US012109257B2

(12) United States Patent
Blair et al.

(10) Patent No.: US 12,109,257 B2
(45) Date of Patent: Oct. 8, 2024

(54) ALPHAVIRUS NEOANTIGEN VECTORS

(71) Applicant: Gritstone bio, Inc., Emeryville, CA (US)

(72) Inventors: Wade Blair, Gaithersburg, MD (US); Karin Jooss, Emeryville, CA (US); Amy Rachel Rappaport, Daly City, CA (US); Ciaran Daniel Scallan, San Francisco, CA (US); Leonid Gitlin, Foster City, CA (US)

(73) Assignee: Gritstone Bio, Inc., Emeryville, CA (US)

( * ) Notice: Subject to any disclaimer, the term of this patent is extended or adjusted under 35 U.S.C. 154(b) by 0 days.

(21) Appl. No.: 18/045,812

(22) Filed: Oct. 11, 2022

(65) Prior Publication Data

US 2024/0024445 A1 Jan. 25, 2024

Related U.S. Application Data

(62) Division of application No. 16/612,352, filed as application No. PCT/US2018/031696 on May 8, 2018, now Pat. No. 11,504,421.

(60) Provisional application No. 62/590,163, filed on Nov. 22, 2017, provisional application No. 62/523,201, filed on Jun. 21, 2017, provisional application No. 62/503,283, filed on May 8, 2017.

(51) Int. Cl.

| | |
|---|---|
| ***A61K 39/12*** | (2006.01) |
| ***A61K 39/00*** | (2006.01) |
| ***A61P 31/12*** | (2006.01) |
| ***C07K 14/47*** | (2006.01) |
| ***C07K 14/74*** | (2006.01) |
| ***C12N 15/86*** | (2006.01) |

(52) U.S. Cl.
CPC ................. *A61K 39/001191* (2018.08); *A61K 39/001188* (2018.08); *A61K 39/12* (2013.01); *A61P 31/12* (2018.01); *C07K 14/4748* (2013.01); *C07K 14/70539* (2013.01); *C12N 15/86* (2013.01); *A61K 2039/53* (2013.01); *A61K 2039/545* (2013.01); *A61K 2039/585* (2013.01); *A61K 2039/6037* (2013.01); *A61K 2039/605* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,656,127 | A | 4/1987 | Mundy |
| 4,722,848 | A | 2/1988 | Paoletti et al. |
| 1,837,028 | A | 6/1989 | Allen |
| 5,019,369 | A | 5/1991 | Presant et al. |
| 5,204,253 | A | 4/1993 | Sanford et al. |
| 5,217,879 | A | 6/1993 | Huang et al. |
| 5,279,833 | A | 1/1994 | Rose |
| 5,505,947 | A | 4/1996 | Johnston et al. |
| 5,580,859 | A | 12/1996 | Felgner et al. |
| 5,589,466 | A | 12/1996 | Felgner et al. |
| 5,622,931 | A | 4/1997 | Edgington et al. |
| 5,643,576 | A | 7/1997 | Johnston et al. |
| 5,662,907 | A | 9/1997 | Kubo et al. |
| 5,814,482 | A | 9/1998 | Dubensky, Jr. et al. |
| 5,843,723 | A | 12/1998 | Dubensky, Jr. et al. |
| 5,849,561 | A | 12/1998 | Falck-Pedersen |
| 5,849,589 | A | 12/1998 | Tedder et al. |
| 5,851,796 | A | 12/1998 | Schatz |
| 5,851,806 | A | 12/1998 | Kovesdi et al. |
| 6,015,686 | A | 1/2000 | Dubensky, Jr. et al. |
| 6,037,135 | A | 3/2000 | Kubo et al. |
| 6,083,716 | A | 7/2000 | Wilson et al. |
| 6,090,406 | A | 7/2000 | Popescu et al. |
| 6,296,854 | B1 | 10/2001 | Pushko et al. |
| 6,312,946 | B1 | 11/2001 | Yeh et al. |
| 6,365,394 | B1 | 4/2002 | Gao et al. |
| 6,376,236 | B1 | 4/2002 | Dubensky, Jr. et al. |
| 6,413,935 | B1 | 7/2002 | Sette et al. |
| 6,475,480 | B1 | 11/2002 | Mehtali et al. |
| 6,531,135 | B1 | 3/2003 | Johnston et al. |
| 6,610,321 | B2 | 8/2003 | Huang et al. |
| 6,770,283 | B1 | 8/2004 | Garoff et al. |
| 6,783,939 | B2 | 8/2004 | Olmsted et al. |
| 7,078,218 | B2 | 7/2006 | Smith et al. |
| 7,202,351 | B1 | 4/2007 | Sette et al. |
| 7,283,337 | B2 | 10/2007 | Sakai et al. |
| 7,285,265 | B2 | 10/2007 | Vogels et al. |
| 7,291,498 | B2 | 11/2007 | Roy et al. |

(Continued)

FOREIGN PATENT DOCUMENTS

| | | | |
|---|---|---|---|
| CA | 2705787 | A1 | 6/2009 |
| CN | 1388247 | A | 1/2003 |

(Continued)

OTHER PUBLICATIONS

Capone et al., Expert Reviews Vaccines, 2013, 12(4):379-393. (Year: 2013).*

(Continued)

*Primary Examiner* — Stacy B Chen
(74) *Attorney, Agent, or Firm* — Goodwin Procter LLP

(57) ABSTRACT

Disclosed herein are alphavirus vectors that include neoantigen-encoding nucleic acid sequences derived from a tumor of a subject. Also disclosed are nucleotides, cells, and methods associated with the vectors including their use as vaccines.

20 Claims, 75 Drawing Sheets

Specification includes a Sequence Listing.

(56) References Cited

U.S. PATENT DOCUMENTS 7,344,872 B2 3/2008 Gao et al.
7,468,181 B2 12/2008 Vogels et al.
7,507,803 B2 3/2009 Sette et al.
7,531,180 B2 5/2009 Polo et al.
7,541,038 B2 6/2009 Kovacs et al.
7,557,200 B2 7/2009 Wu et al.
7,572,453 B2 8/2009 Polo et al.
7,572,628 B2 8/2009 Dubensky, Jr. et al.
7,605,235 B2 10/2009 Anderson et al.
7,732,129 B1 6/2010 Zhang et al.
7,744,900 B2 6/2010 Dubensky, Jr. et al.
7,771,979 B2 8/2010 Polo et al.
7,820,440 B2 10/2010 Vogels et al.
7,820,441 B2 10/2010 Chamberlain et al.
7,838,277 B2 11/2010 Gao et al.
7,850,977 B2 12/2010 Kamrud et al.
7,888,472 B2 2/2011 Sette et al.
8,052,967 B2 11/2011 Vogels et al.
8,093,021 B2 1/2012 Hurtado et al.
8,119,336 B2 2/2012 Sampath et al.
8,158,418 B2 4/2012 Polo et al.
8,216,834 B2 7/2012 Colloca et al.
8,252,574 B2 8/2012 Mason et al.
8,318,677 B2 11/2012 Weinschenk et al.
8,426,188 B2 4/2013 Weaver et al.
8,460,913 B2 6/2013 Kamrud et al.
8,614,082 B2 12/2013 Frolov et al.
8,617,533 B2 12/2013 Smith et al.
8,637,313 B2 1/2014 Chamberlain et al.
8,647,864 B2 2/2014 Polo et al.
8,673,319 B2 3/2014 Colloca et al.
8,680,258 B2 3/2014 Coffield et al.
8,691,563 B2 4/2014 Pushko et al.
8,722,044 B2 5/2014 Almagro et al.
8,951,525 B2 2/2015 Almagro et al.
8,961,995 B2 2/2015 Frolov et al.
8,999,333 B2 4/2015 Almagro et al.
9,017,696 B2 4/2015 Draper et al.
9,024,001 B2 5/2015 Tang et al.
9,101,572 B2 8/2015 Pushko et al.
9,115,402 B2 8/2015 Hacohen et al.
9,187,733 B2 11/2015 O'Shea et al.
9,192,661 B2 11/2015 Jain et al.
9,217,159 B2 12/2015 Roy et al.
9,234,181 B2 1/2016 Tang et al.
9,249,191 B2 2/2016 Ueno et al.
9,254,265 B2 2/2016 Geall et al.
9,255,126 B2 2/2016 Polo et al.
9,273,288 B2 3/2016 Mason et al.
9,295,646 B2 3/2016 Brito et al.
9,340,830 B2 5/2016 Lipson et al.
9,353,353 B2 5/2016 Nabel et al.
9,402,888 B2 8/2016 Ertl et al.
9,416,370 B2 8/2016 Smith et al.
9,453,240 B2 9/2016 Chamberlain et al.
9,486,519 B2 11/2016 Sahin et al.
9,487,563 B2 11/2016 Nabel et al.
9,512,190 B2 12/2016 Ueno et al.
9,580,690 B2 2/2017 Weaver et al.
9,714,435 B2 7/2017 Dicks et al.
9,770,463 B2 9/2017 Geall et al.
9,795,668 B2 10/2017 Jain et al.
9,801,897 B2 10/2017 Geall et al.
9,943,579 B2 4/2018 Weinschenk et al.
10,064,934 B2 9/2018 Ciaramella et al.
10,092,636 B2 10/2018 Binder
10,106,781 B2 10/2018 Barouch et al.
10,238,733 B2 3/2019 Brito et al.
10,240,128 B2 3/2019 Thirion et al.
10,487,332 B2 11/2019 Geall
10,532,067 B2 1/2020 Geall et al.
11,085,084 B2 8/2021 Diehn et al.
11,306,325 B2 4/2022 Gilbert et al.
2002/0065241 A1 5/2002 Shankara
2002/0119127 A1 8/2002 Sette et al.
2002/0137081 A1 9/2002 Bandman
2003/0044774 A1 3/2003 Valenzuela et al.
2003/0072767 A1 4/2003 Gaiger et al.
2003/0114369 A1 6/2003 Takiguchi et al.
2003/0148262 A1 8/2003 Polo et al.
2004/0037843 A1 2/2004 Fikes et al.
2004/0115625 A1 6/2004 Ebner
2004/0248113 A1 12/2004 Sette et al.
2005/0003505 A1 1/2005 Marasco et al.
2005/0123555 A1 6/2005 Olmsted et al.
2005/0196754 A1 9/2005 Drmanac et al.
2005/0271676 A1 12/2005 Sette et al.
2006/0051405 A1 3/2006 MacLachlan et al.
2006/0093623 A1 5/2006 Andrieu et al.
2006/0198854 A1 9/2006 Pushko
2006/0252077 A1 11/2006 Buzby
2006/0292175 A1 12/2006 Polo et al.
2007/0031442 A1 2/2007 Sewell
2007/0055049 A1 3/2007 Grey et al.
2007/0224201 A1 9/2007 Wu et al.
2007/0231347 A1 10/2007 Wilson et al.
2008/0050393 A1 2/2008 Tang et al.
2008/0206837 A1 8/2008 Vogels et al.
2008/0241189 A1 10/2008 Wilson
2009/0075384 A1 3/2009 Kamrud et al.
2009/0081200 A1 3/2009 Wang
2009/0093050 A1 4/2009 Wu et al.
2009/0118181 A1 5/2009 Walker et al.
2009/0215871 A1 8/2009 Wilson et al.
2009/0253184 A1 10/2009 Clarke et al.
2009/0305344 A1 12/2009 Polo et al.
2010/0041737 A1 2/2010 Naldini et al.
2010/0068218 A1 3/2010 Sette et al.
2010/0120897 A1 5/2010 Hurtado et al.
2010/0183665 A1 7/2010 Kamrud et al.
2010/0286070 A1 11/2010 Verheyden et al.
2010/0330121 A1 12/2010 Dubensky, Jr. et al.
2011/0052634 A1 3/2011 Weaver et al.
2011/0091496 A1 4/2011 Graham et al.
2011/0129498 A1 6/2011 Cortese et al.
2011/0142880 A1 6/2011 Lemiale et al.
2011/0217332 A1 9/2011 Colloca et al.
2011/0293637 A1 12/2011 Hacohen et al.
2011/0300205 A1 12/2011 Geall et al.
2012/0027788 A1 2/2012 Colloca et al.
2012/0258126 A1 10/2012 Scholler et al.
2012/0282290 A1 11/2012 Spencer et al.
2012/0328651 A1 12/2012 Colloca et al.
2013/0011426 A1 1/2013 Tureci et al.
2013/0123199 A1 5/2013 Lee
2013/0149375 A1 6/2013 Geall
2013/0171241 A1 7/2013 Geall
2013/0177639 A1 7/2013 Geall et al.
2013/0177640 A1 7/2013 Geall et al.
2013/0189351 A1 7/2013 Geall
2013/0195968 A1 8/2013 Geall et al.
2013/0195969 A1 8/2013 Geall et al.
2013/0202684 A1 8/2013 Geall et al.
2014/0010841 A1 1/2014 Weaver et al.
2014/0141070 A1 5/2014 Geall et al.
2014/0178438 A1 6/2014 Sahin et al.
2014/0227346 A1 8/2014 Geall et al.
2014/0234304 A1 8/2014 Almagro et al.
2014/0242152 A1 8/2014 Geall et al.
2014/0248314 A1 9/2014 Swanson et al.
2014/0255472 A1 9/2014 Geall et al.
2014/0271724 A1 9/2014 Ertl et al.
2014/0271829 A1 9/2014 Lilja et al.
2015/0001108 A1 1/2015 Lee et al.
2015/0110831 A1 4/2015 Gilbert et al.
2015/0125465 A1 5/2015 Binder et al.
2015/0125477 A1 5/2015 Kuttruff-Coqui et al.
2015/0140068 A1 5/2015 Barnett et al.
2015/0167003 A1 6/2015 Naldini et al.
2015/0307897 A1 10/2015 Soden et al.
2015/0337270 A1 11/2015 Lee et al.
2016/0008447 A1 1/2016 Hacohen et al.
2016/0074506 A1 3/2016 Jain et al.
2016/0101170 A1 4/2016 Hacohen et al.

(56) References Cited

U.S. PATENT DOCUMENTS

| | | | |
|---|---|---|---|
| 2016/0199513 | A1 | 7/2016 | Bancel et al. |
| 2016/0289674 | A1 | 10/2016 | Bancel et al. |
| 2016/0331822 | A1 | 11/2016 | Hacohen et al. |
| 2016/0339090 | A1 | 11/2016 | Hacohen et al. |
| 2016/0354409 | A1 | 12/2016 | Wang et al. |
| 2017/0028044 | A1 | 2/2017 | Soon-Shiong et al. |
| 2017/0212984 | A1 | 7/2017 | Yelensky et al. |
| 2017/0340721 | A1 | 11/2017 | Volkmann et al. |
| 2018/0000913 | A1 | 1/2018 | Hacohen et al. |
| 2018/0050059 | A1 | 2/2018 | Geall et al. |
| 2018/0055922 | A1 | 3/2018 | Hacohen et al. |
| 2018/0153975 | A1 | 6/2018 | Fritsch et al. |
| 2018/0363066 | A1 | 12/2018 | Chalmers et al. |
| 2019/0025308 | A1 | 1/2019 | Cummings et al. |
| 2019/0060432 | A1 | 2/2019 | Hacohen et al. |
| 2019/0134184 | A1 | 5/2019 | Yu et al. |
| 2019/0256924 | A1 | 8/2019 | Vogelstein et al. |
| 2019/0270766 | A1 | 9/2019 | Hogrefe et al. |
| 2019/0316184 | A1 | 10/2019 | Zimmermann et al. |
| 2020/0010849 | A1 | 1/2020 | Blair et al. |
| 2020/0197500 | A1 | 6/2020 | Blair et al. |
| 2021/0213122 | A1 | 7/2021 | Blair et al. |
| 2022/0090138 | A1 | 3/2022 | Jooss et al. |
| 2022/0125919 | A1 | 4/2022 | Jooss et al. |
| 2022/0226453 | A1 | 7/2022 | Blair et al. |
| 2022/0265797 | A1 | 8/2022 | Jooss et al. |
| 2023/0040907 | A1 | 2/2023 | Levin et al. |
| 2023/0158134 | A1 | 5/2023 | Ammendola et al. |
| 2024/0067985 | A1 | 2/2024 | Blair et al. |
| 2024/0100139 | A1 | 3/2024 | Juneja |

FOREIGN PATENT DOCUMENTS

| | | | |
|---|---|---|---|
| CN | 101579528 | A | 11/2009 |
| EP | 2044947 | A1 | 4/2009 |
| EP | 2370584 | A1 | 10/2011 |
| EP | 2917353 | A1 | 9/2015 |
| EP | 2947149 | A1 | 11/2015 |
| FR | 2650840 | A1 | 2/1991 |
| KR | 20060017635 | A | 2/2006 |
| RU | 2206329 | C2 | 6/2003 |
| WO | 1991/02087 | A1 | 2/1991 |
| WO | 1991/06309 | A1 | 5/1991 |
| WO | 1992/15712 | A1 | 9/1992 |
| WO | 1993/24640 | A2 | 12/1993 |
| WO | 1995/007994 | A2 | 3/1995 |
| WO | 1995/13392 | A1 | 5/1995 |
| WO | 1996/13597 | A2 | 5/1996 |
| WO | 1996/18373 | A1 | 6/1996 |
| WO | 1997/41241 | A1 | 11/1997 |
| WO | 2000/018433 | A2 | 4/2000 |
| WO | 2001047541 | A1 | 7/2001 |
| WO | 2001/055177 | A2 | 8/2001 |
| WO | 2001/073027 | A2 | 10/2001 |
| WO | 2004/023973 | A2 | 3/2004 |
| WO | 2004/055166 | A2 | 7/2004 |
| WO | 2005/016961 | A1 | 2/2005 |
| WO | 2005/033265 | A2 | 4/2005 |
| WO | 2005/071093 | A2 | 8/2005 |
| WO | 2006/078294 | A2 | 7/2006 |
| WO | 2006/090090 | A2 | 8/2006 |
| WO | 2007/024708 | A2 | 3/2007 |
| WO | 2007/047749 | A1 | 4/2007 |
| WO | 2008/122811 | A2 | 10/2008 |
| WO | 2008/145685 | A1 | 12/2008 |
| WO | 2009/079185 | A2 | 6/2009 |
| WO | 2011/128704 | A1 | 10/2011 |
| WO | 2011/143656 | A2 | 11/2011 |
| WO | 2012/006359 | A1 | 1/2012 |
| WO | 2012/006377 | A2 | 1/2012 |
| WO | 2012/006376 | A3 | 4/2012 |
| WO | 2012/172058 | A1 | 12/2012 |
| WO | 2012/172277 | A1 | 12/2012 |
| WO | 2013/040142 | A2 | 3/2013 |
| WO | 2013/190090 | A1 | 12/2013 |
| WO | 2014/072929 | A1 | 5/2014 |
| WO | 2014/168874 | A2 | 10/2014 |
| WO | 2015/085233 | A1 | 6/2015 |
| WO | 2015/095811 | A2 | 6/2015 |
| WO | 2016/085904 | A1 | 6/2016 |
| WO | 2016/100975 | A1 | 6/2016 |
| WO | 2016/100977 | A1 | 6/2016 |
| WO | 2016/122414 | A1 | 8/2016 |
| WO | 2016/124670 | A1 | 8/2016 |
| WO | 2016/154047 | A2 | 9/2016 |
| WO | 2016/154246 | A1 | 9/2016 |
| WO | 2016/187508 | A3 | 1/2017 |
| WO | 2017/106638 | A1 | 6/2017 |
| WO | 2017/151940 | A2 | 9/2017 |
| WO | 2017/173321 | A1 | 10/2017 |
| WO | 2017/184590 | A1 | 10/2017 |
| WO | 2017/192924 | A1 | 11/2017 |
| WO | 2017/220463 | A1 | 12/2017 |
| WO | 2018/028438 | A1 | 2/2018 |
| WO | 2018/039131 | A1 | 3/2018 |
| WO | 2018/098362 | A1 | 5/2018 |
| WO | 2018/104911 | A1 | 6/2018 |
| WO | 2018/116193 | A1 | 6/2018 |
| WO | 2018/119115 | A1 | 6/2018 |
| WO | 2018102585 | A1 | 6/2018 |
| WO | 2018/187356 | A2 | 10/2018 |
| WO | 2018/227030 | A1 | 12/2018 |
| WO | 2018/232330 | A1 | 12/2018 |
| WO | 2019/090156 | A1 | 5/2019 |
| WO | 2019/170773 | A1 | 9/2019 |
| WO | 2019/226939 | A1 | 11/2019 |
| WO | 2019/226941 | A1 | 11/2019 |
| WO | 2020/097393 | A1 | 5/2020 |
| WO | 2020/243719 | A1 | 12/2020 |
| WO | 2021/003348 | A1 | 1/2021 |
| WO | 2021/092095 | A1 | 5/2021 |
| WO | 2021/119545 | A1 | 6/2021 |
| WO | 2021/142437 | A1 | 7/2021 |
| WO | 2021216775 | A2 | 10/2021 |
| WO | 2022/032196 | A2 | 2/2022 |

OTHER PUBLICATIONS

Cooper et al., "Rescue of splicing-mediated intron loss maximizes expression in lentiviral vectors containing the human ubiquitin C promoter," Nucleic Acids Research vol. 43, No. 1, pp. 682-690, Dec. 17, 2014.

Zufferey et al., "Self-Inactivating Lentivirus Vector for Safe and Efficient In Vivo Gene Delivery," Journal of Virology vol. 72, No. 12, pp. 9873-9880, 1998.

Gros et al., "Prospective identification of neoantigen-specific lymphocytes in the peripheral blood of melanoma patients," Nature Medicine vol. 22, Issue 4, pp. 433-438, Feb. 22, 2016.

Strønen et al., "Targeting of cancer neoantigens with donor-derived T cell receptor repertoires," Science 352, No. 6291 (May 19, 2016): 1337-1341.

Lu et al., "Efficient identification of mutated cancer antigens recognized by T cells associated with durable tumor regressions," Clinical Cancer Research vol. 20, No. 13, pp. 3401-3410, 2014.

Stover et al., "New use of BCG for recombinant vaccines," Nature vol. 351, No. 6326, pp. 456-460, 1991.

Boshart et al., "A Very Strong Enhancer is Located Upstream of an Immediate Early Gene of Human Cytomegalovirus," Cell vol. 41, No. 2, 521-530, 1985.

Kost et al., "The nucleotide sequence of the chick cytoplasmic b-actin gene," Nucleic Acids Research vol. 11, No. 23, pp. 8287-8301, 1983.

Shukla et al., "Comprehensive analysis of cancer-associated somatic mutations in class I HLA genes," Nature Biotechnology vol. 33, No. 11. pp. 1152-1158, Nov. 2015.

Mcgranahan et al., "Allele-specific HLA loss and immune escape in lung cancer evolution," Cell vol. 171, No. 6, pp. 1259-1271, 2017.

Van Loo et al., "Allele-specific copy number analysis of tumors," Proceedings of the National Academy of Sciences, vol. 107, No. 39, pp. 16910-16915, 2010.

(56) References Cited

OTHER PUBLICATIONS

Desrichard et al., "Cancer neoantigens and applications for immunotherapy," Clinical Cancer Research vol. 22, No. 4, pp. 807-812, Feb. 15, 2016.
Gubin et al., "Tumor neoantigens: Building a framework for personalized cancer immunotherapy," The Journal of Clinical Investigation, vol. 125, No. 9, pp. 3413-3421, Sep. 2015.
Rizvi et al., "Mutational landscape determines sensitivity to PD-1 blockade in non-small cell lung cancer," Science vol. 348, No. p. 6230, Apr. 3, 2015.
Snyder et al., "Genetic Basis for Clinical Response to CTLA-4 Blockade in Melanoma," New England Journal of Medicine, vol. 371, No. 23, pp. 2189-2199, 2014.
Carreno et al., "A dendritic cell vaccine increases the breadth and diversity of melanoma neoantigen-specific T cells." Science 348, No. 6236 (Apr. 2, 2015): 9 pages.
Tran et al., "Cancer Immunotherapy Based on Mutation-Specific CD4+ T Cells in a Patient with Epithelial Cancer," Science vol. 344, No. 6184, pp. 641-645, 2014.
Lundegaard et al., "State of the art and challenges in sequence based T-cell epitope prediction," Immunome Research vol. 6, No. 2, pp. 1-14, 2010.
Yadav et al., "Predicting immunogenic tumour mutations by combining mass spectrometry and exome sequencing," Nature, vol. 515, No. 7528, pp. 572-576, 2014.
Bassani-Sternberg et al., "Mass Spectrometry of Human Leukocyte Antigen Class I Peptidomes Reveals Strong Effects of Protein Abundance and Turnover on Antigen Presentation," Molecular & Cellular Proteomics Vo. 14, Issue 3, 658-673, Mar. 1, 2015.
Van Allen et al., "Genomic correlates of response to CTLA-4 blockade in metastatic melanoma," Science vol. 350, No. 6257, pp. 207-211, Nov. 11, 2015.
Yoshida et al., "Splicing factor mutations and cancer," Wiley Interdisciplinary Reviews: RNA 5, No. 4 (2014): 445-459.
Cancer Genome Atlas Research Network, "Comprehensive molecular profiling of lung adenocarcinoma," Nature, vol. 511, pp. 543-550, 2014.
Rajasagi et al., "Systematic identification of personal tumor-specific neoantigens in chronic lymphocytic leukemia," Blood, vol. 124, No. 3, pp. 453-462, 2014.
Cieslik et al., "The use of exome capture RNA-seq for highly degraded RNA with application to clinical cancer sequencing," Genome Research vol. 25, No. 9, 1372-1381, Sep. 1, 2015.
Bodini et al., "The hidden genomic landscape of acute myeloid leukemia: subclonal structure revealed by undetected mutations," Blood, The Journal of the American Society of Hematology vol. 125, No. 4 (Jan. 22, 2015): 600-605.
Saunders et al., Strelka: accurate somatic small-variant calling from sequenced tumor-normal sample pairs, Bioinformatics vol. 28, No. 14, pp. 1811-1817, 2012.
Cibulskis et al., "Sensitive detection of somatic point mutations in impure and heterogeneous cancer samples," Nature Biotechnology vol. 31, No. 3, pp. 213-219, 2013.
Wilkerson et al., "Integrated RNA and DNA sequencing improves mutation detection in low purity tumors," Nucleic Acids Research, vol. 42, p. e107, 2014.
Mose et al., "ABRA: improved coding indel detection via assembly-based realignment," Bioinformatics, vol. 30, No. 19, pp. 2813-2815, 2014.
Ye et al., "Pindel: a pattern growth approach to detect break points of large deletions and medium sized insertions from paired-end short reads," Bioinformatics vol. 25, No. 21, pp. 2865-2871, 2009.
Lam et al., "Nucleotide-resolution analysis of structural variants using BreakSeq and a breakpoint library," Nature Biotechnology vol. 28, No. 1, pp. 47-55 2010.
Frampton et al., "Development and validation of a clinical cancer genomic profiling test based on massively parallel DNA sequencing," Nature Biotechnology vol. 31, No. 11, 2013.
Boegel et al., "HLA typing from RNA-Seq sequence reads," Genome Medicine vol. 4, Issue 12, 2013.
Liu et al., "ATHLATES: accurate typing of human leukocyte antigen through exome sequencing," Nucleic Acids Research vol. 41, No. 14, 2013.
Mayor et al., "HLA typing for the next generation," PLoS One vol. 10, No. 5, May 27, 2015.
Roy et al., "Assessing long-distance RNA sequence connectivity via RNA-templated DNA-DNA ligation," Elife vol. 4, p. e03700, Apr. 13, 2015.
Song et al., "CLASS: constrained transcript assembly of RNA-seq reads," BMC Bioinformatics, vol. 14, Supp. 5, S14, BioMed Central, 2013.
Maretty et al. "Bayesian transcriptome assembly," Genome Biology vol. 15, No. 10, Oct. 2014.
Pertea et al., "StringTie enables improved reconstruction of a transcriptome from RNA-seq reads," Nature Biotechnology vol. 33, No. 3, pp. 290-295, Mar. 2015.
Roberts et al., "Identification of novel transcripts in annotated genomes using RNA-Seq," Bioinformatics vol. 27, No. 17, pp. 2325-2329, 2011.
Vitting-Seerup et al., "spliceR: an R package for classification of alternative splicing and prediction of coding potential from RNA-seq data," BMC Bioinformatics, vol. 15, Issue 1, pp. 1-7, 2014.
Skelly et al., "A powerful and flexible statistical framework for testing hypotheses of allele-specific gene expression from RNA-seq data," Genome Research vol. 21, No. 10, pp. 1728-1737, 2011.
Anders et al., "HTSeq—a Python framework to work with high-throughput sequencing data." Bioinformatics vol. 31, No. 2 (Jan. 15, 2015): 166-169.
Furney et al., "SF3B1 Mutations Are Associated with Alternative Splicing in Uveal Melanoma," Cancer Discovery vol. 3, Issue 10, pp. 1122-1129, 2013.
Zhou et al., "A Chemical Genetics Approach for the Functional Assessment of Novel Cancer Genes," Cancer Research vol. 75, No. 10, pp. 1949-1958, May 15, 2015.
Maguire et al., "SF3B1 mutations constitute a novel therapeutic target in breast cancer," The Journal of Pathology vol. 235, No. 4 pp. 571-580, Mar. 2015.
Carithers et al., "A Novel Approach to High-Quality Postmortem Tissue Procurement: The GTEx Project," Biopreservation and Biobanking, vol. 13, No. 5, 311-319, Oct. 1, 2015.
Xu et al., "RNA Compass: A Dual Approach for Pathogen and Host Transcriptome Analysis of RNA-Seq Datasets," PloS ONE, vol. 9, Issue 2, p. e89445, 2014.
Andreatta et al., "Gapped sequence alignment using artificial neural networks: application to the MHC class I system," Bioinformatics 1 (Feb. 15, 2015): 7 pages.
Jørgensen et al., "NETMHCSTAB-predicting stability of peptide—MHC-I complexes; impacts for cytotoxic T lymphocyte epitope discovery," Immunology vol. 141, No. 1, pp. 18-26, 2014.
Larsen et al., "An integrative approach to CTL epitope prediction: a combined algorithm integrating MHC class I binding, TAP transport efficiency, and proteasomal cleavage predictions," European Journal of Immunology, vol. 35, No. 8, pp. 2295-2303, 2005.
Nielsen et al., "The role of the proteasome in generating cytotoxic T-cell epitopes: insights obtained from improved predictions of proteasomal cleavage," Immunogenetics vol. 57, No. 1-2, pp. 33-41, 2005.
Boisvert et al., "A Quantitative Spatial Proteomics Analysis of Proteome Turnover in Human Cells," Molecular & Cellular Proteomics, vol. 11, Issue. 3, Mar. 1, 2012.
Duan et al., "Genomic and bioinformatic profiling of mutational neoepitopes reveals new rules to predict anticancer immunogenicity," Journal of Experimental Medicine vol. 211, No. 11, Oct. 20, 2014.
Calis et al., "Properties of MHC Class I Presented Peptides That enhance immunogenicity." PLoS Comput Biol. vol. 9, Issue 10 (Oct. 24, 2013): e1003266, 13 pages.
Zhang et al., "Intra-tumor Heterogeneity in Localized Lung Adenocarcinomas Delineated by Multi-region Sequencing," Science vol. 346, No. 6206, pp. 256-259, 2014.
Walter et al., "Clonal Architecture of Secondary Acute Myeloid Leukemia," New England Journal of Medicine, vol. 366, Issue 12, pp. 1090-1098, 2012.

(56) References Cited

OTHER PUBLICATIONS

Hunt et al., "Characterization of Peptides Bound to the Class I MHC Molecule HLA-A2. 1 by Mass Spectrometry," Science vol. 255, pp. 1261-1263, 1992.
Zarling et al., "Identification of class I MHC-associated phosphopeptides as targets for cancer immunotherapy," Proceedings of the National Academy of Sciences, vol. 103, No. 40, pp. 14889-14894, 2006.
Abelin et al., "Complementary IMAC enrichment methods for HLA-associated phosphopeptide identification by mass spectrometry," Nature Protocols 10(9) (2015): 1308-1318.
Barnstable et al., "Production of Monoclonal Antibodies to Group A Erythrocytes, HLA and Other Human Cell Surface Antigens—New Tools for Genetic Analysis," Cell vol. 14, 9-20, 1978.
Goldman et al., "HLA-DA monoclonal antibodies inhibit the proliferation of normal and chronic granulocytic leukaemia myeloid progenitor cell," British Journal of Haematology 52, No. 3 (1982): 411-420.
Eng et al., "Comet: An open-source MS/MS sequence database search tool," Proteomics vol. 13, No. 1, pp. 22-24, 2013.
Eng et al., "A Deeper Look into Comet—Implementation and Features," Journal of the American Society for Mass Spectrometry vol. 26, No. 11, pp. 1865-1874, 2015.
Käll et al., "Semi-supervised learning for peptide identification from shotgun proteomics datasets," Nature Methods vol. 4, No. 11, pp. 923-925, 2007.
Käll et al., "Assigning Significance to Peptides Identified by Tandem Mass Spectrometry Using Decoy Databases," Journal of Proteome Research vol. 7, No. 01, pp. 29-34, 2008.
Käll et al., "Non-parametric estimation of posterior error probabilities associated with peptides identified by tandem mass spectrometry," Bioinformatics vol. 24, No. 16, pp. i42-i48, 2008.
Kinney et al., "Nucleotide sequence of the 26 S mRNA of the virulent Trinidad donkey strain of Venezuelan equine encephalitis virus and deduced sequence of the encoded structural proteins," Virology 152, No. 2 (1986): 400-413.
Slansky et al., "Enhanced Antigen-Specific Antitumor Immunity with Altered Peptide Ligands that Stabilize the MHC-Peptide-TCR Complex," Immunity vol. 13, No. 4, pp. 529-538, 2000.
Huang et al., "The immunodominant major histocompatibility complex class I-restricted antigen of a murine colon tumor derives from an endogenous retroviral gene product," Proceedings of the National Academy of Sciences vol. 93, No. 18, pp. 9730-9735, 1996.
Johnson et al., "Molecular Determinants of Alphavirus Neurovirulence: Nucleotide and Deduced Protein Sequence Changes during Attenuation of Venezuelan Equine Encephalitis Virus," Journal of General Virology vol. 67, Issue 9, pp. 1951-1960, 1986.
Aarnoudse et al., "TCR Reconstitution in Jurkat Reporter Cells Facilitates the Identification of Novel Tumor Antigens By CDNA Expression Cloning," International Journal of Vancer 99, 7013 (2002).
Alexander et al., "Development of High Potency Universal DR-Restricted Helper Epitopes by Modification of High Affinity DR-Blocking Peptides." Immunity vol. 1, Issue 9 (1994): 751-761.
Banu et al., "Building and Optimizing a Virus-specific T Cell Receptor Library for Targeted Immunotherapy in Viral Infections." Scientific Reports vol. 4, pp. 4166, 2014.
Cornet et al., "Optimal organization of a polypeptide-based candidate cancer vaccine composed of cryptic tumor peptides with enhanced immunogenicity," Vaccine vol. 24, No. 12, pp. 2102-2109, 2006.
Depla et al., "Rational Design of a Multiepitope Vaccine Encoding T-Lymphocyte Epitopes for Treatment of Chronic Hepatitis B Virus Infections," Journal of Virology vol. 82, No. 1, pp. 435-450, 2008.
Ishioka et al., "Utilization of MHC Class I Transgenic Mice for Development of Minigene DNA Vaccines Encoding Multiple HLA-Restricted CTL Epitopes," The Journal of Immunology vol. 162, No. 7, pp. 3915-3925, 1999.
Janetzki et al., "Guidelines for the automated evaluation of Elispot assays," Nature Protocols vol. 10, No. 7, pp. 1098-1115, Jul. 2015.
Lyons et al., "Influence of Human CD8 on Antigen Recognition by T-Cell Receptor-Transduced Cells," Cancer Research vol. 66, No. 23, pp. 11455-11461, 2006.
Nagai et al., "Aurora kinase A-specific T-cell receptor gene transfer redirects T lymphocytes to display effective antileukemia reactivity," Blood, The Journal of the American Society of Hematology, vol. 119, No. 2, pp. 368-376, 2012.
Panina-Bordignon et al., "Universally immunogenic T cell epitopes: promiscuous binding to human MHC class II and promiscuous recognition by T cells," European Journal of Immunology 19, No. 12 (1989): 2237-2242.
Vitiello et al., "Analysis of the HLA-restricted Influenza-specific Cytotoxic T Lymphocyte Response in Transgenic Mice Carrying a Chimeric Human-Mouse Class I Major Histocompatibility Complex," The Journal of Experimental Medicine, vol. 173, No. 4, pp. 1007-1015, 1991.
Yachi et al., "Altered Peptide Ligands Induce Delayed CD8-T Cell Receptor Interaction—a Role for CD8 in Distinguishing Antigen Quality," Immunity vol. 25, No. 2, pp. 203-211, 2006.
Pushko et al., "Replicon-Helper Systems from Attenuated Venezuelan Equine Encephalitis Virus: Expression of Heterologous Genes in Vitro and Immunization against Heterologous Pathogens in Vivo," Virology vol. 239, No. 2, pp. 389-401, 1997.
Strauss et al., "The Alphaviruses: Gene Expression, Replication, and Evolution," Microbiological Reviews, vol. 58, No. 3, pp. 491-562, 1994.
Rhême et al., "Alphaviral cytotoxicity and its implication in vector development," Experimental Physiology vol. 90, No. 1, pp. 45-52, 2005.
Riley et al., "Recent advances in nanomaterials for gene delivery—a review," Nanomaterials, vol. 7, No. 5, p. 94, 2017.
Frolov et al., "Cis-acting RNA elements at the 5' end of Sindbis virus genome RNA regulate minus- and plus-strand RNA synthesis," RNA vol. 7, No. 11, pp. 1638-1651, 2001.
Jose et al., "A structural and functional perspective of alphavirus replication and assembly," Future Microbiology, vol. 4, No. 7, pp. 837-856, 2009.
Li et al., "RSEM: accurate transcript quantification from RNA-Seq data with or without a reference genome." BMC bioinformatics 12, No. 1 (2011): 323, 16 pages.
Pearson et al., "MHC class I-associated peptides derive from selective regions of the human genome," The Journal of Clinical Investigation, vol. 126, No. 12, pp. 4690-4701, Dec. 1, 2016.
Mommen et al., "Sampling from the Proteome to the Human Leukocyte Antigen-DR (HLA-DR) Ligandome ProceedsVia High Specificity," Molecular & Cellular Proteomics, vol. 15, No. 4, pp. 1412-1423, Apr. 1, 2016.
Kreiter et al., "Mutant MHC class II epitopes drive therapeutic immune responses to cancer," Nature, vol. 520, No. 7549, pp. 692-696, Apr. 2015.
Andreatta et al., "Accurate pan-specific prediction of peptide-MHC class II binding affinity with improved binding core identification." Immunogenetics 67, No. 11-12 (Nov. 2015): 641-650.
Nielsen et al., "NN-align. An artificial neural network-based alignment algorithm for MHC class II peptide binding prediction," BMC Bioinformatics, vol. 10, No. 1, p. 296, 2009.
Nielsen et al., "Prediction of MHC class II binding affinity using SMM-align, a novel stabilization matrix alignment method," BMC Bioinformatics, vol. 8, No. 1, pp. 238, 2007.
Zhang, et al., "PEAKS DB: De Novo Sequencing Assisted Database Search for Sensitive and Accurate Peptide Identification," Molecular & Cellular Proteomics vol. 11, No. 4, 2012.
Jensen et al., "Improved methods for predicting peptide binding affinity to MHC class II molecules," Immunology vol. 154, Issue 3, pp. 394-406, 2018.
Carter et al., "Absolute quantification of somatic DNA alterations in human cancer," Nature Biotechnology vol. 30, No. 5, 413-421, 2012.
PCT/US18/31696—International Search Report and Written Opinion, Aug. 3, 2018, 12 pages.
Qiu et al., "Reviving virus based cancer vaccines by using cytomegalovirus vectors expressing modified tumor antigens," OncoImmunology vol. 5, No. 1, p. e1056974, Jan. 2, 2016.

(56) References Cited

OTHER PUBLICATIONS

Farina et al., "Replication-Defective Vector Based on a Chimpanzee Adenovirus," Journal of Virology vol. 75, No. 23, pp. 11603-11613, 2001.
Ljungberg et al., "Self-replicating alphavirus RNA vaccines," Expert Review of Vaccines vol. 14, No. 2, pp. 177-194, Feb. 1, 2015.
Lundstrom, "Alphavirus-Based Vaccines," Viruses vol. 6, No. 6, pp. 2392-2415, 2014.
Geall et al., "Nonviral delivery of self-amplifying RNA vaccines," Proceedings of the National Academy of Sciences, vol. 109, Issue 36, pp. 14604-14609, 2012.
Rodriguez et al., "DNA Immunization with Minigenes: Low Frequency of Memory Cytotoxic T Lymphocytes and Inefficient Antiviral Protection Are Rectified by Ubiquitination," Journal of Virology vol. 72, No. 6, pp. 5174-5181, 1998.
Velders et al., "Defined Flanking Spacers and Enhanced Proteolysis Is Essential for Eradication of Established Tumors by an Epitope String DNA Vaccine," The Journal of Immunology, vol. 166, No. 9, pp. 5366-5373, 2001.
Kreiter et al., "Increased Antigen Presentation Efficiency by Coupling Antigens to MHC Class I Trafficking Signals," The Journal of Immunology, vol. 180, No. 1, pp. 309-318, 2008.
Rodriguez et al., "DNA Immunization: Ubiquitination of a Viral Protein Enhances Cytotoxic T-Lymphocyte Induction and Antiviral Protection but Abrogates Antibody Induction," Journal of Virology vol. 71, No. 11, pp. 8497-8503, 1997.
James et al., "Tetramer-guided epitope mapping reveals broad, individualized repertoires of tetanus toxin-specific CD4+ T cells and suggests HLA-based differences in epitope recognition," International Immunology vol. 19, No. 11, pp. 1291-1301, 2007.
Jayaraman et al., "Maximizing the Potency of siRNA Lipid Nanoparticles for Hepatic Gene Silencing In Vivo," Angewandte Chemie vol. 51, pp. 8529-8533, 2012.
Démoulins et al., "Polyethylenimine-based polyplex delivery of self-replicating RNA vaccines," Nanomedicine: Nanotechnology, Biology and Medicine vol. 12, No. 3, pp. 711-722, Apr. 1, 2016.
Chahal et al., "Dendrimer-RNA nanoparticles generate protective immunity against lethal Ebola, H1N1 influenza, and Toxoplasma gondii challenges with a single dose," Proceedings of the National Academy of Sciences vol. 113, No. 29 E4133-E4142, Jul. 19, 2016.
PCT/US18/31696—International Preliminary Report on Patentabilty, Nov. 12, 2019, 9 pages.
Vajdy et al., "Mucosal adjuvants and delivery systems for protein-, DNA- and RNA-based vaccines," Immunology and Cell Biology, vol. 82, No. 6, pp. 617-627, 2004.
Fleeton et al., "Self-Replicative RNA Vaccines Elicit Protection against Influenza A Virus, Respiratory Syncytial Virus, and a Tickborne Encephalitis Virus," The Journal of Infectious Diseases vol. 183, No. 9, pp. 1395-1398, 2001.
Strejan et al., "Suppression of chronic-relapsing experimental allergic encephalomyelitis in strain-13 guinea pigs by administration of liposome-associated myelin basic protein." Journal of Neuroimmunology 7 (1984): 27-41.
Johanning et al., "A Sindbis virus mRNA polynucleotide vector achieves prolonged and high level heterologous gene expression in vivo," Nucleic Aids Research vol. 23, Issue 9, pp. 1495-1501, 1995.
Martinon et al., "Induction of virus-specific cytotoxic T lymphocytes in vivo by liposome-entrapped mRNA," European Journal of Immunology 23, No. 7 (1993): 1719-1722.
Leitner et al., "DNA and RNA-based vaccines: principles, progress and prospects," Vaccine vol. 18, No. 9-10, pp. 765-777, 1999.
Del Val et al., "Efficient Processing of an Antigenic Sequence for Presentation by MHC Class I Molecules Depends on Its Neighboring Residues in the Protein," Cell vol. 66, No. 6, pp. 1145-1153, 1991.
Holzhütter et al., "A Theoretical Approach Towards the Identification of Cleavage-Determining Amino Acid Motifs of the 20S Proteasome," Journal of Molecular Biology, vol. 286, Issue 4, pp. 1251-1265, 1999.
Nussbaum et al., "Cleavage motifs of the yeast 20S proteasome ß subunits deduced from digests of enolase 1," Proceedings of the National Academy of Sciences, vol. 95, No. 21, pp. 12504-12509, 1998.
Eggers et al., "The Cleavage Preference of the Proteasome Governs the Yield of Antigenic Peptides," The Journal of Experimental Medicine vol. 182, No. 6, pp. 1865-1870, 1995.
Borthwick et al., "Vaccine-elicited human T cells recognizing conserved protein regions inhibit HIV-1." Molecular therapy 22, No. 2 (2014): 464-475.
Ager et al., "31st Annual Meeting and Associated Programs of the Society for Immunotherapy of Cancer (SITC 2016): part two," in Journal for Immuno Therapy of Cancer, vol. 4, Supplement 1, p. 73, 2016.
Warimwe et al. "Immunogenicity and efficacy of a chimpanzee adenovirus-vectored Rift Valley fever vaccine in mice," Virology Journal vol. 10, No. 1, pp. 1-9, 2013.
Cappuccini et al. "Immunogenicity and efficacy of the novel cancer vaccine based on simian adenovirus and MVA vectors alone and in combination with PD-1 mAb in a mouse model of prostate cancer," Cancer Immunol. Immunother. vol. 65, No. 6, pp. 701-713, Apr. 6, 2016.
Aurisicchio et al., "Immunogenicity and Therapeutic Efficacy of a Dual-Component Genetic Cancer Vaccine Cotargeting Carcinoembryonic Antigen and HER2/neu in Preclinical Models," Human Gene Therapy, vol. 25, Issue 2, pp. 121-131, Feb. 2014.
Morris et al. "Simian adenoviruses as vaccine vectors." Future Virology, vol. 11, No. 9 pp. 649-659, Sep. 15, 2016.
Letourneau et al. "Design and Pre-Clinical Evaluation of a Universal HIV-1 Vaccine," PloS ONE, vol. 2, No. 10, p. e984, 2007.
Colloca et al., "Vaccine Vectors Derived from a Large Collection of Simian Adenoviruses Induce Potent Cellular Immunity Across Multiple Species," Science Translational Medicine, vol. 4, No. 115, 115ra2, 2012.
Levy et al. "A melanoma multiepitope polypeptide induces specific CD8+ T-cell response," Cellular Immunology, vol. 250, No. 1-2, pp. 24-30, 2007.
Tatsis et al. "Chimpanzee-origin adenovirus vectors as vaccine carriers," Gene Therapy vol. 13, No. 5, pp. 421-429, 2006.
Zappasodi et al., "Alphavirus-based vaccines in melanoma: rationale and potential improvements in immunotherapeutic combinations." Immunotherapy 7, No. 9 (Sep. 2015): 981-997.
Riabov et al., "Anti-tumor effect of the alphavirus-based virus-like particlevector expressing prostate-specific antigen in a HLA-DR transgenic mouse model of prostate cancer." Vaccine 33, No. 41 (Oct. 5, 2015): 5386-5395.
Fang et al., "Stable antibody expression at therapeutic levels using the 2A peptide." Nature biotechnology 23, No. 5 (2005): 584-590.
Wu et al., "Targeting genes: delivery and persistent expression of a foreign gene driven by mammalian regulatory elements in vivo." Journal of Biological Chemistry 264, No. 29 (1989): 16985-16987.
Fisher et al., "The transmembrane domain of diphtheria toxin improves molecular conjugate gene transfer." Biochemical Journal 321, No. 1 (1997): 49-58.
Szoka et al., "Comparative properties and methods of preparation of lipid vesicles (liposomes)." Annual review of biophysics and bioengineering 9, No. 1 (1980): 467-508.
Wolff et al., "Direct gene transfer into mouse muscle in vivo." Science 247, No. 4949 (1990): 1465-1468.
Felgner et al., "Lipofection: a highly efficient, lipid-mediated DNA-transfection procedure." Proceedings of the National Academy of Sciences 84, No. 21 (1987): 7413-7417.
Mannino et al., "Liposome mediated gene transfer." Biotechniques 6, No. 7 (1988): 682-690.
Konarska et al., "Recognition of cap structure in splicing in vitro of mRNA precursors." Cell 38, No. 3 (1984): 731-736.
Huang, "Sindbis virus vectors for expression in animal cells." Current Opinion in Biotechnology 7, No. 5 (1996): 531-535.
Wan et al., "High-sensitivity monitoring of ctDNA by patient-specific sequencing panels and integration of variant reads." bioRxiv (2019): 759399, pp. 1-37.

(56) References Cited

OTHER PUBLICATIONS

Wang et al., "Identification of T Cell Receptors Targeting KRAS-Mutated Human Tumors", Cancer Immunology Research 4(3) Mar. 2016, pp. 204-214.
Hacohen et al., "Getting personal with neoantigen-based therapeutic cancer vaccines." Cancer immunology research 1, No. 1 (2013): 11-15.
Karasaki et al., "Identification of individual cancer-specific somatic mutations for neoantigen-based immunotherapy of lung cancer." Journal of Thoracic Oncology 11, No. 3 (Mar. 2016): 324-333.
Abbas et al., "Structure of human IFIT1 with capped RNA reveals adaptable mRNA binding and mechanisms for sensing N1 and N2 ribose 2?—O methylations." Proceedings of the National Academy of Sciences 114, No. 11 (2017): E2106-E2115.
Nezafat et al., "A novel multi-epitope peptide vaccine against cancer: an in silico approach." Journal of theoretical biology 349 (2014): 121-134.
Mohammed et al., "Phosphorylation-dependent interaction between antigenic peptides and MHC class I: a molecular basis for the presentation of transformed self." Nature immunology 9, No. 11 (2008): 1236-1243.
Toes et al., "Protective anti-tumor immunity induced by vaccination with recombinant adenoviruses encoding multiple tumor-associated cytotoxic T lymphocyte epitopes in a string-of-beads fashion." Proceedings of the National Academy of Sciences 94, No. 26 (1997): 14660-14665.
Wei et al., "Dendritic cells expressing a combined PADRE/MUC4-derived polyepitope DNA vaccine induce multiple cytotoxic T-cell responses." Cancer biotherapy & radiopharmaceuticals 23, No. 1 (2008): 121-128.
Meko'o et al., "Immunopreventive effects against murine H22 hepatocellular carcinoma in vivo by a DNA vaccine targeting a gastrin-releasing peptide." Asian Pacific Journal of Cancer Prevention 15, No. 20 (2014): 9039-9043.
Huang et al., "DNA vaccines for cervical cancer." American journal of translational research 2, No. 1 (2010): 75, 13 pages.
Behrens et al., "Antibody-Drug Conjugates (ADCs) Derived from Interchain Cysteine Cross-Linking Demonstrate Improved Homogeneity and Other Pharmacological Properties over Conventional Heterogeneous ADCs," Molecular Pharmaceutics 12 (11) (): 3986-3998, Nov. 2, 2015.
Koizume et al., "Tissue Factor—Factor VII Complex As a Key Regulator of Ovarian Cancer Phenotypes," Biomarkers in Cancer vol. 7, pp. 1-13, Aug. 5, 2015.
Schumacher et al., "Neoantigens in cancer immunotherapy," Science vol. 348, Issue 6230, pp. 69-74, Apr. 3, 2015.
Rivas et al., "Effect of predicted protein-truncating genetic variants on the human transcriptome," Science vol. 348, No. 6235, pp. 666-669, May 8, 2015.
Lundstrom, Kenneth. "Alphavirus-based vaccines." Current opinion in molecular therapeutics 4, No. 1 (Feb. 2002): 28-34.
Alexander et al., "Linear PADRE T helper epitope and carbohydrate B cell epitope conjugates induce specific high titer IgG antibody responses." The Journal of Immunology 164, No. 3 (Feb. 2000): 1625-1633.
Kim et al., "Neopepsee: accurate genome-level prediction of neoantigens by harnessing sequence and amino acid immunogenicity information." Annals of Oncology 29, No. 4 (Apr. 2018): 1030-1036.
Ott et al., "An immunogenic personal neoantigen vaccine for patients with melanoma." Nature 547, No. 7662 (Jul. 2017): 217-221.
Gen Bank: AF394196.1—Simian adenovirus 25, complete genome, 15 pages, 2001.
Fluet et al., "Effects of rapid antigen degradation and VEE glycoprotein specificity on immune responses induced by a VEE replicon vaccine." Virology 370, No. 1 (Jan. 2008): 22-32.
Ogawa et al., "An Attempt of Cytokine Gene Therapy Using Adenovirus Vectors," Partial Translation of: Biotherapy, 1998, vol. 12 No. 5, p. 785-787.
Nielsen et al., "An in vitro-transcribed-mRNA polyepitope construct encoding 32 distinct HLA class I-restricted epitopes from CMV, EBV, and Influenza for use as a functional control in human immune monitoring studies." Journal of Immunological methods 360, No. 1-2 (2010): 149-156.
Bergmann et al., "Differential effects of flanking residues on presentation of epitopes from chimeric peptides." Journal of virology 68, No. 8 (1994): 5306-5310.
Carroll et al., "Alphavirus replicon-based adjuvants enhance the immunogenicity and effectiveness of Fluzone in rhesus macaques." Vaccine 29, No. 5 (2011): 931-940.
Thompson et al., "The contribution of type I interferon signaling to immunity induced by alphavirus replicon vaccines." Vaccine 26, No. 39 (2008): 4998-5003.
Ljungberg et al,. "Increased immunogenicity of a DNA-launched Venezuelan equine encephalitis virus-based replicon DNA vaccine." Journal of virology 81, No. 24 (2007): 13412-13423.
Channon et al., "Improved adenoviral vectors: cautious optimism for gene therapy." QJM: monthly journal of the Association of Physicians 90, No. 2 (1997): 105-109.
Gao et al., "Biology of adenovirus vectors with E1 and E4 deletions for liver-directed gene therapy." Journal of virology 70, No. 12 (1996): 8934-8943.
Andrews et al., "Generation and characterization of E1/E2a/E3/E4-deficient adenoviral vectors encoding human factor VIII." Molecular Therapy 3, No. 3 (2001): 329-336.
Farina et al., "Replication-defective vector based on a chimpanzee adenovirus." Journal of virology 75, No. 23 (2001): 11603-11613.
Roshorm, et al., "T cells induced by recombinant chimpanzee adenovirus alone and in prime-boost regimens decrease chimeric EcoHIV/NDK challenge virus load," Eur J Immunol. Dec. 2012;42(12):3243-55.
Morris et al., "Simian adenoviruses as vaccine vectors," Future Virol. Sep. 2016; 11(9):649-659.
Leppard, Keith N. "E4 gene function in adenovirus, adenovirus vector and adeno-associated virus infections", Journal of General Virology, 1997, vol. 78, pp. 2131-2138.
Tran et al. "T-Cell Transfer Therapy Targeting Mutant KRAS in Cancer", The New England Journal of Medicine, Dec. 8, 2016;375(23):2255-2262.
Brotto et al., "The usability of allele-specific PCR and reverse-hybridization assays for KRAS genotyping in Serbian colorectal cancer patients," Dig Dis Sci. Apr. 2013;58(4):998-1003.
Shu et al., "Circulating Tumor DNA Mutation Profiling by Targeted Next Generation Sequencing Provides Guidance for Personalized Treatments in Multiple Cancer Types," Sci Rep., Apr. 3, 2017;7(1):583.
Zhou et al., "Untargeted profiling of cell-free circulating DNA," Translational Cancer Research, Mar. 1, 2018, 7(S2):S140-S152.
Volik et al., "Cell-free DNA (cfDNA): Clinical Significance and Utility in Cancer Shaped By Emerging Technologies," Mol Cancer Res. Oct. 2016;14(10):898-908.
Li et al., "Personalized prediction of genes with tumor-causing somatic mutations based on multi-modal deep Boltzmann machine, Neurocomputing," 2019, 324:51-62.
Ngo et al., "CNTO 859, a humanized anti-tissue factor monoclonal antibody, is a potent inhibitor of breast cancer metastasis and tumor growth in xenograft models," International Journal of Cancer, vol. 120, No. 6, pp. 1261-1267, 2007.
Hong et al., Immuno-PET of Tissue Factor in Pancreatic Cancer, J Nucl Med, vol. 53, No. 11, pp. 1748-1754, 2012.
Trail et al., "Antibody drug conjugates for treatment of breast cancer: Novel targets and diverse approaches in ADC design," Pharmacol. Ther., vol. 181, pp. 126-142, 2018.
De Graaf et al., Beta-Glucuronidase-Mediated Drug Release, Curr Pharm Des., vol. 8, pp. 1391-1403, 2002.
Chari et al., Immunoconjugates Containing Novel Maytansinoids: Promising Anticancer Drugs, Cancer Research, vol. 52, pp. 127-131, 1992.
Kovtun et al., "Antibody-Mytansinoid Conjugates Designed to Bypass Multidrug Resistance," Cancer Research vol. 70, No. 6, pp. 2528-2537, 2010.
Vitetta et al., "Redesigning Nature's Poisons to Create Anti-Tumor Reagents," Science vol. 238, No. 4830, pp. 1098-1104, 1987.

(56) References Cited

OTHER PUBLICATIONS

Junutula et al., "Rapid identification of reactive cysteine residues for site-specific labeling of antibody-Fabs," Journal of Immunological Methods 332, No. 1-2 (2008): 41-52.
Junutula et al., "Site-specific conjugation of a cytotoxic drug to an antibody improves the therapeutic index." Nature Biotechnology 26, No. 8 (2008): 925.
Hofer et al., "An engineered selenocysteine defines a unique class of antibody derivatives," Proc. Natl. Acad. Sci. USA, 2008, 105:12451-12456.
Hofer et al., Molecularly defined antibody conjugation through a selenocysteine interface, Biochemistry, vol. 48, No. 50, pp. 12047-12057, 2009.
Hjortoe et al., Tissue factor-factor VIIa-specific up-regulation of IL-8 expression in MDA-MB-231 cells is mediated by PAR-2 and results in increased cell migration, Blood, 2004, vol. 103, No. 8, pp. 3029-3037.
Sakurai et al., "Expression of Tissue Factor in Epithelial Ovarian Carcinoma is Involved in the Development of Venous Thromboembolism," International Journal of Gynecologic Cancer, vol. 27, No. 1, pp. 37-43, 2017.
Cocco et al., "Expression of Tissue factor in Adenocarcinoma and Squamous Cell Carcinoma of the Uterine Cervix: Implications for immunotherapy with hl-con1, a factor VII-IgGFc chimeric protein targeting tissue factor," BMC Cancer, vol. 11 p. 263, 2011.
Christensen et al., Urokinase-type plasminogen activator receptor (uPAR), tissue factor (TF) and epidermal growth factor receptor (EGFR): tumor expression patterns and prognostic value in oral cancer, BMC Cancer, vol. 17, p. 572, 2017.
Yao et al., Tissue Factor and VEGF Expression in Prostate Carcinoma A Tissue Microarray Study, Cancer Invest., vol. 27, pp. 430-434, 2009.
Abdulkadir et al., "Tissue factor expression and angiogenesisin human prostate carcinoma," Human Pathology 31, No. 4 (2000): 443-447.
Zhang et al., "Pathological expression of tissue factor confers promising antitumor response to a novel therapeutic antibody SC1 in triple negative breast cancer and pancreatic adenocarcinoma," Oncotarget vol. 8, No. 35, pp. 59086-59102, 2017.
Guan et al., "Tissue factor expression and angiogenesis in human glioma." Clinical Biochemistry 35, No. 4 (2002): 321-325.
Carneiro-Lobo et al., Ixolaris, a tissue factor inhibitor, blocks primary tumor growth and angiogenesis in a glioblastoma model, J Thromb Haemost, 2009, 7:1855-1864.
Yeh et al., "Upregulation of Tissue Factor by Activated Stat3 Contributes to Malignant Pleural Effusion Generation via Enhancing Tumor Metastasis and Vascular Permeability in Lung Adenocarcinoma," PLoS One, vol. 8, No. 9, p. e75287, 2013.
Regina et al., "Increased tissue factor expression is associated with reduced survival in non-small cell lung cancer and with mutations of TP53 and PTEN," Clinical Chemistry, vol. 55, No. 10, pp. 1834-1842, 2009.
Lo et al., "Tissue factor expression in the metaplasia-adenoma-carcinoma sequence of gastric cancer in a European population," British Journal of Cancer vol. 107, No. 7, pp. 1125-1130, 2012.
Chen et al., "Immunolocalisation of tissue factor in esophageal cancer is correlated with intratumoral angiogenesis and prognosis of the patient." Acta Histochemica 112, No. 3 (2010): 233-239.
Patry et al., "Tissue factor expression correlates with disease-specific survival in patients with node-negative muscle- Invasive bladder cancer," International Journal of Cancer, vol. 122, No. 7, pp. 1592-1597, 2008.
Bromberg et al., Tissue factor promotes melanoma metastasis by a pathway independent of blood coagulation, Proc Natl Acad Sci U S A., 1995, 92:8205-8209.
Silva et al., "Increased Tissue Factor Expression is an Independent Predictor of Mortality in Clear Cell Carcinoma of the Kidney," Int Braz J Urol., 2014, 40:499-506.
Van Den Berg et al., "The relationship between tissue factor and cancer progression: insights from bench and pedside," Blood vol. 119, No. 4, pp. 924-932, 2012.
Tripisciano et al., "Different Potential of Extracellular Vesicles to Support Thrombin Generation: Contributions of Phosphatidylserine, Tissue Factor, and Cellular Origin," Scientific Reports vol. 7, No. 1, pp. 1-11, 2017.
Teplyakov et al., "Crystal structure of tissue factor in complex with antibody 10H10 reveals the signaling epitope," Cellular Signalling vol. 36, pp. 139-144, 2017.
Iepe et al., "A large fraction of HLA class I ligands are proteasome-generated spliced peptides, " Science vol. 354, No. 6310, Oct. 21, 2016.
Smith et al., "Comparison of biosequences," Advances in Applied Mathematics vol. 2, No. 4, pp. 482-489, 1981.
Needleman et al., "A General Method Applicable to the Search for Similarities in the Amino Acid Sequence of Two Proteins," Journal of Molecular Biology, vol. 48, No. 3, pp. 443-453, 1970.
Pearson et al., "Improved tools for biological sequence comparison," Proceedings of the National Academy of Sciences, vol. 85, No. 8, pp. 2444-2448, 1988.
Altschul et al., "Basic Local Alignment Search Tool." Journal of Molecular Biology vol. 215, Issue 3 (1990): 403-410.
Kornher et al., "Mutation detection using nucleotide analogs that alter electrophoretic mobility," Nucleic Acids Research vol. 17, No. 19, pp. 7779-7784, 1989.
Sokolov, "Primer extension technique for the detection of single nucleotide in genomic DNA," Nucleic Acids Research, vol. 18, No. 12, p. 3671, 1990.
SYVÄNEN et al., "A Primer-Guided Nucleotide Incorporation Assay in the Genotyping of Apolipoprotein E," Genomics 3, No. 4 (1990): 684-692.
Kuppuswamy et al., "Single nucleotide primer extension to detect genetic diseases: experimental application to hemophilia B (factor IX) and cystic fibrosis genes," Proceedings of the National Academy of Sciences vol. 88, No. 4, pp. 1143-1147, 1991.
Prezant et al., "Trapped-Oligonucleotide Nucleotide Incorporation (TONI) Assay, a Simple Method for Screening Point Mutations," Human Mutation 1, No. 2 (1992): 159-164.
Ugozzoli et al., "Detection of specific alleles by using allele-specific primer extension followed by capture on solid support," Genetic Analysis: Biomolecular Engineering 9, No. 4 (1992): 107-112.
NYRÉN et al., "Solid phase DNA minisequencing by an enzymatic luminometric inorganic pyrophosphate detection assay." Analytical Biochemistry 208, No. 1 (1993): 171-175.
Syvanen et al., "Identification of Individuals by Analysis of Biallelic DNA Markers, Using PCR and Solid-Phase Minisequencing," American Journal of Human Genetics vol. 52, No. 1, p. 46 1993.
Merrifield, "Solid phase synthesis." Science 232 (1986): 341-348.
Dupuis et al., "Dendritic cells internalize vaccine adjuvant after intramuscular injection," Cellular Immunology 186, No. 1 (1998), 18-27.
Allison, "The mode of action of immunological adjuvants," Developments in Biological Standardization 92 (1998): 3-11.
Gabrilovich et al., "IL-12 and Mutant P53 Peptide-Pulsed Dendritic Cells for the Specific Immunotherapy of Cancer," Journal of Immunotherapy, vol. 19, No. 6 (1996): 414-418.
Tatsis et al., "Adenoviruses as vaccine vectors," Molecular Therapy vol. 10, No. 4, pp. 616-629, 2004.
Hu et al., "Immunization Delivered by Lentiviral Vectors for Cancer and Infectious Diseases," Immunological Reviews, vol. 239, Issue 1, pp. 45-61, 2011.
Sakuma et al., "Lentiviral vectors: basic to translational," Biochemical Journal 443, No. 3 (2012): 603-618.

* cited by examiner

Most recent literature suggests <5% of predicted bound peptides can be found presented on tumor cells

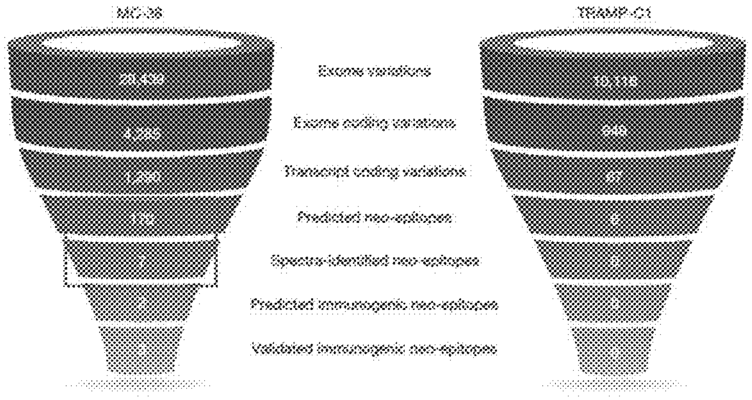

- Only 7/170 (4%) predicted neo-epitopes were eluted and detected by mass-spec
- Possibly due to sensitivity limits of particular mass-spec detection approach Yadav, Nature Vol 515 17 November 2014

| NetMHCcon IC50≤500nM | MS-based identification: HLAp | MS-based identification: Not detected | |
|---|---|---|---|
| Prediction: Binders | 1,579 | 47,777 | 3% |
| Prediction: Non-binders | 153 | 1,140,967 | |

| NetMHCcon IC50≤50nM | MS-based identification: HLAp | MS-based identification: Not detected |
|---|---|---|
| Prediction: Binders | 1,133 | 14,059 |
| Prediction: Non-binders | 599 | 1,174,685 |

Bassani-Sternberg M, Mol Cell Proteomics. 2015;14(3):658-73

FIG 1B

Training Data
170A

| Allele-Dependent ($x^i$) | | | | Allele-Independent ($w^i$) | | |
|---|---|---|---|---|---|---|
| **Peptide Sequence ($p^i$)** | **Affinity ($b^i$-nM)** | **Stability ($s^i$-$h$)** | **Allele ($a^i$)** | **C-Flanking Sequence ($c^i$)** | **mRNA Q. ($m^i$-$FPKM$)** | **Label ($y^i$)** |
| QCEIOWARE | 1000 | 1 | HLA-C*01:03 | FJELFISBOSJFIE | $10^2$ | Not Presented |
| FIEUHFWI | 1500 | 15 | HLA-C*01:03 | FEGRKUOOI | $10^{-3}$ | Presented |
| FEWRHRJTRUJR | 650 | 20 | HLA-C*01:03 | PJFIOEJOIJGEIO | $10^1$ | Presented |
| QIEJOEIJE | 500 | 1 | HLA-B*07:02 | PJFIOEJOIJGEIO | 1 | Presented |
| | 600 | 14 | HLA-C*01:03 | | | |
| | 1200 | 7 | HLA-A*01:01 | | | |

FIG 4A

Training Data
170A

Allele-Dependent ($x^i$)

| Peptide Sequence ($p^i$) | Affinity ($b^i$-nM) | Stability ($s^i$-$h$) | Allele ($a^i$) |
|---|---|---|---|
| QCEIOWAREFLKEIGJ | 1000 | 1 | HLA-DRB3:01:01 |

FIG 4B

| Model | AUC | Log Loss | PPV at 10% Recall |
|---|---|---|---|
| Sigmoid-of-Sums | 0.9278 | $12.2 \cdot 10^{-4}$ | 0.114 |
| Sum-of-Sigmoids | 0.9723 | $5.78 \cdot 10^{-4}$ | 0.152 |
| Hyperbolic Tangent | **0.9734** | $\mathbf{5.72 \cdot 10^{-4}}$ | 0.156 |
| Second Order | 0.9727 | $5.74 \cdot 10^{-4}$ | **0.160** |

FIG 13C

| Model | AUC | Log Loss | PPV at 10% Recall |
|---|---|---|---|
| With A2/B7 Single-Allele Data | **0.9818** | $5.40 \cdot 10^{-4}$ | **0.215** |
| Without A2/B7 Single-Allele Data | 0.9803 | $\mathbf{5.31 \cdot 10^{-4}}$ | 0.211 |

FIG 13D

| Setup | Correlation |
|---|---|
| A2 model predicting B7 | 0.004 |
| A2 model predicting A2 | 0.294 |
| B7 model predicting B7 | 0.366 |
| B7 model predicting A2 | 0.002 |

FIG 13E

| Allele | P2 | P9 |
|---|---|---|
| A2 | L 89% | V 58% |
| | M 5% | L 32% |
| B7 | P 98% | L 76 % |
| | | V 8% |

FIG 13F

| Model | AUC | Log Loss | PPV at 10% Recall |
|---|---|---|---|
| Allele-interacting | 0.9723 | $5.78 \cdot 10^{-4}$ | 0.152 |
| Allele-noninteracting | **0.9732** | $\mathbf{5.53 \cdot 10^{-4}}$ | **0.188** |

FIG 13G

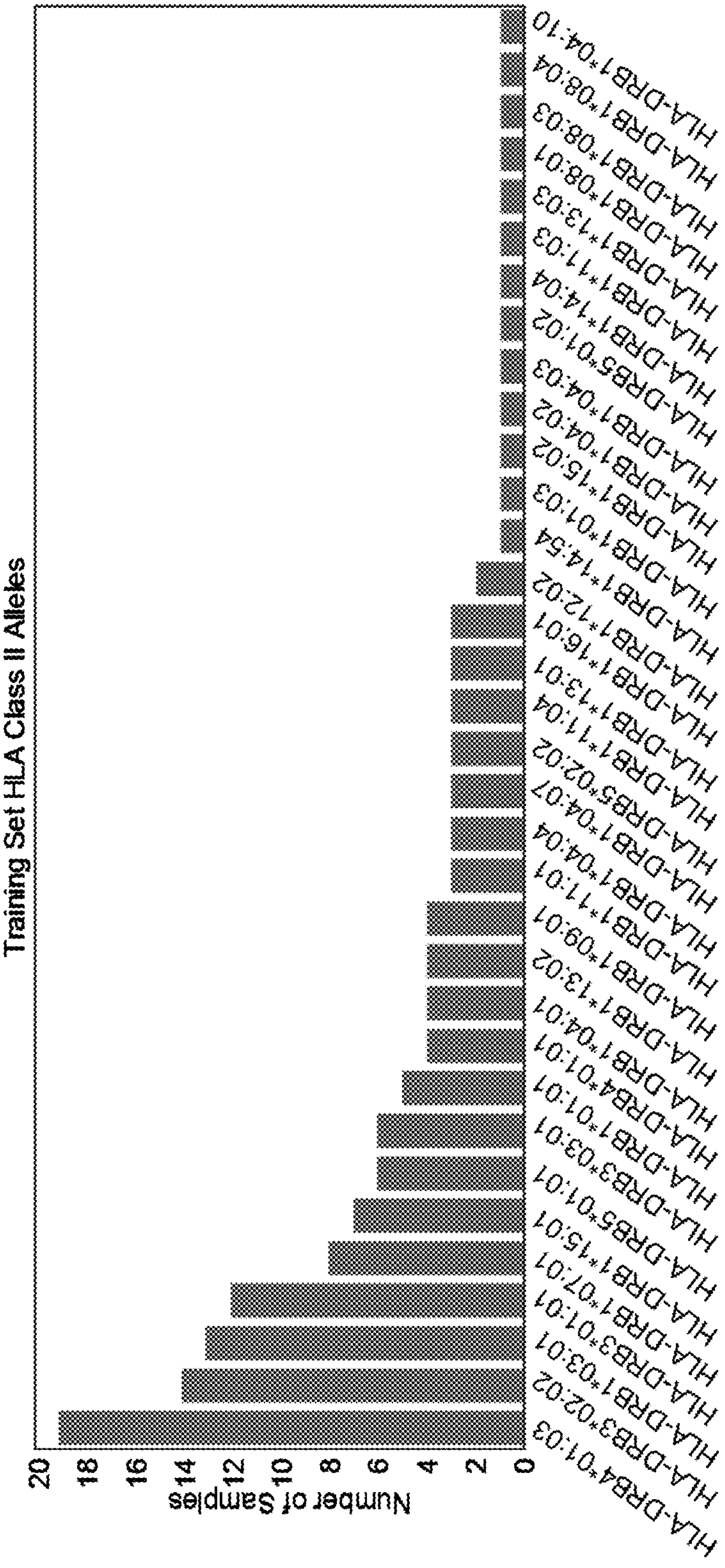
FIG 13-O

| # | HLA | Sequence | Origin |
|---|---|---|---|
| 1 | A*0201 | NLVPMVATV | HCMV pp65 (495– 503) |
| 2 | A*0201 | CLGGLLTMV | EBV LMP2A(426-434) |
| 3 | A*0201 | GLCTLVAML | EBV BMLF1 (280–288) |
| 4 | A*0201 | LLFGYPVYV | HTLV-1 Tax (11-19) |
| 5 | A*0201 | GILGFVFTL | Influenza A Matrix 1 (58– 66) |
| | MHC-II | AKFVAAWTLKAAA | PADRE (artificial seq) |
| | MHC-II | QYIKANSKFIGITE | Tetanus toxoid (830–844) |

| # | HLA | Sequence | Origin |
|---|---|---|---|
| 1 | A*02:01 | NLVPMVATV | HCMV pp65 495-504 |
| 2 | A*02:01 | CLGGLLTMV | EBV LMP-2 426-434 |
| 3 | A*02:01 | GLCTLVAML | EBV BMLF-1 259-267 |
| 4 | A*02:01 | LLFGYPVYV | HTLV1 Tax 11-19 |
| 5 | A*02:01 | GILGFVFTL | Influenza A MP 58-66 |
| 6 | A*02:01 | DLMGYIPAV | HCV core 132-140 |
| 7 | A*02:01 | FLPSDFFPSV | HBV core antigen 18-27 |
| 8 | A*02:01 | FLLTRILTI | HBV envelope 183-191 |
| 9 | A*02:01 | WLSLLVPFV | HBV surface antigen 172-181 |
| 10 | A*02:01 | FLLSLGIHL | HBV polymerase 573-581 |
| 11 | A*02:01 | ILKEPVHGV | HIV-1 RT 476-484 |
| 12 | A*02:01 | YMLDLQPETT | HPV 16 E7 11-20 |
| 13 | A*02:01 | CINGVCWTV | HCV NS3 1073-1081 |
| 14 | A*02:01 | YLLPRRGPRL | HCV core 35-44 |
| 15 | A*02:01 | FLYALALLL | EBV LMP-2 356-364 |
| 16 | A*02:01 | AAGIGILTV | MELAN-A/MART-1 (27-35) |
| 17 | A*02:01 | SLLMWITQV | NY-ESO-1(157-165) C9V |
| 18 | A*03:01 | KLGGALQAK | CVM-IE1 |
| 19 | A*03:01 | RLRAEAQVK | EBV-EBNA-3a |
| 20 | B*44:05 | EENLLDFVRF | EBV EBNASC (281-290) |
| 21 | B*44:05 | EEYLQAFTY | Self ABCD3 protein |

FIG 19B

FIG 20A
1
4
7
10
14
18
linker
NHP
Murine class I MHC epitope
Human
class II MHC epitopes

NHP Epitopes

| | MHC | Sequence |
|---|---|---|
| 1 | Mamu*01 | CTPYDINQM |
| 4 | Mamu*01 | TTPESANL |
| 7 | Mamu*01 | CAPPGYALL |
| 10 | Mamu*01 | SGPKTNIIV |
| 14 | Mamu*01 | LSPRTLNAW |
| 18 | Mamu*01 | TVPWPNASL |

Human Epitopes

| | HLA | Sequence |
|---|---|---|
| 3 | A*02:01 | GILGFVFTL |
| 6 | A*02:01 | LLFGYPVYV |
| 9 | A*02:01 | GLCTLVAML |
| 12 | A*02:01 | NLVPMVATV |
| 16 | A*02:01 | CLGGLLTMV |

Murine MHC-I Epitopes

| | MHC | Sequence |
|---|---|---|
| 2 | H-2Kb | SIINFEKL |
| 5 | H-2Ld | SPSYAYHQF |
| 8 | H-2Db | EGPRNQDWL |
| 11 | H-2Kb | DWENVSPEL |
| 13 | H-2Kb | SIIVFNLL |
| 15 | H-2Db | ASMTNMELM |
| 17 | H-2Db | AQLANDVVL |
| 19 | H-2Kb | SVYDFFVWL |
| 20 | H-2Ld | MNKYAYHML |

Universal MHC-II Epitopes

| | HLA | Sequence |
|---|---|---|
| 1 | MHC-II | AKFVAAWTLKAAA |
| 2 | MHC-II | QYIKANSKFIGITEL |

FIG 20B

ALPHAVIRUS NEOANTIGEN VECTORS

PRIORITY CLAIMS AND RELATED APPLICATIONS

This application is a divisional of U.S. application Ser. No. 16/612,352, filed Nov. 8, 2019, now issued as U.S. Pat. No. 11,504,421, which is the National Stage of International Application No. PCT/US2018/031696, filed Aug. 5, 2018, which claims the benefit of U.S. Provisional Application No. 62/590,163, filed Nov. 22, 2017, U.S. Provisional Application No. 62/523,201, filed Jun. 21, 2017, and U.S. Provisional Application No. 62/503,283, filed May 8, 2017, the entire contents of each is incorporated herein by reference for all purposes.

SEQUENCE LISTING

The instant application contains a Sequence Listing which has been submitted via Patent Center and is hereby incorporated herein by reference in its entirety. The accompanying sequence listing .XML file name GSO-006D2, was created on 7 Nov. 2022, and is 538 kb in size.

BACKGROUND

Therapeutic vaccines based on tumor-specific neoantigens hold great promise as a next-generation of personalized cancer immunotherapy.[1-3] Cancers with a high mutational burden, such as non-small cell lung cancer (NSCLC) and melanoma, are particularly attractive targets of such therapy given the relatively greater likelihood of neoantigen generation.[4,5] Early evidence shows that neoantigen-based vaccination can elicit T-cell responses[6] and that neoantigen targeted cell-therapy can cause tumor regression under certain circumstances in selected patients.[7]

One question for neoantigen vaccine design is which of the many coding mutations present in subject tumors can generate the "best" therapeutic neoantigens, e.g., antigens that can elicit anti-tumor immunity and cause tumor regression.

Initial methods have been proposed incorporating mutation-based analysis using next-generation sequencing, RNA gene expression, and prediction of MHC binding affinity of candidate neoantigen peptides[8]. However, these proposed methods can fail to model the entirety of the epitope generation process, which contains many steps (e.g., TAP transport, proteasomal cleavage, and/or TCR recognition) in addition to gene expression and MHC binding[9]. Consequently, existing methods are likely to suffer from reduced low positive predictive value (PPV). (FIG. 1A)

Indeed, analyses of peptides presented by tumor cells performed by multiple groups have shown that <5% of peptides that are predicted to be presented using gene expression and MHC binding affinity can be found on the tumor surface MHC[10,11] (FIG. 1B). This low correlation between binding prediction and MHC presentation was further reinforced by recent observations of the lack of predictive accuracy improvement of binding-restricted neoantigens for checkpoint inhibitor response over the number of mutations alone.[12]

This low positive predictive value (PPV) of existing methods for predicting presentation presents a problem for neoantigen-based vaccine design. If vaccines are designed using predictions with a low PPV, most patients are unlikely to receive a therapeutic neoantigen and fewer still are likely to receive more than one (even assuming all presented peptides are immunogenic). Thus, neoantigen vaccination with current methods is unlikely to succeed in a substantial number of subjects having tumors. (FIG. 1C)

Additionally, previous approaches generated candidate neoantigens using only cis-acting mutations, and largely neglected to consider additional sources of neo-ORFs, including mutations in splicing factors, which occur in multiple tumor types and lead to aberrant splicing of many genes[13], and mutations that create or remove protease cleavage sites.

Finally, standard approaches to tumor genome and transcriptome analysis can miss somatic mutations that give rise to candidate neoantigens due to suboptimal conditions in library construction, exome and transcriptome capture, sequencing, or data analysis. Likewise, standard tumor analysis approaches can inadvertently promote sequence artifacts or germline polymorphisms as neoantigens, leading to inefficient use of vaccine capacity or auto-immunity risk, respectively.

In addition to the challenges of current neoantigen prediction methods certain challenges also exist with the available vector systems that can be used for neoantigen delivery in humans, many of which are derived from humans. For example, many humans have pre-existing immunity to human viruses as a result of previous natural exposure, and this immunity can be a major obstacle to the use of recombinant human viruses for neoantigen delivery for cancer treatment.

SUMMARY

Disclosed herein is a composition for delivery of a neoantigen expression system, comprising: the neoantigen expression system, wherein the neoantigen expression system comprises one or more vectors, the one or more vectors comprising: (a) an RNA alphavirus backbone, wherein the RNA alphavirus backbone comprises: (i) at least one promoter nucleotide sequence, and (ii) at least one polyadenylation (poly(A)) sequence; and (b) a neoantigen cassette, wherein the neoantigen cassette comprises: (i) at least one neoantigen-encoding nucleic acid sequence derived from a tumor present within a subject, comprising: (I) at least one tumor-specific and subject-specific MHC class I neoantigen-encoding nucleic acid sequence derived from the tumor, and comprising: (A) a MHC class I epitope encoding nucleic acid sequence with at least one alteration that makes the encoded peptide sequence distinct from the corresponding peptide sequence encoded by a wild-type nucleic acid sequence, and (B) optionally, a 5' linker sequence, and (C) optionally, a 3' linker sequence; (ii) optionally, a second promoter nucleotide sequence operably linked to the neoantigen-encoding nucleic acid sequence; and (iii) optionally, at least one MHC class II antigen-encoding nucleic acid sequence; (iv) optionally, at least one nucleic acid sequence encoding a GPGPG amino acid linker sequence (SEQ ID NO:56); and (v) optionally, at least one second poly(A) sequence, wherein the second poly(A) sequence is a native poly(A) sequence or an exogenous poly(A) sequence to the alphavirus.

Also disclosed herein is a composition for delivery of a neoantigen expression system, comprising: the neoantigen expression system, wherein the neoantigen expression system comprises one or more vectors, the one or more vectors comprising: (a) an RNA alphavirus backbone, wherein the RNA alphavirus backbone comprises the nucleic acid sequence set forth in SEQ ID NO:6, wherein the RNA alphavirus backbone sequence comprises a 26S promoter nucleotide sequence and a poly(A) sequence, wherein the 26S promoter sequence is endogenous to the RNA alphavirus backbone, and wherein the poly(A) sequence is endogenous to the RNA alphavirus backbone; and (b) a neoantigen cassette integrated between the 26S promoter nucleotide sequence and the poly(A) sequence, wherein the neoantigen cassette comprises: (i) at least one neoantigen-encoding nucleic acid sequence derived from a tumor present within a subject, comprising: (I) at least 10 tumor-specific and subject-specific MHC class I neoantigen-encoding nucleic acid sequences linearly linked to each other and each comprising: (A) a MHC class I epitope encoding nucleic acid sequence with at least one alteration that makes the encoded peptide sequence distinct from the corresponding peptide sequence encoded by a wild-type nucleic acid sequence, wherein the MHC I epitope encoding nucleic acid sequence encodes a MHC class I epitope 7-15 amino acids in length, (B) a 5' linker sequence, wherein the 5' linker sequence encodes a native N-terminal amino acid sequence of the MHC I epitope, and wherein the 5' linker sequence encodes a peptide that is at least 3 amino acids in length, (C) a 3' linker sequence, wherein the 3' linker sequence encodes a native N-terminal acid sequence of the MHC I epitope, and wherein the 3' linker sequence encodes a peptide that is at least 3 amino acids in length, and wherein the neoantigen cassette is operably linked to the 26S promoter nucleotide sequence, wherein each of the MHC class I neoantigen-encoding nucleic acid sequences encodes a polypeptide that is between 13 and 25 amino acids in length, and wherein each 3' end of each MHC class I neoantigen-encoding nucleic acid sequence is linked to the 5' end of the following MHC class I neoantigen-encoding nucleic acid sequence with the exception of the final MHC class I neoantigen-encoding nucleic acid sequence in the neoantigen cassette; and (ii) at least two MHC class II antigen-encoding nucleic acid sequences comprising: (I) a PADRE MHC class II sequence (SEQ ID NO:48), (II) a Tetanus toxoid MHC class II sequence (SEQ ID NO:46), (III) a first nucleic acid sequence encoding a GPGPG amino acid linker sequence (SEQ ID NO: 56) linking the PADRE MHC class II sequence and the Tetanus toxoid MHC class II sequence, (IV) a second nucleic acid sequence encoding a GPGPG amino acid linker sequence (SEQ ID NO: 56) linking the 5' end of the at least two MHC class II antigen-encoding nucleic acid sequences to the at least 20 tumor-specific and subject-specific MHC class I neoantigen-encoding nucleic acid sequences, (V) optionally, a third nucleic acid sequence encoding a GPGPG amino acid linker sequence (SEQ ID NO: 56) at the 3' end of the at least two MHC class II antigen-encoding nucleic acid sequences.

In some aspects, an ordered sequence of each element of the neoantigen cassette is described in the formula, from 5' to 3', comprising:

*Pa-(L5b-Nc-L3d)X-(G5e-Uf)Y-G3g* wherein P comprises the second promoter nucleotide sequence, where a=0 or 1, N comprises one of the MHC class I epitope encoding nucleic acid sequences, where c=1, L5 comprises the 5' linker sequence, where b=0 or 1, L3 comprises the 3' linker sequence, where d=0 or 1, G5 comprises one of the at least one nucleic acid sequences encoding a GPGPG amino acid linker (SEQ ID NO: 56), where e=0 or 1, G3 comprises one of the at least one nucleic acid sequences encoding a GPGPG amino acid linker (SEQ ID NO: 56), where g=0 or 1, U comprises one of the at least one MHC class II antigen-encoding nucleic acid sequence, where f=1, X=1 to 400, where for each X the corresponding Nc is a epitope encoding nucleic acid sequence, and Y=0, 1, or 2, where for each Y the corresponding Uf is an antigen-encoding nucleic acid sequence. In some aspects, for each X the corresponding Nc is a distinct MHC class I epitope encoding nucleic acid sequence. In some aspects, for each Y the corresponding Uf is a distinct MHC class II antigen-encoding nucleic acid sequence.

In some aspects, a=0, b=1, d=1, e=1, g=1, h=1, X=20, Y=2, the at least one promoter nucleotide sequence is a single 26S promoter nucleotide sequence provided by the RNA alphavirus backbone, the at least one polyadenylation poly(A) sequence is a poly(A) sequence of at least 100 consecutive A nucleotides provided by the RNA alphavirus backbone, each N encodes a MHC class I epitope 7-15 amino acids in length, L5 is a native 5' linker sequence that encodes a native N-terminal amino acid sequence of the MHC I epitope, and wherein the 5' linker sequence encodes a peptide that is at least 3 amino acids in length, L3 is a native 3' linker sequence that encodes a native nucleic-terminal acid sequence of the MHC I epitope, and wherein the 3' linker sequence encodes a peptide that is at least 3 amino acids in length, U is each of a PADRE class II sequence and a Tetanus toxoid MHC class II sequence, the RNA alphavirus backbone is the sequence set forth in SEQ ID NO:6, and each of the MHC class I neoantigen-encoding nucleic acid sequences encodes a polypeptide that is between 13 and 25 amino acids in length.

In some aspects, any of the above compositions further comprise a nanoparticulate delivery vehicle. The nanoparticulate delivery vehicle, in some aspects, may be a lipid nanoparticle (LNP). In some aspects, the LNP comprises ionizable amino lipids. In some aspects, the ionizable amino lipids comprise MC3-like (dilinoleylmethyl-4-dimethylaminobutyrate) molecules. In some aspects, the nanoparticulate delivery vehicle encapsulates the neoantigen expression system.

In some aspects, any of the above compositions further comprise a plurality of LNPs, wherein the LNPs comprise: the neoantigen expression system; a cationic lipid; a non-cationic lipid; and a conjugated lipid that inhibits aggregation of the LNPs, wherein at least about 95% of the LNPs in the plurality of LNPs either: have a non-lamellar morphology; or are electron-dense.

In some aspects, the non-cationic lipid is a mixture of (1) a phospholipid and (2) cholesterol or a cholesterol derivative.

In some aspects, the conjugated lipid that inhibits aggregation of the LNPs is a polyethyleneglycol (PEG)-lipid conjugate. In some aspects, the PEG-lipid conjugate is selected from the group consisting of: a PEG-diacylglycerol (PEG-DAG) conjugate, a PEG dialkyloxypropyl (PEG-DAA) conjugate, a PEG-phospholipid conjugate, a PEG-ceramide (PEG-Cer) conjugate, and a mixture thereof. In some aspects the PEG-DAA conjugate is a member selected from the group consisting of: a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, and a mixture thereof.

In some aspects, the neoantigen expression system is fully encapsulated in the LNPs.

In some aspects, the non-lamellar morphology of the LNPs comprises an inverse hexagonal ($H_{11}$) or cubic phase structure.

In some aspects, the cationic lipid comprises from about 10 mol % to about 50 mol % of the total lipid present in the LNPs. In some aspects, the cationic lipid comprises from about 20 mol % to about 50 mol % of the total lipid present in the LNPs. In some aspects, the cationic lipid comprises from about 20 mol % to about 40 mol % of the total lipid present in the LNPs.

In some aspects, the non-cationic lipid comprises from about 10 mol % to about 60 mol % of the total lipid present in the LNPs. In some aspects, the non-cationic lipid comprises from about 20 mol % to about 55 mol % of the total lipid present in the LNPs. In some aspects, the non-cationic lipid comprises from about 25 mol % to about 50 mol % of the total lipid present in the LNPs.

In some aspects, the conjugated lipid comprises from about 0.5 mol % to about 20 mol % of the total lipid present in the LNPs. In some aspects, the conjugated lipid comprises from about 2 mol % to about 20 mol % of the total lipid present in the LNPs. In some aspects, the conjugated lipid comprises from about 1.5 mol % to about 18 mol % of the total lipid present in the LNPs.

In some aspects, greater than 95% of the LNPs have a non-lamellar morphology. In some aspects, greater than 95% of the LNPs are electron dense.

In some aspects, any of the above compositions further comprise a plurality of LNPs, wherein the LNPs comprise: a cationic lipid comprising from 50 mol % to 65 mol % of the total lipid present in the LNPs; a conjugated lipid that inhibits aggregation of LNPs comprising from 0.5 mol % to 2 mol % of the total lipid present in the LNPs; and a non-cationic lipid comprising either a mixture of a phospholipid and cholesterol or a derivative thereof, wherein the phospholipid comprises from 4 mol % to 10 mol % of the total lipid present in the LNPs and the cholesterol or derivative thereof comprises from 30 mol % to 40 mol % of the total lipid present in the LNPs; a mixture of a phospholipid and cholesterol or a derivative thereof, wherein the phospholipid comprises from 3 mol % to 15 mol % of the total lipid present in the LNPs and the cholesterol or derivative thereof comprises from 30 mol % to 40 mol % of the total lipid present in the LNPs; or up to 49.5 mol % of the total lipid present in the LNPs and comprising a mixture of a phospholipid and cholesterol or a derivative thereof, wherein the cholesterol or derivative thereof comprises from 30 mol % to 40 mol % of the total lipid present in the LNPs.

In some aspects, any of the above compositions further comprise a plurality of LNPs, wherein the LNPs comprise: a cationic lipid comprising from 50 mol % to 85 mol % of the total lipid present in the LNPs; a conjugated lipid that inhibits aggregation of LNPs comprising from 0.5 mol % to 2 mol % of the total lipid present in the LNPs; and a non-cationic lipid comprising from 13 mol % to 49.5 mol % of the total lipid present in the LNPs.

In some aspects, the phospholipid comprises dipalmitoylphosphatidylcholine (DPPC), distearoylphosphatidylcholine (DSPC), or a mixture thereof.

In some aspects, the conjugated lipid comprises a polyethyleneglycol (PEG)-lipid conjugate. In some aspects, the PEG-lipid conjugate comprises a PEG-diacylglycerol (PEG-DAG) conjugate, a PEG-dialkyloxypropyl (PEG-DAA) conjugate, or a mixture thereof. In some aspects, the PEG-DAA conjugate comprises a PEG-dimyristyloxypropyl (PEG-DMA) conjugate, a PEG-distearyloxypropyl (PEG-DSA) conjugate, or a mixture thereof. In some aspects, the PEG portion of the conjugate has an average molecular weight of about 2,000 daltons.

In some aspects, the conjugated lipid comprises from 1 mol % to 2 mol % of the total lipid present in the LNPs.

In some aspects, the LNP comprises a compound having a structure of Formula I:

I

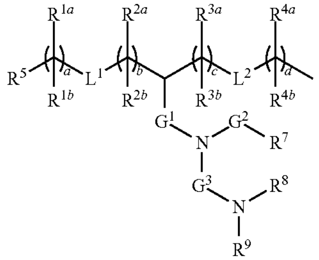

or a pharmaceutically acceptable salt, tautomer, prodrug or stereoisomer thereof, wherein: $L^1$ and $L^2$ are each independently —OC═O)-, —(C═O)O—, —C(═O)-, —O—, —$S(O)_x$-, —S—S—, —C(═O)S—, —SC(═O)-, —$R^a$C(═O)-, —C(═O) $R^a$—, —$R^a$C(═O) $R^a$—, —OC(═O) R—, —$R^a$C(═O)O— or a direct bond; $G^1$ is Ci-$C_2$ alkylene, —(C═O)-, —OC═O)-, —SC(═O)-, —$R^a$C(═O)- or a direct bond: —C(═O)-, —(C═O)O-, —C(═O) S—, —C(═O) $R^a$— or a direct bond; G is $C_1$-$C_6$ alkylene; $R^a$ is H or C1-C12 alkyl; $R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond; $R^2$ and $R^{2b}$ are, at each occurrence, independently either: (a) H or $C_1$-$C_{12}$ alkyl; or (b) $R^2$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond; $R^{3a}$ and $R^{3b}$ are, at each occurrence, independently either (a): H or $C_1$-$C_{12}$ alkyl; or (b) $R^1$ is H or $C_1$-$C_{12}$ alkyl, and $R^{3b}$ together with the carbon atom to which it is bound is taken together with an adjacent R and the carbon atom to which it is bound to form a carbon-carbon double bond; $R^a$ and $R^b$ are, at each occurrence, independently either: (a) H or C1-C12 alkyl; or (b) $R^1$ is H or C1-C12 alkyl, and $R^1$ together with the carbon atom to which it is bound is taken together with an adjacent $R^1$ and the carbon atom to which it is bound to form a carbon-carbon double bond; $R^5$ and $R^6$ are each independently H or methyl; $R^7$ is C4-C20 alkyl; $R^8$ and $R^9$ are each independently C1-C12 alkyl; or $R^8$ and $R^9$, together with the nitrogen atom to which they are attached, form a 5, 6 or 7-membered heterocyclic ring; a, b, c and d are each independently an integer from 1 to 24; and x is 0, 1 or 2.

In some aspects, the LNP comprises a compound having a structure of Formula II:

II

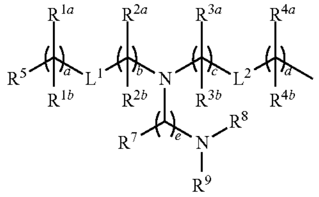

or a pharmaceutically acceptable salt, tautomer, prodrug or stereoisomer thereof, wherein: $L^1$ and $L^2$ are each independently —O(C═O)—, —(C═O)O—or a carbon-carbon double bond; $R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond; $R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond; $R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond; $R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond; $R^5$ and $R^6$ are each independently methyl or cycloalkyl; $R^7$ is, at each occurrence, independently H or $C_1$-$C_{12}$ alkyl; $R^8$ and $R^9$ are each independently unsubstituted C1-C12 alkyl; or $R^8$ and $R^9$, together with the nitrogen atom to which they are attached, form a 5, 6 or 7-membered heterocyclic ring comprising one nitrogen atom; a and d are each independently an integer from 0 to 24; b and c are each independently an integer from 1 to 24; and e is 1 or 2, provided that: at least one of $R^{1a}$, $R^{2a}$, $R^{3a}$ or $R^{4a}$ is C1-C12 alkyl, or at least one of $L^1$ or $L^2$ is —O(C═O)— or —(C═O)O—; and $R^{1a}$ and $R^{1b}$ are not isopropyl when a is 6 or n-butyl when a is 8.

In some aspects, any of the above compositions further comprise one or more excipients comprising a neutral lipid, a steroid, and a polymer conjugated lipid. In some aspects, the neutral lipid comprises at least one of 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), and 1,2-Dioleoyl-sn-glycero-3-phosphoethanolamine (DOPE). In some aspects, the neutral lipid is DSPC.

In some aspects, the molar ratio of the compound to the neutral lipid ranges from about 2:1 to about 8:1.

In some aspects, the steroid is cholesterol. In some aspects, the molar ratio of the compound to cholesterol ranges from about 2:1 to 1:1.

In some aspects, the polymer conjugated lipid is a pegylated lipid. In some aspects, the molar ratio of the compound to the pegylated lipid ranges from about 100:1 to about 25:1. In some aspects, the pegylated lipid is PEG-DAG, a PEG polyethylene (PEG-PE), a PEG-succinoyl-diacylglycerol (PEG-S-DAG), PEG-cer or a PEG dialkyoxypropylcarbamate. In some aspects, the pegylated lipid has the following structure III:

III

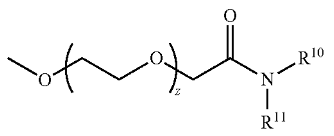

or a pharmaceutically acceptable salt, tautomer or stereoisomer thereof, wherein: $R^{10}$ and $R^{11}$ are each independently a straight or branched, saturated or unsaturated alkyl chain containing from 10 to 30 carbon atoms, wherein the alkyl chain is optionally interrupted by one or more ester bonds; and z has a mean value ranging from 30 to 60. In some aspects, $R^{10}$ and $R^{11}$ are each independently straight, saturated alkyl chains having 12 to 16 carbon atoms. In some aspects, the average z is about 45.

Start Here

In some aspects, the LNP self-assembles into non-bilayer structures when mixed with polyanionic nucleic acid. In some aspects, the non-bilayer structures have a diameter between 60 nm and 120 nm. In some aspects, the non-bilayer structures have a diameter of about 70 nm, about 80 nm, about 90 nm, or about 100 nm. In some aspects, wherein the nanoparticulate delivery vehicle has a diameter of about 100 nm.

In some aspects, the neoantigen cassette is integrated between the at least one promoter nucleotide sequence and the at least one poly(A) sequence. In some aspects, the at least one promoter nucleotide sequence is operably linked to the neoantigen-encoding nucleic acid sequence.

In some aspects, the one or more vectors comprise one or more +-stranded RNA vectors. In some aspects, the one or more +-stranded RNA vectors comprise a 5' 7-methylguanosine (m7g) cap. In some aspects, the one or more +-stranded RNA vectors are produced by in vitro transcription. In some aspects, the one or more vectors are self-replicating within a mammalian cell.

In some aspects, the RNA alphavirus backbone comprises at least one nucleotide sequence of an Aura virus, a Fort Morgan virus, a Venezuelan equine encephalitis virus, a Ross River virus, a Semliki Forest virus, a Sindbis virus, or a Mayaro virus. In some aspects, the RNA alphavirus backbone comprises at least one nucleotide sequence of a Venezuelan equine encephalitis virus. In some aspects, the RNA alphavirus backbone comprises at least sequences for nonstructural protein-mediated amplification, a 26S promoter sequence, a poly(A) sequence, a nonstructural protein 1 (nsP1) gene, a nsP2 gene, a nsP3 gene, and a nsP4 gene encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, the RNA alphavirus backbone comprises at least sequences for nonstructural protein-mediated amplification, a 26S promoter sequence, and a poly(A) sequence encoded by the nucleotide sequence of the Aura virus, the Fort Morgan virus, the Venezuelan equine encephalitis virus, the Ross River virus, the Semliki Forest virus, the Sindbis virus, or the Mayaro virus. In some aspects, sequences for nonstructural protein-mediated amplification are selected from the group consisting of: an alphavirus 5' UTR, a 51-nt CSE, a 24-nt CSE, a 26S subgenomic promoter sequence, a 19-nt CSE, an alphavirus 3' UTR, or combinations thereof.

In some aspects, the RNA alphavirus backbone does not encode structural virion proteins capsid, E2 and E1. In some aspects, the neoantigen cassette is inserted in place of the structural virion proteins within the nucleotide sequence of the Aura virus, the Fort Morgan virus, the Venezuelan equine encephalitis virus, the Ross River virus, the Semliki Forest virus, the Sindbis virus, or the Mayaro virus.

In some aspects, the Venezuelan equine encephalitis virus (VEE) comprises the strain TC-83. In some aspects, the Venezuelan equine encephalitis virus comprises the sequence set forth in SEQ ID NO:3 or SEQ ID NO:5. In some aspects, the Venezuelan equine encephalitis virus comprises the sequence of SEQ ID NO:3 or SEQ ID NO:5 further comprising a deletion between base pair 7544 and 11175. In some aspects, the RNA alphavirus backbone is the sequence set forth in SEQ ID NO:6 or SEQ ID NO:7. In some aspects, the neoantigen cassette is inserted to replace the deletion between base pair 7544 and 11175 set forth in the sequence of SEQ ID NO:3 or SEQ ID NO:5.

In some aspects, the insertion of the neoantigen cassette provides for transcription of a polycistronic RNA comprising the nsP1-4 genes and the at least one of antigen-encoding nucleic acid sequences, wherein the nsP1-4 genes and the at least one of antigen-encoding nucleic acid sequences are in separate open reading frames.

In some aspects, the at least one promoter nucleotide sequence is the native 26S promoter nucleotide sequence encoded by the RNA alphavirus backbone. In some aspects, the at least one promoter nucleotide sequence is an exogenous RNA promoter. In some aspects, the second promoter nucleotide sequence is a 26S promoter nucleotide sequence. In some aspects, the second promoter nucleotide sequence comprises multiple 26S promoter nucleotide sequences, wherein each 26S promoter nucleotide sequence provides for transcription of one or more of the separate open reading frames.

In some aspects, the one or more neoantigen expression vectors are each at least 300 nt in size. In some aspects, the one or more neoantigen expression vectors are each at least 1 kb in size. In some aspects, the one or more neoantigen expression vectors are each 2 kb in size. In some aspects, the one or more neoantigen expression vectors are each less than 5 kb in size.

In some aspects, at least one of the at least one neoantigen-encoding nucleic acid sequences encodes a polypeptide sequence or portion thereof that is presented by MHC class I on the tumor cell. In some aspects, each antigen-encoding nucleic acid sequence is linked directly to one another. In some aspects, at least one of the at least one antigen-encoding nucleic acid sequences is linked to a distinct antigen-encoding nucleic acid sequence with a nucleic acid sequence encoding a linker. In some aspects, the linker links two MHC class I sequences or an MHC class I sequence to an MHC class II sequence. In some aspects, the linker is selected from the group consisting of: (1) consecutive glycine residues, at least 2, 3, 4, 5, 6, 7, 8, 9, or 10 residues in length; (2) consecutive alanine residues, at least 2, 3, 4, 5, 6, 7, 8, 9, or 10 residues in length; (3) two arginine residues (RR); (4) alanine, alanine, tyrosine (AAY); (5) a consensus sequence at least 2, 3, 4, 5, 6, 7, 8, 9, or 10 amino acid residues in length that is processed efficiently by a mammalian proteasome; and (6) one or more native sequences flanking the antigen derived from the cognate protein of origin and that is at least 2, 3, 4, 5, 6, 7, 8, 9, 10, 11, 12, 13, 14, 15, 16, 17, 18, 19, 20, or 2-20 amino acid residues in length. In some aspects, the linker links two MHC class II sequences or an MHC class II sequence to an MHC class I sequence. In some aspects, the linker comprises the sequence GPGPG (SEQ ID NO: 56).

In some aspects, at least one sequence of the at least one antigen-encoding nucleic acid sequences is linked, operably or directly, to a separate or contiguous sequence that enhances the expression, stability, cell trafficking, processing and presentation, and/or immunogenicity of the at least one antigen-encoding nucleic acid sequences. In some aspects, the separate or contiguous sequence comprises at least one of: a ubiquitin sequence, a ubiquitin sequence modified to increase proteasome targeting (e.g., the ubiquitin sequence contains a Gly to Ala substitution at position 76), an immunoglobulin signal sequence (e.g., IgK), a major histocompatibility class I sequence, lysosomal-associated membrane protein (LAMP)-1, human dendritic cell lysosomal-associated membrane protein, and a major histocompatibility class II sequence; optionally wherein the ubiquitin sequence modified to increase proteasome targeting is A76.

In some aspects, at least one of the at least one neoantigen-encoding nucleic acid sequences encodes a polypeptide sequence or portion thereof that has increased binding affinity to its corresponding MHC allele relative to the translated, corresponding wild-type, nucleic acid sequence. In some aspects, at least one of the at least one neoantigen-encoding nucleic acid sequences in the plurality encodes a polypeptide sequence or portion thereof that has increased binding stability to its corresponding MHC allele relative to the translated, corresponding wild-type, nucleic acid sequence. In some aspects, at least one of the at least one neoantigen-encoding nucleic acid sequences in the plurality encodes a polypeptide sequence or portion thereof that has an increased likelihood of presentation on its corresponding MHC allele relative to the translated, corresponding wild-type, nucleic acid sequence.

In some aspects, at least one mutation comprises a point mutation, a frameshift mutation, a non-frameshift mutation, a deletion mutation, an insertion mutation, a splice variant, a genomic rearrangement, or a proteasome-generated spliced antigen.

In some aspects, the tumor is selected from the group consisting of: lung cancer, melanoma, breast cancer, ovarian cancer, prostate cancer, kidney cancer, gastric cancer, colon cancer, testicular cancer, head and neck cancer, pancreatic cancer, bladder cancer, brain cancer, B-cell lymphoma, acute myelogenous leukemia, adult acute lymphoblastic leukemia, chronic myelogenous leukemia, chronic lymphocytic leukemia, T cell lymphocytic leukemia, non-small cell lung cancer, and small cell lung cancer.

In some aspects, the at least one neoantigen-encoding nucleic acid sequence comprises at least 2-10, 2, 3, 4, 5, 6, 7, 8, 9, or 10 nucleic acid sequences. In some aspects, the at least one neoantigen-encoding nucleic acid sequence comprises at least 11-20, 15-20, 11-100, 11-200, 11-300, 11-400, 11, 12, 13, 14, 15, 16, 17, 18, 19, 20 or up to 400 nucleic acid sequences.

In some aspects, the at least one neoantigen-encoding nucleic acid sequence comprises at least 2-400 nucleic acid sequences and wherein at least two of the neoantigen-encoding nucleic acid sequences encode polypeptide sequences or portions thereof that are presented by MHC class I on the tumor cell surface. In some aspects, at least two of the neoantigen-encoding nucleic acid sequences encode polypeptide sequences or portions thereof that are presented by MHC class I on the tumor cell surface. In some aspects, when administered to the subject and translated, at least one of the neoantigens encoded by the at least one neoantigen-encoding nucleic acid sequence are presented on antigen presenting cells resulting in an immune response targeting at least one of the neoantigens on the tumor cell surface. In some aspects, the at least one neoantigen-encoding nucleic acid sequences when administered to the subject and translated, at least one of the MHC class I or class II neoantigens are presented on antigen presenting cells resulting in an immune response targeting at least one of the neoantigens on the tumor cell surface, and optionally wherein the expression of each of the at least one neoantigen-encoding nucleic acid sequences is driven by the at least one promoter nucleotide sequence.

In some aspects, each MHC class I neoantigen-encoding nucleic acid sequence encodes a polypeptide sequence between 8 and 35 amino acids in length, optionally 9-17, 9-25, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids in length.

In some aspects, at least one MHC class II antigen-encoding nucleic acid sequence is present. In some aspects, at least one MHC class II antigen-encoding nucleic acid sequence is present and comprises at least one MHC class II neoantigen-encoding nucleic acid sequence that comprises at least one mutation that makes it distinct from the corresponding wild-type, parental nucleic acid sequence. In some aspects, the at least one MHC class II antigen-encoding nucleic acid sequence is 12-20, 12, 13, 14, 15, 16, 17, 18, 19, 20, or 20-40 amino acids in length. In some aspects, the at least one MHC class II antigen-encoding nucleic acid sequence is present and comprises at least one universal MHC class II antigen-encoding nucleic acid sequence, optionally wherein the at least one universal sequence comprises at least one of Tetanus toxoid and PADRE.

In some aspects, the at least one promoter nucleotide sequence or the second promoter nucleotide sequence is inducible. In some aspects, the at least one promoter nucleotide sequence or the second promoter nucleotide sequence is non-inducible.

In some aspects, the at least one poly(A) sequence comprises a poly(A) sequence native to the alphavirus. In some aspects, the at least one poly(A) sequence comprises a poly(A) sequence exogenous to the alphavirus. In some aspects, the at least one poly(A) sequence is operably linked to at least one of the at least one antigen-encoding nucleic acid sequences. In some aspects, the at least one poly(A) sequence is at least 20, at least 30, at least 40, at least 50, at least 60, at least 70, at least 80, or at least 90 consecutive A nucleotides. In some aspects, the at least one poly(A) sequence is at least 100 consecutive A nucleotides.

In some aspects, the neoantigen cassette further comprises at least one of: an intron sequence, a woodchuck hepatitis virus posttranscriptional regulatory element (WPRE) sequence, an internal ribosome entry sequence (IRES) sequence, a nucleotide sequence encoding a 2A self cleaving peptide sequence, a nucleotide sequence encoding a Furin cleavage site, or a sequence in the 5' or 3' non-coding region known to enhance the nuclear export, stability, or translation efficiency of mRNA that is operably linked to at least one of the at least one antigen-encoding nucleic acid sequences.

In some aspects, the neoantigen cassette further comprises a reporter gene, including but not limited to, green fluorescent protein (GFP), a GFP variant, secreted alkaline phosphatase, luciferase, a luciferase variant, or a detectable peptide or epitope. In some aspects, the detectable peptide or epitope is selected from the group consisting of an HA tag, a Flag tag, a His-tag, or a V5 tag.

In some aspects, the one or more vectors further comprise one or more nucleic acid sequences encoding at least one immune modulator. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the antibody or antigen-binding fragment thereof is a Fab fragment, a Fab' fragment, a single chain Fv (scFv), a single domain antibody (sdAb) either as single specific or multiple specificities linked together (e.g., camelid antibody domains), or full-length single-chain antibody (e.g., full-length IgG with heavy and light chains linked by a flexible linker). In some aspects, the heavy and light chain sequences of the antibody are a contiguous sequence separated by either a self-cleaving sequence such as 2A or IRES; or the heavy and light chain sequences of the antibody are linked by a flexible linker such as consecutive glycine residues.

In some aspects, the immune modulator is a cytokine. In some aspects, the cytokine is at least one of IL-2, IL-7, IL-12, IL-15, or IL-21 or variants thereof of each.

Also, disclosed herein is an adenovirus vector comprising a neoantigen cassette, the neoantigen cassette comprising: a plurality of antigen-encoding nucleic acid sequences derived from a tumor present within a subject, the plurality comprising: at least two MHC class I neoantigen-encoding nucleic acid sequences each comprising at least one alteration that makes it distinct from the corresponding wild-type, parental nucleic acid sequence, and optionally, at least one MHC class II antigen-encoding nucleic acid sequence; and at least one promoter sequence operably linked to at least one sequence of the plurality.

In some aspects, the adenovirus vector is a chimpanzee adenovirus (ChAd) vector, optionally a C68 vector. In some aspects, the adenovirus vector comprises the sequence set forth in SEQ ID NO:1. In some aspects, the adenovirus vector comprises the sequence set forth in SEQ ID NO:1, except that the sequence is fully deleted or functionally deleted in at least one gene selected from the group consisting of the chimpanzee adenovirus E1A, E1B, E2A, E2B, E3, E4, L1, L2, L3, L4, and L5 genes of the sequence set forth in SEQ ID NO: 1, optionally wherein the sequence is fully deleted or functionally deleted in: (1) E1A and E1B; (2) E1A, E1B, and E3; or (3) E1A, E1B, E3, and E4 of the sequence set forth in SEQ ID NO: 1. In some aspects, the adenovirus vector comprises a gene or regulatory sequence obtained from the sequence of SEQ ID NO: 1, optionally wherein the gene is selected from the group consisting of the chimpanzee adenovirus inverted terminal repeat (ITR), E1A, E1B, E2A, E2B, E3, E4, L1, L2, L3, L4, and L5 genes of the sequence set forth in SEQ ID NO: 1.

In some aspects, the neoantigen cassette is inserted in the adenovirus vector at the E1 region, E3 region, and/or any deleted AdV region that allows incorporation of the neoantigen cassette.

In some aspects, the at least one promoter sequence of the adenovirus vector is inducible. In some aspects, the at least one promoter sequence of the adenovirus vector is non-inducible. In some aspects, the at least one promoter sequence of the adenovirus vector is a CMV, SV40, EF-1, RSV, PGK, or EBV promoter sequence.

In some aspects, the neoantigen cassette of the adenovirus vector further comprises at least one polyA sequence operably linked to at least one of the sequences in the plurality, optionally wherein the polyA sequence is located 3' of the at least one sequence in the plurality.

In some aspects, the adenovirus vector is generated from one of a first generation, a second generation, or a helper-dependent adenoviral vector.

In some aspects, the adenovirus vector comprises one or more deletions between base pair number 577 and 3407 and optionally wherein the adenovirus vector further comprises one or more deletions between base pair 27,141 and 32,022 or between base pair 27,816 and 31,332 of the sequence set forth in SEQ ID NO:1. In some aspects, the adenovirus vector further comprises one or more deletions between base pair number 3957 and 10346, base pair number 21787 and 23370, and base pair number 33486 and 36193 of the sequence set forth in SEQ ID NO:1.

In some aspects, the at least one MHC class I neoantigen-encoding nucleic acid sequence is selected by performing the steps of: (a) obtaining at least one of exome, transcriptome, or whole genome tumor nucleotide sequencing data from the tumor, wherein the tumor nucleotide sequencing data is used to obtain data representing peptide sequences of each of a set of neoantigens; (b) inputting the peptide sequence of each neoantigen into a presentation model to generate a set of numerical likelihoods that each of the neoantigens is presented by one or more of the MHC alleles on the tumor cell surface of the tumor, the set of numerical likelihoods having been identified at least based on received mass spectrometry data; and (c) selecting a subset of the set of neoantigens based on the set of numerical likelihoods to generate a set of selected neoantigens which are used to generate the at least one MHC class I neoantigen-encoding nucleic acid sequence.

In some aspects, each of the at least one MHC class I neoantigen-encoding nucleic acid sequence is selected by performing the steps of: (a) obtaining at least one of exome, transcriptome, or whole genome tumor nucleotide sequencing data from the tumor, wherein the tumor nucleotide sequencing data is used to obtain data representing peptide sequences of each of a set of neoantigens; (b) inputting the peptide sequence of each neoantigen into a presentation model to generate a set of numerical likelihoods that each of the neoantigens is presented by one or more of the MHC alleles on the tumor cell surface of the tumor, the set of numerical likelihoods having been identified at least based on received mass spectrometry data; and (c) selecting a subset of the set of neoantigens based on the set of numerical likelihoods to generate a set of selected neoantigens which are used to generate the at least one MHC class I neoantigen-encoding nucleic acid sequence.

In some aspects, a number of the set of selected neoantigens is 2-20.

In some aspects, the presentation model represents dependence between: presence of a pair of a particular one of the MHC alleles and a particular amino acid at a particular position of a peptide sequence; and likelihood of presentation on the tumor cell surface, by the particular one of the MHC alleles of the pair, of such a peptide sequence comprising the particular amino acid at the particular position.

In some aspects, selecting the set of selected neoantigens comprises selecting neoantigens that have an increased likelihood of being presented on the tumor cell surface relative to unselected neoantigens based on the presentation model. In some aspects, selecting the set of selected neoantigens comprises selecting neoantigens that have an increased likelihood of being capable of inducing a tumor-specific immune response in the subject relative to unselected neoantigens based on the presentation model. In some aspects, selecting the set of selected neoantigens comprises selecting neoantigens that have an increased likelihood of being capable of being presented to naïve T cells by professional antigen presenting cells (APCs) relative to unselected neoantigens based on the presentation model, optionally wherein the APC is a dendritic cell (DC). In some aspects, selecting the set of selected neoantigens comprises selecting neoantigens that have a decreased likelihood of being subject to inhibition via central or peripheral tolerance relative to unselected neoantigens based on the presentation model. In some aspects, selecting the set of selected neoantigens comprises selecting neoantigens that have a decreased likelihood of being capable of inducing an autoimmune response to normal tissue in the subject relative to unselected neoantigens based on the presentation model. In some aspects, exome or transcriptome nucleotide sequencing data is obtained by performing sequencing on the tumor tissue. In some aspects, the sequencing is next generation sequencing (NGS) or any massively parallel sequencing approach.

In some aspects, the neoantigen cassette comprises junctional epitope sequences formed by adjacent sequences in the neoantigen cassette. In some aspects, at least one or each junctional epitope sequence has an affinity of greater than 500 nM for MHC. In some aspects, each junctional epitope sequence is non-self. In some aspects, the neoantigen cassette does not encode a non-therapeutic MHC class I or class II epitope nucleic acid sequence comprising a translated, wild-type nucleic acid sequence, wherein the non-therapeutic epitope is predicted to be displayed on an MHC allele of the subject. In some aspects, the non-therapeutic predicted MHC class I or class II epitope sequence is a junctional epitope sequence formed by adjacent sequences in the neoantigen cassette. In some aspects, the prediction is based on presentation likelihoods generated by inputting sequences of the non-therapeutic epitopes into a presentation model. In some aspects, an order of the at least one antigen-encoding nucleic acid sequences in the neoantigen cassette is determined by a series of steps comprising: (a) generating a set of candidate neoantigen cassette sequences corresponding to different orders of the at least one antigen-encoding nucleic acid sequences; (b) determining, for each candidate neoantigen cassette sequence, a presentation score based on presentation of non-therapeutic epitopes in the candidate neoantigen cassette sequence; and (c) selecting a candidate cassette sequence associated with a presentation score below a predetermined threshold as the neoantigen cassette sequence for a neoantigen vaccine.

Also disclosed herein is a pharmaceutical composition comprising any of the compositions disclosed herein (such as an alphavirus-based or ChAd-based vector disclosed herein) and a pharmaceutically acceptable carrier. In some aspects, the pharmaceutical composition further comprises an adjuvant. In some aspects, the pharmaceutical composition further comprises an immune modulator. In some aspects, the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof.

Also disclosed herein is an isolated nucleotide sequence or set of isolated nucleotide sequences comprising the neoantigen cassette of any of the above composition claims and one or more elements obtained from the sequence of SEQ ID NO:3 or SEQ ID NO:5, optionally wherein the one or more elements are selected from the group consisting of the sequences necessary for nonstructural protein-mediated amplification, the 26S promoter nucleotide sequence, the poly(A) sequence, and the nsP1-4 genes of the sequence set forth in SEQ ID NO:3 or SEQ ID NO:5, and optionally wherein the nucleotide sequence is cDNA. In some aspects, the sequence or set of isolated nucleotide sequences comprises a neoantigen cassette disclosed herein inserted at position 7544 of the sequence set forth in SEQ ID NO:6 or SEQ ID NO:7. In some aspects, the isolated nucleotide sequence further comprises a T7 or SP6 RNA polymerase promoter nucleotide sequence 5' of the one or more elements obtained from the sequence of SEQ ID NO:3 or SEQ ID NO:5, and optionally one or more restriction sites 3' of the poly(A) sequence. In some aspects, the the neoantigen cassette disclosed herein is inserted at position 7563 of SEQ ID NO:8 or SEQ ID NO:9. In another aspect, the sequences set forth in SEQ ID NO:8 or SEQ ID NO:9 further comprise an additional adenine nucleotide inserted at position 17.

Also disclosed herein is an isolated nucleotide sequence comprising a neoantigen cassette disclosed herein and at least one promoter disclosed herein. In some aspects, the isolated nucleotide sequence further comprises a ChAd-based gene. In some aspects, the ChAd-based gene is obtained from the sequence of SEQ ID NO: 1, optionally wherein the gene is selected from the group consisting of the chimpanzee adenovirus ITR, E1A, E1B, E2A, E2B, E3, E4, L1, L2, L3, L4, and L5 genes of the sequence set forth in SEQ ID NO: 1, and optionally wherein the nucleotide sequence is cDNA.

Also disclosed herein is an isolated cell comprising an isolated nucleotide sequence disclosed herein, optionally wherein the cell is a BHK-21, CHO, HEK293 or variants thereof, 911, HeLa, A549, LP-293, PER.C6, or AE1-2a cell.

Also disclosed herein is a vector comprising an isolated nucleotide sequence disclosed herein.

Also disclosed herein is a kit comprising a vector or a composition disclosed herein and instructions for use.

Also disclosed herein is a method for treating a subject with cancer, the method comprising administering to the subject a vector disclosed herein or a pharmaceutical composition disclosed herein. In some aspects, the at least one MHC class I neoantigen-encoding nucleic acid sequence derived from a tumor are derived from the tumor of the subject with cancer. In some aspects, the at least one MHC class I neoantigen-encoding nucleic acid sequence are not derived from the tumor of the subject with cancer.

Also disclosed herein is a method for inducing an immune response in a subject, the method comprising administering to the subject any of the compositions, vectors, or pharmaceutical compositions described herein.

In some aspects, the vector or composition is administered intramuscularly (IM), intradermally (ID), or subcutaneously (SC), or intravenously (IV).

In some aspects, the methods described herein further comprise administration of one or more immune modulators, optionally wherein the immune modulator is administered before, concurrently with, or after administration of the composition or pharmaceutical composition. In some aspects, the one or more immune modulators are selected from the group consisting of: an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof. In some aspects, the immune modulator is administered intravenously (IV), intramuscularly (IM), intradermally (ID), or subcutaneously (SC). In some aspects, the subcutaneous administration is near the site of the composition or pharmaceutical composition administration or in close proximity to one or more vector or composition draining lymph nodes.

In some aspects, the methods described herein further comprise administering to the subject a second vaccine composition. In some aspects, the second vaccine composition is administered prior to the administration of the composition or the pharmaceutical composition described above. In some aspects, the second vaccine composition is administered subsequent to the administration of the composition or the pharmaceutical compositions described above. In some aspects, the second vaccine composition is the same as the composition or the pharmaceutical compositions described above. In some aspects, the second vaccine composition is different from the composition or the pharmaceutical compositions described above. In some aspects, the second vaccine composition comprises a chimpanzee adenovirus vector encoding at least one antigen-encoding nucleic acid sequence. In some aspects, the at least one antigen-encoding nucleic acid sequence encoded by the chimpanzee adenovirus vector is the same as the at least one antigen-encoding nucleic acid sequence of any of the above compositions or vectors.

Also disclosed herein is a method of manufacturing the one or more vectors of any of the above compositions, the method comprising: obtaining a linearized DNA sequence comprising the RNA alphavirus backbone and the neoantigen cassette; in vitro transcribing the linearized DNA sequence by addition of the linearized DNA sequence to a in vitro transcription reaction containing all the necessary components to trancribe the linearized DNA sequence into RNA, optionally further comprising in vitro addition of the m7g cap to the resulting RNA; and isolating the one or more vectors from the in vitro transcription reaction. In some aspects, the linearized DNA sequence is generated by linearizing a DNA plasmid sequence or by amplification using PCR. In some aspects, the DNA plasmid sequence is generated using one of bacterial recombination or full genome DNA synthesis or full genome DNA synthesis with amplification of synthesized DNA in bacterial cells. In some aspects, the isolating the one or more vectors from the in vitro transcription reaction involves one or more of phenol chloroform extraction, silica column based purification, or similar RNA purification methods.

Also disclosed herein is a method of manufacturing any of the compositions disclosed herein, the method comprising: providing components for the nanoparticulate delivery vehicle; providing the neoantigen expression system; and providing conditions sufficient for the nanoparticulate delivery vehicle and the neoantigen expression system to produce the composition for delivery of the neoantigen expression system. In some aspects, the conditions are provided by microfluidic mixing.

Also disclosed herein is a method of manufacturing a adenovirus vector disclosed herein, the method comprising: obtaining a plasmid sequence comprising the at least one promoter sequence and the neoantigen cassette; transfecting the plasmid sequence into one or more host cells; and isolating the adenovirus vector from the one or more host cells.

In some aspects, isolating comprises: lysing the host cell to obtain a cell lysate comprising the adenovirus vector, and purifying the adenovirus vector from the cell lysate.

In some aspects, the plasmid sequence is generated using one of bacterial recombination or full genome DNA synthesis or full genome DNA synthesis with amplification of synthesized DNA in bacterial cells. In some aspects, the one or more host cells are at least one of CHO, HEK293 or variants thereof, 911, HeLa, A549, LP-293, PER.C6, and AE1-2a cells. In some aspects, purifying the adenovirus vector from the cell lysate involves one or more of chromatographic separation, centrifugation, virus precipitation, and filtration.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1B shows that <5% of predicted bound peptides are presented on tumor cells.

FIG. 2B discloses SEQ ID NO: 62. FIG. 2C discloses SEQ ID NOS 62-67, respectively, in order of appearance. FIG. 2D discloses SEQ ID NO: 157. FIG. 2E discloses SEQ ID NOS 62-65, 68, and 67, respectively in order of appearance.

FIG. 4A illustrates an example set of training data, according to one embodiment related to MHC class I alleles. FIG. 4A discloses Peptide Sequences as SEQ ID NOS 70-73 and C-Flanking Sequences as SEQ ID NOS 74, 158, 159, and 159, respectively, in order of appearance. FIG. 4B illustrates an example set of training data, according to one embodiment related to an MHC class II allele. FIG. 4B discloses SEQ ID NO: 75.

FIG. 13C shows performance results for peptide presentation determined by mass-spectrometry for an example function-of-sums model (equation (13)), an example sum-of-functions model (equation (19)), and an example second order model (equation (23)) for predicting peptide presentation. The first column refers to the the area-under-curve (AUC) of the receiver operating characteristic (ROC) when each presentation model was applied to the test set, the second column refers to the value of the negative log likelihood loss, and the third column refers to the the positive predictive value (PPV) at a 10% recall rate.

FIG. 13D shows performance results for peptide presentation determined by mass-spectrometry for two example presentation models that are trained with and without single-allele mass spectrometry data. The first column refers to the the area-under-curve (AUC) of the receiver operating characteristic (ROC) when each presentation model was applied to the test set, the second column refers to the value of the negative log likelihood loss, and the third column refers to the the positive predictive value (PPV) at a 10% recall rate.

FIG. 13E shows performance results for peptide presentation determined by mass-spectrometry for two example presentation models that are trained with and without single-allele mass spectrometry data. "Correlation" refers to the correlation between the actual labels that indicate whether the peptide was presented on the corresponding allele in the test data, and the label for prediction.

FIG. 13F shows the frequency of common anchor residues at positions 2 (P2) and 9 (P9) among nonamers predicted by a presentation model trained without single-allele mass spectrometry data.

FIG. 13G shows performance results for peptide presentation determined by mass-spectrometry for an example presentation model that incorporated C- and N-terminal flanking sequences as allele-interacting variables, and an example presentation model that incorporated C- and N-terminal flanking sequences as allele-noninteracting variables. The first column refers to the the area-under-curve (AUC) of the receiver operating characteristic (ROC) when each presentation model was applied to the test set, the second column refers to the value of the negative log likelihood loss, and the third column refers to the the positive predictive value (PPV) at a 10% recall rate.

FIG. 13-O is a histogram that depicts the quantity of samples in which a particular MHC class II molecule allele was identified.

FIG. 19B illustrates in vivo evaluation of the impact of epitope position in long 21-mer cassettes and shows the sequence information on the T cell epitopes used. Figure discloses SEQ ID NOS 132, 133, 136, 135, 134, 162-164, 137, and 165-176, respectively, in order of appearance.

FIG. 20B illustrates final cassette design for preclinical IND-enabling studies and shows the sequence information for the T cell epitopes used that are presented on class I MHC of non-human primate (SEQ ID NOS 177-182, respectively, in order of appearance), mouse (SEQ ID NOS 57, 58 and 183-189, respectively, in order of appearance) and human origin (SEQ ID NOS 134-136, 132, and 133, respectively, in order of appearance), as well as sequences of 2 universal MHC class II epitopes PADRE and Tetanus toxoid (SEQ ID NOS 160 and 190, respectively, in order of appearance).

DETAILED DESCRIPTION

I. Definitions

Figure 1A:
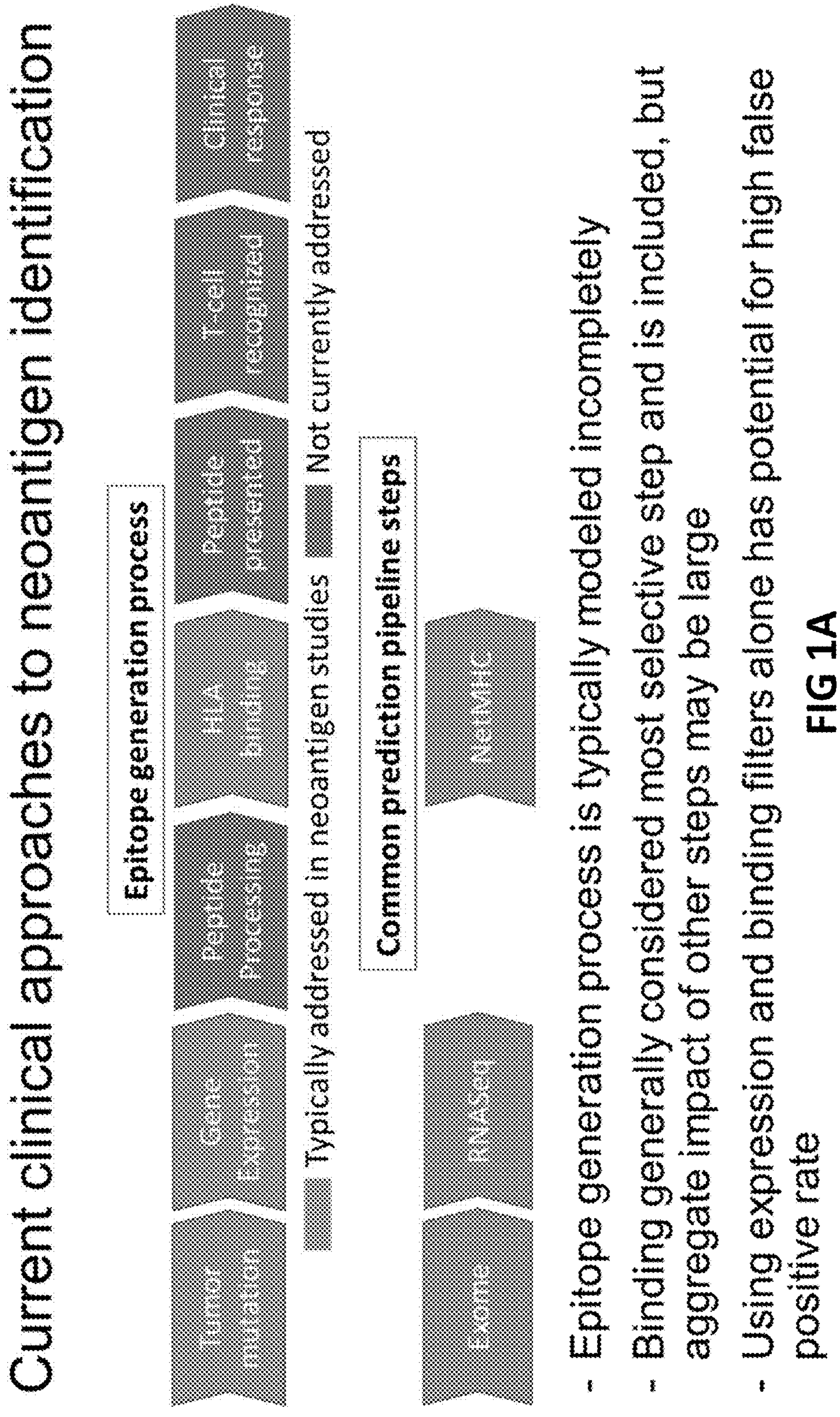
FIG. 1A shows current clinical approaches to neoantigen identification.

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

As used herein the term "antigen" is a substance that induces an immune response.

As used herein the term "neoantigen" is an antigen that has at least one alteration that makes it distinct from the corresponding wild-type antigen, e.g., via mutation in a tumor cell or post-translational modification specific to a tumor cell. A neoantigen can include a polypeptide sequence or a nucleotide sequence. A mutation can include a frameshift or nonframeshift indel, missense or nonsense substitution, splice site alteration, genomic rearrangement or gene fusion, or any genomic or expression alteration giving rise to a neoORF. A mutations can also include a splice variant. Post-translational modifications specific to a tumor cell can include aberrant phosphorylation. Post-translational modifications specific to a tumor cell can also include a proteasome-generated spliced antigen. See Liepe et al., A large fraction of HLA class I ligands are proteasome-generated spliced peptides; Science. 2016 Oct. 21; 354(6310):354-358.

As used herein the term "tumor neoantigen" is a neoantigen present in a subject's tumor cell or tissue but not in the subject's corresponding normal cell or tissue.

As used herein the term "neoantigen-based vaccine" is a vaccine construct based on one or more neoantigens, e.g., a plurality of neoantigens.

As used herein the term "candidate neoantigen" is a mutation or other aberration giving rise to a new sequence that may represent a neoantigen.

As used herein the term "coding region" is the portion(s) of a gene that encode protein.

As used herein the term "coding mutation" is a mutation occurring in a coding region.

As used herein the term "ORF" means open reading frame.

As used herein the term "NEO-ORF" is a tumor-specific ORF arising from a mutation or other aberration such as splicing.

As used herein the term "missense mutation" is a mutation causing a substitution from one amino acid to another.

As used herein the term "nonsense mutation" is a mutation causing a substitution from an amino acid to a stop codon or causing removal of a canonical start codon.

As used herein the term "frameshift mutation" is a mutation causing a change in the frame of the protein.

As used herein the term "indel" is an insertion or deletion of one or more nucleic acids.

As used herein, the term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Alternatively, sequence similarity or dissimilarity can be established by the combined presence or absence of particular nucleotides, or, for translated sequences, amino acids at selected sequence positions (e.g., sequence motifs).

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

As used herein the term "non-stop or read-through" is a mutation causing the removal of the natural stop codon.

As used herein the term "epitope" is the specific portion of an antigen typically bound by an antibody or T cell receptor.

As used herein the term "immunogenic" is the ability to elicit an immune response, e.g., via T cells, B cells, or both.

As used herein the term "HLA binding affinity" "MHC binding affinity" means affinity of binding between a specific antigen and a specific MHC allele.

As used herein the term "bait" is a nucleic acid probe used to enrich a specific sequence of DNA or RNA from a sample.

As used herein the term "variant" is a difference between a subject's nucleic acids and the reference human genome used as a control.

As used herein the term "variant call" is an algorithmic determination of the presence of a variant, typically from sequencing.

As used herein the term "polymorphism" is a germline variant, i.e., a variant found in all DNA-bearing cells of an individual.

As used herein the term "somatic variant" is a variant arising in non-germline cells of an individual.

As used herein the term "allele" is a version of a gene or a version of a genetic sequence or a version of a protein.

As used herein the term "HLA type" is the complement of HLA gene alleles.

As used herein the term "nonsense-mediated decay" or "NMD" is a degradation of an mRNA by a cell due to a premature stop codon.

As used herein the term "truncal mutation" is a mutation originating early in the development of a tumor and present in a substantial portion of the tumor's cells.

As used herein the term "subclonal mutation" is a mutation originating later in the development of a tumor and present in only a subset of the tumor's cells.

As used herein the term "exome" is a subset of the genome that codes for proteins. An exome can be the collective exons of a genome.

As used herein the term "logistic regression" is a regression model for binary data from statistics where the logit of the probability that the dependent variable is equal to one is modeled as a linear function of the dependent variables.

As used herein the term "neural network" is a machine learning model for classification or regression consisting of multiple layers of linear transformations followed by element-wise nonlinearities typically trained via stochastic gradient descent and back-propagation.

As used herein the term "proteome" is the set of all proteins expressed and/or translated by a cell, group of cells, or individual.

As used herein the term "peptidome" is the set of all peptides presented by MHC-I or MHC-II on the cell surface. The peptidome may refer to a property of a cell or a collection of cells (e.g., the tumor peptidome, meaning the union of the peptidomes of all cells that comprise the tumor).

As used herein the term "ELISPOT" means Enzyme-linked immunosorbent spot assay—which is a common method for monitoring immune responses in humans and animals.

As used herein the term "dextramers" is a dextran-based peptide-MHC multimers used for antigen-specific T-cell staining in flow cytometry.

As used herein the term "tolerance or immune tolerance" is a state of immune non-responsiveness to one or more antigens, e.g. self-antigens.

As used herein the term "central tolerance" is a tolerance affected in the thymus, either by deleting self-reactive T-cell clones or by promoting self-reactive T-cell clones to differentiate into immunosuppressive regulatory T-cells (Tregs).

As used herein the term "peripheral tolerance" is a tolerance affected in the periphery by downregulating or anergizing self-reactive T-cells that survive central tolerance or promoting these T cells to differentiate into Tregs.

The term "sample" can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art.

The term "subject" encompasses a cell, tissue, or organism, human or non-human, whether in vivo, ex vivo, or in vitro, male or female. The term subject is inclusive of mammals including humans.

The term "mammal" encompasses both humans and non-humans and includes but is not limited to, humans, non-human primates, canines, felines, murines, bovines, equines, and porcines.

The term "clinical factor" refers to a measure of a condition of a subject, e.g., disease activity or severity. "Clinical factor" encompasses all markers of a subject's health status, including non-sample markers, and/or other characteristics of a subject, such as, without limitation, age and gender. A clinical factor can be a score, a value, or a set of values that can be obtained from evaluation of a sample (or population of samples) from a subject or a subject under a determined condition. A clinical factor can also be predicted by markers and/or other parameters such as gene expression surrogates. Clinical factors can include tumor type, tumor sub-type, and smoking history.

The term "antigen-encoding nucleic acid sequences derived from a tumor" refers to nucleic acid sequences directly extracted from the tumor, e.g. via RT-PCR; or sequence data obtained by sequencing the tumor and then synthesizing the nucleic acid sequences using the sequencing data, e.g., via various synthetic or PCR-based methods known in the art.

The term "alphavirus" refers to members of the family Togaviridae, and are positive-sense single-stranded RNA viruses. Alphaviruses are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis and its derivative strain TC-83. Alphaviruses are typically self-replicating RNA viruses.

The term "alphavirus backbone" refers to minimal sequence(s) of an alphavirus that allow for self-replication of the viral genome. Minimal sequences can include conserved sequences for nonstructural protein-mediated amplification, a nonstructural protein 1 (nsP1) gene, a nsP2 gene, a nsP3 gene, a nsP4 gene, and a polyA sequence, as well as sequences for expression of subgenomic viral RNA including a 26S promoter element.

The term "sequences for nonstructural protein-mediated amplification" includes alphavirus conserved sequence elements (CSE) well known to those in the art. CSEs include, but are not limited to, an alphavirus 5' UTR, a 51-nt CSE, a 24-nt CSE, or other 26S subgenomic promoter sequence, a 19-nt CSE, and an alphavirus 3' UTR.

The term "RNA polymerase" includes polymerases that catalyze the production of RNA polynucleotides from a DNA template. RNA polymerases include, but are not limited to, bacteriophage derived polymerases including T3, T7, and SP6.

The term "lipid" includes hydrophobic and/or amphiphilic molecules. Lipids can be cationic, anionic, or neutral. Lipids can be synthetic or naturally derived, and in some instances biodegradable. Lipids can include cholesterol, phospholipids, lipid conjugates including, but not limited to, polyethyleneglycol (PEG) conjugates (PEGylated lipids), waxes, oils, glycerides, fats, and fat-soluble vitamins. Lipids can also include dilinoleylmethyl-4-dimethylaminobutyrate (MC3) and MC3-like molecules.

The term "lipid nanoparticle" or "LNP" includes vesicle like structures formed using a lipid containing membrane surrounding an aqueous interior, also referred to as liposomes. Lipid nanoparticles includes lipid-based compositions with a solid lipid core stabilized by a surfactant. The core lipids can be fatty acids, acylglycerols, waxes, and mixtures of these surfactants. Biological membrane lipids such as phospholipids, sphingomyelins, bile salts (sodium taurocholate), and sterols (cholesterol) can be utilized as stabilizers. Lipid nanoparticles can be formed using defined ratios of different lipid molecules, including, but not limited to, defined ratios of one or more cationic, anionic, or neutral lipids. Lipid nanoparticles can encapsulate molecules within an outer-membrane shell and subsequently can be contacted with target cells to deliver the encapsulated molecules to the host cell cytosol. Lipid nanoparticles can be modified or functionalized with non-lipid molecules, including on their surface. Lipid nanoparticles can be single-layered (unilamellar) or multi-layered (multilamellar). Lipid nanoparticles can be complexed with nucleic acid. Unilamellar lipid nanoparticles can be complexed with nucleic acid, wherein the nucleic acid is in the aqueous interior. Multilamellar lipid nanoparticles can be complexed with nucleic acid, wherein the nucleic acid is in the aqueous interior, or to form or sandwiched between Abbreviations: MHC: major histocompatibility complex; HLA: human leukocyte antigen, or the human MHC gene locus; NGS: next-generation sequencing; PPV: positive predictive value; TSNA: tumor-specific neoantigen; FFPE: formalin-fixed, paraffin-embedded; NMD: nonsense-mediated decay; NSCLC: non-small-cell lung cancer; DC: dendritic cell.

It should be noted that, as used in the specification and the appended claims, the singular forms "a," "an," and "the" include plural referents unless the context clearly dictates otherwise.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

All references, issued patents and patent applications cited within the body of the specification are hereby incorporated by reference in their entirety, for all purposes.

II. Methods of Identifying Neoantigens

Disclosed herein are methods for identifying neoantigens from a tumor of a subject that are likely to be presented on the cell surface of the tumor or immune cells, including professional antigen presenting cells such as dendritic cells, and/or are likely to be immunogenic. As an example, one such method may comprise the steps of: obtaining at least one of exome, transcriptome or whole genome tumor nucleotide sequencing data from the tumor cell of the subject, wherein the tumor nucleotide sequencing data is used to obtain data representing peptide sequences of each of a set of neoantigens, and wherein the peptide sequence of each neoantigen comprises at least one alteration that makes it distinct from the corresponding wild-type peptide sequence; inputting the peptide sequence of each neoantigen into one or more presentation models to generate a set of numerical likelihoods that each of the neoantigens is presented by one or more MHC alleles on the tumor cell surface of the tumor cell of the subject or cells present in the tumor, the set of numerical likelihoods having been identified at least based on received mass spectrometry data; and selecting a subset of the set of neoantigens based on the set of numerical likelihoods to generate a set of selected neoantigens.

The presentation model can comprise a statistical regression or a machine learning (e.g., deep learning) model trained on a set of reference data (also referred to as a training data set) comprising a set of corresponding labels, wherein the set of reference data is obtained from each of a plurality of distinct subjects where optionally some subjects can have a tumor, and wherein the set of reference data comprises at least one of: data representing exome nucleotide sequences from tumor tissue, data representing exome nucleotide sequences from normal tissue, data representing transcriptome nucleotide sequences from tumor tissue, data representing proteome sequences from tumor tissue, and data representing MHC peptidome sequences from tumor tissue, and data representing MHC peptidome sequences from normal tissue. The reference data can further comprise mass spectrometry data, sequencing data, RNA sequencing data, and proteomics data for single-allele cell lines engineered to express a predetermined MHC allele that are subsequently exposed to synthetic protein, normal and tumor human cell lines, and fresh and frozen primary samples, and T cell assays (e.g., ELISPOT). In certain aspects, the set of reference data includes each form of reference data.

The presentation model can comprise a set of features derived at least in part from the set of reference data, and wherein the set of features comprises at least one of allele dependent-features and allele-independent features. In certain aspects each feature is included.

Also disclosed herein are methods for generating an output for constructing a personalized cancer vaccine by identifying one or more neoantigens from one or more tumor cells of a subject that are likely to be presented on a surface of the tumor cells. As an example, one such method may comprise the steps of: obtaining at least one of exome, transcriptome, or whole genome nucleotide sequencing data from the tumor cells and normal cells of the subject, wherein the nucleotide sequencing data is used to obtain data representing peptide sequences of each of a set of neoantigens identified by comparing the nucleotide sequencing data from the tumor cells and the nucleotide sequencing data from the normal cells, and wherein the peptide sequence of each neoantigen comprises at least one alteration that makes it distinct from the corresponding wild-type, peptide sequence identified from the normal cells of the subject; encoding the peptide sequences of each of the neoantigens into a corresponding numerical vector, each numerical vector including information regarding a plurality of amino acids that make up the peptide sequence and a set of positions of the amino acids in the peptide sequence; inputting the numerical vectors, using a computer processor, into a deep learning presentation model to generate a set of presentation likelihoods for the set of neoantigens, each presentation likelihood in the set representing the likelihood that a corresponding neoantigen is presented by one or more class II MHC alleles on the surface of the tumor cells of the subject, the deep learning presentation model; selecting a subset of the set of neoantigens based on the set of presentation likelihoods to generate a set of selected neoantigens; and generating the output for constructing the personalized cancer vaccine based on the set of selected neoantigens.

In some embodiments, the presentation model comprises a plurality of parameters identified at least based on a training data set and a function representing a relation between the numerical vector received as an input and the presentation likelihood generated as output based on the numerical vector and the parameters. In certain embodiments, the training data set comprises labels obtained by mass spectrometry measuring presence of peptides bound to at least one class II MHC allele identified as present in at least one of a plurality of samples, training peptide sequences encoded as numerical vectors including information regarding a plurality of amino acids that make up the peptide sequence and a set of positions of the amino acids in the peptide sequence, and at least one HLA allele associated with the training peptide sequences.

Dendritic cell presentation to naïve T cell features can comprise at least one of: A feature described above. The dose and type of antigen in the vaccine. (e.g., peptide, mRNA, virus, etc.): (1) The route by which dendritic cells (DCs) take up the antigen type (e.g., endocytosis, micropinocytosis); and/or (2) The efficacy with which the antigen is taken up by DCs. The dose and type of adjuvant in the vaccine. The length of the vaccine antigen sequence. The number and sites of vaccine administration. Baseline patient immune functioning (e.g., as measured by history of recent infections, blood counts, etc). For RNA vaccines: (1) the turnover rate of the mRNA protein product in the dendritic cell; (2) the rate of translation of the mRNA after uptake by dendritic cells as measured in in vitro or in vivo experiments; and/or (3) the number or rounds of translation of the mRNA after uptake by dendritic cells as measured by in vivo or in vitro experiments. The presence of protease cleavage motifs in the peptide, optionally giving additional weight to proteases typically expressed in dendritic cells (as measured by RNA-seq or mass spectrometry). The level of expression of the proteasome and immunoproteasome in typical activated dendritic cells (which may be measured by RNA-seq, mass spectrometry, immunohistochemistry, or other standard techniques). The expression levels of the particular MHC allele in the individual in question (e.g., as measured by RNA-seq or mass spectrometry), optionally measured specifically in activated dendritic cells or other immune cells. The probability of peptide presentation by the particular MHC allele in other individuals who express the particular MHC allele, optionally measured specifically in activated dendritic cells or other immune cells. The probability of peptide presentation by MHC alleles in the same family of molecules (e.g., HLA-A, HLA-B, HLA-C, HLA-DQ, HLA-DR, HLA-DP) in other individuals, optionally measured specifically in activated dendritic cells or other immune cells.

Immune tolerance escape features can comprise at least one of: Direct measurement of the self-peptidome via protein mass spectrometry performed on one or several cell types. Estimation of the self-peptidome by taking the union of all k-mer (e.g. 5-25) substrings of self-proteins. Estimation of the self-peptidome using a model of presentation similar to the presentation model described above applied to all non-mutation self-proteins, optionally accounting for germline variants.

Ranking can be performed using the plurality of neoantigens provided by at least one model based at least in part on the numerical likelihoods. Following the ranking a selecting can be performed to select a subset of the ranked neoantigens according to a selection criteria. After selecting a subset of the ranked peptides can be provided as an output.

A number of the set of selected neoantigens may be 20.

The presentation model may represent dependence between presence of a pair of a particular one of the MHC alleles and a particular amino acid at a particular position of a peptide sequence; and likelihood of presentation on the tumor cell surface, by the particular one of the MHC alleles of the pair, of such a peptide sequence comprising the particular amino acid at the particular position.

A method disclosed herein can also include applying the one or more presentation models to the peptide sequence of the corresponding neoantigen to generate a dependency score for each of the one or more MHC alleles indicating whether the MHC allele will present the corresponding neoantigen based on at least positions of amino acids of the peptide sequence of the corresponding neoantigen.

A method disclosed herein can also include transforming the dependency scores to generate a corresponding per-allele likelihood for each MHC allele indicating a likelihood that the corresponding MHC allele will present the corresponding neoantigen; and combining the per-allele likelihoods to generate the numerical likelihood.

The step of transforming the dependency scores can model the presentation of the peptide sequence of the corresponding neoantigen as mutually exclusive.

A method disclosed herein can also include transforming a combination of the dependency scores to generate the numerical likelihood.

The step of transforming the combination of the dependency scores can model the presentation of the peptide sequence of the corresponding neoantigen as interfering between MHC alleles.

The set of numerical likelihoods can be further identified by at least an allele noninteracting feature, and a method disclosed herein can also include applying an allele noninteracting one of the one or more presentation models to the allele noninteracting features to generate a dependency score for the allele noninteracting features indicating whether the peptide sequence of the corresponding neoantigen will be presented based on the allele noninteracting features.

A method disclosed herein can also include combining the dependency score for each MHC allele in the one or more MHC alleles with the dependency score for the allele noninteracting feature; transforming the combined dependency scores for each MHC allele to generate a corresponding per-allele likelihood for the MHC allele indicating a likelihood that the corresponding MHC allele will present the corresponding neoantigen; and combining the per-allele likelihoods to generate the numerical likelihood.

A method disclosed herein can also include transforming a combination of the dependency scores for each of the MHC alleles and the dependency score for the allele non-interacting features to generate the numerical likelihood.

A set of numerical parameters for the presentation model can be trained based on a training data set including at least a set of training peptide sequences identified as present in a plurality of samples and one or more MHC alleles associated with each training peptide sequence, wherein the training peptide sequences are identified through mass spectrometry on isolated peptides eluted from MHC alleles derived from the plurality of samples.

The samples can also include cell lines engineered to express a single MHC class I or class II allele.

The samples can also include cell lines engineered to express a plurality of MHC class I or class II alleles.

The samples can also include human cell lines obtained or derived from a plurality of patients.

The samples can also include fresh or frozen tumor samples obtained from a plurality of patients.

The samples can also include fresh or frozen tissue samples obtained from a plurality of patients.

The samples can also include peptides identified using T-cell assays.

The training data set can further include data associated with: peptide abundance of the set of training peptides present in the samples; peptide length of the set of training peptides in the samples.

The training data set may be generated by comparing the set of training peptide sequences via alignment to a database comprising a set of known protein sequences, wherein the set of training protein sequences are longer than and include the training peptide sequences.

The training data set may be generated based on performing or having performed nucleotide sequencing on a cell line to obtain at least one of exome, transcriptome, or whole genome sequencing data from the cell line, the sequencing data including at least one nucleotide sequence including an alteration.

The training data set may be generated based on obtaining at least one of exome, transcriptome, and whole genome normal nucleotide sequencing data from normal tissue samples.

The training data set may further include data associated with proteome sequences associated with the samples.

The training data set may further include data associated with MHC peptidome sequences associated with the samples.

The training data set may further include data associated with peptide-MHC binding affinity measurements for at least one of the isolated peptides.

The training data set may further include data associated with peptide-MHC binding stability measurements for at least one of the isolated peptides.

The training data set may further include data associated with transcriptomes associated with the samples.

The training data set may further include data associated with genomes associated with the samples.

The training peptide sequences may be of lengths within a range of k-mers where k is between 8-15, inclusive for MHC class I or 6-30 inclusive for MHC class II.

A method disclosed herein can also include encoding the peptide sequence using a one-hot encoding scheme.

A method disclosed herein can also include encoding the training peptide sequences using a left-padded one-hot encoding scheme.

A method of treating a subject having a tumor, comprising performing the steps of any of the neoantigen identification methods described herein, and further comprising obtaining a tumor vaccine comprising the set of selected neoantigens, and administering the tumor vaccine to the subject.

A method disclosed herein can also include identifying one or more T cells that are antigen-specific for at least one of the neoantigens in the subset. In some embodiments, the identification comprises co-culturing the one or more T cells with one or more of the neoantigens in the subset under conditions that expand the one or more antigen-specific T cells. In further embodiments, the identification comprises contacting the one or more T cells with a tetramer comprising one or more of the neoantigens in the subset under conditions that allow binding between the T cell and the tetramer. In even further embodiments, the method disclosed herein can also include identifying one or more T cell receptors (TCR) of the one or more identified T cells. In certain embodiments, identifying the one or more T cell receptors comprises sequencing the T cell receptor sequences of the one or more identified T cells. The method disclosed herein can further comprise genetically engineering a plurality of T cells to express at least one of the one or more identified T cell receptors; culturing the plurality of T cells under conditions that expand the plurality of T cells; and infusing the expanded T cells into the subject. In some embodiments, genetically engineering the plurality of T cells to express at least one of the one or more identified T cell receptors comprises cloning the T cell receptor sequences of the one or more identified T cells into an expression vector, and transfecting each of the plurality of T cells with the expression vector. In some embodiments, the method disclosed herein further comprises culturing the one or more identified T cells under conditions that expand the one or more identified T cells; and infusing the expanded T cells into the subject.

Also disclosed herein is an isolated T cell that is antigen-specific for at least one selected neoantigen in the subset.

Also disclosed herein is a methods for manufacturing a tumor vaccine, comprising the steps of: obtaining at least one of exome, transcriptome or whole genome tumor nucleotide sequencing data from the tumor cell of the subject, wherein the tumor nucleotide sequencing data is used to obtain data representing peptide sequences of each of a set of neoantigens, and wherein the peptide sequence of each neoantigen comprises at least one alteration that makes it distinct from the corresponding wild-type peptide sequence; inputting the peptide sequence of each neoantigen into one or more presentation models to generate a set of numerical likelihoods that each of the neoantigens is presented by one or more MHC alleles on the tumor cell surface of the tumor cell of the subject, the set of numerical likelihoods having been identified at least based on received mass spectrometry data; and selecting a subset of the set of neoantigens based on the set of numerical likelihoods to generate a set of selected neoantigens; and producing or having produced a tumor vaccine comprising the set of selected neoantigens.

Also disclosed herein is a tumor vaccine including a set of selected neoantigens selected by performing the method comprising the steps of: obtaining at least one of exome, transcriptome or whole genome tumor nucleotide sequencing data from the tumor cell of the subject, wherein the tumor nucleotide sequencing data is used to obtain data representing peptide sequences of each of a set of neoantigens, and wherein the peptide sequence of each neoantigen comprises at least one alteration that makes it distinct from the corresponding wild-type peptide sequence; inputting the peptide sequence of each neoantigen into one or more presentation models to generate a set of numerical likelihoods that each of the neoantigens is presented by one or more MHC alleles on the tumor cell surface of the tumor cell of the subject, the set of numerical likelihoods having been identified at least based on received mass spectrometry data; and selecting a subset of the set of neoantigens based on the set of numerical likelihoods to generate a set of selected neoantigens; and producing or having produced a tumor vaccine comprising the set of selected neoantigens.

The tumor vaccine may include one or more of a nucleotide sequence, a polypeptide sequence, RNA, DNA, a cell, a plasmid, or a vector.

The tumor vaccine may include one or more neoantigens presented on the tumor cell surface.

The tumor vaccine may include one or more neoantigens that is immunogenic in the subject.

The tumor vaccine may not include one or more neoantigens that induce an autoimmune response against normal tissue in the subject.

The tumor vaccine may include an adjuvant.

The tumor vaccine may include an excipient.

A method disclosed herein may also include selecting neoantigens that have an increased likelihood of being presented on the tumor cell surface relative to unselected neoantigens based on the presentation model.

A method disclosed herein may also include selecting neoantigens that have an increased likelihood of being capable of inducing a tumor-specific immune response in the subject relative to unselected neoantigens based on the presentation model.

A method disclosed herein may also include selecting neoantigens that have an increased likelihood of being capable of being presented to naïve T cells by professional antigen presenting cells (APCs) relative to unselected neoantigens based on the presentation model, optionally wherein the APC is a dendritic cell (DC).

A method disclosed herein may also include selecting neoantigens that have a decreased likelihood of being subject to inhibition via central or peripheral tolerance relative to unselected neoantigens based on the presentation model.

A method disclosed herein may also include selecting neoantigens that have a decreased likelihood of being capable of inducing an autoimmune response to normal tissue in the subject relative to unselected neoantigens based on the presentation model.

The exome or transcriptome nucleotide sequencing data may be obtained by performing sequencing on the tumor tissue.

The sequencing may be next generation sequencing (NGS) or any massively parallel sequencing approach.

The set of numerical likelihoods may be further identified by at least MHC-allele interacting features comprising at least one of: the predicted affinity with which the MHC allele and the neoantigen encoded peptide bind; the predicted stability of the neoantigen encoded peptide-MHC complex; the sequence and length of the neoantigen encoded peptide; the probability of presentation of neoantigen encoded peptides with similar sequence in cells from other individuals expressing the particular MHC allele as assessed by mass-spectrometry proteomics or other means; the expression levels of the particular MHC allele in the subject in question (e.g. as measured by RNA-seq or mass spectrometry); the overall neoantigen encoded peptide-sequence-independent probability of presentation by the particular MHC allele in other distinct subjects who express the particular MHC allele; the overall neoantigen encoded peptide-sequence-independent probability of presentation by MHC alleles in the same family of molecules (e.g., HLA-A, HLA-B, HLA-C, HLA-DQ, HLA-DR, HLA-DP) in other distinct subjects.

The set of numerical likelihoods are further identified by at least MHC-allele noninteracting features comprising at least one of: the C- and N-terminal sequences flanking the neoantigen encoded peptide within its source protein sequence; the presence of protease cleavage motifs in the neoantigen encoded peptide, optionally weighted according to the expression of corresponding proteases in the tumor cells (as measured by RNA-seq or mass spectrometry); the turnover rate of the source protein as measured in the appropriate cell type; the length of the source protein, optionally considering the specific splice variants ("isoforms") most highly expressed in the tumor cells as measured by RNA-seq or proteome mass spectrometry, or as predicted from the annotation of germline or somatic splicing mutations detected in DNA or RNA sequence data; the level of expression of the proteasome, immunoproteasome, thymoproteasome, or other proteases in the tumor cells (which may be measured by RNA-seq, proteome mass spectrometry, or immunohistochemistry); the expression of the source gene of the neoantigen encoded peptide (e.g., as measured by RNA-seq or mass spectrometry); the typical tissue-specific expression of the source gene of the neoantigen encoded peptide during various stages of the cell cycle; a comprehensive catalog of features of the source protein and/or its domains as can be found in e.g. uniProt or PDB http://www.rcsb.org/pdb/home/home.do; features describing the properties of the domain of the source protein containing the peptide, for example: secondary or tertiary structure (e.g., alpha helix vs beta sheet); alternative splicing; the probability of presentation of peptides from the source protein of the neoantigen encoded peptide in question in other distinct subjects; the probability that the peptide will not be detected or over-represented by mass spectrometry due to technical biases; the expression of various gene modules/pathways as measured by RNASeq (which need not contain the source protein of the peptide) that are informative about the state of the tumor cells, stroma, or tumor-infiltrating lymphocytes (TILs); the copy number of the source gene of the neoantigen encoded peptide in the tumor cells; the probability that the peptide binds to the TAP or the measured or predicted binding affinity of the peptide to the TAP; the expression level of TAP in the tumor cells (which may be measured by RNA-seq, proteome mass spectrometry, immunohistochemistry); presence or absence of tumor mutations, including, but not limited to: driver mutations in known cancer driver genes such as EGFR, KRAS, ALK, RET, ROS1, TP53, CDKN2A, CDKN2B, NTRK1, NTRK2, NTRK3, and in genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation; presence or absence of functional germline polymorphisms, including, but not limited to: in genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome); tumor type (e.g., NSCLC, melanoma); clinical tumor subtype (e.g., squamous lung cancer vs. non-squamous); smoking history; the typical expression of the source gene of the peptide in the relevant tumor type or clinical subtype, optionally stratified by driver mutation.

The at least one alteration may be a frameshift or non-frameshift indel, missense or nonsense substitution, splice site alteration, genomic rearrangement or gene fusion, or any genomic or expression alteration giving rise to a neoORF.

The tumor cell may be selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

A method disclosed herein may also include obtaining a tumor vaccine comprising the set of selected neoantigens or a subset thereof, optionally further comprising administering the tumor vaccine to the subject.

At least one of neoantigens in the set of selected neoantigens, when in polypeptide form, may include at least one of: a binding affinity with MHC with an IC50 value of less than 1000 nM, for MHC Class I polypeptides a length of 8-15, 8, 9, 10, 11, 12, 13, 14, or 15 amino acids, for MHC Class II polypeptides a length of 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the polypeptide in the parent protein sequence promoting proteasome cleavage, and presence of sequence motifs promoting TAP transport. For MHC Class II, presence of sequence motifs within or near the peptide promoting cleavage by extracellular or lysosomal proteases (e.g., cathepsins) or HLA-DM catalyzed HLA binding.

Also disclosed herein is a methods for generating a model for identifying one or more neoantigens that are likely to be presented on a tumor cell surface of a tumor cell, comprising the steps of: receiving mass spectrometry data comprising data associated with a plurality of isolated peptides eluted from major histocompatibility complex (MHC) derived from a plurality of samples; obtaining a training data set by at least identifying a set of training peptide sequences present in the samples and one or more MHCs associated with each training peptide sequence; training a set of numerical parameters of a presentation model using the training data set comprising the training peptide sequences, the presentation model providing a plurality of numerical likelihoods that peptide sequences from the tumor cell are presented by one or more MHC alleles on the tumor cell surface.

The presentation model may represent dependence between: presence of a particular amino acid at a particular position of a peptide sequence; and likelihood of presentation, by one of the MHC alleles on the tumor cell, of the peptide sequence containing the particular amino acid at the particular position.

The samples can also include cell lines engineered to express a single MHC class I or class II allele.

The samples can also include cell lines engineered to express a plurality of MHC class I or class II alleles.

The samples can also include human cell lines obtained or derived from a plurality of patients.

The samples can also include fresh or frozen tumor samples obtained from a plurality of patients.

The samples can also include peptides identified using T-cell assays.

The training data set may further include data associated with: peptide abundance of the set of training peptides present in the samples; peptide length of the set of training peptides in the samples.

A method disclosed herein can also include obtaining a set of training protein sequences based on the training peptide sequences by comparing the set of training peptide sequences via alignment to a database comprising a set of known protein sequences, wherein the set of training protein sequences are longer than and include the training peptide sequences.

A method disclosed herein can also include performing or having performed mass spectrometry on a cell line to obtain at least one of exome, transcriptome, or whole genome nucleotide sequencing data from the cell line, the nucleotide sequencing data including at least one protein sequence including a mutation.

A method disclosed herein can also include: encoding the training peptide sequences using a one-hot encoding scheme.

A method disclosed herein can also include obtaining at least one of exome, transcriptome, and whole genome normal nucleotide sequencing data from normal tissue samples; and training the set of parameters of the presentation model using the normal nucleotide sequencing data.

The training data set may further include data associated with proteome sequences associated with the samples.

The training data set may further include data associated with MHC peptidome sequences associated with the samples.

The training data set may further include data associated with peptide-MHC binding affinity measurements for at least one of the isolated peptides.

The training data set may further include data associated with peptide-MHC binding stability measurements for at least one of the isolated peptides.

The training data set may further include data associated with transcriptomes associated with the samples.

The training data set may further include data associated with genomes associated with the samples.

A method disclosed herein may also include logistically regressing the set of parameters.

The training peptide sequences may be lengths within a range of k-mers where k is between 8-15, inclusive for MHC class I or 6-30, inclusive for MHC class II.

A method disclosed herein may also include encoding the training peptide sequences using a left-padded one-hot encoding scheme.

A method disclosed herein may also include determining values for the set of parameters using a deep learning algorithm.

Disclosed herein is are methods for identifying one or more neoantigens that are likely to be presented on a tumor cell surface of a tumor cell, comprising executing the steps of: receiving mass spectrometry data comprising data associated with a plurality of isolated peptides eluted from major histocompatibility complex (MHC) derived from a plurality of fresh or frozen tumor samples; obtaining a training data set by at least identifying a set of training peptide sequences present in the tumor samples and presented on one or more MHC alleles associated with each training peptide sequence; obtaining a set of training protein sequences based on the training peptide sequences; and training a set of numerical parameters of a presentation model using the training protein sequences and the training peptide sequences, the presentation model providing a plurality of numerical likelihoods that peptide sequences from the tumor cell are presented by one or more MHC alleles on the tumor cell surface.

The presentation model may represent dependence between: presence of a pair of a particular one of the MHC alleles and a particular amino acid at a particular position of a peptide sequence; and likelihood of presentation on the tumor cell surface, by the particular one of the MHC alleles of the pair, of such a peptide sequence comprising the particular amino acid at the particular position.

A method disclosed herein can also include selecting a subset of neoantigens, wherein the subset of neoantigens is selected because each has an increased likelihood that it is presented on the cell surface of the tumor relative to one or more distinct tumor neoantigens.

A method disclosed herein can also include selecting a subset of neoantigens, wherein the subset of neoantigens is selected because each has an increased likelihood that it is capable of inducing a tumor-specific immune response in the subject relative to one or more distinct tumor neoantigens.

A method disclosed herein can also include selecting a subset of neoantigens, wherein the subset of neoantigens is selected because each has an increased likelihood that it is capable of being presented to naïve T cells by professional antigen presenting cells (APCs) relative to one or more distinct tumor neoantigens, optionally wherein the APC is a dendritic cell (DC).

A method disclosed herein can also include selecting a subset of neoantigens, wherein the subset of neoantigens is selected because each has a decreased likelihood that it is subject to inhibition via central or peripheral tolerance relative to one or more distinct tumor neoantigens.

A method disclosed herein can also include selecting a subset of neoantigens, wherein the subset of neoantigens is selected because each has a decreased likelihood that it is capable of inducing an autoimmune response to normal tissue in the subject relative to one or more distinct tumor neoantigens.

A method disclosed herein can also include selecting a subset of neoantigens, wherein the subset of neoantigens is selected because each has a decreased likelihood that it will be differentially post-translationally modified in tumor cells versus APCs, optionally wherein the APC is a dendritic cell (DC).

The practice of the methods herein will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* 3$^{rd}$ Ed. (Plenum Press) Vols A and B (1992).

III. Identification of Tumor Specific Mutations in Neoantigens

Also disclosed herein are methods for the identification of certain mutations (e.g., the variants or alleles that are present in cancer cells). In particular, these mutations can be present in the genome, transcriptome, proteome, or exome of cancer cells of a subject having cancer but not in normal tissue from the subject.

Genetic mutations in tumors can be considered useful for the immunological targeting of tumors if they lead to changes in the amino acid sequence of a protein exclusively in the tumor. Useful mutations include: (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift mutations or deletions that lead to a new open reading frame with a novel tumor-specific protein sequence. Mutations can also include one or more of nonframeshift indel, missense or nonsense substitution, splice site alteration, genomic rearrangement or gene fusion, or any genomic or expression alteration giving rise to a neoORF.

Peptides with mutations or mutated polypeptides arising from for example, splice-site, frameshift, readthrough, or gene fusion mutations in tumor cells can be identified by sequencing DNA, RNA or protein in tumor versus normal cells.

Also mutations can include previously identified tumor specific mutations. Known tumor mutations can be found at the Catalogue of Somatic Mutations in Cancer (COSMIC) database.

A variety of methods are available for detecting the presence of a particular mutation or allele in an individual's DNA or RNA. Advancements in this field have provided accurate, easy, and inexpensive large-scale SNP genotyping. For example, several techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods utilize amplification of a target genetic region, typically by PCR. Still other methods, based on the generation of small signal molecules by invasive cleavage followed by mass spectrometry or immobilized padlock probes and rolling-circle amplification. Several of the methods known in the art for detecting specific mutations are summarized below.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. For example, a single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide(s) present in the polymorphic site of the target molecule is complementary to that of the nucleotide derivative used in the reaction. This method has the advantage that it does not require the determination of large amounts of extraneous sequence data.

A solution-based method can be used for determining the identity of a nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. can be a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)). These methods differ from GBA in that they utilize incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46-59 (1993)).

A number of initiatives obtain sequence information directly from millions of individual molecules of DNA or RNA in parallel. Real-time single molecule sequencing-by-synthesis technologies rely on the detection of fluorescent nucleotides as they are incorporated into a nascent strand of DNA that is complementary to the template being sequenced. In one method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle consists of adding the polymerase/labeled nucleotide mixture, rinsing, imaging and cleavage of dye. In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain. Other sequencing-by-synthesis technologies also exist.

Any suitable sequencing-by-synthesis platform can be used to identify mutations. As described above, four major sequencing-by-synthesis platforms are currently available: the Genome Sequencers from Roche/454 Life Sciences, the 1 G Analyzer from Illumina/Solexa, the SOLiD system from Applied BioSystems, and the Heliscope system from Helicos Biosciences. Sequencing-by-synthesis platforms have also been described by Pacific BioSciences and VisiGen Biotechnologies. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids can be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., US Patent Application No. 2006/0252077) can be linked to each fragment to be captured on a surface coated with a respective second member of that coupling pair.

Subsequent to the capture, the sequence can be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide can be incorporated and multiple lasers can be utilized for stimulation of incorporated nucleotides.

Sequencing can also include other massively parallel sequencing or next generation sequencing (NGS) techniques and platforms. Additional examples of massively parallel sequencing techniques and platforms are the Illumina HiSeq or MiSeq, Thermo PGM or Proton, the Pac Bio RS II or Sequel, Qiagen's Gene Reader, and the Oxford Nanopore MinION. Additional similar current massively parallel sequencing technologies can be used, as well as future generations of these technologies.

Any cell type or tissue can be utilized to obtain nucleic acid samples for use in methods described herein. For example, a DNA or RNA sample can be obtained from a tumor or a bodily fluid, e.g., blood, obtained by known techniques (e.g. venipuncture) or saliva. Alternatively, nucleic acid tests can be performed on dry samples (e.g. hair or skin). In addition, a sample can be obtained for sequencing from a tumor and another sample can be obtained from normal tissue for sequencing where the normal tissue is of the same tissue type as the tumor. A sample can be obtained for sequencing from a tumor and another sample can be obtained from normal tissue for sequencing where the normal tissue is of a distinct tissue type relative to the tumor.

Tumors can include one or more of lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

Alternatively, protein mass spectrometry can be used to identify or validate the presence of mutated peptides bound to MHC proteins on tumor cells. Peptides can be acid-eluted from tumor cells or from HLA molecules that are immunoprecipitated from tumor, and then identified using mass spectrometry.

IV. Neoantigens

Neoantigens can include nucleotides or polypeptides. For example, a neoantigen can be an RNA sequence that encodes for a polypeptide sequence. Neoantigens useful in vaccines can therefore include nucleotide sequences or polypeptide sequences.

Disclosed herein are isolated peptides that comprise tumor specific mutations identified by the methods disclosed herein, peptides that comprise known tumor specific mutations, and mutant polypeptides or fragments thereof identified by methods disclosed herein. Neoantigen peptides can be described in the context of their coding sequence where a neoantigen includes the nucleotide sequence (e.g., DNA or RNA) that codes for the related polypeptide sequence.

One or more polypeptides encoded by a neoantigen nucleotide sequence can comprise at least one of: a binding affinity with MHC with an IC50 value of less than 1000 nM, for MHC Class I peptides a length of 8-15, 8, 9, 10, 11, 12, 13, 14, or 15 amino acids, presence of sequence motifs within or near the peptide promoting proteasome cleavage, and presence or sequence motifs promoting TAP transport. For MHC Class II peptides a length 6-30, 6, 7, 8, 9, 10, 11, 12, 13, 14, 15, 16, 17, 18, 19, 20, 21, 22, 23, 24, 25, 26, 27, 28, 29, or 30 amino acids, presence of sequence motifs within or near the peptide promoting cleavage by extracellular or lysosomal proteases (e.g., cathepsins) or HLA-DM catalyzed HLA binding.

One or more neoantigens can be presented on the surface of a tumor.

One or more neoantigens can be is immunogenic in a subject having a tumor, e.g., capable of eliciting a T cell response or a B cell response in the subject.

One or more neoantigens that induce an autoimmune response in a subject can be excluded from consideration in the context of vaccine generation for a subject having a tumor.

The size of at least one neoantigenic peptide molecule can comprise, but is not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the neoantigenic peptide molecules are equal to or less than 50 amino acids.

Neoantigenic peptides and polypeptides can be: for MHC Class 115 residues or less in length and usually consist of between about 8 and about 11 residues, particularly 9 or 10 residues; for MHC Class II, 6-30 residues, inclusive.

If desirable, a longer peptide can be designed in several ways. In one case, when presentation likelihoods of peptides on HLA alleles are predicted or known, a longer peptide could consist of either: (1) individual presented peptides with an extensions of 2-5 amino acids toward the N- and C-terminus of each corresponding gene product; (2) a concatenation of some or all of the presented peptides with extended sequences for each. In another case, when sequencing reveals a long (>10 residues) neoepitope sequence present in the tumor (e.g. due to a frameshift, read-through or intron inclusion that leads to a novel peptide sequence), a longer peptide would consist of: (3) the entire stretch of novel tumor-specific amino acids—thus bypassing the need for computational or in vitro test-based selection of the strongest HLA-presented shorter peptide. In both cases, use of a longer peptide allows endogenous processing by patient cells and may lead to more effective antigen presentation and induction of T cell responses.

Neoantigenic peptides and polypeptides can be presented on an HLA protein. In some aspects neoantigenic peptides and polypeptides are presented on an HLA protein with greater affinity than a wild-type peptide. In some aspects, a neoantigenic peptide or polypeptide can have an IC50 of at least less than 5000 nM, at least less than 1000 nM, at least less than 500 nM, at least less than 250 nM, at least less than 200 nM, at least less than 150 nM, at least less than 100 nM, at least less than 50 nM or less.

In some aspects, neoantigenic peptides and polypeptides do not induce an autoimmune response and/or invoke immunological tolerance when administered to a subject.

Also provided are compositions comprising at least two or more neoantigenic peptides. In some embodiments the composition contains at least two distinct peptides. At least two distinct peptides can be derived from the same polypeptide. By distinct polypeptides is meant that the peptide vary by length, amino acid sequence, or both. The peptides are derived from any polypeptide known to or have been found to contain a tumor specific mutation. Suitable polypeptides from which the neoantigenic peptides can be derived can be found for example in the COSMIC database. COSMIC curates comprehensive information on somatic mutations in human cancer. The peptide contains the tumor specific mutation. In some aspects the tumor specific mutation is a driver mutation for a particular cancer type.

Neoantigenic peptides and polypeptides having a desired activity or property can be modified to provide certain desired attributes, e.g., improved pharmacological characteristics, while increasing or at least retaining substantially all of the biological activity of the unmodified peptide to bind the desired MHC molecule and activate the appropriate T cell. For instance, neoantigenic peptide and polypeptides can be subject to various changes, such as substitutions, either conservative or non-conservative, where such changes might provide for certain advantages in their use, such as improved MHC binding, stability or presentation. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications can be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

Modifications of peptides and polypeptides with various amino acid mimetics or unnatural amino acids can be particularly useful in increasing the stability of the peptide and polypeptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half-life of the peptides can be conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4 degrees C.) for 15 minutes and then spun to pellet the precipitated serum proteins. The presence of the peptides is then determined by reversed-phase HPLC using stability-specific chromatography conditions.

The peptides and polypeptides can be modified to provide desired attributes other than improved serum half-life. For instance, the ability of the peptides to induce CTL activity can be enhanced by linkage to a sequence which contains at least one epitope that is capable of inducing a T helper cell response. Immunogenic peptides/T helper conjugates can be linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus can be a hetero- or homo-oligomer. When present, the spacer will usually be at least one or two residues, more usually three to six residues. Alternatively, the peptide can be linked to the T helper peptide without a spacer.

A neoantigenic peptide can be linked to the T helper peptide either directly or via a spacer either at the amino or carboxy terminus of the peptide. The amino terminus of either the neoantigenic peptide or the T helper peptide can be acylated. Exemplary T helper peptides include tetanus toxoid 830-843, influenza 307-319, malaria circumsporozoite 382-398 and 378-389.

Proteins or peptides can be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and can be found at computerized databases known to those of ordinary skill in the art. One such database is the National Center for Biotechnology Information's Genbank and GenPept databases located at the National Institutes of Health website. The coding regions for known genes can be amplified and/or expressed using the techniques disclosed herein or as would be known to those of ordinary skill in the art. Alternatively, various commercial preparations of proteins, polypeptides and peptides are known to those of skill in the art.

In a further aspect a neoantigen includes a nucleic acid (e.g. polynucleotide) that encodes a neoantigenic peptide or portion thereof. The polynucleotide can be, e.g., DNA, cDNA, PNA, CNA, RNA (e.g., mRNA), either single- and/or double-stranded, or native or stabilized forms of polynucleotides, such as, e.g., polynucleotides with a phosphorothiate backbone, or combinations thereof and it may or may not contain introns. A still further aspect provides an expression vector capable of expressing a polypeptide or portion thereof. Expression vectors for different cell types are well known in the art and can be selected without undue experimentation. Generally, DNA is inserted into an expression vector, such as a plasmid, in proper orientation and correct reading frame for expression. If necessary, DNA can be linked to the appropriate transcriptional and translational regulatory control nucleotide sequences recognized by the desired host, although such controls are generally available in the expression vector. The vector is then introduced into the host through standard techniques. Guidance can be found e.g. in Sambrook et al. (1989) Molecular Cloning, A Laboratory Manual, Cold Spring Harbor Laboratory, Cold Spring Harbor, N.Y.

V. Vaccine Compositions

Also disclosed herein is an immunogenic composition, e.g., a vaccine composition, capable of raising a specific immune response, e.g., a tumor-specific immune response. Vaccine compositions typically comprise a plurality of neoantigens, e.g., selected using a method described herein. Vaccine compositions can also be referred to as vaccines.

A vaccine can contain between 1 and 30 peptides, 2, 3, 4, 5, 6, 7, 8, 9, 10, 11, 12, 13, 14, 15, 16, 17, 18, 19, 20, 21, 22, 23, 24, 25, 26, 27, 28, 29, or 30 different peptides, 6, 7, 8, 9, 10 11, 12, 13, or 14 different peptides, or 12, 13 or 14 different peptides. Peptides can include post-translational modifications. A vaccine can contain between 1 and 100 or more nucleotide sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different nucleotide sequences, 6, 7, 8, 9, 10 11, 12, 13, or 14 different nucleotide sequences, or 12, 13 or 14 different nucleotide sequences. A vaccine can contain between 1 and 30 neoantigen sequences, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more different neoantigen sequences, 6, 7, 8, 9, 10 11, 12, 13, or 14 different neoantigen sequences, or 12, 13 or 14 different neoantigen sequences.

In one embodiment, different peptides and/or polypeptides or nucleotide sequences encoding them are selected so that the peptides and/or polypeptides capable of associating with different MHC molecules, such as different MHC class I molecules and/or different MHC class II molecules. In some aspects, one vaccine composition comprises coding sequence for peptides and/or polypeptides capable of associating with the most frequently occurring MHC class I molecules and/or different MHC class II molecules. Hence, vaccine compositions can comprise different fragments capable of associating with at least 2 preferred, at least 3 preferred, or at least 4 preferred MHC class I molecules and/or different MHC class II molecules.

The vaccine composition can be capable of raising a specific cytotoxic T-cells response and/or a specific helper T-cell response.

A vaccine composition can further comprise an adjuvant and/or a carrier. Examples of useful adjuvants and carriers are given herein below. A composition can be associated with a carrier such as e.g. a protein or an antigen-presenting cell such as e.g. a dendritic cell (DC) capable of presenting the peptide to a T-cell.

Adjuvants are any substance whose admixture into a vaccine composition increases or otherwise modifies the immune response to a neoantigen. Carriers can be scaffold structures, for example a polypeptide or a polysaccharide, to which a neoantigen, is capable of being associated. Optionally, adjuvants are conjugated covalently or non-covalently.

The ability of an adjuvant to increase an immune response to an antigen is typically manifested by a significant or substantial increase in an immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th response into a primarily cellular, or Th response.

Suitable adjuvants include, but are not limited to 1018 ISS, alum, aluminium salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Adjuvants such as incomplete Freund's or GM-CSF are useful. Several immunological adjuvants (e.g., MF59) specific for dendritic cells and their preparation have been described previously (Dupuis M, et al., Cell Immunol. 1998; 186(1):18-27; Allison A C; Dev Biol Stand. 1998; 92:3-11). Also cytokines can be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

CpG immunostimulatory oligonucleotides have also been reported to enhance the effects of adjuvants in a vaccine setting. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C)(e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives can readily be determined by the skilled artisan without undue experimentation. Additional adjuvants include colony-stimulating factors, such as Granulocyte Macrophage Colony Stimulating Factor (GM-CSF, sargramostim).

A vaccine composition can comprise more than one different adjuvant. Furthermore, a therapeutic composition can comprise any adjuvant substance including any of the above or combinations thereof. It is also contemplated that a vaccine and an adjuvant can be administered together or separately in any appropriate sequence.

A carrier (or excipient) can be present independently of an adjuvant. The function of a carrier can for example be to increase the molecular weight of in particular mutant to increase activity or immunogenicity, to confer stability, to increase the biological activity, or to increase serum half-life. Furthermore, a carrier can aid presenting peptides to T-cells. A carrier can be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier is generally a physiologically acceptable carrier acceptable to humans and safe. However, tetanus toxoid and/or diptheria toxoid are suitable carriers. Alternatively, the carrier can be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments a vaccine composition additionally contains at least one antigen presenting cell.

Neoantigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.*

(2015) 43 (1): 682-690, Zufferey et al., Self-Inactivating Lentivirus Vector for Safe and Efficient In Vivo Gene Delivery, *J. Virol.* (1998) 72 (12): 9873-9880). Dependent on the packaging capacity of the above mentioned viral vector-based vaccine platforms, this approach can deliver one or more nucleotide sequences that encode one or more neoantigen peptides. The sequences may be flanked by non-mutated sequences, may be separated by linkers or may be preceded with one or more sequences targeting a sub-cellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T cell receptor repertoires, *Science*. (2016) 352 (6291):1337-41, Lu et al., Efficient identification of mutated cancer antigens recognized by T cells associated with durable tumor regressions, *Clin Cancer Res.* (2014) 20(13):3401-10). Upon introduction into a host, infected cells express the neoantigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (*Nature* 351:456-460 (1991)). A wide variety of other vaccine vectors useful for therapeutic administration or immunization of neoantigens, e.g., *Salmonella typhi* vectors, and the like will be apparent to those skilled in the art from the description herein.

V.A. Neoantigen Cassette

The methods employed for the selection of one or more neoantigens, the cloning and construction of a "cassette" and its insertion into a viral vector are within the skill in the art given the teachings provided herein. By "neoantigen cassette" is meant the combination of a selected neoantigen or plurality of neoantigens and the other regulatory elements necessary to transcribe the neoantigen(s) and express the transcribed product. A neoantigen or plurality of neoantigens can be operatively linked to regulatory components in a manner which permits transcription. Such components include conventional regulatory elements that can drive expression of the neoantigen(s) in a cell transfected with the viral vector. Thus the neoantigen cassette can also contain a selected promoter which is linked to the neoantigen(s) and located, with other, optional regulatory elements, within the selected viral sequences of the recombinant vector.

Useful promoters can be constitutive promoters or regulated (inducible) promoters, which will enable control of the amount of neoantigen(s) to be expressed. For example, a desirable promoter is that of the cytomegalovirus immediate early promoter/enhancer [see, e.g., Boshart et al, Cell, 41:521-530 (1985)]. Another desirable promoter includes the Rous sarcoma virus LTR promoter/enhancer. Still another promoter/enhancer sequence is the chicken cytoplasmic beta-actin promoter [T. A. Kost et al, Nucl. Acids Res., 11(23):8287 (1983)]. Other suitable or desirable promoters can be selected by one of skill in the art.

The neoantigen cassette can also include nucleic acid sequences heterologous to the viral vector sequences including sequences providing signals for efficient polyadenylation of the transcript (poly(A), poly-A or pA) and introns with functional splice donor and acceptor sites. A common poly-A sequence which is employed in the exemplary vectors of this invention is that derived from the papovavirus SV-40. The poly-A sequence generally can be inserted in the cassette following the neoantigen-based sequences and before the viral vector sequences. A common intron sequence can also be derived from SV-40, and is referred to as the SV-40 T intron sequence. A neoantigen cassette can also contain such an intron, located between the promoter/enhancer sequence and the neoantigen(s). Selection of these and other common vector elements are conventional [see, e.g., Sambrook et al, "Molecular Cloning. A Laboratory Manual.", 2d edit., Cold Spring Harbor Laboratory, New York (1989) and references cited therein] and many such sequences are available from commercial and industrial sources as well as from Genbank.

A neoantigen cassette can have one or more neoantigens. For example, a given cassette can include 1-10, 1-20, 1-30, 10-20, 15-25, 15-20, 1, 2, 3, 4, 5, 6, 7, 8, 9, 10, 11, 12, 13, 14, 15, 16, 17, 18, 19, 20, or more neoantigens. Neoantigens can be linked directly to one another. Neoantigens can also be linked to one another with linkers. Neoantigens can be in any orientation relative to one another including N to C or C to N.

As above stated, the neoantigen cassette can be located in the site of any selected deletion in the viral vector, such as the site of the E1 gene region deletion or E3 gene region deletion, among others which may be selected.

The neoantigen cassette can be described using the following formula to describe the ordered sequence of each element, from 5' to 3':

$$(P_a\text{-}(L5_b\text{-}N_c\text{-}L3_d)_X)_Z\text{-}(P2_h\text{-}(G5_e\text{-}U_f)_Y)_W\text{-}G3_g$$

wherein P and P2 comprise promoter nucleotide sequences, N comprises an MHC class I epitope encoding nucleic acid sequence, L5 comprises a 5' linker sequence, L3 comprises a 3' linker sequence, G5 comprises a nucleic acid sequences encoding an amino acid linker, G3 comprises one of the at least one nucleic acid sequences encoding an amino acid linker, U comprises an MHC class II antigen-encoding nucleic acid sequence, where for each X the corresponding Nc is a epitope encoding nucleic acid sequence, where for each Y the corresponding Uf is an antigen-encoding nucleic acid sequence. The composition and ordered sequence can be further defined by selecting the number of elements present, for example where a=0 or 1, where b=0 or 1, where c=1, where d=0 or 1, where e=0 or 1, where f=1, where g=0 or 1, where h=0 or 1, X=1 to 400, Y=0, 1, 2, 3, 4 or 5, Z=1 to 400, and W=0, 1, 2, 3, 4 or 5.

In one example, elements present include where a=0, b=1, d=1, e=1, g=1, h=0, X=10, Y=2, Z=1, and W=1, describing where no additional promoter is present (i.e. only the promoter nucleotide sequence provided by the RNA alphavirus backbone is present), 20 MHC class I epitope are present, a 5' linker is present for each N, a 3' linker is present for each N, 2 MHC class II epitopes are present, a linker is present linking the two MHC class II epitopes, a linker is present linking the 5' end of the two MHC class II epitopes to the 3' linker of the final MHC class I epitope, and a linker is present linking the 3' end of the two MHC class II epitopes to the to the RNA alphavirus backbone. Examples of linking the 3' end of the neoantigen cassette to the RNA alphavirus backbone include linking directly to the 3' UTR elements provided by the RNA alphavirus backbone, such as a 3' 19-nt CSE. Examples of linking the 5' end of the neoantigen cassette to the RNA alphavirus backbone include linking directly to a 26S promoter sequence, an alphavirus 5' UTR, a 51-nt CSE, or a 24-nt CSE.

Other examples include: where a=1 describing where a promoter other than the promoter nucleotide sequence provided by the RNA alphavirus backbone is present; where a=1 and Z is greater than 1 where multiple promoters other than the promoter nucleotide sequence provided by the RNA alphavirus backbone are present each driving expression of 1 or more distinct MHC class I epitope encoding nucleic acid sequences; where h=1 describing where a separate promoter is present to drive expression of the MHC class II antigen-encoding nucleic acid sequences; and where g=0 describing the MHC class II antigen-encoding nucleic acid sequence, if present, is directly linked to the RNA alphavirus backbone.

Other examples include where each MHC class I epitope that is present can have a 5' linker, a 3' linker, neither, or both. In examples where more than one MHC class I epitope is present in the same neoantigen cassette, some MHC class I epitopes may have both a 5' linker and a 3' linker, while other MHC class I epitopes may have either a 5' linker, a 3' linker, or neither. In other examples where more than one MHC class I epitope is present in the same neoantigen cassette, some MHC class I epitopes may have either a 5' linker or a 3' linker, while other MHC class I epitopes may have either a 5' linker, a 3' linker, or neither.

In examples where more than one MHC class II epitope is present in the same neoantigen cassette, some MHC class II epitopes may have both a 5' linker and a 3' linker, while other MHC class II epitopes may have either a 5' linker, a 3' linker, or neither. In other examples where more than one MHC class II epitope is present in the same neoantigen cassette, some MHC class II epitopes may have either a 5' linker or a 3' linker, while other MHC class II epitopes may have either a 5' linker, a 3' linker, or neither.

The promoter nucleotide sequences P and/or P2 can be the same as a promoter nucleotide sequence provided by the RNA alphavirus backbone. For example, the promoter sequence provided by the RNA alphavirus backbone, Pn and P2, can each comprise a 26S subgenomic promoter. The promoter nucleotide sequences P and/or P2 can be different from the promoter nucleotide sequence provided by the RNA alphavirus backbone, as well as can be different from each other.

The 5' linker L5 can be a native sequence or a non-natural sequence. Non-natural sequence include, but are not limited to, AAY, RR, and DPP. The 3' linker L3 can also be a native sequence or a non-natural sequence. Additionally, L5 and L3 can both be native sequences, both be non-natural sequences, or one can be native and the other non-natural. For each X, the amino acid linkers can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each X, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G5, for each Y, can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. For each Y, the amino acid linkers can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

The amino acid linker G3 can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. G3 can be also be at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

For each X, each N can encodes a MHC class I epitope 7-15 amino acids in length. For each X, each N can also encodes a MHC class I epitope 5, 6, 7, 8, 9, 10, 11, 12, 13, 14, 15, 16, 17, 18, 19, 20, 21, 22, 23, 24, 25, 26, 27, 28, 29, or 30 amino acids in length. For each X, each N can also encodes a MHC class I epitope at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acids in length.

V.B. Immune Checkpoints

Vectors described herein, such as C68 vectors described herein or alphavirus vectors described herein, can comprise a nucleic acid which encodes at least one neoantigen and the same or a separate vector can comprise a nucleic acid which encodes at least one immune modulator (e.g., an antibody such as an scFv) which binds to and blocks the activity of an immune checkpoint molecule. Vectors can comprise a neoantigen cassette and one or more nucleic acid molecules encoding a checkpoint inhibitor.

Illustrative immune checkpoint molecules that can be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory CD8+ (αβ) T cells), CD160 (also referred to as BY55), and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160, and CGEN-15049. Illustrative immune checkpoint inhibitors include Tremelimumab (CTLA-4 blocking antibody), anti-OX40, PD-L1 monoclonal Antibody (Anti-B7-H1; MEDI4736), ipilimumab, MK-3475 (PD-1 blocker), Nivolumamb (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor). Antibody-encoding sequences can be engineered into vectors such as C68 using ordinary skill in the art. An exemplary method is described in Fang et al., Stable antibody expression at therapeutic levels using the 2A peptide. *Nat Biotechnol.* 2005 May; 23(5):584-90. Epub 2005 Apr. 17; herein incorporated by reference for all purposes.

V.C. Additional Considerations for Vaccine Design and Manufacture

V.C.1. Determination of a Set of Peptides that Cover all Tumor Subclones

Truncal peptides, meaning those presented by all or most tumor subclones, can be prioritized for inclusion into the vaccine.[53] Optionally, if there are no truncal peptides predicted to be presented and immunogenic with high probability, or if the number of truncal peptides predicted to be presented and immunogenic with high probability is small enough that additional non-truncal peptides can be included in the vaccine, then further peptides can be prioritized by estimating the number and identity of tumor subclones and choosing peptides so as to maximize the number of tumor subclones covered by the vaccine.[54]

V.C.2. Neoantigen Prioritization

After all of the above above neoantigen filters are applied, more candidate neoantigens may still be available for vaccine inclusion than the vaccine technology can support. Additionally, uncertainty about various aspects of the neoantigen analysis may remain and tradeoffs may exist between different properties of candidate vaccine neoantigens. Thus, in place of predetermined filters at each step of the selection process, an integrated multi-dimensional model can be considered that places candidate neoantigens in a space with at least the following axes and optimizes selection using an integrative approach.

1. Risk of auto-immunity or tolerance (risk of germline) (lower risk of auto-immunity is typically preferred)
2. Probability of sequencing artifact (lower probability of artifact is typically preferred)
3. Probability of immunogenicity (higher probability of immunogenicity is typically preferred)
4. Probability of presentation (higher probability of presentation is typically preferred)
5. Gene expression (higher expression is typically preferred)
6. Coverage of HLA genes (larger number of HLA molecules involved in the presentation of a set of neoantigens may lower the probability that a tumor will escape immune attack via downregulation or mutation of HLA molecules)
7. Coverage of HLA classes (covering both HLA-I and HLA-II may increase the probability of therapeutic response and decrease the probability of tumor escape)

Additionally, optionally, neoantigens can be deprioritized (e.g., excluded) from the vaccination if they are predicted to be presented by HLA alleles lost or inactivated in either all or part of the patient's tumor. HLA allele loss can occur by either somatic mutation, loss of heterozygosity, or homozygous deletion of the locus. Methods for detection of HLA allele somatic mutation are well known in the art, e.g. (Shukla et al., 2015). Methods for detection of somatic LOH and homozygous deletion (including for HLA locus) are likewise well described. (Carter et al., 2012; McGranahan et al., 2017; Van Loo et al., 2010).

V.D. Alphavirus

V.D.1. Alphavirus Biology

Alphaviruses are members of the family Togaviridae, and are positive-sense single stranded RNA viruses. Alphaviruses can also be referred to as self-replicating RNA or srRNA. Members are typically classified as either Old World, such as Sindbis, Ross River, Mayaro, Chikungunya, and Semliki Forest viruses, or New World, such as eastern equine encephalitis, Aura, Fort Morgan, or Venezuelan equine encephalitis virus and its derivative strain TC-83 (Strauss Microbrial Review 1994). A natural alphavirus genome is typically around 12 kb in length, the first two-thirds of which contain genes encoding non-structural proteins (nsPs) that form RNA replication complexes for self-replication of the viral genome, and the last third of which contains a subgenomic expression cassette encoding structural proteins for virion production (Frolov RNA 2001).

A model lifecycle of an alphavirus involves several distinct steps (Strauss Microbrial Review 1994, Jose Future Microbiol 2009). Following virus attachment to a host cell, the virion fuses with membranes within endocytic compartments resulting in the eventual release of genomic RNA into the cytosol. The genomic RNA, which is in a plus-strand orientation and comprises a 5' methylguanylate cap and 3' polyA tail, is translated to produce non-structural proteins nsP1-4 that form the replication complex. Early in infection, the plus-strand is then replicated by the complex into a minus-stand template. In the current model, the replication complex is further processed as infection progresses, with the resulting processed complex switching to transcription of the minus-strand into both full-length positive-strand genomic RNA, as well as the 26S subgenomic positive-strand RNA containing the structural genes. Several conserved sequence elements (CSEs) of alphavirus have been identified to potentially play a role in the various RNA replication steps including; a complement of the 5' UTR in the replication of plus-strand RNAs from a minus-strand template, a 51-nt CSE in the replication of minus-strand synthesis from the genomic template, a 24-nt CSE in the junction region between the nsPs and the 26S RNA in the transcription of the subgenomic RNA from the minus-strand, and a 3' 19-nt CSE in minus-strand synthesis from the plus-strand template.

Following the replication of the various RNA species, virus particles are then typically assembled in the natural lifecycle of the virus. The 26S RNA is translated and the resulting proteins further processed to produce the structural proteins including capsid protein, glycoproteins E1 and E2, and two small polypeptides E3 and 6K (Strauss 1994). Encapsidation of viral RNA occurs, with capsid proteins normally specific for only genomic RNA being packaged, followed by virion assembly and budding at the membrane surface.

V.D.2. Alphavirus as a Delivery Vector

Alphaviruses have previously been engineered for use as expression vector systems (Pushko 1997, Rheme 2004). Alphaviruses offer several advantages, particularly in a vaccine setting where heterologous antigen expression can be desired. Due to its ability to self-replicate in the host cytosol, alphavirus vectors are generally able to produce high copy numbers of the expression cassette within a cell resulting in a high level of heterologous antigen production. Additionally, the vectors are generally transient, resulting in improved biosafety as well as reduced induction of immunological tolerance to the vector. The public, in general, also lacks pre-existing immunity to alphavirus vectors as compared to other standard viral vectors, such as human adenovirus. Alphavirus based vectors also generally result in cytotoxic responses to infected cells. Cytotoxicity, to a certain degree, can be important in a vaccine setting to properly illicit an immune response to the heterologous antigen expressed. However, the degree of desired cytotoxicity can be a balancing act, and thus several attenuated alphaviruses have been developed, including the TC-83 strain of VEE. Thus, an example of a neoantigen expression vector described herein can utilize an alphavirus backbone that allows for a high level of neoantigen expression, elicits a robust immune response to neoantigen, does not elicit an immune response to the vector itself, and can be used in a safe manner. Furthermore, the neoantigen expression cassette can be designed to elicit different levels of an immune response through optimization of which alphavirus sequences the vector uses, including, but not limited to, sequences derived from VEE or its attenuated derivative TC-83.

Several expression vector design strategies have been engineered using alphavirus sequences (Pushko 1997). In one strategy, a alphavirus vector design includes inserting a second copy of the 26S promoter sequence elements downstream of the structural protein genes, followed by a heterologous gene (Frolov 1993). Thus, in addition to the natural non-structural and structural proteins, an additional subgenomic RNA is produced that expresses the heterologous protein. In this system, all the elements for production of infectious virions are present and, therefore, repeated rounds of infection of the expression vector in non-infected cells can occur.

Another expression vector design makes use of helper virus systems (Pushko 1997). In this strategy, the structural proteins are replaced by a heterologous gene. Thus, following self-replication of viral RNA mediated by still intact non-structural genes, the 26S subgenomic RNA provides for expression of the heterologous protein. Traditionally, additional vectors that expresses the structural proteins are then supplied in trans, such as by co-transfection of a cell line, to produce infectious virus. A system is described in detail in U.S. Pat. No. 8,093,021, which is herein incorporated by reference in its entirety, for all purposes. The helper vector system provides the benefit of limiting the possibility of forming infectious particles and, therefore, improves biosafety. In addition, the helper vector system reduces the total vector length, potentially improving the replication and expression efficiency. Thus, an example of a neoantigen expression vector described herein can utilize an alphavirus backbone wherein the structural proteins are replaced by a neoantigen cassette, the resulting vector both reducing biosafety concerns, while at the same time promoting efficient expression due to the reduction in overall expression vector size.

V.D.3. Alphavirus Production In Vitro

Alphavirus delivery vectors are generally positive-sense RNA polynucleotides. A convenient technique well-known in the art for RNA production is in vitro transcription IVT. In this technique, a DNA template of the desired vector is first produced by techniques well-known to those in the art, including standard molecular biology techniques such as cloning, restriction digestion, ligation, gene synthesis, and polymerase chain reaction (PCR). The DNA template contains a RNA polymerase promoter at the 5' end of the sequence desired to be transcribed into RNA. Promoters include, but are not limited to, bacteriophage polymerase promoters such as T3, T7, or SP6. The DNA template is then incubated with the appropriate RNA polymerase enzyme, buffer agents, and nucleotides (NTPs). The resulting RNA polynucleotide can optionally be further modified including, but limited to, addition of a 5' cap structure such as 7-methylguanosine or a related structure, and optionally modifying the 3' end to include a polyadenylate (polyA) tail. The RNA can then be purified using techniques well-known in the field, such as phenol-chloroform extraction.

V.D.4. Delivery Via Lipid Nanoparticle

An important aspect to consider in vaccine vector design is immunity against the vector itself (Riley 2017). This may be in the form of preexisting immunity to the vector itself, such as with certain human adenovirus systems, or in the form of developing immunity to the vector following administration of the vaccine. The latter is an important consideration if multiple administrations of the same vaccine are performed, such as separate priming and boosting doses, or if the same vaccine vector system is to be used to deliver different neoantigen cassettes.

In the case of alphavirus vectors, the standard delivery method is the previously discussed helper virus system that provides capsid, E1, and E2 proteins in trans to produce infectious viral particles. However, it is important to note that the E1 and E2 proteins are often major targets of neutralizing antibodies (Strauss 1994). Thus, the efficacy of using alphavirus vectors to deliver neoantigens of interest to target cells may be reduced if infectious particles are targeted by neutralizing antibodies.

An alternative to viral particle mediated gene delivery is the use of nanomaterials to deliver expression vectors (Riley 2017). Nanomaterial vehicles, importantly, can be made of non-immunogenic materials and generally avoid eliciting immunity to the delivery vector itself. These materials can include, but are not limited to, lipids, inorganic nanomaterials, and other polymeric materials. Lipids can be cationic, anionic, or neutral. The materials can be synthetic or naturally derived, and in some instances biodegradable. Lipids can include fats, cholesterol, phospholipids, lipid conjugates including, but not limited to, polyethyleneglycol (PEG) conjugates (PEGylated lipids), waxes, oils, glycerides, and fat soulable vitamins.

Lipid nanoparticles (LNPs) are an attractive delivery system due to the amphiphilic nature of lipids enabling formation of membranes and vesicle like structures (Riley 2017). In general, these vesicles deliver the expression vector by absorbing into the membrane of target cells and releasing nucleic acid into the cytosol. In addition, LNPs can be further modified or functionalized to facilitate targeting of specific cell types. Another consideration in LNP design is the balance between targeting efficiency and cytotoxicity. Lipid compositions generally include defined mixtures of cationic, neutral, anionic, and amphipathic lipids. In some instances, specific lipids are included to prevent LNP aggregation, prevent lipid oxidation, or provide functional chemical groups that facilitate attachment of additional moieties. Lipid composition can influence overall LNP size and stability. In an example, the lipid composition comprises dilinoleylmethyl-4-dimethylaminobutyrate (MC3) or MC3-like molecules. MC3 and MC3-like lipid compositions can be formulated to include one or more other lipids, such as a PEG or PEG-conjugated lipid, a sterol, or neutral lipids.

Nucleic-acid vectors, such as expression vectors, exposed directly to serum can have several undesirable consequences, including degradation of the nucleic acid by serum nucleases or off-target stimulation of the immune system by the free nucleic acids. Therefore, encapsulation of the alphavirus vector can be used to avoid degradation, while also avoiding potential off-target affects. In certain examples, an alphavirus vector is fully encapsulated within the delivery vehicle, such as within the aqueous interior of an LNP. Encapsulation of the alphavirus vector within an LNP can be carried out by techniques well-known to those skilled in the art, such as microfluidic mixing and droplet generation carried out on a microfluidic droplet generating device. Such devices include, but are not limited to, standard T-junction devices or flow-focusing devices. In an example, the desired lipid formulation, such as MC3 or MC3-like containing compositions, is provided to the droplet generating device in parallel with the alphavirus delivery vector and other desired agents, such that the delivery vector and desired agents are fully encapsulated within the interior of the MC3 or MC3-like based LNP. In an example, the droplet generating device can control the size range and size distribution of the LNPs produced. For example, the LNP can have a size ranging from 1 to 1000 nanometers in diameter, e.g., 1, 10, 50, 100, 500, or 1000 nanometers. Following droplet generation, the delivery vehicles encapsulating the expression vectors can be further treated or modified to prepare them for administration.

V.E. Chimpanzee Adenovirus (ChAd)

V.E.1. Viral Delivery with Chimpanzee Adenovirus

Vaccine compositions for delivery of one or more neoantigens (e.g., via a neoantigen cassette) can be created by providing adenovirus nucleotide sequences of chimpanzee origin, a variety of novel vectors, and cell lines expressing chimpanzee adenovirus genes. A nucleotide sequence of a chimpanzee C68 adenovirus (also referred to herein as ChAdV68) can be used in a vaccine composition for neoantigen delivery (See SEQ ID NO: 1). Use of C68 adenovirus derived vectors is described in further detail in U.S. Pat. No. 6,083,716, which is herein incorporated by reference in its entirety, for all purposes.

In a further aspect, provided herein is a recombinant adenovirus comprising the DNA sequence of a chimpanzee adenovirus such as C68 and a neoantigen cassette operatively linked to regulatory sequences directing its expression. The recombinant virus is capable of infecting a mammalian, preferably a human, cell and capable of expressing the neoantigen cassette product in the cell. In this vector, the native chimpanzee E1 gene, and/or E3 gene, and/or E4 gene can be deleted. A neoantigen cassette can be inserted into any of these sites of gene deletion. The neoantigen cassette can include a neoantigen against which a primed immune response is desired.

In another aspect, provided herein is a mammalian cell infected with a chimpanzee adenovirus such as C68.

In still a further aspect, a novel mammalian cell line is provided which expresses a chimpanzee adenovirus gene (e.g., from C68) or functional fragment thereof.

In still a further aspect, provided herein is a method for delivering a neoantigen cassette into a mammalian cell comprising the step of introducing into the cell an effective amount of a chimpanzee adenovirus, such as C68, that has been engineered to express the neoantigen cassette.

Still another aspect provides a method for eliciting an immune response in a mammalian host to treat cancer. The method can comprise the step of administering to the host an effective amount of a recombinant chimpanzee adenovirus, such as C68, comprising a neoantigen cassette that encodes one or more neoantigens from the tumor against which the immune response is targeted.

Also disclosed is a non-simian mammalian cell that expresses a chimpanzee adenovirus gene obtained from the sequence of SEQ ID NO: 1. The gene can be selected from the group consisting of the adenovirus E1A, E1B, E2A, E2B, E3, E4, L1, L2, L3, L4 and L5 of SEQ ID NO: 1.

Also disclosed is a nucleic acid molecule comprising a chimpanzee adenovirus DNA sequence comprising a gene obtained from the sequence of SEQ ID NO: 1. The gene can be selected from the group consisting of said chimpanzee adenovirus E1A, E1B, E2A, E2B, E3, E4, L1, L2, L3, L4 and L5 genes of SEQ ID NO: 1. In some aspects the nucleic acid molecule comprises SEQ ID NO: 1. In some aspects the nucleic acid molecule comprises the sequence of SEQ ID NO: 1, lacking at least one gene selected from the group consisting of E1A, E1B, E2A, E2B, E3, E4, L1, L2, L3, L4 and L5 genes of SEQ ID NO: 1.

Also disclosed is a vector comprising a chimpanzee adenovirus DNA sequence obtained from SEQ ID NO: 1 and a neoantigen cassette operatively linked to one or more regulatory sequences which direct expression of the cassette in a heterologous host cell, optionally wherein the chimpanzee adenovirus DNA sequence comprises at least the cis-elements necessary for replication and virion encapsidation, the cis-elements flanking the neoantigen cassette and regulatory sequences. In some aspects, the chimpanzee adenovirus DNA sequence comprises a gene selected from the group consisting of E1A, E1B, E2A, E2B, E3, E4, L1, L2, L3, L4 and L5 gene sequences of SEQ ID NO: 1. In some aspects the vector can lack the E1A and/or E1B gene.

Also disclosed herein is a host cell transfected with a vector disclosed herein such as a C68 vector engineered to expression a neoantigen cassette. Also disclosed herein is a human cell that expresses a selected gene introduced therein through introduction of a vector disclosed herein into the cell.

Also disclosed herein is a method for delivering a neoantigen cassette to a mammalian cell comprising introducing into said cell an effective amount of a vector disclosed herein such as a C68 vector engineered to expression the neoantigen cassette.

Also disclosed herein is a method for producing a neoantigen comprising introducing a vector disclosed herein into a mammalian cell, culturing the cell under suitable conditions and producing the neoantigen.

V.E.2. E1-Expressing Complementation Cell Lines

To generate recombinant chimpanzee adenoviruses (Ad) deleted in any of the genes described herein, the function of the deleted gene region, if essential to the replication and infectivity of the virus, can be supplied to the recombinant virus by a helper virus or cell line, i.e., a complementation or packaging cell line. For example, to generate a replication-defective chimpanzee adenovirus vector, a cell line can be used which expresses the E1 gene products of the human or chimpanzee adenovirus; such a cell line can include HEK293 or variants thereof. The protocol for the generation of the cell lines expressing the chimpanzee E1 gene products (Examples 3 and 4 of U.S. Pat. No. 6,083,716) can be followed to generate a cell line which expresses any selected chimpanzee adenovirus gene.

An AAV augmentation assay can be used to identify a chimpanzee adenovirus E1-expressing cell line. This assay is useful to identify E1 function in cell lines made by using the E1 genes of other uncharacterized adenoviruses, e.g., from other species. That assay is described in Example 4B of U.S. Pat. No. 6,083,716.

A selected chimpanzee adenovirus gene, e.g., E1, can be under the transcriptional control of a promoter for expression in a selected parent cell line. Inducible or constitutive promoters can be employed for this purpose. Among inducible promoters are included the sheep metallothionine promoter, inducible by zinc, or the mouse mammary tumor virus (MMTV) promoter, inducible by a glucocorticoid, particularly, dexamethasone. Other inducible promoters, such as those identified in International patent application WO95/13392, incorporated by reference herein can also be used in the production of packaging cell lines. Constitutive promoters in control of the expression of the chimpanzee adenovirus gene can be employed also.

A parent cell can be selected for the generation of a novel cell line expressing any desired C68 gene. Without limitation, such a parent cell line can be HeLa [ATCC Accession No. CCL 2], A549 [ATCC Accession No. CCL 185], KB [CCL 17], Detroit [e.g., Detroit 510, CCL 72] and WI-38 [CCL 75] cells. Other suitable parent cell lines can be obtained from other sources. Parent cell lines can include CHO, HEK293 or variants thereof, 911, HeLa, A549, LP-293, PER.C6, or AE1-2a.

An E1-expressing cell line can be useful in the generation of recombinant chimpanzee adenovirus E1 deleted vectors. Cell lines constructed using essentially the same procedures that express one or more other chimpanzee adenoviral gene products are useful in the generation of recombinant chimpanzee adenovirus vectors deleted in the genes that encode those products. Further, cell lines which express other human Ad E1 gene products are also useful in generating chimpanzee recombinant Ads.

V.E.3. Recombinant Viral Particles as Vectors

The compositions disclosed herein can comprise viral vectors, that deliver at least one neoantigen to cells. Such vectors comprise a chimpanzee adenovirus DNA sequence such as C68 and a neoantigen cassette operatively linked to regulatory sequences which direct expression of the cassette. The C68 vector is capable of expressing the cassette in an infected mammalian cell. The C68 vector can be functionally deleted in one or more viral genes. A neoantigen cassette comprises at least one neoantigen under the control of one or more regulatory sequences such as a promoter. Optional helper viruses and/or packaging cell lines can supply to the chimpanzee viral vector any necessary products of deleted adenoviral genes.

The term "functionally deleted" means that a sufficient amount of the gene region is removed or otherwise altered, e.g., by mutation or modification, so that the gene region is no longer capable of producing one or more functional products of gene expression. Mutations or modifications that can result in functional deletions include, but are not limited to, nonsense mutations such as introduction of premature stop codons and removal of canonical and non-canonical start codons, mutations that alter mRNA splicing or other transcriptional processing, or combinations thereof. If desired, the entire gene region can be removed.

Modifications of the nucleic acid sequences forming the vectors disclosed herein, including sequence deletions, insertions, and other mutations may be generated using standard molecular biological techniques and are within the scope of this invention.

V.E.4. Construction of the Viral Plasmid Vector

The chimpanzee adenovirus C68 vectors useful in this invention include recombinant, defective adenoviruses, that is, chimpanzee adenovirus sequences functionally deleted in the E1a or E1b genes, and optionally bearing other mutations, e.g., temperature-sensitive mutations or deletions in other genes. It is anticipated that these chimpanzee sequences are also useful in forming hybrid vectors from other adenovirus and/or adeno-associated virus sequences. Homologous adenovirus vectors prepared from human adenoviruses are described in the published literature [see, for example, Kozarsky I and II, cited above, and references cited therein, U.S. Pat. No. 5,240,846].

In the construction of useful chimpanzee adenovirus C68 vectors for delivery of a neoantigen cassette to a human (or other mammalian) cell, a range of adenovirus nucleic acid sequences can be employed in the vectors. A vector comprising minimal chimpanzee C68 adenovirus sequences can be used in conjunction with a helper virus to produce an infectious recombinant virus particle. The helper virus provides essential gene products required for viral infectivity and propagation of the minimal chimpanzee adenoviral vector. When only one or more selected deletions of chimpanzee adenovirus genes are made in an otherwise functional viral vector, the deleted gene products can be supplied in the viral vector production process by propagating the virus in a selected packaging cell line that provides the deleted gene functions in trans.

V.E.5. Recombinant Minimal Adenovirus

A minimal chimpanzee Ad C68 virus is a viral particle containing just the adenovirus cis-elements necessary for replication and virion encapsidation. That is, the vector contains the cis-acting 5' and 3' inverted terminal repeat (ITR) sequences of the adenoviruses (which function as origins of replication) and the native 5' packaging/enhancer domains (that contain sequences necessary for packaging linear Ad genomes and enhancer elements for the E1 promoter). See, for example, the techniques described for preparation of a "minimal" human Ad vector in International Patent Application WO96/13597 and incorporated herein by reference.

V.E.6. Other Defective Adenoviruses

Recombinant, replication-deficient adenoviruses can also contain more than the minimal chimpanzee adenovirus sequences. These other Ad vectors can be characterized by deletions of various portions of gene regions of the virus, and infectious virus particles formed by the optional use of helper viruses and/or packaging cell lines.

As one example, suitable vectors may be formed by deleting all or a sufficient portion of the C68 adenoviral immediate early gene Ela and delayed early gene E1b, so as to eliminate their normal biological functions. Replication-defective E1-deleted viruses are capable of replicating and producing infectious virus when grown on a chimpanzee adenovirus-transformed, complementation cell line containing functional adenovirus E1a and E1b genes which provide the corresponding gene products in trans. Based on the homologies to known adenovirus sequences, it is anticipated that, as is true for the human recombinant E1-deleted adenoviruses of the art, the resulting recombinant chimpanzee adenovirus is capable of infecting many cell types and can express neoantigen(s), but cannot replicate in most cells that do not carry the chimpanzee E1 region DNA unless the cell is infected at a very high multiplicity of infection.

As another example, all or a portion of the C68 adenovirus delayed early gene E3 can be eliminated from the chimpanzee adenovirus sequence which forms a part of the recombinant virus.

Chimpanzee adenovirus C68 vectors can also be constructed having a deletion of the E4 gene. Still another vector can contain a deletion in the delayed early gene E2a.

Deletions can also be made in any of the late genes L1 through L5 of the chimpanzee C68 adenovirus genome. Similarly, deletions in the intermediate genes IX and IVa2 can be useful for some purposes. Other deletions may be made in the other structural or non-structural adenovirus genes.

The above discussed deletions can be used individually, i.e., an adenovirus sequence can contain deletions of E1 only. Alternatively, deletions of entire genes or portions thereof effective to destroy or reduce their biological activity can be used in any combination. For example, in one exemplary vector, the adenovirus C68 sequence can have deletions of the E1 genes and the E4 gene, or of the E1, E2a and E3 genes, or of the E1 and E3 genes, or of E1, E2a and E4 genes, with or without deletion of E3, and so on. As discussed above, such deletions can be used in combination with other mutations, such as temperature-sensitive mutations, to achieve a desired result.

The cassette comprising neoantigen(s) be inserted optionally into any deleted region of the chimpanzee C68 Ad virus. Alternatively, the cassette can be inserted into an existing gene region to disrupt the function of that region, if desired.

V.E.7. Helper Viruses

Depending upon the chimpanzee adenovirus gene content of the viral vectors employed to carry the neoantigen cassette, a helper adenovirus or non-replicating virus fragment can be used to provide sufficient chimpanzee adenovirus gene sequences to produce an infective recombinant viral particle containing the cassette.

Useful helper viruses contain selected adenovirus gene sequences not present in the adenovirus vector construct and/or not expressed by the packaging cell line in which the vector is transfected. A helper virus can be replication-defective and contain a variety of adenovirus genes in addition to the sequences described above. The helper virus can be used in combination with the E1-expressing cell lines described herein.

For C68, the "helper" virus can be a fragment formed by clipping the C terminal end of the C68 genome with SspI, which removes about 1300 bp from the left end of the virus. This clipped virus is then co-transfected into an E1-expressing cell line with the plasmid DNA, thereby forming the recombinant virus by homologous recombination with the C68 sequences in the plasmid.

Helper viruses can also be formed into poly-cation conjugates as described in Wu et al, J. Biol. Chem., 264:16985-16987 (1989); K. J. Fisher and J. M. Wilson, Biochem. J., 299:49 (Apr. 1, 1994). Helper virus can optionally contain a reporter gene. A number of such reporter genes are known to the art. The presence of a reporter gene on the helper virus which is different from the neoantigen cassette on the adenovirus vector allows both the Ad vector and the helper virus to be independently monitored. This second reporter is used to enable separation between the resulting recombinant virus and the helper virus upon purification.

V.E.8. Assembly of Viral Particle and Infection of a Cell Line

Assembly of the selected DNA sequences of the adenovirus, the neoantigen cassette, and other vector elements into various intermediate plasmids and shuttle vectors, and the use of the plasmids and vectors to produce a recombinant viral particle can all be achieved using conventional techniques. Such techniques include conventional cloning techniques of cDNA, in vitro recombination techniques (e.g., Gibson assembly), use of overlapping oligonucleotide sequences of the adenovirus genomes, polymerase chain reaction, and any suitable method which provides the desired nucleotide sequence. Standard transfection and co-transfection techniques are employed, e.g., CaPO4 precipitation techniques or liposome-mediated transfection methods such as lipofectamine. Other conventional methods employed include homologous recombination of the viral genomes, plaquing of viruses in agar overlay, methods of measuring signal generation, and the like.

For example, following the construction and assembly of the desired neoantigen cassette-containing viral vector, the vector can be transfected in vitro in the presence of a helper virus into the packaging cell line. Homologous recombination occurs between the helper and the vector sequences, which permits the adenovirus-neoantigen sequences in the vector to be replicated and packaged into virion capsids, resulting in the recombinant viral vector particles.

The resulting recombinant chimpanzee C68 adenoviruses are useful in transferring a neoantigen cassette to a selected cell. In in vivo experiments with the recombinant virus grown in the packaging cell lines, the E1-deleted recombinant chimpanzee adenovirus demonstrates utility in transferring a cassette to a non-chimpanzee, preferably a human, cell.

V.E.9. Use of the Recombinant Virus Vectors

The resulting recombinant chimpanzee C68 adenovirus containing the neoantigen cassette (produced by cooperation of the adenovirus vector and helper virus or adenoviral vector and packaging cell line, as described above) thus provides an efficient gene transfer vehicle which can deliver neoantigen(s) to a subject in vivo or ex vivo.

The above-described recombinant vectors are administered to humans according to published methods for gene therapy. A chimpanzee viral vector bearing a neoantigen cassette can be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The chimpanzee adenoviral vectors are administered in sufficient amounts to transduce the human cells and to provide sufficient levels of neoantigen transfer and expression to provide a therapeutic benefit without undue adverse or with medically acceptable physiological effects, which can be determined by those skilled in the medical arts.

Conventional and pharmaceutically acceptable routes of administration include, but are not limited to, direct delivery to the liver, intranasal, intravenous, intramuscular, subcutaneous, intradermal, oral and other parental routes of administration. Routes of administration may be combined, if desired.

Dosages of the viral vector will depend primarily on factors such as the condition being treated, the age, weight and health of the patient, and may thus vary among patients. The dosage will be adjusted to balance the therapeutic benefit against any side effects and such dosages may vary depending upon the therapeutic application for which the recombinant vector is employed. The levels of expression of neoantigen(s) can be monitored to determine the frequency of dosage administration.

Recombinant, replication defective adenoviruses can be administered in a "pharmaceutically effective amount", that is, an amount of recombinant adenovirus that is effective in a route of administration to transfect the desired cells and provide sufficient levels of expression of the selected gene to provide a vaccinal benefit, i.e., some measurable level of protective immunity. C68 vectors comprising a neoantigen cassette can be co-administered with adjuvant. Adjuvant can be separate from the vector (e.g., alum) or encoded within the vector, in particular if the adjuvant is a protein. Adjuvants are well known in the art.

Conventional and pharmaceutically acceptable routes of administration include, but are not limited to, intranasal, intramuscular, intratracheal, subcutaneous, intradermal, rectal, oral and other parental routes of administration. Routes of administration may be combined, if desired, or adjusted depending upon the immunogen or the disease. For example, in prophylaxis of rabies, the subcutaneous, intratracheal and intranasal routes are preferred. The route of administration primarily will depend on the nature of the disease being treated.

The levels of immunity to neoantigen(s) can be monitored to determine the need, if any, for boosters. Following an assessment of antibody titers in the serum, for example, optional booster immunizations may be desired

VI. Therapeutic and Manufacturing Methods

Also provided is a method of inducing a tumor specific immune response in a subject, vaccinating against a tumor, treating and or alleviating a symptom of cancer in a subject by administering to the subject one or more neoantigens such as a plurality of neoantigens identified using methods disclosed herein.

In some aspects, a subject has been diagnosed with cancer or is at risk of developing cancer. A subject can be a human, dog, cat, horse or any animal in which a tumor specific immune response is desired. A tumor can be any solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas.

A neoantigen can be administered in an amount sufficient to induce a CTL response.

A neoantigen can be administered alone or in combination with other therapeutic agents. The therapeutic agent is for example, a chemotherapeutic agent, radiation, or immunotherapy. Any suitable therapeutic treatment for a particular cancer can be administered.

In addition, a subject can be further administered an anti-immunosuppressive/immunostimulatory agent such as a checkpoint inhibitor. For example, the subject can be further administered an anti-CTLA antibody or anti-PD-1 or anti-PD-L1. Blockade of CTLA-4 or PD-L1 by antibodies can enhance the immune response to cancerous cells in the patient. In particular, CTLA-4 blockade has been shown effective when following a vaccination protocol.

The optimum amount of each neoantigen to be included in a vaccine composition and the optimum dosing regimen can be determined. For example, a neoantigen or its variant can be prepared for intravenous (i.v.) injection, sub-cutaneous (s.c.) injection, intradermal (i.d.) injection, intraperitoneal (i.p.) injection, intramuscular (i.m.) injection. Methods of injection include s.c., i.d., i.p., i.m., and i.v. Methods of DNA or RNA injection include i.d., i.m., s.c., i.p. and i.v. Other methods of administration of the vaccine composition are known to those skilled in the art.

A vaccine can be compiled so that the selection, number and/or amount of neoantigens present in the composition is/are tissue, cancer, and/or patient-specific. For instance, the exact selection of peptides can be guided by expression patterns of the parent proteins in a given tissue. The selection can be dependent on the specific type of cancer, the status of the disease, earlier treatment regimens, the immune status of the patient, and, of course, the HLA-haplotype of the patient. Furthermore, a vaccine can contain individualized components, according to personal needs of the particular patient. Examples include varying the selection of neoantigens according to the expression of the neoantigen in the particular patient or adjustments for secondary treatments following a first round or scheme of treatment.

For a composition to be used as a vaccine for cancer, neoantigens with similar normal self-peptides that are expressed in high amounts in normal tissues can be avoided or be present in low amounts in a composition described herein. On the other hand, if it is known that the tumor of a patient expresses high amounts of a certain neoantigen, the respective pharmaceutical composition for treatment of this cancer can be present in high amounts and/or more than one neoantigen specific for this particularly neoantigen or pathway of this neoantigen can be included.

Compositions comprising a neoantigen can be administered to an individual already suffering from cancer. In therapeutic applications, compositions are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use will depend on, e.g., the composition, the manner of administration, the stage and severity of the disease being treated, the weight and general state of health of the patient, and the judgment of the prescribing physician. It should be kept in mind that compositions can generally be employed in serious disease states, that is, life-threatening or potentially life threatening situations, especially when the cancer has metastasized. In such cases, in view of the minimization of extraneous substances and the relative nontoxic nature of a neoantigen, it is possible and can be felt desirable by the treating physician to administer substantial excesses of these compositions.

For therapeutic use, administration can begin at the detection or surgical removal of tumors. This is followed by boosting doses until at least symptoms are substantially abated and for a period thereafter.

The pharmaceutical compositions (e.g., vaccine compositions) for therapeutic treatment are intended for parenteral, topical, nasal, oral or local administration. A pharmaceutical compositions can be administered parenterally, e.g., intravenously, subcutaneously, intradermally, or intramuscularly. The compositions can be administered at the site of surgical exiscion to induce a local immune response to the tumor. Disclosed herein are compositions for parenteral administration which comprise a solution of the neoantigen and vaccine compositions are dissolved or suspended in an acceptable carrier, e.g., an aqueous carrier. A variety of aqueous carriers can be used, e.g., water, buffered water, 0.9% saline, 0.3% glycine, hyaluronic acid and the like. These compositions can be sterilized by conventional, well known sterilization techniques, or can be sterile filtered. The resulting aqueous solutions can be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Neoantigens can also be administered via liposomes, which target them to a particular cells tissue, such as lymphoid tissue. Liposomes are also useful in increasing half-life. Liposomes include emulsions, foams, micelles, insoluble monolayers, liquid crystals, phospholipid dispersions, lamellar layers and the like. In these preparations the neoantigen to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired neoantigen can be directed to the site of lymphoid cells, where the liposomes then deliver the selected therapeutic/immunogenic compositions. Liposomes can be formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9; 467 (1980), U.S. Pat. Nos. 4,235,871, 4,501,728, 4,501,728, 4,837,028, and 5,019,369.

For targeting to the immune cells, a ligand to be incorporated into the liposome can include, e.g., antibodies or fragments thereof specific for cell surface determinants of the desired immune system cells. A liposome suspension can be administered intravenously, locally, topically, etc. in a dose which varies according to, inter alia, the manner of administration, the peptide being delivered, and the stage of the disease being treated.

For therapeutic or immunization purposes, nucleic acids encoding a peptide and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Approaches for delivering nucleic acid sequences can include viral vectors, mRNA vectors, and DNA vectors with or without electroporation.

The nucleic acids can also be delivered complexed to cationic compounds, such as cationic lipids. Lipid-mediated gene delivery methods are described, for instance, in 9618372WOAWO 96/18372; 9324640WOAWO 93/24640; Mannino & Gould-Fogerite, BioTechniques 6(7): 682-691 (1988); U.S. Pat. No. 5,279,833 Rose U.S. Pat. Nos. 5,279,833; 9106309WOAWO 91/06309; and Felgner et al., Proc. Natl. Acad. Sci. USA 84: 7413-7414 (1987).

Neoantigens can also be included in viral vector-based vaccine platforms, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuma et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In Vivo Gene Delivery, *J. Virol.* (1998) 72 (12): 9873-9880). Dependent on the packaging capacity of the above mentioned viral vector-based vaccine platforms, this approach can deliver one or more nucleotide sequences that encode one or more neoantigen peptides. The sequences may be flanked by non-mutated sequences, may be separated by linkers or may be preceded with one or more sequences targeting a subcellular compartment (See, e.g., Gros et al., Prospective identification of neoantigen-specific lymphocytes in the peripheral blood of melanoma patients, *Nat Med.* (2016) 22 (4):433-8, Stronen et al., Targeting of cancer neoantigens with donor-derived T cell receptor repertoires, *Science.* (2016) 352 (6291):1337-41, Lu et al., Efficient identification of mutated cancer antigens recognized by T cells associated with durable tumor regressions, *Clin Cancer Res.* (2014) 20(13):3401-10). Upon introduction into a host, infected cells express the neoantigens, and thereby elicit a host immune (e.g., CTL) response against the peptide(s). Vaccinia vectors and methods useful in immunization protocols are described in, e.g., U.S. Pat. No. 4,722,848. Another vector is BCG (Bacille Calmette Guerin). BCG vectors are described in Stover et al. (*Nature* 351:456-460 (1991)). A wide variety of other vaccine vectors useful for therapeutic administration or immunization of neoantigens, e.g., *Salmonella typhi* vectors, and the like will be apparent to those skilled in the art from the description herein.

A means of administering nucleic acids uses minigene constructs encoding one or multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes can be improved by including synthetic (e.g. poly-alanine) or naturally-occurring flanking sequences adjacent to the CTL epitopes. The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Purified plasmid DNA can be prepared for injection using a variety of formulations. The simplest of these is reconstitution of lyophilized DNA in sterile phosphate-buffer saline (PBS). A variety of methods have been described, and new techniques can become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Also disclosed is a method of manufacturing a tumor vaccine, comprising performing the steps of a method disclosed herein; and producing a tumor vaccine comprising a plurality of neoantigens or a subset of the plurality of neoantigens.

Neoantigens disclosed herein can be manufactured using methods known in the art. For example, a method of producing a neoantigen or a vector (e.g., a vector including at least one sequence encoding one or more neoantigens) disclosed herein can include culturing a host cell under conditions suitable for expressing the neoantigen or vector wherein the host cell comprises at least one polynucleotide encoding the neoantigen or vector, and purifying the neoantigen or vector. Standard purification methods include chromatographic techniques, electrophoretic, immunological, precipitation, dialysis, filtration, concentration, and chromatofocusing techniques.

Host cells can include a Chinese Hamster Ovary (CHO) cell, NSO cell, yeast, or a HEK293 cell. Host cells can be transformed with one or more polynucleotides comprising at least one nucleic acid sequence that encodes a neoantigen or vector disclosed herein, optionally wherein the isolated polynucleotide further comprises a promoter sequence operably linked to the at least one nucleic acid sequence that encodes the neoantigen or vector. In certain embodiments the isolated polynucleotide can be cDNA.

VII. Neoantigen Use and Administration

A vaccination protocol can be used to dose a subject with one or more neoantigens. A priming vaccine and a boosting vaccine can be used to dose the subject. The priming vaccine can be based on C68 (e.g., the sequences shown in SEQ ID NO:1 or 2) or srRNA (e.g., the sequences shown in SEQ ID NO:3 or 4) and the boosting vaccine can be based on C68 (e.g., the sequences shown in SEQ ID NO:1 or 2) or srRNA (e.g., the sequences shown in SEQ ID NO:3 or 4). Each vector typically includes a cassette that includes neoantigens. Cassettes can include about 20 neoantigens, separated by spacers such as the natural sequence that normally surrounds each antigen or other non-natural spacer sequences such as AAY. Cassettes can also include MHCII antigens such a tetanus toxoid antigen and PADRE antigen, which can be considered universal class II antigens. Cassettes can also include a targeting sequence such as a ubiquitin targeting sequence. In addition, each vaccine dose can be administered to the subject in conjunction with (e.g., concurrently, before, or after) a checkpoint inhibitor (CPI). CPI's can include those that inhibit CTLA4, PD1, and/or PDL1 such as antibodies or antigen-binding portions thereof. Such antibodies can include tremelimumab or durvalumab.

A priming vaccine can be injected (e.g., intramuscularly) in a subject. Bilateral injections per dose can be used. For example, one or more injections of ChAdV68 (C68) can be used (e.g., total dose $1\times10^{12}$ viral particles); one or more injections of self-replicating RNA (srRNA) at low vaccine dose selected from the range 0.001 to 1 ug RNA, in particular 0.1 or 1 ug can be used; or one or more injections of srRNA at high vaccine dose selected from the range 1 to 100 ug RNA, in particular 10 or 100 ug can be used.

A vaccine boost (boosting vaccine) can be injected (e.g., intramuscularly) after prime vaccination. A boosting vaccine can be administered about every 1, 2, 3, 4, 5, 6, 7, 8, 9, or 10 weeks, e.g., every 4 weeks and/or 8 weeks after the prime. Bilateral injections per dose can be used. For example, one or more injections of ChAdV68 (C68) can be used (e.g., total dose $1\times10^{12}$ viral particles); one or more injections of self-replicating RNA (srRNA) at low vaccine dose selected from the range 0.001 to 1 ug RNA, in particular 0.1 or 1 ug can be used; or one or more injections of srRNA at high vaccine dose selected from the range 1 to 100 ug RNA, in particular 10 or 100 ug can be used.

Anti-CTLA-4 (e.g., tremelimumab) can also be administered to the subject. For example, anti-CTLA4 can be administered subcutaneously near the site of the intramuscular vaccine injection (ChAdV68 prime or srRNA low doses) to ensure drainage into the same lymph node. Tremelimumab is a selective human IgG2 mAb inhibitor of CTLA-4. Target Anti-CTLA-4 (tremelimumab) subcutaneous dose is typically 70-75 mg (in particular 75 mg) with a dose range of, e.g., 1-100 mg or 5-420 mg.

In certain instances an anti-PD-L1 antibody can be used such as durvalumab (MEDI 4736). Durvalumab is a selective, high affinity human IgG1 mAb that blocks PD-L1 binding to PD-1 and CD80. Durvalumab is generally administered at 20 mg/kg i.v. every 4 weeks.

Immune monitoring can be performed before, during, and/or after vaccine administration. Such monitoring can inform safety and efficacy, among other parameters.

To perform immune monitoring, PBMCs are commonly used. PBMCs can be isolated before prime vaccination, and after prime vaccination (e.g. 4 weeks and 8 weeks). PBMCs can be harvested just prior to boost vaccinations and after each boost vaccination (e.g. 4 weeks and 8 weeks).

T cell responses can be assessed as part of an immune monitoring protocol. T cell responses can be measured using one or more methods known in the art such as ELISpot, intracellular cytokine staining, cytokine secretion and cell surface capture, T cell proliferation, MHC multimer staining, or by cytotoxicity assay. T cell responses to epitopes encoded in vaccines can be monitored from PBMCs by measuring induction of cytokines, such as IFN-gamma, using an ELISpot assay. Specific CD4 or CD8 T cell responses to epitopes encoded in vaccines can be monitored from PBMCs by measuring induction of cytokines captured intracellularly or extracellularly, such as IFN-gamma, using flow cytometry. Specific CD4 or CD8 T cell responses to epitopes encoded in the vaccines can be monitored from PBMCs by measuring T cell populations expressing T cell receptors specific for epitope/MHC class I complexes using MHC multimer staining. Specific CD4 or CD8 T cell responses to epitopes encoded in the vaccines can be monitored from PBMCs by measuring the ex vivo expansion of T cell populations following 3H-thymidine, bromodeoxyuridine and carboxyfluoresceine-diacetate-succinimidylester (CFSE) incorporation. The antigen recognition capacity and lytic activity of PBMC-derived T cells that are specific for epitopes encoded in vaccines can be assessed functionally by chromium release assay or alternative colorimetric cytotoxicity assays.

VIII. Neoantigen Identification

VII.A. Neoantigen Candidate Identification

Research methods for NGS analysis of tumor and normal exome and transcriptomes have been described and applied in the neoantigen identification space.[6,14,15] The example below considers certain optimizations for greater sensitivity and specificity for neoantigen identification in the clinical setting. These optimizations can be grouped into two areas, those related to laboratory processes and those related to the NGS data analysis.

VII.A.1. Laboratory Process Optimizations

The process improvements presented here address challenges in high-accuracy neoantigen discovery from clinical specimens with low tumor content and small volumes by extending concepts developed for reliable cancer driver gene assessment in targeted cancer panels[16] to the whole-exome and -transcriptome setting necessary for neoantigen identification. Specifically, these improvements include:

1. Targeting deep (>500×) unique average coverage across the tumor exome to detect mutations present at low mutant allele frequency due to either low tumor content or subclonal state.
2. Targeting uniform coverage across the tumor exome, with <5% of bases covered at <100×, so that the fewest possible neoantigens are missed, by, for instance:
   a. Employing DNA-based capture probes with individual probe QC[17]
   b. Including additional baits for poorly covered regions
3. Targeting uniform coverage across the normal exome, where <5% of bases are covered at <20× so that the fewest neoantigens possible remain unclassified for somatic/germline status (and thus not usable as TSNAs)
4. To minimize the total amount of sequencing required, sequence capture probes will be designed for coding regions of genes only, as non-coding RNA cannot give rise to neoantigens. Additional optimizations include:
   a. supplementary probes for HLA genes, which are GC-rich and poorly captured by standard exome sequencing[18]
   b. exclusion of genes predicted to generate few or no candidate neoantigens, due to factors such as insufficient expression, suboptimal digestion by the proteasome, or unusual sequence features.
5. Tumor RNA will likewise be sequenced at high depth (>100M reads) in order to enable variant detection, quantification of gene and splice-variant ("isoform") expression, and fusion detection. RNA from FFPE samples will be extracted using probe-based enrichment[19], with the same or similar probes used to capture exomes in DNA.

VIII.A.2. NGS Data Analysis Optimizations

Improvements in analysis methods address the suboptimal sensitivity and specificity of common research mutation calling approaches, and specifically consider customizations relevant for neoantigen identification in the clinical setting. These include:

1. Using the HG38 reference human genome or a later version for alignment, as it contains multiple MHC regions assemblies better reflective of population polymorphism, in contrast to previous genome releases.
2. Overcoming the limitations of single variant callers[20] by merging results from different programs[5]
   a. Single-nucleotide variants and indels will be detected from tumor DNA, tumor RNA and normal DNA with a suite of tools including: programs based on comparisons of tumor and normal DNA, such as Strelka[21] and Mutect[22]; and programs that incorporate tumor DNA, tumor RNA and normal DNA, such as UNCeqR, which is particularly advantageous in low-purity samples[23].
   b. Indels will be determined with programs that perform local re-assembly, such as Strelka and ABRA[24].
   c. Structural rearrangements will be determined using dedicated tools such as Pindel[25] or Breakseq[26].
3. In order to detect and prevent sample swaps, variant calls from samples for the same patient will be compared at a chosen number of polymorphic sites.
4. Extensive filtering of artefactual calls will be performed, for instance, by:
   a. Removal of variants found in normal DNA, potentially with relaxed detection parameters in cases of low coverage, and with a permissive proximity criterion in case of indels
   b. Removal of variants due to low mapping quality or low base quality[27].
   c. Removal of variants stemming from recurrent sequencing artifacts, even if not observed in the corresponding normal[27]. Examples include variants primarily detected on one strand.
   d. Removal of variants detected in an unrelated set of controls[27]
5. Accurate HLA calling from normal exome using one of seq2HLA[28], ATHLATES[29] or Optitype and also combining exome and RNA sequencing data[28]. Additional potential optimizations include the adoption of a dedicated assay for HLA typing such as long-read DNA sequencing[30], or the adaptation of a method for joining RNA fragments to retain continuity[31].
6. Robust detection of neo-ORFs arising from tumor-specific splice variants will be performed by assembling transcripts from RNA-seq data using CLASS[32], Bayesembler[33], StringTie[34] or a similar program in its reference-guided mode (i.e., using known transcript structures rather than attempting to recreate transcripts in their entirety from each experiment). While Cufflinks[35] is commonly used for this purpose, it frequently produces implausibly large numbers of splice variants, many of them far shorter than the full-length gene, and can fail to recover simple positive controls. Coding sequences and nonsense-mediated decay potential will be determined with tools such as SpliceR[36] and MAMBA[37], with mutant sequences re-introduced.

Gene expression will be determined with a tool such as Cufflinks[35] or Express (Roberts and Pachter, 2013). Wild-type and mutant-specific expression counts and/or relative levels will be determined with tools developed for these purposes, such as ASE[38] or HTSeq[39]. Potential filtering steps include:

a. Removal of candidate neo-ORFs deemed to be insufficiently expressed.

b. Removal of candidate neo-ORFs predicted to trigger non-sense mediated decay (NMD).

7. Candidate neoantigens observed only in RNA (e.g., neoORFs) that cannot directly be verified as tumor-specific will be categorized as likely tumor-specific according to additional parameters, for instance by considering:

a. Presence of supporting tumor DNA-only cis-acting frameshift or splice-site mutations b. Presence of corroborating tumor DNA-only trans-acting mutation in a splicing factor. For instance, in three independently published experiments with R625-mutant SF3B1, the genes exhibiting the most differentially splicing were concordant even though one experiment examined uveal melanoma patients[40], the second a uveal melanoma cell line[41], and the third breast cancer patients[42].

c. For novel splicing isoforms, presence of corroborating "novel" splice-junction reads in the RNASeq data.

d. For novel re-arrangements, presence of corroborating juxta-exon reads in tumor DNA that are absent from normal DNA e. Absence from gene expression compendium such as GTEx[43] (i.e. making germline origin less likely)

8. Complementing the reference genome alignment-based analysis by comparing assembled DNA tumor and normal reads (or k-mers from such reads) directly to avoid alignment and annotation based errors and artifacts. (e.g. for somatic variants arising near germline variants or repeat-context indels)

In samples with poly-adenylated RNA, the presence of viral and microbial RNA in the RNA-seq data will be assessed using RNA CoMPASS[44] or a similar method, toward the identification of additional factors that may predict patient response.

VIII.B. Isolation and Detection of HLA Peptides

Isolation of HLA-peptide molecules was performed using classic immunoprecipitation (IP) methods after lysis and solubilization of the tissue sample (55-58). A clarified lysate was used for HLA specific IP.

Immunoprecipitation was performed using antibodies coupled to beads where the antibody is specific for HLA molecules. For a pan-Class I HLA immunoprecipitation, a pan-Class I CR antibody is used, for Class II HLA-DR, an HLA-DR antibody is used. Antibody is covalently attached to NHS-sepharose beads during overnight incubation. After covalent attachment, the beads were washed and aliquoted for IP. (59, 60) Immunoprecipitations can also be performed with antibodies that are not covalently attached to beads. Typically this is done using sepharose or magnetic beads coated with Protein A and/or Protein G to hold the antibody to the column. Some antibodies that can be used to selectively enrich MHC/peptide complex are listed below.

| Antibody Name | Specificity |
|---|---|
| W6/32 | Class I HLA-A, B, C |
| L243 | Class II - HLA-DR |
| Tu36 | Class II - HLA-DR |
| LN3 | Class II - HLA-DR |
| Tu39 | Class II - HLA-DR, DP, DQ |

The clarified tissue lysate is added to the antibody beads for the immunoprecipitation. After immunoprecipitation, the beads are removed from the lysate and the lysate stored for additional experiments, including additional IPs. The IP beads are washed to remove non-specific binding and the HLA/peptide complex is eluted from the beads using standard techniques. The protein components are removed from the peptides using a molecular weight spin column or C18 fractionation. The resultant peptides are taken to dryness by SpeedVac evaporation and in some instances are stored at −20° C. prior to MS analysis.

Dried peptides are reconstituted in an HPLC buffer suitable for reverse phase chromatography and loaded onto a C-18 microcapillary HPLC column for gradient elution in a Fusion Lumos mass spectrometer (Thermo). MS1 spectra of peptide mass/charge (m/z) were collected in the Orbitrap detector at high resolution followed by MS2 low resolution scans collected in the ion trap detector after HCD fragmentation of the selected ion. Additionally, MS2 spectra can be obtained using either CID or ETD fragmentation methods or any combination of the three techniques to attain greater amino acid coverage of the peptide. MS2 spectra can also be measured with high resolution mass accuracy in the Orbitrap detector.

MS2 spectra from each analysis are searched against a protein database using Comet (61, 62) and the peptide identification are scored using Percolator (63-65). Additional sequencing is performed using PEAKS studio (Bioinformatics Solutions Inc.) and other search engines or sequencing methods can be used including spectral matching and de novo sequencing (97).

Figure 1C:
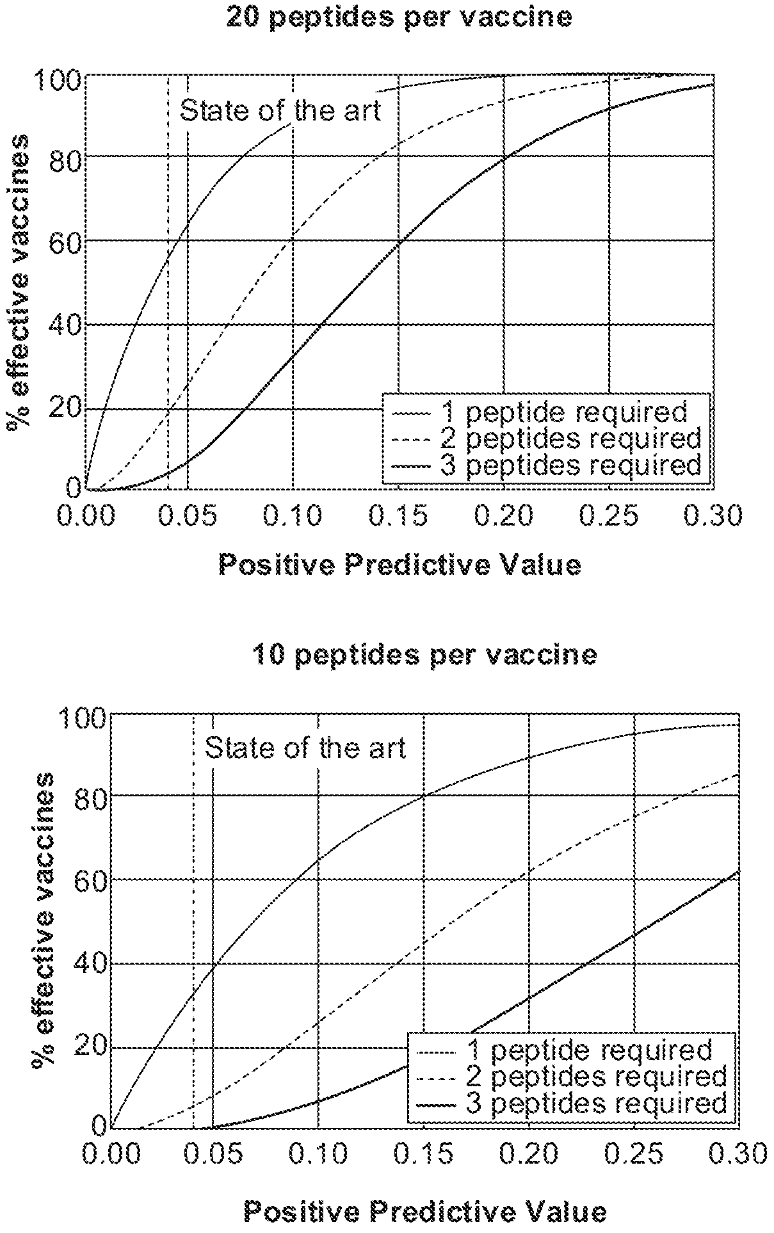
FIG. 1C shows the impact of the neoantigen prediction specificity problem.
Figure 1D:
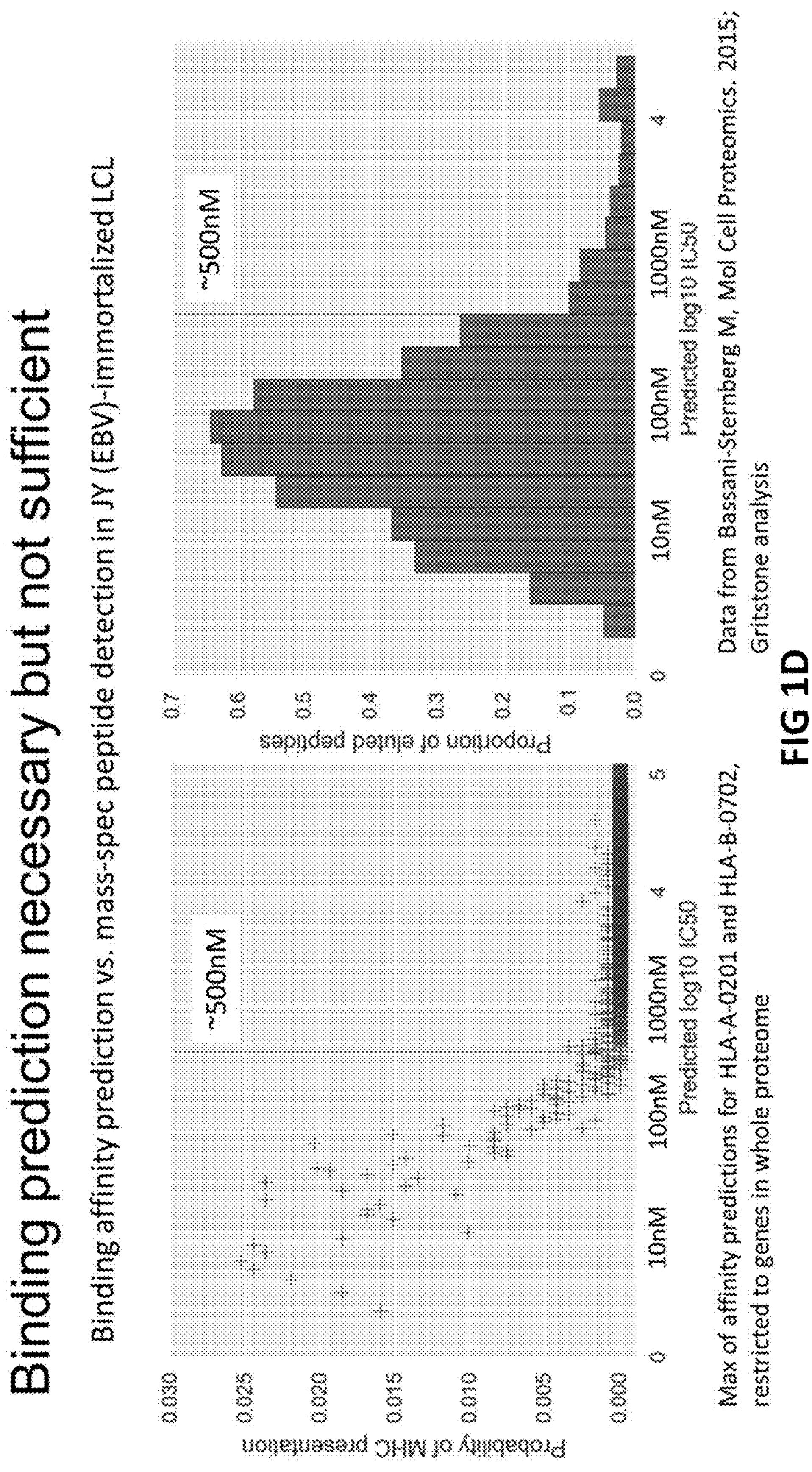
FIG. 1D shows that binding prediction is not sufficient for neoantigen identification.
Figure 1E:
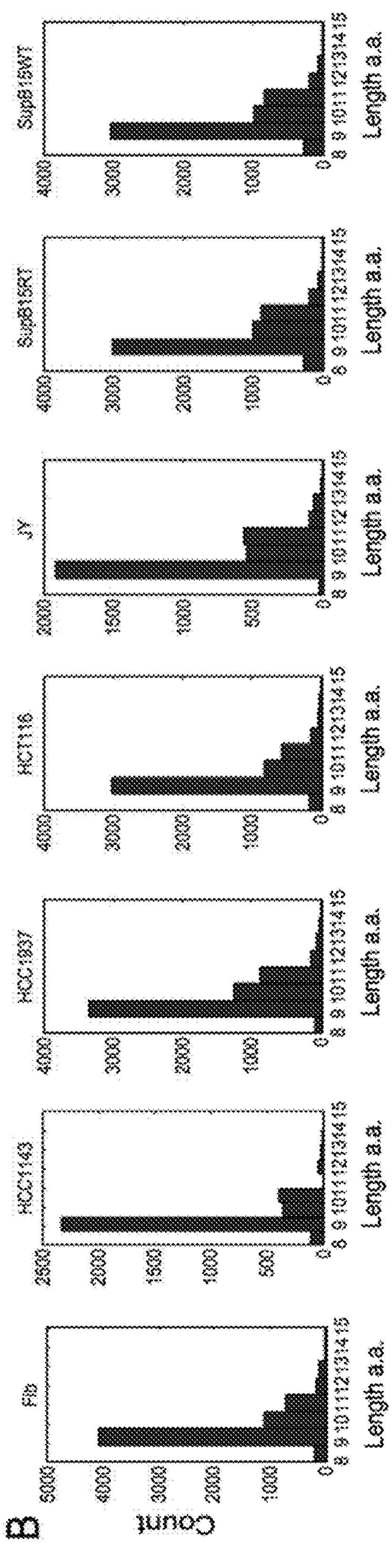
FIG. 1E shows probability of MHC-I presentation as a function of peptide length.
Figure 1F:
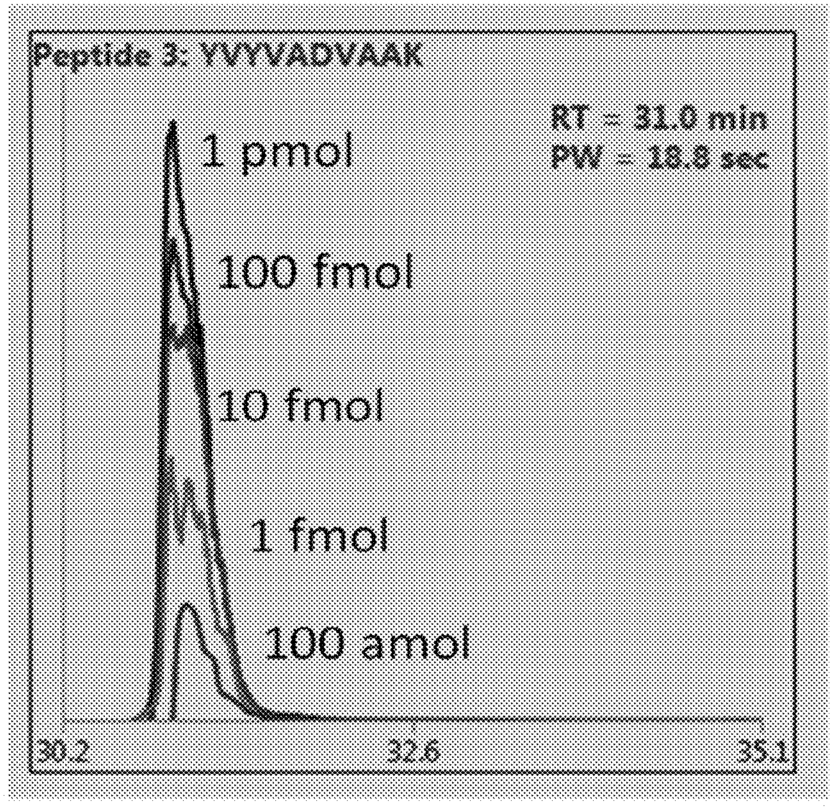
FIG. 1F shows an example peptide spectrum generated from Promega's dynamic range standard. Figure discloses SEQ ID NO: 59.
Figure 1F:
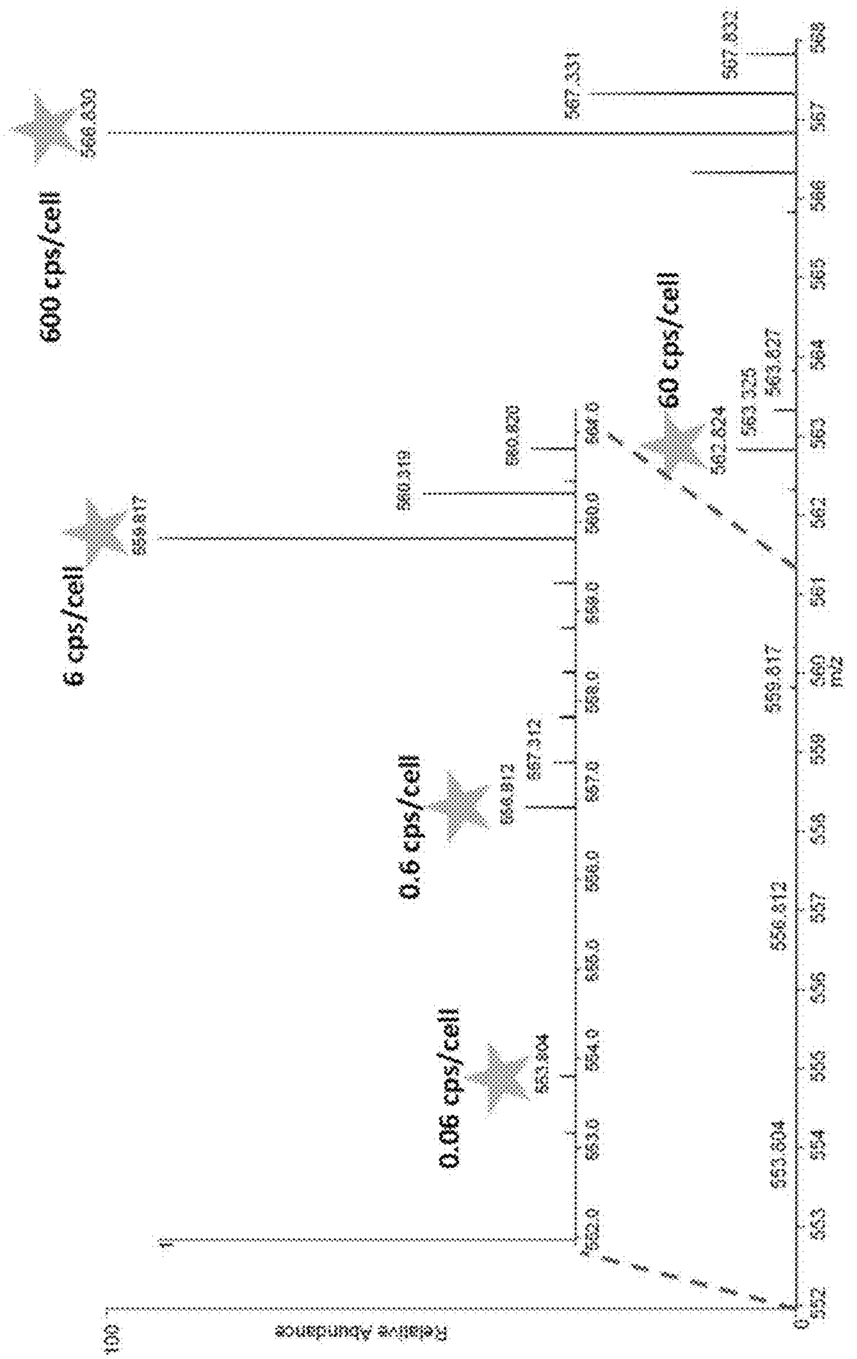
Figure 1G:
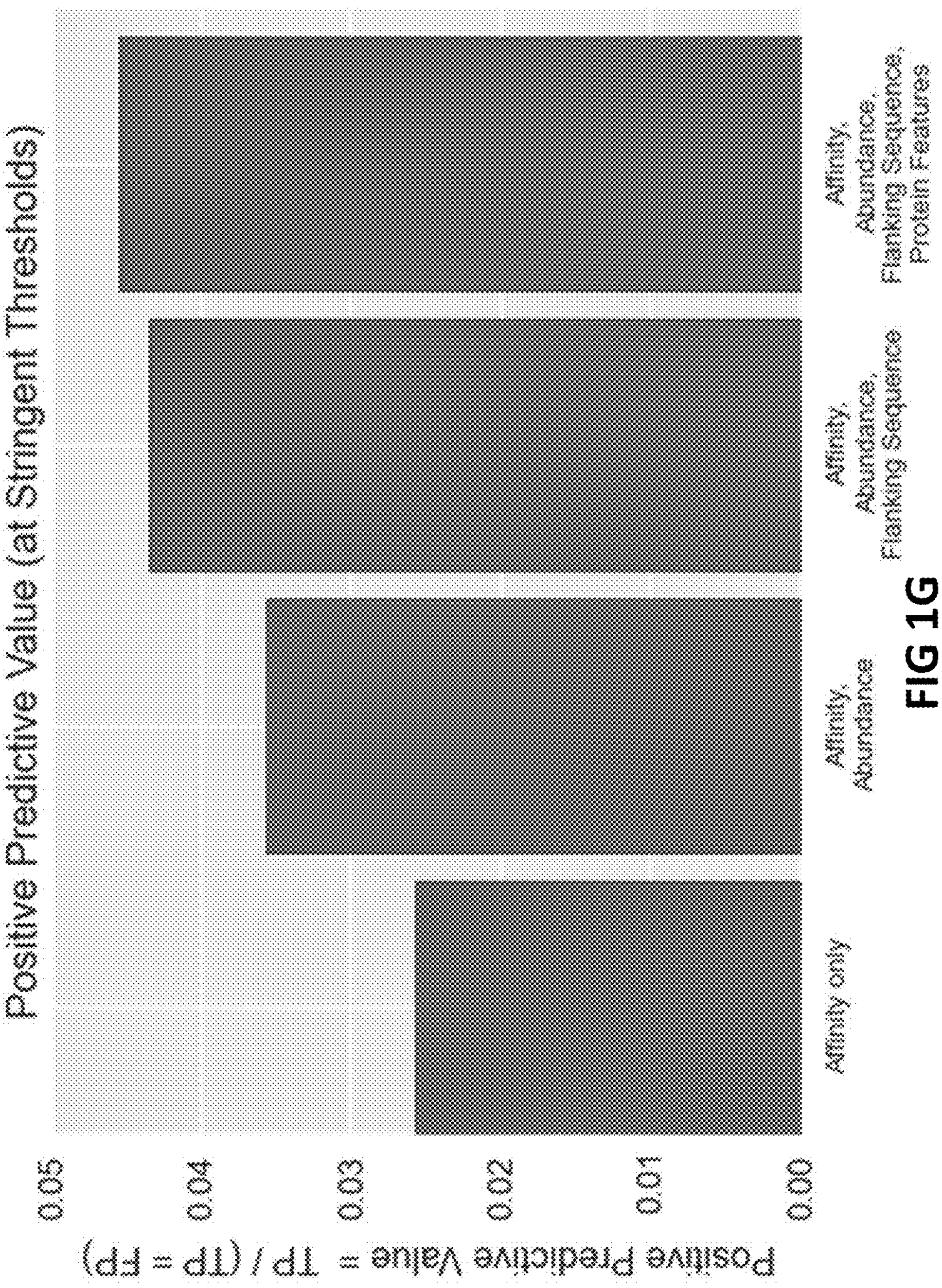
FIG. 1G shows how the addition of features increases the model positive predictive value.

VIII.B.1. MS Limit of Detection Studies in Support of Comprehensive HLA Peptide Sequencing Using the peptide YVYVADVAAK (SEQ ID NO: 59) it was determined what the limits of detection are using different amounts of peptide loaded onto the LC column. The amounts of peptide tested were 1 pmol, 100 fmol, 10 fmol, 1 fmol, and 100 amol. (Table 1) The results are shown in FIG. 1F. These results indicate that the lowest limit of detection (LoD) is in the attomol range ($10^{-18}$), that the dynamic range spans five orders of magnitude, and that the signal to noise appears sufficient for sequencing at low femtomol ranges ($10^{-15}$).

TABLE 1

| Peptide m/z | Loaded on Column | Copies/Cell in 1e9cells |
|---|---|---|
| 566.830 | 1 pmol | 600 |
| 562.823 | 100 fmol | 60 |
| 559.816 | 10 fmol | 6 |
| 556.810 | 1 fmol | 0.6 |
| 553.802 | 100 amol | 0.06 |

IX. Presentation Model

IX.A. System Overview

Figure 2A:
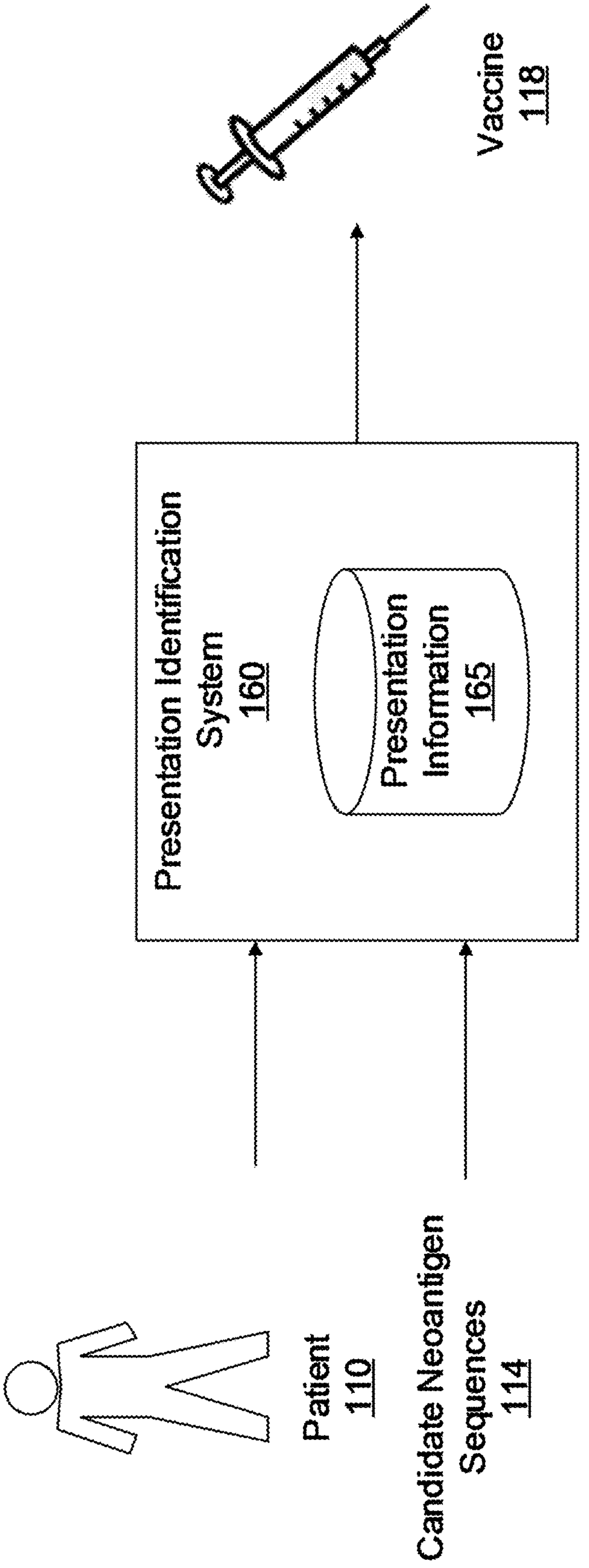
FIG. 2A is an overview of an environment for identifying likelihoods of peptide presentation in patients, in accordance with an embodiment.

FIG. 2A is an overview of an environment 100 for identifying likelihoods of peptide presentation in patients, in accordance with an embodiment. The environment 100 provides context in order to introduce a presentation identification system 160, itself including a presentation information store 165.

The presentation identification system 160 is one or computer models, embodied in a computing system as discussed below with respect to FIG. 14, that receives peptide sequences associated with a set of MHC alleles and determines likelihoods that the peptide sequences will be presented by one or more of the set of associated MHC alleles. The presentation identification system 160 may be applied to both class I and class II MHC alleles. This is useful in a variety of contexts. One specific use case for the presentation identification system 160 is that it is able to receive nucleotide sequences of candidate neoantigens associated with a set of MHC alleles from tumor cells of a patient 110 and determine likelihoods that the candidate neoantigens will be presented by one or more of the associated MHC alleles of the tumor and/or induce immunogenic responses in the immune system of the patient 110. Those candidate neoantigens with high likelihoods as determined by system 160 can be selected for inclusion in a vaccine 118, such an anti-tumor immune response can be elicited from the immune system of the patient 110 providing the tumor cells.

The presentation identification system 160 determines presentation likelihoods through one or more presentation models. Specifically, the presentation models generate likelihoods of whether given peptide sequences will be presented for a set of associated MHC alleles, and are generated based on presentation information stored in store 165. For example, the presentation models may generate likelihoods of whether a peptide sequence "YVYVADVAAK (SEQ ID NO: 59) will be presented for the set of alleles HLA-A*02:01, HLA-A*03:01, HLA-B*07:02, HLA-B*08:03, HLA-C*01:04, HLA-A*06:03, HLA-B*01:04 on the cell surface of the sample. The presentation information 165 contains information on whether peptides bind to different types of MHC alleles such that those peptides are presented by MHC alleles, which in the models is determined depending on positions of amino acids in the peptide sequences. The presentation model can predict whether an unrecognized peptide sequence will be presented in association with an associated set of MHC alleles based on the presentation information 165. As previously mentioned, the presentation models may be applied to both class I and class II MHC alleles.

IX.B. Presentation Information

FIG. 2 illustrates a method of obtaining presentation information, in accordance with an embodiment. The presentation information 165 includes two general categories of information: allele-interacting information and allele-noninteracting information. Allele-interacting information includes information that influence presentation of peptide sequences that are dependent on the type of MHC allele. Allele-noninteracting information includes information that influence presentation of peptide sequences that are independent on the type of MHC allele.

IX.B.1. Allele-Interacting Information

Figure 2B:
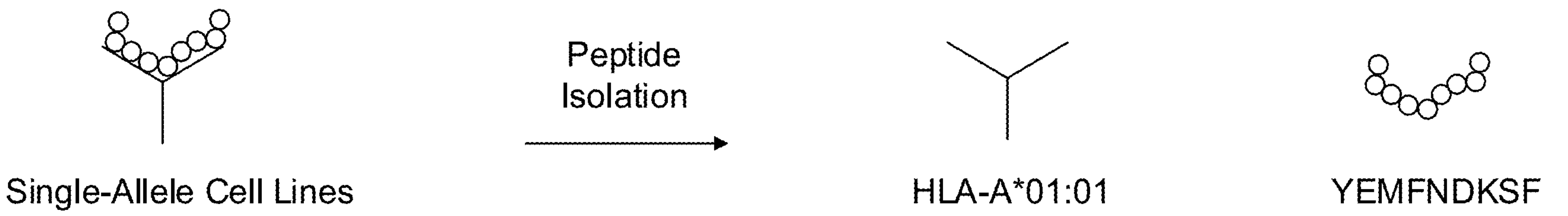
FIG. 2B, FIG. 2C, FIG. 2D, and FIG. 2E illustrate a method of obtaining presentation information, in accordance with an embodiment.
Figure 2C:
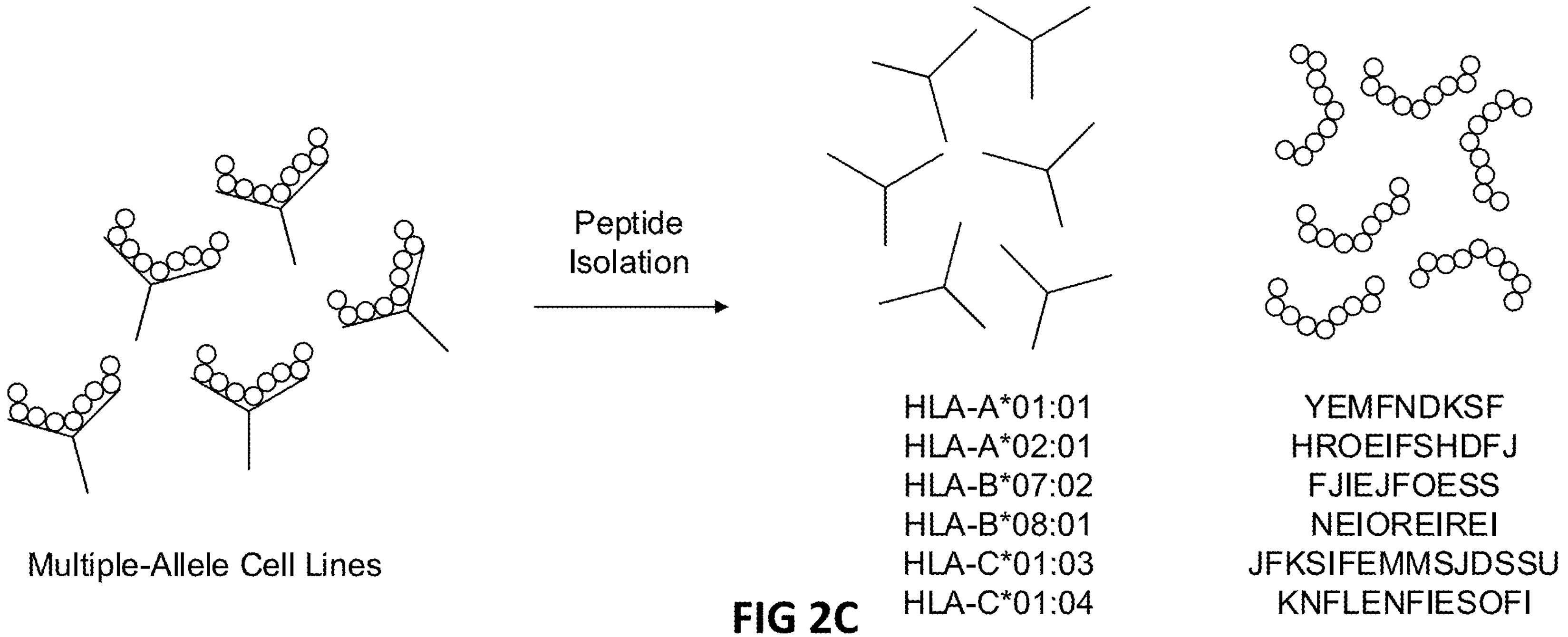
Figure 2D:
Figure 2E:
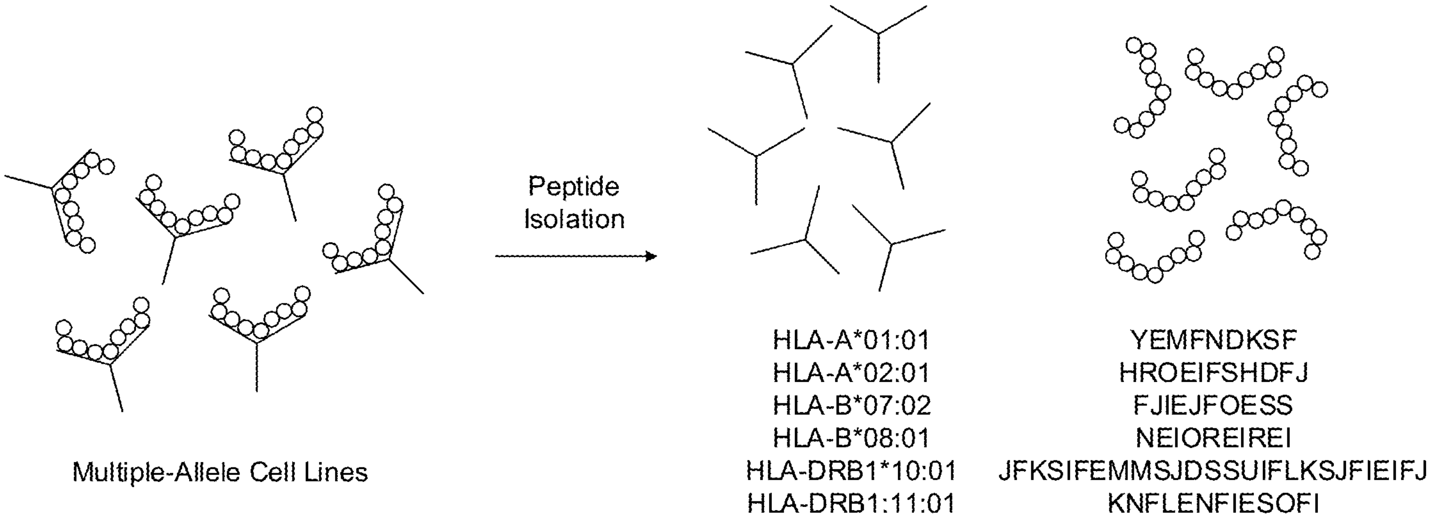

Allele-interacting information primarily includes identified peptide sequences that are known to have been presented by one or more identified MHC molecules from humans, mice, etc. Notably, this may or may not include data obtained from tumor samples. The presented peptide sequences may be identified from cells that express a single MHC allele. In this case the presented peptide sequences are generally collected from single-allele cell lines that are engineered to express a predetermined MHC allele and that are subsequently exposed to synthetic protein. Peptides presented on the MHC allele are isolated by techniques such as acid-elution and identified through mass spectrometry. FIG. 2B shows an example of this, where the example peptide YEMFNDKS (SEQ ID NO:60), presented on the predetermined MHC allele HLA-A*01:01, is isolated and identified through mass spectrometry. FIG. 2D shows another example of this, where the example peptide YEMFNDKSQRAPDDKMF (SEQ ID NO: 61), presented on the predetermined MHC allele HLA-DRB1*12:01, is isolated and identified through mass spectrometry. Since in these situations peptides are identified through cells engineered to express a single predetermined MHC protein, the direct association between a presented peptide and the MHC protein to which it was bound to is definitively known.

The presented peptide sequences may also be collected from cells that express multiple MHC alleles. Typically in humans, 6 different types of MHC-I and up to 12 different types of MHC-II molecules are expressed for a cell. Such presented peptide sequences may be identified from multiple-allele cell lines that are engineered to express multiple predetermined MHC alleles. Such presented peptide sequences may also be identified from tissue samples, either from normal tissue samples or tumor tissue samples. In this case particularly, the MHC molecules can be immunoprecipitated from normal or tumor tissue. Peptides presented on the multiple MHC alleles can similarly be isolated by techniques such as acid-elution and identified through mass spectrometry. FIG. 2C shows an example of this, where the six example peptides, YEMFNDKSF (SEQ ID NO: 62), HROEIFSHDFJ (SEQ ID NO: 63), FJIEJFOESS (SEQ ID NO: 64), NEIOREIREI (SEQ ID NO: 65), JFKSIFEMMSJDSSU (SEQ ID NO: 66), and KNFLENFIESOFI (SEQ ID NO: 67), are presented on identified MHC alleles HLA-A*01:01, HLA-A*02:01, HLA-B*07:02, HLA-B*08:01, HLA-C*01:03, and HLA-C*01:04 and are isolated and identified through mass spectrometry. In another example, FIG. 2C shows where the six example peptides, YEMFNDKSF (SEQ ID NO: 62), HROEIFSHDFJ (SEQ ID NO: 63), FJIEJFOESS (SEQ ID NO: 64), NEIOREIREI (SEQ ID NO: 65), JFKSIFEMMSJDSSUIFLKSJFIEIFJ (SEQ ID NO: 68), and KNFLENFIESOFI (SEQ ID NO: 67), are presented on identified class I MHC alleles HLA-A*01:01, HLA-A*02:01, HLA-B*07:02, HLA-B*08:01, and class II MHC alleles HLA-DRB1*10:01, HLA-DRB1:11:01 and are isolated and identified through mass spectrometry. In contrast to single-allele cell lines, in these examples the direct association between a presented peptide and the MHC protein to which it was bound to may be unknown since the bound peptides are isolated from the MHC molecules before being identified.

Allele-interacting information can also include mass spectrometry ion current which depends on both the concentration of peptide-MHC molecule complexes, and the ionization efficiency of peptides. The ionization efficiency varies from peptide to peptide in a sequence-dependent manner. Generally, ionization efficiency varies from peptide to peptide over approximately two orders of magnitude, while the concentration of peptide-MHC complexes varies over a larger range than that.

Allele-interacting information can also include measurements or predictions of binding affinity between a given MHC allele and a given peptide (94, 95, 96). One or more affinity models can generate such predictions. For example, going back to the example shown in FIG. 1D, presentation information 165 may include a binding affinity prediction of 1000 nM between the peptide YEMFNDKSF (SEQ ID NO: 62) and the class I allele HLA-A*01:01. Few peptides with IC50>1000 nm are presented by the MHC, and lower IC50 values increase the probability of presentation. Presentation information 165 may include a binding affinity prediction between the peptide KNFLENFIESOFI (SEQ ID NO: 67) and the class II allele HLA-DRB1:11:01.

Allele-interacting information can also include measurements or predictions of stability of the MHC complex. One or more stability models that can generate such predictions. More stable peptide-MHC complexes (i.e., complexes with longer half-lives) are more likely to be presented at high copy number on tumor cells and on antigen-presenting cells that encounter vaccine antigen. For example, going back to the example shown in FIG. 2C, presentation information 165 may include a stability prediction of a half-life of 1 h for the class I molecule HLA-A*01:01. Presentation information 165 may also include a stability prediction of a half-life for the class II molecule HLA-DRB1:11:01.

Allele-interacting information can also include the measured or predicted rate of the formation reaction for the peptide-MHC complex. Complexes that form at a higher rate are more likely to be presented on the cell surface at high concentration.

Figure 5:
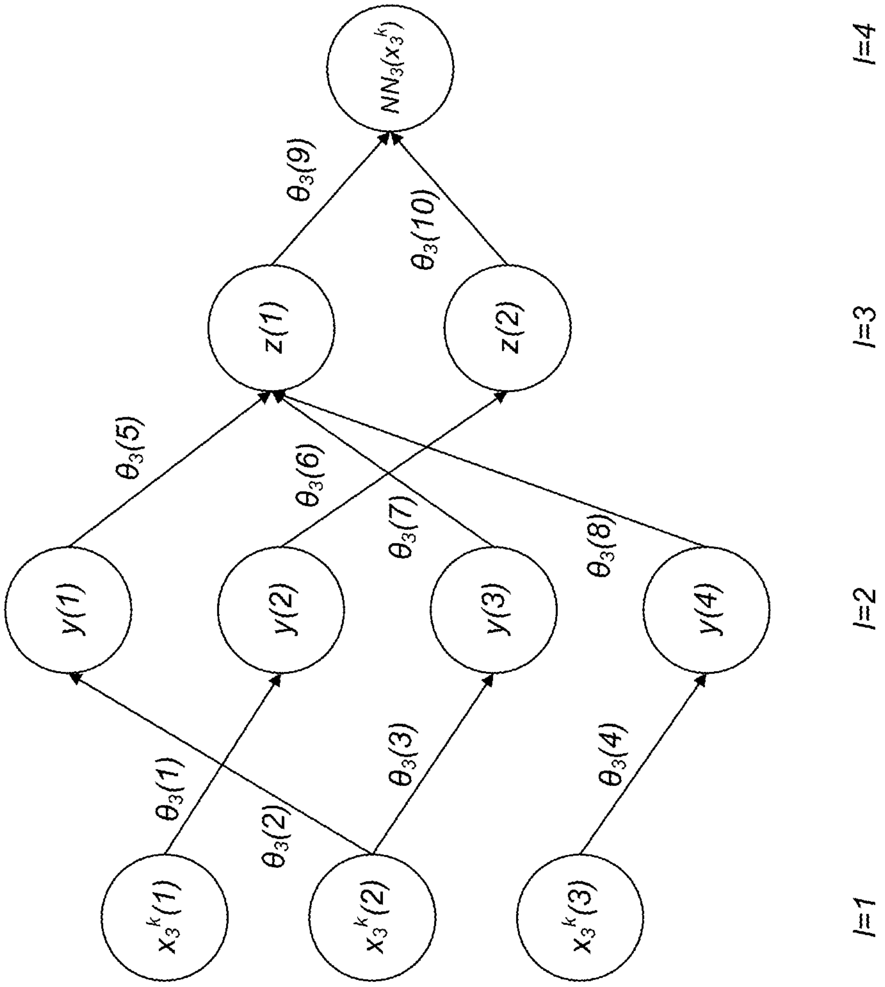
FIG. 5 illustrates an example network model in association with an MHC allele.

Allele-interacting information can also include the sequence and length of the peptide. MHC class I molecules typically prefer to present peptides with lengths between 8 and 15 peptides. 60-80% of presented peptides have length 9. Histograms of presented peptide lengths from several cell lines are shown in FIG. 5. MHC class II molecules typically prefer to present peptides with lengths between 6-30 peptides.

Allele-interacting information can also include the presence of kinase sequence motifs on the neoantigen encoded peptide, and the absence or presence of specific post-translational modifications on the neoantigen encoded peptide. The presence of kinase motifs affects the probability of post-translational modification, which may enhance or interfere with MHC binding.

Allele-interacting information can also include the expression or activity levels of proteins involved in the process of post-translational modification, e.g., kinases (as measured or predicted from RNA seq, mass spectrometry, or other methods).

Allele-interacting information can also include the probability of presentation of peptides with similar sequence in cells from other individuals expressing the particular MHC allele as assessed by mass-spectrometry proteomics or other means.

Allele-interacting information can also include the expression levels of the particular MHC allele in the individual in question (e.g. as measured by RNA-seq or mass spectrometry). Peptides that bind most strongly to an MHC allele that is expressed at high levels are more likely to be presented than peptides that bind most strongly to an MHC allele that is expressed at a low level.

Allele-interacting information can also include the overall neoantigen encoded peptide-sequence-independent probability of presentation by the particular MHC allele in other individuals who express the particular MHC allele.

Allele-interacting information can also include the overall peptide-sequence-independent probability of presentation by MHC alleles in the same family of molecules (e.g., HLA-A, HLA-B, HLA-C, HLA-DQ, HLA-DR, HLA-DP) in other individuals. For example, HLA-C molecules are typically expressed at lower levels than HLA-A or HLA-B molecules, and consequently, presentation of a peptide by HLA-C is a priori less probable than presentation by HLA-A or HLA-B. For another example, HLA-DP is typically expressed at lower levels than HLA-DR or HLA-DQ; consequently, presentation of a peptide by HLA-DP is a prior less probable than presentation by HLA-DR or HLA-DQ.

Allele-interacting information can also include the protein sequence of the particular MHC allele.

Any MHC allele-noninteracting information listed in the below section can also be modeled as an MHC allele-interacting information.

IX.B.2. Allele-Noninteracting Information

Allele-noninteracting information can include C-terminal sequences flanking the neoantigen encoded peptide within its source protein sequence. For MHC-I, C-terminal flanking sequences may impact proteasomal processing of peptides. However, the C-terminal flanking sequence is cleaved from the peptide by the proteasome before the peptide is transported to the endoplasmic reticulum and encounters MHC alleles on the surfaces of cells. Consequently, MHC molecules receive no information about the C-terminal flanking sequence, and thus, the effect of the C-terminal flanking sequence cannot vary depending on MHC allele type. For example, going back to the example shown in FIG. 2C, presentation information 165 may include the C-terminal flanking sequence FOEIFNDKSLDKFJI (SEQ ID NO: 69) of the presented peptide FJIEJFOESS (SEQ ID NO: 64) identified from the source protein of the peptide.

Allele-noninteracting information can also include mRNA quantification measurements. For example, mRNA quantification data can be obtained for the same samples that provide the mass spectrometry training data. As later described in reference to FIG. 13H, RNA expression was identified to be a strong predictor of peptide presentation. In one embodiment, the mRNA quantification measurements are identified from software tool RSEM. Detailed implementation of the RSEM software tool can be found at Bo Li and Colin N. Dewey. *RSEM: accurate transcript quantification from RNA-Seq data with or without a reference genome. BMC Bioinformatics,* 12:323, August 2011. In one embodiment, the mRNA quantification is measured in units of fragments per kilobase of transcript per Million mapped reads (FPKM).

Allele-noninteracting information can also include the N-terminal sequences flanking the peptide within its source protein sequence.

Allele-noninteracting information can also include the source gene of the peptide sequence. The source gene may be defined as the Ensembl protein family of the peptide sequence. In other examples, the source gene may be defined as the source DNA or the source RNA of the peptide sequence. The source gene can, for example, be represented as a string of nucleotides that encode for a protein, or alternatively be more categorically represented based on a named set of known DNA or RNA sequences that are known to encode specific proteins. In another example, allele-noninteracting information can also include the source transcript or isoform or set of potential source transcripts or isoforms of the peptide sequence drawn from a database such as Ensembl or RefSeq.

Allele-noninteracting information can also include the presence of protease cleavage motifs in the peptide, optionally weighted according to the expression of corresponding proteases in the tumor cells (as measured by RNA-seq or mass spectrometry). Peptides that contain protease cleavage motifs are less likely to be presented, because they will be more readily degraded by proteases, and will therefore be less stable within the cell.

Allele-noninteracting information can also include the turnover rate of the source protein as measured in the appropriate cell type. Faster turnover rate (i.e., lower half-life) increases the probability of presentation; however, the predictive power of this feature is low if measured in a dissimilar cell type.

Allele-noninteracting information can also include the length of the source protein, optionally considering the specific splice variants ("isoforms") most highly expressed in the tumor cells as measured by RNA-seq or proteome mass spectrometry, or as predicted from the annotation of germline or somatic splicing mutations detected in DNA or RNA sequence data.

Allele-noninteracting information can also include the level of expression of the proteasome, immunoproteasome, thymoproteasome, or other proteases in the tumor cells (which may be measured by RNA-seq, proteome mass spectrometry, or immunohistochemistry). Different proteasomes have different cleavage site preferences. More weight will be given to the cleavage preferences of each type of proteasome in proportion to its expression level.

Allele-noninteracting information can also include the expression of the source gene of the peptide (e.g., as measured by RNA-seq or mass spectrometry). Possible optimizations include adjusting the measured expression to account for the presence of stromal cells and tumor-infiltrating lymphocytes within the tumor sample. Peptides from more highly expressed genes are more likely to be presented. Peptides from genes with undetectable levels of expression can be excluded from consideration.

Allele-noninteracting information can also include the probability that the source mRNA of the neoantigen encoded peptide will be subject to nonsense-mediated decay as predicted by a model of nonsense-mediated decay, for example, the model from Rivas et al, Science 2015.

Allele-noninteracting information can also include the typical tissue-specific expression of the source gene of the peptide during various stages of the cell cycle. Genes that are expressed at a low level overall (as measured by RNA-seq or mass spectrometry proteomics) but that are known to be expressed at a high level during specific stages of the cell cycle are likely to produce more presented peptides than genes that are stably expressed at very low levels.

Allele-noninteracting information can also include a comprehensive catalog of features of the source protein as given in e.g. uniProt or PDB http://www.rcsb.org/pdb/home/home.do. These features may include, among others: the secondary and tertiary structures of the protein, subcellular localization 11, Gene ontology (GO) terms. Specifically, this information may contain annotations that act at the level of the protein, e.g., 5' UTR length, and annotations that act at the level of specific residues, e.g., helix motif between residues 300 and 310. These features can also include turn motifs, sheet motifs, and disordered residues.

Allele-noninteracting information can also include features describing the properties of the domain of the source protein containing the peptide, for example: secondary or tertiary structure (e.g., alpha helix vs beta sheet); Alternative splicing.

Allele-noninteracting information can also include features describing the presence or absence of a presentation hotspot at the position of the peptide in the source protein of the peptide.

Allele-noninteracting information can also include the probability of presentation of peptides from the source protein of the peptide in question in other individuals (after adjusting for the expression level of the source protein in those individuals and the influence of the different HLA types of those individuals).

Allele-noninteracting information can also include the probability that the peptide will not be detected or over-represented by mass spectrometry due to technical biases.

The expression of various gene modules/pathways as measured by a gene expression assay such as RNASeq, microarray(s), targeted panel(s) such as Nanostring, or single/multi-gene representatives of gene modules measured by assays such as RT-PCR (which need not contain the source protein of the peptide) that are informative about the state of the tumor cells, stroma, or tumor-infiltrating lymphocytes (TILs).

Allele-noninteracting information can also include the copy number of the source gene of the peptide in the tumor cells. For example, peptides from genes that are subject to homozygous deletion in tumor cells can be assigned a probability of presentation of zero.

Allele-noninteracting information can also include the probability that the peptide binds to the TAP or the measured or predicted binding affinity of the peptide to the TAP. Peptides that are more likely to bind to the TAP, or peptides that bind the TAP with higher affinity are more likely to be presented by MHC-I.

Allele-noninteracting information can also include the expression level of TAP in the tumor cells (which may be measured by RNA-seq, proteome mass spectrometry, immunohistochemistry). For MHC-I, higher TAP expression levels increase the probability of presentation of all peptides.

Allele-noninteracting information can also include the presence or absence of tumor mutations, including, but not limited to:

i. Driver mutations in known cancer driver genes such as EGFR, KRAS, ALK, RET, ROS1, TP53, CDKN2A, CDKN2B, NTRK1, NTRK2, NTRK3
ii. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation.

Presence or absence of functional germline polymorphisms, including, but not limited to:

i. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome)

Allele-noninteracting information can also include tumor type (e.g., NSCLC, melanoma).

Allele-noninteracting information can also include known functionality of HLA alleles, as reflected by, for instance HLA allele suffixes. For example, the N suffix in the allele name HLA-A*24:09N indicates a null allele that is not expressed and is therefore unlikely to present epitopes; the full HLA allele suffix nomenclature is described at https://www.ebi.ac.uk/ipd/imgt/hla/nomenclature/suffixes.html.

Allele-noninteracting information can also include clinical tumor subtype (e.g., squamous lung cancer vs. non-squamous).

Allele-noninteracting information can also include smoking history.

Allele-noninteracting information can also include history of sunburn, sun exposure, or exposure to other mutagens.

Allele-noninteracting information can also include the typical expression of the source gene of the peptide in the relevant tumor type or clinical subtype, optionally stratified by driver mutation. Genes that are typically expressed at high levels in the relevant tumor type are more likely to be presented.

Allele-noninteracting information can also include the frequency of the mutation in all tumors, or in tumors of the same type, or in tumors from individuals with at least one shared MHC allele, or in tumors of the same type in individuals with at least one shared MHC allele.

In the case of a mutated tumor-specific peptide, the list of features used to predict a probability of presentation may also include the annotation of the mutation (e.g., missense, read-through, frameshift, fusion, etc.) or whether the mutation is predicted to result in nonsense-mediated decay (NMD). For example, peptides from protein segments that are not translated in tumor cells due to homozygous early-stop mutations can be assigned a probability of presentation of zero. NMD results in decreased mRNA translation, which decreases the probability of presentation.

IX.C. Presentation Identification System

Figure 3:
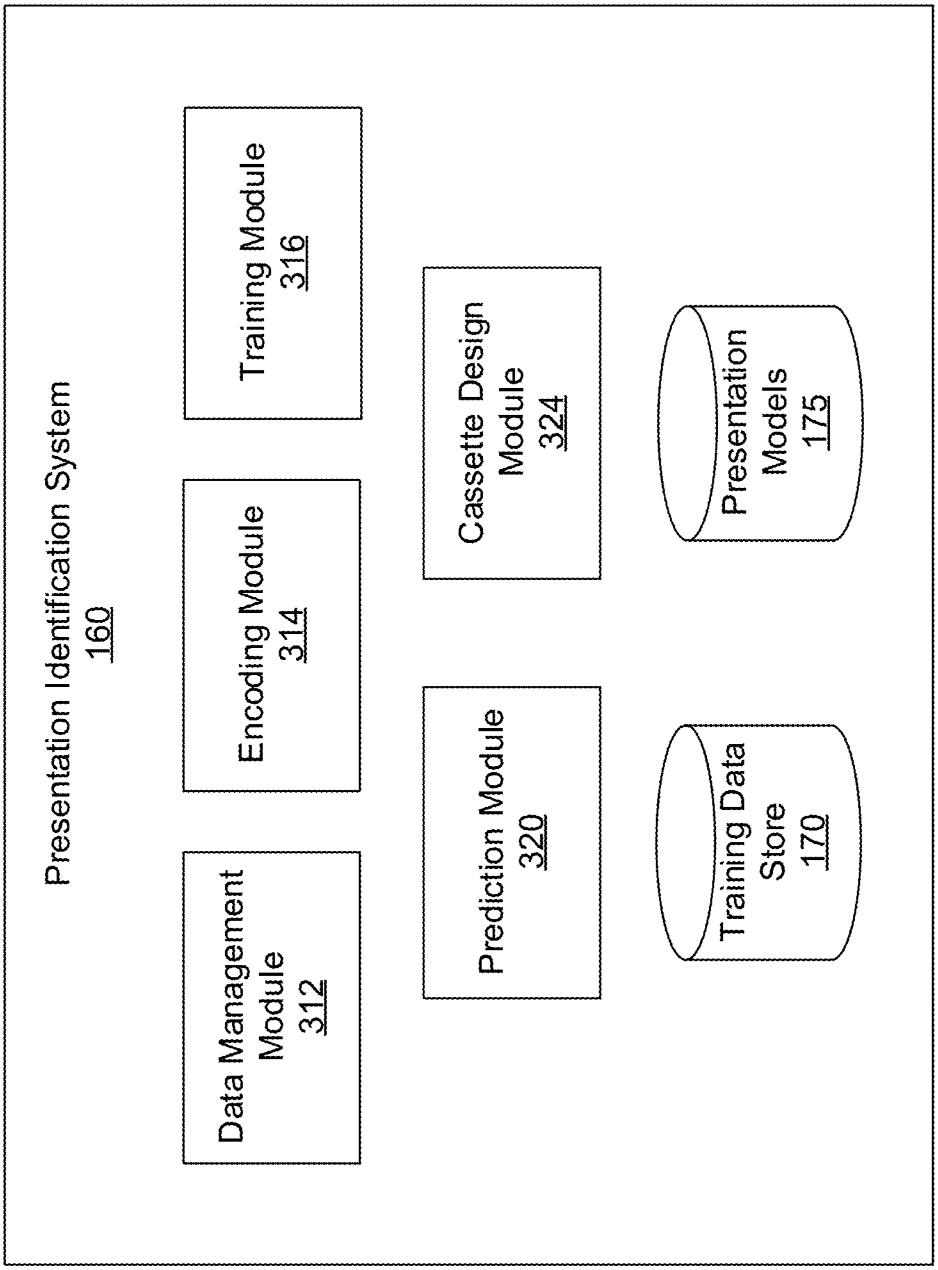
FIG. 3 is a high-level block diagram illustrating the computer logic components of the presentation identification system, according to one embodiment.

FIG. 3 is a high-level block diagram illustrating the computer logic components of the presentation identification system 160, according to one embodiment. In this example embodiment, the presentation identification system 160 includes a data management module 312, an encoding module 314, a training module 316, and a prediction module 320. The presentation identification system 160 is also comprised of a training data store 170 and a presentation models store 175. Some embodiments of the model management system 160 have different modules than those described here. Similarly, the functions can be distributed among the modules in a different manner than is described here.

IX.C.1. Data Management Module

The data management module 312 generates sets of training data 170 from the presentation information 165. Each set of training data contains a plurality of data instances, in which each data instance i contains a set of independent variables $z^i$ that include at least a presented or non-presented peptide sequence $p^i$, one or more associated MHC alleles $a^i$ associated with the peptide sequence $p^i$, and a dependent variable $y^i$ that represents information that the presentation identification system 160 is interested in predicting for new values of independent variables.

In one particular implementation referred throughout the remainder of the specification, the dependent variable $y^i$ is a binary label indicating whether peptide $p^i$ was presented by the one or more associated MHC alleles $a^i$. However, it is appreciated that in other implementations, the dependent variable $y^i$ can represent any other kind of information that the presentation identification system 160 is interested in predicting dependent on the independent variables $z^i$. For example, in another implementation, the dependent variable $y^i$ may also be a numerical value indicating the mass spectrometry ion current identified for the data instance.

The peptide sequence $p^i$ for data instance i is a sequence of $k_i$ amino acids, in which $k_i$ may vary between data instances i within a range. For example, that range may be 8-15 for MHC class I or 6-30 for MHC class II. In one specific implementation of system 160, all peptide sequences $p^i$ in a training data set may have the same length, e.g. 9. The number of amino acids in a peptide sequence may vary depending on the type of MHC alleles (e.g., MHC alleles in humans, etc.). The MHC alleles $a^i$ for data instance i indicate which MHC alleles were present in association with the corresponding peptide sequence $p^i$.

The data management module 312 may also include additional allele-interacting variables, such as binding affinity $b^i$ and stability $s^i$ predictions in conjunction with the peptide sequences $p^i$ and associated MHC alleles a contained in the training data 170. For example, the training data 170 may contain binding affinity predictions $b^i$ between a peptide $p^i$ and each of the associated MHC molecules indicated in $a^i$. As another example, the training data 170 may contain stability predictions $s^i$ for each of the MHC alleles indicated in $a^i$.

The data management module 312 may also include allele-noninteracting variables $w^i$, such as C-terminal flanking sequences and mRNA quantification measurements in conjunction with the peptide sequences $p^i$.

The data management module 312 also identifies peptide sequences that are not presented by MHC alleles to generate the training data 170. Generally, this involves identifying the "longer" sequences of source protein that include presented peptide sequences prior to presentation. When the presentation information contains engineered cell lines, the data management module 312 identifies a series of peptide sequences in the synthetic protein to which the cells were exposed to that were not presented on MHC alleles of the cells. When the presentation information contains tissue samples, the data management module 312 identifies source proteins from which presented peptide sequences originated from, and identifies a series of peptide sequences in the source protein that were not presented on MHC alleles of the tissue sample cells.

The data management module 312 may also artificially generate peptides with random sequences of amino acids and identify the generated sequences as peptides not presented on MHC alleles. This can be accomplished by randomly generating peptide sequences allows the data management module 312 to easily generate large amounts of synthetic data for peptides not presented on MHC alleles. Since in reality, a small percentage of peptide sequences are presented by MHC alleles, the synthetically generated peptide sequences are highly likely not to have been presented by MHC alleles even if they were included in proteins processed by cells.

FIG. 4A illustrates an example set of training data 170A, according to one embodiment. Specifically, the first 3 data instances in the training data 170A indicate peptide presentation information from a single-allele cell line involving the allele HLA-C*01:03 and 3 peptide sequences QCEIOWARE (SEQ ID NO: 70). FIEUHFWI (SEO ID NO: 71), and FEWRHRJTRUJR (SEO ID NO: 72). The fourth data instance in the training data 170A indicates peptide information from a multiple-allele cell line involving the alleles HLA-B*07:02, HLA-C*01:03, HLA-A*01:01 and a peptide sequence QIEJOEUE (SEQ ID NO: 73). The first data instance indicates that peptide sequence QCEIOWARE (SEO ID NO: 70) was not presented by the allele HLA-C*01:03. As discussed in the prior two paragraphs, the peptide sequence may be randomly generated by the data management module 312 or identified from source protein of presented peptides. The training data 170A also includes a binding affinity prediction of 1000 nM and a stability prediction of a half-life of 1 h for the peptide sequence-allele pair. The training data 170A also includes allele-noninteracting variables, such as the C-terminal flanking sequence of the peptide FJELFISBOSJFIE (SEO ID NO: 74), and a mRNA quantification measurement of $10^2$ TPM. The fourth data instance indicates that peptide sequence QIEJOEIE (SEQ ID NO: 73) was presented by one of the alleles HLA-B*07:02, HLA-C*01:03, or HLA-A*01:01. The training data 170A also includes binding affinity predictions and stability predictions for each of the alleles, as well as the C-terminal flanking sequence of the peptide and the mRNA quantification measurement for the peptide.

FIG. 4B illustrates another example set of training data 170A, according to one embodiment. Specifically, the first data instances in the training data 170A indicate peptide presentation information from a single-allele cell line involving the class II allele HLA-DRB3:01:01 and the peptide sequence QCEIOWAREFLKEIGJ (SEQ ID NO: 75). The first data instance indicates that peptide sequence QCEIOWAREFLKEIGJ (SEQ ID NO: 75) was not presented by the allele HLA-DRB3:01:01.

IX.C.2. Encoding Module

The encoding module 314 encodes information contained in the training data 170 into a numerical representation that can be used to generate the one or more presentation models. In one implementation, the encoding module 314 one-hot encodes sequences (e.g., peptide sequences or C-terminal flanking sequences) over a predetermined 20-letter amino acid alphabet. Specifically, a peptide sequence $p^i$ with $k_i$ amino acids is represented as a row vector of $20 \cdot k_i$ elements, where a single element among $p^i_{20(j-1)+1}$, $p^i_{20(j-1)+2}$, . . . , $p^i_{20j}$ that corresponds to the alphabet of the amino acid at the j-th position of the peptide sequence has a value of 1. Otherwise, the remaining elements have a value of 0. As an example, for a given alphabet {A, C, D, E, F, G, H, I, K, L, M, N, P, Q, R, S, T, V, W, Y}, the peptide sequence EAF of 3 amino acids for data instance i may be represented by the row vector of 60 elements $p^i$=[0 0 0 1 0 0 0 0 0 0 0 0 0 0 0 0 0 0 0 0 1 0 0 0 0 0 0 0 0 0 0 0 0 0 0 0 0 0 0 0 0 0 0 0 1 0 0 0 0 0 0 0 0 0 0 0 0 0 0 0]. The C-terminal flanking sequence $c^i$ can be similarly encoded as described above, as well as the protein sequence $d_h$ for MHC alleles, and other sequence data in the presentation information.

When the training data 170 contains sequences of differing lengths of amino acids, the encoding module 314 may further encode the peptides into equal-length vectors by adding a PAD character to extend the predetermined alphabet. For example, this may be performed by left-padding the peptide sequences with the PAD character until the length of the peptide sequence reaches the peptide sequence with the greatest length in the training data 170. Thus, when the peptide sequence with the greatest length has $k_{max}$ amino acids, the encoding module 314 numerically represents each sequence as a row vector of $(20+1) \cdot k_{max}$ elements. As an example, for the extended alphabet {PAD, A, C, D, E, F, G, H, I, K, L, M, N, P, Q, R, S, T, V, W, Y} and a maximum amino acid length of $k_{max}$=5, the same example peptide sequence EAF of 3 amino acids may be represented by the row vector of 105 elements $p^i$=[1 0 0 0 0 0 0 0 0 0 0 0 0 0 0 0 0 0 0 0 0 1 0 0 0 0 0 0 0 0 0 0 0 0 0 0 0 0 0 0 0 0 0 0 0 0 1 0 0 0 0 0 0 0 0 0 0 0 0 0 0 0 0 0 1 0 0 0 0 0 0 0 0 0 0 0 0 0 0 0 0 0 0 0 0 0 0 0 0 1 0 0 0 0 0 0 0 0 0 0 0 0 0 0 0]. The C-terminal flanking sequence $c^i$ or other sequence data can be similarly encoded as described above. Thus, each independent variable or column in the peptide sequence $p^i$ or $c^i$ represents presence of a particular amino acid at a particular position of the sequence.

Although the above method of encoding sequence data was described in reference to sequences having amino acid sequences, the method can similarly be extended to other types of sequence data, such as DNA or RNA sequence data, and the like.

The encoding module 314 also encodes the one or more MHC alleles $a^i$ for data instance i as a row vector of m elements, in which each element h=1, 2, . . . , m corresponds to a unique identified MHC allele. The elements corresponding to the MHC alleles identified for the data instance i have a value of 1. Otherwise, the remaining elements have a value of 0. As an example, the alleles HLA-B*07:02 and HLA-C*01:03 for a data instance i corresponding to a multiple-allele cell line among m=4 unique identified MHC allele types {HLA-A*01:01, HLA-C*01:08, HLA-B*07:02, HLA-C*01:03} may be represented by the row vector of 4 elements $a^i$=[0 0 1 1], in which $a_3^i$=1 and $a_4^i$=1. As another example, the elements corresponding to the MHC alleles identified for the data instance i have a value of 1. Otherwise, the remaining elements have a value of 0. As an example, the alleles HLA-B*07:02 and HLA-DRB1*10:01 for a data instance i corresponding to a multiple-allele cell line among m=4 unique identified MHC allele types {HLA-A*01:01, HLA-C*01:08, HLA-B*07:02, HLA-DRB1*10:01} may be represented by the row vector of 4 elements $a^i$=[0 0 1 1], in which $a_3^i$=1 and $a_4^i$=1. Although the examples described herein with 4 identified MHC allele types, the number of MHC allele types can be hundreds or thousands in practice. As previously discussed, each data instance i typically contains at most 6 different MHC class I allele types in association with the peptide sequence $p_i$, and/or at most 4 different MHC class II DR allele types in association with the peptide sequence $p_i$, and/or at most 12 different MHC class II allele types in association with the peptide sequence $p_i$.

The encoding module 314 also encodes the label $y_i$ for each data instance i as a binary variable having values from the set of {0, 1}, in which a value of 1 indicates that peptide $x^i$ was presented by one of the associated MHC alleles a, and a value of 0 indicates that peptide $x^i$ was not presented by any of the associated MHC alleles a. When the dependent variable $y_i$ represents the mass spectrometry ion current, the encoding module 314 may additionally scale the values using various functions, such as the log function having a range of [−∞, ∞] for ion current values between [0, ∞].

The encoding module 314 may represent a pair of allele-interacting variables $x_h^i$ for peptide $p_i$ and an associated MHC allele h as a row vector in which numerical representations of allele-interacting variables are concatenated one after the other. For example, the encoding module 314 may represent $x_h^i$ as a row vector equal to $[p^i]$, $[p^i\ b_h^i]$, $[p^i\ s_h^i]$, or $[p^i\ b_h^i\ s_h^i]$, where $b_h^i$ is the binding affinity prediction for peptide $p_i$ and associated MHC allele h, and similarly for $s_h^i$ for stability. Alternatively, one or more combination of allele-interacting variables may be stored individually (e.g., as individual vectors or matrices).

In one instance, the encoding module 314 represents binding affinity information by incorporating measured or predicted values for binding affinity in the allele-interacting variables $x_h^i$.

In one instance, the encoding module 314 represents binding stability information by incorporating measured or predicted values for binding stability in the allele-interacting variables $x_h^i$, In one instance, the encoding module 314 represents binding on-rate information by incorporating measured or predicted values for binding on-rate in the allele-interacting variables $x_h^i$.

In one instance, for peptides presented by class I MHC molecules, the encoding module 314 represents peptide length as a vector $T_k=[\mathbb{1}(L_k=8)\ \mathbb{1}(L_k=9)\ \mathbb{1}(L_k=10)\ \mathbb{1}(L_k=11)\ \mathbb{1}(L_k=12)\ \mathbb{1}(L_k=13)\ \mathbb{1}(L_k=14)\ \mathbb{1}(L_k=15)]$ where $\mathbb{1}$ is the indicator function, and $L_k$ denotes the length of peptide $p_k$. The vector $T_k$ can be included in the allele-interacting variables $x_h^i$. In another instance, for peptides presented by class II MHC molecules, the encoding module 314 represents peptide length as a vector $T_k=[\mathbb{1}(L_k=6)\ \mathbb{1}(L_k=7)\ \mathbb{1}(L_k=8)\ \mathbb{1}(L_k=9)\ \mathbb{1}(L_k=10)\ \mathbb{1}(L_k=11)\ \mathbb{1}(L_k=12)\ \mathbb{1}(L_k=13)\ \mathbb{1}(L_k=14)\ \mathbb{1}(L_k=15)\ \mathbb{1}(L_k=16)\ \mathbb{1}(L_k=17)\ \mathbb{1}(L_k=18)\ \mathbb{1}(L_k=19)\ \mathbb{1}(L_k=20)\ \mathbb{1}(L_k=21)\ \mathbb{1}(L_k=22)\ \mathbb{1}(L_k=23)\ \mathbb{1}(L_k=24)\ \mathbb{1}(L_k=25)\ \mathbb{1}(L_k=26)\ \mathbb{1}(L_k=27)\ \mathbb{1}(L_k=28)\ \mathbb{1}(L_k=29)\ \mathbb{1}(L_k=30)]$ where $\mathbb{1}$ is the indicator function, and $L_k$ denotes the length of peptide $p_k$. The vector $T_k$ can be included in the allele-interacting variables $x_h^i$.

In one instance, the encoding module 314 represents RNA expression information of MHC alleles by incorporating RNA-seq based expression levels of MHC alleles in the allele-interacting variables $x_h^i$.

Similarly, the encoding module 314 may represent the allele-noninteracting variables $w^i$ as a row vector in which numerical representations of allele-noninteracting variables are concatenated one after the other. For example, $w^i$ may be a row vector equal to $[c^i]$ or $[c^i\ m^i\ w^i]$ in which $w^i$ is a row vector representing any other allele-noninteracting variables in addition to the C-terminal flanking sequence of peptide $p^i$ and the mRNA quantification measurement $m^i$ associated with the peptide. Alternatively, one or more combination of allele-noninteracting variables may be stored individually (e.g., as individual vectors or matrices).

In one instance, the encoding module 314 represents turnover rate of source protein for a peptide sequence by incorporating the turnover rate or half-life in the allele-noninteracting variables $w^i$.

In one instance, the encoding module 314 represents length of source protein or isoform by incorporating the protein length in the allele-noninteracting variables $w^i$.

In one instance, the encoding module 314 represents activation of immunoproteasome by incorporating the mean expression of the immunoproteasome-specific proteasome subunits including the $\beta1_i$, $\beta2_i$, $\beta5_i$ subunits in the allele-noninteracting variables $w^i$.

In one instance, the encoding module 314 represents the RNA-seq abundance of the source protein of the peptide or gene or transcript of a peptide (quantified in units of FPKM, TPM by techniques such as RSEM) can be incorporating the abundance of the source protein in the allele-noninteracting variables $w^i$.

In one instance, the encoding module 314 represents the probability that the transcript of origin of a peptide will undergo nonsense-mediated decay (NMD) as estimated by the model in, for example, Rivas et. al. *Science,* 2015 by incorporating this probability in the allele-noninteracting variables $w^i$.

In one instance, the encoding module 314 represents the activation status of a gene module or pathway assessed via RNA-seq by, for example, quantifying expression of the genes in the pathway in units of TPM using e.g., RSEM for each of the genes in the pathway then computing a summary statistics, e.g., the mean, across genes in the pathway. The mean can be incorporated in the allele-noninteracting variables $w^i$.

In one instance, the encoding module 314 represents the copy number of the source gene by incorporating the copy number in the allele-noninteracting variables $w^i$.

In one instance, the encoding module 314 represents the TAP binding affinity by including the measured or predicted TAP binding affinity (e.g., in nanomolar units) in the allele-noninteracting variables $w^i$.

In one instance, the encoding module 314 represents TAP expression levels by including TAP expression levels measured by RNA-seq (and quantified in units of TPM by e.g., RSEM) in the allele-noninteracting variables $w^i$.

In one instance, the encoding module 314 represents tumor mutations as a vector of indicator variables (i.e., $d^k=1$ if peptide $p^k$ comes from a sample with a KRAS G12D mutation and 0 otherwise) in the allele-noninteracting variables $w^i$.

In one instance, the encoding module 314 represents germline polymorphisms in antigen presentation genes as a vector of indicator variables (i.e., $d^k=1$ if peptide $p^k$ comes from a sample with a specific germline polymorphism in the TAP). These indicator variables can be included in the allele-noninteracting variables $w^i$.

In one instance, the encoding module 314 represents tumor type as a length-one one-hot encoded vector over the alphabet of tumor types (e.g., NSCLC, melanoma, colorectal cancer, etc). These one-hot-encoded variables can be included in the allele-noninteracting variables $w^i$.

In one instance, the encoding module 314 represents MHC allele suffixes by treating 4-digit HLA alleles with different suffixes. For example, HLA-A*24:09N is considered a different allele from HLA-A*24:09 for the purpose of the model. Alternatively, the probability of presentation by an N-suffixed MHC allele can be set to zero for all peptides, because HLA alleles ending in the N suffix are not expressed.

In one instance, the encoding module 314 represents tumor subtype as a length-one one-hot encoded vector over the alphabet of tumor subtypes (e.g., lung adenocarcinoma, lung squamous cell carcinoma, etc). These one hot-encoded variables can be included in the allele-noninteracting variables $w^i$.

In one instance, the encoding module 314 represents smoking history as a binary indicator variable ($d^k=1$ if the patient has a smoking history, and 0 otherwise), that can be included in the allele-noninteracting variables $w^i$. Alternatively, smoking history can be encoded as a length-one one-hot-encoded variable over an alphabet of smoking severity. For example, smoking status can be rated on a 1-5 scale, where 1 indicates nonsmokers, and 5 indicates current heavy smokers. Because smoking history is primarily relevant to lung tumors, when training a model on multiple tumor types, this variable can also be defined to be equal to 1 if the patient has a history of smoking and the tumor type is lung tumors and zero otherwise.

In one instance, the encoding module 314 represents sunburn history as a binary indicator variable ($d^k$=1 if the patient has a history of severe sunburn, and 0 otherwise), which can be included in the allele-noninteracting variables $w^i$. Because severe sunburn is primarily relevant to melanomas, when training a model on multiple tumor types, this variable can also be defined to be equal to 1 if the patient has a history of severe sunburn and the tumor type is melanoma and zero otherwise.

In one instance, the encoding module 314 represents distribution of expression levels of a particular gene or transcript for each gene or transcript in the human genome as summary statistics (e,g., mean, median) of distribution of expression levels by using reference databases such as TCGA. Specifically, for a peptide $p^k$ in a sample with tumor type melanoma, we can include not only the measured gene or transcript expression level of the gene or transcript of origin of peptide $p^k$ in the allele-noninteracting variables $w^i$, but also the mean and/or median gene or transcript expression of the gene or transcript of origin of peptide $p^k$ in melanomas as measured by TCGA.

In one instance, the encoding module 314 represents mutation type as a length-one one-hot-encoded variable over the alphabet of mutation types (e.g., missense, frameshift, NMD-inducing, etc). These one hot-encoded variables can be included in the allele-noninteracting variables $w^i$.

In one instance, the encoding module 314 represents protein-level features of protein as the value of the annotation (e.g., 5' UTR length) of the source protein in the allele-noninteracting variables $w^i$. In another instance, the encoding module 314 represents residue-level annotations of the source protein for peptide $p^i$ by including an indicator variable, that is equal to 1 if peptide $p^i$ overlaps with a helix motif and 0 otherwise, or that is equal to 1 if peptide $p^i$ is completely contained with within a helix motif in the allele-noninteracting variables $w^i$. In another instance, a feature representing proportion of residues in peptide $p^i$ that are contained within a helix motif annotation can be included in the allele-noninteracting variables $w^i$.

In one instance, the encoding module 314 represents type of proteins or isoforms in the human proteome as an indicator vector $o^k$ that has a length equal to the number of proteins or isoforms in the human proteome, and the corresponding element $o^k_i$ is 1 if peptide $p^k$ comes from protein i and 0 otherwise.

In one instance, the encoding module 314 represents the source gene G=gene($p^i$) of peptide $p^i$ as a categorical variable with L possible categories, where L denotes the upper limit of the number of indexed source genes 1, 2, . . . , L.

The encoding module 314 may also represent the overall set of variables $z^i$ for peptide $p^i$ and an associated MHC allele h as a row vector in which numerical representations of the allele-interacting variables $x^i$ and the allele-noninteracting variables $w^i$ are concatenated one after the other. For example, the encoding module 314 may represent $z_h^i$ as a row vector equal to $[x_h^i\ w^i]$ or $[w^i\ x_h^i]$.

X. Training Module

The training module 316 constructs one or more presentation models that generate likelihoods of whether peptide sequences will be presented by MHC alleles associated with the peptide sequences. Specifically, given a peptide sequence $p^k$ and a set of MHC alleles $a^k$ associated with the peptide sequence $p^k$, each presentation model generates an estimate $u_k$ indicating a likelihood that the peptide sequence $p^k$ will be presented by one or more of the associated MHC alleles $a^k$.

X.A. Overview

The training module 316 constructs the one more presentation models based on the training data sets stored in store 170 generated from the presentation information stored in 165. Generally, regardless of the specific type of presentation model, all of the presentation models capture the dependence between independent variables and dependent variables in the training data 170 such that a loss function is minimized. Specifically, the loss function $\vartheta$ ($y_{i\in S}$ $u_{i\in S}$; θ) represents discrepancies between values of dependent variables $y_{i\in S}$ for one or more data instances S in the training data 170 and the estimated likelihoods $u_{i\in S}$ for the data instances S generated by the presentation model. In one particular implementation referred throughout the remainder of the specification, the loss function ($y_{i\in S}$, $u_{i\in S}$; θ) is the negative log likelihood function given by equation (1a) as follows:

$$\ell(y_{i\in S}, u_{i\in S}; \theta) = \sum_{i\in S}(y_i \log u_i + (1 - y_i)\log(1 - u_i)). \tag{1a}$$

However, in practice, another loss function may be used. For example, when predictions are made for the mass spectrometry ion current, the loss function is the mean squared loss given by equation 1b as follows:

$$\ell(y_{i\in S}, u_{i\in S}; \theta) = \sum_{i\in S}(\|y_i - u_i\|_2^2). \tag{1b}$$

The presentation model may be a parametric model in which one or more parameters θ mathematically specify the dependence between the independent variables and dependent variables. Typically, various parameters of parametric-type presentation models that minimize the loss function ($y_{i\in S}$, $u_{i\in S}$; θ) are determined through gradient-based numerical optimization algorithms, such as batch gradient algorithms, stochastic gradient algorithms, and the like. Alternatively, the presentation model may be a non-parametric model in which the model structure is determined from the training data 170 and is not strictly based on a fixed set of parameters.

X.B. Per-Allele Models

The training module 316 may construct the presentation models to predict presentation likelihoods of peptides on a per-allele basis. In this case, the training module 316 may train the presentation models based on data instances S in the training data 170 generated from cells expressing single MHC alleles.

In one implementation, the training module 316 models the estimated presentation likelihood $u_k$ for peptide $p^k$ for a specific allele h by:

$$u_k^h = Pr(p_k \text{ presented}; MHC \text{ allele } h) = f(g_h(x_h^k; \theta_h)), \quad (2)$$

where peptide sequence $x_h^k$ denotes the encoded allele-interacting variables for peptide $p^k$ and corresponding MHC allele h, $f(\bullet)$ is any function, and is herein throughout is referred to as a transformation function for convenience of description. Further, $g_h(\bullet)$ is any function, is herein throughout referred to as a dependency function for convenience of description, and generates dependency scores for the allele-interacting variables $x_h^k$ based on a set of parameters $\theta_h$ determined for MHC allele h. The values for the set of parameters $\theta_h$ for each MHC allele h can be determined by minimizing the loss function with respect to $\theta_h$, where i is each instance in the subset S of training data 170 generated from cells expressing the single MHC allele h.

The output of the dependency function $g_h(x_h^k; \theta_h)$ represents a dependency score for the MHC allele h indicating whether the MHC allele h will present the corresponding neoantigen based on at least the allele interacting features $x_h^k$, and in particular, based on positions of amino acids of the peptide sequence of peptide $p^k$. For example, the dependency score for the MHC allele h may have a high value if the MHC allele h is likely to present the peptide $p^k$, and may have a low value if presentation is not likely. The transformation function $f(\bullet)$ transforms the input, and more specifically, transforms the dependency score generated by $g_h(x_h^k; \theta_h)$ in this case, to an appropriate value to indicate the likelihood that the peptide $p^k$ will be presented by an MHC allele.

In one particular implementation referred throughout the remainder of the specification, $f(\bullet)$ is a function having the range within [0, 1] for an appropriate domain range. In one example, $f(\bullet)$ is the expit function given by:

$$f(z) = \frac{\exp(z)}{1 + \exp(z)}. \quad (4)$$

As another example, $f(\bullet)$ can also be the hyperbolic tangent function given by:

$$f(z) = \tanh(z) \quad (5)$$

when the values for the domain z is equal to or greater than 0. Alternatively, when predictions are made for the mass spectrometry ion current that have values outside the range [0, 1], $f(\bullet)$ can be any function such as the identity function, the exponential function, the log function, and the like.

Thus, the per-allele likelihood that a peptide sequence $p^k$ will be presented by a MHC allele h can be generated by applying the dependency function $g_h(\bullet)$ for the MHC allele h to the encoded version of the peptide sequence $p^k$ to generate the corresponding dependency score. The dependency score may be transformed by the transformation function $f(\bullet)$ to generate a per-allele likelihood that the peptide sequence $p^k$ will be presented by the MHC allele h.

X.B.1 Dependency Functions for Allele Interacting Variables

In one particular implementation referred throughout the specification, the dependency function $g_h(\bullet)$ is an affine function given by:

$$g_h(x_h^i; \theta_h) = x_h^i \cdot \theta_h. \quad (6)$$

that linearly combines each allele-interacting variable in $x_h^k$ with a corresponding parameter in the set of parameters $\theta_h$ determined for the associated MHC allele h.

In another particular implementation referred throughout the specification, the dependency function $g_h(\bullet)$ is a network function given by:

$$g_h(x_h^i; \theta_h) = NN_h(x_h^i; \theta_h). \quad (7)$$

represented by a network model $NN_h(\bullet)$ having a series of nodes arranged in one or more layers. A node may be connected to other nodes through connections each having an associated parameter in the set of parameters $\theta_h$. A value at one particular node may be represented as a sum of the values of nodes connected to the particular node weighted by the associated parameter mapped by an activation function associated with the particular node. In contrast to the affine function, network models are advantageous because the presentation model can incorporate non-linearity and process data having different lengths of amino acid sequences. Specifically, through non-linear modeling, network models can capture interaction between amino acids at different positions in a peptide sequence and how this interaction affects peptide presentation.

In general, network models $NN_h(\bullet)$ may be structured as feed-forward networks, such as artificial neural networks (ANN), convolutional neural networks (CNN), deep neural networks (DNN), and/or recurrent networks, such as long short-term memory networks (LSTM), bi-directional recurrent networks, deep bi-directional recurrent networks, and the like.

In one instance referred throughout the remainder of the specification, each MHC allele in h=1, 2, . . . , m is associated with a separate network model, and $NN_h(\bullet)$ denotes the output(s) from a network model associated with MHC allele h.

FIG. 5 illustrates an example network model $NN_3(\bullet)$ in association with an arbitrary MHC allele h=3. As shown in FIG. 5, the network model $NN_3(\bullet)$ for MHC allele h=3 includes three input nodes at layer l=1, four nodes at layer l=2, two nodes at layer l=3, and one output node at layer l=4. The network model $NN_3(\bullet)$ is associated with a set of ten parameters $\theta_3(1)$, $\theta_3(2)$, . . . , $\theta_3(10)$. The network model $NN_3(\bullet)$ receives input values (individual data instances including encoded polypeptide sequence data and any other training data used) for three allele-interacting variables $x_3^k(1)$, $x_3^k(2)$, and $x_3^k(3)$ for MHC allele h=3 and outputs the value $NN_3(x_3^k)$. The network function may also include one or more network models each taking different allele interacting variables as input.

In another instance, the identified MHC alleles h=1, 2, . . . , m are associated with a single network model $NN_H(\bullet)$, and $NN_h(\bullet)$ denotes one or more outputs of the single network model associated with MHC allele h. In such an instance, the set of parameters $\theta_h$ may correspond to a set of parameters for the single network model, and thus, the set of parameters $\theta_h$ may be shared by all MHC alleles.

Figure 6A:
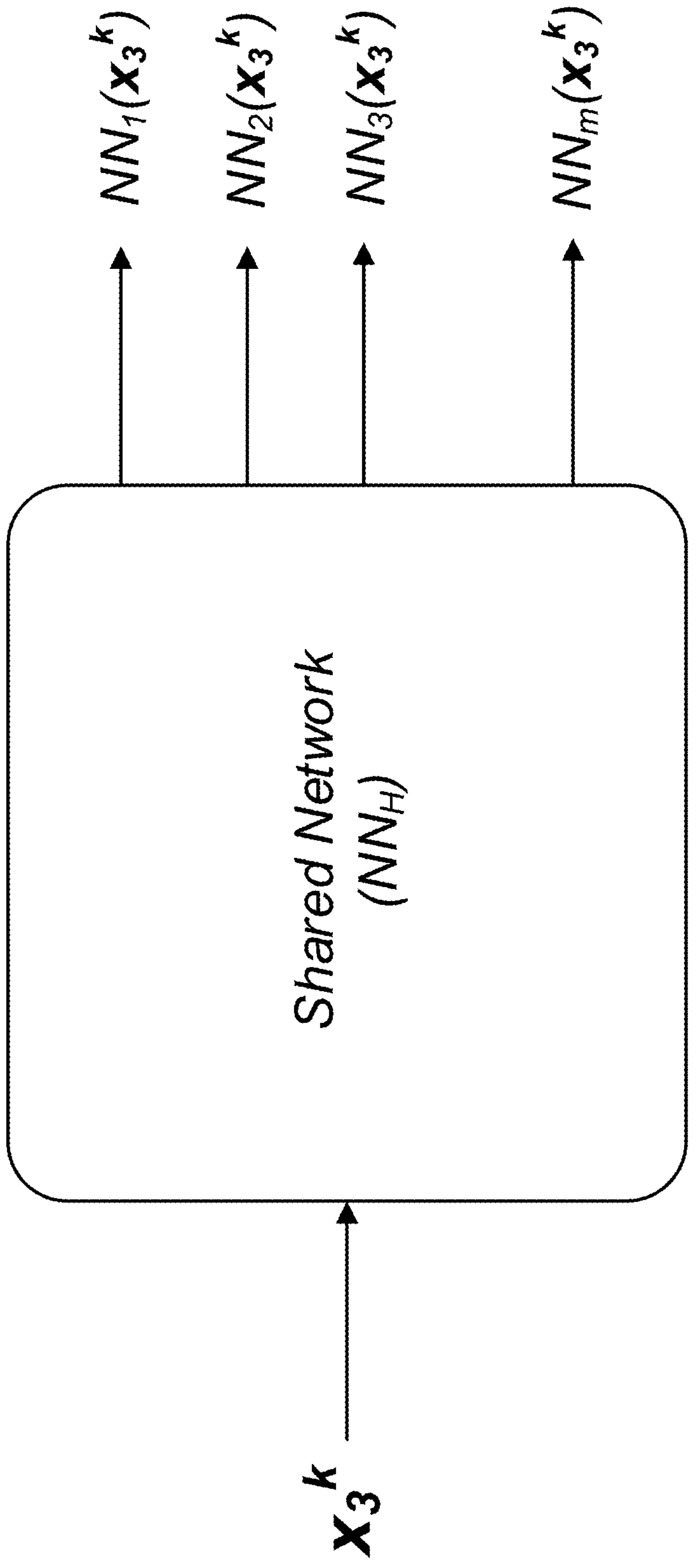
FIG. 6A illustrates an example network model NNH(•) shared by MHC alleles, according to one embodiment.

FIG. 6A illustrates an example network model $NN_H(\bullet)$ shared by MHC alleles h=1, 2, . . . , m. As shown in FIG. 6A, the network model $NN_H(\bullet)$ includes m output nodes each corresponding to an MHC allele. The network model $NN_3(\bullet)$ receives the allele-interacting variables $x_3^k$ for MHC allele h=3 and outputs m values including the value $NN_3(x_3^k)$ corresponding to the MHC allele h=3.

In yet another instance, the single network model $NN_H(\bullet)$ may be a network model that outputs a dependency score given the allele interacting variables $x_h^k$ and the encoded protein sequence $d_h$ of an MHC allele h. In such an instance, the set of parameters $\theta_h$ may again correspond to a set of parameters for the single network model, and thus, the set of parameters $\theta_h$ may be shared by all MHC alleles. Thus, in such an instance, $NN_h(\bullet)$ may denote the output of the single network model $NN_H(\bullet)$ given inputs $[x_k^k\ d_h]$ to the single network model. Such a network model is advantageous because peptide presentation probabilities for MHC alleles that were unknown in the training data can be predicted just by identification of their protein sequence.

Figure 6B:
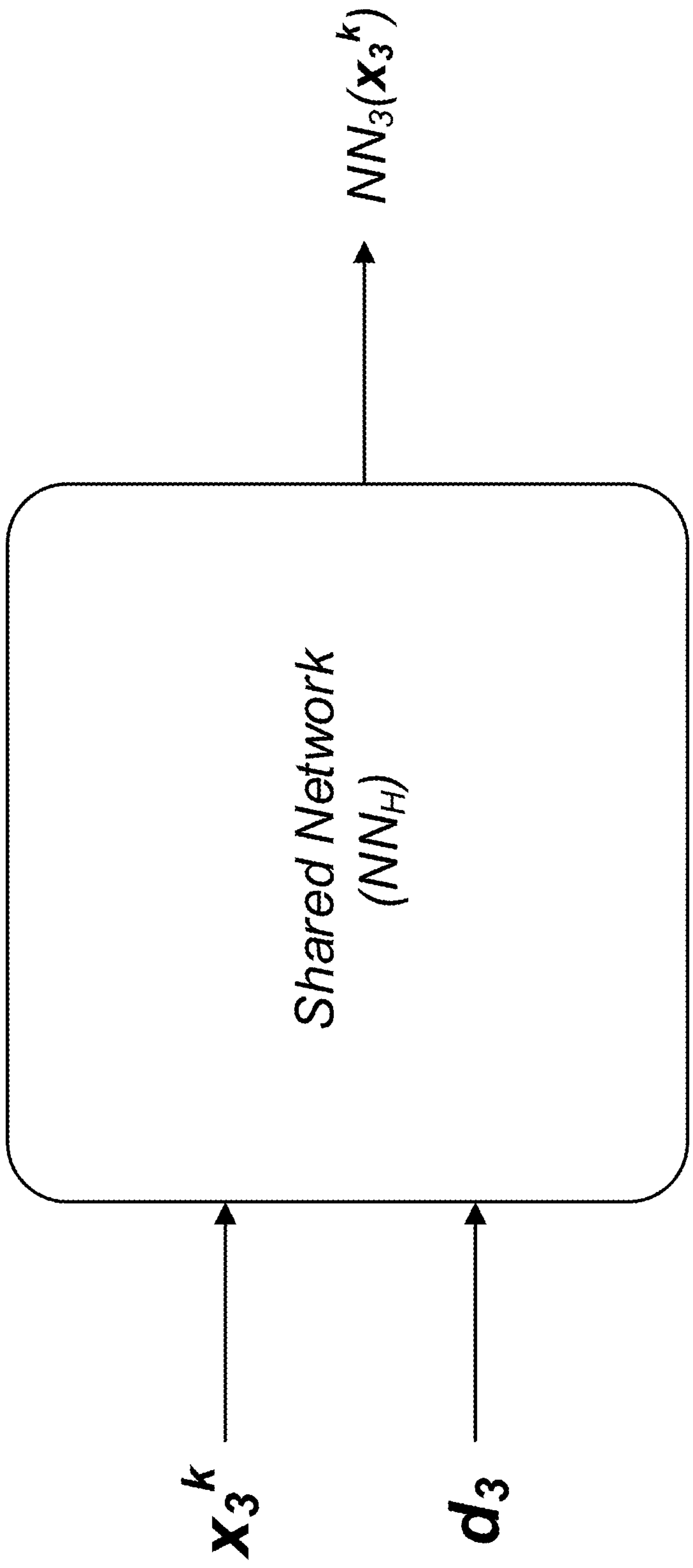
FIG. 6B illustrates an example network model $NN_H(\bullet)$ shared by MHC alleles, according to another embodiment.

FIG. 6B illustrates an example network model $NN_H(\bullet)$ shared by MHC alleles. As shown in FIG. 6B, the network model $NN_H(\bullet)$ receives the allele interacting variables and protein sequence of MHC allele h=3 as input, and outputs a dependency score $NN_3(x_3^k)$ corresponding to the MHC allele h=3.

In yet another instance, the dependency function $g_h(\bullet)$ can be expressed as:

$$g_h(x_h^k;\theta_h)=g'_h(x_h^k;\theta'_h)+\theta$$

where $g'_h(x_h^k;\theta'_h)$ is the affine function with a set of parameters $\theta'_h$, the network function, or the like, with a bias parameter $\theta_h^0$ in the set of parameters for allele interacting variables for the MHC allele that represents a baseline probability of presentation for the MHC allele h.

In another implementation, the bias parameter $\theta_h^0$ may be shared according to the gene family of the MHC allele h. That is, the bias parameter $\theta_h^0$ for MHC allele h may be equal to $\theta_{gene(h)^0}$, where gene(h) is the gene family of MHC allele h. For example, class I MHC alleles HLA-A*02:01, HLA-A*02:02, and HLA-A*02:03 may be assigned to the gene family of "HLA-A," and the bias parameter $\theta_h^0$ for each of these MHC alleles may be shared. As another example, class II MHC alleles HLA-DRB1:10:01, HLA-DRB1:11:01, and HLA-DRB3:01:01 may be assigned to the gene family of "HLA-DRB," and the bias parameter $\theta_h^0$ for each of these MHC alleles may be shared.

Returning to equation (2), as an example, the likelihood that peptide $p^k$ will be presented by MHC allele h=3, among m=4 different identified MHC alleles using the affine dependency function $g_h(\bullet)$, can be generated by:

$$u_k^3=f(x_3^k\cdot\theta_3),$$

where $x_3^k$ are the identified allele-interacting variables for MHC allele h=3, and $\theta_3$ are the set of parameters determined for MHC allele h=3 through loss function minimization.

As another example, the likelihood that peptide $p^k$ will be presented by MHC allele h=3, among m=4 different identified MHC alleles using separate network transformation functions $g_h(\bullet)$, can be generated by:

$$u_k^3=f(NN_3(x_3^k;\theta_3)),$$

where $x_3^k$ are the identified allele-interacting variables for MHC allele h=3, and 03 are the set of parameters determined for the network model $NN_3(\bullet)$ associated with MHC allele h=3.

Figure 7:
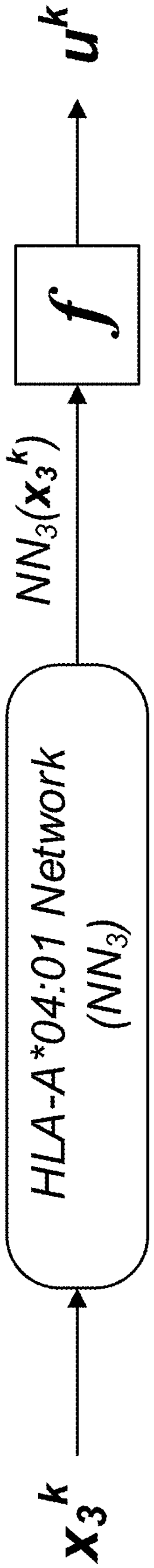
FIG. 7 illustrates generating a presentation likelihood for a peptide in association with an MHC allele using an example network model.

FIG. 7 illustrates generating a presentation likelihood for peptide $p^k$ in association with MHC allele h=3 using an example network model $NN_3(\bullet)$. As shown in FIG. 7, the network model $NN_3(\bullet)$ receives the allele-interacting variables $x_3^k$ for MHC allele h=3 and generates the output $NN_3(x_3^k)$. The output is mapped by function $f(\bullet)$ to generate the estimated presentation likelihood $u_k$.

X.B.2. Per-Allele with Allele-Noninteracting Variables

In one implementation, the training module 316 incorporates allele-noninteracting variables and models the estimated presentation likelihood $u_k$ for peptide $p^k$ by:

$$u_k^h=Pr(p^k\text{ presented})=f(g_w(w^k;\theta_w)+g_h(x_h^i;\theta_h)),\quad(8)$$

where $w^k$ denotes the encoded allele-noninteracting variables for peptide $p^k$, $g_w(\bullet)$ is a function for the allele-noninteracting variables $w^k$ based on a set of parameters $\theta_w$ determined for the allele-noninteracting variables. Specifically, the values for the set of parameters $\theta_h$ for each MHC allele h and the set of parameters $\theta_w$ for allele-noninteracting variables can be determined by minimizing the loss function with respect to $\theta_h$ and $\theta_w$, where i is each instance in the subset S of training data 170 generated from cells expressing single MHC alleles.

The output of the dependency function $g_w(w^k;\theta_w)$ represents a dependency score for the allele noninteracting variables indicating whether the peptide $p^k$ will be presented by one or more MHC alleles based on the impact of allele noninteracting variables. For example, the dependency score for the allele noninteracting variables may have a high value if the peptide $p^k$ is associated with a C-terminal flanking sequence that is known to positively impact presentation of the peptide $p^k$, and may have a low value if the peptide $p^k$ is associated with a C-terminal flanking sequence that is known to negatively impact presentation of the peptide $p^k$.

According to equation (8), the per-allele likelihood that a peptide sequence $p^k$ will be presented by a MHC allele h can be generated by applying the function $g_h(\bullet)$ for the MHC allele h to the encoded version of the peptide sequence $p^k$ to generate the corresponding dependency score for allele interacting variables. The function $g_w(\bullet)$ for the allele noninteracting variables are also applied to the encoded version of the allele noninteracting variables to generate the dependency score for the allele noninteracting variables. Both scores are combined, and the combined score is transformed by the transformation function $f(\bullet)$ to generate a per-allele likelihood that the peptide sequence $p^k$ will be presented by the MHC allele h.

Alternatively, the training module 316 may include allele-noninteracting variables $w^k$ in the prediction by adding the allele-noninteracting variables $w^k$ to the allele-interacting variables $x_h^k$ in equation (2). Thus, the presentation likelihood can be given by:

$$u_k^h=Pr(p^k\text{ presented; allele }h)=f(g_h([x_h^k w^k];\theta_h)).\quad(9)$$

X.B.3 Dependency Functions for Allele-Noninteracting Variables

Similarly to the dependency function $g_h(\bullet)$ for allele-interacting variables, the dependency function $g_w(\bullet)$ for allele noninteracting variables may be an affine function or a network function in which a separate network model is associated with allele-noninteracting variables $w^k$.

Specifically, the dependency function $g_w(\bullet)$ is an affine function given by:

$$g_w(w^k;\theta_w)=w^k\theta_w.$$

that linearly combines the allele-noninteracting variables in $w^k$ with a corresponding parameter in the set of parameters $\theta_w$.

The dependency function $g_w(\bullet)$ may also be a network function given by:

$$g_h(w^k;\theta_w)=NN_w(w^k;\theta_w).$$

represented by a network model $NN_w(\bullet)$ having an associated parameter in the set of parameters $\theta_w$. The network function may also include one or more network models each taking different allele noninteracting variables as input.

In another instance, the dependency function $g_w(\bullet)$ for the allele-noninteracting variables can be given by:

$$g_w(w^k;\theta_w)=g'_w(w^k;\theta'_w)+h(m^k;\theta_w^m), \quad (10)$$

where $g'_w(w^k;\theta'_w)$ is the affine function, the network function with the set of allele noninteracting parameters $\theta'_w$, or the like, $m^k$ is the mRNA quantification measurement for peptide $p^k$, $h(\bullet)$ is a function transforming the quantification measurement, and $\theta_w^m$ is a parameter in the set of parameters for allele noninteracting variables that is combined with the mRNA quantification measurement to generate a dependency score for the mRNA quantification measurement. In one particular embodiment referred throughout the remainder of the specification, $h(\bullet)$ is the log function, however in practice $h(\bullet)$ may be any one of a variety of different functions.

In yet another instance, the dependency function $g_w(\bullet)$ for the allele-noninteracting variables can be given by:

$$g_w(w^k;\theta_w)=g'_w(w^k;\theta'_w)+\theta_w^o\cdot o^k, \quad (11)$$

where $g'_w(w^k;\theta'_w)$ is the affine function, the network function with the set of allele noninteracting parameters $\theta'_w$, or the like, $o^k$ is the indicator vector described above representing proteins and isoforms in the human proteome for peptide $p^k$, and $\theta_w^o$ is a set of parameters in the set of parameters for allele noninteracting variables that is combined with the indicator vector. In one variation, when the dimensionality of $o^k$ and the set of parameters $\theta_w^o$ are significantly high, a parameter regularization term, such as $\lambda\cdot\|\theta_w^o|$, where $\|\bullet\|$ represents L1 norm, L2 norm, a combination, or the like, can be added to the loss function when determining the value of the parameters. The optimal value of the hyperparameter $\lambda$ can be determined through appropriate methods.

In yet another instance, the dependency function $g_w(\bullet)$ for the allele-noninteracting variables can be given by:

$$g_w(w^k;\theta_w)=g'_w(w^k;\theta'_w)+\sum_{l=1}^{L}\mathbb{1}(\text{gene}(p^k=l))\cdot\theta_w^l, \quad (12)$$

where $g'_w(w^k;\theta'_w)$ is the affine function, the network function with the set of allele noninteracting parameters $\theta'_w$, or the like, $\mathbb{1}(\text{gene}(p^k=l))$ is the indicator function that equals to 1 if peptide $p^k$ is from source gene l as describe above in reference to allele noninteracting variables, and $\theta_w^l$ is a parameter indicating "antigenicity" of source gene l. In one variation, when L is significantly high, and thus, the number of parameters $\theta_w^{l=1, 2, \ldots, L}$ are significantly high, a parameter regularization term, such as $\lambda\cdot\|\theta_w^l$, where $\|\bullet\|$ represents L1 norm, L2 norm, a combination, or the like, can be added to the loss function when determining the value of the parameters. The optimal value of the hyperparameter $\lambda$ can be determined through appropriate methods.

In practice, the additional terms of any of equations (10), (11), and (12) may be combined to generate the dependency function $g_w(\bullet)$ for allele noninteracting variables. For example, the term $h(\bullet)$ indicating mRNA quantification measurement in equation (10) and the term indicating source gene antigenicity in equation (12) may be summed together along with any other affine or network function to generate the dependency function for allele noninteracting variables.

Returning to equation (8), as an example, the likelihood that peptide $p^k$ will be presented by MHC allele h=3, among m=4 different identified MHC alleles using the affine transformation functions $g_h(\bullet)$, $g_w(\bullet)$, can be generated by:

$$u_k^3=f(w^k\cdot\theta_w+x_3^k\cdot\theta_3),$$

where $w^k$ are the identified allele-noninteracting variables for peptide $p^k$, and $\theta_w$ are the set of parameters determined for the allele-noninteracting variables.

As another example, the likelihood that peptide $p^k$ will be presented by MHC allele h=3, among m=4 different identified MHC alleles using the network transformation functions $g_h(\bullet)$, $g_w(\bullet)$, can be generated by:

$$u_k^3=f(NN_w(w^k;\theta_w)+NN_3(x_3^k;\theta_3))$$

where $w^k$ are the identified allele-interacting variables for peptide $p^k$, and $\theta_w$ are the set of parameters determined for allele-noninteracting variables.

Figure 8:
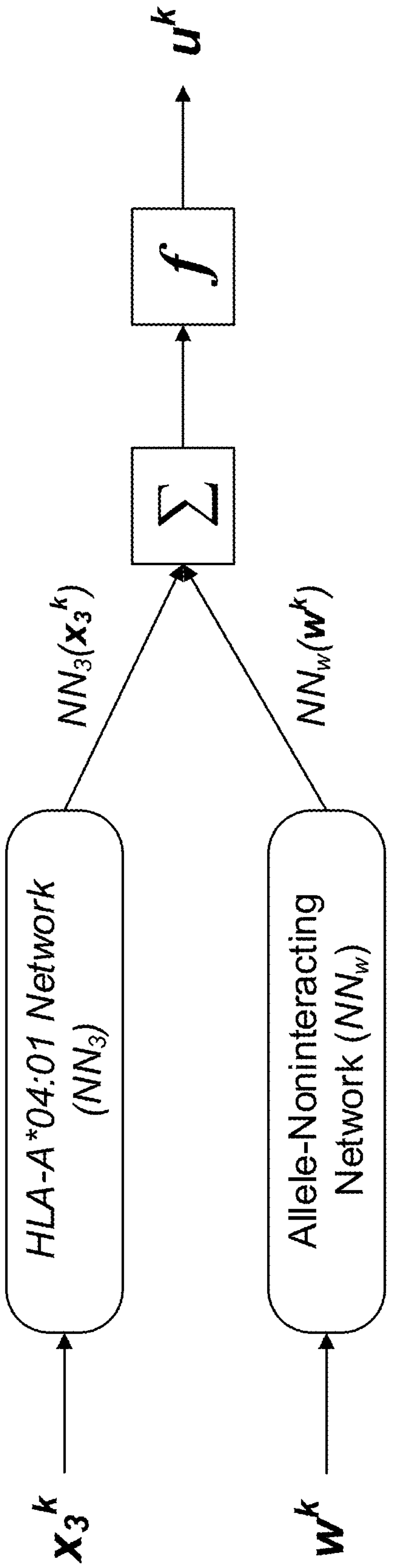
FIG. 8 illustrates generating a presentation likelihood for a peptide in association with a MHC allele using example network models.

FIG. 8 illustrates generating a presentation likelihood for peptide $p^k$ in association with MHC allele h=3 using example network models $NN_3(\bullet)$ and $NN_w(\bullet)$. As shown in FIG. 8, the network model $NN_3(\bullet)$ receives the allele-interacting variables $x_3^k$ for MHC allele h=3 and generates the output $NN_3(x_3^k)$. The network model $NN_w(\bullet)$ receives the allele-noninteracting variables $w^k$ for peptide $p^k$ and generates the output $NN_w(w^k)$. The outputs are combined and mapped by function $f(\bullet)$ to generate the estimated presentation likelihood $u_k$.

X.C. Multiple-Allele Models

The training module 316 may also construct the presentation models to predict presentation likelihoods of peptides in a multiple-allele setting where two or more MHC alleles are present. In this case, the training module 316 may train the presentation models based on data instances S in the training data 170 generated from cells expressing single MHC alleles, cells expressing multiple MHC alleles, or a combination thereof.

X.C.1. Example 1: Maximum of Per-Allele Models

In one implementation, the training module 316 models the estimated presentation likelihood $u_k$ for peptide $p^k$ in association with a set of multiple MHC alleles H as a function of the presentation likelihoods $u_k^{h\in H}$ determined for each of the MHC alleles h in the set H determined based on cells expressing single-alleles, as described above in conjunction with equations (2)-(11). Specifically, the presentation likelihood $u_k$ can be any function of $u_k^{h\in H}$. In one implementation, as shown in equation (12), the function is the maximum function, and the presentation likelihood $u_k$ can be determined as the maximum of the presentation likelihoods for each MHC allele h in the set H.

$$u_k=Pr(p^k\text{ presented; alleles }H)=\max(u_k^{h\in H}).$$

X.C.2. Example 2.1: Function-of-Sums Models

In one implementation, the training module 316 models the estimated presentation likelihood $u_k$ for peptide $p^k$ by:

$$u_k=Pr(p^k\text{ presented})=f\left(\sum_{h=1}^{m}a_h^k\cdot g_h(x_h^k;\theta_h)\right), \quad (13)$$

where elements $a_h^k$ are 1 for the multiple MHC alleles H associated with peptide sequence $p^k$ and $x_h^k$ denotes the encoded allele-interacting variables for peptide $p^k$ and the corresponding MHC alleles. The values for the set of parameters $\theta_h$ for each MHC allele h can be determined by minimizing the loss function with respect to $\theta_h$, where i is each instance in the subset S of training data 170 generated from cells expressing single MHC alleles and/or cells expressing multiple MHC alleles. The dependency function $g_h$ may be in the form of any of the dependency functions $g_h$ introduced above in sections X.B.1.

According to equation (13), the presentation likelihood that a peptide sequence $p^k$ will be presented by one or more MHC alleles h can be generated by applying the dependency function $g_h(\bullet)$ to the encoded version of the peptide sequence $p^k$ for each of the MHC alleles H to generate the corresponding score for the allele interacting variables. The scores for each MHC allele h are combined, and transformed by the transformation function $f(\bullet)$ to generate the presentation likelihood that peptide sequence $p^k$ will be presented by the set of MHC alleles H.

The presentation model of equation (13) is different from the per-allele model of equation (2), in that the number of associated alleles for each peptide $p^k$ can be greater than 1. In other words, more than one element in $a_h^k$ can have values of 1 for the multiple MHC alleles H associated with peptide sequence $p^k$.

As an example, the likelihood that peptide $p^k$ will be presented by MHC alleles h=2, h=3, among m=4 different identified MHC alleles using the affine transformation functions $g_h(\bullet)$, can be generated by:

$$u_k=f(x_2^k\cdot\theta_2+x_3^k\cdot\theta_3),$$

where $x_2^k$, $x_3^k$ are the identified allele-interacting variables for MHC alleles h=2, h=3, and $\theta_2$, $\theta_3$ are the set of parameters determined for MHC alleles h=2, h=3.

As another example, the likelihood that peptide $p^k$ will be presented by MHC alleles h=2, h=3, among m=4 different identified MHC alleles using the network transformation functions $g_h(\bullet)$, $g_w(\bullet)$, can be generated by:

$$u_k=f(NN_2(x_2^k;\theta_2)+NN_3(x_3^k;\theta_3)),$$

where $NN_2(\bullet)$, $NN_3(\bullet)$ are the identified network models for MHC alleles h=2, h=3, and $\theta_2$, $\theta_3$ are the set of parameters determined for MHC alleles h=2, h=3.

Figure 9:
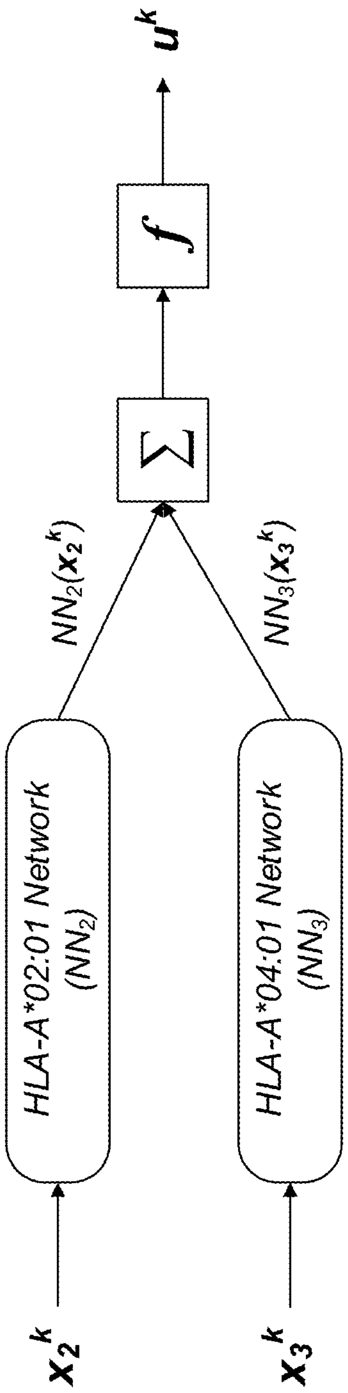
FIG. 9 illustrates generating a presentation likelihood for a peptide in association with MHC alleles using example network models.

FIG. 9 illustrates generating a presentation likelihood for peptide $p^k$ in association with MHC alleles h=2, h=3 using example network models $NN_2(\bullet)$ and $NN_3(\bullet)$. As shown in FIG. 9, the network model $NN_2(\bullet)$ receives the allele-interacting variables $x_3^k$ for MHC allele h=2 and generates the output $NN_2(x_2^k)$ and the network model $NN_3(\bullet)$ receives the allele-interacting variables $x_3^k$ for MHC allele h=3 and generates the output $NN_3(x_3^k)$. The outputs are combined and mapped by function $f(\bullet)$ to generate the estimated presentation likelihood $u_k$.

X.C.3. Example 2.2: Function-of-Sums Models with Allele-Noninteracting Variables In one implementation, the training module 316 incorporates allele-noninteracting variables and models the estimated presentation likelihood $u_k$ for peptide $p^k$ by:

$$u_k = Pr(p^k \text{ presented}) = f\left(g_w(w^k;\theta_w) + \sum_{h=1}^{m} a_h^k \cdot g_h(x_h^k;\theta_h)\right), \tag{14}$$

where $w^k$ denotes the encoded allele-noninteracting variables for peptide $p^k$. Specifically, the values for the set of parameters $\theta_h$ for each MHC allele h and the set of parameters $\theta_w$ for allele-noninteracting variables can be determined by minimizing the loss function with respect to $\theta_h$ and $\theta_w$, where i is each instance in the subset S of training data 170 generated from cells expressing single MHC alleles and/or cells expressing multiple MHC alleles. The dependency function $g_w$ may be in the form of any of the dependency functions $g_w$ introduced above in sections X.B.3.

Thus, according to equation (14), the presentation likelihood that a peptide sequence $p^k$ will be presented by one or more MHC alleles H can be generated by applying the function $g_h(\bullet)$ to the encoded version of the peptide sequence $p^k$ for each of the MHC alleles H to generate the corresponding dependency score for allele interacting variables for each MHC allele h. The function $g_w(\bullet)$ for the allele noninteracting variables is also applied to the encoded version of the allele noninteracting variables to generate the dependency score for the allele noninteracting variables. The scores are combined, and the combined score is transformed by the transformation function $f(\bullet)$ to generate the presentation likelihood that peptide sequence $p^k$ will be presented by the MHC alleles H.

In the presentation model of equation (14), the number of associated alleles for each peptide $p^k$ can be greater than 1. In other words, more than one element in $a_h^k$ can have values of 1 for the multiple MHC alleles H associated with peptide sequence $p^k$.

As an example, the likelihood that peptide $p^k$ will be presented by MHC alleles h=2, h=3, among m=4 different identified MHC alleles using the affine transformation functions $g_h(\bullet)$, $g_w(\bullet)$, can be generated by:

$$u_k=f(w^k\cdot\theta_w+x_2^k\cdot\theta_2+x_3^k\cdot\theta_3),$$

where $w^k$ are the identified allele-noninteracting variables for peptide $p^k$, and $\theta_w$ are the set of parameters determined for the allele-noninteracting variables.

As another example, the likelihood that peptide $p^k$ will be presented by MHC alleles h=2, h=3, among m=4 different identified MHC alleles using the network transformation functions $g_h(\bullet)$, $g_w(\bullet)$, can be generated by:

$$u_k=f(NN_w(w^k;\theta_w)+NN_2(x_2^k;\theta_2)+NN_3(x_3^k;\theta_3))$$

where $w^k$ are the identified allele-interacting variables for peptide $p^k$, and $\theta_w$ are the set of parameters determined for allele-noninteracting variables.

Figure 10:
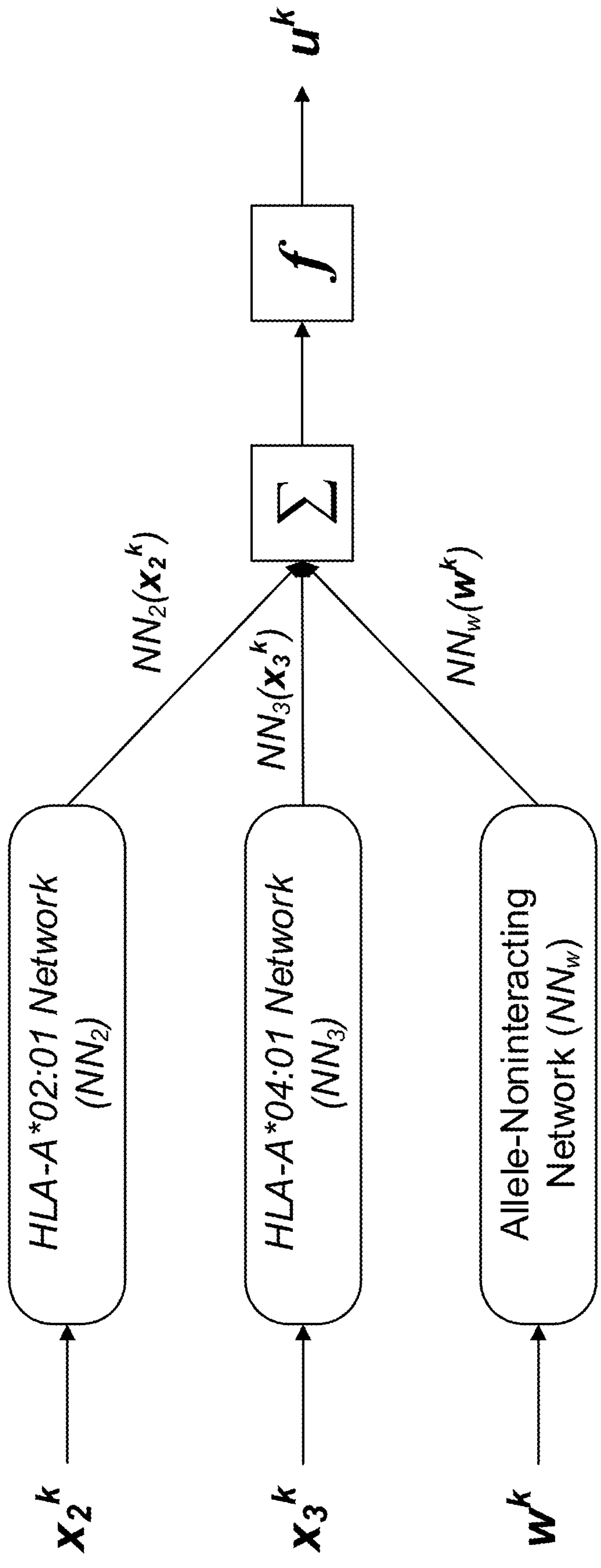
FIG. 10 illustrates generating a presentation likelihood for a peptide in association with MHC alleles using example network models.

FIG. 10 illustrates generating a presentation likelihood for peptide $p^k$ in association with MHC alleles h=2, h=3 using example network models $NN_2(\bullet)$, $NN_3(\bullet)$, and $NN_w(\bullet)$. As shown in FIG. 10, the network model $NN_2(\bullet)$ receives the allele-interacting variables $x_2^k$ for MHC allele h=2 and generates the output $NN_2(x_2^k)$. The network model $NN_3(\bullet)$ receives the allele-interacting variables $x_3^k$ for MHC allele h=3 and generates the output $NN_3(x_3^k)$. The network model $NN_w(\bullet)$ receives the allele-noninteracting variables $w^k$ for peptide $p^k$ and generates the output $NN_w(w^k)$. The outputs are combined and mapped by function $f(\bullet)$ to generate the estimated presentation likelihood $u_k$.

Alternatively, the training module 316 may include allele-noninteracting variables $w^k$ in the prediction by adding the allele-noninteracting variables $w^k$ to the allele-interacting variables $x_h^k$ in equation (15). Thus, the presentation likelihood can be given by:

$$u_k = Pr(p^k \text{ presented}) = f\left(\sum_{h=1}^{m} a_h^k \cdot g_h([x_h^k w^k];\theta_h)\right). \tag{15}$$

X.C.4. Example 3.1: Models Using Implicit Per-Allele Likelihoods

In another implementation, the training module 316 models the estimated presentation likelihood $u_k$ for peptide $p^k$ by:

$$u_k = Pr(p^k \text{ presented}) = r(s(v = [a_1^k \cdot u'_k(\theta) \ldots a_m^k \cdot u'_k{}^m(\theta)])), \quad (16)$$

where elements $a_h^k$ are 1 for the multiple MHC alleles h EH associated with peptide sequence $p^k$, $u'_k{}^h$ is an implicit per-allele presentation likelihood for MHC allele h, vector v is a vector in which element $v_h$ corresponds to $a_h^k \cdot u'_k{}^h$, s(•) is a function mapping the elements of v, and r(•) is a clipping function that clips the value of the input into a given range. As described below in more detail, s(•) may be the summation function or the second-order function, but it is appreciated that in other embodiments, s(•) can be any function such as the maximum function. The values for the set of parameters θ for the implicit per-allele likelihoods can be determined by minimizing the loss function with respect to θ, where i is each instance in the subset S of training data 170 generated from cells expressing single MHC alleles and/or cells expressing multiple MHC alleles.

The presentation likelihood in the presentation model of equation (17) is modeled as a function of implicit per-allele presentation likelihoods $u'_k{}^h$ that each correspond to the likelihood peptide $p^k$ will be presented by an individual MHC allele h. The implicit per-allele likelihood is distinct from the per-allele presentation likelihood of section X.B in that the parameters for implicit per-allele likelihoods can be learned from multiple allele settings, in which direct association between a presented peptide and the corresponding MHC allele is unknown, in addition to single-allele settings. Thus, in a multiple-allele setting, the presentation model can estimate not only whether peptide $p^k$ will be presented by a set of MHC alleles H as a whole, but can also provide individual likelihoods $u'_k{}^{h \in H}$ that indicate which MHC allele h most likely presented peptide $p^k$. An advantage of this is that the presentation model can generate the implicit likelihoods without training data for cells expressing single MHC alleles.

In one particular implementation referred throughout the remainder of the specification, r(⊇) is a function having the range [0, 1]. For example, r(•) may be the clip function:

$$r(z) = \min(\max(z, 0), 1),$$

where the minimum value between z and 1 is chosen as the presentation likelihood $u_k$. In another implementation, r(•) is the hyperbolic tangent function given by:

$$r(z) = \tanh(z)$$

when the values for the domain z is equal to or greater than 0.

X.C.5. Example 3.2: Sum-of-Functions Model

In one particular implementation, s(•) is a summation function, and the presentation likelihood is given by summing the implicit per-allele presentation likelihoods:

$$u_k = Pr(p^k \text{ presented}) = r\left(\sum_{h=1}^{m} a_h^k \cdot u_k'^h(\theta)\right). \quad (17)$$

In one implementation, the implicit per-allele presentation likelihood for MHC allele h is generated by:

$$u'_k{}^h = f(g_h(x_h^k; \theta_h)) \quad (18)$$

such that the presentation likelihood is estimated by:

$$u_k = Pr(p^k \text{ presented}) = r\left(\sum_{h=1}^{m} a_h^k \cdot f(g_h(x_h^k; \theta_h))\right). \quad (19)$$

According to equation (19), the presentation likelihood that a peptide sequence $p^k$ will be presented by one or more MHC alleles H can be generated by applying the function $g_h$(•) to the encoded version of the peptide sequence $p^k$ for each of the MHC alleles H to generate the corresponding dependency score for allele interacting variables. Each dependency score is first transformed by the function $f$(•) to generate implicit per-allele presentation likelihoods $u'_k{}^h$. The per-allele likelihoods $u'_k{}^h$ are combined, and the clipping function may be applied to the combined likelihoods to clip the values into a range [0, 1] to generate the presentation likelihood that peptide sequence $p^k$ will be presented by the set of MHC alleles H. The dependency function $g_h$ may be in the form of any of the dependency functions $g_h$ introduced above in sections X.B.1.

As an example, the likelihood that peptide $p^k$ will be presented by MHC alleles h=2, h=3, among m=4 different identified MHC alleles using the affine transformation functions $g_h$(•), can be generated by:

$$u_k = r(f(x_2^k \cdot \theta_2) + f(x_3^k \cdot \theta_3)),$$

where $x_2^k$, $x_3^k$ are the identified allele-interacting variables for MHC alleles h=2, h=3, and $\theta_2$, $\theta_3$ are the set of parameters determined for MHC alleles h=2, h=3.

As another example, the likelihood that peptide $p^k$ will be presented by MHC alleles h=2, h=3, among m=4 different identified MHC alleles using the network transformation functions $g_h$(•), $g_w$(•), can be generated by:

$$u_k = r(f(NN_2(x_2^k; \theta_2)) + f(NN_3(x_3^k; \theta_3))),$$

where $NN_2$(•), $NN_3$(•) are the identified network models for MHC alleles h=2, h=3, and $\theta_2$, $\theta_3$ are the set of parameters determined for MHC alleles h=2, h=3.

Figure 11:
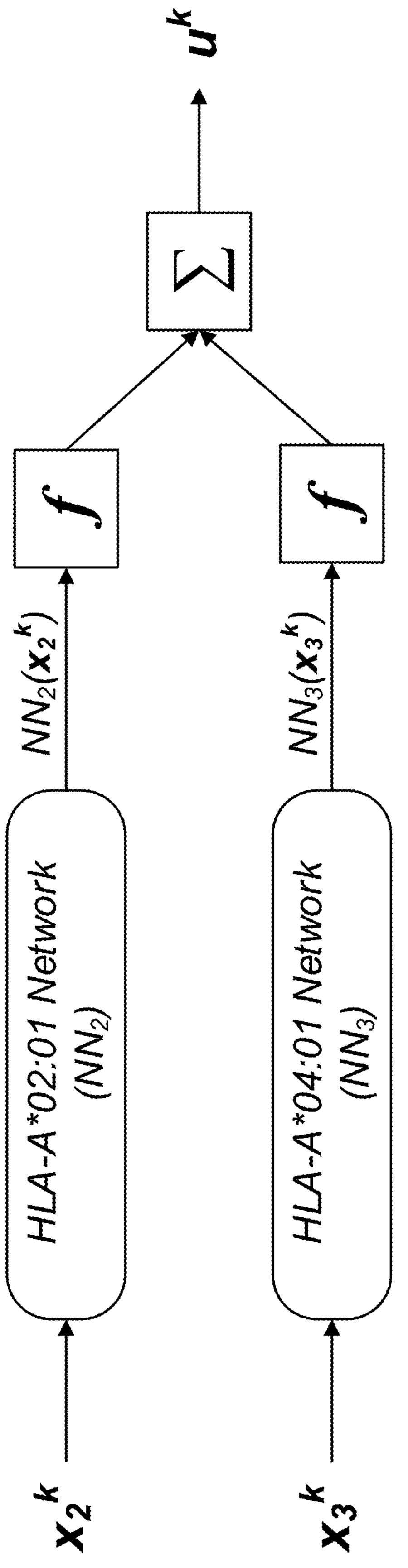
FIG. 11 illustrates generating a presentation likelihood for a peptide in association with MHC alleles using example network models.

FIG. 11 illustrates generating a presentation likelihood for peptide $p^k$ in association with MHC alleles h=2, h=3 using example network models $NN_2$(•) and $NN_3$(•). As shown in FIG. 9, the network model $NN_2$(•) receives the allele-interacting variables $x_3^k$ for MHC allele h=2 and generates the output $NN_2(x_2^k)$ and the network model $NN_3$(•) receives the allele-interacting variables $x_3^k$ for MHC allele h=3 and generates the output $NN_3(x_3^k)$. Each output is mapped by function $f$(•) and combined to generate the estimated presentation likelihood $u_k$.

In another implementation, when the predictions are made for the log of mass spectrometry ion currents, r(•) is the log function and $f$(•) is the exponential function.

X.C.6. Example 3.3: Sum-of-Functions Models with Allele-Noninteracting Variables In one implementation, the implicit per-allele presentation likelihood for MHC allele h is generated by:

$$u'_k{}^h = f(g_h(x_h^k; \theta_h) + g_w(w^k; \theta_w)), \quad (20)$$

such that the presentation likelihood is generated by:

$$u_k = Pr(p^k \text{ presented}) = r\left(\sum_{h=1}^{m} a_h^k \cdot f(g_w(w^k; \theta_w) + g_h(x_h^k; \theta_h))\right), \quad (21)$$

to incorporate the impact of allele noninteracting variables on peptide presentation.

According to equation (21), the presentation likelihood that a peptide sequence $p^k$ will be presented by one or more MHC alleles H can be generated by applying the function $g_h(\bullet)$ to the encoded version of the peptide sequence $p^k$ for each of the MHC alleles H to generate the corresponding dependency score for allele interacting variables for each MHC allele h. The function $g_w(\bullet)$ for the allele noninteracting variables is also applied to the encoded version of the allele noninteracting variables to generate the dependency score for the allele noninteracting variables. The score for the allele noninteracting variables are combined to each of the dependency scores for the allele interacting variables. Each of the combined scores are transformed by the function $f(\bullet)$ to generate the implicit per-allele presentation likelihoods. The implicit likelihoods are combined, and the clipping function may be applied to the combined outputs to clip the values into a range [0,1] to generate the presentation likelihood that peptide sequence $p^k$ will be presented by the MHC alleles H. The dependency function $g_w$ may be in the form of any of the dependency functions $g_w$ introduced above in sections X.B.3.

As an example, the likelihood that peptide $p^k$ will be presented by MHC alleles h=2, h=3, among m=4 different identified MHC alleles using the affine transformation functions $g_h(\bullet)$, $g_w(\bullet)$, can be generated by:

$$u_k=r(f(w^k\cdot\theta_w+x_2{}^k\cdot\theta_2)+f(w^k\cdot\theta_w+x_3{}^k\cdot\theta_3)),$$

where $w^k$ are the identified allele-noninteracting variables for peptide $p^k$, and $\theta_w$ are the set of parameters determined for the allele-noninteracting variables.

As another example, the likelihood that peptide $p^k$ will be presented by MHC alleles h=2, h=3, among m=4 different identified MHC alleles using the network transformation functions $g_h(\bullet)$, $g_w(\bullet)$, can be generated by:

$$u_k=r(f(NN_w(w^k;\theta_w)+NN_2(x_2{}^k;\theta_2))+f(NN_w(w^k;\theta_w)+NN_3(x_3{}^k;\theta 3)))$$

where $w^k$ are the identified allele-interacting variables for peptide $p^k$, and $\theta_w$ are the set of parameters determined for allele-noninteracting variables.

Figure 12:
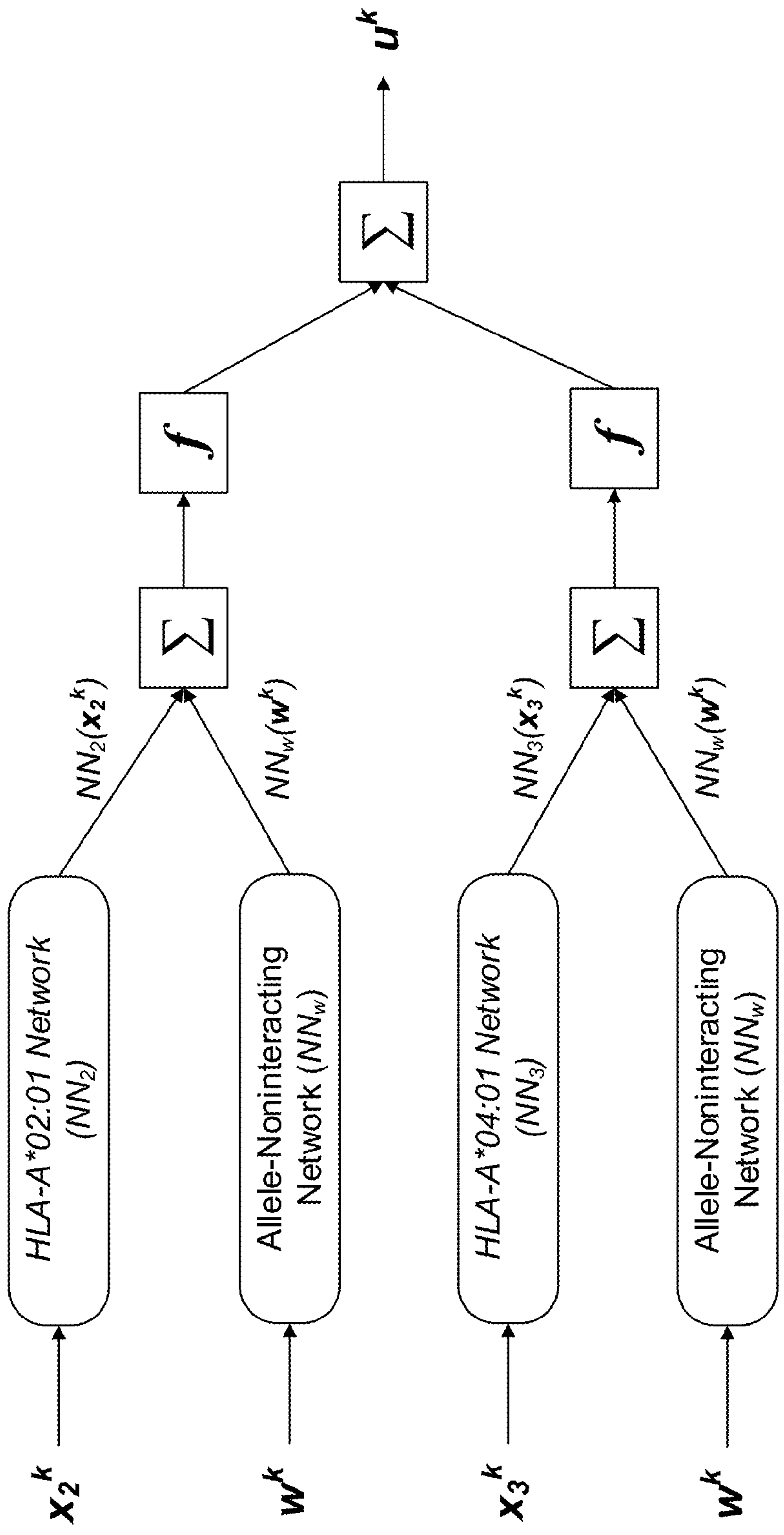
FIG. 12 illustrates generating a presentation likelihood for a peptide in association with MHC alleles using example network models.

FIG. 12 illustrates generating a presentation likelihood for peptide $p^k$ in association with MHC alleles h=2, h=3 using example network models $NN_2(\bullet)$, $NN_3(\bullet)$, and $NN_w(\bullet)$. As shown in FIG. 12, the network model $NN_2(\bullet)$ receives the allele-interacting variables $x_2{}^k$ for MHC allele h=2 and generates the output $NN_2(x_2{}^k)$. The network model $NN_w(\bullet)$ receives the allele-noninteracting variables $w^k$ for peptide $p^k$ and generates the output $NN_w(w^k)$. The outputs are combined and mapped by function $f(\bullet)$. The network model $NN_3(\bullet)$ receives the allele-interacting variables $x_3{}^k$ for MHC allele h=3 and generates the output $NN_3(x_3{}^k)$, which is again combined with the output $NN_w(w^k)$ of the same network model $NN_w(\bullet)$ and mapped by function $f(\bullet)$. Both outputs are combined to generate the estimated presentation likelihood $u_k$.

In another implementation, the implicit per-allele presentation likelihood for MHC allele h is generated by:

$$u'_k{}^h=f(g_h([x_h{}^k w^k];\theta_h)) \tag{22}$$

such that the presentation likelihood is generated by:

$$u_k = Pr(p^k \text{ presented}) = r\left(\sum_{h=1}^{m} a_h^k \cdot f\left(g_h\left(\left[x_h^k w^k\right]; \theta_h\right)\right)\right).$$

X.C.7. Example 4: Second Order Models

In one implementation, s(⊇) is a second-order function, and the estimated presentation likelihood $u_k$ for peptide $p^k$ is given by:

$$u_k = Pr(p^k \text{ presented}) = \sum_{h=1}^{m} a_h^k \cdot u_k'^h(\theta) - \sum_{h=1}^{m} \sum_{j<h} a_h^k \cdot a_j^k \cdot u_k'^h(\theta) \cdot u_k'^j(\theta) \tag{23}$$

where elements $u'_k{}^h$ are the implicit per-allele presentation likelihood for MHC allele h. The values for the set of parameters θ for the implicit per-allele likelihoods can be determined by minimizing the loss function with respect to θ, where i is each instance in the subset S of training data 170 generated from cells expressing single MHC alleles and/or cells expressing multiple MHC alleles. The implicit per-allele presentation likelihoods may be in any form shown in equations (18), (20), and (22) described above.

In one aspect, the model of equation (23) may imply that there exists a possibility peptide $p^k$ will be presented by two MHC alleles simultaneously, in which the presentation by two HLA alleles is statistically independent.

According to equation (23), the presentation likelihood that a peptide sequence $p^k$ will be presented by one or more MHC alleles H can be generated by combining the implicit per-allele presentation likelihoods and subtracting the likelihood that each pair of MHC alleles will simultaneously present the peptide $p^k$ from the summation to generate the presentation likelihood that peptide sequence $p^k$ will be presented by the MHC alleles H.

As an example, the likelihood that peptide $p^k$ will be presented by HLA alleles h=2, h=3, among m=4 different identified HLA alleles using the affine transformation functions $g_h(\bullet)$, can be generated by:

$$u_k=f(x_2{}^k\cdot\theta_2)+f(x_3{}^k\cdot\theta_3)-f(x_2{}^k\cdot\theta_2)\cdot f(x_3{}^k\cdot\theta_3),$$

where $x_2{}^k$, $x_3{}^k$ are the identified allele-interacting variables for HLA alleles h=2, h=3, and $\theta_2$, $\theta_3$ are the set of parameters determined for HLA alleles h=2, h=3.

As another example, the likelihood that peptide $p^k$ will be presented by HLA alleles h=2, h=3, among m=4 different identified HLA alleles using the network transformation functions $g_h(\bullet)$, $g_w(\bullet)$, can be generated by:

$$u_k=f(NN_2(x_2{}^k;\cdot\theta_2))+f(NN_3(x_3{}^k;\theta_3))-f(NN_2(x_2{}^k;\theta_2))\cdot f(NN_3(x_3{}^k;\theta_3)),$$

where $NN_2(\bullet$, $NN_3(\bullet)$ are the identified network models for HLA alleles h=2, h=3, and $\theta_2$, $\theta_3$ are the set of parameters determined for HLA alleles h=2, h=3.

XI.A Example 5: Prediction Module

The prediction module 320 receives sequence data and selects candidate neoantigens in the sequence data using the presentation models. Specifically, the sequence data may be DNA sequences, RNA sequences, and/or protein sequences extracted from tumor tissue cells of patients. The prediction module 320 processes the sequence data into a plurality of peptide sequences $p^k$ having 8-15 amino acids for MHC-I or 6-30 amino acids for MHC-II. For example, the prediction module 320 may process the given sequence "IEFROEIFJEF" (SEQ ID NO: 76) into three peptide sequences having 9 amino acids "IEFROEIFJ," (SEQ ID NO: 77), "EFROEIFJE," (SEQ ID NO: 78), and "FROEIFJEF." (SEQ ID NO: 79) In one embodiment, the prediction module 320 may identify candidate neoantigens that are mutated peptide sequences by comparing sequence data extracted from normal tissue cells of a patient with the sequence data extracted from tumor tissue cells of the patient to identify portions containing one or more mutations.

The presentation module 320 applies one or more of the presentation models to the processed peptide sequences to estimate presentation likelihoods of the peptide sequences. Specifically, the prediction module 320 may select one or more candidate neoantigen peptide sequences that are likely to be presented on tumor HLA molecules by applying the presentation models to the candidate neoantigens. In one implementation, the presentation module 320 selects candidate neoantigen sequences that have estimated presentation likelihoods above a predetermined threshold. In another implementation, the presentation model selects the N candidate neoantigen sequences that have the highest estimated presentation likelihoods (where N is generally the maximum number of epitopes that can be delivered in a vaccine). A vaccine including the selected candidate neoantigens for a given patient can be injected into the patient to induce immune responses.

XI.B. Example 6: Cassette Design Module

XI.B.1 Overview

The cassette design module 324 generates a vaccine cassette sequence based on the v selected candidate peptides for injection into a patient. Specifically, for a set of selected peptides $p^k$, k=1, 2, . . . , v for inclusion in a vaccine of capacity v, the cassette sequence is given by concatenation of a series of therapeutic epitope sequences $p'^k$, k=1, 2, . . . , v that each include the sequence of a corresponding peptide $p^k$. In one embodiment, the cassette design module 324 may concatenate the epitopes directly adjacent to one another. For example, a vaccine cassette C may be represented as:

$$C=[p'^{t1}p'^{t2} \ldots p'^{tv}] \tag{24}$$

where $p'^i$ denotes the i-th epitope of the cassette. Thus, t; corresponds to an index k=1, 2, . . . , v for the selected peptide at the i-th position of the cassette. In another embodiment, the cassette design module 324 may concatenate the epitopes with one or more optional linker sequences in between adjacent epitopes. For example, a vaccine cassette C may be represented as:

$$C=[p'^{t1}l_{(t1,t2)}p'^{t2}l_{(t2,t3)} \ldots l_{(t_{v-1},t_v)}p'^{tv}] \tag{25}$$

where $l_{(ti,tj)}$ denotes a linker sequence placed between the i-th epitope $p'^{ti}$ and the j=i+1-th epitope $p'^{j=i+1}$ of the cassette. The cassette design module 324 determines which of the selected epitopes $p'^k$, k=1, 2, . . . , v are arranged at the different positions of the cassette, as well as any linker sequences placed between the epitopes. A cassette sequence C can be loaded as a vaccine based on any of the methods described in the present specification.

In one embodiment, the set of therapeutic epitopes may be generated based on the selected peptides determined by the prediction module 320 associated with presentation likelihoods above a predetermined threshold, where the presentation likelihoods are determined by the presentation models. However it is appreciated that in other embodiments, the set of therapeutic epitopes may be generated based on any one or more of a number of methods (alone or in combination), for example, based on binding affinity or predicted binding affinity to HLA class I or class II alleles of the patient, binding stability or predicted binding stability to HLA class I or class II alleles of the patient, random sampling, and the like.

In one embodiment, the therapeutic epitopes $p'^k$ may correspond to the selected peptides $p^k$ themselves. In another embodiment, the therapeutic epitopes $p'^k$ may also include C- and/or N-terminal flanking sequences in addition to the selected peptides. For example, an epitope $p'^k$ included in the cassette may be represented as a sequence $[n^k p^k c^k]$ where $c^k$ is a C-terminal flanking sequence attached the C-terminus of the selected peptide $p^k$, and $n^k$ is an N-terminal flanking sequence attached to the N-terminus of the selected peptide $p^k$. In one instance referred throughout the remainder of the specification, the N- and C-terminal flanking sequences are the native N- and C-terminal flanking sequences of the therapeutic vaccine epitope in the context of its source protein. In one instance referred throughout the remainder of the specification, the therapeutic epitope $p'^k$ represents a fixed-length epitope. In another instance, the therapeutic epitope $p'^k$ can represent a variable-length epitope, in which the length of the epitope can be varied depending on, for example, the length of the C- or N-flanking sequence. For example, the C-terminal flanking sequence $c^k$ and the N-terminal flanking sequence $n^k$ can each have varying lengths of 2-5 residues, resulting in 16 possible choices for the epitope $p'^k$.

In one embodiment, the cassette design module 324 generates cassette sequences by taking into account presentation of junction epitopes that span the junction between a pair of therapeutic epitopes in the cassette. Junction epitopes are novel non-self but irrelevant epitope sequences that arise in the cassette due to the process of concatenating therapeutic epitopes and linker sequences in the cassette. The novel sequences of junction epitopes are different from the therapeutic epitopes of the cassette themselves. A junction epitope spanning epitopes $p'^{ti}$ and $p'^{tj}$ may include any epitope sequence that overlaps with both $p'^{ti}$ or $p'^{tj}$ that is different from the sequences of therapeutic epitopes $p'^{ti}$ and $p'^{tj}$ themselves. Specifically, each junction between epitope $p'^{ti}$ and an adjacent epitope $p'^{tj}$ of the cassette with or without an optional linker sequence $l^{(ti,tj)}$ may be associated with $n_{(ti,tj)}$ junction epitopes $e_n^{(ti,tj)}$, n=1, 2, . . . , $n_{(ti,tj)}$. The junction epitopes may be sequences that at least partially overlap with both epitopes $p'^{ti}$ and $p'^{tj}$, or may be sequences that at least partially overlap with linker sequences placed between the epitopes $p'^{ti}$ and $p'^{tj}$. Junction epitopes may be presented by MHC class I, MHC class II, or both.

Figure 38:
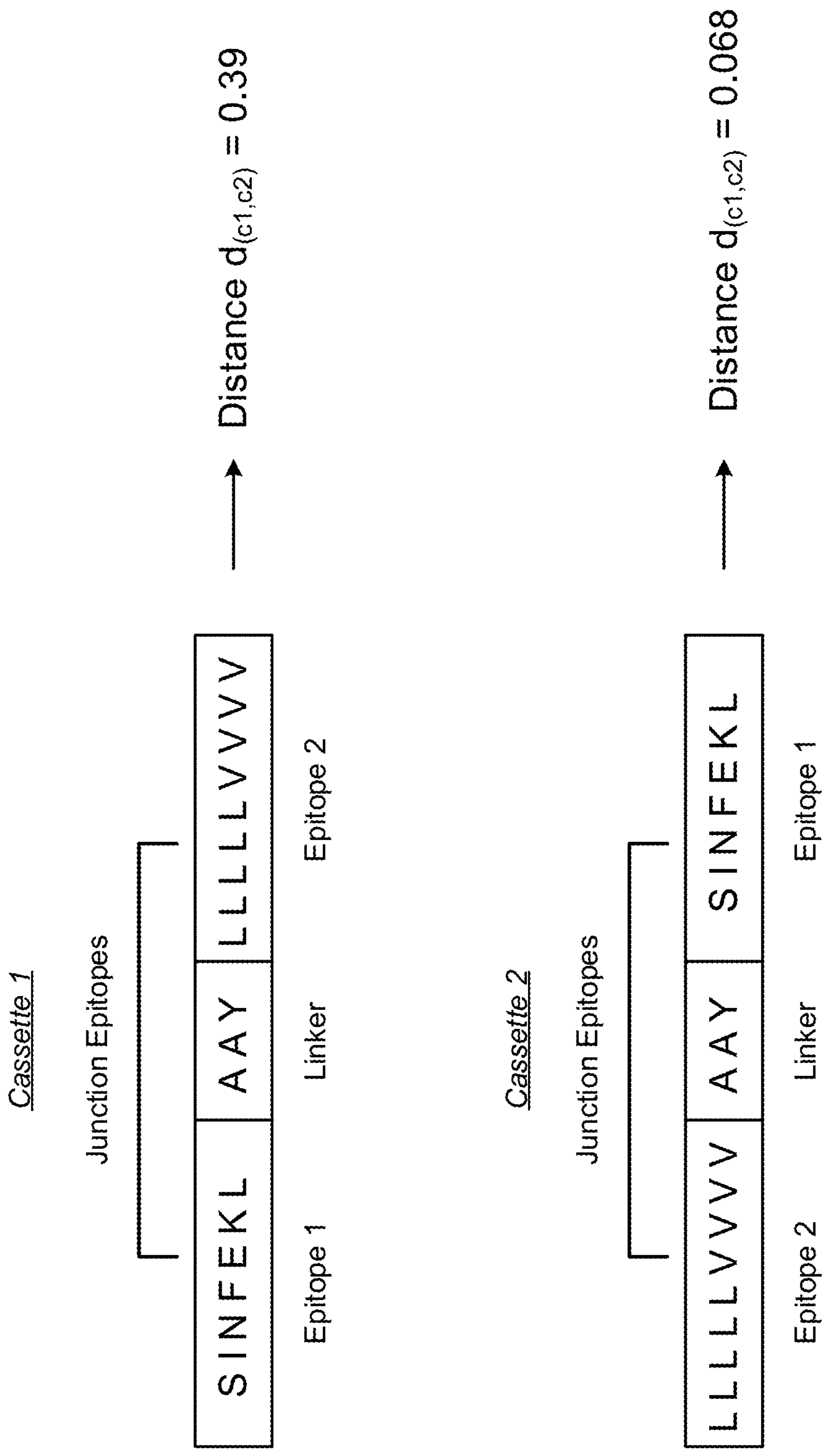
FIG. 38 illustrates determining distance metrics for two example cassette sequences. Figure discloses SEQ ID NOS 191 and 192, respectively, in order of appearance.

FIG. 38 shows two example cassette sequences, cassette 1 ($C_1$) and cassette 2 ($C_2$). Each cassette has a vaccine capacity of v=2, and includes therapeutic epitopes $p'^{t1}=p^1$=SINFEKL (SEQ ID NO: 80) and $p'^{t2}=p^2$=LLLLLVVVV (SEQ ID NO: 81), and a linker sequence $l^{(t1-t2)}$=AAY in between the two epitopes. Specifically, the sequence of cassette $C_1$ is given by $[p^1\ l^{(t1,t2)}\ p^2]$, while the sequence of cassette $C_2$ is given by $[p^2\ l^{(t1,t2)}\ p^1]$. Example junction epitopes $e_n^{(1,2)}$ of cassette $C_1$ may be sequences such as EKLAAYLLL (SEQ ID NO: 82), KLAAYLLLLL (SEQ ID NO: 83), and FEKLAAYL (SEQ ID NO: 84) that span across both epitopes $p'^1$ and $p'^2$ in the cassette, and may be sequences such as AAYLLLLL (SEQ ID NO: 85) and YLLLLLVVV (SEQ ID NO: 86) that span across the linker sequence and a single selected epitope in the cassette. Similarly, example junction epitopes $e_m^{(2,1)}$ of cassette $C_2$ may be sequences such as VVVVAAYSIN (SEQ ID NO: 87), VVVVAAY (SEQ ID NO: 88), and AYSINFEK (SEQ ID NO: 89). Although both cassettes involve the same set of sequences $p^1$, $l^{(c1,c2)}$, and $p^2$, the set of junction epitopes that are identified are different depending on the ordered sequence of the therapeutic epitopes within the cassette.

In one embodiment, the cassette design module 324 generates a cassette sequence that reduces the likelihood that junction epitopes are presented in the patient. Specifically, when the cassette is injected into the patient, junction epitopes have the potential to be presented by HLA class I or HLA class II alleles of the patient, and stimulate a CD8 or CD4 T-cell response, respectively. Such reactions are often times undesirable because T-cells reactive to the junction epitopes have no therapeutic benefit, and may diminish the immune response to the selected therapeutic epitopes in the cassette by antigenic competition.[76]

In one embodiment, the cassette design module 324 iterates through one or more candidate cassettes, and determines a cassette sequence for which a presentation score of junction epitopes associated with that cassette sequence is below a numerical threshold. The junction epitope presentation score is a quantity associated with presentation likelihoods of the junction epitopes in the cassette, and a higher value of the junction epitope presentation score indicates a higher likelihood that junction epitopes of the cassette will be presented by HLA class I or HLA class II or both.

In one embodiment, the cassette design module 324 may determine a cassette sequence associated with the lowest junction epitope presentation score among the candidate cassette sequences. In one instance, the presentation score for a given cassette sequence C is determined based on a set of distance metrics $d(e_n^{(ti,tj)}, n=1, 2, \ldots, n_{(ti,tj)})=d_{(ti,tj)}$ each associated with a junction in the cassette C. Specifically, a distance metric $d_{(ti,tj)}$ specifies a likelihood that one or more of the junction epitopes spanning between the pair of adjacent therapeutic epitopes $p^{ti}$ and $p^{tj}$ will be presented. The junction epitope presentation score for cassette C can then be determined by applying a function (e.g., summation, statistical function) to the set of distance metrics for the cassette C. Mathematically, the presentation score is given by:

$$\text{score}=h(d_{(t_1,t_2)}, d_{(t_2,t_3)}, \ldots, d_{(t_{v-1},t_v)}) \quad (26)$$

where h(•) is some function mapping the distance metrics of each junction to a score. In one particular instance referred throughout the remainder of the specification, the function h(•) is the summation across the distance metrics of the cassette.

The cassette design module 324 may iterate through one or more candidate cassette sequences, determine the junction epitope presentation score for the candidate cassettes, and identify an optimal cassette sequence associated with a junction epitope presentation score below the threshold. In one particular embodiment referred throughout the remainder of the specification, the distance metric d(•) for a given junction may be given by the sum of the presentation likelihoods or the expected number presented junction epitopes as determined by the presentation models described in sections VII and VIII of the specification. However, it is appreciated that in other embodiments, the distance metric may be derived from other factors alone or in combination with the models like the one exemplified above, where these other factors may include deriving the distance metric from any one or more of (alone or in combination): HLA binding affinity or stability measurements or predictions for HLA class I or HLA class II, and a presentation or immunogenicity model trained on HLA mass spectrometry or T-cell epitope data, for HLA class I or HLA class II. In one embodiment, the distance metric may combine information about HLA class I and HLA class II presentation. For example, the distance metric could be the number of junction epitopes predicted to bind any of the patient's HLA class I or HLA class II alleles with binding affinity below a threshold. In another example, the distance metric could be the expected number of epitopes predicted to be presented by any of the patient's HLA class I or HLA class II alleles.

The cassette design module 324 may further check the one or more candidate cassette sequences to identify if any of the junction epitopes in the candidate cassette sequences are self-epitopes for a given patient for whom the vaccine is being designed. To accomplish this, the cassette design module 324 checks the junction epitopes against a known database such as BLAST. In one embodiment, the cassette design module may be configured to design cassettes that avoid junction self-epitopes by setting the distance metric $d_{(ti,tj)}$ to a very large value (e.g., 100) for pairs of epitopes $t_i,t_j$ where contatenating epitope $t_i$ to the N-terminus of epitope t; results in the formation of a junction self-epitope.

Returning to the example in FIG. 38 the cassette design module 324 determines (for example) a distance metric $d_{(t1,t2)}=d_{(1,2)}=0.39$ for the single junction $(t_1,t_2)$ in cassette $C_1$ given by the summation of presentation likelihoods of all possible junction epitopes $e_n^{(t1,t2)}=e_n^{(1,2)}$ having lengths, for example, from 8 to 15 amino acids for MHC class I, or 6-30 amino acids for MHC class II. Since no other junctions are present in cassette $C_1$, the junction epitope presentation score, which is a summation across the distance metrics for cassette $C_1$, is also given by 0.39. The cassette design module 324 also determines a distance metric $d_{(t1,t2)}=d_{(2,1)}=0.068$ for the single junction in cassette $C_2$ given by the summation of presentation likelihoods of all possible junction epitopes $e_n^{(t1,t2)}=e_n^{(2,1)}$ having lengths from 8 to 15 for MHC class I, or 9-30 amino acids for MHC class II. In this example, the junction epitope presentation score for cassette $C_2$ is also given by the distance metric of the single junction 0.068. The cassette design module 324 outputs the cassette sequence of $C_2$ as the optimal cassette since the junction epitope presentation score is lower than the cassette sequence of $C_1$.

In some cases, the cassette design module 324 can perform a brute force approach and iterates through all or most possible candidate cassette sequences to select the sequence with the smallest junction epitope presentation score. However, the number of such candidate cassettes can be prohibitively large as the capacity of the vaccine v increases. For example, for a vaccine capacity of v=20 epitopes, the cassette design module 324 has to iterate through $\sim 10^{18}$ possible candidate cassettes to determine the cassette with the lowest junction epitope presentation score. This determination may be computationally burdensome (in terms of computational processing resources required), and sometimes intractable, for the cassette design module 324 to complete within a reasonable amount of time to generate the vaccine for the patient. Moreover, accounting for the possible junction epitopes for each candidate cassette can be even more burdensome. Thus, the cassette design module 324 may select a cassette sequence based on ways of iterating through a number of candidate cassette sequences that are significantly smaller than the number of candidate cassette sequences for the brute force approach.

In one embodiment, the cassette design module 324 generates a subset of randomly or at least pseudo-randomly generated candidate cassettes, and selects the candidate cassette associated with a junction epitope presentation score below a predetermined threshold as the cassette sequence. Additionally, the cassette design module 324 may select the candidate cassette from the subset with the lowest junction epitope presentation score as the cassette sequence. For example, the cassette design module 324 may generate a subset of ~1 million candidate cassettes for a set of v=20 selected epitopes, and select the candidate cassette with the smallest junction epitope presentation score. Although generating a subset of random cassette sequences and selecting a cassette sequence with a low junction epitope presentation score out of the subset may be sub-optimal relative to the brute force approach, it requires significantly less computational resources thereby making its implementation technically feasible. Further, performing the brute force method as opposed to this more efficient technique may only result in a minor or even negligible improvement in junction epitope presentation score, thus making it not worthwhile from a resource allocation perspective.

In another embodiment, the cassette design module 324 determines an improved cassette configuration by formulating the epitope sequence for the cassette as an asymmetric traveling salesman problem (TSP). Given a list of nodes and distances between each pair of nodes, the TSP determines a sequence of nodes associated with the shortest total distance to visit each node exactly once and return to the original node. For example, given cities A, B, and C with known distances between each other, the solution of the TSP generates a closed sequence of cities, for which the total distance traveled to visit each city exactly once is the smallest among possible routes. The asymmetric version of the TSP determines the optimal sequence of nodes when the distance between a pair of nodes are asymmetric. For example, the "distance" for traveling from node A to node B may be different from the "distance" for traveling from node B to node A.

The cassette design module 324 determines an improved cassette sequence by solving an asymmetric TSP, in which each node corresponds to a therapeutic epitope $p'^{k}$. The distance from a node corresponding to epitope $p'^{k}$ to another node corresponding to epitope $p'^{m}$ is given by the junction epitope distance metric $d_{(k,m)}$, while the distance from the node corresponding to the epitope $p'^{m}$ to the node corresponding to epitope $p'^{k}$ is given by the distance metric $d_{(m,k)}$ that may be different from the distance metric $d_{(k,m)}$. By solving for an improved optimal cassette using an asymmetric TSP, the cassette design module 324 can find a cassette sequence that results in a reduced presentation score across the junctions between epitopes of the cassette. The solution of the asymmetric TSP indicates a sequence of therapeutic epitopes that correspond to the order in which the epitopes should be concatenated in a cassette to minimize the junction epitope presentation score across the junctions of the cassette. Specifically, given the set of therapeutic epitopes k=1, 2, . . . , v, the cassette design module 324 determines the distance metrics $d_{(k,m)}$, k,m=1, 2, . . . , v for each possible ordered pair of therapeutic epitopes in the cassette. In other words, for a given pair k, m of epitopes, both the distance metric $d_{(k,m)}$ for concatenating therapeutic epitope $p'^{m}$ after epitope $p'^{k}$ and the distance metric $d_{(m,k)}$ for concatenating therapeutic epitope $p'^{k}$ after epitope $p'^{m}$ is determined, since these distance metrics may be different from each other.

In one embodiment, the cassette design module 324 solves the asymmetric TSP through an integer linear programming problem. Specifically, the cassette design module 324 generates a (v+1)×(v+1) path matrix P given by the following:

$$P = \begin{bmatrix} 0 & 0^{1\times v} \\ 0^{v\times 1} & D \end{bmatrix}. \tag{26}$$

The v×v matrix D is an asymmetric distance matrix, where each element D(k,m), k=1, 2, . . . , v; m=1, 2, . . . , v corresponds to the distance metric for a junction from epitope $p'^{k}$ to epitope $p'^{m}$. Rows k=2, . . . , v of P correspond to nodes of the original epitopes, while row 1 and column 1 corresponds to a "ghost node" that is at zero distance from all other nodes. The addition of the "ghost node" to the matrix encodes the notion that the vaccine cassette is linear rather than circular, so there is no junction between the first and last epitopes. In other words, the sequence is not circular, and the first epitope is not assumed to be concatenated after the last epitope in the sequence. Let $x_{km}$ denote a binary variable whose value is 1 if there is a directed path (i.e., an epitope-epitope junction in the cassette) where epitope $p'^{k}$ is concatenated to the N-terminus of epitope $p'^{m}$ and 0 otherwise. In addition, let E denote the set of all v therapeutic vaccine epitopes, and let $S \subset E$ denote a subset of epitopes. For any such subset S, let out(S) denote the number of epitope-epitope junctions $x_{km}=1$ where k is an epitope in S and m is an epitope in E\S. Given a known path matrix P, the cassette design module 324 finds a path matrix X that solves the following integer linear programming problem:

$$\min_x \sum_{k=1}^{v+1} \sum_{k\neq m, m=1}^{v+1} P_{km} \cdot x_{km} \tag{27}$$

in which $P_{km}$ denotes element P(k,m) of the path matrix P, subject to the following constraints:

$$\sum_{k=1}^{v+1} x_{km} = 1, \quad m = 1, 2, \ldots, v+1$$

$$\sum_{m=1}^{v+1} x_{km} = 1, \quad k = 1, 2, \ldots, v+1$$

$$x_{kk} = 0, \quad k = 1, 2, \ldots, v+1$$

$$\text{out}(S) \geq 1, S \subset E, 2 \leq |S| \leq |V|/2$$

The first two constraints guarantee that each epitope appears exactly once in the cassette. The last constraint ensures that the cassette is connected. In other words, the cassette encoded by x is a connected linear protein sequence.

The solutions for $x_{km}$, k,m=1, 2, . . . , v+1 in the integer linear programming problem of equation (27) indicates the closed sequence of nodes and ghost nodes that can be used to infer one or more sequences of therapeutic epitopes for the cassette that lower the presentation score of junction epitopes. Specifically, a value of $x_{km}=1$ indicates that a "path" exists from node k to node m, or in other words, that therapeutic epitope $p'^{m}$ should be concatenated after therapeutic epitope $p'^{k}$ in the improved cassette sequence. A solution of $x_{km}=0$ indicates that no such path exists, or in other words, that therapeutic epitope $p'^{m}$ should not be concatenated after therapeutic epitope $p'^{k}$ in the improved cassette sequence. Collectively, the values of $x_{km}$ in the integer programming problem of equation (27) represent a sequence of nodes and the ghost node, in which the path enters and exists each node exactly once. For example, the values of $x_{ghost,1}=1$, $x_{13}=1$, $x_{32}=1$, and $x_{2,ghost}=1$ (0 otherwise) may indicate a sequence ghost→1→3→2→ghost of nodes and ghost nodes.

Once the sequence has been solved for, the ghost nodes are deleted from the sequence to generate a refined sequence with only the original nodes corresponding to therapeutic epitopes in the cassette. The refined sequence indicates the order in which selected epitopes should be concatenated in the cassette to improve the presentation score. For example, continuing from the example in the previous paragraph, the ghost node may be deleted to generate a refined sequence 1→3→2. The refined sequence indicates one possible way to concatenate epitopes in the cassette, namely $p^1 \rightarrow p^3 \rightarrow p^2$.

In one embodiment, when the therapeutic epitopes $p'^k$ are variable-length epitopes, the cassette design module 324 determines candidate distance metrics corresponding to different lengths of the therapeutic epitopes $p'^k$ and $p'^m$, and identifies the distance metric $d_{(k,m)}$ as the smallest candidate distance metric. For example, epitopes $p'^k=[n^k\ p^k\ c^k]$ and $p'^m=[n^m\ p^m\ c^m]$ may each include a corresponding N- and C-terminal flanking sequence that can vary from (in one embodiment) 2-5 amino acids. Thus, the junction between epitopes $p'^k$ and $p'^m$ is associated with 16 different sets of junction epitopes based on the 4 possible length values of $n^k$ and the 4 possible length values of $c^m$ that are placed in the junction. The cassette design module 324 may determine candidate distance metrics for each set of junction epitopes, and determine the distance metric $d_{(k,m)}$ as the smallest value. The cassette design module 324 can then construct the path matrix P and solve for the integer linear programming problem in equation (27) to determine the cassette sequence.

Compared to the random sampling approach, solving for the cassette sequence using the integer programming problem requires determination of $v \times (v-1)$ distance metrics each corresponding to a pair of therapeutic epitopes in the vaccine. A cassette sequence determined through this approach can result in a sequence with significantly less presentation of junction epitopes while potentially requiring significantly less computational resources than the random sampling approach, especially when the number of generated candidate cassette sequences is large.

XI.B.2. Comparison of Junction Epitope Presentation for Cassette Sequences Generated by Random Sampling vs. Asymmetric TSP Two cassette sequences including v=20 therapeutic epitopes were generated by random sampling 1,000,000 permutations (cassette sequence $C_1$), and by solving the integer linear programming problem in equation (27) (cassette sequence $C_2$). The distance metrics, and thus, the presentation score was determined based on the presentation model described in equation (14), in which $f$ is the sigmoid function, $x_h^i$ is the sequence of peptide $p^i$, $g_h(\bullet)$ is the neural network function, w includes the flanking sequence, the log transcripts per kilobase million (TPM) of peptide $p^i$, the antigenicity of the protein of peptide $p^i$, and the sample ID of origin of peptide $p^i$, and $g_w(\bullet)$ of the flanking sequence and the log TPM are neural network functions, respectively. Each of the neural network functions for $g_h(\bullet)$ included one output node of a one-hidden-layer multilayer perceptron (MLP) with input dimensions 231 (11 residues×21 characters per residue, including pad characters), width 256, rectified linear unit (ReLU) activations in the hidden layer, linear activations in the output layer, and one output node per HLA allele in the training data set. The neural network function for the flanking sequence was a one hidden-layer MLP with input dimension 210 (5 residues of N-terminal flanking sequence+5 residues of C-terminal flanking sequence×21 characters per residue, including the pad characters), width 32, ReLU activations in the hidden layer and linear activation in the output layer. The neural network function for the RNA log TPM was a one hidden layer MLP with input dimension 1, width 16, ReLU activations in the hidden layer and linear activation in the output layer. The presentation models were constructed for HLA alleles HLA-A*02:04, HLA-A*02:07, HLA-B*40:01, HLA-B*40:02, HLA-C*16:02, and HLA-C*16:04. The presentation score indicating the expected number of presented junction epitopes of the two cassette sequences were compared. Results showed that the presentation score for the cassette sequence generated by solving the equation of (27) was associated with a ~4 fold improvement over the presentation score for the cassette sequence generated by random sampling.

Specifically, the v=20 epitopes were given by:

$p'^1$ = (SEQ ID NO: 90)
YNYSYWISIFAHTMWYNIWHVQWNK $p'^2$ = (SEQ ID NO: 91)
IEALPYVFLQDQFELRLLKGEQGNN $p'^3$ = (SEQ ID NO: 92)
DSEETNTNYLHYCHFHWTWAQQTTV $p'^4$ = (SEQ ID NO: 93)
GMLSQYELKDCSLGFSWNDPAKYLR $p'^5$ = (SEQ ID NO: 94)
VRIDKFLMYVWYSAPFSAYPLYQDA $p'^6$ = (SEQ ID NO: 95)
CVHIYNNYPRMLGIPFSVMVSGFAM $p'^7$ = (SEQ ID NO: 96)
FTFKGNIWIEMAGQFERTWNYPLSL $p'^8$ = (SEQ ID NO: 97)
ANDDTPDFRKCYIEDHSFRFSQTMN $p'^9$ = (SEQ ID NO: 98)
AAQYIACMVNRQMTIVYHLTRWGMK $p'^{10}$ = (SEQ ID NO: 99)
KYLKEFTQLLTFVDCYMWITFCGPD $p'^{11}$ = (SEQ ID NO: 100)
AMHYRTDIHGYWIEYRQVDNQMWNT $p'^{12}$ = (SEQ ID NO: 101)
THVNEHQLEAVYRFHOVHCRFPYEN $p'^{13}$ = (SEQ ID NO: 102)
QTFSECLFFHCLKVWNNVKYAKSLK $p'^{14}$ = (SEQ ID NO: 103)
SFSSWHYKESHIALLMSPKKNHNNT $p'^{15}$ = (SEQ ID NO: 104)
ILDGIMSRWEKVCTRQTRYSYCQCA

-continued p'[16] =

(SEQ ID NO: 105)
YRAAQMSKWPNKYFDFPEFMAYMPI p'[17] =

(SEQ ID NO: 106)
PRPGMPCQHHNTHGLNDRQAFDDFV p'[18] =

(SEQ ID NO: 107)
HNIISDETEVWEQAPHITWVYMWCR p'[19] =

(SEQ ID NO: 108)
AYSWPVVPMKWIPYRALCANHPPGT p'[20] =

(SEQ ID NO: 109)
HVMPHVAMNICNWYEFLYRISHIGR.

In the first example, 1,000,000 different candidate cassette sequences were randomly generated with the 20 therapeutic epitopes. The presentation score was generated for each of the candidate cassette sequences. The candidate cassette sequence identified to have the lowest presentation score was:

(SEQ ID NO: 110)
$C_1$ = THVNEHQLEAVYRFHQVHCRFPYENAMHYQMWNTYRAAQMSKWPN
KYFDFPEFMAYMPICVHIYNNYPRMLGIPFSVMVSGFAMAYSWPVVPMKW
IPYRALCANHPPGTANDDTPDFRKCYIEDHSFRFSQTMNIEALPYVFLQD
QFELRLLKGEQGNNDSEETNTNYLHYCHFHWTWAQQTTVILDGIMSRWEK
VCTRQTRYSYCQCAFTFKGNIWIEMAGQFERTWNYPLSLSFSSWHYKESH
IALLMSPKKNHNNTQTFSECLFFHCLKVWNNVKYAKSLKHVMPHVAMNIC
NWYEFLYRISHIGRHNIISDETEVWEQAPHITWVYMWCRVRIDKFLMYVW
YSAPFSAYPLYQDAKYLKEFTQLLTFVDCYMWITFCGPDAAQYIACMVNR
QMTIVYHLTRWGMKYNYSYWISIFAHTMWYNIWHVQWNKGMLSQYELKDC
SLGFSWNDPAKYLRPRPGMPCQHHNTHGLNDRQAFDDFV with a presentation score of 6.1 expected number of presented junction epitopes. The median presentation score of the 1,000,000 random sequences was 18.3. The experiment shows that the expected number of presented junction epitopes can be significantly reduced by identifying a cassette sequence among randomly sampled cassettes.

In the second example, a cassette sequence $C_2$ was identified by solving the integer linear programming problem in equation (27). Specifically, the distance metric of each potential junction between a pair of therapeutic epitopes was determined. The distance metrics were used to solve for the solution to the integer programming problem. The cassette sequence identified by this approach was:

(SEQ ID NO: 111)
$C_2$ = IEALPYVFLQDQFELRLLKGEQGNNILDGIMSRWEKVCTRQTRYS
YCQCAHVMPHVAMNICNWYEFLYRISHIGRTHVNEHQLEAVYRFHQVHCR
FPYENFTFKGNIWIEMAGQFERTWNYPLSLAMHYQMWNTSFSSWHYKESH
IALLMSPKKNHNNTVRIDKFLMYVWYSAPFSAYPLYQDAQTFSECLFFHC
LKVWNNVKYAKSLKYRAAQMSKWPNKYFDFPEFMAYMPIAYSWPVVPMKW

-continued

IPYRALCANHPPGTCVHIYNNYPRMLGIPFSVMVSGFAMHNIISDETEVW
EQAPHITWVYMWCRAAQYIACMVNRQMTIVYHLTRWGMKYNYSYWISIFA
HTMWYNIWHVQWNKGMLSQYELKDCSLGFSWNDPAKYLRKYLKEFTQLLT
FVDCYMWITFCGPDANDDTPDFRKCYIEDHSFRFSQTMNDSEETNTNYLH
YCHFHWTWAQQTTVPRPGMPCQHHNTHGLNDRQAFDDFV with a presentation score of 1.7. The presentation score of cassette sequence $C_2$ showed a ~4 fold improvement over the presentation score of cassette sequence $C_1$, and a ~11 fold improvement over the median presentation score of the 1,000,000 randomly generated candidate cassettes. The runtime for generating cassette $C_1$ was 20 seconds on a single thread of a 2.30 GHz Intel Xeon E5-2650 CPU. The runtime for generating cassette $C_2$ was 1 second on a single thread of the same CPU. Thus in this example, the cassette sequence identified by solving the integer programming problem of equation (27) produces a ~4-fold better solution at 20-fold reduced computational cost.

The results show that the integer programming problem can potentially provide a cassette sequence with a lower number of presented junction epitopes than one identified from random sampling, potentially with less computation resources.

XI.B.3. Comparison of Junction Epitope Presentation for Cassette Sequence Selection Generated by MHCflurry and the Presentation Model In this example, cassette sequences including v=20 therapeutic epitopes were selected based off tumor/normal exome sequencing, tumor transcriptome sequencing and HLA typing of a lung cancer sample were generated by random sampling 1,000,000 permutations, and by solving the integer linear programming problem in equation (27). The distance metrics, and thus, the presentation score were determined based on the number of junction epitopes predicted by MHCflurry, an HLA-peptide binding affinity predictor, to bind the patient's HLAs with affinity below a variety of thresholds (e.g., 50-1000 nM, or higher, or lower). In this example, the 20 nonsynoymous somatic mutations chosen as therapeutic epitopes were selected from among the 98 somatic mutations identified in the tumor sample by ranking the mutations according to the presentation model in Section XI.B above. However, it is appreciated that in other embodiments, the therapeutic epitopes may be selected based on other criteria; such as those based stability, or combinations of criteria such as presentation score, affinity, and so on. In addition, it is appreciated that the criteria used for prioritizing therapeutic epitopes for inclusion in the vaccine need not be the same as the criteria used for determining the distance metric D(k,m) used in the cassette design module 324.

The patient's HLA class I alleles were HLA-A*01:01, HLA-A*03:01, HLA-B*07:0 2, HLA-B*35:03, HLA-C*07:02, HLA-C*14:02.

Specifically in this example, the v=20 therapeutic epitopes were (SEQ ID NO: 112)
SSTPYLYYGTSSVSYQFPMVPGGDR (SEQ ID NO: 113)
EMAGKIDLLRDSYIFQLFWREAAEP -continued (SEQ ID NO: 114)
ALKQRTWQALAHKYNSQPSVSLRDF (SEQ ID NO: 115)
VSSHSSQATKDSAVGLKYSASTPVR (SEQ ID NO: 116)
KEAIDAWAPYLPEYIDHVISPGVTS (SEQ ID NO: 117)
SPVITAPPSSPVFDTSDIRKEPMNI (SEQ ID NO: 118)
PAEVAEQYSEKLVYMPHTFFIGDHA (SEQ ID NO: 119)
MADLDKLNIHSIIQRLLEVRGS (SEQ ID NO: 120)
AAAYNEKSGRITLLSLLFQKVFAQI (SEQ ID NO: 121)
KIEEVRDAMENEIRTQLRRQAAAHT (SEQ ID NO: 122)
DRGHYVLCDFGSTTNKFQNPQTEGV (SEQ ID NO: 123)
QVDNRKAEAEEAIKRLSYISQKVSD (SEQ ID NO: 124)
CLSDAGVRKMTAAVRVMKRGLENLT (SEQ ID NO: 125)
LPPRSLPSDPFSQVPASPQSQSSSQ (SEQ ID NO: 126)
ELVLEDLQDGDVKMGGSFRGAFSNS (SEQ ID NO: 127)
VTMDGVREEDLASFSLRKRWESEPH (SEQ ID NO: 128)
IVGVMFFERAFDEGADAIYDHINEG (SEQ ID NO: 129)
TVTPTPTPTGTQSPTPTPITTTTTV (SEQ ID NO: 130)
QEEMPPRPCGGHTSSSLPKSHLEPS (SEQ ID NO: 131)
PNIQAVLLPKKTDSHHKAKGK Results from this example in the table below compare the number of junction epitopes predicted by MHCflurry to bind the patient's HLAs with affinity below the value in the threshold column (where nM stands for nanoMolar) as found via three example methods. For the first method, the optimal cassette found via the traveling salesman problem (ATSP) formulation described above with is run-time. For the second method, the optimal cassette as determined by taking the best cassette found after 1 million random samples. For the third method, the median number of junction epitopes was found in the 1 million random samples.

| Threshold (nM) | ATSP # Binding Junction Epitopes | Random Sampling # Binding Junction Epitopes | Median # Binding Junction Epitopes |
|---|---|---|---|
| 50 | 0 | 0 | 3 |
| 100 | 0 | 0 | 7 |
| 150 | 0 | 1 | 12 |
| 500 | 15 | 26 | 55 |
| 1000 | 68 | 91 | 131 |

The results of this example illustrate that any one of a number of criteria may be used to identify whether or not a given cassette design meets design requirements. Specifically, as demonstrated by prior examples, the selected cassette sequence out of many candidates may be specified by the cassette sequence having a lowest junction epitope presentation score, or at least such a score below an identified threshold. This example represents that another criteria, such as binding affinity, may be used to specify whether or not a given cassette design meets design requirements. For this criteria, a threshold binding affinity (e.g., 50-1000, or greater or lower) may be set specifying that the cassette design sequence should have fewer than some threshold number of junction epitopes above the threshold (e.g., 0), and any one of a number of methods may be used (e.g., methods one through three illustrated in the table) can be used to identify if a given candidate cassette sequence meets those requirements. These example methods further illustrate that depending on the method used, the thresholds may need to be set differently. Other criteria may be envisioned, such as those based stability, or combinations of criteria such as presentation score, affinity, and so on.

In another example, the same cassettes were generated using the same HLA type and 20 therapeutic epitopes from earlier in this section (XI.C), but instead of using distance metrics based off binding affinity prediction, the distance metric for epitopes m, k was the number of peptides spanning the m to k junction predicted to be presented by the patient's HLA class I alleles with probability of presentation above a series of thresholds (between probability of 0.005 and 0.5, or higher, or lower), where the probabilities of presentation were determined by the presentation model in Section XI.B above. This example further illustrates the breadth of criteria that may be considered in identifying whether a given candidate cassette sequence meets design requirements for use in the vaccine.

| Threshold (probability) | ATSP # Junction Epitopes | Random Sampling # Junction Epitopes | Median # Junction Epitopes |
|---|---|---|---|
| 0.005 | 58 | 79 | 118 |
| 0.01 | 39 | 59 | 93 |
| 0.05 | 7 | 33 | 47 |
| 0.1 | 5 | 14 | 35 |
| 0.2 | 1 | 8 | 25 |
| 0.5 | 0 | 2 | 14 |

The examples above have identified that the criteria for determining whether a candidate cassette sequence may vary by implementation. Each of these examples has illustrated that the count of the number of junction epitopes falling above or below the criteria may be a count used in determining whether the candidate cassette sequence meets that criteria. For example, if the criteria is number of epitopes meeting or exceeding a threshold binding affinity for HLA, whether the candidate cassette sequence has greater or fewer than that number may determine whether the candidate cassette sequence meets the criteria for use as the selected cassette for the vaccine. Similarly if the criteria is the number of junction epitopes exceeding a threshold presentation likelihood.

However, in other embodiments, calculations other than counting can be performed to determine whether a candidate cassette sequence meets the design criteria. For example, rather than the count of epitopes exceeding/falling below some threshold, it may instead be determined what proportion of junction epitopes exceed or fall below the threshold, for example whether the top X % of junction epitopes have a presentation likelihood above some threshold Y, or whether X % percent of junction epitopes have an HLA binding affinity less than or greater than Z nM. These are merely examples, generally the criteria may be based on any attribute of either individual junction epitopes, or statistics derived from aggregations of some or all of the junction epitopes. Here, X can generally be any number between 0 and 100% (e.g., 75% or less) and Y can be any value between 0 and 1, and Z can be any number suitable to the criteria in question. These values may be determined empirically, and depend on the models and criteria used, as well as the quality of the training data used.

As such, in certain aspects, junction epitopes with high probabilities of presentation can be removed; junction epitopes with low probabilities of presentation can be retained; junction epitopes that bind tightly, i.e., junction epitopes with binding affinity below 1000 nM or 500 nM or some other threshold can be removed; and/or junction epitopes that bind weakly, i.e., junction epitopes with binding affinity above 1000 nM or 500 nM or some other threshold can be retained.

Although the examples above have identified candidate sequences using an implementation of the presentation model described above, these principles apply equally to an implementation where the epitopes for arrangement in the cassette sequences are identified based on other types of models as well, such as those based on affinity, stability, and so on.

XII. Example 7: Experimentation Results Showing Example Presentation Model Performance The validity of the various presentation models described above were tested on test data T that were subsets of training data 170 that were not used to train the presentation models or a separate dataset from the training data 170 that have similar variables and data structures as the training data 170.

A relevant metric indicative of the performance of a presentation models is:

$$\text{Positive Predictive Value } (PPV) = P(y_{i\in T} = 1 \mid u_{i\in T} \geq t) = \frac{\sum_{i\in T} \mathbb{1}(y_i = 1, u_i \geq t)}{\sum_{i\in T} \mathbb{1}(u_1 \geq t)}$$

that indicates the ratio of the number of peptide instances that were correctly predicted to be presented on associated HLA alleles to the number of peptide instances that were predicted to be presented on the HLA alleles. In one implementation, a $p^i$ in the test data T was predicted to be presented on one or more associated HLA alleles if the corresponding likelihood estimate u; is greater or equal to a given threshold value t. Another relevant metric indicative of the performance of presentation models is:

$$\text{Recall} = P(u_{i\in T} \geq t \mid y_{i\in T} = 1) = \frac{\sum_{i\in T} \mathbb{1}(y_i = 1, u_i \geq t)}{\sum_{i\in T} \mathbb{1}(y_i = 1)}$$

that indicates the ratio of the number of peptide instances that were correctly predicted to be presented on associated HLA alleles to the number of peptide instances that were known to be presented on the HLA alleles. Another relevant metric indicative of the performance of presentation models is the area-under-curve (AUC) of the receiver operating characteristic (ROC). The ROC plots the recall against the false positive rate (FPR), which is given by:

$$FPR = P(u_{i\in T} \geq t \mid y_{i\in T} = 0) = \frac{\sum_{i\in T} \mathbb{1}(y_i = 0, u_i \geq t)}{\sum_{i\in T} \mathbb{1}(y_i = 0)}.$$

Figure 13A:
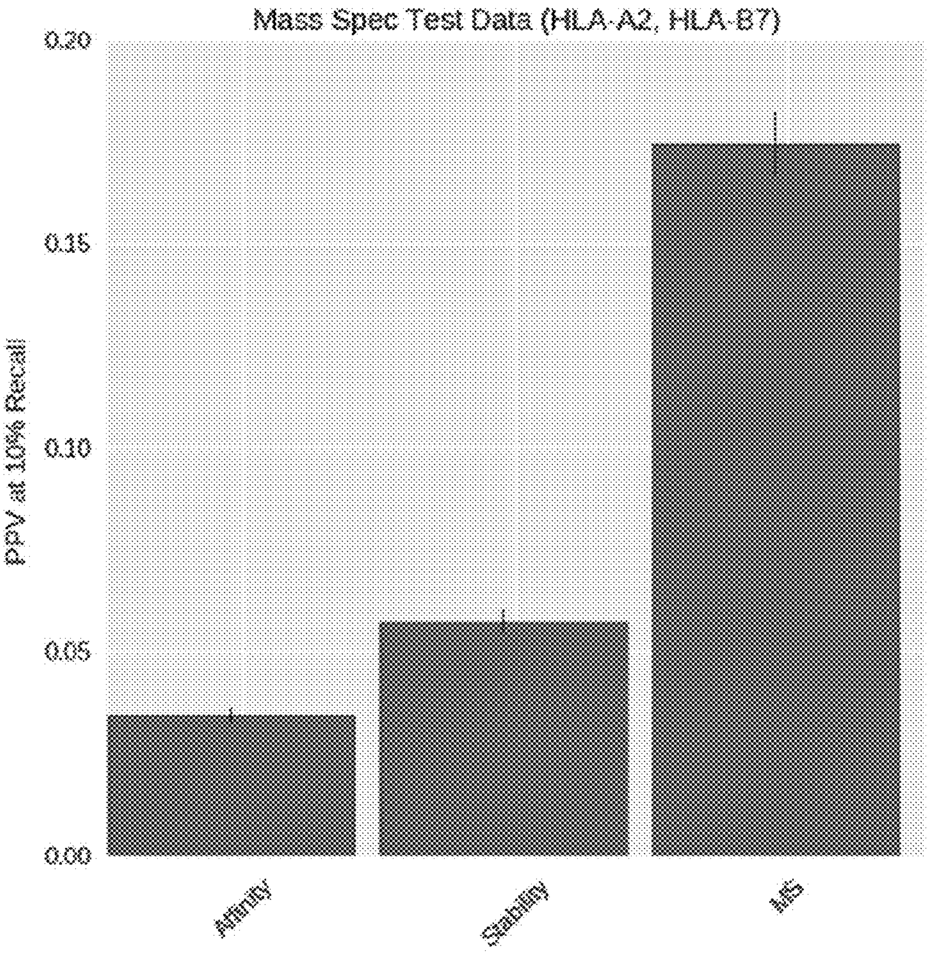
FIG. 13A shows performance results for peptide presentation determined by mass-spectrometry comparing various peptide presentation models. Shown are result for the maximum of per-alleles presentation model shown in equation (12) using the affine dependency function $g_h(\bullet)$ and the expit function $f(\bullet)$ and trained on a subset of mass spectrometry data for HLA-A*02:01 and HLA-B*07:02 ("MS"). Also shown are state-of-the-art models based on affinity predictions NETMHCpan "Affinity" and based on stability predictions NETMHCstab "Stability." The data shows the positive predictive value (PPV) at a 10% recall rate, and error bars (as indicated in solid lines) show 95% confidence intervals.

XII.A. Comparison of Presentation Model Performance on Mass Spectrometry Data Against State-of-the-Art Model FIG. 13A compares performance results of an example presentation model, as presented herein, and state-of-the-art models for predicting peptide presentation on multiple-allele mass spectrometry data. Results showed that the example presentation model performed significantly better at predicting peptide presentation than state-of-the-art models based on affinity and stability predictions.

Specifically, the example presentation model shown in FIG. 13A as "MS" was the maximum of per-alleles presentation model shown in equation (12), using the affine dependency function $g_h(\bullet)$ and the expit function $f(\bullet)$. The example presentation model was trained based on a subset of the single-allele HLA-A*02:01 mass spectrometry data from the IEDB data set (data set "D1") (data can be found at http://www.iedb.org/doc/mhc_ligand_full.zip) and a subset of the single-allele HLA-B*07:02 mass spectrometry from the IEDB data set (data set "D2") (data can be found at http://www.iedb.org/doc/mhc_ligand_full.zip). All peptides from source protein that contain presented peptides in the test set were eliminated from the training data such that the example presentation model could not simply memorize the sequences of presented antigens.

The model shown in FIG. 13A as "Affinity" was a model similar to the current state-of-the-art model that predicts peptide presentation based on affinity predictions NETMHCpan. Implementation of NETMHCpan is provided in detail at http://www.cbs.dtu.dk/services/NetMHCpan/. The model shown in FIG. 13A as "Stability" was a model similar to the current state-of-the-art model that predicts peptide presentation based on stability predictions NETMHCstab. Implementation of NETMHCstab is provided in detail at http://www.cbs.dtu.dk/services/NetMHCstab-1.0/. The test data that is a subset of the multiple-allele JY cell line HLA-A*02:01 and HLA-B*07:02 mass spectrometry data from the Bassani-Sternberg data set (data set "D3") (data can be found at www.ebi.ac.uk/pride/archive/projects/PXD000394). The error bars (as indicated in solid lines) show 95% confidence intervals.

As shown in the results of FIG. 13A, the example presentation model trained on mass spectrometry data had a significantly higher PPV value at 10% recall rate relative to the state-of-the-art models that predict peptide presentation based on MHC binding affinity predictions or MHC binding stability predictions. Specifically, the example presentation model had approximately 14% higher PPV than the model based on affinity predictions, and had approximately 12% higher PPV than the model based on stability predictions.

These results demonstrate that the example presentation model had significantly better performance than the state-of-the-art models that predict peptide presentation based on MHC binding affinity or MHC binding stability predictions even though the example presentation model was not trained based on protein sequences that contained presented peptides.

Figure 13B:
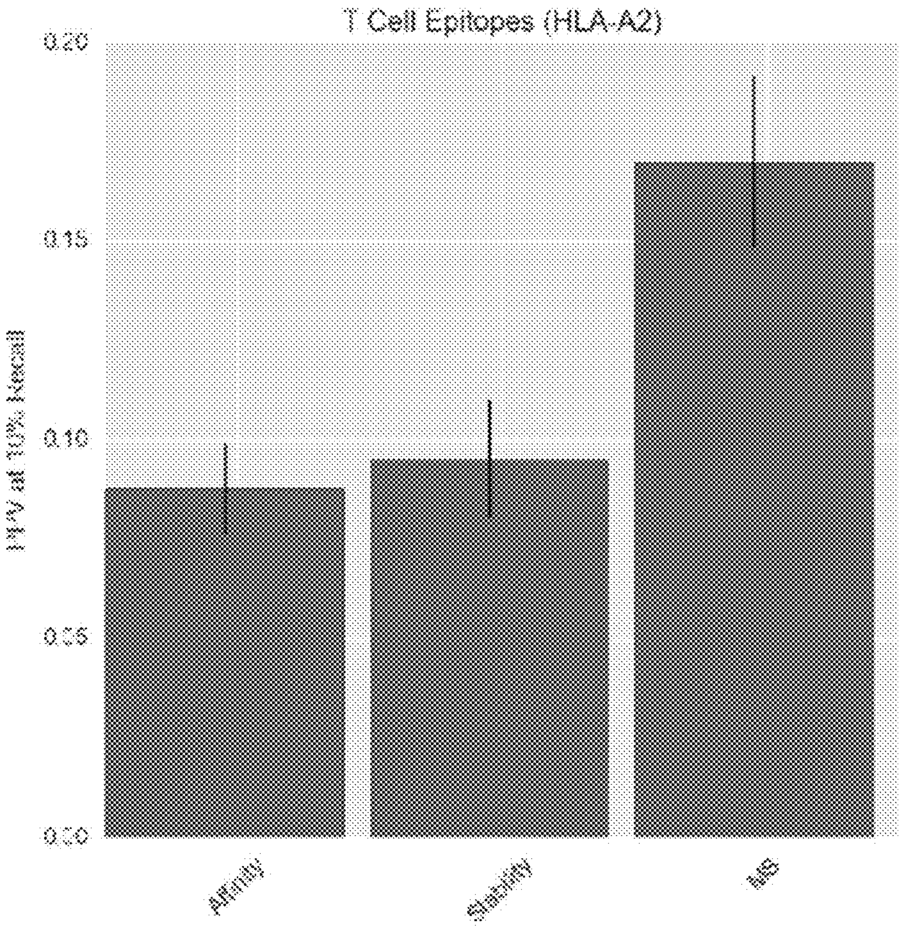
FIG. 13B shows performance results for peptide presentation determined by T-cell epitopes comparing various peptide presentation models. Shown are results for the maximum of per-alleles presentation model shown in equation (12) using the affine dependency function $g_h(\bullet)$ and the expit function $f(\bullet)$ and trained on a subset of mass spectrometry data for HLA-A*02:01. Also shown are state-of-the-art models based on affinity predictions NETMHCpan "Affinity" and based on stability predictions NETMHCstab "Stability." The data shows the positive predictive value (PPV) at a 10% recall rate, and error bars (as indicated in solid lines) show 95% confidence intervals.

XII.B. Comparison of Presentation Model Performance on T-Cell Epitope Data Against State-of-the-Art Models FIG. 13B compares performance results of another example presentation model, as presented herein, and state-of-the-art models for predicting peptide presentation on T-cell epitope data. T-cell epitope data contains peptide sequences that were presented by MHC alleles on the cell surface, and recognized by T-cells. Results showed that even though the example presentation model is trained based on mass spectrometry data, the example presentation model performed significantly better at predicting T-cell epitopes than state-of-the-art models based on affinity and stability predictions. In other words, the results of FIG. 13B indicated that not only did the example presentation model perform better than state-of-the-art models at predicting peptide presentation on mass spectrometry test data, but the example presentation model also performed significantly better than state-of-the-art models at predicting epitopes that were actually recognized by T-cells. This is an indication that the variety of presentation models as presented herein can provide improved identification of antigens that are likely to induce immunogenic responses in the immune system.

Specifically, the example presentation model shown in FIG. 13B as "MS" was the per-allele presentation model shown in equation (2), using the affine transformation function $g_h(\bullet)$ and the expit function $f(\bullet)$ that was trained based on a subset of data set D1. All peptides from source protein that contain presented peptides in the test set were eliminated from the training data such that the presentation model could not simply memorize the sequences of presented antigens.

Each of the models were applied to the test data that is a subset of mass spectrometry data on HLA-A*02:01 T-cell epitope data (data set "D4") (data can be found at www.iedb.org/doc/tcell_full_v3.zip). The model shown in FIG. 13B as "Affinity" was a model similar to the current state-of-the-art model that predicts peptide presentation based on affinity predictions NETMHCpan, and the model shown in FIG. 13B as "Stability" was a model similar to the current state-of-the-art model that predicts peptide presentation based on stability predictions NETMHCstab. The error bars (as indicated in solid lines) show 95% confidence intervals.

As shown in the results of FIG. 13A, the per-allele presentation model trained on mass spectrometry data had a significantly higher PPV value at 10% recall rate than the state-of-the-art models that predict peptide presentation based on MHC binding affinity or MHC binding stability predictions even though the presentation model was not trained based on protein sequences that contained presented peptides. Specifically, the per-allele presentation model had approximately 9% higher PPV than the model based on affinity predictions, and had approximately 8% higher PPV than the model based on stability predictions.

These results demonstrated that the example presentation model trained on mass spectrometry data performed significantly better than state-of-the-art models on predicting epitopes that were recognized by T-cells.

XII.C. Comparison of Different Presentation Model Performances on Mass Spectrometry Data FIG. 13C compares performance results for an example function-of-sums model (equation (13)), an example sum-of-functions model (equation (19)), and an example second order model (equation (23)) for predicting peptide presentation on multiple-allele mass spectrometry data. Results showed that the sum-of-functions model and second order model performed better than the function-of-sums model. This is because the function-of-sums model implies that alleles in a multiple-allele setting can interfere with each other for peptide presentation, when in reality, the presentation of peptides are effectively independent.

Specifically, the example presentation model labeled as "sigmoid-of-sums" in FIG. 13C was the function-of-sums model using a network dependency function $g_h(\bullet)$, the identity function $f(\bullet)$, and the expit function $r(\bullet)$. The example model labeled as "sum-of-sigmoids" was the sum-of-functions model in equation (19) with a network dependency function $g(\bullet)$, the expit function $f(\bullet)$, and the identity function $r(\bullet)$. The example model labeled as "hyperbolic tangent" was the sum-of-functions model in equation (19) with a network dependency function $g_h(\bullet)$, the expit function $f(\bullet)$, and the hyperbolic tangent function $r(\bullet)$. The example model labeled as "second order" was the second order model in equation (23) using an implicit per-allele presentation likelihood form shown in equation (18) with a network dependency function $g_h(\bullet)$ and the expit function $f(\bullet)$. Each model was trained based on a subset of data set D1, D2, and D3. The example presentation models were applied to a test data that is a random subset of data set D3 that did not overlap with the training data.

As shown in FIG. 13C, the first column refers to the AUC of the ROC when each presentation model was applied to the test set, the second column refers to the value of the negative log likelihood loss, and the third column refers to the PPV at 10% recall rate. As shown in FIG. 13C, the performance of presentation models "sum-of-sigmoids," "hyperbolic tangent," and "second order" were approximately tied at approximately 15-16% PPV at 10% recall, while the performance of the model "sigmoid-of-sums" was slightly lower at approximately 11%.

As discussed previously in section X.C.4, the results showed that the presentation models "sum-of-sigmoids," "hyperbolic tangent," and "second order" have high values of PPV compared to the "sigmoid-of-sums" model because the models correctly account for how peptides are presented independently by each MHC allele in a multiple-allele setting.

XII.D. Comparison of Presentation Model Performance with and without Training on Single-Allele Mass Spectrometry Data FIG. 13D compares performance results for two example presentation models that are trained with and without single-allele mass spectrometry data on predicting peptide presentation for multiple-allele mass spectrometry data. The results indicated that example presentation models that are trained without single-allele data achieve comparable performance to that of example presentation models trained with single-allele data.

The example model "with A2/B7 single-allele data" was the "sum-of-sigmoids" presentation model in equation (19) with a network dependency function $g_h(\bullet)$, the expit function $f(\bullet)$, and the identity function $r(\bullet)$. The model was trained based on a subset of data set D3 and single-allele mass spectrometry data for a variety of MHC alleles from the IEDB database (data can be found at: http://www.iedb.org/doc/mhc_ligand_full.zip). The example model "without A2/B7 single-allele data" was the same model, but trained based on a subset of the multiple-allele D3 data set without single-allele mass spectrometry data for alleles HLA-A*02:01 and HLA-B*07:02, but with single-allele mass spectrometry data for other alleles. Within the multiple-allele training data, cell line HCC1937 expressed HLA-B*07:02 but not HLA-A*02:01, and cell line HCT116 expressed HLA-A*02:01 but not HLA-B*07:02. The example presentation models were applied to a test data that was a random subset of data set D3 and did not overlap with the training data.

As shown in FIG. 13D, the predictions based on the implicit per-allele presentation likelihoods for MHC allele HLA-A*02:01 performed significantly better on single-allele test data for MHC allele HLA-A*02:01 rather than for MHC allele HLA-B*07:02. Similar results are shown for MHC allele HLA-B*07:02.

These results indicate that the implicit per-allele presentation likelihoods of the presentation model can correctly predict and distinguish binding motifs to individual MHC alleles, even though direct association between the peptides and each individual MHC allele was not known in the training data.

XII.E. Comparison of Per-Allele Prediction Performance without Training on Single-Allele Mass Spectrometry Data FIG. 13E shows performance for the "without A2/B7 single-allele data" and "with A2/B7 single-allele data" example models shown in FIG. 13D on single-allele mass spectrometry data for alleles HLA-A*02:01 and HLA-B*07:02 that were held out in the analysis shown in FIG. 13D. Results indicate that even through the example presentation model is trained without single-allele mass spectrometry data for these two alleles, the model is able to learn binding motifs for each MHC allele.

The column "Correlation" refers to the correlation between the actual labels that indicate whether the peptide was presented on the corresponding allele in the test data, and the label for prediction. As shown in FIG. 13E, "A2 model predicting B7" indicates the performance of the model when peptide presentation is predicted for single-allele HLA-B*07:02 data based on the implicit per-allele presentation likelihood estimate for MHC allele HLA-A*02:01. Similarly, "A2 model predicting A2" indicates the performance of the model when peptide presentation is predicted for single-allele HLA-A*02:01 based on the implicit per-allele presentation likelihood estimate for MHC allele HLA-A*02:01. "B7 model predicting B7" indicates the performance of the model when peptide presentation is predicted for single-allele HLA-B*07:02 data based on the implicit per-allele presentation likelihood estimate for MHC allele HLA-B*07:02. "B7 model predicting A2" indicates the performance of the model when peptide presentation is predicted for single-allele HLA-A*02:01 based on the implicit per-allele presentation likelihood estimate for MHC allele HLA-B*07:02.

As shown in FIG. 13E, the predictive capacity of implicit per-allele likelihoods for an HLA allele is significantly higher for the intended allele, and significantly lower for the other HLA allele. Similarly to the results shown in FIG. 13D, the example presentation models correctly learned to differentiate peptide presentation of individual alleles HLA-A*02:01 and HLA-B*07:02, even though direct association between peptide presentation and these alleles were not present in the multiple-allele training data.

XII.F. Frequently Occurring Anchor Residues in Per-Allele Predictions Match Known Canonical Anchor Motifs FIG. 13F shows the common anchor residues at positions 2 and 9 among nonamers predicted by the "without A2/B7 single-allele data" example model shown in FIG. 13D. The peptides were predicted to be presented if the estimated likelihood was above 5%. Results show that most common anchor residues in the peptides identified for presentation on the MHC alleles HLA-A*02:01 and HLA-B*07:02 matched previously known anchor motifs for these MHC alleles. This indicates that the example presentation models correctly learned peptide binding based on particular positions of amino acids of the peptide sequences, as expected.

As shown in FIG. 13F, amino acids L/M at position 2 and amino acids V/L at position 9 were known to be canonical anchor residue motifs (as shown in Table 4 of https://link.springer.com/article/10.1186/1745-7580-4-2) for HLA-A*02:01, and amino acid P at position 2 and amino acids UV at position 9 were known to be canonical anchor residue motifs for HLA-B*07:02. The most common anchor residue motifs at positions 2 and 9 for peptides identified the model matched the known canonical anchor residue motifs for both HLA alleles.

XII.G. Comparison of Presentation Model Performances with and Withtout Allele Noninteracting Variables FIG. 13G compares performance results between an example presentation model that incorporated C- and N-terminal flanking sequences as allele-interacting variables, and an example presentation model that incorporated C- and N-terminal flanking sequences as allele-noninteracting variables. Results showed that incorporating C- and N-terminal flanking sequences as allele noninteracting variables significantly improved model performance. More specifically, it is valuable to identify appropriate features for peptide presentation that are common across different MHC alleles, and model them such that statistical strength for these allele-noninteracting variables are shared across MHC alleles to improve presentation model performance.

The example "allele-interacting" model was the sum-of-functions model using the form of implicit per-allele presentation likelihoods in equation (22) that incorporated C- and N-terminal flanking sequences as allele-interacting variables, with a network dependency function $g_h(\bullet)$ and the expit function $f(\bullet)$. The example "allele-noninteracting" model was the sum-of-functions model shown in equation (21) that incorporated C- and N-terminal flanking sequences as allele-noninteracting variables, with a network dependency function $g_h(\bullet)$ and the expit function $f(\bullet)$. The allele-noninteracting variables were modeled through a separate network dependency function $g_w(\bullet)$. Both models were trained on a subset of data set D3 and single-allele mass spectrometry data for a variety of MHC alleles from the IEDB database (data can be found at: http://www.iedb.org/doc/mhc_ligand_full.zip). Each of the presentation models was applied to a test data set that is a random subset of data set D3 that did not overlap with the training data.

As shown in FIG. 13G, incorporating C- and N-terminal flanking sequences in the example presentation model as allele-noninteracting variables achieved an approximately 3% improvement in PPV value relative to modeling them as allele-interacting variables. This is because, in general, the "allele-noninteracting" example presentation model was able to share statistical strength of allele-noninteracting variables across MHC alleles by modeling the effect with a separate network dependency function with very little addition in computing power.

XII.H. Dependency Between Presented Peptides and mRNA Quantification

Figure 13H:
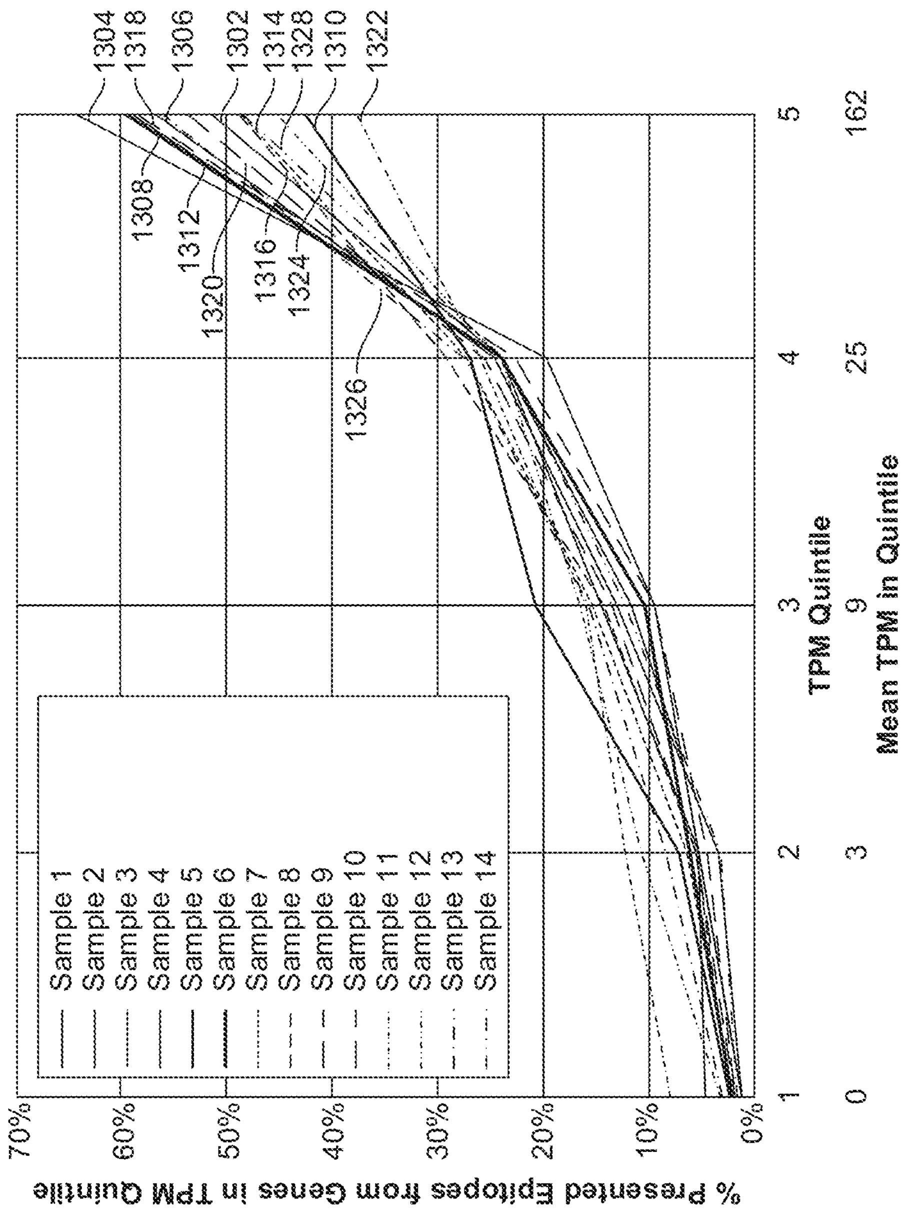
FIG. 13H shows the dependency between mRNA abundance and the frequency of peptides presented on a tumor cell as determined by mass-spectrometry. The horizontal axis indicates mRNA expression in terms of transcripts per million (TPM) quartiles. The vertical axis indicates fraction of presented epitopes from genes in corresponding mRNA expression quartiles. Each solid line is a plot relating the two measurements from a tumor sample that is associated with corresponding mass spectrometry data and mRNA expression measurements.

FIG. 13H shows the dependency between mRNA abundance and the frequency of peptides presented on a tumor cell as determined by mass-spectrometry. Results show that there is a strong dependency between mRNA expression and peptide presentation.

Specifically, the horizontal axis in FIG. 13H indicates mRNA expression in terms of transcripts per million (TPM) quartiles. The vertical axis in FIG. 13H indicates fraction of presented epitopes from genes in corresponding mRNA expression quartiles. Each solid line is a plot relating the two measurements from a tumor sample that is associated with corresponding mass spectrometry data and mRNA expression measurements. As shown in FIG. 13H, there is a strong positive correlation between mRNA expression, and the fraction of peptides in the corresponding gene. Specifically, peptides from genes in the top quartile of RNA expression are more than 20 times likely to be presented than the bottom quartile. Moreover, essentially 0 peptides are presented from genes that are not detected through RNA.

The results indicate that the performance of the presentation model can be greatly improved by incorporating mRNA quantification measurements, as these measurements are strongly predictive of peptide presentation.

Figure 13I:
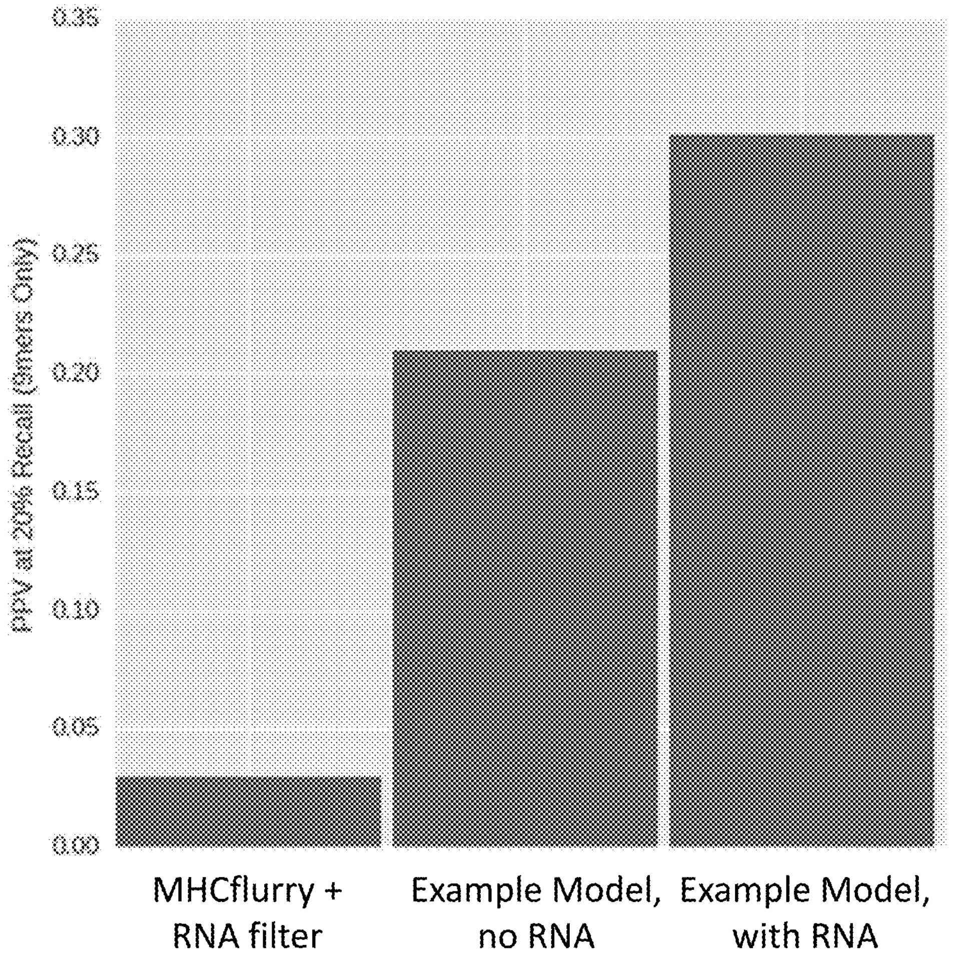
FIG. 13I shows performance performance results for peptide presentation determined by mass-spectrometry for example presentation models "MHCflurry+RNA filter" is a model similar to the current state-of-the-art model that predicts peptide presentation based on affinity predictions with a standard gene expression filter that removed all peptides from proteins with mRNA quantification measurements that were less than 3.2 FPKM. The "Example Model, no RNA" model is the "sum-of-sigmoids" example presentation model shown in equation (21). The "Example Model, with RNA" model is the "sum-of-sigmoids" presentation model shown in equation (19) incorporating mRNA quantification data through a log function. The data shows the positive predictive value (PPV) at a 20% recall rate.

XII.I. Comparison of Presentation Model Performance with Incorporation of RNA Quantification Data FIG. 13I shows performance of two example presentation models, one of which is trained based on mass spectrometry tumor cell data, another of which incorporates mRNA quantification data and mass spectrometry tumor cell data. As expected from FIG. 13H, results indicated that there is a significant improvement in performance by incorporating mRNA quantification measurements in the example presentation model, since the mRNA expression is a strong indicator of peptide presentation.

"MHCflurry+RNA filter" was a model similar to the current state-of-the-art model that predicts peptide presentation based on affinity predictions. It was implemented using MHCflurry along with a standard gene expression filter that removed all peptides from proteins with mRNA quantification measurements that were less than 3.2 FPKM. Implementation of MHCflurry is provided in detail at https://github.com/hammerlab/mhcflurry/, and at http://biorxiv.org/content/early/2016/05/22/054775. The "Example Model, no RNA" model was the "sum-of-sigmoids" example presentation model shown in equation (21) with the network dependency function $g_h(\bullet)$, the network dependency function $g_w(\bullet)$, and the expit function $f(\bullet)$. The "Example Model, no RNA" model incorporated C-terminal flanking sequences as allele-noninteracting variables through a network dependency function $g_w(\bullet)$.

The "Example Model, with RNA" model was the "sum-of-sigmoids" presentation model shown in equation (19) with network dependency function $g_h(\bullet)$, the network dependency function $g_w(\bullet)$ in equation (10) incorporating mRNA quantification data through a log function, and the expit function $f(\bullet)$. The "Example Model, with RNA" model incorporated C-terminal flanking sequences as allele-noninteracting variables through the network dependency functions $g_w(\bullet)$ and incorporated mRNA quantification measurements through the log function.

Each model was trained on a combination of the single-allele mass spectrometry data from the IEDB data set, 7 cell lines from the multiple-allele mass spectrometry data from the Bassani-Sternberg data set, and 20 mass spectrometry tumor samples. Each model was applied to a test set including 5,000 held-out proteins from 7 tumor samples that constituted 9,830 presented peptides from a total of 52,156,840 peptides.

As shown in the first two bar graphs of FIG. 13I, the "Example Model, no RNA" model has a PPV value at 20% Recall of 21%, while that of the state-of-the-art model is approximately 3%, This indicates an initial performance improvement of 18% in PPV value, even without the incorporation of mRNA quantification measurements. As shown in the third bar graph of FIG. 13I, the "Example Model, with RNA" model that incorporates mRNA quantification data into the presentation model shows a PPV value of approximately 30%, which is almost a 10% increase in performance compared to the example presentation model without mRNA quantification measurements.

Thus, results indicate that as expected from the findings in FIG. 13H, mRNA expression is indeed a strong predictor of peptide prediction, that allows significant improvement in the performance of a presentation model with very little addition of computational complexity.

XII.J. Example of Parameters Determined for MHC Allele HLA-C*16:04

Figure 13J:
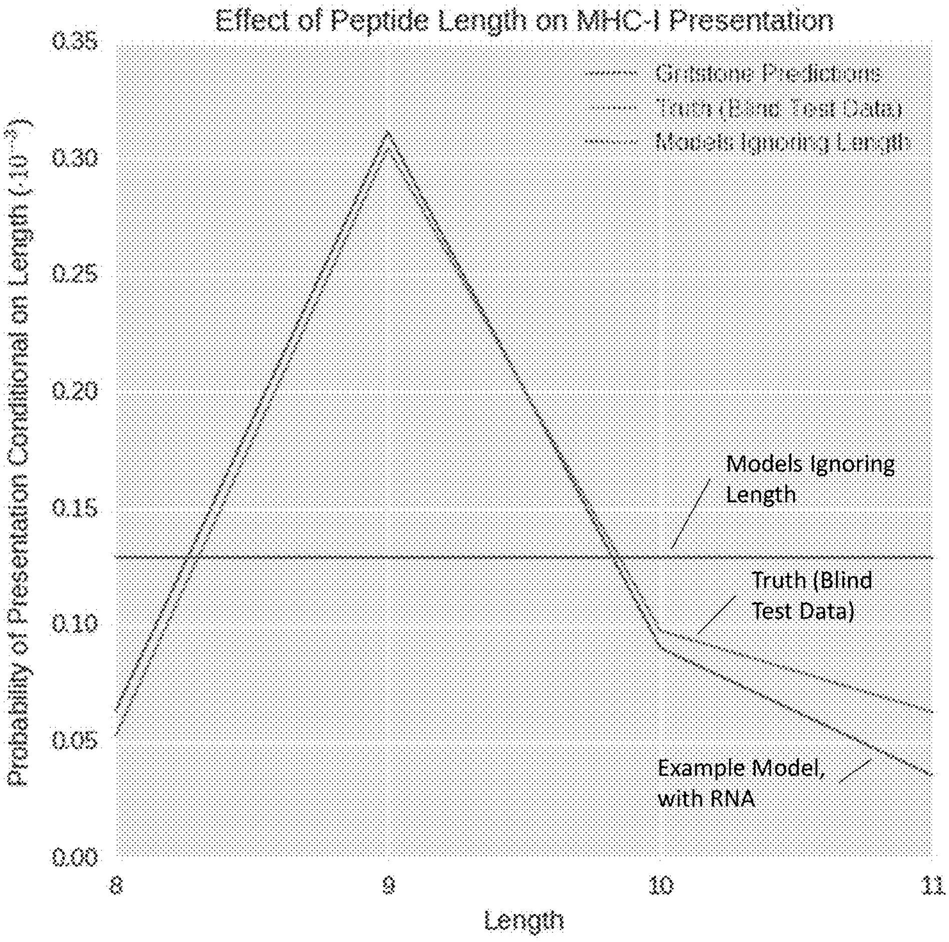
FIG. 13J shows the probability of peptide presentation for different peptide lengths for presentation models that take peptide length into account and state-of-the-art models that do not account for peptide length when predicting peptide presentation. The plot "Truth (Blind Test Data)" showed the proportion of presented peptides according to the length of the peptide in a sample test data set. The plot "Models Ignoring Length" indicated predicted measurements if state-of-the-art models that ignore peptide length applied to the same test data set for presentation prediction. The "Example Model, with RNA" model is the "sum-of-sigmoids" presentation model shown in equation (19) incorporating mRNA quantification data through a log function.

FIG. 13J compares probability of peptide presentation for different peptide lengths between results generated by the "Example Model, with RNA" presentation model described in reference to FIG. 13I, and predicted results by state-of-the-art models that do not account for peptide length when predicting peptide presentation. Results indicated that the "Example Model, with RNA" example presentation model from FIG. 13I captured variation in likelihoods across peptides of differing lengths.

The horizontal axis denoted samples of peptides with lengths 8, 9, 10, and 11. The vertical axis denoted the probability of peptide presentation conditioned on the lengths of the peptide. The plot "Truth (Blind Test Data)" showed the proportion of presented peptides according to the length of the peptide in a sample test data set. The presentation likelihood varied with the length of the peptide. For example, as shown in FIG. 13J, a 10mer peptide with canonical HLA-A2 L/V anchor motifs was approximately 3 times less likely to be presented than a 9mer with the same anchor residues. The plot "Models Ignoring Length" indicated predicted measurements if state-of-the-art models that ignore peptide length were to be applied to the same test data set for presentation prediction. These models may be NetMHC versions before version 4.0, NetMHCpan versions before version 3.0, and MHCflurry, that do not take into account variation in peptide presentation according to peptide length. As shown in FIG. 13J, the proportion of presented peptides would be constant across different values of peptide length, indicating that these models would fail to capture variation in peptide presentation according to length. The plot "Example Model, with RNA" indicated measurements generated from the "Example Model, with RNA" presentation model. As shown in FIG. 13J, the measurements generated by the "Example Model, with RNA" model closely followed those shown in "Truth (Blind Test Data)" and correctly accounted for different degrees of peptide presentation for lengths 8, 9, 10, and 11.

Thus, the results showed that the example presentation models as presented herein generated improved predictions not only for 9mer peptides, but also for peptides of other lengths between 8-15, which account for up to 40% of the presented peptides in HLA class I alleles.

XII.K. Example of Parameters Determined for MHC Allele HLA-C*16:04

The following shows a set of parameters determined for a variation of the per-allele presentation model (equation (2)) for MHC allele HLA-C*16:04 denoted by h:

$$u_k = \text{expit}(\text{relu}(x_h^k \cdot W_h^1 + b_h^1) - W_h^2 + b_h^2),$$

where relu(•) is the rectified linear unit (RELU) function, and $W_h^1$a, $b_h^1$, $W_h^2$, and $b_h^2$ are the set of parameters θ determined for the model. The allele interacting variables $x_h^k$ consist of peptide sequences. The dimensions of $W_h^1$ are (231×256), the dimensions of $b_h^1$ (1×256), the dimensions of $W_h^2$ are (256×1), and $b_h^2$ is a scalar. For demonstration purposes, values for $b_h^1$, $b_h^2$, $W_h^1$, and $W_h^2$ are described in detail in PCT publication WO2017106638, herein incorporated by reference for all that it teaches.

XII.L. MHC II Example 1

Methods for determining MHC class II neoantigens are described in more detail in international application PCT/US2018/028438, herein incorporated by reference for all that it teaches.

Figure 13K:
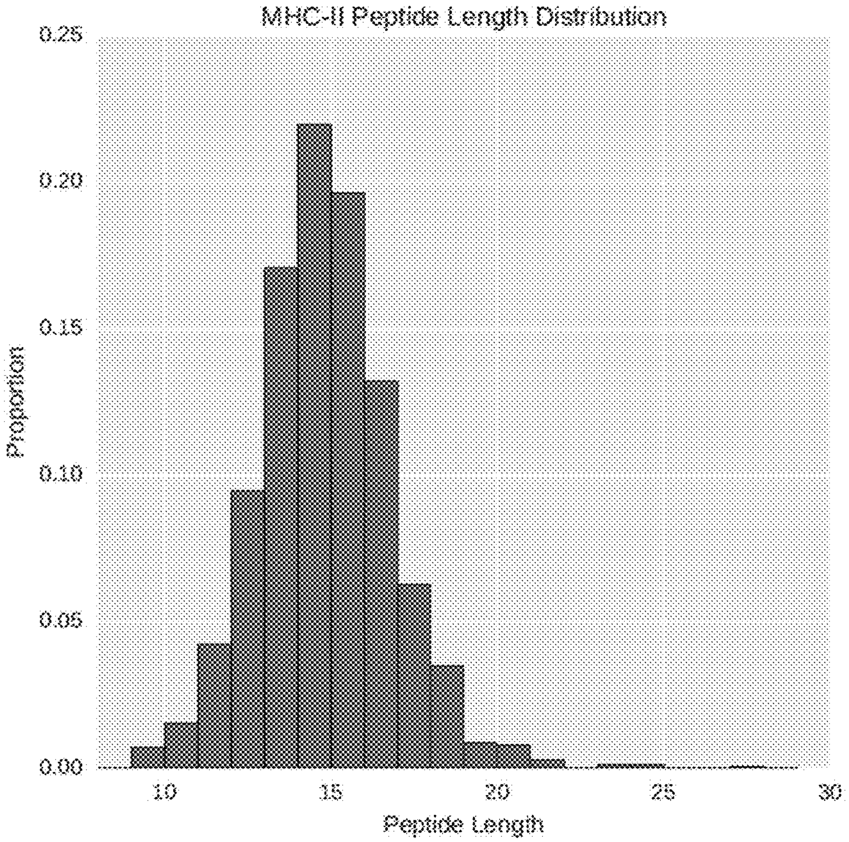
FIG. 13K is a histogram of lengths of peptides eluted from class II MHC alleles on human tumor cells and tumor infiltrating lymphocytes (TIL) using mass spectrometry.

FIG. 13K is a histogram of lengths of peptides eluted from class II MHC alleles on human tumor cells and tumor infiltrating lymphocytes (TIL) using mass spectrometry. Specifically, mass spectrometry peptidomics was performed on HLA-DRB1*12:01 homozygote alleles ("Dataset 1") and HLA-DRB1*12:01, HLA-DRB1*10:01 multi-allele samples ("Dataset 2"). Results show that lengths of peptides eluted from class II MHC alleles range from 6-30 amino acids. The frequency distribution shown in FIG. 13K is similar to that of lengths of peptides eluted from class II MHC alleles using state-of-the-art mass spectrometry techniques, as shown in FIG. 1C of reference 91.

Figure 13L:
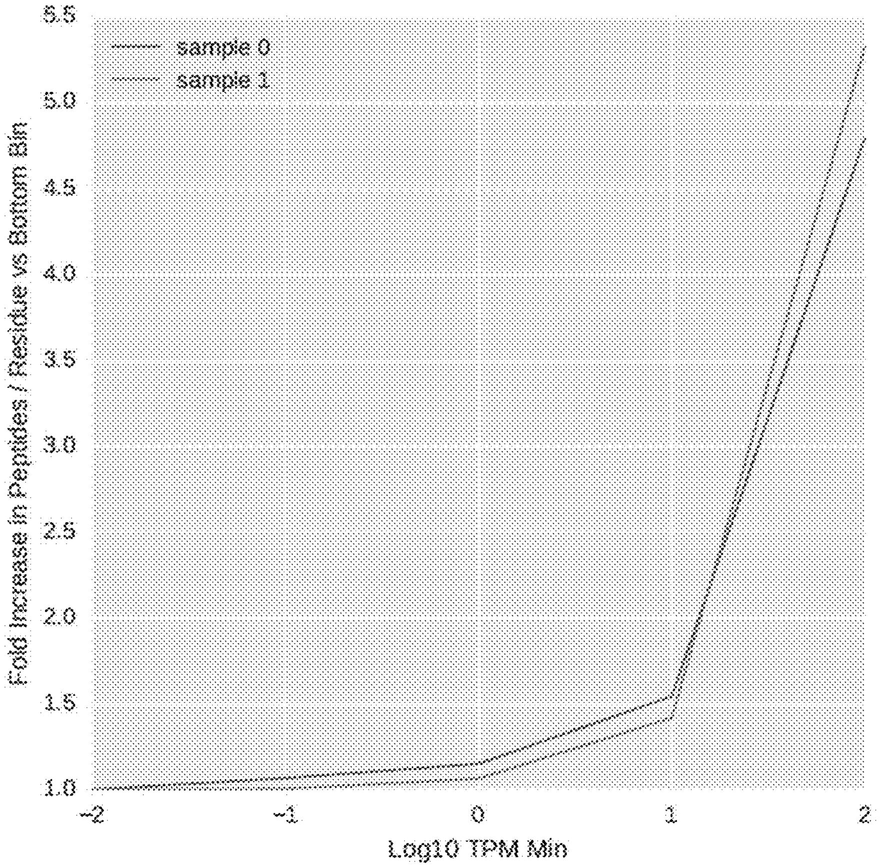
FIG. 13L illustrates the dependency between mRNA quantification and presented peptides per residue for two example datasets.

FIG. 13L illustrates the dependency between mRNA quantification and presented peptides per residue for Dataset 1 and Dataset 2. Results show that there is a strong dependency between mRNA expression and peptide presentation for class II MHC alleles.

Specifically, the horizontal axis in FIG. 13B indicates mRNA expression in terms of $\log_{10}$ transcripts per million (TPM) bins. The vertical axis in FIG. 13L indicates peptide presentation per residue as a multiple of that of the lowest bin corresponding to mRNA expression between $10^{-2}<\log_{10}$ TPM$<10^{-1}$. One solid line is a plot relating mRNA quantification and peptide presentation for Dataset 1, and another is for Dataset 2. As shown in FIG. 13L, there is a strong positive correlation between mRNA expression, and peptide presentation per residue in the corresponding gene. Specifically, peptides from genes in the range of $10^1<\log_{10}$ TPM$<10^2$ of RNA expression are more than 5 times likely to be presented than the bottom bin.

The results indicate that the performance of the presentation model can be greatly improved by incorporating mRNA quantification measurements, as these measurements are strongly predictive of peptide presentation.

Figure 13M:
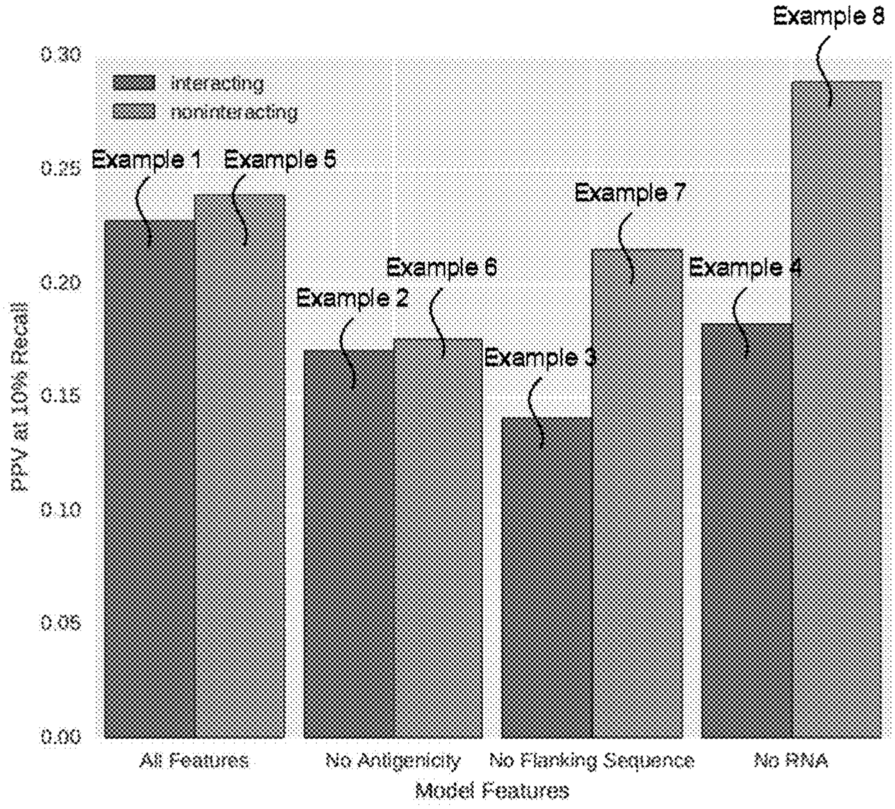
FIG. 13M compares performance results for example presentation models trained and tested using two example datasets.

FIG. 13M compares performance results for example presentation models trained and tested using Dataset 1 and Dataset 2. For each set of model features of the example presentation models, FIG. 13M depicts a PPV value at 10% recall when the features in the set of model features are classified as allele interacting features, and alternatively when the features in the set of model features are classified as allele non-interacting features variables. As seen in FIG. 13M, for each set of model features of the example presentation models, a PPV value at 10% recall that was identified when the features in the set of model features were classified as allele interacting features is shown on the left side, and a PPV value at 10% recall that was identified when the features in the set of model features were classified as allele non-interacting features is shown on the right side. Note that the feature of peptide sequence was always classified as an allele interacting feature for the purposes of FIG. 13M. Results showed that the presentation models achieved a PPV value at 10% recall varying from 14% up to 29%, which are significantly (approximately 500-fold) higher than PPV for a random prediction.

Peptide sequences of lengths 9-20 were considered for this experiment. The data was split into training, validation, and testing sets. Blocks of peptides of 50 residue blocks from both Dataset 1 and Dataset 2 were assigned to training and testing sets. Peptides that were duplicated anywhere in the proteome were removed, ensuring that no peptide sequence appeared both in the training and testing set. The prevalence of peptide presentation in the training and testing set was increased by 50 times by removing non-presented peptides. This is because Dataset 1 and Dataset 2 are from human tumor samples in which only a fraction of the cells are class II HLA alleles, resulting in peptide yields that were roughly 10 times lower than in pure samples of class II HLA alleles, which is still an underestimate due to imperfect mass spectrometry sensitivity. The training set contained 1,064 presented and 3,810,070 non-presented peptides. The test set contained 314 presented and 807,400 non-presented peptides.

Example model 1 was the sum-of-functions model in equation (22) using a network dependency function $g_h(\bullet)$, the expit function $f(\bullet)$, and the identity function $r(\bullet)$. The network dependency function $g_h(\bullet)$ was structured as a multi-layer perceptron (MLP) with 256 hidden nodes and rectified linear unit (ReLU) activations. In addition to the peptide sequence, the allele interacting variables w contained the one-hot encoded C-terminal and N-terminal flanking sequence, a categorical variable indicating index of source gene G=gene($p^i$) of peptide $p^i$, and a variable indicating mRNA quantification measurement. Example model 2 was identical to example model 1, except that the C-terminal and N-terminal flanking sequence was omitted from the allele interacting variables. Example model 3 was identical to example model 1, except that the index of source gene was omitted from the allele interacting variables. Example model 4 was identical to example model 1, except that the mRNA quantification measurement was omitted from the allele interacting variables.

Example model 5 was the sum-of-functions model in equation (20) with a network dependency function $g_h(\bullet)$, the expit function $f(\bullet)$, the identity function $r(\sim)$, and the dependency function $g_w(\bullet)$ of equation (12). The dependency function $g_w(\bullet)$ also included a network model taking mRNA quantification measurement as input, structured as a MLP with 16 hidden nodes and ReLU activations, and a network model taking C-flanking sequence as input, structured as a MLP with 32 hidden nodes and ReLU activations. The network dependency function $g_h(\bullet)$ was structured as a multi-layer perceptron with 256 hidden nodes and rectified linear unit (ReLU) activations. Example model 6 was identical to example model 5, except that the network model for C-terminal and N-terminal flanking sequence was omitted. Example model 7 was identical to example model 5, except that the index of source gene was omitted from the allele noninteracting variables. Example model 8 was identical to example model 5, except that the network model for mRNA quantification measurement was omitted.

The prevalence of presented peptides in the test set was approximately 1/2400, and therefore, the PPV of a random prediction would also be approximately 1/2400=0.00042. As shown in FIG. 13M, the best-performing presentation model achieved a PPV value of approximately 29%, which is roughly 500 times better than the PPV value of a random prediction.

XII.M. MHC II Example 2

Figure 13N:
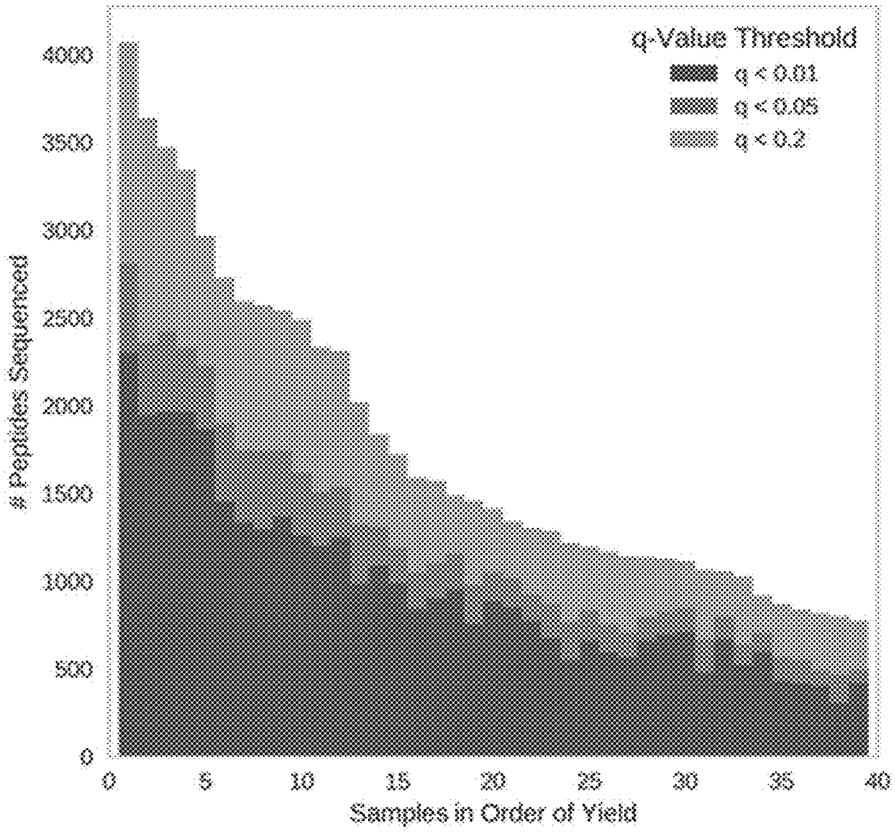
FIG. 13N is a histogram that depicts the quantity of peptides sequenced using mass spectrometry for each sample of a total of 39 samples comprising HLA class II molecules.

FIG. 13N is a histogram that depicts the quantity of peptides sequenced using mass spectrometry for each sample of a total of 39 samples comprising HLA class II molecules. Furthermore, for each sample of the plurality of samples, the histogram shown in FIG. 13N depicts the quantity of peptides sequenced using mass spectrometry at different q-value thresholds. Specifically, for each sample of the plurality of samples, FIG. 13N depicts the quantity of peptides sequenced using mass spectrometry with a q-value of less than 0.01, with a q-value of less than 0.05, and with a q-value of less than 0.2.

As noted above, each sample of the 39 samples of FIG. 13N comprised HLA class II molecules. More specifically, each sample of the 39 samples of FIG. 13N comprised HLA-DR molecules. The HLA-DR molecule is one type of HLA class II molecule. Even more specifically, each sample of the 39 samples of FIG. 13N comprised HLA-DRB1 molecules, HLA-DRB3 molecules, HLA-DRB4 molecules, and/or HLA-DRB5 molecules. The HLA-DRB1 molecule, the HLA-DRB3 molecule, the HLA-DRB4 molecule, and the HLA-DRB5 molecule are types of the HLA-DR molecule.

While this particular experiment was performed using samples comprising HLA-DR molecules, and particularly HLA-DRB1 molecules, HLA-DRB3 molecules, HLA-DRB4 molecules, and HLA-DRB5 molecules, in alternative embodiments, this experiment can be performed using samples comprising one or more of any type(s) of HLA class II molecules. For example, in alterative embodiments, identical experiments can be performed using samples comprising HLA-DP and/or HLA-DQ molecules. This ability to model any type(s) of MHC class II molecules using the same techniques, and still achieve reliable results, is well known by those skilled in the art. For instance, Jensen, Kamilla Kjaergaard, et al.[76] is one example of a recent scientific paper that uses identical methods for modeling binding affinity for HLA-DR molecules as well as for HLA-DQ and HLA-DP molecules. Therefore, one skilled in the art would understand that the experiments and models described herein can be used to separately or simultaneously model not only HLA-DR molecules, but any other MHC class II molecule, while still producing reliable results.

To sequence the peptides of each sample of the 39 total samples, mass spectrometry was performed for each sample. The resulting mass spectrum for the sample was then searched with Comet and scored with Percolator to sequence the peptides. Then, the quantity of peptides sequenced in the sample was identified for a plurality of different Percolator q-value thresholds. Specifically, for the sample, the quantity of peptides sequenced with a Percolator q-value of less than 0.01, with a Percolator q-value of less than 0.05, and with a Percolator q-value of less than 0.2 were determined.

For each sample of the 39 samples, the quantity of peptides sequenced at each of the different Percolator q-value thresholds is depicted in FIG. 13N. For example, as seen in FIG. 13N, for the first sample, approximately 4000 peptides with a q-value of less than 0.2 were sequenced using mass spectrometry, approximately 2800 peptides with a q-value of less than 0.05 were sequenced using mass spectrometry, and approximately 2300 peptides with a q-value of less than 0.01 were sequenced using mass spectrometry.

Overall, FIG. 13N demonstrates the ability to use mass spectrometry to sequence a large quantity of peptides from samples containing MHC class II molecules, at low q-values. In other words, the data depicted in FIG. 13N demonstrate the ability to reliably sequence peptides that may be presented by MHC class II molecules, using mass spectrometry.

FIG. 13O is a histogram that depicts the quantity of samples in which a particular MHC class II molecule allele was identified. More specifically, for the 39 total samples comprising HLA class II molecules, FIG. 13O depicts the quantity of samples in which certain MHC class II molecule alleles were identified.

As discussed above with regard to FIG. 13N, each sample of the 39 samples of FIG. 13N comprised HLA-DRB1 molecules, HLA-DRB3 molecules, HLA-DRB4 molecules, and/or HLA-DRB5 molecules. Therefore, FIG. 13O depicts the quantity of samples in which certain alleles for HLA-DRB1, HLA-DRB3, HLA-DRB4, and HLA-DRB5 molecules were identified. To identify the HLA alleles present in a sample, HLA class II DR typing is performed for the sample. Then, to identify the quantity of samples in which a particular HLA allele was identified, the number of samples in which the HLA allele was identified using HLA class II DR typing is simply summed. For example, as depicted in FIG. 13O, 19 samples of the 39 total samples contained the HLA class II molecule allele HLA-DRB4*01:03. In other words, 19 samples of the 39 total samples contained the allele HLA-DRB4*01:03 for the HLA-DRB4 molecule. Overall, FIG. 13O depicts the ability to identify a wide range of HLA class II molecule alleles from the 39 samples comprising HLA class II molecules.

Figure 13P:
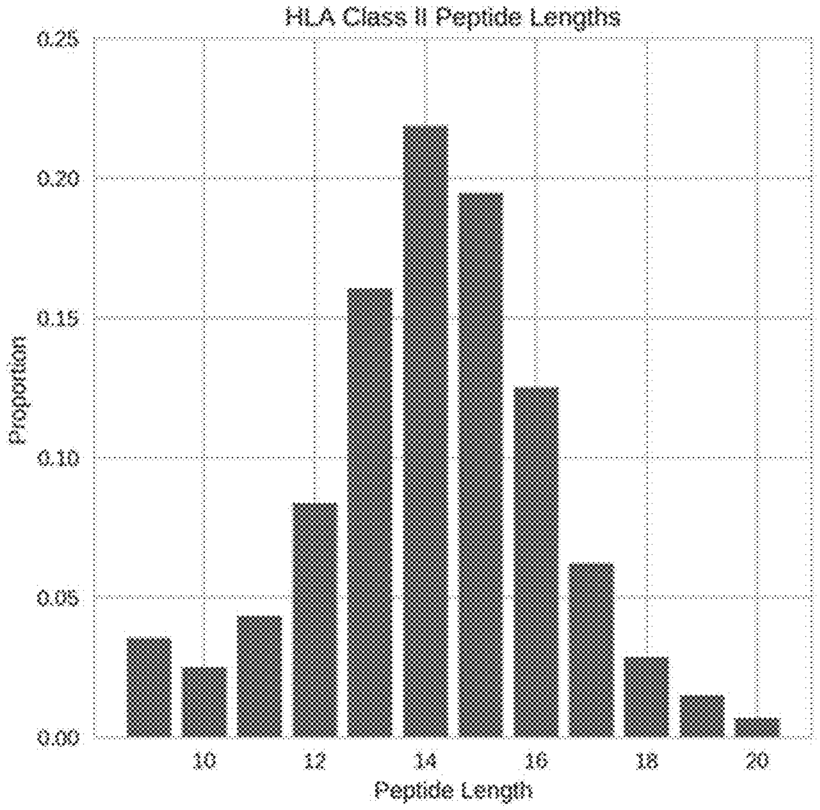
FIG. 13P is a histogram that depicts the proportion of peptides presented by the MHC class II molecules in the 39 total samples, for each peptide length of a range of peptide lengths.

FIG. 13P is a histogram that depicts the proportion of peptides presented by the MHC class II molecules in the 39 total samples, for each peptide length of a range of peptide lengths. To determine the length of each peptide in each sample of the 39 total samples, each peptide was sequenced using mass spectrometry as discussed above with regard to FIG. 13N, and then the number of residues in the sequenced peptide was simply quantified.

As noted above, MHC class II molecules typically present peptides with lengths of between 9-20 amino acids. Accordingly, FIG. 13P depicts the proportion of peptides presented by the MHC class II molecules in the 39 samples for each peptide length between 9-20 amino acids, inclusive. For example, as shown in FIG. 13P, approximately 22% of the peptides presented by the MHC class II molecules in the 39 samples comprise a length of 14 amino acids.

Based on the data depicted in FIG. 13P, modal lengths for the peptides presented by the MHC class II molecules in the 39 samples were identified to be 14 and 15 amino acids in length. These modal lengths identified for the peptides presented by the MHC class II molecules in the 39 samples are consistent with previous reports of modal lengths for peptides presented by MHC class II molecules. Additionally, as also consistent with previous reports, the data of FIG. 13P indicates that more than 60% of the peptides presented by the MHC class II molecules from the 39 samples comprise lengths other than 14 and 15 amino acids. In other words, FIG. 13P indicates that while peptides presented by MHC class II molecules are most frequently 14 or 15 amino acids in length, a large proportion of peptides presented by MHC class II molecules are not 14 or 15 amino acids in length. Accordingly, it is a poor assumption to assume that peptides of all lengths have equal probabilities of being presented by MHC class II molecules, or that only peptides that comprise a length of 14 or 15 amino acids are presented by MHC class II molecules. As discussed in detail below with regard to FIG. 13T, these faulty assumptions are currently used in many state-of-the-art models for predicting peptide presentation by MHC class II molecules, and therefore, the presentation likelihoods predicted by these models are often unreliable.

Figure 13Q:
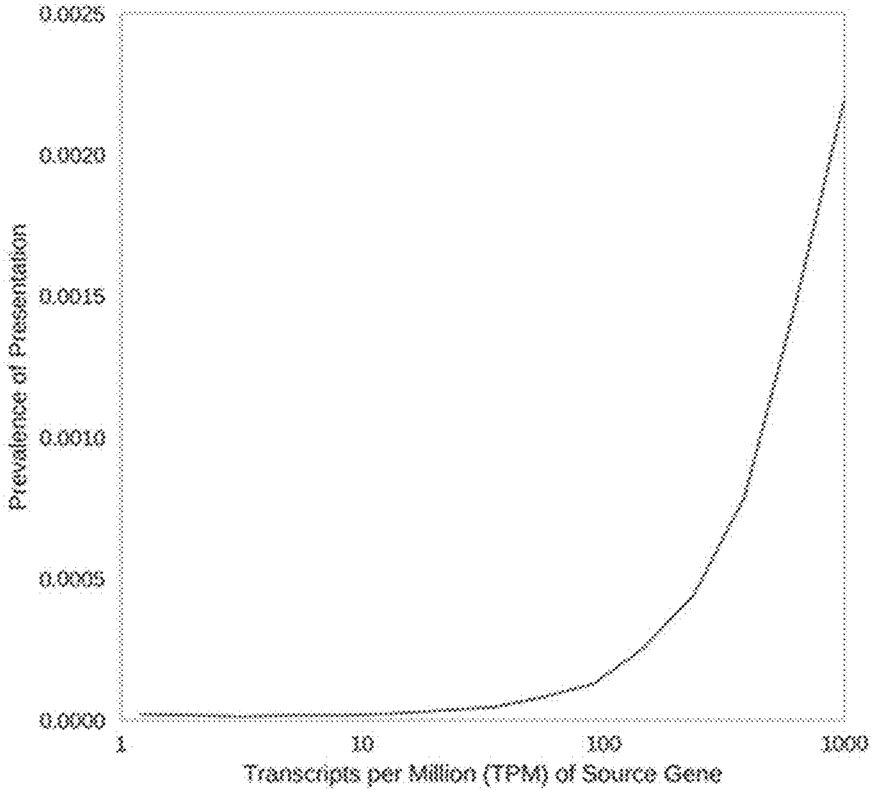
FIG. 13Q is a line graph that depicts the relationship between gene expression and prevalence of presentation of the gene expression product by a MHC class II molecule, for genes present in the 39 samples.

FIG. 13Q is a line graph that depicts the relationship between gene expression and prevalence of presentation of the gene expression product by a MHC class II molecule, for genes present in the 39 samples. More specifically, FIG. 13Q depicts the relationship between gene expression and the proportion of residues resulting from the gene expression that form the N-terminus of a peptide presented by a MHC class II molecule. To quantify gene expression in each sample of the 39 total samples, RNA sequencing is performed on the RNA included in each sample. In FIG. 13Q, gene expression is measured by RNA sequencing in units of transcripts per million (TPM). To identify prevalence of presentation of gene expression products for each sample of the 39 samples, identification of HLA class II DR peptidomic data was performed for each sample.

As depicted in FIG. 13Q, for the 39 samples, there is a strong correlation between gene expression level and presentation of residues of the expressed gene product by a MHC class II molecule. Specifically, as shown in FIG. 13Q, peptides resulting from expression of the least-expressed genes are more than 100-fold less likely to be presented by a MHC class II molecule, than peptides resulting from expression of the most-expressed genes. In simpler terms, the products of more highly expressed genes are more frequently presented by MHC class II molecules.

FIGS. 13H-J are line graphs that compare the performance of various presentation models at predicting the likelihood that peptides in a testing dataset of peptides will be presented by at least one of the MHC class II molecules present in the testing dataset. As shown in FIGS. 13H-J, the performance of a model at predicting the likelihood that a peptide will be presented by at least one of the MHC class II molecules present in the testing dataset is determined by identifying a ratio of a true positive rate to a false positive rate for each prediction made by the model. These ratios identified for a given model can be visualized as a ROC (receiver operator characteristic) curve, in a line graph with an x-axis quantifying false positive rate and a y-axis quantifying true positive rate. An area under the curve (AUC) is used to quantify the performance of the model. Specifically, a model with a greater AUC has a higher performance (i.e., greater accuracy) relative to a model with a lesser AUC. In FIGS. 13H-J, the blacked dashed line with a slope of 1 (i.e., a ratio of true positive rate to false positive rate of 1) depicts the expected curve for randomly guessing likelihoods of peptide presentation. The AUC for the dashed line is 0.5. ROC curves and the AUC metric are discussed in detail with regard to the top portion of Section XII. above.

Figure 13R:
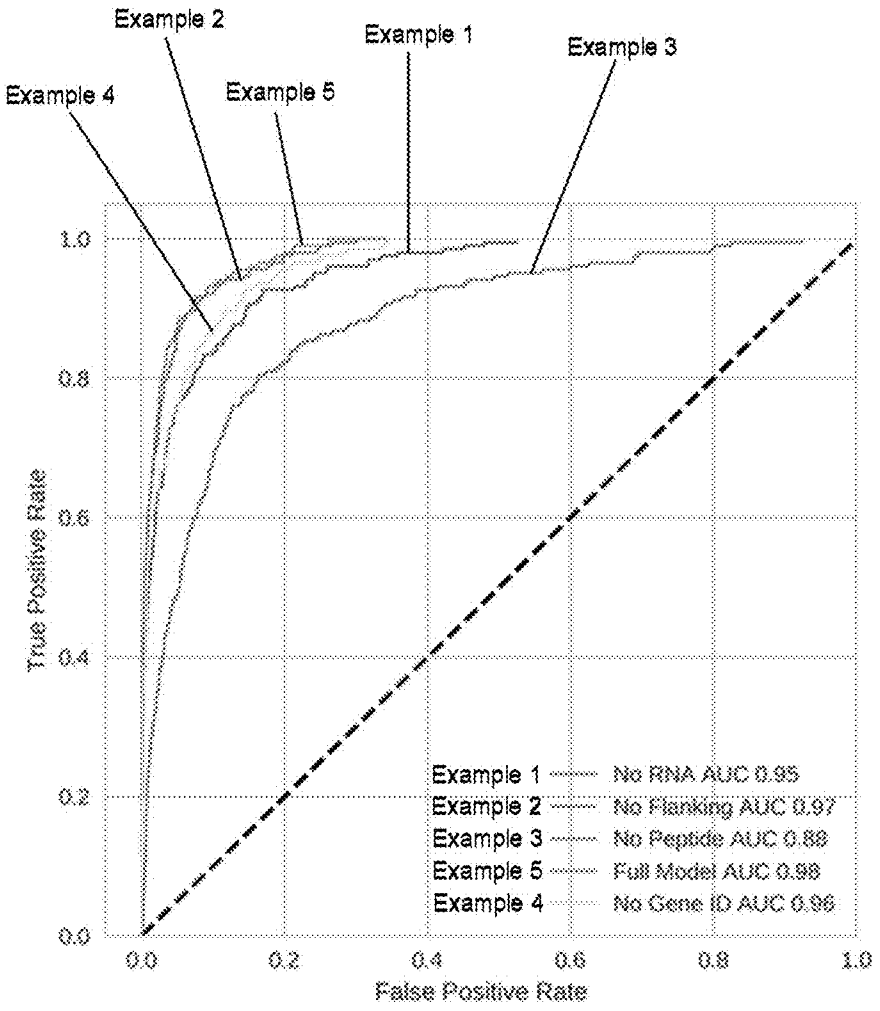
FIG. 13R is a line graph that compares the performance of identical models with varying inputs, at predicting the likelihood that peptides in a testing dataset of peptides will be presented by a MHC class II molecule.

FIG. 13R is a line graph that compares the performance of five example presentation models at predicting the likelihood that peptides in a testing dataset of peptides will be presented by a MHC class II molecule, given different sets of allele interacting and allele non-interacting variables. In other words, FIG. 13R quantifies the relative importance of various allele interacting and allele non-interacting variables for predicting the likelihood that a peptide will be presented by a MHC class II molecule.

The model architecture of each example presentation model of the five example presentations models used to generate the ROC curves of the line graph of FIG. 13R, comprised an ensemble of five sum-of-sigmoids models. Each sum-of-sigmoids model in the ensemble was configured to model peptide presentation for up to four unique HLA-DR alleles per sample. Furthermore, each sum-of-sigmoids model in the ensemble was configured to make predictions of peptide presentation likelihood based on the following allele interacting and allele non-interacting variables: peptide sequence, flanking sequence, RNA expression in units of TPM, gene identifier, and sample identifier. The allele interacting component of each sum-of-sigmoids model in the ensemble was a one-hidden-layer MLP with ReLu activations as 256 hidden units.

Prior to using the example models to predict the likelihood that the peptides in a testing dataset of peptides will be presented by a MHC class II molecule, the example models were trained and validated. To train, validate, and finally test the example models, the data described above for the 39 samples was split into training, validation, and testing datasets.

To ensure that no peptides appeared in more than one of the training, validation, and testing datasets, the following procedure was performed. First all peptides from the 39 total samples that appeared in more than one location in the proteome were removed. Then, the peptides from the 39 total samples were partitioned into blocks of 10 adjacent peptides. Each block of the peptides from the 39 total samples was assigned uniquely to the training dataset, the validation dataset, or the testing dataset. In this way, no peptide appeared in more than one dataset of the training, validation, and testing datasets.

Out of the 28,081,944 peptides in the 39 total samples, the training dataset comprised 21,077 peptides presented by MHC class II molecules from 38 of the 39 total samples. The 21,077 peptides included in the training dataset were between lengths of 9 and 20 amino acids, inclusive. The example models used to generate the ROC curves in FIG. 13R were trained on the training dataset using the ADAM optimizer and early stopping.

The validation dataset consisted of 2,346 peptides presented by MHC class II molecules from the same 38 samples used in the training dataset. The validation set was used only for early stopping.

The testing dataset comprised peptides presented by MHC class II molecules that were identified from a tumor sample using mass spectrometry. Specifically, the testing dataset comprised 203 peptides presented by MHC class II molecules-specifically HLA-DRB1*07:01, HLA-DRB1*15:01, HLA-DRB4*01:03, and HLA-DRB5*01:01 molecules—that were identified from the tumor sample. The peptides included in the testing dataset were held out of the training dataset described above.

As noted above, FIG. 13R quantifies the relative importance of various allele interacting variables and allele non-interacting variables for predicting the likelihood that a peptide will be presented by a MHC class II molecule. As also noted above, the example models used to generate the ROC curves of the line graph of FIG. 13R were configured to make predictions of peptide presentation likelihood based on the following allele interacting and allele non-interacting variables: peptide sequence, flanking sequence, RNA expression in units of TPM, gene identifier, and sample identifier. To quantify the relative importance of four of these five variables (peptide sequence, flanking sequence, RNA expression, and gene identifier) for predicting the likelihood that a peptide will be presented by a MHC class II molecule, each example model of the five the example models described above was tested using data from the testing dataset, with a different combination of the four variables. Specifically, for each peptide of the testing dataset, an example model 1 generated predictions of peptide presentation likelihood based on a peptide sequence, a flanking sequence, a gene identifier, and a sample identifier, but not on RNA expression. Similarly, for each peptide of the testing dataset, an example model 2 generated predictions of peptide presentation likelihood based on a peptide sequence, RNA expression, a gene identifier, and a sample identifier, but not on a flanking sequence. Similarly, for each peptide of the testing dataset, an example model 3 generated predictions of peptide presentation likelihood based on a flanking sequence, RNA expression, a gene identifier, and a sample identifier, but not on a peptide sequence. Similarly, for each peptide of the testing dataset, an example model 4 generated predictions of peptide presentation likelihood based on a flanking sequence, RNA expression, a peptide sequence, and a sample identifier, but not on a gene identifier. Finally, for each peptide of the testing dataset, an example model 5 generated predictions of peptide presentation likelihood based on all five variables of flanking sequence, RNA expression, peptide sequence, sample identifier, and gene identifier.

The performance of each of these five example models is depicted in the line graph of FIG. 13R. Specifically, each of the five example models is associated with a ROC curve that depicts a ratio of a true positive rate to a false positive rate for each prediction made by the model. For instance, FIG. 13R depicts a curve for the example model 1 that generated predictions of peptide presentation likelihood based on a peptide sequence, a flanking sequence, a gene identifier, and a sample identifier, but not on RNA expression. FIG. 13R depicts a curve for the example model 2 that generated predictions of peptide presentation likelihood based on a peptide sequence, RNA expression, a gene identifier, and a sample identifier, but not on a flanking sequence. FIG. 13R also depicts a curve for the example model 3 that generated predictions of peptide presentation likelihood based on a flanking sequence, RNA expression, a gene identifier, and a sample identifier, but not on a peptide sequence. FIG. 13R also depicts a curve for the example model 4 that generated predictions of peptide presentation likelihood based on a flanking sequence, RNA expression, a peptide sequence, and a sample identifier, but not on a gene identifier. And finally FIG. 13R depicts a curve for the example model 5 that generated predictions of peptide presentation likelihood based on all five variables of flanking sequence, RNA expression, peptide sequence, sample identifier, and gene identifier.

As noted above, the performance of a model at predicting the likelihood that a peptide will be presented by a MHC class II molecule is quantified by identifying an AUC for a ROC curve that depicts a ratio of a true positive rate to a false positive rate for each prediction made by the model. A model with a greater AUC has a higher performance (i.e., greater accuracy) relative to a model with a lesser AUC. As shown in FIG. 13R, the curve for the example model 5 that generated predictions of peptide presentation likelihood based on all five variables of flanking sequence, RNA expression, peptide sequence, sample identifier, and gene identifier, achieved the highest AUC of 0.98. Therefore the example model 5 that used all five variables to generate predictions of peptide presentation achieved the best performance. The curve for the example model 2 that generated predictions of peptide presentation likelihood based on a peptide sequence, RNA expression, a gene identifier, and a sample identifier, but not on a flanking sequence, achieved the second highest AUC of 0.97. Therefore, the flanking sequence can be identified as the least important variable for predicting the likelihood that a peptide will be presented by a MHC class II molecule. The curve for the example model 4 generated predictions of peptide presentation likelihood based on a flanking sequence, RNA expression, a peptide sequence, and a sample identifier, but not on a gene identifier, achieved the third highest AUC of 0.96. Therefore, the gene identifier can be identified as the second least important variable for predicting the likelihood that a peptide will be presented by a MHC class II molecule. The curve for the example model 3 that generated predictions of peptide presentation likelihood based on a flanking sequence, RNA expression, a gene identifier, and a sample identifier, but not on a peptide sequence, achieved the lowest AUC of 0.88. Therefore, the peptide sequence can be identified as the most important variable for predicting the likelihood that a peptide will be presented by a MHC class II molecule. The curve for the example model 1 that generated predictions of peptide presentation likelihood based on a peptide sequence, a flanking sequence, a gene identifier, and a sample identifier, but not on RNA expression, achieved the second lowest AUC of 0.95. Therefore, RNA expression can be identified as the second most important variable for predicting the likelihood that a peptide will be presented by a MHC class II molecule.

Figure 13S:
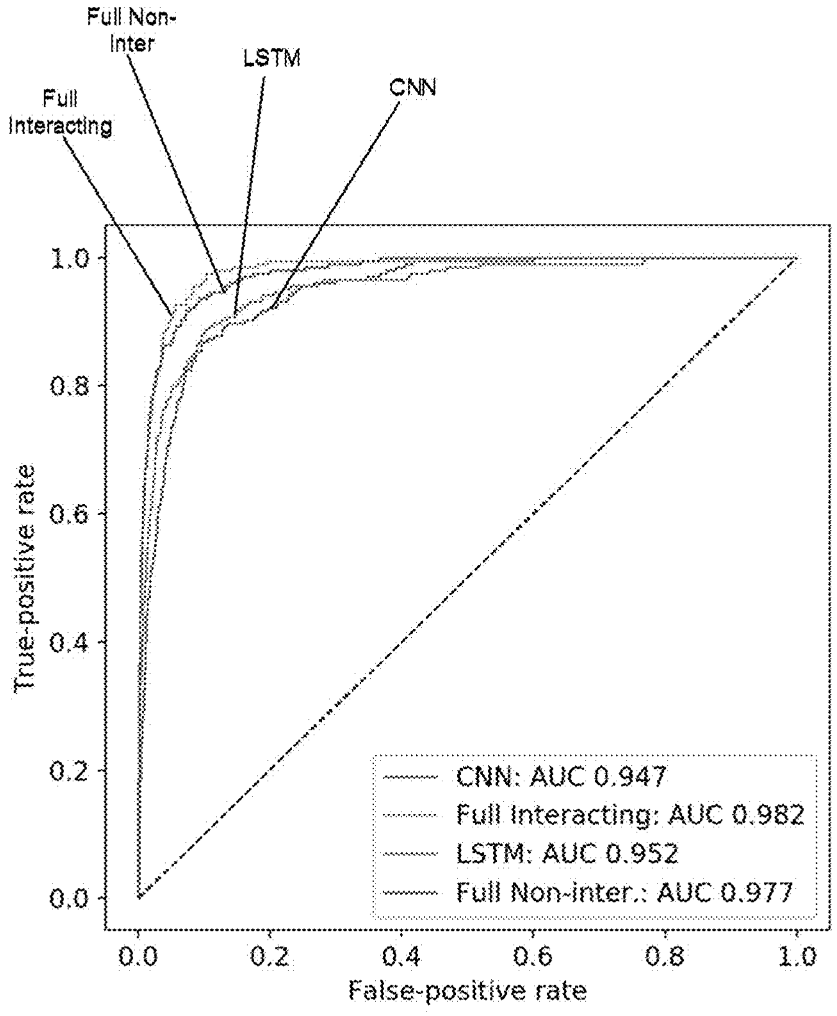
FIG. 13S is a line graph that compares the performance of four different models at predicting the likelihood that peptides in a testing dataset of peptides will be presented by a MHC class II molecule.

FIG. 13S is a line graph that compares the performance of four different presentation models at predicting the likelihood that peptides in a testing dataset of peptides will be presented by a MHC class II molecule.

The first model tested in FIG. 13S is referred to herein as a "full non-interacting model." The full non-interacting model is one embodiment of the presentation models described above in which allele-noninteracting variables $w^k$ and allele-interacting variables $x_h^k$ are input into separate dependency functions such as, for example, a neural network, and then the outputs of these separate dependency functions are added. Specifically, the full non-interacting model is one embodiment of the presentation models described above in which allele-noninteracting variables $w^k$ are input into a dependency function $g_w$, allele-interacting variables $x_h^k$ are input into separate dependency function $g_h$, and the outputs of the dependency function $g_w$ and the dependency function $g_h$ are added together. Therefore, in some embodiments, the full non-interacting model determines the likelihood of peptide presentation using equation 8 as shown above. Furthermore, embodiments of the full non-interacting model in which allele-noninteracting variables $w^k$ are input into a dependency function $g_w$, allele-interacting variables $x_h^k$ are input into separate dependency function $g_h$, and the outputs of the dependency function $g_w$ and the dependency function $g_h$ are added, are discussed in detail above with regard to the top portion of Section X.B.2, the bottom portion of Section X.B.3, the top portion of Section X.C.3, and the top portion of Section X.C.6.

The second model tested in FIG. 13S is referred to herein as a "full interacting model." The full interacting model is one embodiment of the presentation models described above in which allele-noninteracting variables $w^k$ are concatenated directly to allele-interacting variables $x_h^k$ before being input into a dependency function such as, for example, a neural network. Therefore, in some embodiments, the full interacting model determines the likelihood of peptide presentation using equation 9 as shown above. Furthermore, embodiments of the full interacting model in which allele-noninteracting variables $w^k$ are concatenated with allele-interacting variables $x_h^k$ before the variables are input into a dependency function are discussed in detail above with regard to the bottom portion of Section X.B.2, the bottom portion of Section X.C.2, and the bottom portion of Section X.C.5.

The third model tested in FIG. 13S is referred to herein as a "CNN model." The CNN model comprises a convolutional neural network, and is similar to the full non-interacting model described above. However, the layers of the convolutional neural network of the CNN model differ from the layers of the neural network of the full non-interacting model. Specifically, the input layer of the convolutional neural network of the CNN model accepts a 20-mer peptide string and subsequently embeds the 20-mer peptide string as a (n, 20, 21) tensor. The next layers of the convolutional neural network of the CNN model comprise a 1-D convolutional kernel layer of size 5 with a stride of 1, a global max pooling layer, a dropout layer with p=0.2, and finally a dense 34-node layer with a ReLu activation.

The fourth and final model tested in FIG. 13S is referred to herein as a "LSTM model." The LSTM model comprises a long short-term memory neural network. The input layer of the long short-term memory neural network of the LSTM model accepts a 20-mer peptide string and subsequently embeds the 20-mer peptide string as a (n, 20, 21) tensor. The next layers of the long short-term memory neural network of the LSTM model comprise a long short-term memory layer with 128 nodes, a dropout layer with p=0.2, and finally a dense 34-node layer with a ReLu activation.

Prior to using each of the four models of FIG. 13S to predict the likelihood that the peptides in the testing dataset of peptides will be presented by a MHC class II molecule, the models were trained using the 38-sample training dataset described above and validated using the validation dataset described above. Following this training and validation of the models, each of the four models was tested using the held-out $39^{th}$ sample testing dataset described above. Specifically, for each of the four models, each peptide of the testing dataset was input into the model, and the model subsequently output a presentation likelihood for the peptide.

The performance of each of the four models is depicted in the line graph in FIG. 13S. Specifically, each of the four models is associated with a ROC curve that depicts a ratio of a true positive rate to a false positive rate for each prediction made by the model. For instance, FIG. 13S depicts a ROC curve for the CNN model, a ROC curve for the full interacting model, a ROC curve for the LSTM model, and a ROC curve for the full non-interacting model.

As noted above, the performance of a model at predicting the likelihood that a peptide will be presented by a MHC class II molecule is quantified by identifying an AUC for a ROC curve that depicts a ratio of a true positive rate to a false positive rate for each prediction made by the model. A model with a greater AUC has a higher performance (i.e., greater accuracy) relative to a model with a lesser AUC. As shown in FIG. 13S, the curve for the full interacting model achieved the highest AUC of 0.982. Therefore the full interacting model achieved the best performance. The curve for the full non-interacting model achieved the second highest AUC of 0.977. Therefore, the full non-interacting model achieved the second best performance. The curve for the CNN model achieved the lowest AUC of 0.947. Therefore the CNN model achieved the worst performance. The curve for the LSTM model achieved the second lowest AUC of 0.952. Therefore, the LSTM model achieved the second worst performance. However, note that all models tested in FIG. 13S have an AUC that is greater than 0.9. Accordingly, despite the architectural variance between them, all models tested in FIG. 13S are capable of achieving relatively accurate predictions of peptide presentation.

Figure 13T:
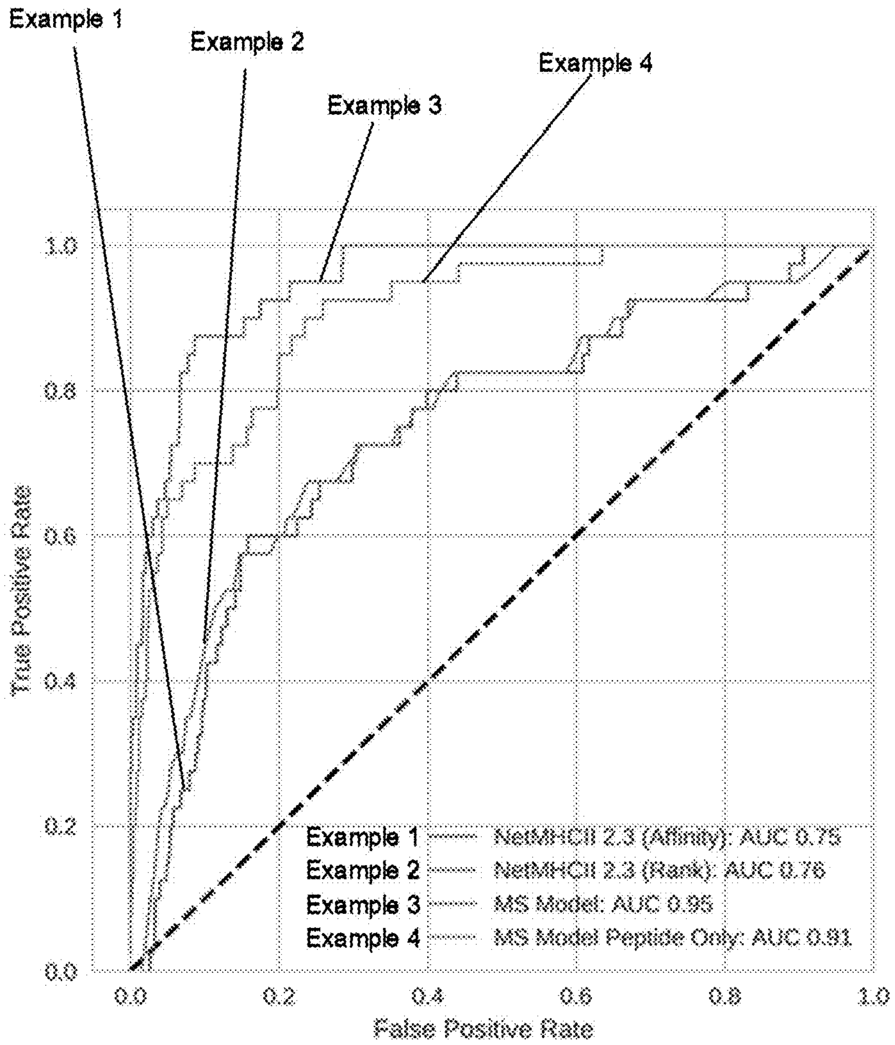
FIG. 13T is a line graph that compares the performance of a best-in-class prior art model using two different criteria and the presentation model disclosed herein with two different inputs, at predicting the likelihood that peptides in a testing dataset of peptides will be presented by a MHC class II molecule.

FIG. 13T is a line graph that compares the performance of two example best-in-class prior art models given two different criteria, and two example presentation models given two different sets of allele interacting and allele non-interacting variables, at predicting the likelihood that peptides in a testing dataset of peptides will be presented by a MHC class II molecule. Specifically, FIG. 13T is a line graph that compares the performance of an example best-in-class prior art model that utilizes minimum NetMHCII 2.3 predicted binding affinity as a criterion to generate predictions (example model 1), an example best-in-class prior art model that utilizes minimum NetMHCII 2.3 predicted binding rank as a criterion to generate predictions (example model 2), an example presentation model that generates predictions of peptide presentation likelihood based on MHC class II molecule type and peptide sequence (example model 4), and an example presentation model that generates predictions of peptide presentation likelihood based on MHC class II molecule type, peptide sequence, RNA expression, gene identifier, and flanking sequence (example model 3).

The best-in-class prior art model used as example model 1 and example model 2 in FIG. 13T is the NetMHCII 2.3 model. The NetMHCII 2.3 model generates predictions of peptide presentation likelihood based on MHC class II molecule type and peptide sequence. The NetMHCII 2.3 model was tested using the NetMHCII 2.3 website (www.cbs.dtu.dk/services/NetMHCII/, PMID 29315598)[76].

As noted above, the NetMHCII 2.3 model was tested according to two different criteria. Specifically, example model 1 model generated predictions of peptide presentation likelihood according to minimum NetMHCII 2.3 predicted binding affinity, and example model 2 generated predictions of peptide presentation likelihood according to minimum NetMHCII 2.3 predicted binding rank.

The presentation model used as example model 3 and example model 4 is an embodiment of the presentation model disclosed herein that is trained using data obtained via mass spectrometry. As noted above, the presentation model generated predictions of peptide presentation likelihood based on two different sets of allele interacting and allele non-interacting variables. Specifically, example model 4 generated predictions of peptide presentation likelihood based on MHC class II molecule type and peptide sequence (the same variable used by the NetMHCII 2.3 model), and example model 3 generated predictions of peptide presentation likelihood based on MHC class II molecule type, peptide sequence, RNA expression, gene identifier, and flanking sequence.

Prior using the example models of FIG. 13T to predict the likelihood that the peptides in the testing dataset of peptides will be presented by a MHC class II molecule, the models were trained and validated. The NetMHCII 2.3 model (example model 1 and example model 2) was trained and validated using its own training and validation datasets based on HLA-peptide binding affinity assays deposited in the immune epitope database (IEDB, www.iedb.org). The training dataset used to train the NetMHCII 2.3 model is known to comprise almost exclusively 15-mer peptides. On the other hand, example models 3 and 4 were trained using the training dataset described above with regard to FIG. 13R and validated and using the validation dataset described above with regard to FIG. 13R.

Following the training and validation of the models, each of the models was tested using a testing dataset. As noted above, the NetMHCII 2.3 model is trained on a dataset comprising almost exclusively 15-mer peptides, meaning that NetMHCII 3.2 does not have the ability to give different priority to peptides of different weights, thereby reducing the predictive performance for NetMHCII 3.2 on HLA class II presentation mass spectrometry data containing peptides of all lengths. Therefore, to provide a fair comparison between the models not affected by variable peptide length, the testing dataset included exclusively 15-mer peptides. Specifically, the testing dataset comprised 933 15-mer peptides. 40 of the 933 peptides in the testing dataset were presented by MHC class II molecules-specifically by HLA-DRB1*07:01, HLA-DRB1*15:01, HLA-DRB4*01:03, and HLA-DRB5*01:01 molecules. The peptides included in the testing dataset were held out of the training datasets described above.

To test the example models using the testing dataset, for each of the example models, for each peptide of the 933 peptides in the testing dataset, the model generated a prediction of presentation likelihood for the peptide. Specifically, for each peptide in the testing dataset, the example 1 model generated a presentation score for the peptide by the MHC class II molecules using MHC class II molecule types and peptide sequence, by ranking the peptide by the minimum NetMHCII 2.3 predicted binding affinity across the four HLA class II DR alleles in the testing dataset. Similarly, for each peptide in the testing dataset, the example 2 model generated a presentation score for the peptide by the MHC class II molecules using MHC class II molecule types and peptide sequence, by ranking the peptide by the minimum NetMHCII 2.3 predicted binding rank (i.e., quantile normalized binding affinity) across the four HLA class II DR alleles in the testing dataset. For each peptide in the testing dataset, the example 4 model generated a presentation likelihood for the peptide by the MHC class II molecules based on MHC class II molecule type and peptide sequence. Similarly, for each peptide in the testing dataset, the example model 3 generated a presentation likelihood for the peptide by the MHC class II molecules based on MHC class II molecule types, peptide sequence, RNA expression, gene identifier, and flanking sequence.

The performance of each of the four example models is depicted in the line graph in FIG. 13T. Specifically, each of the four example models is associated with a ROC curve that depicts a ratio of a true positive rate to a false positive rate for each prediction made by the model. For instance, FIG. 13T depicts a ROC curve for the example 1 model that utilized minimum NetMHCII 2.3 predicted binding affinity to generate predictions, a ROC curve for the example 2 model that utilized minimum NetMHCII 2.3 predicted binding rank to generate predictions, a ROC curve for the example 4 model that generated peptide presentation likelihoods based on MHC class II molecule type and peptide sequence, and a ROC curve for the example 3 model that generated peptide presentation likelihoods based on MHC class II molecule type, peptide sequence, RNA expression, gene identifier, and flanking sequence.

As noted above, the performance of a model at predicting the likelihood that a peptide will be presented by a MHC class II molecule is quantified by identifying an AUC for a ROC curve that depicts a ratio of a true positive rate to a false positive rate for each prediction made by the model. A model with a greater AUC has a higher performance (i.e., greater accuracy) relative to a model with a lesser AUC. As shown in FIG. 13T, the curve for the example 3 model that generated peptide presentation likelihoods based on MHC class II molecule type, peptide sequence, RNA expression, gene identifier, and flanking sequence, achieved the highest AUC of 0.95. Therefore the example 3 model that generated peptide presentation likelihoods based on MHC class II molecule type, peptide sequence, RNA expression, gene identifier, and flanking sequence achieved the best performance. The curve for the example 4 model that generated peptide presentation likelihoods based on MHC class II molecule type and peptide sequence achieved the second highest AUC of 0.91. Therefore, the example 4 model that generated peptide presentation likelihoods based on MHC class II molecule type and peptide sequence achieved the second best performance. The curve for the example 1 model that utilized minimum NetMHCII 2.3 predicted binding affinity to generate predictions achieved the lowest AUC of 0.75. Therefore the example 1 model that utilized minimum NetMHCII 2.3 predicted binding affinity to generate predictions achieved the worst performance. The curve for the example 2 model that utilized minimum NetMHCII 2.3 predicted binding rank to generate predictions achieved the second lowest AUC of 0.76. Therefore, the example 2 model that utilized minimum NetMHCII 2.3 predicted binding rank to generate predictions achieved the second worst performance.

As shown in FIG. 13T, the discrepancy in performance between the example models 1 and 2 and the example models 3 and 4 is large. Specifically, the performance of the NetMHCII 2.3 model (that utilizes either criterion of minimum NetMHCII 2.3 predicted binding affinity or minimum NetMHCII 2.3 predicted binding rank) is almost 25% lower than the performance of the presentation model disclosed herein (that generates peptide presentation likelihoods based on either MHC class II molecule type and peptide sequence, or on MHC class II molecule type, peptide sequence, RNA expression, gene identifier, and flanking sequence). Therefore, FIG. 13T demonstrates that the presentation models disclosed herein are capable of achieving significantly more accurate presentation predictions than the current best-in-class prior art model, the NetMHCII 2.3 model.

Even further, as discussed above, the NetMHCII 2.3 model is trained on a training dataset that comprises almost exclusively 15-mer peptides. As a result, the NetMHCII 2.3 model is not trained to learn which peptides lengths are more likely to be presented by MHC class II molecules. Therefore, the NetMHCII 2.3 model does not weight its predictions of likelihood of peptide presentation by MHC class II molecules according to the length of the peptide. In other words, the NetMHCII 2.3 model does not modify its predictions of likelihood of peptide presentation by MHC class II molecules for peptides that have lengths outside of the modal peptide length of 15 amino acids. As a result, the NetMHCII 2.3 model overpredicts the likelihood of presentation of peptides with lengths greater or less than 15 amino acids.

On the other hand, the presentation models disclosed herein are trained using peptide data obtained via mass spectrometry, and therefore can be trained on training dataset that comprise peptides of all different lengths. As a result, the presentation models disclosed herein are able to learn which peptides lengths are more likely to be presented by MHC class II molecules. Therefore, the presentation models disclosed herein can weight predictions of likelihood of peptide presentation by MHC class II molecules according to the length of the peptide. In other words, the presentation models disclosed herein are able to modify their predictions of likelihood of peptide presentation by MHC class II molecules for peptides that have lengths outside of the modal peptide length of 15 amino acids. As a result, the presentation models disclosed herein are capable of achieving significantly more accurate presentation predictions for peptides of lengths greater than or less than 15 amino acids, than the current best-in-class prior art model, the NetMHCII 2.3 model. This is one advantage of using the presentation models disclosed herein to predict likelihood of peptide presentation by MHC class II molecules.

XII.N. Example of Parameters Determined for MHC II Alleles

The following shows a set of parameters determined for a variation of the multi-allele presentation model (equation (16)) generating implicit per-allele presentation likelihoods for class II MHC alleles HLA-DRB1*12:01 and HLA-DRB1*10:01:

$$u=\text{expit}(\text{relu}(X \cdot W^1+b^1) \cdot W^2+b^2),$$

where relu(•) is the rectified linear unit (RELU) function, $W^1$, $b^1$, $W^2$, and $b^2$ are the set of parameters θ determined for the model. The allele-interacting variables X are contained in a 1×399) matrix consisting of 1 row of one-hot encoded and middle-padded peptide sequences per input peptide. The dimensions of $W^1$ are (399×256), the dimensions of $b^1$ (1×256), the dimensions of $W^2$ are (256×2), and $b^2$ are (1×2). The first column of the output indicates the implicit per-allele probability of presentation for the peptide sequence by the allele HLA-DRB1*12:01, and the second column of the output indicates the implicit per-allele for the peptide sequence by the allele HLA-DRB1*10:01. For demonstration purposes, values for $W^1$, $b^1$, $W^2$, and $b^2$ are described in detail in international application PCT/US2018/028438, herein incorporated by reference for all that it teaches.

XIII. Example Computer

Figure 14:
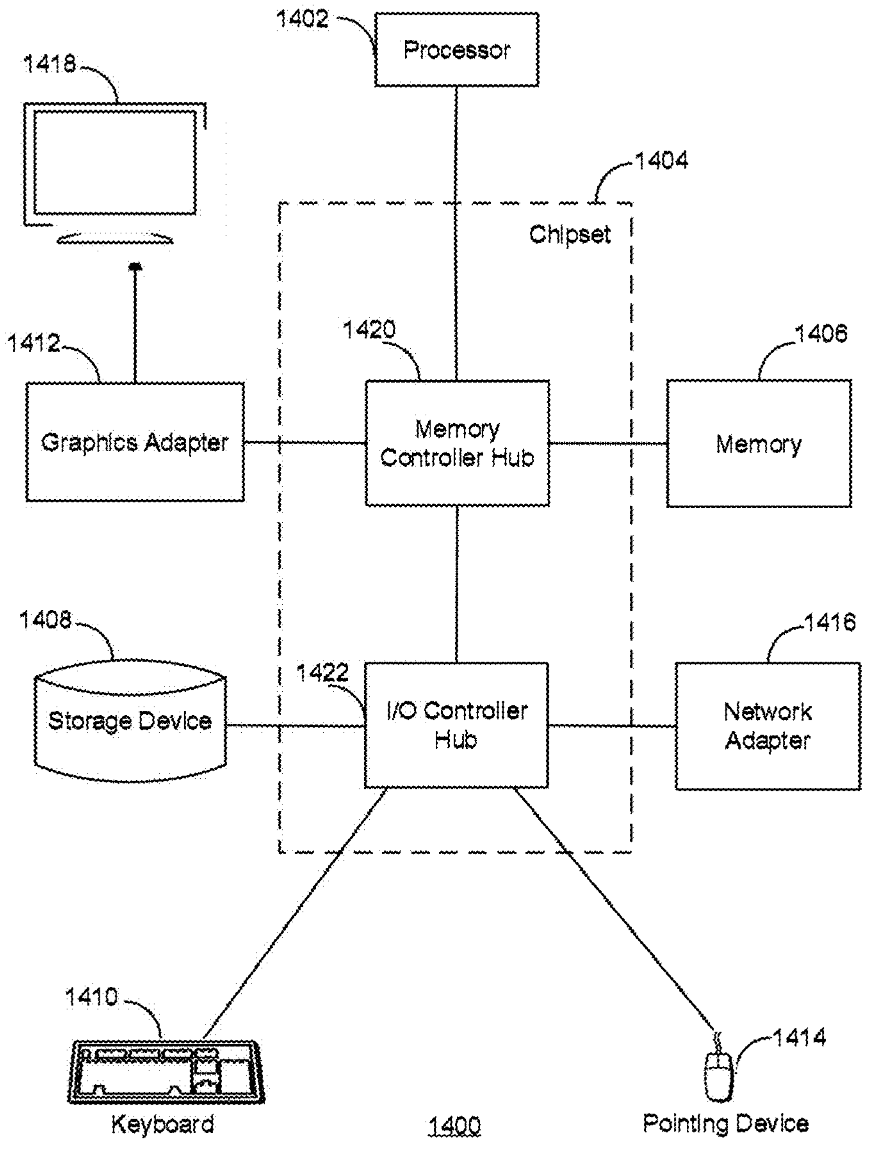
FIG. 14 illustrates an example computer for implementing the entities shown in FIGS. 1 and 3.

FIG. 14 illustrates an example computer 1400 for implementing the entities shown in FIGS. 1 and 3. The computer 1400 includes at least one processor 1402 coupled to a chipset 1404. The chipset 1404 includes a memory controller hub 1420 and an input/output (I/O) controller hub 1422. A memory 1406 and a graphics adapter 1412 are coupled to the memory controller hub 1420, and a display 1418 is coupled to the graphics adapter 1412. A storage device 1408, an input device 1414, and network adapter 1416 are coupled to the I/O controller hub 1422. Other embodiments of the computer 1400 have different architectures.

The storage device 1408 is a non-transitory computer-readable storage medium such as a hard drive, compact disk read-only memory (CD-ROM), DVD, or a solid-state memory device. The memory 1406 holds instructions and data used by the processor 1402. The input interface 1414 is a touch-screen interface, a mouse, track ball, or other type of pointing device, a keyboard, or some combination thereof, and is used to input data into the computer 1400. In some embodiments, the computer 1400 may be configured to receive input (e.g., commands) from the input interface 1414 via gestures from the user. The graphics adapter 1412 displays images and other information on the display 1418. The network adapter 1416 couples the computer 1400 to one or more computer networks.

The computer 1400 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 1408, loaded into the memory 1406, and executed by the processor 1402.

The types of computers 1400 used by the entities of FIG. 1 can vary depending upon the embodiment and the processing power required by the entity. For example, the presentation identification system 160 can run in a single computer 1400 or multiple computers 1400 communicating with each other through a network such as in a server farm. The computers 1400 can lack some of the components described above, such as graphics adapters 1412, and displays 1418.

XIV. Neoantigen Delivery Vector Example

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ Ed. (Plenum Press) Vols A and B (1992).

XIV.A. Neoantigen Cassette Design

Through vaccination, multiple class I MHC restricted tumor-specific neoantigens (TSNAs) that stimulate the corresponding cellular immune response(s) can be delivered. In one example, a vaccine cassette was engineered to encode multiple epitopes as a single gene product where the epitopes were either embedded within their natural, surrounding peptide sequence or spaced by non-natural linker sequences. Several design parameters were identified that could potentially impact antigen processing and presentation and therefore the magnitude and breadth of the TSNA specific CD8 T cell responses. In the present example, several model cassettes were designed and constructed to evaluate: (1) whether robust T cell responses could be generated to multiple epitopes incorporated in a single expression cassette; (2) what makes an optimal linker placed between the TSNAs within the expression cassette—that leads to optimal processing and presentation of all epitopes; (3) if the relative position of the epitopes within the cassette impact T cell responses; (4) whether the number of epitopes within a cassette influences the magnitude or quality of the T cell responses to individual epitopes; (5) if the addition of cellular targeting sequences improves T cell responses.

Two readouts were developed to evaluate antigen presentation and T cell responses specific for marker epitopes within the model cassettes: (1) an in vitro cell-based screen which allowed assessment of antigen presentation as gauged by the activation of specially engineered reporter T cells (Aarnoudse et al., 2002; Nagai et al., 2012); and (2) an in vivo assay that used HLA-A2 transgenic mice (Vitiello et al., 1991) to assess post-vaccination immunogenicity of cassette-derived epitopes of human origin by their corresponding epitope-specific T cell responses (Comet et al., 2006; Depla et al., 2008; Ishioka et al., 1999).

XIV.B. Neoantigen Cassette Design Evaluation

XIV.B.1. Methods and Materials

TCR and Cassette Design and Cloning

The selected TCRs recognize peptides NLVPMVATV (SEQ ID NO: 132) (PDB #5D2N), CLGGLLTMV (SEQ ID NO: 133) (PDB #3REV), GILGFVFTL (SEQ ID NO: 134) (PDB #1OGA) LLFGYPVYV (SEQ ID NO: 135) (PDB #1A07) when presented by A*0201. Transfer vectors were constructed that contain 2A peptide-linked TCR subunits (beta followed by alpha), the EMCV IRES, and 2A-linked CD8 subunits (beta followed by alpha and by the puromycin resistance gene). Open reading frame sequences were codon-optimized and synthesized by GeneArt.

Cell Line Generation for In Vitro Epitope Processing and Presentation Studies

Peptides were purchased from ProImmune or Genscript diluted to 10 mg/mL with 10 mM tris(2-carboxyethyl) phosphine (TCEP) in water/DMSO (2:8, v/v). Cell culture medium and supplements, unless otherwise noted, were from Gibco. Heat inactivated fetal bovine serum (FBShi) was from Seradigm. QUANTI-Luc Substrate, Zeocin, and Puromycin were from InvivoGen. Jurkat-Lucia NFAT Cells (InvivoGen) were maintained in RPMI 1640 supplemented with 10% FBShi, Sodium Pyruvate, and 100 μg/mL Zeocin. Once transduced, these cells additionally received 0.3 μg/mL Puromycin. T2 cells (ATCC CRL-1992) were cultured in Iscove's Medium (IMDM) plus 20% FBShi. U-87 MG (ATCC HTB-14) cells were maintained in MEM Eagles Medium supplemented with 10% FBShi.

Jurkat-Lucia NFAT cells contain an NFAT-inducible Lucia reporter construct. The Lucia gene, when activated by the engagement of the T cell receptor (TCR), causes secretion of a coelenterazine-utilizing luciferase into the culture medium. This luciferase can be measured using the QUANTI-Luc luciferase detection reagent. Jurkat-Lucia cells were transduced with lentivirus to express antigen-specific TCRs. The HIV-derived lentivirus transfer vector was obtained from GeneCopoeia, and lentivirus support plasmids expressing VSV-G (pCMV-VsvG), Rev (pRSV-Rev) and Gag-pol (pCgpV) were obtained from Cell Design Labs.

Lentivirus was prepared by transfection of 50-80% confluent T75 flasks of HEK293 cells with Lipofectamine 2000 (Thermo Fisher), using 40 μl of lipofectamine and 20 μg of the DNA mixture (4:2:1:1 by weight of the transfer plasmid: pCgpV:pRSV-Rev:pCMV-VsvG). 8-10 mL of the virus-containing media were concentrated using the Lenti-X system (Clontech), and the virus resuspended in 100-200 μl of fresh medium. This volume was used to overlay an equal volume of Jurkat-Lucia cells (5–10E4-1–10E6 cells were used in different experiments). Following culture in 0.3 μg/ml puromycin-containing medium, cells were sorted to obtain clonality. These Jurkat-Lucia TCR clones were tested for activity and selectivity using peptide loaded T2 cells.

In Vitro Epitope Processing and Presentation Assay

T2 cells are routinely used to examine antigen recognition by TCRs. T2 cells lack a peptide transporter for antigen processing (TAP deficient) and cannot load endogenous peptides in the endoplasmic reticulum for presentation on the MHC. However, the T2 cells can easily be loaded with exogenous peptides. The five marker peptides (NLVPMVATV (SEQ ID NO: 132), CLGGLLTMV (SEQ ID NO: 133), GLCTLVAML (SEQ ID NO: 136), LLFGYPVYV (SEQ ID NO: 135), GILGFVFTL (SEQ ID NO: 134)) and two irrelevant peptides (WLSLLVPFV (SEQ ID NO: 137), FLLTRICT (SEQ ID NO: 138)) were loaded onto T2 cells. Briefly, T2 cells were counted and diluted to 1×106 cells/mL with IMDM plus 1% FBShi. Peptides were added to result in 10 μg peptide/1×106 cells. Cells were then incubated at 37° C. for 90 minutes. Cells were washed twice with IMDM plus 20% FBShi, diluted to 5×10E5 cells/mL and 100 μL plated into a 96-well Costar tissue culture plate. Jurkat-Lucia TCR clones were counted and diluted to 5×10E5 cells/mL in RPMI 1640 plus 10% FBShi and 100 μL added to the T2 cells. Plates were incubated overnight at 37° C., 5% CO2. Plates were then centrifuged at 400 g for 3 minutes and 20 μL supernatant removed to a white flat bottom Greiner plate. QUANTI-Luc substrate was prepared according to instructions and 50 μL/well added. Luciferase expression was read on a Molecular Devices SpectraMax iE3x.

To test marker epitope presentation by the adenoviral cassettes, U-87 MG cells were used as surrogate antigen presenting cells (APCs) and were transduced with the adenoviral vectors. U-87 MG cells were harvested and plated in culture media as 5×10E5 cells/100 μl in a 96-well Costar tissue culture plate. Plates were incubated for approximately 2 hours at 37° C. Adenoviral cassettes were diluted with MEM plus 10% FBShi to an MOI of 100, 50, 10, 5, 1 and 0 and added to the U-87 MG cells as 5 μl/well. Plates were again incubated for approximately 2 hours at 37° C. Jurkat-Lucia TCR clones were counted and diluted to 5×10E5 cells/mL in RPMI plus 10% FBShi and added to the U-87 MG cells as 100 μL/well. Plates were then incubated for approximately 24 hours at 37° C., 5% C02. Plates were centrifuged at 400 g for 3 minutes and 20 μL supernatant removed to a white flat bottom Greiner plate. QUANTI-Luc substrate was prepared according to instructions and 50 μL/well added. Luciferase expression was read on a Molecular Devices SpectraMax iE3x.

Mouse Strains for Immunogenicity Studies

Transgenic HLA-A2.1 (HLA-A2 Tg) mice were obtained from Taconic Labs, Inc. These mice carry a transgene consisting of a chimeric class I molecule comprised of the human HLA-A2.1 leader, α1, and α2 domains and the murine H2-Kb α3, transmembrane, and cytoplasmic domains (Vitiello et al., 1991). Mice used for these studies were the first generation offspring (F1) of wild type BALB/cAnNTac females and homozygous HLA-A2.1 Tg males on the C57B11/6 background.

Adenovirus Vector (Ad5v) Immunizations

HLA-A2 Tg mice were immunized with $1\times10^{10}$ to $1\times10^{6}$ viral particles of adenoviral vectors via bilateral intramuscular injection into the tibialis anterior. Immune responses were measured at 12 days post-immunization.

Lymphocyte Isolation

Lymphocytes were isolated from freshly harvested spleens and lymph nodes of immunized mice. Tissues were dissociated in RPMI containing 10% fetal bovine serum with penicillin and streptomycin (complete RPMI) using the GentleMACS tissue dissociator according to the manufacturer's instructions.

Ex Vivo Enzyme-Linked Immunospot (ELISPOT) Analysis

ELISPOT analysis was performed according to ELISPOT harmonization guidelines (Janetzki et al., 2015) with the mouse IFNg ELISpotPLUS kit (MABTECH). $1\times10^{5}$ splenocytes were incubated with 10 uM of the indicated peptides for 16 hours in 96-well IFNg antibody coated plates. Spots were developed using alkaline phosphatase. The reaction was timed for 10 minutes and was quenched by running the plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Ex Vivo Intracellular Cytokine Staining (ICS) and Flow Cytometry Analysis

Freshly isolated lymphocytes at a density of 2-5×$10^6$ cells/mL were incubated with 10 uM of the indicated peptides for 2 hours. After two hours, brefeldin A was added to a concentration of 5 ug/ml and cells were incubated with stimulant for an additional 4 hours. Following stimulation, viable cells were labeled with fixable viability dye eFluor780 according to manufacturer's protocol and stained with anti-CD8 APC (clone 53-6.7, BioLegend) at 1:400 dilution. Anti-IFNg PE (clone XMG1.2, BioLegend) was used at 1:100 for intracellular staining. Samples were collected on an Attune NxT Flow Cytometer (Thermo Scientific). Flow cytometry data was plotted and analyzed using FlowJo. To assess degree of antigen-specific response, both the percent IFNg+ of CD8+ cells and the total IFNg+ cell number/1×$10^6$ live cells were calculated in response to each peptide stimulant.

XIV.B.2. In Vitro Evaluation of Neoantigen Cassette Designs

Figure 15:
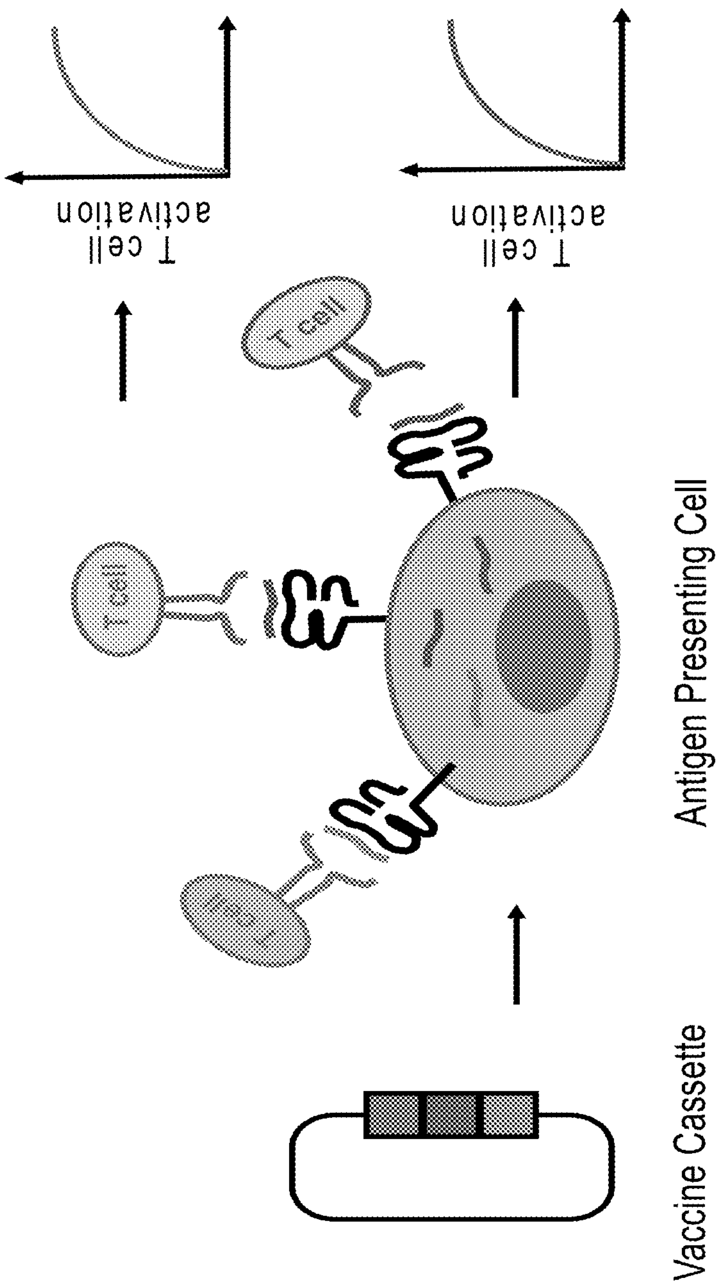
FIG. 15 illustrates development of an in vitro T cell activation assay. Schematic of the assay in which the delivery of a vaccine cassette to antigen presenting cells, leads to expression, processing and MHC-restricted presentation of distinct peptide antigens. Reporter T cells engineered with T cell receptors that match the specific peptide-MHC combination become activated resulting in luciferase expression.

As an example of neoantigen cassette design evaluation, an in vitro cell-based assay was developed to assess whether selected human epitopes within model vaccine cassettes were being expressed, processed, and presented by antigen-presenting cells (FIG. 15). Upon recognition, Jurkat-Lucia reporter T cells that were engineered to express one of five TCRs specific for well-characterized peptide-HLA combinations become activated and translocate the nuclear factor of activated T cells (NFAT) into the nucleus which leads to transcriptional activation of a luciferase reporter gene. Antigenic stimulation of the individual reporter CD8 T cell lines was quantified by bioluminescence.

Individual Jurkat-Lucia reporter lines were modified by lentiviral transduction with an expression construct that includes an antigen-specific TCR beta and TCR alpha chain separated by a P2A ribosomal skip sequence to ensure equimolar amounts of translated product (Banu et al., 2014). The addition of a second CD8 beta-P2A-CD8 alpha element to the lentiviral construct provided expression of the CD8 co-receptor, which the parent reporter cell line lacks, as CD8 on the cell surface is crucial for the binding affinity to target pMHC molecules and enhances signaling through engagement of its cytoplasmic tail (Lyons et al., 2006; Yachi et al., 2006).

After lentiviral transduction, the Jurkat-Lucia reporters were expanded under puromycin selection, subjected to single cell fluorescence assisted cell sorting (FACS), and the monoclonal populations tested for luciferase expression. This yielded stably transduced reporter cell lines for specific peptide antigens 1, 2, 4, and 5 with functional cell responses. (Table 2).

TABLE 2

Development of an in vitro T cell activation assay. Peptide-specific T cell recognition as measured by induction of luciferase indicates effective processing and presentation of the vaccine cassette antigens.

| Epitope | Short Cassette Design AAY |
|---|---|
| 1 | 24.5 ± 0.5 |
| 2 | 11.3 ± 0.4 |
| 3* | n/a |
| 4 | 26.1 ± 3.1 |
| 5 | 46.3 ± 1.9 |

*Reporter T cell for epitope 3 not yet generated

In another example, a series of short cassettes, all marker epitopes were incorporated in the same position (FIG. 16A) and only the linkers separating the HLA-A*0201 restricted epitopes (FIG. 16B) were varied. Reporter T cells were individually mixed with U-87 antigen-presenting cells (APCs) that were infected with adenoviral constructs expressing these short cassettes, and luciferase expression was measured relative to uninfected controls. All four antigens in the model cassettes were recognized by matching reporter T cells, demonstrating efficient processing and presentation of multiple antigens. The magnitude of T cell responses follow largely similar trends for the natural and AAY-linkers. The antigens released from the RR-linker based cassette show lower luciferase inductions (Table 3). The DPP-linker, designed to disrupt antigen processing, produced a vaccine cassette that led to low epitope presentation (Table 3).

TABLE 3

Evaluation of linker sequences in short cassettes. Luciferase induction in the in vitro T cell activation assay indicated that, apart from the DPP-based cassette, all linkers facilitated efficient release of the cassette antigens. T cell epitope only (no linker) = 9AA, natural linker one side = 17AA, natural linker both sides = 25AA, non-natural linkers = AAY, RR, DPP

| | Short Cassette Designs | | | | | |
|---|---|---|---|---|---|---|
| Epitope | 9AA | 17AA | 25AA | AAY | RR | DPP |
| 1 | 33.6 ± 0.9 | 42.8 ± 2.1 | 42.3 ± 2.3 | 24.5 ± 0.5 | 21.7 ± 0.9 | 0.9 ± 0.1 |
| 2 | 12.0 ± 0.9 | 10.3 ± 0.6 | 14.6 ± 04 | 11.3 ± 0.4 | 8.5 ± 0.3 | 1.1 ± 0.2 |
| 3* | n/a | n/a | n/a | n/a | n/a | n/a |
| 4 | 26.6 ± 2.5 | 16.1 ± 0.6 | 16.6 ± 0.8 | 26.1 ± 3.1 | 12.5 ± 0.8 | 1.3 ± 0.2 |
| 5 | 29.7 ± 0.6 | 21.2 ± 0.7 | 24.3 ± 1.4 | 46.3 ± 1.9 | 19.7 ± 0.4 | 1.3 ± 0.1 |

*Reporter T cell for epitope 3 not yet generated

Figure 17:
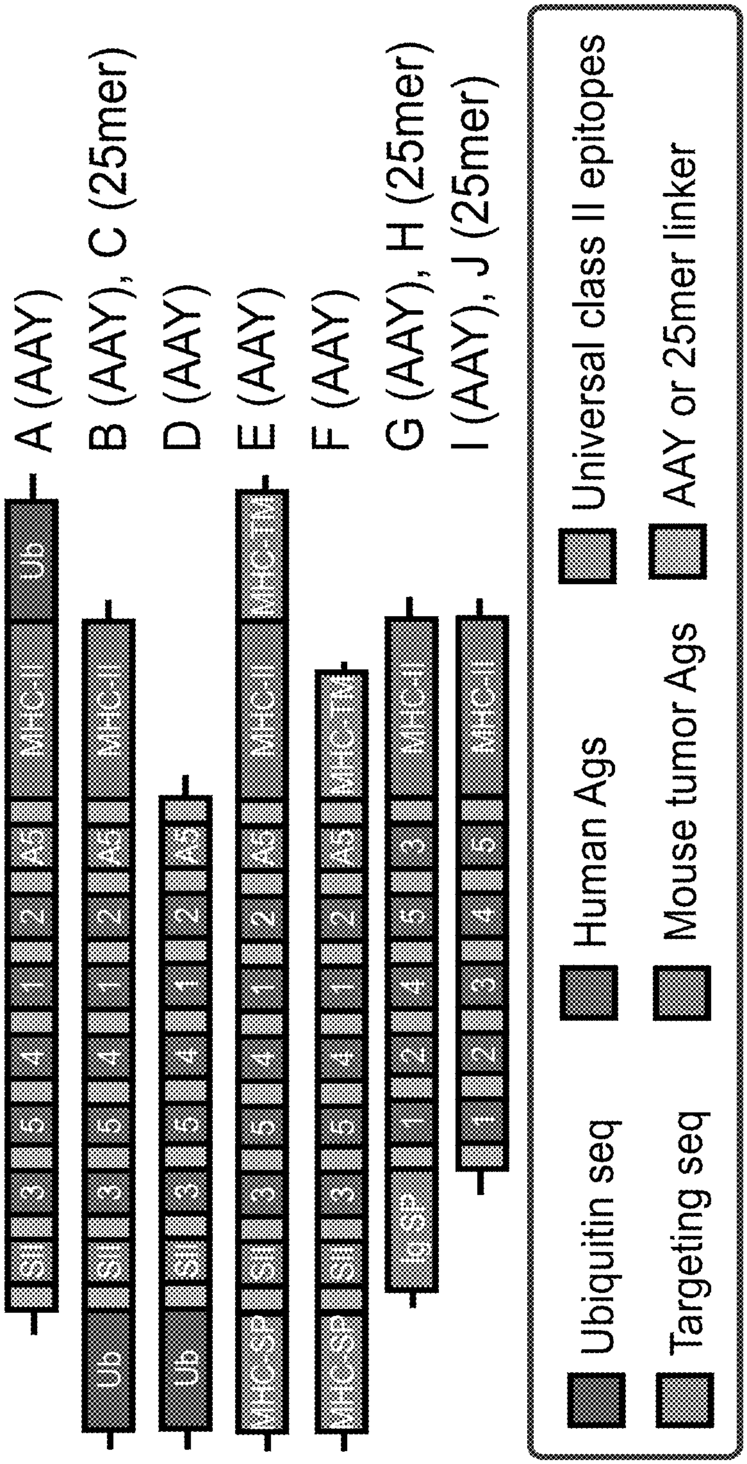
FIG. 17 illustrates evaluation of cellular targeting sequences added to model vaccine cassettes. The targeting cassettes extend the short cassette designs with ubiquitin (Ub), signal peptides (SP) and/or transmembrane (TM) domains, feature next to the five marker human T cell epitopes (epitopes 1 through 5) also two mouse T cell epitopes SIINFEKL (SII) (SEQ ID NO: 57) and SPSYAYHQF (A5) (SEQ ID NO: 58), and use either the non natural linker AAY- or natural linkers flanking the T cell epitopes on both sides (25mer).

In another example, an additional series of short cassettes were constructed that, besides human and mouse epitopes, contained targeting sequences such as ubiquitin (Ub), MHC and Ig-kappa signal peptides (SP), and/or MHC transmembrane (TM) motifs positioned on either the N- or C-terminus of the cassette. (FIG. 17). When delivered to U-87 APCs by adenoviral vector, the reporter T cells again demonstrated efficient processing and presentation of multiple cassette-derived antigens. However, the magnitude of T cell responses were not substantially impacted by the various targeting features (Table 4).

TABLE 4

Evaluation of cellular targeting sequences added to model vaccine cassettes. Employing the in vitro T cell activation assay demonstrated that the four HLA-A*0201 restricted marker epitopes are liberated efficiently from the model cassettes and targeting sequences did not substantially improve T cell recognition and activation.

| | Short Cassette Designs | | | | | | | | | |
|---|---|---|---|---|---|---|---|---|---|---|
| Epitope | A | B | C | D | E | F | G | H | I | J |
| 1 | 32.5 ± 1.5 | 31.8 ± 0.8 | 29.1 ± 1.2 | 29.1 ± 1.1 | 28.4 ± 0.7 | 20.4 ± 0.5 | 35.0 ± 1.3 | 30.3 ± 2.0 | 22.5 ± 0.9 | 38.1 ± 1.6 |
| 2 | 6.1 ± 0.2 | 6.3 ± 0.2 | 7.6 ± 0.4 | 7.0 ± 0.5 | 5.9 ± 0.2 | 3.7 ± 0.2 | 7.6 ± 0.4 | 5.4 ± 0.3 | 6.2 ± 0.4 | 6.4 ± 0.3 |
| 3* | n/a | n/a | n/a | n/a | n/a | n/a | n/a | n/a | n/a | n/a |
| 4 | 12.3 ± 1.1 | 14.1 ± 0.7 | 12.2 ± 0.8 | 13.7 ± 1.0 | 11.7 ± 0.8 | 10.6 ± 0.4 | 11.0 ± 0.6 | 7.6 ± 0.6 | 16.1 ± 0.5 | 8.7 ± 0.5 |
| 5 | 44.4 ± 2.8 | 53.6 ± 1.6 | 49.9 ± 3.3 | 50.5 ± 2.8 | 41.7 ± 2.8 | 36.1 ± 1.1 | 46.5 ± 2.1 | 31.4 ± 0.6 | 75.4 ± 1.6 | 35.7 ± 2.2 |

*Reporter T cell for epitope 3 not yet generated

XIV.B.3. In Vivo Evaluation of Neoantigen Cassette Designs

Figures 16A, 16B:
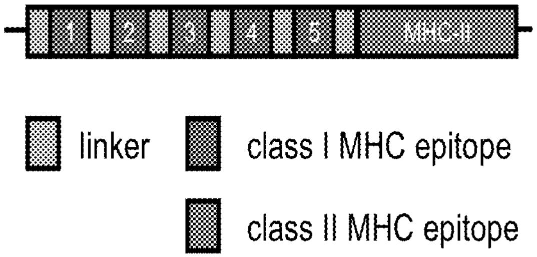
FIG. 16A illustrates evaluation of linker sequences in short cassettes and shows five class I MHC restricted epitopes (epitopes 1 through 5) concatenated in the same position relative to each other followed by two universal class II MHC epitopes (MHC-II). Various iterations were generated using different linkers. In some cases the T cell epitopes are directly linked to each other. In others, the T cell epitopes are flanked on one or both sides by its natural sequence. In other iterations, the T cell epitopes are linked by the non-natural sequences AAY, RR, and DPP.
FIG. 16B illustrates evaluation of linker sequences in short cassettes and shows sequence information on the T cell epitopes embedded in the short cassettes. Figure discloses SEQ ID NOS 132, 133, 136, 135, 134, 160, and 161, respectively, in order of appearance.
Figure 18:
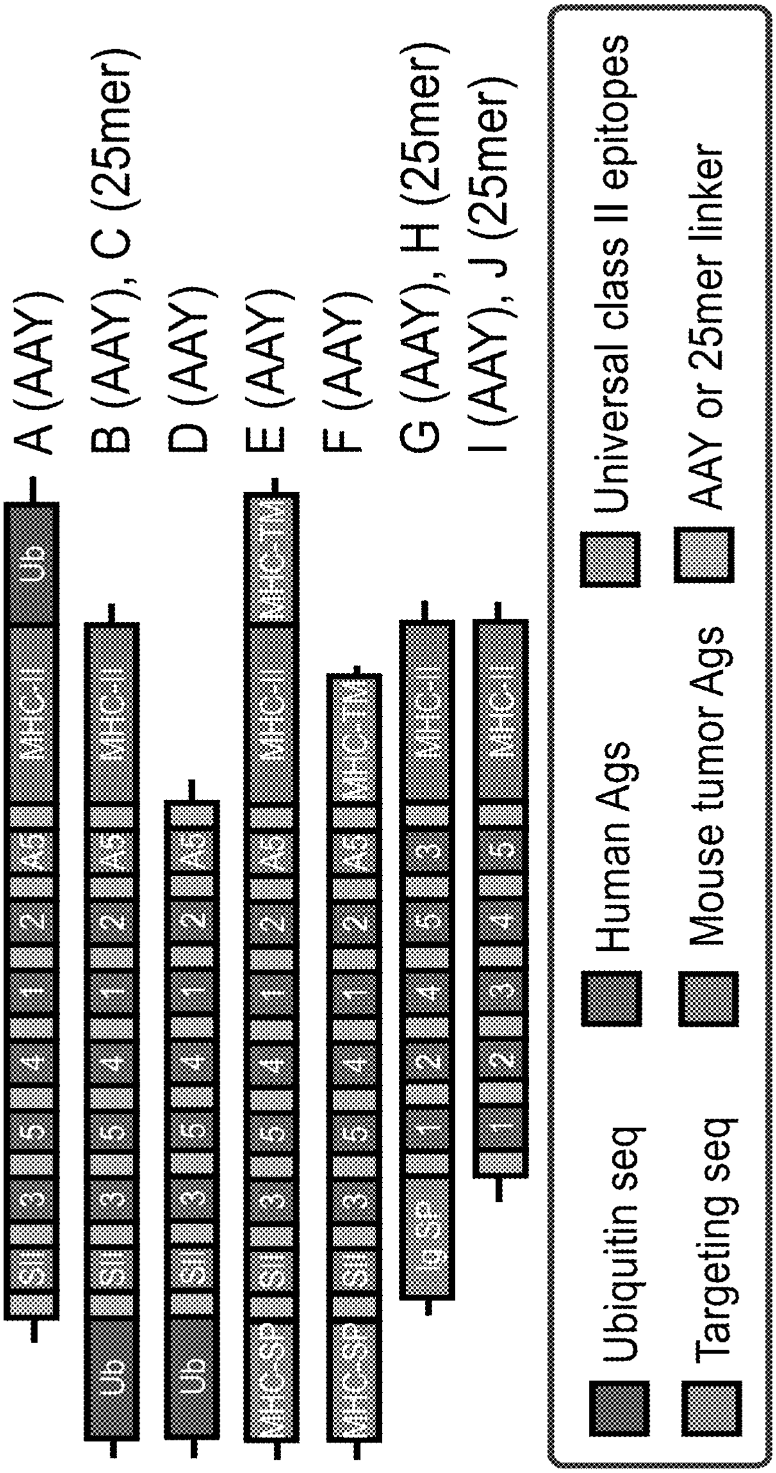
FIG. 18 illustrates in vivo evaluation of linker sequences in short cassettes. A) Experimental design of the in vivo evaluation of vaccine cassettes using HLA-A2 transgenic mice.
Figure 19A:
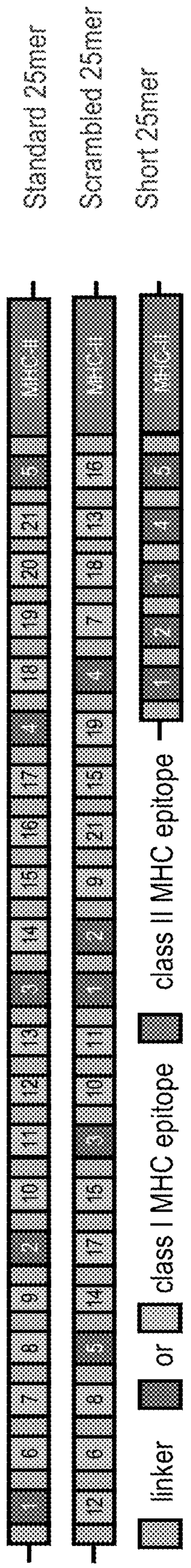
FIG. 19A illustrates in vivo evaluation of the impact of epitope position in long 21-mer cassettes and shows the design of long cassettes entails five marker class I epitopes (epitopes 1 through 5) contained in their 25-mer natural sequence (linker=natural flanking sequences), spaced with additional well-known T cell class I epitopes (epitopes 6 through 21) contained in their 25-mer natural sequence, and two universal class II epitopes (MHC-II0, with only the relative position of the class I epitopes varied.

As another example of neoantigen cassette design evaluation, vaccine cassettes were designed to contain 5 well-characterized human class I MHC epitopes known to stimulate CD8 T cells in an HLA-A*02:01 restricted fashion (FIG. 16A, 17, 19A). For the evaluation of their in vivo immunogenicity, vaccine cassettes containing these marker epitopes were incorporated in adenoviral vectors and used to infect HLA-A2 transgenic mice (FIG. 18). This mouse model carries a transgene consisting partly of human HLA-A*0201 and mouse H2-Kb thus encoding a chimeric class I MHC molecule consisting of the human HLA-A2.1 leader, α1 and α2 domains ligated to the murine 3, transmembrane and cytoplasmic H2-Kb domain (Vitiello et al., 1991). The chimeric molecule allows HLA-A*02:01-restricted antigen presentation whilst maintaining the species-matched interaction of the CD8 co-receptor with the α3 domain on the MHC.

For the short cassettes, all marker epitopes generated a T cell response, as determined by IFN-gamma ELISPOT, that was approximately 10-50× stronger of what has been commonly reported (Comet et al., 2006; Depla et al., 2008; Ishioka et al., 1999). Of all the linkers evaluated, the concatamer of 25mer sequences, each containing a minimal epitope flanked by their natural amino acids sequences, generated the largest and broadest T cell response (Table 5). Intracellular cytokine staining (ICS) and flow cytometry analysis revealed that the antigen-specific T cell responses are derived from CD8 T cells.

TABLE 5

In vivo evaluation of linker sequences in short cassettes. ELISPOT data indicated that HLA-A2 transgenic mice, 17 days post-infection with 1e11 adenovirus viral particles, generated a T cell response to all class I MHC restricted epitopes in the cassette.

| | Short Cassette Designs | | | | | |
|---|---|---|---|---|---|---|
| Epitope | 9AA | 17AA | 25AA | AAY | RR | DPP |
| 1 | 2020 +/− 583 | 2505 +/− 1281 | 6844 +/− 956 | 1489 +/− 762 | 1675 +/− 690 | 1781 +/− 774 |
| 2 | 4472 +/− 755 | 3792 +/− 1319 | 7629 +/− 996 | 3851 +/− 1748 | 4726 +/− 1715 | 5868 +/− 1427 |
| 3 | 5830 +/− 315 | 3629 +/− 862 | 7253 +/− 491 | 4813 +/− 1761 | 6779 +/− 1033 | 7328 +/− 1700 |
| 4 | 5536 +/− 375 | 2446 +/− 955 | 2961 +/− 1487 | 4230 +/− 1759 | 6518 +/− 909 | 7222 +/− 1824 |
| 5 | 8800 +/− 0 | 7943 +/− 821 | 8423 +/− 442 | 8312 +/− 696 | 8800 +/− 0 | 1836 +/− 328 |

In another example, a series of long vaccine cassettes was constructed and incorporated in adenoviral vectors that, next to the original 5 marker epitopes, contained an additional 16 HLA-A*02:01, A*03:01 and B*44:05 epitopes with known CD8 T cell reactivity (FIG. 19A, B). The size of these long cassettes closely mimicked the final clinical cassette design, and only the position of the epitopes relative to each other was varied. The CD8 T cell responses were comparable in magnitude and breadth for both long and short vaccine cassettes, demonstrating that (a) the addition of more epitopes did not substantially impact the magnitude of immune response to the original set of epitopes, and (b) the position of an epitope in a cassette did not substantially influence the ensuing T cell response to it (Table 6).

TABLE 6

In vivo evaluation of the impact of epitope position in long cassettes. ELISPOT data indicated that HLA-A2 transgenic mice, 17 days post-infection with 5e10 adenovirus viral particles, generated a T cell response comparable in magnitude for both long and short vaccine cassettes.

| | Long Cassette Designs | | |
|---|---|---|---|
| Epitope | Standard | Scrambled | Short |
| 1 | 863 +/− 1080 | 804 +/− 1113 | 1871 +/− 2859 |
| 2 | 6425 +/− 1594 | 28 +/− 62 | 5390 +/− 1357 |
| 3* | 23 +/− 30 | 36 +/− 18 | 0 +/− 48 |
| 4 | 2224 +/− 1074 | 2727 +/− 644 | 2637 +/− 1673 |
| 5 | 7952 +/− 297 | 8100 +/− 0 | 8100 +/− 0 |

*Suspected technical error caused an absence of a T cell response.

XIV.B.4. Neoantigen Cassette Design for Immunogenicity and Toxicology Studies In summary, the findings of the model cassette evaluations (FIG. 16-19, Tables 2-6) demonstrated that, for model vaccine cassettes, robustimmunogenicity was achieved when a "string of beads" approach was employed that encodes around 20 epitopes in the context of an adenovirus-based vector. The epitopes were assembled by concatenating 25mer sequences, each embedding a minimal CD8 T cell epitope (e.g. 9 amino acid residues) that were flanked on both sides by its natural, surrounding peptide sequence (e.g. 8 amino acid residues on each side). As used herein, a "natural" or "native" flanking sequence refers to the N- and/or C-terminal flanking sequence of a given epitope in the naturally occurring context of that epitope within its source protein. For example, the HCMV pp65 MHC I epitope NLVPMVATV (SEQ ID NO: 132) is flanked on its 5' end by the native 5' sequence WQAGILAR (SEQ ID NO: 139) and on its 3' end by the native 3' sequence QGQNLKYQ (SEQ ID NO: 140), thus generating the WQAGILARNLVPMVATVQGQNLKYQ (SEQ ID NO: 141) 25mer peptide found within the HCMV pp65 source protein. The natural or native sequence can also refer to a nucleotide sequence that encodes an epitope flanked by native flanking sequence(s). Each 25mer sequence is directly connected to the following 25mer sequence. In instances where the minimal CD8 T cell epitope is greater than or less than 9 amino acids, the flanking peptide length can be adjusted such that the total length is still a 25mer peptide sequence. For example, a 10 amino acid CD8 T cell epitope can be flanked by an 8 amino acid sequence and a 7 amino acid. The concatamer was followed by two universal class II MHC epitopes that were included to stimulate CD4 T helper cells and improve overall in vivo immunogenicity of the vaccine cassette antigens. (Alexander et al., 1994; Panina-Bordignon et al., 1989) The class II epitopes were linked to the final class I epitope by a GPGPG amino acid linker (SEQ ID NO:56). The two class II epitopes were also linked to each other by a GPGPG amino acid linker (SEQ ID NO: 56), as a well as flanked on the C-terminus by a GPGPG amino acid linker (SEQ ID NO: 56). Neither the position nor the number of epitopes appeared to substantially impact T cell recognition or response. Targeting sequences also did not appear to substantially impact the immunogenicity of cassette-derived antigens.

Figure 20A:
FIG. 20A illustrates final cassette design for preclinical IND-enabling studies and shows the design of the final cassettes comprises 20 MHC I epitopes contained in their 25-mer natural sequence (linker=natural flanking sequences), composed of 6 non-human primate (NHP) epitopes, 5 human epitopes, 9 murine epitopes, as well as 2 universal MHC class II epitopes.

As a further example, based on the in vitro and in vivo data obtained with model cassettes (FIG. 16-19, Tables 2-6), a cassette design was generated that alternates well-characterized T cell epitopes known to be immunogenic in non-human primates (NHPs), mice and humans. The 20 epitopes, all embedded in their natural 25mer sequences, are followed by the two universal class II MHC epitopes that were present in all model cassettes evaluated (FIG. 20). This cassette design was used to study immunogenicity as well as pharmacology and toxicology studies in multiple species.

XV. ChAd Neoantigen Cassette Delivery Vector

XV.A. ChAd Neoantigen Cassette Delivery Vector Construction

In one example, Chimpanzee adenovirus (ChAd) was engineered to be a delivery vector for neoantigen cassettes. In a further example, a full-length ChAdV68 vector was synthesized based on AC_000011.1 (sequence 2 from U.S. Pat. No. 6,083,716) with E1 (nt 457 to 3014) and E3 (nt 27,816-31,332) sequences deleted. Reporter genes under the control of the CMV promoter/enhancer were inserted in place of the deleted E1 sequences. Transfection of this clone into HEK293 cells did not yield infectious virus. To confirm the sequence of the wild-type C68 virus, isolate VR-594 was obtained from the ATCC, passaged, and then independently sequenced (SEQ ID NO:10). When comparing the AC_000011.1 sequence to the ATCC VR-594 sequence (SEQ ID NO:10) of wild-type ChAdV68 virus, 6 nucleotide differences were identified. In one example, a modified ChAdV68 vector was generated based on AC_000011.1, with the corresponding ATCC VR-594 nucleotides substituted at five positions (ChAdV68.5WTnt SEQ ID NO:1).

In another example, a modified ChAdV68 vector was generated based on AC_000011.1 with E1 (nt 577 to 3403) and E3 (nt 27,816-31,332) sequences deleted and the corresponding ATCC VR-594 nucleotides substituted at four positions. A GFP reporter (ChAdV68.4WTnt.GFP; SEQ ID NO:11) or model neoantigen cassette (ChAdV68.4WTnt.MAG25mer; SEQ ID NO:12) under the control of the CMV promoter/enhancer was inserted in place of deleted E1 sequences.

In another example, a modified ChAdV68 vector was generated based on AC_000011.1 with E1 (nt 577 to 3403) and E3 (nt 27,125-31,825) sequences deleted and the corresponding ATCC VR-594 nucleotides substituted at five positions. A GFP reporter (ChAdV68.5WTnt.GFP; SEQ ID NO:13) or model neoantigen cassette (ChAdV68.5WTnt.MAG25mer; SEQ ID NO:2) under the control of the CMV promoter/enhancer was inserted in place of deleted E1 sequences.

Full-Length ChAdVC68 sequence "ChAdV68.5WTnt" (SEQ ID NO: 1); AC_000011.1 sequence with corresponding ATCC VR-594 nucleotides substituted at five positions.

CCATCTTCAATAATATACCTCAAACTTTTTGTGCGCGTTAATATGCAAATGAGGCGTTTGAATTT

GGGGAGGAAGGGCGGTGATTGGTCGAGGGATGAGCGACCGTTAGGGGCGGGGCGAGTGACGTTTT

GATGACGTGGTTGCGAGGAGGAGCCAGTTTGCAAGTTCTCGTGGGAAAAGTGACGTCAAACGAGG

TGTGGTTTGAACACGGAAATACTCAATTTTCCCGCGCTCTCTGACAGGAAATGAGGTGTTTCTGG

GCGGATGCAAGTGAAAACGGGCCATTTTCGCGCGAAAACTGAATGAGGAAGTGAAAATCTGAGTA

ATTTCGCGTTTATGGCAGGGAGGAGTATTTGCCGAGGGCCGAGTAGACTTTGACCGATTACGTGG

GGGTTTCGATTACCGTGTTTTTCACCTAAATTTCCGCGTACGGTGTCAAAGTCCGGTGTTTTTAC

GTAGGTGTCAGCTGATCGCCAGGGTATTTAAACCTGCGCTCTCCAGTCAAGAGGCCACTCTTGAG

TGCCAGCGAGAAGAGTTTTCTCCTCCGCGCCGCGAGTCAGATCTACACTTTGAAAGATGAGGCAC

CTGAGAGACCTGCCCGATGAGAAAATCATCATCGCTTCCGGGAACGAGATTCTGGAACTGGTGGT

AAATGCCATGATGGGCGACGACCCTCCGGAGCCCCCCACCCCATTTGAGACACCTTCGCTGCACG

ATTTGTATGATCTGGAGGTGGATGTGCCCGAGGACGATCCCAATGAGGAGGCGGTAAATGATTTT

TTTAGCGATGCCGCGCTGCTAGCTGCCGAGGAGGCTTCGAGCTCTAGCTCAGACAGCGACTCTTC

ACTGCATACCCCTAGACCCGGCAGAGGTGAGAAAAAGATCCCCGAGCTTAAAGGGGAAGAGATGG

ACTTGCGCTGCTATGAGGAATGCTTGCCCCCGAGCGATGATGAGGACGAGCAGGCGATCCAGAAC

GCAGCGAGCCAGGGAGTGCAAGCCGCCAGCGAGAGCTTTGCGCTGGACTGCCCGCCTCTGCCCGG

ACACGGCTGTAAGTCTTGTGAATTTCATCGCATGAATACTGGAGATAAAGCTGTGTTGTGTGCAC

TTTGCTATATGAGAGCTTACAACCATTGTGTTTACAGTAAGTGTGATTAAGTTGAACTTTAGAGG

GAGGCAGAGAGCAGGGTGACTGGGCGATGACTGGTTTATTTATGTATATATGTTCTTTATATAGG

TCCCGTCTCTGACGCAGATGATGAGACCCCCACTACAAAGTCCACTTCGTCACCCCCAGAAATTG

GCACATCTCCACCTGAGAATATTGTTAGACCAGTTCCTGTTAGAGCCACTGGGAGGAGAGCAGCT

GTGGAATGTTTGGATGACTTGCTACAGGGTGGGGTTGAACCTTTGGACTTGTGTACCCGGAAACG

CCCCAGGCACTAAGTGCCACACATGTGTGTTTACTTGAGGTGATGTCAGTATTTATAGGGTGTGG

AGTGCAATAAAAAATGTGTTGACTTTAAGTGCGTGGTTTATGACTCAGGGGTGGGGACTGTGAGT

ATATAAGCAGGTGCAGACCTGTGTGGTTAGCTCAGAGCGGCATGGAGATTTGGACGGTCTTGGAA

GACTTTCACAAGACTAGACAGCTGCTAGAGAACGCCTCGAACGGAGTCTCTTACCTGTGGAGATT

CTGCTTCGGTGGCGACCTAGCTAGGCTAGTCTACAGGGCCAAACAGGATTATAGTGAACAATTTG

AGGTTATTTTGAGAGAGTGTTCTGGTCTTTTTGACGCTCTTAACTTGGGCCATCAGTCTCACTTT

AACCAGAGGATTTCGAGAGCCCTTGATTTTACTACTCCTGGCAGAACCACTGCAGCAGTAGCCTT

TTTTGCTTTTATTCTTGACAAATGGAGTCAAGAAACCCATTTCAGCAGGGATTACCAGCTGGATT

TCTTAGCAGTAGCTTTGTGGAGAACATGGAAGTGCCAGCGCCTGAATGCAATCTCCGGCTACTTG

CCGGTACAGCCGCTAGACACTCTGAGGATCCTGAATCTCCAGGAGAGTCCCAGGGCACGCCAACG

TCGCCAGCAGCAGCAGCAGGAGGAGGATCAAGAAGAGAACCCGAGAGCCGGCCTGGACCCTCCGG

CGGAGGAGGAGGAGTAGCTGACCTGTTTCCTGAACTGCGCCGGGTGCTGACTAGGTCTTCGAGTG

GTCGGGAGAGGGGGATTAAGCGGGAGAGGCATGATGAGACTAATCACAGAACTGAACTGACTGTG

GGTCTGATGAGTCGCAAGCGCCCAGAAACAGTGTGGTGGCATGAGGTGCAGTCGACTGGCACAGA

TGAGGTGTCGGTGATGCATGAGAGGTTTTCTCTAGAACAAGTCAAGACTTGTTGGTTAGAGCCTG

AGGATGATTGGGAGGTAGCCATCAGGAATTATGCCAAGCTGGCTCTGAGGCCAGACAAGAAGTAC

AAGATTACTAAGCTGATAAATATCAGAAATGCCTGCTACATCTCAGGGAATGGGGCTGAAGTGGA

-continued

GATCTGTCTCCAGGAAAGGGTGGCTTTCAGATGCTGCATGATGAATATGTACCCGGGAGTGGTGG

GCATGGATGGGGTTACCTTTATGAACATGAGGTTCAGGGGAGATGGGTATAATGGCACGGTCTTT

ATGGCCAATACCAAGCTGACAGTCCATGGCTGCTCCTTCTTTGGGTTTAATAACACCTGCATCGA

GGCCTGGGGTCAGGTCGGTGTGAGGGGCTGCAGTTTTTCAGCCAACTGGATGGGGGTCGTGGGCA

GGACCAAGAGTATGCTGTCCGTGAAGAAATGCTTGTTTGAGAGGTGCCACCTGGGGGTGATGAGC

GAGGGCGAAGCCAGAATCCGCCACTGCGCCTCTACCGAGACGGGCTGCTTTGTGCTGTGCAAGGG

CAATGCTAAGATCAAGCATAATATGATCTGTGGAGCCTCGGACGAGCGCGGCTACCAGATGCTGA

CCTGCGCCGGCGGGAACAGCCATATGCTGGCCACCGTACATGTGGCTTCCCATGCTCGCAAGCCC

TGGCCCGAGTTCGAGCACAATGTCATGACCAGGTGCAATATGCATCTGGGGTCCCGCCGAGGCAT

GTTCATGCCCTACCAGTGCAACCTGAATTATGTGAAGGTGCTGCTGGAGCCCGATGCCATGTCCA

GAGTGAGCCTGACGGGGGTGTTTGACATGAATGTGGAGGTGTGGAAGATTCTGAGATATGATGAA

TCCAAGACCAGGTGCCGAGCCTGCGAGTGCGGAGGGAAGCATGCCAGGTTCCAGCCCGTGTGTGT

GGATGTGACGGAGGACCTGCGACCCGATCATTTGGTGTTGCCCTGCACCGGGACGGAGTTCGGTT

CCAGCGGGGAAGAATCTGACTAGAGTGAGTAGTGTTCTGGGGCGGGGGAGGACCTGCATGAGGGC

CAGAATAACTGAAATCTGTGCTTTTCTGTGTGTTGCAGCAGCATGAGCGGAAGCGGCTCCTTTGA

GGGAGGGGTATTCAGCCCTTATCTGACGGGGCGTCTCCCCTCCTGGGCGGGAGTGCGTCAGAATG

TGATGGGATCCACGGTGGACGGCCGGCCCGTGCAGCCCGCGAACTCTTCAACCCTGACCTATGCA

ACCCTGAGCTCTTCGTCGTTGGACGCAGCTGCCGCCGCAGCTGCTGCATCTGCCGCCAGCGCCGT

GCGCGGAATGGCCATGGGCGCCGGCTACTACGGCACTCTGGTGGCCAACTCGAGTTCCACCAATA

ATCCCGCCAGCCTGAACGAGGAGAAGCTGTTGCTGCTGATGGCCCAGCTCGAGGCCTTGACCCAG

CGCCTGGGCGAGCTGACCCAGCAGGTGGCTCAGCTGCAGGAGCAGACGCGGGCCGCGGTTGCCAC

GGTGAAATCCAAATAAAAAATGAATCAATAAATAAACGGAGACGGTTGTTGATTTTAACACAGAG

TCTGAATCTTTATTTGATTTTTCGCGCGCGGTAGGCCCTGGACCACCGGTCTCGATCATTGAGCA

CCCGGTGGATCTTTTCCAGGACCCGGTAGAGGTGGGCTTGGATGTTGAGGTACATGGGCATGAGC

CCGTCCCGGGGGTGGAGGTAGCTCCATTGCAGGGCCTCGTGCTCGGGGGTGGTGTTGTAAATCAC

CCAGTCATAGCAGGGGCGCAGGGCATGGTGTTGCACAATATCTTTGAGGAGGAGACTGATGGCCA

CGGGCAGCCCTTTGGTGTAGGTGTTTACAAATCTGTTGAGCTGGGAGGGATGCATGCGGGGGGAG

ATGAGGTGCATCTTGGCCTGGATCTTGAGATTGGCGATGTTACCGCCCAGATCCCGCCTGGGGTT

CATGTTGTGCAGGACCACCAGCACGGTGTATCCGGTGCACTTGGGGAATTTATCATGCAACTTGG

AAGGGAAGGCGTGAAAGAATTTGGCGACGCCTTTGTGCCCGCCCAGGTTTTCCATGCACTCATCC

ATGATGATGGCGATGGGCCCGTGGGCGGCGGCCTGGGCAAAGACGTTTCGGGGGTCGGACACATC

ATAGTTGTGGTCCTGGGTGAGGTCATCATAGGCCATTTTAATGAATTTGGGGCGGAGGGTGCCGG

ACTGGGGGACAAAGGTACCCTCGATCCCGGGGGCGTAGTTCCCCTCACAGATCTGCATCTCCCAG

GCTTTGAGCTCGGAGGGGGGGATCATGTCCACCTGCGGGGCGATAAAGAACACGGTTTCCGGGGC

GGGGGAGATGAGCTGGGCCGAAAGCAAGTTCCGGAGCAGCTGGGACTTGCCGCAGCCGGTGGGGC

CGTAGATGACCCCGATGACCGGCTGCAGGTGGTAGTTGAGGGAGAGACAGCTGCCGTCCTCCCGG

AGGAGGGGGGCCACCTCGTTCATCATCTCGCGCACGTGCATGTTCTCGCGCACCAGTTCCGCCAG

GAGGCGCTCTCCCCCCAGGGATAGGAGCTCCTGGAGCGAGGCGAAGTTTTTCAGCGGCTTGAGTC

CGTCGGCCATGGGCATTTTGGAGAGGGTTTGTTGCAAGAGTTCCAGGCGGTCCCAGAGCTCGGTG

ATGTGCTCTACGGCATCTCGATCCAGCAGACCTCCTCGTTTCGCGGGTTGGGACGGCTGCGGGAG

-continued

TAGGGCACCAGACGATGGGCGTCCAGCGCAGCCAGGGTCCGGTCCTTCCAGGGTCGCAGCGTCCG

CGTCAGGGTGGTCTCCGTCACGGTGAAGGGGTGCGCGCCGGGCTGGGCGCTTGCGAGGGTGCGCT

TCAGGCTCATCCGGCTGGTCGAAAACCGCTCCCGATCGGCGCCCTGCGCGTCGGCCAGGTAGCAA

TTGACCATGAGTTCGTAGTTGAGCGCCTCGGCCGCGTGGCCTTTGGCGCGGAGCTTACCTTTGGA

AGTCTGCCCGCAGGCGGGACAGAGGAGGGACTTGAGGGCGTAGAGCTTGGGGGCGAGGAAGACGG

ACTCGGGGGCGTAGGCGTCCGCGCCGCAGTGGGCGCAGACGGTCTCGCACTCCACGAGCCAGGTG

AGGTCGGGCTGGTCGGGGTCAAAAACCAGTTTCCCGCCGTTCTTTTTGATGCGTTTCTTACCTTT

GGTCTCCATGAGCTCGTGTCCCCGCTGGGTGACAAAGAGGCTGTCCGTGTCCCCGTAGACCGACT

TTATGGGCCGGTCCTCGAGCGGTGTGCCGCGGTCCTCCTCGTAGAGGAACCCCGCCCACTCCGAG

ACGAAAGCCCGGGTCCAGGCCAGCACGAAGGAGGCCACGTGGGACGGGTAGCGGTCGTTGTCCAC

CAGCGGGTCCACCTTTTCCAGGGTATGCAAACACATGTCCCCCTCGTCCACATCCAGGAAGGTGA

TTGGCTTGTAAGTGTAGGCCACGTGACCGGGGGTCCCGGCCGGGGGGGTATAAAAGGGTGCGGGT

CCCTGCTCGTCCTCACTGTCTTCCGGATCGCTGTCCAGGAGCGCCAGCTGTTGGGGTAGGTATTC

CCTCTCGAAGGCGGGCATGACCTCGGCACTCAGGTTGTCAGTTTCTAGAAACGAGGAGGATTTGA

TATTGACGGTGCCGGCGGAGATGCCTTTCAAGAGCCCCTCGTCCATCTGGTCAGAAAAGACGATC

TTTTTGTTGTCGAGCTTGGTGGCGAAGGAGCCGTAGAGGGCGTTGGAGAGGAGCTTGGCGATGGA

GCGCATGGTCTGGTTTTTTTCCTTGTCGGCGCGCTCCTTGGCGGCGATGTTGAGCTGCACGTACT

CGCGCGCCACGCACTTCCATTCGGGGAAGACGGTGGTCAGCTCGTCGGGCACGATTCTGACCTGC

CAGCCCCGATTATGCAGGGTGATGAGGTCCACACTGGTGGCCACCTCGCCGCGCAGGGGCTCATT

AGTCCAGCAGAGGCGTCCGCCCTTGCGCGAGCAGAAGGGGGGCAGGGGGTCCAGCATGACCTCGT

CGGGGGGGTCGGCATCGATGGTGAAGATGCCGGGCAGGAGGTCGGGGTCAAAGTAGCTGATGGAA

GTGGCCAGATCGTCCAGGGCAGCTTGCCATTCGCGCACGGCCAGCGCGCGCTCGTAGGGACTGAG

GGGCGTGCCCCAGGGCATGGGATGGGTAAGCGCGGAGGCGTACATGCCGCAGATGTCGTAGACGT

AGAGGGGCTCCTCGAGGATGCCGATGTAGGTGGGGTAGCAGCGCCCCCCGCGGATGCTGGCGCGC

ACGTAGTCATACAGCTCGTGCGAGGGGGCGAGGAGCCCCGGGCCCAGGTTGGTGCGACTGGGCTT

TTCGGCGCGGTAGACGATCTGGCGGAAAATGGCATGCGAGTTGGAGGAGATGGTGGGCCTTTGGA

AGATGTTGAAGTGGGCGTGGGGCAGTCCGACCGAGTCGCGGATGAAGTGGGCGTAGGAGTCTTGC

AGCTTGGCGACGAGCTCGGCGGTGACTAGGACGTCCAGAGCGCAGTAGTCGAGGGTCTCCTGGAT

GATGTCATACTTGAGCTGTCCCTTTTGTTTCCACAGCTCGCGGTTGAGAAGGAACTCTTCGCGGT

CCTTCCAGTACTCTTCGAGGGGGAACCCGTCCTGATCTGCACGGTAAGAGCCTAGCATGTAGAAC

TGGTTGACGGCCTTGTAGGCGCAGCAGCCCTTCTCCACGGGGAGGGCGTAGGCCTGGGCGGCCTT

GCGCAGGGAGGTGTGCGTGAGGGCGAAAGTGTCCCTGACCATGACCTTGAGGAACTGGTGCTTGA

AGTCGATATCGTCGCAGCCCCCCTGCTCCCAGAGCTGGAAGTCCGTGCGCTTCTTGTAGGCGGGG

TTGGGCAAAGCGAAAGTAACATCGTTGAAGAGGATCTTGCCCGCGCGGGGCATAAAGTTGCGAGT

GATGCGGAAAGGTTGGGGCACCTCGGCCCGGTTGTTGATGACCTGGGCGGCGAGCACGATCTCGT

CGAAGCCGTTGATGTTGTGGCCCACGATGTAGAGTTCCACGAATCGCGGACGGCCCTTGACGTGG

GGCAGTTTCTTGAGCTCCTCGTAGGTGAGCTCGTCGGGGTCGCTGAGCCCGTGCTGCTCGAGCGC

CCAGTCGGCGAGATGGGGGTTGGCGCGGAGGAAGGAAGTCCAGAGATCCACGGCCAGGGCGGTTT

GCAGACGGTCCCGGTACTGACGGAACTGCTGCCCGACGGCCATTTTTTCGGGGGTGACGCAGTAG

-continued

AAGGTGCGGGGGTCCCCGTGCCAGCGATCCCATTTGAGCTGGAGGGCGAGATCGAGGGCGAGCTC
GACGAGCCGGTCGTCCCCGGAGAGTTTCATGACCAGCATGAAGGGGACGAGCTGCTTGCCGAAGG
ACCCCATCCAGGTGTAGGTTTCCACATCGTAGGTGAGGAAGAGCCTTTCGGTGCGAGGATGCGAG
CCGATGGGGAAGAACTGGATCTCCTGCCACCAATTGGAGGAATGGCTGTTGATGTGATGGAAGTA
GAAATGCCGACGGCGCGCCGAACACTCGTGCTTGTGTTTATACAAGCGGCCACAGTGCTCGCAAC
GCTGCACGGGATGCACGTGCTGCACGAGCTGTACCTGAGTTCCTTTGACGAGGAATTTCAGTGGG
AAGTGGAGTCGTGGCGCCTGCATCTCGTGCTGTACTACGTCGTGGTGGTCGGCCTGGCCCTCTTC
TGCCTCGATGGTGGTCATGCTGACGAGCCCGCGCGGGAGGCAGGTCCAGACCTCGGCGCGAGCGG
GTCGGAGAGCGAGGACGAGGGCGCGCAGGCCGGAGCTGTCCAGGGTCCTGAGACGCTGCGGAGTC
AGGTCAGTGGGCAGCGGCGGCGCGCGGTTGACTTGCAGGAGTTTTTCCAGGGCGCGCGGGAGGTC
CAGATGGTACTTGATCTCCACCGCGCCATTGGTGGCGACGTCGATGGCTTGCAGGGTCCCGTGCC
CCTGGGGTGTGACCACCGTCCCCCGTTTCTTCTTGGGCGGCTGGGGCGACGGGGGCGGTGCCTCT
TCCATGGTTAGAAGCGGCGGCGAGGACGCGCGCCGGGCGGCAGGGGCGGCTCGGGGCCCGGAGGC
AGGGGCGGCAGGGGCACGTCGGCGCCGCGCGCGGGTAGGTTCTGGTACTGCGCCCGGAGAAGACT
GGCGTGAGCGACGACGCGACGGTTGACGTCCTGGATCTGACGCCTCTGGGTGAAGGCCACGGGAC
CCGTGAGTTTGAACCTGAAAGAGAGTTCGACAGAATCAATCTCGGTATCGTTGACGGCGGCCTGC
CGCAGGATCTCTTGCACGTCGCCCGAGTTGTCCTGGTAGGCGATCTCGGTCATGAACTGCTCGAT
CTCCTCCTCTTGAAGGTCTCCGCGGCCGGCGCGCTCCACGGTGGCCGCGAGGTCGTTGGAGATGC
GGCCCATGAGCTGCGAGAAGGCGTTCATGCCCGCCTCGTTCCAGACGCGGCTGTAGACCACGACG
CCCTCGGGATCGCgGGCGCGCATGACCACCTGGGCGAGGTTGAGCTCCACGTGGCGCGTGAAGAC
CGCGTAGTTGCAGAGGCGCTGGTAGAGGTAGTTGAGCGTGGTGGCGATGTGCTCGGTGACGAAGA
AATACATGATCCAGCGGCGGAGCGGCATCTCGCTGACGTCGCCCAGCGCCTCCAAACGTTCCATG
GCCTCGTAAAAGTCCACGGCGAAGTTGAAAAACTGGGAGTTGCGCGCCGAGACGGTCAACTCCTC
CTCCAGAAGACGGATGAGCTCGGCGATGGTGGCGCGCACCTCGCGCTCGAAGGCCCCCGGGAGTT
CCTCCACTTCCTCTTCTTCCTCCTCCACTAACATCTCTTCTACTTCCTCCTCAGGCGGCAGTGGT
GGCGGGGGAGGGGGCCTGCGTCGCCGGCGGCGCACGGGCAGACGGTCGATGAAGCGCTCGATGGT
CTCGCCGCGCCGGCGTCGCATGGTCTCGGTGACGGCGCGCCCGTCCTCGCGGGGCCGCAGCGTGA
AGACGCCGCCGCGCATCTCCAGGTGGCCGGGGGGGTCCCCGTTGGGCAGGGAGAGGGCGCTGACG
ATGCATCTTATCAATTGCCCCGTAGGGACTCCGCGCAAGGACCTGAGCGTCTCGAGATCCACGGG
ATCTGAAAACCGCTGAACGAAGGCTTCGAGCCAGTCGCAGTCGCAAGGTAGGCTGAGCACGGTTT
CTTCTGGCGGGTCATGTTGGTTGGGAGCGGGGCGGGCGATGCTGCTGGTGATGAAGTTGAAATAG
GCGGTTCTGAGACGGCGGATGGTGGCGAGGAGCACCAGGTCTTTGGGCCCGGCTTGCTGGATGCG
CAGACGGTCGGCCATGCCCCAGGCGTGGTCCTGACACCTGGCCAGGTCCTTGTAGTAGTCCTGCA
TGAGCCGCTCCACGGGCACCTCCTCCTCGCCCGCGCGGCCGTGCATGCGCGTGAGCCCGAAGCCG
CGCTGGGGCTGGACGAGCGCCAGGTCGGCGACGACGCGCTCGGCGAGGATGGCTTGCTGGATCTG
GGTGAGGGTGGTCTGGAAGTCATCAAAGTCGACGAAGCGGTGGTAGGCTCCGGTGTTGATGGTGT
AGGAGCAGTTGGCCATGACGGACCAGTTGACGGTCTGGTGGCCCGGACGCACGAGCTCGTGGTAC
TTGAGGCGCGAGTAGGCGCGCGTGTCGAAGATGTAGTCGTTGCAGGTGCGCACCAGGTACTGGTA
GCCGATGAGGAAGTGCGGCGGCGGCTGGCGGTAGAGCGGCCATCGCTCGGTGGCGGGGGCGCCGG
GCGCGAGGTCCTCGAGCATGGTGCGGTGGTAGCCGTAGATGTACCTGGACATCCAGGTGATGCCG

-continued

GCGGCGGTGGTGGAGGCGCGCGGGAACTCGCGGACGCGGTTCCAGATGTTGCGCAGCGGCAGGAA

GTAGTTCATGGTGGGCACGGTCTGGCCCGTGAGGCGCGCGCAGTCGTGGATGCTCTATACGGGCA

AAAACGAAAGCGGTCAGCGGCTCGACTCCGTGGCCTGGAGGCTAAGCGAACGGGTTGGGCTGCGC

GTGTACCCCGGTTCGAATCTCGAATCAGGCTGGAGCCGCAGCTAACGTGGTATTGGCACTCCCGT

CTCGACCCAAGCCTGCACCAACCCTCCAGGATACGGAGGCGGGTCGTTTTGCAACTTTTTTTTGG

AGGCCGGATGAGACTAGTAAGCGCGGAAAGCGGCCGACCGCGATGGCTCGCTGCCGTAGTCTGGA

GAAGAATCGCCAGGGTTGCGTTGCGGTGTGCCCCGGTTCGAGGCCGGCCGGATTCCGCGGCTAAC

GAGGGCGTGGCTGCCCCGTCGTTTCCAAGACCCCATAGCCAGCCGACTTCTCCAGTTACGGAGCG

AGCCCCTCTTTTGTTTTGTTTGTTTTTGCCAGATGCATCCCGTACTGCGGCAGATGCGCCCCCAC

CACCCTCCACCGCAACAACAGCCCCCTCCACAGCCGGCGCTTCTGCCCCCGCCCCAGCAGCAACT

TCCAGCCACGACCGCCGCGGCCGCCGTGAGCGGGGCTGGACAGAGTTATGATCACCAGCTGGCCT

TGGAAGAGGGCGAGGGGCTGGCGCGCCTGGGGGCGTCGTCGCCGGAGCGGCACCCGCGCGTGCAG

ATGAAAAGGGACGCTCGCGAGGCCTACGTGCCCAAGCAGAACCTGTTCAGAGACAGGAGCGGCGA

GGAGCCCGAGGAGATGCGCGCGGCCCGGTTCCACGCGGGGGGGGAGCTGCGGCGCGGCCTGGACC

GAAAGAGGGTGCTGAGGGACGAGGATTTCGAGGCGGACGAGCTGACGGGGATCAGCCCCGCGCGC

GCGCACGTGGCCGCGGCCAACCTGGTCACGGCGTACGAGCAGACCGTGAAGGAGGAGAGCAACTT

CCAAAAATCCTTCAACAACCACGTGCGCACCCTGATCGCGCGCGAGGAGGTGACCCTGGGCCTGA

TGCACCTGTGGGACCTGCTGGAGGCCATCGTGCAGAACCCCACCAGCAAGCCGCTGACGGCGCAG

CTGTTCCTGGTGGTGCAGCATAGTCGGGACAACGAAGCGTTCAGGGAGGCGCTGCTGAATATCAC

CGAGCCCGAGGGCCGCTGGCTCCTGGACCTGGTGAACATTCTGCAGAGCATCGTGGTGCAGGAGC

GCGGGCTGCCGCTGTCCGAGAAGCTGGCGGCCATCAACTTCTCGGTGCTGAGTTTGGGCAAGTAC

TACGCTAGGAAGATCTACAAGACCCCGTACGTGCCCATAGACAAGGAGGTGAAGATCGACGGGTT

TTACATGCGCATGACCCTGAAAGTGCTGACCCTGAGCGACGATCTGGGGGTGTACCGCAACGACA

GGATGCACCGTGCGGTGAGCGCCAGCAGGCGGCGCGAGCTGAGCGACCAGGAGCTGATGCATAGT

CTGCAGCGGGCCCTGACCGGGGCCGGGACCGAGGGGGAGAGCTACTTTGACATGGGCGCGGACCT

GCACTGGCAGCCCAGCCGCCGGGCCTTGGAGGCGGCGGCAGGACCCTACGTAGAAGAGGTGGACG

ATGAGGTGGACGAGGAGGGCGAGTACCTGGAAGACTGATGGCGCGACCGTATTTTTGCTAGATGC

AACAACAACAGCCACCTCCTGATCCCGCGATGCGGGCGGCGCTGCAGAGCCAGCCGTCCGGCATT

AACTCCTCGGACGATTGGACCCAGGCCATGCAACGCATCATGGCGCTGACGACCCGCAACCCCGA

AGCCTTTAGACAGCAGCCCCAGGCCAACCGGCTCTCGGCCATCCTGGAGGCCGTGGTGCCCTCGC

GCTCCAACCCCACGCACGAGAAGGTCCTGGCCATCGTGAACGCGCTGGTGGAGAACAAGGCCATC

CGCGGCGACGAGGCCGGCCTGGTGTACAACGCGCTGCTGGAGCGCGTGGCCCGCTACAACAGCAC

CAACGTGCAGACCAACCTGGACCGCATGGTGACCGACGTGCGCGAGGCCGTGGCCCAGCGCGAGC

GGTTCCACCGCGAGTCCAACCTGGGATCCATGGTGGCGCTGAACGCCTTCCTCAGCACCCAGCCC

GCCAACGTGCCCCGGGGCCAGGAGGACTACACCAACTTCATCAGCGCCCTGCGCCTGATGGTGAC

CGAGGTGCCCCAGAGCGAGGTGTACCAGTCCGGGCCGGACTACTTCTTCCAGACCAGTCGCCAGG

GCTTGCAGACCGTGAACCTGAGCCAGGCTTTCAAGAACTTGCAGGGCCTGTGGGGCGTGCAGGCC

CCGGTCGGGGACCGCGCGACGGTGTCGAGCCTGCTGACGCCGAACTCGCGCCTGCTGCTGCTGCT

GGTGGCCCCCTTCACGGACAGCGGCAGCATCAACCGCAACTCGTACCTGGGCTACCTGATTAACC

-continued

TGTACCGCGAGGCCATCGGCCAGGCGCACGTGGACGAGCAGACCTACCAGGAGATCACCCACGTG

AGCCGCGCCCTGGGCCAGGACGACCCGGGCAACCTGGAAGCCACCCTGAACTTTTTGCTGACCAA

CCGGTCGCAGAAGATCCCGCCCCAGTACGCGCTCAGCACCGAGGAGGAGCGCATCCTGCGTTACG

TGCAGCAGAGCGTGGGCCTGTTCCTGATGCAGGAGGGGGCCACCCCCAGCGCCGCGCTCGACATG

ACCGCGCGCAACATGGAGCCCAGCATGTACGCCAGCAACCGCCCGTTCATCAATAAACTGATGGA

CTACTTGCATCGGGCGGCCGCCATGAACTCTGACTATTTCACCAACGCCATCCTGAATCCCCACT

GGCTCCCGCCGCCGGGGTTCTACACGGGCGAGTACGACATGCCCGACCCCAATGACGGGTTCCTG

TGGGACGATGTGGACAGCAGCGTGTTCTCCCCCCGACCGGGTGCTAACGAGCGCCCCTTGTGGAA

GAAGGAAGGCAGCGACCGACGCCCGTCCTCGGCGCTGTCCGGCCGCGAGGGTGCTGCCGCGGCGG

TGCCCGAGGCCGCCAGTCCTTTCCCGAGCTTGCCCTTCTCGCTGAACAGTATCCGCAGCAGCGAG

CTGGGCAGGATCACGCGCCCGCGCTTGCTGGGCGAAGAGGAGTACTTGAATGACTCGCTGTTGAG

ACCCGAGCGGGAGAAGAACTTCCCCAATAACGGGATAGAAAGCCTGGTGGACAAGATGAGCCGCT

GGAAGACGTATGCGCAGGAGCACAGGGACGATCCCCGGGCGTCGCAGGGGGCCACGAGCCGGGGC

AGCGCCGCCCGTAAACGCCGGTGGCACGACAGGCAGCGGGGACAGATGTGGGACGATGAGGACTC

CGCCGACGACAGCAGCGTGTTGGACTTGGGTGGGAGTGGTAACCCGTTCGCTCACCTGCGCCCCC

GTATCGGGCGCATGATGTAAGAGAAACCGAAAATAAATGATACTCACCAAGGCCATGGCGACCAG

CGTGCGTTCGTTTCTTCTCTGTTGTTGTTGTATCTAGTATGATGAGGCGTGCGTACCCGGAGGGT

CCTCCTCCCTCGTACGAGAGCGTGATGCAGCAGGCGATGGCGGCGGCGGCGATGCAGCCCCCGCT

GGAGGCTCCTTACGTGCCCCCGCGGTACCTGGCGCCTACGGAGGGGCGGAACAGCATTCGTTACT

CGGAGCTGGCACCCTTGTACGATACCACCCGGTTGTACCTGGTGGACAACAAGTCGGCGGACATC

GCCTCGCTGAACTACCAGAACGACCACAGCAACTTCCTGACCACCGTGGTGCAGAACAATGACTT

CACCCCCACGGAGGCCAGCACCCAGACCATCAACTTTGACGAGCGCTCGCGGTGGGGCGGCCAGC

TGAAAACCATCATGCACACCAACATGCCCAACGTGAACGAGTTCATGTACAGCAACAAGTTCAAG

GCGCGGGTGATGGTCTCCCGCAAGACCCCCAATGGGGTGACAGTGACAGAGGATTATGATGGTAG

TCAGGATGAGCTGAAGTATGAATGGGTGGAATTTGAGCTGCCCGAAGGCAACTTCTCGGTGACCA

TGACCATCGACCTGATGAACAACGCCATCATCGACAATTACTTGGCGGTGGGGCGGCAGAACGGG

GTGCTGGAGAGCGACATCGGCGTGAAGTTCGACACTAGGAACTTCAGGCTGGGCTGGGACCCCGT

GACCGAGCTGGTCATGCCCGGGGTGTACACCAACGAGGCTTTCCATCCCGATATTGTCTTGCTGC

CCGGCTGCGGGGTGGACTTCACCGAGAGCCGCCTCAGCAACCTGCTGGGCATTCGCAAGAGGCAG

CCCTTCCAGGAAGGCTTCCAGATCATGTACGAGGATCTGGAGGGGGGCAACATCCCCGCGCTCCT

GGATGTCGACGCCTATGAGAAAAGCAAGGAGGATGCAGCAGCTGAAGCAACTGCAGCCGTAGCTA

CCGCCTCTACCGAGGTCAGGGGCGATAATTTTGCAAGCGCCGCAGCAGTGGCAGCGGCCGAGGCG

GCTGAAACCGAAAGTAAGATAGTCATTCAGCCGGTGGAGAAGGATAGCAAGAACAGGAGCTACAA

CGTACTACCGGACAAGATAAACACCGCCTACCGCAGCTGGTACCTAGCCTACAACTATGGCGACC

CCGAGAAGGGCGTGCGCTCCTGGACGCTGCTCACCACCTCGGACGTCACCTGCGGCGTGGAGCAA

GTCTACTGGTCGCTGCCCGACATGATGCAAGACCCGGTCACCTTCCGCTCCACGCGTCAAGTTAG

CAACTACCCGGTGGTGGGCGCCGAGCTCCTGCCCGTCTACTCCAAGAGCTTCTTCAACGAGCAGG

CCGTCTACTCGCAGCAGCTGCGCGCCTTCACCTCGCTTACGCACGTCTTCAACCGCTTCCCCGAG

AACCAGATCCTCGTCCGCCCGCCCGCGCCCACCATTACCACCGTCAGTGAAAACGTTCCTGCTCT

CACAGATCACGGGACCCTGCCGCTGCGCAGCAGTATCCGGGGAGTCCAGCGCGTGACCGTTACTG

-continued

ACGCCAGACGCCGCACCTGCCCCTACGTCTACAAGGCCCTGGGCATAGTCGCGCCGCGCGTCCTC

TCGAGCCGCACCTTCTAAATGTCCATTCTCATCTCGCCCAGTAATAACACCGGTTGGGGCCTGCG

CGCGCCCAGCAAGATGTACGGAGGCGCTCGCCAACGCTCCACGCAACACCCCGTGCGCGTGCGCG

GGCACTTCCGCGCTCCCTGGGGCGCCCTCAAGGGCCGCGTGCGGTCGCGCACCACCGTCGACGAC

GTGATCGACCAGGTGGTGGCCGACGCGCGCAACTACACCCCCGCCGCCGCGCCCGTCTCCACCGT

GGACGCCGTCATCGACAGCGTGGTGGCcGACGCGCGCCGGTACGCCCGCGCCAAGAGCCGGCGGC

GGCGCATCGCCCGGCGGCACCGGAGCACCCCCGCCATGCGCGCGGCGCGAGCCTTGCTGCGCAGG

GCCAGGCGCACGGGACGCAGGGCCATGCTCAGGGCGGCCAGACGCGCGGCTTCAGGCGCCAGCGC

CGGCAGGACCCGGAGACGCGCGGCCACGGCGGCGGCAGCGGCCATCGCCAGCATGTCCCGCCCGC

GGCGAGGGAACGTGTACTGGGTGCGCGACGCCGCCACCGGTGTGCGCGTGCCCGTGCGCACCCGC

CCCCCTCGCACTTGAAGATGTTCACTTCGCGATGTTGATGTGTCCCAGCGGCGAGGAGGATGTCC

AAGCGCAAATTCAAGGAAGAGATGCTCCAGGTCATCGCGCCTGAGATCTACGGCCCTGCGGTGGT

GAAGGAGGAAAGAAAGCCCCGCAAAATCAAGCGGGTCAAAAAGGACAAAAAGGAAGAAGAAAGTG

ATGTGGACGGATTGGTGGAGTTTGTGCGCGAGTTCGCCCCCCGGCGGCGCGTGCAGTGGCGCGGG

CGGAAGGTGCAACCGGTGCTGAGACCCGGCACCACCGTGGTCTTCACGCCCGGCGAGCGCTCCGG

CACCGCTTCCAAGCGCTCCTACGACGAGGTGTACGGGGATGATGATATTCTGGAGCAGGCGGCCG

AGCGCCTGGGCGAGTTTGCTTACGGCAAGCGCAGCCGTTCCGCACCGAAGGAAGAGGCGGTGTCC

ATCCCGCTGGACCACGGCAACCCCACGCCGAGCCTCAAGCCCGTGACCTTGCAGCAGGTGCTGCC

GACCGCGGCGCCGCGCCGGGGGTTCAAGCGCGAGGGCGAGGATCTGTACCCCACCATGCAGCTGA

TGGTGCCCAAGCGCCAGAAGCTGGAAGACGTGCTGGAGACCATGAAGGTGGACCCGGACGTGCAG

CCCGAGGTCAAGGTGCGGCCCATCAAGCAGGTGGCCCCGGGCCTGGGCGTGCAGACCGTGGACAT

CAAGATTCCCACGGAGCCCATGGAAACGCAGACCGAGCCCATGATCAAGCCCAGCACCAGCACCA

TGGAGGTGCAGACGGATCCCTGGATGCCATCGGCTCCTAGTCGAAGACCCCGGCGCAAGTACGGC

GCGGCCAGCCTGCTGATGCCCAACTACGCGCTGCATCCTTCCATCATCCCCACGCCGGGCTACCG

CGGCACGCGCTTCTACCGCGGTCATACCAGCAGCCGCCGCCGCAAGACCACCACTCGCCGCCGCC

GTCGCCGCACCGCCGCTGCAACCACCCCTGCCGCCCTGGTGCGGAGAGTGTACCGCCGCGGCCGC

GCACCTCTGACCCTGCCGCGCGCGCGCTACCACCCGAGCATCGCCATTTAAACTTTCGCCtGCTT

TGCAGATCAATGGCCCTCACATGCCGCCTTCGCGTTCCCATTACGGGCTACCGAGGAAGAAAACC

GCGCCGTAGAAGGCTGGCGGGGAACGGGATGCGTCGCCACCACCACCGGCGGCGGCGCGCCATCA

GCAAGCGGTTGGGGGGAGGCTTCCTGCCCGCGCTGATCCCCATCATCGCCGCGGCGATCGGGGCG

ATCCCCGGCATTGCTTCCGTGGCGGTGCAGGCCTCTCAGCGCCACTGAGACACACTTGGAAACAT

CTTGTAATAAACCaATGGACTCTGACGCTCCTGGTCCTGTGATGTGTTTTCGTAGACAGATGGAA

GACATCAATTTTTCGTCCCTGGCTCCGCGACACGGCACGCGGCCGTTCATGGGCACCTGGAGCGA

CATCGGCACCAGCCAACTGAACGGGGGCGCCTTCAATTGGAGCAGTCTCTGGAGCGGGCTTAAGA

ATTTCGGGTCCACGCTTAAAACCTATGGCAGCAAGGCGTGGAACAGCACCACAGGGCAGGCGCTG

AGGGATAAGCTGAAAGAGCAGAACTTCCAGCAGAAGGTGGTCGATGGGCTCGCCTCGGGCATCAA

CGGGGTGGTGGACCTGGCCAACCAGGCCGTGCAGCGGCAGATCAACAGCCGCCTGGACCCGGTGC

CGCCCGCCGGCTCCGTGGAGATGCCGCAGGTGGAGGAGGAGCTGCCTCCCCTGGACAAGCGGGGC

GAGAAGCGACCCCGCCCCGATGCGGAGGAGACGCTGCTGACGCACACGGACGAGCCGCCCCCGTA

-continued

CGAGGAGGCGGTGAAACTGGGTCTGCCCACCACGCGGCCCATCGCGCCCCTGGCCACCGGGGTGC

TGAAACCCGAAAAGCCCGCGACCCTGGACTTGCCTCCTCCCCAGCCTTCCCGCCCCTCTACAGTG

GCTAAGCCCCTGCCGCCGGTGGCCGTGGCCCGCGCGCGACCCGGGGGCACCGCCCGCCCTCATGC

GAACTGGCAGAGCACTCTGAACAGCATCGTGGGTCTGGGAGTGCAGAGTGTGAAGCGCCGCCGCT

GCTATTAAACCTACCGTAGCGCTTAACTTGCTTGTCTGTGTGTGTATGTATTATGTCGCCGCCGC

CGCTGTCCACCAGAAGGAGGAGTGAAGAGGCGCGTCGCCGAGTTGCAAGATGGCCACCCCATCGA

TGCTGCCCCAGTGGGCGTACATGCACATCGCCGGACAGGACGCTTCGGAGTACCTGAGTCCGGGT

CTGGTGCAGTTTGCCCGCGCCACAGACACCTACTTCAGTCTGGGGAACAAGTTTAGGAACCCCAC

GGTGGCGCCCACGCACGATGTGACCACCGACCGCAGCCAGCGGCTGACGCTGCGCTTCGTGCCCG

TGGACCGCGAGGACAACACCTACTCGTACAAAGTGCGCTACACGCTGGCCGTGGGCGACAACCGC

GTGCTGGACATGGCCAGCACCTACTTTGACATCCGCGGCGTGCTGGATCGGGGCCCTAGCTTCAA

ACCCTACTCCGGCACCGCCTACAACAGTCTGGCCCCCAAGGGAGCACCCAACACTTGTCAGTGGA

CATATAAAGCCGATGGTGAAACTGCCACAGAAAAAACCTATACATATGGAAATGCACCCGTGCAG

GGCATTAACATCACAAAAGATGGTATTCAACTTGGAACTGACACCGATGATCAGCCAATCTACGC

AGATAAAACCTATCAGCCTGAACCTCAAGTGGGTGATGCTGAATGGCATGACATCACTGGTACTG

ATGAAAAGTATGGAGGCAGAGCTCTTAAGCCTGATACCAAAATGAAGCCTTGTTATGGTTCTTTT

GCCAAGCCTACTAATAAAGAAGGAGGTCAGGCAAATGTGAAAACAGGAACAGGCACTACTAAAGA

ATATGACATAGACATGGCTTTCTTTGACAACAGAAGTGCGGCTGCTGCTGGCCTAGCTCCAGAAA

TTGTTTTGTATACTGAAAATGTGGATTTGGAAACTCCAGATACCCATATTGTATACAAAGCAGGC

ACAGATGACAGCAGCTCTTCTATTAATTTGGGTCAGCAAGCCATGCCCAACAGACCTAACTACAT

TGGTTTCAGAGACAACTTTATCGGGCTCATGTACTACAACAGCACTGGCAATATGGGGGTGCTGG

CCGGTCAGGCTTCTCAGCTGAATGCTGTGGTTGACTTGCAAGACAGAAACACCGAGCTGTCCTAC

CAGCTCTTGCTTGACTCTCTGGGTGACAGAACCCGGTATTTCAGTATGTGGAATCAGGCGGTGGA

CAGCTATGATCCTGATGTGCGCATTATTGAAAATCATGGTGTGGAGGATGAACTTCCCAACTATT

GTTTCCCTCTGGATGCTGTTGGCAGAACAGATACTTATCAGGGAATTAAGGCTAATGGAACTGAT

CAAACCACATGGACCAAAGATGACAGTGTCAATGATGCTAATGAGATAGGCAAGGGTAATCCATT

CGCCATGGAAATCAACATCCAAGCCAACCTGTGGAGGAACTTCCTCTACGCCAACGTGGCCCTGT

ACCTGCCCGACTCTTACAAGTACACGCCGGCCAATGTTACCCTGCCCACCAACACCAACACCTAC

GATTACATGAACGGCCGGGTGGTGGCGCCCTCGCTGGTGGACTCCTACATCAACATCGGGGCGCG

CTGGTCGCTGGATCCCATGGACAACGTGAACCCCTTCAACCACCACCGCAATGCGGGGCTGCGCT

ACCGCTCCATGCTCCTGGGCAACGGGCGCTACGTGCCCTTCCACATCCAGGTGCCCCAGAAATTT

TTCGCCATCAAGAGCCTCCTGCTCCTGCCCGGGTCCTACACCTACGAGTGGAACTTCCGCAAGGA

CGTCAACATGATCCTGCAGAGCTCCCTCGGCAACGACCTGCGCACGGACGGGGCCTCCATCTCCT

TCACCAGCATCAACCTCTACGCCACCTTCTTCCCCATGGCGCACAACACGGCCTCCACGCTCGAG

GCCATGCTGCGCAACGACACCAACGACCAGTCCTTCAACGACTACCTCTCGGCGGCCAACATGCT

CTACCCCATCCCGGCCAACGCCACCAACGTGCCCATCTCCATCCCCTCGCGCAACTGGGCCGCCT

TCCGCGGCTGGTCCTTCACGCGTCTCAAGACCAAGGAGACGCCCTCGCTGGGCTCCGGGTTCGAC

CCCTACTTCGTCTACTCGGGCTCCATCCCCTACCTCGACGGCACCTTCTACCTCAACCACACCTT

CAAGAAGGTCTCCATCACCTTCGACTCCTCCGTCAGCTGGCCCGGCAACGACCGGCTCCTGACGC

CCAACGAGTTCGAAATCAAGCGCACCGTCGACGGCGAGGGCTACAACGTGGCCCAGTGCAACATG

-continued

ACCAAGGACTGGTTCCTGGTCCAGATGCTGGCCCACTACAACATCGGCTACCAGGGCTTCTACGT

GCCCGAGGGCTACAAGGACCGCATGTACTCCTTCTTCCGCAACTTCCAGCCCATGAGCCGCCAGG

TGGTGGACGAGGTCAACTACAAGGACTACCAGGCCGTCACCCTGGCCTACCAGCACAACAACTCG

GGCTTCGTCGGCTACCTCGCGCCCACCATGCGCCAGGGCCAGCCCTACCCCGCCAACTACCCCTA

CCCGCTCATCGGCAAGAGCGCCGTCACCAGCGTCACCCAGAAAAAGTTCCTCTGCGACAGGGTCA

TGTGGCGCATCCCCTTCTCCAGCAACTTCATGTCCATGGGCGCGCTCACCGACCTCGGCCAGAAC

ATGCTCTATGCCAACTCCGCCCACGCGCTAGACATGAATTTCGAAGTCGACCCCATGGATGAGTC

CACCCTTCTCTATGTTGTCTTCGAAGTCTTCGACGTCGTCCGAGTGCACCAGCCCCACCGCGGCG

TCATCGAGGCCGTCTACCTGCGCACCCCCTTCTCGGCCGGTAACGCCACCACCTAAGCTCTTGCT

TCTTGCAAGCCATGGCCGCGGGCTCCGGCGAGCAGGAGCTCAGGGCCATCATCCGCGACCTGGGC

TGCGGGCCCTACTTCCTGGGCACCTTCGATAAGCGCTTCCCGGGATTCATGGCCCCGCACAAGCT

GGCCTGCGCCATCGTCAACACGGCCGGCCGCGAGACCGGGGGCGAGCACTGGCTGGCCTTCGCCT

GGAACCCGCGCTCGAACACCTGCTACCTCTTCGACCCCTTCGGGTTCTCGGACGAGCGCCTCAAG

CAGATCTACCAGTTCGAGTACGAGGGCCTGCTGCGCCGCAGCGCCCTGGCCACCGAGGACCGCTG

CGTCACCCTGGAAAAGTCCACCCAGACCGTGCAGGGTCCGCGCTCGGCCGCCTGCGGGCTCTTCT

GCTGCATGTTCCTGCACGCCTTCGTGCACTGGCCCGACCGCCCCATGGACAAGAACCCCACCATG

AACTTGCTGACGGGGGTGCCCAACGGCATGCTCCAGTCGCCCCAGGTGGAACCCACCCTGCGCCG

CAACCAGGAGGCGCTCTACCGCTTCCTCAACTCCCACTCCGCCTACTTTCGCTCCCACCGCGCGC

GCATCGAGAAGGCCACCGCCTTCGACCGCATGAATCAAGACATGTAAACCGTGTGTGTATGTTAA

ATGTCTTTAATAAACAGCACTTTCATGTTACACATGCATCTGAGATGATTTATTTAGAAATCGAA

AGGGTTCTGCCGGGTCTCGGCATGGCCCGCGGGCAGGGACACGTTGCGGAACTGGTACTTGGCCA

GCCACTTGAACTCGGGGATCAGCAGTTTGGGCAGCGGGGTGTCGGGGAAGGAGTCGGTCCACAGC

TTCCGCGTCAGTTGCAGGGCGCCCAGCAGGTCGGGCGCGGAGATCTTGAAATCGCAGTTGGGACC

CGCGTTCTGCGCGCGGGAGTTGCGGTACACGGGGTTGCAGCACTGGAACACCATCAGGGCCGGGT

GCTTCACGCTCGCCAGCACCGTCGCGTCGGTGATGCTCTCCACGTCGAGGTCCTCGGCGTTGGCC

ATCCCGAAGGGGGTCATCTTGCAGGTCTGCCTTCCCATGGTGGGCACGCACCCGGGCTTGTGGTT

GCAATCGCAGTGCAGGGGGATCAGCATCATCTGGGCCTGGTCGGCGTTCATCCCCGGGTACATGG

CCTTCATGAAAGCCTCCAATTGCCTGAACGCCTGCTGGGCCTTGGCTCCCTCGGTGAAGAAGACC

CCGCAGGACTTGCTAGAGAACTGGTTGGTGGCGCACCCGGCGTCGTGCACGCAGCAGCGCGCGTC

GTTGTTGGCCAGCTGCACCACGCTGCGCCCCCAGCGGTTCTGGGTGATCTTGGCCCGGTCGGGGT

TCTCCTTCAGCGCGCGCTGCCCGTTCTCGCTCGCCACATCCATCTCGATCATGTGCTCCTTCTGG

ATCATGGTGGTCCCGTGCAGGCACCGCAGCTTGCCCTCGGCCTCGGTGCACCCGTGCAGCCACAG

CGCGCACCCGGTGCACTCCCAGTTCTTGTGGGCGATCTGGGAATGCGCGTGCACGAAGCCCTGCA

GGAAGCGGCCCATCATGGTGGTCAGGGTCTTGTTGCTAGTGAAGGTCAGCGGAATGCCGCGGTGC

TCCTCGTTGATGTACAGGTGGCAGATGCGGCGGTACACCTCGCCCTGCTCGGGCATCAGCTGGAA

GTTGGCTTTCAGGTCGGTCTCCACGCGGTAGCGGTCCATCAGCATAGTCATGATTTCCATACCCT

TCTCCCAGGCCGAGACGATGGGCAGGCTCATAGGGTTCTTCACCATCATCTTAGCGCTAGCAGCC

GCGGCCAGGGGGTCGCTCTCGTCCAGGGTCTCAAAGCTCCGCTTGCCGTCCTTCTCGGTGATCCG

CACCGGGGGGTAGCTGAAGCCCACGGCCGCCAGCTCCTCCTCGGCCTGTCTTTCGTCCTCGCTGT

-continued

CCTGGCTGACGTCCTGCAGGACCACATGCTTGGTCTTGCGGGGTTTCTTCTTGGGCGGCAGCGGC

GGCGGAGATGTTGGAGATGGCGAGGGGGAGCGCGAGTTCTCGCTCACCACTACTATCTCTTCCTC

TTCTTGGTCCGAGGCCACGCGGCGGTAGGTATGTCTCTTCGGGGGCAGAGGCGGAGGCGACGGGC

TCTCGCCGCCGCGACTTGGCGGATGGCTGGCAGAGCCCCTTCCGCGTTCGGGGGTGCGCTCCCGG

CGGCGCTCTGACTGACTTCCTCCGCGGCCGGCCATTGTGTTCTCCTAGGGAGGAACAACAAGCAT

GGAGACTCAGCCATCGCCAACCTCGCCATCTGCCCCCACCGCCGACGAGAAGCAGCAGCAGCAGA

ATGAAAGCTTAACCGCCCCGCCGCCCAGCCCCGCCACCTCCGACGCGGCCGTCCCAGACATGCAA

GAGATGGAGGAATCCATCGAGATTGACCTGGGCTATGTGACGCCCGCGGAGCACGAGGAGGAGCT

GGCAGTGCGCTTTTCACAAGAAGAGATACACCAAGAACAGCCAGAGCAGGAAGCAGAGAATGAGC

AGAGTCAGGCTGGGCTCGAGCATGACGGCGACTACCTCCACCTGAGCGGGGGGGAGGACGCGCTC

ATCAAGCATCTGGCCCGGCAGGCCACCATCGTCAAGGATGCGCTGCTCGACCGCACCGAGGTGCC

CCTCAGCGTGGAGGAGCTCAGCCGCGCCTACGAGTTGAACCTCTTCTCGCCGCGCGTGCCCCCCA

AGCGCCAGCCCAATGGCACCTGCGAGCCCAACCCGCGCCTCAACTTCTACCCGGTCTTCGCGGTG

CCCGAGGCCCTGGCCACCTACCACATCTTTTTCAAGAACCAAAAGATCCCCGTCTCCTGCCGCGC

CAACCGCACCCGCGCCGACGCCCTTTTCAACCTGGGTCCCGGCGCCCGCCTACCTGATATCGCCT

CCTTGGAAGAGGTTCCCAAGATCTTCGAGGGTCTGGGCAGCGACGAGACTCGGGCCGCGAACGCT

CTGCAAGGAGAAGGAGGAGAGCATGAGCACCACAGCGCCCTGGTCGAGTTGGAAGGCGACAACGC

GCGGCTGGCGGTGCTCAAACGCACGGTCGAGCTGACCCATTTCGCCTACCCGGCTCTGAACCTGC

CCCCCAAAGTCATGAGCGCGGTCATGGACCAGGTGCTCATCAAGCGCGCGTCGCCCATCTCCGAG

GACGAGGGCATGCAAGACTCCGAGGAGGGCAAGCCCGTGGTCAGCGACGAGCAGCTGGCCCGGTG

GCTGGGTCCTAATGCTAGTCCCCAGAGTTTGGAAGAGCGGCGCAAACTCATGATGGCCGTGGTCC

TGGTGACCGTGGAGCTGGAGTGCCTGCGCCGCTTCTTCGCCGACGCGGAGACCCTGCGCAAGGTC

GAGGAGAACCTGCACTACCTCTTCAGGCACGGGTTCGTGCGCCAGGCCTGCAAGATCTCCAACGT

GGAGCTGACCAACCTGGTCTCCTACATGGGCATCTTGCACGAGAACCGCCTGGGGCAGAACGTGC

TGCACACCACCCTGCGCGGGGAGGCCCGGCGCGACTACATCCGCGACTGCGTCTACCTCTACCTC

TGCCACACCTGGCAGACGGGCATGGGCGTGTGGCAGCAGTGTCTGGAGGAGCAGAACCTGAAAGA

GCTCTGCAAGCTCCTGCAGAAGAACCTCAAGGGTCTGTGGACCGGGTTCGACGAGCGCACCACCG

CCTCGGACCTGGCCGACCTCATTTTCCCCGAGCGCCTCAGGCTGACGCTGCGCAACGGCCTGCCC

GACTTTATGAGCCAAAGCATGTTGCAAAACTTTCGCTCTTTCATCCTCGAACGCTCCGGAATCCT

GCCCGCCACCTGCTCCGCGCTGCCCTCGGACTTCGTGCCGCTGACCTTCCGCGAGTGCCCCCCGC

CGCTGTGGAGCCACTGCTACCTGCTGCGCCTGGCCAACTACCTGGCCTACCACTCGGACGTGATC

GAGGACGTCAGCGGCGAGGGCCTGCTCGAGTGCCACTGCCGCTGCAACCTCTGCACGCCGCACCG

CTCCCTGGCCTGCAACCCCCAGCTGCTGAGCGAGACCCAGATCATCGGCACCTTCGAGTTGCAAG

GGCCCAGCGAAGGCGAGGGTTCAGCCGCCAAGGGGGGTCTGAAACTCACCCCGGGGCTGTGGACC

TCGGCCTACTTGCGCAAGTTCGTGCCCGAGGACTACCATCCCTTCGAGATCAGGTTCTACGAGGA

CCAATCCCATCCGCCCAAGGCCGAGCTGTCGGCCTGCGTCATCACCCAGGGGGCGATCCTGGCCC

AATTGCAAGCCATCCAGAAATCCCGCCAAGAATTCTTGCTGAAAAAGGGCCGCGGGGTCTACCTC

GACCCCCAGACCGGTGAGGAGCTCAACCCCGGCTTCCCCCAGGATGCCCCGAGGAAACAAGAAGC

TGAAAGTGGAGCTGCCGCCCGTGGAGGATTTGGAGGAAGACTGGGAGAACAGCAGTCAGGCAGAG

GAGGAGGAGATGGAGGAAGACTGGGACAGCACTCAGGCAGAGGAGGACAGCCTGCAAGACAGTCT

-continued

GGAGGAAGACGAGGAGGAGGCAGAGGAGGAGGTGGAAGAAGCAGCCGCCGCCAGACCGTCGTCCT
CGGCGGGGGAGAAAGCAAGCAGCACGGATACCATCTCCGCTCCGGGTCGGGGTCCCGCTCGACCA
CACAGTAGATGGGACGAGACCGGACGATTCCCGAACCCCACCACCCAGACCGGTAAGAAGGAGCG
GCAGGGATACAAGTCCTGGCGGGGGCACAAAAACGCCATCGTCTCCTGCTTGCAGGCCTGCGGGG
GCAACATCTCCTTCACCCGGCGCTACCTGCTCTTCCACCGCGGGGTGAACTTTCCCCGCAACATC
TTGCATTACTACCGTCACCTCCACAGCCCCTACTACTTCCAAGAAGAGGCAGCAGCAGCAGAAAA
AGACCAGCAGAAAACCAGCAGCTAGAAAATCCACAGCGGCGGCAGCAGGTGGACTGAGGATCGCG
GCGAACGAGCCGGCGCAAACCCGGGAGCTGAGGAACCGGATCTTTCCCACCCTCTATGCCATCTT
CCAGCAGAGTCGGGGGCAGGAGCAGGAACTGAAAGTCAAGAACCGTTCTCTGCGCTCGCTCACCC
GCAGTTGTCTGTATCACAAGAGCGAAGACCAACTTCAGCGCACTCTCGAGGACGCCGAGGCTCTC
TTCAACAAGTACTGCGCGCTCACTCTTAAAGAGTAGCCCGCGCCCGCCCAGTCGCAGAAAAAGGC
GGGAATTACGTCACCTGTGCCCTTCGCCCTAGCCGCCTCCACCCATCATCATGAGCAAAGAGATT
CCCACGCCTTACATGTGGAGCTACCAGCCCCAGATGGGCCTGGCCGCCGGTGCCGCCCAGGACTA
CTCCACCCGCATGAATTGGCTCAGCGCCGGGCCCGCGATGATCTCACGGGTGAATGACATCCGCG
CCCACCGAAACCAGATACTCCTAGAACAGTCAGCGCTCACCGCCACGCCCCGCAATCACCTCAAT
CCGCGTAATTGGCCCGCCGCCCTGGTGTACCAGGAAATTCCCCAGCCCACGACCGTACTACTTCC
GCGAGACGCCCAGGCCGAAGTCCAGCTGACTAACTCAGGTGTCCAGCTGGCGGGCGGCGCCACCC
TGTGTCGTCACCGCCCCGCTCAGGGTATAAAGCGGCTGGTGATCCGGGGCAGAGGCACACAGCTC
AACGACGAGGTGGTGAGCTCTTCGCTGGGTCTGCGACCTGACGGAGTCTTCCAACTCGCCGGATC
GGGGAGATCTTCCTTCACGCCTCGTCAGGCCGTCCTGACTTTGGAGAGTTCGTCCTCGCAGCCCC
GCTCGGGTGGCATCGGCACTCTCCAGTTCGTGGAGGAGTTCACTCCCTCGGTCTACTTCAACCCC
TTCTCCGGCTCCCCCGGCCACTACCCGGACGAGTTCATCCCGAACTTCGACGCCATCAGCGAGTC
GGTGGACGGCTACGATTGAATGTCCCATGGTGGCGCAGCTGACCTAGCTCGGCTTCGACACCTGG
ACCACTGCCGCCGCTTCCGCTGCTTCGCTCGGGATCTCGCCGAGTTTGCCTACTTTGAGCTGCCC
GAGGAGCACCCTCAGGGCCCGGCCCACGGAGTGCGGATCGTCGTCGAAGGGGGCCTCGACTCCCA
CCTGCTTCGGATCTTCAGCCAGCGTCCGATCCTGGTCGAGCGCGAGCAAGGACAGACCCTTCTGA
CTCTGTACTGCATCTGCAACCACCCCGGCCTGCATGAAAGTCTTTGTTGTCTGCTGTGTACTGAG
TATAATAAAAGCTGAGATCAGCGACTACTCCGGACTTCCGTGTGTTCCTGAATCCATCAACCAGT
CTTTGTTCTTCACCGGGAACGAGACCGAGCTCCAGCTCCAGTGTAAGCCCCACAAGAAGTACCTC
ACCTGGCTGTTCCAGGGCTCCCCGATCGCCGTTGTCAACCACTGCGACAACGACGGAGTCCTGCT
GAGCGGCCCTGCCAACCTTACTTTTTCCACCCGCAGAAGCAAGCTCCAGCTCTTCCAACCCTTCC
TCCCCGGGACCTATCAGTGCGTCTCGGGACCCTGCCATCACACCTTCCACCTGATCCCGAATACC
ACAGCGTCGCTCCCCGCTACTAACAACCAAACTAACCTCCACCAACGCCACCGTCGCGACCTTTC
TGAATCTAATACTACCACCCACACCGGAGGTGAGCTCCGAGGTCAACCAACCTCTGGGATTTACT
ACGGCCCCTGGGAGGTGGTTGGGTTAATAGCGCTAGGCCTAGTTGCGGGTGGGCTTTTGGTTCTC
TGCTACCTATACCTCCCTTGCTGTTCGTACTTAGTGGTGCTGTGTTGCTGGTTTAAGAAATGGGG
AAGATCACCCTAGTGAGCTGCGGTGCGCTGGTGGCGGTGTTGCTTTCGATTGTGGGACTGGGCGG
TGCGGCTGTAGTGAAGGAGAAGGCCGATCCCTGCTTGCATTTCAATCCCAACAAATGCCAGCTGA
GTTTTCAGCCCGATGGCAATCGGTGCGCGGTACTGATCAAGTGCGGATGGGAATGCGAGAACGTG

-continued

AGAATCGAGTACAATAACAAGACTCGGAACAATACTCTCGCGTCCGTGTGGCAGCCCGGGGACCC
CGAGTGGTACACCGTCTCTGTCCCCGGTGCTGACGGCTCCCCGCGCACCGTGAATAATACTTTCA
TTTTTGCGCACATGTGCGACACGGTCATGTGGATGAGCAAGCAGTACGATATGTGGCCCCCCACG
AAGGAGAACATCGTGGTCTTCTCCATCGCTTACAGCCTGTGCACGGCGCTAATCACCGCTATCGT
GTGCCTGAGCATTCACATGCTCATCGCTATTCGCCCCAGAAATAATGCCGAAAAAGAAAAACAGC
CATAACGTTTTTTTTCACACCTTTTTCAGACCATGGCCTCTGTTAAATTTTTGCTTTTATTTGCC
AGTCTCATTGCCGTCATTCATGGAATGAGTAATGAGAAAATTACTATTTACACTGGCACTAATCA
CACATTGAAAGGTCCAGAAAAAGCCACAGAAGTTTCATGGTATTGTTATTTTAATGAATCAGATG
TATCTACTGAACTCTGTGGAAACAATAACAAAAAAAATGAGAGCATTACTCTCATCAAGTTTCAA
TGTGGATCTGACTTAACCCTAATTAACATCACTAGAGACTATGTAGGTATGTATTATGGAACTAC
AGCAGGCATTTCGGACATGGAATTTTATCAAGTTTCTGTGTCTGAACCCACCACGCCTAGAATGA
CCACAACCACAAAAACTACACCTGTTACCACTATGCAGCTCACTACCAATAACATTTTTGCCATG
CGTCAAATGGTCAACAATAGCACTCAACCCACCCCACCCAGTGAGGAAATTCCCAAATCCATGAT
TGGCATTATTGTTGCTGTAGTGGTGTGCATGTTGATCATCGCCTTGTGCATGGTGTACTATGCCT
TCTGCTACAGAAAGCACAGACTGAACGACAAGCTGGAACACTTACTAAGTGTTGAATTTTAATTT
TTTAGAACCATGAAGATCCTAGGCCTTTTAATTTTTTCTATCATTACCTCTGCTCTATGCAATTC
TGACAATGAGGACGTTACTGTCGTTGTCGGATCAAATTATACACTGAAAGGTCCAGCGAAGGGTA
TGCTTTCGTGGTATTGCTATTTTGGATCTGACACTACAGAAACTGAATTATGCAATCTTAAGAAT
GGCAAAATTCAAAATTCTAAAATTAACAATTATATATGCAATGGTACTGATCTGATACTCCTCAA
TATCACGAAATCATATGCTGGCAGTTACACCTGCCCTGGAGATGATGCTGACAGTATGATTTTTT
ACAAAGTAACTGTTGTTGATCCCACTACTCCACCTCCACCCACCACAACTACTCACACCACACAC
ACAGATCAAACCGCAGCAGAGGAGGCAGCAAAGTTAGCCTTGCAGGTCCAAGACAGTTCATTTGT
TGGCATTACCCCTACACCTGATCAGCGGTGTCCGGGGCTGCTAGTCAGCGGCATTGTCGGTGTGC
TTTCGGGATTAGCAGTCATAATCATCTGCATGTTCATTTTTGCTTGCTGCTATAGAAGGCTTTAC
CGACAAAAATCAGACCCACTGCTGAACCTCTATGTTTAATTTTTTCCAGAGTCATGAAGGCAGTT
AGCGCTCTAGTTTTTTGTTCTTTGATTGGCATTGTTTTTTGCAATCCTATTCCTAAAGTTAGCTT
TATTAAAGATGTGAATGTTACTGAGGGGGGCAATGTGACACTGGTAGGTGTAGAGGGTGCTGAAA
ACACCACCTGGACAAAATACCACCTCAATGGGTGGAAAGATATTTGCAATTGGAGTGTATTAGTT
TATACATGTGAGGGAGTTAATCTTACCATTGTCAATGCCACCTCAGCTCAAAATGGTAGAATTCA
AGGACAAAGTGTCAGTGTATCTAATGGGTATTTTACCCAACATACTTTTATCTATGACGTTAAAG
TCATACCACTGCCTACGCCTAGCCCACCTAGCACTACCACACAGACAACCCACACTACACAGACA
ACCACATACAGTACATTAAATCAGCCTACCACCACTACAGCAGCAGAGGTTGCCAGCTCGTCTGG
GGTCCGAGTGGCATTTTTGATGTGGGCCCCATCTAGCAGTCCCACTGCTAGTACCAATGAGCAGA
CTACTGAATTTTTGTCCACTGTCGAGAGCCACACCACAGCTACCTCCAGTGCCTTCTCTAGCACC
GCCAATCTCTCCTCGCTTTCCTCTACACCAATCAGTCCCGCTACTACTCCTAGCCCCGCTCCTCT
TCCCACTCCCCTGAAGCAAACAGACGGCGGCATGCAATGGCAGATCACCCTGCTCATTGTGATCG
GGTTGGTCATCCTGGCCGTGTTGCTCTACTACATCTTCTGCCGCCGCATTCCCAACGCGCACCGC
AAGCCGGTCTACAAGCCCATCATTGTCGGGCAGCCGGAGCCGCTTCAGGTGGAAGGGGGTCTAAG
GAATCTTCTCTTCTCTTTTACAGTATGGTGATTGAACTATGATTCCTAGACAATTCTTGATCACT
ATTCTTATCTGCCTCCTCCAAGTCTGTGCCACCCTCGCTCTGGTGGCCAACGCCAGTCCAGACTG

-continued

TATTGGGCCCTTCGCCTCCTACGTGCTCTTTGCCTTCACCACCTGCATCTGCTGCTGTAGCATAG

TCTGCCTGCTTATCACCTTCTTCCAGTTCATTGACTGGATCTTTGTGCGCATCGCCTACCTGCGC

CACCACCCCCAGTACCGCGACCAGCGAGTGGCGCGGCTGCTCAGGCTCCTCTGATAAGCATGCGG

GCTCTGCTACTTCTCGCGCTTCTGCTGTTAGTGCTCCCCCGTCCCGTCGACCCCCGGTCCCCCAC

CCAGTCCCCCGAGGAGGTCCGCAAATGCAAATTCCAAGAACCCTGGAAATTCCTCAAATGCTACC

GCCAAAAATCAGACATGCATCCCAGCTGGATCATGATCATTGGGATCGTGAACATTCTGGCCTGC

ACCCTCATCTCCTTTGTGATTTACCCCTGCTTTGACTTTGGTTGGAACTCGCCAGAGGCGCTCTA

TCTCCCGCCTGAACCTGACACACCACCACAGCAACCTCAGGCACACGCACTACCACCACTACAGC

CTAGGCCACAATACATGCCCATATTAGACTATGAGGCCGAGCCACAGCGACCCATGCTCCCCGCT

ATTAGTTACTTCAATCTAACCGGCGGAGATGACTGACCCACTGGCCAACAACAACGTCAACGACC

TTCTCCTGGACATGGACGGCCGCGCCTCGGAGCAGCGACTCGCCCAACTTCGCATTCGCCAGCAG

CAGGAGAGAGCCGTCAAGGAGCTGCAGGATGCGGTGGCCATCCACCAGTGCAAGAGAGGCATCTT

CTGCCTGGTGAAACAGGCCAAGATCTCCTACGAGGTCACTCCAAACGACCATCGCCTCTCCTACG

AGCTCCTGCAGCAGCGCCAGAAGTTCACCTGCCTGGTCGGAGTCAACCCCATCGTCATCACCCAG

CAGTCTGGCGATACCAAGGGGTGCATCCACTGCTCCTGCGACTCCCCCGACTGCGTCCACACTCT

GATCAAGACCCTCTGCGGCCTCCGCGACCTCCTCCCCATGAACTAATCACCCCCTTATCCAGTGA

AATAAAGATCATATTGATGATGATTTTACAGAAATAAAAAATAATCATTTGATTTGAAATAAAGA

TACAATCATATTGATGATTTGAGTTTAACAAAAAAATAAAGAATCACTTACTTGAAATCTGATAC

CAGGTCTCTGTCCATGTTTTCTGCCAACACCACTTCACTCCCCTCTTCCCAGCTCTGGTACTGCA

GGCCCCGGCGGGCTGCAAACTTCCTCCACACGCTGAAGGGGATGTCAAATTCCTCCTGTCCCTCA

ATCTTCATTTTATCTTCTATCAGATGTCCAAAAAGCGCGTCCGGGTGGATGATGACTTCGACCCC

GTCTACCCCTACGATGCAGACAACGCACCGACCGTGCCCTTCATCAACCCCCCCTTCGTCTCTTC

AGATGGATTCCAAGAGAAGCCCCTGGGGGTGTTGTCCCTGCGACTGGCCGACCCCGTCACCACCA

AGAACGGGGAAATCACCCTCAAGCTGGGAGAGGGGGTGGACCTCGATTCCTCGGGAAAACTCATC

TCCAACACGGCCACCAAGGCCGCCGCCCCTCTCAGTTTTTCCAACAACACCATTTCCCTTAACAT

GGATCACCCCTTTTACACTAAAGATGGAAAATTATCCTTACAAGTTTCTCCACCATTAAATATAC

TGAGAACAAGCATTCTAAACACACTAGCTTTAGGTTTTGGATCAGGTTTAGGACTCCGTGGCTCT

GCCTTGGCAGTACAGTTAGTCTCTCCACTTACATTTGATACTGATGGAAACATAAAGCTTACCTT

AGACAGAGGTTTGCATGTTACAACAGGAGATGCAATTGAAAGCAACATAAGCTGGGCTAAAGGTT

TAAAATTTGAAGATGGAGCCATAGCAACCAACATTGGAAATGGGTTAGAGTTTGGAAGCAGTAGT

ACAGAAACAGGTGTTGATGATGCTTACCCAATCCAAGTTAAACTTGGATCTGGCCTTAGCTTTGA

CAGTACAGGAGCCATAATGGCTGGTAACAAAGAAGACGATAAACTCACTTTGTGGACAACACCTG

ATCCATCACCAAACTGTCAAATACTCGCAGAAAATGATGCAAAACTAACACTTTGCTTGACTAAA

TGTGGTAGTCAAATACTGGCCACTGTGTCAGTCTTAGTTGTAGGAAGTGGAAACCTAAACCCCAT

TACTGGCACCGTAAGCAGTGCTCAGGTGTTTCTACGTTTTGATGCAAACGGTGTTCTTTTAACAG

AACATTCTACACTAAAAAAATACTGGGGGTATAGGCAGGGAGATAGCATAGATGGCACTCCATAT

ACCAATGCTGTAGGATTCATGCCCAATTTAAAAGCTTATCCAAAGTCACAAAGTTCTACTACTAA

AAATAATATAGTAGGGCAAGTATACATGAATGGAGATGTTTCAAAACCTATGCTTCTCACTATAA

CCCTCAATGGTACTGATGACAGCAACAGTACATATTCAATGTCATTTTCATACACCTGGACTAAT

-continued

GGAAGCTATGTTGGAGCAACATTTGGGGCTAACTCTTATACCTTCTCATACATCGCCCAAGAATG

AACACTGTATCCCACCCTGCATGCCAACCCTTCCCACCCCACTCTGTGGAACAAACTCTGAAACA

CAAAATAAAATAAAGTTCAAGTGTTTTATTGATTCAACAGTTTTACAGGATTCGAGCAGTTATTT

TTCCTCCACCCTCCCAGGACATGGAATACACCACCCTCTCCCCCCGCACAGCCTTGAACATCTGA

ATGCCATTGGTGATGGACATGCTTTTGGTCTCCACGTTCCACACAGTTTCAGAGCGAGCCAGTCT

CGGGTCGGTCAGGGAGATGAAACCCTCCGGGCACTCCCGCATCTGCACCTCACAGCTCAACAGCT

GAGGATTGTCCTCGGTGGTCGGGATCACGGTTATCTGGAAGAAGCAGAAGAGCGGCGGTGGGAAT

CATAGTCCGCGAACGGGATCGGCCGGTGGTGTCGCATCAGGCCCCGCAGCAGTCGCTGCCGCCGC

CGCTCCGTCAAGCTGCTGCTCAGGGGGTCCGGGTCCAGGGACTCCCTCAGCATGATGCCCACGGC

CCTCAGCATCAGTCGTCTGGTGCGGCGGGCGCAGCAGCGCATGCGGATCTCGCTCAGGTCGCTGC

AGTACGTGCAACACAGAACCACCAGGTTGTTCAACAGTCCATAGTTCAACACGCTCCAGCCGAAA

CTCATCGCGGGAAGGATGCTACCCACGTGGCCGTCGTACCAGATCCTCAGGTAAATCAAGTGGTG

CCCCCTCCAGAACACGCTGCCCACGTACATGATCTCCTTGGGCATGTGGCGGTTCACCACCTCCC

GGTACCACATCACCCTCTGGTTGAACATGCAGCCCCGGATGATCCTGCGGAACCACAGGGCCAGC

ACCGCCCCGCCCGCCATGCAGCGAAGAGACCCCGGGTCCCGGCAATGGCAATGGAGGACCCACCG

CTCGTACCCGTGGATCATCTGGGAGCTGAACAAGTCTATGTTGGCACAGCACAGGCATATGCTCA

TGCATCTCTTCAGCACTCTCAACTCCTCGGGGGTCAAAACCATATCCCAGGGCACGGGGAACTCT

TGCAGGACAGCGAACCCCGCAGAACAGGGCAATCCTCGCACAGAACTTACATTGTGCATGGACAG

GGTATCGCAATCAGGCAGCACCGGGTGATCCTCCACCAGAGAAGCGCGGGTCTCGGTCTCCTCAC

AGCGTGGTAAGGGGGGCCGGCCGATACGGGTGATGGCGGGACGCGGCTGATCGTGTTCGCGACCGT

GTCATGATGCAGTTGCTTTCGGACATTTTCGTACTTGCTGTAGCAGAACCTGGTCCGGGCGCTGC

ACACCGATCGCCGGCGGCGGTCTCGGCGCTTGGAACGCTCGGTGTTGAAATTGTAAAACAGCCAC

TCTCTCAGACCGTGCAGCAGATCTAGGGCCTCAGGAGTGATGAAGATCCCATCATGCCTGATGGC

TCTGATCACATCGACCACCGTGGAATGGGCCAGACCCAGCCAGATGATGCAATTTTGTTGGGTTT

CGGTGACGGCGGGGGAGGGAAGAACAGGAAGAACCATGATTAACTTTTAATCCAAACGGTCTCGG

AGTACTTCAAAATGAAGATCGCGGAGATGGCACCTCTCGCCCCCGCTGTGTTGGTGGAAAATAAC

AGCCAGGTCAAAGGTGATACGGTTCTCGAGATGTTCCACGGTGGCTTCCAGCAAAGCCTCCACGC

GCACATCCAGAAACAAGACAATAGCGAAAGCGGGAGGGTTCTCTAATTCCTCAATCATCATGTTA

CACTCCTGCACCATCCCCAGATAATTTTCATTTTTCCAGCCTTGAATGATTCGAACTAGTTCcTG

AGGTAAATCCAAGCCAGCCATGATAAAGAGCTCGCGCAGAGCGCCCTCCACCGGCATTCTTAAGC

ACACCCTCATAATTCCAAGATATTCTGCTCCTGGTTCACCTGCAGCAGATTGACAAGCGGAATAT

CAAAATCTCTGCCGCGATCCCTGAGCTCCTCCCTCAGCAATAACTGTAAGTACTCTTTCATATCC

TCTCCGAAATTTTTAGCCATAGGACCACCAGGAATAAGATTAGGGCAAGCCACAGTACAGATAAA

CCGAAGTCCTCCCCAGTGAGCATTGCCAAATGCAAGACTGCTATAAGCATGCTGGCTAGACCCGG

TGATATCTTCCAGATAACTGGACAGAAAATCGCCCAGGCAATTTTTAAGAAAATCAACAAAAGAA

AAATCCTCCAGGTGGACGTTTAGAGCCTCGGGAACAACGATGAAGTAAATGCAAGCGGTGCGTTC

CAGCATGGTTAGTTAGCTGATCTGTAGAAAAAACAAAAATGAACATTAAACCATGCTAGCCTGGC

GAACAGGTGGGTAAATCGTTCTCTCCAGCACCAGGCAGGCCACGGGGTCTCCGGCGCGACCCTCG

TAAAAATTGTCGCTATGATTGAAAACCATCACAGAGAGACGTTCCCGGTGGCCGGCGTGAATGAT

TCGACAAGATGAATACACCCCCGGAACATTGGCGTCCGCGAGTGAAAAAAAGCGCCCGAGGAAGC

-continued

AATAAGGCACTACAATGCTCAGTCTCAAGTCCAGCAAAGCGATGCCATGCGGATGAAGCACAAAA

TTCTCAGGTGCGTACAAAATGTAATTACTCCCCTCCTGCACAGGCAGCAAAGCCCCCGATCCCTC

CAGGTACACATACAAAGCCTCAGCGTCCATAGCTTACCGAGCAGCAGCACACAACAGGCGCAAGA

GTCAGAGAAAGGCTGAGCTCTAACCTGTCCACCCGCTCTCTGCTCAATATATAGCCCAGATCTAC

ACTGACGTAAAGGCCAAAGTCTAAAAATACCCGCCAAATAATCACACACGCCCAGCACACGCCCA

GAAACCGGTGACACACTCAAAAAAATACGCGCACTTCCTCAAACGCCCAAAACTGCCGTCATTTC

CGGGTTCCCACGCTACGTCATCAAAACACGACTTTCAAATTCCGTCGACCGTTAAAAACGTCACC

CGCCCCGCCCCTAACGGTCGCCCGTCTCTCAGCCAATCAGCGCCCCGCATCCCCAAATTCAAACA

CCTCATTTGCATATTAACGCGCACAAAAAGTTTGAGGTATATTATTGATGATGG

ATCC VR-594 C68 (SEQ ID NO: 10); Independently sequenced;
Full-Length C68
CCATCTTCAATAATATACCTCAAACTTTTTGTGCGCGTTAATATGCAAATGAGGCGTTTGAATTT

GGGGAGGAAGGGCGGTGATTGGTCGAGGGATGAGCGACCGTTAGGGGCGGGGCGAGTGACGTTTT

GATGACGTGGTTGCGAGGAGGAGCCAGTTTGCAAGTTCTCGTGGGAAAAGTGACGTCAAACGAGG

TGTGGTTTGAACACGGAAATACTCAATTTTCCCGCGCTCTCTGACAGGAAATGAGGTGTTTCTGG

GCGGATGCAAGTGAAAACGGGCCATTTTCGCGCGAAAACTGAATGAGGAAGTGAAAATCTGAGTA

ATTTCGCGTTTATGGCAGGGAGGAGTATTTGCCGAGGGCCGAGTAGACTTTGACCGATTACGTGG

GGGTTTCGATTACCGTGTTTTTCACCTAAATTTCCGCGTACGGTGTCAAAGTCCGGTGTTTTTAC

GTAGGTGTCAGCTGATCGCCAGGGTATTTAAACCTGCGCTCTCCAGTCAAGAGGCCACTCTTGAG

TGCCAGCGAGAAGAGTTTTCTCCTCCGCGCCGCGAGTCAGATCTACACTTTGAAAGATGAGGCAC

CTGAGAGACCTGCCCGATGAGAAAATCATCATCGCTTCCGGGAACGAGATTCTGGAACTGGTGGT

AAATGCCATGATGGGCGACGACCCTCCGGAGCCCCCCACCCCATTTGAGACACCTTCGCTGCACG

ATTTGTATGATCTGGAGGTGGATGTGCCCGAGGACGATCCCAATGAGGAGGCGGTAAATGATTTT

TTTAGCGATGCCGCGCTGCTAGCTGCCGAGGAGGCTTCGAGCTCTAGCTCAGACAGCGACTCTTC

ACTGCATACCCCTAGACCCGGCAGAGGTGAGAAAAAGATCCCCGAGCTTAAAGGGGAAGAGATGG

ACTTGCGCTGCTATGAGGAATGCTTGCCCCCGAGCGATGATGAGGACGAGCAGGCGATCCAGAAC

GCAGCGAGCCAGGGAGTGCAAGCCGCCAGCGAGAGCTTTGCGCTGGACTGCCCGCCTCTGCCCGG

ACACGGCTGTAAGTCTTGTGAATTTCATCGCATGAATACTGGAGATAAAGCTGTGTTGTGTGCAC

TTTGCTATATGAGAGCTTACAACCATTGTGTTTACAGTAAGTGTGATTAAGTTGAACTTTAGAGG

GAGGCAGAGAGCAGGGTGACTGGGCGATGACTGGTTTATTTATGTATATATGTTCTTTATATAGG

TCCCGTCTCTGACGCAGATGATGAGACCCCCACTACAAAGTCCACTTCGTCACCCCCAGAAATTG

GCACATCTCCACCTGAGAATATTGTTAGACCAGTTCCTGTTAGAGCCACTGGGAGGAGAGCAGCT

GTGGAATGTTTGGATGACTTGCTACAGGGTGGGGTTGAACCTTTGGACTTGTGTACCCGGAAACG

CCCCAGGCACTAAGTGCCACACATGTGTGTTTACTTGAGGTGATGTCAGTATTTATAGGGTGTGG

AGTGCAATAAAAAATGTGTTGACTTTAAGTGCGTGGTTTATGACTCAGGGGTGGGGACTGTGAGT

ATATAAGCAGGTGCAGACCTGTGTGGTTAGCTCAGAGCGGCATGGAGATTTGGACGGTCTTGGAA

GACTTTCACAAGACTAGACAGCTGCTAGAGAACGCCTCGAACGGAGTCTCTTACCTGTGGAGATT

CTGCTTCGGTGGCGACCTAGCTAGGCTAGTCTACAGGGCCAAACAGGATTATAGTGAACAATTTG

AGGTTATTTTGAGAGAGTGTTCTGGTCTTTTTGACGCTCTTAACTTGGGCCATCAGTCTCACTTT

AACCAGAGGATTTCGAGAGCCCTTGATTTTACTACTCCTGGCAGAACCACTGCAGCAGTAGCCTT

-continued

TTTTGCTTTTATTCTTGACAAATGGAGTCAAGAAACCCATTTCAGCAGGGATTACCAGCTGGATT

TCTTAGCAGTAGCTTTGTGGAGAACATGGAAGTGCCAGCGCCTGAATGCAATCTCCGGCTACTTG

CCGGTACAGCCGCTAGACACTCTGAGGATCCTGAATCTCCAGGAGAGTCCCAGGGCACGCCAACG

TCGCCAGCAGCAGCAGCAGGAGGAGGATCAAGAAGAGAACCCGAGAGCCGGCCTGGACCCTCCGG

CGGAGGAGGAGGAGTAGCTGACCTGTTTCCTGAACTGCGCCGGGTGCTGACTAGGTCTTCGAGTG

GTCGGGAGAGGGGGATTAAGCGGGAGAGGCATGATGAGACTAATCACAGAACTGAACTGACTGTG

GGTCTGATGAGTCGCAAGCGCCCAGAAACAGTGTGGTGGCATGAGGTGCAGTCGACTGGCACAGA

TGAGGTGTCGGTGATGCATGAGAGGTTTTCTCTAGAACAAGTCAAGACTTGTTGGTTAGAGCCTG

AGGATGATTGGGAGGTAGCCATCAGGAATTATGCCAAGCTGGCTCTGAGGCCAGACAAGAAGTAC

AAGATTACTAAGCTGATAAATATCAGAAATGCCTGCTACATCTCAGGGAATGGGGCTGAAGTGGA

GATCTGTCTCCAGGAAAGGGTGGCTTTCAGATGCTGCATGATGAATATGTACCCGGGAGTGGTGG

GCATGGATGGGGTTACCTTTATGAACATGAGGTTCAGGGGAGATGGGTATAATGGCACGGTCTTT

ATGGCCAATACCAAGCTGACAGTCCATGGCTGCTCCTTCTTTGGGTTTAATAACACCTGCATCGA

GGCCTGGGGTCAGGTCGGTGTGAGGGGCTGCAGTTTTTCAGCCAACTGGATGGGGGTCGTGGGCA

GGACCAAGAGTATGCTGTCCGTGAAGAAATGCTTGTTTGAGAGGTGCCACCTGGGGGTGATGAGC

GAGGGCGAAGCCAGAATCCGCCACTGCGCCTCTACCGAGACGGGCTGCTTTGTGCTGTGCAAGGG

CAATGCTAAGATCAAGCATAATATGATCTGTGGAGCCTCGGACGAGCGCGGCTACCAGATGCTGA

CCTGCGCCGGCGGGAACAGCCATATGCTGGCCACCGTACATGTGGCTTCCCATGCTCGCAAGCCC

TGGCCCGAGTTCGAGCACAATGTCATGACCAGGTGCAATATGCATCTGGGGTCCCGCCGAGGCAT

GTTCATGCCCTACCAGTGCAACCTGAATTATGTGAAGGTGCTGCTGGAGCCCGATGCCATGTCCA

GAGTGAGCCTGACGGGGGTGTTTGACATGAATGTGGAGGTGTGGAAGATTCTGAGATATGATGAA

TCCAAGACCAGGTGCCGAGCCTGCGAGTGCGGAGGGAAGCATGCCAGGTTCCAGCCCGTGTGTGT

GGATGTGACGGAGGACCTGCGACCCGATCATTTGGTGTTGCCCTGCACCGGGACGGAGTTCGGTT

CCAGCGGGGAAGAATCTGACTAGAGTGAGTAGTGTTCTGGGGCGGGGGAGGACCTGCATGAGGGC

CAGAATAACTGAAATCTGTGCTTTTCTGTGTGTTGCAGCAGCATGAGCGGAAGCGGCTCCTTTGA

GGGAGGGGTATTCAGCCCTTATCTGACGGGGCGTCTCCCCTCCTGGGCGGGAGTGCGTCAGAATG

TGATGGGATCCACGGTGGACGGCCGGCCCGTGCAGCCCGCGAACTCTTCAACCCTGACCTATGCA

ACCCTGAGCTCTTCGTCGTTGGACGCAGCTGCCGCCGCAGCTGCTGCATCTGCCGCCAGCGCCGT

GCGCGGAATGGCCATGGGCGCCGGCTACTACGGCACTCTGGTGGCCAACTCGAGTTCCACCAATA

ATCCCGCCAGCCTGAACGAGGAGAAGCTGTTGCTGCTGATGGCCCAGCTCGAGGCCTTGACCCAG

CGCCTGGGCGAGCTGACCCAGCAGGTGGCTCAGCTGCAGGAGCAGACGCGGGCCGCGGTTGCCAC

GGTGAAATCCAAATAAAAAATGAATCAATAAATAAACGGAGACGGTTGTTGATTTTAACACAGAG

TCTGAATCTTTATTTGATTTTTCGCGCGCGGTAGGCCCTGGACCACCGGTCTCGATCATTGAGCA

CCCGGTGGATCTTTTCCAGGACCCGGTAGAGGTGGGCTTGGATGTTGAGGTACATGGGCATGAGC

CCGTCCCGGGGGTGGAGGTAGCTCCATTGCAGGGCCTCGTGCTCGGGGGTGGTGTTGTAAATCAC

CCAGTCATAGCAGGGGCGCAGGGCATGGTGTTGCACAATATCTTTGAGGAGGAGACTGATGGCCA

CGGGCAGCCCTTTGGTGTAGGTGTTTACAAATCTGTTGAGCTGGGAGGGATGCATGCGGGGGGAG

ATGAGGTGCATCTTGGCCTGGATCTTGAGATTGGCGATGTTACCGCCCAGATCCCGCCTGGGGTT

CATGTTGTGCAGGACCACCAGCACGGTGTATCCGGTGCACTTGGGGAATTTATCATGCAACTTGG

AAGGGAAGGCGTGAAAGAATTTGGCGACGCCTTTGTGCCCGCCCAGGTTTTCCATGCACTCATCC

-continued

ATGATGATGGCGATGGGCCCGTGGGCGGCGGCCTGGGCAAAGACGTTTCGGGGGTCGGACACATC

ATAGTTGTGGTCCTGGGTGAGGTCATCATAGGCCATTTTAATGAATTTGGGGCGGAGGGTGCCGG

ACTGGGGGACAAAGGTACCCTCGATCCCGGGGGCGTAGTTCCCCTCACAGATCTGCATCTCCCAG

GCTTTGAGCTCGGAGGGGGGGATCATGTCCACCTGCGGGGCGATAAAGAACACGGTTTCCGGGGC

GGGGGAGATGAGCTGGGCCGAAAGCAAGTTCCGGAGCAGCTGGGACTTGCCGCAGCCGGTGGGGC

CGTAGATGACCCCGATGACCGGCTGCAGGTGGTAGTTGAGGGAGAGACAGCTGCCGTCCTCCCGG

AGGAGGGGGGCCACCTCGTTCATCATCTCGCGCACGTGCATGTTCTCGCGCACCAGTTCCGCCAG

GAGGCGCTCTCCCCCCAGGGATAGGAGCTCCTGGAGCGAGGCGAAGTTTTTCAGCGGCTTGAGTC

CGTCGGCCATGGGCATTTTGGAGAGGGTTTGTTGCAAGAGTTCCAGGCGGTCCCAGAGCTCGGTG

ATGTGCTCTACGGCATCTCGATCCAGCAGACCTCCTCGTTTCGCGGGTTGGGACGGCTGCGGGAG

TAGGGCACCAGACGATGGGCGTCCAGCGCAGCCAGGGTCCGGTCCTTCCAGGGTCGCAGCGTCCG

CGTCAGGGTGGTCTCCGTCACGGTGAAGGGGTGCGCGCCGGGCTGGGCGCTTGCGAGGGTGCGCT

TCAGGCTCATCCGGCTGGTCGAAAACCGCTCCCGATCGGCGCCCTGCGCGTCGGCCAGGTAGCAA

TTGACCATGAGTTCGTAGTTGAGCGCCTCGGCCGCGTGGCCTTTGGCGCGGAGCTTACCTTTGGA

AGTCTGCCCGCAGGCGGGACAGAGGAGGGACTTGAGGGCGTAGAGCTTGGGGGCGAGGAAGACGG

ACTCGGGGGCGTAGGCGTCCGCGCCGCAGTGGGCGCAGACGGTCTCGCACTCCACGAGCCAGGTG

AGGTCGGGCTGGTCGGGGTCAAAAACCAGTTTCCCGCCGTTCTTTTTGATGCGTTTCTTACCTTT

GGTCTCCATGAGCTCGTGTCCCCGCTGGGTGACAAAGAGGCTGTCCGTGTCCCCGTAGACCGACT

TTATGGGCCGGTCCTCGAGCGGTGTGCCGCGGTCCTCCTCGTAGAGGAACCCCGCCCACTCCGAG

ACGAAAGCCCGGGTCCAGGCCAGCACGAAGGAGGCCACGTGGGACGGGTAGCGGTCGTTGTCCAC

CAGCGGGTCCACCTTTTCCAGGGTATGCAAACACATGTCCCCCTCGTCCACATCCAGGAAGGTGA

TTGGCTTGTAAGTGTAGGCCACGTGACCGGGGGTCCCGGCCGGGGGGGTATAAAAGGGTGCGGGT

CCCTGCTCGTCCTCACTGTCTTCCGGATCGCTGTCCAGGAGCGCCAGCTGTTGGGGTAGGTATTC

CCTCTCGAAGGCGGGCATGACCTCGGCACTCAGGTTGTCAGTTTCTAGAAACGAGGAGGATTTGA

TATTGACGGTGCCGGCGGAGATGCCTTTCAAGAGCCCCTCGTCCATCTGGTCAGAAAAGACGATC

TTTTTGTTGTCGAGCTTGGTGGCGAAGGAGCCGTAGAGGGCGTTGGAGAGGAGCTTGGCGATGGA

GCGCATGGTCTGGTTTTTTTCCTTGTCGGCGCGCTCCTTGGCGGCGATGTTGAGCTGCACGTACT

CGCGCGCCACGCACTTCCATTCGGGGAAGACGGTGGTCAGCTCGTCGGGCACGATTCTGACCTGC

CAGCCCCGATTATGCAGGGTGATGAGGTCCACACTGGTGGCCACCTCGCCGCGCAGGGGCTCATT

AGTCCAGCAGAGGCGTCCGCCCTTGCGCGAGCAGAAGGGGGGCAGGGGGTCCAGCATGACCTCGT

CGGGGGGGTCGGCATCGATGGTGAAGATGCCGGGCAGGAGGTCGGGGTCAAAGTAGCTGATGGAA

GTGGCCAGATCGTCCAGGGCAGCTTGCCATTCGCGCACGGCCAGCGCGCGCTCGTAGGGACTGAG

GGGCGTGCCCCAGGGCATGGGATGGGTAAGCGCGGAGGCGTACATGCCGCAGATGTCGTAGACGT

AGAGGGGCTCCTCGAGGATGCCGATGTAGGTGGGGTAGCAGCGCCCCCCGCGGATGCTGGCGCGC

ACGTAGTCATACAGCTCGTGCGAGGGGGCGAGGAGCCCCGGGCCCAGGTTGGTGCGACTGGGCTT

TTCGGCGCGGTAGACGATCTGGCGGAAAATGGCATGCGAGTTGGAGGAGATGGTGGGCCTTTGGA

AGATGTTGAAGTGGGCGTGGGGCAGTCCGACCGAGTCGCGGATGAAGTGGGCGTAGGAGTCTTGC

AGCTTGGCGACGAGCTCGGCGGTGACTAGGACGTCCAGAGCGCAGTAGTCGAGGGTCTCCTGGAT

GATGTCATACTTGAGCTGTCCCTTTTGTTTCCACAGCTCGCGGTTGAGAAGGAACTCTTCGCGGT

-continued

CCTTCCAGTACTCTTCGAGGGGGAACCCGTCCTGATCTGCACGGTAAGAGCCTAGCATGTAGAAC

TGGTTGACGGCCTTGTAGGCGCAGCAGCCCTTCTCCACGGGGAGGGCGTAGGCCTGGGCGGCCTT

GCGCAGGGAGGTGTGCGTGAGGGCGAAAGTGTCCCTGACCATGACCTTGAGGAACTGGTGCTTGA

AGTCGATATCGTCGCAGCCCCCCTGCTCCCAGAGCTGGAAGTCCGTGCGCTTCTTGTAGGCGGGG

TTGGGCAAAGCGAAAGTAACATCGTTGAAGAGGATCTTGCCCGCGCGGGGCATAAAGTTGCGAGT

GATGCGGAAAGGTTGGGGCACCTCGGCCCGGTTGTTGATGACCTGGGCGGCGAGCACGATCTCGT

CGAAGCCGTTGATGTTGTGGCCCACGATGTAGAGTTCCACGAATCGCGGACGGCCCTTGACGTGG

GGCAGTTTCTTGAGCTCCTCGTAGGTGAGCTCGTCGGGGTCGCTGAGCCCGTGCTGCTCGAGCGC

CCAGTCGGCGAGATGGGGGTTGGCGCGGAGGAAGGAAGTCCAGAGATCCACGGCCAGGGCGGTTT

GCAGACGGTCCCGGTACTGACGGAACTGCTGCCCGACGGCCATTTTTTCGGGGGTGACGCAGTAG

AAGGTGCGGGGGTCCCCGTGCCAGCGATCCCATTTGAGCTGGAGGGCGAGATCGAGGGCGAGCTC

GACGAGCCGGTCGTCCCCGGAGAGTTTCATGACCAGCATGAAGGGGACGAGCTGCTTGCCGAAGG

ACCCCATCCAGGTGTAGGTTTCCACATCGTAGGTGAGGAAGAGCCTTTCGGTGCGAGGATGCGAG

CCGATGGGGAAGAACTGGATCTCCTGCCACCAATTGGAGGAATGGCTGTTGATGTGATGGAAGTA

GAAATGCCGACGGCGCGCCGAACACTCGTGCTTGTGTTTATACAAGCGGCCACAGTGCTCGCAAC

GCTGCACGGGATGCACGTGCTGCACGAGCTGTACCTGAGTTCCTTTGACGAGGAATTTCAGTGGG

AAGTGGAGTCGTGGCGCCTGCATCTCGTGCTGTACTACGTCGTGGTGGTCGGCCTGGCCCTCTTC

TGCCTCGATGGTGGTCATGCTGACGAGCCCGCGCGGGAGGCAGGTCCAGACCTCGGCGCGAGCGG

GTCGGAGAGCGAGGACGAGGGCGCGCAGGCCGGAGCTGTCCAGGGTCCTGAGACGCTGCGGAGTC

AGGTCAGTGGGCAGCGGCGGCGCGCGGTTGACTTGCAGGAGTTTTTCCAGGGCGCGCGGGAGGTC

CAGATGGTACTTGATCTCCACCGCGCCATTGGTGGCGACGTCGATGGCTTGCAGGGTCCCGTGCC

CCTGGGGTGTGACCACCGTCCCCCGTTTCTTCTTGGGCGGCTGGGGCGACGGGGGCGGTGCCTCT

TCCATGGTTAGAAGCGGCGGCGAGGACGCGCGCCGGGCGGCAGGGGCGGCTCGGGGCCCGGAGGC

AGGGGCGGCAGGGGCACGTCGGCGCCGCGCGCGGGTAGGTTCTGGTACTGCGCCCGGAGAAGACT

GGCGTGAGCGACGACGCGACGGTTGACGTCCTGGATCTGACGCCTCTGGGTGAAGGCCACGGGAC

CCGTGAGTTTGAACCTGAAAGAGAGTTCGACAGAATCAATCTCGGTATCGTTGACGGCGGCCTGC

CGCAGGATCTCTTGCACGTCGCCCGAGTTGTCCTGGTAGGCGATCTCGGTCATGAACTGCTCGAT

CTCCTCCTCTTGAAGGTCTCCGCGGCCGGCGCGCTCCACGGTGGCCGCGAGGTCGTTGGAGATGC

GGCCCATGAGCTGCGAGAAGGCGTTCATGCCCGCCTCGTTCCAGACGCGGCTGTAGACCACGACG

CCCTCGGGATCGCgGGCGCGCATGACCACCTGGGCGAGGTTGAGCTCCACGTGGCGCGTGAAGAC

CGCGTAGTTGCAGAGGCGCTGGTAGAGGTAGTTGAGCGTGGTGGCGATGTGCTCGGTGACGAAGA

AATACATGATCCAGCGGCGGAGCGGCATCTCGCTGACGTCGCCCAGCGCCTCCAAACGTTCCATG

GCCTCGTAAAAGTCCACGGCGAAGTTGAAAAACTGGGAGTTGCGCGCCGAGACGGTCAACTCCTC

CTCCAGAAGACGGATGAGCTCGGCGATGGTGGCGCGCACCTCGCGCTCGAAGGCCCCCGGGAGTT

CCTCCACTTCCTCTTCTTCCTCCTCCACTAACATCTCTTCTACTTCCTCCTCAGGCGGCAGTGGT

GGCGGGGGAGGGGGCCTGCGTCGCCGGCGGCGCACGGGCAGACGGTCGATGAAGCGCTCGATGGT

CTCGCCGCGCCGGCGTCGCATGGTCTCGGTGACGGCGCGCCCGTCCTCGCGGGGCCGCAGCGTGA

AGACGCCGCCGCGCATCTCCAGGTGGCCGGGGGGGTCCCCGTTGGGCAGGGAGAGGGCGCTGACG

ATGCATCTTATCAATTGCCCCGTAGGGACTCCGCGCAAGGACCTGAGCGTCTCGAGATCCACGGG

ATCTGAAAACCGCTGAACGAAGGCTTCGAGCCAGTCGCAGTCGCAAGGTAGGCTGAGCACGGTTT

-continued

CTTCTGGCGGGTCATGTTGGTTGGGAGCGGGGGGGGCGATGCTGCTGGTGATGAAGTTGAAATAG

GCGGTTCTGAGACGGCGGATGGTGGCGAGGAGCACCAGGTCTTTGGGCCCGGCTTGCTGGATGCG

CAGACGGTCGGCCATGCCCCAGGCGTGGTCCTGACACCTGGCCAGGTCCTTGTAGTAGTCCTGCA

TGAGCCGCTCCACGGGCACCTCCTCCTCGCCCGCGCGGCCGTGCATGCGCGTGAGCCCGAAGCCG

CGCTGGGGCTGGACGAGCGCCAGGTCGGCGACGACGCGCTCGGCGAGGATGGCTTGCTGGATCTG

GGTGAGGGTGGTCTGGAAGTCATCAAAGTCGACGAAGCGGTGGTAGGCTCCGGTGTTGATGGTGT

AGGAGCAGTTGGCCATGACGGACCAGTTGACGGTCTGGTGGCCCGGACGCACGAGCTCGTGGTAC

TTGAGGCGCGAGTAGGCGCGCGTGTCGAAGATGTAGTCGTTGCAGGTGCGCACCAGGTACTGGTA

GCCGATGAGGAAGTGCGGCGGCGGCTGGCGGTAGAGCGGCCATCGCTCGGTGGCGGGGGCGCCGG

GCGCGAGGTCCTCGAGCATGGTGCGGTGGTAGCCGTAGATGTACCTGGACATCCAGGTGATGCCG

GCGGCGGTGGTGGAGGCGCGCGGGAACTCGCGGACGCGGTTCCAGATGTTGCGCAGCGGCAGGAA

GTAGTTCATGGTGGGCACGGTCTGGCCCGTGAGGCGCGCGCAGTCGTGGATGCTCTATACGGGCA

AAAACGAAAGCGGTCAGCGGCTCGACTCCGTGGCCTGGAGGCTAAGCGAACGGGTTGGGCTGCGC

GTGTACCCCGGTTCGAATCTCGAATCAGGCTGGAGCCGCAGCTAACGTGGTATTGGCACTCCCGT

CTCGACCCAAGCCTGCACCAACCCTCCAGGATACGGAGGCGGGTCGTTTTGCAACTTTTTTTTGG

AGGCCGGATGAGACTAGTAAGCGCGGAAAGCGGCCGACCGCGATGGCTCGCTGCCGTAGTCTGGA

GAAGAATCGCCAGGGTTGCGTTGCGGTGTGCCCCGGTTCGAGGCCGGCCGGATTCCGCGGCTAAC

GAGGGCGTGGCTGCCCCGTCGTTTCCAAGACCCCATAGCCAGCCGACTTCTCCAGTTACGGAGCG

AGCCCCTCTTTTGTTTTGTTTGTTTTTGCCAGATGCATCCCGTACTGCGGCAGATGCGCCCCCAC

CACCCTCCACCGCAACAACAGCCCCCTCCACAGCCGGCGCTTCTGCCCCCGCCCCAGCAGCAACT

TCCAGCCACGACCGCCGCGGCCGCCGTGAGCGGGGCTGGACAGAGTTATGATCACCAGCTGGCCT

TGGAAGAGGGCGAGGGGCTGGCGCGCCTGGGGGCGTCGTCGCCGGAGCGGCACCCGCGCGTGCAG

ATGAAAAGGGACGCTCGCGAGGCCTACGTGCCCAAGCAGAACCTGTTCAGAGACAGGAGCGGCGA

GGAGCCCGAGGAGATGCGCGCGGCCCGGTTCCACGCGGGGGGGGAGCTGCGGCGCGGCCTGGACC

GAAAGAGGGTGCTGAGGGACGAGGATTTCGAGGCGGACGAGCTGACGGGGATCAGCCCCGCGCGC

GCGCACGTGGCCGCGGCCAACCTGGTCACGGCGTACGAGCAGACCGTGAAGGAGGAGAGCAACTT

CCAAAAATCCTTCAACAACCACGTGCGCACCCTGATCGCGCGCGAGGAGGTGACCCTGGGCCTGA

TGCACCTGTGGGACCTGCTGGAGGCCATCGTGCAGAACCCCACCAGCAAGCCGCTGACGGCGCAG

CTGTTCCTGGTGGTGCAGCATAGTCGGGACAACGAAGCGTTCAGGGAGGCGCTGCTGAATATCAC

CGAGCCCGAGGGCCGCTGGCTCCTGGACCTGGTGAACATTCTGCAGAGCATCGTGGTGCAGGAGC

GCGGGCTGCCGCTGTCCGAGAAGCTGGCGGCCATCAACTTCTCGGTGCTGAGTTTGGGCAAGTAC

TACGCTAGGAAGATCTACAAGACCCCGTACGTGCCCATAGACAAGGAGGTGAAGATCGACGGGTT

TTACATGCGCATGACCCTGAAAGTGCTGACCCTGAGCGACGATCTGGGGGTGTACCGCAACGACA

GGATGCACCGTGCGGTGAGCGCCAGCAGGCGGCGCGAGCTGAGCGACCAGGAGCTGATGCATAGT

CTGCAGCGGGCCCTGACCGGGGCCGGGACCGAGGGGGAGAGCTACTTTGACATGGGCGCGGACCT

GCACTGGCAGCCCAGCCGCCGGGCCTTGGAGGCGGCGGCAGGACCCTACGTAGAAGAGGTGGACG

ATGAGGTGGACGAGGAGGGCGAGTACCTGGAAGACTGATGGCGCGACCGTATTTTTGCTAGATGC

AACAACAACAGCCACCTCCTGATCCCGCGATGCGGGCGGCGCTGCAGAGCCAGCCGTCCGGCATT

AACTCCTCGGACGATTGGACCCAGGCCATGCAACGCATCATGGCGCTGACGACCCGCAACCCCGA

-continued

AGCCTTTAGACAGCAGCCCCAGGCCAACCGGCTCTCGGCCATCCTGGAGGCCGTGGTGCCCTCGC

GCTCCAACCCCACGCACGAGAAGGTCCTGGCCATCGTGAACGCGCTGGTGGAGAACAAGGCCATC

CGCGGCGACGAGGCCGGCCTGGTGTACAACGCGCTGCTGGAGCGCGTGGCCCGCTACAACAGCAC

CAACGTGCAGACCAACCTGGACCGCATGGTGACCGACGTGCGCGAGGCCGTGGCCCAGCGCGAGC

GGTTCCACCGCGAGTCCAACCTGGGATCCATGGTGGCGCTGAACGCCTTCCTCAGCACCCAGCCC

GCCAACGTGCCCCGGGGCCAGGAGGACTACACCAACTTCATCAGCGCCCTGCGCCTGATGGTGAC

CGAGGTGCCCCAGAGCGAGGTGTACCAGTCCGGGCCGGACTACTTCTTCCAGACCAGTCGCCAGG

GCTTGCAGACCGTGAACCTGAGCCAGGCTTTCAAGAACTTGCAGGGCCTGTGGGGCGTGCAGGCC

CCGGTCGGGGACCGCGCGACGGTGTCGAGCCTGCTGACGCCGAACTCGCGCCTGCTGCTGCTGCT

GGTGGCCCCCTTCACGGACAGCGGCAGCATCAACCGCAACTCGTACCTGGGCTACCTGATTAACC

TGTACCGCGAGGCCATCGGCCAGGCGCACGTGGACGAGCAGACCTACCAGGAGATCACCCACGTG

AGCCGCGCCCTGGGCCAGGACGACCCGGGCAACCTGGAAGCCACCCTGAACTTTTTGCTGACCAA

CCGGTCGCAGAAGATCCCGCCCCAGTACGCGCTCAGCACCGAGGAGGAGCGCATCCTGCGTTACG

TGCAGCAGAGCGTGGGCCTGTTCCTGATGCAGGAGGGGGCCACCCCCAGCGCCGCGCTCGACATG

ACCGCGCGCAACATGGAGCCCAGCATGTACGCCAGCAACCGCCCGTTCATCAATAAACTGATGGA

CTACTTGCATCGGGCGGCCGCCATGAACTCTGACTATTTCACCAACGCCATCCTGAATCCCCACT

GGCTCCCGCCGCCGGGGTTCTACACGGGCGAGTACGACATGCCCGACCCCAATGACGGGTTCCTG

TGGGACGATGTGGACAGCAGCGTGTTCTCCCCCCGACCGGGTGCTAACGAGCGCCCCTTGTGGAA

GAAGGAAGGCAGCGACCGACGCCCGTCCTCGGCGCTGTCCGGCCGCGAGGGTGCTGCCGCGGCGG

TGCCCGAGGCCGCCAGTCCTTTCCCGAGCTTGCCCTTCTCGCTGAACAGTATCCGCAGCAGCGAG

CTGGGCAGGATCACGCGCCCGCGCTTGCTGGGCGAAGAGGAGTACTTGAATGACTCGCTGTTGAG

ACCCGAGCGGGAGAAGAACTTCCCCAATAACGGGATAGAAAGCCTGGTGGACAAGATGAGCCGCT

GGAAGACGTATGCGCAGGAGCACAGGGACGATCCCCGGGCGTCGCAGGGGGCCACGAGCCGGGGC

AGCGCCGCCCGTAAACGCCGGTGGCACGACAGGCAGCGGGGACAGATGTGGGACGATGAGGACTC

CGCCGACGACAGCAGCGTGTTGGACTTGGGTGGGAGTGGTAACCCGTTCGCTCACCTGCGCCCCC

GTATCGGGCGCATGATGTAAGAGAAACCGAAAATAAATGATACTCACCAAGGCCATGGCGACCAG

CGTGCGTTCGTTTCTTCTCTGTTGTTGTTGTATCTAGTATGATGAGGCGTGCGTACCCGGAGGGT

CCTCCTCCCTCGTACGAGAGCGTGATGCAGCAGGCGATGGCGGCGGCGGCGATGCAGCCCCCGCT

GGAGGCTCCTTACGTGCCCCCGCGGTACCTGGCGCCTACGGAGGGGCGGAACAGCATTCGTTACT

CGGAGCTGGCACCCTTGTACGATACCACCCGGTTGTACCTGGTGGACAACAAGTCGGCGGACATC

GCCTCGCTGAACTACCAGAACGACCACAGCAACTTCCTGACCACCGTGGTGCAGAACAATGACTT

CACCCCCACGGAGGCCAGCACCCAGACCATCAACTTTGACGAGCGCTCGCGGTGGGGCGGCCAGC

TGAAAACCATCATGCACACCAACATGCCCAACGTGAACGAGTTCATGTACAGCAACAAGTTCAAG

GCGCGGGTGATGGTCTCCCGCAAGACCCCCAATGGGGTGACAGTGACAGAGGATTATGATGGTAG

TCAGGATGAGCTGAAGTATGAATGGGTGGAATTTGAGCTGCCCGAAGGCAACTTCTCGGTGACCA

TGACCATCGACCTGATGAACAACGCCATCATCGACAATTACTTGGCGGTGGGGCGGCAGAACGGG

GTGCTGGAGAGCGACATCGGCGTGAAGTTCGACACTAGGAACTTCAGGCTGGGCTGGGACCCCGT

GACCGAGCTGGTCATGCCCGGGGTGTACACCAACGAGGCTTTCCATCCCGATATTGTCTTGCTGC

CCGGCTGCGGGGTGGACTTCACCGAGAGCCGCCTCAGCAACCTGCTGGGCATTCGCAAGAGGCAG

CCCTTCCAGGAAGGCTTCCAGATCATGTACGAGGATCTGGAGGGGGGCAACATCCCCGCGCTCCT

-continued

GGATGTCGACGCCTATGAGAAAAGCAAGGAGGATGCAGCAGCTGAAGCAACTGCAGCCGTAGCTA

CCGCCTCTACCGAGGTCAGGGGCGATAATTTTGCAAGCGCCGCAGCAGTGGCAGCGGCCGAGGCG

GCTGAAACCGAAAGTAAGATAGTCATTCAGCCGGTGGAGAAGGATAGCAAGAACAGGAGCTACAA

CGTACTACCGGACAAGATAAACACCGCCTACCGCAGCTGGTACCTAGCCTACAACTATGGCGACC

CCGAGAAGGGCGTGCGCTCCTGGACGCTGCTCACCACCTCGGACGTCACCTGCGGCGTGGAGCAA

GTCTACTGGTCGCTGCCCGACATGATGCAAGACCCGGTCACCTTCCGCTCCACGCGTCAAGTTAG

CAACTACCCGGTGGTGGGCGCCGAGCTCCTGCCCGTCTACTCCAAGAGCTTCTTCAACGAGCAGG

CCGTCTACTCGCAGCAGCTGCGCGCCTTCACCTCGCTTACGCACGTCTTCAACCGCTTCCCCGAG

AACCAGATCCTCGTCCGCCCGCCCGCGCCCACCATTACCACCGTCAGTGAAAACGTTCCTGCTCT

CACAGATCACGGGACCCTGCCGCTGCGCAGCAGTATCCGGGGAGTCCAGCGCGTGACCGTTACTG

ACGCCAGACGCCGCACCTGCCCCTACGTCTACAAGGCCCTGGGCATAGTCGCGCCGCGCGTCCTC

TCGAGCCGCACCTTCTAAATGTCCATTCTCATCTCGCCCAGTAATAACACCGGTTGGGGCCTGCG

CGCGCCCAGCAAGATGTACGGAGGCGCTCGCCAACGCTCCACGCAACACCCCGTGCGCGTGCGCG

GGCACTTCCGCGCTCCCTGGGGCGCCCTCAAGGGCCGCGTGCGGTCGCGCACCACCGTCGACGAC

GTGATCGACCAGGTGGTGGCCGACGCGCGCAACTACACCCCCGCCGCCGCGCCCGTCTCCACCGT

GGACGCCGTCATCGACAGCGTGGTGGCcGACGCGCGCCGGTACGCCCGCGCCAAGAGCCGGCGGC

GGCGCATCGCCCGGCGGCACCGGAGCACCCCCGCCATGCGCGCGGCGCGAGCCTTGCTGCGCAGG

GCCAGGCGCACGGGACGCAGGGCCATGCTCAGGGCGGCCAGACGCGCGGCTTCAGGCGCCAGCGC

CGGCAGGACCCGGAGACGCGCGGCCACGGCGGCGGCAGCGGCCATCGCCAGCATGTCCCGCCCGC

GGCGAGGGAACGTGTACTGGGTGCGCGACGCCGCCACCGGTGTGCGCGTGCCCGTGCGCACCCGC

CCCCCTCGCACTTGAAGATGTTCACTTCGCGATGTTGATGTGTCCCAGCGGCGAGGAGGATGTCC

AAGCGCAAATTCAAGGAAGAGATGCTCCAGGTCATCGCGCCTGAGATCTACGGCCCTGCGGTGGT

GAAGGAGGAAAGAAAGCCCCGCAAAATCAAGCGGGTCAAAAAGGACAAAAAGGAAGAAGAAAGTG

ATGTGGACGGATTGGTGGAGTTTGTGCGCGAGTTCGCCCCCCGGCGGCGCGTGCAGTGGCGCGGG

CGGAAGGTGCAACCGGTGCTGAGACCCGGCACCACCGTGGTCTTCACGCCCGGCGAGCGCTCCGG

CACCGCTTCCAAGCGCTCCTACGACGAGGTGTACGGGGATGATGATATTCTGGAGCAGGCGGCCG

AGCGCCTGGGCGAGTTTGCTTACGGCAAGCGCAGCCGTTCCGCACCGAAGGAAGAGGCGGTGTCC

ATCCCGCTGGACCACGGCAACCCCACGCCGAGCCTCAAGCCCGTGACCTTGCAGCAGGTGCTGCC

GACCGCGGCGCCGCGCCGGGGGTTCAAGCGCGAGGGCGAGGATCTGTACCCCACCATGCAGCTGA

TGGTGCCCAAGCGCCAGAAGCTGGAAGACGTGCTGGAGACCATGAAGGTGGACCCGGACGTGCAG

CCCGAGGTCAAGGTGCGGCCCATCAAGCAGGTGGCCCCGGGCCTGGGCGTGCAGACCGTGGACAT

CAAGATTCCCACGGAGCCCATGGAAACGCAGACCGAGCCCATGATCAAGCCCAGCACCAGCACCA

TGGAGGTGCAGACGGATCCCTGGATGCCATCGGCTCCTAGTCGAAGACCCCGGCGCAAGTACGGC

GCGGCCAGCCTGCTGATGCCCAACTACGCGCTGCATCCTTCCATCATCCCCACGCCGGGCTACCG

CGGCACGCGCTTCTACCGCGGTCATACCAGCAGCCGCCGCCGCAAGACCACCACTCGCCGCCGCC

GTCGCCGCACCGCCGCTGCAACCACCCCTGCCGCCCTGGTGCGGAGAGTGTACCGCCGCGGCCGC

GCACCTCTGACCCTGCCGCGCGCGCGCTACCACCCGAGCATCGCCATTTAAACTTTCGCCtGCTT

TGCAGATCAATGGCCCTCACATGCCGCCTTCGCGTTCCCATTACGGGCTACCGAGGAAGAAAACC

GCGCCGTAGAAGGCTGGCGGGGAACGGGATGCGTCGCCACCACCACCGGCGGCGGCGCGCCATCA

-continued

GCAAGCGGTTGGGGGGAGGCTTCCTGCCCGCGCTGATCCCCATCATCGCCGCGGCGATCGGGGCG

ATCCCCGGCATTGCTTCCGTGGCGGTGCAGGCCTCTCAGCGCCACTGAGACACACTTGGAAACAT

CTTGTAATAAACCaATGGACTCTGACGCTCCTGGTCCTGTGATGTGTTTTCGTAGACAGATGGAA

GACATCAATTTTTCGTCCCTGGCTCCGCGACACGGCACGCGGCCGTTCATGGGCACCTGGAGCGA

CATCGGCACCAGCCAACTGAACGGGGGCGCCTTCAATTGGAGCAGTCTCTGGAGCGGGCTTAAGA

ATTTCGGGTCCACGCTTAAAACCTATGGCAGCAAGGCGTGGAACAGCACCACAGGGCAGGCGCTG

AGGGATAAGCTGAAAGAGCAGAACTTCCAGCAGAAGGTGGTCGATGGGCTCGCCTCGGGCATCAA

CGGGGTGGTGGACCTGGCCAACCAGGCCGTGCAGCGGCAGATCAACAGCCGCCTGGACCCGGTGC

CGCCCGCCGGCTCCGTGGAGATGCCGCAGGTGGAGGAGGAGCTGCCTCCCCTGGACAAGCGGGGC

GAGAAGCGACCCCGCCCCGATGCGGAGGAGACGCTGCTGACGCACACGGACGAGCCGCCCCCGTA

CGAGGAGGCGGTGAAACTGGGTCTGCCCACCACGCGGCCCATCGCGCCCCTGGCCACCGGGGTGC

TGAAACCCGAAAAGCCCGCGACCCTGGACTTGCCTCCTCCCCAGCCTTCCCGCCCCTCTACAGTG

GCTAAGCCCCTGCCGCCGGTGGCCGTGGCCCGCGCGCGACCCGGGGGCACCGCCCGCCCTCATGC

GAACTGGCAGAGCACTCTGAACAGCATCGTGGGTCTGGGAGTGCAGAGTGTGAAGCGCCGCCGCT

GCTATTAAACCTACCGTAGCGCTTAACTTGCTTGTCTGTGTGTGTATGTATTATGTCGCCGCCGC

CGCTGTCCACCAGAAGGAGGAGTGAAGAGGCGCGTCGCCGAGTTGCAAGATGGCCACCCCATCGA

TGCTGCCCCAGTGGGCGTACATGCACATCGCCGGACAGGACGCTTCGGAGTACCTGAGTCCGGGT

CTGGTGCAGTTTGCCCGCGCCACAGACACCTACTTCAGTCTGGGGAACAAGTTTAGGAACCCCAC

GGTGGCGCCCACGCACGATGTGACCACCGACCGCAGCCAGCGGCTGACGCTGCGCTTCGTGCCCG

TGGACCGCGAGGACAACACCTACTCGTACAAAGTGCGCTACACGCTGGCCGTGGGCGACAACCGC

GTGCTGGACATGGCCAGCACCTACTTTGACATCCGCGGCGTGCTGGATCGGGGCCCTAGCTTCAA

ACCCTACTCCGGCACCGCCTACAACAGTCTGGCCCCCAAGGGAGCACCCAACACTTGTCAGTGGA

CATATAAAGCCGATGGTGAAACTGCCACAGAAAAAACCTATACATATGGAAATGCACCCGTGCAG

GGCATTAACATCACAAAAGATGGTATTCAACTTGGAACTGACACCGATGATCAGCCAATCTACGC

AGATAAAACCTATCAGCCTGAACCTCAAGTGGGTGATGCTGAATGGCATGACATCACTGGTACTG

ATGAAAAGTATGGAGGCAGAGCTCTTAAGCCTGATACCAAAATGAAGCCTTGTTATGGTTCTTTT

GCCAAGCCTACTAATAAAGAAGGAGGTCAGGCAAATGTGAAAACAGGAACAGGCACTACTAAAGA

ATATGACATAGACATGGCTTTCTTTGACAACAGAAGTGCGGCTGCTGCTGGCCTAGCTCCAGAAA

TTGTTTTGTATACTGAAAATGTGGATTTGGAAACTCCAGATACCCATATTGTATACAAAGCAGGC

ACAGATGACAGCAGCTCTTCTATTAATTTGGGTCAGCAAGCCATGCCCAACAGACCTAACTACAT

TGGTTTCAGAGACAACTTTATCGGGCTCATGTACTACAACAGCACTGGCAATATGGGGGTGCTGG

CCGGTCAGGCTTCTCAGCTGAATGCTGTGGTTGACTTGCAAGACAGAAACACCGAGCTGTCCTAC

CAGCTCTTGCTTGACTCTCTGGGTGACAGAACCCGGTATTTCAGTATGTGGAATCAGGCGGTGGA

CAGCTATGATCCTGATGTGCGCATTATTGAAAATCATGGTGTGGAGGATGAACTTCCCAACTATT

GTTTCCCTCTGGATGCTGTTGGCAGAACAGATACTTATCAGGGAATTAAGGCTAATGGAACTGAT

CAAACCACATGGACCAAAGATGACAGTGTCAATGATGCTAATGAGATAGGCAAGGGTAATCCATT

CGCCATGGAAATCAACATCCAAGCCAACCTGTGGAGGAACTTCCTCTACGCCAACGTGGCCCTGT

ACCTGCCCGACTCTTACAAGTACACGCCGGCCAATGTTACCCTGCCCACCAACACCAACACCTAC

GATTACATGAACGGCCGGGTGGTGGCGCCCTCGCTGGTGGACTCCTACATCAACATCGGGGCGCG

CTGGTCGCTGGATCCCATGGACAACGTGAACCCCTTCAACCACCACCGCAATGCGGGGCTGCGCT

-continued

ACCGCTCCATGCTCCTGGGCAACGGGCGCTACGTGCCCTTCCACATCCAGGTGCCCCAGAAATTT

TTCGCCATCAAGAGCCTCCTGCTCCTGCCCGGGTCCTACACCTACGAGTGGAACTTCCGCAAGGA

CGTCAACATGATCCTGCAGAGCTCCCTCGGCAACGACCTGCGCACGGACGGGGCCTCCATCTCCT

TCACCAGCATCAACCTCTACGCCACCTTCTTCCCCATGGCGCACAACACGGCCTCCACGCTCGAG

GCCATGCTGCGCAACGACACCAACGACCAGTCCTTCAACGACTACCTCTCGGCGGCCAACATGCT

CTACCCCATCCCGGCCAACGCCACCAACGTGCCCATCTCCATCCCCTCGCGCAACTGGGCCGCCT

TCCGCGGCTGGTCCTTCACGCGTCTCAAGACCAAGGAGACGCCCTCGCTGGGCTCCGGGTTCGAC

CCCTACTTCGTCTACTCGGGCTCCATCCCCTACCTCGACGGCACCTTCTACCTCAACCACACCTT

CAAGAAGGTCTCCATCACCTTCGACTCCTCCGTCAGCTGGCCCGGCAACGACCGGCTCCTGACGC

CCAACGAGTTCGAAATCAAGCGCACCGTCGACGGCGAGGGCTACAACGTGGCCCAGTGCAACATG

ACCAAGGACTGGTTCCTGGTCCAGATGCTGGCCCACTACAACATCGGCTACCAGGGCTTCTACGT

GCCCGAGGGCTACAAGGACCGCATGTACTCCTTCTTCCGCAACTTCCAGCCCATGAGCCGCCAGG

TGGTGGACGAGGTCAACTACAAGGACTACCAGGCCGTCACCCTGGCCTACCAGCACAACAACTCG

GGCTTCGTCGGCTACCTCGCGCCCACCATGCGCCAGGGCCAGCCCTACCCCGCCAACTACCCCTA

CCCGCTCATCGGCAAGAGCGCCGTCACCAGCGTCACCCAGAAAAAGTTCCTCTGCGACAGGGTCA

TGTGGCGCATCCCCTTCTCCAGCAACTTCATGTCCATGGGCGCGCTCACCGACCTCGGCCAGAAC

ATGCTCTATGCCAACTCCGCCCACGCGCTAGACATGAATTTCGAAGTCGACCCCATGGATGAGTC

CACCCTTCTCTATGTTGTCTTCGAAGTCTTCGACGTCGTCCGAGTGCACCAGCCCCACCGCGGCG

TCATCGAGGCCGTCTACCTGCGCACCCCCTTCTCGGCCGGTAACGCCACCACCTAAGCTCTTGCT

TCTTGCAAGCCATGGCCGCGGGCTCCGGCGAGCAGGAGCTCAGGGCCATCATCCGCGACCTGGGC

TGCGGGCCCTACTTCCTGGGCACCTTCGATAAGCGCTTCCCGGGATTCATGGCCCCGCACAAGCT

GGCCTGCGCCATCGTCAACACGGCCGGCCGCGAGACCGGGGGCGAGCACTGGCTGGCCTTCGCCT

GGAACCCGCGCTCGAACACCTGCTACCTCTTCGACCCCTTCGGGTTCTCGGACGAGCGCCTCAAG

CAGATCTACCAGTTCGAGTACGAGGGCCTGCTGCGCCGCAGCGCCCTGGCCACCGAGGACCGCTG

CGTCACCCTGGAAAAGTCCACCCAGACCGTGCAGGGTCCGCGCTCGGCCGCCTGCGGGCTCTTCT

GCTGCATGTTCCTGCACGCCTTCGTGCACTGGCCCGACCGCCCCATGGACAAGAACCCCACCATG

AACTTGCTGACGGGGGTGCCCAACGGCATGCTCCAGTCGCCCCAGGTGGAACCCACCCTGCGCCG

CAACCAGGAGGCGCTCTACCGCTTCCTCAACTCCCACTCCGCCTACTTTCGCTCCCACCGCGCGC

GCATCGAGAAGGCCACCGCCTTCGACCGCATGAATCAAGACATGTAAACCGTGTGTGTATGTTAA

ATGTCTTTAATAAACAGCACTTTCATGTTACACATGCATCTGAGATGATTTATTTAGAAATCGAA

AGGGTTCTGCCGGGTCTCGGCATGGCCCGCGGGCAGGGACACGTTGCGGAACTGGTACTTGGCCA

GCCACTTGAACTCGGGGATCAGCAGTTTGGGCAGCGGGGTGTCGGGGAAGGAGTCGGTCCACAGC

TTCCGCGTCAGTTGCAGGGCGCCCAGCAGGTCGGGCGCGGAGATCTTGAAATCGCAGTTGGGACC

CGCGTTCTGCGCGCGGGAGTTGCGGTACACGGGGTTGCAGCACTGGAACACCATCAGGGCCGGGT

GCTTCACGCTCGCCAGCACCGTCGCGTCGGTGATGCTCTCCACGTCGAGGTCCTCGGCGTTGGCC

ATCCCGAAGGGGGTCATCTTGCAGGTCTGCCTTCCCATGGTGGGCACGCACCCGGGCTTGTGGTT

GCAATCGCAGTGCAGGGGGATCAGCATCATCTGGGCCTGGTCGGCGTTCATCCCCGGGTACATGG

CCTTCATGAAAGCCTCCAATTGCCTGAACGCCTGCTGGGCCTTGGCTCCCTCGGTGAAGAAGACC

CCGCAGGACTTGCTAGAGAACTGGTTGGTGGCGCACCCGGCGTCGTGCACGCAGCAGCGCGCGTC

-continued

GTTGTTGGCCAGCTGCACCACGCTGCGCCCCCAGCGGTTCTGGGTGATCTTGGCCCGGTCGGGGT

TCTCCTTCAGCGCGCGCTGCCCGTTCTCGCTCGCCACATCCATCTCGATCATGTGCTCCTTCTGG

ATCATGGTGGTCCCGTGCAGGCACCGCAGCTTGCCCTCGGCCTCGGTGCACCCGTGCAGCCACAG

CGCGCACCCGGTGCACTCCCAGTTCTTGTGGGCGATCTGGGAATGCGCGTGCACGAAGCCCTGCA

GGAAGCGGCCCATCATGGTGGTCAGGGTCTTGTTGCTAGTGAAGGTCAGCGGAATGCCGCGGTGC

TCCTCGTTGATGTACAGGTGGCAGATGCGGCGGTACACCTCGCCCTGCTCGGGCATCAGCTGGAA

GTTGGCTTTCAGGTCGGTCTCCACGCGGTAGCGGTCCATCAGCATAGTCATGATTTCCATACCCT

TCTCCCAGGCCGAGACGATGGGCAGGCTCATAGGGTTCTTCACCATCATCTTAGCGCTAGCAGCC

GCGGCCAGGGGGTCGCTCTCGTCCAGGGTCTCAAAGCTCCGCTTGCCGTCCTTCTCGGTGATCCG

CACCGGGGGGTAGCTGAAGCCCACGGCCGCCAGCTCCTCCTCGGCCTGTCTTTCGTCCTCGCTGT

CCTGGCTGACGTCCTGCAGGACCACATGCTTGGTCTTGCGGGGTTTCTTCTTGGGCGGCAGCGGC

GGCGGAGATGTTGGAGATGGCGAGGGGGAGCGCGAGTTCTCGCTCACCACTACTATCTCTTCCTC

TTCTTGGTCCGAGGCCACGCGGCGGTAGGTATGTCTCTTCGGGGGCAGAGGCGGAGGCGACGGGC

TCTCGCCGCCGCGACTTGGCGGATGGCTGGCAGAGCCCCTTCCGCGTTCGGGGGTGCGCTCCCGG

CGGCGCTCTGACTGACTTCCTCCGCGGCCGGCCATTGTGTTCTCCTAGGGAGGAACAACAAGCAT

GGAGACTCAGCCATCGCCAACCTCGCCATCTGCCCCCACCGCCGACGAGAAGCAGCAGCAGCAGA

ATGAAAGCTTAACCGCCCCGCCGCCCAGCCCCGCCACCTCCGACGCGGCCGTCCCAGACATGCAA

GAGATGGAGGAATCCATCGAGATTGACCTGGGCTATGTGACGCCCGCGGAGCACGAGGAGGAGCT

GGCAGTGCGCTTTTCACAAGAAGAGATACACCAAGAACAGCCAGAGCAGGAAGCAGAGAATGAGC

AGAGTCAGGCTGGGCTCGAGCATGACGGCGACTACCTCCACCTGAGCGGGGGGGAGGACGCGCTC

ATCAAGCATCTGGCCCGGCAGGCCACCATCGTCAAGGATGCGCTGCTCGACCGCACCGAGGTGCC

CCTCAGCGTGGAGGAGCTCAGCCGCGCCTACGAGTTGAACCTCTTCTCGCCGCGCGTGCCCCCCA

AGCGCCAGCCCAATGGCACCTGCGAGCCCAACCCGCGCCTCAACTTCTACCCGGTCTTCGCGGTG

CCCGAGGCCCTGGCCACCTACCACATCTTTTTCAAGAACCAAAAGATCCCCGTCTCCTGCCGCGC

CAACCGCACCCGCGCCGACGCCCTTTTCAACCTGGGTCCCGGCGCCCGCCTACCTGATATCGCCT

CCTTGGAAGAGGTTCCCAAGATCTTCGAGGGTCTGGGCAGCGACGAGACTCGGGCCGCGAACGCT

CTGCAAGGAGAAGGAGGAGAGCATGAGCACCACAGCGCCCTGGTCGAGTTGGAAGGCGACAACGC

GCGGCTGGCGGTGCTCAAACGCACGGTCGAGCTGACCCATTTCGCCTACCCGGCTCTGAACCTGC

CCCCCAAAGTCATGAGCGCGGTCATGGACCAGGTGCTCATCAAGCGCGCGTCGCCCATCTCCGAG

GACGAGGGCATGCAAGACTCCGAGGAGGGCAAGCCCGTGGTCAGCGACGAGCAGCTGGCCCGGTG

GCTGGGTCCTAATGCTAGTCCCCAGAGTTTGGAAGAGCGGCGCAAACTCATGATGGCCGTGGTCC

TGGTGACCGTGGAGCTGGAGTGCCTGCGCCGCTTCTTCGCCGACGCGGAGACCCTGCGCAAGGTC

GAGGAGAACCTGCACTACCTCTTCAGGCACGGGTTCGTGCGCCAGGCCTGCAAGATCTCCAACGT

GGAGCTGACCAACCTGGTCTCCTACATGGGCATCTTGCACGAGAACCGCCTGGGGCAGAACGTGC

TGCACACCACCCTGCGCGGGGAGGCCCGGCGCGACTACATCCGCGACTGCGTCTACCTCTACCTC

TGCCACACCTGGCAGACGGGCATGGGCGTGTGGCAGCAGTGTCTGGAGGAGCAGAACCTGAAAGA

GCTCTGCAAGCTCCTGCAGAAGAACCTCAAGGGTCTGTGGACCGGGTTCGACGAGCGCACCACCG

CCTCGGACCTGGCCGACCTCATTTTCCCCGAGCGCCTCAGGCTGACGCTGCGCAACGGCCTGCCC

GACTTTATGAGCCAAAGCATGTTGCAAAACTTTCGCTCTTTCATCCTCGAACGCTCCGGAATCCT

GCCCGCCACCTGCTCCGCGCTGCCCTCGGACTTCGTGCCGCTGACCTTCCGCGAGTGCCCCCCGC

-continued

CGCTGTGGAGCCACTGCTACCTGCTGCGCCTGGCCAACTACCTGGCCTACCACTCGGACGTGATC

GAGGACGTCAGCGGCGAGGGCCTGCTCGAGTGCCACTGCCGCTGCAACCTCTGCACGCCGCACCG

CTCCCTGGCCTGCAACCCCCAGCTGCTGAGCGAGACCCAGATCATCGGCACCTTCGAGTTGCAAG

GGCCCAGCGAAGGCGAGGGTTCAGCCGCCAAGGGGGGTCTGAAACTCACCCCGGGGCTGTGGACC

TCGGCCTACTTGCGCAAGTTCGTGCCCGAGGACTACCATCCCTTCGAGATCAGGTTCTACGAGGA

CCAATCCCATCCGCCCAAGGCCGAGCTGTCGGCCTGCGTCATCACCCAGGGGGCGATCCTGGCCC

AATTGCAAGCCATCCAGAAATCCCGCCAAGAATTCTTGCTGAAAAAGGGCCGCGGGGTCTACCTC

GACCCCCAGACCGGTGAGGAGCTCAACCCCGGCTTCCCCCAGGATGCCCCGAGGAAACAAGAAGC

TGAAAGTGGAGCTGCCGCCCGTGGAGGATTTGGAGGAAGACTGGGAGAACAGCAGTCAGGCAGAG

GAGGAGGAGATGGAGGAAGACTGGGACAGCACTCAGGCAGAGGAGGACAGCCTGCAAGACAGTCT

GGAGGAAGACGAGGAGGAGGCAGAGGAGGAGGTGGAAGAAGCAGCCGCCGCCAGACCGTCGTCCT

CGGCGGGGGAGAAAGCAAGCAGCACGGATACCATCTCCGCTCCGGGTCGGGGTCCCGCTCGACCA

CACAGTAGATGGGACGAGACCGGACGATTCCCGAACCCCACCACCCAGACCGGTAAGAAGGAGCG

GCAGGGATACAAGTCCTGGCGGGGGCACAAAAACGCCATCGTCTCCTGCTTGCAGGCCTGCGGGG

GCAACATCTCCTTCACCCGGCGCTACCTGCTCTTCCACCGCGGGGTGAACTTTCCCCGCAACATC

TTGCATTACTACCGTCACCTCCACAGCCCCTACTACTTCCAAGAAGAGGCAGCAGCAGCAGAAAA

AGACCAGCAGAAAACCAGCAGCTAGAAAATCCACAGCGGCGGCAGCAGGTGGACTGAGGATCGCG

GCGAACGAGCCGGCGCAAACCCGGGAGCTGAGGAACCGGATCTTTCCCACCCTCTATGCCATCTT

CCAGCAGAGTCGGGGGCAGGAGCAGGAACTGAAAGTCAAGAACCGTTCTCTGCGCTCGCTCACCC

GCAGTTGTCTGTATCACAAGAGCGAAGACCAACTTCAGCGCACTCTCGAGGACGCCGAGGCTCTC

TTCAACAAGTACTGCGCGCTCACTCTTAAAGAGTAGCCCGCGCCCGCCCAGTCGCAGAAAAAGGC

GGGAATTACGTCACCTGTGCCCTTCGCCCTAGCCGCCTCCACCCATCATCATGAGCAAAGAGATT

CCCACGCCTTACATGTGGAGCTACCAGCCCCAGATGGGCCTGGCCGCCGGTGCCGCCCAGGACTA

CTCCACCCGCATGAATTGGCTCAGCGCCGGGCCCGCGATGATCTCACGGGTGAATGACATCCGCG

CCCACCGAAACCAGATACTCCTAGAACAGTCAGCGCTCACCGCCACGCCCCGCAATCACCTCAAT

CCGCGTAATTGGCCCGCCGCCCTGGTGTACCAGGAAATTCCCCAGCCCACGACCGTACTACTTCC

GCGAGACGCCCAGGCCGAAGTCCAGCTGACTAACTCAGGTGTCCAGCTGGCGGGCGGCGCCACCC

TGTGTCGTCACCGCCCCGCTCAGGGTATAAAGCGGCTGGTGATCCGGGGCAGAGGCACACAGCTC

AACGACGAGGTGGTGAGCTCTTCGCTGGGTCTGCGACCTGACGGAGTCTTCCAACTCGCCGGATC

GGGGAGATCTTCCTTCACGCCTCGTCAGGCCGTCCTGACTTTGGAGAGTTCGTCCTCGCAGCCCC

GCTCGGGTGGCATCGGCACTCTCCAGTTCGTGGAGGAGTTCACTCCCTCGGTCTACTTCAACCCC

TTCTCCGGCTCCCCCGGCCACTACCCGGACGAGTTCATCCCGAACTTCGACGCCATCAGCGAGTC

GGTGGACGGCTACGATTGAATGTCCCATGGTGGCGCAGCTGACCTAGCTCGGCTTCGACACCTGG

ACCACTGCCGCCGCTTCCGCTGCTTCGCTCGGGATCTCGCCGAGTTTGCCTACTTTGAGCTGCCC

GAGGAGCACCCTCAGGGCCCGGCCCACGGAGTGCGGATCGTCGTCGAAGGGGGCCTCGACTCCCA

CCTGCTTCGGATCTTCAGCCAGCGTCCGATCCTGGTCGAGCGCGAGCAAGGACAGACCCTTCTGA

CTCTGTACTGCATCTGCAACCACCCCGGCCTGCATGAAAGTCTTTGTTGTCTGCTGTGTACTGAG

TATAATAAAAGCTGAGATCAGCGACTACTCCGGACTTCCGTGTGTTCCTGAATCCATCAACCAGT

CTTTGTTCTTCACCGGGAACGAGACCGAGCTCCAGCTCCAGTGTAAGCCCCACAAGAAGTACCTC

-continued

```
ACCTGGCTGTTCCAGGGCTCCCCGATCGCCGTTGTCAACCACTGCGACAACGACGGAGTCCTGCT

GAGCGGCCCTGCCAACCTTACTTTTTCCACCCGCAGAAGCAAGCTCCAGCTCTTCCAACCCTTCC

TCCCCGGGACCTATCAGTGCGTCTCGGGACCCTGCCATCACACCTTCCACCTGATCCCGAATACC

ACAGCGTCGCTCCCCGCTACTAACAACCAAACTAACCTCCACCAACGCCACCGTCGCGACCTTTC

TGAATCTAATACTACCACCCACACCGGAGGTGAGCTCCGAGGTCAACCAACCTCTGGGATTTACT

ACGGCCCCTGGGAGGTGGTTGGGTTAATAGCGCTAGGCCTAGTTGCGGGTGGGCTTTTGGTTCTC

TGCTACCTATACCTCCCTTGCTGTTCGTACTTAGTGGTGCTGTGTTGCTGGTTTAAGAAATGGGG

AAGATCACCCTAGTGAGCTGCGGTGCGCTGGTGGCGGTGTTGCTTTCGATTGTGGGACTGGGCGG

TGCGGCTGTAGTGAAGGAGAAGGCCGATCCCTGCTTGCATTTCAATCCCAACAAATGCCAGCTGA

GTTTTCAGCCCGATGGCAATCGGTGCGCGGTACTGATCAAGTGCGGATGGGAATGCGAGAACGTG

AGAATCGAGTACAATAACAAGACTCGGAACAATACTCTCGCGTCCGTGTGGCAGCCCGGGGACCC

CGAGTGGTACACCGTCTCTGTCCCCGGTGCTGACGGCTCCCCGCGCACCGTGAATAATACTTTCA

TTTTTGCGCACATGTGCGACACGGTCATGTGGATGAGCAAGCAGTACGATATGTGGCCCCCCACG

AAGGAGAACATCGTGGTCTTCTCCATCGCTTACAGCCTGTGCACGGCGCTAATCACCGCTATCGT

GTGCCTGAGCATTCACATGCTCATCGCTATTCGCCCCAGAAATAATGCCGAAAAAGAAAAACAGC

CATAACGTTTTTTTTCACACCTTTTTCAGACCATGGCCTCTGTTAAATTTTTGCTTTTATTTGCC

AGTCTCATTGCCGTCATTCATGGAATGAGTAATGAGAAAATTACTATTTACACTGGCACTAATCA

CACATTGAAAGGTCCAGAAAAAGCCACAGAAGTTTCATGGTATTGTTATTTTAATGAATCAGATG

TATCTACTGAACTCTGTGGAAACAATAACAAAAAAAATGAGAGCATTACTCTCATCAAGTTTCAA

TGTGGATCTGACTTAACCCTAATTAACATCACTAGAGACTATGTAGGTATGTATTATGGAACTAC

AGCAGGCATTTCGGACATGGAATTTTATCAAGTTTCTGTGTCTGAACCCACCACGCCTAGAATGA

CCACAACCACAAAAACTACACCTGTTACCACTATGCAGCTCACTACCAATAACATTTTTGCCATG

CGTCAAATGGTCAACAATAGCACTCAACCCACCCCACCCAGTGAGGAAATTCCCAAATCCATGAT

TGGCATTATTGTTGCTGTAGTGGTGTGCATGTTGATCATCGCCTTGTGCATGGTGTACTATGCCT

TCTGCTACAGAAAGCACAGACTGAACGACAAGCTGGAACACTTACTAAGTGTTGAATTTTAATTT

TTTAGAACCATGAAGATCCTAGGCCTTTTAATTTTTTCTATCATTACCTCTGCTCTATGCAATTC

TGACAATGAGGACGTTACTGTCGTTGTCGGATCAAATTATACACTGAAAGGTCCAGCGAAGGGTA

TGCTTTCGTGGTATTGCTATTTTGGATCTGACACTACAGAAACTGAATTATGCAATCTTAAGAAT

GGCAAAATTCAAAATTCTAAAATTAACAATTATATATGCAATGGTACTGATCTGATACTCCTCAA

TATCACGAAATCATATGCTGGCAGTTACACCTGCCCTGGAGATGATGCTGACAGTATGATTTTTT

ACAAAGTAACTGTTGTTGATCCCACTACTCCACCTCCACCCACCACAACTACTCACACCACACAC

ACAGATCAAACCGCAGCAGAGGAGGCAGCAAAGTTAGCCTTGCAGGTCCAAGACAGTTCATTTGT

TGGCATTACCCCTACACCTGATCAGCGGTGTCCGGGGCTGCTAGTCAGCGGCATTGTCGGTGTGC

TTTCGGGATTAGCAGTCATAATCATCTGCATGTTCATTTTTGCTTGCTGCTATAGAAGGCTTTAC

CGACAAAAATCAGACCCACTGCTGAACCTCTATGTTTAATTTTTTCCAGAGTCATGAAGGCAGTT

AGCGCTCTAGTTTTTTGTTCTTTGATTGGCATTGTTTTTTGCAATCCTATTCCTAAAGTTAGCTT

TATTAAAGATGTGAATGTTACTGAGGGGGGCAATGTGACACTGGTAGGTGTAGAGGGTGCTGAAA

ACACCACCTGGACAAAATACCACCTCAATGGGTGGAAAGATATTTGCAATTGGAGTGTATTAGTT

TATACATGTGAGGGAGTTAATCTTACCATTGTCAATGCCACCTCAGCTCAAAATGGTAGAATTCA

AGGACAAAGTGTCAGTGTATCTAATGGGTATTTTACCCAACATACTTTTATCTATGACGTTAAAG
```

-continued

TCATACCACTGCCTACGCCTAGCCCACCTAGCACTACCACACAGACAACCCACACTACACAGACA

ACCACATACAGTACATTAAATCAGCCTACCACCACTACAGCAGCAGAGGTTGCCAGCTCGTCTGG

GGTCCGAGTGGCATTTTTGATGTtGGCCCCATCTAGCAGTCCCACTGCTAGTACCAATGAGCAGA

CTACTGAATTTTTGTCCACTGTCGAGAGCCACACCACAGCTACCTCCAGTGCCTTCTCTAGCACC

GCCAATCTCTCCTCGCTTTCCTCTACACCAATCAGTCCCGCTACTACTCCTAGCCCCGCTCCTCT

TCCCACTCCCCTGAAGCAAACAGACGGCGGCATGCAATGGCAGATCACCCTGCTCATTGTGATCG

GGTTGGTCATCCTGGCCGTGTTGCTCTACTACATCTTCTGCCGCCGCATTCCCAACGCGCACCGC

AAGCCGGTCTACAAGCCCATCATTGTCGGGCAGCCGGAGCCGCTTCAGGTGGAAGGGGGTCTAAG

GAATCTTCTCTTCTCTTTTACAGTATGGTGATTGAACTATGATTCCTAGACAATTCTTGATCACT

ATTCTTATCTGCCTCCTCCAAGTCTGTGCCACCCTCGCTCTGGTGGCCAACGCCAGTCCAGACTG

TATTGGGCCCTTCGCCTCCTACGTGCTCTTTGCCTTCACCACCTGCATCTGCTGCTGTAGCATAG

TCTGCCTGCTTATCACCTTCTTCCAGTTCATTGACTGGATCTTTGTGCGCATCGCCTACCTGCGC

CACCACCCCCAGTACCGCGACCAGCGAGTGGCGCGGCTGCTCAGGCTCCTCTGATAAGCATGCGG

GCTCTGCTACTTCTCGCGCTTCTGCTGTTAGTGCTCCCCCGTCCCGTCGACCCCCGGTCCCCCAC

CCAGTCCCCCGAGGAGGTCCGCAAATGCAAATTCCAAGAACCCTGGAAATTCCTCAAATGCTACC

GCCAAAAATCAGACATGCATCCCAGCTGGATCATGATCATTGGGATCGTGAACATTCTGGCCTGC

ACCCTCATCTCCTTTGTGATTTACCCCTGCTTTGACTTTGGTTGGAACTCGCCAGAGGCGCTCTA

TCTCCCGCCTGAACCTGACACACCACCACAGCAACCTCAGGCACACGCACTACCACCACTACAGC

CTAGGCCACAATACATGCCCATATTAGACTATGAGGCCGAGCCACAGCGACCCATGCTCCCCGCT

ATTAGTTACTTCAATCTAACCGGCGGAGATGACTGACCCACTGGCCAACAACAACGTCAACGACC

TTCTCCTGGACATGGACGGCCGCGCCTCGGAGCAGCGACTCGCCCAACTTCGCATTCGCCAGCAG

CAGGAGAGAGCCGTCAAGGAGCTGCAGGATGCGGTGGCCATCCACCAGTGCAAGAGAGGCATCTT

CTGCCTGGTGAAACAGGCCAAGATCTCCTACGAGGTCACTCCAAACGACCATCGCCTCTCCTACG

AGCTCCTGCAGCAGCGCCAGAAGTTCACCTGCCTGGTCGGAGTCAACCCCATCGTCATCACCCAG

CAGTCTGGCGATACCAAGGGGTGCATCCACTGCTCCTGCGACTCCCCCGACTGCGTCCACACTCT

GATCAAGACCCTCTGCGGCCTCCGCGACCTCCTCCCCATGAACTAATCACCCCCTTATCCAGTGA

AATAAAGATCATATTGATGATGATTTTACAGAAATAAAAAATAATCATTTGATTTGAAATAAAGA

TACAATCATATTGATGATTTGAGTTTAACAAAAAAATAAAGAATCACTTACTTGAAATCTGATAC

CAGGTCTCTGTCCATGTTTTCTGCCAACACCACTTCACTCCCCTCTTCCCAGCTCTGGTACTGCA

GGCCCCGGCGGGCTGCAAACTTCCTCCACACGCTGAAGGGGATGTCAAATTCCTCCTGTCCCTCA

ATCTTCATTTTATCTTCTATCAGATGTCCAAAAAGCGCGTCCGGGTGGATGATGACTTCGACCCC

GTCTACCCCTACGATGCAGACAACGCACCGACCGTGCCCTTCATCAACCCCCCCTTCGTCTCTTC

AGATGGATTCCAAGAGAAGCCCCTGGGGGTGTTGTCCCTGCGACTGGCCGACCCCGTCACCACCA

AGAACGGGGAAATCACCCTCAAGCTGGGAGAGGGGGTGGACCTCGATTCCTCGGGAAAACTCATC

TCCAACACGGCCACCAAGGCCGCCGCCCCTCTCAGTTTTTCCAACAACACCATTTCCCTTAACAT

GGATCACCCCTTTTACACTAAAGATGGAAAATTATCCTTACAAGTTTCTCCACCATTAAATATAC

TGAGAACAAGCATTCTAAACACACTAGCTTTAGGTTTTGGATCAGGTTTAGGACTCCGTGGCTCT

GCCTTGGCAGTACAGTTAGTCTCTCCACTTACATTTGATACTGATGGAAACATAAAGCTTACCTT

AGACAGAGGTTTGCATGTTACAACAGGAGATGCAATTGAAAGCAACATAAGCTGGGCTAAAGGTT

-continued

TAAAATTTGAAGATGGAGCCATAGCAACCAACATTGGAAATGGGTTAGAGTTTGGAAGCAGTAGT

ACAGAAACAGGTGTTGATGATGCTTACCCAATCCAAGTTAAACTTGGATCTGGCCTTAGCTTTGA

CAGTACAGGAGCCATAATGGCTGGTAACAAAGAAGACGATAAACTCACTTTGTGGACAACACCTG

ATCCATCACCAAACTGTCAAATACTCGCAGAAAATGATGCAAAACTAACACTTTGCTTGACTAAA

TGTGGTAGTCAAATACTGGCCACTGTGTCAGTCTTAGTTGTAGGAAGTGGAAACCTAAACCCCAT

TACTGGCACCGTAAGCAGTGCTCAGGTGTTTCTACGTTTTGATGCAAACGGTGTTCTTTTAACAG

AACATTCTACACTAAAAAAATACTGGGGGTATAGGCAGGGAGATAGCATAGATGGCACTCCATAT

ACCAATGCTGTAGGATTCATGCCCAATTTAAAAGCTTATCCAAAGTCACAAAGTTCTACTACTAA

AAATAATATAGTAGGGCAAGTATACATGAATGGAGATGTTTCAAAACCTATGCTTCTCACTATAA

CCCTCAATGGTACTGATGACAGCAACAGTACATATTCAATGTCATTTTCATACACCTGGACTAAT

GGAAGCTATGTTGGAGCAACATTTGGGGCTAACTCTTATACCTTCTCATACATCGCCCAAGAATG

AACACTGTATCCCACCCTGCATGCCAACCCTTCCCACCCCACTCTGTGGAACAAACTCTGAAACA

CAAAATAAAATAAAGTTCAAGTGTTTTATTGATTCAACAGTTTTACAGGATTCGAGCAGTTATTT

TTCCTCCACCCTCCCAGGACATGGAATACACCACCCTCTCCCCCCGCACAGCCTTGAACATCTGA

ATGCCATTGGTGATGGACATGCTTTTGGTCTCCACGTTCCACACAGTTTCAGAGCGAGCCAGTCT

CGGGTCGGTCAGGGAGATGAAACCCTCCGGGCACTCCCGCATCTGCACCTCACAGCTCAACAGCT

GAGGATTGTCCTCGGTGGTCGGGATCACGGTTATCTGGAAGAAGCAGAAGAGCGGCGGTGGGAAT

CATAGTCCGCGAACGGGATCGGCCGGTGGTGTCGCATCAGGCCCCGCAGCAGTCGCTGCCGCCGC

CGCTCCGTCAAGCTGCTGCTCAGGGGGTCCGGGTCCAGGGACTCCCTCAGCATGATGCCCACGGC

CCTCAGCATCAGTCGTCTGGTGCGGCGGGCGCAGCAGCGCATGCGGATCTCGCTCAGGTCGCTGC

AGTACGTGCAACACAGAACCACCAGGTTGTTCAACAGTCCATAGTTCAACACGCTCCAGCCGAAA

CTCATCGCGGGAAGGATGCTACCCACGTGGCCGTCGTACCAGATCCTCAGGTAAATCAAGTGGTG

CCCCCTCCAGAACACGCTGCCCACGTACATGATCTCCTTGGGCATGTGGCGGTTCACCACCTCCC

GGTACCACATCACCCTCTGGTTGAACATGCAGCCCCGGATGATCCTGCGGAACCACAGGGCCAGC

ACCGCCCCGCCCGCCATGCAGCGAAGAGACCCCGGGTCCCGGCAATGGCAATGGAGGACCCACCG

CTCGTACCCGTGGATCATCTGGGAGCTGAACAAGTCTATGTTGGCACAGCACAGGCATATGCTCA

TGCATCTCTTCAGCACTCTCAACTCCTCGGGGGTCAAAACCATATCCCAGGGCACGGGGAACTCT

TGCAGGACAGCGAACCCCGCAGAACAGGGCAATCCTCGCACAGAACTTACATTGTGCATGGACAG

GGTATCGCAATCAGGCAGCACCGGGTGATCCTCCACCAGAGAAGCGCGGGTCTCGGTCTCCTCAC

AGCGTGGTAAGGGGGCCGGCCGATACGGGTGATGGCGGGACGCGGCTGATCGTGTTCGCGACCGT

GTCATGATGCAGTTGCTTTCGGACATTTTCGTACTTGCTGTAGCAGAACCTGGTCCGGGCGCTGC

ACACCGATCGCCGGCGGCGGTCTCGGCGCTTGGAACGCTCGGTGTTGAAATTGTAAAACAGCCAC

TCTCTCAGACCGTGCAGCAGATCTAGGGCCTCAGGAGTGATGAAGATCCCATCATGCCTGATGGC

TCTGATCACATCGACCACCGTGGAATGGGCCAGACCCAGCCAGATGATGCAATTTTGTTGGGTTT

CGGTGACGGCGGGGGAGGGAAGAACAGGAAGAACCATGATTAACTTTTAATCCAAACGGTCTCGG

AGTACTTCAAAATGAAGATCGCGGAGATGGCACCTCTCGCCCCCGCTGTGTTGGTGGAAAATAAC

AGCCAGGTCAAAGGTGATACGGTTCTCGAGATGTTCCACGGTGGCTTCCAGCAAAGCCTCCACGC

GCACATCCAGAAACAAGACAATAGCGAAAGCGGGAGGGTTCTCTAATTCCTCAATCATCATGTTA

CACTCCTGCACCATCCCCAGATAATTTTCATTTTTCCAGCCTTGAATGATTCGAACTAGTTCcTG

AGGTAAATCCAAGCCAGCCATGATAAAGAGCTCGCGCAGAGCGCCCTCCACCGGCATTCTTAAGC

-continued

ACACCCTCATAATTCCAAGATATTCTGCTCCTGGTTCACCTGCAGCAGATTGACAAGCGGAATAT

CAAAATCTCTGCCGCGATCCCTGAGCTCCTCCCTCAGCAATAACTGTAAGTACTCTTTCATATCC

TCTCCGAAATTTTTAGCCATAGGACCACCAGGAATAAGATTAGGGCAAGCCACAGTACAGATAAA

CCGAAGTCCTCCCCAGTGAGCATTGCCAAATGCAAGACTGCTATAAGCATGCTGGCTAGACCCGG

TGATATCTTCCAGATAACTGGACAGAAAATCGCCCAGGCAATTTTTAAGAAAATCAACAAAAGAA

AAATCCTCCAGGTGGACGTTTAGAGCCTCGGGAACAACGATGAAGTAAATGCAAGCGGTGCGTTC

CAGCATGGTTAGTTAGCTGATCTGTAGAAAAAACAAAAATGAACATTAAACCATGCTAGCCTGGC

GAACAGGTGGGTAAATCGTTCTCTCCAGCACCAGGCAGGCCACGGGGTCTCCGGCGCGACCCTCG

TAAAAATTGTCGCTATGATTGAAAACCATCACAGAGAGACGTTCCCGGTGGCCGGCGTGAATGAT

TCGACAAGATGAATACACCCCCGGAACATTGGCGTCCGCGAGTGAAAAAAAGCGCCCGAGGAAGC

AATAAGGCACTACAATGCTCAGTCTCAAGTCCAGCAAAGCGATGCCATGCGGATGAAGCACAAAA

TTCTCAGGTGCGTACAAAATGTAATTACTCCCCTCCTGCACAGGCAGCAAAGCCCCCGATCCCTC

CAGGTACACATACAAAGCCTCAGCGTCCATAGCTTACCGAGCAGCAGCACACAACAGGCGCAAGA

GTCAGAGAAAGGCTGAGCTCTAACCTGTCCACCCGCTCTCTGCTCAATATATAGCCCAGATCTAC

ACTGACGTAAAGGCCAAAGTCTAAAAATACCCGCCAAATAATCACACACGCCCAGCACACGCCCA

GAAACCGGTGACACACTCAAAAAAATACGCGCACTTCCTCAAACGCCCAAAACTGCCGTCATTTC

CGGGTTCCCACGCTACGTCATCAAAACACGACTTTCAAATTCCGTCGACCGTTAAAAACGTCACC

CGCCCCGCCCCTAACGGTCGCCCGTCTCTCAGCCAATCAGCGCCCCGCATCCCCAAATTCAAACA

CCTCATTTGCATATTAACGCGCACAAAAAGTTTGAGGTATATTATTGATGATGG

ChAdV68.4WTnt.GFP (SEQ ID NO: 11); AC_000011.1 with E1
(nt 577 to 3403) and E3 (nt 27,816-31,332) sequences
deleted; corresponding ATCC VR-594 nucleotides substituted
at four positions, GFP reporter under the control of the
CMV promoter/enhancer inserted in place of deleted E1
CCATCTTCAATAATATACCTCAAACTTTTTGTGCGCGTTAATATGCAAATGAGGCGTTTGAATTT

GGGGAGGAAGGGCGGTGATTGGTCGAGGGATGAGCGACCGTTAGGGGGGGGGCGAGTGACGTTTT

GATGACGTGGTTGCGAGGAGGAGCCAGTTTGCAAGTTCTCGTGGGAAAAGTGACGTCAAACGAGG

TGTGGTTTGAACACGGAAATACTCAATTTTCCCGCGCTCTCTGACAGGAAATGAGGTGTTTCTGG

GCGGATGCAAGTGAAAACGGGCCATTTTCGCGCGAAAACTGAATGAGGAAGTGAAAATCTGAGTA

ATTTCGCGTTTATGGCAGGGAGGAGTATTTGCCGAGGGCCGAGTAGACTTTGACCGATTACGTGG

GGGTTTCGATTACCGTGTTTTTCACCTAAATTTCCGCGTACGGTGTCAAAGTCCGGTGTTTTTAC

GTAGGTGTCAGCTGATCGCCAGGGTATTTAAACCTGCGCTCTCCAGTCAAGAGGCCACTCTTGAG

TGCCAGCGAGAAGAGTTTTCTCCTCCGCGCCGCGAGTCAGATCTACACTTTGAAAGTAGGGATAA

CAGGGTAATgacattgattattgactagttGttaaTAGTAATCAATTACGGGGTCATTAGTTCAT

AGCCCATATATGGAGTTCCGCGTTACATAACTTACGGTAAATGGCCCGCCTGGCTGACCGCCCAA

CGACCCCCGCCCATTGACGTCAATAATGACGTATGTTGCCATAGTAACGCCAATAGGGACTTTCC

ATTGACGTCAATGGGTGGAGTATTTACGGTAAACTGCCCACTTGGCAGTACATCAAGTGTATCAT

ATGCCAAGTCCGCCCCCTATTGACGTCAATGACGGTAAATGGCCCGCCTGGCATTATGCCCAGTA

CATGACCTTACGGGACTTTCCTACTTGGCAGTACATCTACGTATTAGTCATCGCTATTACCATGg

TGATGCGGTTTTGGCAGTACACCAATGGGCGTGGATAGCGGTTTGACTCACGGGGATTTCCAAGT

CTCCACCCCATTGACGTCAATGGGAGTTTGTTTTGGCACCAAAATCAACGGGACTTTCCAAAATG

TCGTAATAACCCCGCCCCGTTGACGCAAATGGGCGGTAGGCGTGTACGGTGGGAGGTCTATATAA

-continued

GCAGAgcTCGTTTAGTGAACCGTCAGATCGCCTGGAACGCCATCCACGCTGTTTTGACCTCCATA

GAAGACAGCGATCGCGccacCATGGTGAGCAAGGGCGAGGAGCTGTTCACCGGGGTGGTGCCCAT

CCTGGTCGAGCTGGACGGCGACGTAAACGGCCACAAGTTCAGCGTGTCCGGCGAGGGCGAGGGCG

ATGCCACCTACGGCAAGCTGACCCTGAAGTTCATCTGCACCACCGGCAAGCTGCCCGTGCCCTGG

CCCACCCTCGTGACCACCCTGACCTACGGCGTGCAGTGCTTCAGCCGCTACCCCGACCACATGAA

GCAGCACGACTTCTTCAAGTCCGCCATGCCCGAAGGCTACGTCCAGGAGCGCACCATCTTCTTCA

AGGACGACGGCAACTACAAGACCCGCGCCGAGGTGAAGTTCGAGGGCGACACCCTGGTGAACCGC

ATCGAGCTGAAGGGCATCGACTTCAAGGAGGACGGCAACATCCTGGGGCACAAGCTGGAGTACAA

CTACAACAGCCACAACGTCTATATCATGGCCGACAAGCAGAAGAACGGCATCAAGGTGAACTTCA

AGATCCGCCACAACATCGAGGACGGCAGCGTGCAGCTCGCCGACCACTACCAGCAGAACACCCCC

ATCGGCGACGGCCCCGTGCTGCTGCCCGACAACCACTACCTGAGCACCCAGTCCGCCCTGAGCAA

AGACCCCAACGAGAAGCGCGATCACATGGTCCTGCTGGAGTTCGTGACCGCCGCCGGGATCACTC

TCGGCATGGACGAGCTtTACAAGTAGtgaGTTTAAACTCCCATTTAAATGTGAGGGTTAATGCTT

CGAGCAGACATGATAAGATACATTGATGAGTTTGGACAAACCACAACTAGAATGCAGTGAAAAAA

ATGCTTTATTTGTGAAATTTGTGATGCTATTGCTTTATTTGTAACCATTATAAGCTGCAATAAAC

AAGTTAACAACAACAATTGCATTCATTTTATGTTTCAGGTTCAGGGGGAGATGTGGGAGGTTTTT

TAAAGCAAGTAAAACCTCTACAAATGTGGTAAAATAACTATAACGGTCCTAAGGTAGCGAGTGAG

TAGTGTTCTGGGGCGGGGGAGGACCTGCATGAGGGCCAGAATAACTGAAATCTGTGCTTTTCTGT

GTGTTGCAGCAGCATGAGCGGAAGCGGCTCCTTTGAGGGAGGGGTATTCAGCCCTTATCTGACGG

GGCGTCTCCCCTCCTGGGCGGGAGTGCGTCAGAATGTGATGGGATCCACGGTGGACGGCCGGCCC

GTGCAGCCCGCGAACTCTTCAACCCTGACCTATGCAACCCTGAGCTCTTCGTCGTTGGACGCAGC

TGCCGCCGCAGCTGCTGCATCTGCCGCCAGCGCCGTGCGCGGAATGGCCATGGGCGCCGGCTACT

ACGGCACTCTGGTGGCCAACTCGAGTTCCACCAATAATCCCGCCAGCCTGAACGAGGAGAAGCTG

TTGCTGCTGATGGCCCAGCTCGAGGCCTTGACCCAGCGCCTGGGCGAGCTGACCCAGCAGGTGGC

TCAGCTGCAGGAGCAGACGCGGGCCGCGGTTGCCACGGTGAAATCCAAATAAAAAATGAATCAAT

AAATAAACGGAGACGGTTGTTGATTTTAACACAGAGTCTGAATCTTTATTTGATTTTTCGCGCGC

GGTAGGCCCTGGACCACCGGTCTCGATCATTGAGCACCCGGTGGATCTTTTCCAGGACCCGGTAG

AGGTGGGCTTGGATGTTGAGGTACATGGGCATGAGCCCGTCCCGGGGGTGGAGGTAGCTCCATTG

CAGGGCCTCGTGCTCGGGGGTGGTGTTGTAAATCACCCAGTCATAGCAGGGGCGCAGGGCATGGT

GTTGCACAATATCTTTGAGGAGGAGACTGATGGCCACGGGCAGCCCTTTGGTGTAGGTGTTTACA

AATCTGTTGAGCTGGGAGGGATGCATGCGGGGGGAGATGAGGTGCATCTTGGCCTGGATCTTGAG

ATTGGCGATGTTACCGCCCAGATCCCGCCTGGGGTTCATGTTGTGCAGGACCACCAGCACGGTGT

ATCCGGTGCACTTGGGGAATTTATCATGCAACTTGGAAGGGAAGGCGTGAAAGAATTTGGCGACG

CCTTTGTGCCCGCCCAGGTTTTCCATGCACTCATCCATGATGATGGCGATGGGCCCGTGGGCGGC

GGCCTGGGCAAAGACGTTTCGGGGGTCGGACACATCATAGTTGTGGTCCTGGGTGAGGTCATCAT

AGGCCATTTTAATGAATTTGGGGCGGAGGGTGCCGGACTGGGGGACAAAGGTACCCTCGATCCCG

GGGGCGTAGTTCCCCTCACAGATCTGCATCTCCCAGGCTTTGAGCTCGGAGGGGGGGATCATGTC

CACCTGCGGGGCGATAAAGAACACGGTTTCCGGGGCGGGGGAGATGAGCTGGGCCGAAAGCAAGT

TCCGGAGCAGCTGGGACTTGCCGCAGCCGGTGGGGCCGTAGATGACCCCGATGACCGGCTGCAGG

-continued

TGGTAGTTGAGGGAGAGACAGCTGCCGTCCTCCCGGAGGAGGGGGGCCACCTCGTTCATCATCTC

GCGCACGTGCATGTTCTCGCGCACCAGTTCCGCCAGGAGGCGCTCTCCCCCCAGGGATAGGAGCT

CCTGGAGCGAGGCGAAGTTTTTCAGCGGCTTGAGTCCGTCGGCCATGGGCATTTTGGAGAGGGTT

TGTTGCAAGAGTTCCAGGCGGTCCCAGAGCTCGGTGATGTGCTCTACGGCATCTCGATCCAGCAG

ACCTCCTCGTTTCGCGGGTTGGGACGGCTGCGGGAGTAGGGCACCAGACGATGGGCGTCCAGCGC

AGCCAGGGTCCGGTCCTTCCAGGGTCGCAGCGTCCGCGTCAGGGTGGTCTCCGTCACGGTGAAGG

GGTGCGCGCCGGGCTGGGCGCTTGCGAGGGTGCGCTTCAGGCTCATCCGGCTGGTCGAAAACCGC

TCCCGATCGGCGCCCTGCGCGTCGGCCAGGTAGCAATTGACCATGAGTTCGTAGTTGAGCGCCTC

GGCCGCGTGGCCTTTGGCGCGGAGCTTACCTTTGGAAGTCTGCCCGCAGGCGGGACAGAGGAGGG

ACTTGAGGGCGTAGAGCTTGGGGGCGAGGAAGACGGACTCGGGGGCGTAGGCGTCCCCGCCGCAG

TGGGCGCAGACGGTCTCGCACTCCACGAGCCAGGTGAGGTCGGGCTGGTCGGGGTCAAAAACCAG

TTTCCCGCCGTTCTTTTTGATGCGTTTCTTACCTTTGGTCTCCATGAGCTCGTGTCCCCGCTGGG

TGACAAAGAGGCTGTCCGTGTCCCCGTAGACCGACTTTATGGGCCGGTCCTCGAGCGGTGTGCCG

CGGTCCTCCTCGTAGAGGAACCCCGCCCACTCCGAGACGAAAGCCCGGGTCCAGGCCAGCACGAA

GGAGGCCACGTGGGACGGGTAGCGGTCGTTGTCCACCAGCGGGTCCACCTTTTCCAGGGTATGCA

AACACATGTCCCCCTCGTCCACATCCAGGAAGGTGATTGGCTTGTAAGTGTAGGCCACGTGACCG

GGGGTCCCGGCCGGGGGGGTATAAAAGGGTGCGGGTCCCTGCTCGTCCTCACTGTCTTCCGGATC

GCTGTCCAGGAGCGCCAGCTGTTGGGGTAGGTATTCCCTCTCGAAGGCGGGCATGACCTCGGCAC

TCAGGTTGTCAGTTTCTAGAAACGAGGAGGATTTGATATTGACGGTGCCGGCGGAGATGCCTTTC

AAGAGCCCCTCGTCCATCTGGTCAGAAAAGACGATCTTTTTGTTGTCGAGCTTGGTGGCGAAGGA

GCCGTAGAGGGCGTTGGAGAGGAGCTTGGCGATGGAGCGCATGGTCTGGTTTTTTTCCTTGTCGG

CGCGCTCCTTGGCGGCGATGTTGAGCTGCACGTACTCGCGCGCCACGCACTTCCATTCGGGGAAG

ACGGTGGTCAGCTCGTCGGGCACGATTCTGACCTGCCAGCCCCGATTATGCAGGGTGATGAGGTC

CACACTGGTGGCCACCTCGCCGCGCAGGGGCTCATTAGTCCAGCAGAGGCGTCCGCCCTTGCGCG

AGCAGAAGGGGGGCAGGGGGTCCAGCATGACCTCGTCGGGGGGGTCGGCATCGATGGTGAAGATG

CCGGGCAGGAGGTCGGGGTCAAAGTAGCTGATGGAAGTGGCCAGATCGTCCAGGGCAGCTTGCCA

TTCGCGCACGGCCAGCGCGCtCTCGTAGGGACTGAGGGGCGTGCCCCAGGGCATGGGATGGGTAA

GCGCGGAGGCGTACATGCCGCAGATGTCGTAGACGTAGAGGGGCTCCTCGAGGATGCCGATGTAG

GTGGGGTAGCAGCGCCCCCCGCGGATGCTGGCGCGCACGTAGTCATACAGCTCGTGCGAGGGGGC

GAGGAGCCCCGGGCCCAGGTTGGTGCGACTGGGCTTTTCGGCGCGGTAGACGATCTGGCGGAAAA

TGGCATGCGAGTTGGAGGAGATGGTGGGCCTTTGGAAGATGTTGAAGTGGGCGTGGGGCAGTCCG

ACCGAGTCGCGGATGAAGTGGGCGTAGGAGTCTTGCAGCTTGGCGACGAGCTCGGCGGTGACTAG

GACGTCCAGAGCGCAGTAGTCGAGGGTCTCCTGGATGATGTCATACTTGAGCTGTCCCTTTTGTT

TCCACAGCTCGCGGTTGAGAAGGAACTCTTCGCGGTCCTTCCAGTACTCTTCGAGGGGGAACCCG

TCCTGATCTGCACGGTAAGAGCCTAGCATGTAGAACTGGTTGACGGCCTTGTAGGCGCAGCAGCC

CTTCTCCACGGGGAGGGCGTAGGCCTGGGCGGCCTTGCGCAGGGAGGTGTGCGTGAGGGCGAAAG

TGTCCCTGACCATGACCTTGAGGAACTGGTGCTTGAAGTCGATATCGTCGCAGCCCCCCTGCTCC

CAGAGCTGGAAGTCCGTGCGCTTCTTGTAGGCGGGGTTGGGCAAAGCGAAAGTAACATCGTTGAA

GAGGATCTTGCCCGCGCGGGGCATAAAGTTGCGAGTGATGCGGAAAGGTTGGGGCACCTCGGCCC

GGTTGTTGATGACCTGGGCGGCGAGCACGATCTCGTCGAAGCCGTTGATGTTGTGGCCCACGATG

-continued

TAGAGTTCCACGAATCGCGGACGGCCCTTGACGTGGGGCAGTTTCTTGAGCTCCTCGTAGGTGAG

CTCGTCGGGGTCGCTGAGCCCGTGCTGCTCGAGCGCCCAGTCGGCGAGATGGGGGTTGGCGCGGA

GGAAGGAAGTCCAGAGATCCACGGCCAGGGCGGTTTGCAGACGGTCCCGGTACTGACGGAACTGC

TGCCCGACGGCCATTTTTTCGGGGGTGACGCAGTAGAAGGTGCGGGGGTCCCCGTGCCAGCGATC

CCATTTGAGCTGGAGGGCGAGATCGAGGGCGAGCTCGACGAGCCGGTCGTCCCCGGAGAGTTTCA

TGACCAGCATGAAGGGGACGAGCTGCTTGCCGAAGGACCCCATCCAGGTGTAGGTTTCCACATCG

TAGGTGAGGAAGAGCCTTTCGGTGCGAGGATGCGAGCCGATGGGGAAGAACTGGATCTCCTGCCA

CCAATTGGAGGAATGGCTGTTGATGTGATGGAAGTAGAAATGCCGACGGCGCGCCGAACACTCGT

GCTTGTGTTTATACAAGCGGCCACAGTGCTCGCAACGCTGCACGGGATGCACGTGCTGCACGAGC

TGTACCTGAGTTCCTTTGACGAGGAATTTCAGTGGGAAGTGGAGTCGTGGCGCCTGCATCTCGTG

CTGTACTACGTCGTGGTGGTCGGCCTGGCCCTCTTCTGCCTCGATGGTGGTCATGCTGACGAGCC

CGCGCGGGAGGCAGGTCCAGACCTCGGCGCGAGCGGGTCGGAGAGCGAGGACGAGGGCGCGCAGG

CCGGAGCTGTCCAGGGTCCTGAGACGCTGCGGAGTCAGGTCAGTGGGCAGCGGCGGCGCGCGGTT

GACTTGCAGGAGTTTTTCCAGGGCGCGCGGGAGGTCCAGATGGTACTTGATCTCCACCGCGCCAT

TGGTGGCGACGTCGATGGCTTGCAGGGTCCCGTGCCCCTGGGGTGTGACCACCGTCCCCCGTTTC

TTCTTGGGCGGCTGGGGCGACGGGGGGGGTGCCTCTTCCATGGTTAGAAGCGGCGGCGAGGACGC

GCGCCGGGCGGCAGGGGCGGCTCGGGGCCCGGAGGCAGGGGCGGCAGGGGCACGTCGGCGCCGCG

CGCGGGTAGGTTCTGGTACTGCGCCCGGAGAAGACTGGCGTGAGCGACGACGCGACGGTTGACGT

CCTGGATCTGACGCCTCTGGGTGAAGGCCACGGGACCCGTGAGTTTGAACCTGAAAGAGAGTTCG

ACAGAATCAATCTCGGTATCGTTGACGGCGGCCTGCCGCAGGATCTCTTGCACGTCGCCCGAGTT

GTCCTGGTAGGCGATCTCGGTCATGAACTGCTCGATCTCCTCCTCTTGAAGGTCTCCGCGGCCGG

CGCGCTCCACGGTGGCCGCGAGGTCGTTGGAGATGCGGCCCATGAGCTGCGAGAAGGCGTTCATG

CCCGCCTCGTTCCAGACGCGGCTGTAGACCACGACGCCCTCGGGATCGCgGGCGCGCATGACCAC

CTGGGCGAGGTTGAGCTCCACGTGGCGCGTGAAGACCGCGTAGTTGCAGAGGCGCTGGTAGAGGT

AGTTGAGCGTGGTGGCGATGTGCTCGGTGACGAAGAAATACATGATCCAGCGGCGGAGCGGCATC

TCGCTGACGTCGCCCAGCGCCTCCAAACGTTCCATGGCCTCGTAAAAGTCCACGGCGAAGTTGAA

AAACTGGGAGTTGCGCGCCGAGACGGTCAACTCCTCCTCCAGAAGACGGATGAGCTCGGCGATGG

TGGCGCGCACCTCGCGCTCGAAGGCCCCCGGGAGTTCCTCCACTTCCTCTTCTTCCTCCTCCACT

AACATCTCTTCTACTTCCTCCTCAGGCGGCAGTGGTGGCGGGGGAGGGGGCCTGCGTCGCCGGCG

GCGCACGGGCAGACGGTCGATGAAGCGCTCGATGGTCTCGCCGCGCCGGCGTCGCATGGTCTCGG

TGACGGCGCGCCCGTCCTCGCGGGGCCGCAGCGTGAAGACGCCGCCGCGCATCTCCAGGTGGCCG

GGGGGGTCCCCGTTGGGCAGGGAGAGGGCGCTGACGATGCATCTTATCAATTGCCCCGTAGGGAC

TCCGCGCAAGGACCTGAGCGTCTCGAGATCCACGGGATCTGAAAACCGCTGAACGAAGGCTTCGA

GCCAGTCGCAGTCGCAAGGTAGGCTGAGCACGGTTTCTTCTGGCGGGTCATGTTGGTTGGGAGCG

GGGGGGGCGATGCTGCTGGTGATGAAGTTGAAATAGGCGGTTCTGAGACGGCGGATGGTGGCGAG

GAGCACCAGGTCTTTGGGCCCGGCTTGCTGGATGCGCAGACGGTCGGCCATGCCCCAGGCGTGGT

CCTGACACCTGGCCAGGTCCTTGTAGTAGTCCTGCATGAGCCGCTCCACGGGCACCTCCTCCTCG

CCCGCGCGGCCGTGCATGCGCGTGAGCCCGAAGCCGCGCTGGGGCTGGACGAGCGCCAGGTCGGC

GACGACGCGCTCGGCGAGGATGGCTTGCTGGATCTGGGTGAGGGTGGTCTGGAAGTCATCAAAGT

-continued

CGACGAAGCGGTGGTAGGCTCCGGTGTTGATGGTGTAGGAGCAGTTGGCCATGACGGACCAGTTG

ACGGTCTGGTGGCCCGGACGCACGAGCTCGTGGTACTTGAGGCGCGAGTAGGCGCGCGTGTCGAA

GATGTAGTCGTTGCAGGTGCGCACCAGGTACTGGTAGCCGATGAGGAAGTGCGGCGGCGGCTGGC

GGTAGAGCGGCCATCGCTCGGTGGCGGGGGCGCCGGGCGCGAGGTCCTCGAGCATGGTGCGGTGG

TAGCCGTAGATGTACCTGGACATCCAGGTGATGCCGGCGGCGGTGGTGGAGGCGCGCGGGAACTC

GCGGACGCGGTTCCAGATGTTGCGCAGCGGCAGGAAGTAGTTCATGGTGGGCACGGTCTGGCCCG

TGAGGCGCGCGCAGTCGTGGATGCTCTATACGGGCAAAAACGAAAGCGGTCAGCGGCTCGACTCC

GTGGCCTGGAGGCTAAGCGAACGGGTTGGGCTGCGCGTGTACCCCGGTTCGAATCTCGAATCAGG

CTGGAGCCGCAGCTAACGTGGTATTGGCACTCCCGTCTCGACCCAAGCCTGCACCAACCCTCCAG

GATACGGAGGCGGGTCGTTTTGCAACTTTTTTTTGGAGGCCGGATGAGACTAGTAAGCGCGGAAA

GCGGCCGACCGCGATGGCTCGCTGCCGTAGTCTGGAGAAGAATCGCCAGGGTTGCGTTGCGGTGT

GCCCCGGTTCGAGGCCGGCCGGATTCCGCGGCTAACGAGGGCGTGGCTGCCCCGTCGTTTCCAAG

ACCCCATAGCCAGCCGACTTCTCCAGTTACGGAGCGAGCCCCTCTTTTGTTTTGTTTGTTTTTGC

CAGATGCATCCCGTACTGCGGCAGATGCGCCCCCACCACCCTCCACCGCAACAACAGCCCCCTCC

ACAGCCGGCGCTTCTGCCCCCGCCCCAGCAGCAACTTCCAGCCACGACCGCCGCGGCCGCCGTGA

GCGGGGCTGGACAGAGTTATGATCACCAGCTGGCCTTGGAAGAGGGCGAGGGGCTGGCGCGCCTG

GGGGCGTCGTCGCCGGAGCGGCACCCGCGCGTGCAGATGAAAAGGGACGCTCGCGAGGCCTACGT

GCCCAAGCAGAACCTGTTCAGAGACAGGAGCGGCGAGGAGCCCGAGGAGATGCGCGCGGCCCGGT

TCCACGCGGGGCGGGAGCTGCGGCGCGGCCTGGACCGAAAGAGGGTGCTGAGGGACGAGGATTTC

GAGGCGGACGAGCTGACGGGGATCAGCCCCGCGCGCGCGCACGTGGCCGCGGCCAACCTGGTCAC

GGCGTACGAGCAGACCGTGAAGGAGGAGAGCAACTTCCAAAAATCCTTCAACAACCACGTGCGCA

CCCTGATCGCGCGCGAGGAGGTGACCCTGGGCCTGATGCACCTGTGGGACCTGCTGGAGGCCATC

GTGCAGAACCCCACCAGCAAGCCGCTGACGGCGCAGCTGTTCCTGGTGGTGCAGCATAGTCGGGA

CAACGAAGCGTTCAGGGAGGCGCTGCTGAATATCACCGAGCCCGAGGGCCGCTGGCTCCTGGACC

TGGTGAACATTCTGCAGAGCATCGTGGTGCAGGAGCGCGGGCTGCCGCTGTCCGAGAAGCTGGCG

GCCATCAACTTCTCGGTGCTGAGTTTGGGCAAGTACTACGCTAGGAAGATCTACAAGACCCCGTA

CGTGCCCATAGACAAGGAGGTGAAGATCGACGGGTTTTACATGCGCATGACCCTGAAAGTGCTGA

CCCTGAGCGACGATCTGGGGGTGTACCGCAACGACAGGATGCACCGTGCGGTGAGCGCCAGCAGG

CGGCGCGAGCTGAGCGACCAGGAGCTGATGCATAGTCTGCAGCGGGCCCTGACCGGGGCCGGGAC

CGAGGGGGAGAGCTACTTTGACATGGGCGCGGACCTGCACTGGCAGCCCAGCCGCCGGGCCTTGG

AGGCGGCGGCAGGACCCTACGTAGAAGAGGTGGACGATGAGGTGGACGAGGAGGGCGAGTACCTG

GAAGACTGATGGCGCGACCGTATTTTTGCTAGATGCAACAACAACAGCCACCTCCTGATCCCGCG

ATGCGGGCGGCGCTGCAGAGCCAGCCGTCCGGCATTAACTCCTCGGACGATTGGACCCAGGCCAT

GCAACGCATCATGGCGCTGACGACCCGCAACCCCGAAGCCTTTAGACAGCAGCCCCAGGCCAACC

GGCTCTCGGCCATCCTGGAGGCCGTGGTGCCCTCGCGCTCCAACCCCACGCACCAGAAGGTCCTG

GCCATCGTGAACGCGCTGGTGGAGAACAAGGCCATCCGCGGCGACGAGGCCGGCCTGGTGTACAA

CGCGCTGCTGGAGCGCGTGGCCCGCTACAACAGCACCAACGTGCAGACCAACCTGGACCGCATGG

TGACCGACGTGCGCGAGGCCGTGGCCCAGCGCGAGCGGTTCCACCGCGAGTCCAACCTGGGATCC

ATGGTGGCGCTGAACGCCTTCCTCAGCACCCAGCCCGCCAACGTGCCCCGGGGCCAGGAGGACTA

CACCAACTTCATCAGCGCCCTGCGCCTGATGGTGACCGAGGTGCCCCAGAGCGAGGTGTACCAGT

-continued

CCGGGCCGGACTACTTCTTCCAGACCAGTCGCCAGGGCTTGCAGACCGTGAACCTGAGCCAGGCT

TTCAAGAACTTGCAGGGCCTGTGGGGCGTGCAGGCCCCGGTCGGGGACCGCGCGACGGTGTCGAG

CCTGCTGACGCCGAACTCGCGCCTGCTGCTGCTGCTGGTGGCCCCCTTCACGGACAGCGGCAGCA

TCAACCGCAACTCGTACCTGGGCTACCTGATTAACCTGTACCGCGAGGCCATCGGCCAGGCGCAC

GTGGACGAGCAGACCTACCAGGAGATCACCCACGTGAGCCGCGCCCTGGGCCAGGACGACCCGGG

CAACCTGGAAGCCACCCTGAACTTTTTGCTGACCAACCGGTCGCAGAAGATCCCGCCCCAGTACG

CGCTCAGCACCGAGGAGGAGCGCATCCTGCGTTACGTGCAGCAGAGCGTGGGCCTGTTCCTGATG

CAGGAGGGGGCCACCCCCAGCGCCGCGCTCGACATGACCGCGCGCAACATGGAGCCCAGCATGTA

CGCCAGCAACCCCCCGTTCATCAATAAACTGATGGACTACTTGCATCGGGCGGCCGCCATGAACT

CTGACTATTTCACCAACGCCATCCTGAATCCCCACTGGCTCCCCCCGCCGGGGTTCTACACGGGC

GAGTACGACATGCCCGACCCCAATGACGGGTTCCTGTGGGACGATGTGGACAGCAGCGTGTTCTC

CCCCCGACCGGGTGCTAACGAGCGCCCCTTGTGGAAGAAGGAAGGCAGCGACCGACGCCCGTCCT

CGGCGCTGTCCGGCCGCGAGGGTGCTGCCGCGGCGGTGCCCGAGGCCGCCAGTCCTTTCCCGAGC

TTGCCCTTCTCGCTGAACAGTATCCGCAGCAGCGAGCTGGGCAGGATCACGCGCCCGCGCTTGCT

GGGCGAAGAGGAGTACTTGAATGACTCGCTGTTGAGACCCGAGCGGGAGAAGAACTTCCCCAATA

ACGGGATAGAAAGCCTGGTGGACAAGATGAGCCGCTGGAAGACGTATGCGCAGGAGCACAGGGAC

GATCCCCGGGCGTCGCAGGGGGCCACGAGCCGGGGCAGCGCCGCCCGTAAACGCCGGTGGCACGA

CAGGCAGCGGGGACAGATGTGGGACGATGAGGACTCCGCCGACGACAGCAGCGTGTTGGACTTGG

GTGGGAGTGGTAACCCGTTCGCTCACCTGCGCCCCCGTATCGGGCGCATGATGTAAGAGAAACCG

AAAATAAATGATACTCACCAAGGCCATGGCGACCAGCGTGCGTTCGTTTCTTCTCTGTTGTTGTT

GTATCTAGTATGATGAGGCGTGCGTACCCGGAGGGTCCTCCTCCCTCGTACGAGAGCGTGATGCA

GCAGGCGATGGCGGCGGCGGCGATGCAGCCCCCGCTGGAGGCTCCTTACGTGCCCCCGCGGTACC

TGGCGCCTACGGAGGGGCGGAACAGCATTCGTTACTCGGAGCTGGCACCCTTGTACGATACCACC

CGGTTGTACCTGGTGGACAACAAGTCGGCGGACATCGCCTCGCTGAACTACCAGAACGACCACAG

CAACTTCCTGACCACCGTGGTGCAGAACAATGACTTCACCCCCACGGAGGCCAGCACCCAGACCA

TCAACTTTGACGAGCGCTCGCGGTGGGGCGGCCAGCTGAAAACCATCATGCACACCAACATGCCC

AACGTGAACGAGTTCATGTACAGCAACAAGTTCAAGGCGCGGGTGATGGTCTCCCGCAAGACCCC

CAATGGGGTGACAGTGACAGAGGATTATGATGGTAGTCAGGATGAGCTGAAGTATGAATGGGTGG

AATTTGAGCTGCCCGAAGGCAACTTCTCGGTGACCATGACCATCGACCTGATGAACAACGCCATC

ATCGACAATTACTTGGCGGTGGGGGGCAGAACGGGGTGCTGGAGAGCGACATCGGCGTGAAGTTC

GACACTAGGAACTTCAGGCTGGGCTGGGACCCCGTGACCGAGCTGGTCATGCCCGGGGTGTACAC

CAACGAGGCTTTCCATCCCGATATTGTCTTGCTGCCCGGCTGCGGGGTGGACTTCACCGAGAGCC

GCCTCAGCAACCTGCTGGGCATTCGCAAGAGGCAGCCCTTCCAGGAAGGCTTCCAGATCATGTAC

GAGGATCTGGAGGGGGGCAACATCCCCGCGCTCCTGGATGTCGACGCCTATGAGAAAAGCAAGGA

GGATGCAGCAGCTGAAGCAACTGCAGCCGTAGCTACCGCCTCTACCGAGGTCAGGGGCGATAATT

TTGCAAGCGCCGCAGCAGTGGCAGCGGCCGAGGCGGCTGAAACCGAAAGTAAGATAGTCATTCAG

CCGGTGGAGAAGGATAGCAAGAACAGGAGCTACAACGTACTACCGGACAAGATAAACACCGCCTA

CCGCAGCTGGTACCTAGCCTACAACTATGGCGACCCCGAGAAGGGCGTGCGCTCCTGGACGCTGC

TCACCACCTCGGACGTCACCTGCGGCGTGGAGCAAGTCTACTGGTCGCTGCCCGACATGATGCAA

-continued

GACCCGGTCACCTTCCGCTCCACGCGTCAAGTTAGCAACTACCCGGTGGTGGGCGCCGAGCTCCT

GCCCGTCTACTCCAAGAGCTTCTTCAACGAGCAGGCCGTCTACTCGCAGCAGCTGCGCGCCTTCA

CCTCGCTTACGCACGTCTTCAACCGCTTCCCCGAGAACCAGATCCTCGTCCGCCCGCCCGCGCCC

ACCATTACCACCGTCAGTGAAAACGTTCCTGCTCTCACAGATCACGGGACCCTGCCGCTGCGCAG

CAGTATCCGGGGAGTCCAGCGCGTGACCGTTACTGACGCCAGACGCCGCACCTGCCCCTACGTCT

ACAAGGCCCTGGGCATAGTCGCGCCGCGCGTCCTCTCGAGCCGCACCTTCTAAATGTCCATTCTC

ATCTCGCCCAGTAATAACACCGGTTGGGGCCTGCGCGCGCCCAGCAAGATGTACGGAGGCGCTCG

CCAACGCTCCACGCAACACCCCGTGCGCGTGCGCGGGCACTTCCGCGCTCCCTGGGGCGCCCTCA

AGGGCCGCGTGCGGTCGCGCACCACCGTCGACGACGTGATCGACCAGGTGGTGGCCGACGCGCGC

AACTACACCCCCGCCGCCGCGCCCGTCTCCACCGTGGACGCCGTCATCGACAGCGTGGTGGCcGA

CGCGCGCCGGTACGCCCGCGCCAAGAGCCGGCGGCGGCGCATCGCCCGGCGGCACCGGAGCACCC

CCGCCATGCGCGCGGCGCGAGCCTTGCTGCGCAGGGCCAGGCGCACGGGACGCAGGGCCATGCTC

AGGGCGGCCAGACGCGCGGCTTCAGGCGCCAGCGCCGGCAGGACCCGGAGACGCGCGGCCACGGC

GGCGGCAGCGGCCATCGCCAGCATGTCCCGCCCGCGGCGAGGGAACGTGTACTGGGTGCGCGACG

CCGCCACCGGTGTGCGCGTGCCCGTGCGCACCCGCCCCCCTCGCACTTGAAGATGTTCACTTCGC

GATGTTGATGTGTCCCAGCGGCGAGGAGGATGTCCAAGCGCAAATTCAAGGAAGAGATGCTCCAG

GTCATCGCGCCTGAGATCTACGGCCCTGCGGTGGTGAAGGAGGAAAGAAAGCCCCGCAAAATCAA

GCGGGTCAAAAAGGACAAAAAGGAAGAAGAAAGTGATGTGGACGGATTGGTGGAGTTTGTGCGCG

AGTTCGCCCCCCGGCGGCGCGTGCAGTGGCGCGGGCGGAAGGTGCAACCGGTGCTGAGACCCGGC

ACCACCGTGGTCTTCACGCCCGGCGAGCGCTCCGGCACCGCTTCCAAGCGCTCCTACGACGAGGT

GTACGGGGATGATGATATTCTGGAGCAGGCGGCCGAGCGCCTGGGCGAGTTTGCTTACGGCAAGC

GCAGCCGTTCCGCACCGAAGGAAGAGGCGGTGTCCATCCCGCTGGACCACGGCAACCCCACGCCG

AGCCTCAAGCCCGTGACCTTGCAGCAGGTGCTGCCGACCGCGGCGCCGCGCCGGGGGTTCAAGCG

CGAGGGCGAGGATCTGTACCCCACCATGCAGCTGATGGTGCCCAAGCGCCAGAAGCTGGAAGACG

TGCTGGAGACCATGAAGGTGGACCCGGACGTGCAGCCCGAGGTCAAGGTGCGGCCCATCAAGCAG

GTGGCCCCGGGCCTGGGCGTGCAGACCGTGGACATCAAGATTCCCACGGAGCCCATGGAAACGCA

GACCGAGCCCATGATCAAGCCCAGCACCAGCACCATGGAGGTGCAGACGGATCCCTGGATGCCAT

CGGCTCCTAGTCGAAGACCCCGGCGCAAGTACGGCGCGGCCAGCCTGCTGATGCCCAACTACGCG

CTGCATCCTTCCATCATCCCCACGCCGGGCTACCGCGGCACGCGCTTCTACCGCGGTCATACCAG

CAGCCGCCGCCGCAAGACCACCACTCGCCGCCGCCGTCGCCGCACCGCCGCTGCAACCACCCCTG

CCGCCCTGGTGCGGAGAGTGTACCGCCGCGGCCGCGCACCTCTGACCCTGCCGCGCGCGCGCTAC

CACCCGAGCATCGCCATTTAAACTTTCGCCTGCTTTGCAGATCAATGGCCCTCACATGCCCCCTT

CGCGTTCCCATTACGGGCTACCGAGGAAGAAAACCGCGCCGTAGAAGGCTGGCGGGGAACGGGAT

GCGTCGCCACCACCACCGGCGGCGGCGCGCCATCAGCAAGCGGTTGGGGGGAGGCTTCCTGCCCG

CGCTGATCCCCATCATCGCCGCGGCGATCGGGGCGATCCCCGGCATTGCTTCCGTGGCGGTGCAG

GCCTCTCAGCGCCACTGAGACACACTTGGAAACATCTTGTAATAAACCaATGGACTCTGACGCTC

CTGGTCCTGTGATGTGTTTTCGTAGACAGATGGAAGACATCAATTTTTCGTCCCTGGCTCCGCGA

CACGGCACGCGGCCGTTCATGGGCACCTGGAGCGACATCGGCACCAGCCAACTGAACGGGGGCGC

CTTCAATTGGAGCAGTCTCTGGAGCGGGCTTAAGAATTTCGGGTCCACGCTTAAAACCTATGGCA

GCAAGGCGTGGAACAGCACCACAGGGCAGGCGCTGAGGGATAAGCTGAAAGAGCAGAACTTCCAG

-continued

CAGAAGGTGGTCGATGGGCTCGCCTCGGGCATCAACGGGGTGGTGGACCTGGCCAACCAGGCCGT

GCAGCGGCAGATCAACAGCCGCCTGGACCCGGTGCCGCCCGCCGGCTCCGTGGAGATGCCGCAGG

TGGAGGAGGAGCTGCCTCCCCTGGACAAGCGGGGCGAGAAGCGACCCCGCCCCGATGCGGAGGAG

ACGCTGCTGACGCACACGGACGAGCCGCCCCCGTACGAGGAGGCGGTGAAACTGGGTCTGCCCAC

CACGCGGCCCATCGCGCCCCTGGCCACCGGGGTGCTGAAACCCGAAAAGCCCGCGACCCTGGACT

TGCCTCCTCCCCAGCCTTCCCGCCCCTCTACAGTGGCTAAGCCCCTGCCGCCGGTGGCCGTGGCC

CGCGCGCGACCCGGGGGCACCGCCCGCCCTCATGCGAACTGGCAGAGCACTCTGAACAGCATCGT

GGGTCTGGGAGTGCAGAGTGTGAAGCGCCGCCGCTGCTATTAAACCTACCGTAGCGCTTAACTTG

CTTGTCTGTGTGTGTATGTATTATGTCGCCGCCGCCGCTGTCCACCAGAAGGAGGAGTGAAGAGG

CGCGTCGCCGAGTTGCAAGATGGCCACCCCATCGATGCTGCCCCAGTGGGCGTACATGCACATCG

CCGGACAGGACGCTTCGGAGTACCTGAGTCCGGGTCTGGTGCAGTTTGCCCGCGCCACAGACACC

TACTTCAGTCTGGGGAACAAGTTTAGGAACCCCACGGTGGCGCCCACGCACGATGTGACCACCGA

CCGCAGCCAGCGGCTGACGCTGCGCTTCGTGCCCGTGGACCGCGAGGACAACACCTACTCGTACA

AAGTGCGCTACACGCTGGCCGTGGGCGACAACCGCGTGCTGGACATGGCCAGCACCTACTTTGAC

ATCCGCGGCGTGCTGGATCGGGGCCCTAGCTTCAAACCCTACTCCGGCACCGCCTACAACAGTCT

GGCCCCCAAGGGAGCACCCAACACTTGTCAGTGGACATATAAAGCCGATGGTGAAACTGCCACAG

AAAAAACCTATACATATGGAAATGCACCCGTGCAGGGCATTAACATCACAAAAGATGGTATTCAA

CTTGGAACTGACACCGATGATCAGCCAATCTACGCAGATAAAACCTATCAGCCTGAACCTCAAGT

GGGTGATGCTGAATGGCATGACATCACTGGTACTGATGAAAAGTATGGAGGCAGAGCTCTTAAGC

CTGATACCAAAATGAAGCCTTGTTATGGTTCTTTTGCCAAGCCTACTAATAAAGAAGGAGGTCAG

GCAAATGTGAAAACAGGAACAGGCACTACTAAAGAATATGACATAGACATGGCTTTCTTTGACAA

CAGAAGTGCGGCTGCTGCTGGCCTAGCTCCAGAAATTGTTTTGTATACTGAAAATGTGGATTTGG

AAACTCCAGATACCCATATTGTATACAAAGCAGGCACAGATGACAGCAGCTCTTCTATTAATTTG

GGTCAGCAAGCCATGCCCAACAGACCTAACTACATTGGTTTCAGAGACAACTTTATCGGGCTCAT

GTACTACAACAGCACTGGCAATATGGGGGTGCTGGCCGGTCAGGCTTCTCAGCTGAATGCTGTGG

TTGACTTGCAAGACAGAAACACCGAGCTGTCCTACCAGCTCTTGCTTGACTCTCTGGGTGACAGA

ACCCGGTATTTCAGTATGTGGAATCAGGCGGTGGACAGCTATGATCCTGATGTGCGCATTATTGA

AAATCATGGTGTGGAGGATGAACTTCCCAACTATTGTTTCCCTCTGGATGCTGTTGGCAGAACAG

ATACTTATCAGGGAATTAAGGCTAATGGAACTGATCAAACCACATGGACCAAAGATGACAGTGTC

AATGATGCTAATGAGATAGGCAAGGGTAATCCATTCGCCATGGAAATCAACATCCAAGCCAACCT

GTGGAGGAACTTCCTCTACGCCAACGTGGCCCTGTACCTGCCCGACTCTTACAAGTACACGCCGG

CCAATGTTACCCTGCCCACCAACACCAACACCTACGATTACATGAACGGCCGGGTGGTGGCCCCC

TCGCTGGTGGACTCCTACATCAACATCGGGGCGCGCTGGTCGCTGGATCCCATGGACAACGTGAA

CCCCTTCAACCACCACCGCAATGCGGGGCTGCGCTACCGCTCCATGCTCCTGGGCAACGGGCGCT

ACGTGCCCTTCCACATCCAGGTGCCCCAGAAATTTTTCGCCATCAAGAGCCTCCTGCTCCTGCCC

GGGTCCTACACCTACGAGTGGAACTTCCGCAAGGACGTCAACATGATCCTGCAGAGCTCCCTCGG

CAACGACCTGCGCACGGACGGGGCCTCCATCTCCTTCACCAGCATCAACCTCTACGCCACCTTCT

TCCCCATGGCGCACAACACGGCCTCCACGCTCGAGGCCATGCTGCGCAACGACACCAACGACCAG

TCCTTCAACGACTACCTCTCGGCGGCCAACATGCTCTACCCCATCCCGGCCAACGCCACCAACGT

-continued

GCCCATCTCCATCCCCTCGCGCAACTGGGCCGCCTTCCGCGGCTGGTCCTTCACGCGTCTCAAGA

CCAAGGAGACGCCCTCGCTGGGCTCCGGGTTCGACCCCTACTTCGTCTACTGGGGCTCCATCCCC

TACCTCGACGGCACCTTCTACCTCAACCACACCTTCAAGAAGGTCTCCATCACCTTCGACTCCTC

CGTCAGCTGGCCCGGCAACGACCGGCTCCTGACGCCCAACGAGTTCGAAATCAAGCGCACCGTCG

ACGGCGAGGGCTACAACGTGGCCCAGTGCAACATGACCAAGGACTGGTTCCTGGTCCAGATGCTG

GCCCACTACAACATCGGCTACCAGGGCTTCTACGTGCCCGAGGGCTACAAGGACCGCATGTACTC

CTTCTTCCGCAACTTCCAGCCCATGAGCCGCCAGGTGGTGGACGAGGTCAACTACAAGGACTACC

AGGCCGTCACCCTGGCCTACCAGCACAACAACTGGGGCTTCGTCGGCTACCTCGCGCCCACCATG

CGCCAGGGCCAGCCCTACCCCGCCAACTACCCCTACCCGCTCATCGGCAAGAGCGCCGTCACCAG

CGTCACCCAGAAAAAGTTCCTCTGCGACAGGGTCATGTGGCGCATCCCCTTCTCCAGCAACTTCA

TGTCCATGGGCGCGCTCACCGACCTCGGCCAGAACATGCTCTATGCCAACTCCGCCCACGCGCTA

GACATGAATTTCGAAGTCGACCCCATGGATGAGTCCACCCTTCTCTATGTTGTCTTCGAAGTCTT

CGACGTCGTCCGAGTGCACCAGCCCCACCGCGGCGTCATCGAGGCCGTCTACCTGCGCACCCCCT

TCTCGGCCGGTAACGCCACCACCTAAGCTCTTGCTTCTTGCAAGCCATGGCCGCGGGCTCCGGCG

AGCAGGAGCTCAGGGCCATCATCCGCGACCTGGGCTGCGGGCCCTACTTCCTGGGCACCTTCGAT

AAGCGCTTCCCGGGATTCATGGCCCCGCACAAGCTGGCCTGCGCCATCGTCAACACGGCCGGCCG

CGAGACCGGGGGCGAGCACTGGCTGGCCTTCGCCTGGAACCCGCGCTCGAACACCTGCTACCTCT

TCGACCCCTTCGGGTTCTCGGACGAGCGCCTCAAGCAGATCTACCAGTTCGAGTACGAGGGCCTG

CTGCGCCGCAGCGCCCTGGCCACCGAGGACCGCTGCGTCACCCTGGAAAAGTCCACCCAGACCGT

GCAGGGTCCGCGCTCGGCCGCCTGCGGGCTCTTCTGCTGCATGTTCCTGCACGCCTTCGTGCACT

GGCCCGACCGCCCCATGGACAAGAACCCCACCATGAACTTGCTGACGGGGGTGCCCAACGGCATG

CTCCAGTCGCCCCAGGTGGAACCCACCCTGCGCCGCAACCAGGAGGCGCTCTACCGCTTCCTCAA

CTCCCACTCCGCCTACTTTCGCTCCCACCGCGCGCGCATCGAGAAGGCCACCGCCTTCGACCGCA

TGAATCAAGACATGTAAACCGTGTGTGTATGTTAAATGTCTTTAATAAACAGCACTTTCATGTTA

CACATGCATCTGAGATGATTTATTTAGAAATCGAAAGGGTTCTGCCGGGTCTCGGCATGGCCCGC

GGGCAGGGACACGTTGCGGAACTGGTACTTGGCCAGCCACTTGAACTCGGGGATCAGCAGTTTGG

GCAGCGGGGTGTCGGGGAAGGAGTCGGTCCACAGCTTCCGCGTCAGTTGCAGGGCGCCCAGCAGG

TCGGGCGCGGAGATCTTGAAATCGCAGTTGGGACCCGCGTTCTGCGCGCGGGAGTTGCGGTACAC

GGGGTTGCAGCACTGGAACACCATCAGGGCCGGGTGCTTCACGCTCGCCAGCACCGTCGCGTCGG

TGATGCTCTCCACGTCGAGGTCCTCGGCGTTGGCCATCCCGAAGGGGGTCATCTTGCAGGTCTGC

CTTCCCATGGTGGGCACGCACCCGGGCTTGTGGTTGCAATCGCAGTGCAGGGGGATCAGCATCAT

CTGGGCCTGGTCGGCGTTCATCCCCGGGTACATGGCCTTCATGAAAGCCTCCAATTGCCTGAACG

CCTGCTGGGCCTTGGCTCCCTCGGTGAAGAAGACCCCGCAGGACTTGCTAGAGAACTGGTTGGTG

GCGCACCCGGCGTCGTGCACGCAGCAGCGCGCGTCGTTGTTGGCCAGCTGCACCACGCTGCGCCC

CCAGCGGTTCTGGGTGATCTTGGCCCGGTCGGGGTTCTCCTTCAGCGCGCGCTGCCCGTTCTCGC

TCGCCACATCCATCTCGATCATGTGCTCCTTCTGGATCATGGTGGTCCCGTGCAGGCACCGCAGC

TTGCCCTCGGCCTCGGTGCACCCGTGCAGCCACAGCGCGCACCCGGTGCACTCCCAGTTCTTGTG

GGCGATCTGGGAATGCGCGTGCACGAAGCCCTGCAGGAAGCGGCCCATCATGGTGGTCAGGGTCT

TGTTGCTAGTGAAGGTCAGCGGAATGCCGCGGTGCTCCTCGTTGATGTACAGGTGGCAGATGCGG

CGGTACACCTCGCCCTGCTCGGGCATCAGCTGGAAGTTGGCTTTCAGGTCGGTCTCCACGCGGTA

-continued

GCGGTCCATCAGCATAGTCATGATTTCCATACCCTTCTGCCAGGCCGAGACGATGGGCAGGCTCA

TAGGGTTCTTCACCATCATCTTAGCGCTAGCAGCCGCGGCCAGGGGGTCGCTCTCGTCCAGGGTC

TCAAAGCTCCGCTTGCCGTCCTTCTCGGTGATCCGCACCGGGGGGTAGCTGAAGCCCACGGCCGC

CAGCTCCTCCTCGGCCTGTCTTTCGTCCTCGCTGTCCTGGCTGACGTCCTGCAGGACCACATGCT

TGGTCTTGCGGGGTTTCTTCTTGGGCGGCAGCGGCGGCGGAGATGTTGGAGATGGCGAGGGGGAG

CGCGAGTTCTCGCTCACCACTACTATCTCTTCCTCTTCTTGGTCCGAGGCCACGCGGCGGTAGGT

ATGTCTCTTCGGGGGCAGAGGCGGAGGCGACGGGCTCTCGCCGCCGCGACTTGGGGGATGGCTGG

CAGAGCCCCTTCCGCGTTCGGGGGTGCGCTCCCGGCGGCGCTCTGACTGACTTCCTCCGCGGCCG

GCCATTGTGTTCTCCTAGGGAGGAACAACAAGCATGGAGACTCAGCCATCGCCAACCTCGCCATC

TGCCCCCACCGCCGACGAGAAGCAGCAGCAGCAGAATGAAAGCTTAACCGCCCCGCCGCCCAGCC

CCGCCACCTCCGACGCGGCCGTCCCAGACATGCAAGAGATGGAGGAATCCATCGAGATTGACCTG

GGCTATGTGACGCCCGCGGAGCACGAGGAGGAGCTGGCAGTGCGCTTTTCACAAGAAGAGATACA

CCAAGAACAGCCAGAGCAGGAAGCAGAGAATGAGCAGAGTCAGGCTGGGCTCGAGCATGACGGCG

ACTACCTCCACCTGAGCGGGGGGGAGGACGCGCTCATCAAGCATCTGGCCCGGCAGGCCACCATC

GTCAAGGATGCGCTGCTCGACCGCACCGAGGTGCCCCTCAGCGTGGAGGAGCTCAGCCGCGCCTA

CGAGTTGAACCTCTTCTCGCCGCGCGTGCCCCCCAAGCGCCAGCCCAATGGCACCTGCGAGCCCA

ACCCGCGCCTCAACTTCTACCCGGTCTTCGCGGTGCCCGAGGCCCTGGCCACCTACCACATCTTT

TTCAAGAACCAAAAGATCCCCGTCTCCTGCCGCGCCAACCGCACCCGCGCCGACGCCCTTTTCAA

CCTGGGTCCCGGCGCCCCCCTACCTGATATCGCCTCCTTGGAAGAGGTTCCCAAGATCTTCGAGG

GTCTGGGCAGCGACGAGACTCGGGCCCCGAACGCTCTGCAAGGAGAAGGAGGAGAGCATGAGCAC

CACAGCGCCCTGGTCGAGTTGGAAGGCGACAACGCGCGGCTGGCGGTGCTCAAACGCACGGTCGA

GCTGACCCATTTCGCCTACCCGGCTCTGAACCTGCCCCCCAAAGTCATGAGCGCGGTCATGGACC

AGGTGCTCATCAAGCGCGCGTCGCCCATCTCCGAGGACGAGGGCATGCAAGACTCCGAGGAGGGC

AAGCCCGTGGTCAGCGACGAGCAGCTGGCCCGGTGGCTGGGTCCTAATGCTAGTCCCCAGAGTTT

GGAAGAGCGGCGCAAACTCATGATGGCCGTGGTCCTGGTGACCGTGGAGCTGGAGTGCCTGCGCC

GCTTCTTCGCCGACGCGGAGACCCTGCGCAAGGTCGAGGAGAACCTGCACTACCTCTTCAGGCAC

GGGTTCGTGCGCCAGGCCTGCAAGATCTCCAACGTGGAGCTGACCAACCTGGTCTCCTACATGGG

CATCTTGCACGAGAACCGCCTGGGGCAGAACGTGCTGCACACCACCCTGCGCGGGGAGGCCCGGC

GCGACTACATCCGCGACTGCGTCTACCTCTACCTCTGCCACACCTGGCAGACGGGCATGGGCGTG

TGGCAGCAGTGTCTGGAGGAGCAGAACCTGAAAGAGCTCTGCAAGCTCCTGCAGAAGAACCTCAA

GGGTCTGTGGACCGGGTTCGACGAGCGCACCACCGCCTCGGACCTGGCCGACCTCATTTTCCCCG

AGCGCCTCAGGCTGACGCTGCGCAACGGCCTGCCCGACTTTATGAGCCAAAGCATGTTGCAAAAC

TTTCGCTCTTTCATCCTGGAACGCTCCGGAATCCTGCCCGCCACCTGCTCCGCGCTGCCCTCGGA

CTTCGTGCCGCTGACCTTCCGCGAGTGCCCCCCGCCGCTGTGGAGCCACTGCTACCTGCTGCGCC

TGGCCAACTACCTGGCCTACCACTCGGACGTGATCGAGGACGTCAGCGGCGAGGGCCTGCTCGAG

TGCCACTGCCGCTGCAACCTCTGCACGCCGCACCGCTCCCTGGCCTGCAACCCCCAGCTGCTGAG

CGAGACCCAGATCATCGGCACCTTCGAGTTGCAAGGGCCCAGCGAAGGCGAGGGTTCAGCCGCCA

AGGGGGGTCTGAAACTCACCCCGGGGCTGTGGACCTCGGCCTACTTGCGCAAGTTCGTGCCCGAG

GACTACCATCCCTTCGAGATCAGGTTCTACGAGGACCAATCCCATCCGCCCAAGGCCGAGCTGTC

-continued

GGCCTGCGTCATCACCCAGGGGGCGATCCTGGCCCAATTGCAAGCCATCCAGAAATCCCGCCAAG

AATTCTTGCTGAAAAAGGGCCGCGGGGTCTACCTCGACCCCCAGACCGGTGAGGAGCTCAACCCC

GGCTTCCCCCAGGATGCCCCGAGGAAACAAGAAGCTGAAAGTGGAGCTGCCCCCCGTGGAGGATT

TGGAGGAAGACTGGGAGAACAGCAGTCAGGCAGAGGAGGAGGAGATGGAGGAAGACTGGGACAGC

ACTCAGGCAGAGGAGGACAGCCTGCAAGACAGTCTGGAGGAAGACGAGGAGGAGGCAGAGGAGGA

GGTGGAAGAAGCAGCCGCCGCCAGACCGTCGTCCTCGGCGGGGGAGAAAGCAAGCAGCACGGATA

CCATCTCCGCTCCGGGTCGGGGTCCCGCTCGACCACACAGTAGATGGGACGAGACCGGACGATTC

CCGAACCCCACCACCCAGACCGGTAAGAAGGAGCGGCAGGGATACAAGTCCTGGCGGGGGCACAA

AAACGCCATCGTCTCCTGCTTGCAGGCCTGCGGGGGCAACATCTCCTTCACCCGGCGCTACCTGC

TCTTCCACCGCGGGGTGAACTTTCCCCGCAACATCTTGCATTACTACCGTCACCTCCACAGCCCC

TACTACTTCCAAGAAGAGGCAGCAGCAGCAGAAAAAGACCAGCAGAAAACCAGCAGCTAGAAAAT

CCACAGCGGCGGCAGCAGGTGGACTGAGGATCGCGGCGAACGAGCCGGCGCAAACCCGGGAGCTG

AGGAACCGGATCTTTCCCACCCTCTATGCCATCTTCCAGCAGAGTCGGGGGCAGGAGCAGGAACT

GAAAGTCAAGAACCGTTCTCTGCGCTCGCTCACCCGCAGTTGTCTGTATCACAAGAGCGAAGACC

AACTTCAGCGCACTCTCGAGGACGCCGAGGCTCTCTTCAACAAGTACTGCGCGCTCACTCTTAAA

GAGTAGCCCGCGCCCGCCCAGTCGCAGAAAAAGGCGGGAATTACGTCACCTGTGCCCTTCGCCCT

AGCCGCCTCCACCCATCATCATGAGCAAAGAGATTCCCACGCCTTACATGTGGAGCTACCAGCCC

CAGATGGGCCTGGCCGCCGGTGCCGCCCAGGACTACTCCACCCGCATGAATTGGCTCAGCGCCGG

GCCCGCGATGATCTCACGGGTGAATGACATCCGCGCCCACCGAAACCAGATACTCCTAGAACAGT

CAGCGCTCACCGCCACGCCCCGCAATCACCTCAATCCGCGTAATTGGCCCGCCGCCCTGGTGTAC

CAGGAAATTCCCCAGCCCACGACCGTACTACTTCCGCGAGACGCCCAGGCCGAAGTCCAGCTGAC

TAACTCAGGTGTCCAGCTGGCGGGCGGCGCCACCCTGTGTCGTCACCGCCCCGCTCAGGGTATAA

AGCGGCTGGTGATCCGGGGCAGAGGCACACAGCTCAACGACGAGGTGGTGAGCTCTTCGCTGGGT

CTGCGACCTGACGGAGTCTTCCAACTCGCCGGATCGGGGAGATCTTCCTTCACGCCTCGTCAGGC

CGTCCTGACTTTGGAGAGTTCGTCCTCGCAGCCCCGCTCGGGTGGCATCGGCACTCTCCAGTTCG

TGGAGGAGTTCACTCCCTCGGTCTACTTCAACCCCTTCTCCGGCTCCCCCGGCCACTACCCGGAC

GAGTTCATCCCGAACTTCGACGCCATCAGCGAGTCGGTGGACGGCTACGATTGAATGTCCCATGG

TGGCGCAGCTGACCTAGCTCGGCTTCGACACCTGGACCACTGCCGCCGCTTCCGCTGCTTCGCTC

GGGATCTCGCCGAGTTTGCCTACTTTGAGCTGCCCGAGGAGCACCCTCAGGGCCCGGCCCACGGA

GTGCGGATCGTCGTCGAAGGGGGCCTCGACTCCCACCTGCTTCGGATCTTCAGCCAGCGTCCGAT

CCTGGTCGAGCGCGAGCAAGGACAGACCCTTCTGACTCTGTACTGCATCTGCAACCACCCCGGCC

TGCATGAAAGTCTTTGTTGTCTGCTGTGTACTGAGTATAATAAAAGCTGAGATCAGCGACTACTC

CGGACTTCCGTGTGTTCCTGAATCCATCAACCAGTCTTTGTTCTTCACCGGGAACGAGACCGAGC

TCCAGCTCCAGTGTAAGCCCCACAAGAAGTACCTCACCTGGCTGTTCCAGGGCTCCCCGATCGCC

GTTGTCAACCACTGCGACAACGACGGAGTCCTGCTGAGCGGCCCTGCCAACCTTACTTTTTCCAC

CCGCAGAAGCAAGCTCCAGCTCTTCCAACCCTTCCTCCCCGGGACCTATCAGTGCGTCTCGGGAC

CCTGCCATCACACCTTCCACCTGATCCCGAATACCACAGCGTCGCTCCCCGCTACTAACAACCAA

ACTAACCTCCACCAACGCCACCGTCGCGACGGCCACAATACATGCCCATATTAGACTATGAGGCC

GAGCCACAGCGACCCATGCTCCCCGCTATTAGTTACTTCAATCTAACCGGCGGAGATGACTGACC

CACTGGCCAACAACAACGTCAACGACCTTCTCCTGGACATGGACGGCCGCGCCTCGGAGCAGCGA

-continued

CTCGCCCAACTTCGCATTCGCCAGCAGCAGGAGAGAGCCGTCAAGGAGCTGCAGGATGCGGTGGC

CATCCACCAGTGCAAGAGAGGCATCTTCTGCCTGGTGAAACAGGCCAAGATCTCCTACGAGGTCA

CTCCAAACGACCATCGCCTCTCCTACGAGCTCCTGCAGCAGCGCCAGAAGTTCACCTGCCTGGTC

GGAGTCAACCCCATCGTCATCACCCAGCAGTCTGGCGATACCAAGGGGTGCATCCACTGCTCCTG

CGACTCCCCCGACTGCGTCCACACTCTGATCAAGACCCTCTGCGGCCTCCCCGACCTCCTCCCCA

TGAACTAATCACCCCCTTATCCAGTGAAATAAAGATCATATTGATGATGATTTTACAGAAATAAA

AAATAATCATTTGATTTGAAATAAAGATACAATCATATTGATGATTTGAGTTTAACAAAAAAATA

AAGAATCACTTACTTGAAATCTGATACCAGGTCTCTGTCCATGTTTTCTGCCAACACCACTTCAC

TCCCCTCTTCCCAGCTCTGGTACTGCAGGCCCCGGCGGGCTGCAAACTTCCTCCACACGCTGAAG

GGGATGTCAAATTCCTCCTGTCCCTCAATCTTCATTTTATCTTCTATCAGATGTCCAAAAAGCGC

GTCCGGGTGGATGATGACTTCGACCCCGTCTACCCCTACGATGCAGACAACGCACCGACCGTGCC

CTTCATCAACCCCCCCTTCGTCTCTTCAGATGGATTCCAAGAGAAGCCCCTGGGGGTGTTGTCCC

TGCGACTGGCCGACCCCGTCACCACCAAGAACGGGGAAATCACCCTCAAGCTGGGAGAGGGGGTG

GACCTCGATTCCTCGGGAAAACTCATCTCCAACACGGCCACCAAGGCCGCCGCCCCTCTCAGTTT

TTCCAACAACACCATTTCCCTTAACATGGATCACCCCTTTTACACTAAAGATGGAAAATTATCCT

TACAAGTTTCTCCACCATTAAATATACTGAGAACAAGCATTCTAAACACACTAGCTTTAGGTTTT

GGATCAGGTTTAGGACTCCGTGGCTCTGCCTTGGCAGTACAGTTAGTCTCTCCACTTACATTTGA

TACTGATGGAAACATAAAGCTTACCTTAGACAGAGGTTTGCATGTTACAACAGGAGATGCAATTG

AAAGCAACATAAGCTGGGCTAAAGGTTTAAAATTTGAAGATGGAGCCATAGCAACCAACATTGGA

AATGGGTTAGAGTTTGGAAGCAGTAGTACAGAAACAGGTGTTGATGATGCTTACCCAATCCAAGT

TAAACTTGGATCTGGCCTTAGCTTTGACAGTACAGGAGCCATAATGGCTGGTAACAAAGAAGACG

ATAAACTCACTTTGTGGACAACACCTGATCCATCACCAAACTGTCAAATACTCGCAGAAAATGAT

GCAAAACTAACACTTTGCTTGACTAAATGTGGTAGTCAAATACTGGCCACTGTGTCAGTCTTAGT

TGTAGGAAGTGGAAACCTAAACCCCATTACTGGCACCGTAAGCAGTGCTCAGGTGTTTCTACGTT

TTGATGCAAACGGTGTTCTTTTAACAGAACATTCTACACTAAAAAAATACTGGGGGTATAGGCAG

GGAGATAGCATAGATGGCACTCCATATACCAATGCTGTAGGATTCATGCCCAATTTAAAAGCTTA

TCCAAAGTCACAAAGTTCTACTACTAAAAATAATATAGTAGGGCAAGTATACATGAATGGAGATG

TTTCAAAACCTATGCTTCTCACTATAACCCTCAATGGTACTGATGACAGCAACAGTACATATTCA

ATGTCATTTTCATACACCTGGACTAATGGAAGCTATGTTGGAGCAACATTTGGGGCTAACTCTTA

TACCTTCTCATACATCGCCCAAGAATGAACACTGTATCCCACCCTGCATGCCAACCCTTCCCACC

CCACTCTGTGGAACAAACTCTGAAACACAAAATAAAATAAAGTTCAAGTGTTTTATTGATTCAAC

AGTTTTACAGGATTCGAGCAGTTATTTTTCCTCCACCCTCCCAGGACATGGAATACACCACCCTC

TCCCCCCGCACAGCCTTGAACATCTGAATGCCATTGGTGATGGACATGCTTTTGGTCTCCACGTT

CCACACAGTTTCAGAGCGAGCCAGTCTCGGGTCGGTCAGGGAGATGAAACCCTCCGGGCACTCCC

GCATCTGCACCTCACAGCTCAACAGCTGAGGATTGTCCTCGGTGGTCGGGATCACGGTTATCTGG

AAGAAGCAGAAGAGCGGCGGTGGGAATCATAGTCCGCGAACGGGATCGGCCGGTGGTGTCGCATC

AGGCCCCGCAGCAGTCGCTGCCGCCGCCGCTCCGTCAAGCTGCTGCTCAGGGGGTCCGGGTCCAG

GGACTCCCTCAGCATGATGCCCACGGCCCTCAGCATCAGTCGTCTGGTGCGGCGGGCGCAGCAGC

GCATGCGGATCTCGCTCAGGTCGCTGCAGTACGTGCAACACAGAACCACCAGGTTGTTCAACAGT

-continued

CCATAGTTCAACACGCTCCAGCCGAAACTCATCGCGGGAAGGATGCTACCCACGTGGCCGTCGTA

CCAGATCCTCAGGTAAATCAAGTGGTGCCCCCTCCAGAACACGCTGCCCACGTACATGATCTCCT

TGGGCATGTGGCGGTTCACCACCTCCCGGTACCACATCACCCTCTGGTTGAACATGCAGCCCCGG

ATGATCCTGCGGAACCACAGGGCCAGCACCGCCCCGCCCGCCATGCAGCGAAGAGACCCCGGGTC

CCGGCAATGGCAATGGAGGACCCACCGCTCGTACCCGTGGATCATCTGGGAGCTGAACAAGTCTA

TGTTGGCACAGCACAGGCATATGCTCATGCATCTCTTCAGCACTCTCAACTCCTCGGGGGTCAAA

ACCATATCCCAGGGCACGGGGAACTCTTGCAGGACAGCGAACCCCGCAGAACAGGGCAATCCTCG

CACAGAACTTACATTGTGCATGGACAGGGTATCGCAATCAGGCAGCACCGGGTGATCCTCCACCA

GAGAAGCGCGGGTCTCGGTCTCCTCACAGCGTGGTAAGGGGGCCGGCCGATACGGGTGATGGCGG

GACGCGGCTGATCGTGTTCGCGACCGTGTCATGATGCAGTTGCTTTCGGACATTTTCGTACTTGC

TGTAGCAGAACCTGGTCCGGGCGCTGCACACCGATCGCCGGCGGCGGTCTCGGCGCTTGGAACGC

TCGGTGTTGAAATTGTAAAACAGCCACTCTCTCAGACCGTGCAGCAGATCTAGGGCCTCAGGAGT

GATGAAGATCCCATCATGCCTGATGGCTCTGATCACATCGACCACCGTGGAATGGGCCAGACCCA

GCCAGATGATGCAATTTTGTTGGGTTTCGGTGACGGCGGGGGAGGGAAGAACAGGAAGAACCATG

ATTAACTTTTAATCCAAACGGTCTCGGAGTACTTCAAAATGAAGATCGCGGAGATGGCACCTCTC

GCCCCCGCTGTGTTGGTGGAAAATAACAGCCAGGTCAAAGGTGATACGGTTCTCGAGATGTTCCA

CGGTGGCTTCCAGCAAAGCCTCCACGCGCACATCCAGAAACAAGACAATAGCGAAAGCGGGAGGG

TTCTCTAATTCCTCAATCATCATGTTACACTCCTGCACCATCCCCAGATAATTTTCATTTTTCCA

GCCTTGAATGATTCGAACTAGTTCGTGAGGTAAATCCAAGCCAGCCATGATAAAGAGCTCGCGCA

GAGCGCCCTCCACCGGCATTCTTAAGCACACCCTCATAATTCCAAGATATTCTGCTCCTGGTTCA

CCTGCAGCAGATTGACAAGCGGAATATCAAAATCTCTGCCGCGATCCCTGAGCTCCTCCCTCAGC

AATAACTGTAAGTACTCTTTCATATCCTCTCCGAAATTTTTAGCCATAGGACCACCAGGAATAAG

ATTAGGGCAAGCCACAGTACAGATAAACCGAAGTCCTCCCCAGTGAGCATTGCCAAATGCAAGAC

TGCTATAAGCATGCTGGCTAGACCCGGTGATATCTTCCAGATAACTGGACAGAAAATCGCCCAGG

CAATTTTTAAGAAAATCAACAAAAGAAAAATCCTCCAGGTGGACGTTTAGAGCCTCGGGAACAAC

GATGAAGTAAATGCAAGCGGTGCGTTCCAGCATGGTTAGTTAGCTGATCTGTAGAAAAAACAAAA

ATGAACATTAAACCATGCTAGCCTGGCGAACAGGTGGGTAAATCGTTCTCTCCAGCACCAGGCAG

GCCACGGGGTCTCCGGCGCGACCCTCGTAAAAATTGTCGCTATGATTGAAAACCATCACAGAGAG

ACGTTCCCGGTGGCCGGCGTGAATGATTCGACAAGATGAATACACCCCCGGAACATTGGCGTCCG

CGAGTGAAAAAAAGCGCCCGAGGAAGCAATAAGGCACTACAATGCTCAGTCTCAAGTCCAGCAAA

GCGATGCCATGCGGATGAAGCACAAAATTCTCAGGTGCGTACAAAATGTAATTACTCCCCTGCTG

CACAGGCAGCAAAGCCCCCGATCCCTCCAGGTACACATACAAAGCCTCAGCGTCCATAGCTTACC

GAGCAGCAGCACACAACAGGCGCAAGAGTCAGAGAAAGGCTGAGCTCTAACCTGTCCACCCGCTC

TCTGCTCAATATATAGCCCAGATCTACACTGACGTAAAGGCCAAAGTCTAAAAATACCCGCCAAA

TAATCACACACGCCCAGCACACGCCCAGAAACCGGTGACACACTCAAAAAAATACGCGCACTTCC

TCAAACGCCCAAAACTGCCGTCATTTCCGGGTTCCCACGCTACGTCATCAAAACACGACTTTCAA

ATTCCGTCGACCGTTAAAAACGTCACCCGCCCCGCCCCTAACGGTCGCCCGTCTCTCAGCCAATC

AGCGCCCCGCATCCCCAAATTCAAACACCTCATTTGCATATTAACGCGCACAAAAAGTTTGAGGT

ATATTATTGATGATGG

ChAdV68.4WTnt.MAG25mer (SEQ ID NO: 12); AC_000011.1 with
E1 (nt 577 to 3403) and E3 (nt 27,816-31,332) sequences
deleted; corresponding ATCC VR-594 nucleotides substituted
at four positions; model neoantigen cassette under the
control of the CMV promoter/enhancer inserted in place
of deleted E1

CCATCTTCAATAATATACCTCAAACTTTTTGTGCGCGTTAATATGCAAATGAGGCGTTTGAATTT

GGGGAGGAAGGGCGGTGATTGGTCGAGGGATGAGCGACCGTTAGGGGGGGGGCGAGTGACGTTTT

GATGACGTGGTTGCGAGGAGGAGCCAGTTTGCAAGTTCTCGTGGGAAAAGTGACGTCAAACGAGG

TGTGGTTTGAACACGGAAATACTCAATTTTCCCGCGCTCTCTGACAGGAAATGAGGTGTTTCTGG

GCGGATGCAAGTGAAAACGGGCCATTTTCGCGCGAAAACTGAATGAGGAAGTGAAAATCTGAGTA

ATTTCGCGTTTATGGCAGGGAGGAGTATTTGCCGAGGGCCGAGTAGACTTTGACCGATTACGTGG

GGGTTTCGATTACCGTGTTTTTCACCTAAATTTCCGCGTACGGTGTCAAAGTCCGGTGTTTTTAC

GTAGGTGTCAGCTGATCGCCAGGGTATTTAAACCTGCGCTCTCCAGTCAAGAGGCCACTCTTGAG

TGCCAGCGAGAAGAGTTTTCTCCTCCGCGCCGCGAGTCAGATCTACACTTTGAAAGTAGGGATAA

CAGGGTAATgacattgattattgactagttGttaaTAGTAATCAATTACGGGGTCATTAGTTCAT

AGCCCATATATGGAGTTCCGCGTTACATAACTTACGGTAAATGGCCCGCCTGGCTGACCGCCCAA

CGACCCCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGTATCAT

ATGCCAAGTCCGCCCCCTATTGACGTCAATGACGGTAAATGGCCCGCCTGGCATTATGCCCAGTA

CATGACCTTACGGGACTTTCCTACTTGGCAGTACATCTACGTATTAGTCATCGCTATTACCATGg

TGATGCGGTTTTGGCAGTACACCAATGGGCGTGGATAGCGGTTTGACTCACGGGGATTTCCAAGT

CTCCACCCCATTGACGTCAATGGGAGTTTGTTTTGGCACCAAAATCAACGGGACTTTCCAAAATG

TCGTAATAACCCCGCCCCGTTGACGCAAATGGGCGGTAGGCGTGTACGGTGGGAGGTCTATATAA

GCAGAgcTCGTTTAGTGAACCGTCAGATCGCCTGGAACGCCATCCACGCTGTTTTGACCTCCATA

GAAGACAGCGATCGCGccacCATGGCCGGGATGTTCCAGGCACTGTCCGAAGGCTGCACACCCTA

TGATATTAACCAGATGCTGAATGTCCTGGGAGACCACCAGGTCTCTGGCCTGGAGCAGCTGGAGA

GCATCATCAACTTCGAGAAGCTGACCGAGTGGACAAGCTCCAATGTGATGCCTATCCTGTCCCCA

CTGACCAAGGGCATCCTGGGCTTCGTGTTTACCCTGACAGTGCCTTCTGAGCGGGGCCTGTCTTG

CATCAGCGAGGCAGACGCAACCACACCAGAGTCCGCCAATCTGGGCGAGGAGATCCTGTCTCAGC

TGTACCTGTGGCCCCGGGTGACATATCACTCCCCTTCTTACGCCTATCACCAGTTCGAGCGGAGA

GCCAAGTACAAGAGACACTTCCCAGGCTTTGGCCAGTCTCTGCTGTTCGGCTACCCCGTGTACGT

GTTCGGCGATTGCGTGCAGGGCGACTGGGATGCCATCCGGTTTAGATACTGCGCACCACCTGGAT

ATGCACTGCTGAGGTGTAACGACACCAATTATTCCGCCCTGCTGGCAGTGGGCGCCCTGGAGGGC

CCTCGCAATCAGGATTGGCTGGGCGTGCCAAGGCAGCTGGTGACACGCATGCAGGCCATCCAGAA

CGCAGGCCTGTGCACCCTGGTGGCAATGCTGGAGGAGACAATCTTCTGGCTGCAGGCCTTTCTGA

TGGCCCTGACCGACAGCGGCCCCAAGACAAACATCATCGTGGATTCCCAGTACGTGATGGGCATC

TCCAAGCCTTCTTTCCAGGAGTTTGTGGACTGGGAGAACGTGAGCCCAGAGCTGAATTCCACCGA

TCAGCCATTCTGGCAGGCAGGAATCCTGGCAAGGAACCTGGTGCCTATGGTGGCCACAGTGCAGG

GCCAGAATCTGAAGTACCAGGGCCAGAGCCTGGTCATCAGCGCCTCCATCATCGTGTTTAACCTG

CTGGAGCTGGAGGGCGACTATCGGGACGATGGCAACGTGTGGGTGCACACCCCACTGAGCCCCAG

AACACTGAACGCCTGGGTGAAGGCCGTGGAGGAGAAGAAGGGCATCCCAGTGCACCTGGAGCTGG

-continued

CCTCCATGACCAATATGGAGCTGATGTCTAGCATCGTGCACCAGCAGGTGAGGACATACGGACCC

GTGTTCATGTGCCTGGGAGGCCTGCTGACCATGGTGGCAGGAGCCGTGTGGCTGACAGTGCGGGT

GCTGGAGCTGTTCAGAGCCGCCCAGCTGGCCAACGATGTGGTGCTGCAGATCATGGAGCTGTGCG

GAGCAGCCTTTCGCCAGGTGTGCCACACCACAGTGCCATGGCCCAATGCCTCCCTGACCCCCAAG

TGGAACAATGAGACAACACAGCCTCAGATCGCCAACTGTAGCGTGTACGACTTCTTCGTGTGGCT

GCACTACTATAGCGTGAGGGATACCCTGTGGCCCCCCGTGACATACCACATGAATAAGTACGCCT

ATCACATGCTGGAGAGGCGCGCCAAGTATAAGAGAGGCCCTGGCCCAGGCGCAAAGTTTGTGGCA

GCATGGACCCTGAAGGCCGCCGCCGGCCCCGGCCCCGGCCAGTATATCAAGGCTAACAGTAAGTT

CATTGGAATCACAGAGCTGGGACCCGGACCTGGATAATGAGTTTAAACTCCCATTTAAATGTGAG

GGTTAATGCTTCGAGCAGACATGATAAGATACATTGATGAGTTTGGACAAACCACAACTAGAATG

CAGTGAAAAAAATGCTTTATTTGTGAAATTTGTGATGCTATTGCTTTATTTGTAACCATTATAAG

CTGCAATAAACAAGTTAACAACAACAATTGCATTCATTTTATGTTTCAGGTTCAGGGGGAGATGT

GGGAGGTTTTTTAAAGCAAGTAAAACCTCTACAAATGTGGTAAAATAACTATAACGGTCCTAAGG

TAGCGAGTGAGTAGTGTTCTGGGGCGGGGGAGGACCTGCATGAGGGCCAGAATAACTGAAATCTG

TGCTTTTCTGTGTGTTGCAGCAGCATGAGCGGAAGCGGCTCCTTTGAGGGAGGGGTATTCAGCCC

TTATCTGACGGGGCGTCTCCCCTCCTGGGCGGGAGTGCGTCAGAATGTGATGGGATCCACGGTGG

ACGGCCGGCCCGTGCAGCCCGCGAACTCTTCAACCCTGACCTATGCAACCCTGAGCTCTTCGTCG

TTGGACGCAGCTGCCGCCGCAGCTGCTGCATCTGCCGCCAGCGCCGTGCGCGGAATGGCCATGGG

CGCCGGCTACTACGGCACTCTGGTGGCCAACTCGAGTTCCACCAATAATCCCGCCAGCCTGAACG

AGGAGAAGCTGTTGCTGCTGATGGCCCAGCTCGAGGCCTTGACCCAGCGCCTGGGCGAGCTGACC

CAGCAGGTGGCTCAGCTGCAGGAGCAGACGCGGGCCGCGGTTGCCACGGTGAAATCCAAATAAAA

AATGAATCAATAAATAAACGGAGACGGTTGTTGATTTTAACACAGAGTCTGAATCTTTATTTGAT

TTTTCGCGCGCGGTAGGCCCTGGACCACCGGTCTCGATCATTGAGCACCCGGTGGATCTTTTCCA

GGACCCGGTAGAGGTGGGCTTGGATGTTGAGGTACATGGGCATGAGCCCGTCCCGGGGGTGGAGG

TAGCTCCATTGCAGGGCCTCGTGCTCGGGGGTGGTGTTGTAAATCACCCAGTCATAGCAGGGGCG

CAGGGCATGGTGTTGCACAATATCTTTGAGGAGGAGACTGATGGCCACGGGCAGCCCTTTGGTGT

AGGTGTTTACAAATCTGTTGAGCTGGGAGGGATGCATGCGGGGGGAGATGAGGTGCATCTTGGCC

TGGATCTTGAGATTGGCGATGTTACCGCCCAGATCCCGCCTGGGGTTCATGTTGTGCAGGACCAC

CAGCACGGTGTATCCGGTGCACTTGGGGAATTTATCATGCAACTTGGAAGGGAAGGCGTGAAAGA

ATTTGGCGACGCCTTTGTGCCCGCCCAGGTTTTCCATGCACTCATCCATGATGATGGCGATGGGC

CCGTGGGGGGGGCCTGGGCAAAGACGTTTCGGGGGTCGGACACATCATAGTTGTGGTCCTGGGTG

AGGTCATCATAGGCCATTTTAATGAATTTGGGGCGGAGGGTGCCGGACTGGGGGACAAAGGTACC

CTCGATCCCGGGGGCGTAGTTCCCCTCACAGATCTGCATCTCCCAGGCTTTGAGCTCGGAGGGGG

GGATCATGTCCACCTGCGGGGCGATAAAGAACACGGTTTCCGGGGCGGGGGAGATGAGCTGGGCC

GAAAGCAAGTTCCGGAGCAGCTGGGACTTGCCGCAGCCGGTGGGGCCGTAGATGACCCCGATGAC

CGGCTGCAGGTGGTAGTTGAGGGAGAGACAGCTGCCGTCCTCCCGGAGGAGGGGGGCCACCTCGT

TCATCATCTCGCGCACGTGCATGTTCTCGCGCACCAGTTCCGCCAGGAGGCGCTCTCCCCCCAGG

GATAGGAGCTCCTGGAGCGAGGCGAAGTTTTTCAGCGGCTTGAGTCCGTCGGCCATGGGCATTTT

GGAGAGGGTTTGTTGCAAGAGTTCCAGGCGGTCCCAGAGCTCGGTGATGTGCTCTACGGCATCTC

GATCCAGCAGACCTCCTCGTTTCGCGGGTTGGGACGGCTGCGGGAGTAGGGCACCAGACGATGGG

-continued

CGTCCAGCGCAGCCAGGGTCCGGTCCTTCCAGGGTCGCAGCGTCCGCGTCAGGGTGGTCTCCGTC

ACGGTGAAGGGGTGCGCGCCGGGCTGGGCGCTTGCGAGGGTGCGCTTCAGGCTCATCCGGCTGGT

CGAAAACCGCTCCCGATCGGCGCCCTGCGCGTCGGCCAGGTAGCAATTGACCATGAGTTCGTAGT

TGAGCGCCTCGGCCGCGTGGCCTTTGGCGCGGAGCTTACCTTTGGAAGTCTGCCCGCAGGCGGGA

CAGAGGAGGGACTTGAGGGCGTAGAGCTTGGGGGCGAGGAAGACGGACTCGGGGGCGTAGGCGTC

CGCGCCGCAGTGGGCGCAGACGGTCTCGCACTCCACGAGCCAGGTGAGGTCGGGCTGGTCGGGGT

CAAAAACCAGTTTCCCGCCGTTCTTTTTGATGCGTTTCTTACCTTTGGTCTCCATGAGCTCGTGT

CCCCGCTGGGTGACAAAGAGGCTGTCCGTGTCCCCGTAGACCGACTTTATGGGCCGGTCCTCGAG

CGGTGTGCCGCGGTCCTCCTCGTAGAGGAACCCCGCCCACTCCGAGACGAAAGCCCGGGTCCAGG

CCAGCACGAAGGAGGCCACGTGGGACGGGTAGCGGTCGTTGTCCACCAGCGGGTCCACCTTTTCC

AGGGTATGCAAACACATGTCCCCCTCGTCCACATCCAGGAAGGTGATTGGCTTGTAAGTGTAGGC

CACGTGACCGGGGGTCCCGGCCGGGGGGGTATAAAAGGGTGCGGGTCCCTGCTCGTCCTCACTGT

CTTCCGGATCGCTGTCCAGGAGCGCCAGCTGTTGGGGTAGGTATTCCCTCTCGAAGGCGGGCATG

ACCTCGGCACTCAGGTTGTCAGTTTCTAGAAACGAGGAGGATTTGATATTGACGGTGCCGGCGGA

GATGCCTTTCAAGAGCCCCTCGTCCATCTGGTCAGAAAAGACGATCTTTTTGTTGTCGAGCTTGG

TGGCGAAGGAGCCGTAGAGGGCGTTGGAGAGGAGCTTGGCGATGGAGCGCATGGTCTGGTTTTTT

TCCTTGTCGGCGCGCTCCTTGGCGGCGATGTTGAGCTGCACGTACTCGCGCGCCACGCACTTCCA

TTCGGGGAAGACGGTGGTCAGCTCGTCGGGCACGATTCTGACCTGCCAGCCCCGATTATGCAGGG

TGATGAGGTCCACACTGGTGGCCACCTCGCCGCGCAGGGGCTCATTAGTCCAGCAGAGGCGTCCG

CCCTTGCGCGAGCAGAAGGGGGGCAGGGGGTCCAGCATGACCTCGTCGGGGGGGTCGGCATCGAT

GGTGAAGATGCCGGGCAGGAGGTCGGGGTCAAAGTAGCTGATGGAAGTGGCCAGATCGTCCAGGG

CAGCTTGCCATTCGCGCACGGCCAGCGCGCCTCGTAGGGACTGAGGGGCGTGCCCCAGGGCATGG

GATGGGTAAGCGCGGAGGCGTACATGCCGCAGATGTCGTAGACGTAGAGGGGCTCCTCGAGGATG

CCGATGTAGGTGGGGTAGCAGCGCCCCCCGCGGATGCTGGCGCGCACGTAGTCATACAGCTCGTG

CGAGGGGGCGAGGAGCCCCGGGCCCAGGTTGGTGCGACTGGGCTTTTCGGCGCGGTAGACGATCT

GGCGGAAAATGGCATGCGAGTTGGAGGAGATGGTGGGCCTTTGGAAGATGTTGAAGTGGGCGTGG

GGCAGTCCGACCGAGTCGCGGATGAAGTGGGCGTAGGAGTCTTGCAGCTTGGCGACGAGCTCGGC

GGTGACTAGGACGTCCAGAGCGCAGTAGTCGAGGGTCTCCTGGATGATGTCATACTTGAGCTGTC

CCTTTTGTTTCCACAGCTCGCGGTTGAGAAGGAACTCTTCGCGGTCCTTCCAGTACTCTTCGAGG

GGGAACCCGTCCTGATCTGCACGGTAAGAGCCTAGCATGTAGAACTGGTTGACGGCCTTGTAGGC

GCAGCAGCCCTTCTCCACGGGGAGGGCGTAGGCCTGGGCGGCCTTGCGCAGGGAGGTGTGCGTGA

GGGCGAAAGTGTCCCTGACCATGACCTTGAGGAACTGGTGCTTGAAGTCGATATCGTCGCAGCCC

CCCTGCTCCCAGAGCTGGAAGTCCGTGCGCTTCTTGTAGGCGGGGTTGGGCAAAGCGAAAGTAAC

ATCGTTGAAGAGGATCTTGCCCGCGCGGGGCATAAAGTTGCGAGTGATGCGGAAAGGTTGGGGCA

CCTCGGCCCGGTTGTTGATGACCTGGGCGGCGAGCACGATCTCGTCGAAGCCGTTGATGTTGTGG

CCCACGATGTAGAGTTCCACGAATCGCGGACGGCCCTTGACGTGGGGCAGTTTCTTGAGCTCCTC

GTAGGTGAGCTCGTCGGGGTCGCTGAGCCCGTGCTGCTCGAGCGCCCAGTCGGCGAGATGGGGGT

TGGCGCGGAGGAAGGAAGTCCAGAGATCCACGGCCAGGGCGGTTTGCAGACGGTCCCGGTACTGA

CGGAACTGCTGCCCGACGGCCATTTTTTCGGGGGTGACGCAGTAGAAGGTGCGGGGGTCCCCGTG

-continued

CCAGCGATCCCATTTGAGCTGGAGGGCGAGATCGAGGGCGAGCTCGACGAGCCGGTCGTCCCCGG

AGAGTTTCATGACCAGCATGAAGGGGACGAGCTGCTTGCCGAAGGACCCCATCCAGGTGTAGGTT

TCCACATCGTAGGTGAGGAAGAGCCTTTCGGTGCGAGGATGCGAGCCGATGGGGAAGAACTGGAT

CTCCTGCCACCAATTGGAGGAATGGCTGTTGATGTGATGGAAGTAGAAATGCCGACGGCGCGCCG

AACACTCGTGCTTGTGTTTATACAAGCGGCCACAGTGCTCGCAACGCTGCACGGGATGCACGTGC

TGCACGAGCTGTACCTGAGTTCCTTTGACGAGGAATTTCAGTGGGAAGTGGAGTCGTGGCGCCTG

CATCTCGTGCTGTACTACGTCGTGGTGGTCGGCCTGGCCCTCTTCTGCCTCGATGGTGGTCATGC

TGACGAGCCCGCGCGGGAGGCAGGTCCAGACCTCGGCGCGAGCGGGTCGGAGAGCGAGGACGAGG

GCGCGCAGGCCGGAGCTGTCCAGGGTCCTGAGACGCTGCGGAGTCAGGTCAGTGGGCAGCGGCGG

CGCGCGGTTGACTTGCAGGAGTTTTTCCAGGGCGCGCGGGAGGTCCAGATGGTACTTGATCTCCA

CCGCGCCATTGGTGGCGACGTCGATGGCTTGCAGGGTCCCGTGCCCCTGGGGTGTGACCACCGTC

CCCCGTTTCTTCTTGGGCGGCTGGGGCGACGGGGGCGGTGCCTCTTCCATGGTTAGAAGCGGCGG

CGAGGACGCGCGCCGGGCGGCAGGGGCGGCTCGGGGCCCGGAGGCAGGGGCGGCAGGGGCACGTC

GGCGCCGCGCGCGGGTAGGTTCTGGTACTGCGCCCGGAGAAGACTGGCGTGAGCGACGACGCGAC

GGTTGACGTCCTGGATCTGACGCCTCTGGGTGAAGGCCACGGGACCCGTGAGTTTGAACCTGAAA

GAGAGTTCGACAGAATCAATCTCGGTATCGTTGACGGCGGCCTGCCGCAGGATCTCTTGCACGTC

GCCCGAGTTGTCCTGGTAGGCGATCTCGGTCATGAACTGCTCGATCTCCTCCTCTTGAAGGTCTC

CGCGGCCGGCGCGCTCCACGGTGGCCGCGAGGTCGTTGGAGATGCGGCCCATGAGCTGCGAGAAG

GCGTTCATGCCCGCCTCGTTCCAGACGCGGCTGTAGACCACGACGCCCTCGGGATCGCgGGCGCG

CATGACCACCTGGGCGAGGTTGAGCTCCACGTGGCGCGTGAAGACCGCGTAGTTGCAGAGGCGCT

GGTAGAGGTAGTTGAGCGTGGTGGCGATGTGCTCGGTGACGAAGAAATACATGATCCAGCGGCGG

AGCGGCATCTCGCTGACGTCGCCCAGCGCCTCCAAACGTTCCATGGCCTCGTAAAAGTCCACGGC

GAAGTTGAAAAACTGGGAGTTGCGCGCCGAGACGGTCAACTCCTCCTCCAGAAGACGGATGAGCT

CGGCGATGGTGGCGCGCACCTCGCGCTCGAAGGCCCCCGGGAGTTCCTCCACTTCCTCTTCTTCC

TCCTCCACTAACATCTCTTCTACTTCCTCCTCAGGCGGCAGTGGTGGCGGGGGAGGGGGCCTGCG

TCGCCGGCGGCGCACGGGCAGACGGTCGATGAAGCGCTCGATGGTCTCGCCGCGCCGGCGTCGCA

TGGTCTCGGTGACGGCGCGCCCGTCCTCGCGGGGCCGCAGCGTGAAGACGCCGCCGCGCATCTCC

AGGTGGCCGGGGGGGTCCCCGTTGGGCAGGGAGAGGGCGCTGACGATGCATCTTATCAATTGCCC

CGTAGGGACTCCGCGCAAGGACCTGAGCGTCTCGAGATCCACGGGATCTGAAAACCGCTGAACGA

AGGCTTCGAGCCAGTCGCAGTCGCAAGGTAGGCTGAGCACGGTTTCTTCTGGCGGGTCATGTTGG

TTGGGAGCGGGGGGGCGATGCTGCTGGTGATGAAGTTGAAATAGGCGGTTCTGAGACGGCGGAT

GGTGGCGAGGAGCACCAGGTCTTTGGGCCCGGCTTGCTGGATGCGCAGACGGTCGGCCATGCCCC

AGGCGTGGTCCTGACACCTGGCCAGGTCCTTGTAGTAGTCCTGCATGAGCCGCTCCACGGGCACC

TCCTCCTCGCCCGCGCGGCCGTGCATGCGCGTGAGCCCGAAGCCGCGCTGGGGCTGGACGAGCGC

CAGGTCGGCGACGACGCGCTCGGCGAGGATGGCTTGCTGGATCTGGGTGAGGGTGGTCTGGAAGT

CATCAAAGTCGACGAAGCGGTGGTAGGCTCCGGTGTTGATGGTGTAGGAGCAGTTGGCCATGACG

GACCAGTTGACGGTCTGGTGGCCCGGACGCACGAGCTCGTGGTACTTGAGGCGCGAGTAGGCGCG

CGTGTCGAAGATGTAGTCGTTGCAGGTGCGCACCAGGTACTGGTAGCCGATGAGGAAGTGCGGCG

GCGGCTGGCGGTAGAGCGGCCATCGCTCGGTGGCGGGGGCGCCGGGCGCGAGGTCCTCGAGCATG

GTGCGGTGGTAGCCGTAGATGTACCTGGACATCCAGGTGATGCCGGCGGCGGTGGTGGAGGCGCG

-continued

CGGGAACTCGCGGACGCGGTTCCAGATGTTGCGCAGCGGCAGGAAGTAGTTCATGGTGGGCACGG

TCTGGCCCGTGAGGCGCGCGCAGTCGTGGATGCTCTATACGGGCAAAAACGAAAGCGGTCAGCGG

CTCGACTCCGTGGCCTGGAGGCTAAGCGAACGGGTTGGGCTGCGCGTGTACCCCGGTTCGAATCT

CGAATCAGGCTGGAGCCGCAGCTAACGTGGTATTGGCACTCCCGTCTCGACCCAAGCCTGCACCA

ACCCTCCAGGATACGGAGGCGGGTCGTTTTGCAACTTTTTTTTGGAGGCCGGATGAGACTAGTAA

GCGCGGAAAGCGGCCGACCGCGATGGCTCGCTGCCGTAGTCTGGAGAAGAATCGCCAGGGTTGCG

TTGCGGTGTGCCCCGGTTCGAGGCCGGCCGGATTCCGCGGCTAACGAGGGCGTGGCTGCCCCGTC

GTTTCCAAGACCCCATAGCCAGCCGACTTCTCCAGTTACGGAGCGAGCCCCTCTTTTGTTTTGTT

TGTTTTTGCCAGATGCATCCCGTACTGCGGCAGATGCGCCCCCACCACCCTCCACCGCAACAACA

GCCCCCTCCACAGCCGGCGCTTCTGCCCCCGCCCCAGCAGCAACTTCCAGCCACGACCGCCGCGG

CCGCCGTGAGCGGGGCTGGACAGAGTTATGATCACCAGCTGGCCTTGGAAGAGGGCGAGGGGCTG

GCGCGCCTGGGGGCGTCGTCGCCGGAGCGGCACCCGCGCGTGCAGATGAAAAGGGACGCTCGCGA

GGCCTACGTGCCCAAGCAGAACCTGTTCAGAGACAGGAGCGGCGAGGAGCCCGAGGAGATGCGCG

CGGCCCGGTTCCACGCGGGGCGGGAGCTGCGGCGCGGCCTGGACCGAAAGAGGGTGCTGAGGGAC

GAGGATTTCGAGGCGGACGAGCTGACGGGGATCAGCCCCGCGCGCGCGCACGTGGCCGCGGCCAA

CCTGGTCACGGCGTACGAGCAGACCGTGAAGGAGGAGAGCAACTTCCAAAAATCCTTCAACAACC

ACGTGCGCACCCTGATCGCGCGCGAGGAGGTGACCCTGGGCCTGATGCACCTGTGGGACCTGCTG

GAGGCCATCGTGCAGAACCCCACCAGCAAGCCGCTGACGGCGCAGCTGTTCCTGGTGGTGCAGCA

TAGTCGGGACAACGAAGCGTTCAGGGAGGCGCTGCTGAATATCACCGAGCCCGAGGGCCGCTGGC

TCCTGGACCTGGTGAACATTCTGCAGAGCATCGTGGTGCAGGAGCGCGGGCTGCCGCTGTCCGAG

AAGCTGGCGGCCATCAACTTCTCGGTGCTGAGTTTGGGCAAGTACTACGCTAGGAAGATCTACAA

GACCCCGTACGTGCCCATAGACAAGGAGGTGAAGATCGACGGGTTTTACATGCGCATGACCCTGA

AAGTGCTGACCCTGAGCGACGATCTGGGGGTGTACCGCAACGACAGGATGCACCGTGCGGTGAGC

GCCAGCAGGCGGCGCGAGCTGAGCGACCAGGAGCTGATGCATAGTCTGCAGCGGGCCCTGACCGG

GGCCGGGACCGAGGGGGAGAGCTACTTTGACATGGGCGCGGACCTGCACTGGCAGCCCAGCCGCC

GGGCCTTGGAGGCGGCGGCAGGACCCTACGTAGAAGAGGTGGACGATGAGGTGGACGAGGAGGGC

GAGTACCTGGAAGACTGATGGCGCGACCGTATTTTTGCTAGATGCAACAACAACAGCCACCTCCT

GATCCCGCGATGCGGGCGGCGCTGCAGAGCCAGCCGTCCGGCATTAACTCCTCGGACGATTGGAC

CCAGGCCATGCAACGCATCATGGCGCTGACGACCCGCAACCCCGAAGCCTTTAGACAGCAGCCCC

AGGCCAACCGGCTCTCGGCCATCCTGGAGGCCGTGGTGCCCTCGCGCTCCAACCCCACGCACGAG

AAGGTCCTGGCCATCGTGAACGCGCTGGTGGAGAACAAGGCCATCCGCGGCGACGAGGCCGGCCT

GGTGTACAACGCGCTGCTGGAGCGCGTGGCCCGCTACAACAGCACCAACGTGCAGACCAACCTGG

ACCGCATGGTGACCGACGTGCGCGAGGCCGTGGCCCAGCGCGAGCGGTTCCACCGCGAGTCCAAC

CTGGGATCCATGGTGGCGCTGAACGCCTTCCTCAGCACCCAGCCCGCCAACGTGCCCCGGGGCCA

GGAGGACTACACCAACTTCATCAGCGCCCTGCGCCTGATGGTGACCGAGGTGCCCCAGAGCGAGG

TGTACCAGTCCGGGCCGGACTACTTCTTCCAGACCAGTCGCCAGGGCTTGCAGACCGTGAACCTG

AGCCAGGCTTTCAAGAACTTGCAGGGCCTGTGGGGCGTGCAGGCCCCGGTCGGGGACCGCGCGAC

GGTGTCGAGCCTGCTGACGCCGAACTCGCGCCTGCTGCTGCTGCTGGTGGCCCCCTTCACGGACA

GCGGCAGCATCAACCGCAACTCGTACCTGGGCTACCTGATTAACCTGTACCGCGAGGCCATCGGC

-continued

CAGGCGCACGTGGACGAGCAGACCTACCAGGAGATCACCCACGTGAGCCGCGCCCTGGGCCAGGA

CGACCCGGGCAACCTGGAAGCCACCCTGAACTTTTTGCTGACCAACCGGTCGCAGAAGATCCCGC

CCCAGTACGCGCTCAGCACCGAGGAGGAGCGCATCCTGCGTTACGTGCAGCAGAGCGTGGGCCTG

TTCCTGATGCAGGAGGGGGCCACCCCCAGCGCCGCGCTCGACATGACCGCGCGCAACATGGAGCC

CAGCATGTACGCCAGCAACCGCCCGTTCATCAATAAACTGATGGACTACTTGCATCGGGCGGCCG

CCATGAACTCTGACTATTTCACCAACGCCATCCTGAATCCCCACTGGCTCCCGCCGCCGGGGTTC

TACACGGGCGAGTACGACATGCCCGACCCCAATGACGGGTTCCTGTGGGACGATGTGGACAGCAG

CGTGTTCTCCCCCCGACCGGGTGCTAACGAGCGCCCCTTGTGGAAGAAGGAAGGCAGCGACCGAC

GCCCGTCCTCGGCGCTGTCCGGCCGCGAGGGTGCTGCCGCGGCGGTGCCCGAGGCCGCCAGTCCT

TTCCCGAGCTTGCCCTTCTCGCTGAACAGTATCCGCAGCAGCGAGCTGGGCAGGATCACGCGCCC

GCGCTTGCTGGGCGAAGAGGAGTACTTGAATGACTCGCTGTTGAGACCCGAGCGGGAGAAGAACT

TCCCCAATAACGGGATAGAAAGCCTGGTGGACAAGATGAGCCGCTGGAAGACGTATGCGCAGGAG

CACAGGGACGATCCCCGGGCGTCGCAGGGGGCCACGAGCCGGGGCAGCGCCGCCCGTAAACGCCG

GTGGCACGACAGGCAGCGGGGACAGATGTGGGACGATGAGGACTCCCCCGACGACAGCAGCGTGT

TGGACTTGGGTGGGAGTGGTAACCCGTTCGCTCACCTGCGCCCCCGTATCGGGCGCATGATGTAA

GAGAAACCGAAAATAAATGATACTCACCAAGGCCATGGCGACCAGCGTGCGTTCGTTTCTTCTCT

GTTGTTGTTGTATCTAGTATGATGAGGCGTGCGTACCCGGAGGGTCCTCCTCCCTCGTACGAGAG

CGTGATGCAGCAGGCGATGGCGGCGGCGGCGATGCAGCCCCCGCTGGAGGCTCCTTACGTGCCCC

CGCGGTACCTGGCGCCTACGGAGGGGCGGAACAGCATTCGTTACTCGGAGCTGGCACCCTTGTAC

GATACCACCCGGTTGTACCTGGTGGACAACAAGTCGGCGGACATCGCCTCGCTGAACTACCAGAA

CGACCACAGCAACTTCCTGACCACCGTGGTGCAGAACAATGACTTCACCCCCACGGAGGCCAGCA

CCCAGACCATCAACTTTGACGAGCGCTCGCGGTGGGGCGGCCAGCTGAAAACCATCATGCACACC

AACATGCCCAACGTGAACGAGTTCATGTACAGCAACAAGTTCAAGGCGCGGGTGATGGTCTCCCG

CAAGACCCCCAATGGGGTGACAGTGACAGAGGATTATGATGGTAGTCAGGATGAGCTGAAGTATG

AATGGGTGGAATTTGAGCTGCCCGAAGGCAACTTCTCGGTGACCATGACCATCGACCTGATGAAC

AACGCCATCATCGACAATTACTTGGCGGTGGGGCGGCAGAACGGGGTGCTGGAGAGCGACATCGG

CGTGAAGTTCGACACTAGGAACTTCAGGCTGGGCTGGGACCCCGTGACCGAGCTGGTCATGCCCG

GGGTGTACACCAACGAGGCTTTCCATCCCGATATTGTCTTGCTGCCCGGCTGCGGGGTGGACTTC

ACCGAGAGCCCCCTCAGCAACCTGCTGGGCATTCGCAAGAGGCAGCCCTTCCAGGAAGGCTTCCA

GATCATGTACGAGGATCTGGAGGGGGGCAACATCCCCCCGCTCCTGGATGTCGACGCCTATGAGA

AAAGCAAGGAGGATGCAGCAGCTGAAGCAACTGCAGCCGTAGCTACCGCCTCTACCGAGGTCAGG

GGCGATAATTTTGCAAGCGCCGCAGCAGTGGCAGCGGCCGAGGCGGCTGAAACCGAAAGTAAGAT

AGTCATTCAGCCGGTGGAGAAGGATAGCAAGAACAGGAGCTACAACGTACTACCGGACAAGATAA

ACACCGCCTACCGCAGCTGGTACCTAGCCTACAACTATGGCGACCCCGAGAAGGGCGTGCGCTCC

TGGACGCTGCTCACCACCTCGGACGTCACCTGCGGCGTGGAGCAAGTCTACTGGTCGCTGCCCGA

CATGATGCAAGACCCGGTCACCTTCCGCTCCACGCGTCAAGTTAGCAACTACCCGGTGGTGGGCG

CCGAGCTCCTGCCCGTCTACTCCAAGAGCTTCTTCAACGAGCAGGCCGTCTACTCGCAGCAGCTG

CGGGCCTTCACCTCGCTTACGCACGTCTTCAACCGCTTCCCCGAGAACCAGATCCTCGTCCGCCC

GCCCGCGCCCACCATTACCACCGTCAGTGAAAACGTTCCTGCTCTCACAGATCACGGGACCCTGC

CGCTGCGCAGCAGTATCCGGGGAGTCCAGCGCGTGACCGTTACTGACGCCAGACGCCGCACCTGC

-continued

CCCTACGTCTACAAGGCCCTGGGCATAGTCGCGCCGCGCGTCCTCTCGAGCCGCACCTTCTAAAT

GTCCATTCTCATCTCGCCCAGTAATAACACCGGTTGGGGCCTGCGCGCGCCCAGCAAGATGTACG

GAGGCGCTCGCCAACGCTCCACGCAACACCCCGTGCGCGTGCGCGGGCACTTCCGCGCTCCCTGG

GGCGCCCTCAAGGGCCGCGTGCGGTCGCGCACCACCGTCGACGACGTGATCGACCAGGTGGTGGC

CGACGCGCGCAACTACACCCCCGCCGCCGCGCCCGTCTCCACCGTGGACGCCGTCATCGACAGCG

TGGTGGCCGACGCGCGCCGGTACGCCCGCGCCAAGAGCCGGCGGCGGCGCATCGCCCGGCGGCAC

CGGAGCACCCCCGCCATGCGCGCGGCGCGAGCCTTGCTGCGCAGGGCCAGGCGCACGGGACGCAG

GGCCATGCTCAGGGCGGCCAGACGCGCGGCTTCAGGCGCCAGCGCCGGCAGGACCCGGAGACGCG

CGGCCACGGCGGCGGCAGCGGCCATCGCCAGCATGTCCCGCCCGCGGCGAGGGAACGTGTACTGG

GTGCGCGACGCCGCCACCGGTGTGCGCGTGCCCGTGCGCACCCGCCCCCCTCGCACTTGAAGATG

TTCACTTCGCGATGTTGATGTGTCCCAGCGGCGAGGAGGATGTCCAAGCGCAAATTCAAGGAAGA

GATGCTCCAGGTCATCGCGCCTGAGATCTACGGCCCTGCGGTGGTGAAGGAGGAAAGAAAGCCCC

GCAAAATCAAGCGGGTCAAAAAGGACAAAAAGGAAGAAGAAAGTGATGTGGACGGATTGGTGGAG

TTTGTGCGCGAGTTCGCCCCCCGGCGGCGCGTGCAGTGGCGCGGGCGGAAGGTGCAACCGGTGCT

GAGACCCGGCACCACCGTGGTCTTCACGCCCGGCGAGCGCTCCGGCACCGCTTCCAAGCGCTCCT

ACGACGAGGTGTACGGGGATGATGATATTCTGGAGCAGGCGGCCGAGCGCCTGGGCGAGTTTGCT

TACGGCAAGCGCAGCCGTTCCGCACCGAAGGAAGAGGCGGTGTCCATCCCGCTGGACCACGGCAA

CCCCACGCCGAGCCTCAAGCCCGTGACCTTGCAGCAGGTGCTGCCGACCGCGGCGCCGCGCCGGG

GGTTCAAGCGCGAGGGCGAGGATCTGTACCCCACCATGCAGCTGATGGTGCCCAAGCGCCAGAAG

CTGGAAGACGTGCTGGAGACCATGAAGGTGGACCCGGACGTGCAGCCCGAGGTCAAGGTGCGGCC

CATCAAGCAGGTGGCCCCGGGCCTGGGCGTGCAGACCGTGGACATCAAGATTGCCACGGAGCCCA

TGGAAACGCAGACCGAGCCCATGATCAAGCCCAGCACCAGCACCATGGAGGTGCAGACGGATCCC

TGGATGCCATCGGCTCCTAGTCGAAGACCCCGGCGCAAGTACGGCGCGGCCAGCCTGCTGATGCC

CAACTACGCGCTGCATCCTTCCATCATCCCCACGCCGGGCTACCGCGGCACGCGCTTCTACCGCG

GTCATACCAGCAGCCGCCGCCGCAAGACCACCACTCGCCGCCGCCGTCGCCGCACCGCCGCTGCA

ACCACCCCTGCCGCCCTGGTGCGGAGAGTGTACCGCCGCGGCCGCGCACCTCTGACCCTGCCGCG

CGCGCGCTACCACCCGAGCATCGCCATTTAAACTTTCGCCTGCTTTGCAGATCAATGGCCCTCAC

ATGCCGCCTTCGCGTTCCCATTACGGGCTACCGAGGAAGAAAACCGCGCCGTAGAAGGCTGGCGG

GGAACGGGATGCGTCGCCACCACCACCGGCGGCGGCGCGCCATCAGCAAGCGGTTGGGGGGAGGC

TTCCTGCCCGCGCTGATCCCCATCATCGCCGCGGCGATCGGGGCGATCCCCGGCATTGCTTCCGT

GGCGGTGCAGGCCTCTCAGCGCCACTGAGACACACTTGGAAACATCTTGTAATAAACCaATGGAC

TCTGACGCTCCTGGTCCTGTGATGTGTTTTCGTAGACAGATGGAAGACATCAATTTTTCGTCCCT

GGCTCCGCGACACGGCACGCGGCCGTTCATGGGCACCTGGAGCGACATCGGCACCAGCCAACTGA

ACGGGGGCGCCTTCAATTGGAGCAGTCTCTGGAGCGGGCTTAAGAATTTCGGGTCCACGCTTAAA

ACCTATGGCACCAAGGCGTGGAACAGCACCACAGGGCAGGCGCTGAGGGATAAGCTGAAAGAGCA

GAACTTCCAGCAGAAGGTGGTCGATGGGCTCGCCTCGGGCATCAACGGGGTGGTGGACCTGGCCA

ACCAGGCCGTGCAGCGGCAGATCAACAGCCGCCTGGACCCGGTGCCGCCCGCCGGCTCCGTGGAG

ATGCCGCAGGTGGAGGAGGAGCTGCCTCCCCTGGACAAGCGGGGCGAGAAGCGACCCCGCCCCGA

TGCGGAGGAGACGCTGCTGACGCACACGGACGAGCCCCCCCCGTACGAGGAGGCGGTGAAACTGG

-continued

GTCTGCCCACCACGCGGCCCATCGCGCCCCTGGCCACCGGGGTGCTGAAACCCGAAAAGCCCGCG

ACCCTGGACTTGCCTCCTCCCCAGCCTTCCCGCCCCTCTACAGTGGCTAAGCCCCTGCCGCCGGT

GGCCGTGGCCCGCGCGCGACCCGGGGGCACCGCCCGCCCTCATGCGAACTGGCAGAGCACTCTGA

ACAGCATCGTGGGTCTGGGAGTGCAGAGTGTGAAGCGCCGCCGCTGCTATTAAACCTACCGTAGC

GCTTAACTTGCTTGTCTGTGTGTGTATGTATTATGTCGCCGCCGCCGCTGTCCACCAGAAGGAGG

AGTGAAGAGGCGCGTCGCCGAGTTGCAAGATGGCCACCCCATCGATGCTGCCCCAGTGGGCGTAC

ATGCACATCGCCGGACAGGACGCTTCGGAGTACCTGAGTCCGGGTCTGGTGCAGTTTGCCCGCGC

CACAGACACCTACTTCAGTCTGGGGAACAAGTTTAGGAACCCCACGGTGGCGCCCACGCACGATG

TGACCACCGACCGCAGCCAGCGGCTGACGCTGCGCTTCGTGCCCGTGGACCGCGAGGACAACACC

TACTCGTACAAAGTGCGCTACACGCTGGCCGTGGGCGACAACCGCGTGCTGGACATGGCCAGCAC

CTACTTTGACATCCGCGGCGTGCTGGATCGGGGCCCTAGCTTCAAACCCTACTCCGGCACCGCCT

ACAACAGTCTGGCCCCCAAGGGAGCACCCAACACTTGTCAGTGGACATATAAAGCCGATGGTGAA

ACTGCCACAGAAAAAACCTATACATATGGAAATGCACCCGTGCAGGGCATTAACATCACAAAAGA

TGGTATTCAACTTGGAACTGACACCGATGATCAGCCAATCTACGCAGATAAAACCTATCAGCCTG

AACCTCAACTGGGTGATGCTGAATGGCATGACATCACTGGTACTGATGAAAAGTATGGAGGCAGA

GCTCTTAAGCCTGATACCAAAATGAAGCCTTGTTATGGTTCTTTTGCCAAGCCTACTAATAAAGA

AGGAGGTCAGGCAAATGTGAAAACAGGAACAGGCACTACTAAAGAATATGACATAGACATGGCTT

TCTTTGACAACAGAAGTGCGGCTGCTGCTGGCCTAGCTCCAGAAATTGTTTTGTATACTGAAAAT

GTGGATTTGGAAACTCCAGATACCCATATTGTATACAAAGCAGGCACAGATGACAGCAGCTCTTC

TATTAATTTGGGTCAGCAAGCCATGCCCAACAGACCTAACTACATTGGTTTCAGAGACAACTTTA

TCGGGCTCATGTACTACAACAGCACTGGCAATATGGGGGTGCTGGCCGGTCAGGCTTCTCAGCTG

AATGCTGTGGTTGACTTGCAAGACAGAAACACCGAGCTGTCCTACCAGCTCTTGCTTGACTCTCT

GGGTGACAGAACCCGGTATTTCAGTATGTGGAATCAGGCGGTGGACAGCTATGATCCTGATGTGC

GCATTATTGAAAATCATGGTGTGGAGGATGAACTTCCCAACTATTGTTTCCCTCTGGATGCTGTT

GGCAGAACAGATACTTATCAGGGAATTAAGGCTAATGGAACTGATCAAACCACATGGACCAAAGA

TGACAGTGTCAATGATGCTAATGAGATAGGCAAGGGTAATCCATTCGCCATGGAAATCAACATCC

AAGCCAACCTGTGGAGGAACTTCCTCTACGCCAACGTGGCCCTGTACCTGCCCGACTCTTACAAG

TACACGCCGGCCAATGTTACCCTGCCCACCAACACCAACACCTACGATTACATGAACGGCCGGGT

GGTGGCGCCCTCGCTGGTGGACTCCTACATCAACATCGGGGCGCGCTGGTCGCTGGATCCCATGG

ACAACGTGAACCCCTTCAACCACCACCGCAATGCGGGGCTGCGCTACCGCTCCATGCTCCTGGGC

AACGGGCGCTACGTGCCCTTCCACATCCAGGTGCCCCAGAAATTTTTCGCCATCAAGAGCCTCCT

GCTCCTGCCCGGGTCCTACACCTACGAGTGGAACTTCCGCAAGGACGTCAACATGATCCTGCAGA

GCTCCCTCGGCAACGACCTGCGCACGGACGGGGCCTCCATCTCCTTCACCAGCATCAACCTCTAC

GCCACCTTCTTCCCCATGGCGCACAACACGGCCTCCACGCTCGAGGCCATGCTGCGCAACGACAC

CAACGACCAGTCCTTCAACGACTACCTCTCGGCGGCCAACATGCTCTACCCCATCCCGGCCAACG

CCACCAACGTGCCCATCTCCATCCCCTCGCGCAACTGGGCCGCCTTCCGCGGCTGGTCCTTCACG

CGTCTCAAGACCAAGGAGACGCCCTCGCTGGGCTCCGGGTTCGACCCCTACTTCGTCTACTCGGG

CTCCATCCCCTACCTCGACGGCACCTTCTACCTCAACCACACCTTCAAGAAGGTCTCCATCACCT

TCGACTCCTCCGTCAGCTGGCCCGGCAACGACCGGCTCCTGACGCCCAACGAGTTCGAAATCAAG

CGCACCGTCGACGGCGAGGGCTACAACGTGGCCCAGTGCAACATGACCAAGGACTGGTTCCTGGT

-continued

CCAGATGCTGGCCCACTACAACATCGGCTACCAGGGCTTCTACGTGCCCGAGGGCTACAAGGACC

GCATGTACTCCTTCTTCCGCAACTTCCAGCCCATGAGCCGCCAGGTGGTGGACGAGGTCAACTAC

AAGGACTACCAGGCCGTCACCCTGGCCTACCAGCACAACAACTCGGGCTTCGTCGGCTACCTCGC

GCCCACCATGCGCCAGGGCCAGCCCTACCCCGCCAACTACCCCTACCCGCTCATCGGCAAGAGCG

CCGTCACCAGCGTCACCCAGAAAAAGTTCCTCTGCGACAGGGTCATGTGGCGCATCCCCTTCTCC

AGCAACTTCATGTCCATGGGCGCGCTCACCGACCTCGGCCAGAACATGCTCTATGCCAACTCCGC

CCACGCGCTAGACATGAATTTCGAAGTCGACCCCATGGATGAGTCCACCCTTCTCTATGTTGTCT

TCGAAGTCTTCGACGTCGTCCGAGTGCACCAGCCCCACCGCGGCGTCATCGAGGCCGTCTACCTG

CGCACCCCCTTCTCGGCCGGTAACGCCACCACCTAAGCTCTTGCTTCTTGCAAGCCATGGCCGCG

GGCTCCGGCGAGCAGGAGCTCAGGGCCATCATCCGCGACCTGGGCTGCGGGCCCTACTTCCTGGG

CACCTTCGATAAGCGCTTCCCGGGATTCATGGCCCCGCACAAGCTGGCCTGCGCCATCGTCAACA

CGGCCGGCCGCGAGACCGGGGGCGAGCACTGGCTGGCCTTCGCCTGGAACCCGCGCTCGAACACC

TGCTACCTCTTCGACCCCTTCGGGTTCTCGGACGAGCGCCTCAAGCAGATCTACCAGTTCGAGTA

CGAGGGCCTGCTGCGCCGCAGCGCCCTGGCCACCGAGGACCGCTGCGTCACCCTGGAAAAGTCCA

CCCAGACCGTGCAGGGTCCGCGCTCGGCCGCCTGCGGGCTCTTCTGCTGCATGTTCCTGCACGCC

TTCGTGCACTGGCCCGACCGCCCCATGGACAAGAACCCCACCATGAACTTGCTGACGGGGGTGCC

CAACGGCATGCTCCAGTCCCCCCAGGTGGAACCCACCCTGCGCCGCAACCAGGAGGCGCTCTACC

GCTTCCTCAACTCCCACTCCCCCTACTTTCGCTCCCACCGCGCGCGCATCGAGAAGGCCACCGCC

TTCGACCGCATGAATCAAGACATGTAAACCGTGTGTGTATGTTAAATGTCTTTAATAAACAGCAC

TTTCATGTTACACATGCATCTGAGATGATTTATTTAGAAATCGAAAGGGTTCTGCCGGGTCTCGG

CATGGCCCGCGGGCAGGGACACGTTGCGGAACTGGTACTTGGCCAGCCACTTGAACTCGGGGATC

AGCAGTTTGGGCAGCGGGGTGTCGGGGAAGGAGTCGGTCCACAGCTTCCGCGTCAGTTGCAGGGC

GCCCAGCAGGTCGGGCGCGGAGATCTTGAAATCGCAGTTGGGACCCGCGTTCTGCGCGCGGGAGT

TGCGGTACACGGGGTTGCAGCACTGGAACACCATCAGGGCCGGGTGCTTCACGCTCGCCAGCACC

GTCGCGTCGGTGATGCTCTCCACGTCGAGGTCCTCGGCGTTGGCCATCCCGAAGGGGGTCATCTT

GCAGGTCTGCCTTCCCATGGTGGGCACGCACCCGGGCTTGTGGTTGCAATCGCAGTGCAGGGGGA

TCAGCATCATCTGGGCCTGGTCGGCGTTCATCCCCGGGTACATGGCCTTCATGAAAGCCTCCAAT

TGCCTGAACGCCTGCTGGGCCTTGGCTCCCTCGGTGAAGAAGACCCCGCAGGACTTGCTAGAGAA

CTGGTTGGTGGCGCACCCGGCGTCGTGCACGCAGCAGCGCGCGTCGTTGTTGGCCAGCTGCACCA

CGCTGCGCCCCCAGCGGTTCTGGGTGATCTTGGCCCGGTCGGGGTTCTCCTTCAGCGCGCGCTGC

CCGTTCTCGCTCGCCACATCCATCTCGATCATGTGCTCCTTCTGGATCATGGTGGTCCCGTGCAG

GCACCGCAGCTTGCCCTCGGCCTCGGTGCACCCGTGCAGCCACAGCGCGCACCCGGTGCACTCCC

AGTTCTTGTGGGCGATCTGGGAATGCGCGTGCACGAAGCCCTGCAGGAAGCGGCCCATCATGGTG

GTCAGGGTCTTGTTGCTAGTGAAGGTCAGCGGAATGCCGCGGTGCTCCTCGTTGATGTACAGGTG

GCAGATGCGGCGGTACACCTCGCCCTGCTCGGGCATCAGCTGGAAGTTGGCTTTCAGGTCGGTCT

CCACGCGGTAGCGGTCCATCAGCATAGTCATGATTTCCATACCCTTCTCCCAGGCCGAGACGATG

GGCAGGCTCATAGGGTTCTTCACCATCATCTTAGCGCTAGCAGCCGCGGCCAGGGGGTCGCTCTC

GTCCAGGGTCTCAAAGCTGCGCTTGCCGTCCTTCTCGGTGATCCGCACCGGGGGGTAGCTGAAGC

CCACGGCCGCCAGCTCCTCCTCGGCCTGTCTTTCGTCCTCGCTGTCCTGGCTGACGTCCTGCAGG

-continued

ACCACATGCTTGGTCTTGCGGGGTTTCTTCTTGGGCGGCAGCGGCGGCGGAGATGTTGGAGATGG

CGAGGGGGAGCGCGAGTTCTCGCTCACCACTACTATCTCTTCCTCTTCTTGGTCCGAGGCCACGC

GGCGGTAGGTATGTCTCTTCGGGGGCAGAGGCGGAGGCGACGGGCTCTCGCCGCCGCGACTTGGC

GGATGGCTGGCAGAGCCCCTTCCGCGTTCGGGGGTGCGCTCCCGGCGGCGCTCTGACTGACTTCC

TCCGCGGCCGGCCATTGTGTTCTCCTAGGGAGGAACAACAAGCATGGAGACTCAGCCATCGCCAA

CCTCGCCATCTGCCCCCACCGCCGACGAGAAGCAGCAGCAGCAGAATGAAAGCTTAACCGCCCCG

CCGCCCAGCCCCGCCACCTCCGACGCGGCCGTCCCAGACATGCAAGAGATGGAGGAATCCATCGA

GATTGACCTGGGCTATGTGACGCCCGCGGAGCACGAGGAGGAGCTGGCAGTGCGCTTTTCACAAG

AAGAGATACACCAAGAACAGCCAGAGCAGGAAGCAGAGAATGAGCAGAGTCAGGCTGGGCTCGAG

CATGACGGCGACTACCTCCACCTGAGCGGGGGGGAGGACGCGCTCATCAAGCATCTGGCCCGGCA

GGCCACCATCGTCAAGGATGCGCTGCTCGACCGCACCGAGGTGCCCCTCAGCGTGGAGGAGCTCA

GCCGCGCCTACGAGTTGAACCTCTTCTCGCCGCGCGTGCCCCCCAAGCGCCAGCCCAATGGCACC

TGCGAGCCCAACCCGCGCCTCAACTTCTACCCGGTCTTCGCGGTGCCCGAGGCCCTGGCCACCTA

CCACATCTTTTTCAAGAACCAAAAGATCCCCGTCTCCTGCCGCGCCAACCGCACCCGCGCCGACG

CCCTTTTCAACCTGGGTCCCGGCGCCCGCCTACCTGATATCGCCTCCTTGGAAGAGGTTCCCAAG

ATCTTCGAGGGTCTGGGCAGCGACGAGACTCGGGCCGCGAACGCTCTGCAAGGAGAAGGAGGAGA

GCATGAGCACCACAGCGCCCTGGTCGAGTTGGAAGGCGACAACGCGCGGCTGGCGGTGCTCAAAC

GCACGGTCGAGCTGACCCATTTCGCCTACCCGGCTCTGAACCTGCCCCCCAAAGTCATGAGCGCG

GTCATGGACCAGGTGCTCATCAAGCGCGCGTCGCCCATCTCCGAGGACGAGGGCATGCAAGACTC

CGAGGAGGGCAAGCCCGTGGTCAGCGACGAGCAGCTGGCCCGGTGGCTGGGTCCTAATGCTAGTC

CCCAGAGTTTGGAAGAGCGGCGCAAACTCATGATGGCCGTGGTCCTGGTGACCGTGGAGCTGGAG

TGCCTGCGCCGCTTCTTCGCCGACGCGGAGACCCTGCGCAAGGTCGAGGAGAACCTGCACTACCT

CTTCAGGCACGGGTTCGTGCGCCAGGCCTGCAAGATCTCCAACGTGGAGCTGACCAACCTGGTCT

CCTACATGGGCATCTTGCACGAGAACCGCCTGGGGCAGAACGTGCTGCACACCACCCTGCGCGGG

GAGGCCCGGCGCGACTACATCCGCGACTGCGTCTACCTCTACCTCTGCCACACCTGGCAGACGGG

CATGGGCGTGTGGCAGCAGTGTCTGGAGGAGCAGAACCTGAAAGAGCTCTGCAAGCTCCTGCAGA

AGAACCTCAAGGGTCTGTGGACCGGGTTCGACGAGCGCACCACCGCCTCGGACCTGGCCGACCTC

ATTTTCCCCGAGCGCCTCAGGCTGACGCTGCGCAACGGCCTGCCCGACTTTATGAGCCAAAGCAT

GTTGCAAAACTTTCGCTCTTTCATCCTCGAACGCTCCGGAATCCTGCCCGCCACCTGCTCCGCGC

TGCCCTCGGACTTCGTGCCGCTGACCTTCCGCGAGTGCCCCCCGCCGCTGTGGAGCCACTGCTAC

CTGCTGCGCCTGGCCAACTACCTGGCCTACCACTCGGACGTGATCGAGGACGTCAGCGGCGAGGG

CCTGCTCGAGTGCCACTGCCGCTGCAACCTCTGCACGCCGCACCGCTCCCTGGCCTGCAACCCCC

AGCTGCTGAGCGAGACCCAGATCATCGGCACCTTCGAGTTGCAAGGGCCCAGCGAAGGCGAGGGT

TCAGCCGCCAAGGGGGGTCTGAAACTCACCCCGGGGCTGTGGACCTCGGCCTACTTGCGCAAGTT

CGTGCCCGAGGACTACCATCCCTTCGAGATCAGGTTCTACGAGGACCAATCCCATCCGCCCAAGG

CCGAGCTGTCGGCCTGCGTCATCACCCAGGGGGCGATCCTGGCCCAATTGCAAGCCATCCAGAAA

TCCCGCCAAGAATTCTTGCTGAAAAAGGGCCGCGGGGTCTACCTCGACCCCCAGACCGGTGAGGA

GCTCAACCCCGGCTTCCCCCAGGATGCCCCGAGGAAACAAGAAGCTGAAAGTGGAGCTGCCGCCC

GTGGAGGATTTGGAGGAAGACTGGGAGAACAGCAGTCAGGCAGAGGAGGAGGAGATGGAGGAAGA

CTGGGACAGCACTCAGGCAGAGGAGGACAGCCTGCAAGACAGTCTGGAGGAAGACGAGGAGGAGG

-continued

CAGAGGAGGAGGTGGAAGAAGCAGCCGCCGCCAGACCGTCGTCCTCGGCGGGGGAGAAAGCAAGC

AGCACGGATACCATCTCCGCTCCGGGTCGGGGTCCCGCTCGACCACACAGTAGATGGGACGAGAC

CGGACGATTCCCGAACCCCACCACCCAGACCGGTAAGAAGGAGCGGCAGGGATACAAGTCCTGGG

GGGGGCACAAAAACGCCATCGTCTCCTGCTTGCAGGCCTGCGGGGGCAACATCTCCTTCACCCGG

CGCTACCTGCTCTTCCACCCCGGGGTGAACTTTCCCCGCAACATCTTGCATTACTACCGTCACCT

CCACAGCCCCTACTACTTCCAAGAAGAGGCAGCAGCAGCAGAAAAAGACCAGCAGAAAACCAGCA

GCTAGAAAATCCACAGCGGCGGCAGCAGGTGGACTGAGGATCGCGGCGAACGAGCCGGCGCAAAC

CCGGGAGCTGAGGAACCGGATCTTTCCCACCCTCTATGCCATCTTCCAGCAGAGTCGGGGGCAGG

AGCAGGAACTGAAAGTCAAGAACCGTTCTCTGCGCTCGCTCACCCGCAGTTGTCTGTATCACAAG

AGCGAAGACCAACTTCAGCGCACTCTCGAGGACGCCGAGGCTCTCTTCAACAAGTACTGCGCGCT

CACTCTTAAAGAGTAGCCCGCGCCCGCCCAGTCGCAGAAAAAGGCGGGAATTACGTCACCTGTGC

CCTTCGCCCTAGCCGCCTCCACCCATCATCATGAGCAAAGAGATTCCCACGCCTTACATGTGGAG

CTACCAGCCCCAGATGGGCCTGGCCGCCGGTGCCGCCCAGGACTACTCCACCCGCATGAATTGGC

TCAGCGCCGGGCCCGCGATGATCTCACGGGTGAATGACATCCGCGCCCACCGAAACCAGATACTC

CTAGAACAGTCAGCGCTCACCGCCACGCCCCGCAATCACCTCAATCCGCGTAATTGGCCCGCCGC

CCTGGTGTACCAGGAAATTCCCCAGCCCACGACCGTACTACTTCCGCGAGACGCCCAGGCCGAAG

TCCAGCTGACTAACTCAGGTGTCCAGCTGGCGGGGGGCGCCACCCTGTGTCGTCACCGCCCCGCT

CAGGGTATAAAGCGGCTGGTGATCCGGGGCAGAGGCACACAGCTCAACGACGAGGTGGTGAGCTC

TTCGCTGGGTCTGCGACCTGACGGAGTCTTCCAACTCGCCGGATCGGGGAGATCTTCCTTCACGC

CTCGTCAGGCCGTCCTGACTTTGGAGAGTTCGTCCTCGCAGCCCCGCTCGGGTGGCATCGGCACT

CTCCAGTTCGTGGAGGAGTTCACTCCCTCGGTCTACTTCAACCCCTTCTCCGGCTCCCCCGGCCA

CTACCCGGACGAGTTCATCCCGAACTTCGACGCCATCAGCGAGTCGGTGGACGGCTACGATTGAA

TGTCCCATGGTGGCGCAGCTGACCTAGCTCGGCTTCGACACCTGGACCACTGCCGCCGCTTCCGC

TGCTTCGCTCGGGATCTCGCCGAGTTTGCCTACTTTGAGCTGCCCGAGGAGCACCCTCAGGGCCC

GGCCCACGGAGTGCGGATCGTCGTCGAAGGGGGCCTCGACTCCCACCTGCTTCGGATCTTCAGCC

AGCGTCCGATCCTGGTCGAGCGCGAGCAAGGACAGACCCTTCTGACTCTGTACTGCATCTGCAAC

CACCCCGGCCTGCATGAAAGTCTTTGTTGTCTGCTGTGTACTGAGTATAATAAAAGCTGAGATCA

GCGACTACTCCGGACTTCCGTGTGTTCCTGAATCCATCAACCAGTCTTTGTTCTTCACCGGGAAC

GAGACCGAGCTCCAGCTCCAGTGTAAGCCCCACAAGAAGTACCTCACCTGGCTGTTCCAGGGCTC

CCCGATCGCCGTTGTCAACCACTGCGACAACGACGGAGTCCTGCTGAGCGGCCCTGCCAACCTTA

CTTTTTCCACCCGCAGAAGCAAGCTCCAGCTCTTCCAACCCTTCCTCCCCGGGACCTATCAGTGC

GTCTCGGGACCCTGCCATCACACCTTCCACCTGATCCCGAATACCACAGCGTCGCTCCCCGCTAC

TAACAACCAAACTAACCTCCACCAACGCCACCGTCGCGACGGCCACAATACATGCCCATATTAGA

CTATGAGGCCGAGCCACAGCGACCCATGCTCCCCGCTATTAGTTACTTCAATCTAACCGGCGGAG

ATGACTGACCCACTGGCCAACAACAACGTCAACGACCTTCTCCTGGACATGGACGGCCGCGCCTC

GGAGCAGCGACTGGCCCAACTTCGCATTCGCCAGCAGCAGGAGAGAGCCGTCAAGGAGCTGCAGG

ATGCGGTGGCCATCCACCAGTGCAAGAGAGGCATCTTCTGCCTGGTGAAACAGGCCAAGATCTCC

TACGAGGTCACTCCAAACGACCATCGCCTCTCCTACGAGCTCCTGCAGCAGCGCCAGAAGTTCAC

CTGCCTGGTCGGAGTCAACCCCATCGTCATCACCCAGCAGTCTGGCGATACCAAGGGGTGCATCC

-continued

ACTGCTCCTGCGACTCCCCCGACTGCGTCCACACTCTGATCAAGACCCTCTGCGGCCTCCGCGAC

CTCCTCCCCATGAACTAATCACCCCCTTATCCAGTGAAATAAAGATCATATTGATGATGATTTTA

CAGAAATAAAAAATAATCATTTGATTTGAAATAAAGATACAATCATATTGATGATTTGAGTTTAA

CAAAAAAATAAAGAATCACTTACTTGAAATCTGATACCAGGTCTCTGTCCATGTTTTCTGCCAAC

ACCACTTCACTCCCCTCTTCCCAGCTCTGGTACTGCAGGCCCCGGCGGGCTGCAAACTTCCTCCA

CACGCTGAAGGGGATGTCAAATTCCTCCTGTCCCTCAATCTTCATTTTATCTTCTATCAGATGTC

CAAAAAGCGCGTCCGGGTGGATGATGACTTCGACCCCGTCTACCCCTACGATGCAGACAACGCAC

CGACCGTGCCCTTCATCAACCCCCCCTTCGTCTCTTCAGATGGATTCCAAGAGAAGCCCCTGGGG

GTGTTGTCCCTGCGACTGGCCGACCCCGTCACCACCAAGAACGGGGAAATCACCCTCAAGCTGGG

AGAGGGGGTGGACCTCGATTCCTCGGGAAAACTCATCTCCAACACGGCCACCAAGGCCGCCGCCC

CTCTCAGTTTTTCCAACAACACCATTTCCCTTAACATGGATCACCCCTTTTACACTAAAGATGGA

AAATTATCCTTACAAGTTTCTCCACCATTAAATATACTGAGAACAAGCATTCTAAACACACTAGC

TTTAGGTTTTGGATCAGGTTTAGGACTCCGTGGCTCTGCCTTGGCAGTACAGTTAGTCTCTCCAC

TTACATTTGATACTGATGGAAACATAAAGCTTACCTTAGACAGAGGTTTGCATGTTACAACAGGA

GATGCAATTGAAAGCAACATAAGCTGGGCTAAAGGTTTAAAATTTGAAGATGGAGCCATAGCAAC

CAACATTGGAAATGGGTTAGAGTTTGGAAGCAGTAGTACAGAAACAGGTGTTGATGATGCTTACC

CAATCCAAGTTAAACTTGGATCTGGCCTTAGCTTTGACAGTACAGGAGCCATAATGGCTGGTAAC

AAAGAAGACGATAAACTCACTTTGTGGACAACACCTGATCCATCACCAAACTGTCAAATACTCGC

AGAAAATGATGCAAAACTAACACTTTGCTTGACTAAATGTGGTAGTCAAATACTGGCCACTGTGT

CAGTCTTAGTTGTAGGAAGTGGAAACCTAAACCCCATTACTGGCACCGTAAGCAGTGCTCAGGTG

TTTCTACGTTTTGATGCAAACGGTGTTCTTTTAACAGAACATTCTACACTAAAAAAATACTGGGG

GTATAGGCAGGGAGATAGCATAGATGGCACTCCATATACCAATGCTGTAGGATTCATGCCCAATT

TAAAAGCTTATCCAAAGTCACAAAGTTCTACTACTAAAAATAATATAGTAGGGCAAGTATACATG

AATGGAGATGTTTCAAAACCTATGCTTCTCACTATAACCCTCAATGGTACTGATGACAGCAACAG

TACATATTCAATGTCATTTTCATACACCTGGACTAATGGAAGCTATGTTGGAGCAACATTTGGGG

CTAACTCTTATACCTTCTCATACATCGCCCAAGAATGAACACTGTATCCCACCCTGCATGCCAAC

CCTTCCCACCCCACTCTGTGGAACAAACTCTGAAACACAAAATAAAATAAAGTTCAAGTGTTTTA

TTGATTCAACAGTTTTACAGGATTCGAGCAGTTATTTTTCCTCCACCCTCCCAGGACATGGAATA

CACCACCCTCTCCCCCCGCACAGCCTTGAACATCTGAATGCCATTGGTGATGGACATGCTTTTGG

TCTCCACGTTCCACACAGTTTCAGAGCGAGCCAGTCTCGGGTCGGTCAGGGAGATGAAACCCTCC

GGGCACTCCCGCATCTGCACCTCACAGCTCAACAGCTGAGGATTGTCCTCGGTGGTCGGGATCAC

GGTTATCTGGAAGAAGCAGAAGAGCGGCGGTGGGAATCATAGTCCGCGAACGGGATCGGCCGGTG

GTGTCGCATCAGGCCCCGCAGCAGTCGCTGCCGCCGCCGCTCCGTCAAGCTGCTGCTCAGGGGGT

CCGGGTCCAGGGACTCCCTCAGCATGATGCCCACGGCCCTCAGCATCAGTCGTCTGGTGCGGGGG

CGCAGCAGCGCATGCGGATCTCGCTCAGGTCGCTGCAGTACGTGCAACACAGAACCACCAGGTTG

TTCAACAGTCCATAGTTCAACACGCTCCAGCCGAAACTCATCGCGGGAAGGATGCTACCCACGTG

GCCGTCGTACCAGATCCTCAGGTAAATCAAGTGGTGCCCCCTCCAGAACACGCTGCCCACGTACA

TGATCTCCTTGGGCATGTGGCGGTTCACCACCTCCCGGTACCACATCACCCTCTGGTTGAACATG

CAGCCCCGGATGATCCTGCGGAACCACAGGGCCAGCACCGCCCCGCCCGCCATGCAGCGAAGAGA

CCCCGGGTCCCGGCAATGGCAATGGAGGACCCACCGCTCGTACCCGTGGATCATCTGGGAGCTGA

-continued

ACAAGTCTATGTTGGCACAGCACAGGCATATGCTCATGCATCTCTTCAGCACTCTCAACTCCTCG

GGGGTCAAAACCATATGCCAGGGCACGGGGAACTCTTGCAGGACAGCGAACCCCGCAGAACAGGG

CAATCCTCGCACAGAACTTACATTGTGCATGGACAGGGTATCGCAATCAGGCAGCACCGGGTGAT

CCTCCACCAGAGAAGCGCGGGTCTCGGTCTCCTCACAGCGTGGTAAGGGGGCCGGCCGATACGGG

TGATGGCGGGACGCGGCTGATCGTGTTCGCGACCGTGTCATGATGCAGTTGCTTTCGGACATTTT

CGTACTTGCTGTAGCAGAACCTGGTCCGGGCGCTGCACACCGATCGCCGGCGGCGGTCTCGGCGC

TTGGAACGCTCGGTGTTGAAATTGTAAAACAGCCACTCTCTCAGACCGTGCAGCAGATCTAGGGC

CTCAGGAGTGATGAAGATCCCATCATGCCTGATGGCTCTGATCACATCGACCACCGTGGAATGGG

CCAGACCCAGCCAGATGATGCAATTTTGTTGGGTTTCGGTGACGGCGGGGGAGGGAAGAACAGGA

AGAACCATGATTAACTTTTAATCCAAACGGTCTCGGAGTACTTCAAAATGAAGATCGCGGAGATG

GCACCTCTCGCCCCCGCTGTGTTGGTGGAAAATAACAGCCAGGTCAAAGGTGATACGGTTCTCGA

GATGTTCCACGGTGGCTTCCAGCAAAGCCTCCACGCGCACATCCAGAAACAAGACAATAGCGAAA

GCGGGAGGGTTCTCTAATTCCTCAATCATCATGTTACACTCCTGCACCATCCCCAGATAATTTTC

ATTTTTCCAGCCTTGAATGATTCGAACTAGTTCGTGAGGTAAATCCAAGCCAGCCATGATAAAGA

GCTCGCGCAGAGCGCCCTCCACCGGCATTCTTAAGCACACCCTCATAATTCCAAGATATTCTGCT

CCTGGTTCACCTGCAGCAGATTGACAAGCGGAATATCAAAATCTCTGCCGCGATCCCTGAGCTCC

TCCCTCAGCAATAACTGTAAGTACTCTTTCATATCCTCTCCGAAATTTTTAGCCATAGGACCACC

AGGAATAAGATTAGGGCAAGCCACAGTACAGATAAACCGAAGTCCTCCCCAGTGAGCATTGCCAA

ATGCAAGACTGCTATAAGCATGCTGGCTAGACCCGGTGATATCTTCCAGATAACTGGACAGAAAA

TCGCCCAGGCAATTTTTAAGAAAATCAACAAAAGAAAAATCCTCCAGGTGGACGTTTAGAGCCTC

GGGAACAACGATGAAGTAAATGCAAGCGGTGCGTTCCAGCATGGTTAGTTAGCTGATCTGTAGAA

AAAACAAAAATGAACATTAAACCATGCTAGCCTGGCGAACAGGTGGGTAAATCGTTCTCTCCAGC

ACCAGGCAGGCCACGGGGTCTCCGGCGCGACCCTCGTAAAAATTGTCGCTATGATTGAAAACCAT

CACAGAGAGACGTTCCCGGTGGCCGGCGTGAATGATTCGACAAGATGAATACACCCCCGGAACAT

TGGCGTCCGCGAGTGAAAAAAAGCGCCCGAGGAAGCAATAAGGCACTACAATGCTCAGTCTCAAG

TCCAGCAAAGCGATGCCATGCGGATGAAGCACAAAATTCTCAGGTGCGTACAAAATGTAATTACT

CCCCTCCTGCACAGGCAGCAAAGCCCCCGATCCCTCCAGGTACACATACAAAGCCTCAGCGTCCA

TAGCTTACCGAGCAGCAGCACACAACAGGCGCAAGAGTCAGAGAAAGGCTGAGCTCTAACCTGTC

CACCCGCTCTCTGCTCAATATATAGCCCAGATCTACACTGACGTAAAGGCCAAAGTCTAAAAATA

CCCGCCAAATAATCACACACGCCCAGCACACGCCCAGAAACCGGTGACACACTCAAAAAAATACG

CGCACTTCCTCAAACGCCCAAAACTGCCGTCATTTCCGGGTTCCCACGCTACGTCATCAAAACAC

GACTTTCAAATTCCGTCGACCGTTAAAAACGTCACCCGCCCCGCCCCTAACGGTCGCCCGTCTCT

CAGCCAATCAGCGCCCCGCATCCCCAAATTCAAACACCTCATTTGCATATTAACGCGCACAAAAA

GTTTGAGGTATATTATTGATGATGG

ChAdV68.5WTnt.GFP (SEQ ID NO: 13); AC_000011.1 with E1 (nt 577 to 3403) and E3 (nt 27,125- 31,825) sequences deleted; corresponding ATCC VR-594 nucleotides substituted at five positions; GFP reporter under the control of the CMV promoter/enhancer inserted in place of deleted E1

CCATCTTCAATAATATACCTCAAACTTTTTGTGCGCGTTAATATGCAAATGAGGCGTTTGAATTT

GGGGAGGAAGGGCGGTGATTGGTCGAGGGATGAGCGACCGTTAGGGGGGGGCGAGTGACGTTTTG

ATGACGTGGTTGCGAGGAGGAGCCAGTTTGCAAGTTCTCGTGGGAAAAGTGACGTCAAACGAGGT

-continued

GTGGTTTGAACACGGAAATACTCAATTTTCCCGCGCTCTCTGACAGGAAATGAGGTGTTTCTGGG

CGGATGCAAGTGAAAACGGGCCATTTTCGCGCGAAAACTGAATGAGGAAGTGAAAATCTGAGTAA

TTTCGCGTTTATGGCAGGGAGGAGTATTTGCCGAGGGCCGAGTAGACTTTGACCGATTACGTGGG

GGTTTCGATTACCGTGTTTTTCACCTAAATTTCCGCGTACGGTGTCAAAGTCCGGTGTTTTTACG

TAGGTGTCAGCTGATCGCCAGGGTATTTAAACCTGCGCTCTCCAGTCAAGAGGCCACTCTTGAGT

GCCAGCGAGAAGAGTTTTCTCCTCCGCGCCGCGAGTCAGATCTACACTTTGAAAGTAGGGATAAC

AGGGTAATgacattgattattgactagttGttaaTAGTAATCAATTACGGGGTCATTAGTTCATA

GCCCATATATGGAGTTCCGCGTTACATAACTTACGGTAAATGGCCCGCCTGGCTGACCGCCCAAC

CACCCCCGCCCATTGACGTCAATAATGACGTATGTTCCCATAGTAACGCCAATAGGGACTTTCCA

TTGACGTCAATGGGTGGAGTATTTACGGTAAACTGCCCACTTGGCAGTACATCAAGTGTATCATA

TGCCAAGTCCGCCCCCTATTGACGTCAATGACGGTAAATGGCCCCCCTGGCATTATGCCCAGTAC

ATGACCTTACGGGACTTTCCTACTTGGCAGTACATCTACGTATTAGTCATCGCTATTACCATGgT

GATGCGGTTTTGGCAGTACACCAATGGGCGTGGATAGCGGTTTGACTCACGGGGATTTCCAAGTC

TCCACCCCATTGACGTCAATGGGAGTTTGTTTTGGCACCAAAATCAACGGGACTTTCCAAAATGT

CGTAATAACCCCGCCCCGTTGACGCAAATGGGCGGTAGGCGTGTACGGTGGGAGGTCTATATAAG

CAGAgcTCGTTTAGTGAACCGTCAGATCGCCTGGAACGCCATCCACGCTGTTTTGACCTCCATAG

AAGACAGCGATCGCGecacCATGGTGAGCAAGGGCGAGGAGCTGTTCACCGGGGGGTGCCCATCC

TGGTCGAGCTGGACGGCGACGTAAACGGCCACAAGTTCAGCGTGTCCGGCGAGGGCGAGGGCGAT

GCCACCTACGGCAAGCTGACCCTGAAGTTCATCTGCACCACCGGCAAGCTGCCCGTGCCCTGGCC

CACCCTCGTGACCACCCTGACCTACGGCGTGCAGTGCTTCAGCCGCTACCCCGACCACATGAAGC

AGCACGACTTCTTCAAGTCCCCCATGCCCGAAGGCTACGTCCAGGAGCGCACCATCTTCTTCAAG

GACGACGGCAACTACAAGACCCGCGCCGAGGTGAAGTTCGAGGGCGACACCCTGGTGAACCGCAT

CGAGCTGAAGGGCATCGACTTCAAGGAGGACGGCAACATCCTGGGGCACAAGCTGGAGTACAACT

ACAACAGCCACAACGTCTATATCATGGCCGACAAGCAGAAGAACGGCATCAAGGTGAACTTCAAG

ATCCGCCACAACATCGAGGACGGCAGCGTGCAGCTCGCCGACCACTACCAGCAGAACACCCCCAT

CGGCGACGGCCCCGTGCTGCTGCCCGACAACCACTACCTGAGCACCCAGTCCGCCCTGAGCAAAG

ACCCCAACGAGAAGCGCGATCACATGGTCCTGCTGGAGTTCGTGACCGCCGCCGGGATCACTCTC

GGCATGGACGAGCTTTACAAGTAGtgaGTTTAAACTCCCATTTAAATGTGAGGGTTAATGCTTCG

AGCAGACATGATAAGATACATTGATGAGTTTGGACAAACCACAACTAGAATGCAGTGAAAAAAAT

GCTTTATTTGTGAAATTTGTGATGCTATTGCTTTATTTGTAACCATTATAAGCTGCAATAAACAA

GTTAACAACAACAATTGCATTCATTTTATGTTTCAGGTTCAGGGGGAGATGTGGGAGGTTTTTTA

AAGCAAGTAAAACCTCTACAAATGTGGTAAAATAACTATAACGGTCCTAAGGTAGCGAGTGAGTA

GTGTTCTGGGGCGGGGGAGGACCTGCATGAGGGCCAGAATAACTGAAATCTGTGCTTTTCTGTGT

GTTGCAGCAGCATGAGCGGAAGCGGCTCCTTTGAGGGAGGGGTATTCAGCCCTTATCTGACGGGG

CGTCTCCCCTCCTGGGCGGGAGTGCGTCAGAATGTGATGGGATCCACGGTGGACGGCCGGCCCGT

GCAGCCCGCGAACTCTTCAACCCTGACCTATGCAACCCTGAGCTCTTCGTCGTTGGACGCAGCTG

CCGCCGCAGCTGCTGCATCTGCCGCCAGCGCCGTGCGCGGAATGGCCATGGGCGCCGGCTACTAC

GGCACTCTGGTGGCCAACTCGAGTTCCACCAATAATCCCGCCAGCCTGAACGAGGAGAAGCTGTT

GCTGCTGATGGCCCAGCTCGAGGCCTTGACCCAGCGCCTGGGCGAGCTGACCCAGCAGGTGGCTC

-continued

AGCTGCAGGAGCAGACGCGGGCCGCGGTTGCCACGGTGAAATCCAAATAAAAAATGAATCAATAA

ATAAACGGAGACGGTTGTTGATTTTAACACAGAGTCTGAATCTTTATTTGATTTTTCGCGCGCGG

TAGGCCCTGGACCACCGGTCTCGATCATTGAGCACCCGGTGGATCTTTTCCAGGACCCGGTAGAG

GTGGGCTTGGATGTTGAGGTACATGGGCATGAGCCCGTCCCGGGGGTGGAGGTAGCTCCATTGCA

GGGCCTCGTGCTCGGGGGTGGTGTTGTAAATCACCCAGTCATAGCAGGGGCGCAGGGCATGGTGT

TGCACAATATCTTTGAGGAGGAGACTGATGGCCACGGGCAGCCCTTTGGTGTAGGTGTTTACAAA

TCTGTTGAGCTGGGAGGGATGCATGCGGGGGGAGATGAGGTGCATCTTGGCCTGGATCTTGAGAT

TGGCGATGTTACCGCCCAGATCCCGCCTGGGGTTCATGTTGTGCAGGACCACCAGCACGGTGTAT

CCGGTGCACTTGGGGAATTTATCATGCAACTTGGAAGGGAAGGCGTGAAAGAATTTGGCGACGCC

TTTGTGCCCGCCCAGGTTTTCCATGCACTCATCCATGATGATGGCGATGGGCCCGTGGGCGGCGG

CCTGGGCAAAGACGTTTCGGGGGTCGGACACATCATAGTTGTGGTCCTGGGTGAGGTCATCATAG

GCCATTTTAATGAATTTGGGGCGGAGGGTGCCGGACTGGGGGACAAAGGTACCCTCGATCCCGGG

GGCGTAGTTCCCCTCACAGATCTGCATCTCCCAGGCTTTGAGCTCGGAGGGGGGGATCATGTCCA

CCTGCGGGGCGATAAAGAACACGGTTTCCGGGGCGGGGGAGATGAGCTGGGCCGAAAGCAAGTTC

CGGAGCAGCTGGGACTTGCCGCAGCCGGTGGGGCCGTAGATGACCCCGATGACCGGCTGCAGGTG

GTAGTTGAGGGAGAGACAGCTGCCGTCCTCCCGGAGGAGGGGGGCCACCTCGTTCATCATCTCGC

GCACGTGCATGTTCTCGCGCACCAGTTCCGCCAGGAGGCGCTCTCCCCCCAGGGATAGGAGCTCC

TGGAGCGAGGCGAAGTTTTTCAGCGGCTTGAGTCCGTCGGCCATGGGCATTTTGGAGAGGGTTTG

TTGCAAGAGTTCCAGGCGGTCCCAGAGCTCGGTGATGTGCTCTACGGCATCTCGATCCAGCAGAC

CTCCTCGTTTCGCGGGTTGGGACGGCTGCGGGAGTAGGGCACCAGACGATGGGCGTCCAGCGCAG

CCAGGGTCCGGTCCTTCCAGGGTCGCAGCGTCCGCGTCAGGGTGGTCTCCGTCACGGTGAAGGGG

TGCGCGCCGGGCTGGGCGCTTGCGAGGGTGCGCTTCAGGCTCATCCGGCTGGTCGAAAACCGCTC

CCGATCGGCGCCCTGCGCGTCGGCCAGGTAGCAATTGACCATGAGTTCGTAGTTGAGCGCCTCGG

CCGCGTGGCCTTTGGCGCGGAGCTTACCTTTGGAAGTCTGCCCGCAGGCGGGACAGAGGAGGGAC

TTGAGGGCGTAGAGCTTGGGGGCGAGGAAGACGGACTCGGGGGCGTAGGCGTCCGCGCCGCAGTG

GGCGCAGACGGTCTCGCACTCCACGAGCCAGGTGAGGTCGGGCTGGTCGGGGTCAAAAACCAGTT

TCCCGCCGTTCTTTTTGATGCGTTTCTTACCTTTGGTCTCCATGAGCTCGTGTCCCCGCTGGGTG

ACAAAGAGGCTGTCCGTGTCCCCGTAGACCGACTTTATGGGCCGGTCCTCGAGCGGTGTGCCGCG

GTCCTCCTCGTAGAGGAACCCCGCCCACTCCGAGACGAAAGCCCGGGTCCAGGCCAGCACGAAGG

AGGCCACGTGGGACGGGTAGCGGTCGTTGTCCACCAGCGGGTCCACCTTTTCCAGGGTATGCAAA

CACATGTCCCCCTCGTCCACATCCAGGAAGGTGATTGGCTTGTAAGTGTAGGCCACGTGACCGGG

GGTCCCGGCCGGGGGGGTATAAAAGGGGGGGGTCCCTGCTCGTCCTCACTGTCTTCCGGATCGCT

GTCCAGGAGCGCCAGCTGTTGGGGTAGGTATTCCCTCTCGAAGGCGGGCATGACCTCGGCACTCA

GGTTGTCAGTTTCTAGAAACGAGGAGGATTTGATATTGACGGTGCCGGCGGAGATGCCTTTCAAG

AGCCCCTCGTCCATCTGGTCAGAAAAGACGATCTTTTTGTTGTCGAGCTTGGTGGCGAAGGAGCC

GTAGAGGGCGTTGGAGAGGAGCTTGGCGATGGAGCGCATGGTCTGGTTTTTTTCCTTGTCGGCGC

GCTCCTTGGCGGCGATGTTGAGCTGCACGTACTCGCGCGCCACGCACTTCCATTCGGGGAAGACG

GTGGTCAGCTCGTCGGGCACGATTCTGACCTGCCAGCCCCGATTATGCAGGGTGATGAGGTCCAC

ACTGGTGGCCACCTCGCCGCGCAGGGGCTCATTAGTCCAGCAGAGGCGTCCGCCCTTGCGCGAGC

AGAAGGGGGGCAGGGGGTCCAGCATGACCTCGTCGGGGGGGTCGGCATCGATGGTGAAGATGCCG

-continued

GGCAGGAGGTCGGGGTCAAAGTAGCTGATGGAAGTGGCCAGATCGTCCAGGGCAGCTTGCCATTC

GCGCACGGCCAGCGCGCGCTCGTAGGGACTGAGGGGCGTGCCCCAGGGCATGGGATGGGTAAGCG

CGGAGGCGTACATGCCGCAGATGTCGTAGACGTAGAGGGGCTCCTCGAGGATGCCGATGTAGGTG

GGGTAGCAGCGCCCCCCGCGGATGCTGGCGCGCACGTAGTCATACAGCTCGTGCGAGGGGGCGAG

GAGCCCCGGGCCCAGGTTGGTGCGACTGGGCTTTTCGGCGCGGTAGACGATCTGGCGGAAAATGG

CATGCGAGTTGGAGGAGATGGTGGGCCTTTGGAAGATGTTGAAGTGGGCGTGGGGCAGTCCGACC

GAGTCGCGGATGAAGTGGGCGTAGGAGTCTTGCAGCTTGGCGACGAGCTCGGCGGTGACTAGGAC

GTCCAGAGCGCAGTAGTCGAGGGTCTCCTGGATGATGTCATACTTGAGCTGTCCCTTTTGTTTCC

ACAGCTCGCGGTTGAGAAGGAACTCTTCGCGGTCCTTCCAGTACTCTTCGAGGGGGAACCCGTCC

TGATCTGCACGGTAAGAGCCTAGCATGTAGAACTGGTTGACGGCCTTGTAGGCGCAGCAGCCCTT

CTCCACGGGGAGGGCGTAGGCCTGGGCGGCCTTGCGCAGGGAGGTGTGCGTGAGGGCGAAAGTGT

CCCTGACCATGACCTTGAGGAACTGGTGCTTGAAGTCGATATCGTCGCAGCCCCCCTGCTCCCAG

AGCTGGAAGTCCGTGCGCTTCTTGTAGGCGGGGTTGGGCAAAGCGAAAGTAACATCGTTGAAGAG

GATCTTGCCCGCGCGGGGCATAAAGTTGCGAGTGATGCGGAAAGGTTGGGGCACCTCGGCCCGGT

TGTTGATGACCTGGGCGGCGAGCACGATCTCGTCGAAGCCGTTGATGTTGTGGCCCACGATGTAG

AGTTCCACGAATCGCGGACGGCCCTTGACGTGGGGCAGTTTCTTGAGCTCCTCGTAGGTGAGCTC

GTCGGGGTCGCTGAGCCCGTGCTGCTCGAGCGCCCAGTCGGCGAGATGGGGGTTGGCGCGGAGGA

AGGAAGTCCAGAGATCCACGGCCAGGGCGGTTTGCAGACGGTCCCGGTACTGACGGAACTGCTGC

CCGACGGCCATTTTTTCGGGGGTGACGCAGTAGAAGGTGCGGGGGTCCCCGTGCCAGCGATCCCA

TTTGAGCTGGAGGGCGAGATCGAGGGCGAGCTCGACGAGCCGGTCGTCCCCGGAGAGTTTCATGA

CCAGCATGAAGGGGACGAGCTGCTTGCCGAAGGACCCCATCCAGGTGTAGGTTTCCACATCGTAG

GTGAGGAAGAGCCTTTCGGTGCGAGGATGCGAGCCGATGGGGAAGAACTGGATCTCCTGCCACCA

ATTGGAGGAATGGCTGTTGATGTGATGGAAGTAGAAATGCCGACGGCGCGCCGAACACTCGTGCT

TGTGTTTATACAAGCGGCCACAGTGCTCGCAACGCTGCACGGGATGCACGTGCTGCACGAGCTGT

ACCTGAGTTCCTTTGACGAGGAATTTCAGTGGGAAGTGGAGTCGTGGCGCCTGCATCTCGTGCTG

TACTACGTCGTGGTGGTCGGCCTGGCCCTCTTCTGCCTCGATGGTGGTCATGCTGACGAGCCCGC

GCGGGAGGCAGGTCCAGACCTCGGCGCGAGCGGGTCGGAGAGCGAGGACGAGGGCGCGCAGGCCG

GAGCTGTCCAGGGTCCTGAGACGCTGCGGAGTCAGGTCAGTGGGCAGCGGCGGCGCGCGGTTGAC

TTGCAGGAGTTTTTCCAGGGCGCGCGGGAGGTCCAGATGGTACTTGATCTCCACCGCGCCATTGG

TGGCGACGTCGATGGCTTGCAGGGTCCCGTGCCCCTGGGGTGTGACCACCGTCCCCCGTTTCTTC

TTGGGCGGCTGGGGCGACGGGGGGGGTGCCTCTTCCATGGTTAGAAGCGGCGGCGAGGACGCGCG

CCGGGCGGCAGGGGCGGCTCGGGGCCCGGAGGCAGGGGCGGCAGGGGCACGTCGGCGCCGCGCGC

GGGTAGGTTCTGGTACTGCGCCCGGAGAAGACTGGCGTGAGCGACGACGCGACGGTTGACGTCCT

GGATCTGACGCCTCTGGGTGAAGGCCACGGGACCCGTGAGTTTGAACCTGAAAGAGAGTTCGACA

GAATCAATCTCGGTATCGTTGACGGCGGCCTGCCGCAGGATCTCTTGCACGTCGCCCGAGTTGTC

CTGGTAGGCGATCTCGGTCATGAACTGCTCGATCTCCTCCTCTTGAAGGTCTCCGCGGCCGGCGC

GCTCCACGGTGGCCGCGAGGTCGTTGGAGATGCGGCCCATGAGCTGCGAGAAGGCGTTCATGCCC

GCCTCGTTCCAGACGCGGCTGTAGACCACGACGCCCTCGGGATCGCgGGCGCGCATGACCACCTG

GGCGAGGTTGAGCTCCACGTGGCGCGTGAAGACCGCGTAGTTGCAGAGGCGCTGGTAGAGGTAGT

-continued

TGAGCGTGGTGGCGATGTGCTCGGTGACGAAGAAATACATGATCCAGCGGCGGAGCGGCATCTCG

CTGACGTCGCCCAGCGCCTCCAAACGTTCCATGGCCTCGTAAAAGTCCACGGCGAAGTTGAAAAA

CTGGGAGTTGCGCGCCGAGACGGTCAACTCCTCCTCCAGAAGACGGATGAGCTCGGCGATGGTGG

CGCGCACCTCGCGCTCGAAGGCCCCCGGGAGTTCCTCCACTTCCTCTTCTTCCTCCTCCACTAAC

ATCTCTTCTACTTCCTCCTCAGGCGGCAGTGGTGGCGGGGGAGGGGGCCTGCGTCGCCGGCGGCG

CACGGGCAGACGGTCGATGAAGCGCTCGATGGTCTCGCCGCGCCGGCGTCGCATGGTCTCGGTGA

CGGCGCGCCCGTCCTCGCGGGGCCGCAGCGTGAAGACGCCGCCGCGCATCTCCAGGTGGCCGGGG

GGGTCCCCGTTGGGCAGGGAGAGGGCGCTGACGATGCATCTTATCAATTGCCCCGTAGGGACTCC

GCGCAAGGACCTGAGCGTCTCGAGATCCACGGGATCTGAAAACCGCTGAACGAAGGCTTCGAGCC

AGTCGCAGTCGCAAGGTAGGCTGAGCACGGTTTCTTCTGGGGGGTCATGTTGGTTGGGAGCGGGG

GGGGCGATGCTGCTGGTGATGAAGTTGAAATAGGCGGTTCTGAGACGGCGGATGGTGGCGAGGAG

CACCAGGTCTTTGGGCCCGGCTTGCTGGATGCGCAGACGGTCGGCCATGCCCCAGGCGTGGTCCT

GACACCTGGCCAGGTCCTTGTAGTAGTCCTGCATGAGCCGCTCCACGGGCACCTCCTCCTCGCCC

GCGCGGCCGTGCATGCGCGTGAGCCCGAAGCCGCGCTGGGGCTGGACGAGCGCCAGGTCGGCGAC

GACGCGCTCGGCGAGGATGGCTTGCTGGATCTGGGTGAGGGTGGTCTGGAAGTCATCAAAGTCGA

CGAAGCGGTGGTAGGCTCCGGTGTTGATGGTGTAGGAGCAGTTGGCCATGACGGACCAGTTGACG

GTCTGGTGGCCCGGACGCACGAGCTCGTGGTACTTGAGGCGCGAGTAGGCGCGCGTGTCGAAGAT

GTAGTCGTTGCAGGTGCGCACCAGGTACTGGTAGCCGATGAGGAAGTGCGGCGGCGGCTGGCGGT

AGAGCGGCCATCGCTCGGTGGCGGGGGCGCCGGGCGCGAGGTCCTCGAGCATGGTGCGGTGGTAG

CCGTAGATGTACCTGGACATCCAGGTGATGCCGGCGGCGGTGGTGGAGGCGCGCGGGAACTCGCG

GACGCGGTTCCAGATGTTGCGCAGCGGCAGGAAGTAGTTCATGGTGGGCACGGTCTGGCCCGTGA

GGCGCGCGCAGTCGTGGATGCTCTATACGGGCAAAAACGAAAGCGGTCAGCGGCTCGACTCCGTG

GCCTGGAGGCTAAGCGAACGGGTTGGGCTGCGCGTGTACCCCGGTTCGAATCTCGAATCAGGCTG

GAGCCGCAGCTAACGTGGTATTGGCACTCCCGTCTCGACCCAAGCCTGCACCAACCCTCCAGGAT

ACGGAGGCGGGTCGTTTTGCAACTTTTTTTTGGAGGCCGGATGAGACTAGTAAGCGCGGAAAGCG

GCCGACCGCGATGGCTCGCTGCCGTAGTCTGGAGAAGAATCGCCAGGGTTGCGTTGCGGTGTGCC

CCGGTTCGAGGCCGGCCGGATTCCGCGGCTAACGAGGGCGTGGCTGCCCCGTCGTTTCCAAGACC

CCATAGCCAGCCGACTTCTCCAGTTACGGAGCGAGCCCCTCTTTTGTTTTGTTTGTTTTTGCCAG

ATGCATCCCGTACTGCGGCAGATGCGCCCCCACCACCCTCCACCGCAACAACAGCCCCCTCCACA

GCCGGCGCTTCTGCCCCCGCCCCAGCAGCAACTTCCAGCCACGACCGCCGCGGCCGCCGTGAGCG

GGGCTGGACAGAGTTATGATCACCAGCTGGCCTTGGAAGAGGGCGAGGGGCTGGCGCGCCTGGGG

GCGTCGTCGCCGGAGCGGCACCCGCGCGTGCAGATGAAAAGGGACGCTCGCGAGGCCTACGTGCC

CAAGCAGAACCTGTTCAGAGACAGGAGCGGCGAGGAGCCCGAGGAGATGCGCGCGGCCCGGTTCC

ACGCGGGGCGGGAGCTGCGGCGCGGCCTGGACCGAAAGAGGGTGCTGAGGGACGAGGATTTCGAG

GCGGACGAGCTGACGGGGATCAGCCCCGCGCGCGCGCACGTGGCCGCGGCCAACCTGGTCACGGC

GTACGAGCAGACCGTGAAGGAGGAGAGCAACTTCCAAAAATCCTTCAACAACCACGTGCGCACCC

TGATCGCGCGCGAGGAGGTGACCCTGGGCCTGATGCACCTGTGGGACCTGCTGGAGGCCATCGTG

CAGAACCCCACCAGCAAGCCGCTGACGGCGCAGCTGTTCCTGGTGGTGCAGCATAGTCGGGACAA

CGAAGCGTTCAGGGAGGCGCTGCTGAATATCACCGAGCCCGAGGGCCGCTGGCTCCTGGACCTGG

TGAACATTCTGCAGAGCATCGTGGTGCAGGAGCGCGGGCTGCCGCTGTCCGAGAAGCTGGCGGCC

-continued

ATCAACTTCTCGGTGCTGAGTTTGGGCAAGTACTACGCTAGGAAGATCTACAAGACCCCGTACGT

GCCCATAGACAAGGAGGTGAAGATCGACGGGTTTTACATGCGCATGACCCTGAAAGTGCTGACCC

TGAGCGACGATCTGGGGGTGTACCGCAACGACAGGATGCACCGTGCGGTGAGCGCCAGCAGGCGG

CGCGAGCTGAGCGACCAGGAGCTGATGCATAGTCTGCAGCGGGCCCTGACCGGGGCCGGGACCGA

GGGGGAGAGCTACTTTGACATGGGCGCGGACCTGCACTGGCAGCCCAGCCGCCGGGCCTTGGAGG

CGGCGGCAGGACCCTACGTAGAAGAGGTGGACGATGAGGTGGACGAGGAGGGCGAGTACCTGGAA

GACTGATGGCGCGACCGTATTTTTGCTAGATGCAACAACAACAGCCACCTCCTGATCCCGCGATG

CGGGCGGCGCTGCAGAGCCAGCCGTCCGGCATTAACTCCTCGGACGATTGGACCCAGGCCATGCA

ACGCATCATGGCGCTGACGACCCGCAACCCCGAAGCCTTTAGACAGCAGCCCCAGGCCAACCGGC

TCTCGGCCATCCTGGAGGCCGTGGTGCCCTCGCGCTCCAACCCCACGCACGAGAAGGTCCTGGCC

ATCGTGAACGCGCTGGTGGAGAACAAGGCCATCCGCGGCGACGAGGCCGGCCTGGTGTACAACGC

GCTGCTGGAGCGCGTGGCCCGCTACAACAGCACCAACGTGCAGACCAACCTGGACCGCATGGTGA

CCGACGTGCGCGAGGCCGTGGCCCAGCGCGAGCGGTTCCACCGCGAGTCCAACCTGGGATCCATG

GTGGCGCTGAACGCCTTCCTCAGCACCCAGCCCGCCAACGTGCCCCGGGGCCAGGAGGACTACAC

CAACTTCATCAGCGCCCTGCGCCTGATGGTGACCGAGGTGCCCCAGAGCGAGGTGTACCAGTCCG

GGCCGGACTACTTCTTCCAGACCAGTCGCCAGGGCTTGCAGACCGTGAACCTGAGCCAGGCTTTC

AAGAACTTGCAGGGCCTGTGGGGCGTGCAGGCCCCGGTCGGGGACCGCGCGACGGTGTCGAGCCT

GCTGACGCCGAACTCGCGCCTGCTGCTGCTGCTGGTGGCCCCCTTCACGGACAGCGGCAGCATCA

ACCGCAACTCGTACCTGGGCTACCTGATTAACCTGTACCGCGAGGCCATCGGCCAGGCGCACGTG

GACGAGCAGACCTACCAGGAGATCACCCACGTGAGCCGCGCCCTGGGCCAGGACGACCCGGGCAA

CCTGGAAGCCACCCTGAACTTTTTGCTGACCAACCGGTCGCAGAAGATCCCCCCCCAGTACGCGC

TCAGCACCGAGGAGGAGCGCATCCTGCGTTACGTGCAGCAGAGCGTGGGCCTGTTCCTGATGCAG

GAGGGGGCCACCCCCAGCGCCGCGCTCGACATGACCGCGCGCAACATGGAGCCCAGCATGTACGC

CAGCAACCGCCCGTTCATCAATAAACTGATGGACTACTTGCATCGGGCGGCCGCCATGAACTCTG

ACTATTTCACCAACGCCATCCTGAATCCCCACTGGCTCCCGCCGCCGGGGTTCTACACGGGCGAG

TACGACATGCCCGACCCCAATGACGGGTTCCTGTGGGACGATGTGGACAGCAGCGTGTTCTCCCC

CCGACCGGGTGCTAACGAGCGCCCCTTGTGGAAGAAGGAAGGCAGCGACCGACGCCCGTCCTCGG

CGCTGTCCGGCCGCGAGGGTGCTGCCGCGGCGGTGCCCGAGGCCGCCAGTCCTTTCCCGAGCTTG

CCCTTCTCGCTGAACAGTATCCGCAGCAGCGAGCTGGGCAGGATCACGCGCCCGCGCTTGCTGGG

CGAAGAGGAGTACTTGAATGACTCGCTGTTGAGACCCGAGCGGGAGAAGAACTTCCCCAATAACG

GGATAGAAAGCCTGGTGGACAAGATGAGCCGCTGGAAGACGTATGCGCAGGAGCACAGGGACGAT

CCCCGGGCGTCGCAGGGGGCCACGAGCCGGGGCAGCGCCGCCCGTAAACGCCGGTGGCACGACAG

GCAGCGGGGACAGATGTGGGACGATGAGGACTCCGCCGACGACAGCAGCGTGTTGGACTTGGGTG

GGAGTGGTAACCCGTTCGCTCACCTGCGCCCCCGTATCGGGCGCATGATGTAAGAGAAACCGAAA

ATAAATGATACTCACCAAGGCCATGGCGACCAGCGTGCGTTCGTTTCTTCTCTGTTGTTGTTGTA

TCTAGTATGATGAGGCGTGCGTACCCGGAGGGTCCTCCTCCCTCGTACGAGAGCGTGATGCAGCA

GGCGATGGCGGCGGCGGCGATGCAGCCCCCGCTGGAGGCTCCTTACGTGCCCCCGCGGTACCTGG

CGCCTACGGAGGGGCGGAACAGCATTCGTTACTCGGAGCTGGCACCCTTGTACGATACCACCCGG

TTGTACCTGGTGGACAACAAGTCGGCGGACATCGCCTCGCTGAACTACCAGAACGACCACAGCAA

-continued

CTTCCTGACCACCGTGGTGCAGAACAATGACTTCACCCCCACGGAGGCCAGCACCCAGACCATCA

ACTTTGACGAGCGCTCGCGGTGGGGCGGCCAGCTGAAAACCATCATGCACACCAACATGCCCAAC

GTGAACGAGTTCATGTACAGCAACAAGTTCAAGGCGCGGGTGATGGTCTCCCGCAAGACCCCCAA

TGGGGTGACAGTGACAGAGGATTATGATGGTAGTCAGGATGAGCTGAAGTATGAATGGGTGGAAT

TTGAGCTGCCCGAAGGCAACTTCTCGGTGACCATGACCATCGACCTGATGAACAACGCCATCATC

GACAATTACTTGGCGGTGGGGCGGCAGAACGGGGTGCTGGAGAGCGACATCGGCGTGAAGTTCGA

CACTAGGAACTTCAGGCTGGGCTGGGACCCCGTGACCGAGCTGGTCATGCCCGGGGTGTACACCA

ACGAGGCTTTCCATCCCGATATTGTCTTGCTGCCCGGCTGCGGGGTGGACTTCACCGAGAGCCGC

CTCAGCAACCTGCTGGGCATTCGCAAGAGGCAGCCCTTCCAGGAAGGCTTCCAGATCATGTACGA

GGATCTGGAGGGGGGCAACATCCCCGCGCTCCTGGATGTCGACGCCTATGAGAAAAGCAAGGAGG

ATGCAGCAGCTGAAGCAACTGCAGCCGTAGCTACCGCCTCTACCGAGGTCAGGGGCGATAATTTT

GCAAGCGCCGCAGCAGTGGCAGCGGCCGAGGCGGCTGAAACCGAAAGTAAGATAGTCATTCAGCC

GGTGGAGAAGGATAGCAAGAACAGGAGCTACAACGTACTACCGGACAAGATAAACACCGCCTACC

GCAGCTGGTACCTAGCCTACAACTATGGCGACCCCGAGAAGGGCGTGCGCTCCTGGACGCTGCTC

ACCACCTCGGACGTCACCTGCGGCGTGGAGCAAGTCTACTGGTCGCTGCCCGACATGATGCAAGA

CCCGGTCACCTTCCGCTCCACGCGTCAAGTTAGCAACTACCCGGTGGTGGGCGCCGAGCTCCTGC

CCGTCTACTCCAAGAGCTTCTTCAACGAGCAGGCCGTCTACTCGCAGCAGCTGCGCGCCTTCACC

TCGCTTACGCACGTCTTCAACCGCTTCCCCGAGAACCAGATCCTCGTCCGCCCGCCCGCGCCCAC

CATTACCACCGTCAGTGAAAACGTTCCTGCTCTCACAGATCACGGGACCCTGCCGCTGCGCAGCA

GTATCCGGGGAGTCCAGCGCGTGACCGTTACTGACGCCAGACGCCGCACCTGCCCCTACGTCTAC

AAGGCCCTGGGCATAGTCGCGCCGCGCGTCCTCTCGAGCCGCACCTTCTAAATGTCCATTCTCAT

CTCGCCCAGTAATAACACCGGTTGGGGCCTGCGCGCGCCCAGCAAGATGTACGGAGGCGCTCGCC

AACGCTCCACGCAACACCCCGTGCGCGTGCGCGGGCACTTCCGCGCTCCCTGGGGCGCCCTCAAG

GGCCGCGTGCGGTCGCGCACCACCGTCGACGACGTGATCGACCAGGTGGTGGCCGACGCGCGCAA

CTACACCCCCGCCGCCGCGCCCGTCTCCACCGTGGACGCCGTCATCGACAGCGTGGTGGCCGACG

CGCGCCGGTACGCCCGCGCCAAGAGCCGGCGGCGGCGCATCGCCCGGCGGCACCGGAGCACCCCC

GCCATGCGCGCGGCGCGAGCCTTGCTGCGCAGGGCCAGGCGCACGGGACGCAGGGCCATGCTCAG

GGCGGCCAGACGCGCGGCTTCAGGCGCCAGCGCCGGCAGGACCCGGAGACGCGCGGCCACGGCGG

CGGCAGCGGCCATCGCCAGCATGTCCCGCCCGCGGCGAGGGAACGTGTACTGGGTGCGCGACGCC

GCCACCGGTGTGCGCGTGCCCGTGCGCACCCGCCCCCCTCGCACTTGAAGATGTTCACTTCGCGA

TGTTGATGTGTCCCAGCGGCGAGGAGGATGTCCAAGCGCAAATTCAAGGAAGAGATGCTCCAGGT

CATCGCGCCTGAGATCTACGGCCCTGCGGTGGTGAAGGAGGAAAGAAAGCCCCGCAAAATCAAGC

GGGTCAAAAAGGACAAAAAGGAAGAAGAAAGTGATGTGGACGGATTGGTGGAGTTTGTGCGCGAG

TTCGCCCCCCGGCGGCGCGTGCAGTGGCGCGGGCGGAAGGTGCAACCGGTGCTGAGACCCGGCAC

CACCGTGGTCTTCACGCCCGGCGAGCGCTCCGGCACCGCTTCCAAGCGCTCCTACGACGAGGTGT

ACGGGGATGATGATATTCTGGAGCAGGCGGCCGAGCGCCTGGGCGAGTTTGCTTACGGCAAGCGC

AGCCGTTCCGCACCGAAGGAAGAGGCGGTGTCCATCCCGCTGGACCACGGCAACCCCACGCCGAG

CCTCAAGCCCGTGACCTTGCAGCAGGTGCTGCCGACCGCGGCGCCGCGCCGGGGGTTCAAGCGCG

AGGGCGAGGATCTGTACCCCACCATGCAGCTGATGGTGCCCAAGCGCCAGAAGCTGGAAGACGTG

CTGGAGACCATGAAGGTGGACCCGGACGTGCAGCCCGAGGTCAAGGTGCGGCCCATCAAGCAGGT

-continued

GGCCCCGGGCCTGGGCGTGCAGACCGTGGACATCAAGATTCCCACGGAGCCCATGGAAACGCAGA

CCGAGCCCATGATCAAGCCCAGCACCAGCACCATGGAGGTGCAGACGGATCCCTGGATGCCATCG

GCTCCTAGTCGAAGACCCCGGCGCAAGTACGGCGCGGCCAGCCTGCTGATGCCCAACTACGCGCT

GCATCCTTCCATCATCCCCACGCCGGGCTACCGCGGCACGCGCTTCTACCGCGGTCATACCAGCA

GCCGCCGCCGCAAGACCACCACTCGCCGCCGCCGTCGCCGCACCGCCGCTGCAACCACCCCTGCC

GCCCTGGTGCGGAGAGTGTACCGCCGCGGCCGCGCACCTCTGACCCTGCCGCGCGCGCGCTACCA

CCCGAGCATCGCCATTTAAACTTTCGCCTGCTTTGCAGATCAATGGCCCTCACATGCCGCCTTCG

CGTTCCCATTACGGGCTACCGAGGAAGAAAACCGCGCCGTAGAAGGCTGGCGGGGAACGGGATGC

GTCGCCACCACCACCGGCGGCGGCGCGCCATCAGCAAGCGGTTGGGGGGAGGCTTCCTGCCCGCG

CTGATCCCCATCATCGCCGCGGCGATCGGGGCGATCCCCGGCATTGCTTCCGTGGCGGTGCAGGC

CTCTCAGCGCCACTGAGACACACTTGGAAACATCTTGTAATAAACCaATGGACTCTGACGCTCCT

GGTCCTGTGATGTGTTTTCGTAGACAGATGGAAGACATCAATTTTTCGTCCCTGGCTCCGCGACA

CGGCACGCGGCCGTTCATGGGCACCTGGAGCGACATCGGCACCAGCCAACTGAACGGGGGCGCCT

TCAATTGGAGCAGTCTCTGGAGCGGGCTTAAGAATTTCGGGTCCACGCTTAAAACCTATGGCAGC

AAGGCGTGGAACAGCACCACAGGGCAGGCGCTGAGGGATAAGCTGAAAGAGCAGAACTTCCAGCA

GAAGGTGGTCGATGGGCTCGCCTCGGGCATCAACGGGGTGGTGGACCTGGCCAACCAGGCCGTGC

AGCGGCAGATCAACAGCCGCCTGGACCCGGTGCCGCCCGCCGGCTCCGTGGAGATGCCCCAGGTG

GAGGAGGAGCTGCCTCCCCTGGACAAGCGGGGCGAGAAGCGACCCCGCCCCGATGCGGAGGAGAC

GCTGCTGACGCACACGGACGAGCCGCCCCCGTACGAGGAGGCGGTGAAACTGGGTCTGCCCACCA

CGCGGCCCATCGCGCCCCTGGCCACCGGGGTGCTGAAACCCGAAAAGCCCGCGACCCTGGACTTG

CCTCCTCCCCAGCCTTCCCGCCCCTCTACAGTGGCTAAGCCCCTGCCGCCGGTGGCCGTGGCCCG

CGCGCGACCCGGGGGCACCGCCCGCCCTCATGCGAACTGGCAGAGCACTCTGAACAGCATCGTGG

GTCTGGGAGTGCAGAGTGTGAAGCGCCGCCGCTGCTATTAAACCTACCGTAGCGCTTAACTTGCT

TGTCTGTGTGTGTATGTATTATGTCGCCGCCGCCGCTGTCCACCAGAAGGAGGAGTGAAGAGGCG

CGTCGCCGAGTTGCAAGATGGCCACCCCATCGATGCTGCCCCAGTGGGCGTACATGCACATCGCC

GGACAGGACGCTTCGGAGTACCTGAGTCCGGGTCTGGTGCAGTTTGCCCGCGCCACAGACACCTA

CTTCAGTCTGGGGAACAAGTTTAGGAACCCCACGGTGGCGCCCACGCACGATGTGACCACCGACC

GCAGCCAGCGGCTGACGCTGCGCTTCGTGCCCGTGGACCGCGAGGACAACACCTACTCGTACAAA

GTGCGCTACACGCTGGCCGTGGGCGACAACCGCGTGCTGGACATGGCCAGCACCTACTTTGACAT

CCGCGGCGTGCTGGATCGGGGCCCTAGCTTCAAACCCTACTCCGGCACCGCCTACAACAGTCTGG

CCCCCAAGGGAGCACCCAACACTTGTCAGTGGACATATAAAGCCGATGGTGAAACTGCCACAGAA

AAAACCTATACATATGGAAATGCACCCGTGCAGGGCATTAACATCACAAAAGATGGTATTCAACT

TGGAACTGACACCGATGATCAGCCAATCTACGCAGATAAAACCTATCAGCCTGAACCTCAAGTGG

GTGATGCTGAATGGCATGACATCACTGGTACTGATGAAAAGTATGGAGGCAGAGCTCTTAAGCCT

GATACCAAAATGAAGCCTTGTTATGGTTCTTTTGCCAAGCCTACTAATAAAGAAGGAGGTCAGGC

AAATGTGAAAACAGGAACAGGCACTACTAAAGAATATGACATAGACATGGCTTTCTTTGACAACA

GAAGTGCGGCTGCTGCTGGCCTAGCTCCAGAAATTGTTTTGTATACTGAAAATGTGGATTTGGAA

ACTCCAGATACCCATATTGTATACAAAGCAGGCACAGATGACAGCAGCTCTTCTATTAATTTGGG

TCAGCAAGCCATGCCCAACAGACCTAACTACATTGGTTTCAGAGACAACTTTATCGGGCTCATGT

-continued

ACTACAACAGCACTGGCAATATGGGGGTGCTGGCCGGTCAGGCTTCTCAGCTGAATGCTGTGGTT

GACTTGCAAGACAGAAACACCGAGCTGTCCTACCAGCTCTTGCTTGACTCTCTGGGTGACAGAAC

CCGGTATTTCAGTATGTGGAATCAGGCGGTGGACAGCTATGATCCTGATGTGCGCATTATTGAAA

ATCATGGTGTGGAGGATGAACTTCCCAACTATTGTTTCCCTCTGGATGCTGTTGGCAGAACAGAT

ACTTATCAGGGAATTAAGGCTAATGGAACTGATCAAACCACATGGACCAAAGATGACAGTGTCAA

TGATGCTAATGAGATAGGCAAGGGTAATCCATTCGCCATGGAAATCAACATCCAAGCCAACCTGT

GGAGGAACTTCCTCTACGCCAACGTGGCCCTGTACCTGCCCGACTCTTACAAGTACACGCCGGCC

AATGTTACCCTGCCCACCAACACCAACACCTACGATTACATGAACGGCCGGGTGGTGGCGCCCTC

GCTGGTGGACTCCTACATCAACATCGGGGCGCGCTGGTCGCTGGATCCCATGGACAACGTGAACC

CCTTCAACCACCACCGCAATGCGGGGCTGCGCTACCGCTCCATGCTCCTGGGCAACGGGCGCTAC

GTGCCCTTCCACATCCAGGTGCCCCAGAAATTTTTCGCCATCAAGAGCCTCCTGCTCCTGCCCGG

GTCCTACACCTACGAGTGGAACTTCCGCAAGGACGTCAACATGATCCTGCAGAGCTCCCTCGCCA

ACGACCTGCGCACGGACGGGGCCTCCATCTCCTTCACCAGCATCAACCTCTACGCCACCTTCTTC

CCCATGGCGCACAACACGGCCTCCACGCTCGAGGCCATGCTGCGCAACGACACCAACGACCAGTC

CTTCAACGACTACCTCTCGGCGGCCAACATGCTCTACCCCATCCCGGCCAACGCCACCAACGTGC

CCATCTCCATCCCCTCGCGCAACTGGGCCGCCTTCCGCGGCTGGTCCTTCACGCGTCTCAAGACC

AAGGAGACGCCCTCGCTGGGCTCCGGGTTCGACCCCTACTTCGTCTACTCGGGCTCCATCCCCTA

CCTCGACGGCACCTTCTACCTCAACCACACCTTCAAGAAGGTCTCCATCACCTTCGACTCCTCCG

TCAGCTGGCCCGGCAACGACCGGCTCCTGACGCCCAACGAGTTCGAAATCAAGCGCACCGTCGAC

GGCGAGGGCTACAACGTGGCCCAGTGCAACATGACCAAGGACTGGTTCCTGGTCCAGATGCTGGC

CCACTACAACATCGGCTACCAGGGCTTCTACGTGCCCGAGGGCTACAAGGACCGCATGTACTCCT

TCTTCCGCAACTTCCAGCCCATGAGCCGCCAGGTGGTGGACGAGGTCAACTACAAGGACTACCAG

GCCGTCACCCTGGCCTACCAGCACAACAACTGGGGCTTCGTCGGCTACCTCGCGCCCACCATGCG

CCAGGGCCAGCCCTACCCCGCCAACTACCCCTACCCGCTCATCGGCAAGAGCGCCGTCACCAGCG

TCACCCAGAAAAAGTTCCTCTGCGACAGGGTCATGTGGCGCATCCCCTTCTCCAGCAACTTCATG

TCCATGGGCGCGCTCACCGACCTCGGCCAGAACATGCTCTATGCCAACTCCGCCCACGCGCTAGA

CATGAATTTCGAAGTCGACCCCATGGATGAGTCCACCCTTCTCTATGTTGTCTTCGAAGTCTTCG

ACGTCGTCCGAGTGCACCACCCCCACCGCGGCGTCATCGAGGCCGTCTACCTGCGCACCCCCTTC

TCGGCCGGTAACGCCACCACCTAAGCTCTTGCTTCTTGCAAGCCATGGCCGCGGGCTCCGGCGAG

CAGGAGCTCAGGGCCATCATCCGCGACCTGGGCTGCGGGCCCTACTTCCTGGGCACCTTCGATAA

GCGCTTCCCGGGATTCATGGCCCCGCACAAGCTGGCCTGCGCCATCGTCAACACGGCCGGCCGCG

AGACCGGGGGCGAGCACTGGCTGGCCTTCGCCTGGAACCCGCGCTCGAACACCTGCTACCTCTTC

GACCCCTTCGGGTTCTCGGACGAGCGCCTCAAGCAGATCTACCAGTTCGAGTACGAGGGCCTGCT

GCGCCGCAGCGCCCTGGCCACCGAGGACCGCTGCGTCACCCTGGAAAAGTCCACCCAGACCGTGC

AGGGTCCGCGCTCGGCCGCCTGCGGGCTCTTCTGCTGCATGTTCCTGCACGCCTTCGTGCACTGG

CCCGACCGCCCCATGGACAAGAACCCCACCATGAACTTGCTGACGGGGGTGCCCAACGGCATGCT

CCAGTCGCCCCAGGTGGAACCCACCCTGCGCCGCAACCAGGAGGCGCTCTACCGCTTCCTCAACT

CCCACTCCGCCTACTTTCGCTCCCACCGCGCGCGCATCGAGAAGGCCACCGCCTTCGACCGCATG

AATCAAGACATGTAAACCGTGTGTGTATGTTAAATGTCTTTAATAAACAGCACTTTCATGTTACA

CATGCATCTGAGATGATTTATTTAGAAATCGAAAGGGTTCTGCCGGGTCTCGGCATGGCCCGCGG

-continued

GCAGGGACACGTTGCGGAACTGGTACTTGGCCAGCCACTTGAACTCGGGGATCAGCAGTTTGGGC

AGCGGGGTGTCGGGGAAGGAGTCGGTCCACAGCTTCCGCGTCAGTTGCAGGGCGCCCAGCAGGTC

GGGCGCGGAGATCTTGAAATCGCAGTTGGGACCCGCGTTCTGCGCGCGGGAGTTGCGGTACACGG

GGTTGCAGCACTGGAACACCATCAGGGCCGGGTGCTTCACGCTCGCCAGCACCGTCGCGTCGGTG

ATGCTCTCCACGTCGAGGTCCTCGGCGTTGGCCATCCCGAAGGGGGTCATCTTGCAGGTCTGCCT

TCCCATGGTGGGCACGCACCCGGGCTTGTGGTTGCAATCGCAGTGCAGGGGGATCAGCATCATCT

GGGCCTGGTCGGCGTTCATCCCCGGGTACATGGCCTTCATGAAAGCCTCCAATTGCCTGAACGCC

TGCTGGGCCTTGGCTCCCTCGGTGAAGAAGACCCCGCAGGACTTGCTAGAGAACTGGTTGGTGGC

GCACCCGGCGTCGTGCACGCAGCAGCGCGCGTCGTTGTTGGCCAGCTGCACCACGCTGCGCCCCC

AGCGGTTCTGGGTGATCTTGGCCCGGTCGGGGTTCTCCTTCAGCGCGCGCTGCCCGTTCTCGCTC

GCCACATCCATCTCGATCATGTGCTCCTTCTGGATCATGGTGGTCCCGTGCAGGCACCGCAGCTT

GCCCTCGGCCTCGGTGCACCCGTGCAGCCACAGCGCGCACCCGGTGCACTCCCAGTTCTTGTGGG

CGATCTGGGAATGCGCGTGCACGAAGCCCTGCAGGAAGCGGCCCATCATGGTGGTCAGGGTCTTG

TTGCTAGTGAAGGTCAGCGGAATGCCGCGGTGCTCCTCGTTGATGTACAGGTGGCAGATGCGGCG

GTACACCTCGCCCTGCTCGGGCATCAGCTGGAAGTTGGCTTTCAGGTCGGTCTCCACGCGGTAGC

GGTCCATCAGCATAGTCATGATTTCCATACCCTTCTGCCAGGCCGAGACGATGGGCAGGCTCATA

GGGTTCTTCACCATCATCTTAGCGCTAGCAGCCGCGGCCAGGGGGTCGCTCTCGTCCAGGGTCTC

AAAGCTCCGCTTGCCGTCCTTCTCGGTGATCCGCACCGGGGGGTAGCTGAAGCCCACGGCCGCCA

GCTCCTCCTCGGCCTGTCTTTCGTCCTCGCTGTCCTGGCTGACGTCCTGCAGGACCACATGCTTG

GTCTTGCGGGGTTTCTTCTTGGGCGGCAGCGGCGGCGGAGATGTTGGAGATGGCGAGGGGGAGCG

CGAGTTCTCGCTCACCACTACTATCTCTTCCTCTTCTTGGTCCGAGGCCACGCGGCGGTAGGTAT

GTCTCTTCGGGGGCAGAGGCGGAGGCGACGGGCTCTCGCCGCCGCGACTTGGGGGATGGCTGGCA

GAGCCCCTTCCGCGTTCGGGGGTGCGCTCCCGGCGGCGCTCTGACTGACTTCCTCCGCGGCCGGC

CATTGTGTTCTCCTAGGGAGGAACAACAAGCATGGAGACTCAGCCATCGCCAACCTCGCCATCTG

CCCCCACCGCCGACGAGAAGCAGCAGCAGCAGAATGAAAGCTTAACCGCCCCGCCGCCCAGCCCC

GCCACCTCCGACGCGGCCGTCCCAGACATGCAAGAGATGGAGGAATCCATCGAGATTGACCTGGG

CTATGTGACGCCCGCGGAGCACGAGGAGGAGCTGGCAGTGCGCTTTTCACAAGAAGAGATACACC

AAGAACAGCCAGAGCAGGAAGCAGAGAATGAGCAGAGTCAGGCTGGGCTCGAGCATGACGGCGAC

TACCTCCACCTGAGCGGGGGGGAGGACGCGCTCATCAAGCATCTGGCCCGGCAGGCCACCATCGT

CAAGGATGCGCTGCTCGACCGCACCGAGGTGCCCCTCAGCGTGGAGGAGCTCAGCCGCGCCTACG

AGTTGAACCTCTTCTCGCCGCGCGTGCCCCCCAAGCGCCAGCCCAATGGCACCTGCGAGCCCAAC

CCGCGCCTCAACTTCTACCCGGTCTTCGCGGTGCCCGAGGCCCTGGCCACCTACCACATCTTTTT

CAAGAACCAAAAGATCCCCGTCTCCTGCCGCGCCAACCGCACCCGCGCCGACGCCCTTTTCAACC

TGGGTCCCGGCGCCCCCCTACCTGATATCGCCTCCTTGGAAGAGGTTCCCAAGATCTTCGAGGGT

CTGGGCAGCGACGAGACTCGGGCCCCGAACGCTCTGCAAGGAGAAGGAGGAGAGCATGAGCACCA

CAGCGCCCTGGTCGAGTTGGAAGGCGACAACGCGCGGCTGGCGGTGCTCAAACGCACGGTCGAGC

TGACCCATTTCGCCTACCCGGCTCTGAACCTGCCCCCCAAAGTCATGAGCGCGGTCATGGACCAG

GTGCTCATCAAGCGCGCGTCGCCCATCTCCGAGGACGAGGGCATGCAAGACTCCGAGGAGGGCAA

GCCCGTGGTCAGCGACGAGCAGCTGGCCCGGTGGCTGGGTCCTAATGCTAGTCCCCAGAGTTTGG

-continued

AAGAGCGGCGCAAACTCATGATGGCCGTGGTCCTGGTGACCGTGGAGCTGGAGTGCCTGCGCCGC

TTCTTCGCCGACGCGGAGACCCTGCGCAAGGTCGAGGAGAACCTGCACTACCTCTTCAGGCACGG

GTTCGTGCGCCAGGCCTGCAAGATCTCCAACGTGGAGCTGACCAACCTGGTCTCCTACATGGGCA

TCTTGCACGAGAACCGCCTGGGGCAGAACGTGCTGCACACCACCCTGCGCGGGGAGGCCCGGCGC

GACTACATCCGCGACTGCGTCTACCTCTACCTCTGCCACACCTGGCAGACGGGCATGGGCGTGTG

GCAGCAGTGTCTGGAGGAGCAGAACCTGAAAGAGCTCTGCAAGCTCCTGCAGAAGAACCTCAAGG

GTCTGTGGACCGGGTTCGACGAGCGCACCACCGCCTCGGACCTGGCCGACCTCATTTTCCCCGAG

CGCCTCAGGCTGACGCTGCGCAACGGCCTGCCCGACTTTATGAGCCAAAGCATGTTGCAAAACTT

TCGCTCTTTCATCCTCGAACGCTCCGGAATCCTGCCCGCCACCTGCTCCGCGCTGCCCTCGGACT

TCGTGCCGCTGACCTTCCGCGAGTGCCCCCCGCCGCTGTGGAGCCACTGCTACCTGCTGCGCCTG

GCCAACTACCTGGCCTACCACTCGGACGTGATCGAGGACGTCAGCGGCGAGGGCCTGCTCGAGTG

CCACTGCCGCTGCAACCTCTGCACGCCGCACCGCTCCCTGGCCTGCAACCCCCAGCTGCTGAGCG

AGACCCAGATCATCGGCACCTTCGAGTTGCAAGGGCCCAGCGAAGGCGAGGGTTCAGCCGCCAAG

GGGGGTCTGAAACTCACCCCGGGGCTGTGGACCTCGGCCTACTTGCGCAAGTTCGTGCCCGAGGA

CTACCATCCCTTCGAGATCAGGTTCTACGAGGACCAATCCCATCCGCCCAAGGCCGAGCTGTCGG

CCTGCGTCATCACCCAGGGGGCGATCCTGGCCCAATTGCAAGCCATCCAGAAATCCCGCCAAGAA

TTCTTGCTGAAAAAGGGCCGCGGGGTCTACCTCGACCCCCAGACCGGTGAGGAGCTCAACCCCGG

CTTCCCCCAGGATGCCCCGAGGAAACAAGAAGCTGAAAGTGGAGCTGCCCCCCGTGGAGGATTTG

GAGGAAGACTGGGAGAACAGCAGTCAGGCAGAGGAGGAGGAGATGGAGGAAGACTGGGACAGCAC

TCAGGCAGAGGAGGACAGCCTGCAAGACAGTCTGGAGGAAGACGAGGAGGAGGCAGAGGAGGAGG

TGGAAGAAGCAGCCGCCGCCAGACCGTCGTCCTCGGGGGGGGAGAAAGCAAGCAGCACGGATACC

ATCTCCGCTCCGGGTCGGGGTCCCGCTCGACCACACAGTAGATGGGACGAGACCGGACGATTCCC

GAACCCCACCACCCAGACCGGTAAGAAGGAGCGGCAGGGATACAAGTCCTGGCGGGGGCACAAAA

ACGCCATCGTCTCCTGCTTGCAGGCCTGCGGGGGCAACATCTCCTTCACCCGGCGCTACCTGCTC

TTCCACCGCGGGGTGAACTTTCCCCGCAACATCTTGCATTACTACCGTCACCTCCACAGCCCCTA

CTACTTCCAAGAAGAGGCAGCAGCAGCAGAAAAAGACCAGCAGAAAACCAGCAGCTAGAAAATCC

ACAGCGGCGGCAGCAGGTGGACTGAGGATCGCGGCGAACGAGCCGGCGCAAACCCGGGAGCTGAG

GAACCGGATCTTTCCCACCCTCTATGCCATCTTCCAGCAGAGTCGGGGGCAGGAGCAGGAACTGA

AAGTCAAGAACCGTTCTCTGCGCTCGCTCACCCGCAGTTGTCTGTATCACAAGAGCGAAGACCAA

CTTCAGCGCACTCTCGAGGACGCCGAGGCTCTCTTCAACAAGTACTGCGCGCTCACTCTTAAAGA

GTAGCCCGCGCCCGCCCAGTCGCAGAAAAAGGCGGGAATTACGTCACCTGTGCCCTTCGCCCTAG

CCGCCTCCACCCATCATCATGAGCAAAGAGATTCCCACGCCTTACATGTGGAGCTACCAGCCCCA

GATGGGCCTGGCCGCCGGTGCCGCCCAGGACTACTCCACCCGCATGAATTGGCTCAGCGCCGGGC

CCGCGATGATCTCACGGGTGAATGACATCCGCGCCCACCGAAACCAGATACTCCTAGAACAGTCA

GCGCTCACCGCCACGCCCCGCAATCACCTCAATCCGCGTAATTGGCCCGCCGCCCTGGTGTACCA

GGAAATTCCCCAGCCCACGACCGTACTACTTCCGCGAGACGCCCAGGCCGAAGTCCAGCTGACTA

ACTCAGGTGTCCAGCTGGCGGGCGGCGCCACCCTGTGTCGTCACCGCCCCGCTCAGGGTATAAAG

CGGCTGGTGATCCGGGGCAGAGGCACACAGCTCAACGACGAGGTGGTGAGCTCTTCGCTGGGTCT

GCGACCTGACGGAGTCTTCCAACTCGCCGGATCGGGGAGATCTTCCTTCACGCCTCGTCAGGCCG

TCCTGACTTTGGAGAGTTCGTCCTCGCAGCCCCGCTCGGGTGGCATCGGCACTCTCCAGTTCGTG

-continued

GAGGAGTTCACTCCCTCGGTCTACTTCAACCCCTTCTCCGGCTCCCCCGGCCACTACCCGGACGA

GTTCATCCCGAACTTCGACGCCATCAGCGAGTCGGTGGACGGCTACGATTGAAACTAATCACCCC

CTTATCCAGTGAAATAAAGATCATATTGATGATGATTTTACAGAAATAAAAAATAATCATTTGAT

TTGAAATAAAGATACAATCATATTGATGATTTGAGTTTAACAAAAAAATAAAGAATCACTTACTT

GAAATCTGATACCAGGTCTCTGTCCATGTTTTCTGCCAACACCACTTCACTCCCCTCTTCCCAGC

TCTGGTACTGCAGGCCCCGGGGGCTGCAAACTTCCTCCACACGCTGAAGGGGATGTCAAATTCCT

CCTGTCCCTCAATCTTCATTTTATCTTCTATCAGATGTCCAAAAAGCGCGTCCGGGTGGATGATG

ACTTCGACCCCGTCTACCCCTACGATGCAGACAACGCACCGACCGTGCCCTTCATCAACCCCCCC

TTCGTCTCTTCAGATGGATTCCAAGAGAAGCCCCTGGGGGTGTTGTCCCTGCGACTGGCCGACCC

CGTCACCACCAAGAACGGGGAAATCACCCTCAAGCTGGGAGAGGGGGTGGACCTCGATTCCTCGG

GAAAACTCATCTCCAACACGGCCACCAAGGCCGCCGCCCCTCTCAGTTTTTCCAACAACACCATT

TCCCTTAACATGGATCACCCCTTTTACACTAAAGATGGAAAATTATCCTTACAAGTTTCTCCACC

ATTAAATATACTGAGAACAAGCATTCTAAACACACTAGCTTTAGGTTTTGGATCAGGTTTAGGAC

TCCGTGGCTCTGCCTTGGCAGTACAGTTAGTCTCTCCACTTACATTTGATACTGATGGAAACATA

AAGCTTACCTTAGACAGAGGTTTGCATGTTACAACAGGAGATGCAATTGAAAGCAACATAAGCTG

GGCTAAAGGTTTAAAATTTGAAGATGGAGCCATAGCAACCAACATTGGAAATGGGTTAGAGTTTG

GAAGCAGTAGTACAGAAACAGGTGTTGATGATGCTTACCCAATCCAAGTTAAACTTGGATCTGGC

CTTAGCTTTGACAGTACAGGAGCCATAATGGCTGGTAACAAAGAAGACGATAAACTCACTTTGTG

GACAACACCTGATCCATCACCAAACTGTCAAATACTCGCAGAAAATGATGCAAAACTAACACTTT

GCTTGACTAAATGTGGTAGTCAAATACTGGCCACTGTGTCAGTCTTAGTTGTAGGAAGTGGAAAC

CTAAACCCCATTACTGGCACCGTAAGCAGTGCTCAGGTGTTTCTACGTTTTGATGCAAACGGTGT

TCTTTTAACAGAACATTCTACACTAAAAAAATACTGGGGGTATAGGCAGGGAGATAGCATAGATG

GCACTCCATATACCAATGCTGTAGGATTCATGCCCAATTTAAAAGCTTATCCAAAGTCACAAAGT

TCTACTACTAAAAATAATATAGTAGGGCAAGTATACATGAATGGAGATGTTTCAAAACCTATGCT

TCTCACTATAACCCTCAATGGTACTGATGACAGCAACAGTACATATTCAATGTCATTTTCATACA

CCTGGACTAATGGAAGCTATGTTGGAGCAACATTTGGGGCTAACTCTTATACCTTCTCATACATC

GCCCAAGAATGAACACTGTATCCCACCCTGCATGCCAACCCTTCCCACCCCACTCTGTGGAACAA

ACTCTGAAACACAAAATAAAATAAAGTTCAAGTGTTTTATTGATTCAACAGTTTTACAGGATTCG

AGCAGTTATTTTTCCTCCACCCTCCCAGGACATGGAATACACCACCCTCTCCCCCCGCACAGCCT

TGAACATCTGAATGCCATTGGTGATGGACATGCTTTTGGTCTCCACGTTCCACACAGTTTCAGAG

CGAGCCAGTCTCGGGTCGGTCAGGGAGATGAAACCCTCCGGGCACTCCCGCATCTGCACCTCACA

GCTCAACAGCTGAGGATTGTCCTCGGTGGTCGGGATCACGGTTATCTGGAAGAAGCAGAAGAGCG

GCGGTGGGAATCATAGTCCGCGAACGGGATCGGCCGGTGGTGTCGCATCAGGCCCCGCAGCAGTC

GCTGCCGCCGCCGCTCCGTCAAGCTGCTGCTCAGGGGGTCCGGGTCCAGGGACTCCCTCAGCATG

ATGCCCACGGCCCTCAGCATCAGTCGTCTGGTGCGGCGGGCGCAGCAGCGCATGCGGATCTCGCT

-continued

CAGGTCGCTGCAGTACGTGCAACACAGAACCACCAGGTTGTTCAACAGTCCATAGTTCAACACGC

TCCAGCCGAAACTCATCGCGGGAAGGATGCTACCCACGTGGCCGTCGTACCAGATCCTCAGGTAA

ATCAAGTGGTGCCCCCTCCAGAACACGCTGCCCACGTACATGATCTCCTTGGGCATGTGGCGGTT

CACCACCTCCCGGTACCACATCACCCTCTGGTTGAACATGCAGCCCCGGATGATCCTGCGGAACC

ACAGGGCCAGCACCGCCCCCCCCGCCATGCAGCGAAGAGACCCCGGGTCCCGGCAATGGCAATGG

AGGACCCACCGCTCGTACCCGTGGATCATCTGGGAGCTGAACAAGTCTATGTTGGCACAGCACAG

GCATATGCTCATGCATCTCTTCAGCACTCTCAACTCCTCGGGGGTCAAAACCATATCCCAGGGCA

CGGGGAACTCTTGCAGGACAGCGAACCCCGCAGAACAGGGCAATCCTCGCACAGAACTTACATTG

TGCATGGACAGGGTATCGCAATCAGGCAGCACCGGGTGATCCTCCACCAGAGAAGCGCGGGTCTC

GGTCTCCTCACAGCGTGGTAAGGGGGCCGGCCGATACGGGTGATGGCGGGACGCGGCTGATCGTG

TTCGCGACCGTGTCATGATGCAGTTGCTTTCGGACATTTTCGTACTTGCTGTAGCAGAACCTGGT

CCGGGCGCTGCACACCGATCGCCGGCGGCGGTCTCGGCGCTTGGAACGCTCGGTGTTGAAATTGT

AAAACAGCCACTCTCTCAGACCGTGCAGCAGATCTAGGGCCTCAGGAGTGATGAAGATCCCATCA

TGCCTGATGGCTCTGATCACATCGACCACCGTGGAATGGGCCAGACCCAGCCAGATGATGCAATT

TTGTTGGGTTTCGGTGACGGCGGGGGAGGGAAGAACAGGAAGAACCATGATTAACTTTTAATCCA

AACGGTCTCGGAGTACTTCAAAATGAAGATCGCGGAGATGGCACCTCTCGCCCCCGCTGTGTTGG

TGGAAAATAACAGCCAGGTCAAAGGTGATACGGTTCTCGAGATGTTCCACGGTGGCTTCCAGCAA

AGCCTCCACGCGCACATCCAGAAACAAGACAATAGCGAAAGCGGGAGGGTTCTCTAATTCCTCAA

TCATCATGTTACACTCCTGCACCATCCCCAGATAATTTTCATTTTTCCAGCCTTGAATGATTCGA

ACTAGTTCCTGAGGTAAATCCAAGCCAGCCATGATAAAGAGCTCGCGCAGAGCGCCCTCCACCGG

CATTCTTAAGCACACCCTCATAATTCCAAGATATTCTGCTCCTGGTTCACCTGCAGCAGATTGAC

AAGCGGAATATCAAAATCTCTGCCGCGATCCCTGAGCTCCTCCCTCAGCAATAACTGTAAGTACT

CTTTCATATCCTCTCCGAAATTTTTAGCCATAGGACCACCAGGAATAAGATTAGGGCAAGCCACA

GTACAGATAAACCGAAGTGCTGCCCAGTGAGCATTGCCAAATGCAAGACTGCTATAAGCATGCTG

GCTAGACCCGGTGATATCTTCCAGATAACTGGACAGAAAATCGCCCAGGCAATTTTTAAGAAAAT

CAACAAAAGAAAAATCCTCCAGGTGGACGTTTAGAGCCTCGGGAACAACGATGAAGTAAATGCAA

GCGGTGCGTTCCAGCATGGTTAGTTAGCTGATCTGTAGAAAAAACAAAAATGAACATTAAACCAT

GCTAGCCTGGCGAACAGGTGGGTAAATCGTTCTCTCCAGCACCAGGCAGGCCACGGGGTCTCCGG

CGCGACCCTCGTAAAAATTGTCGCTATGATTGAAAACCATCACAGAGAGACGTTCCCGGTGGCCG

GCGTGAATGATTCGACAAGATGAATACACCCCCGGAACATTGGCGTCCGCGAGTGAAAAAAAGCG

CCCGAGGAAGCAATAAGGCACTACAATGCTCAGTCTCAAGTCCAGCAAAGCGATGCCATGCGGAT

GAAGCACAAAATTCTCAGGTGCGTACAAAATGTAATTACTCCCCTCCTGCACAGGCAGCAAAGCC

CCCGATCCCTCCAGGTACACATACAAAGCCTCAGCGTCCATAGCTTACCGAGCAGCAGCACACAA

CAGGCGCAAGAGTCAGAGAAAGGCTGAGCTCTAACCTGTCCACCCGCTCTCTGCTCAATATATAG

CCCAGATCTACACTGACGTAAAGGCCAAAGTCTAAAAATACCCGCCAAATAATCACACACGCCCA

GCACACGCCCAGAAACCGGTGACACACTCAAAAAAATACGCGCACTTCCTCAAACCCCCAAAACT

GCCGTCATTTCCGGGTTCCCACGCTACGTCATCAAAACACGACTTTCAAATTCCGTCGACCGTTA

AAAACGTCACCCGCCCCGCCCCTAACGGTCGCCCGTCTCTCAGCCAATCAGCGCCCCGCATCCCC

AAATTCAAACACCTCATTTGCATATTAACGCGCACAAAAAGTTTGAGGTATATTATTGATGATGG

XV.B. ChAd Neoandigen Cassette Delivery Vector Testing

XV.B.1. ChAd Vector Evaluation Methods and Materials

Transfection of HEK293A Cells Using Lipofectamine

DNA for the ChAdV68 constructs (ChAdV68.4WTnt.GFP, ChAdV68.5WTnt.GFP, ChAdV68.4WTnt.MAG25mer and ChAdV68.5WTnt.MAG25mer) was prepared and transfected into HEK293A cells using the following protocol.

10 ug of plasmid DNA was digested with PacI to liberate the viral genome. DNA was then purified using GeneJet DNA cleanup Micro columns (Thermo Fisher) according to manufacturer's instructions for long DNA fragments, and eluted in 20 ul of pre-heated water, columns were left at 37 degrees for 0.5-1 hours before the elution step.

HEK293A cells were introduced into 6-well plates at a cell density of $10^6$ cells/well 14-18 hours prior to transfection. Cells were overlaid with 1 ml of fresh medium (DMEM-10% hiFBS with pen/strep and glutamate) per well. 1-2 ug of purified DNA was used per well in a transfection with twice the ul volume (2-4 ul) of Lipofectamine2000, according to the manufacturer's protocol. 0.5 ml of OPTI-MEM medium containing the transfection mix was added to the 1 ml of normal growth medium in each well, and left on cells overnight.

Transfected cell cultures were incubated at 37° C. for at least 5-7 days. If viral plaques were not visible by day 7 post-transfection, cells were split 1:4 or 1:6, and incubated at 37° C. to monitor for plaque development. Alternatively, transfected cells were harvested and subjected to 3 cycles of freezing and thawing and the cell lysates were used to infect HEK293A cells and the cells were incubated until virus plaques were observed.

Transfection of ChAdV68 Vectors into HEK293A Cells Using Calcium Phosphate and Generation of the Tertiary Viral Stock DNA for the ChAdV68 constructs (ChAdV68.4WTnt.GFP, ChAdV68.5WTnt.GFP, ChAdV68.4WTnt.MAG25mer, ChAdV68.5WTnt.MAG25mer) was prepared and transfected into HEK293A cells using the following protocol.

HEK293A cells were seeded one day prior to the transfection at $10^6$ cells/well of a 6 well plate in 5% BS/DMEM/1×P/S, 1×Glutamax. Two wells are needed per transfection. Two to four hours prior to transfection the media was changed to fresh media. The ChAdV68.4WTnt.GFP plasmid was linearized with PacI. The linearized DNA was then phenol chloroform extracted and precipitated using one tenth volume of 3M Sodium acetate pH 5.3 and two volumes of 100% ethanol. The precipitated DNA was pelleted by centrifugation at 12,000×g for 5 min before washing 1× with 70% ethanol. The pellet was air dried and re-suspended in 50 μL of sterile water. The DNA concentration was determined using a NanoDrop™ (ThermoFisher) and the volume adjusted to 5 μg of DNA/50 μL.

169 μL of sterile water was added to a microfuge tube. 5 μL of 2M $CaCl_2$ was then added to the water and mixed gently by pipetting. 50 μL of DNA was added dropwise to the $CaCl_2$ water solution. Twenty six μL of 2M $CaCl_2$ was then added and mixed gently by pipetting twice with a micro-pipetor. This final solution should consist of 5 μg of DNA in 250 μL of 0.25M $CaCl_2$. A second tube was then prepared containing 250 μL of 2×HBS (Hepes buffered solution). Using a 2 mL sterile pipette attached to a Pipet-Aid air was slowly bubbled through the 2×HBS solution. At the same time the DNA solution in the 0.25M $CaCl_2$ solution was added in a dropwise fashion. Bubbling was continued for approximately 5 seconds after addition of the final DNA droplet. The solution was then incubated at room temperature for up to 20 minutes before adding to 293A cells. 250 μL of the DNA/Calcium phosphate solution was added dropwise to a monolayer of 293A cells that had been seeded one day prior at $10^6$ cells per well of a 6 well plate. The cells were returned to the incubator and incubated overnight. The media was changed 24 h later. After 72 h the cells were split 1:6 into a 6 well plate. The monolayers were monitored daily by light microscopy for evidence of cytopathic effect (CPE). 7-10 days post transfection viral plaques were observed and the monolayer harvested by pipetting the media in the wells to lift the cells. The harvested cells and media were transferred to a 50 mL centrifuge tube followed by three rounds of freeze thawing (at −80° C. and 37° C.). The subsequent lysate, called the primary virus stock was clarified by centrifugation at full speed on a bench top centrifuge (4300×g) and a proportion of the lysate 10-50%) used to infect 293A cells in a T25 flask. The infected cells were incubated for 48 h before harvesting cells and media at complete CPE. The cells were once again harvested, freeze thawed and clarified before using this secondary viral stock to infect a T150 flask seeded at $1.5\times10^7$ cells per flask. Once complete CPE was achieved at 72 h the media and cells were harvested and treated as with earlier viral stocks to generate a tertiary stock.

Production in 293F Cells

ChAdV68 virus production was performed in 293F cells grown in 293 FreeStyle™ (ThermoFisher) media in an incubator at 8% $CO_2$. On the day of infection cells were diluted to $10^6$ cells per mL, with 98% viability and 400 mL were used per production run in 1 L Shake flasks (Corning). 4 mL of the tertiary viral stock with a target MOI of >3.3 was used per infection. The cells were incubated for 48-72 h until the viability was <70% as measured by Trypan blue. The infected cells were then harvested by centrifugation, full speed bench top centrifuge and washed in 1×PBS, re-centrifuged and then re-suspended in 20 mL of 10 mM Tris pH7.4. The cell pellet was lysed by freeze thawing 3× and clarified by centrifugation at 4,300×g for 5 minutes.

Purification by CsCl Centrifugation

Viral DNA was purified by CsCl centrifugation. Two discontinuous gradient runs were performed. The first to purify virus from cellular components and the second to further refine separation from cellular components and separate defective from infectious particles.

10 mL of 1.2 (26.8 g CsCl dissolved in 92 mL of 10 mM Tris pH 8.0) CsCl was added to polyallomer tubes. Then 8 mL of 1.4 CsCl (53 g CsCl dissolved in 87 mL of 10 mM Tris pH 8.0) was carefully added using a pipette delivering to the bottom of the tube. The clarified virus was carefully layered on top of the 1.2 layer. If needed more 10 mM Tris was added to balance the tubes. The tubes were then placed in a SW-32Ti rotor and centrifuged for 2 h 30 min at 10° C. The tube was then removed to a laminar flow cabinet and the virus band pulled using an 18 guage needle and a 10 mL syringe. Care was taken not to remove contaminating host cell DNA and protein. The band was then diluted at least 2× with 10 mM Tris pH 8.0 and layered as before on a discontinuous gradient as described above. The run was performed as described before except that this time the run was performed overnight. The next day the band was pulled with care to avoid pulling any of the defective particle band. The virus was then dialyzed using a Slide-a-Lyzer™ Cassette (Pierce) against ARM buffer (20 mM Tris pH 8.0, 25 mM NaCl, 2.5% Glycerol). This was performed 3×, 1 h per buffer exchange. The virus was then aliquoted for storage at −80° C.

Viral Assays

VP concentration was performed by using an OD 260 assay based on the extinction coefficient of $1.1\times10^{12}$ viral particles (VP) is equivalent to an Absorbance value of 1 at OD260 nm. Two dilutions (1:5 and 1:10) of adenovirus were made in a viral lysis buffer (0.1% SDS, 10 mM Tris pH 7.4, 1 mM EDTA). OD was measured in duplicate at both dilutions and the VP concentration/mL was measured by multiplying the OD260 value X dilution factor X $1.1\times10^{12}$VP.

An infectious unit (IU) titer was calculated by a limiting dilution assay of the viral stock. The virus was initially diluted 100× in DMEM/5% NS/1×PS and then subsequently diluted using 10-fold dilutions down to $1\times10^{-7}$. 100 μL of these dilutions were then added to 293A cells that were seeded at least an hour before at 3e5 cells/well of a 24 well plate. This was performed in duplicate. Plates were incubated for 48 h in a CO2 (5%) incubator at 37° C. The cells were then washed with 1×PBS and were then fixed with 100% cold methanol (−20° C.). The plates were then incubated at −20° C. for a minimum of 20 minutes. The wells were washed with 1×PBS then blocked in 1×PBS/0.1% BSA for 1 h at room temperature. A rabbit anti-Ad antibody (Abcam, Cambridge, MA) was added at 1:8,000 dilution in blocking buffer (0.25 ml per well) and incubated for 1 h at room temperature. The wells were washed 4× with 0.5 mL PBS per well. A HRP conjugated Goat anti-Rabbit antibody (Bethyl Labs, Montgomery Texas) diluted 1000× was added per well and incubated for 1 h prior to a final round of washing. 5 PBS washes were performed and the plates were developed using DAB (Diaminobenzidine tetrahydrochloride) substrate in Tris buffered saline (0.67 mg/mL DAB in 50 mM Tris pH 7.5, 150 mM NaCl) with 0.01% $H_2O_2$. Wells were developed for 5 min prior to counting. Cells were counted under a 10× objective using a dilution that gave between 4-40 stained cells per field of view. The field of view that was used was a 0.32 $mm^2$ grid of which there are equivalent to 625 per field of view on a 24 well plate. The number of infectious viruses/mL can be determined by the number of stained cells per grid multiplied by the number of grids per field of view multiplied by a dilution factor 10. Similarly, when working with GFP expressing cells florescent can be used rather than capsid staining to determine the number of GFP expressing virions per mL.

Immunizations

C57BL/6J female mice and Balb/c female mice were injected with $1\times10^{8}$ viral particles (VP) of ChAdV68.5WTnt.MAG25mer in 100 uL volume, bilateral intramuscular injection (50 uL per leg).

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM $NH_4Cl$, 10 mM $KHCO_3$, 0.1 mM $Na_2EDTA$). Cells were filtered again through a 30 micron filter and then resuspended in complete RPMI. Cells were counted on the Attune N×T flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). $5\times10^{4}$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Figure 21C:
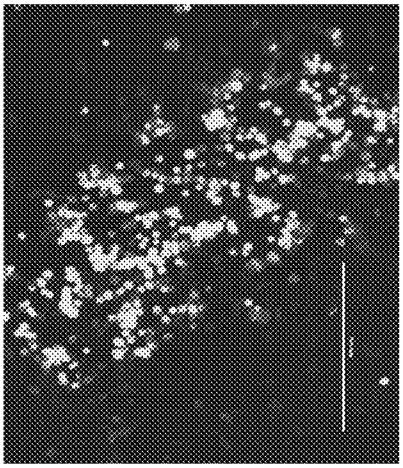
FIG. 21C illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using fluorescent microscopy at 100× magnification.
Figure 21B:
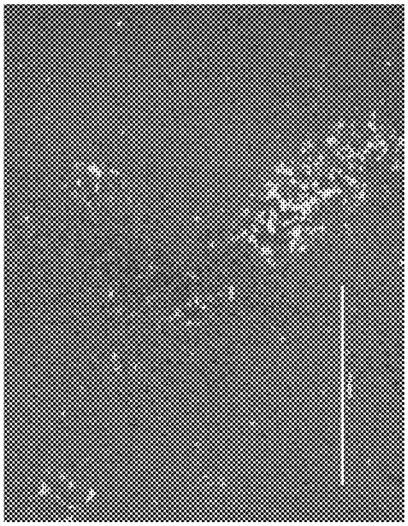
FIG. 21B illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using fluorescent microscopy at 40× magnification.
Figure 21A:
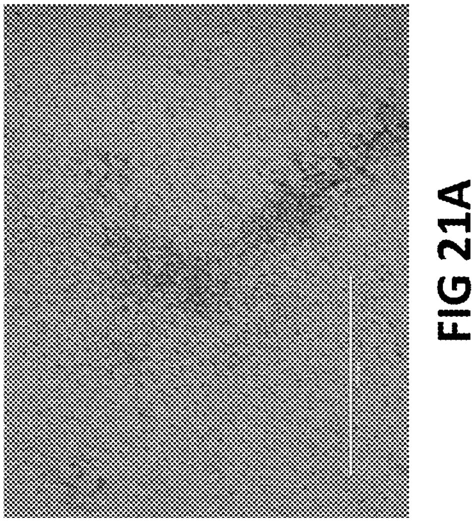
FIG. 21A illustrates ChAdV68.4WTnt.GFP virus production after transfection. HEK293A cells were transfected with ChAdV68.4WTnt.GFP DNA using the calcium phosphate protocol. Viral replication was observed 10 days after transfection and ChAdV68.4WTnt.GFP viral plaques were visualized using light microscopy (40× magnification).
Figure 22C:
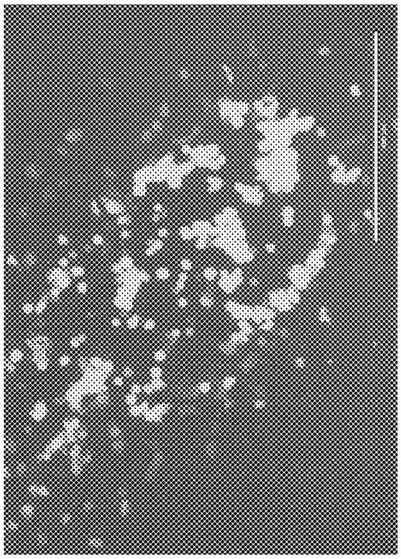
FIG. 22C illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using fluorescent microscopy at 100× magnification.
Figure 22B:
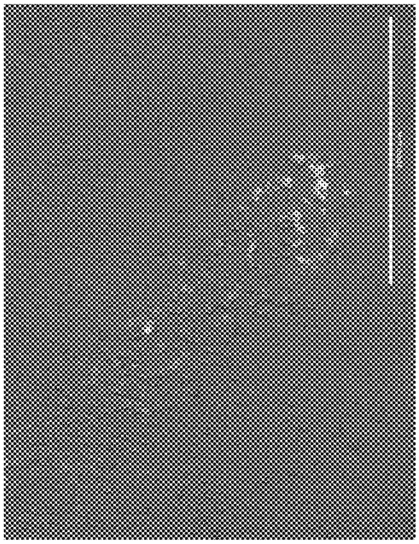
FIG. 22B illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using fluorescent microscopy at 40× magnification.
Figure 22A:
FIG. 22A illustrates ChAdV68.5WTnt.GFP virus production after transfection. HEK293A cells were transfected with ChAdV68.5WTnt.GFP DNA using the lipofectamine protocol. Viral replication (plaques) was observed 10 days after transfection. A lysate was made and used to reinfect a T25 flask of 293A cells. ChAdV68.5WTnt.GFP viral plaques were visualized and photographed 3 days later using light microscopy (40× magnification)

XV.B.2. Production of ChAdV68 Viral Delivery Particles after DNA Transfection In one example, ChAdV68.4WTnt.GFP (FIG. 21) and ChAdV68.5WTnt.GFP (FIG. 22) DNA was transfected into HEK293A cells and virus replication (viral plaques) was observed 7-10 days after transfection. ChAdV68 viral plaques were visualized using light (FIGS. 21A and 22A) and fluorescent microscopy (FIGS. 21B-C and FIGS. 22B-C). GFP denotes productive ChAdV68 viral delivery particle production.

XV.B.3. ChAdV68 Viral Delivery Particles Expansion

Figure 23:
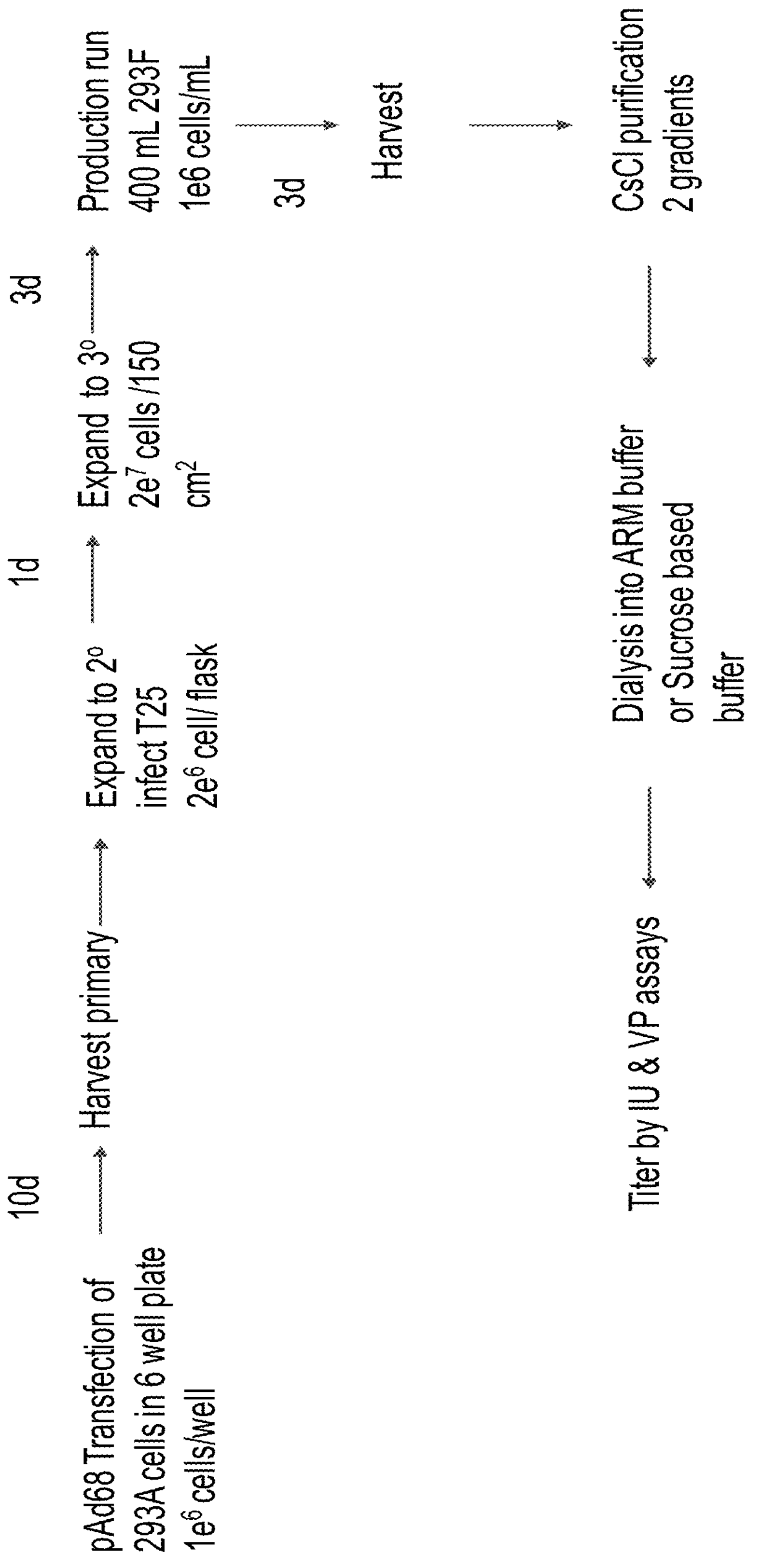
FIG. 23 illustrates the viral particle production scheme.

In one example, ChAdV68.4WTnt.GFP, ChAdV68.5WTnt.GFP, and ChAdV68.5WTnt.MAG25mer viruses were expanded in HEK293F cells and a purified virus stock produced 18 days after transfection (FIG. 23). Viral particles were quantified in the purified ChAdV68 virus stocks and compared to adenovirus type 5 (Ad5) and ChAdVY25 (a closely related ChAdV; Dicks, 2012, PloS ONE 7, e40385) viral stocks produced using the same protocol. ChAdV68 viral titers were comparable to Ad5 and ChAdVY25 (Table 7).

TABLE 7

Adenoviral vector production in 293F suspension cells

| Construct | Average VP/cell +/− SD |
|---|---|
| Ad5-Vectors (Multiple vectors) | 2.96e4 +/− 2.26e4 |
| Ad5-GFP | 3.89e4 |
| chAdY25-GFP | 1.75e3 +/− 6.03e1 |
| ChAdV68.4WTnt.GFP | 1.2e4 +/− 6.5e32 |
| ChAdV68.5WTnt.GFP | 1.8e3 |
| ChAdV68.5WTnt.MAG25mer | 1.39e3 +/− 1.1e3 |

*SD is only reported where multiple Production runs have been performed

XV.B.4. Evaluation of Immunogenicity in Tumor Models

Figure 29:
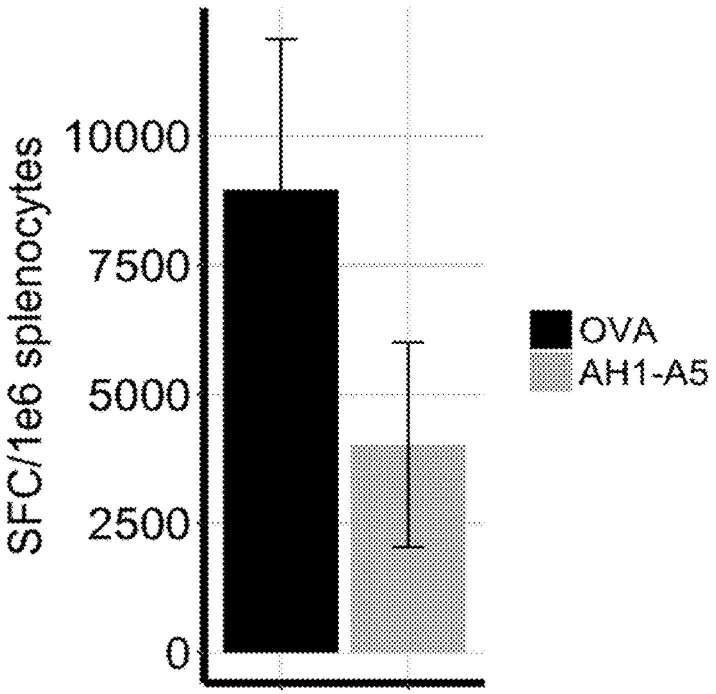
FIG. 29 illustrates ChAdV68 eliciting T-Cell responses to mouse tumor antigens in mice. Mice were immunized with ChAdV68.5WTnt.MAG25mer, and T-cell responses to the MHC class I epitope SIINFEKL (OVA) (SEQ ID NO: 57) were measured in C57BL/6J female mice and the MHC class I epitope AH1-A5 measured in Balb/c mice. Mean spot forming cells (SFCs) per $10^6$ splenocytes measured in ELISpot assays presented. Error bars represent standard deviation.

C68 vector expressing mouse tumor antigens were evaluated in mouse immunogenicity studies to demonstrate the C68 vector elicits T-cell responses. T-cell responses to the MHC class I epitope SIINFEKL (SEQ ID NO: 57) were measured in C57BL/6J female mice and the MHC class I epitope AH1-A5 (Slansky et al., 2000, Immunity 13:529-538) measured in Balb/c mice. As shown in FIG. 29, strong T-cell responses relative to control were measured after immunization of mice with ChAdV68.5WTnt.MAG25mer. Mean cellular immune responses of 8957 or 4019 spot forming cells (SFCs) per $10^6$ splenocytes were observed in ELISpot assays when C57BL/6J or Balb/c mice were immunized with ChAdV68.5WTnt.MAG25mer, respectively, 10 days after immunization.

XVI. Alphavirus Neoantigen Cassette Delivery Vector

XVI.A. Alphavirus Delivery Vector Evaluation Materials and Methods

In Vitro Transcription to Generate RNA

For in vitro testing: plasmid DNA was linearized by restriction digest with PmeI, column purified following manufacturer's protocol (GeneJet DNA cleanup kit, Thermo) and used as template. In vitro transcription was performed using the RiboMAX Large Scale RNA production System (Promega) with the $m^7G$ cap analog (Promega) according to manufacturer's protocol. mRNA was purified using the RNeasy kit (Qiagen) according to manufacturer's protocol.

For in vivo studies: RNA was generated and purified by TriLInk Biotechnologies and capped with Enzymatic Cap1.

Transfection of RNA

HEK293A cells were seeded at 6e4 cells/well for 96 wells and 2e5 cells/well for 24 wells, ~16 hours prior to transfection. Cells were transfected with mRNA using MessengerMAX lipofectamine (Invitrogen) and following manufacturer's protocol. For 96-wells, 0.15 uL of lipofectamine and 10 ng of mRNA was used per well, and for 24-wells, 0.75 uL of lipofectamine and 150 ng of mRNA was used per well. A GFP expressing mRNA (TriLink Biotechnologies) was used as a transfection control.

Luciferase Assay

Luciferase reporter assay was performed in white-walled 96-well plates with each condition in triplicate using the ONE-Glo luciferase assay (Promega) following manufacturer's protocol. Luminescence was measured using the SpectraMax.

qRT-PCR

Transfected cells were rinsed and replaced with fresh media 2 hours post transfection to remove any untransfected mRNA. Cells were then harvested at various timepoints in RLT plus lysis buffer (Qiagen), homogenized using a QiaShredder (Qiagen) and RNA was extracted using the RNeasy kit (Qiagen), all according to manufacturer's protocol. Total RNA was quantified using a Nanodrop (Thermo Scientific). qRT-PCR was performed using the Quantitect Probe One-Step RT-PCR kit (Qiagen) on the qTower[3] (Analytik Jena) according to manufacturer's protocol, using 20 ng of total RNA per reaction. Each sample was run in triplicate for each probe. Actin or GusB were used as reference genes. Custom primer/probes were generated by IDT (Table 8).

TABLE 8 qPCR primers/probes

| Target | | | SEQ ID NO: |
|---|---|---|---|
| Luci | Primer1 | GTGGTGTGCAGCGAGAATAG | 142 |
| | Primer2 | CGCTCGTTGTAGATGTCGTTAG | 143 |
| | Probe | /56-FAM/TTGCAGTTC/ZEN/TTCATGCCCGTGTTG/3IABkFQ/ | 144 |
| GusB | Primer1 | GTTTTTGATCCAGACCCAGATG | 145 |
| | Primer2 | GCCCATTATTCAGAGCGAGTA | 146 |
| | Probe | /56-FAM/TGCAGGGTT/ZEN/TCACCAGGATCCAC/3IABkFQ/ | 147 |
| ActB | Primer1 | CCTTGCACATGCCGGAG | 148 |
| | Primer2 | ACAGAGCCTCGCCTTTG | 149 |
| | Probe | /56-FAM/TCATCCATG/ZEN/GTGAGCTGGCGG/3IABkFQ/ | 150 |
| MAG-25 mer Set1 | Primer1 | CTGAAAGCTCGGTTTGCTAATG | 151 |
| | Primer2 | CCATGCTGGAAGAGACAATCT | 152 |
| | Probe | /56-FAM/CGTTTCTGA/ZEN/TGGCGCTGACCGATA/3IABkFQ/ | 153 |
| MAG-25 mer Set2 | Primer1 | TATGCCTATCCTGTCTCCTCTG | 154 |
| | Primer2 | GCTAATGCAGCTAAGTCCTCTC | 155 |
| | Probe | /56-FAM/TGTTTACCC/ZEN/TGACCGTGCCTTCTG/3IABkFQ/ | 156 |

B16-OVA Tumor Model

C57B1J6J mice were injected in the lower left abdominal flank with $10^5$ B16-OVA cells/animal. Tumors were allowed to grow for 3 days prior to immunization.

CT26 Tumor Model

Balb/c mice were injected in the lower left abdominal flank with $10^6$ CT26 cells/animal. Tumors were allowed to grow for 7 days prior to immunization.

Immunizations

For srRNA vaccine, mice were injected with 10 ug of RNA in 100 uL volume, bilateral intramuscular injection (50 uL per leg). For Ad5 vaccine, mice were injected with $5\times10^{10}$ viral particles (VP) in 100 uL volume, bilateral intramuscular injection (50 uL per leg). Animals were injected with anti-CTLA-4 (clone 9D39, BioXcell), anti- PD-1 (clone RMP1-14, BioXcell) or anti-IgG (clone MPC-11, BioXcell), 250 ug dose, 2 times per week, via intraperitoneal injection.

In Vivo Bioluminescent Imaging

At each timepoint mice were injected with 150 mg/kg luciferin substrate via intraperitoneal injection and bioluminescence was measured using the IVIS In vivo imaging system (PerkinElmer) 10-15 minutes after injection.

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM $NH_4Cl$, 10 mM $KHCO_3$, 0.1 mM $Na_2EDTA$). Cells were filtered again through a 30 micron filter and then resuspended in complete RPMI. Cells were counted on the Attune N×T flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). $5\times10^4$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

XVI.B. Alphavirus Vector

XVI.B.1. Alphavirus Vector In Vitro Evaluation

Figure 24:
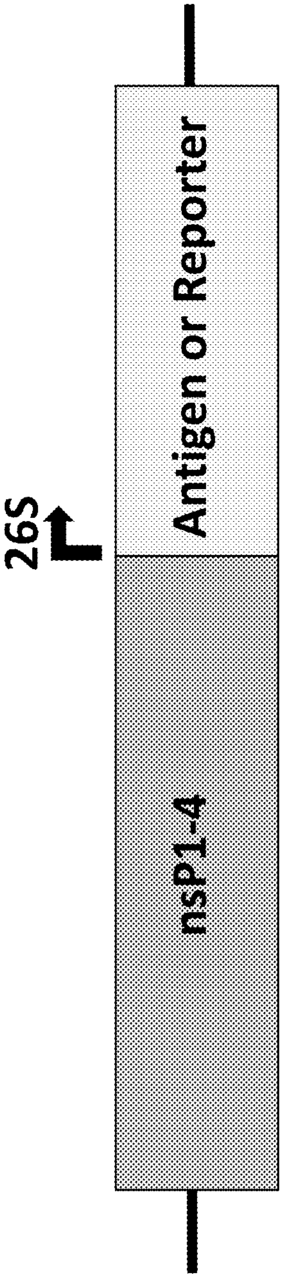
FIG. 24 illustrates the alphavirus derived VEE self-replicating RNA (srRNA) vector.

In one implementation of the present invention, a RNA alphavirus backbone for the neoantigen expression system was generated from a Venezuelan Equine Encephalitis (VEE) (Kinney, 1986, Virology 152: 400-413) based self-replicating RNA (srRNA) vector. In one example, the sequences encoding the structural proteins of VEE located 3' of the 26S subgenomic promoter were deleted (VEE sequences 7544 to 11,175 deleted; numbering based on Kinney et al 1986; SEQ ID NO:6) and replaced by antigen sequences (SEQ ID NO:14 and SEQ ID NO:4) or a luciferase reporter (e.g., VEE-Luciferase, SEQ ID NO:15) (FIG. 24). RNA was transcribed from the srRNA DNA vector in vitro, transfected into HEK293A cells and luciferase reporter expression was measured. In addition, an (non-replicating) mRNA encoding luciferase was transfected for comparison. An ~30,000-fold increase in srRNA reporter signal was observed for VEE-Luciferase srRNA when comparing the 23 hour measurement vs the 2 hour measurement (Table 9). In contrast, the mRNA reporter exhibited a less than 10-fold increase in signal over the same time period (Table 9).

TABLE 9

Expression of luciferase from VEE self-replicating vector increases over time. HEK293A cells transfected with 10 ng of VEE-Luciferase srRNA or 10 ng of non-replicating luciferase mRNA (TriLink L-6307) per well in 96 wells. Luminescence was measured at various times post transfection. Luciferase expression is reported as relative luminescence units (RLU). Each data point is the mean +/− SD of 3 transfected wells.

| Construct | Timepoint (hr) | Mean RLU | Standard Dev (triplicate wells) |
|---|---|---|---|
| mRNA | 2 | 878.6666667 | 120.7904522 |
| mRNA | 5 | 1847.333333 | 978.515372 |
| mRNA | 9 | 4847 | 868.3271273 |
| mRNA | 23 | 8639.333333 | 751.6816702 |
| SRRNA | 2 | 27 | 15 |
| SRRNA | 5 | 4884.333333 | 2955.158935 |
| SRRNA | 9 | 182065.5 | 16030.81784 |
| SRRNA | 23 | 783658.3333 | 68985.05538 |

In another example, replication of the srRNA was confirmed directly by measuring RNA levels after transfection of either the luciferase encoding srRNA (VEE-Luciferase) or an srRNA encoding a multi-epitope cassette (VEE-MAG25mer) using quantitative reverse transcription polymerase chain reaction (qRT-PCR). An ~150-fold increase in RNA was observed for the VEE-luciferase srRNA (Table 10), while a 30-50-fold increase in RNA was observed for the VEE-MAG25mer srRNA (Table 11). These data confirm that the VEE srRNA vectors replicate when transfected into cells.

TABLE 10

Direct measurement of RNA replication in VEE-Luciferase srRNA transfected cells. HEK293A cells transfected with VEE-Luciferase srRNA (150 ng per well, 24-well) and RNA levels quantified by qRT-PCR at various times after transfection. Each measurement was normalized based on the Actin reference gene and fold-change relative to the 2 hour timepoint is presented.

| Timepoint (hr) | Luciferase Ct | Actin Ct | dCt | Ref dCt | ddCt | Relative Fold change |
|---|---|---|---|---|---|---|
| 2 | 20.51 | 18.14 | 2.38 | 2.38 | 0.00 | 1.00 |
| 4 | 20.09 | 18.39 | 1.70 | 2.38 | −0.67 | 1.59 |
| 6 | 15.50 | 18.19 | −2.69 | 2.38 | −5.07 | 33.51 |
| 8 | 13.51 | 18.36 | −4.85 | 2.38 | −7.22 | 149.43 |

TABLE 11

Direct measurement of RNA replication in VEE-MAG25mer srRNA transfected cells. HEK293 cells transfected with VEE-MAG25mer srRNA (150 ng per well, 24-well) and RNA levels quantified by qRT-PCR at various times after transfection. Each measurement was normalized based on the GusB reference gene and fold-change relative to the 2 hour timepoint is presented. Different lines on the graph represent 2 different qPCR primer/probe sets, both of which detect the epitope cassette region of the srRNA.

| Primer/ probe | Timepoint (hr) | Ct | GusB Ct | dCt | Ref dCt | ddCt | Relative Fold-Change |
|---|---|---|---|---|---|---|---|
| Set1 | 2 | 18.96 | 22.41 | −3.45 | −3.45 | 0.00 | 1.00 |
| Set1 | 4 | 17.46 | 22.27 | −4.81 | −3.45 | −1.37 | 2.58 |
| Set1 | 6 | 14.87 | 22.04 | −7.17 | −3.45 | −3.72 | 13.21 |
| Set1 | 8 | 14.16 | 22.19 | −8.02 | −3.45 | −4.58 | 23.86 |
| Set1 | 24 | 13.16 | 22.01 | −8.86 | −3.45 | −5.41 | 42.52 |
| Set1 | 36 | 13.53 | 22.63 | −9.10 | −3.45 | −5.66 | 50.45 |
| Set2 | 2 | 17.75 | 22.41 | −4.66 | −4.66 | 0.00 | 1.00 |
| Set2 | 4 | 16.66 | 22.27 | −5.61 | −4.66 | −0.94 | 1.92 |
| Set2 | 6 | 14.22 | 22.04 | −7.82 | −4.66 | −3.15 | 8.90 |
| Set2 | 8 | 13.18 | 22.19 | −9.01 | −4.66 | −4.35 | 20.35 |
| Set2 | 24 | 12.22 | 22.01 | −9.80 | −4.66 | −5.13 | 35.10 |
| Set2 | 36 | 13.08 | 22.63 | −9.55 | −4.66 | −4.89 | 29.58 |

XVI.B.2. Alphavirus Vector In Vivo Evaluation

Figure 25:
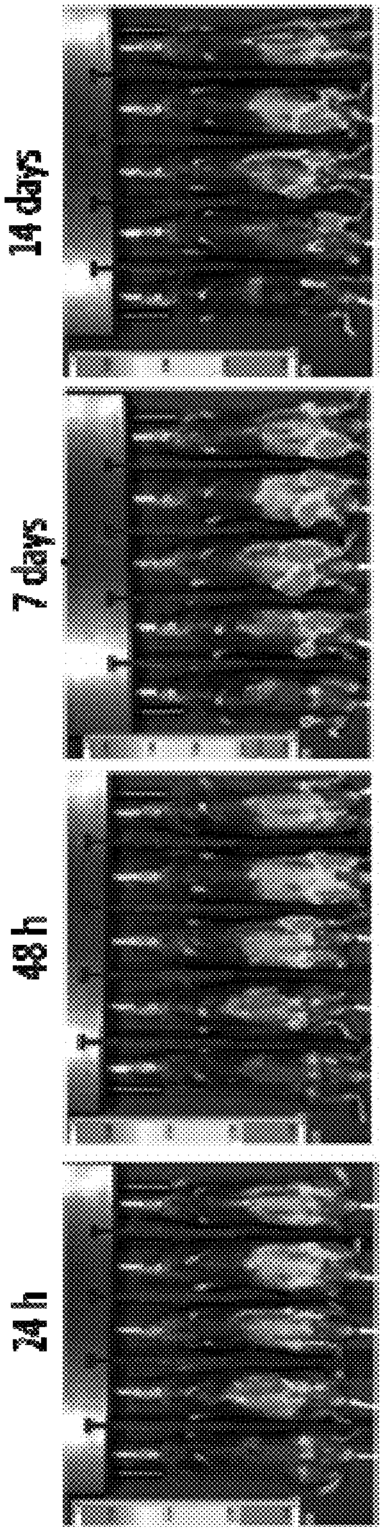
FIG. 25 illustrates in vivo reporter expression after inoculation of C57BL/6J mice with VEE-Luciferase srRNA. Shown are representative images of luciferase signal following immunization of C57BL/6J mice with VEE-Luciferase srRNA (10 ug per mouse, bilateral intramuscular injection, MC3 encapsulated) at various timepoints.

In another example, VEE-Luciferase reporter expression was evaluated in vivo. Mice were injected with 10 ug of VEE-Luciferase srRNA encapsulated in lipid nanoparticle (MC3) and imaged at 24 and 48 hours, and 7 and 14 days post injection to determine bioluminescent signal. Luciferase signal was detected at 24 hours post injection and increased over time and appeared to peak at 7 days after srRNA injection (FIG. 25).

XVI.B.3. Alphavirus Vector Tumor Model Evaluation

In one implementation, to determine if the VEE srRNA vector directs antigen-specific immune responses in vivo, a VEE srRNA vector was generated (VEE-UbAAY, SEQ ID NO:14) that expresses 2 different MHC class I mouse tumor epitopes, SIINFEKL (SEQ ID NO: 57) and AH1-A5 (Slansky et al., 2000, Immunity 13:529-538). The SFL (SIINFEKL (SEQ ID NO: 57)) epitope is expressed by the B16-OVA melanoma cell line, and the AH1-A5 (SPSYAYHQF (SEQ ID NO: 58); Slansky et al., 2000, Immunity) epitope induces T cells targeting a related epitope (AH1/SPSYVYHQF (SEQ ID NO: 193); Huang et al., 1996, Proc Natl Acad Sci USA 93:9730-9735) that is expressed by the CT26 colon carcinoma cell line. In one example, for in vivo studies, VEE-UbAAY srRNA was generated by in vitro transcription using T7 polymerase (TriLink Biotechnologies) and encapsulated in a lipid nanoparticle (MC3).

Figure 26A:
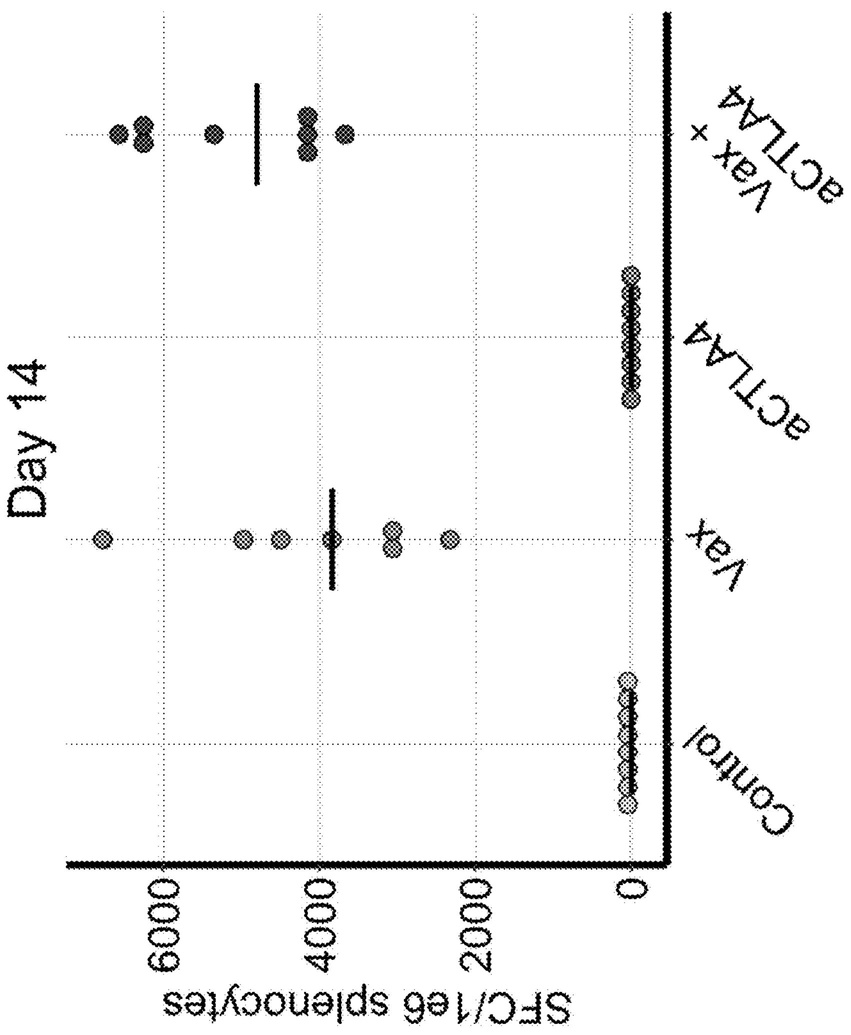
FIG. 26A illustrates T-cell responses measured 14 days after immunization with VEE srRNA formulated with MC3 LNP in B16-OVA tumor bearing mice. B16-OVA tumor bearing C57BL/6J mice were injected with 10 ug of VEE-Luciferase srRNA (control), VEE-UbAAY srRNA (Vax), VEE-Luciferase srRNA and anti-CTLA-4 (aCTLA-4) or VEE-UbAAY srRNA and anti-CTLA-4 (Vax+aCTLA-4). In addition, all mice were treated with anti-PD1 mAb starting at day 7. Each group consisted of 8 mice. Mice were sacrificed and spleens and lymph nodes were collected 14 days after immunization. SIINFEKL-specific T-cell responses ("SIINFEKL" disclosed as SEQ ID NO: 57) were assessed by IFN-gamma ELISPOT and are reported as spot-forming cells (SFC) per 106 splenocytes. Lines represent medians.
Figure 26B:
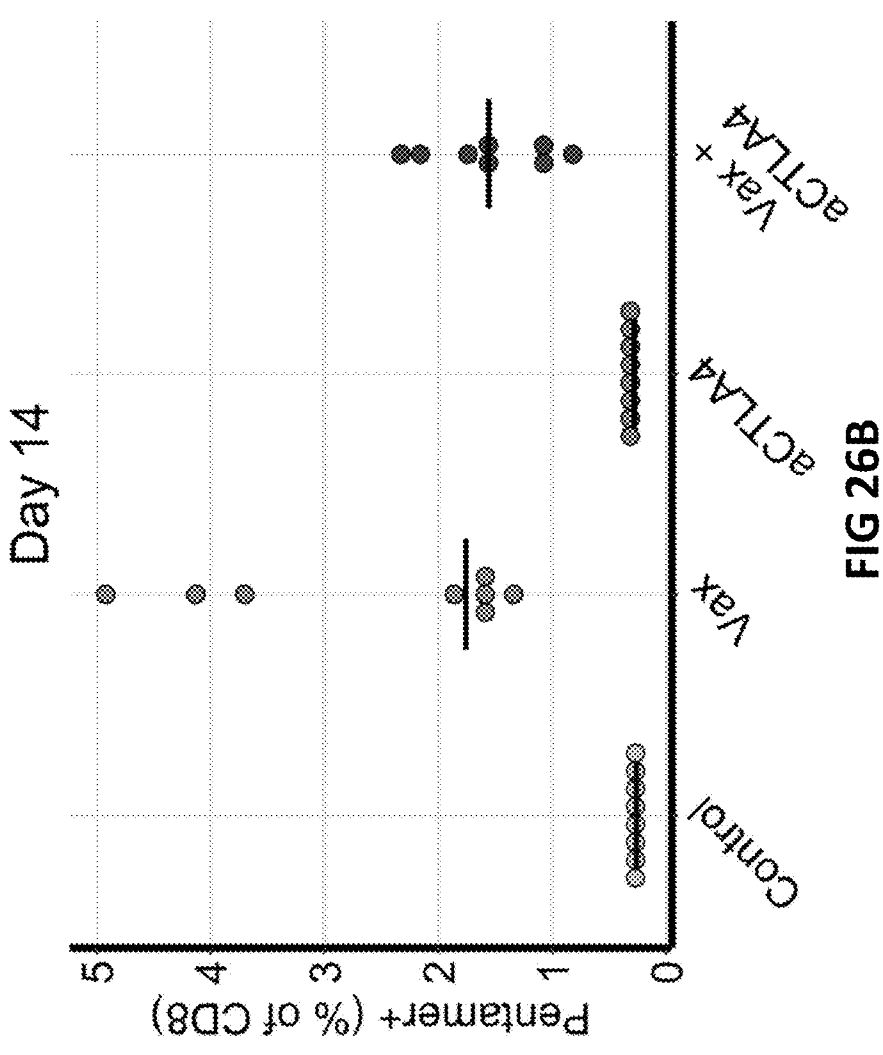
FIG. 26B illustrates T-cell responses measured 14 days after immunization with VEE srRNA formulated with MC3 LNP in B16-OVA tumor bearing mice. B16-OVA tumor bearing C57BL/6J mice were injected with 10 ug of VEE-Luciferase srRNA (control), VEE-UbAAY srRNA (Vax), VEE-Luciferase srRNA and anti-CTLA-4 (aCTLA-4) or VEE-UbAAY srRNA and anti-CTLA-4 (Vax+aCTLA-4). In addition, all mice were treated with anti-PD1 mAb starting at day 7. Each group consisted of 8 mice. Mice were sacrificed and spleens and lymph nodes were collected 14 days after immunization. SIINFEKL-specific T-cell responses ("SIINFEKL" disclosed as SEQ ID NO: 57) were assessed by MHCI-pentamer staining, reported as pentamer positive cells as a percent of CD8 positive cells. Lines represent medians.

A strong antigen-specific T-cell response targeting SFL, relative to control, was observed two weeks after immunization of B16-OVA tumor bearing mice with MC3 formulated VEE-UbAAY srRNA. In one example, a median of 3835 spot forming cells (SFC) per $10^6$ splenocytes was measured after stimulation with the SFL peptide in ELISpot assays (FIG. 26A, Table 12) and 1.8% (median) of CD8 T-cells were SFL antigen-specific as measured by pentamer staining (FIG. 26B, Table 12). In another example, co-administration of an anti-CTLA-4 monoclonal antibody (mAb) with the VEE srRNA vaccine resulted in a moderate increase in overall T-cell responses with a median of 4794.5 SFCs per $10^6$ splenocytes measured in the ELISpot assay (FIG. 26A, Table 12).

TABLE 12

Results of ELISPOT and MHCI-pentamer staining assays 14 days post VEE srRNA immunization in B16-OVA tumor bearing C57BL/6J mice.

| Group | Mouse | SFC/1e6 splenocytes | Pentamer positive (% of CD8) | Group | Mouse | SFC/1e6 splenocytes | Pentamer positive (% of CD8) |
|---|---|---|---|---|---|---|---|
| Control | 1 | 47 | 0.22 | Vax | 1 | 6774 | 4.92 |
| | 2 | 80 | 0.32 | | 2 | 2323 | 1.34 |
| | 3 | 0 | 0.27 | | 3 | 2997 | 1.52 |
| | 4 | 0 | 0.29 | | 4 | 4492 | 1.86 |
| | 5 | 0 | 0.27 | | 5 | 4970 | 3.7 |
| | 6 | 0 | 0.25 | | 6 | | 4.13 |
| | 7 | 0 | 0.23 | | 7 | 3835 | 1.66 |
| | 8 | 87 | 0.25 | | 8 | 3119 | 1.64 |
| aCTLA4 | 1 | 0 | 0.24 | Vax + aCTLA4 | 1 | 6232 | 2.16 |
| | 2 | 0 | 0.26 | | 2 | 4242 | 0.82 |
| | 3 | 0 | 0.39 | | 3 | 5347 | 1.57 |
| | 4 | 0 | 0.28 | | 4 | 6568 | 2.33 |
| | 5 | 0 | 0.28 | | 5 | 6269 | 1.55 |
| | 6 | 0 | 0.28 | | 6 | 4056 | 1.74 |
| | 7 | 0 | 0.31 | | 7 | 4163 | 1.14 |
| | 8 | 6 | 0.26 | | 8 | 3667 | 1.01 |

*Note that results from mouse #6 in the Vax group were excluded from analysis due to high variability between triplicate wells.

Figure 27A:
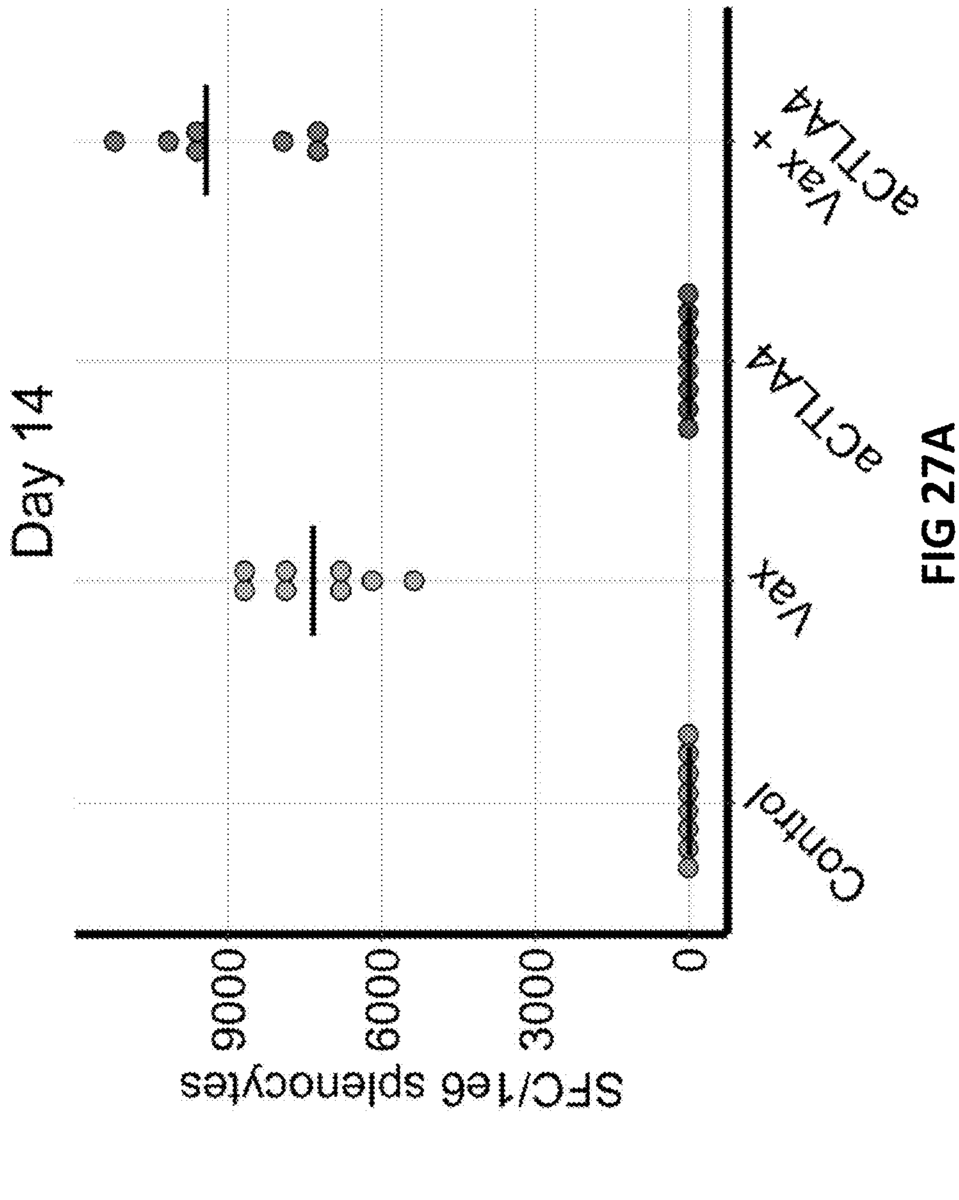
FIG. 27A illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by IFN-gamma ELISPOT. Mice were sacrificed and spleens and lymph nodes collected at 14 days post immunization with adenovirus.
Figure 27B:
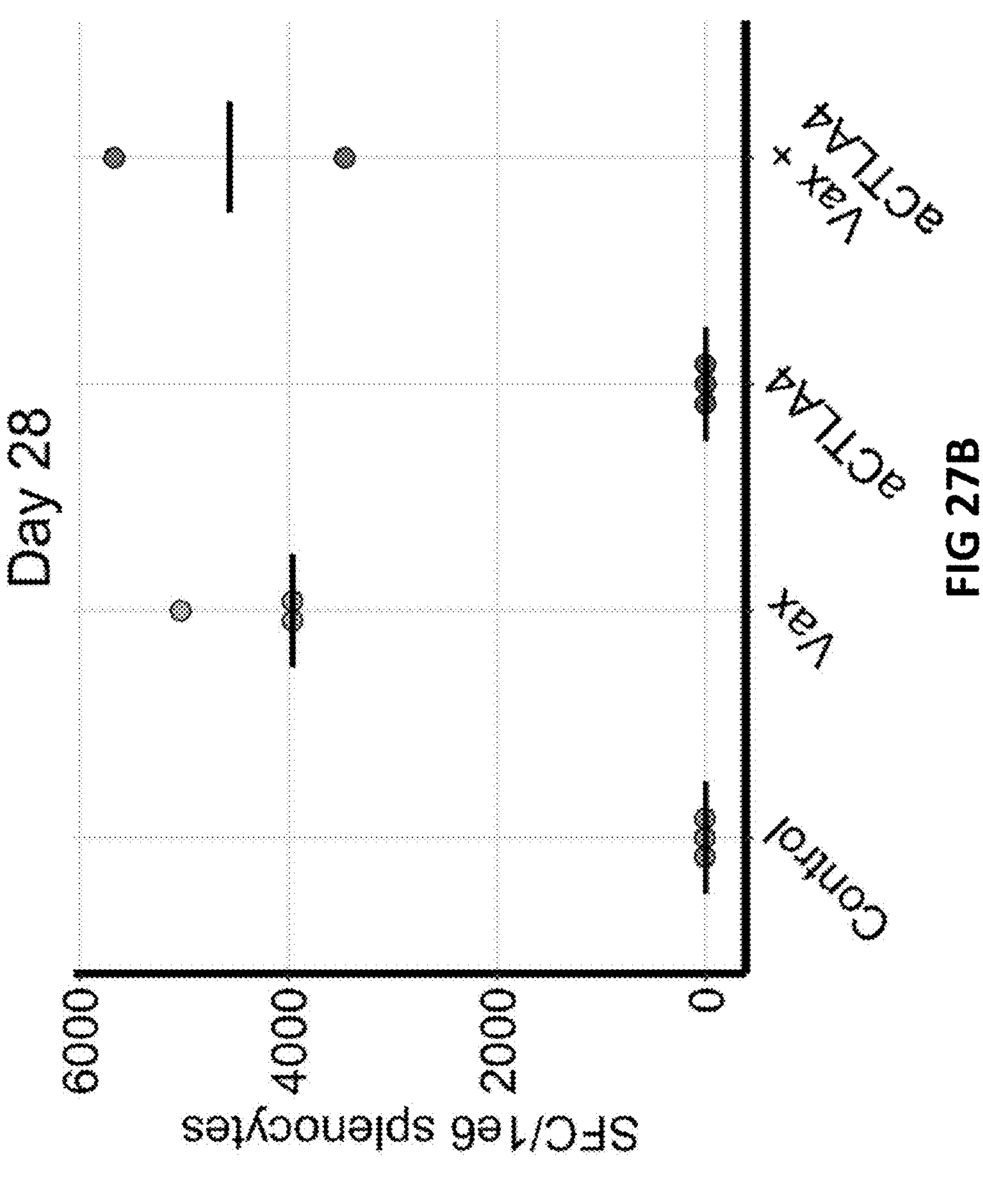
FIG. 27B illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by IFN-gamma ELISPOT. Mice were sacrificed and spleens and lymph nodes collected at 14 days post immunization with adenovirus and 14 days post boost with srRNA (day 28 after prime).
Figure 27C:
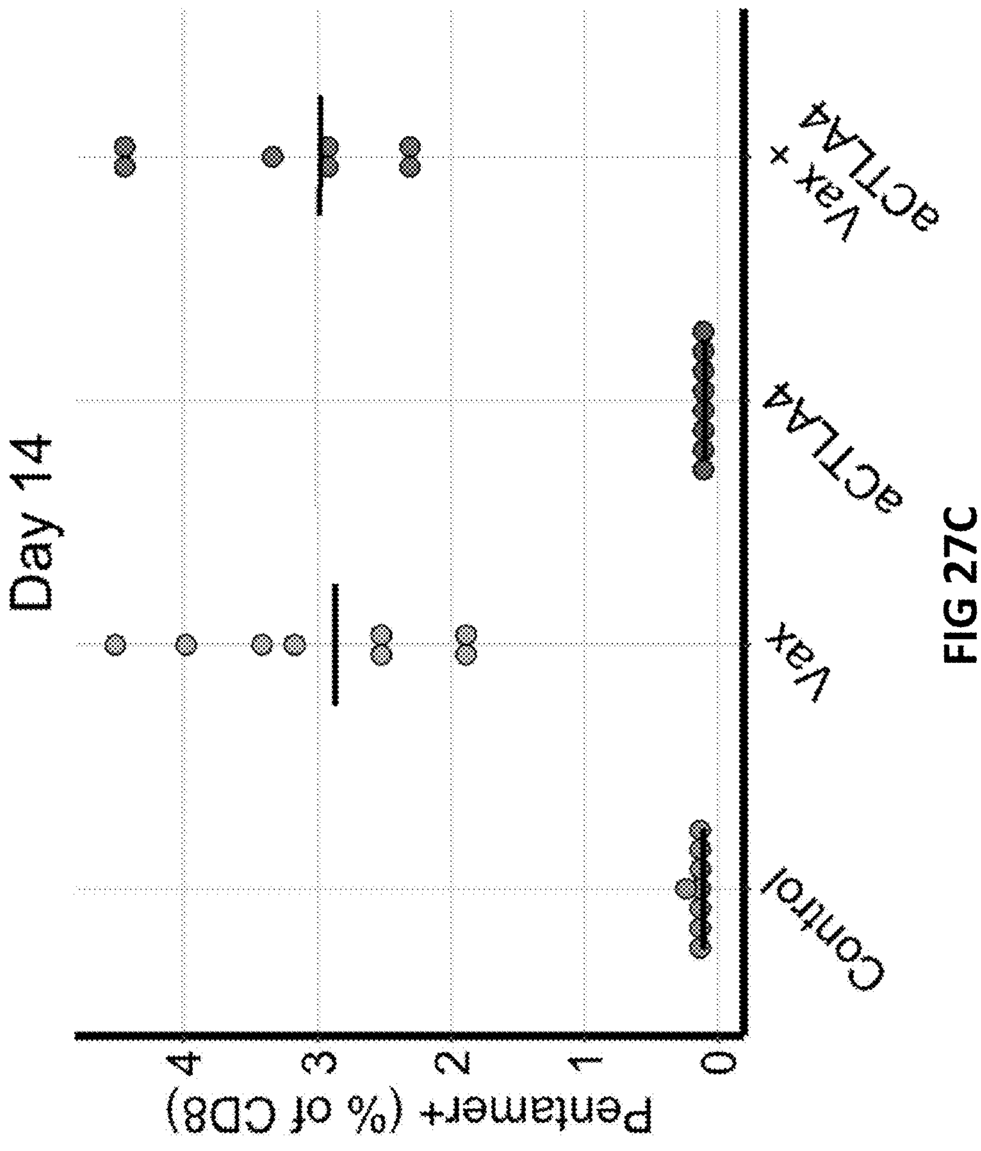
FIG. 27C illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti- CTLA-4 (Vax+aCTLA-4). In addition, all mice were treated with anti-PD-1 mAb starting at day 21. T-cell responses were measured by MHC class I pentamer staining. Mice were sacrificed and spleens and lymph nodes collected at 14 days post immunization with adenovirus.
Figure 27D:
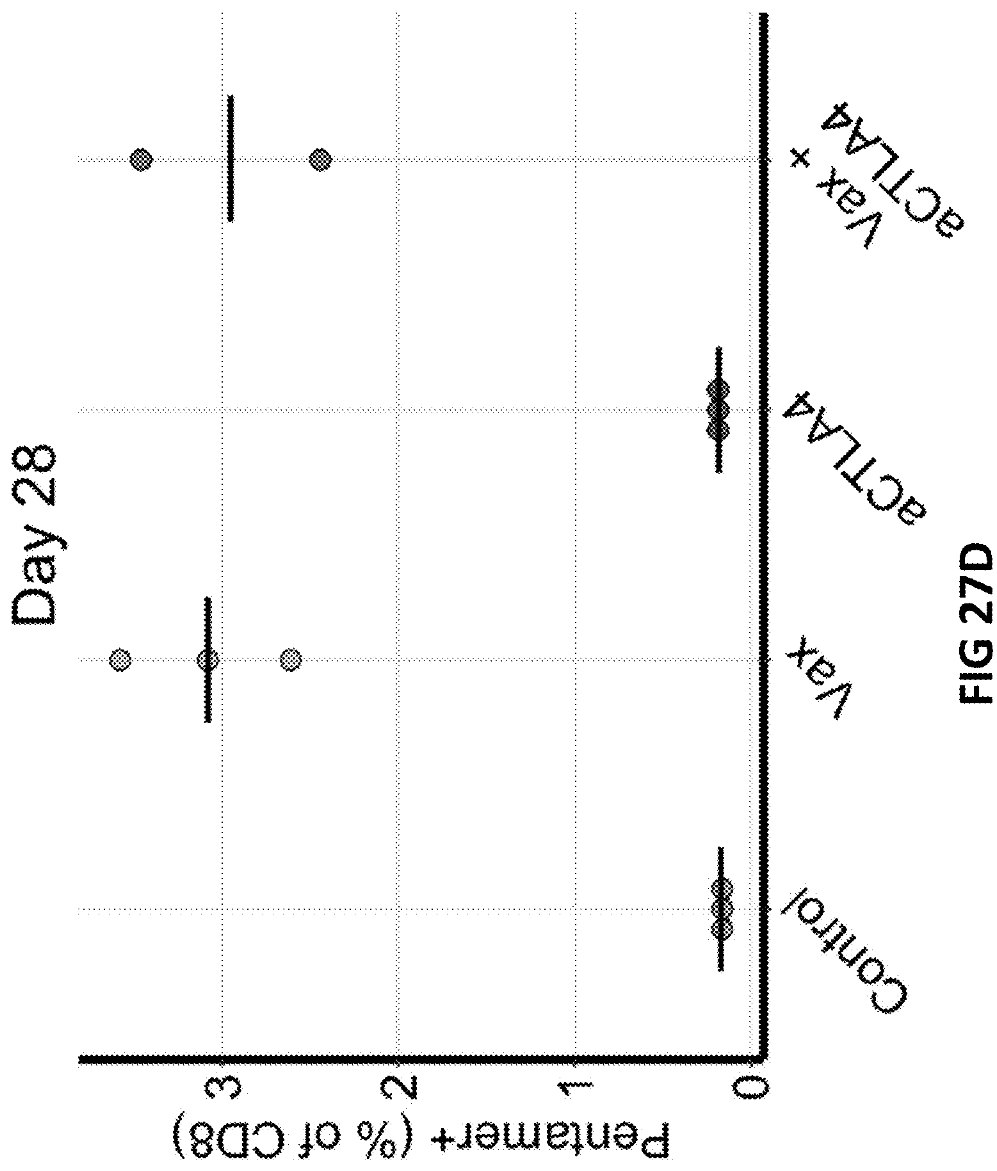
FIG. 27D illustrates antigen-specific T-cell responses following heterologous prime/boost in B16-OVA tumor bearing mice. B16-OVA tumor bearing C57BL/6J mice were injected with adenovirus expressing GFP (Ad5-GFP) and boosted with VEE-Luciferase srRNA formulated with MC3 LNP (Control) or Ad5-UbAAY and boosted with VEE-UbAAY srRNA (Vax). Both the Control and Vax groups were also treated with an IgG control mAb. A third group was treated with the Ad5-GFP prime/VEE-Luciferase srRNA boost in combination with anti-CTLA-4 (aCTLA-4), while the fourth group was treated with the Ad5-UbAAY prime/VEE-UbAAY boost in combination with anti-CTLA-4 (Vax+aCTLA-4). In addition, all mice were treated with anti-PD-1 mAb starting at day 21. T-cell responses were measured by MHC class I pentamer staining. Mice were sacrificed and spleens and lymph nodes collected at 14 days post immunization with adenovirus and 14 days post boost with srRNA (day 28 after prime).

In another implementation, to mirror a clinical approach, a heterologous prime/boost in the B16-OVA and CT26 mouse tumor models was performed, where tumor bearing mice were immunized first with adenoviral vector expressing the same antigen cassette (Ad5-UbAAY), followed by a boost immunization with the VEE-UbAAY srRNA vaccine 14 days after the Ad5-UbAAY prime. In one example, an antigen-specific immune response was induced by the Ad5-UbAAY vaccine resulting in 7330 (median) SFCs per $10^6$ splenocytes measured in the ELISpot assay (FIG. 27A, Table 13) and 2.9% (median) of CD8 T-cells targeting the SFL antigen as measured by pentamer staining (FIG. 27C, Table 13). In another example, the T-cell response was maintained 2 weeks after the VEE-UbAAY srRNA boost in the B16-OVA model with 3960 (median) SFL-specific SFCs per $10^6$ splenocytes measured in the ELISpot assay (FIG. 27B, Table 13) and 3.1% (median) of CD8 T-cells targeting the SFL antigen as measured by pentamer staining (FIG. 27D, Table 13).

TABLE 13

Immune monitoring of B16-OVA mice following heterologous prime/boost with Ad5 vaccine prime and srRNA boost.

| Group | Mouse | SFC/1e6 splenocytes | Pentamer positive (% of CD8) | Group | Mouse | SFC/1e6 splenocytes | Pentamer positive (% of CD8) |
|---|---|---|---|---|---|---|---|
| Day 14 | | | | | | | |
| Control | 1 | 0 | 0.10 | Vax | 1 | 8514 | 1.87 |
| | 2 | 0 | 0.09 | | 2 | 7779 | 1.91 |
| | 3 | 0 | 0.11 | | 3 | 6177 | 3.17 |
| | 4 | 46 | 0.18 | | 4 | 7945 | 3.41 |
| | 5 | 0 | 0.11 | | 5 | 8821 | 4.51 |
| | 6 | 16 | 0.11 | | 6 | 6881 | 2.48 |
| | 7 | 0 | 0.24 | | 7 | 5365 | 2.57 |
| | 8 | 37 | 0.10 | | 8 | 6705 | 3.98 |
| aCTLA4 | 1 | 0 | 0.08 | Vax + | 1 | 9416 | 2.35 |
| | 2 | 29 | 0.10 | aCTLA4 | 2 | 7918 | 3.33 |
| | 3 | 0 | 0.09 | | 3 | 10153 | 4.50 |
| | 4 | 29 | 0.09 | | 4 | 7212 | 2.98 |
| | 5 | 0 | 0.10 | | 5 | 11203 | 4.38 |
| | 6 | 49 | 0.10 | | 6 | 9784 | 2.27 |
| | 7 | 0 | 0.10 | | 8 | 7267 | 2.87 |
| | 8 | 31 | 0.14 | | | | |
| Day 28 | | | | | | | |
| Control | 2 | 0 | 0.17 | Vax | 1 | 5033 | 2.61 |
| | 4 | 0 | 0.15 | | 2 | 3958 | 3.08 |
| | 6 | 20 | 0.17 | | 4 | 3960 | 3.58 |
| aCTLA4 | 1 | 7 | 0.23 | Vax + | 4 | 3460 | 2.44 |
| | 2 | 0 | 0.18 | aCTLA4 | 5 | 5670 | 3.46 |
| | 3 | 0 | 0.14 | | | | |

Figure 28A:
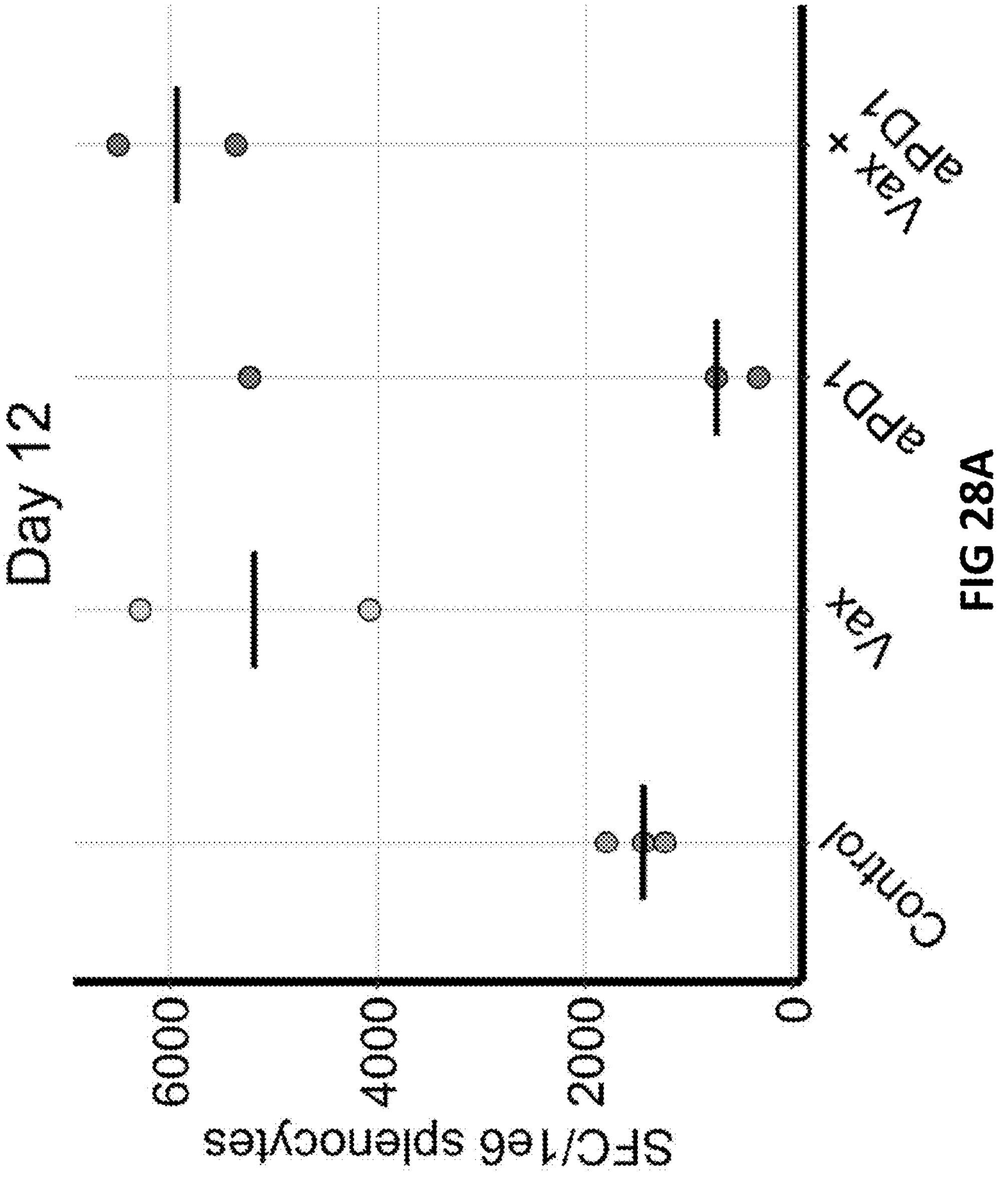
FIG. 28A illustrates antigen-specific T-cell responses following heterologous prime/boost in CT26 (Balb/c) tumor bearing mice. Mice were immunized with Ad5-GFP and boosted 15 days after the adenovirus prime with VEE-Luciferase srRNA formulated with MC3 LNP (Control) or primed with Ad5-UbAAY and boosted with VEE-UbAAY srRNA (Vax). Both the Control and Vax groups were also treated with an IgG control mAb. A separate group was administered the Ad5-GFPNEE-Luciferase srRNA prime/boost in combination with anti-PD-1 (aPD1), while a fourth group received the Ad5-UbAAY/VEE-UbAAY srRNA prime/boost in combination with an anti-PD-1 mAb (Vax+aPD1). T-cell responses to the AH1 peptide were measured using IFN-gamma ELISPOT. Mice were sacrificed and spleens and lymph nodes collected at 12 days post immunization with adenovirus.
Figure 28B:
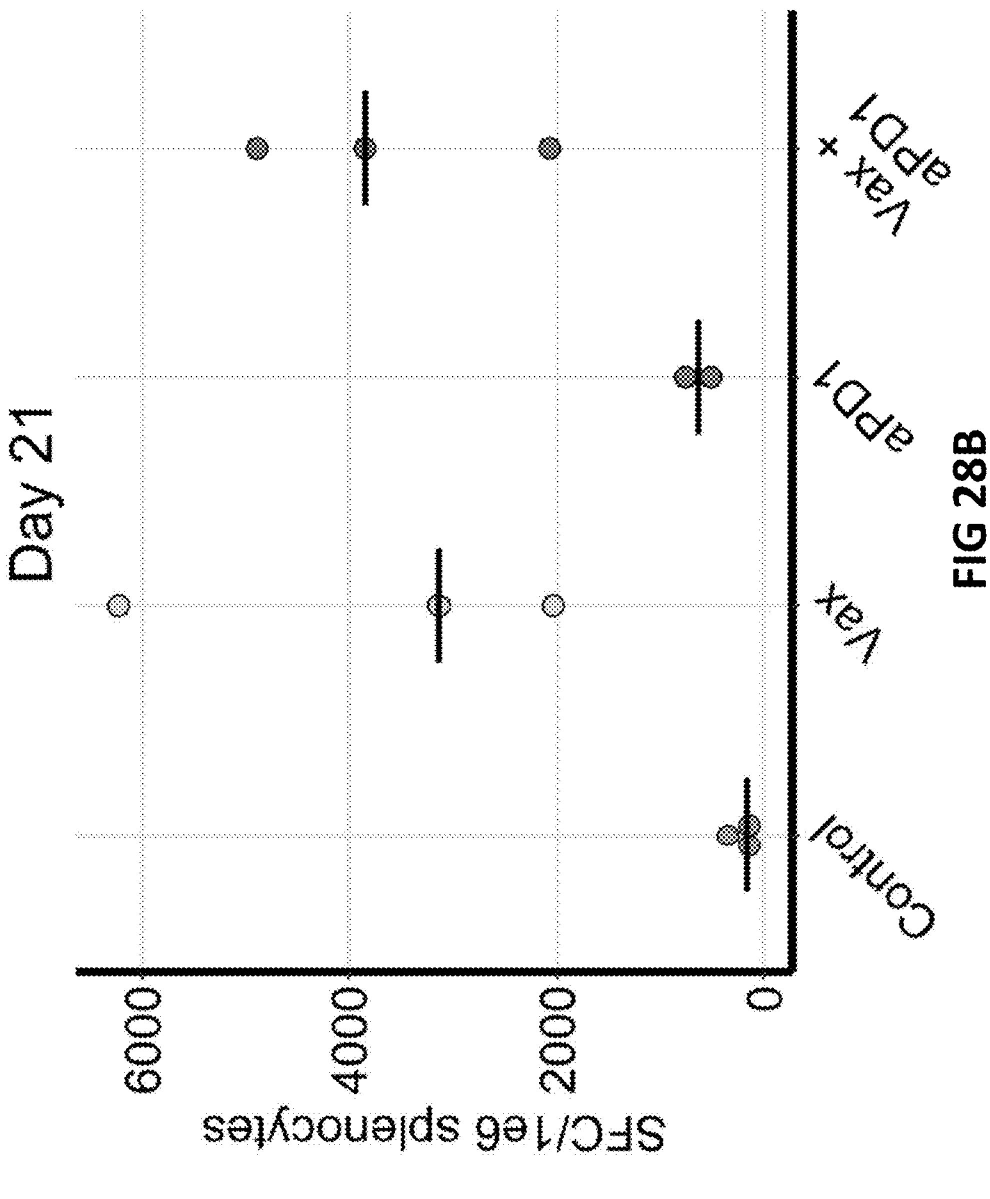
FIG. 28B illustrates antigen-specific T-cell responses following heterologous prime/boost in CT26 (Balb/c) tumor bearing mice. Mice were immunized with Ad5-GFP and boosted 15 days after the adenovirus prime with VEE-Luciferase srRNA formulated with MC3 LNP (Control) or primed with Ad5-UbAAY and boosted with VEE-UbAAY srRNA (Vax). Both the Control and Vax groups were also treated with an IgG control mAb. A separate group was administered the Ad5-GFPNEE-Luciferase srRNA prime/boost in combination with anti-PD-1 (aPD1), while a fourth group received the Ad5-UbAAY/VEE-UbAAY srRNA prime/boost in combination with an anti-PD-1 mAb (Vax+aPD1). T-cell responses to the AH1 peptide were measured using IFN-gamma ELISPOT. Mice were sacrificed and spleens and lymph nodes collected at 12 days post immunization with adenovirus and 6 days post boost with srRNA (day 21 after prime).

In another implementation, similar results were observed after an Ad5-UbAAY prime and VEE-UbAAY srRNA boost in the CT26 mouse model. In one example, an AH1 antigen-specific response was observed after the Ad5-UbAAY prime (day 14) with a mean of 5187 SFCs per $10^6$ splenocytes measured in the ELISpot assay (FIG. 28A, Table 14) and 3799 SFCs per $10^6$ splenocytes measured in the ELISpot assay after the VEE-UbAAY srRNA boost (day 28) (FIG. 28B, Table 14).

TABLE 14

Immune monitoring after heterologous prime/boost in CT26 tumor mouse model.

| Day 12 | | | Day 21 | | |
|---|---|---|---|---|---|
| Group | Mouse | SFC/1e6 splenocytes | Group | Mouse | SFC/1e6 splenocytes |
| Control | 1 | 1799 | Control | 9 | 167 |
| | 2 | 1442 | | 10 | 115 |
| | 3 | 1235 | | 11 | 347 |
| aPD1 | 1 | 737 | aPD1 | 8 | 511 |
| | 2 | 5230 | | 11 | 758 |
| | 3 | 332 | Vax | 9 | 3133 |
| Vax | 1 | 6287 | | 10 | 2036 |
| | 2 | 4086 | | 11 | 6227 |
| Vax + | 1 | 5363 | Vax + | 8 | 3844 |

TABLE 14-continued

Immune monitoring after heterologous prime/boost in CT26 tumor mouse model.

| Day 12 | | | Day 21 | | |
|---|---|---|---|---|---|
| Group | Mouse | SFC/1e6 splenocytes | Group | Mouse | SFC/1e6 splenocytes |
| aPD1 | 2 | 6500 | aPD1 | 9 | 2071 |
| | | | | 11 | 4888 |

XVII. ChAdV/srRNA Combination Tumor Model Evaluation

Various dosing protocols using ChAdV68 and self-replicating RNA (srRNA) were evaluated in murine CT26 tumor models.

XVII.A ChAdV/srRNA Combination Tumor Model Evaluation Methods and Materials

Tumor Injection

Balb/c mice were injected with the CT26 tumor cell line. 7 days after tumor cell injection, mice were randomized to the different study arms (28-40 mice per group) and treatment initiated. Balb/c mice were injected in the lower left abdominal flank with $10^6$ CT26 cells/animal. Tumors were allowed to grow for 7 days prior to immunization. The study arms are described in detail in Table 15.

TABLE 15

| ChAdV/srRNA Combination Tumor Model Evaluation Study Arms | | | | | | |
|---|---|---|---|---|---|---|
| Group | N | Treatment | Dose | Volume | Schedule | Route |
| 1 | 40 | chAd68 control | 1e11 vp | 2 × 50 uL | day 0 | IM |
| | | srRNA control | 10 ug | 50 uL | day 14, 28, 42 | IM |
| | | Anti-PD1 | 250 ug | 100 uL | 2x/week (start day 0) | IP |
| 2 | 40 | chAd68 control | 1e11 vp | 2 × 50 uL | day 0 | IM |
| | | srRNA control | 10 ug | 50 uL | day 14, 28, 42 | IM |
| | | Anti-IgG | 250 ug | 100 uL | 2x/week (start day 0) | IP |
| 3 | 28 | chAd68 vaccine | 1e11 vp | 2 × 50 uL | day 0 | IM |
| | | srRNA vaccine | 10 ug | 50 uL | day 14, 28, 42 | IM |
| | | Anti-PD1 | 250 ug | 100 uL | 2x/week (start day 0) | IP |
| 4 | 28 | chAd68 vaccine | 1e11 vp | 2 × 50 uL | day 0 | IM |
| | | srRNA vaccine | 10 ug | 50 uL | day 14, 28, 42 | IM |
| | | Anti-IgG | 250 ug | 100 uL | 2x/week (start day 0) | IP |
| 5 | 28 | srRNA vaccine | 10 ug | 50 uL | day 0, 28, 42 | IM |
| | | chAd68 vaccine | 1e11 vp | 2 × 50 uL | day 14 | IM |
| | | Anti-PD1 | 250 ug | 100 uL | 2x/week (start day 0) | IP |
| 6 | 28 | srRNA vaccine | 10 ug | 50 uL | day 0, 28, 42 | IM |
| | | chAd68 vaccine | 1e11 vp | 2 × 50 uL | day 14 | IM |
| | | Anti-IgG | 250 ug | 100 uL | 2x/week (start day 0) | IP |
| 7 | 40 | srRNA vaccine | 10 ug | 50 uL | day 0, 14, 28, 42 | IM |
| | | Anti-PD1 | 250 ug | 100 uL | 2x/week (start day 0) | IP |
| 8 | 40 | srRNA vaccine | 10 ug | 50 uL | day 0, 14, 28, 42 | IM |
| | | Anti-IgG | 250 ug | 100 uL | 2x/week (start day 0) | IP |

Immunizations

For srRNA vaccine, mice were injected with 10 ug of VEE-MAG25mer srRNA in 100 uL volume, bilateral intramuscular injection (50 uL per leg). For C68 vaccine, mice were injected with $1\times10^{11}$ viral particles (VP) of ChAdV68.5WTnt.MAG25mer in 100 uL volume, bilateral intramuscular injection (50 uL per leg). Animals were injected with anti-PD-1 (clone RMP1-14, BioXcell) or anti-IgG (clone MPC-11, BioXcell), 250 ug dose, 2 times per week, via intraperitoneal injection.

Splenocyte Dissociation

Spleen and lymph nodes for each mouse were pooled in 3 mL of complete RPMI (RPMI, 10% FBS, penicillin/streptomycin). Mechanical dissociation was performed using the gentleMACS Dissociator (Miltenyi Biotec), following manufacturer's protocol. Dissociated cells were filtered through a 40 micron filter and red blood cells were lysed with ACK lysis buffer (150 mM $NH_4Cl$, 10 mM $KHCO_3$, 0.1 mM $Na_2EDTA$). Cells were filtered again through a 30 micron filter and then resuspended in complete RPMI. Cells were counted on the Attune NxT flow cytometer (Thermo Fisher) using propidium iodide staining to exclude dead and apoptotic cells. Cell were then adjusted to the appropriate concentration of live cells for subsequent analysis.

Ex Vivo Enzyme-Linked Immunospot (ELISPOT) Analysis

ELISPOT analysis was performed according to ELISPOT harmonization guidelines {DOI: 10.1038/nprot.2015.068} with the mouse IFNg ELISpotPLUS kit (MABTECH). $5\times10^4$ splenocytes were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as "too numerous to count". Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

XVH.B ChAdV/srRNA Combination Evaluation in a CT26 Tumor Model

The immunogenicity and efficacy of the ChAdV68.5WTnt.MAG25mer/VEE-MAG25mer srRNA heterologous prime/boost or VEE-MAG25mer srRNA homologous prime/boost vaccines were evaluated in the CT26 mouse tumor model. Balb/c mice were injected with the CT26 tumor cell line. 7 days after tumor cell injection, mice were randomized to the different study arms and treatment initiated. The study arms are described in detail in Table 15 and more generally in Table 16.

TABLE 16

| Prime/Boost Study Arms | | |
|---|---|---|
| Group | Prime | Boost |
| 1 | Control | Control |
| 2 | Control + anti-PD-1 | Control + anti-PD-1 |
| 3 | ChAdV68.5WTnt.MAG25mer | VEE-MAG25mer srRNA |
| 4 | ChAdV68.5WTnt.MAG25mer + anti-PD-1 | VEE-MAG25mer srRNA + anti-PD-1 |
| 5 | VEE-MAG25mer srRNA | ChAdV68.5WTnt.MAG25mer |
| 6 | VEE-MAG25mer srRNA + anti-PD-1 | ChAdV68.5WTnt.MAG25mer + anti-PD-1 |

TABLE 16-continued

| Prime/Boost Study Arms | | |
|---|---|---|
| Group | Prime | Boost |
| 7 | VEE-MAG25mer srRNA | VEE-MAG25mer srRNA |
| 8 | VEE-MAG25mer srRNA + anti-PD-1 | VEE-MAG25mer srRNA + anti-PD-1 |

Figure 30:
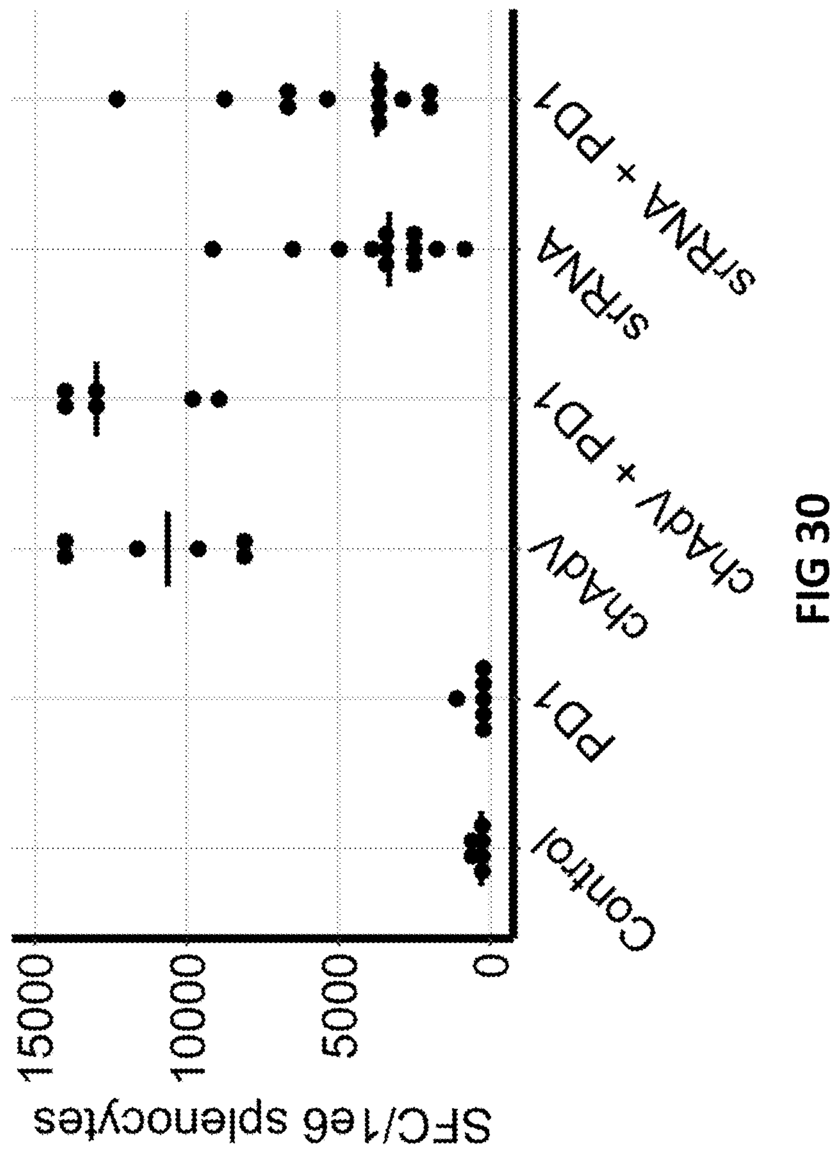
FIG. 30 illustrates cellular immune responses in a CT26 tumor model following a single immunization with either ChAdV6, ChAdV+anti-PD-1, srRNA, srRNA+anti-PD-1, or anti-PD-1 alone. Antigen-specific IFN-gamma production was measured in splenocytes for 6 mice from each group using ELISpot. Results are presented as spot forming cells (SFC) per $10^6$ splenocytes. Median for each group indicated by horizontal line. P values determined using the Dunnett's multiple comparison test; *P<0.0001, P<0.001, *P<0.05. ChAdV=ChAdV68.5WTnt.MAG25mer; srRNA=VEE-MAG25mer srRNA.

Spleens were harvested 14 days after the prime vaccination for immune monitoring. Tumor and body weight measurements were taken twice a week and survival was monitored. Strong immune responses relative to control were observed in all active vaccine groups. Median cellular immune responses of 10,630, 12,976, 3319, or 3745 spot forming cells (SFCs) per $10^6$ splenocytes were observed in ELISpot assays in mice immunized with ChAdV68.5WTnt.MAG25mer (ChAdV/group 3), ChAdV68.5WTnt.MAG25mer+anti-PD-1 (ChAdV+PD-1/group 4), VEE-MAG25mer srRNA (srRNA/median for groups 5 & 7 combined), or VEE-MAG25mer srRNA+anti-PD-1 (srRNA+PD-1/median for groups 6 & 8 combined), respectively, 14 days after the first immunization (FIG. 30 and Table 17). In contrast, the vaccine control (group 1) or vaccine control with anti-PD-1 (group 2) exhibited median cellular immune responses of 296 or 285 SFC per $10^6$ splenocytes, respectively.

TABLE 17

| Cellular immune responses in a CT26 tumor model | |
|---|---|
| Treatment | Median SFC/$10^6$ Splenocytes |
| Control | 296 |
| PD1 | 285 |
| ChAdV68.5WTnt.MAG25mer (ChAdV) | 10630 |
| ChAdV68.5WTnt.MAG25mer + PD1 (ChAdV + PD-1) | 12976 |
| VEE-MAG25mer srRNA (srRNA) | 3319 |
| VEE-MAG25mer srRNA + PD-1 (srRNA + PD1) | 3745 |

Figure 31:
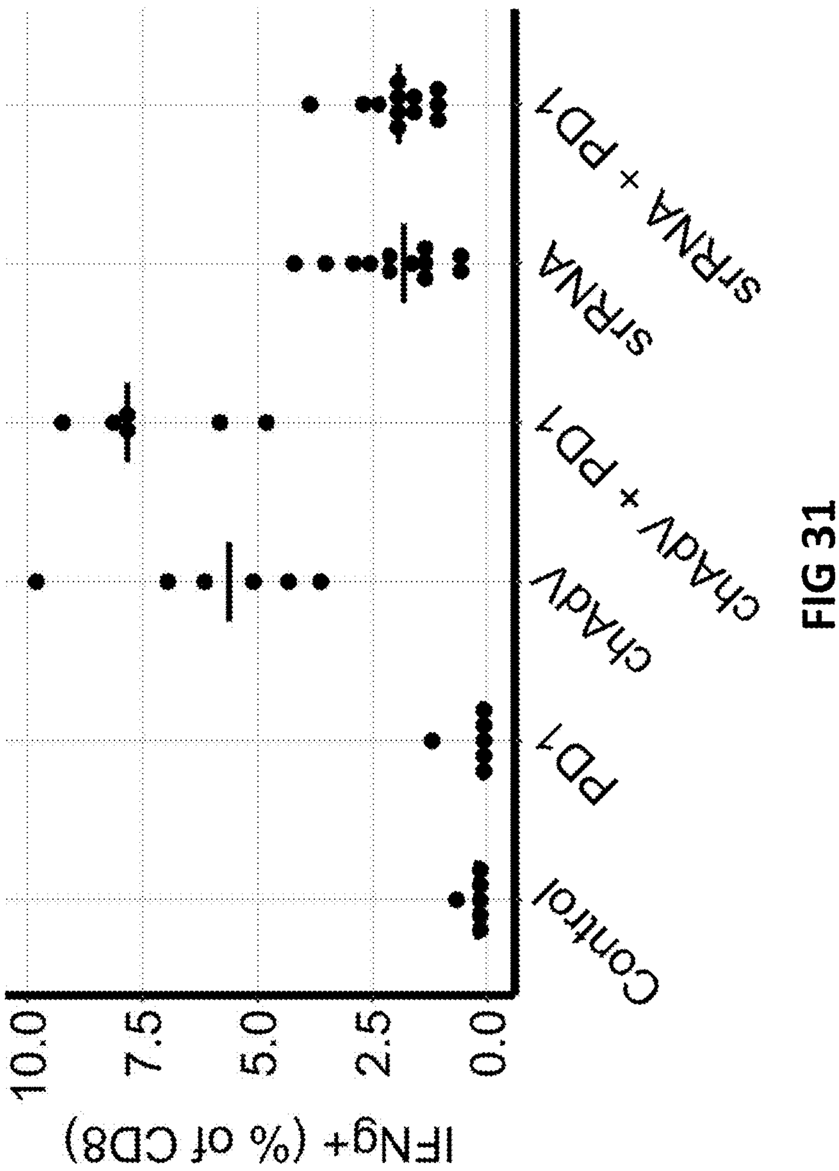
FIG. 31 illustrates CD8 T-Cell responses in a CT26 tumor model following a single immunization with either ChAdV6, ChAdV+anti-PD-1, srRNA, srRNA+anti-PD-1, or anti-PD-1 alone. Antigen-specific IFN-gamma production in CD8 T cells measured using ICS and results presented as antigen-specific CD8 T cells as a percentage of total CD8 T cells. Median for each group indicated by horizontal line. P values determined using the Dunnett's multiple comparison test; *P<0.0001, P<0.001, *P<0.05. ChAdV=ChAdV68.5WTnt.MAG25mer, srRNA=VEE-MAG25mer srRNA.

Consistent with the ELISpot data, 5.6, 7.8, 1.8 or 1.9% of CD8 T cells (median) exhibited antigen-specific responses in intracellular cytokine staining (ICS) analyses for mice immunized with ChAdV68.5WTnt.MAG25mer (ChAdV/group 3), ChAdV68.5WTnt.MAG25mer+anti-PD-1 (ChAdV+PD-1/group 4), VEE-MAG25mer srRNA (srRNA/median for groups 5 & 7 combined), or VEE-MAG25mer srRNA+anti-PD-1 (srRNA+PD-1/median for groups 6 & 8 combined), respectively, 14 days after the first immunization (FIG. 31 and Table 18). Mice immunized with the vaccine control or vaccine control combined with anti-PD-1 showed antigen-specific CD8 responses of 0.2 and 0.1%, respectively.

TABLE 18

| CD8 T-Cell responses in a CT26 tumor model | |
|---|---|
| Treatment | Median % CD8 IFN-gamma Positive |
| Control | 0.21 |
| PD1 | 0.1 |
| ChAdV68.5WTnt.MAG25mer (ChAdV) | 5.6 |
| ChAdV68.5WTnt.MAG25mer + PD1 (ChAdV + PD-1) | 7.8 |
| VEE-MAG25mer srRNA (srRNA) | 1.8 |
| VEE-MAG25mer srRNA + PD-1 (srRNA + PD1) | 1.9 |

Figure 32:
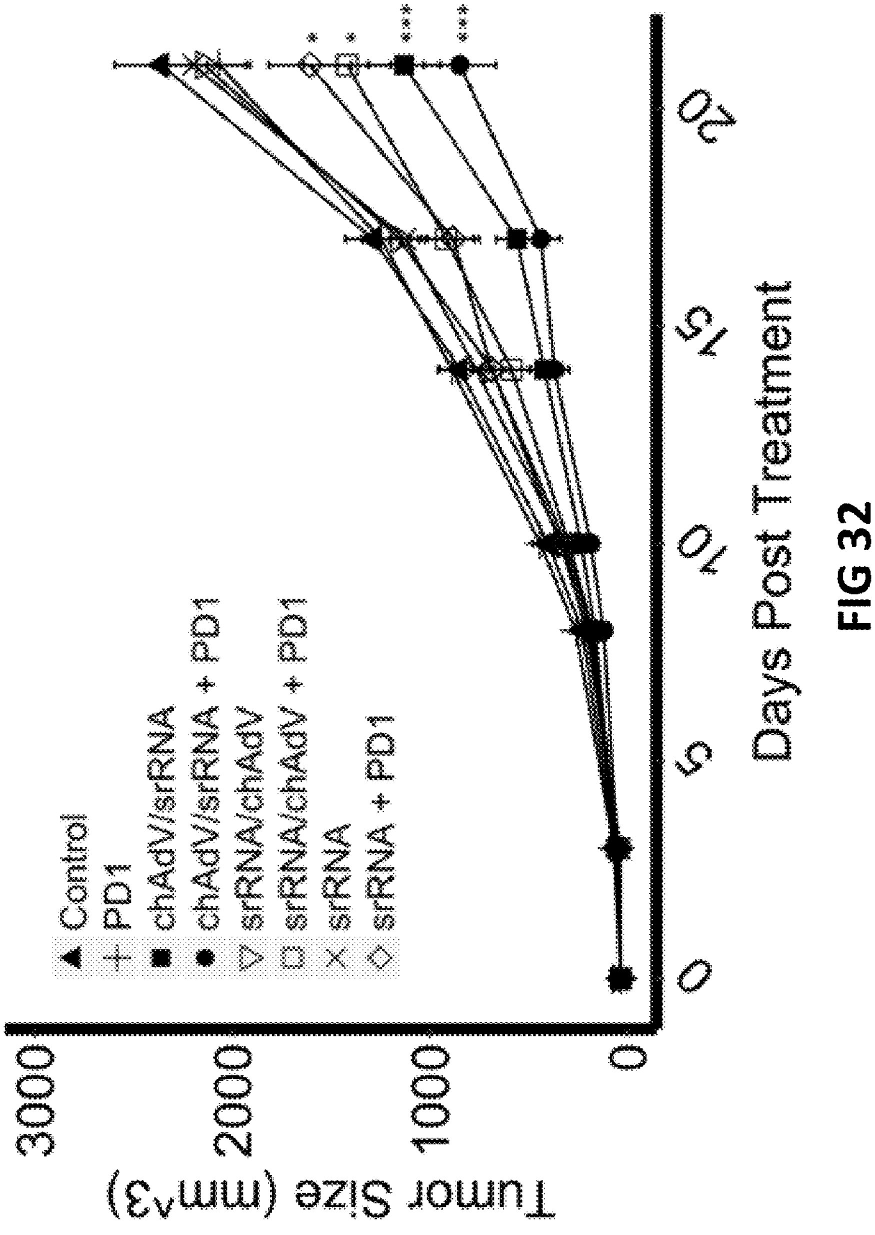
FIG. 32 illustrates tumor growth in a CT26 tumor model following immunization with a ChAdV/srRNA heterologous prime/boost, a srRNA/ChAdV heterologous prime/boost, or a srRNA/srRNA homologous primer/boost. Also illustrated in a comparison of the prime/boost immunizations with or without administration of anti-PD1 during prime and boost. Tumor volumes measured twice per week and mean tumor volumes presented for the first 21 days of the study. 22-28 mice per group at study initiation. Error bars represent standard error of the mean (SEM). P values determined using the Dunnett's test; *P<0.0001, P<0.001, *P<0.05. ChAdV=ChAdV68.5WTnt.MAG25mer, srRNA=VEE-MAG25mer srRNA.

Tumor growth was measured in the CT26 colon tumor model for all groups, and tumor growth up to 21 days after treatment initiation (28 days after injection of CT-26 tumor cells) is presented. Mice were sacrificed 21 days after treatment initiation based on large tumor sizes (>2500 $mm^3$); therefore, only the first 21 days are presented to avoid analytical bias. Mean tumor volumes at 21 days were 1129, 848, 2142, 1418, 2198 and 1606 $mm^3$ for ChAdV68.5WTnt.MAG25mer prime/VEE-MAG25mer srRNA boost (group 3), ChAdV68.5WTnt.MAG25mer prime/VEE-MAG25mer srRNA boost+anti-PD-1 (group 4), VEE-MAG25mer srRNA prime/ChAdV68.5WTnt.MAG25mer boost (group 5), VEE-MAG25mer srRNA prime/ChAdV68.5WTnt.MAG25mer boost+anti-PD-1 (group 6), VEE-MAG25mer srRNA prime/VEE-MAG25mer srRNA boost (group 7) and VEE-MAG25mer srRNA prime/VEE-MAG25mer srRNA boost+anti-PD-1 (group 8), respectively (FIG. 32 and Table 19). The mean tumor volumes in the vaccine control or vaccine control combined with anti-PD-1 were 2361 or 2067 $mm^3$, respectively. Based on these data, vaccine treatment with ChAdV68.5WTnt.MAG25mer/VEE-MAG25mer srRNA (group 3), ChAdV68.5WTnt.MAG25mer/VEE-MAG25mer srRNA+anti-PD-1 (group 4), VEE-MAG25mer srRNA/ChAdV68.5WTnt.MAG25mer+anti-PD-1 (group 6) and VEE-MAG25mer srRNA/VEE-MAG25mer srRNA+anti-PD-1 (group 8) resulted in a reduction of tumor growth at 21 days that was significantly different from the control (group 1).

TABLE 19

| Tumor size at day 21 measured in the CT26 model | | |
|---|---|---|
| Treatment | Tumor Size ($mm^3$) | SEM |
| Control | 2361 | 235 |
| PD1 | 2067 | 137 |
| chAdV/srRNA | 1129 | 181 |
| chAdV/srRNA + PD1 | 848 | 182 |
| srRNA/chAdV | 2142 | 233 |
| srRNA/chAdV + PD1 | 1418 | 220 |
| srRNA | 2198 | 134 |
| srRNA + PD1 | 1606 | 210 |

Figure 33:
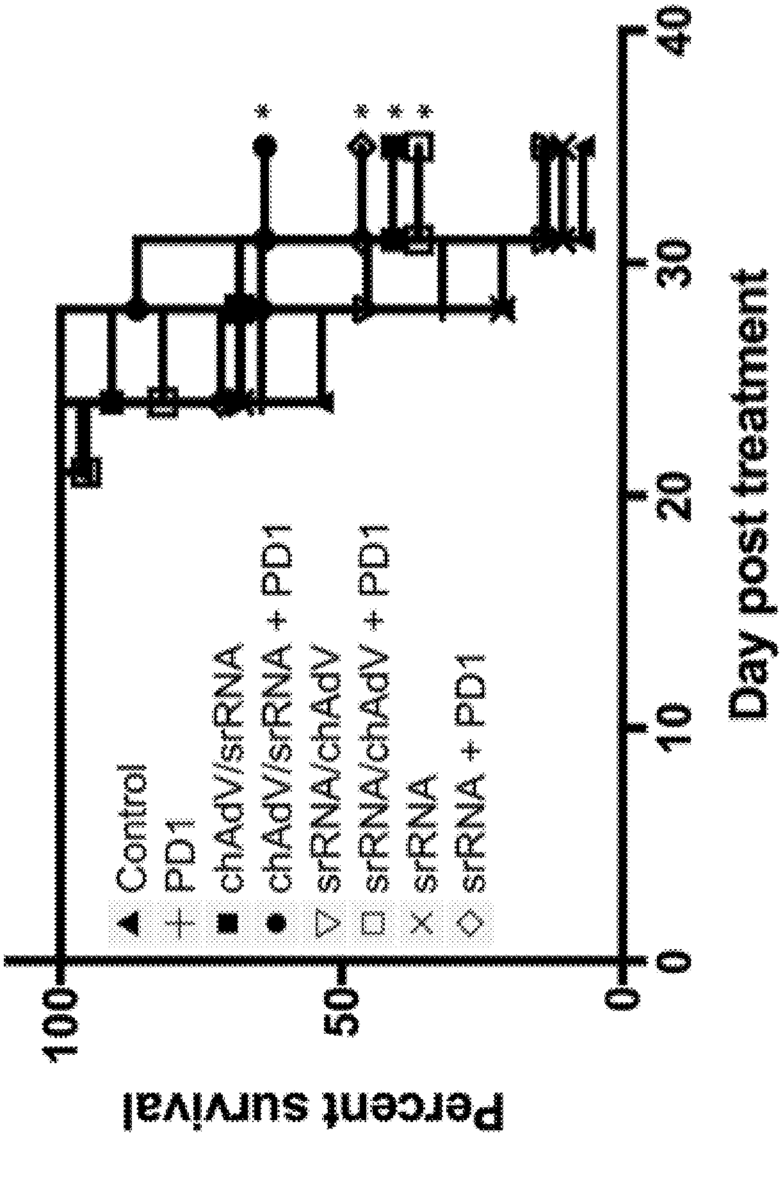
FIG. 33 illustrates survival in a CT26 tumor model following immunization with a ChAdV/srRNA heterologous prime/boost, a srRNA/ChAdV heterologous prime/boost, or a srRNA/srRNA homologous primer/boost. Also illustrated in a comparison of the prime/boost immunizations with or without administration of anti-PD1 during prime and boost. P values determined using the log-rank test; *P<0.0001, P<0.001, *P<0.01. ChAdV=ChAdV68.5WTnt.MAG25mer; srRNA=VEE-MAG25mer srRNA.

Survival was monitored for 35 days after treatment initiation in the CT-26 tumor model (42 days after injection of CT-26 tumor cells). Improved survival was observed after vaccination of mice with 4 of the combinations tested. After vaccination, 64%, 46%, 41% and 36% of mice survived with ChAdV68.5WTnt.MAG25mer prime/VEE-MAG25mer srRNA boost in combination with anti-PD-1 (group 4; P<0.0001 relative to control group 1), VEE-MAG25mer srRNA prime/VEE-MAG25mer srRNA boost in combination with anti-PD-1 (group 8; P=0.0006 relative to control group 1), ChAdV68.5WTnt.MAG25mer prime/VEE-MAG25mer srRNA boost (group 3; P=0.0003 relative to control group 1) and VEE-MAG25mer srRNA prime/ChAdV68.5WTnt.MAG25mer boost in combination with anti-PD-1 (group 6; P=0.0016 relative to control group 1), respectively (FIG. 33 and Table 20). Survival was not significantly different from the control group 1 (514%) for the remaining treatment groups [VEE-MAG25mer srRNA-prime/ChAdV68.5WTnt.MAG25mer boost (group 5), VEE-MAG25mer srRNA prime/VEE-MAG25mer srRNA boost (group 7) and anti-PD-1 alone (group 2)].

TABLE 20

Survival in the CT26 model

| Timepoint | Control | PD1 | chAdV/ srRNA | chAdV/ srRNA + PD1 | srRNA/ chAdV | srRNA/ chAdV + PD1 | srRNA | srRNA + PD1 |
|---|---|---|---|---|---|---|---|---|
| 0 | 100 | 100 | 100 | 100.00 | 100.00 | 100 | 100 | 100 |
| 21 | 96 | 100 | 100 | 100 | 100 | 95 | 100 | 100 |
| 24 | 54 | 64 | 91 | 100 | 68 | 82 | 68 | 71 |
| 28 | 21 | 32 | 68 | 86 | 45 | 68 | 21 | 64 |
| 31 | 7 | 14 | 41 | 64 | 14 | 36 | 11 | 46 |
| 35 | 7 | 14 | 41 | 64 | 14 | 36 | 11 | 46 |

In conclusion, ChAdV68.5WTnt.MAG25mer and VEE-MAG25mer srRNA elicited strong T-cell responses to mouse tumor antigens encoded by the vaccines, relative to control. Administration of a ChAdV68.5WTnt.MAG25mer prime and VEE-MAG25mer srRNA boost with or without co-administration of anti-PD-1, VEE-MAG25mer srRNA prime and ChAdV68.5WTnt.MAG25mer boost in combination with anti-PD-1 or administration of VEE-MAG25mer srRNA as a homologous prime boost immunization in combination with anti-PD-1 to tumor bearing mice resulted in improved survival.

XVIII. Non-Human Primate Studies

Various dosing protocols using ChAdV68 and self-replicating RNA (srRNA) were evaluated in non-human primates (NHP).

Materials and Methods

A priming vaccine was injected intramuscularly (IM) in each NHP to initiate the study (vaccine prime). One or more boosting vaccines (vaccine boost) were also injected intramuscularly in each NHP. Bilateral injections per dose were administered according to groups outlined in tables and summarized below.

Immunizations

Mamu-A*01 Indian rhesus macaques were immunized bilaterally with $1\times10^{12}$ viral particles ($5\times10^{11}$ viral particles per injection) of ChAdV68.5WTnt.MAG25mer, 30 ug of VEE-MAG25MER srRNA, 100 ug of VEE-MAG25mer srRNA or 300 ug of VEE-MAG25mer srRNA formulated in LNP-1 or LNP-2. Vaccine boosts of 30 ug, 100 ug or 300 ug VEE-MAG25mer srRNA were administered intramuscularly at the indicated time after prime vaccination.

Immune Monitoring

PBMCs were isolated at indicated times after prime vaccination using Lymphocyte Separation Medium (LSM, MP Biomedicals) and LeucoSep separation tubes (Greiner Bio-One) and resuspended in RPMI containing 10% FBS and penicillin/streptomycin. Cells were counted on the Attune N×T flow cytometer (Thermo Fisher) using propidium iodide staining to exclude dead and apoptotic cells. Cell were then adjusted to the appropriate concentration of live cells for subsequent analysis. For each monkey in the studies, T cell responses were measured using ELISpot or flow cytometry methods. T cell responses to 6 different rhesus macaque Mamu-A*01 class I epitopes encoded in the vaccines were monitored from PBMCs by measuring induction of cytokines, such as IFN-gamma, using ex vivo enzyme-linked immunospot (ELISpot) analysis. ELISpot analysis was performed according to ELISPOT harmonization guidelines {DOI: 10.1038/nprot.2015.068} with the monkey IFNg ELISpotPLUS kit (MABTECH). 200,000 PBMCs were incubated with 10 uM of the indicated peptides for 16 hours in 96-well IFNg antibody coated plates. Spots were developed using alkaline phosphatase. The reaction was timed for 10 minutes and was terminated by running plate under tap water. Spots were counted using an AID vSpot Reader Spectrum. For ELISPOT analysis, wells with saturation >50% were recorded as “too numerous to count”. Samples with deviation of replicate wells >10% were excluded from analysis. Spot counts were then corrected for well confluency using the formula: spot count+2×(spot count×% confluence/[100%−% confluence]). Negative background was corrected by subtraction of spot counts in the negative peptide stimulation wells from the antigen stimulated wells. Finally, wells labeled too numerous to count were set to the highest observed corrected value, rounded up to the nearest hundred.

Specific CD4 and CD8 T cell responses to 6 different rhesus macaque Mamu-A*01 class I epitopes encoded in the vaccines were monitored from PBMCs by measuring induction of intracellular cytokines, such as IFN-gamma, using flow cytometry. The results from both methods indicate that cytokines were induced in an antigen-specific manner to epitopes.

Immunogenicity in Rhesus Macaques

This study was designed to (a) evaluate the immunogenicity and preliminary safety of VEE-MAG25mer srRNA 30 μg and 100 μg doses as a homologous prime/boost or heterologous prime/boost in combination with ChAdV68.5WTnt.MAG25mer; (b) compare the immune responses of VEE-MAG25mer srRNA in lipid nanoparticles using LNP1 versus LNP2; (c) evaluate the kinetics of T-cell responses to VEE-MAG25mer srRNA and ChAdV68.5WTnt.MAG25mer immunizations.

The study arm was conducted in Mamu-A*01 Indian rhesus macaques to demonstrate immunogenicity. Select antigens used in this study are only recognized in Rhesus macaques, specifically those with a Mamu-A*01 MHC class I haplotype. Mamu-A*01 Indian rhesus macaques were randomized to the different study arms (6 macaques per group) and administered an IM injection bilaterally with either ChAdV68.5WTnt.MAG25mer or VEE-MAG25mer srRNA vector encoding model antigens that includes multiple Mamu-A*01 restricted epitopes. The study arms were as described below.

TABLE 21

Non-GLP immunogenicity study in Indian Rhesus Macaques

| Group | Prime | Boost 1 | Boost 2 |
|---|---|---|---|
| 1 | VEE-MAG25mer srRNA-LNP1(30 μg) | VEE-MAG25mer srRNA-LNP1 (30 μg) | VEE-MAG25mer srRNA-LNP1 (30 μg) |
| 2 | VEE-MAG25mer srRNA-LNP1 (100 μg) | VEE-MAG25mer srRNA-LNP1 (100 μg) | VEE-MAG25mer srRNA-LNP1 (100 μg) |
| 3 | VEE-MAG25mer srRNA-LNP2 (100 μg) | VEE-MAG25mer srRNA-LNP2 (100 μg) | VEE-MAG25mer srRNA-LNP2 (100 μg) |
| 4 | ChAdV68.5WTnt.MAG25mer | VEE-MAG25mer srRNA-LNP1 (100 μg) | VEE-MAG25mer srRNA-LNP1 (100 μg) |

PBMCs were collected prior to immunization and on weeks 1, 2, 3, 4, 5, 6, 8, 9, and 10 after the initial immunization for immune monitoring.

Results

Antigen-specific cellular immune responses in peripheral blood mononuclear cells (PBMCs) were measured to six different Mamu-A*01 restricted epitopes prior to immunization and 1, 2, 3, 4, 5, 6, 8, 9, and 10 weeks after the initial immunization. Animals received a boost immunization with VEE-MAG25mer srRNA on weeks 4 and 8 with either 30 μg or 100 μg doses, and either formulated with LNP1 or LNP2, as described in Table 21. Combined immune responses to all six epitopes were plotted for each immune monitoring timepoint (FIGS. 34A-D and Tables 22-25).

Figure 34A:
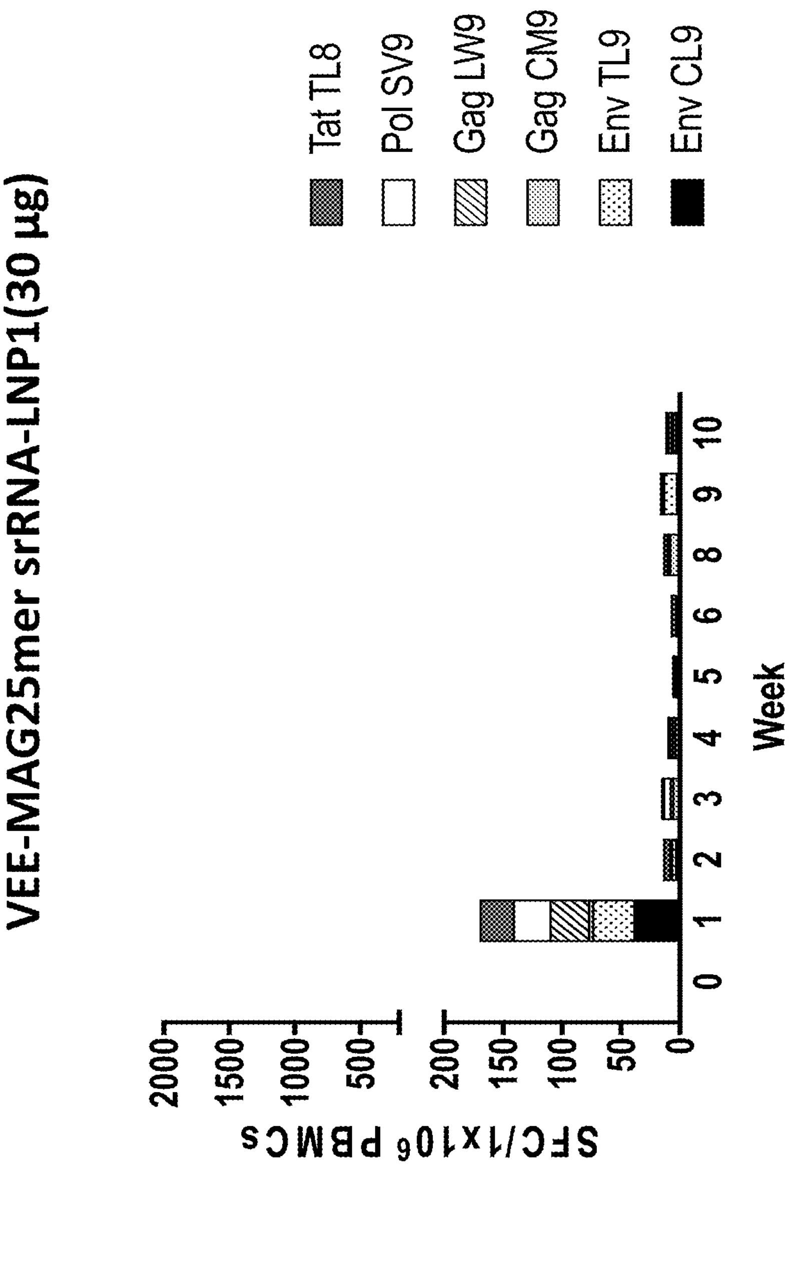
FIG. 34A, FIG. 34B, FIG. 34C, and FIG. 34D illustrates antigen-specific cellular immune responses measured using ELISpot. Antigen-specific IFN-gamma production to six different mamu A01 restricted epitopes was measured in PBMCs for the VEE-MAG25mer srRNA-LNP1 (30 μg) (FIG. 34A), VEE-MAG25mer srRNA-LNP1 (100 μg) (FIG. 34B), or VEE-MAG25mer srRNA-LNP2 (100 μg) (FIG. 34C) homologous prime/boost or the ChAdV68.5WTnt.MAG25mer NEE-MAG25mer srRNA heterologous prime/boost group (FIG. 34D) using ELISpot 1, 2, 3, 4, 5, 6, 8, 9, or 10 weeks after the first boost immunization (6 rhesus macaques per group). Results are presented as mean spot forming cells (SFC) per $10^6$ PBMCs for each epitope in a stacked bar graph format. Values for each animal were normalized to the levels at pre-bleed (week 0).
Figure 34B:
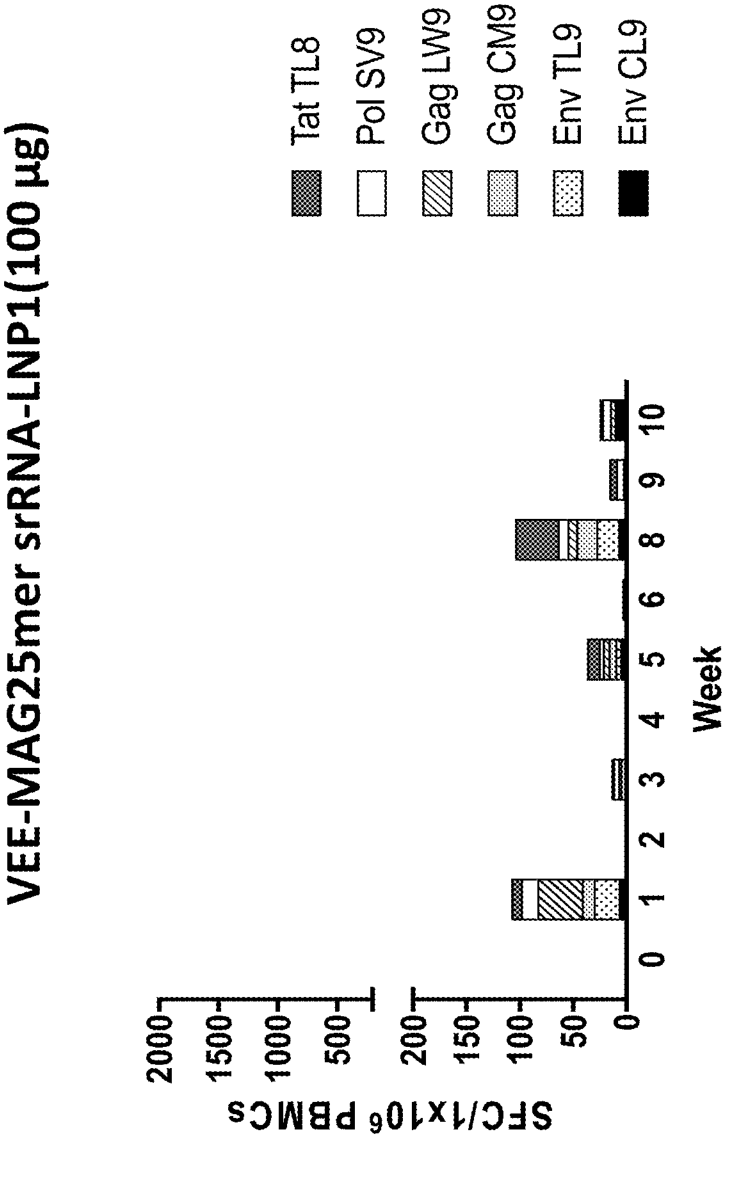
Figure 34C:
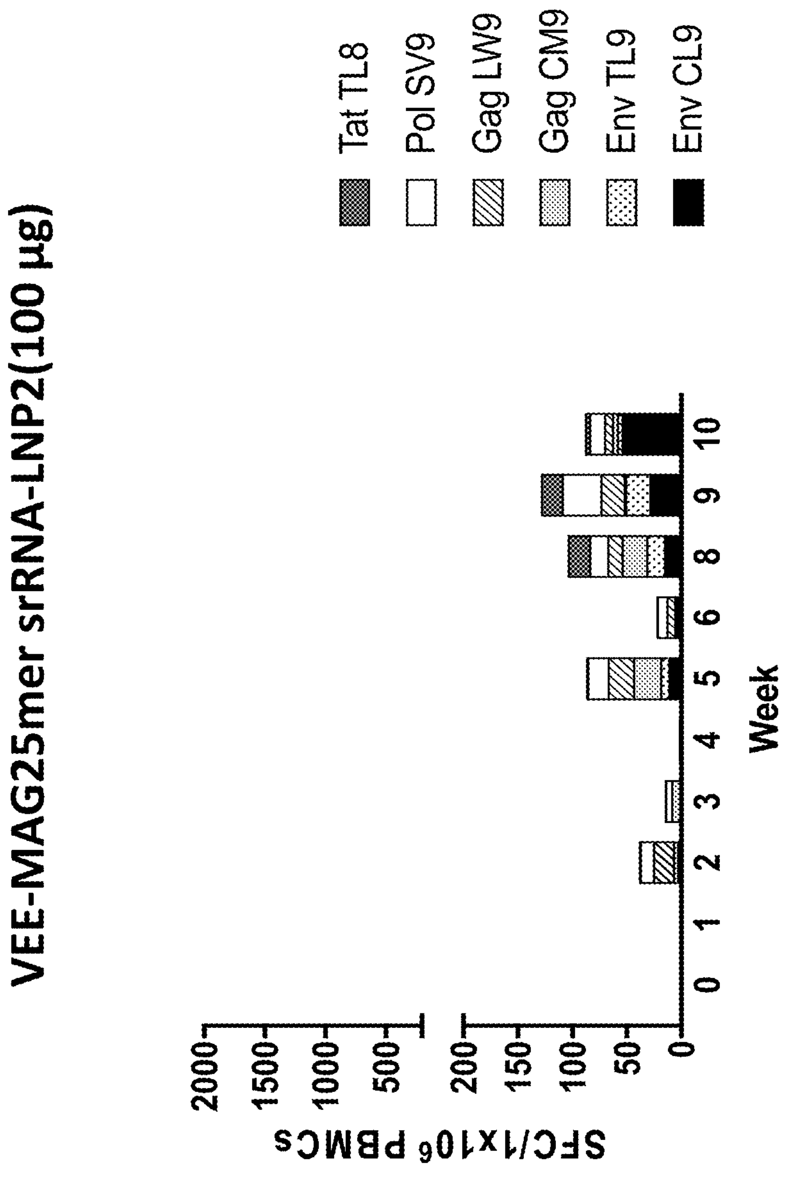

Combined antigen-specific immune responses were observed at all measurements with 170, 14, 15, 11, 7, 8, 14, 17, 12 SFCs per $10^6$ PBMCs (six epitopes combined) 1, 2, 3, 4, 5, 6, 8, 9, or 10 weeks after an initial VEE-MAG25mer srRNA-LNP1(30 μg) prime immunization, respectively (FIG. 34A). Combined antigen-specific immune responses were observed at all measurements with 108, −3, 14, 1, 37, 4, 105, 17, 25 SFCs per $10^6$ PBMCs (six epitopes combined) 1, 2, 3, 4, 5, 6, 8, 9, or 10 weeks after an initial VEE-MAG25mer srRNA-LNP1(100 μg) prime immunization, respectively (FIG. 34B). Combined antigen-specific immune responses were observed at all measurements with −17, 38, 14, −2, 87, 21, 104, 129, 89 SFCs per $10^6$ PBMCs (six epitopes combined) 1, 2, 3, 4, 5, 6, 8, 9, or 10 weeks after an initial VEE-MAG25mer srRNA-LNP2(100 μg) prime immunization, respectively (FIG. 34C). Negative values are a result of normalization to pre-bleed values for each epitope/animal.

Figure 34D:
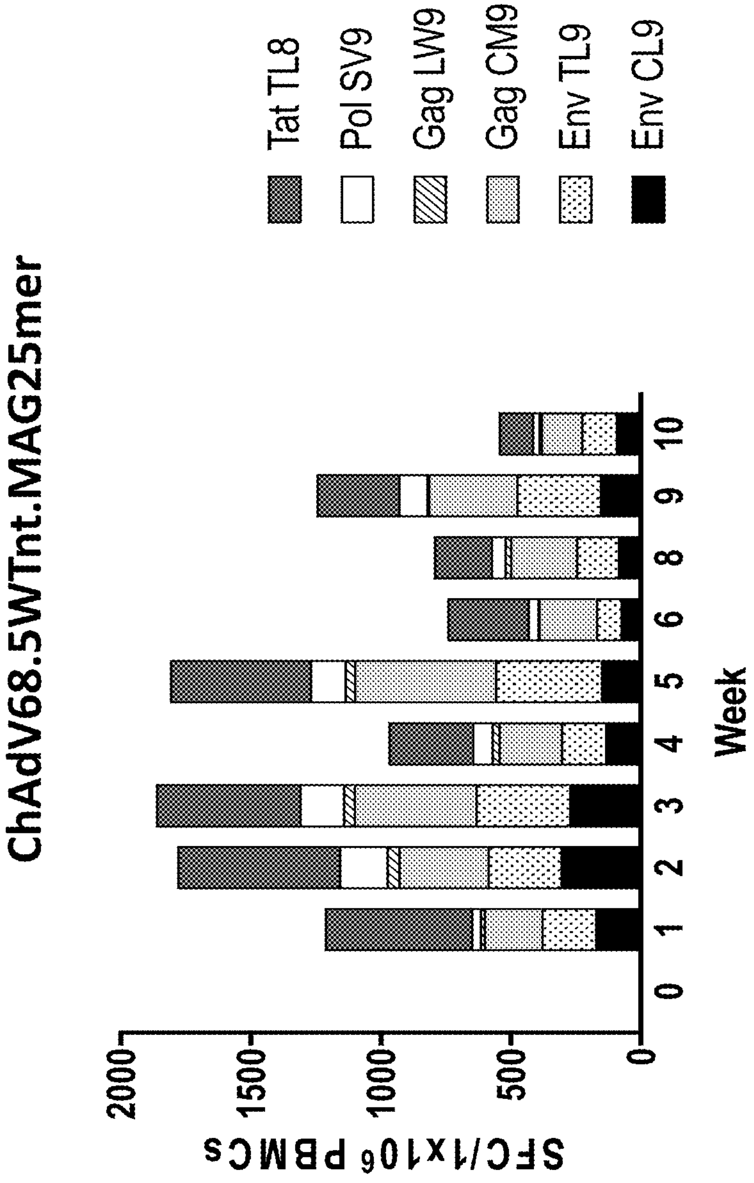

Combined antigen-specific immune responses were observed at all measurements with 1218, 1784, 1866, 973, 1813, 747, 797, 1249, and 547 SFCs per $10^6$ PBMCs (six epitopes combined) 1, 2, 3, 4, 5, 6, 8, 9, or 10 weeks after an initial ChAdV68.5WTnt.MAG25mer prime immunization, respectively (FIG. 34D). The immune response showed the expected profile with peak immune responses measured ~2-3 weeks after the prime immunization followed by a contraction in the immune response after 4 weeks. Combined antigen-specific cellular immune responses of 1813 SFCs per $10^6$ PBMCs (six epitopes combined) were measured 5 weeks after the initial immunization with ChAdV68.5WTnt.MAG25mer (i.e., 1 week after the first boost with VEE-MAG25mer srRNA). The immune response measured 1 week after the first boost with VEE-MAG25mer srRNA (week 5) was comparable to the peak immune response measured for the ChAdV68.5WTnt.MAG25mer prime immunization (week 3) (FIG. 34D). Combined antigen-specific cellular immune responses of 1249 SFCs per $10^6$ PBMCs (six epitopes combined) was measured 9 weeks after the initial immunization with ChAdV68.5WTnt.MAG25mer, respectively (i.e., 1 week after the second boost with VEE-MAG25mer srRNA). The immune responses measured 1 week after the second boost with VEE-MAG25mer srRNA (week 9) was ~2-fold higher than that measured just before the boost immunization (FIG. 34D).

TABLE 22

Mean spot forming cells (SFC) per $10^6$ PBMCs for each epitope ± SEM for VEE-MAG25mer srRNA-LNP1(30 μg) (Group 1)

| | Antigen | | | | | |
|---|---|---|---|---|---|---|
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | 39.7 ± 22.7 | 35.4 ± 25.1 | 3.2 ± 3.6 | 33 ± 28.1 | 30.9 ± 20.3 | 28.3 ± 17.5 |
| 3 | 2 ± 2.4 | 0.2 ± 1.8 | 1.8 ± 2.4 | 3.7 ± 1.9 | 1.7 ± 2.8 | 4.9 ± 2.3 |
| 4 | 1 ± 1.8 | 0.3 ± 1.2 | 5.5 ± 3.6 | 2.3 ± 2.2 | 5.7 ± 2.7 | 0.8 ± 0.8 |
| 5 | 0.5 ± 0.9 | 1.4 ± 3.8 | 3.1 ± 1.6 | 2.3 ± 2.7 | 1.9 ± 2 | 1.4 ± 1.2 |
| 6 | 1.9 ± 1.8 | −0.3 ± 3 | 1.7 ± 1.2 | 1.4 ± 1.4 | 0.8 ± 1.1 | 1.1 ± 1 |
| 8 | −0.4 ± 0.8 | −0.9 ± 2.9 | 0.5 ± 1.3 | 3 ± 1.1 | 2.2 ± 2.1 | 3.7 ± 2 |
| 9 | 1 ± 1.7 | 1.2 ± 4.2 | 7.2 ± 3.9 | 0.5 ± 0.7 | 1.6 ± 3 | 3 ± 1 |
| 10 | 3.8 ± 1.8 | 11 ± 5 | −1.1 ± 1.1 | 1.9 ± 0.9 | 1.3 ± 1.6 | 0.2 ± 0.5 |

TABLE 23

| Mean spot forming cells (SFC) per $10^6$ PBMCs for each epitope ± SEM for VEE-MAG25mer srRNA-LNP1(100 μg) (Group 2) | | | | | | |
|---|---|---|---|---|---|---|
| | Antigen | | | | | |
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | 7.9 ± 17.2 | 23.2 ± 17.4 | 11.4 ± 4.9 | 41.7 ± 16.5 | 15 ± 13.5 | 8.9 ± 6.2 |
| 3 | −3.1 ± 4.6 | −7.2 ± 6.5 | 2.3 ± 2.3 | −0.3 ± 2.7 | 2.7 ± 5.1 | 2.2 ± 1.4 |
| 4 | 1.9 ± 3.8 | −6.2 ± 7.6 | 10.5 ± 4.1 | 1.2 ± 2.9 | 5.6 ± 4.9 | 1.1 ± 0.8 |
| 5 | −2.6 ± 7 | −8 ± 5.9 | 1.5 ± 1.7 | 6.4 ± 2.3 | 0.7 ± 4.3 | 3.3 ± 1.3 |
| 6 | 6.3 ± 6.3 | 4.4 ± 8.3 | 6.6 ± 4.4 | 5.2 ± 5.2 | 3.9 ± 5 | 10.8 ± 6.9 |
| 8 | −3.6 ± 7.2 | −6.8 ± 7.3 | −0.8 ± 1.2 | 3.4 ± 4.2 | 6.4 ± 7.5 | 5.7 ± 2.7 |
| 9 | 8.1 ± 2.4 | 20.6 ± 23.4 | 18.9 ± 5.7 | 8.1 ± 8.9 | 9 ± 11.2 | 40 ± 17.6 |
| 10 | 3.1 ± 8 | −3.9 ± 8.5 | 3.3 ± 1.8 | 0.6 ± 2.9 | 7.4 ± 6.4 | 6.1 ± 2.5 |

TABLE 24

| Mean spot forming cells (SFC) per $10^6$ PBMCs for each epitope ± SEM for VEE-MAG25mer srRNA-LNP2(100 μg) (Group 3) | | | | | | |
|---|---|---|---|---|---|---|
| | Antigen | | | | | |
| Wk | Env CL9 | Env TL9 | Gag CM9 | Gag LW9 | Pol SV9 | Tat TL8 |
| 1 | 0 ± 0 | 0 ± 0 | 0 ± 0 | 0 ± 0 | 0 ± 0 | 0 ± 0 |
| 2 | −5.9 ± 3.8 | −0.3 ± 0.5 | −0.5 ± 1.5 | −5.7 ± 6.1 | −1 ± 1.3 | −3.2 ± 5.5 |
| 3 | 0.7 ± 5.2 | 3.4 ± 2.4 | 4.2 ± 4.6 | 18.3 ± 15.5 | 11.9 ± 5.1 | −0.4 ± 8.2 |
| 4 | −3.8 ± 5.5 | 2.3 ± 1.8 | 11.3 ± 6.1 | −3.1 ± 5.6 | 8.5 ± 4 | −1.5 ± 6.1 |
| 5 | −3.7 ± 5.7 | −0.1 ± 0.7 | −0.2 ± 1.6 | 3.4 ± 8.5 | 3 ± 3.1 | −4.6 ± 5 |
| 6 | 12.3 ± 15 | 7.8 ± 4.9 | 24.7 ± 19.8 | 23.2 ± 22.5 | 18.7 ± 15.8 | 0.5 ± 6.2 |
| 8 | 5.9 ± 12.3 | −0.1 ± 0.7 | −0.5 ± 1.3 | 8.8 ± 14.4 | 8.7 ± 8 | −1.3 ± 4 |
| 9 | 16.1 ± 13.4 | 16.5 ± 4 | 22.9 ± 4.2 | 13 ± 13.2 | 16.4 ± 7.8 | 19.6 ± 9.2 |
| 10 | 29.9 ± 21.8 | 22 ± 19.5 | 0.5 ± 2.6 | 22.2 ± 22.6 | 35.3 ± 15.8 | 19.4 ± 17.3 |

TABLE 25

| Mean spot forming cells (SFC) per $10^6$ PBMCs for each epitope ± SEM for ChAdV68.5WTnt.MAG25mer prime | | | | | | |
|---|---|---|---|---|---|---|
| | Antigen | | | | | |
| Wk | Env CL9 | Env TL9 | Gag CM9 | Gag LW9 | Pol SV9 | Tat TL8 |
| 1 | 178 ± 68.7 | 206.5 ± 94.8 | 221.2 ± 120 | 15.4 ± 16.7 | 33.3 ± 25.9 | 563.5 ± 174.4 |
| 2 | 311.2 ± 165.5 | 278.8 ± 100.9 | 344.6 ± 110.8 | 46.3 ± 13.5 | 181.6 ± 76.8 | 621.4 ± 220.9 |
| 3 | 277.3 ± 101.1 | 359.6 ± 90.5 | 468.2 ± 106.6 | 41.7 ± 11.1 | 169.8 ± 57.8 | 549.4 ± 115.7 |
| 4 | 140 ± 46.5 | 169.6 ± 46.8 | 239.4 ± 37 | 26.5 ± 11.4 | 75 ± 31.6 | 322.2 ± 50.7 |
| 5 | 155.6 ± 62.1 | 406.7 ± 96.4 | 542.7 ± 143.3 | 35.1 ± 16.6 | 134.2 ± 53.7 | 538.5 ± 91.9 |
| 6 | 78.9 ± 42.5 | 95.5 ± 29.4 | 220.9 ± 75.3 | −1.4 ± 5.3 | 43.4 ± 19.6 | 308.1 ± 42.6 |
| 8 | 88.4 ± 30.4 | 162.1 ± 30.3 | 253.4 ± 78.6 | 21.4 ± 11.2 | 53.7 ± 22.3 | 217.8 ± 45.2 |
| 9 | 158.5 ± 69 | 322.3 ± 87.2 | 338.2 ± 137.1 | 5.6 ± 12.4 | 109.2 ± 17.9 | 314.8 ± 43.4 |
| 10 | 97.3 ± 32.5 | 133.2 ± 27 | 154.9 ± 59.2 | 10 ± 6 | 26 ± 16.7 | 125.5 ± 27.7 |

Non-GLP RNA Dose Ranging Study (Higher Doses) in Indian Rhesus Macaques

This study was designed to (a) evaluate the immunogenicity of VEE-MAG25mer srRNAat a dose of 300 μg as a homologous prime/boost or heterologous prime/boost in combination with ChAdV68.5WTnt.MAG25mer; (b) compare the immune responses of VEE-MAG25mer srRNA in lipid nanoparticles using LNP1 versus LNP2 at the 300 μg dose; and (c) evaluate the kinetics of T-cell responses to VEE-MAG25mer srRNA and ChAdV68.5WTnt.MAG25mer immunizations.

The study arm was conducted in Mamu-A*01 Indian rhesus macaques to demonstrate immunogenicity. Vaccine immunogenicity in nonhuman primate species, such as Rhesus, is the best predictor of vaccine potency in humans. Furthermore, select antigens used in this study are only recognized in Rhesus macaques, specifically those with a Mamu-A*01 MHC class I haplotype. Mamu-A*01 Indian rhesus macaques were randomized to the different study arms (6 macaques per group) and administered an IM injection bilaterally with either ChAdV68.5-WTnt.MAG25mer or VEE-MAG25mer srRNA encoding model antigens that includes multiple Mamu-A*01 restricted antigens. The study arms were as described below.

PBMCs were collected prior to immunization and 4, 5, 6, 7, 8, 10, 11, 12, 13, 14, 15, 16, 17, 18, 19, 20, 21, 22, 23 or 24 weeks after the initial immunization for immune monitoring for group 1 (heterologous prime/boost). PBMCs were collected prior to immunization and 4, 5, 7, 8, 10, 11, 12, 13, 14, or 15 weeks after the initial immunization for immune monitoring for groups 2 and 3 (homologous prime/boost).

TABLE 26

| Non-GLP immunogenicity study in Indian Rhesus Macaques | | | | |
|---|---|---|---|---|
| Group | Prime | Boost 1 | Boost 2 | Boost 3 |
| 1 | ChAdV68.5WTnt.MAG25mer | VEE-MAG25mer srRNA-LNP2 (300 μg) | VEE-MAG25mer srRNA-LNP2 (300 μg) | VEE-MAG25mer srRNA-LNP2 (300 μg) |
| 2 | VEE-MAG25mer srRNA-LNP2 (300 μg) | VEE-MAG25mer srRNA-LNP2 (300 μg) | VEE-MAG25mer srRNA-LNP2 (300 μg) | |
| 3 | VEE-MAG25mer srRNA-LNP1 (300 μg) | VEE-MAG25mer srRNA-LNP1 (300 μg) | VEE-MAG25mer srRNA-LNP1 (300 μg) | |

Results

Figure 35:
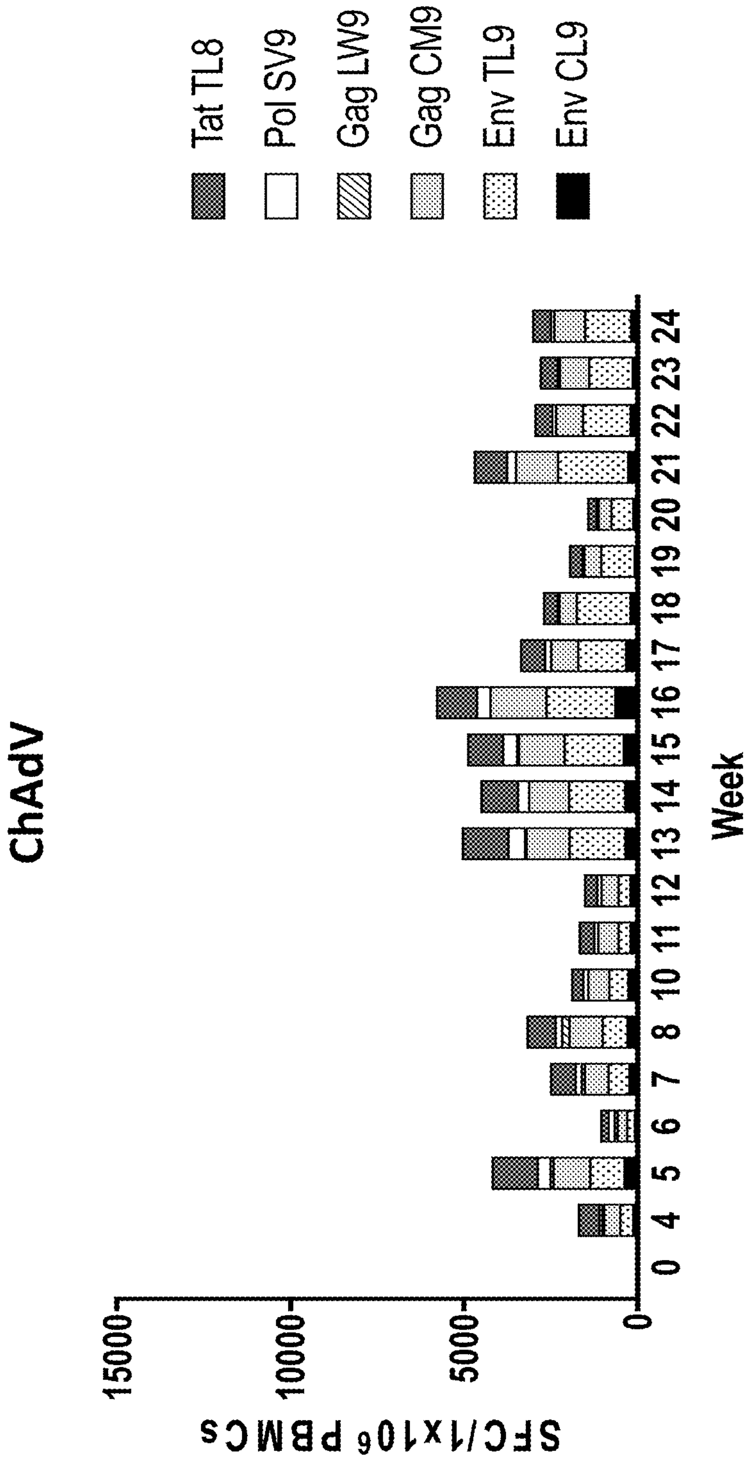
FIG. 35 shows antigen-specific cellular immune response measured using ELISpot. Antigen-specific IFN-gamma production to six different mamu A01 restricted epitopes was measured in PBMCs after immunization with the ChAdV68.5WTnt.MAG25mer NEE-MAG25mer srRNA heterologous prime/boost regimen using ELISpot prior to immunization and 4, 5, 6, 7, 8, 10, 11, 12, 13, 14, 15, 16, 17, 18, 19, 20, 21, 22, 23 or 24 weeks after the initial immunization. Results are presented as mean spot forming cells (SFC) per $10^6$ PBMCs for each epitope (6 rhesus macaques per group) in a stacked bar graph format.

Mamu-A*01 Indian rhesus macaques were immunized with ChAdV68.5-WTnt.MAG25mer. Antigen-specific cellular immune responses in peripheral blood mononuclear cells (PBMCs) were measured to six different Mamu-A*01 restricted epitopes prior to immunization and 4, 5, 6, 7, 8, 10, 11, 12, 13, 14, 15, 16, 17, 18, 19, 20, 21, 22, 23 or 24 weeks after the initial immunization (FIG. 35 and Table 27). Animals received boost immunizations with VEE-MAG25mer srRNA using the LNP2 formulation on weeks 4, 12, and 20. Combined antigen-specific immune responses of 1750, 4225, 1100, 2529, 3218, 1915, 1708, 1561, 5077, 4543, 4920, 5820, 3395, 2728, 1996, 1465, 4730, 2984, 2828, or 3043 SFCs per $10^6$ PBMCs (six epitopes combined) were measured 4, 5, 6, 7, 8, 10, 11, 12, 13, 14, 15, 16, 17, 18, 19, 20, 21, 22, 23 or 24 weeks after the initial immunization with ChAdV68.5WTnt.MAG25mer (FIG. 35). Immune responses measured 1 week after the second boost immunization (week 13) with VEE-MAG25mer srRNA were ~3-fold higher than that measured just before the boost immunization (week 12). Immune responses measured 1 week after the third boost immunization (week 21) with VEE-MAG25mer srRNA, were ~3-fold higher than that measured just before the boost immunization (week 20), similar to the response observed for the second boost.

Figure 36:
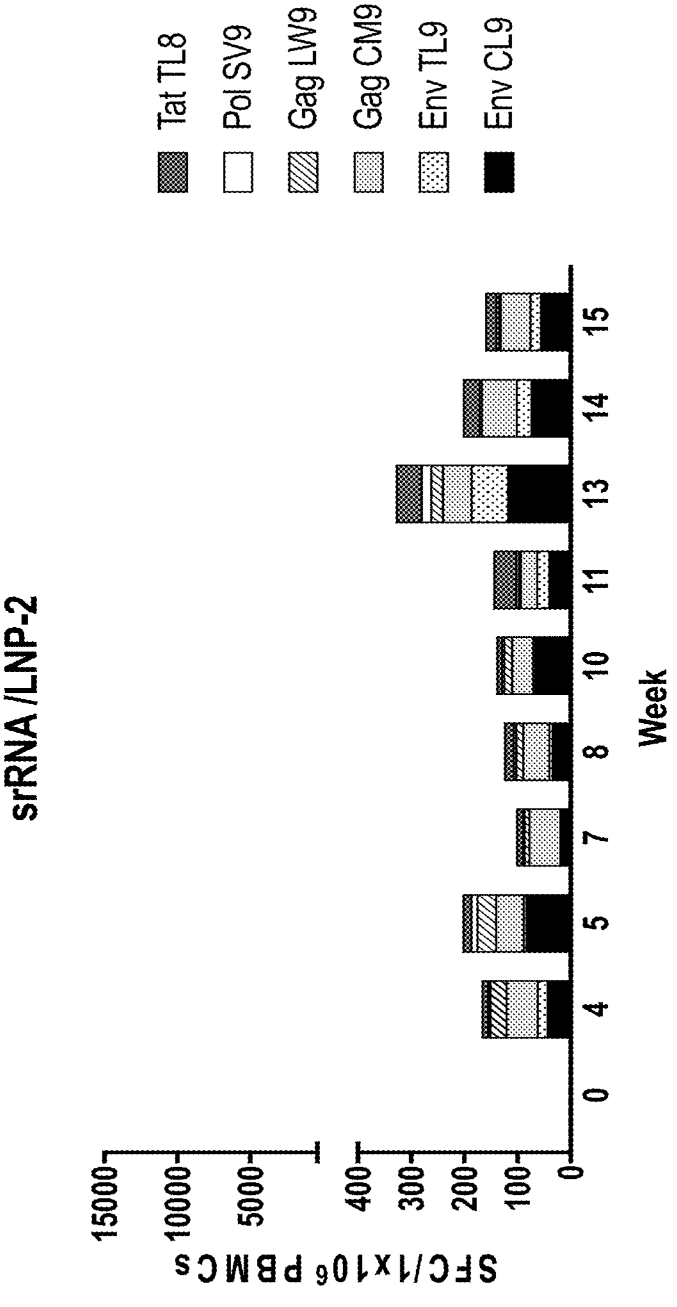
FIG. 36 shows antigen-specific cellular immune response measured using ELISpot. Antigen-specific IFN-gamma production to six different mamu A01 restricted epitopes was measured in PBMCs after immunization with the VEE-MAG25mer srRNA LNP2 homologous prime/boost regimen using ELISpot prior to immunization and 4, 5, 6, 7, 8, 10, 11, 12, 13, 14, or 15 weeks after the initial immunization. Results are presented as mean spot forming cells (SFC) per $10^6$ PBMCs for each epitope (6 rhesus macaques per group) in a stacked bar graph format.
Figure 37:
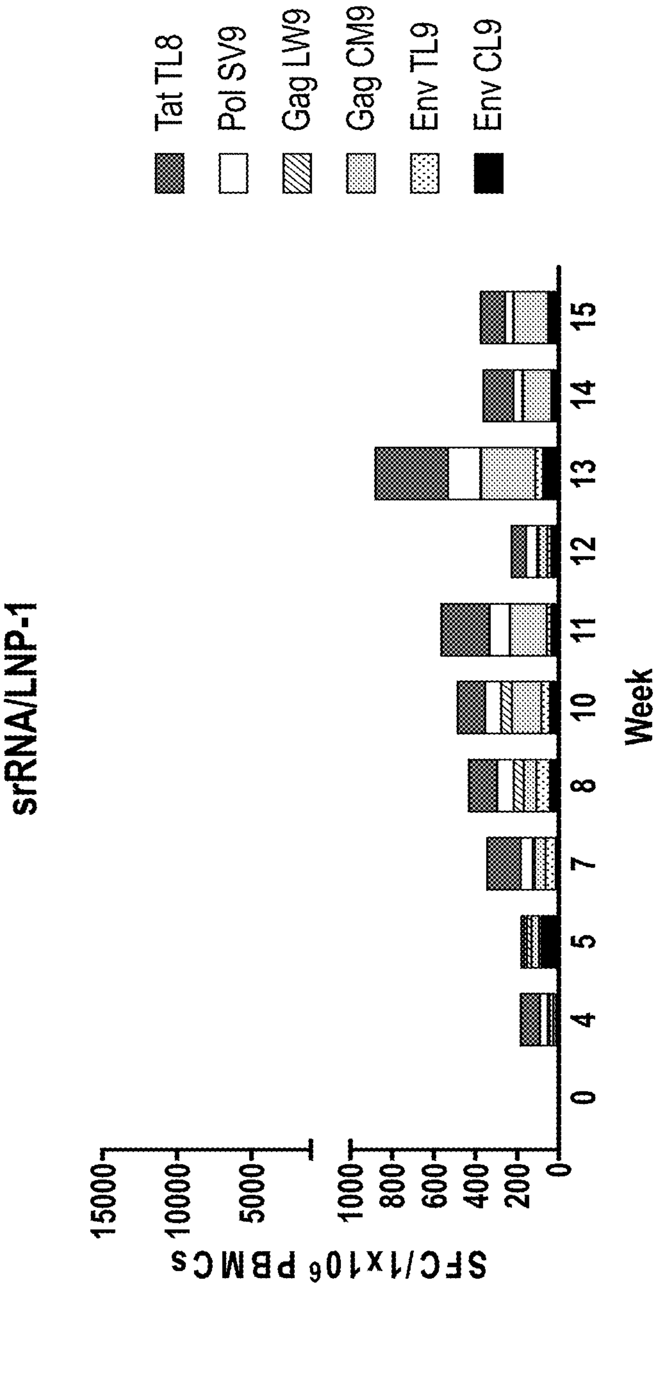
FIG. 37 shows antigen-specific cellular immune response measured using ELISpot. Antigen-specific IFN-gamma production to six different mamu A01 restricted epitopes was measured in PBMCs after immunization with the VEE-MAG25mer srRNA LNP1 homologous prime/boost regimen using ELISpot prior to immunization and 4, 5, 6, 7, 8, 10, 11, 12, 13, 14, or 15 weeks after the initial immunization. Results are presented as mean spot forming cells (SFC) per $10^6$ PBMCs for each epitope (6 rhesus macaques per group) in a stacked bar graph format.

Mamu-A*01 Indian rhesus macaques were also immunized with VEE-MAG25mer srRNA using two different LNP formulations (LNP1 and LNP2). Antigen-specific cellular immune responses in peripheral blood mononuclear cells (PBMCs) were measured to six different Mamu-A*01 restricted epitopes prior to immunization and 4, 5, 6, 7, 8, 10, 11, 12, 13, 14, or 15 weeks after the initial immunization (FIGS. 36 and 37, Tables 28 and 29). Animals received boost immunizations with VEE-MAG25mer srRNA using the respective LNP1 or LNP2 formulation on weeks 4 and 12. Combined antigen-specific immune responses of 168, 204, 103, 126, 140, 145, 330, 203, and 162 SFCs per 106 PBMCs (six epitopes combined) were measured 4, 5, 7, 8, 10, 11, 13, 14, 15 weeks after the immunization with VEE-MAG25mer srRNA-LNP2 (FIG. 36). Combined antigen-specific immune responses of 189, 185, 349, 437, 492, 570, 233, 886, 369, and 381 SFCs per $10^6$ PBMCs (six epitopes combined) were measured 4, 5, 7, 8, 10, 11, 12, 13, 14, 15 weeks after the immunization with VEE-MAG25mer srRNA-LNP1 (FIG. 37).

TABLE 27

Mean spot forming cells (SFC) per $10^6$ PBMCs for each epitope ± SEM for priming vaccination with ChAdV68.5WTnt.MAG25mer (Group 1)

| | Antigen | | | | | |
|---|---|---|---|---|---|---|
| Wk | Env CL9 | Env TL9 | Gag CM9 | Gag LW9 | Pol SV9 | Tat TL8 |
| 4 | 173 ± 41.6 | 373.5 ± 87.3 | 461.4 ± 74.2 | 38.4 ± 26.1 | 94.5 ± 26 | 609.2 ± 121.9 |
| 5 | 412.7 ± 138.4 | 987.8 ± 283.3 | 1064.4 ± 266.9 | 85.6 ± 31.2 | 367.2 ± 135.2 | 1306.8 ± 332.8 |
| 6 | 116.2 ± 41.2 | 231.1 ± 46.3 | 268.3 ± 90.7 | 86.1 ± 42 | 174.3 ± 61 | 223.9 ± 38.1 |
| 7 | 287.4 ± 148.7 | 588.9 ± 173.9 | 693.2 ± 224.8 | 92.1 ± 33.5 | 172.9 ± 55.6 | 694.6 ± 194.8 |
| 8 | 325.4 ± 126.6 | 735.8 ± 212 | 948.9 ± 274.5 | 211.3 ± 62.7 | 179.1 ± 50 | 817.3 ± 185.2 |
| 10 | 312 ± 129.7 | 543.2 ± 188.4 | 618.6 ± 221.7 | −5.7 ± 4.1 | 136.5 ± 51.3 | 309.9 ± 85.6 |
| 11 | 248.5 ± 81.1 | 348.7 ± 129.8 | 581.1 ± 205.5 | −3.1 ± 4.4 | 119 ± 51.2 | 413.7 ± 144.8 |
| 12 | 261.9 ± 68.2 | 329.9 ± 83 | 486.5 ± 118.6 | −1.2 ± 5.1 | 132.8 ± 31.8 | 350.9 ± 69.3 |
| 13 | 389.3 ± 167.7 | 1615.8 ± 418.3 | 1244.3 ± 403.6 | 1.3 ± 8.1 | 522.5 ± 155 | 1303.3 ± 385.6 |
| 14 | 406.3 ± 121.6 | 1616 ± 491.7 | 1142.3 ± 247.2 | 6.6 ± 11.1 | 322.7 ± 94.1 | 1048.6 ± 215.6 |
| 15 | 446.8 ± 138.7 | 1700.8 ± 469.1 | 1306.3 ± 294.4 | 43 ± 24.5 | 421.2 ± 87.9 | 1001.5 ± 236.4 |
| 16 | 686.8 ± 268.8 | 1979.5 ± 541.7 | 1616.8 ± 411.8 | 2.4 ± 7.8 | 381.9 ± 116.4 | 1152.8 ± 352.7 |
| 17 | 375.8 ± 109.3 | 1378.6 ± 561.2 | 773.1 ± 210.3 | −1.4 ± 4.3 | 177.6 ± 93.7 | 691.7 ± 245 |
| 18 | 255.9 ± 99.7 | 1538.4 ± 498.1 | 498.7 ± 152.3 | −5.3 ± 3.3 | 26.2 ± 13.4 | 413.9 ± 164.8 |
| 19 | 133 ± 62.6 | 955.9 ± 456.8 | 491.1 ± 121.8 | −5.7 ± 4.1 | 50.3 ± 25.4 | 371.2 ± 123.7 |
| 20 | 163.7 ± 55.8 | 641.7 ± 313.5 | 357.9 ± 91.1 | 2.6 ± 7.5 | 41.4 ± 24.2 | 257.8 ± 68.9 |
| 21 | 319.9 ± 160.5 | 2017.1 ± 419.9 | 1204.8 ± 335.2 | −3.7 ± 5.1 | 268.1 ± 109.6 | 924.1 ± 301 |
| 22 | 244.7 ± 105.6 | 1370.9 ± 563.5 | 780.3 ± 390 | −3.6 ± 5.1 | 118.2 ± 68.1 | 473.3 ± 249.3 |
| 23 | 176.7 ± 81.8 | 1263.7 ± 527.3 | 838.6 ± 367.9 | −5.7 ± 4.1 | 73.6 ± 49 | 480.9 ± 163.9 |
| 24 | 236.5 ± 92 | 1324.7 ± 589.3 | 879.7 ± 321 | −0.4 ± 5.7 | 104 ± 53.1 | 498 ± 135.8 |

TABLE 28

Mean spot forming cells (SFC) per $10^6$ PBMCs for each epitope ± SEM for priming vaccination with VEE-MAG25mer srRNA-LNP2 (300 μg) (Group 2)

| | Antigen | | | | | |
|---|---|---|---|---|---|---|
| Wk | Env CL9 | Env TL9 | Gag CM9 | Gag LW9 | Pol SV9 | Tat TL8 |
| 4 | 46 ± 27.1 | 18.4 ± 6.8 | 58.3 ± 45.8 | 29.9 ± 20.8 | 4.9 ± 2.3 | 10.7 ± 4 |
| 5 | 85.4 ± 54 | 5.2 ± 5.8 | 52.4 ± 51.2 | 34.5 ± 35 | 11.8 ± 12.2 | 14.4 ± 7.9 |
| 7 | 18.6 ± 32.5 | 1.9 ± 1.7 | 59.4 ± 55.7 | 9.3 ± 10.7 | 3.3 ± 3 | 10.7 ± 6.1 |
| 8 | 36.6 ± 39.4 | 6.3 ± 3.9 | 48.7 ± 39.9 | 13.5 ± 8.8 | 3.8 ± 3.6 | 17.2 ± 9.7 |
| 10 | 69.1 ± 59.1 | 4.4 ± 1.9 | 39.3 ± 38 | 14.7 ± 10.8 | 4.4 ± 5.3 | 8.5 ± 5.3 |
| 11 | 43 ± 38.8 | 22.6 ± 21.1 | 30.2 ± 26.2 | 3.3 ± 2.2 | 5.8 ± 3.5 | 40.3 ± 25.5 |
| 13 | 120.4 ± 78.3 | 68.2 ± 43.9 | 54.2 ± 36.8 | 21.8 ± 7.4 | 17.7 ± 6.1 | 47.4 ± 27.3 |
| 14 | 76 ± 44.8 | 28 ± 19.5 | 65.9 ± 64.3 | −0.3 ± 1.3 | 2.5 ± 2 | 31.1 ± 26.5 |
| 15 | 58.9 ± 41.4 | 19.5 ± 15.1 | 55.4 ± 51 | 2.5 ± 2 | 5.5 ± 3.6 | 20.1 ± 15.7 |

TABLE 29

Mean spot forming cells (SFC) per $10^6$ PBMCs for each epitope ± SEM for priming vaccination with VEE-MAG25mer srRNA-LNP1 (300 μg) (Group 3)

| | Antigen | | | | | |
|---|---|---|---|---|---|---|
| Wk | Env CL9 | Env TL9 | Gag CM9 | Gag LW9 | Pol SV9 | Tat TL8 |
| 4 | 19.5 ± 8.7 | 13.3 ± 13.1 | 16.5 ± 15.3 | 10.5 ± 7.3 | 35.9 ± 24.8 | 92.9 ± 91.6 |
| 5 | 87.9 ± 43.9 | 12.7 ± 11.7 | 37.2 ± 31.9 | 21.1 ± 23.8 | 13.2 ± 13.7 | 12.6 ± 13.7 |
| 7 | 21.1 ± 13.3 | 48.8 ± 48.4 | 51.7 ± 39.5 | 9.1 ± 10.5 | 58.6 ± 55.8 | 159.4 ± 159 |
| 8 | 47.7 ± 21.7 | 66.4 ± 52.2 | 59.8 ± 57.4 | 49.4 ± 28 | 79.4 ± 63 | 133.8 ± 132.1 |
| 10 | 49 ± 30.2 | 42.2 ± 41.1 | 139.3 ± 139.3 | 51.6 ± 51.2 | 78.2 ± 75.8 | 131.7 ± 131.6 |
| 11 | 42 ± 26.8 | 20.9 ± 21.4 | 177.1 ± 162 | −6.3 ± 4.3 | 104.3 ± 104.1 | 231.5 ± 230.1 |
| 12 | 40.2 ± 19 | 20.3 ± 11.9 | 42.2 ± 46.7 | 3.7 ± 6.7 | 57 ± 44.7 | 70 ± 69.2 |
| 13 | 81.2 ± 48.9 | 38.2 ± 37.6 | 259.4 ± 222.2 | −4 ± 4.1 | 164.1 ± 159.3 | 347.3 ± 343.5 |
| 14 | 34.5 ± 31.8 | 5.3 ± 11.6 | 138.6 ± 137.3 | −4.7 ± 5.2 | 52.3 ± 52.9 | 142.6 ± 142.6 |
| 15 | 49 ± 24 | 6.7 ± 9.8 | 167.1 ± 163.8 | −6.4 ± 4.2 | 47.8 ± 42.3 | 116.6 ± 114.5 |

srRNA Dose Ranging Study

In one implementation of the present invention, an srRNA dose ranging study can be conducted in mamu A01 Indian rhesus macaques to identify which srRNA dose to progress to NHP immunogenicity studies. In one example, Mamu A01 Indian rhesus macaques can be administered with an srRNA vector encoding model antigens that includes multiple mamu A01 restricted epitopes by IM injection. In another example, an anti-CTLA-4 monoclonal antibody can be administered SC proximal to the site of IM vaccine injection to target the vaccine draining lymph node in one group of animals. PBMCs can be collected every 2 weeks after the initial vaccination for immune monitoring. The study arms are described in below (Table 30).

TABLE 30

Non-GLP RNA dose ranging study in Indian Rhesus Macaques

| Group | Prime | Boost 1 | Boost 2 |
|---|---|---|---|
| 1 | srRNA-LNP (Low Dose) | srRNA-LNP (Low Dose) | srRNA-LNP (Low Dose) |
| 2 | srRNA-LNP (Mid Dose) | srRNA-LNP (Mid Dose) | srRNA-LNP (Mid Dose) |
| 3 | srRNA-LNP (High Dose) | srRNA-LNP (High Dose) | srRNA-LNP (High Dose) |
| 4 | srRNA-LNP (High Dose) + anti-CTLA-4 | srRNA-LNP (High Dose) + anti-CTLA-4 | srRNA-LNP (High Dose) + anti-CTLA-4 |

* Dose range of srRNA to be determined with the high dose ≤300 μg.

Immunogenicity Study in Indian Rhesus Macaques

In one implementation of the present invention, vaccine studies can be conducted in mamu A01 Indian rhesus macaques to demonstrate immunogenicity. In one example, Mamu A01 Indian rhesus macaques can be administered an IM injection with a ChAdV and/or srRNA vector encoding model antigens that includes multiple mamu A01 restricted antigens. In another example, an anti-CTLA-4 monoclonal antibody will be administered SC proximal to the site of IM vaccine injection to some of the groups. PBMCs can be collected every 2 weeks after the initial vaccination for immune monitoring. The study arms are described in below (Table 31).

TABLE 31

Non-GLP immunogenicity study in Indian Rhesus Macaques

| Group | Prime | Boost 1 | Boost 2 |
|---|---|---|---|
| 1 | ChAdV | srRNA-LNP* | srRNA-LNP |
| 2 | srRNA-LNP | ChAdV | srRNA-LNP |
| 3 | srRNA-LNP | srRNA-LNP | ChAdV |
| 4 | srRNA-LNP + anti-CTLA-4 | srRNA-LNP + anti-CTLA-4 | srRNA-LNP + anti-CTLA-4 |
| 5 | ChAdV + anti-CTLA-4 | srRNA-LNP + anti-CTLA-4 | srRNA-LNP + anti-CTLA-4 |
| 6 | srRNA-LNP + anti-CTLA-4 | ChAdV + anti-CTLA-4 | srRNA-LNP + anti-CTLA-4 |

*srRNA dose to be determined based on srRNA dose range study.

XIX. Identification of MHC/Peptide Target-Reactive T Cells and TCRs

T cells can be isolated from blood, lymph nodes, or tumors of patients. T cells can be enriched for antigen-specific T cells, e.g., by sorting antigen-MHC tetramer binding cells or by sorting activated cells stimulated in an in vitro co-culture of T cells and antigen-pulsed antigen presenting cells. Various reagents are known in the art for antigen-specific T cell identification including antigen-loaded tetramers and other MHC-based reagents.

Antigen-relevant alpha-beta (or gamma-delta) TCR dimers can be identified by single cell sequencing of TCRs of antigen-specific T cells. Alternatively, bulk TCR sequencing of antigen-specific T cells can be performed and alpha-beta pairs with a high probability of matching can be determined using a TCR pairing method known in the art.

Alternatively or in addition, antigen-specific T cells can be obtained through in vitro priming of naïve T cells from healthy donors. T cells obtained from PBMCs, lymph nodes, or cord blood can be repeatedly stimulated by antigen-pulsed antigen presenting cells to prime differentiation of antigen-experienced T cells. TCRs can then be identified similarly as described above for antigen-specific T cells from patients.

Certain Sequences

Sequences for vectors, cassettes, and antibodies are shown below.

Tremelimumab VL (SEQ ID NO: 16)
PSSLSASVGDRVTITCRASQSINSYLDWYQQKPCKAPKLLIYAASSLQSGVPSRFSGSGSGTDF
TLTISSLQPEDFATYYCQQYYSTPFTFGPGTKVEIKRTVAAPSVFIFPPSDEQLKSGTASVVCLLNNFYPR
EAKV Tremelimumab VH (SEQ ID NO: 17)
GVVQPGRSLRLSCAASGFTFSSYGMHWVRQAPGKGLEWVAVIWYDGSNKYYADSVKGRFTI
SRDNSKNTLYLQMNSLRAEDTAVYYCARDPRGATLYYYYYGMDVWGQGTTVTVSSASTKGPSVFPL
APCSRSTSESTAALGCLVKDYFPEPVTVSWNSGALTSGVH Tremelimumab VH CDR1 (SEQ ID NO: 18)
GFTFSSYGMH Tremelimumab VH CDR2 (SEQ ID NO: 19)
VIWYDGSNKYYADSV Tremelimumab VH CDR3 (SEQ ID NO: 20)
DPRGATLYYYYYGMDV Tremelimumab VL CDR1 (SEQ ID NO: 21)
RASQSINSYLD Tremelimumab VL CDR2 (SEQ ID NO: 22)
AASSLQS Tremelimumab VL CDR3 (SEQ ID NO: 23)
QQYYSTPFT Durvalumab (MEDI4736) VL (SEQ ID NO: 24)
EIVLTQSPGTLSLSPGERATLSCRASQRVSSSYLAWYQQKPGQAPRLLIYDASSRATGIPDRFSGSGSGT
DFTLTISRLEPEDFAVYYCQQYGSLPWTFGQGTKVEIK MEDI4736 VH (SEQ ID NO: 25)
EVQLVESGGGLVQPGGSLRLSCAASGFTFSRYWMSWVRQAPGKGLEWVANIKQDGSEKYYVDSVKG
RFTISRDNAKNSLYLQMNSLRAEDTAVYYCAREGGWFGELAFDYWGQGTLVTVSS

MEDI4736 VH CDR1 (SEQ ID NO: 26)
RYWMS

MEDI4736 VH CDR2 (SEQ ID NO: 27)
NIKQDGSEKYYVDSVKG

MEDI4736 VH CDR3 (SEQ ID NO: 28)
EGGWFGELAFDY

MEDI4736 VL CDR1 (SEQ ID NO: 29)
RASQRVSSSYLA

MEDI4736 VL CDR2 (SEQ ID NO: 30)
DASSRAT

MEDI4736 VL CDR3 (SEQ ID NO: 31)

-continued

QQYGSLPWT

UbA76-25 merPDTT nucleotide (SEQ ID NO: 32)
GCCCGGGCATTTAAATGCGATCGCATCGATtacgactctagaatagtctagtccgcaggccaccatgCAGATCT
TCGTGAAGACCCTGACCGGCAAGACCATCACCCTAGAGGTGGAGCCCAGTGACACCATCGAGAA
CGTGAAGGCCAAGATCCAGGATAAAGAGGGCATCCCCCCTGACCAGCAGAGGCTGATCTTTGCCG
GCAAGCAGCTGGAAGATGGCCGCACCCTCTCTGATTACAACATCCAGAAGGAGTCAACCCTGCAC
CTGGTCCTTCGCCTGAGAGGTGcCatgtttcaggcgctgagcgaaggctgcaccccgtatgatattaaccagatgctgaacgtgctgggcga
tcatcaggtctcaggccttgagcagcttgagagtataatcaactttgaaaaactgactgaatggaccagttctaatgttatgCCTATCCTGTCTCCTCT
GACAAAGGGCATCCTGGGCTTCGTGTTTACCCTGACCGTGCCTTCTGAGAGAGGACTTagctgcattagc
gaagcggatgcgaccaccccggaaagcgcgaacctgggcgaagaaattctgagccagctgtatctttggccaagggtgacctaccattcccctagttatgcttac
caccaatttgaaagacgagccaaatataaaagaCACTTCCCCGGCTTTGGCCAGAGCCTGCTGTTTGGCTACCCTGTGT
ACGTGTTCGGCGATTGCGTGCAGGGCGATtgggatgcgattcgctttcgctattgcgcgccgccgggctatgcgctgctgcgctgcaa
cgataccaactatagcgctctgctggctgtgggggccctagaaggacccaggaatcaggactggcttggtgtcccaagacaacttgtaactCGGATGCA
GGCTATTCAGAATGCCGGCCTGTGTACCCTGGTGGCCATGCTGGAAGAGACAATCTTCTGGCTGC
AAgcgtttctgatggcgctgaccgatagcggcccgaaaaccaacattattgtggatagccagtatgtgatgggcattagcaaaccgagctttcaggaatttgtgg
attgggaaaacgtgagcccggaactgaacagcaccgatcagccgtttTGGCAAGCCGGAATCCTGGCCAGAAATCTGGTGCC
TATGGTGGCCACAGTGCAGGGCCAGAACCTGAAGTACCAGggtcagtcactagtcatctctgcttctatcattgtcttcaacct
gCtggaactggaaggtgattatcgagatgatggcaacgtgtgggtgcataccccgctgagcccgcgcaccctgaacgcgtgggtgaaagcggtggaagaaaa
aaaaggtattccagttcacctagagctggccagtatgaccaacaTggagctcatgagcagtattgtgcatcagcaggtcAGAACATACGGCCCCG
TGTTCATGTGTCTCGGCGGACTGCTTACAATGGTGGCTGGTGCTGTGTGGCTGACAGTGcgagtgctcga
gctgttccgggccgcgcagctggccaacgacgtggtcctccagatcatggagctttgtggtgcagcgtttcgccaggtgtgccataccaccgtgccgtggccga
acgcgagcctgaccccgaaatggaacaacgaaaccacccagccccagatcgccaactgcagcgtgtatgactttttgtgtggctccattattattctgttcgagac
acactttggccaagggtgacctaccatatgaacaaatatgcgtatcatatgctggaaagacgagccaaatataaaagaGGACCAGGACCTGGCGC
TAAATTTGTGGCCGCCTGGACACTGAAAGCCGCTGCTGGTCCTGGACCTGGCCAGTACATCAAGG
CCAACAGCAAGTTCATCGGCATCACCGAACTCGGACCCGGACCAGGCTGATGATTTCGAAATTTA
AATAAGCTTGCGGCCGCTAGGGATAACAGGGTAATtatcacgcccaaacatttacagccgcggtgtcaaaaaccgcgtgg UbA76-25 merPDTT polypeptide (SEQ ID NO: 33)
MQIFVKTLTGKTITLEVEPSDTIENVKAKIQDKEGIPPDQQRLIFAGKQLEDGRTLSDYNIQKES
TLHLVLRLRGAMFQALSEGCTPYDINQMLNVLGDHQVSGLEQLESIINFEKLTEWTSSNVMPILSPLTK
GILGFVFTLTVPSERGLSCISEADATTPESANLGEEILSQLYLWPRVTYHSPSYAYHQFERRAKYKRHFP
GFGQSLLFGYPVYVFGDCVQGDWDAIRFRYCAPPGYALLRCNDTNYSALLAVGALEGPRNQDWLGV
PRQLVTRMQAIQNAGLCTLVAMLEETIFWLQAFLMALTDSGPKTNIIVDSQYVMGISKPSFQEFVDWE
NVSPELNSTDQPFWQAGILARNLVPMVATVQGQNLKYQGQSLVISASIIVFNLLELEGDYRDDGNVW
VHTPLSPRTLNAWVKAVEEKKGIPVHLELASMTNMELMSSIVHQQVRTYGPVFMCLGGLLTMVAGA
VWLTVRVLELFRAAQLANDVVLQIMELCGAAFRQVCHTTVPWPNASLTPKWNNETTQPQIANCSVY
DFFVWLHYYSVRDTLWPRVTYHMNKYAYHMLERRAKYKRGPGPGAKFVAAWTLKAAAGPGPGQY
IKANSKFIGITELGPGPG MAG-25 merPDTT nucleotide (SEQ ID NO: 34)
ATGGCCGGGATGTTCCAGGCACTGTCCGAAGGCTGCACACCCTATGATATTAACCAGATGCTGAA
TGTCCTGGGAGACCACCAGGTCTCTGGCCTGGAGCAGCTGGAGAGCATCATCAACTTCGAGAAGC
TGACCGAGTGGACAAGCTCCAATGTGATGCCTATCCTGTCCCCACTGACCAAGGGCATCCTGGGC
TTCGTGTTTACCCTGACAGTGCCTTCTGAGCGGGGCCTGTCTTGCATCAGCGAGGCAGACGCAACC
ACACCAGAGTCCGCCAATCTGGGCGAGGAGATCCTGTCTCAGCTGTACCTGTGGCCCCGGGTGAC
ATATCACTCCCCTTCTTACGCCTATCACCAGTTCGAGCGGAGAGCCAAGTACAAGAGACACTTCCC
AGGCTTTGGCCAGTCTCTGCTGTTCGGCTACCCCGTGTACGTGTTCGGCGATTGCGTGCAGGGCGA
CTGGGATGCCATCCGGTTTAGATACTGCGCACCACCTGGATATGCACTGCTGAGGTGTAACGACA
CCAATTATTCCCCCCTGCTGGCAGTGGGCGCCCTGGAGGGCCCTCGCAATCAGGATTGGCTGGGC
GTGCCAAGGCAGCTGGTGACACGCATGCAGGCCATCCAGAACGCAGGCCTGTGCACCCTGGTGGC
AATGCTGGAGGAGACAATCTTCTGGCTGCAGGCCTTTCTGATGGCCCTGACCGACAGCGGCCCCA
AGACAAACATCATCGTGGATTCCCAGTACGTGATGGGCATCTCCAAGCCTTCTTTCCAGGAGTTTG
TGGACTGGGAGAACCTGAGCCCAGAGCTGAATTCCACCGATCAGCCATTCTGGCAGGCAGGAATC -continued CTGGCAAGGAACCTGGTGCCTATGGTGGCCACAGTGCAGGGCCAGAATCTGAAGTACCAGGGCC
AGAGCCTGGTCATCAGCGCCTCCATCATCGTGTTTAACCTGCTGGAGCTGGAGGGCGACTATCGG
GACGATGGCAACGTGTGGGTGCACACCCCACTGAGCCCCAGAACACTGAACGCCTGGGTGAAGG
CCGTGGAGGAGAAGAAGGGCATCCCAGTGCACCTGGAGCTGGCCTCCATGACCAATATGGAGCT
GATGTCTAGCATCGTGCACCAGCAGGTGAGGACATACGGACCCGTGTTCATGTGCCTGGGAGGCC
TGCTGACCATGGTGGCAGGAGCCGTGTGGCTGACAGTGCGGGTGCTGGAGCTGTTCAGAGCCGCC
CAGCTGGCCAACGATGTGGTGCTGCAGATCATGGAGCTGTGCGGAGCAGCCTTTCGCCAGGTGTG
CCACACCACAGTGCCATGGCCCAATGCCTCCCTGACCCCCAAGTQGAACAATGAGACAACACAGC
CTCAGATCGCCAACTGTAGCGTGTACGACTTCTTCGTGTGGCTGCACTACTATAGCGTGAGGGATA
CCCTGTGGCCCCCCGTGACATACCACATGAATAAGTACGCCTATCACATGCTGGAGAGGCGCGCC
AAGTATAAGAGAGGCCCTGGCCCAGGCGCAAAGTTTGTGGCAGCATGGACCCTGAAGGCCGCCG
CCGGCCCCGGCCCCGGCCAGTATATCAAGGCTAACAGTAAGTTCATTGGAATCACAGAGCTGGGA
CCCGGACCTGGA MAG-25 merPDTT polypeptide (SEQ ID NO: 35)
MAGMFQALSEGCTPYDINQMLNVLGDHQVSGLEQLESIINFEKLTEWTSSNVMPILSPLTKGIL
GFVFTLTVPSERGLSCISEADATTPESANLGEEILSQLYLWPRVTYHSPSYAYHQFERRAKYKRHFPGF
GQSLLFGYPVYVFGDCVQGDWDAIRFRYCAPPGYALLRCNDTNYSALLAVGALEGPRNQDWLGVPR
QLVTRMQAIQNAGLCTLVAMLEETIFWLQAFLMALTDSGPKTNIIVDSQYVMGISKPSFQEFVDWENV
SPELNSTDQPFWQAGILARNLVPMVATVQGQNLKYQGQSLVISASIIVFNLLELEGDYRDDGNVWVHT
PLSPRTLNAWVKAVEEKKGIPVHLELASMTNMELMSSIVHQQVRTYGPVFMCLGGLLTMVAGAVWL
TVRVLELFRAAQLANDVVLQIMELCGAAFRQVCHTTVPWPNASLTPKWNNETTQPQIANCSVYDFFV
WLHYYSVRDTLWPRVTYHMNKYAYHMLERRAKYKRGPGPGAKFVAAWTLKAAAGPGPGQYIKAN
SKFIGITELGPGPG Ub7625 merPDTT_NoSFL nucleotide (SEQ ID NO: 36)
GCCCGGGCATTTAAATGCGATCGCATCGATtacgactctagaatagtctagtccgcaggccaccatgCAGATCT
TCGTGAAGACCCTGACCGGCAAGACCATCACCCTAGAGGTGGAGCCCAGTGACACCATCGAGAA
CGTGAAGGCCAAGATCCAGGATAAAGAGGGCATCCCCCCTGACCAGCAGAGGCTGATCTTTGCCG
GCAAGCAGCTGGAAGATGGCCGCACCCTCTCTGATTACAACATCCAGAAGGAGTCAACCCTGCAC
CTGGTCCTTCGCCTGAGAGGTGcCatgtttcaggcgctgagcgaaggctgcaccccgtatgatattaaccagatgctgaacgtgctgggcga
tcatcagtttaagcacatcaaagcctttgaccggacatttgctaacaacccaggtcccatggttgtgtttgccacacctgggCCTATCCTGTCTCCTCT
GACAAAGGGCATCCTGGGCTTCGTGTTTACCCTGACCGTGCCTTCTGAGAGAGGACTTagctgcattagc
gaagcggatgcgaccaccccggaaagcgcgaacctgggcgaagaaattctgagccagctgtatctttggccaagggtgacctaccattcccctagttatgcttac
caccaatttgaaagacgagccaaatataaaagaCACTTCCCCGGCTTTGGCCAGAGCCTGCTGTTTGGCTACCCTGTGT
ACGTGTTCGGCGATTGCGTGCAGGGCGATtgggatgcgattcgctttcgctattgcgcgccgccgggctatgcgctgctgcgctgcaa
cgataccaactatagcgctctgctggctgtgggggccctagaaggacccaggaatcaggactggcttggtgtcccaagacaacttgtaactCGGATGCA
GGCTATTCAGAATGCCGGCCTGTGTACCCTGGTGGCCATGCTGGAAGAGACAATCTTCTGGCTGC
AAgcgtttctgatggcgctgaccgatagcggcccgaaaaccaacattattgtggatagccagtatgtgatgggcattagcaaaccgagctttcaggaatttgtgg
attgggaaaacgtgagcccggaactgaacagcaccgatcagccgtttTGGCAAGCCGGAATCCTGGCCAGAAATCTGGTGCC
TATGGTGGCCACAGTGCAGGGCCAGAACCTGAAGTACCAGggtcagtcactagtcatctctgcttctatcattgtcttcaacct
gCtggaactggaaggtgattatcgagatgatggcaacgtgtgggtgcataccccgctgagcccgcgcaccctgaacgcgtgggtgaaagcggtggaagaaaa
aaaaggtattccagttcacctagagctggccagtatgaccaacaTggagctcatgagcagtattgtgcatcagcaggtcAGAACATACGGCCCCG
TGTTCATGTGTCTCGGCGGACTGCTTACAATGGTGGCTGGTGCTGTGTGGCTGACAGTGcgagtgctcga
gctgttccgggccgcgcagctggccaacgacgtggtcctccagatcatggagctttgtggtgcagcgtttcgccaggtgtgccataccaccgtgccgtggccga
acgcgagcctgaccccgaaatggaacaacgaaaccacccagccccagatcgccaactgcagcgtgtatgactttttttgtgtggctccattattattctgttcgagac
acactttggccaagggtgacctaccatatgaacaaatatgcgtatcatatgctggaaagacgagccaaatataaaagaGGACCAGGACCTGGCGC
TAAATTTGTGGCCGCCTGGACACTGAAAGCCGCTGCTGGTCCTGGACCTGGCCAGTACATCAAGG
CCAACAGCAAGTTCATCGGCATCACCGAACTCGGACCCGGACCAGGCTGATGATTTCGAAATTTA
AATAAGCTTGCGGCCGCTAGGGATAACAGGGTAATtatcacgcccaaacatttacagccgcggtgtcaaaaaccgcgtgg Ub7625 merPDTT_NoSFL polypeptide (SEQ ID NO: 37)
MQIFVKTLTGKTITLEVEPSDTIENVKAKIQDKEGIPPDQQRLIFAGKQLEDGRTLSDYNIQKES
TLHLVLRLRGAMFQALSEGCTPYDINQMLNVLGDHQFKHIKAFDRTFANNPGPMVVFATPGPILSPLT -continued KGILGFVFTLTVPSERGLSCISEADATTPESANLGEEILSQLYLWPRVTYHSPSYAYHQFERRAKYKRHF
PGFGQSLLFGYPVYVFGDCVQGDWDAIRFRYCAPPGYALLRCNDTNYSALLAVGALEGPRNQDWLG
VPRQLVTRMQAIQNAGLCTLVAMLEETIFWLQAFLMALTDSGPKTNIIVDSQYVMGISKPSFQEFVDW
ENVSPELNSTDQPFWQAGILARNLVPMVATVQGQNLKYQGQSLVISASIIVFNLLELEGDYRDDGNVW
VHTPLSPRTLNAWVKAVEEKKGIPVHLELASMTNMELMSSIVHQQVRTYGPVFMCLGGLLTMVAGA
VWLTVRVLELFRAAQLANDVVLQIMELCGAAFRQVCHTTVPWPNASLTPKWNNETTQPQIANCSVY
DFFVWLHYYSVRDTLWPRVTYHMNKYAYHMLERRAKYKRGPGPGAKFVAAWTLKAAAGPGPGQY
IKANSKFIGITELGPGPG ChAdV68.5WTnt.MAG25 mer (SEQ ID NO: 2); AC_000011.1 with El (nt 577 to 3403) and E3 (nt 27,125-31,825) sequences deleted; corresponding ATCC VR-594 nucleotides substituted at five positions; model neoantigen cassette under the control of the CMV promoter/enhancer inserted in place of deleted E1; SV40 polyA 3' of cassette CCATCTTCAATAATATACCTCAAACTTTTTGTGCGCGTTAATATGCAAATGAGGCGTTTGA
ATTTGGGGAGGAAGGGCGGTGATTGGTCGAGGGATGAGCGACCGTTAGGGGCGGGGCGAGTGAC
GTTTTGATGACGTGGTTGCGAGGAGGAGCCAGTTTGCAAGTTCTCGTGGGAAAAGTGACGTCAAA
CGAGGTGTGGTTTGAACACGGAAATACTCAATTTTCCCGCGCTCTCTGACAGGAAATGAGGTGTTT
CTGGGCGGATGCAAGTGAAAACGGGCCATTTTCGCGCGAAAACTGAATGAGGAAGTGAAAATCT
GAGTAATTTCGCGTTTATGGCAGGGAGGAGTATTTGCCGAGGGCCGAGTAGACTTTGACCGATTA
CGTGGGGGTTTCGATTACCGTGTTTTTCACCTAAATTTCCGCGTACGGTGTCAAAGTCCGGTGTTTT
TACGTAGGTGTCAGCTGATCGCCAGGGTATTTAAACCTGCGCTCTCCAGTCAAGAGGCCACTCTTG
AGTGCCAGCGAGAAGAGTTTTCTCCTCCGCGCCGCGAGTCAGATCTACACTTTGAAAGTAGGGAT
AACAGGGTAATgacattgattattgactagttGttaaTAGTAATCAATTACGGGGTCATTAGTTCATAGCCCATAT
ATGGAGTTCCGCGTTACATAACTTACGGTAAATGGCCCCCCTGGCTGACCGCCCAACGACCCCCG
CCCATTGACGTCAATAATGACGTATGTTCCCATAGTAACGCCAATAGGGACTTTCCATTGACGTCA
ATGGGTGGAGTATTTACGGTAAACTGCCCACTTGGCAGTACATCAAGTGTATCATATGCCAAGTC
CGCCCCCTATTGACGTCAATGACGGTAAATGGCCCGCCTGGCATTATGCCCAGTACATGACCTTAC
GGGACTTTCCTACTTGGCAGTACATCTACGTATTAGTCATCGCTATTACCATGgTGATGCGGTTTTG
GCAGTACACCAATGGGCGTGGATAGCGGTTTGACTCACGGGGATTTCCAAGTCTCCACCCCATTG
ACGTCAATGGGAGTTTGTTTTGGCACCAAAATCAACGGGACTTTCCAAAATGTCGTAATAACCCC
GCCCCGTTGACGCAAATGGGCGGTAGGCGTGTACGGTGGGAGGTCTATATAAGCAGAgcTCGTTTA
GTGAACCGTCAGATCGCCTGGAACGCCATCCACGCTGTTTTGACCTCCATAGAAGACAGCGATCG
CGccaccATGGCCGGGATGTTCCAGGCACTGTCCGAAGGCTGCACACCCTATGATATTAACCAGATG
CTGAATGTCCTGGGAGACCACCAGGTCTCTGGCCTGGAGCAGCTGGAGAGCATCATCAACTTCGA
GAAGCTGACCGAGTGGACAAGCTCCAATGTGATGCCTATCCTGTCCCCACTGACCAAGGGCATCC
TGGGCTTCGTGTTTACCCTGACAGTGCCTTCTGAGCGGGGCCTGTCTTGCATCAGCGAGGCAGACG
CAACCACACCAGAGTCCGCCAATCTGGGCGAGGAGATCCTGTCTCAGCTGTACCTGTGGCCCCGG
GTGACATATCACTCCCCTTCTTACGCCTATCACCAGTTCGAGCGGAGAGCCAAGTACAAGAGACA
CTTCCCAGGCTTTGGCCAGTCTCTGCTGTTCGGCTACCCCGTGTACGTGTTCGGCGATTGCGTGCA
GGGCGACTGGGATGCCATCCGGTTTAGATACTGCGCACCACCTGGATATGCACTGCTGAGGTGTA
ACGACACCAATTATTCCGCCCTGCTGGCAGTGGGCGCCCTGGAGGGCCCTCGCAATCAGGATTGG
CTGGGCGTGCCAAGGCAGCTGGTGACACGCATGCAGGCCATCCAGAACGCAGGCCTGTGCACCCT
GGTGGCAATGCTGGAGGAGACAATCTTCTGGCTGCAGGCCTTTCTGATGGCCCTGACCGACAGCG
GCCCCAAGACAAACATCATCGTGGATTCCCAGTACGTGATGGGCATCTCCAAGCCTTCTTTCCAGG
AGTTTGTGGACTGGGAGAACGTGAGCCCAGAGCTGAATTCCACCGATCAGCCATTCTGGCAGGCA
GGAATCCTGGCAAGGAACCTGGTGCCTATGGTGGCCACAGTGCAGGGCCAGAATCTGAAGTACCA
GGGCCAGAGCCTGGTCATCAGCGCCTCCATCATCGTGTTTAACCTGCTGGAGCTGGAGGGCGACT
ATCGGGACGATGGCAACGTGTGGGTGCACACCCCACTGAGCCCCAGAACACTGAACGCCTGGGTG
AAGGCCGTGGAGGAGAAGAAGGGCATCCCAGTGCACCTGGAGCTGGCCTCCATGACCAATATGG
AGCTGATGTCTAGCATCGTGCACCAGCAGGTGAGGACATACGGACCCGTGTTCATGTGCCTGGGA
GGCCTGCTGACCATGGTGGCAGGAGCCGTGTGGCTGACAGTGCGGGTGCTGGAGCTGTTCAGAGC
CGCCCAGCTGGCCAACGATGTGGTGCTGCAGATCATGGAGCTGTGCGGAGCAGCCTTTCGCCAGG
TGTGCCACACCACAGTGCCATGGCCCAATGCCTCCCTGACCCCCAAGTGGAACAATGAGACAACA
CAGCCTCAGATCGCCAACTGTAGCGTGTACGACTTCTTCGTGTGGCTGCACTACTATAGCGTGAGG -continued GATACCCTGTGGCCCCGCGTGACATACCACATGAATAAGTACGCCTATCACATGCTGGAGAGGCG
CGCCAAGTATAAGAGAGGCCCTGGCCCAGGCGCAAAGTTTGTGGCAGCATGGACCCTGAAGGCC
GCCGCCGGCCCCGGCCCCGGCCAGTATATCAAGGCTAACAGTAAGTTCATTGGAATCACAGAGCT
GGGACCCGGACCTGGATAATGAGTTTAAACTCCCATTTAAATGTGAGGGTTAATGCTTCGAGCAG
ACATGATAAGATACATTGATGAGTTTGGACAAACCACAACTAGAATGCAGTGAAAAAAATGCTTT
ATTTGTGAAATTTGTGATGCTATTGCTTTATTTGTAACCATTATAAGCTGCAATAAACAAGTTAAC
AACAACAATTGCATTCATTTTATGTTTCAGGTTCAGGGGGAGATGTGGGAGGTTTTTTAAAGCAAG
TAAAACCTCTACAAATGTGGTAAAATAACTATAACGGTCCTAAGGTAGCGAGTGAGTAGTGTTCT
GGGGCGGGGGAGGACCTGCATGAGGGCCAGAATAACTGAAATCTGTGCTTTTCTGTGTGTTGCAG
CAGCATGAGCGGAAGCGGCTCCTTTGAGGGAGGGGTATTCAGCCCTTATCTGACGGGGCGTCTCC
CCTCCTGGGCGGGAGTGCGTCAGAATGTGATGGGATCCACGGTGGACGGCCGGCCCGTGCAGCCC
GCGAACTCTTCAACCCTGACCTATGCAACCCTGAGCTCTTCGTCGTTGGACGCAGCTGCCGCCGCA
GCTGCTGCATCTGCCGCCAGCGCCGTGCGCGGAATGGCCATGGGCGCCGGCTACTACGGCACTCT
GGTGGCCAACTCGAGTTCCACCAATAATCCCGCCAGCCTGAACGAGGAGAAGCTGTTGCTGCTGA
TGGCCCAGCTCGAGGCCTTGACCCAGCGCCTGGGCGAGCTGACCCAGCAGGTGGCTCAGCTGCAG
GAGCAGACGCGGGCCGCGGTTGCCACGGTGAAATCCAAATAAAAAATGAATCAATAAATAAACG
GAGACGGTTGTTGATTTTAACACAGAGTCTGAATCTTTATTTGATTTTTCGCGCGCGGTAGGCCCT
GGACCACCGGTCTCGATCATTGAGCACCCGGTGGATCTTTTCCAGGACCCGGTAGAGGTGGGCTT
GGATGTTGAGGTACATGGGCATGAGCCCGTCCCGGGGGTGGAGGTAGCTCCATTGCAGGGCCTCG
TGCTCGGGGGTGGTGTTGTAAATCACCCAGTCATAGCAGGGGCGCAGGGCATGGTGTTGCACAAT
ATCTTTGAGGAGGAGACTGATGGCCACGGGCAGCCCTTTGGTGTAGGTGTTTACAAATCTGTTGA
GCTGGGAGGGATGCATGCGGGGGGAGATGAGGTGCATCTTGGCCTGGATCTTGAGATTGGCGATG
TTACCGCCCAGATCCCGCCTGGGGTTCATGTTGTGCAGGACCACCAGCACGGTGTATCCGGTGCA
CTTGGGGAATTTATCATGCAACTTGGAAGGGAAGGCGTGAAAGAATTTGGCGACGCCTTTGTGCC
CGCCCAGGTTTTCCATGCACTCATCCATGATGATGGCGATGGGCCCGTGGGGGGGGCCTGGGCA
AAGACGTTTCGGGGGTCGGACACATCATAGTTGTGGTCCTGGGTGAGGTCATCATAGGCCATTTT
AATGAATTTGGGGCGGAGGGTGCCGGACTGGGGGACAAAGGTACCCTCGATCCCGGGGGCGTAG
TTCCCCTCACAGATCTGCATCTCCCAGGCTTTGAGCTCGGAGGGGGGGATCATGTCCACCTGCGGG
GCGATAAAGAACACGGTTTCCGGGGCGGGGGAGATGAGCTGGGCCGAAAGCAAGTTCCGGAGCA
GCTGGGACTTGCCGCAGCCGGTGGGGCCGTAGATGACCCCGATGACCGGCTGCAGGTGGTAGTTG
AGGGAGAGACAGCTGCCGTCCTCCCGGAGGAGGGGGGCCACCTCGTTCATCATCTCGCGCACGTG
CATGTTCTCGCCCACCAGTTCCGCCAGGAGGCGCTCTCCCCCCAGGGATAGGAGCTCCTGGAGCG
AGGCGAAGTTTTTCAGCGGCTTGAGTCCGTCGGCCATGGGCATTTTGGAGAGGGTTTGTTGCAAG
AGTTCCAGGCGGTCCCAGAGCTCGGTGATGTGCTCTACGGCATCTCGATCCAGCAGACCTCCTCGT
TTCGCGGGTTGGGACGGCTGCGGGAGTAGGGCACCAGACGATGGGCGTCCAGCGCAGCCAGGGT
CCGGTCCTTCCAGGGTCGCAGCGTCCGCGTCAGGGTGGTCTCCGTCACGGTGAAGGGGTGCGCGC
CGGGCTGGGCGCTTGCGAGGGTGCGCTTCAGGCTCATCCGGCTGGTCGAAAACCGCTCCCGATCG
GCGCCCTGCGCGTCGGCCAGGTAGCAATTGACCATGAGTTCGTAGTTGAGCGCCTCGGCCGCGTG
GCCTTTGGCGCGGAGCTTACCTTTGGAAGTCTGCCCGCAGGCGGGACAGAGGAGGGACTTGAGGG
CGTAGAGCTTGGGGGCGAGGAAGACGGACTCGGGGGCGTAGGCGTCCGCGCCGCAGTGGGCGCA
GACGGTCTCGCACTCCACGAGCCAGGTGAGGTCGGGCTGGTCGGGGTCAAAAACCAGTTTCCCGC
CGTTCTTTTTGATGCCTTTCTTACCTTTGGTCTCCATGAGCTCGTGTCCCCGCTGGGTGACAAAGAG
GCTGTCCGTGTCCCCGTAGACCGACTTTATGGGCCGGTCCTCGAGCGGTGTGCCGCGGTCCTCCTC
GTAGAGGAACCCCGCCCACTCCGAGACGAAAGCCCGGGTCCAGGCCAGCACGAAGGAGGCCACG
TGGGACGGGTAGCGGTCGTTGTCCACCAGCGGGTCCACCTTTTCCAGGGTATGCAAACACATGTC
CCCCTCGTCCACATCCAGGAAGGTGATTGGCTTGTAAGTGTAGGCCACGTGACCGGGGGTCCCGG
CCGGGGGGGTATAAAAGGGTGCGGGTCCCTGCTCGTCCTCACTGTCTTCCGGATCGCTGTCCAGG
AGCGCCAGCTGTTGGGGTAGGTATTCCCTCTCGAAGGCGGGCATGACCTCGGCACTCAGGTTGTC
AGTTTCTAGAAACGAGGAGGATTTGATATTGACGGTGCCGGCGGAGATGCCTTTCAAGAGCCCCT
CGTCCATCTGGTCAGAAAAGACGATCTTTTTGTTGTCGAGCTTGGTGGCGAAGGAGCCGTAGAGG
GCGTTGGAGAGGAGCTTGGCGATGGAGCGCATGGTCTGGTTTTTTTCCTTGTCGGCGCGCTCCTTG
GCGGCGATGTTGAGCTGCACGTACTCGCGCGCCACGCACTTCCATTCGGGGAAGACGGTGGTCAG
CTCGTCGGGCACGATTCTGACCTGCCAGCCCCGATTATGCAGGGTGATGAGGTCCACACTGGTGG
CCACCTCGCCGCGCAGGGGCTCATTAGTCCAGCAGAGGCGTCCGCCCTTGCGCGAGCAGAAGGGG -continued GGCAGGGGGTCCAGCATGACCTCGTCGGGGGGGTCGGCATCGATGGTGAAGATGCCGGGCAGGA
GGTCGGGGTCAAAGTAGCTGATGGAAGTGGCCAGATCGTCCAGGGCAGCTTGCCATTCGCGCACG
GCCAGCGCGCGCTCGTAGGGACTGAGGGGCGTGCCCCAGGGCATGGGATGGGTAAGCGCGGAGG
CGTACATGCCGCAGATGTCGTAGACGTAGAGGGGCTCCTCGAGGATGCCGATGTAGGTGGGGTAG
CAGCGCCCCCCGCGGATGCTGGCGCGCACGTAGTCATACAGCTCGTGCGAGGGGGCGAGGAGCC
CCGGGCCCAGGTTGGTGCGACTGGGCTTTTCGGCGCGGTAGACGATCTGGCGGAAAATGGCATGC
GAGTTGGAGGAGATGGTGGGCCTTTGGAAGATGTTGAAGTGGGCGTGGGGCAGTCCGACCGAGT
CGCGGATGAAGTGGGCGTAGGAGTCTTGCAGCTTGGCGACGAGCTCGGCGGTGACTAGGACGTCC
AGAGCGCAGTAGTCGAGGGTCTCCTGGATGATGTCATACTTGAGCTGTCCCTTTTGTTTCCACAGC
TCGCGGTTGAGAAGGAACTCTTCGCGGTCCTTCCAGTACTCTTCGAGGGGGAACCCGTCCTGATCT
GCACGGTAAGAGCCTAGCATGTAGAACTGGTTGACGGCCTTGTAGGCGCAGCAGCCCTTCTCCAC
GGGGAGGGCGTAGGCCTGGGCGGCCTTGCGCAGGGAGGTGTGCGTGAGGGCGAAAGTGTCCCTG
ACCATGACCTTGAGGAACTGGTGCTTGAAGTCGATATCGTCGCAGCCCCCCTGCTCCCAGAGCTG
GAAGTCCGTGCGCTTCTTGTAGGCGGGGTTGGGCAAAGCGAAAGTAACATCGTTGAAGAGGATCT
TGCCCGCGCGGGGCATAAAGTTGCGAGTGATGCGGAAAGGTTGGGGCACCTCGGCCCGGTTGTTG
ATGACCTGGGCGGCGAGCACGATCTCGTCGAAGCCGTTGATGTTGTGGCCCACGATGTAGAGTTC
CACGAATCGCGGACGGCCCTTGACGTGGGGCAGTTTCTTGAGCTCCTCGTAGGTGAGCTCGTCGG
GGTCGCTGAGCCCGTGCTGCTCGAGCGCCCAGTCGGCGAGATGGGGGTTGGCGCGGAGGAAGGA
AGTCCAGAGATCCACGGCCAGGGCGGTTTGCAGACGGTCCCGGTACTGACGGAACTGCTGCCCGA
CGGCCATTTTTTCGGGGGTGACGCAGTAGAAGGTGCGGGGGTCCCCGTGCCAGCGATCCCATTTG
AGCTGGAGGGCGAGATCGAGGGCGAGCTCGACGAGCCGGTCGTCCCCGGAGAGTTTCATGACCA
GCATGAAGGGGACGAGCTGCTTGCCGAAGGACCCCATCCAGGTGTAGGTTTCCACATCGTAGGTG
AGGAAGAGCCTTTCGGTGCGAGGATGCGAGCCGATGGGGAAGAACTGGATCTCCTGCCACCAATT
GGAGGAATGGCTGTTGATGTGATGGAAGTAGAAATGCCGACGGCGCGCCGAACACTCGTGCTTGT
GTTTATACAAGCGGCCACAGTGCTCGCAACGCTGCACGGGATGCACGTGCTGCACGAGCTGTACC
TGAGTTCCTTTGACGAGGAATTTCAGTGGGAAGTGGAGTCGTGGCGCCTGCATCTCGTGCTGTACT
ACGTCGTGGTGGTCGGCCTGGCCCTCTTCTGCCTCGATGGTGGTCATGCTGACGAGCCCGCGCGGG
AGGCAGGTCCAGACCTCGGCGCGAGCGGGTCGGAGAGCGAGGACGAGGGCGCGCAGGCCGGAG
CTGTCCAGGGTCCTGAGACGCTGCGGAGTCAGGTCAGTGGGCAGCGGCGGCGCGCGGTTGACTTG
CAGGAGTTTTTCCAGGGCGCGCGGGAGGTCCAGATGGTACTTGATCTCCACCGCGCCATTGGTGG
CGACGTCGATGGCTTGCAGGGTCCCGTGCCCCTGGGGTGTGACCACCGTCCCCCGTTTCTTCTTGG
GCGGCTGGGGCGACGGGGGGGGTGCCTCTTCCATGGTTAGAAGCGGCGGCGAGGACGCGCGCCG
GGCGGCAGGGGCGGCTCGGGGCCCGGAGGCAGGGGCGGCAGGGGCACGTCGGCGCCGCGCGCG
GGTAGGTTCTGGTACTGCGCCCGGAGAAGACTGGCGTGAGCGACGACGCGACGGTTGACGTCCTG
GATCTGACGCCTCTGGGTGAAGGCCACGGGACCCGTGAGTTTGAACCTGAAAGAGAGTTCGACAG
AATCAATCTCGGTATCGTTGACGGCGGCCTGCCGCAGGATCTCTTGCACGTCGCCCGAGTTGTCCT
GGTAGGCGATCTCGGTCATGAACTGCTCGATCTCCTCCTCTTGAAGGTCTCCGCGGCCGGCGCGCT
CCACGGTGGCCGCGAGGTCGTTGGAGATGCGGCCCATGAGCTGCGAGAAGGCGTTCATGCCCGCC
TCGTTCCAGACGCGGCTGTAGACCACGACGCCCTCGGGATCGC&GGCGCGCATGACCACCTGGGC
GAGGTTGAGCTCCACGTGGCGCGTGAAGACCGCGTAGTTGCAGAGGCGCTGGTAGAGGTAGTTGA
GCGTGGTGGCGATGTGCTCGGTGACGAAGAAATACATGATCCAGCGGCGGAGCGGCATCTCGCTG
ACGTCGCCCAGCGCCTCCAAACGTTCCATGGCCTCGTAAAAGTCCACGGCGAAGTTGAAAAACTG
GGAGTTGCGCGCCGAGACGGTCAACTCCTCCTCCAGAAGACGGATGAGCTCGGCGATGGTGGCGC
GCACCTCGCGCTCGAAGGCCCCCGGGAGTTCCTCCACTTCCTCTTCTTCCTCCTCCACTAACATCTC
TTCTACTTCCTCCTCAGGCGGCAGTGGTGGCGGGGGAGGGGGCCTGCGTCGCCGGCGGCGCACGG
GCAGACGGTCGATGAAGCGCTCGATGGTCTCGCCGCGCCGGCGTCGCATGGTCTCGGTGACGGCG
CGCCCGTCCTCGCGGGGCCGCAGCGTGAAGACGCCGCCGCGCATCTCCAGGTGGCCGGGGGGGTC
CCCGTTGGGCAGGGAGAGGGCGCTGACGATGCATCTTATCAATTGCCCCGTAGGGACTCCGCGCA
AGGACCTGAGCGTCTCGAGATCCACGGGATCTGAAAACCGCTGAACGAAGGCTTCGAGCCAGTCG
CAGTCGCAAGGTAGGCTGAGCACGGTTTCTTCTGGCGGGTCATGTTGGTTGGGAGCGGGGGGGGC
GATGCTGCTGGTGATGAAGTTGAAATAGGCGGTTCTGAGACGGCGGATGGTGGCGAGGAGCACC
AGGTCTTTGGGCCCGGCTTGCTGGATGCGCAGACGGTCGGCCATGCCCCAGGCGTGGTCCTGACA
CCTGGCCAGGTCCTTGTAGTAGTCCTGCATGAGCCGCTCCACGGGCACCTCCTCCTCGCCCGCGCG
GCCGTGCATGCGCGTGAGCCCGAAGCCGCGCTGGGGCTGGACGAGCGCCAGGTCGGCGACGACG -continued

```
CGCTCGGCGAGGATGGCTTGCTGGATCTGGGTGAGGGTGGTCTGGAAGTCATCAAAGTCGACGAA
GCGGTGGTAGGCTCCGGTGTTGATGGTGTAGGAGCAGTTGGCCATGACGGACCAGTTGACGGTCT
GGTGGCCCGGACGCACGAGCTCGTGGTACTTGAGGCGCGAGTAGGCGCGCGTGTCGAAGATGTA
GTCGTTGCAGGTGCGCACCAGGTACTGGTAGCCGATGAGGAAGTGCGGCGGCGGCTGGCGGTAG
AGCGGCCATCGCTCGGTGGCGGGGGCGCCGGGCGCGAGGTCCTCGAGCATGGTGCGGTGGTAGC
CGTAGATGTACCTGGACATCCAGGTGATGCCGGCGGCGGTGGTGGAGGCGCGCGGGAACTCGCG
GACGCGGTTCCAGATGTTGCGCAGCGGCAGGAAGTAGTTCATGGTGGGCACGGTCTGGCCCGTGA
GGCGCGCGCAGTCGTGGATGCTCTATACGGGCAAAAACGAAAGCGGTCAGCGGCTCGACTCCGTG
GCCTGGAGGCTAAGCGAACGGGTTGGGCTGCGCGTGTACCCCGGTTCGAATCTCGAATCAGGCTG
GAGCCGCAGCTAACGTGGTATTGGCACTCCCGTCTCGACCCAAGCCTGCACCAACCCTCCAGGAT
ACGGAGGCGGGTCGTTTTGCAACTTTTTTTTGGAGGCCGGATGAGACTAGTAAGCGCGGAAAGCG
GCCGACCGCGATGGCTCGCTGCCGTAGTCTGGAGAAGAATCGCCAGGGTTGCGTTGCGGTGTGCC
CCGGTTCGAGGCCGGCCGGATTCCGCGGCTAACGAGGGCGTGGCTGCCCCGTCGTTTCCAAGACC
CCATAGCCAGCCGACTTCTCCAGTTACGGAGCGAGCCCCTCTTTTGTTTTGTTTGTTTTTGCCAGAT
GCATCCCGTACTGCGGCAGATGCGCCCCCACCACCCTCCACCGCAACAACAGCCCCCTCCACAGC
CGGCGCTTCTGCCCCCGCCCCAGCAGCAACTTCCAGCCACGACCGCCGCGGCCGCCGTGAGCGGG
GCTGGACAGAGTTATGATCACCAGCTGGCCTTGGAAGAGGGCGAGGGGCTGGCGCGCCTGGGGG
CGTCGTCGCCGGAGCGGCACCCGCGCGTGCAGATGAAAAGGGACGCTCGCGAGGCCTACGTGCC
CAAGCAGAACCTGTTCAGAGACAGGAGCGGCGAGGAGCCCGAGGAGATGCGCGCGGCCCGGTTC
CACGCGGGGGGGGAGCTGCGGCGCGGCCTGGACCGAAAGAGGGTGCTGAGGGACGAGGATTTCG
AGGCGGACGAGCTGACGGGGATCAGCCCCGCGCGCGCGCACGTGGCCGCGGCCAACCTGGTCAC
GGCGTACGAGCAGACCGTGAAGGAGGAGAGCAACTTCCAAAAATCCTTCAACAACCACGTGCGC
ACCCTGATCGCGCGCGAGGAGGTGACCCTGGGCCTGATGCACCTGTGGGACCTGCTGGAGGCCAT
CGTGCAGAACCCCACCAGCAAGCCGCTGACGGCGCAGCTGTTCCTGGTGGTGCAGCATAGTCGGG
ACAACGAAGCGTTCAGGGAGGCGCTGCTGAATATCACCGAGCCCGAGGGCCGCTGGCTCCTGGAC
CTGGTGAACATTCTGCAGAGCATCGTGGTGCAGGAGCGCGGGCTGCCGCTGTCCGAGAAGCTGGC
GGCCATCAACTTCTCGGTGCTGAGTTTGGGCAAGTACTACGCTAGGAAGATCTACAAGACCCCGT
ACGTGCCCATAGACAAGGAGGTGAAGATCGACGGGTTTTACATGCGCATGACCCTGAAAGTGCTG
ACCCTGAGCGACGATCTGGGGGTGTACCGCAACGACAGGATGCACCGTGCGGTGAGCGCCAGCA
GGCGGCGCGAGCTGAGCGACCAGGAGCTGATGCATAGTCTGCAGCGGGCCCTGACCGGGGCCGG
GACCGAGGGGGAGAGCTACTTTGACATGGGCGCGGACCTGCACTGGCAGCCCAGCCGCCGGGCC
TTGGAGGCGGCGGCAGGACCCTACGTAGAAGAGGTGGACGATGAGGTGGACGAGGAGGGCGAGT
ACCTGGAAGACTGATGGCGCGACCGTATTTTTGCTAGATGCAACAACAACAGCCACCTCCTGATC
CCGCGATGCGGGCGGCGCTGCAGAGCCAGCCGTCCGGCATTAACTCCTCGGACCATTGGACCCAG
GCCATGCAACGCATCATGGCGCTGACGACCCGCAACCCCGAAGCCTTTAGACAGCAGCCCCAGGC
CAACCGGCTCTCGGCCATCCTGGAGGCCGTGGTGCCCTCGCGCTCCAACCCCACGCACGAGAAGG
TCCTGGCCATCGTGAACGCGCTGGTGGAGAACAAGGCCATCCGCGGCGACGAGGCCGGCCTGGTG
TACAACGCGCTGCTGGAGCGCGTGGCCCGCTACAACAGCACCAACGTGCAGACCAACCTGGACCG
CATGGTGACCGACGTGCGCGAGGCCGTGGCCCAGCGCGAGCGGTTCCACCGCGAGTCCAACCTGG
GATCCATGGTGGCGCTGAACGCCTTCCTCAGCACCCAGCCCGCCAACGTGCCCCGGGGCCAGGAG
GACTACACCAACTTCATCAGCGCCCTGCGCCTGATGGTGACCGAGGTGCCCCAGAGCGAGGTGTA
CCAGTCCGGGCCGGACTACTTCTTCCAGACCAGTCGCCAGGGCTTGCAGACCGTGAACCTGAGCC
AGGCTTTCAAGAACTTGCAGGGCCTGTGGGGCGTGCAGGCCCCGGTCGGGGACCGCGCGACGGTG
TCGAGCCTGCTGACGCCGAACTCGCGCCTGCTGCTGCTGCTGGTGGCCCCCTTCACGGACAGCGG
CAGCATCAACCGCAACTCGTACCTGGGCTACCTGATTAACCTGTACCGCGAGGCCATCGGCCAGG
CGCACGTGGACGAGCAGACCTACCAGGAGATCACCCACGTGAGCCGCGCCCTGGGCCAGGACGA
CCCGGGCAACCTGGAAGCCACCCTGAACTTTTTGCTGACCAACCGGTCGCAGAAGATCCCGCCCC
AGTACGCGCTCAGCACCGAGGAGGAGCGCATCCTGCGTTACGTGCAGCAGAGCGTGGGCCTGTTC
CTGATGCAGGAGGGGGCCACCCCCAGCGCCGCGCTCGACATGACCGCGCGCAACATGGAGCCCA
GCATGTACGCCAGCAACCGCCCGTTCATCAATAAACTGATGGACTACTTGCATCGGGCGGCCGCC
ATGAACTCTGACTATTTCACCAACGCCATCCTGAATCCCCACTGGCTCCCGCCGCCGGGGTTCTAC
ACGGGCGAGTACGACATGCCCGACCCCAATACGGGTTCCTGTGGGACGATGTGGACAGCAGCGT
GTTCTCCCCCCGACCGGGTGCTAACGAGCGCCCCTTGTGGAAGAAGGAAGGCAGCGACCGACGCC
CGTCCTCGGCGCTGTCCGGCCGCGAGGGTGCTGCCGCGGCGGTGCCCGAGGCCGCCAGTCCTTTC
```

-continued

CCGAGCTTGCCCTTCTCGCTGAACAGTATCCGCAGCAGCGAGCTGGGCAGGATCACGCGCCCGCG
CTTGCTGGGCGAAGAGGAGTACTTGAATGACTCGCTGTTGAGACCCGAGCGGGAGAAGAACTTCC
CCAATAACGGGATAGAAAGCCTGGTGGACAAGATGAGCCGCTGGAAGACGTATGCGCAGGAGCA
CAGGGACGATCCCCGGGCGTCGCAGGGGGCCACGAGCCGGGGCAGCGCCGCCCGTAAACGCCGG
TGGCACGACAGGCAGCGGGGACAGATGTGGGACGATGAGGACTCCGCCGACGACAGCAGCGTGT
TGGACTTGGGTGGGAGTGGTAACCCGTTCGCTCACCTGCGCCCCCGTATCGGGCGCATGATGTAA
GAGAAACCGAAAATAAATGATACTCACCAAGGCCATGGCGACCAGCGTGCGTTCGTTTCTTCTCT
GTTGTTGTTGTATCTAGTATGATGAGGCGTGCGTACCCGGAGGGTCCTCCTCCCTCGTACGAGAGC
GTGATGCAGCAGGCGATGGCGGCGGCGGCGATGCAGCCCCCGCTGGAGGCTCCTTACGTGCCCCC
GCGGTACCTGGCGCCTACGGAGGGGCGGAACAGCATTCGTTACTCGGAGCTGGCACCCTTGTACG
ATACCACCCGGTTGTACCTGGTGGACAACAAGTCGGCGGACATCGCCTCGCTGAACTACCAGAAC
GACCACAGCAACTTCCTGACCACCGTGGTGCAGAACAATGACTTCACCCCCACGGAGGCCAGCAC
CCAGACCATCAACTTTGACGAGCGCTCGCGGTGGGGGGCCAGCTGAAAACCATCATGCACACCA
ACATGCCCAACGTGAACGAGTTCATGTACAGCAACAAGTTCAAGGCGCGGGTGATGGTCTCCCGC
AAGACCCCCAATGGGGTGACAGTGACAGAGGATTATGATGGTAGTCAGGATGAGCTGAAGTATG
AATGGGTGGAATTTGAGCTGCCCGAAGGCAACTTCTCGGTGACCATGACCATCGACCTGATGAAC
AACGCCATCATCGACAATTACTTGGCGGTGGGGCGGCAGAACGGGGTGCTGGAGAGCGACATCG
GCGTGAAGTTCGACACTAGGAACTTCAGGCTGGGCTGGGACCCCGTGACCGAGCTGGTCATGCCC
GGGGTGTACACCAACGAGGCTTTCCATCCCGATATTGTCTTGCTGCCCGGCTGCGGGGTGGACTTC
ACCGAGAGCCGCCTCAGCAACCTGCTGGGCATTCGCAAGAGGCAGCCCTTCCAGGAAGGCTTCCA
GATCATGTACGAGGATCTGGAGGGGGGCAACATCCCCGCGCTCCTGGATGTCGACGCCTATGAGA
AAAGCAAGGAGGATGCAGCAGCTGAAGCAACTGCAGCCGTAGCTACCGCCTCTACCGAGGTCAG
GGGCGATAATTTTGCAAGCGCCGCAGCAGTGGCAGCGGCCGAGGCGGCTGAAACCGAAAGTAAG
ATAGTCATTCAGCCGGTGGAGAAGGATAGCAAGAACAGGAGCTACAACGTACTACCGGACAAGA
TAAACACCGCCTACCGCAGCTGGTACCTAGCCTACAACTATGGCGACCCCGAGAAGGGCGTGCGC
TCCTGGACGCTGCTCACCACCTCGGACGTCACCTGCGGCGTGGAGCAAGTCTACTGGTCGCTGCCC
GACATGATGCAAGACCCGGTCACCTTCCGCTCCACGCGTCAAGTTAGCAACTACCCGGTGGTGGG
CGCCGAGCTCCTGCCCGTCTACTCCAAGAGCTTCTTCAACGAGCAGGCCGTCTACTCGCAGCAGCT
GCGCGCCTTCACCTCGCTTACGCACGTCTTCAACCGCTTCCCCGAGAACCAGATCCTCGTCCGCCC
GCCCGCGCCCACCATTACCACCGTCAGTGAAAACGTTCCTGCTCTCACAGATCACGGGACCCTGC
CGCTGCGCAGCAGTATCCGGGGAGTCCAGCGCGTGACCGTTACTGACGCCAGACGCCGCACCTGC
CCCTACGTCTACAAGGCCCTGGGCATAGTCGCGCCGCGCGTCCTCTCGAGCCGCACCTTCTAAATG
TCCATTCTCATCTCGCCCAGTAATAACACCGGTTGGGGCCTGCGCGCGCCCAGCAAGATGTACGG
AGGCGCTCGCCAACGCTCCACGCAACACCCCGTGCGCGTGCGCGGGCACTTCCGCGCTCCCTGGG
GCGCCCTCAAGGGCCGCGTGCGGTCGCGCACCACCGTCGACGACGTGATCGACCAGGTGGTGGCC
GACGCGCGCAACTACACCCCCGCCGCCGCGCCCGTCTCCACCGTGGACGCCGTCATCGACAGCGT
GGTGGCcGACGCGCGCCGGTACGCCCGCGCCAAGAGCCGGCGGCGGCGCATCGCCCGGCGGCACC
GGAGCACCCCCGCCATGCGCGCGGCGCGAGCCTTGCTGCGCAGGGCCAGGCGCACGGGACGCAG
GGCCATGCTCAGGGCGGCCAGACGCGCGGCTTCAGGCGCCAGCGCCGGCAGGACCCGGAGACGC
GCGGCCACGGCGGCGGCAGCGGCCATCGCCAGCATGTCCCGCCCGCGGCGAGGGAACGTGTACT
GGGTGCGCGACGCCGCCACCGGTGTGCGCGTGCCCGTGCGCACCCGCCCCCCTCGCACTTGAAGA
TGTTCACTTCGCGATGTTGATGTGTCCCAGCGGCGAGGAGGATGTCCAAGCGCAAATTCAAGGAA
GAGATGCTCCAGGTCATCGCGCCTGAGATCTACGGCCCTGCGGTGGTGAAGGAGGAAAGAAAGC
CCCCCAAAATCAAGCGGGTCAAAAAGGACAAAAAGGAAGAAGAAAGTGATGTGGACGGATTGGT
GGAGTTTGTGCGCGAGTTCGCCCCCCGGCGGCGCGTGCAGTGGCGCGGGCGGAAGGTGCAACCG
GTGCTGAGACCCGGCACCACCGTGGTCTTCACGCCCGGCGAGCGCTCCGGCACCGCTTCCAAGCG
CTCCTACGACGAGGTGTACGGGGATGATGATATTCTGGAGCAGGCGGCCGAGCGCCTGGGCGAGT
TTGCTTACGGCAAGCGCAGCCGTTCCGCACCGAAGGAAGAGGCGGTGTCCATCCCGCTGGACCAC
GGCAACCCCACGCCGAGCCTCAAGCCCGTGACCTTGCAGCAGGTGCTGCCGACCGCGGCGCCGCG
CCGGGGGTTCAAGCGCGAGGGCGAGGATCTGTACCCCACCATGCAGCTGATGGTGCCCAAGCGCC
AGAAGCTGGAAGACGTGCTGGAGACCATGAAGGTGGACCCGGACGTGCAGCCCGAGGTCAAGGT
GCGGCCCATCAAGCAGGTGGCCCCGGGCCTGGGCGTGCAGACCGTGGACATCAAGATTCCCACGG
AGCCCATGGAAACGCAGACCGAGCCCATGATCAAGCCCAGCACCAGCACCATGGAGGTGCAGAC
GGATCCCTGGATGCCATCGGCTCCTAGTCGAAGACCCCGGCGCAAGTACGGCGCGGCCAGCCTGC

-continued

TGATGCCCAACTACGCGCTGCATCCTTCCATCATCCCCACGCCGGGCTACCGCGGCACGCGCTTCT
ACCGCGGTCATACCAGCAGCCGCCGCCGCAAGACCACCACTCGCCGCCGCCGTCGCCGCACCGCC
GCTGCAACCACCCCTGCCGCCCTGGTGCGGAGAGTGTACCGCCGCGGCCGCGCACCTCTGACCCT
GCCGCGCGCGCGCTACCACCCGAGCATCGCCATTTAAACTTTCGCCTGCTTTGCAGATCAATGGCC
CTCACATGCCGCCTTCGCGTTCCCATTACGGGCTACCGAGGAAGAAAACCGCGCCGTAGAAGGCT
GGCGGGGAACGGGATGCGTCGCCACCACCACCGGCGGCGGCGCGCCATCAGCAAGCGGTTGGGG
GGAGGCTTCCTGCCCGCGCTGATCCCCATCATCGCCGCGGCGATCGGGGCGATCCCCGGCATTGC
TTCCGTGGCGGTGCAGGCCTCTCAGCGCCACTGAGACACACTTGGAAACATCTTGTAATAAACCaA
TGGACTCTGACGCTCCTGGTCCTGTGATGTGTTTTCGTAGACAGATGGAAGACATCAATTTTTCGT
CCCTGGCTCCGCGACACGGCACGCGGCCGTTCATGGGCACCTGGAGCGACATCGGCACCAGCCAA
CTGAACGGGGGCGCCTTCAATTGGAGCAGTCTCTGGAGCGGGCTTAAGAATTTCGGGTCCACGCT
TAAAACCTATGGCAGCAAGGCGTGGAACAGCACCACAGGGCAGGCGCTGAGGGATAAGCTGAAA
GAGCAGAACTTCCAGCAGAAGGTGGTCGATGGGCTCGCCTCGGGCATCAACGGGGGGGGACCT
GGCCAACCAGGCCGTGCAGCGGCAGATCAACAGCCGCCTGGACCCGGTGCCGCCCGCCGGCTCCG
TGGAGATGCCGCAGGTGGAGGAGGAGCTGCCTCCCCTGGACAAGCGGGGCGAGAAGCGACCCCG
CCCCGATGCGGAGGAGACGCTGCTGACGCACACGGACGAGCCGCCCCCGTACGAGGAGGCGGTG
AAACTGGGTCTGCCCACCACGCGGCCCATCGCGCCCCTGGCCACCGGGGTGCTGAAACCCGAAAA
GCCCGCGACCCTGGACTTGCCTCCTCCCCAGCCTTCCCGCCCCTCTACAGTGGCTAAGCCCCTGCC
GCCGGTGGCCGTGGCCCGCGCGCGACCCGGGGGCACCGCCCGCCCTCATGCGAACTGGCAGAGC
ACTCTGAACAGCATCGTGGGTCTGGGAGTGCAGAGTGTGAAGCGCCGCCGCTGCTATTAAACCTA
CCGTAGCGCTTAACTTGCTTGTCTGTGTGTGTATGTATTATGTCGCCGCCGCCGCTGTCCACCAGA
AGGAGGAGTGAAGAGGCGCGTCGCCGAGTTGCAAGATGGCCACCCCATCGATGCTGCCCCAGTG
GGCGTACATGCACATCGCCGGACAGGACGCTTCGGAGTACCTGAGTCCGGGTCTGGTGCAGTTTG
CCCGCGCCACAGACACCTACTTCAGTCTGGGGAACAAGTTTAGGAACCCCACGGTGGCGCCCACG
CACGATGTGACCACCGACCGCAGCCAGCGGCTGACGCTGCGCTTCGTGCCCGTGGACCGCGAGGA
CAACACCTACTCGTACAAAGTGCGCTACACGCTGGCCGTGGGCGACAACCGCGTGCTGGACATGG
CCAGCACCTACTTTGACATCCGCGGCGTGCTGGATCGGGGCCCTAGCTTCAAACCCTACTCCGGCA
CCGCCTACAACAGTCTGGCCCCCAAGGGAGCACCCAACACTTGTCAGTGGACATATAAAGCCGAT
GGTGAAACTGCCACAGAAAAAACCTATACATATGGAAATGCACCCGTGCAGGGCATTAACATCAC
AAAAGATGGTATTCAACTTGGAACTGACACCGATGATCAGCCAATCTACGCAGATAAAACCTATC
AGCCTGAACCTCAAGTGGGTGATGCTGAATGGCATGACATCACTGGTACTGATGAAAAGTATGGA
GGCAGAGCTCTTAAGCCTGATACCAAAATGAAGCCTTGTTATGGTTCTTTTGCCAAGCCTACTAAT
AAAGAAGGAGGTCAGGCAAATGTGAAAACAGGAACAGGCACTACTAAAGAATATGACATAGACA
TGGCTTTCTTTGACAACAGAAGTGCGGCTGCTGCTGGCCTAGCTCCAGAAATTGTTTTGTATACTG
AAAATGTGGATTTGGAAACTCCAGATACCCATATTGTATACAAAGCAGGCACAGATGACAGCAGC
TCTTCTATTAATTTGGGTCAGCAAGCCATGCCCAACAGACCTAACTACATTGGTTTCAGAGACAAC
TTTATCGGGCTCATGTACTACAACAGCACTGGCAATATGGGGGTGCTGGCCGGTCAGGCTTCTCA
GCTGAATGCTGTGGTTGACTTGCAAGACAGAAACACCGAGCTGTCCTACCAGCTCTTGCTTGACTC
TCTGGGTGACAGAACCCGGTATTTCAGTATGTGGAATCAGGCGGTGGACAGCTATGATCCTGATG
TGCGCATTATTGAAAATCATGGTGTGGAGGATGAACTTCCCAACTATTGTTTCCCTCTGGATGCTG
TTGGCAGAACAGATACTTATCAGGGAATTAAGGCTAATGGAACTGATCAAACCACATGGACCAAA
GATGACAGTGTCAATGATGCTAATGAGATAGGCAAGGGTAATCCATTCGCCATGGAAATCAACAT
CCAAGCCAACCTGTGGAGGAACTTCCTCTACGCCAACGTGGCCCTGTACCTGCCCGACTCTTACAA
GTACACGCCGGCCAATGTTACCCTGCCCACCAACACCAACACCTACGATTACATGAACGGCCGGG
TGGTGGCGCCCTCGCTGGTGGACTCCTACATCAACATCGGGGCGCGCTGGTCGCTGGATCCCATG
GACAACGTGAACCCCTTCAACCACCACCGCAATGCGGGGCTGCGCTACCGCTCCATGCTCCTGGG
CAACGGGCGCTACGTGCCCTTCCACATCCAGGTGCCCCAGAAATTTTTCGCCATCAAGAGCCTCCT
GCTCCTGCCCGGGTCCTACACCTACGAGTGGAACTTCCGCAAGGACGTCAACATGATCCTGCAGA
GCTCCCTCGGCAACGACCTGCGCACGGACGGGGCCTCCATCTCCTTCACCAGCATCAACCTCTACG
CCACCTTCTTCCCCATGGCGCACAACACGGCCTCCACGCTCGAGGCCATGCTGCGCAACGACACC
AACGACCAGTCCTTCAACGACTACCTCTCGGCGGCCAACATGCTCTACCCCATCCCGGCCAACGC
CACCAACGTGCCCATCTCCATCCCCTCGCGCAACTGGGCCGCCTTCCGCGGCTGGTCCTTCACGCG
TCTCAAGACCAAGGAGACGCCCTCGCTGGGCTCCGGGTTCGACCCCTACTTCGTCTACTCGGGCTC
CATCCCCTACCTCGACGGCACCTTCTACCTCAACCACACCTTCAAGAAGGTCTCCATCACCTTCGA

-continued

CTCCTCCGTCAGCTGGCCCGGCAACGACCGGCTCCTGACGCCCAACGAGTTCGAAATCAAGCGCA
CCGTCGACGGCGAGGGCTACAACGTGGCCCAGTGCAACATGACCAAGGACTGGTTCCTGGTCCAG
ATGCTGGCCCACTACAACATCGGCTACCAGGGCTTCTACGTGCCCGAGGGCTACAAGGACCGCAT
GTACTCCTTCTTCCGCAACTTCCAGCCCATGAGCCGCCAGGTGGTGGACGAGGTCAACTACAAGG
ACTACCAGGCCGTCACCCTGGCCTACCAGCACAACAACTCGGGCTTCGTCGGCTACCTCGCGCCC
ACCATGCGCCAGGGCCAGCCCTACCCCGCCAACTACCCCTACCCGCTCATCGGCAAGAGCGCCGT
CACCAGCGTCACCCAGAAAAAGTTCCTCTGCGACAGGGTCATGTGGCGCATCCCCTTCTCCAGCA
ACTTCATGTCCATGGGCGCGCTCACCGACCTCGGCCAGAACATGCTCTATGCCAACTCCGCCCACG
CGCTAGACATGAATTTCGAAGTCGACCCCATGGATGAGTCCACCCTTCTCTATGTTGTCTTCGAAG
TCTTCGACGTCGTCCGAGTGCACCAGCCCCACCGCGGCGTCATCGAGGCCGTCTACCTGCGCACCC
CCTTCTCGGCCGGTAACGCCACCACCTAAGCTCTTGCTTCTTGCAAGCCATGGCCGCGGGCTCCGG
CGAGCAGGAGCTCAGGGCCATCATCCGCGACCTGGGCTGCGGGCCCTACTTCCTGGGCACCTTCG
ATAAGCGCTTCCCGGGATTCATGGCCCCGCACAAGCTGGCCTGCGCCATCGTCAACACGGCCGGC
CGCGAGACCGGGGGCGAGCACTGGCTGGCCTTCGCCTGGAACCCGCGCTCGAACACCTGCTACCT
CTTCGACCCCTTCGGGTTCTCGGACGAGCGCCTCAAGCAGATCTACCAGTTCGAGTACGAGGGCC
TGCTGCGCCGCAGCGCCCTGGCCACCGAGGACCGCTGCGTCACCCTGGAAAAGTCCACCCAGACC
GTGCAGGGTCCGCGCTCGGCCGCCTGCGGGCTCTTCTGCTGCATGTTCCTGCACGCCTTCGTGCAC
TGGCCCGACCGCCCCATGGACAAGAACCCCACCATGAACTTGCTGACGGGGGTGCCCAACGGCAT
GCTCCAGTCGCCCCAGGTGGAACCCACCCTGCGCCGCAACCAGGAGGCGCTCTACCGCTTCCTCA
ACTCCCACTCCGCCTACTTTCGCTCCCACCGCGCGCGCATCGAGAAGGCCACCGCCTTCGACCGCA
TGAATCAAGACATGTAAACCGTGTGTGTATGTTAAATGTCTTTAATAAACAGCACTTTCATGTTAC
ACATGCATCTGAGATGATTTATTTAGAAATCGAAAGGGTTCTGCCGGGTCTCGGCATGGCCCGCG
GGCAGGGACACGTTGCGGAACTGGTACTTGGCCAGCCACTTGAACTCGGGGATCAGCAGTTTGGG
CAGCGGGGTGTCGGGGAAGGAGTCGGTCCACAGCTTCCGCGTCAGTTGCAGGGCGCCCAGCAGGT
CGGGCGCGGAGATCTTGAAATCGCAGTTGGGACCCGCGTTCTGCGCGCGGGAGTTGCGGTACACG
GGGTTGCAGCACTGGAACACCATCAGGGCCGGGTGCTTCACGCTCGCCAGCACCGTCGCGTCGGT
GATGCTCTCCACGTCGAGGTCCTCGGCGTTGGCCATCCCGAAGGGGGTCATCTTGCAGGTCTGCCT
TCCCATGGTGGGCACGCACCCGGGCTTGTGGTTGCAATCGCAGTGCAGGGGGATCAGCATCATCT
GGGCCTGGTCGGCGTTCATCCCCGGGTACATGGCCTTCATGAAAGCCTCCAATTGCCTGAACGCCT
GCTGGGCCTTGGCTCCCTCGGTGAAGAAGACCCCGCAGGACTTGCTAGAGAACTGGTTGGTGGCG
CACCCGGCGTCGTGCACGCAGCAGCGCGCGTCGTTGTTGGCCAGCTGCACCACGCTGCGCCCCCA
GCGGTTCTGGGTGATCTTGGCCCGGTCGGGGTTCTCCTTCAGCGCGCGCTGCCCGTTCTCGCTCGC
CACATCCATCTCGATCATGTGCTCCTTCTGGATCATGGTGGTCCCGTGCAGGCACCGCAGCTTGCC
CTCGGCCTCGGTGCACCCGTGCAGCCACAGCGCGCACCCGGTGCACTCCCAGTTCTTGTGGGCGA
TCTGGGAATGCGCGTGCACGAAGCCCTGCAGGAAGCGGCCCATCATGGTGGTCAGGGTCTTGTTG
CTAGTGAAGGTCAGCGGAATGCCGCGGTGCTCCTCGTTGATGTACAGGTGGCAGATGCGGCGGTA
CACCTCGCCCTGCTCGGGCATCAGCTGGAAGTTGGCTTTCAGGTCGGTCTCCACGCGGTAGCGGTC
CATCAGCATAGTCATGATTTCCATACCCTTCTCCCAGGCCGAGACGATGGGCAGGCTCATAGGGTT
CTTCACCATCATCTTAGCGCTAGCAGCCGCGGCCAGGGGGTCGCTCTCGTCCAGGGTCTCAAAGCT
CCGCTTGCCGTCCTTCTCGGTGATCCGCACCGGGGGGTAGCTGAAGCCCACGGCCGCCAGCTCCTC
CTCGGCCTGTCTTTCGTCCTCGCTGTCCTGGCTGACGTCCTGCAGGACCACATGCTTGGTCTTGCG
GGGTTTCTTCTTGGGCGGCAGCGGCGGCGGAGATGTTGGAGATGGCGAGGGGGAGCGCGAGTTCT
CGCTCACCACTACTATCTCTTCCTCTTCTTGGTCCGAGGCCACGCGGCGGTAGGTATGTCTCTTCG
GGGGCAGAGGCGGAGGCGACGGGCTCTCGCCGCCGCGACTTGGCGGATGGCTGGCAGAGCCCCT
TCCGCCTTCGGGGGTGCGCTCCCGGCGGCGCTCTGACTGACTTCCTCCGCGGCCGGCCATTGTGTT
CTCCTAGGGAGGAACAACAAGCATGGAGACTCAGCCATCGCCAACCTCGCCATCTGCCCCCACCG
CCGACGAGAAGCAGCAGCAGCAGAATGAAAGCTTAACCGCCCCGCCGCCCAGCCCCGCCACCTC
CGACGCGGCCGTCCCAGACATGCAAGAGATGGAGGAATCCATCGAGATTGACCTGGGCTATGTGA
CCCCCGCGGAGCACGAGGAGGAGCTGGCAGTGCGCTTTTCACAAGAAGAGATACACCAAGAACA
GCCAGAGCAGGAAGCAGAGAATGAGCAGAGTCAGGCTGGGCTCGAGCATGACGGCGACTACCTC
CACCTGAGCGGGGGGGAGGACGCGCTCATCAAGCATCTGGCCCGGCAGGCCACCATCGTCAAGG
ATGCGCTGCTCGACCGCACCGAGGTGCCCCTCAGCGTGGAGGAGCTCAGCCGCGCCTACGAGTTG
AACCTCTTCTCGCCGCGCGTGCCCCCCAAGCGCCAGCCCAATGGCACCTGCGAGCCCAACCCGCG
CCTCAACTTCTACCCGGTCTTCGCGGTGCCCGAGGCCCTGGCCACCTACCACATCTTTTTCAAGAA

-continued

CCAAAAGATCCCCGTCTCCTGCCGCGCCAACCGCACCCGCGCCGACGCCCTTTTCAACCTGGGTCC
CGGCGCCCGCCTACCTGATATCGCCTCCTTGGAAGAGGTTCCCAAGATCTTCGAGGGTCTGGGCA
GCGACGAGACTCGGGCCGCGAACGCTCTGCAAGGAGAAGGAGGAGAGCATGAGCACCACAGCGC
CCTGGTCGAGTTGGAAGGCGACAACGCGCGGCTGGCGGTGCTCAAACGCACGGTCGAGCTGACCC
ATTTCGCCTACCCGGCTCTGAACCTGCCCCCCAAAGTCATGAGCGCGGTCATGGACCAGGTGCTC
ATCAAGCGCGCGTCGCCCATCTCCGAGGACGAGGGCATGCAAGACTCCGAGGAGGGCAAGCCCG
TGGTCAGCGACGAGCAGCTGGCCCGGTGGCTGGGTCCTAATGCTAGTCCCCAGAGTTTGGAAGAG
CGGCGCAAACTCATGATGGCCGTGGTCCTGGTGACCGTGGAGCTGGAGTGCCTGCGCCGCTTCTT
CGCCGACGCGGAGACCCTGCGCAAGGTCGAGGAGAACCTGCACTACCTCTTCAGGCACGGGTTCG
TGCGCCAGGCCTGCAAGATCTCCAACGTGGAGCTGACCAACCTGGTCTCCTACATGGGCATCTTG
CACGAGAACCGCCTGGGGCAGAACGTGCTGCACACCACCCTGCGCGGGGAGGCCCGGCGCGACT
ACATCCGCGACTGCGTCTACCTCTACCTCTGCCACACCTGGCAGACGGGCATGGGCGTGTGGCAG
CAGTGTCTGGAGGAGCAGAACCTGAAAGAGCTCTGCAAGCTCCTGCAGAAGAACCTCAAGGGTCT
GTGGACCGGGTTCGACGAGCGCACCACCGCCTCGGACCTGGCCGACCTCATTTTCCCCGAGCGCC
TCAGGCTGACGCTGCGCAACGGCCTGCCCGACTTTATGAGCCAAAGCATGTTGCAAAACTTTCGC
TCTTTCATCCTCGAACGCTCCGGAATCCTGCCCGCCACCTGCTCCGCGCTGCCCTCGGACTTCGTG
CCGCTGACCTTCCGCGAGTGCCCCCCGCCGCTGTGGAGCCACTGCTACCTGCTGCGCCTGGCCAAC
TACCTGGCCTACCACTCGGACGTGATCGAGGACGTCAGCGGCGAGGGCCTGCTCGAGTGCCACTG
CCGCTGCAACCTCTGCACGCCGCACCGCTCCCTGGCCTGCAACCCCCAGCTGCTGAGCGAGACCC
AGATCATCGGCACCTTCGAGTTGCAAGGGCCCAGCGAAGGCGAGGGTTCAGCCGCCAAGGGGGG
TCTGAAACTCACCCCGGGGCTGTGGACCTCGGCCTACTTGCGCAAGTTCGTGCCCGAGGACTACC
ATCCCTTCGAGATCAGGTTCTACGAGGACCAATCCCATCCGCCCAAGGCCGAGCTGTCGGCCTGC
GTCATCACCCAGGGGGCGATCCTGGCCCAATTGCAAGCCATCCAGAAATCCCGCCAAGAATTCTT
GCTGAAAAAGGGCCGCGGGGTCTACCTCGACCCCCAGACCGGTGAGGAGCTCAACCCCGGCTTCC
CCCAGGATGCCCCGAGGAAACAAGAAGCTGAAAGTGGAGCTGCCGCCCGTGGAGGATTTGGAGG
AAGACTGGGAGAACAGCAGTCAGGCAGAGGAGGAGGAGATGGAGGAAGACTGGGACAGCACTC
AGGCAGAGGAGGACAGCCTGCAAGACAGTCTGGAGGAAGACGAGGAGGAGGCAGAGGAGGAGG
TGGAAGAAGCAGCCGCCGCCAGACCGTCGTCCTCGGCGGGGGAGAAAGCAAGCAGCACGGATAC
CATCTCCGCTCCGGGTCGGGGTCCCGCTCGACCACACAGTAGATGGGACGAGACCGGACGATTCC
CGAACCCCACCACCCAGACCGGTAAGAAGGAGCGGCAGGGATACAAGTCCTGGCGGGGGCACAA
AAACGCCATCGTCTCCTGCTTGCAGGCCTGCGGGGGCAACATCTCCTTCACCCGGCGCTACCTGCT
CTTCCACCGCGGGGTGAACTTTCCCCGCAACATCTTGCATTACTACCGTCACCTCCACAGCCCCTA
CTACTTCCAAGAAGAGGCAGCAGCAGCAGAAAAAGACCAGCAGAAAACCAGCAGCTAGAAAATC
CACAGCGGCGGCAGCAGGTGGACTGAGGATCGCGGCGAACGAGCCGGCGCAAACCCGGGAGCTG
AGGAACCGGATCTTTCCCACCCTCTATGCCATCTTCCAGCAGAGTCGGGGGCAGGAGCAGGAACT
GAAAGTCAAGAACCGTTCTCTGCGCTCGCTCACCCGCAGTTGTCTGTATCACAAGAGCGAAGACC
AACTTCAGCGCACTCTCGAGGACGCCGAGGCTCTCTTCAACAAGTACTGCGCGCTCACTCTTAAA
GAGTAGCCCGCGCCCGCCCAGTCGCAGAAAAAGGCGGGAATTACGTCACCTGTGCCCTTCGCCCT
AGCCGCCTCCACCCATCATCATGAGCAAAGAGATTCCCACGCCTTACATGTGGAGCTACCAGCCC
CAGATGGGCCTGGCCGCCGGTGCCGCCCAGGACTACTCCACCCGCATGAATTGGCTCAGCGCCGG
GCCCGCGATGATCTCACGGGTGAATGACATCCGCGCCCACCGAAACCAGATACTCCTAGAACAGT
CAGCGCTCACCGCCACGCCCCGCAATCACCTCAATCCGCGTAATTGGCCCGCCGCCCTGGTGTACC
AGGAAATTCCCCAGCCCACGACCGTACTACTTCCGCGAGACGCCCAGGCCGAAGTCCAGCTGACT
AACTCAGGTGTCCAGCTGGCGGGCGGCGCCACCCTGTGTCGTCACCGCCCCGCTCAGGGTATAAA
GCGGCTGGTGATCCGGGGCAGAGGCACACAGCTCAACGACGAGGTGGTGAGCTCTTCGCTGGGTC
TGCGACCTGACGGAGTCTTCCAACTCGCCGGATCGGGGAGATCTTCCTTCACGCCTCGTCAGGCCG
TCCTGACTTTGGAGAGTTCGTCCTCGCAGCCCCGCTCGGGTGGCATCGGCACTCTCCAGTTCGTGG
AGGAGTTCACTCCCTCGGTCTACTTCAACCCCTTCTCCGGCTCCCCCGGCCACTACCCGGACGAGT
TCATCCCGAACTTCGACGCCATCAGCGAGTCGGTGGACGGCTACGATTGAAACTAATCACCCCCT
TATCCAGTGAAATAAAGATCATATTGATGATGATTTTACAGAAATAAAAAATAATCATTTGATTTG
AAATAAAGATACAATCATATTGATGATTTGAGTTTAACAAAAAAATAAAGAATCACTTACTTGAA
ATCTGATACCAGGTCTCTGTCCATGTTTTCTGCCAACACCACTTCACTCCCCTCTTCCCAGCTCTGG
TACTGCAGGCCCCGGCGGGCTGCAAACTTCCTCCACACGCTGAAGGGGATGTCAAATTCCTCCTG
TCCCTCAATCTTCATTTTATCTTCTATCAGATGTCCAAAAAGCGCGTCCGGGTGGATGATGACTTC

-continued

GACCCCGTCTACCCCTACGATGCAGACAACGCACCGACCGTGCCCTTCATCAACCCCCCCTTCGTC
TCTTCAGATGGATTCCAAGAGAAGCCCCTGGGGGTGTTGTCCCTGCGACTGGCCGACCCCGTCAC
CACCAAGAACGGGGAAATCACCCTCAAGCTGGGAGAGGGGGTGGACCTCGATTCCTCGGGAAAA
CTCATCTCCAACACGGCCACCAAGGCCGCCGCCCCTCTCAGTTTTTCCAACAACACCATTTCCCTT
AACATGGATCACCCCTTTTACACTAAAGATGGAAAATTATCCTTACAAGTTTCTCCACCATTAAAT
ATACTGAGAACAAGCATTCTAAACACACTAGCTTTAGGTTTTGGATCAGGTTTAGGACTCCGTGGC
TCTGCCTTGGCAGTACAGTTAGTCTCTCCACTTACATTTGATACTGATGGAAACATAAAGCTTACC
TTAGACAGAGGTTTGCATGTTACAACAGGAGATGCAATTGAAAGCAACATAAGCTGGGCTAAAG
GTTTAAAATTTGAAGATGGAGCCATAGCAACCAACATTGGAAATGGGTTAGAGTTTGGAAGCAGT
AGTACAGAAACAGGTGTTGATGATGCTTACCCAATCCAAGTTAAACTTGGATCTGGCCTTAGCTTT
GACAGTACAGGAGCCATAATGGCTGGTAACAAAGAAGACGATAAACTCACTTTGTGGACAACAC
CTGATCCATCACCAAACTGTCAAATACTCGCAGAAAATGATGCAAAACTAACACTTTGCTTGACT
AAATGTGGTAGTCAAATACTGGCCACTGTGTCAGTCTTAGTTGTAGGAAGTGGAAACCTAAACCC
CATTACTGGCACCGTAAGCAGTGCTCAGGTGTTTCTACGTTTTGATGCAAACGGTGTTCTTTTAAC
AGAACATTCTACACTAAAAAAATACTGGGGGTATAGGCAGGGAGATAGCATAGATGGCACTCCA
TATACCAATGCTGTAGGATTCATGCCCAATTTAAAAGCTTATCCAAAGTCACAAAGTTCTACTACT
AAAAATAATATAGTAGGGCAAGTATACATGAATGGAGATGTTTCAAAACCTATGCTTCTCACTAT
AACCCTCAATGGTACTGATGACAGCAACAGTACATATTCAATGTCATTTTCATACACCTGGACTAA
TGGAAGCTATGTTGGAGCAACATTTGGGGCTAACTCTTATACCTTCTCATACATCGCCCAAGAATG
AACACTGTATCCCACCCTGCATGCCAACCCTTCCCACCCCACTCTGTGGAACAAACTCTGAAACAC
AAAATAAAATAAAGTTCAAGTGTTTTATTGATTCAACAGTTTTACAGGATTCGAGCAGTTATTTTT
CCTCCACCCTCCCAGGACATGGAATACACCACCCTCTCCCCCCGCACAGCCTTGAACATCTGAATG
CCATTGGTGATGGACATGCTTTTGGTCTCCACGTTCCACACAGTTTCAGAGCGAGCCAGTCTCGGG
TCGGTCAGGGAGATGAAACCCTCCGGGCACTCCCGCATCTGCACCTCACAGCTCAACAGCTGAGG
ATTGTCCTCGGTGGTCGGGATCACGGTTATCTGGAAGAAGCAGAAGAGCGGCGGTGGGAATCATA
GTCCGCGAACGGGATCGGCCGGTGGTGTCGCATCAGGCCCCGCAGCAGTCGCTGCCGCCGCCGCT
CCGTCAAGCTGCTGCTCAGGGGGTCCGGGTCCAGGGACTCCCTCAGCATGATGCCCACGGCCCTC
AGCATCAGTCGTCTGGTGCGGCGGGCGCAGCAGCGCATGCGGATCTCGCTCAGGTCGCTGCAGTA
CGTGCAACACAGAACCACCAGGTTGTTCAACAGTCCATAGTTCAACACGCTCCAGCCGAAACTCA
TCGCGGGAAGGATGCTACCCACGTGGCCGTCGTACCAGATCCTCAGGTAAATCAAGTGGTGCCCC
CTCCAGAACACGCTGCCCACGTACATGATCTCCTTGGGCATGTGGCGGTTCACCACCTCCCGGTAC
CACATCACCCTCTGGTTGAACATGCAGCCCCGGATGATCCTGCGGAACCACAGGGCCAGCACCGC
CCCGCCCGCCATGCAGCGAAGAGACCCCGGGTCCCGGCAATGGCAATGGAGGACCCACCGCTCGT
ACCCGTGGATCATCTGGGAGCTGAACAAGTCTATGTTGGCACAGCACAGGCATATGCTCATGCAT
CTCTTCAGCACTCTCAACTCCTCGGGGGTCAAAACCATATGCCAGGGCACGGGGAACTCTTGCAG
GACAGCGAACCCCGCAGAACAGGGCAATCCTCGCACAGAACTTACATTGTGCATGGACAGGGTAT
CGCAATCAGGCAGCACCGGGTGATCCTCCACCAGAGAAGCGCGGGTCTCGGTCTCCTCACAGCGT
GGTAAGGGGGCCGGCCGATACGGGTGATGGGGACGCGGCTGATCGTGTTCGCGACCGTGTCAT
GATGCAGTTGCTTTCGGACATTTTCGTACTTGCTGTAGCAGAACCTGGTCCGGGCGCTGCACACCG
ATCGCCGGCGGCGGTCTCGGCGCTTGGAACGCTCGGTGTTGAAATTGTAAAACAGCCACTCTCTC
AGACCGTGCAGCAGATCTAGGGCCTCAGGAGTGATGAAGATCCCATCATGCCTGATGGCTCTGAT
CACATCGACCACCGTGGAATGGGCCAGACCCAGCCAGATGATGCAATTTTGTTGGGTTTCGGTGA
CGGCGGGGGAGGGAAGAACAGGAAGAACCATGATTAACTTTTAATCCAAACGGTCTCGGAGTAC
TTCAAAATGAAGATCGCGGAGATGGCACCTCTCGCCCCCGCTGTGTTGGTGGAAAATAACAGCCA
GGTCAAAGGTGATACGGTTCTCGAGATGTTCCACGGTGGCTTCCAGCAAAGCCTCCACGCGCACA
TCCAGAAACAAGACAATAGCGAAAGCGGGAGGGTTCTCTAATTCCTCAATCATCATGTTACACTC
CTGCACCATCCCCAGATAATTTTCATTTTTCCAGCCTTGAATGATTCGAACTAGTTCCTGAGGTAAA
TCCAAGCCAGCCATGATAAAGAGCTCGCGCAGAGCGCCCTCCACCGGCATTCTTAAGCACACCCT
CATAATTCCAAGATATTCTGCTCCTGGTTCACCTGCAGCAGATTGACAAGCGGAATATCAAAATCT
CTGCCGCGATCCCTGAGCTCCTCCCTCAGCAATAACTGTAAGTACTCTTTCATATCCTCTCCGAAA
TTTTTAGCCATAGGACCACCAGGAATAAGATTAGGGCAAGCCACAGTACAGATAAACCGAAGTCC
TCCCCAGTGAGCATTGCCAAATGCAAGACTGCTATAAGCATGCTGGCTAGACCCGGTGATATCTT
CCAGATAACTGGACAGAAAATCGCCCAGGCAATTTTTAAGAAAATCAACAAAAGAAAAATCCTC
CAGGTGGACGTTTAGAGCCTCGGGAACAACGATGAAGTAAATGCAAGCGGTGCGTTCCAGCATG

-continued

GTTAGTTAGCTGATCTGTAGAAAAAACAAAAATGAACATTAAACCATGCTAGCCTGGCGAACAGG
TGGGTAAATCGTTCTCTCCAGCACCAGGCAGGCCACGGGGTCTCCGGCGCGACCCTCGTAAAAT
TGTCGCTATGATTGAAAACCATCACAGAGAGACGTTCCCGGTGGCCGGCGTGAATGATTCGACAA
GATGAATACACCCCCGGAACATTGGCGTCCGCGAGTGAAAAAAAGCGCCCGAGGAAGCAATAAG
GCACTACAATGCTCAGTCTCAAGTCCAGCAAAGCGATGCCATGCGGATGAAGCACAAAATTCTCA
GGTGCGTACAAAATGTAATTACTCCCCTCCTGCACAGGCAGCAAAGCCCCCGATCCCTCCAGGTA
CACATACAAAGCCTCAGCGTCCATAGCTTACCGAGCAGCAGCACACAACAGGCGCAAGAGTCAG
AGAAAGGCTGAGCTCTAACCTGTCCACCCGCTCTCTGCTCAATATATAGCCCAGATCTACACTGAC
GTAAAGGCCAAAGTCTAAAAATACCCGCCAAATAATCACACACGCCCAGCACACGCCCAGAAAC
CGGTGACACACTCAAAAAAATACGCGCACTTCCTCAAACGCCCAAAACTGCCGTCATTTCCGGGT
TCCCACGCTACGTCATCAAAACACGACTTTCAAATTCCGTCGACCGTTAAAAACGTCACCCGCCCC
GCCCCTAACGGTCGCCCGTCTCTCAGCCAATCAGCGCCCCGCATCCCCAAATTCAAACACCTCATT
TGCATATTAACGCGCACAAAAAGTTTGAGG

Venezuelan equine encephalitis virus [VEE] (SEQ ID NO: 3) GenBank: L01442.2
atgggcggcg catgagagaa gcccagacca attacctacc caaaatggag aaagttcacg ttgacatcga ggaagacagc ccattcctca
gagctttgca gcggagcttc ccgcagtttg aggtagaagc caagcaggtc actgataatg accatgctaa tgccagagcg ttttcgcatc tggcttcaaa
actgatcgaa acggaggtgg acccatccga cacgatcctt gacattggaa gtgcgcccgc ccgcagaatg tattctaagc acaagtatca ttgtatctgt
ccgatgagat gtgcggaaga tccggacaga ttgtataagt atgcaactaa gctgaagaaa aactgtaagg aaataactga taaggaattg
gacaagaaaa tgaaggagct cgccgccgtc atgagcgacc ctgacctgga aactgagact atgtgcctcc acgacgacga gtcgtgtcgc
tacgaagggc aagtcgctgt ttaccaggat gtatacgcgg ttgacggacc gacaagtctc tatcaccaag ccaataaggg agttagagtc gcctactgga
taggctttga caccacccct tttatgttta agaacttggc tggagcatat ccatcatact ctaccaactg ggccgacgaa accgtgttaa cggctcgtaa
cataggccta tgcagctctg acgttatgga gcggtcacgt agagggatgt ccattcttag aaagaagtat ttgaaaccat ccaacaatgt tctattctct
gttggctcga ccatctacca cgagaagagg gacttactga ggagctggca cctgccgtct gtatttcact tacgtggcaa gcaaaattac acatgtcggt
gtgagactat agttagttgc gacgggtacg tcgttaaaag aatagctatc agtccaggcc tgtatgggaa gccttcaggc tatgctgcta cgatgcaccg
cgagggattc ttgtgctgca aagtgacaga cacattgaac ggggagaggg tctcttttcc cgtgtgcacg tatgtgccag ctacattgtg tgaccaaatg
actggcatac tggcaacaga tgtcagtgcg gacgacgcgc aaaaactgct ggttgggctc aaccagcgta tagtcgtcaa cggtcgcacc
cagagaaaca ccaataccat gaaaaattac cttttgcccg tagtggccca ggcatttgct aggtgggcaa aggaatataa ggaagatcaa gaagatgaaa
ggccactagg actacgagat agacagttag tcatggggtg ttgttgggct tttagaaggc acaagataac atctatttat aagcgcccgg atacccaaac
catcatcaaa gtgaacagcg atttccactc attcgtgctg cccaggatag gcagtaacac attggagatc gggctgagaa caagaatcag gaaaatgtta
gaggagcaca aggagccgtc acctctcatt accgccgagg acgtacaaga agctaagtgc gcagccgatg aggctaagga ggtgcgtgaa
gccgaggagt tgcgcgcagc tctaccacct ttggcagctg atgttgagga gcccactctg gaagccgatg tcgacttgat gttacaagag
gctggggccg gctcagtgga gacacctcgt ggcttgataa aggttaccag ctacgctggc gaggacaaga tcggctctta cgctgtgctt tctccgcagg
ctgtactcaa gagtgaaaaa ttatcttgca tccaccctct cgctgaacaa gtcatagtga taacacactc tggccgaaaa gggcgttatg ccgtggaacc
ataccatggt aaagtagtgg tgccagaggg acatgcaata cccgtccagg actttcaagc tctgagtgaa agtgccacca ttgtgtacaa cgaacgtgag
ttcgtaaaca ggtacctgca ccatattgcc acacatggag gagcgctgaa cactgatgaa gaatattaca aaactgtcaa gcccagcgag
cacgacggcg aatacctgta cgacatcgac aggaaacagt gcgtcaagaa agaactagtc actgggctag ggctcacagg cgagctggtg
gatcctccct tccatgaatt cgcctacgag agtctgagaa cacgaccagc cgctccttac caagtaccaa ccataggggt gtatggcgtg ccaggatcag
gcaagtctgg catcattaaa agcgcagtca ccaaaaaaga tctagtggtg agcgccaaga aagaaaactg tgcagaaatt ataagggacg
tcaagaaaat gaaagggctg gacgtcaatg ccagaactgt ggactcagtg ctcttgaatg gatgcaaaca ccccgtagag accctgtata ttgacgaagc
ttttgcttgt catgcaggta ctctcagagc gctcatagcc attataagac ctaaaaaggc agtgctctgc ggggatccca aacagtgcgg ttttttttaac
atgatgtgcc tgaaagtgca ttttaaccac gagatttgca cacaagtctt ccacaaaagc atctctcgcc gttgcactaa atctgtgact tcggtcgtct
caaccttgtt ttacgacaaa aaaatgagaa cgacgaatcc gaaagagact aagattgtga ttgacactac cggcagtacc aaacctaagc aggacgatct
cattctcact tgtttcagag ggtgggtgaa gcagttgcaa atagattaca aaggcaacga aataatgacg gcagctgcct ctcaagggct gacccgtaaa
ggtgtgtatg ccgttcggta caaggtgaat gaaaatcctc tgtacgcacc cacctcagaa catgtgaacg tcctactgac ccgcacggag gaccgcatcg
tgtggaaaac actagccggc gacccatgga taaaaacact gactgccaag taccctggga atttcactgc cacgatagag gagtggcaag
cagagcatga tgccatcatg aggcacatct tggagagacc ggaccctacc gacgtcttcc agaataaggc aaacgtgtgt tgggccaagg
ctttagtgcc ggtgctgaag accgctggca tagacatgac cactgaacaa tggaacactg tggattattt tgaaacggac aaagctcact cagcagagat
agtattgaac caactatgcg tgaggttctt tggactcgat ctggactccg gtctattttc tgcacccact gttccgttat ccattaggaa taatcactgg
gataactccc cgtcgcctaa catgtacggg ctgaataaag aagtggtccg tcagctctct cgcaggtacc cacaactgcc tcgggcagtt gccactggaa
gagtctatga catgaacact ggtacactgc gcaattatga tccgcgcata aacctagtac ctgtaaacag aagactgcct catgctttag tcctccacca
taatgaacac ccacagagtg actttcttc attcgtcagc aaattgaagg gcagaactgt cctggtggtc ggggaaaagt tgtccgtccc aggcaaaatg
gttgactggt tgtcagaccg gcctgaggct accttcagag ctcggctgga tttaggcatc ccaggtgatg tgcccaaata tgacataata tttgttaatg
tgaggacccc atataaatac catcactatc agcagtgtga agaccatgcc attaagctta gcatgttgac caagaaagct tgtctgcatc tgaatcccgg -continued

```
cggaacctgt gtcagcatag gttatggtta cgctgacagg gccagcgaaa gcatcattgg tgctatagcg cggcagttca agttttcccg ggtatgcaaa
ccgaaatcct cacttgaaga gacggaagtt ctgtttgtat tcattgggta cgatcgcaag gcccgtacgc acaatcctta caagctttca tcaaccttga
ccaacattta tacaggttcc agactccacg aagccggatg tgcaccctca tatcatgtgg tgcgagggga tattgccacg gccaccgaag gagtgattat
aaatgctgct aacagcaaag gacaacctgg cggaggggtg tgcggagcgc tgtataagaa attcccggaa agcttcgatt tacagccgat
cgaagtagga aaagcgcgac tggtcaaagg tgcagctaaa catatcattc atgccgtagg accaaacttc aacaaagttt cggaggttga
aggtgacaaa cagttggcag aggcttatga gtccatcgct aagattgtca acgataacaa ttacaagtca gtagcgattc cactgttgtc caccggcatc
ttttccggga acaaagatcg actaacccaa tcattgaacc atttgctgac agctttagac accactgatg cagatgtagc catatactgc agggacaaga
aatgggaaat gactctcaag gaagcagtgg ctaggagaga agcagtggag gagatatgca tatccgacga ctcttcagtg acagaacctg
atgcagagct ggtgagggtg catccgaaga gttctttggc tggaaggaag ggctacagca caagcgatgg caaaactttc tcatatttgg
aagggaccaa gtttcaccag gcggccaagg atatagcaga aattaatgcc atgtggcccg ttgcaacgga ggccaatgag caggtatgca
tgtatatcct cggagaaagc atgagcagta ttaggtcgaa atgccccgtc gaagagtcgg aagcctccac accacctagc acgctgcctt gcttgtgcat
ccatgccatg actccagaaa gagtacagcg cctaaaagcc tcacgtccag aacaaattac tgtgtgctca tcctttccat tgccgaagta tagaatcact
ggtgtgcaga agatccaatg ctcccagcct atattgttct caccgaaagt gcctgcgtat attcatccaa ggaagtatct cgtggaaaca ccaccggtag
acgagactcc ggagccatcg gcagagaacc aatccacaga ggggacacct gaacaaccac cacttataac cgaggatgag accaggacta
gaacgcctga gccgatcatc atcgaagagg aagaagagga tagcataagt ttgctgtcag atggcccgac ccaccaggtg ctgcaagtcg
aggcagacat tcacgggccg ccctctgtat ctagctcatc ctggtccatt cctcatgcat ccgactttga tgtggacagt ttatccatac ttgacaccct
ggagggagct agcgtgacca gcggggcaac gtcagccgag actaactctt acttcgcaaa gagtatggag tttctggcgc gaccggtgcc
tgcgcctcga acagtattca ggaaccctcc acatcccgct ccgcgcacaa gaacaccgtc acttgcaccc agcagggcct gctcgagaac
cagcctagtt tccaccccgc caggcgtgaa tagggtgatc actagagagg agctcgaggc gcttaccccg tcacgcactc ctagcaggtc
ggtctcgaga accagcctgg tctccaaccc gccaggcgta aatagggtga ttacaagaga ggagtttgag gcgttcgtag cacaacaaca
atgacggttt gatgcgggtg catacatctt ttcctccgac accggtcaag ggcatttaca acaaaaatca gtaaggcaaa cggtgctatc cgaagtggtg
ttggagagga ccgaattgga gatttcgtat gccccgcgcc tcgaccaaga aaaagaagaa ttactacgca agaaattaca gttaaatccc acacctgcta
acagaagcag ataccagtcc aggaaggtgg agaacatgaa agccataaca gctagacgta ttctgcaagg cctagggcat tatttgaagg
cagaaggaaa agtggagtgc taccgaaccc tgcatcctgt tcctttgtat tcatctagtg tgaaccgtgc cttttcaagc cccaaggtcg cagtggaagc
ctgtaacgcc atgttgaaag agaactttcc gactgtggct tcttactgta ttattccaga gtacgatgcc tatttggaca tggttgacgg agcttcatgc
tgcttagaca ctgccagttt ttgccctgca aagctgcgca gctttccaaa gaaacactcc tatttggaac ccacaatacg atcggcagtg ccttcagcga
tccagaacac gctccagaac gtcctggcag ctgccacaaa aagaaattgc aatgtcacgc aaatgagaga attgcccgta ttggattcgg cggcctttaa
tgtggaatgc ttcaagaaat atgcgtgtaa taatgaatat tgggaaacgt ttaaagaaaa ccccatcagg cttactgaag aaaacgtggt aaattacatt
accaaattaa aaggaccaaa agctgctgct ctttttgcga agacacataa tttgaatatg ttgcaggaca taccaatgga caggtttgta atggacttaa
agagagacgt gaaagtgact ccaggaacaa aacatactga agaacggccc aaggtacagg tgatccaggc tgccgatccg ctagcaacag
cgtatctgtg cggaatccac cgagagctgg ttaggagatt aaatgcggtc ctgcttccga acattcatac actgtttgat atgtcggctg aagactttga
cgctattata gccgagcact tccagcctgg ggattgtgtt ctggaaactg acatcgcgtc gtttgataaa agtgaggacg acgccatggc tctgaccgcg
ttaatgattc tggaagactt aggtgtggac gcagagctgt tgacgctgat tgaggcggct ttcggcgaaa tttcatcaat acatttgccc actaaaacta
aatttaaatt cggagccatg atgaaatctg gaatgttcct cacactgttt gtgaacacag tcattaacat tgtaatcgca agcagagtgt tgagagaacg
gctaaccgga tcaccatgtg cagcattcat tggagatgac aatatcgtga aaggagtcaa atcggacaaa ttaatggcag acaggtgcgc cacctggttg
aatatggaag tcaagattat agatgctgtg gtgggcgaga aagcgcctta tttctgtgga gggtttattt tgtgtgactc cgtgaccggc acagcgtgcc
gtgtggcaga ccccctaaaa aggctgttta agcttggcaa acctctggca gcagacgatg aacatgatga tgacaggaga agggcattgc
atgaagagtc aacacgctgg aaccgagtgg gtattctttc agagctgtgc aaggcagtag aatcaaggta tgaaaccgta ggaacttcca tcatagttat
ggccatgact actctagcta gcagtgttaa atcattcagc tacctgagag ggcccctat aactctctac ggctaacctg aatggactac gacatagtct
agtccgccaa gatgttcccg ttccagccaa tgtatccgat gcagccaatg ccctatcgca acccgttcgc ggccccgcgc aggccctggt
tccccagaac cgacccttt ctggcgatgc aggtgcagga attaacccgc tcgatggcta acctgacgtt caagcaacgc cgggacgcgc
cacctgaggg gccatccgct aagaaaccga agaaggaggc ctcgcaaaaa cagaaagggg gaggccaagg gaagaagaag aagaaccaag
ggaagaagaa ggctaagaca gggccgccta atccgaaggc acagaatgga aacaagaaga agaccaacaa gaaaccaggc aagagacagc
gcatggtcat gaaattggaa tctgacaaga cgttcccaat catgttggaa gggaagataa acggctacgc ttgtgtggtc ggagggaagt tattcaggcc
gatgcatgtg gaaggcaaga tcgacaacga cgttctggcc gcgcttaaga cgaagaaagc atccaaatac gatcttgagt atgcagatgt
gccacagaac atgcgggccg atacattcaa atacacccat gagaaacccc aaggctatta cagctggcat catggagcag tccaatatga
aaatgggcgt ttcacggtgc cgaaaggagt tggggccaag ggagacagcg gacgacccat tctggataac cagggacggg tggtcgctat
tgtgctggga ggtgtgaatg aaggatctag gacagccctt tcagtcgtca tgtggaacga gaagggagtt accgtgaagt atactccgga
gaactgcgag caatggtcac tagtgaccac catgtgtctg ctcgccaatg tgacgttccc atgtgctcaa ccaccaattt gctacgacag aaaaccagca
gagactttgg ccatgctcag cgttaacgtt gacaacccgg gctacgatga gctgctggaa gcagctgtta agtgccccgg aaggaaaagg
agatccaccg aggagctgtt taaggagtat aagctaacgc gcccttacat ggccagatgc atcagatgtg cagttgggag ctgccatagt ccaatagcaa
tcgaggcagt aaagagcgac gggcacgacg gttatgttag acttcagact tcctcgcagt atggcctgga ttcctccggc aacttaaagg gcaggaccat
gcggtatgac atgcacggga ccattaaaga gataccacta catcaagtgt cactccatac atctcgcccg tgtcacattg tggatgggca cggttatttc
ctgcttgcca ggtgcccggc aggggactcc atcaccatgg aatttaagaa agattccgtc acacactcct gctcggtgcc gtatgaagtg aaatttaatc
```

-continued ctgtaggcag agaactctat actcatcccc cagaacacgg agtagagcaa gcgtgccaag tctacgcaca tgatgcacag aacagaggag
cttatgtcga gatgcacctc ccgggctcag aagtggacag cagtttggtt tccttgagcg gcagttcagt caccgtgaca cctcctgttg ggactagcgc
cctggtggaa tgcgagtgtg gcggcacaaa gatctccgag accatcaaca agacaaaaca gttcagccag tgcacaaaga aggagcagtg
cagagcatat cggctgcaga acgataagtg ggtgtataat tctgacaaac tgcccaaagc agcgggagcc accttaaaag gaaaactgca tgtcccattc
ttgctggcag acggcaaatg caccgtgcct ctagcaccag aacctatgat aacctttggt ttcagatcag tgtcactgaa actgcaccct aagaatccca
catatctaac cacccgccaa cttgctgatg agcctcacta cacgcacgag ctcatatctg aaccagctgt taggaatttt accgtcaccg aaaaagggtg
ggagtttgta tggggaaacc acccgccgaa aaggttttgg gcacaggaaa cagcacccgg aaatccacat gggctaccgc acgaggtgat
aactcattat taccacagat accctatgtc caccatcctg ggtttgtcaa tttgtgccgc cattgcaacc gtttccgttg cagcgtctac ctggctgttt
tgcagatcta gagttgcgtg cctaactcct taccggctaa cacctaacgc taggatacca ttttgtctgg ctgtgctttg ctgcgcccgc actgcccggg
ccgagaccac ctgggagtcc ttggatcacc tatggaacaa taaccaacag atgttctgga ttcaattgct gatccctctg gccgccttga tcgtagtgac
tcgcctgctc aggtgcgtgt gctgtgtcgt gcctttttta gtcatggccg gcgccgcagg cgccggcgcc tacgagcacg cgaccacgat
gccgagccaa gcgggaatct cgtataacac tatagtcaac agagcaggct acgcaccact ccctatcagc ataacaccaa caaagatcaa
gctgatacct acagtgaact tggagtacgt cacctgccac tacaaaacag gaatggattc accagccatc aaatgctgcg gatctcagga atgcactcca
acttacaggc ctgatgaaca gtgcaaagtc ttcacagggg tttacccgtt catgtggggt ggtgcatatt gcttttgcga cactgagaac acccaagtca
gcaaggccta cgtaatgaaa tctgacgact gccttgcgga tcatgctgaa gcatataaag cgcacacagc ctcagtgcag gcgttcctca acatcacagt
gggagaacac tctattgtga ctaccgtgta tgtgaatgga gaaactcctg tgaatttcaa tggggtcaaa ttaactgcag gtccgctttc cacagcttgg
acaccctttg atcgcaaaat cgtgcagtat gccggggaga tctataatta tgattttcct gagtatgggg caggacaacc aggagcattt ggagatatac
aatccagaac agtctcaagc tcagatctgt atgccaatac caacctagtg ctgcagagac ccaaagcagg agcgatccac gtgccataca
ctcaggcacc ttcgggtttt gagcaatgga agaaagataa agctccatca ttgaaattta ccgccccttt cggatgcgaa atatatacaa accccattcg
cgccgaaaac tgtgctgtag ggtcaattcc attagccttt gacattcccg acgccttgtt caccagggtg tcagaaacac cgacactttc agcggccgaa
tgcactctta acgagtgcgt gtattcttcc gactttggtg ggatcgccac ggtcaagtac tcggccagca agtcaggcaa gtgcgcagtc catgtgccat
cagggactgc taccctaaaa gaagcagcag tcgagctaac cgagcaaggg tcggcgacta tccatttctc gaccgcaaat atccacccgg
agttcaggct ccaaatatgc acatcatatg ttacgtgcaa aggtgattgt caccccccga aagaccatat tgtgacacac cctcagtatc acgcccaaac
atttacagcc gcggtgtcaa aaaccgcgtg gacgtggtta acatccctgc tgggaggatc agccgtaatt attataattg gcttggtgct ggctactatt
gtggccatgt acgtgctgac caaccagaaa cataattgaa tacagcagca attggcaagc tgcttacata gaactcgcgg cgattggcat gccgccttaa
aatttttatt ttatttttc ttttcttttc cgaatcggat tttgttttta atatttc VEE-MAG25 mer (SEQ ID NO: 4); contains MAG-25 merPDTT nucleotide (bases 30-1755)

atgggcggcgcatgagagaagcccagaccaattacctacccaaaatggagaaagttcacgttgacatcgaggaagacagcccattcctcagagct
ttgcagcggagcttcccgcagtttgaggtagaagccaagcaggtcactgataatgaccatgctaatgccagagcgttttcgcatctggcttcaaaactgatcgaaac
ggaggtggacccatccgacacgatccttgacattggaagtgcgcccgcccgcagaatgtattctaagcacaagtatcattgtatctgtccgatgagatgtgcggaa
gatccggacagattgtataagtatgcaactaagctgaagaaaaactgtaaggaaataactgataaggaattggacaagaaaatgaaggagctcgccgccgtcatg
agcgaccctgacctggaaactgagactatgtgcctccacgacgacgagtcgtgtcgctacgaagggcaagtcgctgtttaccaggatgtatacgcggttgacgg
accgacaagtctctatcaccaagccaataagggagttagagtcgcctactggataggctttgacaccaccccttttatgtttaagaacttggctggagcatatccatc
atactctaccaactgggccgacgaaaccgtgttaacggctcgtaacataggcctatgcagctctgacgttatggagcggtcacgtagagggatgtccattcttaga
aagaagtatttgaaaccatccaacaatgttctattctctgttggctcgaccatctaccacgagaagagggacttactgaggagctggcacctgccgtctgtatttcact
tacgtggcaagcaaaattacacatgtcggtgtgagactatagttagttgcgacgggtacgtcgttaaaagaatagctatcagtccaggcctgtatgggaagccttca
ggctatgctgctacgatgcaccgcgagggattcttgtgctgcaaagtgacagacacattgaacggggagagggtctcttttcccgtgtgcacgtatgtgccagcta
cattgtgtgaccaaatgactggcatactggcaacagatgtcagtgcggacgacgcgcaaaaactgctggttgggctcaaccagcgtatagtcgtcaacggtcgca
cccagagaaacaccaataccatgaaaaattaccttttgcccgtagtggcccaggcatttgctaggtgggcaaaggaatataaggaagatcaagaagatgaaagg
ccactaggactacgagatagacagttagtcatggggtgttgttgggcttttagaaggcacaagataacatctatttataagcgcccggatacccaaaccatcatcaa
agtgaacagcgatttccactcattcgtgctgcccaggataggcagtaacacattggagatcgggctgagaacaagaatcaggaaaatgttagaggagcacaagg
agccgtcacctctcattaccgccgaggacgtacaagaagctaagtgcgcagccgatgaggctaaggaggtgcgtgaagccgaggagttgcgcgcagctctac
cacctttggcagctgatgttgaggagcccactctggaagccgatgtcgacttgatgttacaagaggctggggccggctcagtggagacacctcgtggcttgataa
aggttaccagctacgctggcgaggacaagatcggctcttacgctgtgctttctccgcaggctgtactcaagagtgaaaaattatcttgcatccaccctctcgctgaac
aagtcatagtgataacacactctggccgaaaagggcgttatgccgtggaaccataccatggtaaagtagtggtgccagagggacatgcaatacccgtccaggac
tttcaagctctgagtgaaagtgccaccattgtgtacaacgaacgtgagttcgtaaacaggtacctgcaccatattgccacacatggaggagcgctgaacactgatg
aagaatattacaaaactgtcaagcccagcgagcacgacggcgaatacctgtacgacatcgacaggaaacagtgcgtcaagaaagaactagtcactgggctagg
gctcacaggcgagctggtggatcctcccttccatgaattcgcctacgagagtctgagaacacgaccagccgctccttaccaagtaccaaccataggggtgtatgg
cgtgccaggatcaggcaagtctggcatcattaaaagcgcagtcaccaaaaaagatctagtggtgagcgccaagaaagaaaactgtgcagaaattataagggac
gtcaagaaaatgaaagggctggacgtcaatgccagaactgtggactcagtgctcttgaatggatgcaaacaccccgtagagaccctgtatattgacgaagcttttg
cttgtcatgcaggtactctcagagcgctcatagccattataagacctaaaaaggcagtgctctgcggggatcccaaacagtgcggtttttttaacatgatgtgcctga
aagtgcattttaaccacgagatttgcacacaagtcttccacaaaagcatctctcgccgttgcactaaatctgtgacttcggtcgtctcaaccttgttttacgacaaaaaa
atgagaacgacgaatccgaaagagactaagattgtgattgacactaccggcagtaccaaacctaagcaggacgatctcattctcacttgtttcagagggggtga -continued agcagttgcaaatagattacaaaggcaacgaaataatgacggcagctgcctctcaagggctgacccgtaaaggtgtgtatgccgttcggtacaaggtgaatgaaa
atcctctgtacgcacccacctcagaacatgtgaacgtcctactgacccgcacggaggaccgcatcgtgtggaaaacactagccggcgacccatggataaaaaca
ctgactgccaagtaccctgggaatttcactgccacgatagaggagtggcaagcagagcatgatgccatcatgaggcacatcttggagagaccggaccctaccga
cgtcttccagaataaggcaaacgtgtgttgggccaaggctttagtgccggtgctgaagaccgctggcatagacatgaccactgaacaatggaacactgtggattat
tttgaaacggacaaagctcactcagcagagatagtattgaaccaactatgcgtgaggttctttggactcgatctggactccggtctattttctgcacccactgttccgtt
atccattaggaataatcactgggataactccccgtcgcctaacatgtacgggctgaataaagaagtggtccgtcagctctctcgcaggtacccacaactgcctcgg
gcagttgccactggaagagtctatgacatgaacactggtacactgcgcaattatgatccgcgcataaacctagtacctgtaaacagaagactgcctcatgctttagt
cctccaccataatgaacacccacagagtgacttttcttcattcgtcagcaaattgaagggcagaactgtcctggtggtcggggaaaagttgtccgtcccaggcaaa
atggttgactggttgtcagaccggcctgaggctaccttcagagctcggctggatttaggcatcccaggtgatgtgcccaaatatgacataatatttgttaatgtgagg
accccatataaataccatcactatcagcagtgtgaagaccatgccattaagcttagcatgttgaccaagaaagcttgtctgcatctgaatcccggcggaacctgtgtc
agcataggttatggttacgctgacagggccagcgaaagcatcattggtgctatagcgcggcagttcaagttttcccgggtatgcaaaccgaaatcctcacttgaag
agacggaagttctgtttgtattcattgggtacgatcgcaaggcccgtacgcacaatccttacaagctttcatcaaccttgaccaacatttatacaggttccagactcca
cgaagccggatgtgcaccctcatatcatgtggtgcgaggggatattgccacggccaccgaaggagtgattataaatgctgctaacagcaaaggacaacctggcg
gaggggtgtgcggagcgctgtataagaaattcccggaaagcttcgatttacagccgatcgaagtaggaaaagcgcgactggtcaaaggtgcagctaaacatatc
attcatgccgtaggaccaaacttcaacaaagtttcggaggttgaaggtgacaaacagttggcagaggcttatgagtccatcgctaagattgtcaacgataacaatta
caagtcagtagcgattccactgttgtccaccggcatcttttccgggaacaaagatcgactaacccaatcattgaaccatttgctgacagctttagacaccactgatgc
agatgtagccatatactgcagggacaagaaatgggaaatgactctcaaggaagcagtggctaggagagaagcagtggaggagatatgcatatccgacgactctt
cagtgacagaacctgatgcagagctggtgagggtgcatccgaagagttctttggctggaaggaagggctacagcacaagcgatggcaaaactttctcatatttgg
aagggaccaagtttcaccaggcggccaaggatatagcagaaattaatgccatgtggcccgttgcaacggaggccaatgagcaggtatgcatgtatatcctcgga
gaaagcatgagcagtattaggtcgaaatgccccgtcgaagagtcggaagcctccacaccacctagcacgctgccttgcttgtgcatccatgccatgactccagaa
agagtacagcgcctaaaagcctcacgtccagaacaaattactgtgtgctcatcctttccattgccgaagtatagaatcactggtgtgcagaagatccaatgctccca
gcctatattgttctcaccgaaagtgcctgcgtatattcatccaaggaagtatctcgtggaaacaccaccggtagacgagactccggagccatcggcagagaacca
atccacagaggggacacctgaacaaccaccacttataaccgaggatgagaccaggactagaacgcctgagccgatcatcatcgaagaggaagaagaggatag
cataagtttgctgtcagatggcccgacccaccaggtgctgcaagtcgaggcagacattcacgggccgccctctgtatctagctcatcctggtccattcctcatgcat
ccgactttgatgtggacagtttatccatacttgacaccctggagggagctagcgtgaccagcggggcaacgtcagccgagactaactcttacttcgcaaagagtat
ggagtttctggcgcgaccggtgcctgcgcctcgaacagtattcaggaaccctccacatcccgctccgcgcacaagaacaccgtcacttgcacccagcagggcct
gctcgagaaccagcctagtttccaccccgccaggcgtgaatagggtgatcactagagaggagctcgaggcgcttaccccgtcacgcactcctagcaggtcggtc
tcgagaaccagcctggtctccaacccgccaggcgtaaatagggtgattacaagagaggagtttgaggcgttcgtagcacaacaacaatgacggtttgatgcggg
tgcatacatcttttcctccgacaccggtcaagggcatttacaacaaaaatcagtaaggcaaacggtgctatccgaagtggtgttggagaggaccgaattggagattt
cgtatgccccgcgcctcgaccaagaaaaagaagaattactacgcaagaaattacagttaaatcccacacctgctaacagaagcagataccagtccaggaaggtg
gagaacatgaaagccataacagctagacgtattctgcaaggcctagggcattatttgaaggcagaaggaaaagtggagtgctaccgaaccctgcatcctgttcctt
tgtattcatctagtgtgaaccgtgccttttcaagccccaaggtcgcagtggaagcctgtaacgccatgttgaaagagaactttccgactgtggcttcttactgtattattc
cagagtacgatgcctatttggacatggttgacggagcttcatgctgcttagacactgccagtttttgccctgcaaagctgcgcagctttccaaagaaacactcctattt
ggaacccacaatacgatcggcagtgccttcagcgatccagaacacgctccagaacgtcctggcagctgccacaaaaagaaattgcaatgtcacgcaaatgaga
gaattgcccgtattggattcggcggcctttaatgtggaatgcttcaagaaatatgcgtgtaataatgaatattgggaaacgtttaaagaaaaccccatcaggcttactg
aagaaaacgtggtaaattacattaccaaattaaaaggaccaaaagctgctgctctttttgcgaagacacataatttgaatatgttgcaggacataccaatggacaggt
ttgtaatggacttaaagagagacgtgaaagtgactccaggaacaaaacatactgaagaacggcccaaggtacaggtgatccaggctgccgatccgctagcaaca
gcgtatctgtgcggaatccaccgagagctggttaggagattaaatgcggtcctgcttccgaacattcatacactgtttgatatgtcggctgaagactttgacgctatta
tagccgagcacttccagcctggggattgtgttctggaaactgacatcgcgtcgtttgataaaagtgaggacgacgccatggctctgaccgcgttaatgattctggaa
gacttaggtgtggacgcagagctgttgacgctgattgaggcggctttcggcgaaatttcatcaatacatttgcccactaaaactaaatttaaattcggagccatgatg
aaatctggaatgttcctcacactgtttgtgaacacagtcattaacattgtaatcgcaagcagagtgttgagagaacggctaaccggatcaccatgtgcagcattcatt
ggagatgacaatatcgtgaaaggagtcaaatcggacaaattaatggcagacaggtgcgccacctggttgaatatggaagtcaagattatagatgctgtggtgggc
gagaaagcgccttatttctgtggagggtttattttgtgtgactccgtgaccggcacagcgtgccgtgtggcagacccccctaaaaaggctgtttaagcttggcaaacct
ctggcagcagacgatgaacatgatgatgacaggagaagggcattgcatgaagagtcaacacgctggaaccgagtgggtattctttcagagctgtgcaaggcagt
agaatcaaggtatgaaaccgtaggaacttccatcatagttatggccatgactactctagctagcagtgttaaatcattcagctacctgagaggggcccctataactct
ctacggctaacctgaatggactacgactctagaatagtctttaatTAAGCCACCATGGCAGGCATGTTTCAGGCGCTGAGCGA
AGGCTGCACCCCGTATGATATTAACCAGATGCTGAACGTGCTGGGCGATCATCAGGTCTCAGGCC
TTGAGCAGCTTGAGAGTATAATCAACTTTGAAAAACTGACTGAATGGACCAGTTCTAATGTTATG
CCTATCCTGTCTCCTCTGACAAAGGGCATCCTGGGCTTCGTGTTTACCCTGACCGTGCCTTCTGAG
AGAGGACTTAGCTGCATTAGCGAAGCGGATGCGACCACCCCGGAAAGCGCGAACCTGGGCGAAG
AAATTCTGAGCCAGCTGTATCTTTGGCCAAGGGTGACCTACCATTCCCCTAGTTATGCTTACCACC
AATTTGAAAGACGAGCCAAATATAAAAGACACTTCCCCGGCTTTGGCCAGAGCCTGCTGTTTGGC
TACCCTGTGTACGTGTTCGGCGATTGCGTGCAGGGCGATTGGGATGCGATTCGCTTTCGCTATTGC
GCGCCGCCGGGCTATGCGCTGCTGCGCTGCAACGATACCAACTATAGCGCTCTGCTGGCTGTGGG -continued GGCCCTAGAAGGACCCAGGAATCAGGACTGGCTTGGTGTCCCAAGACAACTTGTAACTCGGATGC
AGGCTATTCAGAATGCCGGCCTGTGTACCCTGGTGGCCATGCTGGAAGAGACAATCTTCTGGCTG
CAAGCGTTTCTGATGGCGCTGACCGATAGCGGCCCGAAAACCAACATTATTGTGGATAGCCAGTA
TGTGATGGGCATTAGCAAACCGAGCTTTCAGGAATTTGTGGATTGGGAAAACGTGAGCCCGGAAC
TGAACAGCACCGATCAGCCGTTTTGGCAAGCCGGAATCCTGGCCAGAAATCTGGTGCCTATGGTG
GCCACAGTGCAGGGCCAGAACCTGAAGTACCAGGGTCAGTCACTAGTCATCTCTGCTTCTATCATT
GTCTTCAACCTGCTGGAACTGGAAGGTGATTATCGAGATGATGGCAACGTGTGGGTGCATACCCC
GCTGAGCCCGCGCACCCTGAACGCGTGGGTGAAAGCGGTGGAAGAAAAAAAAGGTATTCCAGTT
CACCTAGAGCTGGCCAGTATGACCAACATGGAGCTCATGAGCAGTATTGTGCATCAGCAGGTCAG
AACATACGGCCCCGTGTTCATGTGTCTCGGCGGACTGCTTACAATGGTGGCTGGTGCTGTGTGGCT
GACAGTGCGAGTGCTCGAGCTGTTCCGGGCCGCGCAGCTGGCCAACGACGTGGTCCTCCAGATCA
TGGAGCTTTGTGGTGCAGCGTTTCGCCAGGTGTGCCATACCACCGTGCCGTGGCCGAACGCGAGC
CTGACCCCGAAATGGAACAACGAAACCACCCAGCCCCAGATCGCCAACTGCAGCGTGTATGACTT
TTTTGTGTGGCTCCATTATTATTCTGTTCGAGACACACTTTGGCCAAGGGTGACCTACCATATGAA
CAAATATGCGTATCATATGCTGGAAAGACGAGCCAAATATAAAAGAGGACCAGGACCTGGCGCT
AAATTTGTGGCCGCCTGGACACTGAAAGCCGCTGCTGGTCCTGGACCTGGCCAGTACATCAAGGC
CAACAGCAAGTTCATCGGCATCACCGAACTCGGACCCGGACCAGGCTGATGATTcgaacggccgtatcacg
cccaaacatttacagccgcggtgtcaaaaaccgcgtggacgtggttaacatccctgctgggaggatcagccgtaattattataattggcttggtgctggctactattg
tggccatgtacgtgctgaccaaccagaaacataattgaatacagcagcaattggcaagctgcttacatagaactcgcggcgattggcatgccgccttaaaatttttat
tttatttttcttttcttttccgaatcggattttgtttttaatatttcaaaaaaaaaaaaaaaaaaaaaaaaaaaaaaaaaaaaaaaaaaaaaaaaaaaaaaaaa
aaaaaaaaaaaaaaaa Venezuelan equine encephalitis virus strain TC-83 [TC-83](SEQ ID NO: 5) GenBank: L01443.1
atgggcggcg catgagagaa gcccagacca attacctacc caaaatggag aaagttcacg ttgacatcga ggaagacagc ccattcctca
gagctttgca gcggagcttc ccgcagtttg aggtagaagc caagcaggtc actgataatg accatgctaa tgccagagcg ttttcgcatc tggcttcaaa
actgatcgaa acggaggtgg acccatccga cacgatcctt gacattggaa gtgcgcccgc ccgcagaatg tattctaagc acaagtatca ttgtatctgt
ccgatgagat gtgcggaaga tccggacaga ttgtataagt atgcaactaa gctgaagaaa aactgtaagg aaataactga taaggaattg
gacaagaaaa tgaaggagct cgccgccgtc atgagcgacc ctgacctgga aactgagact atgtgcctcc acgacgacga gtcgtgtcgc
tacgaagggc aagtcgctgt ttaccaggat gtatacgcgg ttgacggacc gacaagtctc tatcaccaag ccaataaggg agttagagtc gcctactgga
taggctttga caccacccct tttatgttta agaacttggc tggagcatat ccatcatact ctaccaactg ggccgacgaa accgtgttaa cggctcgtaa
cataggccta tgcagctctg acgttatgga gcggtcacgt agagggatgt ccattcttag aaagaagtat ttgaaaccat ccaacaatgt tctattctct
gttggctcga ccatctacca cgagaagagg gacttactga ggagctggca cctgccgtct gtatttcact tacgtggcaa gcaaaattac acatgtcggt
gtgagactat agttagttgc gacgggtacg tcgttaaaag aatagctatc agtccaggcc tgtatgggaa gccttcaggc tatgctgcta cgatgcaccg
cgagggattc ttgtgctgca aagtgacaga cacattgaac ggggagaggg tctcttttcc cgtgtgcacg tatgtgccag ctacattgtg tgaccaaatg
actggcatac tggcaacaga tgtcagtgcg gacgacgcgc aaaaactgct ggttgggctc aaccagcgta tagtcgtcaa cggtcgcacc
cagagaaaca ccaataccat gaaaaattac cttttgcccg tagtggccca ggcatttgct aggtgggcaa aggaatataa ggaagatcaa gaagatgaaa
ggccactagg actacgagat agacagttag tcatggggtg ttgttgggct tttagaaggc acaagataac atctatttat aagcgcccgg atacccaaac
catcatcaaa gtgaacagcg atttccactc attcgtgctg cccaggatag gcagtaacac attggagatc gggctgagaa caagaatcag gaaaatgtta
gaggagcaca aggagccgtc acctctcatt accgccgagg acgtacaaga agctaagtgc gcagccgatg aggctaagga ggtgcgtgaa
gccgaggagt tgcgcgcagc tctaccacct ttggcagctg atgttgagga gcccactctg gaagccgatg tcgacttgat gttacaagag
gctggggccg gctcagtgga gacacctcgt ggcttgataa aggttaccag ctacgctggc gaggacaaga tcggctctta cgctgtgctt tctccgcagg
ctgtactcaa gagtgaaaaa ttatcttgca tccaccctct cgctgaacaa gtcatagtga taacacactc tggccgaaaa gggcgttatg ccgtggaacc
ataccatggt aaagtagtgg tgccagaggg acatgcaata cccgtccagg actttcaagc tctgagtgaa agtgccacca ttgtgtacaa cgaacgtgag
ttcgtaaaca ggtacctgca ccatattgcc acacatggag gagcgctgaa cactgatgaa gaatattaca aaactgtcaa gcccagcgag
cacgacggcg aatacctgta cgacatcgac aggaaacagt gcgtcaagaa agaactagtc actgggctag ggctcacagg cgagctggtg
gatcctccct tccatgaatt cgcctacgag agtctgagaa cacgaccagc cgctccttac caagtaccaa ccataggggt gtatggcgtg ccaggatcag
gcaagtctgg catcattaaa agcgcagtca ccaaaaaaga tctagtggtg agcgccaaga aagaaaactg tgcagaaatt ataagggacg
tcaagaaaat gaaagggctg gacgtcaatg ccagaactgt ggactcagtg ctcttgaatg gatgcaaaca ccccgtagag accctgtata ttgacgaagc
ttttgcttgt catgcaggta ctctcagagc gctcatagcc attataagac ctaaaaaggc agtgctctgc ggggatccca aacagtgcgg tttttttaac
atgatgtgcc tgaaagtgca ttttaaccac gagatttgca cacaagtctt ccacaaaagc atctctcgcc gttgcactaa atctgtgact tcggtcgtct
caaccttgtt ttacgacaaa aaaatgagaa cgacgaatcc gaaagagact aagattgtga ttgacactac cggcagtacc aaacctaagc aggacgatct
cattctcact tgtttcagag ggtgggtgaa gcagttgcaa atagattaca aaggcaacga aataatgacg gcagctgcct ctcaagggct gacccgtaaa
ggtgtgtatg ccgttcggta caaggtgaat gaaaatcctc tgtacgcacc cacctcagaa catgtgaacg tcctactgac ccgcacggag gaccgcatcg
tgtggaaaac actagccggc gacccatgga taaaaacact gactgccaag taccctggga atttcactgc cacgatagag gagtggcaag -continued

```
cagagcatga tgccatcatg aggcacatct tggagagacc ggaccctacc gacgtcttcc agaataaggc aaacgtgtgt tgggccaagg
ctttagtgcc ggtgctgaag accgctggca tagacatgac cactgaacaa tggaacactg tggattattt tgaaacggac aaagctcact cagcagagat
agtattgaac caactatgcg tgaggttctt tggactcgat ctggactccg gtctattttc tgcacccact gttccgttat ccattaggaa taatcactgg
gataactccc cgtcgcctaa catgtacggg ctgaataaag aagtggtccg tcagctctct cgcaggtacc cacaactgcc tcgggcagtt gccactggaa
gagtctatga catgaacact ggtacactgc gcaattatga tccgcgcata aacctagtac ctgtaaacag aagactgcct catgctttag tcctccacca
taatgaacac ccacagagtg acttttcttc attcgtcagc aaattgaagg gcagaactgt cctggtggtc ggggaaaagt tgtccgtccc aggcaaaatg
gttgactggt tgtcagaccg gcctgaggct accttcagag ctcggctgga tttaggcatc ccaggtgatg tgcccaaata tgacataata tttgttaatg
tgaggacccc atataaatac catcactatc agcagtgtga agaccatgcc attaagctta gcatgttgac caagaaagct tgtctgcatc tgaatcccgg
cggaacctgt gtcagcatag gttatggtta cgctgacagg gccagcgaaa gcatcattgg tgctatagcg cggcagttca agttttcccg ggtatgcaaa
ccgaaatcct cacttgaaga gacggaagtt ctgtttgtat tcattgggta cgatcgcaag gcccgtacgc acaatcctta caagctttca tcaaccttga
ccaacattta tacaggttcc agactccacg aagccggatg tgcaccctca tatcatgtgg tgcgagggga tattgccacg gccaccgaag gagtgattat
aaatgctgct aacagcaaag gacaacctgg cggaggggtg tgcggagcgc tgtataagaa attcccggaa agcttcgatt tacagccgat
cgaagtagga aaagcgcgac tggtcaaagg tgcagctaaa catatcattc atgccgtagg accaaacttc aacaaagttt cggaggttga
aggtgacaaa cagttggcag aggcttatga gtccatcgct aagattgtca acgataacaa ttacaagtca gtagcgattc cactgttgtc caccggcatc
ttttccggga acaaagatcg actaacccaa tcattgaacc atttgctgac agctttagac accactgatg cagatgtagc catatactgc agggacaaga
aatgggaaat gactctcaag gaagcagtgg ctaggagaga agcagtggag gagatatgca tatccgacga ctcttcagtg acagaacctg
atgcagagct ggtgagggtg catccgaaga gttctttggc tggaaggaag ggctacagca caagcgatgg caaaactttc tcatatttgg
aagggaccaa gtttcaccag gcggccaagg atatagcaga aattaatgcc atgtggcccg ttgcaacgga ggccaatgag caggtatgca
tgtatatcct cggagaaagc atgagcagta ttaggtcgaa atgccccgtc gaagagtcgg aagcctccac accacctagc acgctgcctt gcttgtgcat
ccatgccatg actccagaaa gagtacagcg cctaaaagcc tcacgtccag aacaaattac tgtgtgctca tcctttccat tgccgaagta tagaatcact
ggtgtgcaga agatccaatg ctcccagcct atattgttct caccgaaagt gcctgcgtat attcatccaa ggaagtatct cgtggaaaca ccaccggtag
acgagactcc ggagccatcg gcagagaacc aatccacaga ggggacacct gaacaaccac cacttataac cgaggatgag accaggacta
gaacgcctga gccgatcatc atcgaagagg aagaagagga tagcataagt ttgctgtcag atggcccgac ccaccaggtg ctgcaagtcg
aggcagacat tcacgggccg ccctctgtat ctagctcatc ctggtccatt cctcatgcat ccgactttga tgtggacagt ttatccatac ttgacaccct
ggagggagct agcgtgacca gcggggcaac gtcagccgag actaactctt acttcgcaaa gagtatggag tttctggcgc gaccggtgcc
tgcgcctcga acagtattca ggaaccctcc acatcccgct ccgcgcacaa gaacaccgtc acttgcaccc agcagggcct gctcgagaac
cagcctagtt tccaccccgc caggcgtgaa tagggtgatc actagagagg agctcgaggc gcttaccccg tcacgcactc ctagcaggtc
ggtctcgaga accagcctgg tctccaaccc gccaggcgta aatagggtga ttacaagaga ggagtttgag gcgttcgtag cacaacaaca
atgacggttt gatgcgggtg catacatctt ttcctccgac accggtcaag ggcatttaca acaaaaatca gtaaggcaaa cggtgctatc cgaagtggtg
ttggagagga ccgaattgga gatttcgtat gccccgcgcc tcgaccaaga aaaagaagaa ttactacgca agaaattaca gttaaatccc acacctgcta
acagaagcag ataccagtcc aggaaggtgg agaacatgaa agccataaca gctagacgta ttctgcaagg cctagggcat tatttgaagg
cagaaggaaa agtggagtgc taccgaaccc tgcatcctgt tcctttgtat tcatctagtg tgaaccgtgc cttttcaagc cccaaggtcg cagtggaagc
ctgtaacgcc atgttgaaag agaactttcc gactgtggct tcttactgta ttattccaga gtacgatgcc tatttggaca tggttgacgg agcttcatgc
tgcttagaca ctgccagttt ttgccctgca aagctgcgca gctttccaaa gaaacactcc tatttggaac ccacaatacg atcggcagtg ccttcagcga
tccagaacac gctccagaac gtcctggcag ctgccacaaa aagaaattgc aatgtcacgc aaatgagaga attgcccgta ttggattcgg cggcctttaa
tgtggaatgc ttcaagaaat atgcgtgtaa taatgaatat tgggaaacgt ttaaagaaaa ccccatcagg cttactgaag aaaacgtggt aaattacatt
accaaattaa aaggaccaaa agctgctgct ctttttgcga agacacataa tttgaatatg ttgcaggaca taccaatgga caggtttgta atggacttaa
agagagacgt gaaagtgact ccaggaacaa aacatactga agaacggccc aaggtacagg tgatccaggc tgccgatccg ctagcaacag
cgtatctgtg cggaatccac cgagagctgg ttaggagatt aaatgcggtc ctgcttccga acattcatac actgtttgat atgtcggctg aagactttga
cgctattata gccgagcact tccagcctgg ggattgtgtt ctggaaactg acatcgcgtc gtttgataaa agtgaggacg acgccatggc tctgaccgcg
ttaatgattc tggaagactt aggtgtggac gcagagctgt tgacgctgat tgaggcggct ttcggcgaaa tttcatcaat acatttgccc actaaaacta
aatttaaatt cggagccatg atgaaatctg gaatgttcct cacactgttt gtgaacacag tcattaacat tgtaatcgca agcagagtgt tgagagaacg
gctaaccgga tcaccatgtg cagcattcat tggagatgac aatatcgtga aaggagtcaa atcggacaaa ttaatggcag acaggtgcgc cacctggttg
aatatggaag tcaagattat agatgctgtg gtgggcgaga aagcgcctta tttctgtgga gggtttattt tgtgtgactc cgtgaccggc acagcgtgcc
gtgtggcaga ccccctaaaa aggctgttta agcttggcaa acctctggca gcagacgatg aacatgatga tgacaggaga agggcattgc
atgaagagtc aacacgctgg aaccgagtgg gtattctttc agagctgtgc aaggcagtag aatcaaggta tgaaaccgta ggaacttcca tcatagttat
ggccatgact actctagcta gcagtgttaa atcattcagc tacctgagag ggcccctat aactctctac ggctaacctg aatggactac gacatagtct
agtccgccaa gatgttcccg ttccagccaa tgtatccgat gcagccaatg ccctatcgca acccgttcgc ggccccgcgc aggccctggt
tccccagaac cgaccctttt ctggcgatgc aggtgcagga attaacccgc tcgatggcta acctgacgtt caagcaacgc cgggacgcgc
cacctgaggg gccatccgct aagaaaccga agaaggaggc ctcgcaaaaa cagaaagggg gaggccaagg gaagaagaag aagaaccaag
ggaagaagaa ggctaagaca gggccgccta atccgaaggc acagaatgga aacaagaaga agaccaacaa gaaaccaggc aagagacagc
gcatggtcat gaaattggaa tctgacaaga cgttcccaat catgttggaa gggaagataa acggctacgc ttgtgtggtc ggagggaagt tattcaggcc
gatgcatgtg gaaggcaaga tcgacaacga cgttctggcc gcgcttaaga cgaagaaagc atccaaatac gatcttgagt atgcagatgt
gccacagaac atgcgggccg atacattcaa atacacccat gagaaacccc aaggctatta cagctggcat catggagcag tccaatatga
```

-continued aaatgggcgt ttcacggtgc cgaaaggagt tggggccaag ggagacagcg gacgacccat tctggataac cagggacggg tggtcgctat
tgtgctggga ggtgtgaatg aaggatctag gacagccctt tcagtcgtca tgtggaacga gaagggagtt accgtgaagt atactccgga
gaactgcgag caatggtcac tagtgaccac catgtgtctg ctcgccaatg tgacgttccc atgtgctcaa ccaccaattt gctacgacag aaaaccagca
gagactttgg ccatgctcag cgttaacgtt gacaacccgg gctacgatga gctgctggaa gcagctgtta agtgccccgg aaggaaaagg
agatccaccg aggagctgtt taaggagtat aagctaacgc gcccttacat ggccagatgc atcagatgtg cagttgggag ctgccatagt ccaatagcaa
tcgaggcagt aaagagcgac gggcacgacg gttatgttag acttcagact tcctcgcagt atggcctgga ttcctccggc aacttaaagg gcaggaccat
gcggtatgac atgcacggga ccattaaaga gataccacta catcaagtgt cactccatac atctcgcccg tgtcacattg tggatgggca cggttatttc
ctgcttgcca ggtgcccggc aggggactcc atcaccatgg aatttaagaa agattccgtc acacactcct gctaggtgcc gtatgaagtg aaatttaatc
ctgtaggcag agaactctat actcatcccc cagaacacgg agtagagcaa gcgtgccaag tctacgcaca tgatgcacag aacagaggag
cttatgtcga gatgcacctc ccgggctcag aagtggacag cagtttggtt tccttgagcg gcagttcagt caccgtgaca cctcctgttg ggactagcgc
cctggtggaa tgcgagtgtg gcggcacaaa gatctccgag accatcaaca agacaaaaca gttcagccag tgcacaaaga aggagcagtg
cagagcatat cggctgcaga acgataagtg ggtgtataat tctgacaaac tgcccaaagc agcgggagcc accttaaaag gaaaactgca tgtcccattc
ttgctggcag acggcaaatg caccgtgcct ctagcaccag aacctatgat aacctttggt ttcagatcag tgtcactgaa actgcaccct aagaatccca
catatctaac cacccgccaa cttgctgatg agcctcacta cacgcacgag ctcatatctg aaccagctgt taggaatttt accgtcaccg aaaaagggtg
ggagtttgta tggggaaacc acccgccgaa aaggttttgg gcacaggaaa cagcacccgg aaatccacat gggctaccgc acgaggtgat
aactcattat taccacagat accctatgtc caccatcctg ggtttgtcaa tttgtgccgc cattgcaacc gtttccgttg cagcgtctac ctggctgttt
tgcagatcta gagttgcgtg cctaactcct taccggctaa cacctaacgc taggatacca ttttgtctgg ctgtgctttg ctgcgcccgc actgcccggg
ccgagaccac ctgggagtcc ttggatcacc tatggaacaa taaccaacag atgttctgga ttcaattgct gatccctctg gccgccttga tcgtagtgac
tcgcctgctc aggtgcgtgt gctgtgtcgt gccttttta gtcatggccg gcgccgcagg cgccggcgcc tacgagcacg cgaccacgat
gccgagccaa gcgggaatct cgtataacac tatagtcaac agagcaggct acgcaccact ccctatcagc ataacaccaa caaagatcaa
gctgatacct acagtgaact tggagtacgt cacctgccac tacaaaacag gaatggattc accagccatc aaatgctgcg gatctcagga atgcactcca
acttacaggc ctgatgaaca gtgcaaagtc ttcacagggg tttacccgtt catgtggggt ggtgcatatt gcttttgcga cactgagaac acccaagtca
gcaaggccta cgtaatgaaa tctgacgact gccttgcgga tcatgctgaa gcatataaag cgcacacagc ctcagtgcag gcgttcctca acatcacagt
gggagaacac tctattgtga ctaccgtgta tgtgaatgga gaaactcctg tgaatttcaa tggggtcaaa ttaactgcag gtccgctttc cacagcttgg
acaccctttg atcgcaaaat cgtgcagtat gccggggaga tctataatta tgattttcct gagtatgggg caggacaacc aggagcattt ggagatatac
aatccagaac agtctcaagc tcagatctgt atgccaatac caacctagtg ctgcagagac ccaaagcagg agcgatccac gtgccataca
ctcaggcacc ttcgggtttt gagcaatgga agaaagataa agctccatca ttgaaattta ccgccccttt cggatgcgaa atatatacaa accccattcg
cgccgaaaac tgtgctgtag ggtcaattcc attagccttt gacattcccg acgccttgtt caccagggtg tcagaaacac cgacactttc agcggccgaa
tgcactctta acgagtgcgt gtattcttcc gactttggtg ggatcgccac ggtcaagtac tcggccagca agtcaggcaa gtgcgcagtc catgtgccat
cagggactgc taccctaaaa gaagcagcag tcgagctaac cgagcaaggg tcggcgacta tccatttctc gaccgcaaat atccacccgg
agttcaggct ccaaatatgc acatcatatg ttacgtgcaa aggtgattgt caccccccga aagaccatat tgtgacacac cctcagtatc acgcccaaac
atttacagcc gcggtgtcaa aaaccgcgtg gacgtggtta acatccctgc tgggaggatc agccgtaatt attataattg gcttggtgct ggctactatt
gtggccatgt acgtgctgac caaccagaaa cataattgaa tacagcagca attggcaagc tgcttacata gaactcgcgg cgattggcat gccgccttaa
aatttttatt ttattttttc ttttcttttc cgaatcggat tttgttttta atatttc VEE Delivery Vector (SEQ ID NO: 6); VEE genome with nucleotides 7544-11175 deleted [alphavirus structural proteins removed]

ATGggcggcgcatgagagaagcccagaccaattacctacccaaaATGGagaaagttcacgttgacatcgaggaagacagcccattcctcagagctttgca
gcggagcttcccgcagtttgaggtagaagccaagcaggtcactgataatgaccatgctaatgccagagcgttttcgcatctggcttcaaaactgatcgaaacggag
gtggacccatccgacacgatccttgacattggaagtgcgcccgcccgcagaatgtattctaagcacaagtatcattgtatctgtccgatgagatgtgcggaagatcc
ggacagattgtataagtatgcaactaagctgaagaaaaactgtaaggaaataactgataaggaattggacaagaaaatgaaggagctcgccgccgtcatgagcg
accctgacctggaaactgagactatgtgcctccacgacgacgagtcgtgtcgctacgaagggcaagtcgctgtttaccaggatgtatacgcggttgacggaccga
caagtctctatcaccaagccaataagggagttagagtcgcctactggataggctttgacaccacccctttttatgtttaagaacttggctggagcatatccatcatactct
accaactgggccgacgaaaccgtgttaacggctcgtaacataggcctatgcagctctgacgttatggagcggtcacgtagagggatgtccattcttagaaagaag
tatttgaaaccatccaacaatgttctattctctgttggctcgaccatctaccacgagaagagggacttactgaggagctggcacctgccgtctgtatttcacttacgtgg
caagcaaaattacacatgtcggtgtgagactatagttagttgcgacgggtacgtcgttaaaagaatagctatcagtccaggcctgtatgggaagccttcaggctatg
ctgctacgatgcaccgcgagggattcttgtgctgcaaagtgacagacacattgaacggggagagggtctcttttcccgtgtgcacgtatgtgccagctacattgtgt
gaccaaatgactggcatactggcaacagatgtcagtgcggacgacgcgcaaaaactgctggttgggctcaaccagcgtatagtcgtcaacggtcgcacccaga
gaaacaccaataccatgaaaaattaccttttgcccgtagtggcccaggcatttgctaggtgggcaaaggaatataaggaagatcaagaagatgaaaggccactag
gactacgagatagacagttagtcatggggtgttgttgggcttttagaaggcacaagataacatctatttataagcgcccggatacccaaaccatcatcaaagtgaac
agcgatttccactcattcgtgctgcccaggataggcagtaacacattggagatcgggctgagaacaagaatcaggaaaatgttagaggagcacaaggagccgtc
acctctcattaccgccgaggacgtacaagaagctaagtgcgcagccgatgaggctaaggaggtgcgtgaagccgaggagttgcgcgcagctctaccacctttg
gcagctgatgttgaggagcccactctggaagccgatgtcgacttgatgttacaagaggctggggccggctcagtggagacacctcgtggcttgataaaggttacc
agctacgctggcgaggacaagatcggctcttacgctgtgctttctccgcaggctgtactcaagagtgaaaaattatcttgcatccaccctctcgctgaacaagtcata -continued gtgataacacactctggccgaaaagggcgttatgccgtggaaccataccatggtaaagtagtggtgccagagggacatgcaatacccgtccaggactttcaagct
ctgagtgaaagtgccaccattgtgtacaacgaacgtgagttcgtaaacaggtacctgcaccatattgccacacatggaggagcgctgaacactgatgaagaatatt
acaaaactgtcaagcccagcgagcacgacggcgaatacctgtacgacatcgacaggaaacagtgcgtcaagaaagaactagtcactgggctagggctcacag
gcgagctggtggatcctcccttccatgaattcgcctacgagagtctgagaacacgaccagccgctccttaccaagtaccaaccataggggtgtatggcgtgccag
gatcaggcaagtctggcatcattaaaagcgcagtcaccaaaaaagatctagtggtgagcgccaagaaagaaaactgtgcagaaattataagggacgtcaagaaa
atgaaagggctggacgtcaatgccagaactgtggactcagtgctcttgaatggatgcaaacaccccgtagagaccctgtatattgacgaagcttttgcttgtcatgc
aggtactctcagagcgctcatagccattataagacctaaaaaggcagtgctctgcggggatcccaaacagtgcggtttttttaacatgatgtgcctgaaagtgcatttt
aaccacgagatttgcacacaagtcttccacaaaagcatctctcgccgttgcactaaatctgtgacttcggtcgtctcaaccttgttttacgacaaaaaaatgagaacg
acgaatccgaaagagactaagattgtgattgacactaccggcagtaccaaacctaagcaggacgatctcattctcacttgtttcagagggggtgaagcagttgc
aaatagattacaaaggcaacgaaataatgacggcagctgcctctcaagggctgacccgtaaaggtgtgtatgccgttcggtacaaggtgaatgaaaatcctctgta
cgcacccacctcagaacatgtgaacgtcctactgacccgcacggaggaccgcatcgtgtggaaaacactagccggcgacccatggataaaaacactgactgcc
aagtaccctgggaatttcactgccacgatagaggagtggcaagcagagcatgatgccatcatgaggcacatcttggagagaccggaccctaccgacgtcttcca
gaataaggcaaacgtgtgttgggccaaggctttagtgccggtgctgaagaccgctggcatagacatgaccactgaacaatggaacactgtggattattttgaaacg
gacaaagctcactcagcagagatagtattgaaccaactatgcgtgaggttctttggactcgatctggactccggtctattttctgcacccactgttccgttatccattag
gaataatcactgggataactccccgtcgcctaacatgtacgggctgaataaagaagtggtccgtcagctctctcgcaggtacccacaactgcctcgggcagttgcc
actggaagagtctatgacatgaacactggtacactgcgcaattatgatccgcgcataaacctagtacctgtaaacagaagactgcctcatgctttagtcctccaccat
aatgaacacccacagagtgacttttcttcattcgtcagcaaattgaagggcagaactgtcctggtggtcggggaaaagttgtccgtcccaggcaaaatggttgactg
gttgtcagaccggcctgaggctaccttcagagctcggctggatttaggcatcccaggtgatgtgcccaaatatgacataatatttgttaatgtgaggaccccatataa
ataccatcactatcagcagtgtgaagaccatgccattaagcttagcatgttgaccaagaaagcttgtctgcatctgaatcccggcggaacctgtgtcagcataggtta
tggttacgctgacagggccagcgaaagcatcattggtgctatagcgcggcagttcaagttttcccgggtatgcaaaccgaaatcctcacttgaagagacggaagtt
ctgtttgtattcattgggtacgatcgcaaggcccgtacgcacaatccttacaagctttcatcaaccttgaccaacatttatacaggttccagactccacgaagccggat
gtgcaccctcatatcatgtggtgcgaggggatattgccacggccaccgaaggagtgattataaatgctgctaacagcaaaggacaacctggcggaggggtgtgc
ggagcgctgtataagaaattcccggaaagcttcgatttacagccgatcgaagtaggaaaagcgcgactggtcaaaggtgcagctaaacatatcattcatgccgta
ggaccaaacttcaacaaagtttcggaggttgaaggtgacaaacagttggcagaggcttatgagtccatcgctaagattgtcaacgataacaattacaagtcagtag
cgattccactgttgtccaccggcatcttttccgggaacaaagatcgactaacccaatcattgaaccatttgctgacagctttagacaccactgatgcagatgtagccat
atactgcagggacaagaaatgggaaatgactctcaaggaagcagtggctaggagagaagcagtggaggagatatgcatatccgacgactcttcagtgacagaa
cctgatgcagagctggtgagggtgcatccgaagagttctttggctggaaggaagggctacagcacaagcgatggcaaaactttctcatatttggaagggaccaag
tttcaccaggcggccaaggatatagcagaaattaatgccatgtggcccgttgcaacggaggccaatgagcaggtatgcatgtatatcctcggagaaagcatgagc
agtattaggtcgaaatgccccgtcgaagagtcggaagcctccacaccacctagcacgctgccttgcttgtgcatccatgccatgactccagaaagagtacagcgc
ctaaaagcctcacgtccagaacaaattactgtgtgctcatcctttccattgccgaagtatagaatcactggtgtgcagaagatccaatgctcccagcctatattgttctc
accgaaagtgcctgcgtatattcatccaaggaagtatctcgtggaaacaccaccggtagacgagactccggagccatcggcagagaaccaatccacagagggg
acacctgaacaaccaccacttataaccgaggatgagaccaggactagaacgcctgagccgatcatcatcgaagaggaagaagaggatagcataagtttgctgtc
agatggcccgacccaccaggtgctgcaagtcgaggcagacattcacgggccgccctctgtatctagctcatcctggtccattcctcatgcatccgactttgatgtgg
acagtttatccatacttgacaccctggagggagctagcgtgaccagcggggcaacgtcagccgagactaactcttacttcgcaaagagtatggagtttctggcgc
gaccggtgcctgcgcctcgaacagtattcaggaaccctccacatcccgctccgcgcacaagaacaccgtcacttgcacccagcagggcctgctcgagaaccag
cctagtttccaccccgccaggcgtgaatagggtgatcactagagaggagctcgaggcgcttaccccgtcacgcactcctagcaggtcggtctcgagaaccagcc
tggtctccaacccgccaggcgtaaatagggtgattacaagagaggagtttgaggcgttcgtagcacaacaacaatgacggtttgatgcgggtgcatacatcttttcc
tccgacaccggtcaagggcatttacaacaaaaatcagtaaggcaaacggtgctatccgaagtggtgttggagaggaccgaattggagatttcgtatgccccgcgc
ctcgaccaagaaaaagaagaattactacgcaagaaattacagttaaatcccacacctgctaacagaagcagataccagtccaggaaggtggagaacatgaaagc
cataacagctagacgtattctgcaaggcctagggcattatttgaaggcagaaggaaaagtggagtgctaccgaaccctgcatcctgttcctttgtattcatctagtgt
gaaccgtgccttttcaagccccaaggtcgcagtggaagcctgtaacgccatgttgaaagagaactttccgactgtggcttcttactgtattattccagagtacgatgc
ctatttggacatggttgacggagcttcatgctgcttagacactgccagtttttgccctgcaaagctgcgcagctttccaaagaaacactcctatttggaacccacaata
cgatcggcagtgccttcagcgatccagaacacgctccagaacgtcctggcagctgccacaaaaagaaattgcaatgtcacgcaaatgagagaattgcccgtattg
gattcggcggcctttaatgtggaatgcttcaagaaatatgcgtgtaataatgaatattgggaaacgtttaaagaaaaccccatcaggcttactgaagaaaacgtggta
aattacattaccaaattaaaaggaccaaaagctgctgctctttttgcgaagacacataatttgaatatgttgcaggacataccaatggacaggtttgtaatggacttaaa
gagagacgtgaaagtgactccaggaacaaaacatactgaagaacggcccaaggtacaggtgatccaggctgccgatccgctagcaacagcgtatctgtgcgg
aatccaccgagagctggttaggagattaaatgcggtcctgcttccgaacattcatacactgtttgatatgtcggctgaagactttgacgctattatagccgagcacttc
cagcctggggattgtgttctggaaactgacatcgcgtcgtttgataaaagtgaggacgacgccatggctctgaccgcgttaatgattctggaagacttaggtgtgga
cgcagagctgttgacgctgattgaggcggctttcggcgaaatttcatcaatacatttgcccactaaaactaaatttaaattcggagccatgatgaaatctggaatgttc
ctcacactgtttgtgaacacagtcattaacattgtaatcgcaagcagagtgttgagagaacggctaaccggatcaccatgtgcagcattcattggagatgacaatatc
gtgaaaggagtcaaatcggacaaattaatggcagacaggtgcgccacctggttgaatatggaagtcaagattatagatgctgtggtgggcgagaaagcgccttat
ttctgtggagggtttattttgtgtgactccgtgaccggcacagcgtgccgtgtggcagacccccctaaaaaggctgtttaagcttggcaaacctctggcagcagacga
tgaacatgatgatgacaggagaagggcattgcatgaagagtcaacacgctggaaccgagtgggtattctttcagagctgtgcaaggcagtagaatcaaggtatga
aaccgtaggaacttccatcatagttatggccatgactactctagctagcagtgttaaatcattcagctacctgagaggggcccctataactctctacggcTAAcct -continued gaatggactacgactatcacgcccaaacatttacagccgcggtgtcaaaaaccgcgtggacgtggttaacatccctgctgggaggatcagccgtaattattataatt
ggcttggtgctggctactattgtggccatgtacgtgctgaccaaccagaaacataattgaatacagcagcaattggcaagctgcttacatagaactcgcggcgattg
gcatgccgccttaaaatttttattttatttttttcttttcttttccgaatcggattttgtttttaatatttcAAAAAAAAAAAAAAAAAAAAAAAAAA
AAAAAAAAAAAAAAAAAAAAAAAAAAAAAAAAAAAAAAAAAAAAAAAAAAAAAA TC-83 Delivery Vector(SEQ ID NO: 7); TC-83 genome with nucleotides 7544-11175 deleted [alphavirus structural proteins removed]

ATAGGCGGCGCATGAGAGAAGCCCAGACCAATTACCTACCCAAAATGGAGAAAGTTCACGTTGA
CATCGAGGAAGACAGCCCATTCCTCAGAGCTTTGCAGCGGAGCTTCCCGCAGTTTGAGGTAGAAG
CCAAGCAGGTCACTGATAATGACCATGCTAATGCCAGAGCGTTTTCGCATCTGGCTTCAAAACTG
ATCGAAACGGAGGTGGACCCATCCGACACGATCCTTGACATTGGAAGTGCGCCCGCCCGCAGAAT
GTATTCTAAGCACAAGTATCATTGTATCTGTCCGATGAGATGTGCGGAAGATCCGGACAGATTGT
ATAAGTATGCAACTAAGCTGAAGAAAAACTGTAAGGAAATAACTGATAAGGAATTGGACAAGAA
AATGAAGGAGCTCGCCGCCGTCATGAGCGACCCTGACCTGGAAACTGAGACTATGTGCCTCCACG
ACGACGAGTCGTGTCGCTACGAAGGGCAAGTCGCTGTTTACCAGGATGTATACGCGGTTGACGGA
CCGACAAGTCTCTATCACCAAGCCAATAAGGGAGTTAGAGTCGCCTACTGGATAGGCTTTGACAC
CACCCCTTTTATGTTTAAGAACTTGGCTGGAGCATATCCATCATACTCTACCAACTGGGCCGACGA
AACCGTGTTAACGGCTCGTAACATAGGCCTATGCAGCTCTGACGTTATGGAGCGGTCACGTAGAG
GGATGTCCATTCTTAGAAAGAAGTATTTGAAACCATCCAACAATGTTCTATTCTCTGTTGGCTCGA
CCATCTACCACGAGAAGAGGGACTTACTGAGGAGCTGGCACCTGCCGTCTGTATTTCACTTACGT
GGCAAGCAAAATTACACATGTCGGTGTGAGACTATAGTTAGTTGCGACGGGTACGTCGTTAAAAG
AATAGCTATCAGTCCAGGCCTGTATGGGAAGCCTTCAGGCTATGCTGCTACGATGCACCGCGAGG
GATTCTTGTGCTGCAAAGTGACAGACACATTGAACGGGGAGAGGGTCTCTTTTCCCGTGTGCACG
TATGTGCCAGCTACATTGTGTGACCAAATGACTGGCATACTGGCAACAGATGTCAGTGCGGACGA
CGCGCAAAAACTGCTGGTTGGGCTCAACCAGCGTATAGTCGTCAACGGTCGCACCCAGAGAAACA
CCAATACCATGAAAAATTACCTTTTGCCCGTAGTGGCCCAGGCATTTGCTAGGTGGGCAAAGGAA
TATAAGGAAGATCAAGAAGATGAAAGGCCACTAGGACTACGAGATAGACAGTTAGTCATGGGGT
GTTGTTGGGCTTTTAGAAGGCACAAGATAACATCTATTTATAAGCGCCCGGATACCCAAACCATC
ATCAAAGTGAACAGCGATTTCCACTCATTCGTGCTGCCCAGGATAGGCAGTAACACATTGGAGAT
CGGGCTGAGAACAAGAATCAGGAAAATGTTAGAGGAGCACAAGGAGCCGTCACCTCTCATTACC
GCCGAGGACGTACAAGAAGCTAAGTGCGCAGCCGATGAGGCTAAGGAGGTGCGTGAAGCCGAGG
AGTTGCGCGCAGCTCTACCACCTTTGGCAGCTGATGTTGAGGAGCCCACTCTGGAAGCCGATGTC
GACTTGATGTTACAAGAGGCTGGGGCCGGCTCAGTGGAGACACCTCGTGGCTTGATAAAGGTTAC
CAGCTACGATGGCGAGGACAAGATCGGCTCTTACGCTGTGCTTTCTCCGCAGGCTGTACTCAAGA
GTGAAAAATTATCTTGCATCCACCCTCTCGCTGAACAAGTCATAGTGATAACACACTCTGGCCGA
AAAGGGCGTTATGCCGTGGAACCATACCATGGTAAAGTAGTGGTGCCAGAGGGACATGCAATAC
CCGTCCAGGACTTTCAAGCTCTGAGTGAAAGTGCCACCATTGTGTACAACGAACGTGAGTTCGTA
AACAGGTACCTGCACCATATTGCCACACATGGAGGAGCGCTGAACACTGATGAAGAATATTACAA
AACTGTCAAGCCCAGCGAGCACGACGGCGAATACCTGTACGACATCGACAGGAAACAGTGCGTC
AAGAAAGAACTAGTCACTGGGCTAGGGCTCACAGGCGAGCTGGTGGATCCTCCCTTCCATGAATT
CGCCTACGAGAGTCTGAGAACACGACCAGCCGCTCCTTACCAAGTACCAACCATAGGGGTGTATG
GCGTGCCAGGATCAGGCAAGTCTGGCATCATTAAAAGCGCAGTCACCAAAAAAGATCTAGTGGTG
AGCGCCAAGAAAGAAAACTGTGCAGAAATTATAAGGGACGTCAAGAAAATGAAAGGGCTGGACG
TCAATGCCAGAACTGTGGACTCAGTGCTCTTGAATGGATGCAAACACCCCGTAGAGACCCTGTAT
ATTGACGAAGCTTTTGCTTGTCATGCAGGTACTCTCAGAGCGCTCATAGCCATTATAAGACCTAAA
AAGGCAGTGCTCTGCGGGGATCCCAAACAGTGCGGTTTTTTTAACATGATGTGCCTGAAAGTGCA
TTTTAACCACGAGATTTGCACACAAGTCTTCCACAAAAGCATCTCTCGCCGTTGCACTAAATCTGT
GACTTCGGTCGTCTCAACCTTGTTTTACGACAAAAAAATGAGAACGACGAATCCGAAAGAGACTA
AGATTGTGATTGACACTACCGGCAGTACCAAACCTAAGCAGGACGATCTCATTCTCACTTGTTTCA
GAGGGTGGGTGAAGCAGTTGCAAATAGATTACAAAGGCAACGAAATAATGACGGCAGCTGCCTC
TCAAGGGCTGACCCGTAAAGGTGTGTATGCCGTTCGGTACAAGGTGAATGAAAATCCTCTGTACG
CACCCACCTCAGAACATGTGAACGTCCTACTGACCCGCACGGAGGACCGCATCGTGTGGAAAACA
CTAGCCGGCGACCCATGGATAAAAACACTGACTGCCAAGTACCCTGGGAATTTCACTGCCACGAT
AGAGGAGTGGCAAGCAGAGCATGATGCCATCATGAGGCACATCTTGGAGAGACCGGACCCTACC

-continued

```
GACGTCTTCCAGAATAAGGCAAACGTGTGTTGGGCCAAGGCTTTAGTGCCGGTGCTGAAGACCGC
TGGCATAGACATGACCACTGAACAATGGAACACTGTGGATTATTTTGAAACGGACAAAGCTCACT
CAGCAGAGATAGTATTGAACCAACTATGCGTGAGGTTCTTTGGACTCGATCTGGACTCCGGTCTAT
TTTCTGCACCCACTGTTCCGTTATCCATTAGGAATAATCACTGGGATAACTCCCCGTCGCCTAACA
TGTACGGGCTGAATAAAGAAGTGGTCCGTCAGCTCTCTCGCAGGTACCCACAACTGCCTCGGGCA
GTTGCCACTGGAAGAGTCTATGACATGAACACTGGTACACTGCGCAATTATGATCCGCGCATAAA
CCTAGTACCTGTAAACAGAAGACTGCCTCATGCTTTAGTCCTCCACCATAATGAACACCCACAGA
GTGACTTTTCTTCATTCGTCAGCAAATTGAAGGGCAGAACTGTCCTGGTGGTCGGGGAAAAGTTGT
CCGTCCCAGGCAAAATGGTTGACTGGTTGTCAGACCGGCCTGAGGCTACCTTCAGAGCTCGGCTG
GATTTAGGCATCCCAGGTGATGTGCCCAAATATGACATAATATTTGTTAATGTGAGGACCCCATAT
AAATACCATCACTATCAGCAGTGTGAAGACCATGCCATTAAGCTTAGCATGTTGACCAAGAAAGC
TTGTCTGCATCTGAATCCCGGCGGAACCTGTGTCAGCATAGGTTATGGTTACGCTGACAGGGCCA
GCGAAAGCATCATTGGTGCTATAGCGCGGCAGTTCAAGTTTTCCCGGGTATGCAAACCGAAATCC
TCACTTGAAGAGACGGAAGTTCTGTTTGTATTCATTGGGTACGATCGCAAGGCCCGTACGCACAA
TCCTTACAAGCTTTCATCAACCTTGACCAACATTTATACAGGTTCCAGACTCCACGAAGCCGGATG
TGCACCCTCATATCATGTGGTGCGAGGGGATATTGCCACGGCCACCGAAGGAGTGATTATAAATG
CTGCTAACAGCAAAGGACAACCTGGCGGAGGGGTGTGCGGAGCGCTGTATAAGAAATTCCCGGA
AAGCTTCGATTTACAGCCGATCGAAGTAGGAAAAGCGCGACTGGTCAAAGGTGCAGCTAAACAT
ATCATTCATGCCGTAGGACCAAACTTCAACAAAGTTTCGGAGGTTGAAGGTGACAAACAGTTGGC
AGAGGCTTATGAGTCCATCGCTAAGATTGTCAACGATAACAATTACAAGTCAGTAGCGATTCCAC
TGTTGTCCACCGGCATCTTTTCCGGGAACAAAGATCGACTAACCCAATCATTGAACCATTTGCTGA
CAGCTTTAGACACCACTGATGCAGATGTAGCCATATACTGCAGGGACAAGAAATGGGAAATGACT
CTCAAGGAAGCAGTGGCTAGGAGAGAAGCAGTGGAGGAGATATGCATATCCGACGACTCTTCAG
TGACAGAACCTGATGCAGAGCTGGTGAGGGTGCATCCGAAGAGTTCTTTGGCTGGAAGGAAGGG
CTACAGCACAAGCGATGGCAAAACTTTCTCATATTTGGAAGGGACCAAGTTTCACCAGGCGGCCA
AGGATATAGCAGAAATTAATGCCATGTGGCCCGTTGCAACGGAGGCCAATGAGCAGGTATGCATG
TATATCCTCGGAGAAAGCATGAGCAGTATTAGGTCGAAATGCCCCGTCGAAGAGTCGGAAGCCTC
CACACCACCTAGCACGCTGCCTTGCTTGTGCATCCATGCCATGACTCCAGAAAGAGTACAGCGCC
TAAAAGCCTCACGTCCAGAACAAATTACTGTGTGCTCATCCTTTCCATTGCCGAAGTATAGAATCA
CTGGTGTGCAGAAGATCCAATGCTCCCAGCCTATATTGTTCTCACCGAAAGTGCCTGCGTATATTC
ATCCAAGGAAGTATCTCGTGGAAACACCACCGGTAGACGAGACTCCGGAGCCATCGGCAGAGAA
CCAATCCACAGAGGGGACACCTGAACAACCACCACTTATAACCGAGGATGAGACCAGGACTAGA
ACGCCTGAGCCGATCATCATCGAAGAGGAAGAAGAGGATAGCATAAGTTTGCTGTCAGATGGCCC
GACCCACCAGGTGCTGCAAGTCGAGGCAGACATTCACGGGCCGCCCTCTGTATCTAGCTCATCCT
GGTCCATTCCTCATGCATCCGACTTTGATGTGGACAGTTTATCCATACTTGACACCCTGGAGGGAG
CTAGCGTGACCAGCGGGGCAACGTCAGCCGAGACTAACTCTTACTTCGCAAAGAGTATGGAGTTT
CTGGCGCGACCGGTGCCTGCGCCTCGAACAGTATTCAGGAACCCTCCACATCCCGCTCCGCGCAC
AAGAACACCGTCACTTGCACCCAGCAGGGCCTGCTCGAGAACCAGCCTAGTTTCCACCCCGCCAG
GCGTGAATAGGGTGATCACTAGAGAGGAGCTCGAGGCGCTTACCCCGTCACGCACTCCTAGCAGG
TCGGTCTCGAGAACCAGCCTGGTCTCCAACCCGCCAGGCGTAAATAGGGTGATTACAAGAGAGGA
GTTTGAGGCGTTCGTAGCACAACAACAATGACGGTTTGATGCGGGTGCATACATCTTTTCCTCCGA
CACCGGTCAAGGGCATTTACAACAAAAATCAGTAAGGCAAACGGTGCTATCCGAAGTGGTGTTGG
AGAGGACCGAATTGGAGATTTCGTATGCCCCGCGCCTCGACCAAGAAAAAGAAGAATTACTACGC
AAGAAATTACAGTTAAATCCCACACCTGCTAACAGAAGCAGATACCAGTCCAGGAAGGTGGAGA
ACATGAAAGCCATAACAGCTAGACGTATTCTGCAAGGCCTAGGGCATTATTTGAAGGCAGAAGGA
AAAGTGGAGTGCTACCGAACCCTGCATCCTGTTCCTTTGTATTCATCTAGTGTGAACCGTGCCTTT
TCAAGCCCCAAGGTCGCAGTGGAAGCCTGTAACGCCATGTTGAAAGAGAACTTTCCGACTGTGGC
TTCTTACTGTATTATTCCAGAGTACGATGCCTATTTGGACATGGTTGACGGAGCTTCATGCTGCTT
AGACACTGCCAGTTTTTGCCCTGCAAAGCTGCGCAGCTTTCCAAAGAAACACTCCTATTTGGAACC
CACAATACGATCGGCAGTGCCTTCAGCGATCCAGAACACGCTCCAGAACGTCCTGGCAGCTGCCA
CAAAAAGAAATTGCAATGTCACGCAAATGAGAGAATTGCCCGTATTGGATTCGGCGGCCTTTAAT
GTGGAATGCTTCAAGAAATATGCGTGTAATAATGAATATTGGGAAACGTTTAAAGAAAACCCCAT
CAGGCTTACTGAAGAAAACGTGGTAAATTACATTACCAAATTAAAAGGACCAAAAGCTGCTGCTC
TTTTTGCGAAGACACATAATTTGAATATGTTGCAGGACATACCAATGGACAGGTTTGTAATGGACT
```

-continued

TAAAGAGAGACGTGAAAGTGACTCCAGGAACAAAACATACTGAAGAACGGCCCAAGGTACAGGT
GATCCAGGCTGCCGATCCGCTAGCAACAGCGTATCTGTGCGGAATCCACCGAGAGCTGGTTAGGA
GATTAAATGCGGTCCTGCTTCCGAACATTCATACACTGTTTGATATGTCGGCTGAAGACTTTGACG
CTATTATAGCCGAGCACTTCCAGCCTGGGGATTGTGTTCTGGAAACTGACATCGCGTCGTTTGATA
AAAGTGAGGACGACGCCATGGCTCTGACCGCGTTAATGATTCTGGAAGACTTAGGTGTGGACGCA
GAGCTGTTGACGCTGATTGAGGCGGCTTTCGGCGAAATTTCATCAATACATTTGCCCACTAAAACT
AAATTTAAATTCGGAGCCATGATGAAATCTGGAATGTTCCTCACACTGTTTGTGAACACAGTCATT
AACATTGTAATCGCAAGCAGAGTGTTGAGAGAACGGCTAACCGGATCACCATGTGCAGCATTCAT
TGGAGATGACAATATCGTGAAAGGAGTCAAATCGGACAAATTAATGGCAGACAGGTGCGCCACC
TGGTTGAATATGGAAGTCAAGATTATAGATGCTGTGGTGGGCGAGAAAGCGCCTTATTTCTGTGG
AGGGTTTATTTTGTGTGACTCCGTGACCGGCACAGCGTGCCGTGTGGCAGACCCCCTAAAAAGGC
TGTTTAAGCTTGGCAAACCTCTGGCAGCAGACGATGAACATGATGATGACAGGAGAAGGGCATTG
CATGAAGAGTCAACACGCTGGAACCGAGTGGGTATTCTTTCAGAGCTGTGCAAGGCAGTAGAATC
AAGGTATGAAACCGTAGGAACTTCCATCATAGTTATGGCCATGACTACTCTAGCTAGCAGTGTTA
AATCATTCAGCTACCTGAGAGGGGCCCCTATAACTCTCTACGGCTAACCTGAATGGACTACGACT
ATCACGCCCAAACATTTACAGCCGCGGTGTCAAAAACCGCGTGGACGTGGTTAACATCCCTGCTG
GGAGGATCAGCCGTAATTATTATAATTGGCTTGGTGCTGGCTACTATTGTGGCCATGTACGTGCTG
ACCAACCAGAAACATAATTGAATACAGCAGCAATTGGCAAGCTGCTTACATAGAACTCGCGGCGA
TTGGCATGCCGCCTTAAAATTTTTATTTTATTTTTCTTTTCTTTTCCGAATCGGATTTTGTTTTTAAT
ATTTCAAAAAAAAAAAAAAAAAAAAAAAAAAAAAAAAAAAAAAAAAAAAAAAAAAAA
AAAAAAAAAAAAAAAAAAAAA

VEE Production Vector (SEQ ID NO: 8); VEE genome with nucleotides 7544-11175 deleted, plus 5' T7-promoter, plus 3' restriction sites
TAATACGACTCACTATAGGATGggcggcgcatgagagaagcccagaccaattacctacccaaaATGGagaaagttcacgttgacatcg
aggaagacagcccattcctcagagctttgcagcggagcttcccgcagtttgaggtagaagccaagcaggtcactgataatgaccatgctaatgccagagcgttttc
gcatctggcttcaaaactgatcgaaacggaggtggacccatccgacacgatccttgacattggaagtgcgcccgcccgcagaatgtattctaagcacaagtatcat
tgtatctgtccgatgagatgtgcggaagatccggacagattgtataagtatgcaactaagctgaagaaaaactgtaaggaaataactgataaggaattggacaaga
aaatgaaggagctcgccgccgtcatgagcgaccctgacctggaaactgagactatgtgcctccacgacgacgagtcgtgtcgctacgaagggcaagtcgctgtt
taccaggatgtatacgcggttgacggaccgacaagtctctatcaccaagccaataagggagttagagtcgcctactggataggctttgacaccacccctttttatgttt
aagaacttggctggagcatatccatcatactctaccaactgggccgacgaaaccgtgttaacggctcgtaacataggcctatgcagctctgacgttatggagcggt
cacgtagagggatgtccattcttagaaagaagtatttgaaaccatccaacaatgttctattctctgttggctcgaccatctaccacgagaagagggacttactgagga
gctggcacctgccgtctgtatttcacttacgtggcaagcaaaattacacatgtcggtgtgagactatagttagttgcgacgggtacgtcgttaaaagaatagctatca
gtccaggcctgtatgggaagccttcaggctatgctgctacgatgcaccgcgagggattcttgtgctgcaaagtgacagacacattgaacggggagagggtctcttt
tcccgtgtgcacgtatgtgccagctacattgtgtgaccaaatgactggcatactggcaacagatgtcagtgcggacgacgcgcaaaaactgctggttgggctcaa
ccagcgtatagtcgtcaacggtcgcacccagagaaacaccaataccatgaaaaattacctttttgcccgtagtggcccaggcatttgctaggtgggcaaaggaatat
aaggaagatcaagaagatgaaaggccactaggactacgagatagacagttagtcatggggtgttgttgggcttttagaaggcacaagataacatctatttataagc
gcccggatacccaaaccatcatcaaagtgaacagcgatttccactcattcgtgctgcccaggataggcagtaacacattggagatcgggctgagaacaagaatca
ggaaaatgttagaggagcacaaggagccgtcacctctcattaccgccgaggacgtacaagaagctaagtgcgcagccgatgaggctaaggaggtgcgtgaag
ccgaggagttgcgcgcagctctaccacctttggcagctgatgttgaggagcccactctggaagccgatgtcgacttgatgttacaagaggctggggccggctca
gtggagacacctcgtggcttgataaaggttaccagctacgctggcgaggacaagatcggctcttacgctgtgctttctccgcaggctgtactcaagagtgaaaaatt
atcttgcatccaccctctcgctgaacaagtcatagtgataacacactctggccgaaaagggcgttatgccgtggaaccataccatggtaaagtagtggtgccagag
ggacatgcaatacccgtccaggactttcaagctctgagtgaaagtgccaccattgtgtacaacgaacgtgagttcgtaaacaggtacctgcaccatattgccacac
atggaggagcgctgaacactgatgaagaatattacaaaactgtcaagcccagcgagcacgacggcgaatacctgtacgacatcgacaggaaacagtgcgtcaa
gaaagaactagtcactgggctagggctcacaggcgagctggtggatcctcccttccatgaattcgcctacgagagtctgagaacacgaccagccgctccttacca
agtaccaaccataggggtgtatggcgtgccaggatcaggcaagtctggcatcattaaaagcgcagtcaccaaaaaagatctagtggtgagcgccaagaaagaa
aactgtgcagaaattataagggacgtcaagaaaatgaaagggctggacgtcaatgccagaactgtggactcagtgctcttgaatggatgcaaacaccccgtaga
gaccctgtatattgacgaagcttttgcttgtcatgcaggtactctcagagcgctcatagccattataagacctaaaaaggcagtgctctgcggggatcccaaacagt
gcggtttttttaacatgatgtgcctgaaagtgcattttaaccacgagatttgcacacaagtcttccacaaaagcatctctcgccgttgcactaaatctgtgacttcggtcg
tctcaaccttgttttacgacaaaaaaatgagaacgacgaatccgaaagagactaagattgtgattgacactaccggcagtaccaaacctaagcaggacgatctcatt
ctcacttgtttcagagggtgggtgaagcagttgcaaatagattacaaaggcaacgaaataatgacggcagctgcctctcaagggctgacccgtaaaggtgtgtatg
ccgttcggtacaaggtgaatgaaaatcctctgtacgcacccacctcagaacatgtgaacgtcctactgacccgcacggaggaccgcatcgtgtggaaaacactag
ccggcgacccatggataaaaacactgactgccaagtaccctgggaatttcactgccacgatagaggagtggcaagcagagcatgatgccatcatgaggcacatc
ttggagagaccggaccctaccgacgtcttccagaataaggcaaacgtgtgttgggccaaggctttagtgccggtgctgaagaccgctggcatagacatgaccact -continued gaacaatggaacactgtggattattttgaaacggacaaagctcactcagcagagatagtattgaaccaactatgcgtgaggttctttggactcgatctggactccggt
ctattttctgcacccactgttccgttatccattaggaataatcactgggataactccccgtcgcctaacatgtacgggctgaataaagaagtggtccgtcagctctctc
gcaggtacccacaactgcctcgggcagttgccactggaagagtctatgacatgaacactggtacactgcgcaattatgatccgcgcataaacctagtacctgtaaa
cagaagactgcctcatgctttagtcctccaccataatgaacacccacagagtgacttttcttcattcgtcagcaaattgaagggcagaactgtcctggtggtcgggga
aaagttgtccgtcccaggcaaaatggttgactggttgtcagaccggcctgaggctaccttcagagctcggctggatttaggcatcccaggtgatgtgcccaaatat
gacataatatttgttaatgtgaggaccccatataaataccatcactatcagcagtgtgaagaccatgccattaagcttagcatgttgaccaagaaagcttgtctgcatct
gaatcccggcggaacctgtgtcagcataggttatggttacgctgacagggccagcgaaagcatcattggtgctatagcgcggcagttcaagttttcccgggtatgc
aaaccgaaatcctcacttgaagagacggaagttctgtttgtattcattgggtacgatcgcaaggcccgtacgcacaatccttacaagctttcatcaaccttgaccaac
atttatacaggttccagactccacgaagccggatgtgcaccctcatatcatgtggtgcgaggggatattgccacggccaccgaaggagtgattataaatgctgcta
acagcaaaggacaacctggcggaggggtgtgcggagcgctgtataagaaattcccggaaagcttcgatttacagccgatcgaagtaggaaaagcgcgactggt
caaaggtgcagctaaacatatcattcatgccgtaggaccaaacttcaacaaagtttcggaggttgaaggtgacaaacagttggcagaggcttatgagtccatcgct
aagattgtcaacgataacaattacaagtcagtagcgattccactgttgtccaccggcatcttttccgggaacaaagatcgactaacccaatcattgaaccatttgctga
cagctttagacaccactgatgcagatgtagccatatactgcagggacaagaaatgggaaatgactctcaaggaagcagtggctaggagagaagcagtggagga
gatatgcatatccgacgactcttcagtgacagaacctgatgcagagctggtgagggtgcatccgaagagttctttggctggaaggaagggctacagcacaagcg
atggcaaaactttctcatatttggaagggaccaagtttcaccaggcggccaaggatatagcagaaattaatgccatgtggcccgttgcaacggaggccaatgagc
aggtatgcatgtatatcctcggagaaagcatgagcagtattaggtcgaaatgccccgtcgaagagtcggaagcctccacaccacctagcacgctgccttgcttgtg
catccatgccatgactccagaaagagtacagcgcctaaaagcctcacgtccagaacaaattactgtgtgctcatcctttccattgccgaagtatagaatcactggtgt
gcagaagatccaatgctcccagcctatattgttctcaccgaaagtgcctgcgtatattcatccaaggaagtatctcgtggaaacaccaccggtagacgagactccg
gagccatcggcagagaaccaatccacagaggggacacctgaacaaccaccacttataaccgaggatgagaccaggactagaacgcctgagccgatcatcatc
gaagaggaagaagaggatagcataagtttgctgtcagatggcccgacccaccaggtgctgcaagtcgaggcagacattcacgggccgccctctgtatctagctc
atcctggtccattcctcatgcatccgactttgatgtggacagtttatccatacttgacaccctggagggagctagcgtgaccagcggggcaacgtcagccgagact
aactcttacttcgcaaagagtatggagtttctggcgcgaccggtgcctgcgcctcgaacagtattcaggaaccctccacatcccgctccgcgcacaagaacaccg
tcacttgcacccagcagggcctgctcgagaaccagcctagtttccaccccgccaggcgtgaatagggtgatcactagagaggagctcgaggcgcttaccccgtc
acgcactcctagcaggtcggtctcgagaaccagcctggtctccaacccgccaggcgtaaatagggtgattacaagagaggagtttgaggcgttcgtagcacaac
aacaatgacggtttgatgcgggtgcatacatcttttcctccgacaccggtcaagggcatttacaacaaaaatcagtaaggcaaacggtgctatccgaagtggtgttg
gagaggaccgaattggagatttcgtatgccccgcgcctcgaccaagaaaaagaagaattactacgcaagaaattacagttaaatcccacacctgctaacagaagc
agataccagtccaggaaggtggagaacatgaaagccataacagctagacgtattctgcaaggcctagggcattatttgaaggcagaaggaaaagtggagtgcta
ccgaaccctgcatcctgttcctttgtattcatctagtgtgaaccgtgccttttcaagccccaaggtcgcagtggaagcctgtaacgccatgttgaaagagaactttccg
actgtggcttcttactgtattattccagagtacgatgcctatttggacatggttgacggagcttcatgctgcttagacactgccagttttgccctgcaaagctgcgcag
ctttccaaagaaacactcctatttggaacccacaatacgatcggcagtgccttcagcgatccagaacacgctccagaacgtcctggcagctgccacaaaaagaaa
ttgcaatgtcacgcaaatgagagaattgcccgtattggattcggcggcctttaatgtggaatgcttcaagaaatatgcgtgtaataatgaatattgggaaacgtttaaa
gaaaaccccatcaggcttactgaagaaaacgtggtaaattacattaccaaattaaaaggaccaaaagctgctgctctttttgcgaagacacataatttgaatatgttgc
aggacataccaatggacaggtttgtaatggacttaaagagagacgtgaaagtgactccaggaacaaaacatactgaagaacggcccaaggtacaggtgatcca
ggctgccgatccgctagcaacagcgtatctgtgcggaatccaccgagagctggttaggagattaaatgcggtcctgcttccgaacattcatacactgtttgatatgtc
ggctgaagactttgacgctattatagccgagcacttccagcctggggattgtgttctggaaactgacatcgcgtcgtttgataaaagtgaggacgacgccatggctc
tgaccgcgttaatgattctggaagacttaggtgtggacgcagagctgttgacgctgattgaggcggctttcggcgaaatttcatcaatacatttgcccactaaaacta
aatttaaattcggagccatgatgaaatctggaatgttcctcacactgtttgtgaacacagtcattaacattgtaatcgcaagcagagtgttgagagaacggctaaccg
gatcaccatgtgcagcattcattggagatgacaatatcgtgaaaggagtcaaatcggacaaattaatggcagacaggtgcgccacctggttgaatatggaagtcaa
gattatagatgctgtggtgggcgagaaagcgccttatttctgtggagggtttattttgtgtgactccgtgaccggcacagcgtgccgtgtggcagacccccctaaaaa
ggctgtttaagcttggcaaacctctggcagcagacgatgaacatgatgatgacaggagaagggcattgcatgaagagtcaacacgctggaaccgagtgggtatt
ctttcagagctgtgcaaggcagtagaatcaaggtatgaaaccgtaggaacttccatcatagttatggccatgactactctagctagcagtgttaaatcattcagctacc
tgagaggggcccctataactctctacggcTAAcctgaatggactacgactatcacgcccaaacatttacagccgcggtgtcaaaaaccgcgtggacgtggtta
acatccctgctgggaggatcagccgtaattattataattggcttggtgctggctactattgtggccatgtacgtgctgaccaaccagaaacataattgaatacagcag
caattggcaagctgcttacatagaactcgcggcgattggcatgccgccttaaaatttttatttatttttttcttttcttttccgaatcggattttgtttttaatatttcAAAAA
AAAAAAAAAAAAAAAAAAAAAAAAAAAAAAAAAAAAAAAAAAAAAAAAAAAAAAAAAAAAAA
AAAAAAAAAAAAAtacgtagtttaaac TC-83 Production Vector(SEQ ID NO: 9); TC-83 genome with nucleotides 7544-11175 deleted, plus 5' T7-promoter, plus 3' restriction sites TAATACGACTCACTATAGGATAGGCGGCGCATGAGAGAAGCCCAGACCAATTACCTACCCAAAAT
GGAGAAAGTTCACGTTGACATCGAGGAAGACAGCCCATTCCTCAGAGCTTTGCAGCGGAGCTTCC
CGCAGTTTGAGGTAGAAGCCAAGCAGGTCACTGATAATGACCATGCTAATGCCAGAGCGTTTTCG
CATCTGGCTTCAAAACTGATCGAAACGGAGGTGGACCCATCCGACACGATCCTTGACATTGGAAG
TGCGCCCGCCCGCAGAATGTATTCTAAGCACAAGTATCATTGTATCTGTCCGATGAGATGTGCGG -continued AAGATCCGGACAGATTGTATAAGTATGCAACTAAGCTGAAGAAAAACTGTAAGGAAATAACTGA
TAAGGAATTGGACAAGAAAATGAAGGAGCTCGCCGCCGTCATGAGCGACCCTGACCTGGAAACT
GAGACTATGTGCCTCCACGACGACGAGTCGTGTCGCTACGAAGGGCAAGTCGCTGTTTACCAGGA
TGTATACGCGGTTGACGGACCGACAAGTCTCTATCACCAAGCCAATAAGGGAGTTAGAGTCGCCT
ACTGGATAGGCTTTGACACCACCCCTTTTATGTTTAAGAACTTGGCTGGAGCATATCCATCATACT
CTACCAACTGGGCCGACGAAACCGTGTTAACGGCTCGTAACATAGGCCTATGCAGCTCTGACGTT
ATGGAGCGGTCACGTAGAGGGATGTCCATTCTTAGAAAGAAGTATTTGAAACCATCCAACAATGT
TCTATTCTCTGTTGGCTCGACCATCTACCACGAGAAGAGGGACTTACTGAGGAGCTGGCACCTGCC
GTCTGTATTTCACTTACGTGGCAAGCAAAATTACACATGTCGGTGTGAGACTATAGTTAGTTGCGA
CGGGTACGTCGTTAAAAGAATAGCTATCAGTCCAGGCCTGTATGGGAAGCCTTCAGGCTATGCTG
CTACGATGCACCGCGAGGGATTCTTGTGCTGCAAAGTGACAGACACATTGAACGGGGAGAGGGTC
TCTTTTCCCGTGTGCACGTATGTGCCAGCTACATTGTGTGACCAAATGACTGGCATACTGGCAACA
GATGTCAGTGCGGACGACGCGCAAAAACTGCTGGTTGGGCTCAACCAGCGTATAGTCGTCAACGG
TCGCACCCAGAGAAACACCAATACCATGAAAAATTACCTTTTGCCCGTAGTGGCCCAGGCATTTG
CTAGGTGGGCAAAGGAATATAAGGAAGATCAAGAAGATGAAAGGCCACTAGGACTACGAGATAG
ACAGTTAGTCATGGGGTGTTGTTGGGCTTTTAGAAGGCACAAGATAACATCTATTTATAAGCGCCC
GGATACCCAAACCATCATCAAAGTGAACAGCGATTTCCACTCATTCGTGCTGCCCAGGATAGGCA
GTAACACATTGGAGATCGGGCTGAGAACAAGAATCAGGAAAATGTTAGAGGAGCACAAGGAGCC
GTCACCTCTCATTACCGCCGAGGACGTACAAGAAGCTAAGTGCGCAGCCGATGAGGCTAAGGAG
GTGCGTGAAGCCGAGGAGTTGCGCGCAGCTCTACCACCTTTGGCAGCTGATGTTGAGGAGCCCAC
TCTGGAAGCCGATGTCGACTTGATGTTACAAGAGGCTGGGGCCGGCTCAGTGGAGACACCTCGTG
GCTTGATAAAGGTTACCAGCTACGATGGCGAGGACAAGATCGGCTCTTACGCTGTGCTTTCTCCGC
AGGCTGTACTCAAGAGTGAAAAATTATCTTGCATCCACCCTCTCGCTGAACAAGTCATAGTGATA
ACACACTCTGGCCGAAAAGGGCGTTATGCCGTGGAACCATACCATGGTAAAGTAGTGGTGCCAGA
GGGACATGCAATACCCGTCCAGGACTTTCAAGCTCTGAGTGAAAGTGCCACCATTGTGTACAACG
AACGTGAGTTCGTAAACAGGTACCTGCACCATATTGCCACACATGGAGGAGCGCTGAACACTGAT
GAAGAATATTACAAAACTGTCAAGCCCAGCGAGCACGACGGCGAATACCTGTACGACATCGACA
GGAAACAGTGCGTCAAGAAAGAACTAGTCACTGGGCTAGGGCTCACAGGCGAGCTGGTGGATCC
TCCCTTCCATGAATTCGCCTACGAGAGTCTGAGAACACGACCAGCCGCTCCTTACCAAGTACCAA
CCATAGGGGTGTATGGCGTGCCAGGATCAGGCAAGTCTGGCATCATTAAAAGCGCAGTCACCAAA
AAAGATCTAGTGGTGAGCGCCAAGAAAGAAAACTGTGCAGAAATTATAAGGGACGTCAAGAAAA
TGAAAGGGCTGGACGTCAATGCCAGAACTGTGGACTCAGTGCTCTTGAATGGATGCAAACACCCC
GTAGAGACCCTGTATATTGACGAAGCTTTTGCTTGTCATGCAGGTACTCTCAGAGCGCTCATAGCC
ATTATAAGACCTAAAAAGGCAGTGCTCTGCGGGGATCCCAAACAGTGCGGTTTTTTAACATGAT
GTGCCTGAAAGTGCATTTTAACCACGAGATTTGCACACAAGTCTTCCACAAAAGCATCTCTCGCCG
TTGCACTAAATCTGTGACTTCGGTCGTCTCAACCTTGTTTTACGACAAAAAAATGAGAACGACGA
ATCCGAAAGAGACTAAGATTGTGATTGACACTACCGGCAGTACCAAACCTAAGCAGGACGATCTC
ATTCTCACTTGTTTCAGAGGGTGGGTGAAGCAGTTGCAAATAGATTACAAAGGCAACGAAATAAT
GACGGCAGCTGCCTCTCAAGGGCTGACCCGTAAAGGTGTGTATGCCGTTCGGTACAAGGTGAATG
AAAATCCTCTGTACGCACCCACCTCAGAACATGTGAACGTCCTACTGACCCGCACGGAGGACCGC
ATCGTGTGGAAAACACTAGCCGGCGACCCATGGATAAAAACACTGACTGCCAAGTACCCTGGGA
ATTTCACTGCCACGATAGAGGAGTGGCAAGCAGAGCATGATGCCATCATGAGGCACATCTTGGAG
AGACCGGACCCTACCGACGTCTTCCAGAATAAGGCAAACGTGTGTTGGGCCAAGGCTTTAGTGCC
GGTGCTGAAGACCGCTGGCATAGACATGACCACTGAACAATGGAACACTGTGGATTATTTTGAAA
CGGACAAAGCTCACTCAGCAGAGATAGTATTGAACCAACTATGCGTGAGGTTCTTTGGACTCGAT
CTGGACTCCGGTCTATTTTCTGCACCCACTGTTCCGTTATCCATTAGGAATAATCACTGGGATAAC
TCCCCGTCGCCTAACATGTACGGGCTGAATAAAGAAGTGGTCCGTCAGCTCTCTCGCAGGTACCC
ACAACTGCCTCGGGCAGTTGCCACTGGAAGAGTCTATGACATGAACACTGGTACACTGCGCAATT
ATGATCCGCGCATAAACCTAGTACCTGTAAACAGAAGACTGCCTCATGCTTTAGTCCTCCACCATA
ATGAACACCCACAGAGTGACTTTTCTTCATTCGTCAGCAAATTGAAGGGCAGAACTGTCCTGGTG
GTCGGGGAAAAGTTGTCCGTCCCAGGCAAAATGGTTGACTGGTTGTCAGACCGGCCTGAGGCTAC
CTTCAGAGCTCGGCTGGATTTAGGCATCCCAGGTGATGTGCCCAAATATGACATAATATTTGTTAA
TGTGAGGACCCCATATAAATACCATCACTATCAGCAGTGTGAAGACCATGCCATTAAGCTTAGCA
TGTTGACCAAGAAAGCTTGTCTGCATCTGAATCCCGGCGGAACCTGTGTCAGCATAGGTTATGGTT -continued ACGCTGACAGGGCCAGCGAAAGCATCATTGGTGCTATAGCGCGGCAGTTCAAGTTTTCCCGGGTA
TGCAAACCGAAATCCTCACTTGAAGAGACGGAAGTTCTGTTTGTATTCATTGGGTACGATCGCAA
GGCCCGTACGCACAATCCTTACAAGCTTTCATCAACCTTGACCAACATTTATACAGGTTCCAGACT
CCACGAAGCCGGATGTGCACCCTCATATCATGTGGTGCGAGGGGATATTGCCACGGCCACCGAAG
GAGTGATTATAAATGCTGCTAACAGCAAAGGACAACCTGGCGGAGGGGTGTGCGGAGCGCTGTA
TAAGAAATTCCCGGAAAGCTTCGATTTACAGCCGATCGAAGTAGGAAAAGCGCGACTGGTCAAA
GGTGCAGCTAAACATATCATTCATGCCGTAGGACCAAACTTCAACAAAGTTTCGGAGGTTGAAGG
TGACAAACAGTTGGCAGAGGCTTATGAGTCCATCGCTAAGATTGTCAACGATAACAATTACAAGT
CAGTAGCGATTCCACTGTTGTCCACCGGCATCTTTTCCGGGAACAAAGATCGACTAACCCAATCAT
TGAACCATTTGCTGACAGCTTTAGACACCACTGATGCAGATGTAGCCATATACTGCAGGGACAAG
AAATGGGAAATGACTCTCAAGGAAGCAGTGGCTAGGAGAGAAGCAGTGGAGGAGATATGCATAT
CCGACGACTCTTCAGTGACAGAACCTGATGCAGAGCTGGTGAGGGTGCATCCGAAGAGTTCTTTG
GCTGGAAGGAAGGGCTACAGCACAAGCGATGGCAAAACTTTCTCATATTTGGAAGGGACCAAGTT
TCACCAGGCGGCCAAGGATATAGCAGAAATTAATGCCATGTGGCCCGTTGCAACGGAGGCCAATG
AGCAGGTATGCATGTATATCCTCGGAGAAAGCATGAGCAGTATTAGGTCGAAATGCCCCGTCGAA
GAGTCGGAAGCCTCCACACCACCTAGCACGCTGCCTTGCTTGTGCATCCATGCCATGACTCCAGA
AAGAGTACAGCGCCTAAAAGCCTCACGTCCAGAACAAATTACTGTGTGCTCATCCTTTCCATTGCC
GAAGTATAGAATCACTGGTGTGCAGAAGATCCAATGCTCCCAGCCTATATTGTTCTCACCGAAAG
TGCCTGCGTATATTCATCCAAGGAAGTATCTCGTGGAAACACCACCGGTAGACGAGACTCCGGAG
CCATCGGCAGAGAACCAATCCACAGAGGGGACACCTGAACAACCACCACTTATAACCGAGGATG
AGACCAGGACTAGAACGCCTGAGCCGATCATCATCGAAGAGGAAGAAGAGGATAGCATAAGTTT
GCTGTCAGATGGCCCGACCCACCAGGTGCTGCAAGTCGAGGCAGACATTCACGGGCCGCCCTCTG
TATCTAGCTCATCCTGGTCCATTCCTCATGCATCCGACTTTGATGTGGACAGTTTATCCATACTTGA
CACCCTGGAGGGAGCTAGCGTGACCAGCGGGGCAACGTCAGCCGAGACTAACTCTTACTTCGCAA
AGAGTATGGAGTTTCTGGCGCGACCGGTGCCTGCGCCTCGAACAGTATTCAGGAACCCTCCACAT
CCCGCTCCGCGCACAAGAACACCGTCACTTGCACCCAGCAGGGCCTGCTCGAGAACCAGCCTAGT
TTCCACCCCGCCAGGCGTGAATAGGGTGATCACTAGAGAGGAGCTCGAGGCGCTTACCCCGTCAC
GCACTCCTAGCAGGTCGGTCTCGAGAACCAGCCTGGTCTCCAACCCGCCAGGCGTAAATAGGGTG
ATTACAAGAGAGGAGTTTGAGGCGTTCGTAGCACAACAACAATGACGGTTTGATGCGGGTGCATA
CATCTTTTCCTCCGACACCGGTCAAGGGCATTTACAACAAAAATCAGTAAGGCAAACGGTGCTAT
CCGAAGTGGTGTTGGAGAGGACCGAATTGGAGATTTCGTATGCCCCGCGCCTCGACCAAGAAAAA
GAAGAATTACTACGCAAGAAATTACAGTTAAATCCCACACCTGCTAACAGAAGCAGATACCAGTC
CAGGAAGGTGGAGAACATGAAAGCCATAACAGCTAGACGTATTCTGCAAGGCCTAGGGCATTATT
TGAAGGCAGAAGGAAAAGTGGAGTGCTACCGAACCCTGCATCCTGTTCCTTTGTATTCATCTAGT
GTGAACCGTGCCTTTTCAAGCCCCAAGGTCGCAGTGGAAGCCTGTAACGCCATGTTGAAAGAGAA
CTTTCCGACTGTGGCTTCTTACTGTATTATTCCAGAGTACGATGCCTATTTGGACATGGTTGACGG
AGCTTCATGCTGCTTAGACACTGCCAGTTTTTGCCCTGCAAAGCTGCGCAGCTTTCCAAAGAAACA
CTCCTATTTGGAACCCACAATACGATCGGCAGTGCCTTCAGCGATCCAGAACACGCTCCAGAACG
TCCTGGCAGCTGCCACAAAAAGAAATTGCAATGTCACGCAAATGAGAGAATTGCCCGTATTGGAT
TCGGCGGCCTTTAATGTGGAATGCTTCAAGAAATATGCGTGTAATAATGAATATTGGGAAACGTT
TAAAGAAAACCCCATCAGGCTTACTGAAGAAAACGTGGTAAATTACATTACCAAATTAAAAGGAC
CAAAAGCTGCTGCTCTTTTTGCGAAGACACATAATTTGAATATGTTGCAGGACATACCAATGGAC
AGGTTTGTAATGGACTTAAAGAGAGACGTGAAAGTGACTCCAGGAACAAAACATACTGAAGAAC
GGCCCAAGGTACAGGTGATCCAGGCTGCCGATCCGCTAGCAACAGCGTATCTGTGCGGAATCCAC
CGAGAGCTGGTTAGGAGATTAAATGCGGTCCTGCTTCCGAACATTCATACACTGTTTGATATGTCG
GCTGAAGACTTTGACGCTATTATAGCCGAGCACTTCCAGCCTGGGGATTGTGTTCTGGAAACTGAC
ATCGCGTCGTTTGATAAAAGTGAGGACGACGCCATGGCTCTGACCGCGTTAATGATTCTGGAAGA
CTTAGGTGTGGACGCAGAGCTGTTGACGCTGATTGAGGCGGCTTTCGGCGAAATTTCATCAATAC
ATTTGCCCACTAAAACTAAATTTAAATTCGGAGCCATGATGAAATCTGGAATGTTCCTCACACTGT
TTGTGAACACAGTCATTAACATTGTAATCGCAAGCAGAGTGTTGAGAGAACGGCTAACCGGATCA
CCATGTGCAGCATTCATTGGAGATGACAATATCGTGAAAGGAGTCAAATCGGACAAATTAATGGC
AGACAGGTGCGCCACCTGGTTGAATATGGAAGTCAAGATTATAGATGCTGTGGTGGGCGAGAAA
GCGCCTTATTTCTGTGGAGGGTTTATTTTGTGTGACTCCGTGACCGGCACAGCGTGCCGTGTGGCA
GACCCCCTAAAAAGGCTGTTTAAGCTTGGCAAACCTCTGGCAGCAGACGATGAACATGATGATGA -continued CAGGAGAAGGGCATTGCATGAAGAGTCAACACGCTGGAACCGAGTGGGTATTCTTTCAGAGCTGT
GCAAGGCAGTAGAATCAAGGTATGAAACCGTAGGAACTTCCATCATAGTTATGGCCATGACTACT
CTAGCTAGCAGTGTTAAATCATTCAGCTACCTGAGAGGGGCCCCTATAACTCTCTACGGCTAACCT
GAATGGACTACGACTATCACGCCCAAACATTTACAGCCGCGGTGTCAAAAACCGCGTGGACGTGG
TTAACATCCCTGCTGGGAGGATCAGCCGTAATTATTATAATTGGCTTGGTGCTGGCTACTATTGTG
GCCATGTACGTGCTGACCAACCAGAAACATAATTGAATACAGCAGCAATTGGCAAGCTGCTTACA
TAGAACTCGCGGCGATTGGCATGCCGCCTTAAAATTTTTATTTTATTTTTCTTTTCTTTTCCGAATC
GGATTTTGTTTTTAATATTTCAAAAAAAAAAAAAAAAAAAAAAAAAAAAAAAAAAAAAAAAA
AAAAAAAAAAAAAAAAAAAAAAAAAAAAAAAAAAAAAtacgtagtttaaac VEE-UbAAY (SEQ ID NO: 14); VEE delivery vector with MHC class I mouse tumor epitopes SIINFEKL (SEQ ID NO: 57)_and AH1-A5 inserted ATGggcggcgcatgagagaagcccagaccaattacctacccaaaatggagaaagttcacgttgacatcgaggaagacagcccattcctcagag
ctttgcagcggagcttcccgcagtttgaggtagaagccaagcaggtcactgataatgaccatgctaatgccagagcgttttcgcatctggcttcaaaactgatcgaa
acggaggtggacccatccgacacgatccttgacattggaagtgcgcccgcccgcagaatgtattctaagcacaagtatcattgtatctgtccgatgagatgtgcgg
aagatccggacagattgtataagtatgcaactaagctgaagaaaaactgtaaggaaataactgataaggaattggacaagaaaatgaaggagctcgccgccgtc
atgagcgaccctgacctggaaactgagactatgtgcctccacgacgacgagtcgtgtcgctacgaagggcaagtcgctgtttaccaggatgtatacgcggttgac
ggaccgacaagtctctatcaccaagccaataagggagttagagtcgcctactggataggctttgacaccaccccttttatgtttaagaacttggctggagcatatcca
tcatactctaccaactgggccgacgaaaccgtgttaacggctcgtaacataggcctatgcagctctgacgttatggagcggtcacgtagagggatgtccattcttag
aaagaagtatttgaaaccatccaacaatgttctattctctgttggctcgaccatctaccacgagaagagggacttactgaggagctggcacctgccgtctgtatttcac
ttacgtggcaagcaaaattacacatgtcggtgtgagactatagttagttgcgacgggtacgtcgttaaaagaatagctatcagtccaggcctgtatgggaagccttc
aggctatgctgctacgatgcaccgcgagggattcttgtgctgcaaagtgacagacacattgaacggggagagggtctcttttcccgtgtgcacgtatgtgccagct
acattgtgtgaccaaatgactggcatactggcaacagatgtcagtgcggacgacgcgcaaaaactgctggttgggctcaaccagcgtatagtcgtcaacggtcgc
acccagagaaacaccaataccatgaaaaattaccttttgcccgtagtggcccaggcatttgctaggtgggcaaaggaatataaggaagatcaagaagatgaaag
gccactaggactacgagatagacagttagtcatggggtgttgttgggcttttagaaggcacaagataacatctatttataagcgcccggatacccaaaccatcatca
aagtgaacagcgatttccactcattcgtgctgcccaggataggcagtaacacattggagatcgggctgagaacaagaatcaggaaaatgttagaggagcacaag
gagccgtcacctctcattaccgccgaggacgtacaagaagctaagtgcgcagccgatgaggctaaggaggtgcgtgaagccgaggagttgcgcgcagctcta
ccacctttggcagctgatgttgaggagcccactctggaagccgatgtcgacttgatgttacaagaggctggggccggctcagtggagacacctcgtggcttgata
aaggttaccagctacgctggcgaggacaagatcggctcttacgctgtgctttctccgcaggctgtactcaagagtgaaaaattatcttgcatccaccctctcgctgaa
caagtcatagtgataacacactctggccgaaaagggcgttatgccgtggaaccataccatggtaaagtagtggtgccagagggacatgcaatacccgtccagga
ctttcaagctctgagtgaaagtgccaccattgtgtacaacgaacgtgagttcgtaaacaggtacctgcaccatattgccacacatggaggagcgctgaacactgat
gaagaatattacaaaactgtcaagcccagcgagcacgacggcgaatacctgtacgacatcgacaggaaacagtgcgtcaagaaagaactagtcactgggctag
ggctcacaggcgagctggtggatcctcccttccatgaattcgcctacgagagtctgagaacacgaccagccgctccttaccaagtaccaaccataggggtgtatg
gcgtgccaggatcaggcaagtctggcatcattaaaagcgcagtcaccaaaaaagatctagtggtgagcgccaagaaagaaaactgtgcagaaattataaggga
cgtcaagaaaatgaaagggctggacgtcaatgccagaactgtggactcagtgctcttgaatggatgcaaacaccccgtagagaccctgtatattgacgaagctttt
gcttgtcatgcaggtactctcagagcgctcatagccattataagacctaaaaaggcagtgctctgcggggatcccaaacagtgcggtttttttaacatgatgtgcctg
aaagtgcattttaaccacgagatttgcacacaagtcttccacaaaagcatctctcgccgttgcactaaatctgtgacttcggtcgtctcaaccttgttttacgacaaaaa
aatgagaacgacgaatccgaaagagactaagattgtgattgacactaccggcagtaccaaacctaagcaggacgatctcattctcacttgtttcagagggtgggtg
aagcagttgcaaatagattacaaaggcaacgaaataatgacggcagctgcctctcaagggctgacccgtaaaggtgtgtatgccgttcggtacaaggtgaatgaa
aatcctctgtacgcacccacctcagaacatgtgaacgtcctactgacccgcacggaggaccgcatcgtgtggaaaacactagccggcgacccatggataaaaac
actgactgccaagtaccctgggaatttcactgccacgatagaggagtggcaagcagagcatgatgccatcatgaggcacatcttggagagaccggaccctaccg
acgtcttccagaataaggcaaacgtgtgttgggccaaggctttagtgccggtgctgaagaccgctggcatagacatgaccactgaacaatggaacactgtggatt
attttgaaacggacaaagctcactcagcagagatagtattgaaccaactatgcgtgaggttctttggactcgatctggactccggtctattttctgcacccactgttccg
ttatccattaggaataatcactgggataactccccgtcgcctaacatgtacgggctgaataaagaagtggtccgtcagctctctcgcaggtacccacaactgcctcg
ggcagttgccactggaagagtctatgacatgaacactggtacactgcgcaattatgatccgcgcataaacctagtacctgtaaacagaagactgcctcatgctttag
tcctccaccataatgaacacccacagagtgacttttcttcattcgtcagcaaattgaagggcagaactgtcctggtggtcggggaaaagttgtccgtcccaggcaaa
atggttgactggttgtcagaccggcctgaggctaccttcagagctcggctggatttaggcatcccaggtgatgtgcccaaatatgacataatatttgttaatgtgagg
accccatataaataccatcactatcagcagtgtgaagaccatgccattaagcttagcatgttgaccaagaaagcttgtctgcatctgaatcccggcggaacctgtgtc
agcataggttatggttacgctgacagggccagcgaaagcatcattggtgctatagcgcggcagttcaagttttcccgggtatgcaaaccgaaatcctcacttgaag
agacggaagttctgtttgtattcattgggtacgatcgcaaggcccgtacgcacaatccttacaagctttcatcaaccttgaccaacatttatacaggttccagactcca
cgaagccggatgtgcaccctcatatcatgtggtgcgaggggatattgccacggccaccgaaggagtgattataaatgctgctaacagcaaaggacaacctggcg
gaggggtgtgcggagcgctgtataagaaattcccggaaagcttcgatttacagccgatcgaagtaggaaaagcgcgactggtcaaaggtgcagctaaacatatc
attcatgccgtaggaccaaacttcaacaaagtttcggaggttgaaggtgacaaacagttggcagaggcttatgagtccatcgctaagattgtcaacgataacaatta
caagtcagtagcgattccactgttgtccaccggcatcttttccgggaacaaagatcgactaacccaatcattgaaccatttgctgacagctttagacaccactgatgc -continued agatgtagccatatactgcagggacaagaaatgggaaatgactctcaaggaagcagtggctaggagagaagcagtggaggagatatgcatatccgacgactctt
cagtgacagaacctgatgcagagctggtgagggtgcatccgaagagttctttggctggaaggaagggctacagcacaagcgatggcaaaactttctcatatttgg
aagggaccaagtttcaccaggcggccaaggatatagcagaaattaatgccatgtggcccgttgcaacggaggccaatgagcaggtatgcatgtatatcctcgga
gaaagcatgagcagtattaggtcgaaatgccccgtcgaagagtcggaagcctccacaccacctagcacgctgccttgcttgtgcatccatgccatgactccagaa
agagtacagcgcctaaaagcctcacgtccagaacaaattactgtgtgctcatcctttccattgccgaagtatagaatcactggtgtgcagaagatccaatgctccca
gcctatattgttctcaccgaaagtgcctgcgtatattcatccaaggaagtatctcgtggaaacaccaccggtagacgagactccggagccatcggcagagaacca
atccacagaggggacacctgaacaaccaccacttataaccgaggatgagaccaggactagaacgcctgagccgatcatcatcgaagaggaagaagaggatag
cataagtttgctgtcagatggcccgacccaccaggtgctgcaagtcgaggcagacattcacgggccgccctctgtatctagctcatcctggtccattcctcatgcat
ccgactttgatgtggacagtttatccatacttgacaccctggagggagctagcgtgaccagcggggcaacgtcagccgagactaactcttacttcgcaaagagtat
ggagtttctggcgcgaccggtgcctgcgcctcgaacagtattcaggaaccctccacatcccgctccgcgcacaagaacaccgtcacttgcacccagcagggcct
gctcgagaaccagcctagtttccaccccgccaggcgtgaatagggtgatcactagagaggagctcgaggcgcttaccccgtcacgcactcctagcaggtcggtc
tcgagaaccagcctggtctccaacccgccaggcgtaaatagggtgattacaagagaggagtttgaggcgttcgtagcacaacaacaatgacggtttgatgcggg
tgcatacatcttttcctccgacaccggtcaagggcatttacaacaaaaatcagtaaggcaaacggtgctatccgaagtggtgttggagaggaccgaattggagattt
cgtatgccccgcgcctcgaccaagaaaaagaagaattactacgcaagaaattacagttaaatcccacacctgctaacagaagcagataccagtccaggaaggtg
gagaacatgaaagccataacagctagacgtattctgcaaggcctagggcattatttgaaggcagaaggaaaagtggagtgctaccgaaccctgcatcctgttcctt
tgtattcatctagtgtgaaccgtgccttttcaagccccaaggtcgcagtggaagcctgtaacgccatgttgaaagagaactttccgactgtggcttcttactgtattattc
cagagtacgatgcctatttggacatggttgacggagcttcatgctgcttagacactgccagttttgccctgcaaagctgcgcagctttccaaagaaacactcctattt
ggaacccacaatacgatcggcagtgccttcagcgatccagaacacgctccagaacgtcctggcagctgccacaaaaagaaattgcaatgtcacgcaaatgaga
gaattgcccgtattggattcggcggcctttaatgtggaatgcttcaagaaatatgcgtgtaataatgaatattgggaaacgtttaaagaaaaccccatcaggcttactg
aagaaaacgtggtaaattacattaccaaattaaaaggaccaaaagctgctgctctttttgcgaagacacataatttgaatatgttgcaggacataccaatggacaggt
ttgtaatggacttaaagagagacgtgaaagtgactccaggaacaaaacatactgaagaacggcccaaggtacaggtgatccaggctgccgatccgctagcaaca
gcgtatctgtgcggaatccaccgagagctggttaggagattaaatgcggtcctgcttccgaacattcatacactgtttgatatgtcggctgaagactttgacgctatta
tagccgagcacttccagcctggggattgtgttctggaaactgacatcgcgtcgtttgataaaagtgaggacgacgccatggctctgaccgcgttaatgattctggaa
gacttaggtgtggacgcagagctgttgacgctgattgaggcggctttcggcgaaatttcatcaatacatttgcccactaaaactaaatttaaattcggagccatgatg
aaatctggaatgttcctcacactgtttgtgaacacagtcattaacattgtaatcgcaagcagagtgttgagagaacggctaaccggatcaccatgtgcagcattcatt
ggagatgacaatatcgtgaaaggagtcaaatcggacaaattaatggcagacaggtgcgccacctggttgaatatggaagtcaagattatagatgctgtggtgggc
gagaaagcgccttatttctgtggagggtttattttgtgtgactccgtgaccggcacagcgtgccgtgtggcagacccccctaaaaaggctgtttaagcttggcaaacct
ctggcagcagacgatgaacatgatgatgacaggagaagggcattgcatgaagagtcaacacgctggaaccgagtgggtattctttcagagctgtgcaaggcagt
agaatcaaggtatgaaaccgtaggaacttccatcatagttatggccatgactactctagctagcagtgttaaatcattcagctacctgagaggggcccctataactct
ctacggctaacctgaatggactacgactctagaatagtctttaattaaagtccgccatatgaggccaccatgCAGATCTTCGTGAAGACCCTGA
CCGGCAAGACCATCACCCTAGAGGTGGAGCCCAGTGACACCATCGAGAACGTGAAGGCCAAGAT
CCAGGATAAAGAGGGCATCCCCCCTGACCAGCAGAGGCTGATCTTTGCCGGCAAGCAGCTGGAA
GATGGCCGCACCCTCTCTGATTACAACATCCAGAAGGAGTCAACCCTGCACCTGGTCCTTCGCCTG
AGAGGTGGCGCTGCTTACAGTATAATCAACTTTGAAAAACTGGCTGCTTACGGCATCCTGGGCTTT
GTGTTTACACTGGCTGCCTACCTGCTGTTTGGCTATCCTGTGTACGTGGCCGCTTATGGACTGTGTA
CCCTGGTGGCCATGCTGGCTGCTTACAATCTGGTGCCTATGGTGGCCACAGTGGCCGCCTATTGTC
TTGGCGGACTGCTGACAATGGTGGCAGCCTACAgcccgagctatgcgtatcatcagtttGCAGCCTACGGCCCAG
GACCAGGCgCTAAATTTGTGGCTGCCTGGACACTGAAAGCCGCCGCTGGACCAGGTCCTGGACAG
TACATCAAGGCCAACAGCAAGTTCATCGGCATCACCGAACTCGGCCCAGGACCAGGCTATCCCTA
CGATGTGCCTGATTACGCCTGATagTGATGATTCGAACGGCCGtatcacgcccaaacatttacagccgcggtgtcaaaaac
cgcgtggacgtggttaacatccctgctgggaggatcagccgtaattattataattggcttggtgctggctactattgtggccatgtacgtgctgaccaaccagaaaca
taattgaatacagcagcaattggcaagctgcttacatagaactcgcggcgattggcatgccgccttaaaattttatttatttttttcttttcttttccgaatcggattttgtttt
taatatttcAAAAAAAAAAAAAAAAAAAAAAAAAAAAAAAAAAAAAAAAAAAAAAAAAAAAAAAAA
AAAAAAAAAAAAAAAAAAAAAAA VEE-Luciferase (SEQ ID NO: 15); VEE delivery vector with luciferase gene inserted at 7545
ATGggcggcgcatgagagaagcccagaccaattacctacccaaaATGGagaaagttcacgttgacatcgaggaagacagcccattcctcagagctttgca
gcggagcttcccgcagtttgaggtagaagccaagcaggtcactgataatgaccatgctaatgccagagcgttttcgcatctggcttcaaaactgatcgaaacggag
gtggacccatccgacacgatccttgacattggaagtgcgcccgcccgcagaatgtattctaagcacaagtatcattgtatctgtccgatgagatgtgcggaagatcc
ggacagattgtataagtatgcaactaagctgaagaaaaactgtaaggaaataactgataaggaattggacaagaaaatgaaggagctcgccgccgtcatgagcg
accctgacctggaaactgagactatgtgcctccacgacgacgagtcgtgtcgctacgaagggcaagtcgctgtttaccaggatgtatacgcggttgacggaccga
caagtctctatcaccaagccaataagggagttagagtcgcctactggataggctttgacaccaccccttttatgtttaagaacttggctggagcatatccatcatactct
accaactgggccgacgaaaccgtgttaacggctcgtaacataggcctatgcagctctgacgttatggagcggtcacgtagagggatgtccattcttagaaagaag
tatttgaaaccatccaacaatgttctattctctgttggctcgaccatctaccacgagaagagggacttactgaggagctggcacctgccgtctgtatttcacttacgtgg -continued caagcaaaattacacatgtcggtgtgagactatagttagttgcgacgggtacgtcgttaaaagaatagctatcagtccaggcctgtatgggaagccttcaggctatg
ctgctacgatgcaccgcgagggattcttgtgctgcaaagtgacagacacattgaacggggagagggtctcttttcccgtgtgcacgtatgtgccagctacattgtgt
gaccaaatgactggcatactggcaacagatgtcagtgcggacgacgcgcaaaaactgctggttgggctcaaccagcgtatagtcgtcaacggtcgcacccaga
gaaacaccaataccatgaaaaattaccttttgcccgtagtggcccaggcatttgctaggtgggcaaaggaatataaggaagatcaagaagatgaaaggccactag
gactacgagatagacagttagtcatggggtgttgttgggcttttagaaggcacaagataacatctatttataagcgcccggatacccaaaccatcatcaaagtgaac
agcgatttccactcattcgtgctgcccaggataggcagtaacacattggagatcgggctgagaacaagaatcaggaaaatgttagaggagcacaaggagccgtc
acctctcattaccgccgaggacgtacaagaagctaagtgcgcagccgatgaggctaaggaggtgcgtgaagccgaggagttgcgcgcagctctaccacctttg
gcagctgatgttgaggagcccactctggaagccgatgtcgacttgatgttacaagaggctggggccggctcagtggagacacctcgtggcttgataaaggttacc
agctacgctggcgaggacaagatcggctcttacgctgtgctttctccgcaggctgtactcaagagtgaaaaattatcttgcatccaccctctcgctgaacaagtcata
gtgataacacactctggccgaaaagggcgttatgccgtggaaccataccatggtaaagtagtggtgccagagggacatgcaatacccgtccaggactttcaagct
ctgagtgaaagtgccaccattgtgtacaacgaacgtgagttcgtaaacaggtacctgcaccatattgccacacatggaggagcgctgaacactgatgaagaatatt
acaaaactgtcaagcccagcgagcacgacggcgaatacctgtacgacatcgacaggaaacagtgcgtcaagaaagaactagtcactgggctagggctcacag
gcgagctggtggatcctcccttccatgaattcgcctacgagagtctgagaacacgaccagccgctccttaccaagtaccaaccataggggtgtatggcgtgccag
gatcaggcaagtctggcatcattaaaagcgcagtcaccaaaaaagatctagtggtgagcgccaagaaagaaaactgtgcagaaattataagggacgtcaagaaa
atgaaagggctggacgtcaatgccagaactgtggactcagtgctcttgaatggatgcaaacaccccgtagagaccctgtatattgacgaagcttttgcttgtcatgc
aggtactctcagagcgctcatagccattataagacctaaaaaggcagtgctctgcggggatcccaaacagtgcggtttttttaacatgatgtgcctgaaagtgcatttt
aaccacgagatttgcacacaagtcttccacaaaagcatctctcgccgttgcactaaatctgtgacttcggtcgtctcaaccttgttttacgacaaaaaaatgagaacg
acgaatccgaaagagactaagattgtgattgacactaccggcagtaccaaacctaagcaggacgatctcattctcacttgtttcagagggtgggtgaagcagttgc
aaatagattacaaaggcaacgaaataatgacggcagctgcctctcaagggctgacccgtaaaggtgtgtatgccgttcggtacaaggtgaatgaaaatcctctgta
cgcacccacctcagaacatgtgaacgtcctactgacccgcacggaggaccgcatcgtgtggaaaacactagccggcgacccatggataaaaacactgactgcc
aagtaccctgggaatttcactgccacgatagaggagtggcaagcagagcatgatgccatcatgaggcacatcttggagagaccggaccctaccgacgtcttcca
gaataaggcaaacgtgtgttgggccaaggctttagtgccggtgctgaagaccgctggcatagacatgaccactgaacaatggaacactgtggattatttgaaacg
gacaaagctcactcagcagagatagtattgaaccaactatgcgtgaggttctttggactcgatctggactccggtctattttctgcacccactgttccgttatccattag
gaataatcactgggataactccccgtcgcctaacatgtacgggctgaataaagaagtggtccgtcagctctctcgcaggtacccacaactgcctcgggcagttgcc
actggaagagtctatgacatgaacactggtacactgcgcaattatgatccgcgcataaacctagtacctgtaaacagaagactgcctcatgctttagtcctccaccat
aatgaacacccacagagtgacttttcttcattcgtcagcaaattgaagggcagaactgtcctggtggtcggggaaaagttgtccgtcccaggcaaaatggttgactg
gttgtcagaccggcctgaggctaccttcagagctcggctggatttaggcatcccaggtgatgtgcccaaatatgacataatatttgttaatgtgaggaccccatataa
ataccatcactatcagcagtgtgaagaccatgccattaagcttagcatgttgaccaagaaagcttgtctgcatctgaatcccggcggaacctgtgtcagcataggtta
tggttacgctgacagggccagcgaaagcatcattggtgctatagcgcggcagttcaagttttcccgggtatgcaaaccgaaatcctcacttgaagagacggaagtt
ctgtttgtattcattgggtacgatcgcaaggcccgtacgcacaatccttacaagctttcatcaaccttgaccaacatttatacaggttccagactccacgaagccggat
gtgcaccctcatatcatgtggtgcgaggggatattgccacggccaccgaaggagtgattataaatgctgctaacagcaaaggacaacctggcggaggggtgtgc
ggagcgctgtataagaaattcccggaaagcttcgatttacagccgatcgaagtaggaaaagcgcgactggtcaaaggtgcagctaaacatatcattcatgccgta
ggaccaaacttcaacaaagtttcggaggttgaaggtgacaaacagttggcagaggcttatgagtccatcgctaagattgtcaacgataacaattacaagtcagtag
cgattccactgttgtccaccggcatcttttccgggaacaaagatcgactaacccaatcattgaaccatttgctgacagctttagacaccactgatgcagatgtagccat
atactgcagggacaagaaatgggaaatgactctcaaggaagcagtggctaggagagaagcagtggaggagatatgcatatccgacgactcttcagtgacagaa
cctgatgcagagctggtgagggtgcatccgaagagttctttggctggaaggaagggctacagcacaagcgatggcaaaactttctcatatttggaagggaccaag
tttcaccaggcggccaaggatatagcagaaattaatgccatgtggcccgttgcaacggaggccaatgagcaggtatgcatgtatatcctcggagaaagcatgagc
agtattaggtcgaaatgccccgtcgaagagtcggaagcctccacaccacctagcacgctgccttgcttgtgcatccatgccatgactccagaaagagtacagcgc
ctaaaagcctcacgtccagaacaaattactgtgtgctcatcctttccattgccgaagtatagaatcactggtgtgcagaagatccaatgctcccagcctatattgttctc
accgaaagtgcctgcgtatattcatccaaggaagtatctcgtggaaacaccaccggtagacgagactccggagccatcggcagagaaccaatccacagagggg
acacctgaacaaccaccacttataaccgaggatgagaccaggactagaacgcctgagccgatcatcatcgaagaggaagaagaggatagcataagtttgctgtc
agatggcccgacccaccaggtgctgcaagtcgaggcagacattcacgggccgccctctgtatctagctcatcctggtccattcctcatgcatccgactttgatgtgg
acagtttatccatacttgacaccctggagggagctagcgtgaccagcggggcaacgtcagccgagactaactcttacttcgcaaagagtatggagtttctggcgc
gaccggtgcctgcgcctcgaacagtattcaggaaccctccacatcccgctccgcgcacaagaacaccgtcacttgcacccagcagggcctgctcgagaaccag
cctagtttccaccccgccaggcgtgaatagggtgatcactagagaggagctcgaggcgcttaccccgtcacgcactcctagcaggtcggtctcgagaaccagcc
tggtctccaacccgccaggcgtaaatagggtgattacaagagaggagtttgaggcgttcgtagcacaacaacaatgacggtttgatgcgggtgcatacatcttttcc
tccgacaccggtcaagggcatttacaacaaaaatcagtaaggcaaacggtgctatccgaagtggtgttggagaggaccgaattggagatttcgtatgccccgcgc
ctcgaccaagaaaaagaagaattactacgcaagaaattacagttaaatcccacacctgctaacagaagcagataccagtccaggaaggtggagaacatgaaagc
cataacagctagacgtattctgcaaggcctagggcattatttgaaggcagaaggaaaagtggagtgctaccgaaccctgcatcctgttcctttgtattcatctagtgt
gaaccgtgccttttcaagccccaaggtcgcagtggaagcctgtaacgccatgttgaaagagaactttccgactgtggcttcttactgtattattccagagtacgatgc
ctatttggacatggttgacggagcttcatgctgcttagacactgccagtttttgccctgcaaagctgcgcagctttccaaagaaacactcctatttggaacccacaata
cgatcggcagtgccttcagcgatccagaacacgctccagaacgtcctggcagctgccacaaaaagaaattgcaatgtcacgcaaatgagagaattgcccgtattg
gattcggcggcctttaatgtggaatgcttcaagaaatatgcgtgtaataatgaatattgggaaacgtttaaagaaaaccccatcaggcttactgaagaaaacgtggta
aattacattaccaaattaaaaggaccaaaagctgctgctctttttgcgaagacacataatttgaatatgttgcaggacataccaatggacaggtttgtaatggacttaaa -continued gagagacgtgaaagtgactccaggaacaaaacatactgaagaacggcccaaggtacaggtgatccaggctgccgatccgctagcaacagcgtatctgtgcgg
aatccaccgagagctggttaggagattaaatgcggtcctgcttccgaacattcatacactgtttgatatgtcggctgaagactttgacgctattatagccgagcacttc
cagcctggggattgtgttctggaaactgacatcgcgtcgtttgataaaagtgaggacgacgccatggctctgaccgcgttaatgattctggaagacttaggtgtgga
cgcagagctgttgacgctgattgaggcggctttcggcgaaatttcatcaatacatttgcccactaaaactaaatttaaattcggagccatgatgaaatctggaatgttc
ctcacactgtttgtgaacacagtcattaacattgtaatcgcaagcagagtgttgagagaacggctaaccggatcaccatgtgcagcattcattggagatgacaatatc
gtgaaaggagtcaaatcggacaaattaatggcagacaggtgcgccacctggttgaatatggaagtcaagattatagatgctgtggtgggcgagaaagcgccttat
ttctgtggagggtttattttgtgtgactccgtgaccggcacagcgtgccgtgtggcagacccccctaaaaaggctgtttaagcttggcaaacctctggcagcagacga
tgaacatgatgatgacaggagaagggcattgcatgaagagtcaacacgctggaaccgagtgggtattctttcagagctgtgcaaggcagtagaatcaaggtatga
aaccgtaggaacttccatcatagttatggccatgactactctagctagcagtgttaaatcattcagctacctgagaggggcccctataactctctacggcTAAcct
gaatggactacgactctagaatagtctttaattaaagtccgccatatgagatggaagatgccaaaaacattaagaagggcccagcgccattctacccactcgaaga
cgggaccgccggcgagcagctgcacaaagccatgaagcgctacgccctggtgcccggcaccatcgcctttaccgacgcacatatcgaggtggacattacctac
gccgagtacttcgagatgagcgttcggctggcagaagctatgaagcgctatgggctgaatacaaaccatcggatcgtggtgtgcagcgagaatagcttgcagttc
ttcatgcccgtgttgggtgccctgttcatcggtgtggctgtggccccagctaacgacatctacaacgagcgcgagctgctgaacagcatgggcatcagccagccc
accgtcgtattcgtgagcaagaaagggctgcaaaagatcctcaacgtgcaaaagaagctaccgatcatacaaaagatcatcatcatggatagcaagaccgactac
cagggcttccaaagcatgtacaccttcgtgacttcccatttgccacccggcttcaacgagtacgacttcgtgcccgagagcttcgaccgggacaaaaccatcgccc
tgatcatgaacagtagtggcagtaccggattgcccaagggcgtagccctaccgcaccgcaccgcttgtgtccgattcagtcatgcccgcgaccccatcttcggca
accagatcatccccgacaccgctatcctcagcgtggtgccatttcaccacggcttcggcatgttcaccacgctgggctacttgatctgcggctttcgggtcgtgctc
atgtaccgcttcgaggaggagctattcttgcgcagcttgcaagactataagattcaatctgccctgctggtgcccacactatttagcttcttcgctaagagcactctcat
cgacaagtacgacctaagcaacttgcacgagatcgccagcgggggcgccgctcagcaaggaggtaggtgaggccgtggccaaacgcttccacctaccag
gcatccgccagggctacggcctgacagaaacaaccagcgccattctgatcacccccgaaggggacgacaagcctggcgcagtaggcaaggtggtgcccttct
tcgaggctaaggtggtggacttggacaccggtaagacactgggtgtgaaccagcgcggcgagctgtgcgtccgtggccccatgatcatgagcggctacgttaa
caaccccgaggctacaaacgctctcatcgacaaggacggctggctgcacagcggcgacatcgcctactgggacgaggacgagcacttcttcatcgtggaccg
gctgaagagcctgatcaaatacaagggctaccaggtagccccagccgaactggagagcatcctgctgcaacaccccaacatcttcgacgccggggtcgccgg
cctgcccgacgacgatgccggcgagctgcccgccgcagtcgtcgtgctggaacacggtaaaaccatgaccgagaaggagatcgtggactatgtggccagcca
ggttacaaccgccaagaagctgcgcggtggtgttgtgttcgtggacgaggtgcctaaaggactgaccggcaagttggacgcccgcaagatccgcgagattctca
ttaaggccaagaagggggcaagatcgccgtgtaaTTCGAACGGCCGtatcacgcccaaacatttacagccgcggtgtcaaaaaccgcgtggacgt
ggttaacatccctgctgggaggatcagccgtaattattataattggcttggtgctggctactattgtggccatgtacgtgctgaccaaccagaaacataattgaataca
gcagcaattggcaagctgcttacatagaactcgcggcgattggcatgccgccttaaaatttttatttatttttttcttttcttttccgaatcggattttgtttttaatatttcAA
AAAAAAAAAAAAAAAAAAAAAAAAAAAAAAAAAAAAAAAAAAAAAAAAAAAAAAAAAAAAAA
AAAAAAAAAAAAAAAA ubiquitin (SEQ ID NO: 38)
>UbG76 0-228
ATGCAGATCTTCGTGAAGACCCTGACCGGCAAGACCATCACCCTAGAGGTGGAGCCCAGTGACACC
ATCGAGAACGTGAAGGCCAAGATCCAGGATAAAGAGGGCATCCCCCCTGACCAGCAGAGGCTGATC
TTTGCCGGCAAGCAGCTGGAAGATGGCCGCACCCTCTCTGATTACAACATCCAGAAGGAGTCAACCC
TGCACCTGGTCCTTCGCCTGAGAGGTGGC Ubiquitin A76 (SEQ ID NO: 39)
>UbA76 0-228
ATGCAGATCTTCGTGAAGACCCTGACCGGCAAGACCATCACCCTAGAGGTGGAGCCCAGTGACACC
ATCGAGAACGTGAAGGCCAAGATCCAGGATAAAGAGGGCATCCCCCCTGACCAGCAGAGGCTGATC
TTTGCCGGCAAGCAGCTGGAAGATGGCCGCACCCTCTCTGATTACAACATCCAGAAGGAGTCAACCC
TGCACCTGGTCCTTCGCCTGAGAGGTGCC HLA-A2 (MHC class I) signal peptide (SEQ ID NO: 40)
>MHC SignalPep 0-78
atggccgtcatggcgccccgaaccctcgtcctgctactctcgggggctctggccctgacccagacctgggggctct HLA-A2 (MHC class I) Trans Membrane domain (SEQ ID NO: 41)
>HLA A2 TM Domain 0-201
CCGtcttcccagcccaccatccCCATCGTGGGCAtcattgctggcctggttctctttggagctgtgatcactggagctgtggtcgctgctgtgatgtggagg
aggaagagctcagatagaaaaggagggagctactctcaggctgcaagcagtgacagtgcccagggctctgatgtgtctctcacagcttgtaaagtgtga -continued IgK Leader Seq (SEQ ID NO: 42)
>IgK Leader Seq 0-60
atggagaccgatacactgctgctgtgggtgctgctcctgtgggtgccaggaagcacaggc Human DC-Lamp (SEQ ID NO: 43)
>HumanDCLAMP 0-3178
ggcaccgattcggggcctgcccggacttcgccgcacgctgcagaacctcgcccagcgcccaccatgccccggcagctcagcgcggcggccgcgctcttcgcgtc
cctggccgtaattttgcacgatggcagtcaaatgagagcaaaagcatttccagaaaccagagattattctcaacctactgcagcagcaacagtacaggacataaaaaa
acctgtccagcaaccagctaagcaagcacctcaccaaactttagcagcaagattcatggatggtcatatcacctttcaaacagcggccacagtaaaaattccaacaact
accccagcaactacaaaaaacactgcaaccaccagcccaattacctacaccctggtcacaacccaggccacacccaacaactcacacacagctcctccagttactga
agttacagtcggccctagcttagccccttattcactgccacccaccatcaccccaccagctcatacagctggaaccagttcatcaaccgtcagccacacaactgggaa
caccactcaacccagtaaccagaccacccttccagcaactttatcgatagcactgcacaaaagcacaaccggtcagaagcctgatcaacccacccatgccccaggaa
caacggcagctgcccacaataccacccgcacagctgcacctgcctccacggttcctgggcccaccccttgcacctcagccatcgtcagtcaagactggaatttatcag
gttctaaacggaagcagactctgtataaaagcagagatggggatacagctgattgttcaagacaaggagtcggtttttttcacctcggagatacttcaacatcgaccccaa
cgcaacgcaagcctctgggaactgtggcacccgaaaatccaaccttctgttgaattttcagggcggatttgtgaatctcacatttaccaaggatgaagaatcatattatat
cagtgaagtgggagcctatttgaccgtctcagatccagagacagtttaccaaggaatcaaacatgcggtggtgatgttccagacagcagtcgggcattccttcaagtgc
gtgagtgaacagagcctccagttgtcagcccacctgcaggtgaaaacaaccgatgtccaacttcaagcctttgattttgaagatgaccactttggaaatgtggatgagtg
ctcgtctgactacacaattgtgcttcctgtgattggggccatcgtggttggtctctgccttatgggtatgggtgtctataaaatccgcctaaggtgtcaatcatctggatacc
agagaatctaattgttgcccggggggaatgaaaataatggaatttagagaactctttcatcccttccaggatggatgttgggaaattccctcagagtgtgggtccttcaaa
caatgtaaaccaccatcttctattcaaatgaagtgagtcatgtgtgatttaagttcaggcagcacatcaatttctaaatactttttgtttattttatgaaagatatagtgagctgttt
attttctagtttcctttagaatattttagccactcaaagtcaacatttgagatatgttgaattaacataatatatgtaaagtagaataagccttcaaattataaaccaagggtcaat
tgtaactaatactactgtgtgtgcattgaagattttattttacccttgatcttaacaaagcctttgctttgttatcaaatggactttcagtgcttttactatctgtgttttatggtttcat
gtaacatacatattcctggtgtagcacttaactccttttccactttaaatttgtttttgtttttttgagacggagtttcactcttgtcacccaggctggagtacagtggcacgatctc
ggcttatggcaacctccgcctcccgggttcaagtgattctcctgcttcagcttcccgagtagctgggattacaggcacacactaccacgcctggctaatttttgtatttttatt
atagacgggtttcaccatgttggccagactggtcttgaactcttgacctcaggtgatccacccacctcagcctcccaaagtgctgggattacaggcatgagccattgcg
cccggccttaaatgtttttttaatcatcaaaaagaacaacatatctcaggttgtctaagtgtttttatgtaaaaccaacaaaaagaacaaatcagcttatatttttttatcttgatg
actcctgctccagaattgctagactaagaattaggtggctacagatggtagaactaaacaataagcaagagacaataataatggcccttaattattaacaaagtgccaga
gtctaggctaagcactttatctatatctcatttcattctcacaacttataagtgaatgagtaaactgagacttaagggaactgaatcacttaaatgtcacctggctaactgatg
gcagagccagagcttgaattcatgttggtctgacatcaaggtctttggtcttctccctacaccaagttacctacaagaacaatgacaccacactctgcctgaaggctcaca
cctcataccagcatacgctcaccttacagggaaatgggtttatccaggatcatgagacattagggtagatgaaaggagagctttgcagataacaaaatagcctatcctta
ataaatcctccactctctggaaggagactgaggggctttgtaaaacattagtcagttgctcatttttatgggattgcttagctgggctgtaaagatgaaggcatcaaataaa
ctcaaagtattttaaatttttttgataatagagaaacttcgctaaccaactgttctttcttgagtgtatagccccatcttgtggtaacttgctgcttctgcacttcatatccatattt
cctattgttcactttattctgtagagcagcctgccaagaattttatttctgctgtttttttttgctgctaaagaaaggaactaagtcaggatgttaacagaaaagtccacataacc
ctagaattcttagtcaaggaataattcaagtcagcctagagaccatgttgactttcctcatgtgtttccttatgactcagtaagttggcaaggtcctgactttagtcttaataaa
acattgaattgtagtaaaggtttttgcaataaaaacttactttgg Mouse LAMP1 (SEQ ID NO: 44)
>MouseLamp1 0-1858
attccggaggtgaaaaacaatggcacaacgtgtataatggccagcttctctgcctcctttctgaccacctacgagactgcgaatggttctcagatcgtgaacatttccctg
ccagcctctgcagaagtactgaaaaatggcagttcttgtggtaaagaaaatgtttctgaccccagcctcacaattacttttggaagaggatatttactgacactcaacttca
caaaaaatacaacacgttacagtgtccagcatatgtattttacatataacttgtcagatacagaacattttcccaatgccatcagcaaagagatctacaccatggattccac
aactgacatcaaggcagacatcaacaaagcataccggtgtgtcagtgatatccgggtctacatgaagaatgtgaccgttgtgctccgggatgccactatccaggccta
cctgtcgagtggcaacttcagcaaggaagagacacactgcacacaggatggaccttccccaaccactgggccacccagcccctcaccaccacttgtgcccacaaac
cccactgtatccaagtacaatgttactggtaacaacggaacctgcctgctggcctctatggcactgcaactgaatatcacctacctgaaaaaggacaacaagacggtga
ccagagcgttcaacatcagcccaaatgacacatctagtgggagttgcggtatcaacttggtgaccctgaaagtggagaacaagaacagagccctggaattgcagtttg
ggatgaatgccagctctagcctgtttttcttgcaaggagtgcgcttgaatatgactcttcctgatgccctagtgcccacattcagcatctccaaccattcactgaaagctctt
caggccactgtgggaaactcatacaagtgcaacactgaggaacacatctttgtcagcaagatgctctccctcaatgtcttcagtgtgcaggtccaggctttcaaggtgg
acagtgacaggtttgggtctgtggaagagtgtgttcaggatggtaacaacatgttgatccccattgctgtgggcggtgccctggcagggctgatcctcatcgtcctcatt
gcctacctcattggcaggaagaggagtcacgccggctatcagaccatctagcctggtgggcaggtgcaccagagatgcacaggggcctgttctcacatccccaagc
ttagataggtgtggaagggaggcacactttctggcaaactgttttaaaatctgctttatcaaatgtgaagttcatcttgcaacatttactatgcacaaaggaataactattgaa
atgacggtgttaattttgctaactgggttaaatattgatgagaaggctccactgatttgacttttaagacttggtgtttggttcttcattcttttactcagatttaagcctatcaaag
ggatactctggtccagaccttggcctggcaagggtggctgatggttaggctgcacacacttaagaagcaacgggagcagggaaggcttgcacacaggcacgcaca
gggtcaacctctggacacttggcttgggctacctggccttggggggctgaactctggcatctggctgggtacacacccccccaatttctgtgctctgccacccgtgag
ctgccactttcctaaatagaaaatggcattatttttatttactttttgtaaagtgatttccagtcttgtgttggcgttcagggtggccctgtctctgcactgtgtacaataatagat -continued tcacactgctgacgtgtcttgcagcgtaggtgggttgtacactgggcatcagctcacgtaatgcattgcctgtaacgatgctaataaaaa Human Lamp1 cDNA (SEQ ID NO: 45)
>Human Lamp1 0-2339
ggcccaaccgccgcccgcgcccccgctctccgcaccgtacccggccgcctcgcgccatggcggcccccggcagcgcccggcgacccctgctgctgctactgct
gttgctgctgctcggcctcatgcattgtgcgtcagcagcaatgtttatggtgaaaaatggcaacgggaccgcgtgcataatggccaacttctctgctgccttctcagtgaa
ctacgacaccaagagtggccctaagaacatgacctttgacctgccatcagatgccacagtggtgctcaaccgcagctcctgtggaaaagagaacacttctgacccca
gtctcgtgattgcttttggaagaggacatacactcactctcaatttcacgagaaatgcaacacgttacagcgtccagctcatgagttttgtttataacttgtcagacacacac
cttttccccaatgcgagctccaaagaaatcaagactgtggaatctataactgacatcagggcagatatagataaaaaatacagatgtgttagtggcacccaggtccacat
gaacaacgtgaccgtaacgctccatgatgccaccatccaggcgtacctttccaacagcagcttcagcaggggagagacacgctgtgaacaagacaggccttcccca
accacagcgcccccctgcgccacccagcccctcgccctcacccgtgcccaagagcccctctgtggacaagtacaacgtgagcggcaccaacgggacctgcctgct
ggccagcatggggctgcagctgaacctcacctatgagaggaaggacaacacgacggtgacaaggcttctcaacatcaaccccaacaagacctcggccagcggga
gctgcggcgcccacctggtgactctggagctgcacagcgagggcaccaccgtcctgctcttccagttcgggatgaatgcaagttctagccggtttttcctacaaggaat
ccagttgaatacaattcttcctgacgccagagaccctgcctttaaagctgccaacggctccctgcgagcgctgcaggccacagtcggcaattcctacaagtgcaacgc
ggaggagcacgtccgtgtcacgaaggcgttttcagtcaatatattcaaagtgtgggtccaggctttcaaggtggaaggtggccagtttggctctgtggaggagtgtctg
ctggacgagaacagcatgctgatccccatcgctgtgggtggtgccctggcggggctggtcctcatcgtcctcatcgcctacctcgtcggcaggaagaggagtcacgc
aggctaccagactatctagcctggtgcacgcaggcacagcagctgcaggggcctctgttcctttctctgggcttagggtcctgtcgaaggggaggcacactttctggc
aaacgtttctcaaatctgcttcatccaatgtgaagttcatcttgcagcatttactatgcacaacagagtaactatcgaaatgacggtgttaattttgctaactgggttaaatattt
tgctaactggttaaacattaatatttaccaaagtaggattttgagggggggggtgctctctctgagggggtgggggtgccgctgtctctgagggggggggtgccgctgt
ctctgaggggtgggggtgccgctctctctgagggggtgggggtgccgctttctctgagggggtgggggtgccgctctctctgagggggtgggggtgctgctctctcc
gaggggtggaatgccgctgtctctgaggggtgggggtgccgctctaaattggctccatatcatttgagtttagggttctggtgtttggtttcttcattctttactgcactcaga
tttaagccttacaaagggaaagcctctggccgtcacacgtaggacgcatgaaggtcactcgtggtgaggctgacatgctcacacattacaacagtagagagggaaaa
tcctaagacagaggaactccagagatgagtgtctggagcgcttcagttcagctttaaaggccaggacgggccacacgtggctggcggcctcgttccagtggcggca
cgtccttgggcgtctctaatgtctgcagctcaagggctggcactttttaaatataaaaatgggtgttattttatttttttttgtaaagtgattttggtcttctgttgacattcggg
gtgatcctgttctgcgctgtgtacaatgtgagatcggtgcgttctcctgatgttttgccgtggcttggggattgtacacgggaccagctcacgtaatgcattgcctgtaaca
atgtaataaaaagcctctttcttttaaaaaaaaaaaaaaaaaaaaaaaa Tetanus toxoid nulceic acid sequence (SEQ ID NO: 46)
CAGTACATCAAGGCCAACAGCAAGTTCATCGGCATCACCGAACTC Tetanus toxoid amino acid sequence (SEQ ID NO: 47)
QYIKANSKFIGITEL PADRE nulceotide sequence (SEQ ID NO: 48)
GCTAAATTTGTGGCTGCCTGGACACTGAAAGCCGCCGCT PADRE amino acid sequence (SEQ ID NO: 49)
AKFVAAWTLKAAA WPRE (SEQ ID NO: 50)
>WPRE 0-593
aatcaacctctggattacaaaatttgtgaaagattgactggtattcttaactatgttgctccttttacgctatgtggatacgctgctttaatgcctttgtatcatgctattgcttccc
gtatggctttcattttctcctccttgtataaatcctggttgctgtctctttatgaggagttgtggcccgttgtcaggcaacgtggcgtggtgtgcactgtgtttgctgacgcaac
ccccactggttggggcattgccaccacctgtcagctcctttccgggactttcgctttccccctccctattgccacggcggaactcatcgccgcctgccttgcccgctgct
ggacaggggctcggctgttgggcactgacaattccgtggtgttgtcggggaagctgacgtcctttccatggctgctcgcctgtgttgccacctggattctgcgcgggac
gtccttctgctacgtcccttcggccctcaatccagcggaccttccttcccgcggcctgctgccggctctgcggcctcttccgcgtcttcgccttcgccctcagacgagtc
ggatctccctttgggccgcctccccgcctgt IRES (SEQ ID NO: 51)
>eGFP_IRES_SEAP_Insert 1746-2335
tctcccccccccccctctccctcccccccccctaacgttactggccgaagccgcttggaataaggccggtgtgcgtttgtctatatgttattttccaccatattgccgtctttt
ggcaatgtgagggcccggaaacctggccctgtcttcttgacgagcattcctaggggtctttcccctctcgccaaaggaatgcaaggtctgttgaatgtcgtgaaggaag
cagttcctctggaagcttcttgaagacaaacaacgtctgtagcgaccctttgcaggcagcggaaccccccacctggcgacaggtgcctctgcggccaaaagccacgt
gtataagatacacctgcaaaggcggcacaaccccagtgccacgttgtgagttggatagttgtggaaagagtcaaatggctctcctcaagcgtattcaacaaggggctg -continued

```
aaggatgcccagaaggtaccccattgtatgggatctgatctggggcctcggtgcacatgctttacatgtgtttagtcgaggttaaaaaaacgtctaggccccccgaacc
acggggacgtggttttcctttgaaaaacacgatgataatatg
```

GFP (SEQ ID NO: 52)

```
atggtgagcaagggcgaggagctgttcaccggggtggtgcccatcctggtcgagctggacggcgacgtaaacggccacaagttcagcgtgtccggcgagggcga
gggcgatgccacctacggcaagctgaccctgaagttcatctgcaccaccggcaagctgcccgtgccctggcccaccctcgtgaccaccctgacctacggcgtgcag
tgcttcagccgctaccccgaccacatgaagcagcacgacttcttcaagtccgccatgcccgaaggctacgtccaggagcgcaccatcttcttcaaggacgacggcaa
ctacaagacccgcgccgaggtgaagttcgagggcgacaccctggtgaaccgcatcgagctgaagggcatcgacttcaaggaggacggcaacatcctggggcaca
agctggagtacaactacaacagccacaacgtctatatcatggccgacaagcagaagaacggcatcaaggtgaacttcaagatccgccacaacatcgaggacggca
gcgtgcagctcgccgaccactaccagcagaacacccccatcggcgacggccccgtgctgctgcccgacaaccactacctgagcacccagtccgccctgagcaaa
gaccccaacgagaagcgcgatcacatggtcctgctggagttcgtgaccgccgccgggatcactctcggcatggacgagctgtacaagtag
```

SEAP (SEQ ID NO: 53)

```
atgctgctgctgctgctgctgctgggcctgaggctacagctctccctgggcatcatcccagttgaggaggagaacccggacttctggaaccgcgaggcagccgagg
ccctgggtgccgccaagaagctgcagcctgcacagacagccgccaagaacctcatcatcttcctgggcgatgggatgggggtgtctacggtgacagctgccaggat
cctaaaagggcagaagaaggacaaactggggcctgagataccccctggccatggaccgcttcccatatgtggctctgtccaagacatacaatgtagacaaacatgtgc
cagacagtggagccacagccacggcctacctgtgcggggtcaagggcaacttccagaccattggcttgagtgcagccgcccgctttaaccagtgcaacacgacac
gcggcaacgaggtcatctccgtgatgaatcgggccaagaaagcagggaagtcagtgggagtggtaaccaccacacgagtgcagcacgcctcgccagccggcac
ctacgcccacacggtgaaccgcaactggtactcggacgccgacgtgcctgcctcggcccgccaggaggggtgccaggacatcgctacgcagctcatctccaacat
ggacattgacgtgatcctaggtggaggccgaaagtacatgtttcgcatgggaaccccagaccctgagtacccagatgactacagccaaggtgggaccaggctggac
gggaagaatctggtgcaggaatggctggcgaagcgccagggtgcccggtatgtgtggaaccgcactgagctcatgcaggcttccctggacccgtctgtgacccatc
tcatgggtctctttgagcctggagacatgaaatacgagatccaccgagactccacactggacccctccctgatggagatgacagaggctgccctgcgcctgctgagc
aggaacccccgcggcttcttcctcttcgtggagggtggtcgcatcgaccatggtcatcatgaaagcagggcttaccgggcactgactgagacgatcatgttcgacgac
gccattgagagggggggccagctcaccagcgaggaggacacgctgagcctcgtcactgccgaccactcccacgtcttctccttcggaggctaccccctgcgaggg
agctccatcttcgggctggcccctggcaaggcccgggacaggaaggcctacacggtcctcctatacggaaacggtccaggctatgtgctcaaggacggcgcccgg
ccggatgttaccgagagcgagagcgggagccccgagtatcggcagcagtcagcagtgcccctggacgaagagacccacgcaggcgaggacgtggcggtgttcg
cgcgcggcccgcaggcgcacctggttcacggcgtgcaggagcagaccttcatagcgcacgtcatggccttcgccgcctgcctggagccctacaccgcctgcgacc
tggcgcccccgccggcaccaccgacgccgcgcacccgggttactctagagtcgggggccggccgcttcgagcagacatgataa
```

Firefly Luciferase (SEQ ID NO: 54)

```
atggaagatgccaaaaacattaagaagggcccagcgccattctacccactcgaagacgggaccgccggcgagcagctgcacaaagccatgaagcgctacgccct
ggtgcccggcaccatcgcctttaccgacgcacatatcgaggtggacattacctacgccgagtacttcgagatgagcgttcggctggcagaagctatgaagcgctatg
ggctgaatacaaaccatcggatcgtggtgtgcagcgagaatagcttgcagttcttcatgcccgtgttgggtgccctgttcatcggtgtggctgtggccccagctaacga
catctacaacgagcgcgagctgctgaacagcatgggcatcagccagcccaccgtcgtattcgtgagcaagaaagggctgcaaaagatcctcaacgtgcaaaagaa
gctaccgatcatacaaaagatcatcatcatggatagcaagaccgactaccagggcttccaaagcatgtacaccttcgtgacttcccatttgccacccggcttcaacgagt
acgacttcgtgcccgagagcttcgaccgggacaaaaccatcgccctgatcatgaacagtagtggcagtaccggattgcccaaggggtagccctaccgcaccgcac
cgcttgtgtccgattcagtcatgcccgcgaccccatcttcggcaaccagatcatccccgacaccgctatcctcagcgtggtgccatttcaccacggcttcggcatgttca
ccacgctgggctacttgatctgcggctttcgggtcgtgctcatgtaccgcttcgaggaggagctattcttgcgcagcttgcaagactataagattcaatctgccctgctgg
tgcccacactatttagcttcttcgctaagagcactctcatcgacaagtacgacctaagcaacttgcacgagatcgccagcggcggggcgccgctcagcaaggaggta
ggtgaggccgtggccaaacgcttccacctaccaggcatccgccagggctacggcctgacagaaacaaccagcgccattctgatcacccccgaaggggacgacaa
gcctggcgcagtaggcaaggtggtgcccttcttcgaggctaaggtggtggacttggacaccggtaagacactgggtgtgaaccagcgcggcgagctgtgcgtccgt
ggccccatgatcatgagcggctacgttaacaaccccgaggctacaaacgctctcatcgacaaggacggctggctgcacagcggcgacatcgcctactgggacgag
gacgagcacttcttcatcgtggaccggctgaagagcctgatcaaatacaagggctaccaggtagccccagccgaactggagagcatcctgctgcaacaccccaaca
tcttcgacgccggggtcgccggcctgcccgacgacgatgccggcgagctgcccgccgcagtcgtcgtgctggaacacggtaaaaccatgaccgagaaggagatc
gtggactatgtggccagccaggttacaaccgccaagaagctgcgcggtggtgttgtgttcgtggacgaggtgcctaaaggactgaccggcaagttggacgcccgca
agatccgcgagattctcattaaggccaagaagggcggcaagatcgccgtgtaa
```

FMDV 2A (SEQ ID NO: 55)

```
GTAAAGCAAACACTGAACTTTGACCTTCTCAAGTTGGCTGGAGACGTTGAGTCCAATCCTGGGCCC
```

REFERENCES

1. Desrichard, A., Snyder, A. & Chan, T. A. Cancer Neoantigens and Applications for Immunotherapy. *Clin. Cancer Res. Off J. Am. Assoc. Cancer Res.* (2015). doi:10.1158/1078-0432.CCR-14-3175
2. Schumacher, T. N. & Schreiber, R. D. Neoantigens in cancer immunotherapy. *Science* 348, 69-74 (2015).
3. Gubin, M. M., Artyomov, M. N., Mardis, E. R. & Schreiber, R. D. Tumor neoantigens: building a framework for personalized cancer immunotherapy. *J. Clin. Invest.* 125, 3413-3421 (2015).
4. Rizvi, N. A. et al. Cancer immunology. Mutational landscape determines sensitivity to PD-1 blockade in non-small cell lung cancer. *Science* 348, 124-128 (2015).
5. Snyder, A. et al. Genetic basis for clinical response to CTLA-4 blockade in melanoma. *N. Engl. J. Med.* 371, 2189-2199 (2014).
6. Carreno, B. M. et al. Cancer immunotherapy. A dendritic cell vaccine increases the breadth and diversity of melanoma neoantigen-specific T cells. *Science* 348, 803-808 (2015).
7. Tran, E. et al. Cancer immunotherapy based on mutation-specific CD4+ T cells in a patient with epithelial cancer. *Science* 344, 641-645 (2014).
8. Hacohen, N. & Wu, C. J.-Y. United States Patent Application 010293637-COMPOSITIONS AND METHODS OF IDENTIFYING TUMOR SPECIFIC NEOANTIGENS. (A1). at <http://appftl.uspto.gov/netacgi/nph-Parser?Sect1=PTO1&Sect2=HITOFF&d=PG01&p=1&u=/netahtmiLPTO/srchnum.html&r=1&f=G&l=50&s1=20110293637.PGNR.>
9. Lundegaard, C., Hoof, I., Lund, O. & Nielsen, M. State of the art and challenges in sequence based T-cell epitope prediction. *Immunome Res.* 6 SuppL 2, S3 (2010).
10. Yadav, M. et al. Predicting immunogenic tumour mutations by combining mass spectrometry and exome sequencing. *Nature* 515, 572-576 (2014).
11. Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. *Mol. Cell. Proteomics* MCP 14, 658-673 (2015).
12. Van Allen, E. M. et al. Genomic correlates of response to CTLA-4 blockade in metastatic melanoma. *Science* 350, 207-211 (2015).
13. Yoshida, K. & Ogawa, S. Splicing factor mutations and cancer. *Wiley Interdiscip. Rev. RNA* 5, 445-459 (2014).
14. Cancer Genome Atlas Research Network. Comprehensive molecular profiling of lung adenocarcinoma. *Nature* 511, 543-550 (2014).
15. Rajasagi, M. et al. Systematic identification of personal tumor-specific neoantigens in chronic lymphocytic leukemia. *Blood* 124, 453-462 (2014).
16. Downing, S. R. et al. United States Patent Application 0120208706-OPTIMIZATION OF MULTIGENE ANALYSIS OF TUMOR SAMPLES. (A1). at <http://appftl.uspto.gov/netacgi/nph-Parser?Sect1=PTO1&Sect2=HITOFF&d=PG01&p=1&u=/netahtmiLPTO/srchnum.html&r=1&f=G&l=50&s1=20120208706.PGNR.>
17. Target Capture for NextGen Sequencing—IDT. at <http://www.idtdna.com/pages/products/nextgen/target-capture>
18. Shukla, S. A. et al. Comprehensive analysis of cancer-associated somatic mutations in class I HLA genes. *Nat. Biotechnol.* 33, 1152-1158 (2015).
19. Cieslik, M. et al. The use of exome capture RNA-seq for highly degraded RNA with application to clinical cancer sequencing. *Genome Res.* 25, 1372-1381 (2015).
20. Bodini, M. et al. The hidden genomic landscape of acute myeloid leukemia: subclonal structure revealed by undetected mutations. *Blood* 125, 600-605 (2015).
21. Saunders, C. T. et al. Strelka: accurate somatic small-variant calling from sequenced tumor-normal sample pairs. *Bioinforma. Oxf Engl.* 28, 1811-1817 (2012).
22. Cibulskis, K. et al. Sensitive detection of somatic point mutations in impure and heterogeneous cancer samples. *Nat. Biotechnol.* 31, 213-219 (2013).
23. Wilkerson, M. D. et al. Integrated RNA and DNA sequencing improves mutation detection in low purity tumors. *Nucleic Acids Res.* 42, e107 (2014).
24. Mose, L. E., Wilkerson, M. D., Hayes, D. N., Perou, C. M. & Parker, J. S. ABRA: improved coding indel detection via assembly-based realignment. *Bioinforma. Oxf Engl.* 30, 2813-2815 (2014).
25. Ye, K., Schulz, M. H., Long, Q., Apweiler, R. & Ning, Z. Pindel: a pattern growth approach to detect break points of large deletions and medium sized insertions from paired-end short reads. *Bioinforma. Oxf Engl.* 25, 2865-2871 (2009).
26. Lam, H. Y. K. et al. Nucleotide-resolution analysis of structural variants using BreakSeq and a breakpoint library. *Nat. Biotechnol.* 28, 47-55 (2010).
27. Frampton, G. M. et al. Development and validation of a clinical cancer genomic profiling test based on massively parallel DNA sequencing. *Nat. Biotechnol.* 31, 1023-1031 (2013).
28. Boegel, S. et al. HLA typing from RNA-Seq sequence reads. *Genome Med.* 4, 102 (2012).
29. Liu, C. et al. ATHLATES: accurate typing of human leukocyte antigen through exome sequencing. *Nucleic Acids Res.* 41, e142 (2013).
30. Mayor, N. P. et al. HLA Typing for the Next Generation. *PloS One* 10, e0127153 (2015).
31. Roy, C. K., Olson, S., Graveley, B. R., Zamore, P. D. & Moore, M. J. Assessing long-distance RNA sequence connectivity via RNA-templated DNA-DNA ligation. *eLife* 4, (2015).
32. Song, L. & Florea, L. CLASS: constrained transcript assembly of RNA-seq reads. *BMC Bioinformatics* 14 Suppl 5, S14 (2013).
33. Maretty, L., Sibbesen, J. A. & Krogh, A. Bayesian transcriptome assembly. *Genome Biol.* 15, 501 (2014).
34. Pertea, M. et al. StringTie enables improved reconstruction of a transcriptome from RNA-seq reads. *Nat. Biotechnol.* 33, 290-295 (2015).
35. Roberts, A., Pimentel, H., Trapnell, C. & Pachter, L. Identification of novel transcripts in annotated genomes using RNA-Seq. *Bioinforma. Oxf Engl.* (2011). doi:10.1093/bioinformatics/btr355
36. Vitting-Seerup, K., Porse, B. T., Sandelin, A. & Waage, J. spliceR: an R package for classification of alternative splicing and prediction of coding potential from RNA-seq data. *BMC Bioinformatics* 15, 81 (2014).
37. Rivas, M. A. et al. Human genomics. Effect of predicted protein-truncating genetic variants on the human transcriptome. *Science* 348, 666-669 (2015).
38. Skelly, D. A., Johansson, M., Madeoy, J., Wakefield, J. & Akey, J. M. A powerful and flexible statistical framework for testing hypotheses of allele-specific gene expression from RNA-seq data. *Genome Res.* 21, 1728-1737 (2011).

39. Anders, S., Pyl, P. T. & Huber, W. HTSeq—a Python framework to work with high-throughput sequencing data. *Bioinforma. Oxf Engl.* 31, 166-169 (2015).
40. Furney, S. J. et al. SF3B1 mutations are associated with alternative splicing in uveal melanoma. Cancer Discov. (2013). doi:10.1158/2159-8290.CD-13-0330
41. Zhou, Q. et al. A chemical genetics approach for the functional assessment of novel cancer genes. *Cancer Res.* (2015). doi:10.1158/0008-5472.CAN-14-2930
42. Maguire, S. L. et al. SF3B1 mutations constitute a novel therapeutic target in breast cancer. *J. Pathol.* 235, 571-580 (2015).
43. Carithers, L. J. et al. A Novel Approach to High-Quality Postmortem Tissue Procurement: The GTEx Project. *Biopreservation Biobanking* 13, 311-319 (2015).
44. Xu, G. et al. RNA CoMPASS: a dual approach for pathogen and host transcriptome analysis of RNA-seq datasets. *PloS One* 9, e89445 (2014).
45. Andreatta, M. & Nielsen, M. Gapped sequence alignment using artificial neural networks: application to the MHC class I system. *Bioinforma. Oxf Engl.* (2015). doi:10.1093/bioinformatics/btv639
46. Jorgensen, K. W., Rasmussen, M., Buus, S. & Nielsen, M. NetMHCstab-predicting stability of peptide-MHC-I complexes; impacts for cytotoxic T lymphocyte epitope discovery. *Immunology* 141, 18-26 (2014).
47. Larsen, M. V. et al. An integrative approach to CTL epitope prediction: a combined algorithm integrating MHC class I binding, TAP transport efficiency, and proteasomal cleavage predictions. *Eur. J. Immunol.* 35, 2295-2303 (2005).
48. Nielsen, M., Lundegaard, C., Lund, O. & Keşmir, C. The role of the proteasome in generating cytotoxic T-cell epitopes: insights obtained from improved predictions of proteasomal cleavage. *Immunogenetics* 57, 33-41 (2005).
49. Boisvert, F.-M. et al. A Quantitative Spatial Proteomics Analysis of Proteome Turnover in Human Cells. *Mol. Cell. Proteomics* 11, M111.011429-M 111.011429 (2012).
50. Duan, F. et al. Genomic and bioinformatic profiling of mutational neoepitopes reveals new rules to predict anticancer immunogenicity. *J. Exp. Med.* 211, 2231-2248 (2014).
51. Janeway's Immunobiology: 9780815345312: Medicine & Health Science Books @ Amazon.com. at <http://www.amazon.com/Janeways-Immunobiology-Kenneth-Murphy/dp/0815345313>
52. Calis, J. J. A. et al. Properties of MHC Class I Presented Peptides That Enhance Immunogenicity. *PLoS Comput. Biol.* 9, e1003266 (2013).
53. Zhang, J. et al. Intratumor heterogeneity in localized lung adenocarcinomas delineated by multiregion sequencing. *Science* 346, 256-259 (2014)
54. Walter, M. J. et al. Clonal architecture of secondary acute myeloid leukemia. *N. Engl. J. Med.* 366, 1090-1098 (2012).
55. Hunt D F, Henderson R A, Shabanowitz J, Sakaguchi K, Michel H, Sevilir N, Cox A L, Appella E, Engelhard V H. Characterization of peptides bound to the class I MHC molecule HLA-A2.1 by mass spectrometry. Science 1992. 255: 1261-1263.
56. Zarling A L, Polefrone J M, Evans A M, Mikesh L M, Shabanowitz J, Lewis S T, Engelhard V H, Hunt D F. Identification of class I MHC-associated phosphopeptides as targets for cancer immunotherapy. Proc Natl Acad Sci USA. 2006 Oct. 3; 103(40):14889-94.
57. Bassani-Sternberg M, Pletscher-Frankild S, Jensen L J, Mann M. Mass spectrometry of human leukocyte antigen class I peptidomes reveals strong effects of protein abundance and turnover on antigen presentation. Mol Cell Proteomics. 2015 March; 14(3):658-73. doi: 10.1074/mcp.M114.042812.
58. Abelin J G, Trantham P D, Penny S A, Patterson A M, Ward S T, Hildebrand W H, Cobbold M, Bai D L, Shabanowitz J, Hunt D F. Complementary IMAC enrichment methods for HLA-associated phosphopeptide identification by mass spectrometry. Nat Protoc. 2015 September; 10(9):1308-18. doi: 10.1038/nprot.2015.086. Epub 2015 Aug. 6
59. Barnstable C J, Bodmer W F, Brown G, Galfre G, Milstein C, Williams A F, Ziegler A. Production of monoclonal antibodies to group A erythrocytes, HLA and other human cell surface antigens-new tools for genetic analysis. Cell. 1978 May; 14(1):9-20.
60. Goldman J M, Hibbin J, Kearney L, Orchard K, Th'ng KH. HLA-DR monoclonal antibodies inhibit the proliferation of normal and chronic granulocytic leukaemia myeloid progenitor cells. Br J Haematol. 1982 November; 52(3):411-20.
61. Eng J K, Jahan T A, Hoopmann M R. Comet: an open-source MS/MS sequence database search tool. Proteomics. 2013 January; 13(1):22-4. doi: 10.1002/pmic.201200439. Epub 2012 Dec. 4.
62. Eng J K, Hoopmann M R, Jahan T A, Egertson J D, Noble W S, MacCoss MJ. A deeper look into Comet—implementation and features. J Am Soc Mass Spectrom. 2015 November; 26(11):1865-74. doi: 10.1007/s13361-015-1179-x. Epub 2015 Jun. 27.
63. Lukas Kill, Jesse Canterbury, Jason Weston, William Stafford Noble and Michael J. MacCoss. Semi-supervised learning for peptide identification from shotgun proteomics datasets. Nature Methods 4:923-925, November 2007
64. Lukas Kill, John D. Storey, Michael J. MacCoss and William Stafford Noble. Assigning confidence measures to peptides identified by tandem mass spectrometry. Journal of Proteome Research, 7(1):29-34, January 2008
65. Lukas Käll, John D. Storey and William Stafford Noble. Nonparametric estimation of posterior error probabilities associated with peptides identified by tandem mass spectrometry. Bioinformatics, 24(16): i42-i48, August 2008
66. Kinney R M, BJ Johnson, VL Brown, DW Trent. Nucleotide Sequence of the 26 S mRNA of the Virulent Trinidad Donkey Strain of Venezuelan Equine Encephalitis Virus and Deduced Sequence of the Encoded Structural Proteins. Virology 152 (2), 400-413. 1986 Jul. 30.
67. Jill E Slansky, Frédérique M Rattis, Lisa F Boyd, Tarek Fahmy, Elizabeth M Jaffee, Jonathan P Schneck, David H Margulies, Drew M Pardoll. Enhanced Antigen-Specific Antitumor Immunity with Altered Peptide Ligands that Stabilize the MHC-Peptide-TCR Complex. Immunity, Volume 13, Issue 4, 1 Oct. 2000, Pages 529-538.
68. A Y Huang, P H Gulden, A S Woods, M C Thomas, C D Tong, W Wang, V H Engelhard, G Pasternack, R Cotter, D Hunt, D M Pardoll, and E M Jaffee. The immunodominant major histocompatibility complex class I-restricted antigen of a murine colon tumor derives from an endogenous retroviral gene product. Proc Natl Acad Sci USA.; 93(18): 9730-9735, 1996 Sep. 3.
69. JOHNSON, BARBARA J. B., RICHARD M. KINNEY, CRYSTLE L. KOST AND DENNIS W. TRENT. Molecular Determinants of Alphavirus Neurovirulence: Nucleotide and Deduced Protein Sequence Changes during Attenuation of Venezuelan Equine Encephalitis Virus. J Gen Virol 67:1951-1960, 1986.

70. Aarnoudse, C. A., Krüse, M., Konopitzky, R., Brouwenstijn, N., and Schrier, P. I. (2002). TCR reconstitution in Jurkat reporter cells facilitates the identification of novel tumor antigens by cDNA expression cloning. Int J Cancer 99, 7-13.

71. Alexander, J., Sidney, J., Southwood, S., Ruppert, J., Oseroff, C., Maewal, A., Snoke, K., Serra, H. M., Kubo, R. T., and Sette, A. (1994). Development of high potency universal DR-restricted helper epitopes by modification of high affinity DR-blocking peptides. Immunity 1, 751-761.

72. Banu, N., Chia, A., Ho, Z. Z., Garcia, A. T., Paravasivam, K., Grotenbreg, G. M., Bertoletti, A., and Gehring, A. J. (2014). Building and optimizing a virus-specific T cell receptor library for targeted immunotherapy in viral infections. Scientific Reports 4, 4166.

73. Cornet, S., Miconnet, I., Menez, J., Lemonnier, F., and Kosmatopoulos, K. (2006). Optimal organization of a polypeptide-based candidate cancer vaccine composed of cryptic tumor peptides with enhanced immunogenicity. Vaccine 24, 2102-2109.

74. Depla, E., van der Aa, A., Livingston, B. D., Crimi, C., Allosery, K., de Brabandere, V., Krakover, J., Murthy, S., Huang, M., Power, S., et al. (2008). Rational design of a multiepitope vaccine encoding T-lymphocyte epitopes for treatment of chronic hepatitis B virus infections. Journal of Virology 82, 435-450.

75. Ishioka, G. Y., Fikes, J., Hermanson, G., Livingston, B., Crimi, C., Qin, M., del Guercio, M. F., Oseroff, C., Dahlberg, C., Alexander, J., et al. (1999). Utilization of MHC class I transgenic mice for development of minigene DNA vaccines encoding multiple HLA-restricted CTL epitopes. J Immunol 162, 3915-3925.

76. Janetzki, S., Price, L., Schroeder, H., Britten, C. M., Welters, M. J. P., and Hoos, A. (2015). Guidelines for the automated evaluation of Elispot assays. Nat Protoc 10, 1098-1115.

77. Lyons, G. E., Moore, T., Brasic, N., Li, M., Roszkowski, J. J., and Nishimura, M. I. (2006). Influence of human CD8 on antigen recognition by T-cell receptor-transduced cells. Cancer Res 66, 11455-11461.

78. Nagai, K., Ochi, T., Fujiwara, H., An, J., Shirakata, T., Mineno, J., Kuzushima, K., Shiku, H., Melenhorst, J. J., Gostick, E., et al. (2012). Aurora kinase A-specific T-cell receptor gene transfer redirects T lymphocytes to display effective antileukemia reactivity. Blood 119, 368-376.

79. Panina-Bordignon, P., Tan, A., Termijtelen, A., Demotz, S., Corradin, G., and Lanzavecchia, A. (1989). Universally immunogenic T cell epitopes: promiscuous binding to human MHC class II and promiscuous recognition by T cells. Eur J Immunol 19, 2237-2242.

80. Vitiello, A., Marchesini, D., Furze, J., Sherman, L. A., and Chesnut, R. W. (1991). Analysis of the HLA-restricted influenza-specific cytotoxic T lymphocyte response in transgenic mice carrying a chimeric human-mouse class I major histocompatibility complex. J Exp Med 173, 1007-1015.

81. Yachi, P. P., Ampudia, J., Zal, T., and Gascoigne, N. R. J. (2006). Altered peptide ligands induce delayed CD8-T cell receptor interaction—a role for CD8 in distinguishing antigen quality. Immunity 25, 203-211.

82. Pushko P, Parker M, Ludwig G V, Davis N L, Johnston R E, Smith J F. Replicon-helper systems from attenuated Venezuelan equine encephalitis virus: expression of heterologous genes in vitro and immunization against heterologous pathogens in vivo. Virology. 1997 Dec. 22; 239(2):389-401.

83. Strauss, JH and E G Strauss. The alphaviruses: gene expression, replication, and evolution. Microbiol Rev. 1994 September; 58(3): 491-562.

84. Rhême C, Ehrengruber M U, Grandgirard D. Alphaviral cytotoxicity and its implication in vector development. Exp Physiol. 2005 January; 90(1):45-52. Epub 2004 Nov. 12.

85. Riley, Michael K. II, and Wilfred Vermerris. Recent Advances in Nanomaterials for Gene Delivery—A Review. Nanomaterials 2017, 7(5), 94.

86. Frolov I, Hardy R, Rice C M. Cis-acting RNA elements at the 5' end of Sindbis virus genome RNA regulate minus- and plus-strand RNA synthesis. RNA. 2001 November; 7(11):1638-51.

87. Jose J, Snyder J E, Kuhn R J. A structural and functional perspective of alphavirus replication and assembly. Future Microbiol. 2009 September; 4(7):837-56.

88. Bo Li and C. olin N. Dewey. RSEM: accurate transcript quantification from RNA-Seq data with or without a referenfe genome. BMC Bioinformatics, 12:323, August 2011

89. Hillary Pearson, Tariq Daouda, Diana Paola Granados, Chantal Durette, Eric Bonneil, Mathieu Courcelles, Anja Rodenbrock, Jean-Philippe Laverdure, Caroline Côté, Sylvie Mader, Sëbastien Lemieux, Pierre Thibault, and Claude Perreault. MHC class I-associated peptides derive from selective regions of the human genome. The Journal of Clinical Investigation, 2016, 90. Juliane Liepe, Fabio Marino, John Sidney, Anita Jeko, Daniel E. Bunting, Alessandro Sette, Peter M. Kloetzel, Michael P. H. Stumpf, Albert J. R. Heck, Michele Mishto. A large fraction of HLA class I ligands are proteasome-generated spliced peptides. Science, 21, October 2016.

91. Mommen G P., Marino, F., Meiring H D., Poelen, MC., van Gaans-van den Brink, JA., Mohammed S., Heck A J., and van Els C A. Sampling From the Proteome to the Human Leukocyte Antigen-DR (HLA-DR) Ligandome Proceeds Via High Specificity. Mol Cell Proteomics 15(4): 1412-1423, April 2016.

92. Sebastian Kreiter, Mathias Vormehr, Niels van de Roemer, Mustafa Diken, Martin Löwer, Jan Diekmann, Sebastian Boegel, Barbara Schrörs, Fulvia Vascotto, John C. Castle, Arbel D. Tadmor, Stephen P. Schoenberger, Christoph Huber, Özlem Türeci, and Ugur Sahin. Mutant MHC class II epitopes drive therapeutic immune responses to caner. Nature 520, 692-696, April 2015.

93. Tran E., Turcotte S., Gros A., Robbins P. F., Lu Y. C., Dudley M. E., Wunderlich J. R., Somerville R. P., Hogan K., Hinrichs C. S., Parkhurst M. R., Yang J. C., Rosenberg S. A. Cancer immunotherapy based on mutation-specific CD4+ T cells in a patient with epithelial cancer. Science 344(6184) 641-645, May 2014.

94. Andreatta M., Karosiene E., Rasmussen M., Stryhn A., Buus S., Nielsen M. Accurate pan-specific prediction of peptide-MHC class II binding affinity with improved binding core identification. Immunogenetics 67(11-12) 641-650, November 2015.

95. Nielsen, M., Lund, O. NN-align. An artificial neural network-based alignment algorithm for MHC class II peptide binding prediction. BMC Bioinformatics 10:296, September 2009.

96. Nielsen, M., Lundegaard, C., Lund, O. Prediction of MHC class II binding affinity using SMM-align, a novel stabilization matrix alignment method. BMC Bioinformatics 8:238, July 2007.

97. Zhang, J., et al. PEAKS DB: de novo sequencing assisted database search for sensitive and accurate peptide identification. Molecular & Cellular Proteomics. 11(4):1-8. Jan. 2, 2012.
98. Jensen, Kamilla Kjaergaard, et al. "Improved Methods for Prediting Peptide Binding Affinity to MHC Class II Molecules." Immunology, 2018, doi:10.111 limm.12889.
99. Carter, S. L., Cibulskis, K., Helman, E., McKenna, A., Shen, H., Zack, T., Laird, P. W., Onofrio, R. C., Winckler, W., Weir, B. A., et al. (2012). Absolute quantification of somatic DNA alterations in human cancer. Nat. Biotechnol. 30, 413-421
100. McGranahan, N., Rosenthal, R., Hiley, C. T., Rowan, A. J., Watkins, T. B. K., Wilson, G. A., Birkbak, N. J., Veeriah, S., Van Loo, P., Herrero, J., et al. (2017). Allele-Specific HLA Loss and Immune Escape in Lung Cancer Evolution. Cell 171, 1259-1271.e11.
101. Shukla, S. A., Rooney, M. S., Rajasagi, M., Tiao, G., Dixon, P. M., Lawrence, M. S., Stevens, J., Lane, W. J., Dellagatta, J. L., Steelman, S., et al. (2015). Comprehensive analysis of cancer-associated somatic mutations in class I HLA genes. Nat. Biotechnol. 33, 1152-1158.
102. Van Loo, P., Nordgard, S. H., Lingjwrde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A 107, 16910-16915.
103. Van Loo, P., Nordgard, S. H., Lingjwrde, O. C., Russnes, H. G., Rye, I. H., Sun, W., Weigman, V. J., Marynen, P., Zetterberg, A., Naume, B., et al. (2010). Allele-specific copy number analysis of tumors. Proc. Natl. Acad. Sci. U.S.A. 107, 16910-16915.

VARIOUS EMBODIMENTS

1. Disclosed herein is a viral vector comprising a neoantigen or plurality of neoantigens. In certain embodiments, a neoantigen is identified using a method disclosed herein, e.g., below. In certain embodiments, a neoantigen has at least one characteristic or property as disclosed herein, e.g., below.
2. Disclosed herein is a method for identifying one or more neoantigens from a tumor cell of a subject that are likely to be presented on the tumor cell surface, comprising the steps of:
   obtaining at least one of exome, transcriptome or whole genome tumor nucleotide sequencing data from the tumor cell of the subject, wherein the tumor nucleotide sequencing data is used to obtain data representing peptide sequences of each of a set of neoantigens, and wherein the peptide sequence of each neoantigen comprises at least one alteration that makes it distinct from the corresponding wild-type, parental peptide sequence;
   inputting the peptide sequence of each neoantigen into one or more presentation models to generate a set of numerical likelihoods that each of the neoantigens is presented by one or more MHC alleles on the tumor cell surface of the tumor cell of the subject, the set of numerical likelihoods having been identified at least based on received mass spectrometry data; and
   selecting a subset of the set of neoantigens based on the set of numerical likelihoods to generate a set of selected neoantigens.
3. In certain embodiments, a number of the set of selected neoantigens is 20.
4. In certain embodiments, the presentation model represents dependence between:
   presence of a pair of a particular one of the MHC alleles and a particular amino acid at a particular position of a peptide sequence; and
   likelihood of presentation on the tumor cell surface, by the particular one of the MHC alleles of the pair, of such a peptide sequence comprising the particular amino acid at the particular position.
5. In certain embodiments, inputting the peptide sequence comprises:
   applying the one or more presentation models to the peptide sequence of the corresponding neoantigen to generate a dependency score for each of the one or more MHC alleles indicating whether the MHC allele will present the corresponding neoantigen based on at least positions of amino acids of the peptide sequence of the corresponding neoantigen.
6. In certain embodiments, the method further comprises:
   transforming the dependency scores to generate a corresponding per-allele likelihood for each MHC allele indicating a likelihood that the corresponding MHC allele will present the corresponding neoantigen; and
   combining the per-allele likelihoods to generate the numerical likelihood.
7. In certain embodiments, the transforming the dependency scores model the presentation of the peptide sequence of the corresponding neoantigen as mutually exclusive.
8. In certain embodiments, the method further comprises:
   transforming a combination of the dependency scores to generate the numerical likelihood.
9. In certain embodiments, the transforming the combination of the dependency scores models the presentation of the peptide sequence of the corresponding neoantigen as interfering between MHC alleles.
10. In certain embodiments, the set of numerical likelihoods are further identified by at least an allele noninteracting feature, and further comprising:
    applying an allele noninteracting one of the one or more presentation models to the allele noninteracting features to generate a dependency score for the allele noninteracting features indicating whether the peptide sequence of the corresponding neoantigen will be presented based on the allele noninteracting features.
11. In certain embodiments, the method further comprises:
    combining the dependency score for each MHC allele in the one or more MHC alleles with the dependency score for the allele noninteracting feature;
    transforming the combined dependency scores for each MHC allele to generate a corresponding per-allele likelihood for the MHC allele indicating a likelihood that the corresponding MHC allele will present the corresponding neoantigen; and
    combining the per-allele likelihoods to generate the numerical likelihood.
12. In certain embodiments, the method further comprises:
    transforming a combination of the dependency scores for each of the MHC alleles and the dependency score for the allele noninteracting features to generate the numerical likelihood.
13. In certain embodiments, a set of numerical parameters for the presentation model is trained based on a training data set including at least a set of training peptide sequences identified as present in a plurality of samples and one or more MHC alleles associated with each training peptide sequence, wherein the training peptide sequences are identified through mass spectrometry on isolated peptides eluted from MHC alleles derived from the plurality of samples.

14. In certain embodiments, the training data set further includes data on mRNA expression levels of the tumor cell.

15. In certain embodiments, the samples comprise cell lines engineered to express a single MHC class I or class II allele.

16. In certain embodiments, the samples comprise cell lines engineered to express a plurality of MHC class I or class II alleles.

17. In certain embodiments, the samples comprise human cell lines obtained or derived from a plurality of patients.

18. In certain embodiments, the samples comprise fresh or frozen tumor samples obtained from a plurality of patients.

19. In certain embodiments, the samples comprise fresh or frozen tissue samples obtained from a plurality of patients.

20. In certain embodiments, the samples comprise peptides identified using T-cell assays.

21. In certain embodiments, the training data set further comprises data associated with:
 peptide abundance of the set of training peptides present in the samples;
 peptide length of the set of training peptides in the samples.

22. In certain embodiments, the training data set is generated by comparing the set of training peptide sequences via alignment to a database comprising a set of known protein sequences, wherein the set of training protein sequences are longer than and include the training peptide sequences.

23. In certain embodiments, the training data set is generated based on performing or having performed mass spectrometry on a cell line to obtain at least one of exome, transcriptome, or whole genome peptide sequencing data from the cell line, the peptide sequencing data including at least one protein sequence including an alteration.

24. In certain embodiments, the training data set is generated based on obtaining at least one of exome, transcriptome, and whole genome normal nucleotide sequencing data from normal tissue samples.

25. In certain embodiments, the training data set further comprises data associated with proteome sequences associated with the samples.

26. In certain embodiments, the training data set further comprises data associated with MHC peptidome sequences associated with the samples.

27. In certain embodiments, the training data set further comprises data associated with peptide-MHC binding affinity measurements for at least one of the isolated peptides.

28. In certain embodiments, the training data set further comprises data associated with peptide-MHC binding stability measurements for at least one of the isolated peptides.

29. In certain embodiments, the training data set further comprises data associated with transcriptomes associated with the samples.

30. In certain embodiments, the training data set further comprises data associated with genomes associated with the samples.

31. In certain embodiments, the training peptide sequences are of lengths within a range of k-mers where k is between 8-15, inclusive.

32. In certain embodiments, the method further comprises encoding the peptide sequence using a one-hot encoding scheme.

33. In certain embodiments, the method further comprises encoding the training peptide sequences using a left-padded one-hot encoding scheme.

34. Also disclosed herein is a method of treating a subject having a tumor, comprising performing any of the steps of the methods disclosed herein, and further comprising obtaining a tumor vaccine comprising the set of selected neoantigens, and administering the tumor vaccine to the subject.

35. Also disclosed herein is a method of manufacturing a tumor vaccine, comprising performing any of the steps a method disclosed herein, and further comprising producing or having produced a tumor vaccine comprising the set of selected neoantigens.

36. Also disclosed herein is a tumor vaccine comprising a set of selected neoantigens, selected by performing a method disclosed herein.

37. In certain embodiments, the tumor vaccine comprises one or more of a nucleotide sequence, a polypeptide sequence, RNA, DNA, a cell, a plasmid, or a vector.

38. In certain embodiments, the tumor vaccine comprises one or more neoantigens presented on the tumor cell surface.

39. In certain embodiments, the tumor vaccine comprises one or more neoantigens that is immunogenic in the subject.

40. In certain embodiments, the tumor vaccine does not comprise one or more neoantigens that induce an autoimmune response against normal tissue in the subject.

41. In certain embodiments, the tumor vaccine further comprises an adjuvant.

42. In certain embodiments, the tumor vaccine further comprises an excipient.

43. In certain embodiments, selecting the set of selected neoantigens comprises selecting neoantigens that have an increased likelihood of being presented on the tumor cell surface relative to unselected neoantigens based on the presentation model.

44. In certain embodiments, selecting the set of selected neoantigens comprises selecting neoantigens that have an increased likelihood of being capable of inducing a tumor-specific immune response in the subject relative to unselected neoantigens based on the presentation model.

45. In certain embodiments, selecting the set of selected neoantigens comprises selecting neoantigens that have an increased likelihood of being capable of being presented to naïve T cells by professional antigen presenting cells (APCs) relative to unselected neoantigens based on the presentation model, optionally wherein the APC is a dendritic cell (DC).

46. In certain embodiments, selecting the set of selected neoantigens comprises selecting neoantigens that have a decreased likelihood of being subject to inhibition via central or peripheral tolerance relative to unselected neoantigens based on the presentation model.

47. In certain embodiments, selecting the set of selected neoantigens comprises selecting neoantigens that have a decreased likelihood of being capable of inducing an autoimmune response to normal tissue in the subject relative to unselected neoantigens based on the presentation model.
48. In certain embodiments, exome or transcriptome nucleotide sequencing data is obtained by performing sequencing on the tumor tissue.
49. In certain embodiments, sequencing is next generation sequencing (NGS) or any massively parallel sequencing approach.
50. In certain embodiments, the set of numerical likelihoods are further identified by at least MHC-allele interacting features comprising at least one of:
   a. The predicted affinity with which the MHC allele and the neoantigen encoded peptide bind.
   b. The predicted stability of the neoantigen encoded peptide-MHC complex.
   c. The sequence and length of the neoantigen encoded peptide.
   d. The probability of presentation of neoantigen encoded peptides with similar sequence in cells from other individuals expressing the particular MHC allele as assessed by mass-spectrometry proteomics or other means.
   e. The expression levels of the particular MHC allele in the subject in question (e.g. as measured by RNA-seq or mass spectrometry).
   f. The overall neoantigen encoded peptide-sequence-independent probability of presentation by the particular MHC allele in other distinct subjects who express the particular MHC allele.
   g. The overall neoantigen encoded peptide-sequence-independent probability of presentation by MHC alleles in the same family of molecules (e.g., HLA-A, HLA-B, HLA-C, HLA-DQ, HLA-DR, HLA-DP) in other distinct subjects.
51. In certain embodiments, the set of numerical likelihoods are further identified by at least MHC-allele noninteracting features comprising at least one of:
   a. The C- and N-terminal sequences flanking the neoantigen encoded peptide within its source protein sequence.
   b. The presence of protease cleavage motifs in the neoantigen encoded peptide, optionally weighted according to the expression of corresponding proteases in the tumor cells (as measured by RNA-seq or mass spectrometry).
   c. The turnover rate of the source protein as measured in the appropriate cell type.
   d. The length of the source protein, optionally considering the specific splice variants ("isoforms") most highly expressed in the tumor cells as measured by RNA-seq or proteome mass spectrometry, or as predicted from the annotation of germline or somatic splicing mutations detected in DNA or RNA sequence data.
   e. The level of expression of the proteasome, immunoproteasome, thymoproteasome, or other proteases in the tumor cells (which may be measured by RNA-seq, proteome mass spectrometry, or immunohistochemistry).
   f. The expression of the source gene of the neoantigen encoded peptide (e.g., as measured by RNA-seq or mass spectrometry).
   g. The typical tissue-specific expression of the source gene of the neoantigen encoded peptide during various stages of the cell cycle.
   h. A comprehensive catalog of features of the source protein and/or its domains as can be found in e.g. uniProt or PDB http://www.rcsb.org/pdb/home/home.do.
   i. Features describing the properties of the domain of the source protein containing the peptide, for example: secondary or tertiary structure (e.g., alpha helix vs beta sheet); Alternative splicing.
   j. The probability of presentation of peptides from the source protein of the neoantigen encoded peptide in question in other distinct subjects.
   k. The probability that the peptide will not be detected or over-represented by mass spectrometry due to technical biases.
   l. The expression of various gene modules/pathways as measured by RNASeq (which need not contain the source protein of the peptide) that are informative about the state of the tumor cells, stroma, or tumor-infiltrating lymphocytes (TILs).
   m. The copy number of the source gene of the neoantigen encoded peptide in the tumor cells.
   n. The probability that the peptide binds to the TAP or the measured or predicted binding affinity of the peptide to the TAP.
   o. The expression level of TAP in the tumor cells (which may be measured by RNA-seq, proteome mass spectrometry, immunohistochemistry).
   p. Presence or absence of tumor mutations, including, but not limited to:
      i. Driver mutations in known cancer driver genes such as EGFR, KRAS, ALK, RET, ROS1, TP53, CDKN2A, CDKN2B, NTRK1, NTRK2, NTRK3
      ii. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome). Peptides whose presentation relies on a component of the antigen-presentation machinery that is subject to loss-of-function mutation in the tumor have reduced probability of presentation.
   q. Presence or absence of functional germline polymorphisms, including, but not limited to:
      i. In genes encoding the proteins involved in the antigen presentation machinery (e.g., B2M, HLA-A, HLA-B, HLA-C, TAP-1, TAP-2, TAPBP, CALR, CNX, ERP57, HLA-DM, HLA-DMA, HLA-DMB, HLA-DO, HLA-DOA, HLA-DOB, HLA-DP, HLA-DPA1, HLA-DPB1, HLA-DQ, HLA-DQA1, HLA-DQA2, HLA-DQB1, HLA-DQB2, HLA-DR, HLA-DRA, HLA-DRB1, HLA-DRB3, HLA-DRB4, HLA-DRB5 or any of the genes coding for components of the proteasome or immunoproteasome)
   r. Tumor type (e.g., NSCLC, melanoma).
   s. Clinical tumor subtype (e.g., squamous lung cancer vs. non-squamous).

t. Smoking history.

u. The typical expression of the source gene of the peptide in the relevant tumor type or clinical subtype, optionally stratified by driver mutation.

52. In certain embodiments, the at least one mutation is a frameshift or nonframeshift indel, missense or nonsense substitution, splice site alteration, genomic rearrangement or gene fusion, or any genomic or expression alteration giving rise to a neoORF.

53. In certain embodiments, the tumor cell is selected from the group consisting of: lung cancer, melanoma, breast cancer, ovarian cancer, prostate cancer, kidney cancer, gastric cancer, colon cancer, testicular cancer, head and neck cancer, pancreatic cancer, brain cancer, B-cell lymphoma, acute myelogenous leukemia, chronic myelogenous leukemia, chronic lymphocytic leukemia, and T cell lymphocytic leukemia, non-small cell lung cancer, and small cell lung cancer.

54. In certain embodiments, the method further comprises obtaining a tumor vaccine comprising the set of selected neoantigens or a subset thereof, optionally further comprising administering the tumor vaccine to the subject.

55. In certain embodiments, at least one of neoantigens in the set of selected neoantigens, when in polypeptide form, comprises at least one of: a binding affinity with MHC with an IC50 value of less than 1000 nM, for MHC Class I polypeptides a length of 8-15, 8, 9, 10, 11, 12, 13, 14, or 15 amino acids, presence of sequence motifs within or near the polypeptide in the parent protein sequence promoting proteasome cleavage, and presence of sequence motifs promoting TAP transport.

56. Also disclosed herein is a method for generating a model for identifying one or more neoantigens that are likely to be presented on a tumor cell surface of a tumor cell, comprising executing the steps of:

receiving mass spectrometry data comprising data associated with a plurality of isolated peptides eluted from major histocompatibility complex (MHC) derived from a plurality of samples;

obtaining a training data set by at least identifying a set of training peptide sequences present in the samples and one or more MHCs associated with each training peptide sequence;

training a set of numerical parameters of a presentation model using the training data set comprising the training peptide sequences, the presentation model providing a plurality of numerical likelihoods that peptide sequences from the tumor cell are presented by one or more MHC alleles on the tumor cell surface.

57. In certain embodiments, the presentation model represents dependence between: presence of a particular amino acid at a particular position of a peptide sequence; and likelihood of presentation, by one of the MHC alleles on the tumor cell, of the peptide sequence containing the particular amino acid at the particular position.

58. In certain embodiments, the samples comprise cell lines engineered to express a single MHC class I or class II allele.

59. In certain embodiments, the samples comprise cell lines engineered to express a plurality of MHC class I or class II alleles.

60. In certain embodiments, the samples comprise human cell lines obtained or derived from a plurality of patients.

61. In certain embodiments, the samples comprise fresh or frozen tumor samples obtained from a plurality of patients.

62. In certain embodiments, the samples comprise peptides identified using T-cell assays.

63. In certain embodiments, the training data set further comprises data associated with:

peptide abundance of the set of training peptides present in the samples;

peptide length of the set of training peptides in the samples.

64. In certain embodiments, obtaining the training data set comprises:

obtaining a set of training protein sequences based on the training peptide sequences by comparing the set of training peptide sequences via alignment to a database comprising a set of known protein sequences, wherein the set of training protein sequences are longer than and include the training peptide sequences.

65. In certain embodiments, obtaining the training data set comprises:

performing or having performed mass spectrometry on a cell line to obtain at least one of exome, transcriptome, or whole genome nucleotide sequencing data from the cell line, the nucleotide sequencing data including at least one protein sequence including a mutation.

66. In certain embodiments, training the set of parameters of the presentation model comprises: encoding the training peptide sequences using a one-hot encoding scheme.

67. In certain embodiments, the method further comprises:

obtaining at least one of exome, transcriptome, and whole genome normal nucleotide sequencing data from normal tissue samples; and training the set of parameters of the presentation model using the normal nucleotide sequencing data.

68. In certain embodiments, the training data set further comprises data associated with proteome sequences associated with the samples.

69. In certain embodiments, the training data set further comprises data associated with MHC peptidome sequences associated with the samples.

70. In certain embodiments, the training data set further comprises data associated with peptide-MHC binding affinity measurements for at least one of the isolated peptides.

71. In certain embodiments, the training data set further comprises data associated with peptide-MHC binding stability measurements for at least one of the isolated peptides.

72. In certain embodiments, the training data set further comprises data associated with transcriptomes associated with the samples.

73. In certain embodiments, the training data set further comprises data associated with genomes associated with the samples.

74. In certain embodiments, training the set of numerical parameters further comprises: logistically regressing the set of parameters.

75. In certain embodiments, the training peptide sequences are of lengths within a range of k-mers where k is between 8-15, inclusive.

76. In certain embodiments, training the set of numerical parameters of the presentation model comprises:

encoding the training peptide sequences using a left-padded one-hot encoding scheme.

77. In certain embodiments, training the set of numerical parameters further comprises: determining values for the set of parameters using a deep learning algorithm.

78. Also disclosed herein is a method for generating a model for identifying one or more neoantigens that are likely to be presented on a tumor cell surface of a tumor cell, comprising executing the steps of:

receiving mass spectrometry data comprising data associated with a plurality of isolated peptides eluted from major histocompatibility complex (MHC) derived from a plurality of fresh or frozen tumor samples;

obtaining a training data set by at least identifying a set of training peptide sequences present in the tumor samples and presented on one or more MHC alleles associated with each training peptide sequence;

obtaining a set of training protein sequences based on the training peptide sequences; and training a set of numerical parameters of a presentation model using the training protein sequences and the training peptide sequences, the presentation model providing a plurality of numerical likelihoods that peptide sequences from the tumor cell are presented by one or more MHC alleles on the tumor cell surface.

79. In certain embodiments, the presentation model represents dependence between:

presence of a pair of a particular one of the MHC alleles and a particular amino acid at a particular position of a peptide sequence; and likelihood of presentation on the tumor cell surface, by the particular one of the MHC alleles of the pair, of such a peptide sequence comprising the particular amino acid at the particular position.

SEQUENCE LISTING

```
Sequence total quantity: 193
SEQ ID NO: 1            moltype = DNA  length = 36519
FEATURE                 Location/Qualifiers
misc_feature            1..36519
                        note = Description of Artificial Sequence: Synthetic
                         polynucleotide
source                  1..36519
                        mol_type = other DNA
                        organism = synthetic construct
SEQUENCE: 1
ccatcttcaa taatatacct caaacttttt gtgcgcgtta atatgcaaat gaggcgtttg  60
aatttgggga ggaagggcgg tgattggtcg agggatgagc gaccgttagg ggcggggcga  120
gtgacgtttt gatgacgtgg ttgcgaggag gagccagttt gcaagttctc gtgggaaaag  180
tgacgtcaaa cgaggtgtgg tttgaacacg gaaatactca atttcccgc gctctctgac  240
aggaaatgag gtgtttctgg gcggatgcaa gtgaaaacgg gccattttcg cgcgaaaact  300
gaatgaggaa gtgaaaatct gagtaatttc gcgtttatgg cagggaggag tatttgccga  360
gggccgagta gactttgacc gattacgtgg gggtttcgat taccgtgttt ttcacctaaa  420
tttccgcgta cggtgtcaaa gtccggtgtt tttacgtagg tgtcagctga tcgccagggt  480
atttaaacct gcgctctcca gtcaagaggc cactcttgag tgccagcgag aagagttttc  540
tcctccgcgc cgcgagtcag atctacactt tgaaagatga ggcacctgag agacctgccc  600
gatgagaaaa tcatcatcgc ttccgggaac gagattctgg aactggtggt aaatgccatg  660
atgggcgacg accctccgga gccccccacc ccatttgaga caccttcgct gcacgatttg  720
tatgatctgg aggtggatgt gcccgaggac gatcccaatg aggaggcggt aaatgatttt  780
tttagcgatg ccgcgctgct agctgccgag gaggcttcga gctctagctc agacagcgac  840
tcttcactgc atacccctag acccggcaga ggtgagaaaa agatccccga gcttaaaggg  900
gaagagatgg acttgcgctg ctatgaggaa tgcttgcccc cgagcgatga tgaggacgag  960
caggcgatcc agaacgcagc gagccaggga gtgcaagccg ccagcgagag ctttgcgctg  1020
gactgcccgc ctctgcccgg acacggctgt aagtcttgtg aatttcatcg catgaatact  1080
ggagataaag ctgtgttgtg tgcactttgc tatatgagag cttacaacca ttgtgtttac  1140
agtaagtgtg attaagttga actttagagg gaggcagaga gcagggtgac tgggcgatga  1200
ctggtttatt tatgtatata tgttctttat ataggtcccg tctctgacgc agatgatgag  1260
acccccacta caaagtccac ttcgtcaccc ccagaaattg gcacatctcc acctgagaat  1320
attgttagac cagttcctgt tagagccact gggaggagag cagctgtgga atgtttggat  1380
gacttgctac agggtggggt tgaacctttg gacttgtgta cccggaaacg ccccaggcac  1440
taagtgccac acatgtgtgt ttacttgagg tgatgtcagt atttataggg tgtggagtgc  1500
aataaaaaat gtgttgactt taagtgcgtg gtttatgact caggggtggg gactgtgagt  1560
atataagcag gtgcagacct gtgtggttag ctcagagcgg catggagatt tggacggtct  1620
tggaagactt tcacaagact agacagctgc tagagaacgc ctcgaacgga gtctcttacc  1680
tgtggagatt ctgcttcggt ggcgacctag ctaggctagt ctacagggcc aaacaggatt  1740
atagtgaaca atttgaggtt attttgagag agtgttctgg tctttttgac gctcttaact  1800
tgggccatca gtctcacttt aaccagagga tttcgagagc ccttgatttt actactcctg  1860
gcagaaccac tgcagcagta gcctttttttg cttttattct tgacaaatgg agtcaagaaa  1920
cccatttcag cagggattac cagctggatt tcttagcagt agctttgtgg agaacatgga  1980
agtgccagcg cctgaatgca atctccggct acttgccggt acagccgcta gacactctga  2040
ggatcctgaa tctccaggag agtcccaggg cacgccaacg tcgccagcag cagcagcagg  2100
aggaggatca agaagagaac ccgagagccg gcctggaccc tccggcggag gaggaggagt  2160
agctgacctg tttcctgaac tgcgccgggt gctgactagg tcttcgagtg gtcgggagag  2220
ggggattaag cgggagaggc atgatgagac taatcacaga actgaactga ctgtgggtct  2280
gatgagtcgc aagcgcccag aaacagtgtg gtggcatgag gtgcagtcga ctggcacaga  2340
tgaggtgtcg gtgatgcatg agaggttttc tctagaacaa gtcaagactt gttggttaga  2400
gcctgaggat gattgggagg tagccatcag gaattatgcc aagctggctc tgaggccaga  2460
caagaagtac aagattacta agctgataaa tatcagaaat gcctgctaca tctcagggaa  2520
tggggctgaa gtggagatct gtctccagga aagggtggct ttcagatgct gcatgatgaa  2580
tatgtacccg ggagtggtgg gcatggatgg ggttaccttt atgaacatga ggttcagggg  2640
agatgggtat aatggcacgg tctttatggc caataccaag ctgacagtcc atggctgctc  2700
```

-continued

```
cttctttggg tttaataaca cctgcatcga ggcctggggt caggtcggtg tgaggggctg  2760
cagtttttca gccaactgga tgggggtcgt gggcaggacc aagagtatgc tgtccgtgaa  2820
gaaatgcttg tttgagaggt gccacctggg ggtgatgagc gagggcgaag ccagaatccg  2880
ccactgcgcc tctaccgaga cgggctgctt tgtgctgtgc aagggcaatg ctaagatcaa  2940
gcataaatatg atctgtggag cctcggacga gcgcggctac cagatgctga cctgcgccgg  3000
cgggaacagc catatgctgg ccaccgtaca tgtggcttcc catgctcgca agccctggcc  3060
cgagttcgag cacaatgtca tgaccaggtg caatatgcat ctggggtccc gccgaggcat  3120
gttcatgccc taccagtgca acctgaatta tgtgaaggtg ctgctggagc ccgatgccat  3180
gtccagagtg agcctgacgg gggtgtttga catgaatgtg gaggtgtgga agattctgag  3240
atatgatgaa tccaagacca ggtgccgagc ctgcgagtgc ggagggaagc atgccaggtt  3300
ccagcccgtg tgtgtggatg tgacggagga cctgcgaccc gatcatttgg tgttgccctg  3360
caccgggacg gagttcggtt ccagcgggga agaatctgac tagagtgagt agtgttctgg  3420
ggcgggggag gacctgcatg agggccagaa taactgaaat ctgtgctttt ctgtgtgttg  3480
cagcagcatg agcggaagcg gctcctttga gggaggggta ttcagccctt atctgacggg  3540
gcgtctcccc tcctgggcgg gagtgcgtca gaatgtgatg ggatccacgg tggacggccg  3600
gcccgtgcag cccgcgaact cttcaaccct gacctatgca accctgagct cttcgtcgtt  3660
ggacgcagct gccgccgcag ctgctgcatc tgccgccagc gccgtgcgcg gaatggccat  3720
gggcgccggc tactacggca ctctggtggc caactcgagt tccaccaata atcccgccag  3780
cctgaacgag gagaagctgt tgctgctgat ggcccagctc gaggccttga cccagcgcct  3840
gggcgagctg acccagcagg tggctcagct gcaggagcag acgcgggccg cggttgccac  3900
ggtgaaatcc aaataaaaaa tgaatcaata aataaacgga gacggttgtt gattttaaca  3960
cagagtctga atctttattt gatttttcgc gcgcggtagg ccctggacca ccggtctcga  4020
tcattgagca cccggtggat cttttccagg acccggtaga ggtgggcttg gatgttgagg  4080
tacatgggca tgagcccgtc ccgggggtgg aggtagctcc attgcagggc ctcgtgctcg  4140
ggggtggtgt tgtaaatcac ccagtcatag caggggcgca gggcatggtg ttgcacaata  4200
tctttgagga ggagactgat ggccacgggc agcccttttgg tgtaggtgtt tacaaatctg  4260
ttgagctggg agggatgcat gcggggggag atgaggtgca tcttggcctg gatcttgaga  4320
ttggcgatgt taccgcccag atcccgcctg ggttcatgt tgtgcaggac caccagcacg  4380
gtgtatccgg tgcacttggg gaatttatca tgcaacttgg aagggaaggc gtgaaagaat  4440
ttggcgacgc ctttgtgccc gcccaggttt tccatgcact catccatgat gatggcgatg  4500
ggcccgtggg cggcggcctg ggcaaagacg tttcgggggt cggacacatc atagttgtgg  4560
tcctgggtga ggtcatcata ggccatttta atgaatttgg ggcggagggt gccggactgg  4620
gggacaaagg taccctcgat cccgggggcg tagttcccct cacagatctg catctcccag  4680
gctttgagct cggagggggg gatcatgtcc acctgcgggg cgataaagaa cacggtttcc  4740
ggggcggggg agatgagctg ggccgaaagc aagttccgga gcagctggga cttgccgcag  4800
ccggtggggc cgtagatgac cccgatgacc ggctgcaggt ggtagttgag ggagagacag  4860
ctgccgtcct cccggaggag gggggccacc tcgttcatca tctcgcgcac gtgcatgttc  4920
tcgcgcacca gttccgccag gaggcgctct ccccccaggg ataggagctc ctggagcgag  4980
gcgaagtttt tcagcggctt gagtccgtcg gccatgggca ttttggagag ggtttgttgc  5040
aagagttcca ggcggtccca gagctcggtg atgtgctcta cggcatctcg atccagcaga  5100
cctcctcgtt tcgcgggttg ggacggctgc gggagtaggg caccagacga tgggcgtcca  5160
gcgcagccag ggtccggtcc ttccagggtc gcagcgtccg cgtcagggtg gtctccgtca  5220
cggtgaaggg gtgcgcgccg ggctgggcgc ttgcgagggt gcgcttcagg ctcatccggc  5280
tggtcgaaaa ccgctcccga tcggcgccct gcgcgtcggc caggtagcaa ttgaccatga  5340
gttcgtagtt gagcgcctcg gccgcgtggc ctttggcgcg gagcttacct ttggaagtct  5400
gcccgcaggc gggacagagg agggacttga gggcgtagag cttgggggcg aggaagacgg  5460
actcgggggc gtaggcgtcc gcgccgcagt gggcgcagac ggtctcgcac tccacgagcc  5520
aggtgaggtc gggctggtcg gggtcaaaaa ccagtttccc gccgttcttt ttgatgcgtt  5580
tcttaccttt ggtctccatg agctcgtgtc cccgctgggt gacaaagagg ctgtccgtgt  5640
ccccgtagac cgactttatg ggccggtcct cgagcggtgt gccgcggtcc tcctcgtaga  5700
ggaaccccgc ccactccgag acgaaagccc gggtccaggc cagcacgaag gaggccacgt  5760
gggacgggta gcggtcgttg tccaccagcg ggtccacctt ttccagggta tgcaaacaca  5820
tgtccccctc gtccacatcc aggaaggtga ttggcttgta agtgtaggcc acgtgaccgg  5880
gggtcccggc cggggggta taaaagggtg cgggtccctg ctcgtcctca ctgtcttccg  5940
gatcgctgtc caggagcgcc agctgttggg gtaggtattc cctctcgaag gcgggcatga  6000
cctcggcact caggttgtca gtttctagaa acgaggagga tttgatattg acggtgccgg  6060
cggagatgcc tttcaagagc ccctcgtcca tctggtcaga aaagacgatc tttttgttgt  6120
cgagcttggt ggcgaaggag ccgtagaggg cgttggagag gagcttggcg atggagcgca  6180
tggtctggtt tttttccttg tcggcgcgct ccttggcggc gatgttgagc tgcacgtact  6240
cgcgcgccac gcacttccat tcggggaaga cggtggtcag ctcgtcgggc acgattctga  6300
cctgccagcc ccgattatgc aggtgatga ggtccacact ggtggccacc tcgccgcgca  6360
ggggctcatt agtccagcag aggcgtccgc ccttgcgcga gcagaagggg ggcagggggt  6420
ccagcatgac ctcgtcgggg gggtcggcat cgatggtgaa gatgccgggc aggaggtcgg  6480
ggtcaaagta gctgatggaa gtggccagat cgtccagggc agcttgccat tcgcgcacgg  6540
ccagcgcgcg ctcgtaggga ctgaggggcg tgccccaggg catgggatgg gtaagcgcgg  6600
aggcgtacat gccgcagatg tcgtagacgt agaggggctc ctcgaggatg ccgatgtagg  6660
tggggtagca gcgccccccg cggatgctgg cgcgcacgta gtcatacagc tcgtgcgagg  6720
gggcgaggag ccccgggccc aggttggtgc gactgggctt ttcggcgcgg tagacgatct  6780
ggcggaaaat ggcatgcgag ttggaggaga tggtgggcct ttggaagatg ttgaagtggg  6840
cgtggggcag tccgaccgag tcgcggatga agtgggcgta ggagtcttgc agcttggcga  6900
cgagctcggc ggtgactagg acgtccagag cgcagtagtc gagggtctcc tggatgatgt  6960
catacttgag ctgtcccttt tgtttccaca gctcgcggtt gagaaggaac tcttcgcggt  7020
ccttccagta ctcttcgagg gggaacccgt cctgatctgc acggtaagag cctagcatgt  7080
agaactggtt gacggccttg taggcgcagc agcccttctc cacggggagg gcgtaggcct  7140
gggcggcctt gcgcagggag gtgtgcgtga gggcgaaagt gtccctgacc atgaccttga  7200
ggaactggtg cttgaagtcg atatcgtcgc agcccccctg ctcccagagc tggaagtccg  7260
tgcgcttctt gtaggcgggg ttgggcaaag cgaaagtaac atcgttgaag aggatcttgc  7320
ccgcgcgggg cataaagttg cgagtgatgc ggaaaggttg ggcacctcg gcccggttgt  7380
tgatgacctg ggcggcgagc acgatctcgt cgaagccgtt gatgttgtgg cccacgatgt  7440
```

-continued

```
agagttccac gaatcgcgga cggcccttga cgtggggcag tttcttgagc tcctcgtagg  7500
tgagctcgtc ggggtcgctg agcccgtgct gctcgagcgc ccagtcggcg agatgggggt  7560
tggcgcggag gaaggaagtc cagagatcca cggccagggc ggtttgcaga cggtcccggt  7620
actgacggaa ctgctgcccg acggccattt tttcgggggt gacgcagtag aaggtgcggg  7680
ggtccccgtg ccagcgatcc catttgagct ggagggcgag atcgagggcg agctcgacga  7740
gccggtcgtc cccggagagt ttcatgacca gcatgaaggg gacgagctgc ttgccgaagg  7800
accccatcca ggtgtaggtt tccacatcgt aggtgaggaa gagcctttcg gtgcgaggat  7860
gcgagccgat ggggaagaac tggatctcct gccaccaatt ggaggaatgg ctgttgatgt  7920
gatggaagta gaaatgccga cggcgcgccg aacactcgtg cttgtgttta tacaagcggc  7980
cacagtgctc gcaacgctgc acgggatgca cgtgctgcac gagctgtacc tgagttcctt  8040
tgacgaggaa tttcagtggg aagtggagtc gtggcgcctg catctcgtgc tgtactacgt  8100
cgtggtggtc ggcctggccc tcttctgcct cgatggtggt catgctgacg agcccgcgcg  8160
ggaggcaggt ccagacctcg gcgcgagcgg gtcggagagc gaggacgagg gcgcgcaggc  8220
cggagctgtc cagggtcctg agacgctgcg gagtcaggtc agtgggcagc ggcggcgcgc  8280
ggttgacttg caggagtttt tccagggcgc gcgggaggtc cagatggtac ttgatctcca  8340
ccgcgccatt ggtggcgacg tcgatggctt gcagggtccc gtgcccctgg ggtgtgacca  8400
ccgtccccccg tttcttcttg ggcggctggg gcgacggggg cggtgcctct tccatggtta  8460
gaagcggcgg cgaggacgcg cgccgggcgg caggggcggc tcggggcccg gaggcagggg  8520
cggcaggggc acgtcggcgc cgcgcgcggg taggttctgg tactgcgccc ggagaagact  8580
ggcgtgagcg acgacgcgac ggttgacgtc ctggatctga cgcctctggg tgaaggccac  8640
gggacccgtg agtttgaacc tgaaagagag ttcgacagaa tcaatctcgg tatcgttgac  8700
ggcggcctgc cgcaggatct cttgcacgtc gcccgagttg tcctggtagg cgatctcggt  8760
catgaactgc tcgatctcct cctcttgaag gtctccgcgg ccggcgcgct ccacggtggc  8820
cgcgaggtcg ttggagatgc ggcccatgag ctgcgagaag gcgttcatgc ccgcctcgtt  8880
ccagacgcgg ctgtagacca cgacgccctc gggatcgcgg gcgcgcatga ccacctgggc  8940
gaggttgagc tccacgtggc gcgtgaagac cgcgtagttg cagaggcgct ggtagaggta  9000
gttgagcgtg gtggcgatgt gctcggtgac gaagaaatac atgatccagc ggcggagcgg  9060
catctcgctg acgtcgccca gcgcctccaa acgttccatg gcctcgtaaa agtccacggc  9120
gaagttgaaa aactgggagt tgcgcgccga gacggtcaac tcctcctcca gaagacggat  9180
gagctcggcg atggtggcgc gcacctcgcg ctcgaaggcc cccgggagtt cctccacttc  9240
ctcttcttcc tcctccacta acatctcttc tacttcctcc tcaggcggca gtggtggcgg  9300
gggagggggc ctgcgtcgcc ggcggcgcac gggcagacgg tcgatgaagc gctcgatggt  9360
ctcgccgcgc cggcgtcgca tggtctcggt gacggcgcgc ccgtcctcgc ggggccgcag  9420
cgtgaagacg ccgccgcgca tctccaggtg gccgggggggg tccccgttgg gcagggagag  9480
ggcgctgacg atgcatctta tcaattgccc cgtagggact ccgcgcaagg acctgagcgt  9540
ctcgagatcc acgggatctg aaaaccgctg aacgaaggct tcgagccagt cgcagtcgca  9600
aggtaggctg agcacggttt cttctggcgg gtcatgttgg ttgggagcgg ggcgggcgat  9660
gctgctggtg atgaagttga aataggcggt tctgagacgg cggatggtgg cgaggagcac  9720
caggtctttg ggcccggctt gctggatgcg cagacggtcg gccatgcccc aggcgtggtc  9780
ctgacacctg gccaggtcct tgtagtagtc ctgcatgagc cgctccacgg gcacctcctc  9840
ctcgcccgcg cggccgtgca tgcgcgtgag cccgaagccg cgctggggct ggacgagcgc  9900
caggtcggcg acgacgcgct cggcgaggat ggcttgctgg atctgggtga gggtggtctg  9960
gaagtcatca aagtcgacga agcggtggta ggctccggtg ttgatggtgt aggagcagtt  10020
ggccatgacg gaccagttga cggtctggtg gcccggacgc acgagctcgt ggtacttgag  10080
gcgcgagtag gcgcgcgtgt cgaagatgta gtcgttgcag gtgcgcacca ggtactggta  10140
gccgatgagg aagtgcggcg gcggctggcg gtagagcggc catcgctcgg tggcgggggc  10200
gccgggcgcg aggtcctcga gcatggtgcg gtggtagccg tagatgtacc tggacatcca  10260
ggtgatgccg gcggcggtgg tggaggcgcg cgggaactcg cggacgcggt tccagatgtt  10320
gcgcagcggc aggaagtagt tcatggtggg cacggtctgg cccgtgaggc gcgcgcagtc  10380
gtggatgctc tatacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtattg gcactcccgt ctcgacccaa gcctgcacca accctccagg  10560
atacggaggc gggtcgtttt gcaacttttt tttggaggcc ggatgagact agtaagcgcg  10620
gaaagcggcc gaccgcgatg gctcgctgcc gtagtctgga gaagaatcgc caggggttgcg  10680
ttgcggtgtg ccccggttcg aggccggccg gattccgcgg ctaacgaggg cgtggctgcc  10740
ccgtcgtttc caagacccca tagccagccg acttctccag ttacggagcg agcccctctt  10800
ttgttttgtt tgtttttgcc agatgcatcc cgtactgcgg cagatgcgcc cccaccaccc  10860
tccaccgcaa caacagcccc ctccacagcc ggcgcttctg cccccgcccc agcagcaact  10920
tccagccacg accgccgcgg ccgccgtgag cggggctgga cagagttatg atcaccagct  10980
ggccttggaa gagggcgagg ggctggcgcg cctgggggcg tcgtcgccgg agcggcaccc  11040
gcgcgtgcag atgaaaaggg acgctcgcga ggcctacgtg cccaagcaga acctgttcag  11100
agacaggagc ggcgaggagc ccgaggagat gcgcgcggcc cggttccacg cggggcggga  11160
gctgcggcgc ggcctggacc gaaagagggt gctgagggac gaggatttcg aggcggacga  11220
gctgacgggg atcagccccg cgcgcgcgca cgtggccgcg gccaacctgg tcacggcgta  11280
cgagcagacc gtgaaggagg agagcaactt ccaaaaatcc ttcaacaacc acgtgcgcac  11340
cctgatcgcg cgcgaggagg tgaccctggg cctgatgcac ctgtgggacc tgctggaggc  11400
catcgtgcag aaccccacca gcaagccgct gacggcgcag ctgttcctgg tggtgcagca  11460
tagtcgggac aacgaagcgt tcagggaggc gctgctgaat atcaccgagc ccgagggccg  11520
ctggctcctg gacctggtga acattctgca gagcatcgtg gtgcaggagc gcgggctgcc  11580
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctggggg tgtaccgcaa  11760
cgacaggatg caccgtgcgg tgagcgccag caggcggcgc gagctgagcg accaggagct  11820
gatgcatagt ctgcagcggg ccctgaccgg ggccgggacc gagggggaga gctactttga  11880
catgggcgcg gacctgcact ggcagcccag ccgccgggcc ttggaggcgg cggcaggacc  11940
ctacgtagaa gaggtggacg atgaggtgga cgaggagggc gagtacctgg aagactgatg  12000
gcgcgaccgt atttttgcta gatgcaacaa caacagccac ctcctgatcc cgcgatgcgg  12060
gcggcgctgc agagccagcc gtccggcatt aactcctcgg acgattggac ccaggccatg  12120
caacgcatca tggcgctgac gacccgcaac cccgaagcct ttagacagca gccccaggcc  12180
```

```
aaccggctct cggccatcct ggaggccgtg gtgccctcgc gctccaaccc cacgcacgag  12240
aaggtcctgg ccatcgtgaa cgcgctggtg gagaacaagg ccatccgcgg cgacgaggcc  12300
ggcctggtgt acaacgcgct gctggagcgc gtggcccgct acaacagcac caacgtgcag  12360
accaacctgg accgcatggt gaccgacgtg cgcgaggccg tggcccagcg cgagcggttc  12420
caccgcgagt ccaacctggg atccatggtg gcgctgaacg ccttcctcag cacccagccc  12480
gccaacgtgc cccggggcca ggaggactac accaacttca tcagcgccct gcgcctgatg  12540
gtgaccgagg tgccccagag cgaggtgtac cagtccgggc cggactactt cttccagacc  12600
agtcgccagg gcttgcagac cgtgaacctg agccaggctt tcaagaactt gcagggcctg  12660
tggggcgtgc aggccccggt cggggaccgc gcgacggtgt cgagcctgct gacgccgaac  12720
tcgcgcctgc tgctgctgct ggtggccccc ttcacggaca gcggcagcat caaccgcaac  12780
tcgtacctgg gctacctgat taacctgtac cgcgaggcca tcggccaggc gcacgtggac  12840
gagcagacct accaggagat cacccacgtg agccgcgccc tgggccagga cgacccgggc  12900
aacctggaag ccaccctgaa ctttttgctg accaaccggt cgcagaagat cccgccccag  12960
tacgcgctca gcaccgagga ggagcgcatc ctgcgttacg tgcagcagag cgtgggcctg  13020
ttcctgatgc aggagggggc cacccccagc gccgcgctcg acatgaccgc gcgcaacatg  13080
gagcccagca tgtacgccag caaccgcccg ttcatcaata aactgatgga ctacttgcat  13140
cgggcggccg ccatgaactc tgactatttc accaacgcca tcctgaatcc ccactggctc  13200
ccgccgccgg ggttctacac gggcgagtac gacatgcccg accccaatga cgggttcctg  13260
tgggacgatg tggacagcag cgtgttctcc ccccgaccgg gtgctaacga gcgcccccttg  13320
tggaagaagg aaggcagcga ccgacgcccg tcctcggcgc tgtccggccg cgagggtgct  13380
gccgcggcgg tgcccgaggc cgccagtcct ttcccgagct tgcccttctc gctgaacagt  13440
atccgcagca gcgagctggg caggatcacg cgcccgcgct tgctgggcga agaggagtac  13500
ttgaatgact cgctgttgag acccgagcgg gagaagaact tccccaataa cgggatagaa  13560
agcctggtgg acaagatgag ccgctggaag acgtatgcgc aggagcacag ggacgatccc  13620
cgggcgtcgc agggggccac gagccggggc agcgccgccc gtaaacgccg gtggcacgac  13680
aggcagcggg gacagatgtg ggacgatgag gactccgccg acgacagcag cgtgttggac  13740
ttgggtggga gtggtaaccc gttcgctcac ctgcgccccc gtatcgggcg catgatgtaa  13800
gagaaaccga aaataaatga tactcaccaa ggccatggcg accagcgtgc gttcgtttct  13860
tctctgttgt tgttgtatct agtatgatga ggcgtgcgta cccggagggt cctcctccct  13920
cgtacgagag cgtgatgcag caggcgatgg cggcggcggc gatgcagccc ccgctggagg  13980
ctccttacgt gcccccgcgg tacctggcgc ctacggaggg gcggaacagc attcgttact  14040
cggagctggc acccttgtac gataccaccc ggttgtacct ggtggacaac aagtcggcgg  14100
acatcgcctc gctgaactac cagaacgacc acagcaactt cctgaccacc gtggtgcaga  14160
acaatgactt cacccccacg gaggccagca cccagaccat caactttgac gagcgctcgc  14220
ggtggggcgg ccagctgaaa accatcatgc acaccaacat gcccaacgtg aacgagttca  14280
tgtacagcaa caagttcaag gcgcgggtga tggtctcccg caagaccccc aatggggtga  14340
cagtgacaga ggattatgat ggtagtcagg atgagctgaa gtatgaatgg gtggaatttg  14400
agctgcccga aggcaacttc tcggtgacca tgaccatcga cctgatgaac aacgccatca  14460
tcgacaatta cttggcggtg gggcggcaga acggggtgct ggagagcgac atcggcgtga  14520
agttcgacac taggaacttc aggctgggct gggaccccgt gaccgagctg gtcatgcccg  14580
gggtgtacac caacgaggct ttccatcccg atattgtctt gctgcccggc tgcggggtgg  14640
acttcaccga gagccgcctc agcaacctgc tgggcattcg caagaggcag cccttccagg  14700
aaggcttcca gatcatgtac gaggatctgg agggggggcaa catccccgcg ctcctggatg  14760
tcgacgccta tgagaaaagc aaggaggatg cagcagctga agcaactgca gccgtagcta  14820
ccgcctctac cgaggtcagg ggcgataatt ttgcaagcgc cgcagcagtg gcagcggccg  14880
aggcggctga aaccgaaagt aagatagtca ttcagccggt ggagaaggat agcaagaaca  14940
ggagctacaa cgtactaccg gacaagataa acaccgccta ccgcagctgg tacctagcct  15000
acaactatgg cgaccccgag aagggcgtgc gctcctggac gctgctcacc acctcggacg  15060
tcacctgcgg cgtggagcaa gtctactggt cgctgcccga catgatgcaa gacccggtca  15120
ccttccgctc cacgcgtcaa gttagcaact acccggtggt gggcgccgag ctcctgcccg  15180
tctactccaa gagcttcttc aacgagcagg ccgtctactc gcagcagctg cgcgccttca  15240
cctcgcttac gcacgtcttc aaccgcttcc ccgagaacca gatcctcgtc cgcccgcccg  15300
cgcccaccat taccaccgtc agtgaaaacg ttcctgctct cacagatcac gggaccctgc  15360
cgctgcgcag cagtatccgg ggagtccagc gcgtgaccgt tactgacgcc agacgccgca  15420
cctgccccta cgtctacaag gccctgggca tagtcgcgcc gcgcgtcctc tcgagccgca  15480
ccttctaaat gtccattctc atctcgccca gtaataacac cggttggggc ctgcgcgcgc  15540
ccagcaagat gtacggaggc gctcgccaac gctccacgca acaccccgtg cgcgtgcgcg  15600
ggcacttccg cgctccctgg ggcgccctca agggccgcgt gcggtcgcgc accaccgtcg  15660
acgacgtgat cgaccaggtg gtggccgacg cgcgcaacta cacccccgcc gccgcgcccg  15720
tctccaccgt ggacgccgtc atcgacagcg tggtggccga cgcgcgccgg tacgcccgcg  15780
ccaagagccg gcggcggcgc atcgcccggc ggcaccggag cacccccgcc atgcgcgcgg  15840
cgcgagcctt gctgcgcagg gccaggcgca cgggacgcag ggccatgctc agggcggcca  15900
gacgcgcggc ttcaggcgcc agcgccggca ggacccggag acgcgcggcc acggcggcgg  15960
cagcggccat cgccagcatg tcccgcccgc ggcgagggaa cgtgtactgg gtgcgcgacg  16020
ccgccaccgg tgtgcgcgtg cccgtgcgca cccgcccccc tcgcacttga agatgttcac  16080
ttcgcgatgt tgatgtgtcc cagcggcgag gaggatgtcc aagcgcaaat tcaaggaaga  16140
gatgctccag gtcatcgcgc ctgagatcta cggccctgcg gtggtgaagg aggaaagaaa  16200
gccccgcaaa atcaagcggg tcaaaaagga caaaaaggaa gaagaaagtg atgtggacgg  16260
attggtggag tttgtgcgcg agttcgcccc ccggcggcgc gtgcagtggc gcgggcggaa  16320
ggtgcaaccg gtgctgagac ccggcaccac cgtggtcttc acgcccggcg agcgctccgg  16380
caccgcttcc aagcgctcct acgacgaggt gtacggggat gatgatattc tggagcaggc  16440
ggccgagcgc ctgggcgagt ttgcttacgg caagcgcagc cgttccgcac cgaaggaaga  16500
ggcggtgtcc atcccgctgg accacggcaa ccccacgccg agcctcaagc ccgtgacctt  16560
gcagcaggtg ctgccgaccg cggcgccgcg ccgggggttc aagcgcgagg gcgaggatct  16620
gtaccccacc atgcagctga tggtgcccaa gcgccagaag ctggaagacg tgctggagac  16680
catgaaggtg gacccggacg tgcagcccga ggtcaaggtg cggcccatca agcaggtggc  16740
cccgggcctg ggcgtgcaga ccgtggacat caagattccc acggagccca tggaaacgca  16800
gaccgagccc atgatcaagc ccagcaccag caccatggag gtgcagacgg atccctggat  16860
gccatcggct cctagtcgaa gaccccggcg caagtacggc gcggccagcc tgctgatgcc  16920
```

```
caactacgcg ctgcatcctt ccatcatccc cacgccgggc taccgcggca cgcgcttcta  16980
ccgcggtcat accagcagcc gccgccgcaa gaccaccact cgccgccgcc gtcgccgcac  17040
cgcccgctgca accacccctg ccgccctggt gcggagagtg taccgccgcg gccgcgcacc  17100
tctgaccctg ccgcgcgcgc gctaccaccc gagcatcgcc atttaaactt tcgcctgctt  17160
tgcagatcaa tggccctcac atgccgcctt cgcgttccca ttacgggcta ccgaggaaga  17220
aaaccgcgcc gtagaaggct ggcggggaac gggatgcgtc gccaccacca ccggcggcgg  17280
cgcgccatca gcaagcggtt gggggggaggc ttcctgcccg cgctgatccc catcatcgcc  17340
gcggcgatcg gggcgatccc cggcattgct tccgtggcgg tgcaggcctc tcagcgccac  17400
tgagacacac ttggaaacat cttgtaataa accaatggac tctgacgctc ctggtcctgt  17460
gatgtgtttt cgtagacaga tggaagacat caatttttcg tccctggctc cgcgacacgg  17520
cacgcggccg ttcatgggca cctggagcga catcggcacc agccaactga acgggggcgc  17580
cttcaattgg agcagtctct ggagcgggct taagaatttc gggtccacgc ttaaaaccta  17640
tggcagcaag gcgtggaaca gcaccacagg gcaggcgctg agggataagc tgaaagagca  17700
gaacttccag cagaaggtgg tcgatgggct cgcctcgggc atcaacgggg tggtggacct  17760
ggccaaccag gccgtgcagc ggcagatcaa cagccgcctg gacccggtgc cgcccgccgg  17820
ctccgtggag atgccgcagg tggaggagga gctgcctccc ctggacaagc ggggcgagaa  17880
gcgacccccgc cccgatgcgg aggagacgct gctgacgcac acggacgagc cgcccccgta  17940
cgaggaggcg gtgaaactgg gtctgcccac cacgcggccc atcgcgcccc tggccaccgg  18000
ggtgctgaaa cccgaaaagc ccgcgaccct ggacttgcct cctccccagc cttcccgccc  18060
ctctacagtg gctaagcccc tgccgccggt ggccgtggcc cgcgcgcgac ccgggggcac  18120
cgcccgccct catgcgaact ggcagagcac tctgaacagc atcgtgggtc tgggagtgca  18180
gagtgtgaag cgccgccgct gctattaaac ctaccgtagc gcttaacttg cttgtctgtg  18240
tgtgtatgta ttatgtcgcc gccgccgctg tccaccagaa ggaggagtga agaggcgcgt  18300
cgccgagttg caagatggcc accccatcga tgctgcccca gtgggcgtac atgcacatcg  18360
ccggacagga cgcttcggag tacctgagtc cgggtctggt gcagtttgcc cgcgccacag  18420
acacctactt cagtctgggg aacaagttta ggaaccccac ggtggcgccc acgcacgatg  18480
tgaccaccga ccgcagccag cggctgacgc tgcgcttcgt gcccgtggac cgcgaggaca  18540
acacctactc gtacaaagtg cgctacacgc tggccgtggg cgacaaccgc gtgctggaca  18600
tggccagcac ctactttgac atccgcggcg tgctggatcg gggccctagc ttcaaaccct  18660
actccggcac cgcctacaac agtctggccc ccaagggagc acccaacact tgtcagtgga  18720
catataaagc cgatggtgaa actgccacag aaaaaaccta tacatatgga aatgcacccg  18780
tgcagggcat taacatcaca aaagatggta ttcaacttgg aactgacacc gatgatcagc  18840
caatctacgc agataaaacc tatcagcctg aacctcaagt gggtgatgct gaatggcatg  18900
acatcactgg tactgatgaa aagtatggag gcagagctct taagcctgat accaaaatga  18960
agccttgtta tggttctttt gccaagccta ctaataaaga aggaggtcag gcaaatgtga  19020
aaacaggaac aggcactact aaagaatatg acatagacat ggctttcttt gacaacagaa  19080
gtgcggctgc tgctggccta gctccagaaa ttgttttgta tactgaaaat gtggatttgg  19140
aaactccaga tacccatatt gtatacaaag caggcacaga tgacagcagc tcttctatta  19200
atttgggtca gcaagccatg cccaacagac ctaactacat tggtttcaga gacaacttta  19260
tcgggctcat gtactacaac agcactggca atatgggggt gctggccggt caggcttctc  19320
agctgaatgc tgtggttgac ttgcaagaca gaaacaccga gctgtcctac cagctcttgc  19380
ttgactctct gggtgacaga acccggtatt tcagtatgtg gaatcaggcg gtggacagct  19440
atgatcctga tgtgcgcatt attgaaaatc atggtgtgga ggatgaactt cccaactatt  19500
gtttccctct ggatgctgtt ggcagaacag atacttatca gggaattaag gctaatggaa  19560
ctgatcaaac cacatggacc aaagatgaca gtgtcaatga tgctaatgag ataggcaagg  19620
gtaatccatt cgccatggaa atcaacatcc aagccaacct gtggaggaac ttcctctacg  19680
ccaacgtggc cctgtacctg cccgactctt acaagtacac gccggccaat gttaccctgc  19740
ccaccaacac caacacctac gattacatga acggccgggt ggtggcgccc tcgctggtgg  19800
actcctacat caacatcggg gcgcgctggt cgctggatcc catggacaac gtgaacccct  19860
tcaaccacca ccgcaatgcg gggctgcgct accgctccat gctcctgggc aacgggcgct  19920
acgtgccctt ccacatccag gtgccccaga aatttttcgc catcaagagc ctcctgctcc  19980
tgcccgggtc ctacacctac gagtggaact tccgcaagga cgtcaacatg atcctgcaga  20040
gctccctcgg caacgacctg cgcacggacg gggcctccat ctccttcacc agcatcaacc  20100
tctacgccac cttcttcccc atggcgcaca acacggcctc cacgctcgag gccatgctgc  20160
gcaacgacac caacgaccag tccttcaacg actacctctc ggcggccaac atgctctacc  20220
ccatcccggc caacgccacc aacgtgccca tctccatccc ctcgcgcaac tgggccgcct  20280
tccgcggctg gtccttcacg cgtctcaaga ccaaggagac gccctcgctg ggctccgggt  20340
tcgaccccta cttcgtctac tcgggctcca tcccctacct cgacggcacc ttctacctca  20400
accacacctt caagaaggtc tccatcacct tcgactcctc cgtcagctgg cccggcaacg  20460
accggctcct gacgcccaac gagttcgaaa tcaagcgcac cgtcgacggc gagggctaca  20520
acgtggccca gtgcaacatg accaaggact ggttcctggt ccagatgctg gcccactaca  20580
acatcggcta ccagggcttc tacgtgcccg agggctacaa ggaccgcatg tactccttct  20640
tccgcaactt ccagcccatg agccgccagg tggtggacga ggtcaactac aaggactacc  20700
aggccgtcac cctggcctac cagcacaaca actcgggctt cgtcggctac ctcgcgccca  20760
ccatgcgcca gggccagccc taccccgcca actaccccta cccgctcatc ggcaagagcg  20820
ccgtcaccag cgtcacccag aaaaagttcc tctgcgacag ggtcatgtgg cgcatcccct  20880
tctccagcaa cttcatgtcc atgggcgcgc tcaccgacct cggccagaac atgctctatg  20940
ccaactccgc ccacgcgcta gacatgaatt tcgaagtcga ccccatggat gagtccaccc  21000
ttctctatgt tgtcttcgaa gtcttcgacg tcgtccgagt gcaccagccc caccgcggcg  21060
tcatcgaggc cgtctacctg cgcacccccct tctcggccgg taacgccacc acctaagctc  21120
ttgcttcttg caagccatgg ccgcgggctc cggcgagcag gagctcaggg ccatcatccg  21180
cgacctgggc tgcgggccct acttcctggg caccttcgat aagcgcttcc cgggattcat  21240
ggccccgcac aagctggcct gcgccatcgt caacacggcc ggccgcgaga ccgggggcga  21300
gcactggctg gccttcgcct ggaacccgcg ctcgaacacc tgctacctct tcgacccctt  21360
cgggttctcg gacgagcgcc tcaagcagat ctaccagttc gagtacgagg gcctgctgcg  21420
ccgcagcgcc ctggccaccg aggaccgctg cgtcaccctg gaaaagtcca cccagaccgt  21480
gcagggtccg cgctcggccg cctgcgggct cttctgctgc atgttcctgc acgccttcgt  21540
gcactggccc gaccgcccca tggacaagaa ccccaccatg aacttgctga cgggggtgcc  21600
caacggcatg ctccagtcgc cccaggtgga acccaccctg cgccgcaacc aggaggcgct  21660
```

-continued

```
ctaccgcttc ctcaactccc actccgccta ctttcgctcc caccgcgcgc gcatcgagaa  21720
ggccaccgcc ttcgaccgca tgaatcaaga catgtaaacc gtgtgtgtat gttaaatgtc  21780
tttaataaac agcactttca tgttacacat gcatctgaga tgatttattt agaaatcgaa  21840
agggttctgc cgggtctcgg catggcccgc gggcagggac acgttgcgga actggtactt  21900
ggccagccac ttgaactcgg ggatcagcag tttgggcagc ggggtgtcgg ggaaggagtc  21960
ggtccacagc ttccgcgtca gttgcagggc gcccagcagg tcgggcgcgg agatcttgaa  22020
atcgcagttg ggacccgcgt tctgcgcgcg ggagttgcgg tacacggggt tgcagcactg  22080
gaacaccatc agggccgggt gcttcacgct cgccagcacc gtcgcgtcgg tgatgctctc  22140
cacgtcgagg tcctcggcgt tggccatccc gaagggggtc atcttgcagg tctgccttcc  22200
catggtgggc acgcacccgg gcttgtggtt gcaatcgcag tgcaggggga tcagcatcat  22260
ctgggcctgg tcggcgttca tccccgggta catggccttc atgaaagcct ccaattgcct  22320
gaacgcctgc tgggccttgg ctccctcggt gaagaagacc ccgcaggact tgctagagaa  22380
ctggttggtg gcgcacccgg cgtcgtgcac gcagcagcgc gcgtcgttgt tggccagctg  22440
caccacgctg cgcccccagc ggttctgggt gatcttggcc cggtcggggt tctccttcag  22500
cgcgcgctgc ccgttctcgc tcgccacatc catctcgatc atgtgctcct tctggatcat  22560
ggtggtcccg tgcaggcacc gcagcttgcc ctcggcctcg gtgcacccgt gcagccacag  22620
cgcgcacccg gtgcactccc agttcttgtg ggcgatctgg gaatgcgcgt gcacgaagcc  22680
ctgcaggaag cggcccatca tggtggtcag ggtcttgttg ctagtgaagg tcagcggaat  22740
gccgcggtgc tcctcgttga tgtacaggtg gcagatgcgg cggtacacct cgccctgctc  22800
gggcatcagc tggaagttgg ctttcaggtc ggtctccacg cggtagcggt ccatcagcat  22860
agtcatgatt tccataccct tctcccaggc cgagacgatg ggcaggctca tagggttctt  22920
caccatcatc ttagcgctag cagccgcggc caggggggtcg ctctcgtcca gggtctcaaa  22980
gctccgcttg ccgtccttct cggtgatccg caccgggggg tagctgaagc ccacggccgc  23040
cagctcctcc tcggcctgtc tttcgtcctc gctgtcctgg ctgacgtcct gcaggaccac  23100
atgcttggtc ttgcggggtt tcttcttggg cggcagcggc ggcggagatg ttggagatgg  23160
cgagggggag cgcgagttct cgctcaccac tactatctct tcctcttctt ggtccgaggc  23220
cacgcggcgg taggtatgtc tcttcggggg cagaggcgga ggcgacgggc tctcgccgcc  23280
gcgacttggc ggatggctgg cagagcccct tccgcgttcg ggggtgcgct cccggcggcg  23340
ctctgactga cttcctccgc ggccggccat tgtgttctcc tagggaggaa caacaagcat  23400
ggagactcag ccatcgccaa cctcgccatc tgcccccacc gccgacgaga agcagcagca  23460
gcagaatgaa agcttaaccg ccccgccgcc cagccccgcc acctccgacg cggccgtccc  23520
agacatgcaa gagatggagg aatccatcga gattgacctg ggctatgtga cgcccgcgga  23580
gcacgaggag gagctggcag tgcgcttttc acaagaagag atacaccaag aacagccaga  23640
gcaggaagca gagaatgagc agagtcaggc tgggctcgag catgacggcg actacctcca  23700
cctgagcggg ggggaggacg cgctcatcaa gcatctggcc cggcaggcca ccatcgtcaa  23760
ggatgcgctg ctcgaccgca ccgaggtgcc cctcagcgtg gaggagctca gccgcgccta  23820
cgagttgaac ctcttctcgc cgcgcgtgcc ccccaagcgc cagcccaatg gcacctgcga  23880
gcccaacccg cgcctcaact tctacccggt cttcgcggtg cccgaggccc tggccaccta  23940
ccacatcttt ttcaagaacc aaaagatccc cgtctcctgc cgcgccaacc gcacccgcgc  24000
cgacgccctt ttcaacctgg gtcccggcgc ccgcctacct gatatcgcct ccttggaaga  24060
ggttcccaag atcttcgagg gtctgggcag cgacgagact cgggccgcga acgctctgca  24120
aggagaagga ggagagcatg agcaccacag cgccctggtc gagttggaag gcgacaacgc  24180
gcggctggcg gtgctcaaac gcacggtcga gctgacccat ttcgcctacc cggctctgaa  24240
cctgcccccc aaagtcatga gcgcggtcat ggaccaggtg ctcatcaagc gcgcgtcgcc  24300
catctccgag gacgagggca tgcaagactc cgaggagggc aagcccgtgg tcagcgacga  24360
gcagctggcc cggtggctgg gtcctaatgc tagtccccag agtttggaag agcggcgcaa  24420
actcatgatg gccgtggtcc tggtgaccgt ggagctggag tgcctgcgcc gcttcttcgc  24480
cgacgcggag accctgcgca aggtcgagga gaacctgcac tacctcttca ggcacgggtt  24540
cgtgcgccag gcctgcaaga tctccaacgt ggagctgacc aacctggtct cctacatggg  24600
catcttgcac gagaaccgcc tggggcagaa cgtgctgcac accaccctgc gcggggaggc  24660
ccggcgcgac tacatccgcg actgcgtcta cctctacctc tgccacacct ggcagacggg  24720
catgggcgtg tggcagcagt gtctggagga gcagaacctg aaagagctct gcaagctcct  24780
gcagaagaac ctcaagggtc tgtggaccgg gttcgacgag cgcaccaccg cctcggacct  24840
ggccgacctc attttccccg agcgcctcag gctgacgctg cgcaacggcc tgcccgactt  24900
tatgagccaa agcatgttgc aaaactttcg ctctttcatc ctcgaacgct ccggaatcct  24960
gcccgccacc tgctccgcgc tgccctcgga cttcgtgccg ctgaccttcc gcgagtgccc  25020
cccgccgctg tggagccact gctacctgct gcgcctggcc aactacctgg cctaccactc  25080
ggacgtgatc gaggacgtca gcggcgaggg cctgctcgag tgccactgcc gctgcaacct  25140
ctgcacgccg caccgctccc tggcctgcaa cccccagctg ctgagcgaga cccagatcat  25200
cggcaccttc gagttgcaag ggcccagcga aggcgagggt tcagccgcca agggggggtct  25260
gaaactcacc ccggggctgt ggacctcggc ctacttgcgc aagttcgtgc ccgaggacta  25320
ccatcccttc gagatcaggt tctacgagga ccaatcccat ccgcccaagg ccgagctgtc  25380
ggcctgcgtc atcacccagg gggcgatcct ggcccaattg caagccatcc agaaatcccg  25440
ccaagaattc ttgctgaaaa agggccgcgg ggtctacctc gacccccaga ccggtgagga  25500
gctcaacccc ggcttccccc aggatgcccc gaggaaacaa gaagctgaaa gtggagctgc  25560
cgcccgtgga ggatttggag gaagactggg agaacagcag tcaggcagag gaggaggaga  25620
tggaggaaga ctgggacagc actcaggcag aggaggacag cctgcaagac agtctggagg  25680
aagacgagga ggaggcagag gaggaggtgg aagaagcagc cgccgccaga ccgtcgtcct  25740
cggcggggga gaaagcaagc agcacggata ccatctccgc tccgggtcgg ggtcccgctc  25800
gaccacacag tagatgggac gagaccggac gattcccgaa ccccaccacc cagaccggta  25860
agaaggagcg gcagggatac aagtcctggc gggggcacaa aaacgccatc gtctcctgct  25920
tgcaggcctg cgggggcaac atctccttca cccggcgcta cctgctcttc caccgcgggg  25980
tgaactttcc ccgcaacatc ttgcattact accgtcacct ccacagcccc tactacttcc  26040
aagaagaggc agcagcagca gaaaaagacc agcagaaaac cagcagctag aaaatccaca  26100
gcggcggcag caggtggact gaggatcgcg gcgaacgagc cggcgcaaac ccgggagctg  26160
aggaaccgga tctttcccac cctctatgcc atcttccagc agagtcgggg gcaggagcag  26220
gaactgaaag tcaagaaccg ttctctgcgc tcgctcaccc gcagttgtct gtatcacaag  26280
agcgaagacc aacttcagcg cactctcgag gacgccgagg ctctcttcaa caagtactgc  26340
gcgctcactc ttaaagagta gcccgcgccc gcccagtcgc agaaaaaggc gggaattacg  26400
```

-continued

```
tcacctgtgc ccttcgccct agccgcctcc acccatcatc atgagcaaag agattcccac  26460
gccttacatg tggagctacc agccccagat gggcctggcc gccggtgccg cccaggacta  26520
ctccacccgc atgaattggc tcagcgccgg gcccgcgatg atctcacggg tgaatgacat  26580
ccgcgcccac cgaaaccaga tactcctaga acagtcagcg ctcaccgcca cgccccgcaa  26640
tcacctcaat ccgcgtaatt ggcccgccgc cctggtgtac caggaaattc cccagcccac  26700
gaccgtacta cttccgcgag acgcccaggc cgaagtccag ctgactaact caggtgtcca  26760
gctggcgggc ggcgccaccc tgtgtcgtca ccgccccgct cagggtataa agcggctggt  26820
gatccggggc agaggcacac agctcaacga cgaggtggtg agctcttcgc tgggtctgcg  26880
acctgacgga gtcttccaac tcgccggatc ggggagatct tccttcacgc ctcgtcaggc  26940
cgtcctgact ttggagagtt cgtcctcgca gccccgctcg ggtggcatcg gcactctcca  27000
gttcgtggag gagttcactc cctcggtcta cttcaacccc ttctccggct cccccggcca  27060
ctacccggac gagttcatcc cgaacttcga cgccatcagc gagtcggtgg acggctacga  27120
ttgaatgtcc catggtggcg cagctgacct agctcggctt cgacacctgg accactgccg  27180
ccgcttccgc tgcttcgctc gggatctcgc cgagtttgcc tactttgagc tgcccgagga  27240
gcaccctcag ggcccggccc acggagtgcg gatcgtcgtc gaagggggcc tcgactccca  27300
cctgcttcgg atcttcagcc agcgtccgat cctggtcgag cgcgagcaag gacagaccct  27360
tctgactctg tactgcatct gcaaccaccc cggcctgcat gaaagtcttt gttgtctgct  27420
gtgtactgag tataataaaa gctgagatca gcgactactc cggacttccg tgtgttcctg  27480
aatccatcaa ccagtctttg ttcttcaccg ggaacgagac cgagctccag ctccagtgta  27540
agccccacaa gaagtacctc acctggctgt tccagggctc cccgatcgcc gttgtcaacc  27600
actgcgacaa cgacggagtc ctgctgagcg gccctgccaa ccttactttt tccacccgca  27660
gaagcaagct ccagctcttc caacccttcc tccccgggac ctatcagtgc gtctcgggac  27720
cctgccatca caccttccac ctgatcccga ataccacagc gtcgctcccc gctactaaca  27780
accaaactaa cctccaccaa cgccaccgtc gcgacctttc tgaatctaat actaccaccc  27840
acaccggagg tgagctccga ggtcaaccaa cctctgggat ttactacggc ccctgggagg  27900
tggttgggtt aatagcgcta ggcctagttg cgggtgggct tttggttctc tgctacctat  27960
acctcccttg ctgttcgtac ttagtggtgc tgtgttgctg gtttaagaaa tggggaagat  28020
caccctagtg agctgcggtg cgctggtggc ggtgttgctt tcgattgtgg gactgggcgg  28080
tgcggctgta gtgaaggaga aggccgatcc ctgcttgcat ttcaatccca acaaatgcca  28140
gctgagtttt cagcccgatg gcaatcggtg cgcggtactg atcaagtgcg gatgggaatg  28200
cgagaacgtg agaatcgagt acaataacaa gactcggaac aatactctcg cgtccgtgtg  28260
gcagcccggg gaccccgagt ggtacaccgt ctctgtcccc ggtgctgacg gctccccgcg  28320
caccgtgaat aatactttca tttttgcgca catgtgcgac acggtcatgt ggatgagcaa  28380
gcagtacgat atgtggcccc ccacgaagga gaacatcgtg gtcttctcca tcgcttacag  28440
cctgtgcacg gcgctaatca ccgctatcgt gtgcctgagc attcacatgc tcatcgctat  28500
tcgccccaga aataatgccg aaaaagaaaa acagccataa cgtttttttt cacacctttt  28560
tcagaccatg gcctctgtta aatttttgct tttatttgcc agtctcattg ccgtcattca  28620
tggaatgagt aatgagaaaa ttactattta cactggcact aatcacacat tgaaaggtcc  28680
agaaaaagcc acagaagttt catggtattg ttattttaat gaatcagatg tatctactga  28740
actctgtgga aacaataaca aaaaaaatga gagcattact ctcatcaagt ttcaatgtgg  28800
atctgactta accctaatta acatcactag agactatgta ggtatgtatt atggaactac  28860
agcaggcatt tcggacatgg aattttatca agtttctgtg tctgaaccca ccacgcctag  28920
aatgaccaca accacaaaaa ctacacctgt taccactatg cagctcacta ccaataacat  28980
ttttgccatg cgtcaaatgg tcaacaatag cactcaaccc accccaccca gtgaggaaat  29040
tcccaaatcc atgattggca ttattgttgc tgtagtggtg tgcatgttga tcatcgcctt  29100
gtgcatggtg tactatgcct tctgctacag aaagcacaga ctgaacgaca agctggaaca  29160
cttactaagt gttgaatttt aatttttttag aaccatgaag atcctaggcc ttttaatttt  29220
ttctatcatt acctctgctc tatgcaattc tgacaatgag gacgttactg tcgttgtcgg  29280
atcaaattat acactgaaag gtccagcgaa gggtatgctt tcgtggtatt gctattttgg  29340
atctgacact acagaaactg aattatgcaa tcttaagaat ggcaaaattc aaaattctaa  29400
aattaacaat tatatatgca atggtactga tctgatactc ctcaatatca cgaaatcata  29460
tgctggcagt tacacctgcc ctggagatga tgctgacagt atgatttttt acaaagtaac  29520
tgttgttgat cccactactc cacctccacc caccacaact actcacacca cacacacaga  29580
tcaaaccgca gcagaggagg cagcaaagtt agccttgcag gtccaagaca gttcatttgt  29640
tggcattacc cctacacctg atcagcggtg tccggggctg ctagtcagcg gcattgtcgg  29700
tgtgctttcg ggattagcag tcataatcat ctgcatgttc atttttgctt gctgctatag  29760
aaggctttac cgacaaaaat cagacccact gctgaacctc tatgtttaat tttttccaga  29820
gtcatgaagg cagttagcgc tctagttttt tgttctttga ttggcattgt tttttgcaat  29880
cctattccta aagttagctt tattaaagat gtgaatgtta ctgagggggg caatgtgaca  29940
ctggtaggtg tagagggtgc tgaaaacacc acctggacaa aataccacct caatgggtgg  30000
aaagatattt gcaattggag tgtattagtt tatacatgtg agggagttaa tcttaccatt  30060
gtcaatgcca cctcagctca aaatggtaga attcaaggac aaagtgtcag tgtatctaat  30120
gggtatttta cccaacatac ttttatctat gacgttaaag tcataccact gcctacgcct  30180
agcccaccta gcactaccac acagacaacc cacactacac agacaaccac atacagtaca  30240
ttaaatcagc ctaccaccac tacagcagca gaggttgcca gctcgtctgg ggtccgagtg  30300
gcatttttga tgtgggcccc atctagcagt cccactgcta gtaccaatga gcagactact  30360
gaatttttgt ccactgtcga gagccacacc acagctacct ccagtgcctt ctctagcacc  30420
gccaatctct cctcgctttc ctctacacca atcagtcccg ctactactcc tagccccgct  30480
cctcttccca ctcccctgaa gcaaacagac ggcggcatgc aatggcagat caccctgctc  30540
attgtgatcg ggttggtcat cctggccgtg ttgctctact acatcttctg ccgccgcatt  30600
cccaacgcgc accgcaagcc ggtctacaag cccatcattg tcgggcagcc ggagccgctt  30660
caggtggaag gggtctaagg gaatcttctc ttctctttta cagtatggtg attgaactat  30720
gattcctaga caattcttga tcactattct tatctgcctc ctccaagtct gtgccaccct  30780
cgctctggtg gccaacgcca gtccagactg tattgggccc ttcgcctcct acgtgctctt  30840
tgccttcacc acctgcatct gctgctgtag catagtctgc ctgcttatca ccttcttcca  30900
gttcattgac tggatctttg tgcgcatcgc ctacctgcgc caccaccccc agtaccgcga  30960
ccagcgagtg gcgcggctgc tcaggctcct ctgataagca tgcgggctct gctacttctc  31020
gcgcttctgc tgttagtgct cccccgtccc gtcgaccccc ggtcccccac ccagtccccc  31080
gaggaggtcc gcaaatgcaa attccaagaa ccctggaaat tcctcaaatg ctaccgccaa  31140
```

-continued

```
aaatcagaca tgcatcccag ctggatcatg atcattggga tcgtgaacat tctggcctgc  31200
accctcatct cctttgtgat ttacccctgc tttgactttg gttggaactc gccagaggcg  31260
ctctatctcc cgcctgaacc tgacacacca ccacagcaac ctcaggcaca cgcactacca  31320
ccactacagc ctaggccaca atacatgccc atattagact atgaggccga gccacagcga  31380
cccatgctcc ccgctattag ttacttcaat ctaaccggcg gagatgactg acccactggc  31440
caacaacaac gtcaacgacc ttctcctgga catggacggc cgcgcctcgg agcagcgact  31500
cgcccaactt cgcattcgcc agcagcagga gagagccgtc aaggagctgc aggatgcggt  31560
ggccatccac cagtgcaaga gaggcatctt ctgcctggtg aaacaggcca agatctccta  31620
cgaggtcact ccaaacgacc atcgcctctc ctacgagctc ctgcagcagc gccagaagtt  31680
cacctgcctg gtcggagtca accccatcgt catcacccag cagtctggcg ataccaaggg  31740
gtgcatccac tgctcctgcg actcccccga ctgcgtccac actctgatca agaccctctg  31800
cggcctccgc gacctcctcc ccatgaacta atcaccccct tatccagtga aataaagatc  31860
atattgatga tgattttaca gaaataaaaa ataatcattt gatttgaaat aaagatacaa  31920
tcatattgat gatttgagtt taacaaaaaa ataaagaatc acttacttga aatctgatac  31980
caggtctctg tccatgtttt ctgccaacac cacttcactc ccctcttccc agctctggta  32040
ctgcaggccc cggcgggctg caaacttcct ccacacgctg aaggggatgt caaattcctc  32100
ctgtccctca atcttcattt tatcttctat cagatgtcca aaaagcgcgt ccgggtggat  32160
gatgacttcg accccgtcta cccctacgat gcagacaacg caccgaccgt gcccttcatc  32220
aaccccccct tcgtctcttc agatggattc caagagaagc cccctggggggt gttgtccctg  32280
cgactggccg accccgtcac caccaagaac ggggaaatca ccctcaagct gggagagggg  32340
gtggacctcg attcctcggg aaaactcatc tccaacacgg ccaccaaggc cgccgcccct  32400
ctcagttttt ccaacaacac catttccctt aacatggatc accccttttta cactaaagat  32460
ggaaaattat ccttacaagt ttctccacca ttaaatatac tgagaacaag cattctaaac  32520
acactagctt taggttttgg atcaggttta ggactccgtg gctctgcctt ggcagtacag  32580
ttagtctctc cacttacatt tgatactgat ggaaacataa agcttacctt agacagaggt  32640
ttgcatgtta caacaggaga tgcaattgaa agcaacataa gctgggctaa aggtttaaaa  32700
tttgaagatg gagccatagc aaccaacatt ggaaatgggt tagagtttgg aagcagtagt  32760
acagaaacag gtgttgatga tgcttaccca atccaagtta aacttggatc tggccttagc  32820
tttgacagta caggagccat aatggctggt aacaaagaag acgataaact cactttgtgg  32880
acaacacctg atccatcacc aaactgtcaa atactcgcag aaaatgatgc aaaactaaca  32940
ctttgcttga ctaaatgtgg tagtcaaata ctggccactg tgtcagtctt agttgtagga  33000
agtggaaacc taaaccccat tactggcacc gtaagcagtg ctcaggtgtt tctacgtttt  33060
gatgcaaacg gtgttctttt aacagaacat tctacactaa aaaaatactg gggtatagg  33120
cagggagata gcatagatgg cactccatat accaatgctg taggattcat gcccaattta  33180
aaagcttatc caaagtcaca aagttctact actaaaaata atatagtagg gcaagtatac  33240
atgaatggag atgtttcaaa acctatgctt ctcactataa ccctcaatgg tactgatgac  33300
agcaacagta catattcaat gtcattttca tacacctgga ctaatggaag ctatgttgga  33360
gcaacatttg gggctaactc ttataccttc tcatacatcg cccaagaatg aacactgtat  33420
cccaccctgc atgccaaccc ttcccacccc actctgtgga acaaactctg aaacacaaaa  33480
taaaataaag ttcaagtgtt ttattgattc aacagtttta caggattcga gcagttattt  33540
ttcctccacc ctcccaggac atggaataca ccaccctctc cccccgcaca gccttgaaca  33600
tctgaatgcc attggtgatg gacatgcttt tggtctccac gttccacaca gtttcagagc  33660
gagccagtct cgggtcggtc agggagatga aaccctccgg gcactcccgc atctgcacct  33720
cacagctcaa cagctgagga ttgtcctcgg tggtcgggat cacggttatc tggaagaagc  33780
agaagagcgg cggtgggaat catagtccgc gaacgggatc ggccggtggt gtcgcatcag  33840
gccccgcagc agtcgctgcc gccgccgctc cgtcaagctg ctgctcaggg ggtccgggtc  33900
cagggactcc ctcagcatga tgcccacggc cctcagcatc agtcgtctgg tgcggcgggc  33960
gcagcagcgc atgcggatct cgctcaggtc gctgcagtac gtgcaacaca gaaccaccag  34020
gttgttcaac agtccatagt tcaacacgct ccagccgaaa ctcatcgcgg gaaggatgct  34080
acccacgtgg ccgtcgtacc agatcctcag gtaaatcaag tggtgccccc tccagaacac  34140
gctgcccacg tacatgatct ccttgggcat gtggcggttc accacctccc ggtaccacat  34200
caccctctgg ttgaacatgc agccccggat gatcctgcgg aaccacaggg ccagcaccgc  34260
cccgcccgcc atgcagcgaa gagaccccgg gtcccggcaa tggcaatgga ggacccaccg  34320
ctcgtacccg tggatcatct gggagctgaa caagtctatg ttggcacagc acaggcatat  34380
gctcatgcat ctcttcagca ctctcaactc ctcgggggtc aaaaccatat cccagggcac  34440
ggggaactct tgcaggacag cgaaccccgc agaacagggc aatcctcgca cagaacttac  34500
attgtgcatg gacagggtat cgcaatcagg cagcaccggg tgatcctcca ccagagaagc  34560
gcgggtctcg gtctcctcac agcgtggtaa gggggccggc cgatacgggt gatggcggga  34620
cgcggctgat cgtgttcgcg accgtgtcat gatgcagttg ctttcggaca ttttcgtact  34680
tgctgtagca gaacctggtc cgggcgctgc acaccgatcg ccggcggcgg tctcggcgct  34740
tggaacgctc ggtgttgaaa ttgtaaaaca gccactctct cagaccgtgc agcagatcta  34800
gggcctcagg agtgatgaag atcccatcat gcctgatggc tctgatcaca tcgaccaccg  34860
tggaatgggc cagacccagc cagatgatgc aattttgttg ggtttcggtg acggcggggg  34920
agggaagaac aggaagaacc atgattaact tttaatccaa acggtctcgg agtacttcaa  34980
aatgaagatc gcggagatgg cacctctcgc ccccgctgtg ttggtggaaa ataacagcca  35040
ggtcaaaggt gatacggttc tcgagatgtt ccacggtggc ttccagcaaa gcctccacgc  35100
gcacatccag aaacaagaca atagcgaaag cgggagggtt ctctaattcc tcaatcatca  35160
tgttacactc ctgcaccatc cccagataat ttcatttttt ccagccttga atgattcgaa  35220
ctagttcctg aggtaaatcc aagccagcca tgataaagag ctcgcgcaga gcgccctcca  35280
ccggcattct taagcacacc ctcataattc caagatattc tgctcctggt tcacctgcag  35340
cagattgaca agcggaatat caaaatctct gccgcgatcc ctgagctcct ccctcagcaa  35400
taactgtaag tactctttca tatcctctcc gaaattttta gccataggac caccaggaat  35460
aagattaggg caagccacag tacagataaa ccgaagtcct ccccagtgag cattgccaaa  35520
tgcaagactg ctataagcat gctggctaga cccggtgata tcttccagat aactggacag  35580
aaaatcgccc aggcaatttt taagaaaatc aacaaaagaa aaatcctcca ggtggacgtt  35640
tagagcctcg ggaacaacga tgaagtaaat gcaagcggtg cgttccagca tggttagtta  35700
gctgatctgt agaaaaaaca aaaatgaaca ttaaaccatg ctagcctggc gaacaggtgg  35760
gtaaatcgtt ctctccagca ccaggcaggc cacggggtct ccggcgcgac cctcgtaaaa  35820
attgtcgcta tgattgaaaa ccatcacaga gagacgttcc cggtggccgg cgtgaatgat  35880
```

-continued

```
tcgacaagat gaatacaccc ccggaacatt ggcgtccgcg agtgaaaaaa agcgcccgag  35940
gaagcaataa ggcactacaa tgctcagtct caagtccagc aaagcgatgc catgcggatg  36000
aagcacaaaa ttctcaggtg cgtacaaaat gtaattactc ccctcctgca caggcagcaa  36060
agcccccgat ccctccaggt acacatacaa agcctcagcg tccatagctt accgagcagc  36120
agcacacaac aggcgcaaga gtcagagaaa ggctgagctc taacctgtcc acccgctctc  36180
tgctcaatat atagcccaga tctacactga cgtaaaggcc aaagtctaaa aatacccgcc  36240
aaataatcac acacgcccag cacacgccca gaaaccggtg acacactcaa aaaaatacgc  36300
gcacttcctc aaacgcccaa aactgccgtc atttccgggt tcccacgcta cgtcatcaaa  36360
acacgacttt caaattccgt cgaccgttaa aaacgtcacc cgccccgccc ctaacggtcg  36420
cccgtctctc agccaatcag cgccccgcat ccccaaattc aaacacctca tttgcatatt  36480
aacgcgcaca aaaagtttga ggtatattat tgatgatgg                        36519

SEQ ID NO: 2           moltype = DNA  length = 31588
FEATURE                Location/Qualifiers
misc_feature           1..31588
                       note = Description of Artificial Sequence: Synthetic
                        polynucleotide
source                 1..31588
                       mol_type = other DNA
                       organism = synthetic construct
SEQUENCE: 2
ccatcttcaa taatatacct caaacttttt gtgcgcgtta atatgcaaat gaggcgtttg  60
aatttgggga ggaagggcgg tgattggtcg agggatgagc gaccgttagg ggcggggcga  120
gtgacgtttt gatgacgtgg ttgcgaggag gagccagttt gcaagttctc gtgggaaaag  180
tgacgtcaaa cgaggtgtgg tttgaacacg gaaatactca attttcccgc gctctctgac  240
aggaaatgag gtgtttctgg gcggatgcaa gtgaaaacgg gccattttcg cgcgaaaact  300
gaatgaggaa gtgaaaatct gagtaatttc gcgtttatgg cagggaggag tatttgccga  360
gggccgagta gactttgacc gattacgtgg gggtttcgat taccgtgttt ttcacctaaa  420
tttccgcgta cggtgtcaaa gtccggtgtt tttacgtagg tgtcagctga tcgccagggt  480
atttaaacct gcgctctcca gtcaagaggc cactcttgag tgccagcgag aagagttttc  540
tcctccgcgc cgcgagtcag atctacactt tgaaagtagg gataacaggg taatgacatt  600
gattattgac tagttgttaa tagtaatcaa ttacggggtc attagttcat agcccatata  660
tggagttccg cgttacataa cttacggtaa atggcccgcc tggctgaccg cccaacgacc  720
cccgcccatt gacgtcaata atgacgtatg ttcccatagt aacgccaata gggactttcc  780
attgacgtca atgggtggag tatttacggt aaactgccca cttggcagta catcaagtgt  840
atcatatgcc aagtccgccc cctattgacg tcaatgacgg taaatggccc gcctggcatt  900
atgcccagta catgacctta cgggactttc ctacttggca gtacatctac gtattagtca  960
tcgctattac catggtgatg cggttttggc agtacaccaa tgggcgtgga tagcggtttg  1020
actcacgggg atttccaagt ctccacccca ttgacgtcaa tgggagtttg ttttggcacc  1080
aaaatcaacg ggactttcca aaatgtcgta ataaccccgc cccgttgacg caaatgggcg  1140
gtaggcgtgt acggtgggag gtctatataa gcagagctcg tttagtgaac cgtcagatcg  1200
cctggaacgc catccacgct gttttgacct ccatagaaga cagcgatcgc gccaccatgg  1260
ccgggatgtt ccaggcactg tccgaaggct gcacaccccta tgatattaac cagatgctga  1320
atgtcctggg agaccaccag gtctctggcc tggagcagct ggagagcatc atcaacttcg  1380
agaagctgac cgagtggaca agctccaatg tgatgcctat cctgtcccca ctgaccaagg  1440
gcatcctggg cttcgtgttt accctgacag tgccttctga gcggggcctg tcttgcatca  1500
gcgaggcaga cgcaaccaca ccagagtccg ccaatctggg cgaggagatc ctgtctcagc  1560
tgtacctgtg gccccgggtg acatatcact ccccttctta cgcctatcac cagttcgagc  1620
ggagagccaa gtacaagaga cacttcccag gctttggcca gtctctgctg ttcggctacc  1680
ccgtgtacgt gttcggcgat tgcgtgcagg gcgactggga tgccatccgg tttagatact  1740
gcgcaccacc tggatatgca ctgctgaggt gtaacgacac caattattcc gccctgctgg  1800
cagtgggcgc cctggagggc cctcgcaatc aggattggct gggcgtgcca aggcagctgg  1860
tgacacgcat gcaggccatc cagaacgcag gcctgtgcac cctggtggca atgctggagg  1920
agacaatctt ctggctgcag gcctttctga tggccctgac cgacagcggc cccaagacaa  1980
acatcatcgt ggattcccag tacgtgatgg gcatctccaa gccttctttc caggagtttg  2040
tggactggga gaacgtgagc ccagagctga attccaccga tcagccattc tggcaggcag  2100
gaatcctggc aaggaacctg gtgcctatgg tggccacagt gcagggccag aatctgaagt  2160
accagggcca gagcctggtc atcagcgcct ccatcatcgt gtttaacctg ctggagctgg  2220
agggcgacta tcgggacgat ggcaacgtgt gggtgcacac cccactgagc cccagaacac  2280
tgaacgcctg ggtgaaggcc gtggaggaga agaagggcat cccagtgcac ctggagctgg  2340
cctccatgac caatatggag ctgatgtcta gcatcgtgca ccagcaggtg aggacatacg  2400
gacccgtgtt catgtgcctg ggaggcctgc tgaccatggt ggcaggagcc gtgtggctga  2460
cagtgcgggt gctggagctg ttcagagccg cccagctggc caacgatgtg gtgctgcaga  2520
tcatggagct gtgcggagca gcctttcgcc aggtgtgcca caccacagtg ccatggccca  2580
atgcctccct gacccccaag tggaacaatg agacaacaca gcctcagatc gccaactgta  2640
gcgtgtacga cttcttcgtg tggctgcact actatagcgt gagggatacc ctgtggcccc  2700
gcgtgacata ccacatgaat aagtacgcct atcacatgct ggagaggcgc gccaagtata  2760
agagaggccc tggcccaggc gcaaagtttg tggcagcatg gaccctgaag gccgccgccg  2820
gccccggccc cggccagtat atcaaggcta acagtaagtt cattggaatc acagagctgg  2880
gacccggacc tggataatga gtttaaactc ccatttaaat gtgagggtta atgcttcgag  2940
cagacatgat aagatacatt gatgagtttg gacaaaccac aactagaatg cagtgaaaaa  3000
aatgctttat ttgtgaaatt tgtgatgcta ttgctttatt tgtaaccatt ataagctgca  3060
ataaacaagt taacaacaac aattgcattc attttatgtt tcaggttcag ggggagatgt  3120
gggaggtttt ttaaagcaag taaaacctct acaaatgtgg taaaataact ataacggtcc  3180
taaggtagcg agtgagtagt gttctggggc gggggaggac ctgcatgagg gccagaataa  3240
ctgaaatctg tgcttttctg tgtgttgcag cagcatgagc ggaagcggct cctttgaggg  3300
aggggtattc agcccttatc tgacggggcg tctcccctcc tgggcgggag tgcgtcagaa  3360
tgtgatggga tccacggtgg acggccggcc cgtgcagccc gcgaactctt caaccctgac  3420
ctatgcaacc ctgagctctt cgtcgttgga cgcagctgcc gccgcagctg ctgcatctgc  3480
```

-continued

| | | | | | | |
|---|---|---|---|---|---|---|
| cgccagcgcc | gtgcgcggaa | tggccatggg | cgccggctac | tacggcactc | tggtggccaa | 3540 |
| ctcgagttcc | accaataatc | ccgccagcct | gaacgaggag | aagctgttgc | tgctgatggc | 3600 |
| ccagctcgag | gccttgaccc | agcgcctggg | cgagctgacc | cagcaggtgg | ctcagctgca | 3660 |
| ggagcagacg | cgggccgcgg | ttgccacggt | gaaatccaaa | taaaaaatga | atcaataaat | 3720 |
| aaacggagac | ggttgttgat | tttaacacag | agtctgaatc | tttatttgat | ttttcgcgcg | 3780 |
| cggtaggccc | tggaccaccg | gtctcgatca | ttgagcaccc | ggtggatctt | ttccaggacc | 3840 |
| cggtagaggt | gggcttggat | gttgaggtac | atgggcatga | gcccgtcccg | ggggtggagg | 3900 |
| tagctccatt | gcagggcctc | gtgctcgggg | gtggtgttgt | aaatcaccca | gtcatagcag | 3960 |
| gggcgcaggg | catggtgttg | cacaatatct | ttgaggagga | gactgatggc | cacgggcagc | 4020 |
| cctttggtgt | aggtgtttac | aaatctgttg | agctgggagg | gatgcatgcg | gggggagatg | 4080 |
| aggtgcatct | tggcctggat | cttgagattg | gcgatgttac | cgcccagatc | ccgcctgggg | 4140 |
| ttcatgttgt | gcaggaccac | cagcacggtg | tatccggtgc | acttggggaa | tttatcatgc | 4200 |
| aacttggaag | ggaaggcgtg | aaagaatttg | gcgacgcctt | tgtgcccgcc | caggttttcc | 4260 |
| atgcactcat | ccatgatgat | ggcgatgggc | ccgtgggcgg | cggcctgggc | aaagacgttt | 4320 |
| cgggggtcgg | acacatcata | gttgtggtcc | tgggtgaggt | catcataggc | cattttaatg | 4380 |
| aatttggggc | ggagggtgcc | ggactggggg | acaaaggtac | cctcgatccc | gggggcgtag | 4440 |
| ttcccctcac | agatctgcat | ctcccaggct | ttgagctcgg | aggggggat | catgtccacc | 4500 |
| tgcggggcga | taaagaacac | ggtttccggg | gcgggggaga | tgagctgggc | cgaaagcaag | 4560 |
| ttccggagca | gctgggactt | gccgcagccg | gtggggccgt | agatgacccc | gatgaccggc | 4620 |
| tgcaggtggt | agttgaggga | gagacagctg | ccgtcctccc | ggaggagggg | ggccacctcg | 4680 |
| ttcatcatct | cgcgcacgtg | catgttctcg | cgcaccagtt | ccgccaggag | gcgctctccc | 4740 |
| cccagggata | ggagctcctg | gagcgaggcg | aagtttttca | gcggcttgag | tccgtcggcc | 4800 |
| atgggcattt | tggagagggt | ttgttgcaag | agttccaggc | ggtcccagag | ctcggtgatg | 4860 |
| tgctctacgg | catctcgatc | cagcagacct | cctcgtttcg | cgggttggga | cggctgcggg | 4920 |
| agtagggcac | cagacgatgg | gcgtccagcg | cagccagggt | ccggtccttc | cagggtcgca | 4980 |
| gcgtccgcgt | cagggtggtc | tccgtcacgg | tgaaggggtg | cgcgccgggc | tgggcgcttg | 5040 |
| cgagggtgcg | cttcaggctc | atccggctgg | tcgaaaaccg | ctcccgatcg | gcgccctgcg | 5100 |
| cgtcggccag | gtagcaattg | accatgagtt | cgtagttgag | cgcctcggcc | gcgtggcctt | 5160 |
| tggcgcggag | cttacctttg | gaagtctgcc | cgcaggcggg | acagaggagg | gacttgaggg | 5220 |
| cgtagagctt | gggggcgagg | aagacggact | cgggggcgta | ggcgtccgcg | ccgcagtggg | 5280 |
| cgcagacggt | ctcgcactcc | acgagccagg | tgaggtcggg | ctggtcgggg | tcaaaaacca | 5340 |
| gtttcccgcc | gttctttttg | atgcgtttct | tacctttggt | ctccatgagc | tcgtgtcccc | 5400 |
| gctgggtgac | aaagaggctg | tccgtgtccc | cgtagaccga | ctttatgggc | cggtcctcga | 5460 |
| gcggtgtgcc | gcggtcctcc | tcgtagagga | accccgccca | ctccgagacg | aaagcccggg | 5520 |
| tccaggccag | cacgaaggag | gccacgtggg | acgggtagcg | gtcgttgtcc | accagcgggt | 5580 |
| ccaccttttc | cagggtatgc | aaacacatgt | ccccctcgtc | cacatccagg | aaggtgattg | 5640 |
| gcttgtaagt | gtaggccacg | tgaccggggg | tcccggccgg | gggggtataa | aagggtgcgg | 5700 |
| gtccctgctc | gtcctcactg | tcttccggat | cgctgtccag | gagcgccagc | tgttggggta | 5760 |
| ggtattccct | ctcgaaggcg | ggcatgacct | cggcactcag | gttgtcagtt | tctagaaacg | 5820 |
| aggaggattt | gatattgacg | gtgccggcgg | agatgccttt | caagagcccc | tcgtccatct | 5880 |
| ggtcagaaaa | gacgatcttt | ttgttgtcga | gcttggtggc | gaaggagccg | tagagggcgt | 5940 |
| tggagaggag | cttggcgatg | gagcgcatgg | tctggttttt | ttccttgtcg | gcgcgctcct | 6000 |
| tggcggcgat | gttgagctgc | acgtactcgc | gcgccacgca | cttccattcg | gggaagacgg | 6060 |
| tggtcagctc | gtcgggcacg | attctgacct | gccagccccg | attatgcagg | gtgatgaggt | 6120 |
| ccacactggt | ggccacctcg | ccgcgcaggg | gctcattagt | ccagcagagg | cgtccgccct | 6180 |
| tgcgcgagca | gaaggggggc | agggggtcca | gcatgacctc | gtcggggggg | tcggcatcga | 6240 |
| tggtgaagat | gccgggcagg | aggtcggggt | caaagtagct | gatggaagtg | gccagatcgt | 6300 |
| ccagggcagc | ttgccattcg | cgcacggcca | gcgcgcgctc | gtagggactg | aggggcgtgc | 6360 |
| cccagggcat | gggatgggta | agcgcggagg | cgtacatgcc | gcagatgtcg | tagacgtaga | 6420 |
| ggggctcctc | gaggatgccg | atgtaggtgg | ggtagcagcg | ccccccgcgg | atgctggcgc | 6480 |
| gcacgtagtc | atacagctcg | tgcgaggggg | cgaggagccc | cgggcccagg | ttggtgcgac | 6540 |
| tgggcttttc | ggcgcggtag | acgatctggc | ggaaaatggc | atgcgagttg | gaggagatgg | 6600 |
| tgggcctttg | gaagatgttg | aagtgggcgt | ggggcagtcc | gaccgagtcg | cggatgaagt | 6660 |
| gggcgtagga | gtcttgcagc | ttggcgacga | gctcggcggt | gactaggacg | tccagagcgc | 6720 |
| agtagtcgag | ggtctcctgg | atgatgtcat | acttgagctg | tccctttttgt | ttccacagct | 6780 |
| cgcggttgag | aaggaactct | tcgcggtcct | tccagtactc | ttcgaggggg | aacccgtcct | 6840 |
| gatctgcacg | gtaagagcct | agcatgtaga | actggttgac | ggccttgtag | gcgcagcagc | 6900 |
| ccttctccac | ggggagggcg | taggcctggg | cggccttgcg | cagggaggtg | tgcgtgaggg | 6960 |
| cgaaagtgtc | cctgaccatg | accttgagga | actggtgctt | gaagtcgata | tcgtcgcagc | 7020 |
| cccccctgctc | ccagagctgg | aagtccgtgc | gcttcttgta | ggcggggttg | ggcaaagcga | 7080 |
| aagtaacatc | gttgaagagg | atcttgcccg | cgcggggcat | aaagttgcga | gtgatgcgga | 7140 |
| aaggttgggg | cacctcggcc | cggttgttga | tgacctgggc | ggcgagcacg | atctcgtcga | 7200 |
| agccgttgat | gttgtggccc | acgatgtaga | gttccacgaa | tcgcggacgg | cccttgacgt | 7260 |
| ggggcagttt | cttgagctcc | tcgtaggtga | gctcgtcggg | gtcgctgagc | ccgtgctgct | 7320 |
| cgagcgccca | gtcggcgaga | tgggggttgg | cgcggaggaa | ggaagtccag | agatccacgg | 7380 |
| ccagggcggt | ttgcagacgg | tcccggtact | gacggaactg | ctgcccgacg | gccatttttt | 7440 |
| cgggggtgac | gcagtagaag | gtgcgggggt | ccccgtgcca | gcgatcccat | ttgagctgga | 7500 |
| gggcgagatc | gagggcgagc | tcgacgagcc | ggtcgtcccc | ggagagtttc | atgaccagca | 7560 |
| tgaaggggac | gagctgcttg | ccgaaggacc | ccatccaggt | gtaggtttcc | acatcgtagg | 7620 |
| tgaggaagag | cctttcggtg | cgaggatgcg | agccgatggg | gaagaactgg | atctcctgcc | 7680 |
| accaattgga | ggaatggctg | ttgatgtgat | ggaagtagaa | atgccgacgg | cgcgccgaac | 7740 |
| actcgtgctt | gtgtttatac | aagcggccac | agtgctcgca | acgctgcacg | ggatgcacgt | 7800 |
| gctgcacgag | ctgtacctga | gttcctttga | cgaggaattt | cagtgggaag | tggagtcgtg | 7860 |
| gcgcctgcat | ctcgtgctgt | actacgtcgt | ggtggtcggc | ctggccctct | tctgcctcga | 7920 |
| tggtggtcat | gctgacgagc | ccgcgcggga | ggcaggtcca | gacctcggcg | cgagcgggtc | 7980 |
| ggagagcgag | gacgagggcg | cgcaggccgg | agctgtccag | ggtcctgaga | cgctgcggag | 8040 |
| tcaggtcagt | gggcagcggc | ggcgcgcggt | tgacttgcag | gagtttttcc | agggcgcgcg | 8100 |
| ggaggtccag | atggtacttg | atctccaccg | cgccattggt | ggcgacgtcg | atggcttgca | 8160 |
| gggtcccgtg | cccctggggt | gtgaccaccg | tcccccgttt | cttcttgggc | ggctggggcg | 8220 |

-continued

```
acgggggcgg tgcctcttcc atggttagaa gcggcggcga ggacgcgcgc cgggcggcag  8280
gggcggctcg gggcccggag gcaggggcgg caggggcacg tcggcgccgc gcgcgggtag  8340
gttctggtac tgcgcccgga gaagactggc gtgagcgacg acgcgacggt tgacgtcctg  8400
gatctgacgc ctctgggtga aggccacggg acccgtgagt ttgaacctga aagagagttc  8460
gacagaatca atctcggtat cgttgacggc ggcctgccgc aggatctctt gcacgtcgcc  8520
cgagttgtcc tggtaggcga tctcggtcat gaactgctcg atctcctcct cttgaaggtc  8580
tccgcggccg gcgcgctcca cggtggccgc gaggtcgttg gagatgcggc ccatgagctg  8640
cgagaaggcg ttcatgcccg cctcgttcca gacgcggctg tagaccacga cgccctcggg  8700
atcgcgggcg cgcatgacca cctgggcgag gttgagctcc acgtggcgcg tgaagaccgc  8760
gtagttgcag aggcgctggt agaggtagtt gagcgtggtg gcgatgtgct cggtgacgaa  8820
gaaatacatg atccagcggc ggagcggcat ctcgctgacg tcgcccagcg cctccaaacg  8880
ttccatggcc tcgtaaaagt ccacggcgaa gttgaaaaac tgggagttgc gcgccgagac  8940
ggtcaactcc tcctccagaa gacggatgag ctcggcgatg gtggcgcgca cctcgcgctc  9000
gaaggccccc gggagttcct ccacttcctc ttcttcctcc tccactaaca tctcttctac  9060
ttcctcctca ggcggcagtg gtggcggggg agggggcctg cgtcgccggc ggcgcacggg  9120
cagacggtcg atgaagcgct cgatggtctc gccgcgccgg cgtcgcatgg tctcggtgac  9180
ggcgcgcccg tcctcgcggg gccgcagcgt gaagacgccg ccgcgcatct ccaggtggcc  9240
gggggggtcc ccgttgggca gggagagggc gctgacgatg catcttatca attgccccgt  9300
agggactccg cgcaaggacc tgagcgtctc gagatccacg ggatctgaaa accgctgaac  9360
gaaggcttcg agccagtcgc agtcgcaagg taggctgagc acggtttctt ctggcgggtc  9420
atgttggttg ggagcggggc gggcgatgct gctggtgatg aagttgaaat aggcggttct  9480
gagacggcgg atggtggcga ggagcaccag gtctttgggc ccggcttgct ggatgcgcag  9540
acggtcggcc atgccccagg cgtggtcctg acacctggcc aggtccttgt agtagtcctg  9600
catgagccgc tccacgggca cctcctcctc gcccgcgcgg ccgtgcatgc gcgtgagccc  9660
gaagccgcgc tggggctgga cgagcgccag gtcggcgacg acgcgctcgg cgaggatggc  9720
ttgctggatc tgggtgaggg tggtctggaa gtcatcaaag tcgacgaagc ggtggtaggc  9780
tccggtgttg atggtgtagg agcagttggc catgacggac cagttgacgg tctggtggcc  9840
cggacgcacg agctcgtggt acttgaggcg cgagtaggcg cgcgtgtcga agatgtagtc  9900
gttgcaggtg cgcaccaggt actggtagcc gatgaggaag tgcggcggcg gctggcggta  9960
gagcggccat cgctcggtgg cgggggcgcc gggcgcgagg tcctcgagca tggtgcggtg  10020
gtagccgtag atgtacctgg acatccaggt gatgccggcg gcggtggtgg aggcgcgcgg  10080
gaactcgcgg acgcggttcc agatgttgcg cagcggcagg aagtagttca tggtgggcac  10140
ggtctggccc gtgaggcgcg cgcagtcgtg gatgctctat acgggcaaaa acgaaagcgg  10200
tcagcggctc gactccgtgg cctggaggct aagcgaacgg gttgggctgc gcgtgtaccc  10260
cggttcgaat ctcgaatcag gctggagccg cagctaacgt ggtattggca ctcccgtctc  10320
gacccaagcc tgcaccaacc ctccaggata cggaggcggg tcgttttgca acttttttt  10380
ggaggccgga tgagactagt aagcgcggaa agcggccgac cgcgatggct cgctgccgta  10440
gtctggagaa gaatcgccag ggttgcgttg cggtgtgccc cggttcgagg ccggccggat  10500
tccgcggcta acgagggcgt ggctgccccg tcgtttccaa gaccccatag ccagccgact  10560
tctccagtta cggagcgagc ccctctttg ttttgtttgt ttttgccaga tgcatcccgt  10620
actgcggcag atgcgccccc accaccctcc accgcaacaa cagccccctc cacagccggc  10680
gcttctgccc ccgccccagc agcaacttcc agccacgacc gccgcggccg ccgtgagcgg  10740
ggctggacag agttatgatc accagctggc cttggaagag ggcgaggggc tggcgcgcct  10800
gggggcgtcg tcgccggagc ggcacccgcg cgtgcagatg aaaagggacg ctcgcgaggc  10860
ctacgtgccc aagcagaacc tgttcagaga caggagcggc gaggagcccg aggagatgcg  10920
cgcggcccgg ttccacgcgg ggcgggagct gcggcgcggc ctggaccgaa agagggtgct  10980
gagggacgag gatttcgagg cggacgagct gacggggatc agccccgcgc gcgcgcacgt  11040
ggccgcggcc aacctggtca cggcgtacga gcagaccgtg aaggaggaga gcaacttcca  11100
aaaatccttc aacaaccacg tgcgcaccct gatcgcgcgc gaggaggtga ccctgggcct  11160
gatgcacctg tgggacctgc tggaggccat cgtgcagaac cccaccagca agccgctgac  11220
ggcgcagctg ttcctggtgg tgcagcatag tcgggacaac gaagcgttca gggaggcgct  11280
gctgaatatc accgagcccg agggccgctg gctcctggac ctggtgaaca ttctgcagag  11340
catcgtggtg caggagcgcg ggctgccgct gtccgagaag ctggcggcca tcaacttctc  11400
ggtgctgagt ttgggcaagt actacgctag gaagatctac aagaccccgt acgtgcccat  11460
agacaaggag gtgaagatcg acgggtttta catgcgcatg accctgaaag tgctgaccct  11520
gagcgacgat ctgggggtgt accgcaacga caggatgcac cgtgcggtga gcgccagcag  11580
gcggcgcgag ctgagcgacc aggagctgat gcatagtctg cagcgggccc tgaccggggc  11640
cgggaccgag ggggagagct actttgacat gggcgcggac ctgcactggc agcccagccg  11700
ccgggccttg gaggcggcgg caggacccta cgtagaagag gtggacgatg aggtggacga  11760
ggagggcgag tacctggaag actgatggcg cgaccgtatt tttgctagat gcaacaacaa  11820
cagccacctc ctgatcccgc gatgcgggcg gcgctgcaga gccagccgtc cggcattaac  11880
tcctcggacg attggaccca ggccatgcaa cgcatcatgg cgctgacgac ccgcaacccc  11940
gaagccttta gacagcagcc ccaggccaac cggctctcgg ccatcctgga ggccgtggtg  12000
ccctcgcgct ccaaccccac gcacgagaag gtcctggcca tcgtgaacgc gctggtggag  12060
aacaaggcca tccgcggcga cgaggccggc ctggtgtaca acgcgctgct ggagcgcgtg  12120
gcccgctaca acagcaccaa cgtgcagacc aacctggacc gcatggtgac cgacgtgcgc  12180
gaggccgtgg cccagcgcga gcggttccac cgcgagtcca acctgggatc catggtggcg  12240
ctgaacgcct tcctcagcac ccagcccgcc aacgtgcccc ggggccagga ggactacacc  12300
aacttcatca gcgccctgcg cctgatggtg accgaggtgc cccagagcga ggtgtaccag  12360
tccgggccgg actacttctt ccagaccagt cgccagggct tgcagaccgt gaacctgagc  12420
caggctttca agaacttgca gggcctgtgg ggcgtgcagg ccccggtcgg ggaccgcgcg  12480
acggtgtcga gcctgctgac gccgaactcg cgcctgctgc tgctgctggt ggcccccttc  12540
acggacagcg gcagcatcaa ccgcaactcg tacctgggct acctgattaa cctgtaccgc  12600
gaggccatcg gccaggcgca cgtggacgag cagacctacc aggagatcac ccacgtgagc  12660
cgcgccctgg gccaggacga cccgggcaac ctggaagcca ccctgaactt tttgctgacc  12720
aaccggtcgc agaagatccc gccccagtac gcgctcagca ccgaggagga gcgcatcctg  12780
cgttacgtgc agcagagcgt gggcctgttc ctgatgcagg agggggccac ccccagcgcc  12840
gcgctcgaca tgaccgcgcg caacatggag cccagcatgt acgccagcaa ccgcccgttc  12900
atcaataaac tgatggacta cttgcatcgg gcggccgcca tgaactctga ctatttcacc  12960
```

-continued

```
aacgccatcc tgaatcccca ctggctcccg ccgccggggt tctacacggg cgagtacgac  13020
atgcccgacc ccaatgacgg gttcctgtgg gacgatgtgg acagcagcgt gttctccccc  13080
cgaccgggtg ctaacgagcg ccccttgtgg aagaaggaag gcagcgaccg acgcccgtcc  13140
tcggcgctgt ccggccgcga gggtgctgcc gcggcggtgc ccgaggccgc cagtcctttc  13200
ccgagcttgc ccttctcgct gaacagtatc cgcagcagcg agctgggcag gatcacgcgc  13260
ccgcgcttgc tgggcgaaga ggagtacttg aatgactcgc tgttgagacc cgagcgggag  13320
aagaacttcc ccaataacgg gatagaaagc ctggtggaca agatgagccg ctggaagacg  13380
tatgcgcagg agcacaggga cgatccccgg gcgtcgcagg gggccacgag ccggggcagc  13440
gccgcccgta aacgccggtg gcacgacagg cagcggggac agatgtggga cgatgaggac  13500
tccgccgacg acagcagcgt gttggacttg ggtgggagtg gtaacccgtt cgctcacctg  13560
cgcccccgta tcgggcgcat gatgtaagag aaaccgaaaa taaatgatac tcaccaaggc  13620
catggcgacc agcgtgcgtt cgtttcttct ctgttgttgt tgtatctagt atgatgaggc  13680
gtgcgtaccc ggagggtcct cctccctcgt acgagagcgt gatgcagcag gcgatggcgg  13740
cggcggcgat gcagcccccg ctggaggctc cttacgtgcc cccgcggtac ctggcgccta  13800
cggaggggcg gaacagcatt cgttactcgg agctggcacc cttgtacgat accacccggt  13860
tgtacctggt ggacaacaag tcggcggaca tcgcctcgct gaactaccag aacgaccaca  13920
gcaacttcct gaccaccgtg gtgcagaaca atgacttcac ccccacggag gccagcaccc  13980
agaccatcaa ctttgacgag cgctcgcggt ggggcggcca gctgaaaacc atcatgcaca  14040
ccaacatgcc caacgtgaac gagttcatgt acagcaacaa gttcaaggcg cgggtgatgg  14100
tctcccgcaa gacccccaat ggggtgacag tgacagagga ttatgatggt agtcaggatg  14160
agctgaagta tgaatgggtg gaatttgagc tgcccgaagg caacttctcg gtgaccatga  14220
ccatcgacct gatgaacaac gccatcatcg acaattactt ggcggtgggg cggcagaacg  14280
gggtgctgga gagcgacatc ggcgtgaagt tcgacactag gaacttcagg ctgggctggg  14340
accccgtgac cgagctggtc atgcccgggg tgtacaccaa cgaggctttc catcccgata  14400
ttgtcttgct gcccggctgc ggggtggact tcaccgagag ccgcctcagc aacctgctgg  14460
gcattcgcaa gaggcagccc ttccaggaag gcttccagat catgtacgag gatctggagg  14520
ggggcaacat ccccgcgctc ctggatgtcg acgcctatga gaaaagcaag gaggatgcag  14580
cagctgaagc aactgcagcc gtagctaccg cctctaccga ggtcaggggc gataattttg  14640
caagcgccgc agcagtggca gcggccgagg cggctgaaac cgaaagtaag atagtcattc  14700
agccggtgga gaaggatagc aagaacagga gctacaacgt actaccggac aagataaaca  14760
ccgcctaccg cagctggtac ctagcctaca actatggcga ccccgagaag ggcgtgcgct  14820
cctggacgct gctcaccacc tcggacgtca cctgcggcgt ggagcaagtc tactggtcgc  14880
tgcccgacat gatgcaagac ccggtcacct tccgctccac gcgtcaagtt agcaactacc  14940
cggtggtggg cgccgagctc ctgcccgtct actccaagag cttcttcaac gagcaggccg  15000
tctactcgca gcagctgcgc gccttcacct cgcttacgca cgtcttcaac cgcttccccg  15060
agaaccagat cctcgtccgc ccgcccgcgc ccaccattac caccgtcagt gaaaacgttc  15120
ctgctctcac agatcacggg accctgccgc tgcgcagcag tatccgggga gtccagcgcg  15180
tgaccgttac tgacgccaga cgccgcacct gcccctacgt ctacaaggcc ctgggcatag  15240
tcgcgccgcg cgtcctctcg agccgcacct tctaaatgtc cattctcatc tcgcccagta  15300
ataacaccgg ttggggcctg cgcgcgccca gcaagatgta cggaggcgct cgccaacgct  15360
ccacgcaaca ccccgtgcgc gtgcgcgggc acttccgcgc tccctggggc gccctcaagg  15420
gccgcgtgcg gtcgcgcacc accgtcgacg acgtgatcga ccaggtggtg gccgacgcgc  15480
gcaactacac ccccgccgcc gcgcccgtct ccaccgtgga cgccgtcatc gacagcgtgg  15540
tggccgacgc gcgccggtac gcccgcgcca agagccggcg gcggcgcatc gcccggcggc  15600
accggagcac ccccgccatg cgcgcggcgc gagccttgct gcgcagggcc aggcgcacgg  15660
gacgcagggc catgctcagg gcggccagac gcgcggcttc aggcgccagc gccggcagga  15720
cccggagacg cgcggccacg gcggcggcag cggccatcgc cagcatgtcc cgcccgcggc  15780
gagggaacgt gtactgggtg cgcgacgccg ccaccggtgt gcgcgtgccc gtgcgcaccc  15840
gcccccctcg cacttgaaga tgttcacttc gcgatgttga tgtgtcccag cggcgaggag  15900
gatgtccaag cgcaaattca aggaagagat gctccaggtc atcgcgcctg agatctacgg  15960
ccctgcggtg gtgaaggagg aaagaaagcc ccgcaaaatc aagcgggtca aaaaggacaa  16020
aaaggaagaa gaaagtgatg tggacggatt ggtggagttt gtgcgcgagt tcgccccccg  16080
gcggcgcgtg cagtggcgcg ggcggaaggt gcaaccggtg ctgagacccg gcaccaccgt  16140
ggtcttcacg cccggcgagc gctccggcac cgcttccaag cgctcctacg acgaggtgta  16200
cggggatgat gatattctgg agcaggcggc cgagcgcctg ggcgagtttg cttacggcaa  16260
gcgcagccgt tccgcaccga aggaagaggc ggtgtccatc ccgctggacc acggcaaccc  16320
cacgccgagc ctcaagcccg tgaccttgca gcaggtgctg ccgaccgcgg cgccgcgccg  16380
ggggttcaag cgcgagggcg aggatctgta ccccaccatg cagctgatgg tgcccaagcg  16440
ccagaagctg gaagacgtgc tggagaccat gaaggtggac ccggacgtgc agcccgaggt  16500
caaggtgcgg cccatcaagc aggtggcccc gggcctgggc gtgcagaccg tggacatcaa  16560
gattcccacg gagcccatgg aaacgcagac cgagcccatg atcaagccca gcaccagcac  16620
catggaggtg cagacggatc cctggatgcc atcggctcct agtcgaagac cccggcgcaa  16680
gtacggcgcg gccagcctgc tgatgcccaa ctacgcgctg catccttcca tcatccccac  16740
gccgggctac cgcggcacgc gcttctaccg cggtcatacc agcagccgcc gccgcaagac  16800
caccactcgc cgccgccgtc gccgcaccgc cgctgcaacc acccctgccg ccctggtgcg  16860
gagagtgtac cgccgcggcc gcgcacctct gaccctgccg cgcgcgcgct accacccgag  16920
catcgccatt taaactttcg cctgctttgc agatcaatgg ccctcacatg ccgccttcgc  16980
gttcccatta cgggctaccg aggaagaaaa ccgcgcccgta gaaggctggc ggggaacggg  17040
atgcgtcgcc accaccaccg gcggcggcgc gccatcagca agcggttggg gggaggcttc  17100
ctgcccgcgc tgatccccat catcgccgcg gcgatcgggg cgatccccgg cattgcttcc  17160
gtggcggtgc aggcctctca gcgccactga gacacacttg gaaacatctt gtaataaacc  17220
aatggactct gacgctcctg gtcctgtgat gtgttttcgt agacagatgg aagacatcaa  17280
tttttcgtcc ctggctccgc gacacggcac gcggccgttc atgggcacct ggagcgacat  17340
cggcaccagc caactgaacg gggcgccctt caattggagc agtctctgga gcgggcttaa  17400
gaatttcggg tccacgctta aacctatgg cagcaaggcg tggaacagca ccacagggca  17460
ggcgctgagg gataagctga aagagcagaa cttccagcag aaggtggtcg atgggctcgc  17520
ctcgggcatc aacggggtgg tggacctggc caaccaggcc gtgcagcggc agatcaacag  17580
ccgcctggac ccggtgccgc ccgccggctc cgtggagatg ccgcaggtgg aggaggagct  17640
gcctcccctg gacaagcggg gcgagaagcg accccgcccc gatgcggagg agacgctgct  17700
```

-continued

```
gacgcacacg gacgagccgc ccccgtacga ggaggcggtg aaactgggtc tgcccaccac  17760
gcggcccatc gcgcccctgg ccaccggggt gctgaaaccc gaaaagcccg cgaccctgga  17820
cttgcctcct ccccagcctt cccgcccctc tacagtggct aagcccctgc cgccggtggc  17880
cgtggcccgc gcgcgacccg ggggcaccgc ccgccctcat gcgaactggc agagcactct  17940
gaacagcatc gtgggtctgg gagtgcagag tgtgaagcgc cgccgctgct attaaaccta  18000
ccgtagcgct taacttgctt gtctgtgtgt gtatgtatta tgtcgccgcc gccgctgtcc  18060
accagaagga ggagtgaaga ggcgcgtcgc cgagttgcaa gatggccacc ccatcgatgc  18120
tgccccagtg ggcgtacatg cacatcgccg gacaggacgc ttcggagtac ctgagtccgg  18180
gtctggtgca gtttgcccgc gccacagaca cctacttcag tctggggaac aagtttagga  18240
accccacggt ggcgcccacg cacgatgtga ccaccgaccg cagccagcgg ctgacgctgc  18300
gcttcgtgcc cgtggaccgc gaggacaaca cctactcgta caaagtgcgc tacacgctgg  18360
ccgtgggcga caaccgcgtg ctggacatgg ccagcaccta ctttgacatc cgcggcgtgc  18420
tggatcgggg ccctagcttc aaaccctact ccggcaccgc ctacaacagt ctggccccca  18480
agggagcacc caacacttgt cagtggacat ataaagccga tggtgaaact gccacagaaa  18540
aaacctatac atatggaaat gcacccgtgc agggcattaa catcacaaaa gatggtattc  18600
aacttggaac tgacaccgat gatcagccaa tctacgcaga taaaacctat cagcctgaac  18660
ctcaagtggg tgatgctgaa tggcatgaca tcactggtac tgatgaaaag tatggaggca  18720
gagctcttaa gcctgatacc aaaatgaagc cttgttatgg ttcttttgcc aagcctacta  18780
ataaagaagg aggtcaggca aatgtgaaaa caggaacagg cactactaaa gaatatgaca  18840
tagacatggc tttctttgac aacagaagtg cggctgctgc tggcctagct ccagaaattg  18900
ttttgtatac tgaaaatgtg gatttggaaa ctccagatac ccatattgta tacaaagcag  18960
gcacagatga cagcagctct tctattaatt tgggtcagca agccatgccc aacagaccta  19020
actacattgg tttcagagac aactttatcg ggctcatgta ctacaacagc actggcaata  19080
tgggggtgct ggccggtcag gcttctcagc tgaatgctgt ggttgacttg caagacagaa  19140
acaccgagct gtcctaccag ctcttgcttg actctctggg tgacagaacc cggtatttca  19200
gtatgtggaa tcaggcggtg gacagctatg atcctgatgt gcgcattatt gaaaatcatg  19260
gtgtggagga tgaacttccc aactattgtt tccctctgga tgctgttggc agaacagata  19320
cttatcaggg aattaaggct aatggaactg atcaaaccac atggaccaaa gatgacagtg  19380
tcaatgatgc taatgagata ggcaagggta atccattcgc catggaaatc aacatccaag  19440
ccaacctgtg gaggaacttc ctctacgcca acgtggccct gtacctgccc gactcttaca  19500
agtacacgcc ggccaatgtt accctgccca ccaacaccaa cacctacgat tacatgaacg  19560
gccgggtggt ggcgccctcg ctggtggact cctacatcaa catcggggcg cgctggtcgc  19620
tggatcccat ggacaacgtg aaccccttca accaccaccg caatgcgggg ctgcgctacc  19680
gctccatgct cctgggcaac gggcgctacg tgcccttcca catccaggtg ccccagaaat  19740
ttttcgccat caagagcctc ctgctcctgc ccgggtccta cacctacgag tggaacttcc  19800
gcaaggacgt caacatgatc ctgcagagct ccctcggcaa cgacctgcgc acggacgggg  19860
cctccatctc cttcaccagc atcaacctct acgccacctt cttccccatg gcgcacaaca  19920
cggcctccac gctcgaggcc atgctgcgca acgacaccaa cgaccagtcc ttcaacgact  19980
acctctcggc ggccaacatg ctctacccca tcccggccaa cgccaccaac gtgcccatct  20040
ccatcccctc gcgcaactgg gccgccttcc gcggctggtc cttcacgcgt ctcaagacca  20100
aggagacgcc ctcgctgggc tccgggttcg acccctactt cgtctactcg ggctccatcc  20160
cctacctcga cggcaccttc tacctcaacc acaccttcaa gaaggtctcc atcaccttcg  20220
actcctccgt cagctggccc ggcaacgacc ggctcctgac gcccaacgag ttcgaaatca  20280
agcgcaccgt cgacggcgag ggctacaacg tggcccagtg caacatgacc aaggactggt  20340
tcctggtcca gatgctggcc cactacaaca tcggctacca gggcttctac gtgcccgagg  20400
gctacaagga ccgcatgtac tccttcttcc gcaacttcca gcccatgagc cgccaggtgg  20460
tggacgaggt caactacaag gactaccagg ccgtcaccct ggcctaccag cacaacaact  20520
cgggcttcgt cggctacctc gcgcccacca tgcgccaggg ccagccctac cccgccaact  20580
acccctaccc gctcatcggc aagagcgccg tcaccagcgt cacccagaaa aagttcctct  20640
gcgacagggt catgtggcgc atccccttct ccagcaactt catgtccatg ggcgcgctca  20700
ccgacctcgg ccagaacatg ctctatgcca actccgccca cgcgctagac atgaatttcg  20760
aagtcgaccc catggatgag tccacccttc tctatgttgt cttcgaagtc ttcgacgtcg  20820
tccgagtgca ccagccccac cgcggcgtca tcgaggccgt ctacctgcgc acccccttct  20880
cggccggtaa cgccaccacc taagctcttg cttcttgcaa gccatggccg cgggctccgg  20940
cgagcaggag ctcagggcca tcatccgcga cctgggctgc gggccctact tcctgggcac  21000
cttcgataag cgcttcccgg gattcatggc ccccgcacaag ctggcctgcg ccatcgtcaa  21060
cacggccggc cgcgagaccg gggcgagca ctggctggcc ttcgcctgga acccgcgctc  21120
gaacacctgc tacctcttcg acccettcgg gttctcggac gagcgcctca agcagatcta  21180
ccagttcgag tacgagggcc tgctgcgccg cagcgccctg gccaccgagg accgctgcgt  21240
caccctggaa aagtccaccc agaccgtgca gggtccgcgc tcggccgcct gcgggctctt  21300
ctgctgcatg ttcctgcacg ccttcgtgca ctggcccgac cgccccatgg acaagaaccc  21360
caccatgaac ttgctgacgg gggtgcccaa cggcatgctc cagtcgcccc aggtggaacc  21420
caccctgcgc cgcaaccagg aggcgctcta ccgcttcctc aactcccact ccgcctactt  21480
tcgctcccac cgcgcgcgca tcgagaaggc caccgccttc gaccgcatga atcaagacat  21540
gtaaaccgtg tgtgtatgtt aaatgtcttt aataaacagc actttcatgt tacacatgca  21600
tctgagatga tttatttaga aatcgaaagg gttctgccgg gtctcggcat ggcccgcggg  21660
cagggacacg ttgcggaact ggtacttggc cagccacttg aactcgggga tcagcagttt  21720
gggcagcggg gtgtcgggga aggagtcggt ccacagcttc cgcgtcagtt gcagggcgcc  21780
cagcaggtcg ggcgcggaga tcttgaaatc gcagttggga cccgcgttct gcgcgcggga  21840
gttgcggtac acggggttgc agcactggaa caccatcagg gccgggtgct tcacgctcgc  21900
cagcaccgtc gcgtcggtga tgctctccac gtcgaggtcc tcggcgttgg ccatcccgaa  21960
gggggtcatc ttgcaggtct gccttcccat ggtgggcacg cacccgggct tgtggttgca  22020
atcgcagtgc agggggatca gcatcatctg ggcctggtcg gcgttcatcc ccgggtacat  22080
ggccttcatg aaagcctcca attgcctgaa cgcctgctgg gccttggctc cctcggtgaa  22140
gaagaccccg caggacttgc tagagaactg gttggtggcg cacccggcgt cgtgcacgca  22200
gcagcgcgcg tcgttgttgg ccagctgcac cacgctgcgc ccccagcggt tctgggtgat  22260
cttggcccgg tcggggttct ccttcagcgc gcgctgcccg ttctcgctcg ccacatccat  22320
ctcgatcatg tgctccttct ggatcatggt ggtcccgtgc aggcaccgca gcttgccctc  22380
ggcctcggtg cacccgtgca gccacagcgc gcacccggtg cactcccagt tcttgtgggc  22440
```

```
gatctgggaa tgcgcgtgca cgaagccctg caggaagcgg cccatcatgg tggtcagggt  22500
cttgttgcta gtgaaggtca gcggaatgcc gcggtgctcc tcgttgatgt acaggtggca  22560
gatgcggcgg tacacctcgc cctgctcggg catcagctgg aagttggctt tcaggtcggt  22620
ctccacgcgg tagcggtcca tcagcatagt catgatttcc atacccttct cccaggccga  22680
gacgatgggc aggctcatag ggttcttcac catcatctta gcgctagcag ccgcggccag  22740
ggggtcgctc tcgtccaggg tctcaaagct ccgcttgccg tccttctcgg tgatccgcac  22800
cggggggtag ctgaagccca cggccgccag ctcctcctcg gcctgtcttt cgtcctcgct  22860
gtcctggctg acgtcctgca ggaccacatg cttggtcttg cggggtttct tcttgggcgg  22920
cagcggcggc ggagatgttg gagatggcga gggggagcgc gagttctcgc tcaccactac  22980
tatctcttcc tcttcttggt ccgaggccac gcggcggtag gtatgtctct tcgggggcag  23040
aggcggaggc gacgggctct cgccgccgcg acttggcgga tggctggcag agccccttcc  23100
gcgttcgggg gtgcgctccc ggcggcgctc tgactgactt cctccgcggc cggccattgt  23160
gttctcctag ggaggaacaa caagcatgga gactcagcca tcgccaacct cgccatctgc  23220
ccccaccgcc gacgagaagc agcagcagca gaatgaaagc ttaaccgccc cgccgcccag  23280
ccccgccacc tccgacgcgg ccgtcccaga catgcaagag atggaggaat ccatcgagat  23340
tgacctgggc tatgtgacgc ccgcggagca cgaggaggag ctggcagtgc gcttttcaca  23400
agaagagata caccaagaac agccagagca ggaagcagag aatgagcaga gtcaggctgg  23460
gctcgagcat gacggcgact acctccacct gagcgggggg gaggacgcgc tcatcaagca  23520
tctggcccgg caggccacca tcgtcaagga tgcgctgctc gaccgcaccg aggtgcccct  23580
cagcgtggag gagctcagcc gcgcctacga gttgaacctc ttctcgccgc gcgtgccccc  23640
caagcgccag cccaatggca cctgcgagcc caacccgcgc ctcaacttct acccggtctt  23700
cgcggtgccc gaggccctgg ccacctacca catctttttc aagaaccaaa agatccccgt  23760
ctcctgccgc gccaaccgca cccgcgccga cgcccttttc aacctgggtc ccggcgcccg  23820
cctacctgat atcgcctcct tggaagaggt tcccaagatc ttcgagggtc tgggcagcga  23880
cgagactcgg gccgcgaacg ctctgcaagg agaaggagga gagcatgagc accacagcgc  23940
cctggtcgag ttggaaggcg acaacgcgcg gctggcggtg ctcaaacgca cggtcgagct  24000
gacccatttc gcctacccgg ctctgaacct gccccccaaa gtcatgagcg cggtcatgga  24060
ccaggtgctc atcaagcgcg cgtcgcccat ctccgaggac gagggcatgc aagactccga  24120
ggagggcaag cccgtggtca gcgacgagca gctggcccgg tggctgggtc ctaatgctag  24180
tccccagagt ttggaagagc ggcgcaaact catgatggcc gtggtcctgg tgaccgtgga  24240
gctggagtgc ctgcgccgct tcttcgccga cgcggagacc ctgcgcaagg tcgaggagaa  24300
cctgcactac ctcttcaggc acgggttcgt gcgccaggcc tgcaagatct ccaacgtgga  24360
gctgaccaac ctggtctcct acatgggcat cttgcacgag aaccgcctgg ggcagaacgt  24420
gctgcacacc accctgcgcg gggaggcccg gcgcgactac atccgcgact gcgtctacct  24480
ctacctctgc cacacctggc agacgggcat gggcgtgtgg cagcagtgtc tggaggagca  24540
gaacctgaaa gagctctgca agctcctgca gaagaacctc aagggtctgt ggaccgggtt  24600
cgacgagcgc accaccgcct cggacctggc cgacctcatt ttccccgagc gcctcaggct  24660
gacgctgcgc aacggcctgc ccgactttat gagccaaagc atgttgcaaa actttcgctc  24720
tttcatcctc gaacgctccg gaatcctgcc cgccacctgc tccgcgctgc cctcggactt  24780
cgtgccgctg accttccgcg agtgcccccc gccgctgtgg agccactgct acctgctgcg  24840
cctggccaac tacctggcct accactcgga cgtgatcgag gacgtcagcg gcgagggcct  24900
gctcgagtgc cactgccgct gcaacctctg cacgccgcac cgctccctgg cctgcaaccc  24960
ccagctgctg agcgagaccc agatcatcgg caccttcgag ttgcaagggc ccagcgaagg  25020
cgagggttca gccgccaagg ggggtctgaa actcaccccg gggctgtgga cctcggccta  25080
cttgcgcaag ttcgtgcccg aggactacca tcccttcgag atcaggttct acgaggacca  25140
atcccatccg cccaaggccg agctgtcggc ctgcgtcatc acccaggggg cgatcctggc  25200
ccaattgcaa gccatccaga aatcccgcca agaattcttg ctgaaaaagg gccgcggggt  25260
ctacctcgac ccccagaccg gtgaggagct caaccccggc ttcccccagg atgccccgag  25320
gaaacaagaa gctgaaagtg gagctgccgc ccgtggagga tttggaggaa gactgggaga  25380
acagcagtca ggcagaggag gaggagatgg aggaagactg ggacagcact caggcagagg  25440
aggacagcct gcaagacagt ctggaggaag acgaggagga ggcagaggag gaggtggaag  25500
aagcagccgc cgccagaccg tcgtcctcgg cgggggagaa agcaagcagc acggatacca  25560
tctccgctcc gggtcggggt cccgctcgac cacacagtag atgggacgag accggacgat  25620
tcccgaaccc caccacccag accggtaaga aggagcggca gggatacaag tcctggcggg  25680
ggcacaaaaa cgccatcgtc tcctgcttgc aggcctgcgg gggcaacatc tccttcaccc  25740
ggcgctacct gctcttccac cgcggggtga actttccccg caacatcttg cattactacc  25800
gtcacctcca cagcccctac tacttccaag aagaggcagc agcagcagaa aaagaccagc  25860
agaaaaccag cagctagaaa atccacagcg gcggcagcag gtggactgag gatcgcggcg  25920
aacgagccgg cgcaaacccg ggagctgagg aaccggatct ttcccaccct ctatgccatc  25980
ttccagcaga gtcgggggca ggagcaggaa ctgaaagtca agaaccgttc tctgcgctcg  26040
ctcacccgca gttgtctgta tcacaagagc gaagaccaac ttcagcgcac tctcgaggac  26100
gccgaggctc tcttcaacaa gtactgcgcg ctcactctta aagagtagcc cgcgcccgcc  26160
cagtcgcaga aaaaggcggg aattacgtca cctgtgccct tcgccctagc cgcctccacc  26220
catcatcatg agcaaagaga ttcccacgcc ttacatgtgg agctaccagc cccagatggg  26280
cctggccgcc ggtgccgccc aggactactc cacccgcatg aattggctca gcgccgggcc  26340
cgcgatgatc tcacgggtga atgacatccg cgcccaccga aaccagatac tcctagaaca  26400
gtcagcgctc accgccacgc cccgcaatca cctcaatccg cgtaattggc ccgccgccct  26460
ggtgtaccag gaaattcccc agcccacgac cgtactactt ccgcgagacg cccaggccga  26520
agtccagctg actaactcag gtgtccagct ggcgggcggc gccaccctgt gtcgtcaccg  26580
ccccgctcag ggtataaagc ggctggtgat ccggggcaga ggcacacagc tcaacgacga  26640
ggtggtgagc tcttcgctgg gtctgcgacc tgacggagtc ttccaactcg ccggatcggg  26700
gagatcttcc ttcacgcctc gtcaggccgt cctgactttg gagagttcgt cctcgcagcc  26760
ccgctcgggt ggcatcggca ctctccagtt cgtggaggag ttcactccct cggtctactt  26820
caaccccttc tccggctccc ccggccacta cccggacgag ttcatcccga acttcgacgc  26880
catcagcgag tcggtggacg gctacgattg aaactaatca cccccttatc cagtgaaata  26940
aagatcatat tgatgatgat tttacagaaa taaaaaaataa tcatttgatt tgaaataaag  27000
atacaatcat attgatgatt tgagtttaac aaaaaaataa agaatcactt acttgaaatc  27060
tgataccagg tctctgtcca tgttttctgc caacaccact tcactcccct cttcccagct  27120
ctggtactgc aggccccggc gggctgcaaa cttcctccac acgctgaagg ggatgtcaaa  27180
```

-continued

```
ttcctcctgt ccctcaatct tcattttatc ttctatcaga tgtccaaaaa gcgcgtccgg  27240
gtggatgatg acttcgaccc cgtctacccc tacgatgcag acaacgcacc gaccgtgccc  27300
ttcatcaacc ccccttcgt ctcttcagat ggattccaag agaagcccct gggggtgttg  27360
tccctgcgac tggccgaccc cgtcaccacc aagaacgggg aaatcaccct caagctggga  27420
gagggggtgg acctcgattc ctcgggaaaa ctcatctcca acacggccac caaggccgcc  27480
gcccctctca gtttttccaa caacaccatt tcccttaaca tggatcaccc cttttacact  27540
aaagatggaa aattatcctt acaagtttct ccaccattaa atatactgag aacaagcatt  27600
ctaaacacac tagctttagg ttttggatca ggtttaggac tccgtggctc tgccttggca  27660
gtacagttag tctctccact tacatttgat actgatggaa acataaagct taccttagac  27720
agaggtttgc atgttacaac aggagatgca attgaaagca acataagctg ggctaaaggt  27780
ttaaaatttg aagatggagc catagcaacc aacattggaa atgggttaga gtttggaagc  27840
agtagtacag aaacaggtgt tgatgatgct tacccaatcc aagttaaact tggatctggc  27900
cttagctttg acagtacagg agccataatg gctggtaaca aagaagacga taaactcact  27960
ttgtggacaa cacctgatcc atcaccaaac tgtcaaatac tcgcagaaaa tgatgcaaaa  28020
ctaacacttt gcttgactaa atgtggtagt caaatactgg ccactgtgtc agtcttagtt  28080
gtaggaagtg gaaacctaaa ccccattact ggcaccgtaa gcagtgctca ggtgtttcta  28140
cgttttgatg caaacggtgt tcttttaaca gaacattcta cactaaaaaa atactggggg  28200
tataggcagg gagatagcat agatggcact ccatatacca atgctgtagg attcatgccc  28260
aatttaaaag cttatccaaa gtcacaaagt tctactacta aaaataatat agtagggcaa  28320
gtatacatga atggagatgt ttcaaaacct atgcttctca ctataaccct caatggtact  28380
gatgacagca acagtacata ttcaatgtca ttttcataca cctggactaa tggaagctat  28440
gttggagcaa catttggggc taactcttat accttctcat acatcgccca agaatgaaca  28500
ctgtatccca ccctgcatgc caacccttcc caccccactc tgtggaacaa actctgaaac  28560
acaaaataaa ataaagttca agtgttttat tgattcaaca gttttacagg attcgagcag  28620
ttatttttcc tccaccctcc caggacatgg aatacaccac cctctccccc cgcacagcct  28680
tgaacatctg aatgccattg gtgatggaca tgcttttggt ctccacgttc cacacagttt  28740
cagagcgagc cagtctcggg tcggtcaggg agatgaaacc ctccgggcac tcccgcatct  28800
gcacctcaca gctcaacagc tgaggattgt cctcggtggt cgggatcacg gttatctgga  28860
agaagcagaa gagcggcggt gggaatcata gtccgcgaac gggatcggcc ggtggtgtcg  28920
catcaggccc cgcagcagtc gctgccgccg ccgctccgtc aagctgctgc tcagggggtc  28980
cgggtccagg gactccctca gcatgatgcc cacggccctc agcatcagtc gtctggtgcg  29040
gcgggcgcag cagcgcatgc ggatctcgct caggtcgctg cagtacgtgc aacacagaac  29100
caccaggttg ttcaacagtc catagttcaa cacgctccag ccgaaactca tcgcgggaag  29160
gatgctaccc acgtggccgt cgtaccagat cctcaggtaa atcaagtggt gccccctcca  29220
gaacacgctg cccacgtaca tgatctcctt gggcatgtgg cggttcacca cctcccggta  29280
ccacatcacc ctctggttga acatgcagcc ccggatgatc ctgcggaacc acagggccag  29340
caccgccccg cccgccatgc agcgaagaga ccccgggtcc cggcaatggc aatggaggac  29400
ccaccgctcg tacccgtgga tcatctggga gctgaacaag tctatgttgg cacagcacag  29460
gcatatgctc atgcatctct tcagcactct caactcctcg gggtcaaaa ccatatccca  29520
gggcacgggg aactcttgca ggacagcgaa ccccgcagaa cagggcaatc ctcgcacaga  29580
acttacattg tgcatggaca gggtatcgca atcaggcagc accgggtgat cctccaccag  29640
agaagcgcgg gtctcggtct cctcacagcg tggtaagggg gccggccgat acgggtgatg  29700
gcgggacgcg gctgatcgtg ttcgcgaccg tgtcatgatg cagttgcttt cggacatttt  29760
cgtacttgct gtagcagaac ctggtccggg cgctgcacac cgatcgccgg cggcggtctc  29820
ggcgcttgga acgctcggtg ttgaaattgt aaaacagcca ctctctcaga ccgtgcagca  29880
gatctagggc ctcaggagtg atgaagatcc catcatgcct gatggctctg atcacatcga  29940
ccaccgtgga atgggccaga cccagccaga tgatgcaatt ttgttgggtt tcggtgacgg  30000
cgggggaggg aagaacagga agaaccatga ttaactttta atccaaacgg tctcggagta  30060
cttcaaaatg aagatcgcgg agatggcacc tctcgccccc gctgtgttgg tggaaaataa  30120
cagccaggtc aaaggtgata cggttctcga gatgttccac ggtggcttcc agcaaagcct  30180
ccacgcgcac atccagaaac aagacaatag cgaaagcggg agggttctct aattcctcaa  30240
tcatcatgtt acactcctgc accatcccca gataattttc atttttccag ccttgaatga  30300
ttcgaactag ttcctgaggt aaatccaagc cagccatgat aaagagctcg cgcagagcgc  30360
cctccaccgg cattcttaag cacaccctca taattccaag atattctgct cctggttcac  30420
ctgcagcaga ttgacaagcg gaatatcaaa atctctgccg cgatccctga gctcctccct  30480
cagcaataac tgtaagtact ctttcatatc ctctccgaaa tttttagcca taggaccacc  30540
aggaataaga ttagggcaag ccacagtaca gataaaccga agtcctcccc agtgagcatt  30600
gccaaatgca agactgctat aagcatgctg gctagacccg gtgatatctt ccagataact  30660
ggacagaaaa tcgcccaggc aatttttaag aaaatcaaca aaagaaaaat cctccaggtg  30720
gacgtttaga gcctcgggaa caacgatgaa gtaaatgcaa gcggtgcgtt ccagcatggt  30780
tagttagctg atctgtagaa aaaacaaaaa tgaacattaa accatgctag cctggcgaac  30840
aggtgggtaa atcgttctct ccagcaccag gcaggccacg gggtctccgg cgcgaccctc  30900
gtaaaaattg tcgctatgat tgaaaaccat cacagagaga cgttcccggt ggccggcgtg  30960
aatgattcga caagatgaat acacccccgg aacattggcg tccgcgagtg aaaaaaagcg  31020
cccgaggaag caataaggca ctacaatgct cagtctcaag tccagcaaag cgatgccatg  31080
cggatgaagc acaaaattct caggtgcgta caaaatgtaa ttactcccct cctgcacagg  31140
cagcaaagcc cccgatccct ccaggtacac atacaaagcc tcagcgtcca tagcttaccg  31200
agcagcagca cacaacaggc gcaagagtca gagaaaggct gagctctaac ctgtccaccc  31260
gctctctgct caatatatag cccagatcta cactgacgta aaggccaaag tctaaaaata  31320
cccgccaaat aatcacacac gcccagcaca cgcccagaaa ccggtgacac actcaaaaaa  31380
atacgcgcac ttcctcaaac gcccaaaact gccgtcattt ccgggttccc acgctacgtc  31440
atcaaaacac gactttcaaa ttccgtcgac cgttaaaaac gtcacccgcc ccgcccctaa  31500
cggtcgcccg tctctcagcc aatcagcgcc ccgcatcccc aaattcaaac acctcatttg  31560
catattaacg cgcacaaaaa gtttgagg                                    31588
```

```
SEQ ID NO: 3            moltype = DNA  length = 11447
FEATURE                 Location/Qualifiers
source                  1..11447
                        mol_type = other DNA
```

-continued

```
                    organism = Venezuelan equine encephalitis virus
```

SEQUENCE: 3

```
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct cgccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa catatggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaagccgatg  1620
tcgacttgat gttacaagag gctggggccg gctcagtgga gacacctcgt ggcttgataa  1680
aggttaccag ctacgctggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
```

-continued

```
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gatgttcccg ttccagccaa tgtatccgat gcagccaatg ccctatcgca acccgttcgc  7620
ggccccgcgc aggccctggt tccccagaac cgaccctttt ctggcgatgc aggtgcagga  7680
attaacccgc tcgatggcta acctgacgtt caagcaacgc cgggacgcgc cacctgaggg  7740
gccatccgct aagaaaccga agaaggaggc ctcgcaaaaa cagaaagggg gaggccaagg  7800
gaagaagaag aagaaccaag ggaagaagaa ggctaagaca gggccgccta atccgaaggc  7860
acagaatgga aacaagaaga agaccaacaa gaaaccaggc aagagacagc gcatggtcat  7920
gaaattggaa tctgacaaga cgttcccaat catgttggaa gggaagataa acggctacgc  7980
ttgtgtggtc ggagggaagt tattcaggcc gatgcatgtg gaaggcaaga tcgacaacga  8040
cgttctggcc gcgcttaaga cgaagaaagc atccaaatac gatcttgagt atgcagatgt  8100
gccacagaac atgcgggccg atacattcaa atacacccat gagaaacccc aaggctatta  8160
cagctggcat catggagcag tccaatatga aaatgggcgt ttcacggtgc cgaaaggagt  8220
tggggccaag ggagacagcg gacgacccat tctggataac cagggacggg tggtcgctat  8280
tgtgctggga ggtgtgaatg aaggatctag gacagccctt tcagtcgtca tgtggaacga  8340
gaagggagtt accgtgaagt atactccgga gaactgcgag caatggtcac tagtgaccac  8400
catgtgtctg ctcgccaatg tgacgttccc atgtgctcaa ccaccaattt gctacgacag  8460
aaaaccagca gagactttgg ccatgctcag cgttaacgtt gacaacccgg gctacgatga  8520
gctgctggaa gcagctgtta agtgccccgg aaggaaaagg agatccaccg aggagctgtt  8580
taaggagtat aagctaacgc gcccttacat ggccagatgc atcagatgtg cagttgggag  8640
ctgccatagt ccaatagcaa tcgaggcagt aaagagcgac gggcacgacg gttatgttag  8700
acttcagact tcctcgcagt atggcctgga ttcctccggc aacttaaagg gcaggaccat  8760
gcggtatgac atgcacggga ccattaaaga gataccacta catcaagtgt cactccatac  8820
atctcgcccg tgtcacattg tggatgggca cggttatttc ctgcttgcca ggtgcccggc  8880
aggggactcc atcaccatgg aatttaagaa agattccgtc acacactcct gctcggtgcc  8940
gtatgaagtg aaatttaatc ctgtaggcag agaactctat actcatcccc cagaacacgg  9000
agtagagcaa gcgtgccaag tctacgcaca tgatgcacag aacagaggag cttatgtcga  9060
gatgcacctc ccgggctcag aagtggacag cagtttggtt tccttgagcg gcagttcagt  9120
caccgtgaca cctcctgttg ggactagcgc cctggtggaa tgcgagtgtg gcggcacaaa  9180
gatctccgag accatcaaca agacaaaaca gttcagccag tgcacaaaga aggagcagtg  9240
cagagcatat cggctgcaga acgataagtg ggtgtataat tctgacaaac tgcccaaagc  9300
agcgggagcc accttaaaag gaaaactgca tgtcccattc ttgctggcag acggcaaatg  9360
```

-continued

```
caccgtgcct ctagcaccag aacctatgat aacctttggt ttcagatcag tgtcactgaa  9420
actgcaccct aagaatccca catatctaac cacccgccaa cttgctgatg agcctcacta  9480
cacgcacgag ctcatatctg aaccagctgt taggaatttt accgtcaccg aaaaagggtg  9540
ggagtttgta tggggaaacc acccgccgaa aaggttttgg gcacaggaaa cagcacccgg  9600
aaatccacat gggctaccgc acgaggtgat aactcattat taccacagat accctatgtc  9660
caccatcctg ggtttgtcaa tttgtgccgc cattgcaacc gtttccgttg cagcgtctac  9720
ctggctgttt tgcagatcta gagttgcgtg cctaactcct taccggctaa cacctaacgc  9780
taggatacca ttttgtctgg ctgtgctttg ctgcgcccgc actgcccggg ccgagaccac  9840
ctgggagtcc ttggatcacc tatggaacaa taaccaacag atgttctgga ttcaattgct  9900
gatccctctg gccgccttga tcgtagtgac tcgcctgctc aggtgcgtgt gctgtgtcgt  9960
gccttttta gtcatggccg gcgccgcagg cgccggcgcc tacgagcacg cgaccacgat  10020
gccgagccaa gcgggaatct cgtataacac tatagtcaac agagcaggct acgcaccact  10080
ccctatcagc ataacaccaa caaagatcaa gctgataccc acagtgaact tggagtacgt  10140
cacctgccac tacaaaacag gaatggattc accagccatc aaatgctgcg gatctcagga  10200
atgcactcca acttacaggc ctgatgaaca gtgcaaagtc ttcacagggg tttacccgtt  10260
catgtggggt ggtgcatatt gcttttgcga cactgagaac acccaagtca gcaaggccta  10320
cgtaatgaaa tctgacgact gccttgcgga tcatgctgaa gcatataaag cgcacacagc  10380
ctcagtgcag gcgttcctca acatcacagt gggagaacac tctattgtga ctaccgtgta  10440
tgtgaatgga gaaactcctg tgaatttcaa tggggtcaaa ttaactgcag gtccgctttc  10500
cacagcttgg acaccctttg atcgcaaaat cgtgcagtat gccgggggaga tctataatta  10560
tgattttcct gagtatgggg caggacaacc aggagcattt ggagatatac aatccagaac  10620
agtctcaagc tcagatctgt atgccaatac caacctagtg ctgcagagac ccaaagcagg  10680
agcgatccac gtgccataca ctcaggcacc ttcgggtttt gagcaatgga agaaagataa  10740
agctccatca ttgaaattta ccgccccttt cggatgcgaa atatatacaa accccattcg  10800
cgccgaaaac tgtgctgtag ggtcaattcc attagccttt gacattcccg acgccttgtt  10860
caccagggtg tcagaaacac cgacactttc agcggccgaa tgcactctta acgagtgcgt  10920
gtattcttcc gactttggtg ggatcgccac ggtcaagtac tcggccagca agtcaggcaa  10980
gtgcgcagtc catgtgccat cagggactgc taccctaaaa gaagcagcag tcgagctaac  11040
cgagcaaggg tcggcgacta tccatttctc gaccgcaaat atccacccgg agttcaggct  11100
ccaaatatgc acatcatatg ttacgtgcaa aggtgattgt cacccccccga aagaccatat  11160
tgtgacacac cctcagtatc acgcccaaac atttacagcc gcggtgtcaa aaaccgcgtg  11220
gacgtggtta acatccctgc tgggaggatc agccgtaatt attataattg gcttggtgct  11280
ggctactatt gtggccatgt acgtgctgac caaccagaaa cataattgaa tacagcagca  11340
attggcaagc tgcttacata gaactcgcgg cgattggcat gccgccttaa aattttttatt  11400
ttatttttc ttttcttttc cgaatcggat tttgttttta atatttc                11447
```

```
SEQ ID NO: 4            moltype = DNA  length = 9577
FEATURE                 Location/Qualifiers
misc_feature            1..9577
                        note = Description of Artificial Sequence: Synthetic
                         polynucleotide
source                  1..9577
                        mol_type = other DNA
                        organism = synthetic construct
SEQUENCE: 4
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct cgccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaagccgatg  1620
tcgacttgat gttacaagag gctggggccg gctcagtgga gacacctcgt ggcttgataa  1680
aggttaccag ctacgctggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
```

-continued

```
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccacccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
```

```
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gactctagaa tagtctttaa  7560
ttaagccacc atggcaggca tgtttcaggc gctgagcgaa ggctgcaccc cgtatgatat  7620
taaccagatg ctgaacgtgc tgggcgatca tcaggtctca ggccttgagc agcttgagag  7680
tataatcaac tttgaaaaac tgactgaatg gaccagttct aatgttatgc ctatcctgtc  7740
tcctctgaca aagggcatcc tgggcttcgt gtttaccctg accgtgcctt ctgagagagg  7800
acttagctgc attagcgaag cggatgcgac caccccggaa agcgcgaacc tgggcgaaga  7860
aattctgagc cagctgtatc tttggccaag ggtgacctac cattccccta gttatgctta  7920
ccaccaattt gaaagacgag ccaaatataa aagacacttc cccggctttg gccagagcct  7980
gctgtttggc taccctgtgt acgtgttcgg cgattgcgtg cagggcgatt gggatgcgat  8040
tcgctttcgc tattgcgcgc cgccgggcta tgcgctgctg cgctgcaacg ataccaacta  8100
tagcgctctg ctggctgtgg gggccctaga aggacccagg aatcaggact ggcttggtgt  8160
cccaagacaa cttgtaactc ggatgcaggc tattcagaat gccggcctgt gtaccctggt  8220
ggccatgctg gaagagacaa tcttctggct gcaagcgttt ctgatggcgc tgaccgatag  8280
cggcccgaaa accaacatta ttgtggatag ccagtatgtg atgggcatta gcaaaccgag  8340
ctttcaggaa tttgtggatt gggaaaacgt gagcccggaa ctgaacagca ccgatcagcc  8400
gttttggcaa gccggaatcc tggccagaaa tctggtgcct atggtggcca cagtgcaggg  8460
ccagaacctg aagtaccagg gtcagtcact agtcatctct gcttctatca ttgtcttcaa  8520
cctgctggaa ctggaaggtg attatcgaga tgatggcaac gtgtgggtgc ataccccgct  8580
gagcccgcgc accctgaacg cgtgggtgaa agcggtggaa gaaaaaaaag gtattccagt  8640
tcacctagag ctggccagta tgaccaacat ggagctcatg agcagtattg tgcatcagca  8700
ggtcagaaca tacggccccg tgttcatgtg tctcggcgga ctgcttacaa tggtggctgg  8760
tgctgtgtgg ctgacagtgc gagtgctcga gctgttccgg gccgcgcagc tggccaacga  8820
cgtggtcctc cagatcatgg agctttgtgg tgcagcgttt cgccaggtgt gccataccac  8880
cgtgccgtgg ccgaacgcga gcctgacccc gaaatggaac aacgaaacca cccagcccca  8940
gatcgccaac tgcagcgtgt atgacttttt tgtgtggctc cattattatt ctgttcgaga  9000
cacactttgg ccaagggtga cctaccatat gaacaaatat gcgtatcata tgctggaaag  9060
acgagccaaa tataaaagag gaccaggacc tggcgctaaa tttgtggccg cctggacact  9120
gaaagccgct gctggtcctg gacctggcca gtacatcaag gccaacagca agttcatcgg  9180
catcaccgaa ctcggacccg gaccaggctg atgattcgaa cggccgtatc acgcccaaac  9240
atttacagcc gcggtgtcaa aaaccgcgtg gacgtggtta acatccctgc tgggaggatc  9300
agccgtaatt attataattg gcttggtgct ggctactatt gtggccatgt acgtgctgac  9360
caaccagaaa cataattgaa tacagcagca attggcaagc tgcttacata gaactcgcgg  9420
cgattggcat gccgccttaa aatttttatt ttattttttc ttttcttttc cgaatcggat  9480
tttgttttta atatttcaaa aaaaaaaaaa aaaaaaaaaa aaaaaaaaaa aaaaaaaaaa  9540
aaaaaaaaaa aaaaaaaaaa aaaaaaaaaa aaaaaaa                           9577

SEQ ID NO: 5            moltype = DNA  length = 11447
FEATURE                 Location/Qualifiers
source                  1..11447
                        mol_type = other DNA
                        organism = Venezuelan equine encephalitis virus
SEQUENCE: 5
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct cgccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
```

-continued

```
acgtacaaga agctaagtgc gcagccgatg aggctaagga ggtgcgtgaa gccgaggagt  1560
tgcgcgcagc tctaccacct ttggcagctg atgttgagga gcccactctg gaagccgatg  1620
tcgacttgat gttacaagag gctggggccg gctcagtgga gacacctcgt ggcttgataa  1680
aggttaccag ctacgctggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccatagggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
```

-continued

```
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gacatagtct agtccgccaa  7560
gatgttcccg ttccagccaa tgtatccgat gcagccaatg ccctatcgca acccgttcgc  7620
ggccccgcgc aggccctggt tccccagaac cgaccctttt ctggcgatgc aggtgcagga  7680
attaacccgc tcgatggcta acctgacgtt caagcaacgc cgggacgcgc cacctgaggg  7740
gccatccgct aagaaaccga agaaggaggc ctcgcaaaaa cagaaagggg gaggccaagg  7800
gaagaagaag aagaaccaag ggaagaagaa ggctaagaca gggccgccta atccgaaggc  7860
acagaatgga aacaagaaga agaccaacaa gaaaccaggc aagagacagc gcatggtcat  7920
gaaattggaa tctgacaaga cgttcccaat catgttggaa gggaagataa acggctacgc  7980
ttgtgtggtc ggagggaagt tattcaggcc gatgcatgtg gaaggcaaga tcgacaacga  8040
cgttctggcc gcgcttaaga cgaagaaagc atccaaatac gatcttgagt atgcagatgt  8100
gccacagaac atgcgggccg atacattcaa atacacccat gagaaacccc aaggctatta  8160
cagctggcat catggagcag tccaatatga aaatgggcgt ttcacggtgc cgaaaggagt  8220
tggggccaag ggagacagcg gacgacccat tctggataac cagggacggg tggtcgctat  8280
tgtgctggga ggtgtgaatg aaggatctag gacagccctt tcagtcgtca tgtggaacga  8340
gaagggagtt accgtgaagt atactccgga gaactgcgag caatggtcac tagtgaccac  8400
catgtgtctg ctcgccaatg tgacgttccc atgtgctcaa ccaccaattt gctacgacag  8460
aaaaccagca gagactttgg ccatgctcag cgttaacgtt gacaacccgg gctacgatga  8520
gctgctggaa gcagctgtta agtgccccgg aaggaaaagg agatccaccg aggagctgtt  8580
taaggagtat aagctaacgc gcccttacat ggccagatgc atcagatgtg cagttgggag  8640
ctgccatagt ccaatagcaa tcgaggcagt aaagagcgac gggcacgacg gttatgttag  8700
acttcagact tcctcgcagt atggcctgga ttcctccggc aacttaaagg gcaggaccat  8760
gcggtatgac atgcacggga ccattaaaga gataccacta catcaagtgt cactccatac  8820
atctcgcccg tgtcacattg tggatgggca cggttatttc ctgcttgcca ggtgcccggc  8880
aggggactcc atcaccatgg aatttaagaa agattccgtc acacactcct gctcggtgcc  8940
gtatgaagtg aaatttaatc ctgtaggcag agaactctat actcatcccc cagaacacgg  9000
agtagagcaa gcgtgccaag tctacgcaca tgatgcacag aacagaggag cttatgtcga  9060
gatgcacctc ccgggctcag aagtggacag cagtttggtt tccttgagcg gcagttcagt  9120
caccgtgaca cctcctgttg ggactagcgc cctggtggaa tgcgagtgtg gcggcacaaa  9180
gatctccgag accatcaaca agacaaaaca gttcagccag tgcacaaaga aggagcagtg  9240
cagagcatat cggctgcaga acgataagtg ggtgtataat tctgacaaac tgcccaaagc  9300
agcgggagcc accttaaaag gaaaactgca tgtcccattc ttgctggcag acggcaaatg  9360
caccgtgcct ctagcaccag aacctatgat aacctttggt ttcagatcag tgtcactgaa  9420
actgcaccct aagaatccca catatctaac cacccgccaa cttgctgatg agcctcacta  9480
cacgcacgag ctcatatctg aaccagctgt taggaatttt accgtcaccg aaaaagggtg  9540
ggagtttgta tggggaaacc acccgccgaa aaggttttgg gcacaggaaa cagcacccgg  9600
aaatccacat gggctaccgc acgaggtgat aactcattat taccacagat accctatgtc  9660
caccatcctg ggtttgtcaa tttgtgccgc cattgcaacc gtttccgttg cagcgtctac  9720
ctggctgttt tgcagatcta gagttgcgtg cctaactcct taccggctaa cacctaacgc  9780
taggatacca ttttgtctgg ctgtgctttg ctgcgcccgc actgcccggg ccgagaccac  9840
ctgggagtcc ttggatcacc tatggaacaa taaccaacag atgttctgga ttcaattgct  9900
gatccctctg gccgccttga tcgtagtgac tcgcctgctc aggtgcgtgt gctgtgtcgt  9960
gccttttttta gtcatggccg gcgccgcagg cgccggcgcc tacgagcacg cgaccacgat  10020
gccgagccaa gcgggaatct cgtataacac tatagtcaac agagcaggct acgcaccact  10080
ccctatcagc ataacaccaa caaagatcaa gctgatacct acagtgaact tggagtacgt  10140
cacctgccac tacaaaacag gaatggattc accagccatc aaatgctgcg gatctcagga  10200
atgcactcca acttacaggc ctgatgaaca gtgcaaagtc ttcacagggg tttacccgtt  10260
catgtggggt ggtgcatatt gcttttgcga cactgagaac acccaagtca gcaaggccta  10320
cgtaatgaaa tctgacgact gccttgcgga tcatgctgaa gcatataaag cgcacacagc  10380
ctcagtgcag gcgttcctca acatcacagt gggagaacac tctattgtga ctaccgtgta  10440
tgtgaatgga gaaactcctg tgaatttcaa tggggtcaaa ttaactgcag gtccgctttc  10500
cacagcttgg acaccctttg atcgcaaaat cgtgcagtat gccggggaga tctataatta  10560
tgattttcct gagtatgggg caggacaacc aggagcattt ggagatatac aatccagaac  10620
agtctcaagc tcagatctgt atgccaatac caacctagtg ctgcagagac ccaaagcagg  10680
agcgatccac gtgccataca ctcaggcacc ttcgggtttt gagcaatgga agaaagataa  10740
agctccatca ttgaaattta ccgccccttt cggatgcgaa atatatacaa accccattcg  10800
cgccgaaaac tgtgctgtag ggtcaattcc attagccttt gacattcccg acgccttgtt  10860
caccagggtg tcagaaacac cgacactttc agcggccgaa tgcactctta acgagtgcgt  10920
gtattcttcc gactttggtg ggatcgccac ggtcaagtac tcggccagca agtcaggcaa  10980
```

```
gtgcgcagtc catgtgccat cagggactgc taccctaaaa gaagcagcag tcgagctaac  11040
cgagcaaggg tcggcgacta tccatttctc gaccgcaaat atccacccgg agttcaggct  11100
ccaaatatgc acatcatatg ttacgtgcaa aggtgattgt caccccccga aagaccatat  11160
tgtgacacac cctcagtatc acgcccaaac atttacagcc gcggtgtcaa aaaccgcgtg  11220
gacgtggtta acatccctgc tgggaggatc agccgtaatt attataattg gcttggtgct  11280
ggctactatt gtggccatgt acgtgctgac caaccagaaa cataattgaa tacagcagca  11340
attggcaagc tgcttacata gaactcgcgg cgattggcat gccgccttaa aatttttatt  11400
ttattttttc ttttcttttc cgaatcggat tttgttttta atatttc                11447

SEQ ID NO: 6            moltype = DNA  length = 7894
FEATURE                 Location/Qualifiers
misc_feature            1..7894
                        note = Description of Artificial Sequence: Synthetic
                         polynucleotide
source                  1..7894
                        mol_type = other DNA
                        organism = synthetic construct
SEQUENCE: 6
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct cgccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaagccgatg  1620
tcgacttgat gttacaagag gctggggccg gctcagtgga gacacctcgt ggcttgataa  1680
aggttaccag ctacgctggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccatagggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
```

-continued

```
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgagggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgcccacaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gactatcacg cccaaacatt  7560
tacagccgcg gtgtcaaaaa ccgcgtggac gtggttaaca tccctgctgg gaggatcagc  7620
cgtaattatt ataattggct tggtgctggc tactattgtg gccatgtacg tgctgaccaa  7680
ccagaaacat aattgaatac agcagcaatt ggcaagctgc ttacatagaa ctcgcggcga  7740
ttggcatgcc gccttaaaat ttttatttta tttttctttt tcttttccga atcggatttt  7800
gtttttaata tttcaaaaaa aaaaaaaaaa aaaaaaaaaa aaaaaaaaaa aaaaaaaaaa  7860
aaaaaaaaaa aaaaaaaaaa aaaaaaaaaa aaaa                              7894
```

```
SEQ ID NO: 7           moltype = DNA  length = 7893
FEATURE                Location/Qualifiers
misc_feature           1..7893
                       note = Description of Artificial Sequence: Synthetic
                        polynucleotide
source                 1..7893
                       mol_type = other DNA
```

organism = synthetic construct
SEQUENCE: 7
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatggag 1980
gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg tttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg actttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620

-continued

```
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gactatcacg cccaaacatt  7560
tacagccgcg gtgtcaaaaa ccgcgtggac gtggttaaca tccctgctgg gaggatcagc  7620
cgtaattatt ataattggct tggtgctggc tactattgtg gccatgtacg tgctgaccaa  7680
ccagaaacat aattgaatac agcagcaatt ggcaagctgc ttacatagaa ctcgcggcga  7740
ttggcatgcc gccttaaaat ttttatttta tttttctttt cttttccgaa tcggattttg  7800
tttttaatat ttcaaaaaaa aaaaaaaaaa aaaaaaaaaa aaaaaaaaaa aaaaaaaaaa  7860
aaaaaaaaaa aaaaaaaaaa aaaaaaaaaa aaa                                7893

SEQ ID NO: 8           moltype = DNA  length = 7927
FEATURE                Location/Qualifiers
misc_feature           1..7927
                       note = Description of Artificial Sequence: Synthetic
                        polynucleotide
source                 1..7927
                       mol_type = other DNA
                       organism = synthetic construct
SEQUENCE: 8
taatacgact cactatagga tggcggcgc atgagagaag cccagaccaa ttacctaccc  60
aaaatggaga aagttcacgt tgacatcgag gaagacagcc cattcctcag agctttgcag  120
cggagcttcc cgcagtttga ggtagaagcc aagcaggtca ctgataatga ccatgctaat  180
gccagagcgt tttcgcatct ggcttcaaaa ctgatcgaaa cggaggtgga cccatccgac  240
acgatccttg acattggaag tgcgcccgcc cgcagaatgt attctaagca caagtatcat  300
tgtatctgtc cgatgagatg tgcggaagat ccggacagat tgtataagta tgcaactaag  360
ctgaagaaaa actgtaagga aataactgat aaggaattgg acaagaaaat gaaggagctc  420
gccgccgtca tgagcgaccc tgacctggaa actgagacta tgtgcctcca cgacgacgag  480
tcgtgtcgct acgaagggca agtcgctgtt taccaggatg tatacgcggt tgacggaccg  540
acaagtctct atcaccaagc caataaggga gttagagtcg cctactggat aggctttgac  600
accacccctt ttatgtttaa gaacttggct ggagcatatc catcatactc taccaactgg  660
gccgacgaaa ccgtgttaac ggctcgtaac ataggcctat gcagctctga cgttatggag  720
cggtcacgta gagggatgtc cattcttaga aagaagtatt tgaaaccatc caacaatgtt  780
ctattctctg ttggctcgac catctaccac gagaagaggg acttactgag gagctggcac  840
```

-continued

```
ctgccgtctg tatttcactt acgtggcaag caaaattaca catgtcggtg tgagactata  900
gttagttgcg acgggtacgt cgttaaaaga atagctatca gtccaggcct gtatgggaag  960
ccttcaggct atgctgctac gatgcaccgc gagggattct tgtgctgcaa agtgacagac  1020
acattgaacg gggagagggt ctcttttccc gtgtgcacgt atgtgccagc tacattgtgt  1080
gaccaaatga ctggcatact ggcaacagat gtcagtgcgg acgacgcgca aaaactgctg  1140
gttgggctca accagcgtat agtcgtcaac ggtcgcaccc agagaaacac caataccatg  1200
aaaaattacc ttttgcccgt agtggcccag gcatttgcta ggtgggcaaa ggaatataag  1260
gaagatcaag aagatgaaag gccactagga ctacgagata gacagttagt catggggtgt  1320
tgttgggctt ttagaaggca caagataaca tctatttata agcgcccgga tacccaaacc  1380
atcatcaaag tgaacagcga tttccactca ttcgtgctgc ccaggatagg cagtaacaca  1440
ttggagatcg ggctgagaac aagaatcagg aaaatgttag aggagcacaa ggagccgtca  1500
cctctcatta ccgccgagga cgtacaagaa gctaagtgcg cagccgatga ggctaaggag  1560
gtgcgtgaag ccgaggagtt gcgcgcagct ctaccacctt tggcagctga tgttgaggag  1620
cccactctgg aagccgatgt cgacttgatg ttacaagagg ctggggccgg ctcagtggag  1680
acacctcgtg gcttgataaa ggttaccagc tacgctggcg aggacaagat cggctcttac  1740
gctgtgcttt ctccgcaggc tgtactcaag agtgaaaaat tatcttgcat ccaccctctc  1800
gctgaacaag tcatagtgat aacacactct ggccgaaaag ggcgttatgc cgtggaacca  1860
taccatggta aagtagtggt gccagaggga catgcaatac ccgtccagga ctttcaagct  1920
ctgagtgaaa gtgccaccat tgtgtacaac gaacgtgagt tcgtaaacag gtacctgcac  1980
catattgcca cacatggagg agcgctgaac actgatgaag aatattacaa aactgtcaag  2040
cccagcgagc acgacggcga atacctgtac gacatcgaca ggaaacagtg cgtcaagaaa  2100
gaactagtca ctgggctagg gctcacaggc gagctggtgg atcctccctt ccatgaattc  2160
gcctacgaga gtctgagaac acgaccagcc gctccttacc aagtaccaac catagggggtg  2220
tatggcgtgc caggatcagg caagtctggc atcattaaaa gcgcagtcac caaaaaagat  2280
ctagtggtga gcgccaagaa agaaaactgt gcagaaatta taagggacgt caagaaaatg  2340
aaagggctgg acgtcaatgc cagaactgtg gactcagtgc tcttgaatgg atgcaaacac  2400
cccgtagaga ccctgtatat tgacgaagct tttgcttgtc atgcaggtac tctcagagcg  2460
ctcatagcca ttataagacc taaaaaggca gtgctctgcg gggatcccaa acagtgcggt  2520
tttttaaca tgatgtgcct gaaagtgcat tttaaccacg agatttgcac acaagtcttc  2580
cacaaaagca tctctcgccg ttgcactaaa tctgtgactt cggtcgtctc aaccttgttt  2640
tacgacaaaa aaatgagaac gacgaatccg aaagagacta agattgtgat tgacactacc  2700
ggcagtacca aacctaagca ggacgatctc attctcactt gtttcagagg gtgggtgaag  2760
cagttgcaaa tagattacaa aggcaacgaa ataatgacgg cagctgcctc tcaagggctg  2820
acccgtaaag gtgtgtatgc cgttcggtac aaggtgaatg aaaatcctct gtacgcaccc  2880
acctcagaac atgtgaacgt cctactgacc cgcacggagg accgcatcgt gtggaaaaca  2940
ctagccggcg acccatggat aaaaacactg actgccaagt accctgggaa tttcactgcc  3000
acgatagagg agtggcaagc agagcatgat gccatcatga ggcacatctt ggagagaccg  3060
gaccctaccg acgtcttcca gaataaggca aacgtgtgtt gggccaaggc tttagtgccg  3120
gtgctgaaga ccgctggcat agacatgacc actgaacaat ggaacactgt ggattatttt  3180
gaaacggaca aagctcactc agcagagata gtattgaacc aactatgcgt gaggttcttt  3240
ggactcgatc tggactccgg tctattttct gcacccactg ttccgttatc cattaggaat  3300
aatcactggg ataactcccc gtcgcctaac atgtacgggc tgaataaaga agtggtccgt  3360
cagctctctc gcaggtaccc acaactgcct cgggcagttg ccactggaag agtctatgac  3420
atgaacactg gtacactgcg caattatgat ccgcgcataa acctagtacc tgtaaacaga  3480
agactgcctc atgctttagt cctccaccat aatgaacacc cacagagtga cttttcttca  3540
ttcgtcagca aattgaaggg cagaactgtc ctggtggtcg gggaaaagtt gtccgtccca  3600
ggcaaaatgg ttgactggtt gtcagaccgg cctgaggcta ccttcagagc tcggctggat  3660
ttaggcatcc caggtgatgt gcccaaatat gacataaatat ttgttaatgt gaggacccca  3720
tataaatacc atcactatca gcagtgtgaa gaccatgcca ttaagcttag catgttgacc  3780
aagaaagctt gtctgcatct gaatcccggc ggaacctgtg tcagcatagg ttatggttac  3840
gctgacaggg ccagcgaaag catcattggt gctatagcgc ggcagttcaa gttttcccgg  3900
gtatgcaaac cgaaatcctc acttgaagag acggaagttc tgtttgtatt cattgggtac  3960
gatcgcaagg cccgtacgca caatccttac aagctttcat caaccttgac caacatttat  4020
acaggttcca gactccacga agccggatgt gcaccctcat atcatgtggt gcgaggggat  4080
attgccacgg ccaccgaagg agtgattata aatgctgcta acagcaaagg acaacctggc  4140
ggaggggtgt gcggagcgct gtataagaaa ttcccggaaa gcttcgattt acagccgatc  4200
gaagtaggaa aagcgcgact ggtcaaaggt gcagctaaac atatcattca tgccgtagga  4260
ccaaacttca acaaagtttc ggaggttgaa ggtgacaaac agttggcaga ggcttatgag  4320
tccatcgcta agattgtcaa cgataacaat tacaagtcag tagcgattcc actgttgtcc  4380
accggcatct tttccgggaa caaagatcga ctaacccaat cattgaacca tttgctgaca  4440
gctttagaca ccactgatgc agatgtagcc atatactgca gggacaagaa atgggaaatg  4500
actctcaagg aagcagtggc taggagagaa gcagtggagg agatatgcat atccgacgac  4560
tcttcagtga cagaacctga tgcagagctg gtgagggtgc atccgaagag ttctttggct  4620
ggaaggaagg gctacagcac aagcgatggc aaaactttct catatttgga agggaccaag  4680
tttcaccagg cggccaagga tatagcagaa attaatgcca tgtggcccgt tgcaacggag  4740
gccaatgagc aggtatgcat gtatatcctc ggagaaagca tgagcagtat taggtcgaaa  4800
tgccccgtcg aagagtcgga agcctccaca ccacctagca cgctgccttg cttgtgcatc  4860
catgccatga ctccagaaag agtacagcgc ctaaaagcct cacgtccaga acaaattact  4920
gtgtgctcat cctttccatt gccgaagtat agaatcactg gtgtgcagaa gatccaatgc  4980
tcccagccta tattgttctc accgaaagtg cctgcgtata ttcatccaag gaagtatctc  5040
gtggaaacac caccggtaga cgagactccg gagccatcgg cagagaacca atccacagag  5100
gggacacctg aacaaccacc acttataacc gaggatgaga ccaggactag aacgcctgag  5160
ccgatcatca tcgaagagga agaagaggat agcataagtt tgctgtcaga tggcccgacc  5220
caccaggtgc tgcaagtcga ggcagacatt cacgggccgc cctctgtatc tagctcatcc  5280
tggtccattc ctcatgcatc cgactttgat gtggacagtt tatccatact tgacaccctg  5340
gagggagcta gcgtgaccag cggggcaacg tcagccgaga ctaactctta cttcgcaaag  5400
agtatggagt ttctggcgcg accggtgcct gcgcctcgaa cagtattcag gaaccctcca  5460
catcccgctc cgcgcacaag aacaccgtca cttgcaccca gcagggcctg ctcgagaacc  5520
agcctagttt ccaccccgcc aggcgtgaat agggtgatca ctagagagga gctcgaggcg  5580
```

-continued

```
cttaccccgt cacgcactcc tagcaggtcg gtctcgagaa ccagcctggt ctccaacccg  5640
ccaggcgtaa atagggtgat tacaagagag gagtttgagg cgttcgtagc acaacaacaa  5700
tgacggtttg atgcgggtgc atacatcttt tcctccgaca ccggtcaagg gcatttacaa  5760
caaaaatcag taaggcaaac ggtgctatcc gaagtggtgt tggagaggac cgaattggag  5820
atttcgtatg ccccgcgcct cgaccaagaa aaagaagaat tactacgcaa gaaattacag  5880
ttaaatccca cacctgctaa cagaagcaga taccagtcca ggaaggtgga gaacatgaaa  5940
gccataacag ctagacgtat tctgcaaggc ctagggcatt atttgaaggc agaaggaaaa  6000
gtggagtgct accgaaccct gcatcctgtt cctttgtatt catctagtgt gaaccgtgcc  6060
ttttcaagcc ccaaggtcgc agtggaagcc tgtaacgcca tgttgaaaga gaactttccg  6120
actgtggctt cttactgtat tattccagag tacgatgcct atttggacat ggttgacgga  6180
gcttcatgct gcttagacac tgccagtttt tgccctgcaa agctgcgcag ctttccaaag  6240
aaacactcct atttggaacc cacaatacga tcggcagtgc cttcagcgat ccagaacacg  6300
ctccagaacg tcctggcagc tgccacaaaa agaaattgca atgtcacgca aatgagagaa  6360
ttgcccgtat tggattcggc ggcctttaat gtggaatgct tcaagaaata tgcgtgtaat  6420
aatgaatatt gggaaacgtt taaagaaaac cccatcaggc ttactgaaga aaacgtggta  6480
aattacatta ccaaattaaa aggaccaaaa gctgctgctc tttttgcgaa gacacataat  6540
ttgaatatgt tgcaggacat accaatggac aggtttgtaa tggacttaaa gagagacgtg  6600
aaagtgactc caggaacaaa acatactgaa gaacggccca aggtacaggt gatccaggct  6660
gccgatccgc tagcaacagc gtatctgtgc ggaatccacc gagagctggt taggagatta  6720
aatgcggtcc tgcttccgaa cattcataca ctgtttgata tgtcggctga agactttgac  6780
gctattatag ccgagcactt ccagcctggg gattgtgttc tggaaactga catcgcgtcg  6840
tttgataaaa gtgaggacga cgccatggct ctgaccgcgt taatgattct ggaagactta  6900
ggtgtggacg cagagctgtt gacgctgatt gaggcggctt tcggcgaaat ttcatcaata  6960
catttgccca ctaaaactaa atttaaattc ggagccatga tgaaatctgg aatgttcctc  7020
acactgtttg tgaacacagt cattaacatt gtaatcgcaa gcagagtgtt gagagaacgg  7080
ctaaccggat caccatgtgc agcattcatt ggagatgaca atatcgtgaa aggagtcaaa  7140
tcggacaaat taatggcaga caggtgcgcc acctggttga atatggaagt caagattata  7200
gatgctgtgg tgggcgagaa agcgccttat ttctgtggag ggtttatttt gtgtgactcc  7260
gtgaccggca cagcgtgccg tgtggcagac cccctaaaaa ggctgtttaa gcttggcaaa  7320
cctctggcag cagacgatga acatgatgat gacaggagaa gggcattgca tgaagagtca  7380
acacgctgga accgagtggg tattctttca gagctgtgca aggcagtaga atcaaggtat  7440
gaaaccgtag gaacttccat catagttatg gccatgacta ctctagctag cagtgttaaa  7500
tcattcagct acctgagagg ggcccctata actctctacg gctaacctga atggactacg  7560
actatcacgc ccaaacattt acagccgcgg tgtcaaaaac cgcgtggacg tggttaacat  7620
ccctgctggg aggatcagcc gtaattatta taattggctt ggtgctggct actattgtgg  7680
ccatgtacgt gctgaccaac cagaaacata attgaataca gcagcaattg gcaagctgct  7740
tacatagaac tcgcggcgat tggcatgccg ccttaaaatt tttattttat tttttctttt  7800
cttttccgaa tcggattttg tttttaatat ttcaaaaaaa aaaaaaaaaa aaaaaaaaaa  7860
aaaaaaaaaa aaaaaaaaaa aaaaaaaaaa aaaaaaaaaa aaaaaaaaaa aaatacgtag  7920
tttaaac                                                            7927
```

```
SEQ ID NO: 9            moltype = DNA  length = 7926
FEATURE                 Location/Qualifiers
misc_feature            1..7926
                        note = Description of Artificial Sequence: Synthetic
                         polynucleotide
source                  1..7926
                        mol_type = other DNA
                        organism = synthetic construct
SEQUENCE: 9
taatacgact cactatagga taggcggcgc atgagagaag cccagaccaa ttacctaccc  60
aaaatggaga aagttcacgt tgacatcgag gaagacagcc cattcctcag agctttgcag  120
cggagcttcc cgcagtttga ggtagaagcc aagcaggtca ctgataatga ccatgctaat  180
gccagagcgt tttcgcatct ggcttcaaaa ctgatcgaaa cggaggtgga cccatccgac  240
acgatccttg acattggaag tgcgcccgcc cgcagaatgt attctaagca caagtatcat  300
tgtatctgtc cgatgagatg tgcggaagat ccggacagat tgtataagta tgcaactaag  360
ctgaagaaaa actgtaagga aataactgat aaggaattgg acaagaaaat gaaggagctc  420
gccgccgtca tgagcgaccc tgacctggaa actgagacta tgtgcctcca cgacgacgag  480
tcgtgtcgct acgaagggca agtcgctgtt taccaggatg tatacgcggt tgacggaccg  540
acaagtctct atcaccaagc caataaggga gttagagtcg cctactggat aggctttgac  600
accacccctt ttatgtttaa gaacttggct ggagcatatc catcatactc taccaactgg  660
gccgacgaaa ccgtgttaac ggctcgtaac ataggcctat gcagctctga cgttatggag  720
cggtcacgta gagggatgtc cattcttaga aagaagtatt tgaaaccatc caacaatgtt  780
ctattctctg ttggctcgac catctaccac gagaagaggg acttactgag gagctggcac  840
ctgccgtctg tatttcactt acgtggcaag caaaattaca catgtcggtg tgagactata  900
gttagttgcg acgggtacgt cgttaaaaga atagctatca gtccaggcct gtatgggaag  960
ccttcaggct atgctgctac gatgcaccgc gagggattct tgtgctgcaa agtgacagac  1020
acattgaacg gggagagggt ctcttttccc gtgtgcacgt atgtgccagc tacattgtgt  1080
gaccaaatga ctggcatact ggcaacagat gtcagtgcgg acgacgcgca aaaactgctg  1140
gttgggctca accagcgtat agtcgtcaac ggtcgcaccc agagaaacac caataccatg  1200
aaaaattacc ttttgcccgt agtggcccag gcatttgcta ggtgggcaaa ggaatataag  1260
gaagatcaag aagatgaaag gccactagga ctacgagata gacagttagt catggggtgt  1320
tgttgggctt ttagaaggca caagataaca tctatttata agcgcccgga tacccaaacc  1380
atcatcaaag tgaacagcga tttccactca ttcgtgctgc ccaggatagg cagtaacaca  1440
ttggagatcg ggctgagaac aagaatcagg aaaatgttag aggagcacaa ggagccgtca  1500
cctctcatta ccgccgagga cgtacaagaa gctaagtgcg cagccgatga ggctaaggag  1560
gtgcgtgaag ccgaggagtt gcgcgcagct ctaccacctt tggcagctga tgttgaggag  1620
cccactctgg aagccgatgt cgacttgatg ttacaagagg ctggggccgg ctcagtggag  1680
acacctcgtg gcttgataaa ggttaccagc tacgatggcg aggacaagat cggctcttac  1740
```

-continued

```
gctgtgcttt ctccgcaggc tgtactcaag agtgaaaaat tatcttgcat ccaccctctc  1800
gctgaacaag tcatagtgat aacacactct ggccgaaaag ggcgttatgc cgtggaacca  1860
taccatggta aagtagtggt gccagaggga catgcaatac ccgtccagga ctttcaagct  1920
ctgagtgaaa gtgccaccat tgtgtacaac gaacgtgagt tcgtaaacag gtacctgcac  1980
catattgcca cacatggagg agcgctgaac actgatgaag aatattacaa aactgtcaag  2040
cccagcgagc acgacggcga atacctgtac gacatcgaca ggaaacagtg cgtcaagaaa  2100
gaactagtca ctgggctagg gctcacaggc gagctggtgg atcctccctt ccatgaattc  2160
gcctacgaga gtctgagaac acgaccagcc gctccttacc aagtaccaac cataggggtg  2220
tatggcgtgc caggatcagg caagtctggc atcattaaaa gcgcagtcac caaaaaagat  2280
ctagtggtga gcgccaagaa agaaaactgt gcagaaatta taagggacgt caagaaaatg  2340
aaagggctgg acgtcaatgc cagaactgtg gactcagtgc tcttgaatgg atgcaaacac  2400
cccgtagaga ccctgtatat tgacgaagct tttgcttgtc atgcaggtac tctcagagcg  2460
ctcatagcca ttataagacc taaaaaggca gtgctctgcg gggatcccaa acagtgcggt  2520
tttttaaca tgatgtgcct gaaagtgcat tttaaccacg agatttgcac acaagtcttc  2580
cacaaaagca tctctcgccg ttgcactaaa tctgtgactt cggtcgtctc aaccttgttt  2640
tacgacaaaa aaatgagaac gacgaatccg aaagagacta agattgtgat tgacactacc  2700
ggcagtacca aacctaagca ggacgatctc attctcactt gtttcagagg gtgggtgaag  2760
cagttgcaaa tagattacaa aggcaacgaa ataatgacgg cagctgcctc tcaagggctg  2820
acccgtaaag gtgtgtatgc cgttcggtac aaggtgaatg aaaatcctct gtacgcaccc  2880
acctcagaac atgtgaacgt cctactgacc cgcacggagg accgcatcgt gtggaaaaca  2940
ctagccggcg acccatggat aaaaacactg actgccaagt accctgggaa tttcactgcc  3000
acgatagagg agtggcaagc agagcatgat gccatcatga ggcacatctt ggagagaccg  3060
gaccctaccg acgtcttcca gaataaggca aacgtgtgtt gggccaaggc tttagtgccg  3120
gtgctgaaga ccgctggcat agacatgacc actgaacaat ggaacactgt ggattatttt  3180
gaaacggaca aagctcactc agcagagata gtattgaacc aactatgcgt gaggttcttt  3240
ggactcgatc tggactccgg tctattttct gcacccactg ttccgttatc cattaggaat  3300
aatcactggg ataactcccc gtcgcctaac atgtacgggc tgaataaaga agtggtccgt  3360
cagctctctc gcaggtaccc acaactgcct cgggcagttg ccactggaag agtctatgac  3420
atgaacactg gtacactgcg caattatgat ccgcgcataa acctagtacc tgtaaacaga  3480
agactgcctc atgctttagt cctccaccat aatgaacacc cacagagtga cttttcttca  3540
ttcgtcagca aattgaaggg cagaactgtc ctggtggtcg gggaaaagtt gtccgtccca  3600
ggcaaaatgg ttgactggtt gtcagaccgg cctgaggcta ccttcagagc tcggctggat  3660
ttaggcatcc caggtgatgt gcccaaatat gacataatat ttgttaatgt gaggacccca  3720
tataaatacc atcactatca gcagtgtgaa gaccatgcca ttaagcttag catgttgacc  3780
aagaaagctt gtctgcatct gaatcccggc ggaacctgtg tcagcatagg ttatggttac  3840
gctgacaggg ccagcgaaag catcattggt gctatagcgc ggcagttcaa gttttcccgg  3900
gtatgcaaac cgaaatcctc acttgaagag acggaagttc tgtttgtatt cattgggtac  3960
gatcgcaagg cccgtacgca caatccttac aagctttcat caaccttgac caacatttat  4020
acaggttcca gactccacga agccggatgt gcaccctcat atcatgtggt gcgaggggat  4080
attgccacgg ccaccgaagg agtgattata aatgctgcta acagcaaagg acaacctggc  4140
ggaggggtgt gcggagcgct gtataagaaa ttcccggaaa gcttcgattt acagccgatc  4200
gaagtaggaa aagcgcgact ggtcaaaggt gcagctaaac atatcattca tgccgtagga  4260
ccaaacttca acaaagtttc ggaggttgaa ggtgacaaac agttggcaga ggcttatgag  4320
tccatcgcta agattgtcaa cgataacaat tacaagtcag tagcgattcc actgttgtcc  4380
accggcatct ttcccgggaa caaagatcga ctaacccaat cattgaacca tttgctgaca  4440
gctttagaca ccactgatgc agatgtagcc atatactgca gggacaagaa atgggaaatg  4500
actctcaagg aagcagtggc taggagagaa gcagtggagg agatatgcat atccgacgac  4560
tcttcagtga cagaacctga tgcagagctg gtgagggtgc atccgaagag ttctttggct  4620
ggaaggaagg gctacagcac aagcgatggc aaaactttct catatttgga agggaccaag  4680
tttcaccagg cggccaagga tatagcagaa attaatgcca tgtggcccgt tgcaacggag  4740
gccaatgagc aggtatgcat gtatatcctc ggagaaagca tgagcagtat taggtcgaaa  4800
tgccccgtcg aagagtcgga agcctccaca ccacctagca cgctgccttg cttgtgcatc  4860
catgccatga ctccagaaag agtacagcgc ctaaaagcct cacgtccaga acaaattact  4920
gtgtgctcat cctttccatt gccgaagtat agaatcactg gtgtgcagaa gatccaatgc  4980
tcccagccta tattgttctc accgaaagtg cctgcgtata ttcatccaag gaagtatctc  5040
gtggaaacac caccggtaga cgagactccg gagccatcgg cagagaacca atccacagag  5100
gggacacctg aacaaccacc acttataacc gaggatgaga ccaggactag aacgcctgag  5160
ccgatcatca tcgaagagga agaagaggat agcataagtt tgctgtcaga tggcccgacc  5220
caccaggtgc tgcaagtcga ggcagacatt cacgggccgc cctctgtatc tagctcatcc  5280
tggtccattc ctcatgcatc cgactttgat gtggacagtt tatccatact tgacaccctg  5340
gagggagcta gcgtgaccag cggggcaacg tcagccgaga ctaactctta cttcgcaaag  5400
agtatggagt ttctggcgcg accggtgcct gcgcctcgaa cagtattcag gaaccctcca  5460
catcccgctc cgcgcacaag aacaccgtca cttgcaccca gcagggcctg ctcgagaacc  5520
agcctagttt ccaccccgcc aggcgtgaat agggtgatca ctagagagga gctcgaggcg  5580
cttaccccgt cacgcactcc tagcaggtcg gtctcgagaa ccagcctggt ctccaacccg  5640
ccaggcgtaa atagggtgat tacaagagag gagtttgagg cgttcgtagc acaacaacaa  5700
tgacggtttg atgcgggtgc atacatcttt tcctccgaca ccggtcaagg gcatttacaa  5760
caaaaatcag taaggcaaac ggtgctatcc gaagtggtgt tggagaggac cgaattggag  5820
atttcgtatg ccccgcgcct cgaccaagaa aaagaagaat tactacgcaa gaaattacag  5880
ttaaatccca cacctgctaa cagaagcaga taccagtcca ggaaggtgga gaacatgaaa  5940
gccataacag ctagacgtat tctgcaaggc ctagggcatt atttgaaggc agaaggaaaa  6000
gtggagtgct accgaaccct gcatcctgtt cctttgtatt catctagtgt gaaccgtgcc  6060
ttttcaagcc ccaaggtcgc agtggaagcc tgtaacgcca tgttgaaaga gaactttccg  6120
actgtggctt cttactgtat tattccagag tacgatgcct atttggacat ggttgacgga  6180
gcttcatgct gcttagacac tgccagtttt tgccctgcaa agctgcgcag ctttccaaag  6240
aaacactcct atttggaacc cacaatacga tcggcagtgc cttcagcgat ccagaacacg  6300
ctccagaacg tcctggcagc tgccacaaaa agaaattgca atgtcacgca aatgagagaa  6360
ttgcccgtat tggattcggc ggcctttaat gtggaatgct tcaagaaata tgcgtgtaat  6420
aatgaatatt gggaaacgtt taaagaaaac cccatcaggc ttactgaaga aaacgtggta  6480
```

-continued

```
aattacatta ccaaattaaa aggaccaaaa gctgctgctc tttttgcgaa gacacataat  6540
ttgaatatgt tgcaggacat accaatggac aggtttgtaa tggacttaaa gagagacgtg  6600
aaagtgactc caggaacaaa acatactgaa gaacggccca aggtacaggt gatccaggct  6660
gccgatccgc tagcaacagc gtatctgtgc ggaatccacc gagagctggt taggagatta  6720
aatgcggtcc tgcttccgaa cattcataca ctgtttgata tgtcggctga agactttgac  6780
gctattatag ccgagcactt ccagcctggg gattgtgttc tggaaactga catcgcgtcg  6840
tttgataaaa gtgaggacga cgccatggct ctgaccgcgt taatgattct ggaagactta  6900
ggtgtggacg cagagctgtt gacgctgatt gaggcggctt tcggcgaaat ttcatcaata  6960
catttgccca ctaaaactaa atttaaattc ggagccatga tgaaatctgg aatgttcctc  7020
acactgtttg tgaacacagt cattaacatt gtaatcgcaa gcagagtgtt gagagaacgg  7080
ctaaccggat caccatgtgc agcattcatt ggagatgaca atatcgtgaa aggagtcaaa  7140
tcggacaaat taatggcaga caggtgcgcc acctggttga atatggaagt caagattata  7200
gatgctgtgg tgggcgagaa agcgccttat ttctgtggag ggtttatttt gtgtgactcc  7260
gtgaccggca cagcgtgccg tgtggcagac cccctaaaaa ggctgtttaa gcttggcaaa  7320
cctctggcag cagacgatga acatgatgat gacaggagaa gggcattgca tgaagagtca  7380
acacgctgga accgagtggg tattctttca gagctgtgca aggcagtaga atcaaggtat  7440
gaaaccgtag gaacttccat catagttatg gccatgacta ctctagctag cagtgttaaa  7500
tcattcagct acctgagagg ggcccctata actctctacg gctaacctga atggactacg  7560
actatcacgc ccaaacattt acagccgcgg tgtcaaaaac cgcgtggacg tggttaacat  7620
ccctgctggg aggatcagcc gtaattatta taattggctt ggtgctggct actattgtgg  7680
ccatgtacgt gctgaccaac cagaaacata attgaataca gcagcaattg gcaagctgct  7740
tacatagaac tcgcggcgat tggcatgccg ccttaaaatt tttattttat ttttcttttc  7800
ttttccgaat cggattttgt ttttaatatt tcaaaaaaaa aaaaaaaaaa aaaaaaaaaa  7860
aaaaaaaaaa aaaaaaaaaa aaaaaaaaaa aaaaaaaaaa aaaaaaaaaa aatacgtagt  7920
ttaaac                                                             7926

SEQ ID NO: 10          moltype = DNA  length = 36519
FEATURE                Location/Qualifiers
misc_feature           1..36519
                       note = Description of Artificial Sequence: Synthetic
                        polynucleotide
source                 1..36519
                       mol_type = other DNA
                       organism = synthetic construct
SEQUENCE: 10
ccatcttcaa taatatacct caaacttttt gtgcgcgtta atatgcaaat gaggcgtttg  60
aatttgggga ggaagggcgg tgattggtcg agggatgagc gaccgttagg ggcggggcga  120
gtgacgtttt gatgacgtgg ttgcgaggag gagccagttt gcaagttctc gtgggaaaag  180
tgacgtcaaa cgaggtgtgg tttgaacacg gaaatactca attttcccgc gctctctgac  240
aggaaatgag gtgtttctgg gcggatgcaa gtgaaaacgg gccattttcg cgcgaaaact  300
gaatgaggaa gtgaaaatct gagtaatttc gcgtttatgg cagggaggag tatttgccga  360
gggccgagta gactttgacc gattacgtgg gggtttcgat taccgtgttt ttcacctaaa  420
tttccgcgta cggtgtcaaa gtccggtgtt tttacgtagg tgtcagctga tcgccagggt  480
atttaaacct gcgctctcca gtcaagaggc cactcttgag tgccagcgag aagagttttc  540
tcctccgcgc cgcgagtcag atctacactt tgaaagatga ggcacctgag agacctgccc  600
gatgagaaaa tcatcatcgc ttccgggaac gagattctgg aactggtggt aaatgccatg  660
atgggcgacg accctccgga gcccccccacc ccatttgaga caccttcgct gcacgatttg  720
tatgatctgg aggtggatgt gcccgaggac gatcccaatg aggaggcggt aaatgatttt  780
tttagcgatg ccgcgctgct agctgccgag gaggcttcga gctctagctc agacagcgac  840
tcttcactgc ataccccctag acccggcaga ggtgagaaaa agatccccga gcttaaaggg  900
gaagagatgg acttgcgctg ctatgaggaa tgcttgcccc cgagcgatga tgaggacgag  960
caggcgatcc agaacgcagc gagccaggga gtgcaagccg ccagcgagag ctttgcgctg  1020
gactgcccgc ctctgcccgg acacggctgt aagtcttgtg aatttcatcg catgaatact  1080
ggagataaag ctgtgttgtg tgcactttgc tatatgagag cttacaacca ttgtgtttac  1140
agtaagtgtg attaagttga actttagagg gaggcagaga gcagggtgac tgggcgatga  1200
ctggtttatt tatgtatata tgttctttat ataggtcccg tctctgacgc agatgatgag  1260
acccccacta caaagtccac ttcgtcaccc ccagaaattg gcacatctcc acctgagaat  1320
attgttagac cagttcctgt tagagccact gggaggagag cagctgtgga atgtttggat  1380
gacttgctac agggtggggt tgaacctttg gacttgtgta cccggaaacg ccccaggcac  1440
taagtgccac acatgtgtgt ttacttgagg tgatgtcagt atttataggg tgtggagtgc  1500
aataaaaaat gtgttgactt taagtgcgtg gtttatgact caggggtggg gactgtgagt  1560
atataagcag gtgcagacct gtgtggttag ctcagagcgg catggagatt tggacggtct  1620
tggaagactt tcacaagact agacagctgc tagagaacgc ctcgaacgga gtctcttacc  1680
tgtggagatt ctgcttcggt ggcgacctag ctaggctagt ctacagggcc aaacaggatt  1740
atagtgaaca atttgaggtt attttgagag agtgttctgg tctttttgac gctcttaact  1800
tgggccatca gtctcacttt aaccagagga tttcgagagc ccttgatttt actactcctg  1860
gcagaaccac tgcagcagta gccttttttg cttttattct tgacaaatgg agtcaagaaa  1920
cccatttcag cagggattac cagctggatt tcttagcagt agctttgtgg agaacatgga  1980
agtgccagcg cctgaatgca atctccggct acttgccggt acagccgcta gacactctga  2040
ggatcctgaa tctccaggag agtcccaggg cacgccaacg tcgccagcag cagcagcagg  2100
aggaggatca agaagagaac ccgagagccg gcctggaccc tccggcggag gaggaggagt  2160
agctgacctg tttcctgaac tgcgccgggt gctgactagg tcttcgagtg gtcgggagag  2220
ggggattaag cgggagaggc atgatgagac taatcacaga actgaactga ctgtgggtct  2280
gatgagtcgc aagcgcccag aaacagtgtg gtggcatgag gtgcagtcga ctggcacaga  2340
tgaggtgtcg gtgatgcatg agaggttttc tctagaacaa gtcaagactt gttggttaga  2400
gcctgaggat gattgggagg tagccatcag gaattatgcc aagctggctc tgaggccaga  2460
caagaagtac aagattacta agctgataaa tatcagaaat gcctgctaca tctcagggaa  2520
tggggctgaa gtggagatct gtctccagga aagggtggct ttcagatgct gcatgatgaa  2580
tatgtacccg ggagtggtgg gcatggatgg ggttaccttt atgaacatga ggttcagggg  2640
```

-continued

```
agatgggtat aatggcacgg tctttatggc caataccaag ctgacagtcc atggctgctc 2700
cttctttggg tttaataaca cctgcatcga ggcctggggt caggtcggtg tgaggggctg 2760
cagtttttca gccaactgga tgggggtcgt gggcaggacc aagagtatgc tgtccgtgaa 2820
gaaatgcttg tttgagaggt gccacctggg ggtgatgagc gagggcgaag ccagaatccg 2880
ccactgcgcc tctaccgaga cggctgcttt tgtgctgtgc aagggcaatg ctaagatcaa 2940
gcataatatg atctgtggag cctcggacga gcgcggctac cagatgctga cctgcgccgg 3000
cgggaacagc catatgctgg ccaccgtaca tgtggcttcc catgctcgca agccctggcc 3060
cgagttcgag cacaatgtca tgaccaggtg caatatgcat ctggggtccc gccgaggcat 3120
gttcatgccc taccagtgca acctgaatta tgtgaaggtg ctgctggagc ccgatgccat 3180
gtccagagtg agcctgacgg gggtgtttga catgaatgtg gaggtgtgga agattctgag 3240
atatgatgaa tccaagacca ggtgccgagc ctgcgagtgc ggagggaagc atgccaggtt 3300
ccagcccgtg tgtgtggatg tgacggagga cctgcgaccc gatcatttgg tgttgccctg 3360
caccgggacg gagttcggtt ccagcgggga agaatctgac tagagtgagt agtgttctgg 3420
ggcgggggag gacctgcatg agggccagaa taactgaaat ctgtgctttt ctgtgtgttg 3480
cagcagcatg agcggaagcg gctcctttga gggaggggta ttcagccctt atctgacggg 3540
gcgtctcccc tcctgggcgg gagtgcgtca gaatgtgatg ggatccacgg tggacggccg 3600
gcccgtgcag cccgcgaact cttcaaccct gacctatgca accctgagct cttcgtcgtt 3660
ggacgcagct gccgccgcag ctgctgcatc tgccgccagc gccgtgcgcg gaatggccat 3720
gggcgccggc tactacggca ctctggtggc caactcgagt tccaccaata atcccgccag 3780
cctgaacgag gagaagctgt tgctgctgat ggcccagctc gaggccttga cccagcgcct 3840
gggcgagctg acccagcagg tggctcagct gcaggagcag acgcgggccg cggttgccac 3900
ggtgaaatcc aaataaaaaa tgaatcaata aataaacgga gacggttgtt gattttaaca 3960
cagagtctga atctttattt gatttttcgc gcgcggtagg ccctggacca ccggtctcga 4020
tcattgagca cccggtggat cttttccagg acccggtaga ggtgggcttg gatgttgagg 4080
tacatgggca tgagcccgtc ccgggggtgg aggtagctcc attgcagggc ctcgtgctcg 4140
ggggtggtgt tgtaaatcac ccagtcatag caggggcgca gggcatggtg ttgcacaata 4200
tctttgagga ggagactgat ggccacgggc agccctttgg tgtaggtgtt tacaaatctg 4260
ttgagctggg agggatgcat gcgggggag atgaggtgca tcttggcctg gatcttgaga 4320
ttggcgatgt taccgcccag atcccgcctg ggttcatgt tgtgcaggac caccagcacg 4380
gtgtatccgg tgcacttggg gaatttatca tgcaacttgg aagggaaggc gtgaaagaat 4440
ttggcgacgc ctttgtgccc gcccaggttt tccatgcact catccatgat gatggcgatg 4500
ggcccgtggg cggcggcctg ggcaaagacg tttcgggggt cggacacatc atagttgtgg 4560
tcctgggtga ggtcatcata ggccatttta atgaatttgg ggcggagggt gccggactgg 4620
gggacaaagg taccctcgat cccgggggcg tagttcccct cacagatctg catctcccag 4680
gctttgagct cggaggggg gatcatgtcc acctgcgggg cgataaagaa cacggtttcc 4740
ggggcggggg agatgagctg ggccgaaagc aagttccgga gcagctggga cttgccgcag 4800
ccggtggggc cgtagatgac cccgatgacc ggctgcaggt ggtagttgag ggagagacag 4860
ctgccgtcct cccggaggag gggggccacc tcgttcatca tctcgcgcac gtgcatgttc 4920
tcgcgcacca gttccgccag gaggcgctct ccccccaggg ataggagctc ctggagcgag 4980
gcgaagtttt tcagcggctt gagtccgtcg gccatgggca ttttggagag ggtttgttgc 5040
aagagttcca ggcggtccca gagctcggtg atgtgctcta cggcatctcg atccagcaga 5100
cctcctcgtt tcgcgggttg ggacggctgc gggagtaggg caccagacga tgggcgtcca 5160
gcgcagccag ggtccggtcc ttccagggtc gcagcgtccg cgtcagggtg gtctccgtca 5220
cggtgaaggg gtgcgcgccg ggctgggcgc ttgcgagggt gcgcttcagg ctcatccggc 5280
tggtcgaaaa ccgctcccga tcggcgccct gcgcgtcggc caggtagcaa ttgaccatga 5340
gttcgtagtt gagcgcctcg gccgcgtggc ctttggcgcg gagcttacct ttggaagtct 5400
gcccgcaggc gggacagagg agggacttga gggcgtagag cttgggggcg aggaagacgg 5460
actcgggggc gtaggcgtcc gcgccgcagt gggcgcagac ggtctcgcac tccacgagcc 5520
aggtgaggtc gggctggtcg gggtcaaaaa ccagtttccc gccgttcttt ttgatgcgtt 5580
tcttaccttt ggtctccatg agctcgtgtc cccgctgggt gacaaagagg ctgtccgtgt 5640
ccccgtagac cgactttatg ggccggtcct cgagcggtgt gccgcggtcc tcctcgtaga 5700
ggaaccccgc ccactccgag acgaaagccc gggtccaggc cagcacgaag gaggccacgt 5760
gggacgggta gcggtcgttg tccaccagcg ggtccacctt ttccagggta tgcaaacaca 5820
tgtccccctc gtccacatcc aggaaggtga ttggcttgta agtgtaggcc acgtgaccgg 5880
gggtcccggc cgggggggta taaaagggtg cgggtccctg ctcgtcctca ctgtcttccg 5940
gatcgctgtc caggagcgcc agctgttggg gtaggtattc cctctcgaag gcgggcatga 6000
cctcggcact caggttgtca gtttctagaa acgaggagga tttgatattg acggtgccgg 6060
cggagatgcc tttcaagagc ccctcgtcca tctggtcaga aaagacgatc tttttgttgt 6120
cgagcttggt ggcgaaggag ccgtagaggg cgttggagag gagcttggcg atggagcgca 6180
tggtctggtt tttttccttg tcggcgcgct ccttggcggc gatgttgagc tgcacgtact 6240
cgcgcgccac gcacttccat tcggggaaga cggtggtcag ctcgtcgggc acgattctga 6300
cctgccagcc ccgattatgc agggtgatga ggtccacact ggtggccacc tcgccgcgca 6360
ggggctcatt agtccagcag aggcgtccgc ccttgcgcga gcagaagggg ggcagggggt 6420
ccagcatgac ctcgtcgggg gggtcggcat cgatggtgaa gatgccgggc aggaggtcgg 6480
ggtcaaagta gctgatggaa gtggccagat cgtccagggc agcttgccat tcgcgcacgg 6540
ccagcgcgcg ctcgtaggga ctgaggggcg tgccccaggg catgggatgg gtaagcgcgg 6600
aggcgtacat gccgcagatg tcgtagacgt agaggggctc ctcgaggatg ccgatgtagg 6660
tggggtagca gcgccccccg cggatgctgg cgcgcacgta gtcatacagc tcgtgcgagg 6720
gggcgaggag ccccgggccc aggttggtgc gactgggctt ttcggcgcgg tagacgatct 6780
ggcggaaaat ggcatgcgag ttggaggaga tggtgggcct ttggaagatg ttgaagtggg 6840
cgtggggcag tccgaccgag tcgcggatga agtgggcgta ggagtcttgc agcttggcga 6900
cgagctcggc ggtgactagg acgtccagag cgcagtagtc gagggtctcc tggatgatgt 6960
catacttgag ctgtcccttt tgtttccaca gctcgcggtt gagaaggaac tcttcgcggt 7020
ccttccagta ctcttcgagg gggaacccgt cctgatctgc acggtaagag cctagcatgt 7080
agaactggtt gacggccttg taggcgcagc agcccttctc cacggggagg gcgtaggcct 7140
gggcggcctt gcgcagggag gtgtgcgtga gggcgaaagt gtccctgacc atgaccttga 7200
ggaactggtg cttgaagtcg atatcgtcgc agccccccctg ctcccagagc tggaagtccg 7260
tgcgcttctt gtaggcgggg ttgggcaaag cgaaagtaac atcgttgaag aggatcttgc 7320
ccgcgcgggg cataaagttg cgagtgatgc ggaaaggttg gggcacctcg gcccggttgt 7380
```

-continued

```
tgatgacctg ggcggcgagc acgatctcgt cgaagccgtt gatgttgtgg cccacgatgt  7440
agagttccac gaatcgcgga cggcccttga cgtggggcag tttcttgagc tcctcgtagg  7500
tgagctcgtc ggggtcgctg agcccgtgct gctcgagcgc ccagtcggcg agatgggggt  7560
tggcgcggag gaaggaagtc cagagatcca cggccagggc ggtttgcaga cggtcccggt  7620
actgacggaa ctgctgcccg acggccattt tttcgggggt gacgcagtag aaggtgcggg  7680
ggtccccgtg ccagcgatcc catttgagct ggagggcgag atcgagggcg agctcgacga  7740
gccggtcgtc cccggagagt ttcatgacca gcatgaaggg gacgagctgc ttgccgaagg  7800
accccatcca ggtgtaggtt tccacatcgt aggtgaggaa gagcctttcg gtgcgaggat  7860
gcgagccgat ggggaagaac tggatctcct gccaccaatt ggaggaatgg ctgttgatgt  7920
gatggaagta gaaatgccga cggcgcgccg aacactcgtg cttgtgttta tacaagcggc  7980
cacagtgctc gcaacgctgc acgggatgca cgtgctgcac gagctgtacc tgagttcctt  8040
tgacgaggaa tttcagtggg aagtggagtc gtggcgcctg catctcgtgc tgtactacgt  8100
cgtggtggtc ggcctggccc tcttctgcct cgatggtggt catgctgacg agcccgcgcg  8160
ggaggcaggt ccagacctcg gcgcgagcgg gtcggagagc gaggacgagg gcgcgcaggc  8220
cggagctgtc cagggtcctg agacgctgcg gagtcaggtc agtgggcagc ggcggcgcgc  8280
ggttgacttg caggagtttt tccagggcgc gcgggaggtc cagatggtac ttgatctcca  8340
ccgcgccatt ggtggcgacg tcgatggctt gcagggtccc gtgcccctgg ggtgtgacca  8400
ccgtcccccg tttcttcttg ggcggctggg gcgacggggg cggtgcctct tccatggtta  8460
gaagcggcgg cgaggacgcg cgccgggcgg caggggcggc tcggggcccg gaggcagggg  8520
cggcaggggc acgtcggcgc cgcgcgcggg taggttctgg tactgcgccc ggagaagact  8580
ggcgtgagcg acgacgcgac ggttgacgtc ctggatctga cgcctctggg tgaaggccac  8640
gggacccgtg agtttgaacc tgaaagagag ttcgacagaa tcaatctcgg tatcgttgac  8700
ggcggcctgc cgcaggatct cttgcacgtc gcccgagttg tcctggtagg cgatctcggt  8760
catgaactgc tcgatctcct cctcttgaag gtctccgcgg ccggcgcgct ccacggtggc  8820
cgcgaggtcg ttggagatgc ggcccatgag ctgcgagaag gcgttcatgc ccgcctcgtt  8880
ccagacgcgg ctgtagacca cgacgccctc gggatcgcgg gcgcgcatga ccacctgggc  8940
gaggttgagc tccacgtggc gcgtgaagac cgcgtagttg cagaggcgct ggtagaggta  9000
gttgagcgtg gtggcgatgt gctcggtgac gaagaaatac atgatccagc ggcggagcgg  9060
catctcgctg acgtcgccca gcgcctccaa acgttccatg gcctcgtaaa agtccacggc  9120
gaagttgaaa aactgggagt tgcgcgccga gacggtcaac tcctcctcca gaagacggat  9180
gagctcggcg atggtggcgc gcacctcgcg ctcgaaggcc cccgggagtt cctccacttc  9240
ctcttcttcc tcctccacta acatctcttc tacttcctcc tcaggcggca gtggtggcgg  9300
gggagggggc ctgcgtcgcc ggcggcgcac gggcagacgg tcgatgaagc gctcgatggt  9360
ctcgccgcgc cggcgtcgca tggtctcggt gacggcgcgc ccgtcctcgc ggggccgcag  9420
cgtgaagacg ccgccgcgca tctccaggtg gccggggggg tccccgttgg gcagggagag  9480
ggcgctgacg atgcatctta tcaattgccc cgtagggact ccgcgcaagg acctgagcgt  9540
ctcgagatcc acgggatctg aaaaccgctg aacgaaggct tcgagccagt cgcagtcgca  9600
aggtaggctg agcacggttt cttctggcgg gtcatgttgg ttgggagcgg ggcgggcgat  9660
gctgctggtg atgaagttga aataggcggt tctgagacgg cggatggtgg cgaggagcac  9720
caggtctttg ggcccggctt gctggatgcg cagacggtcg gccatgcccc aggcgtggtc  9780
ctgacacctg gccaggtcct tgtagtagtc ctgcatgagc cgctccacgg gcacctcctc  9840
ctcgcccgcg cggccgtgca tgcgcgtgag cccgaagccg cgctggggct ggacgagcgc  9900
caggtcggcg acgacgcgct cggcgaggat ggcttgctgg atctgggtga gggtggtctg  9960
gaagtcatca aagtcgacga agcggtggta ggctccggtg ttgatggtgt aggagcagtt  10020
ggccatgacg gaccagttga cggtctggtg gcccggacgc acgagctcgt ggtacttgag  10080
gcgcgagtag gcgcgcgtgt cgaagatgta gtcgttgcag gtgcgcacca ggtactggta  10140
gccgatgagg aagtgcggcg gcggctggcg gtagagcggc catcgctcgg tggcgggggc  10200
gccgggcgcg aggtcctcga gcatggtgcg gtggtagccg tagatgtacc tggacatcca  10260
ggtgatgccg gcggcggtgg tggaggcgcg cgggaactcg cggacgcggt tccagatgtt  10320
gcgcagcggc aggaagtagt tcatggtggg cacggtctgg cccgtgaggc gcgcgcagtc  10380
gtggatgctc tatacgggca aaaacgaaag cggtcagcgg ctcgactccg tggcctggag  10440
gctaagcgaa cgggttgggc tgcgcgtgta ccccggttcg aatctcgaat caggctggag  10500
ccgcagctaa cgtggtattg gcactcccgt ctcgacccaa gcctgcacca accctccagg  10560
atacggaggc gggtcgtttt gcaacttttt tttggaggcc ggatgagact agtaagcgcg  10620
gaaagcggcc gaccgcgatg gctcgctgcc gtagtctgga gaagaatcgc cagggttgcg  10680
ttgcggtgtg ccccggttcg aggccggccg gattccgcgg ctaacgaggg cgtggctgcc  10740
ccgtcgtttc caagacccca tagccagccg acttctccag ttacggagcg agcccctctt  10800
ttgttttgtt tgtttttgcc agatgcatcc cgtactgcgg cagatgcgcc cccaccaccc  10860
tccaccgcaa caacagcccc ctccacagcc ggcgcttctg cccccgcccc agcagcaact  10920
tccagccacg accgccgcgg ccgccgtgag cggggctgga cagagttatg atcaccagct  10980
ggccttggaa gagggcgagg ggctggcgcg cctgggggcg tcgtcgccgg agcggcaccc  11040
gcgcgtgcag atgaaaaggg acgctcgcga ggcctacgtg cccaagcaga acctgttcag  11100
agacaggagc ggcgaggagc ccgaggagat gcgcgcggcc cggttccacg cggggcggga  11160
gctgcggcgc ggcctggacc gaaagagggt gctgagggac gaggatttcg aggcggacga  11220
gctgacgggg atcagccccg cgcgcgcgca cgtggccgcg gccaacctgg tcacggcgta  11280
cgagcagacc gtgaaggagg agagcaactt ccaaaaatcc ttcaacaacc acgtgcgcac  11340
cctgatcgcg cgcgaggagg tgaccctggg cctgatgcac ctgtgggacc tgctggaggc  11400
catcgtgcag aaccccacca gcaagccgct gacggcgcag ctgttcctgg tggtgcagca  11460
tagtcgggac aacgaagcgt tcagggaggc gctgctgaat atcaccgagc ccgagggccg  11520
ctggctcctg gacctggtga acattctgca gagcatcgtg gtgcaggagc gcgggctgcc  11580
gctgtccgag aagctggcgg ccatcaactt ctcggtgctg agtttgggca agtactacgc  11640
taggaagatc tacaagaccc cgtacgtgcc catagacaag gaggtgaaga tcgacgggtt  11700
ttacatgcgc atgaccctga aagtgctgac cctgagcgac gatctggggg tgtaccgcaa  11760
cgacaggatg caccgtgcgg tgagcgccag caggcggcgc gagctgagcg accaggagct  11820
gatgcatagt ctgcagcggg ccctgaccgg ggccgggacc gagggggaga gctactttga  11880
catgggcgcg gacctgcact ggcagcccag ccgccgggcc ttggaggcgg cggcaggacc  11940
ctacgtagaa gaggtggacg atgaggtgga cgaggagggc gagtacctgg aagactgatg  12000
gcgcgaccgt atttttgcta gatgcaacaa caacagccac ctcctgatcc cgcgatgcgg  12060
gcggcgctgc agagccagcc gtccggcatt aactcctcgg acgattggac ccaggccatg  12120
```

-continued caacgcatca tggcgctgac gacccgcaac cccgaagcct ttagacagca gccccaggcc 12180
aaccggctct cggccatcct ggaggccgtg gtgccctcgc gctccaaccc cacgcacgag 12240
aaggtcctgg ccatcgtgaa cgcgctggtg gagaacaagg ccatccgcgg cgacgaggcc 12300
ggcctggtgt acaacgcgct gctggagcgc gtggcccgct acaacagcac caacgtgcag 12360
accaacctgg accgcatggt gaccgacgtg cgcgaggccg tggcccagcg cgagcggttc 12420
caccgcgagt ccaacctggg atccatggtg gcgctgaacg ccttcctcag cacccagccc 12480
gccaacgtgc cccggggcca ggaggactac accaacttca tcagcgccct gcgcctgatg 12540
gtgaccgagg tgccccagag cgaggtgtac cagtccgggc cggactactt cttccagacc 12600
agtcgccagg gcttgcagac cgtgaacctg agccaggctt tcaagaactt gcagggcctg 12660
tggggcgtgc aggccccggt cggggaccgc gcgacggtgt cgagcctgct gacgccgaac 12720
tcgcgcctgc tgctgctgct ggtggccccc ttcacggaca gcggcagcat caaccgcaac 12780
tcgtacctgg gctacctgat taacctgtac cgcgaggcca tcggccaggc gcacgtggac 12840
gagcagacct accaggagat cacccacgtg agccgcgccc tgggccagga cgacccgggc 12900
aacctggaag ccaccctgaa ctttttgctg accaaccggt cgcagaagat cccgccccag 12960
tacgcgctca gcaccgagga ggagcgcatc ctgcgttacg tgcagcagag cgtgggcctg 13020
ttcctgatgc aggagggggc cacccccagc gccgcgctcg acatgaccgc gcgcaacatg 13080
gagcccagca tgtacgccag caaccgcccg ttcatcaata aactgatgga ctacttgcat 13140
cgggcggccg ccatgaactc tgactatttc accaacgcca tcctgaatcc ccactggctc 13200
ccgccgccgg ggttctacac gggcgagtac gacatgcccg accccaatga cgggttcctg 13260
tgggacgatg tggacagcag cgtgttctcc ccccgaccgg gtgctaacga gcgcccettg 13320
tggaagaagg aaggcagcga ccgacgcccg tcctcggcgc tgtccggccg cgagggtgct 13380
gccgcggcgg tgcccgaggc cgccagtcct ttcccgagct tgcccttctc gctgaacagt 13440
atccgcagca gcgagctggg caggatcacg cgcccgcgct tgctgggcga agaggagtac 13500
ttgaatgact cgctgttgag acccgagcgg gagaagaact tccccaataa cgggatagaa 13560
agcctggtgg acaagatgag ccgctggaag acgtatgcgc aggagcacag ggacgatccc 13620
cgggcgtcgc agggggccac gagccggggc agcgccgccc gtaaacgccg gtggcacgac 13680
aggcagcggg gacagatgtg ggacgatgag gactccgccg acgacagcag cgtgttggac 13740
ttgggtggga gtggtaaccc gttcgctcac ctgcgccccc gtatcgggcg catgatgtaa 13800
gagaaaccga aaataaatga tactcaccaa ggccatggcg accagcgtgc gttcgtttct 13860
tctctgttgt tgttgtatct agtatgatga ggcgtgcgta cccggagggt cctcctccct 13920
cgtacgagag cgtgatgcag caggcgatgg cggcggcggc gatgcagccc ccgctggagg 13980
ctccttacgt gcccccgcgg tacctggcgc ctacggaggg gcggaacagc attcgttact 14040
cggagctggc acccttgtac gataccaccc ggttgtacct ggtggacaac aagtcggcgg 14100
acatcgcctc gctgaactac cagaacgacc acagcaactt cctgaccacc gtggtgcaga 14160
acaatgactt caccccacg gaggccagca cccagaccat caactttgac gagcgctcgc 14220
ggtggggcgg ccagctgaaa accatcatgc acaccaacat gcccaacgtg aacgagttca 14280
tgtacagcaa caagttcaag gcgcgggtga tggtctcccg caagaccccc aatggggtga 14340
cagtgacaga ggattatgat ggtagtcagg atgagctgaa gtatgaatgg gtggaatttg 14400
agctgcccga aggcaacttc tcggtgacca tgaccatcga cctgatgaac aacgccatca 14460
tcgacaatta cttggcggtg gggcggcaga acggggtgct ggagagcgac atcggcgtga 14520
agttcgacac taggaacttc aggctgggct gggaccccgt gaccgagctg gtcatgcccg 14580
gggtgtacac caacgaggct ttccatcccg atattgtctt gctgcccggc tgcggggtgg 14640
acttcaccga gagccgcctc agcaacctgc tgggcattcg caagaggcag cccttccagg 14700
aaggcttcca gatcatgtac gaggatctgg aggggggcaa catccccgcg ctcctggatg 14760
tcgacgccta tgagaaaagc aaggaggatg cagcagctga agcaactgca gccgtagcta 14820
ccgcctctac cgaggtcagg ggcgataatt ttgcaagcgc cgcagcagtg gcagcggccg 14880
aggcggctga aaccgaaagt aagatagtca ttcagccggt ggagaaggat agcaagaaca 14940
ggagctacaa cgtactaccg gacaagataa acaccgccta ccgcagctgg tacctagcct 15000
acaactatgg cgaccccgag aagggcgtgc gctcctggac gctgctcacc acctcggacg 15060
tcacctgcgg cgtggagcaa gtctactggt cgctgcccga catgatgcaa gacccggtca 15120
ccttccgctc cacgcgtcaa gttagcaact acccggtggt gggcgccgag ctcctgcccg 15180
tctactccaa gagcttcttc aacgagcagg ccgtctactc gcagcagctg cgcgccttca 15240
cctcgcttac gcacgtcttc aaccgcttcc ccgagaacca gatcctcgtc cgcccgcccg 15300
cgcccaccat taccaccgtc agtgaaaacg ttcctgctct cacagatcac gggaccctgc 15360
cgctgcgcag cagtatccgg ggagtccagc gcgtgaccgt tactgacgcc agacgccgca 15420
cctgccccta cgtctacaag gccctgggca tagtcgcgcc gcgcgtcctc tcgagccgca 15480
ccttctaaat gtccattctc atctcgccca gtaataacac cggttggggc ctgcgcgcgc 15540
ccagcaagat gtacggaggc gctcgccaac gctccacgca acaccccgtg cgcgtgcgcg 15600
ggcacttccg cgctccctgg ggcgccctca agggccgcgt gcggtcgcgc accaccgtcg 15660
acgacgtgat cgaccaggtg gtggccgacg cgcgcaacta cacccccgcc gccgcgcccg 15720
tctccaccgt ggacgccgtc atcgacagcg tggtggccga cgcgcgccgg tacgcccgcg 15780
ccaagagccg gcggcggcgc atcgcccggc ggcaccggag cacccccgcc atgcgcgcgg 15840
cgcgagcctt gctgcgcagg gccaggcgca cgggacgcag ggccatgctc agggcggcca 15900
gacgcgcggc ttcaggcgcc agcgccggca ggacccggag acgcgcggcc acggcggcgg 15960
cagcggccat cgccagcatg tcccgcccgc ggcgagggaa cgtgtactgg gtgcgcgacg 16020
ccgccaccgg tgtgcgcgtg cccgtgcgca cccgcccccc tcgcacttga agatgttcac 16080
ttcgcgatgt tgatgtgtcc cagcggcgag gaggatgtcc aagcgcaaat tcaaggaaga 16140
gatgctccag gtcatcgcgc ctgagatcta cggccctgcg gtggtgaagg aggaaagaaa 16200
gccccgcaaa atcaagcggg tcaaaaagga caaaaaggaa gaagaaagtg atgtggacgg 16260
attggtggag tttgtgcgcg agttcgcccc ccggcggcgc gtgcagtggc gcgggcggaa 16320
ggtgcaaccg gtgctgagac ccggcaccac cgtggtcttc acgcccggcg agcgctccgg 16380
caccgcttcc aagcgctcct acgacgaggt gtacggggat gatgatattc tggagcaggc 16440
ggccgagcgc ctgggcgagt ttgcttacgg caagcgcagc cgttccgcac cgaaggaaga 16500
ggcggtgtcc atcccgctgg accacggcaa ccccacgccg agcctcaagc ccgtgacctt 16560
gcagcaggtg ctgccgaccg cggcgccgcg ccgggggttc aagcgcgagg gcgaggatct 16620
gtaccccacc atgcagctga tggtgcccaa gcgccagaag ctggaagacg tgctggagac 16680
catgaaggtg gacccggacg tgcagcccga ggtcaaggtg cggcccatca agcaggtggc 16740
cccgggcctg ggcgtgcaga ccgtggacat caagattccc acggagccca tggaaacgca 16800
gaccgagccc atgatcaagc ccagcaccag caccatggag gtgcagacgg atccctggat 16860

-continued

```
gccatcggct cctagtcgaa gaccccggcg caagtacggc gcggccagcc tgctgatgcc  16920
caactacgcg ctgcatcctt ccatcatccc cacgccgggc taccgcggca cgcgcttcta  16980
ccgcggtcat accagcagcc gccgccgcaa gaccaccact cgccgccgcc gtcgccgcac  17040
cgccgctgca accacccctg ccgccctggt gcggagagtg taccgccgcg gccgcgcacc  17100
tctgaccctg ccgcgcgcgc gctaccaccc gagcatcgcc atttaaactt tcgcctgctt  17160
tgcagatcaa tggccctcac atgccgcctt cgcgttccca ttacgggcta ccgaggaaga  17220
aaaccgcgcc gtagaaggct ggcggggaac gggatgcgtc gccaccacca ccggcggcgg  17280
cgcgccatca gcaagcggtt gggggaggc ttcctgcccg cgctgatccc catcatcgcc  17340
gcggcgatcg gggcgatccc cggcattgct tccgtggcgg tgcaggcctc tcagcgccac  17400
tgagacacac ttggaaacat cttgtaataa accaatggac tctgacgctc ctggtcctgt  17460
gatgtgtttt cgtagacaga tggaagacat caatttttcg tccctggctc cgcgacacgg  17520
cacgcggccg ttcatgggca cctggagcga catcggcacc agccaactga acgggggcgc  17580
cttcaattgg agcagtctct ggagcgggct taagaatttc gggtccacgc ttaaaaccta  17640
tggcagcaag gcgtggaaca gcaccacagg gcaggcgctg agggataagc tgaaagagca  17700
gaacttccag cagaaggtgg tcgatgggct cgcctcgggc atcaacgggg tggtggacct  17760
ggccaaccag gccgtgcagc ggcagatcaa cagccgcctg gacccggtgc cgcccgccgg  17820
ctccgtggag atgccgcagg tggaggagga gctgcctccc ctggacaagc ggggcgagaa  17880
gcgaccccgc cccgatgcgg aggagacgct gctgacgcac acggacgagc cgcccccgta  17940
cgaggaggcg gtgaaactgg gtctgcccac cacgcggccc atcgcgcccc tggccaccgg  18000
ggtgctgaaa cccgaaaagc ccgcgaccct ggacttgcct cctccccagc cttcccgccc  18060
ctctacagtg gctaagcccc tgccgccggt ggccgtggcc cgcgcgcgac ccgggggcac  18120
cgcccgccct catgcgaact ggcagagcac tctgaacagc atcgtgggtc tgggagtgca  18180
gagtgtgaag cgccgccgct gctattaaac ctaccgtagc gcttaacttg cttgtctgtg  18240
tgtgtatgta ttatgtcgcc gccgccgctg tccaccagaa ggaggagtga agaggcgcgt  18300
cgccgagttg caagatggcc accccatcga tgctgcccca gtgggcgtac atgcacatcg  18360
ccggacagga cgcttcggag tacctgagtc cgggtctggt gcagtttgcc cgcgccacag  18420
acacctactt cagtctgggg aacaagttta ggaaccccac ggtggcgccc acgcacgatg  18480
tgaccaccga ccgcagccag cggctgacgc tgcgcttcgt gcccgtggac cgcgaggaca  18540
acacctactc gtacaaagtg cgctacacgc tggccgtggg cgacaaccgc gtgctggaca  18600
tggccagcac ctactttgac atccgcggcg tgctggatcg gggccctagc ttcaaaccct  18660
actccggcac cgcctacaac agtctggccc ccaagggagc acccaacact tgtcagtgga  18720
catataaagc cgatggtgaa actgccacag aaaaaaccta tacatatgga aatgcacccg  18780
tgcagggcat taacatcaca aaagatggta ttcaacttgg aactgacacc gatgatcagc  18840
caatctacgc agataaaacc tatcagcctg aacctcaagt gggtgatgct gaatggcatg  18900
acatcactgg tactgatgaa aagtatggag gcagagctct taagcctgat accaaaatga  18960
agccttgtta tggttctttt gccaagccta ctaataaaga aggaggtcag gcaaatgtga  19020
aaacaggaac aggcactact aaagaatatg acatagacat ggctttcttt gacaacagaa  19080
gtgcggctgc tgctggccta gctccagaaa ttgttttgta tactgaaaat gtggatttgg  19140
aaactccaga tacccatatt gtatacaaag caggcacaga tgacagcagc tcttctatta  19200
atttgggtca gcaagccatg cccaacagac ctaactacat tggtttcaga gacaacttta  19260
tcgggctcat gtactacaac agcactggca atatgggggt gctggccggt caggcttctc  19320
agctgaatgc tgtggttgac ttgcaagaca gaaacaccga gctgtcctac cagctcttgc  19380
ttgactctct gggtgacaga acccggtatt tcagtatgtg gaatcaggcg gtggacagct  19440
atgatcctga tgtgcgcatt attgaaaatc atggtgtgga ggatgaactt cccaactatt  19500
gtttccctct ggatgctgtt ggcagaacag atacttatca gggaattaag gctaatggaa  19560
ctgatcaaac cacatggacc aaagatgaca gtgtcaatga tgctaatgag ataggcaagg  19620
gtaatccatt cgccatggaa atcaacatcc aagccaacct gtggaggaac ttcctctacg  19680
ccaacgtggc cctgtacctg cccgactctt acaagtacac gccggccaat gttaccctgc  19740
ccaccaacac caacacctac gattacatga acggccgggt ggtggcgccc tcgctggtgg  19800
actcctacat caacatcggg gcgcgctggt cgctggatcc catggacaac gtgaacccct  19860
tcaaccacca ccgcaatgcg gggctgcgct accgctccat gctcctgggc aacgggcgct  19920
acgtgccctt ccacatccag gtgccccaga aatttttcgc catcaagagc ctcctgctcc  19980
tgcccgggtc ctacacctac gagtggaact tccgcaagga cgtcaacatg atcctgcaga  20040
gctccctcgg caacgacctg cgcacggacg gggcctccat ctccttcacc agcatcaacc  20100
tctacgccac cttcttcccc atggcgcaca acacggcctc cacgctcgag gccatgctgc  20160
gcaacgacac caacgaccag tccttcaacg actacctctc ggcggccaac atgctctacc  20220
ccatcccggc caacgccacc aacgtgccca tctccatccc ctcgcgcaac tgggccgcct  20280
tccgcggctg gtccttcacg cgtctcaaga ccaaggagac gccctcgctg ggctccgggt  20340
tcgaccccta cttcgtctac tcgggctcca tcccctacct cgacggcacc ttctacctca  20400
accacacctt caagaaggtc tccatcacct tcgactcctc cgtcagctgg cccggcaacg  20460
accggctcct gacgcccaac gagttcgaaa tcaagcgcac cgtcgacggc gagggctaca  20520
acgtggccca gtgcaacatg accaaggact ggttcctggt ccagatgctg gcccactaca  20580
acatcggcta ccagggcttc tacgtgcccg agggctacaa ggaccgcatg tactccttct  20640
tccgcaactt ccagcccatg agccgccagg tggtggacga ggtcaactac aaggactacc  20700
aggccgtcac cctggcctac cagcacaaca actcgggctt cgtcggctac ctcgcgccca  20760
ccatgcgcca gggccagccc taccccgcca actaccccta cccgctcatc ggcaagagcg  20820
ccgtcaccag cgtcacccag aaaaagttcc tctgcgacag ggtcatgtgg cgcatcccct  20880
tctccagcaa cttcatgtcc atgggcgcgc tcaccgacct cggccagaac atgctctatg  20940
ccaactccgc ccacgcgcta gacatgaatt tcgaagtcga ccccatggat gagtccaccc  21000
ttctctatgt tgtcttcgaa gtcttcgacg tcgtccgagt gcaccagccc caccgcggcg  21060
tcatcgaggc cgtctacctg cgcacccct tctcggccgg taacgccacc acctaagctc  21120
ttgcttcttg caagccatgg ccgcgggctc cggcgagcag gagctcaggg ccatcatccg  21180
cgacctgggc tgcgggccct acttcctggg caccttcgat aagcgcttcc cgggattcat  21240
ggccccgcac aagctggcct gcgccatcgt caacacggcc ggccgcgaga ccgggggcga  21300
gcactggctg gccttcgcct ggaacccgcg ctcgaacacc tgctacctct tcgacccctt  21360
cgggttctcg gacgagcgcc tcaagcagat ctaccagttc gagtacgagg gcctgctgcg  21420
ccgcagcgcc ctggccaccg aggaccgctg cgtcaccctg gaaaagtcca cccagaccgt  21480
gcagggtccg cgctcggccg cctgcgggct cttctgctgc atgttcctgc acgccttcgt  21540
gcactggccc gaccgcccca tggacaagaa ccccaccatg aacttgctga cgggggtgcc  21600
```

-continued

```
caacggcatg ctccagtcgc cccaggtgga acccaccctg cgccgcaacc aggaggcgct  21660
ctaccgcttc ctcaactccc actccgccta ctttcgctcc caccgcgcgc gcatcgagaa  21720
ggccaccgcc ttcgaccgca tgaatcaaga catgtaaacc gtgtgtgtat gttaaatgtc  21780
tttaataaac agcactttca tgttacacat gcatctgaga tgatttattt agaaatcgaa  21840
agggttctgc cgggtctcgg catggcccgc gggcagggac acgttgcgga actggtactt  21900
ggccagccac ttgaactcgg ggatcagcag tttgggcagc ggggtgtcgg ggaaggagtc  21960
ggtccacagc ttccgcgtca gttgcagggc gcccagcagg tcgggcgcgg agatcttgaa  22020
atcgcagttg ggacccgcgt tctgcgcgcg ggagttgcgg tacacggggt tgcagcactg  22080
gaacaccatc agggccgggt gcttcacgct cgccagcacc gtcgcgtcgg tgatgctctc  22140
cacgtcgagg tcctcggcgt tggccatccc gaagggggtc atcttgcagg tctgccttcc  22200
catggtgggc acgcacccgg gcttgtggtt gcaatcgcag tgcaggggga tcagcatcat  22260
ctgggcctgg tcggcgttca tccccgggta catggccttc atgaaagcct ccaattgcct  22320
gaacgcctgc tgggccttgg ctccctcggt gaagaagacc ccgcaggact tgctagagaa  22380
ctggttggtg gcgcacccgg cgtcgtgcac gcagcagcgc gcgtcgttgt tggccagctg  22440
caccacgctg cgcccccagc ggttctgggt gatcttggcc cggtcggggt tctccttcag  22500
cgcgcgctgc ccgttctcgc tcgccacatc catctcgatc atgtgctcct tctggatcat  22560
ggtggtcccg tgcaggcacc gcagcttgcc ctcggcctcg gtgcacccgt gcagccacag  22620
cgcgcacccg gtgcactccc agttcttgtg ggcgatctgg gaatgcgcgt gcacgaagcc  22680
ctgcaggaag cggcccatca tggtggtcag ggtcttgttg ctagtgaagg tcagcggaat  22740
gccgcggtgc tcctcgttga tgtacaggtg gcagatgcgg cggtacacct cgccctgctc  22800
gggcatcagc tggaagttgg ctttcaggtc ggtctccacg cggtagcggt ccatcagcat  22860
agtcatgatt tccataccct tctcccaggc cgagacgatg ggcaggctca tagggttctt  22920
caccatcatc ttagcgctag cagccgcggc caggggggtcg ctctcgtcca gggtctcaaa  22980
gctccgcttg ccgtccttct cggtgatccg caccgggggg tagctgaagc ccacggccgc  23040
cagctcctcc tcggcctgtc tttcgtcctc gctgtcctgg ctgacgtcct gcaggaccac  23100
atgcttggtc ttgcggggtt tcttcttggg cggcagcggc ggcggagatg ttggagatgg  23160
cgagggggag cgcgagttct cgctcaccac tactatctct tcctcttctt ggtccgaggc  23220
cacgcggcgg taggtatgtc tcttcggggg cagaggcgga ggcgacgggc tctcgccgcc  23280
gcgacttggc ggatggctgg cagagcccct tccgcgttcg ggggtgcgct cccggcggcg  23340
ctctgactga cttcctccgc ggccggccat tgtgttctcc tagggaggaa caacaagcat  23400
ggagactcag ccatcgccaa cctcgccatc tgcccccacc gccgacgaga agcagcagca  23460
gcagaatgaa agcttaaccg ccccgccgcc cagccccgcc acctccgacg cggccgtccc  23520
agacatgcaa gagatggagg aatccatcga gattgacctg ggctatgtga cgcccgcgga  23580
gcacgaggag gagctggcag tgcgcttttc acaagaagag atacaccaag aacagccaga  23640
gcaggaagca gagaatgagc agagtcaggc tggcctcgag catgacggcg actacctcca  23700
cctgagcggg ggggaggacg cgctcatcaa gcatctggcc cggcaggcca ccatcgtcaa  23760
ggatgcgctg ctcgaccgca ccgaggtgcc cctcagcgtg gaggagctca gccgcgccta  23820
cgagttgaac ctcttctcgc cgcgcgtgcc ccccaagcgc cagcccaatg gcacctgcga  23880
gcccaacccg cgcctcaact tctacccggt cttcgcggtg cccgaggccc tggccaccta  23940
ccacatcttt ttcaagaacc aaaagatccc cgtctcctgc cgcgccaacc gcacccgcgc  24000
cgacgccctt ttcaacctgg gtcccggcgc ccgcctacct gatatcgcct ccttggaaga  24060
ggttcccaag atcttcgagg gtctgggcag cgacgagact cgggccgcga acgctctgca  24120
aggagaagga ggagagcatg agcaccacag cgccctggtc gagttggaag gcgacaacgc  24180
gcggctggcg gtgctcaaac gcacggtcga gctgacccat ttcgcctacc cggctctgaa  24240
cctgcccccc aaagtcatga gcgcggtcat ggaccaggtg ctcatcaagc gcgcgtcgcc  24300
catctccgag gacgagggca tgcaagactc cgaggagggc aagcccgtgg tcagcgacga  24360
gcagctggcc cggtggctgg gtcctaatgc tagtccccag agtttggaag agcggcgcaa  24420
actcatgatg gccgtggtcc tggtgaccgt ggagctggag tgcctgcgcc gcttcttcgc  24480
cgacgcggag accctgcgca aggtcgagga gaacctgcac tacctcttca ggcacgggtt  24540
cgtgcgccag gcctgcaaga tctccaacgt ggagctgacc aacctggtct cctacatggg  24600
catcttgcac gagaaccgcc tggggcagaa cgtgctgcac accaccctgc gcggggaggc  24660
ccggcgcgac tacatccgcg actgcgtcta cctctacctc tgccacacct ggcagacggg  24720
catgggcgtg tggcagcagt gtctggagga gcagaacctg aaagagctct gcaagctcct  24780
gcagaagaac ctcaagggtc tgtggaccgg gttcgacgag cgcaccaccg cctcggacct  24840
ggccgacctc attttccccg agcgcctcag gctgacgctg cgcaacggcc tgcccgactt  24900
tatgagccaa agcatgttgc aaaactttcg ctctttcatc ctcgaacgct ccggaatcct  24960
gcccgccacc tgctccgcgc tgccctcgga cttcgtgccg ctgaccttcc gcgagtgccc  25020
cccgccgctg tggagccact gctacctgct gcgcctggcc aactacctgg cctaccactc  25080
ggacgtgatc gaggacgtca gcggcgaggg cctgctcgag tgccactgcc gctgcaacct  25140
ctgcacgccg caccgctccc tggcctgcaa cccccagctg ctgagcgaga cccagatcat  25200
cggcaccttc gagttgcaag ggcccagcga aggcgagggt tcagccgcca aggggggtct  25260
gaaactcacc ccggggctgt ggacctcggc ctacttgcgc aagttcgtgc ccgaggacta  25320
ccatcccttc gagatcaggt tctacgagga ccaatcccat ccgcccaagg ccgagctgtc  25380
ggcctgcgtc atcacccagg gggcgatcct ggcccaattg caagccatcc agaaatcccg  25440
ccaagaattc ttgctgaaaa agggccgcgg ggtctacctc gacccccaga ccggtgagga  25500
gctcaacccc ggcttccccc aggatgcccc gaggaaacaa gaagctgaaa gtggagctgc  25560
cgcccgtgga ggatttggag gaagactggg agaacagcag tcaggcagag gaggaggaga  25620
tggaggaaga ctgggacagc actcaggcag aggaggacag cctgcaagac agtctggagg  25680
aagacgagga ggaggcagag gaggaggtgg aagaagcagc cgccgccaga ccgtcgtcct  25740
cggcggggga gaaagcaagc agcacggata ccatctccgc tccgggtcgg ggtcccgctc  25800
gaccacacag tagatgggac gagaccggac gattcccgaa ccccaccacc cagaccggta  25860
agaaggagcg gcagggatac aagtcctggc gggggcacaa aaacgccatc gtctcctgct  25920
tgcaggcctg cgggggcaac atctccttca cccggcgcta cctgctcttc caccgcgggg  25980
tgaactttcc ccgcaacatc ttgcattact accgtcacct ccacagcccc tactacttcc  26040
aagaagaggc agcagcagca gaaaaagacc agcagaaaac cagcagctag aaaatccaca  26100
gcggcggcag caggtggact gaggatcgcg gcgaacgagc cggcgcaaac ccgggagctg  26160
aggaaccgga tctttcccac cctctatgcc atcttccagc agagtcgggg gcaggagcag  26220
gaactgaaag tcaagaaccg ttctctgcgc tcgctcaccc gcagttgtct gtatcacaag  26280
agcgaagacc aacttcagcg cactctcgag gacgccgagg ctctcttcaa caagtactgc  26340
```

-continued

```
gcgctcactc ttaaagagta gcccgcgccc gcccagtcgc agaaaaaggc gggaattacg  26400
tcacctgtgc ccttcgccct agccgcctcc acccatcatc atgagcaaag agattcccac  26460
gccttacatg tggagctacc agccccagat gggcctggcc gccggtgccg cccaggacta  26520
ctccacccgc atgaattggc tcagcgccgg gcccgcgatg atctcacggg tgaatgacat  26580
ccgcgcccac cgaaaccaga tactcctaga acagtcagcg ctcaccgcca cgccccgcaa  26640
tcacctcaat ccgcgtaatt ggcccgccgc cctggtgtac caggaaattc cccagcccac  26700
gaccgtacta cttccgcgag acgcccaggc cgaagtccag ctgactaact caggtgtcca  26760
gctggcgggc ggcgccaccc tgtgtcgtca ccgccccgct cagggtataa agcggctggt  26820
gatccggggc agaggcacac agctcaacga cgaggtggtg agctcttcgc tgggtctgcg  26880
acctgacgga gtcttccaac tcgccggatc ggggagatct tccttcacgc ctcgtcaggc  26940
cgtcctgact ttggagagtt cgtcctcgca gccccgctcg ggtggcatcg gcactctcca  27000
gttcgtggag gagttcactc cctcggtcta cttcaacccc ttctccggct cccccggcca  27060
ctacccggac gagttcatcc cgaacttcga cgccatcagc gagtcggtgg acggctacga  27120
ttgaatgtcc catggtggcg cagctgacct agctcggctt cgacacctgg accactgccg  27180
ccgcttccgc tgcttcgctc gggatctcgc cgagtttgcc tactttgagc tgcccgagga  27240
gcaccctcag ggcccggccc acggagtgcg gatcgtcgtc gaagggggcc tcgactccca  27300
cctgcttcgg atcttcagcc agcgtccgat cctggtcgag cgcgagcaag gacagaccct  27360
tctgactctg tactgcatct gcaaccaccc cggcctgcat gaaagtcttt gttgtctgct  27420
gtgtactgag tataataaaa gctgagatca gcgactactc cggacttccg tgtgttcctg  27480
aatccatcaa ccagtctttg ttcttcaccg ggaacgagac cgagctccag ctccagtgta  27540
agccccacaa gaagtacctc acctggctgt tccagggctc cccgatcgcc gttgtcaacc  27600
actgcgacaa cgacggagtc ctgctgagcg gccctgccaa ccttactttt tccacccgca  27660
gaagcaagct ccagctcttc caacccttcc tccccgggac ctatcagtgc gtctcgggac  27720
cctgccatca caccttccac ctgatcccga ataccacagc gtcgctcccc gctactaaca  27780
accaaactaa cctccaccaa cgccaccgtc gcgacctttc tgaatctaat actaccaccc  27840
acaccggagg tgagctccga ggtcaaccaa cctctgggat ttactacggc ccctgggagg  27900
tggttgggtt aatagcgcta ggcctagttg cgggtgggct tttggttctc tgctacctat  27960
acctcccttg ctgttcgtac ttagtggtgc tgtgttgctg gtttaagaaa tggggaagat  28020
caccctagtg agctgcggtg cgctggtggc ggtgttgctt tcgattgtgg gactgggcgg  28080
tgcggctgta gtgaaggaga aggccgatcc ctgcttgcat ttcaatccca acaaatgcca  28140
gctgagtttt cagcccgatg gcaatcggtg cgcggtactg atcaagtgcg gatgggaatg  28200
cgagaacgtg agaatcgagt acaataacaa gactcggaac aatactctcg cgtccgtgtg  28260
gcagcccggg gaccccgagt ggtacaccgt ctctgtcccc ggtgctgacg gctccccgcg  28320
caccgtgaat aatactttca tttttgcgca catgtgcgac acggtcatgt ggatgagcaa  28380
gcagtacgat atgtggcccc ccacgaagga gaacatcgtg gtcttctcca tcgcttacag  28440
cctgtgcacg gcgctaatca ccgctatcgt gtgcctgagc attcacatgc tcatcgctat  28500
tcgccccaga aataatgccg aaaaagaaaa acagccataa cgtttttttt cacacctttt  28560
tcagaccatg gcctctgtta aatttttgct tttatttgcc agtctcattg ccgtcattca  28620
tggaatgagt aatgagaaaa ttactattta cactggcact aatcacacat tgaaaggtcc  28680
agaaaaagcc acagaagttt catggtattg ttattttaat gaatcagatg tatctactga  28740
actctgtgga aacaataaca aaaaaaatga gagcattact ctcatcaagt ttcaatgtgg  28800
atctgactta accctaatta acatcactag agactatgta ggtatgtatt atggaactac  28860
agcaggcatt tcggacatgg aattttatca agtttctgtg tctgaaccca ccacgcctag  28920
aatgaccaca accacaaaaa ctacacctgt taccactatg cagctcacta ccaataacat  28980
ttttgccatg cgtcaaatgg tcaacaatag cactcaaccc accccaccca gtgaggaaat  29040
tcccaaatcc atgattggca ttattgttgc tgtagtggtg tgcatgttga tcatcgcctt  29100
gtgcatggtg tactatgcct tctgctacag aaagcacaga ctgaacgaca agctggaaca  29160
cttactaagt gttgaatttt aattttttag aaccatgaag atcctaggcc ttttaatttt  29220
ttctatcatt acctctgctc tatgcaattc tgacaatgag gacgttactg tcgttgtcgg  29280
atcaaattat acactgaaag gtccagcgaa gggtatgctt tcgtggtatt gctattttgg  29340
atctgacact acagaaactg aattatgcaa tcttaagaat ggcaaaattc aaaattctaa  29400
aattaacaat tatatatgca atggtactga tctgatactc ctcaatatca cgaaatcata  29460
tgctggcagt tacacctgcc ctggagatga tgctgacagt atgatttttt acaaagtaac  29520
tgttgttgat cccactactc cacctccacc caccacaact actcacacca cacacacaga  29580
tcaaaccgca gcagaggagg cagcaaagtt agccttgcag gtccaagaca gttcatttgt  29640
tggcattacc cctacacctg atcagcggtg tccggggctg ctagtcagcg gcattgtcgg  29700
tgtgctttcg ggattagcag tcataatcat ctgcatgttc atttttgctt gctgctatag  29760
aaggctttac cgacaaaaat cagacccact gctgaacctc tatgtttaat tttttccaga  29820
gtcatgaagg cagttagcgc tctagttttt tgttctttga ttggcattgt tttttgcaat  29880
cctattccta aagttagctt tattaaagat gtgaatgtta ctgagggggg caatgtgaca  29940
ctggtaggtg tagagggtgc tgaaaacacc acctggacaa aataccacct caatgggtgg  30000
aaagatattt gcaattggag tgtattagtt tatacatgtg agggagttaa tcttaccatt  30060
gtcaatgcca cctcagctca aaatggtaga attcaaggac aaagtgtcag tgtatctaat  30120
gggtatttta cccaacatac ttttatctat gacgttaaag tcataccact gcctacgcct  30180
agcccaccta gcactaccac acagacaacc cacactacac agacaaccac atacagtaca  30240
ttaaatcagc ctaccaccac tacagcagca gaggttgcca gctcgtctgg ggtccgagtg  30300
gcatttttga tgttggcccc atctagcagt cccactgcta gtaccaatga gcagactact  30360
gaatttttgt ccactgtcga gagccacacc acagctacct ccagtgcctt ctctagcacc  30420
gccaatctct cctcgctttc ctctacacca atcagtcccg ctactactcc tagccccgct  30480
cctcttccca ctcccctgaa gcaaacagac ggcggcatgc aatggcagat caccctgctc  30540
attgtgatcg ggttggtcat cctggccgtg ttgctctact acatcttctg ccgccgcatt  30600
cccaacgcgc accgcaagcc ggtctacaag cccatcattg tcgggcagcc ggagccgctt  30660
caggtggaag gggtctaagg gaatcttctc ttctctttta cagtatggtg attgaactat  30720
gattcctaga caattcttga tcactattct tatctgcctc ctccaagtct gtgccaccct  30780
cgctctggtg gccaacgcca gtccagactg tattgggccc ttcgcctcct acgtgctctt  30840
tgccttcacc acctgcatct gctgctgtag catagtctgc ctgcttatca ccttcttcca  30900
gttcattgac tggatctttg tgcgcatcgc ctacctgcgc caccaccccc agtaccgcga  30960
ccagcgagtg gcgcggctgc tcaggctcct ctgataagca tgcgggctct gctacttctc  31020
gcgcttctgc tgttagtgct cccccgtccc gtcgaccccc ggtcccccac ccagtccccc  31080
```

```
gaggaggtcc gcaaatgcaa attccaagaa ccctggaaat tcctcaaatg ctaccgccaa  31140
aaatcagaca tgcatcccag ctggatcatg atcattggga tcgtgaacat tctggcctgc  31200
accctcatct cctttgtgat ttacccctgc tttgactttg gttggaactc gccagaggcg  31260
ctctatctcc cgcctgaacc tgacacacca ccacagcaac ctcaggcaca cgcactacca  31320
ccactacagc ctaggccaca atacatgccc atattagact atgaggccga gccacagcga  31380
cccatgctcc ccgctattag ttacttcaat ctaaccggcg gagatgactg acccactggc  31440
caacaacaac gtcaacgacc ttctcctgga catggacggc cgcgcctcgg agcagcgact  31500
cgcccaactt cgcattcgcc agcagcagga gagagccgtc aaggagctgc aggatgcggt  31560
ggccatccac cagtgcaaga gaggcatctt ctgcctggtg aaacaggcca agatctccta  31620
cgaggtcact ccaaacgacc atcgcctctc ctacgagctc ctgcagcagc gccagaagtt  31680
cacctgcctg gtcggagtca accccatcgt catcacccag cagtctggcg ataccaaggg  31740
gtgcatccac tgctcctgcg actcccccga ctgcgtccac actctgatca agaccctctg  31800
cggcctccgc gacctcctcc ccatgaacta atcacccccct tatccagtga aataaagatc  31860
atattgatga tgattttaca gaaataaaaa ataatcattt gatttgaaat aaagatacaa  31920
tcatattgat gatttgagtt taacaaaaaa ataaagaatc acttacttga aatctgatac  31980
caggtctctg tccatgtttt ctgccaacac cacttcactc ccctcttccc agctctggta  32040
ctgcaggccc cggcgggctg caaacttcct ccacacgctg aaggggatgt caaattcctc  32100
ctgtccctca atcttcattt tatcttctat cagatgtcca aaaagcgcgt ccgggtggat  32160
gatgacttcg accccgtcta cccctacgat gcagacaacg caccgaccgt gcccttcatc  32220
aacccccccct tcgtctcttc agatggattc caagagaagc cctgggggt gttgtccctg  32280
cgactggccg accccgtcac caccaagaac ggggaaatca ccctcaagct gggagagggg  32340
gtggacctcg attcctcggg aaaactcatc tccaacacgg ccaccaaggc cgccgcccct  32400
ctcagttttt ccaacaacac catttccctt aacatggatc accccttta cactaaagat  32460
ggaaaattat ccttacaagt ttctccacca ttaaatatac tgagaacaag cattctaaac  32520
acactagctt taggttttgg atcaggttta ggactccgtg gctctgcctt ggcagtacag  32580
ttagtctctc cacttacatt tgatactgat ggaaacataa agcttacctt agacagaggt  32640
ttgcatgtta caacaggaga tgcaattgaa agcaacataa gctgggctaa aggtttaaaa  32700
tttgaagatg gagccatagc aaccaacatt ggaaatgggt tagagtttgg aagcagtagt  32760
acagaaacag gtgttgatga tgcttaccca atccaagtta aacttggatc tggccttagc  32820
tttgacagta caggagccat aatggctggt aacaaagaag acgataaact cactttgtgg  32880
acaacacctg atccatcacc aaactgtcaa atactcgcag aaaatgatgc aaaactaaca  32940
ctttgcttga ctaaatgtgg tagtcaaata ctggccactg tgtcagtctt agttgtagga  33000
agtggaaacc taaaccccat tactggcacc gtaagcagtg ctcaggtgtt tctacgtttt  33060
gatgcaaacg gtgttctttt aacagaacat tctacactaa aaaaatactg gggtatagg  33120
cagggagata gcatagatgg cactccatat accaatgctg taggattcat gcccaattta  33180
aaagcttatc caaagtcaca aagttctact actaaaaata atatagtagg gcaagtatac  33240
atgaatggag atgtttcaaa acctatgctt ctcactataa ccctcaatgg tactgatgac  33300
agcaacagta catattcaat gtcattttca tacacctgga ctaatggaag ctatgttgga  33360
gcaacatttg ggggctaactc ttatacttc tcatacatcg cccaagaatg aacactgtat  33420
cccaccctgc atgccaaccc ttcccacccc actctgtgga acaaactctg aaacacaaaa  33480
taaaataaag ttcaagtgtt ttattgattc aacagtttta caggattcga gcagttattt  33540
ttcctccacc ctcccaggac atggaataca ccaccctctc cccccgcaca gccttgaaca  33600
tctgaatgcc attggtgatg gacatgcttt tggtctccac gttccacaca gtttcagagc  33660
gagccagtct cgggtcggtc agggagatga aaccctccgg gcactcccgc atctgcacct  33720
cacagctcaa cagctgagga ttgtcctcgg tggtcgggat cacggttatc tggaagaagc  33780
agaagagcgg cggtgggaat catagtccgc gaacgggatc ggccggtggt gtcgcatcag  33840
gccccgcagc agtcgctgcc gccgccgctc cgtcaagctg ctgctcaggg ggtccgggtc  33900
cagggactcc ctcagcatga tgcccacggc cctcagcatc agtcgtctgg tgcggcgggc  33960
gcagcagcgc atgcggatct cgctcaggtc gctgcagtac gtgcaacaca gaaccaccag  34020
gttgttcaac agtccatagt tcaacacgct ccagccgaaa ctcatcgcgg gaaggatgct  34080
acccacgtgg ccgtcgtacc agatcctcag gtaaatcaag tggtgccccc tccagaacac  34140
gctgcccacg tacatgatct ccttgggcat gtggcggttc accacctccc ggtaccacat  34200
caccctctgg ttgaacatgc agccccggat gatcctgcgg aaccacaggg ccagcaccgc  34260
cccgcccgcc atgcagcgaa gagaccccgg gtcccggcaa tggcaatgga ggacccaccg  34320
ctcgtacccg tggatcatct gggagctgaa caagtctatg ttggcacagc acaggcatat  34380
gctcatgcat ctcttcagca ctctcaactc ctcgggggtc aaaaccatat cccagggcac  34440
ggggaactct tgcaggacag cgaaccccgc agaacagggc aatcctcgca cagaacttac  34500
attgtgcatg gacagggtat cgcaatcagg cagcaccggg tgatcctcca ccagagaagc  34560
gcgggtctcg gtctcctcac agcgtggtaa gggggccggc cgatacgggt gatggcggga  34620
cgcggctgat cgtgttcgcg accgtgtcat gatgcagttg ctttcggaca ttttcgtact  34680
tgctgtagca gaacctggtc cgggcgctgc acaccgatcg ccggcggcgg tctcggcgct  34740
tggaacgctc ggtgttgaaa ttgtaaaaca gccactctct cagaccgtgc agcagatcta  34800
gggcctcagg agtgatgaag atcccatcat gcctgatggc tctgatcaca tcgaccaccg  34860
tggaatgggc cagacccagc cagatgatgc aattttgttg ggtttcggtg acggcggggg  34920
agggaagaac aggaagaacc atgattaact tttaatccaa acggtctcgg agtacttcaa  34980
aatgaagatc gcggagatgg cacctctcgc ccccgctgtg ttggtggaaa ataacagcca  35040
ggtcaaaggt gatacggttc tcgagatgtt ccacggtggc ttccagcaaa gcctccacgc  35100
gcacatccag aaacaagaca atagcgaaag cgggagggtt ctctaattcc tcaatcatca  35160
tgttacactc ctgcaccatc cccagataat tttcattttt ccagccttga atgattcgaa  35220
ctagttcctg aggtaaatcc aagccagcca tgataaagag ctcgcgcaga gcgccctcca  35280
ccggcattct taagcacacc ctcataattc caagatattc tgctcctggt tcacctgcag  35340
cagattgaca agcggaatat caaaatctct gccgcgatcc ctgagctcct ccctcagcaa  35400
taactgtaag tactctttca tatcctctcc gaaattttta gccataggac caccaggaat  35460
aagattaggg caagccacag tacagataaa ccgaagtcct ccccagtgag cattgccaaa  35520
tgcaagactg ctataagcat gctggctaga cccggtgata tcttccagat aactggacag  35580
aaaatcgccc aggcaatttt taagaaaatc aacaaaagaa aaatcctcca ggtggacgtt  35640
tagagcctcg ggaacaacga tgaagtaaat gcaagcggtg cgttccagca tggttagtta  35700
gctgatctgt agaaaaaaca aaaatgaaca ttaaaccatg ctagcctggc gaacaggtgg  35760
gtaaatcgtt ctctccagca ccaggcaggc cacggggtct ccggcgcgac cctcgtaaaa  35820
```

-continued

```
attgtcgcta tgattgaaaa ccatcacaga gagacgttcc cggtggccgg cgtgaatgat  35880
tcgacaagat gaatacaccc ccggaacatt ggcgtccgcg agtgaaaaaa agcgcccgag  35940
gaagcaataa ggcactacaa tgctcagtct caagtccagc aaagcgatgc catgcggatg  36000
aagcacaaaa ttctcaggtg cgtacaaaat gtaattactc ccctcctgca caggcagcaa  36060
agcccccgat ccctccaggt acacatacaa agcctcagcg tccatagctt accgagcagc  36120
agcacacaac aggcgcaaga gtcagagaaa ggctgagctc taacctgtcc acccgctctc  36180
tgctcaatat atagcccaga tctacactga cgtaaaggcc aaagtctaaa aatacccgcc  36240
aaataatcac acacgcccag cacacgccca gaaaccggtg acacactcaa aaaaatacgc  36300
gcacttcctc aaacgcccaa aactgccgtc atttccgggt tcccacgcta cgtcatcaaa  36360
acacgacttt caaattccgt cgaccgttaa aaacgtcacc cgccccgccc ctaacggtcg  36420
cccgtctctc agccaatcag cgccccgcat ccccaaattc aaacacctca tttgcatatt  36480
aacgcgcaca aaaagtttga ggtatattat tgatgatgg                         36519

SEQ ID NO: 11          moltype = DNA  length = 31867
FEATURE                Location/Qualifiers
misc_feature           1..31867
                       note = Description of Artificial Sequence: Synthetic
                        polynucleotide
source                 1..31867
                       mol_type = other DNA
                       organism = synthetic construct
SEQUENCE: 11
ccatcttcaa taatatacct caaacttttt gtgcgcgtta atatgcaaat gaggcgtttg  60
aatttgggga ggaagggcgg tgattggtcg agggatgagc gaccgttagg ggcggggcga  120
gtgacgtttt gatgacgtgg ttgcgaggag gagccagttt gcaagttctc gtgggaaaag  180
tgacgtcaaa cgaggtgtgg tttgaacacg gaaatactca atttcccgc gctctctgac  240
aggaaatgag gtgtttctgg gcggatgcaa gtgaaaacgg gccattttcg cgcgaaaact  300
gaatgaggaa gtgaaaatct gagtaatttc gcgtttatgg cagggaggag tatttgccga  360
gggccgagta gactttgacc gattacgtgg gggtttcgat taccgtgttt ttcacctaaa  420
tttccgcgta cggtgtcaaa gtccggtgtt tttacgtagg tgtcagctga tcgccagggt  480
atttaaacct gcgctctcca gtcaagaggc cactcttgag tgccagcgag aagagttttc  540
tcctccgcgc cgcgagtcag atctacactt tgaaagtagg gataacaggg taatgacatt  600
gattattgac tagttgttaa tagtaatcaa ttacggggtc attagttcat agcccatata  660
tggagttccg cgttacataa cttacggtaa atggcccgcc tggctgaccg cccaacgacc  720
cccgcccatt gacgtcaata atgacgtatg ttcccatagt aacgccaata gggactttcc  780
attgacgtca atgggtggag tatttacggt aaactgccca cttggcagta catcaagtgt  840
atcatatgcc aagtccgccc cctattgacg tcaatgacgg taaatggccc gcctggcatt  900
atgcccagta catgacctta cggactttc ctacttggca gtacatctac gtattagtca  960
tcgctattac catggtgatg cggttttggc agtacaccaa tgggcgtgga tagcggtttg  1020
actcacgggg atttccaagt ctccacccca ttgacgtcaa tgggagtttg ttttggcacc  1080
aaaatcaacg ggactttcca aaatgtcgta ataaccccgc cccgttgacg caaatgggcg  1140
gtaggcgtgt acggtgggag gtctatataa gcagagctcg tttagtgaac cgtcagatcg  1200
cctggaacgc catccacgct gttttgacct ccatagaaga cagcgatcgc gccaccatgg  1260
tgagcaaggg cgaggagctg ttcaccgggg tggtgcccat cctggtcgag ctggacggcg  1320
acgtaaacgg ccacaagttc agcgtgtccg gcgagggcga gggcgatgcc acctacggca  1380
agctgaccct gaagttcatc tgcaccaccg gcaagctgcc cgtgccctgg cccaccctcg  1440
tgaccaccct gacctacggc gtgcagtgct tcagccgcta ccccgaccac atgaagcagc  1500
acgacttctt caagtccgcc atgcccgaag gctacgtcca ggagcgcacc atcttcttca  1560
aggacgacgg caactacaag acccgcgccg aggtgaagtt cgagggcgac accctggtga  1620
accgcatcga gctgaagggc atcgacttca aggaggacgg caacatcctg gggcacaagc  1680
tggagtacaa ctacaacagc cacaacgtct atatcatggc cgacaagcag aagaacggca  1740
tcaaggtgaa cttcaagatc cgccacaaca tcgaggacgg cagcgtgcag ctcgccgacc  1800
actaccagca gaacaccccc atcggcgacg gccccgtgct gctgcccgac aaccactacc  1860
tgagcaccca gtccgccctg agcaaagacc ccaacgagaa gcgcgatcac atggtcctgc  1920
tggagttcgt gaccgccgcc gggatcactc tcggcatgga cgagctttac aagtagtgag  1980
tttaaactcc catttaaatg tgagggttaa tgcttcgagc agacatgata agatacattg  2040
atgagtttgg acaaaccaca actagaatgc agtgaaaaaa atgctttatt tgtgaaattt  2100
gtgatgctat tgctttattt gtaaccatta taagctgcaa taaacaagtt aacaacaaca  2160
attgcattca ttttatgttt caggttcagg gggagatgtg ggaggttttt taaagcaagt  2220
aaaacctcta caaatgtggt aaaataacta taacggtcct aaggtagcga gtgagtagtg  2280
ttctggggcg gggaggacc tgcatgaggg ccagaataac tgaaatctgt gcttttctgt  2340
gtgttgcagc agcatgagcg gaagcggctc ctttgaggga ggggtattca gcccttatct  2400
gacggggcgt ctcccctcct gggcgggagt gcgtcagaat gtgatgggat ccacggtgga  2460
cggccggccc gtgcagcccg cgaactcttc aaccctgacc tatgcaaccc tgagctcttc  2520
gtcgttggac gcagctgccg ccgcagctgc tgcatctgcc gccagcgccg tgcgcggaat  2580
ggccatgggc gccggctact acggcactct ggtggccaac tcgagttcca ccaataatcc  2640
cgccagcctg aacgaggaga agctgttgct gctgatggcc cagctcgagg ccttgaccca  2700
gcgcctgggc gagctgaccc agcaggtggc tcagctgcag gagcagacgc gggccgcggt  2760
tgccacggtg aaatccaaat aaaaaatgaa tcaataaata aacggagacg gttgttgatt  2820
ttaacacaga gtctgaatct ttatttgatt tttcgcgcgc ggtaggccct ggaccaccgg  2880
tctcgatcat tgagcacccg gtggatcttt tccaggaccc ggtagaggtg ggcttggatg  2940
ttgaggtaca tgggcatgag cccgtcccgg gggtggaggt agctccattg cagggcctcg  3000
tgctcggggg tggtgttgta aatcacccag tcatagcagg ggcgcagggc atggtgttgc  3060
acaatatctt tgaggaggag actgatggcc acgggcagcc ctttggtgta ggtgtttaca  3120
aatctgttga gctgggaggg atgcatgcgg ggggagatga ggtgcatctt ggcctggatc  3180
ttgagattgg cgatgttacc gcccagatcc cgcctggggt tcatgttgtg caggaccacc  3240
agcacggtgt atccggtgca cttggggaat ttatcatgca acttggaagg gaaggcgtga  3300
aagaatttgg cgacgccttt gtgcccgccc aggttttcca tgcactcatc catgatgatg  3360
gcgatgggcc cgtgggcggc ggcctgggca aagacgtttc gggggtcgga cacatcatag  3420
```

-continued

```
ttgtggtcct gggtgaggtc atcataggcc attttaatga atttggggcg gagggtgccg  3480
gactggggga caaaggtacc ctcgatcccg ggggcgtagt tcccctcaca gatctgcatc  3540
tcccaggctt tgagctcgga ggggggggatc atgtccacct gcggggcgat aaagaacacg  3600
gtttccgggg cgggggagat gagctgggcc gaaagcaagt tccggagcag ctgggacttg  3660
ccgcagccgg tggggccgta gatgaccccg atgaccggct gcaggtggta gttgagggag  3720
agacagctgc cgtcctcccg gaggaggggg gccacctcgt tcatcatctc gcgcacgtgc  3780
atgttctcgc gcaccagttc cgccaggagg cgctctcccc ccagggatag gagctcctgg  3840
agcgaggcga agtttttcag cggcttgagt ccgtcggcca tgggcatttt ggagagggtt  3900
tgttgcaaga gttccaggcg gtcccagagc tcggtgatgt gctctacggc atctcgatcc  3960
agcagacctc ctcgtttcgc gggttgggac ggctgcggga gtagggcacc agacgatggg  4020
cgtccagcgc agccagggtc cggtccttcc agggtcgcag cgtccgcgtc agggtggtct  4080
ccgtcacggt gaaggggtgc gcgccgggct gggcgcttgc gagggtgcgc ttcaggctca  4140
tccggctggt cgaaaaccgc tcccgatcgg cgccctgcgc gtcggccagg tagcaattga  4200
ccatgagttc gtagttgagc gcctcggccg cgtggccttt ggcgcggagc ttacctttgg  4260
aagtctgccc gcaggcggga cagaggaggg acttgagggc gtagagcttg ggggcgagga  4320
agacggactc gggggcgtag gcgtccgcgc cgcagtgggc gcagacggtc tcgcactcca  4380
cgagccaggt gaggtcgggc tggtcggggt caaaaaccag tttcccgccg ttctttttga  4440
tgcgtttctt acctttggtc tccatgagct cgtgtccccg ctgggtgaca aagaggctgt  4500
ccgtgtcccc gtagaccgac tttatgggcc ggtcctcgag cggtgtgccg cggtcctcct  4560
cgtagaggaa ccccgcccac tccgagacga aagcccgggt ccaggccagc acgaaggagg  4620
ccacgtggga cgggtagcgg tcgttgtcca ccagcgggtc caccttttcc agggtatgca  4680
aacacatgtc ccctcgtcc acatccagga aggtgattgg cttgtaagtg taggccacgt  4740
gaccgggggt cccggccggg ggggtataaa agggtgcggg tccctgctcg tcctcactgt  4800
cttccggatc gctgtccagg agcgccagct gttggggtag gtattccctc tcgaaggcgg  4860
gcatgacctc ggcactcagg ttgtcagttt ctagaaacga ggaggatttg atattgacgg  4920
tgccggcgga gatgcctttc aagagcccct cgtccatctg gtcagaaaag acgatctttt  4980
tgttgtcgag cttggtggcg aaggagccgt agagggcgtt ggagaggagc ttggcgatgg  5040
agcgcatggt ctggtttttt tccttgtcgg cgcgctcctt ggcggcgatg ttgagctgca  5100
cgtactcgcg cgccacgcac ttccattcgg ggaagacggt ggtcagctcg tcgggcacga  5160
ttctgacctg ccagccccga ttatgcaggg tgatgaggtc cacactggtg gccacctcgc  5220
cgcgcagggg ctcattagtc cagcagaggc gtccgccctt gcgcgagcag aagggggggca  5280
gggggtccag catgacctcg tcgggggggt cggcatcgat ggtgaagatg ccgggcagga  5340
ggtcggggtc aaagtagctg atggaagtgg ccagatcgtc cagggcagct tgccattcgc  5400
gcacggccag cgcgctctcg tagggactga ggggcgtgcc ccagggcatg ggatgggtaa  5460
gcgcggaggc gtacatgccg cagatgtcgt agacgtagag gggctcctcg aggatgccga  5520
tgtaggtggg gtagcagcgc cccccgcgga tgctggcgcg cacgtagtca tacagctcgt  5580
gcgagggggc gaggagcccc gggcccaggt tggtgcgact gggcttttcg gcgcggtaga  5640
cgatctggcg gaaaatggca tgcgagttgg aggagatggt gggcctttgg aagatgttga  5700
agtgggcgtg gggcagtccg accgagtcgc ggatgaagtg ggcgtaggag tcttgcagct  5760
tggcgacgag ctcggcggtg actaggacgt ccagagcgca gtagtcgagg gtctcctgga  5820
tgatgtcata cttgagctgt ccctttttgtt tccacagctc gcggttgaga aggaactctt  5880
cgcggtcctt ccagtactct tcgaggggga acccgtcctg atctgcacgg taagagccta  5940
gcatgtagaa ctggttgacg gccttgtagg cgcagcagcc cttctccacg ggagggcgt  6000
aggcctgggc ggccttgcgc agggaggtgt gcgtgagggc gaaagtgtcc ctgaccatga  6060
ccttgaggaa ctggtgcttg aagtcgatat cgtcgcagcc cccctgctcc cagagctgga  6120
agtccgtgcg cttcttgtag gcggggttgg gcaaagcgaa agtaacatcg ttgaagagga  6180
tcttgcccgc gcggggcata aagttgcgag tgatgcggaa aggttggggc acctcggccc  6240
ggttgttgat gacctgggcg gcgagcacga tctcgtcgaa gccgttgatg ttgtggccca  6300
cgatgtagag ttccacgaat cgcggacggc ccttgacgtg gggcagtttc ttgagctcct  6360
cgtaggtgag ctcgtcgggg tcgctgagcc cgtgctgctc gagcgcccag tcggcgagat  6420
gggggttggc gcggaggaag gaagtccaga gatccacggc cagggcggtt tgcagacggt  6480
cccggtactg acggaactgc tgcccgacgg ccatttttttc gggggtgacg cagtagaagg  6540
tgcgggggtc cccgtgccag cgatcccatt tgagctggag ggcgagatcg agggcgagct  6600
cgacgagccg gtcgtccccg gagagtttca tgaccagcat gaaggggacg agctgcttgc  6660
cgaaggaccc catccaggtg taggtttcca catcgtaggt gaggaagagc ctttcggtgc  6720
gaggatgcga gccgatgggg aagaactgga tctcctgcca ccaattggag gaatggctgt  6780
tgatgtgatg gaagtagaaa tgccgacggc gcgccgaaca ctcgtgcttg tgtttataca  6840
agcggccaca gtgctcgcaa cgctgcacgg gatgcacgtg ctgcacgagc tgtacctgag  6900
ttcctttgac gaggaatttc agtgggaagt ggagtcgtgg cgcctgcatc tcgtgctgta  6960
ctacgtcgtg gtggtcggcc tggccctctt ctgcctcgat ggtggtcatg ctgacgagcc  7020
cgcgcgggag gcaggtccag acctcggcgc gagcgggtcg gagagcgagg acgagggcgc  7080
gcaggccgga gctgtccagg gtcctgagac gctgcggagt caggtcagtg ggcagcggcg  7140
gcgcgcggtt gacttgcagg agtttttcca gggcgcgcgg gaggtccaga tggtacttga  7200
tctccaccgc gccattggtg gcgacgtcga tggcttgcag ggtcccgtgc cctggggtg  7260
tgaccaccgt cccccgtttc ttcttgggcg gctggggcga cgggggcggt gcctcttcca  7320
tggttagaag cggcggcgag gacgcgcgcc gggcggcagg ggcggctcgg ggcccggagg  7380
caggggcggc aggggcacgt cggcgccgcg cgcgggtagg ttctggtact gcgcccggag  7440
aagactggcg tgagcgacga cgcgacggtt gacgtcctgg atctgacgcc tctgggtgaa  7500
ggccacggga cccgtgagtt tgaacctgaa agagagttcg acagaatcaa tctcggtatc  7560
gttgacggcg gcctgccgca ggatctcttg cacgtcgccc gagttgtcct ggtaggcgat  7620
ctcggtcatg aactgctcga tctcctcctc ttgaaggtct ccgcggccgg cgcgctccac  7680
ggtggccgcg aggtcgttgg agatgcggcc catgagctgc gagaaggcgt tcatgcccgc  7740
ctcgttccag acgcggctgt agaccacgac gccctcggga tcgcgggcgc gcatgaccac  7800
ctgggcgagg ttgagctcca cgtggcgcgt gaagaccgcg tagttgcaga ggcgctggta  7860
gaggtagttg agcgtggtgg cgatgtgctc ggtgacgaag aaatacatga tccagcggcg  7920
gagcggcatc tcgctgacgt cgcccagcgc ctccaaacgt tccatggcct cgtaaaagtc  7980
cacggcgaag ttgaaaaact gggagttgcg cgccgagacg gtcaactcct cctccagaag  8040
acggatgagc tcggcgatgg tggcgcgcac ctcgcgctcg aaggcccccg ggagttcctc  8100
cacttcctct tcttcctcct ccactaacat ctcttctact tcctcctcag gcggcagtgg  8160
```

```
tggcggggga gggggcctgc gtcgccggcg gcgcacgggc agacggtcga tgaagcgctc  8220
gatggtctcg ccgcgccggc gtcgcatggt ctcggtgacg gcgcgcccgt cctcgcgggg  8280
ccgcagcgtg aagacgccgc cgcgcatctc caggtggccg ggggggtccc cgttgggcag  8340
ggagagggcg ctgacgatgc atcttatcaa ttgccccgta gggactccgc gcaaggacct  8400
gagcgtctcg agatccacgg gatctgaaaa ccgctgaacg aaggcttcga gccagtcgca  8460
gtcgcaaggt aggctgagca cggtttcttc tggcgggtca tgttggttgg gagcggggcg  8520
ggcgatgctg ctggtgatga agttgaaata ggcggttctg agacggcgga tggtggcgag  8580
gagcaccagg tctttgggcc cggcttgctg gatgcgcaga cggtcggcca tgccccaggc  8640
gtggtcctga cacctggcca ggtccttgta gtagtcctgc atgagccgct ccacgggcac  8700
ctcctcctcg cccgcgcggc cgtgcatgcg cgtgagcccg aagccgcgct ggggctggac  8760
gagcgccagg tcggcgacga cgcgctcggc gaggatggct tgctggatct gggtgagggt  8820
ggtctggaag tcatcaaagt cgacgaagcg gtggtaggct ccggtgttga tggtgtagga  8880
gcagttggcc atgacggacc agttgacggt ctggtggccc ggacgcacga gctcgtggta  8940
cttgaggcgc gagtaggcgc gcgtgtcgaa gatgtagtcg ttgcaggtgc gcaccaggta  9000
ctggtagccg atgaggaagt gcggcggcgg ctggcggtag agcggccatc gctcggtggc  9060
gggggcgccg ggcgcgaggt cctcgagcat ggtgcggtgg tagccgtaga tgtacctgga  9120
catccaggtg atgccggcgg cggtggtgga ggcgcgcggg aactcgcgga cgcggttcca  9180
gatgttgcgc agcggcagga agtagttcat ggtgggcacg gtctggcccg tgaggcgcgc  9240
gcagtcgtgg atgctctata cggcaaaaa cgaaagcggt cagcggctcg actccgtggc  9300
ctggaggcta agcgaacggg ttgggctgcg cgtgtacccc ggttcgaatc tcgaatcagg  9360
ctggagccgc agctaacgtg gtattggcac tcccgtctcg acccaagcct gcaccaaccc  9420
tccaggatac ggaggcgggt cgttttgcaa cttttttttg gaggccggat gagactagta  9480
agcgcggaaa gcggccgacc gcgatggctc gctgccgtag tctggagaag aatcgccagg  9540
gttgcgttgc ggtgtgcccc ggttcgaggc cggccggatt ccgcggctaa cgagggcgtg  9600
gctgccccgt cgtttccaag accccatagc cagccgactt ctccagttac ggagcgagcc  9660
cctcttttgt tttgtttgtt tttgccagat gcatcccgta ctgcggcaga tgcgccccca  9720
ccaccctcca ccgcaacaac agccccctcc acagccggcg cttctgcccc cgccccagca  9780
gcaacttcca gccacgaccg ccgcggccgc cgtgagcggg gctggacaga gttatgatca  9840
ccagctggcc ttggaagagg gcgaggggct ggcgcgcctg gggcgtcgt  cgccggagcg  9900
gcacccgcgc gtgcagatga aaagggacgc tcgcgaggcc tacgtgccca agcagaacct  9960
gttcagagac aggagcggcg aggagcccga ggagatgcgc gcggcccggt tccacgcggg  10020
gcgggagctg cggcgcggcc tggaccgaaa gagggtgctg agggacgagg atttcgaggc  10080
ggacgagctg acggggatca gccccgcgcg cgcgcacgtg gccgcggcca acctggtcac  10140
ggcgtacgag cagaccgtga aggaggagag caacttccaa aaatccttca acaaccacgt  10200
gcgcaccctg atcgcgcgcg aggaggtgac cctgggcctg atgcacctgt gggacctgct  10260
ggaggccatc gtgcagaacc ccaccagcaa gccgctgacg gcgcagctgt tcctggtggt  10320
gcagcatagt cgggacaacg aagcgttcag ggaggcgctg ctgaatatca ccgagcccga  10380
gggccgctgg ctcctggacc tggtgaacat tctgcagagc atcgtggtgc aggagcgcgg  10440
gctgccgctg tccgagaagc tggcggccat caacttctcg gtgctgagtt tgggcaagta  10500
ctacgctagg aagatctaca agaccccgta cgtgcccata gacaaggagg tgaagatcga  10560
cgggttttac atgcgcatga ccctgaaagt gctgaccctg agcgacgatc tgggggtgta  10620
ccgcaacgac aggatgcacc gtgcggtgag cgccagcagg cggcgcgagc tgagcgacca  10680
ggagctgatg catagtctgc agcgggccct gaccggggcc gggaccgagg gggagagcta  10740
ctttgacatg ggcgcggacc tgcactggca gcccagccgc cgggccttgg aggcggcggc  10800
aggaccctac gtagaagagg tggacgatga ggtggacgag gagggcgagt acctggaaga  10860
ctgatggcgc gaccgtattt ttgctagatg caacaacaac agccacctcc tgatcccgcg  10920
atgcgggcgg cgctgcagag ccagccgtcc ggcattaact cctcggacga ttggacccag  10980
gccatgcaac gcatcatggc gctgacgacc cgcaaccccg aagcctttag acagcagccc  11040
caggccaacc ggctctcggc catcctggag gccgtggtgc cctcgcgctc caaccccacg  11100
cacgagaagg tcctggccat cgtgaacgcg ctggtggaga acaaggccat ccgcggcgac  11160
gaggccggcc tggtgtacaa cgcgctgctg gagcgcgtgg cccgctacaa cagcaccaac  11220
gtgcagacca acctggaccg catggtgacc gacgtgcgcg aggccgtggc ccagcgcgag  11280
cggttccacc gcgagtccaa cctgggatcc atggtggcgc tgaacgcctt cctcagcacc  11340
cagcccgcca acgtgccccg gggccaggag gactacacca acttcatcag cgccctgcgc  11400
ctgatggtga ccgaggtgcc ccagagcgag gtgtaccagt ccgggccgga ctacttcttc  11460
cagaccagtc gccagggctt gcagaccgtg aacctgagcc aggctttcaa gaacttgcag  11520
ggcctgtggg gcgtgcaggc cccggtcggg gaccgcgcga cggtgtcgag cctgctgacg  11580
ccgaactcgc gcctgctgct gctgctggtg gccccttca  cggacagcgg cagcatcaac  11640
cgcaactcgt acctgggcta cctgattaac ctgtaccgcg aggccatcgg ccaggcgcac  11700
gtggacgagc agacctacca ggagatcacc cacgtgagcc gcgccctggg ccaggacgac  11760
ccgggcaacc tggaagccac cctgaacttt ttgctgacca accggtcgca gaagatcccg  11820
ccccagtacg cgctcagcac cgaggaggag cgcatcctgc gttacgtgca gcagagcgtg  11880
ggcctgttcc tgatgcagga gggggccacc cccagcgccg cgctcgacat gaccgcgcgc  11940
aacatggagc ccagcatgta cgccagcaac cgcccgttca tcaataaact gatggactac  12000
ttgcatcggg cggccgccat gaactctgac tatttcacca acgccatcct gaatccccac  12060
tggctcccgc cgccggggtt ctacacgggc gagtacgaca tgcccgaccc caatgacggg  12120
ttcctgtggg acgatgtgga cagcagcgtg ttctccccc  gaccgggtgc taacgagcgc  12180
cccttgtgga agaaggaagg cagcgaccga cgcccgtcct cggcgctgtc cggccgcgag  12240
ggtgctgccg cggcggtgcc cgaggccgcc agtcctttcc cgagcttgcc cttctcgctg  12300
aacagtatcc gcagcagcga gctgggcagg atcacgcgcc cgcgcttgct gggcgaagag  12360
gagtacttga atgactcgct gttgagaccc gagcgggaga agaacttccc caataacggg  12420
atagaaagcc tggtggacaa gatgagccgc tggaagacgt atgcgcagga gcacagggac  12480
gatccccggg cgtcgcaggg ggccacgagc cggggcagcg ccgcccgtaa acgccggtgg  12540
cacgacaggc agcggggaca gatgtgggac gatgaggact ccgccgacga cagcagcgtg  12600
ttggacttgg gtgggagtgg taacccgttc gctcacctgc gcccccgtat cgggcgcatg  12660
atgtaagaga aaccgaaaat aaatgatact caccaaggcc atggcgacca gcgtgcgttc  12720
gtttcttctc tgttgttgtt gtatctagta tgatgaggcg tgcgtacccg gagggtcctc  12780
ctccctcgta cgagagcgtg atgcagcagg cgatggcggc ggcggcgatg cagcccccgc  12840
tggaggctcc ttacgtgccc ccgcggtacc tggcgcctac ggaggggcgg aacagcattc  12900
```

-continued

```
gttactcgga gctggcaccc ttgtacgata ccacccggtt gtacctggtg gacaacaagt  12960
cggcggacat cgcctcgctg aactaccaga acgaccacag caacttcctg accaccgtgg  13020
tgcagaacaa tgacttcacc cccacggagg ccagcaccca gaccatcaac tttgacgagc  13080
gctcgcggtg gggcggccag ctgaaaacca tcatgcacac caacatgccc aacgtgaacg  13140
agttcatgta cagcaacaag ttcaaggcgc gggtgatggt ctcccgcaag acccccaatg  13200
gggtgacagt gacagaggat tatgatggta gtcaggatga gctgaagtat gaatgggtgg  13260
aatttgagct gcccgaaggc aacttctcgg tgaccatgac catcgacctg atgaacaacg  13320
ccatcatcga caattacttg gcggtggggc ggcagaacgg ggtgctggag agcgacatcg  13380
gcgtgaagtt cgacactagg aacttcaggc tgggctggga ccccgtgacc gagctggtca  13440
tgcccggggt gtacaccaac gaggctttcc atcccgatat tgtcttgctg cccggctgcg  13500
gggtggactt caccgagagc cgcctcagca acctgctggg cattcgcaag aggcagccct  13560
tccaggaagg cttccagatc atgtacgagg atctggaggg gggcaacatc cccgcgctcc  13620
tggatgtcga cgcctatgag aaaagcaagg aggatgcagc agctgaagca actgcagccg  13680
tagctaccgc ctctaccgag gtcaggggcg ataattttgc aagcgccgca gcagtggcag  13740
cggccgaggc ggctgaaacc gaaagtaaga tagtcattca gccggtggag aaggatagca  13800
agaacaggag ctacaacgta ctaccggaca agataaacac cgcctaccgc agctggtacc  13860
tagcctacaa ctatggcgac cccgagaagg gcgtgcgctc ctggacgctg ctcaccacct  13920
cggacgtcac ctgcggcgtg gagcaagtct actggtcgct gcccgacatg atgcaagacc  13980
cggtcacctt ccgctccacg cgtcaagtta gcaactaccc ggtggtgggc gccgagctcc  14040
tgcccgtcta ctccaagagc ttcttcaacg agcaggccgt ctactcgcag cagctgcgcg  14100
ccttcacctc gcttacgcac gtcttcaacc gcttccccga gaaccagatc ctcgtccgcc  14160
cgcccgcgcc caccattacc accgtcagtg aaaacgttcc tgctctcaca gatcacggga  14220
ccctgccgct gcgcagcagt atccggggag tccagcgcgt gaccgttact gacgccagac  14280
gccgcacctg cccctacgtc tacaaggccc tgggcatagt cgcgccgcgc gtcctctcga  14340
gccgcacctt ctaaatgtcc attctcatct cgcccagtaa taacaccggt tggggcctgc  14400
gcgcgcccag caagatgtac ggaggcgctc gccaacgctc cacgcaacac cccgtgcgcg  14460
tgcgcgggca cttccgcgct ccctggggcg ccctcaaggg ccgcgtgcgg tcgcgcacca  14520
ccgtcgacga cgtgatcgac caggtggtgg ccgacgcgcg caactacacc cccgccgccg  14580
cgcccgtctc caccgtggac gccgtcatcg acagcgtggt ggccgacgcg cgccggtacg  14640
cccgcgccaa gagccggcgg cggcgcatcg cccggcggca ccggagcacc cccgccatgc  14700
gcgcggcgcg agccttgctg cgcagggcca ggcgcacggg acgcagggcc atgctcaggg  14760
cggccagacg cgcggcttca ggcgccagcg ccggcaggac ccggagacgc gcggccacgg  14820
cggcggcagc ggccatcgcc agcatgtccc gcccgcggcg agggaacgtg tactgggtgc  14880
gcgacgccgc caccggtgtg cgcgtgcccg tgcgcacccg ccccccctcgc acttgaagat  14940
gttcacttcg cgatgttgat gtgtcccagc ggcgaggagg atgtccaagc gcaaattcaa  15000
ggaagagatg ctccaggtca tcgcgcctga gatctacggc cctgcggtgg tgaaggagga  15060
aagaaagccc cgcaaaatca agcgggtcaa aaaggacaaa aaggaagaag aaagtgatgt  15120
ggacggattg gtggagtttg tgcgcgagtt cgccccccgg cggcgcgtgc agtggcgcgg  15180
gcggaaggtg caaccggtgc tgagacccgg caccaccgtg gtcttcacgc ccggcgagcg  15240
ctccggcacc gcttccaagc gctcctacga cgaggtgtac ggggatgatg atattctgga  15300
gcaggcggcc gagcgcctgg gcgagtttgc ttacggcaag cgcagccgtt ccgcaccgaa  15360
ggaagaggcg gtgtccatcc cgctggacca cggcaacccc acgccgagcc tcaagcccgt  15420
gaccttgcag caggtgctgc cgaccgcggc gccgcgccgg gggttcaagc gcgagggcga  15480
ggatctgtac cccaccatgc agctgatggt gcccaagcgc cagaagctgg aagacgtgct  15540
ggagaccatg aaggtggacc cggacgtgca gcccgaggtc aaggtgcggc ccatcaagca  15600
ggtggccccg ggcctgggcg tgcagaccgt ggacatcaag attcccacgg agcccatgga  15660
aacgcagacc gagcccatga tcaagcccag caccagcacc atggaggtgc agacggatcc  15720
ctggatgcca tcggctccta gtcgaagacc ccggcgcaag tacggcgcgg ccagcctgct  15780
gatgcccaac tacgcgctgc atccttccat catccccacg ccgggctacc gcggcacgcg  15840
cttctaccgc ggtcatacca gcagccgccg ccgcaagacc accactcgcc gccgccgtcg  15900
ccgcaccgcc gctgcaacca cccctgccgc cctggtgcgg agagtgtacc gccgcggccg  15960
cgcacctctg accctgccgc gcgcgcgcta ccacccgagc atcgccattt aaactttcgc  16020
ctgctttgca gatcaatggc cctcacatgc cgccttcgcg ttcccattac gggctaccga  16080
ggaagaaaac cgcgccgtag aaggctggcg gggaacggga tgcgtcgcca ccaccaccgg  16140
cggcggcgcg ccatcagcaa gcggttgggg ggaggcttcc tgcccgcgct gatccccatc  16200
atcgccgcgg cgatcggggc gatccccggc attgcttccg tggcggtgca ggcctctcag  16260
cgccactgag acacacttgg aaacatcttg taataaacca atggactctg acgctcctgg  16320
tcctgtgatg tgttttcgta gacagatgga agacatcaat ttttcgtccc tggctccgcg  16380
acacggcacg cggccgttca tgggcacctg gagcgacatc ggcaccagcc aactgaacgg  16440
gggcgccttc aattggagca gtctctggag cgggcttaag aatttcgggt ccacgcttaa  16500
aacctatggc agcaaggcgt ggaacagcac cacagggcag gcgctgaggg ataagctgaa  16560
agagcagaac ttccagcaga aggtggtcga tgggctcgcc tcgggcatca acggggtggt  16620
ggacctggcc aaccaggccg tgcagcggca gatcaacagc cgcctggacc cggtgccgcc  16680
cgccggctcc gtggagatgc cgcaggtgga ggaggagctg cctcccctgg acaagcgggg  16740
cgagaagcga ccccgccccg atgcggagga gacgctgctg acgcacacgg acgagccgcc  16800
cccgtacgag gaggcggtga aactgggtct gcccaccacg cggcccatcg cgcccctggc  16860
caccggggtg ctgaaacccg aaaagcccgc gaccctggac ttgcctcctc cccagccttc  16920
ccgcccctct acagtggcta agcccctgcc gccggtggcc gtggcccgcg cgcgacccgg  16980
gggcaccgcc cgccctcatg cgaactggca gagcactctg aacagcatcg tgggtctggg  17040
agtgcagagt gtgaagcgcc gccgctgcta ttaaacctac cgtagcgctt aacttgcttg  17100
tctgtgtgtg tatgtattat gtcgccgccg ccgctgtcca ccagaaggag gagtgaagag  17160
gcgcgtcgcc gagttgcaag atggccaccc catcgatgct gccccagtgg gcgtacatgc  17220
acatcgccgg acaggacgct tcggagtacc tgagtccggg tctggtgcag tttgcccgcg  17280
ccacagacac ctacttcagt ctggggaaca agtttaggaa ccccacggtg gcgcccacgc  17340
acgatgtgac caccgaccgc agccagcggc tgacgctgcg cttcgtgccc gtggaccgcg  17400
aggacaacac ctactcgtac aaagtgcgct acacgctggc cgtgggcgac aaccgcgtgc  17460
tggacatggc cagcacctac tttgacatcc gcggcgtgct ggatcggggc cctagcttca  17520
aaccctactc cggcaccgcc tacaacagtc tggcccccaa gggagcaccc aacacttgtc  17580
agtggacata taaagccgat ggtgaaactg ccacagaaaa aacctataca tatggaaatg  17640
```

-continued

```
cacccgtgca gggcattaac atcacaaaag atggtattca acttggaact gacaccgatg  17700
atcagccaat ctacgcagat aaaacctatc agcctgaacc tcaagtgggt gatgctgaat  17760
ggcatgacat cactggtact gatgaaaagt atggaggcag agctcttaag cctgatacca  17820
aaatgaagcc ttgttatggt tcttttgcca agcctactaa taaagaagga ggtcaggcaa  17880
atgtgaaaac aggaacaggc actactaaag aatatgacat agacatggct ttctttgaca  17940
acagaagtgc ggctgctgct ggcctagctc cagaaattgt tttgtatact gaaaatgtgg  18000
atttggaaac tccagatacc catattgtat acaaagcagg cacagatgac agcagctctt  18060
ctattaattt gggtcagcaa gccatgccca acagacctaa ctacattggt ttcagagaca  18120
actttatcgg gctcatgtac tacaacagca ctggcaatat gggggtgctg gccggtcagg  18180
cttctcagct gaatgctgtg gttgacttgc aagacagaaa caccgagctg tcctaccagc  18240
tcttgcttga ctctctgggt gacagaaccc ggtatttcag tatgtggaat caggcggtgg  18300
acagctatga tcctgatgtg cgcattattg aaaatcatgg tgtggaggat gaacttccca  18360
actattgttt ccctctggat gctgttggca gaacagatac ttatcaggga attaaggcta  18420
atggaactga tcaaaccaca tggaccaaag atgacagtgt caatgatgct aatgagatag  18480
gcaagggtaa tccattcgcc atggaaatca acatccaagc caacctgtgg aggaacttcc  18540
tctacgccaa cgtggccctg tacctgcccg actcttacaa gtacacgccg gccaatgtta  18600
ccctgcccac caacaccaac acctacgatt acatgaacgg ccgggtggtg gcgccctcgc  18660
tggtggactc ctacatcaac atcggggcgc gctggtcgct ggatcccatg gacaacgtga  18720
acccctcaa ccaccaccgc aatgcggggc tgcgctaccg ctccatgctc ctgggcaacg  18780
ggcgctacgt gcccttccac atccaggtgc cccagaaatt tttcgccatc aagagcctcc  18840
tgctcctgcc cgggtcctac acctacgagt ggaacttccg caaggacgtc aacatgatcc  18900
tgcagagctc cctcggcaac gacctgcgca cggacggggc ctccatctcc ttcaccagca  18960
tcaacctcta cgccaccttc ttccccatgg cgcacaacac ggcctccacg ctcgaggcca  19020
tgctgcgcaa cgacaccaac gaccagtcct tcaacgacta cctctcggcg gccaacatgc  19080
tctaccccat cccggccaac gccaccaacg tgcccatctc catcccctcg cgcaactggg  19140
ccgccttccg cggctggtcc ttcacgcgtc tcaagaccaa ggagacgccc tcgctgggct  19200
ccgggttcga cccctacttc gtctactcgg gctccatccc ctacctcgac ggcaccttct  19260
acctcaacca caccttcaag aaggtctcca tcaccttcga ctcctccgtc agctggcccg  19320
gcaacgaccg gctcctgacg cccaacgagt tcgaaatcaa gcgcaccgtc gacggcgagg  19380
gctacaacgt ggcccagtgc aacatgacca aggactggtt cctggtccag atgctggccc  19440
actacaacat cggctaccag ggcttctacg tgcccgaggg ctacaaggac cgcatgtact  19500
ccttcttccg caacttccag cccatgagcc gccaggtggt ggacgaggtc aactacaagg  19560
actaccaggc cgtcaccctg gcctaccagc acaacaactc gggcttcgtc ggctacctcg  19620
cgcccaccat gcgccagggc cagccctacc ccgccaacta cccctacccg ctcatcggca  19680
agagcgccgt caccagcgtc acccagaaaa agttcctctg cgacagggtc atgtggcgca  19740
tccccttctc cagcaacttc atgtccatgg gcgcgctcac cgacctcggc cagaacatgc  19800
tctatgccaa ctccgcccac gcgctagaca tgaatttcga agtcgacccc atggatgagt  19860
ccacccttct ctatgttgtc ttcgaagtct tcgacgtcgt ccgagtgcac cagccccacc  19920
gcggcgtcat cgaggccgtc tacctgcgca cccccttctc ggccggtaac gccaccacct  19980
aagctcttgc ttcttgcaag ccatggccgc gggctccggc gagcaggagc tcagggccat  20040
catccgcgac ctgggctgcg ggccctactt cctgggcacc ttcgataagc gcttcccggg  20100
attcatggcc ccgcacaagc tggcctgcgc catcgtcaac acggccggcc gcgagaccgg  20160
gggcgagcac tggctggcct tcgcctggaa cccgcgctcg aacacctgct acctcttcga  20220
ccccttcggg ttctcggacg agcgcctcaa gcagatctac cagttcgagt acgagggcct  20280
gctgcgccgc agcgccctgg ccaccgagga ccgctgcgtc accctggaaa agtccaccca  20340
gaccgtgcag ggtccgcgct cggccgcctg cgggctcttc tgctgcatgt tcctgcacgc  20400
cttcgtgcac tggcccgacc gccccatgga caagaacccc accatgaact tgctgacggg  20460
ggtgccccaac ggcatgctcc agtcgcccca ggtggaaccc accctgcgcc gcaaccagga  20520
ggcgctctac cgcttcctca actcccactc cgcctacttt cgctcccacc gcgcgcgcat  20580
cgagaaggcc accgccttcg accgcatgaa tcaagacatg taaaccgtgt gtgtatgtta  20640
aatgtcttta ataaacagca ctttcatgtt acacatgcat ctgagatgat ttatttagaa  20700
atcgaaaggg ttctgccggg tctcggcatg gcccgcgggc agggacacgt tgcggaactg  20760
gtacttggcc agccacttga actcggggat cagcagtttg ggcagcgggg tgtcggggaa  20820
ggagtcggtc cacagcttcc gcgtcagttg cagggcgccc agcaggtcgg gcgcggagat  20880
cttgaaatcg cagttgggac ccgcgttctg cgcgcgggag ttgcggtaca cggggttgca  20940
gcactggaac accatcaggg ccgggtgctt cacgctcgcc agcaccgtcg cgtcggtgat  21000
gctctccacg tcgaggtcct cggcgttggc catcccgaag gggtcatct tgcaggtctg  21060
ccttcccatg gtgggcacgc acccgggctt gtggttgcaa tcgcagtgca gggggatcag  21120
catcatctgg gcctggtcgg cgttcatccc cgggtacatg gccttcatga aagcctccaa  21180
ttgcctgaac gcctgctggg ccttggctcc ctcggtgaag aagaccccgc aggacttgct  21240
agagaactgg ttggtggcgc acccggcgtc gtgcacgcag cagcgcgcgt cgttgttggc  21300
cagctgcacc acgctgcgcc cccagcggtt ctgggtgatc ttggcccggt cggggttctc  21360
cttcagcgcg cgctgcccgt tctcgctcgc cacatccatc tcgatcatgt gctccttctg  21420
gatcatggtg gtcccgtgca ggcaccgcag cttgccctcg gcctcggtgc acccgtgcag  21480
ccacagcgcg cacccggtgc actcccagtt cttgtgggcg atctgggaat gcgcgtgcac  21540
gaagccctgc aggaagcggc ccatcatggt ggtcagggtc ttgttgctag tgaaggtcag  21600
cggaatgccg cggtgctcct cgttgatgta caggtggcag atgcggcggt acacctcgcc  21660
ctgctcgggc atcagctgga agttggcttt caggtcggtc tccacgcggt agcggtccat  21720
cagcatagtc atgatttcca tacccttctc ccaggccgag acgatgggca ggctcatagg  21780
gttcttcacc atcatcttag cgctagcagc cgcggccagg gggtcgctct cgtccagggt  21840
ctcaaagctc cgcttgccgt ccttctcggt gatccgcacc ggggggtagc tgaagcccac  21900
ggccgccagc tcctcctcgg cctgtctttc gtcctcgctg tcctggctga cgtcctgcag  21960
gaccacatgc ttggtcttgc ggggtttctt cttgggcggc agcggcggcg gagatgttgg  22020
agatggcgag gggagcgcg agttctcgct caccactact atctcttcct cttcttggtc  22080
cgaggccacg cggcggtagg tatgtctctt cgggggcaga ggcggaggcg acgggctctc  22140
gccgccgcga cttggcggat ggctggcaga gccccttccg cgttcggggg tgcgctcccg  22200
gcggcgctct gactgacttc ctccgcggcc ggccattgtg ttctcctagg gaggaacaac  22260
aagcatggag actcagccat cgccaacctc gccatctgcc cccaccgccg acgagaagca  22320
gcagcagcag aatgaaagct taaccgcccc gccgcccagc cccgccacct ccgacgcggc  22380
```

-continued

```
cgtcccagac atgcaagaga tggaggaatc catcgagatt gacctgggct atgtgacgcc  22440
cgcggagcac gaggaggagc tggcagtgcg cttttcacaa gaagagatac accaagaaca  22500
gccagagcag gaagcagaga atgagcagag tcaggctggg ctcgagcatg acggcgacta  22560
cctccacctg agcggggggg aggacgcgct catcaagcat ctggcccggc aggccaccat  22620
cgtcaaggat gcgctgctcg accgcaccga ggtgcccctc agcgtggagg agctcagccg  22680
cgcctacgag ttgaacctct tctcgccgcg cgtgcccccc aagcgccagc ccaatggcac  22740
ctgcgagccc aacccgcgcc tcaacttcta cccggtcttc gcggtgcccg aggccctggc  22800
cacctaccac atctttttca agaaccaaaa gatccccgtc tcctgccgcg ccaaccgcac  22860
ccgcgccgac gccctttca acctgggtcc cggcgcccgc ctacctgata tcgcctcctt  22920
ggaagaggtt cccaagatct tcgagggtct gggcagcgac gagactcggg ccgcgaacgc  22980
tctgcaagga gaaggaggag agcatgagca ccacagcgcc ctggtcgagt tggaaggcga  23040
caacgcgcgg ctggcggtgc tcaaacgcac ggtcgagctg acccatttcg cctacccggc  23100
tctgaacctg ccccccaaag tcatgagcgc ggtcatggac caggtgctca tcaagcgcgc  23160
gtcgcccatc tccgaggacg agggcatgca agactccgag gagggcaagc ccgtggtcag  23220
cgacgagcag ctggcccggt ggctgggtcc taatgctagt ccccagagtt tggaagagcg  23280
gcgcaaactc atgatggccg tggtcctggt gaccgtggag ctggagtgcc tgcgccgctt  23340
cttcgccgac gcggagaccc tgcgcaaggt cgaggagaac ctgcactacc tcttcaggca  23400
cgggttcgtg cgccaggcct gcaagatctc caacgtggag ctgaccaacc tggtctccta  23460
catgggcatc ttgcacgaga accgcctggg gcagaacgtg ctgcacacca ccctgcgcgg  23520
ggaggcccgg cgcgactaca tccgcgactg cgtctacctc tacctctgcc acacctggca  23580
gacgggcatg ggcgtgtggc agcagtgtct ggaggagcag aacctgaaag agctctgcaa  23640
gctcctgcag aagaacctca agggtctgtg gaccgggttc gacgagcgca ccaccgcctc  23700
ggacctggcc gacctcattt tccccgagcg cctcaggctg acgctgcgca acggcctgcc  23760
cgactttatg agccaaagca tgttgcaaaa ctttcgctct ttcatcctcg aacgctccgg  23820
aatcctgccc gccacctgct ccgcgctgcc ctcggacttc gtgccgctga ccttccgcga  23880
gtgccccccg ccgctgtgga gccactgcta cctgctgcgc ctggccaact acctggccta  23940
ccactcggac gtgatcgagg acgtcagcgg cgagggcctg ctcgagtgcc actgccgctg  24000
caacctctgc acgccgcacc gctccctggc ctgcaacccc cagctgctga gcgagaccca  24060
gatcatcggc accttcgagt tgcaagggcc cagcgaaggc gagggttcag ccgccaaggg  24120
gggtctgaaa ctcaccccgg ggctgtggac ctcggcctac ttgcgcaagt tcgtgcccga  24180
ggactaccat cccttcgaga tcaggttcta cgaggaccaa tcccatccgc ccaaggccga  24240
gctgtcggcc tgcgtcatca cccagggggc gatcctggcc caattgcaag ccatccagaa  24300
atcccgccaa gaattcttgc tgaaaaaggg ccgcggggtc tacctcgacc cccagaccgg  24360
tgaggagctc aaccccggct tcccccagga tgccccgagg aaacaagaag ctgaaagtgg  24420
agctgccgcc cgtggaggat ttggaggaag actgggagaa cagcagtcag gcagaggagg  24480
aggagatgga ggaagactgg gacagcactc aggcagagga ggacagcctg caagacagtc  24540
tggaggaaga cgaggaggag gcagaggagg aggtggaaga agcagccgcc gccagaccgt  24600
cgtcctcggc gggggagaaa gcaagcagca cggataccat ctccgctccg ggtcggggtc  24660
ccgctcgacc acacagtaga tgggacgaga ccggacgatt cccgaacccc accacccaga  24720
ccggtaagaa ggagcggcag ggatacaagt cctggcgggg gcacaaaaac gccatcgtct  24780
cctgcttgca ggcctgcggg ggcaacatct ccttcacccg gcgctacctg ctcttccacc  24840
gcggggtgaa ctttccccgc aacatcttgc attactaccg tcacctccac agcccctact  24900
acttccaaga agaggcagca gcagcagaaa aagaccagca gaaaaccagc agctagaaaa  24960
tccacagcgg cggcagcagg tggactgagg atcgcggcga acgagccggc gcaaacccgg  25020
gagctgagga accggatctt tcccaccctc tatgccatct tccagcagag tcgggggcag  25080
gagcaggaac tgaaagtcaa gaaccgttct ctgcgctcgc tcacccgcag ttgtctgtat  25140
cacaagagcg aagaccaact tcagcgcact ctcgaggacg ccgaggctct cttcaacaag  25200
tactgcgcgc tcactcttaa agagtagccc gcgcccgccc agtcgcagaa aaaggcggga  25260
attacgtcac ctgtgccctt cgccctagcc gcctccaccc atcatcatga gcaaagagat  25320
tcccacgcct tacatgtgga gctaccagcc ccagatgggc ctggccgccg gtgccgccca  25380
ggactactcc acccgcatga attggctcag cgccgggccc gcgatgatct cacgggtgaa  25440
tgacatccgc gcccaccgaa accagatact cctagaacag tcagcgctca ccgccacgcc  25500
ccgcaatcac ctcaatccgc gtaattggcc cgccgccctg gtgtaccagg aaattcccca  25560
gcccacgacc gtactacttc cgcgagacgc ccaggccgaa gtccagctga ctaactcagg  25620
tgtccagctg gcgggcggcg ccaccctgtg tcgtcaccgc cccgctcagg gtataaagcg  25680
gctggtgatc cggggcagag gcacacagct caacgacgag gtggtgagct cttcgctggg  25740
tctgcgacct gacggagtct tccaactcgc cggatcgggg agatcttcct tcacgcctcg  25800
tcaggccgtc ctgactttgg agagttcgtc ctcgcagccc cgctcgggtg gcatcggcac  25860
tctccagttc gtggaggagt tcactccctc ggtctacttc aacccctctc ccggctcccc  25920
cggccactac ccggacgagt tcatcccgaa cttcgacgcc atcagcgagt cggtggacgg  25980
ctacgattga atgtcccatg gtggcgcagc tgacctagct cggcttcgac acctggacca  26040
ctgccgccgc ttccgctgct tcgctcggga tctcgccgag tttgcctact ttgagctgcc  26100
cgaggagcac cctcagggcc cggcccacgg agtgcggatc gtcgtcgaag gggcctcga  26160
ctcccacctg cttcggatct tcagccagcg tccgatcctg gtcgagcgcg agcaaggaca  26220
gacccttctg actctgtact gcatctgcaa ccaccccggc ctgcatgaaa gtctttgttg  26280
tctgctgtgt actgagtata ataaaagctg agatcagcga ctactccgga cttccgtgtg  26340
ttcctgaatc catcaaccag tctttgttct tcaccgggaa cgagaccgag ctccagctcc  26400
agtgtaagcc ccacaagaag tacctcacct ggctgttcca gggctccccg atcgccgttg  26460
tcaaccactg cgacaacgac ggagtcctgc tgagcggccc tgccaacctt actttttcca  26520
cccgcagaag caagctccag ctcttccaac ccttcctccc cgggacctat cagtgcgtct  26580
cgggaccctg ccatcacacc ttccacctga tcccgaatac cacagcgtcg ctcccccgcta  26640
ctaacaacca aactaacctc caccaacgcc accgtcgcga cggccacaat acatgcccat  26700
attagactat gaggccgagc cacagcgacc catgctcccc gctattagtt acttcaatct  26760
aaccggcgga gatgactgac ccactggcca acaacaacgt caacgacctt ctcctggaca  26820
tggacggccg cgcctcggag cagcgactcg cccaacttcg cattcgccag cagcaggaga  26880
gagccgtcaa ggagctgcag gatgcggtgg ccatccacca gtgcaagaga ggcatcttct  26940
gcctggtgaa acaggccaag atctcctacg aggtcactcc aaacgaccat cgcctctcct  27000
acgagctcct gcagcagcgc cagaagttca cctgcctggt cggagtcaac cccatcgtca  27060
tcacccagca gtctggcgat accaaggggt gcatccactg ctcctgcgac tcccccgact  27120
```

-continued

```
gcgtccacac tctgatcaag accctctgcg gcctccgcga cctcctcccc atgaactaat  27180
cacccccttta tccagtgaaa taaagatcat attgatgatg attttacaga aataaaaaat  27240
aatcatttga tttgaaataa agatacaatc atattgatga tttgagttta acaaaaaaat  27300
aaagaatcac ttacttgaaa tctgatacca ggtctctgtc catgttttct gccaacacca  27360
cttcactccc ctcttcccag ctctggtact gcaggccccg gcgggctgca aacttcctcc  27420
acacgctgaa ggggatgtca aattcctcct gtccctcaat cttcatttta tcttctatca  27480
gatgtccaaa aagcgcgtcc gggtggatga tgacttcgac cccgtctacc cctacgatgc  27540
agacaacgca ccgaccgtgc ccttcatcaa cccccccttc gtctcttcag atggattcca  27600
agagaagccc ctgggggtgt tgtccctgcg actggccgac cccgtcacca ccaagaacgg  27660
ggaaatcacc ctcaagctgg gagaggggggt ggacctcgat tcctcgggaa aactcatctc  27720
caacacggcc accaaggccg ccgcccctct cagtttttcc aacaacacca tttcccttaa  27780
catggatcac ccctttttaca ctaaagatgg aaaattatcc ttacaagttt ctccaccatt  27840
aaatatactg agaacaagca ttctaaacac actagcttta ggttttggat caggtttagg  27900
actccgtggc tctgccttgg cagtacagtt agtctctcca cttacatttg atactgatgg  27960
aaacataaag cttaccttag acagaggttt gcatgttaca acaggagatg caattgaaag  28020
caacataagc tgggctaaag gtttaaaatt tgaagatgga gccatagcaa ccaacattgg  28080
aaatgggtta gagtttggaa gcagtagtac agaaacaggt gttgatgatg cttacccaat  28140
ccaagttaaa cttggatctg gccttagctt tgacagtaca ggagccataa tggctggtaa  28200
caaagaagac gataaactca ctttgtggac aacacctgat ccatcaccaa actgtcaaat  28260
actcgcagaa aatgatgcaa aactaacact ttgcttgact aaatgtggta gtcaaatact  28320
ggccactgtg tcagtcttag ttgtaggaag tggaaaccta aaccccatta ctggcaccgt  28380
aagcagtgct caggtgtttc tacgttttga tgcaaacggt gttcttttaa cagaacattc  28440
tacactaaaa aaatactggg ggtataggca gggagatagc atagatggca ctccatatac  28500
caatgctgta ggattcatgc ccaatttaaa agcttatcca aagtcacaaa gttctactac  28560
taaaaataat atagtagggc aagtatacat gaatggagat gtttcaaaac ctatgcttct  28620
cactataacc ctcaatggta ctgatgacag caacagtaca tattcaatgt cattttcata  28680
cacctggact aatggaagct atgttggagc aacatttggg gctaactctt ataccttctc  28740
atacatcgcc caagaatgaa cactgtatcc caccctgcat gccaaccctt cccaccccac  28800
tctgtggaac aaactctgaa acacaaaata aaataaagtt caagtgtttt attgattcaa  28860
cagttttaca ggattcgagc agttattttt cctccaccct cccaggacat ggaatacacc  28920
accctctccc cccgcacagc cttgaacatc tgaatgccat tggtgatgga catgcttttg  28980
gtctccacgt tccacacagt ttcagagcga gccagtctcg ggtcggtcag ggagatgaaa  29040
ccctccgggc actcccgcat ctgcacctca cagctcaaca gctgaggatt gtcctcggtg  29100
gtcgggatca cggttatctg gaagaagcag aagagcggcg gtgggaatca tagtccgcga  29160
acgggatcgg ccggtggtgt cgcatcaggc cccgcagcag tcgctgccgc cgccgctccg  29220
tcaagctgct gctcaggggg tccgggtcca gggactccct cagcatgatg cccacggccc  29280
tcagcatcag tcgtctggtg cggcgggcgc agcagcgcat gcggatctcg ctcaggtcgc  29340
tgcagtacgt gcaacacaga accaccaggt tgttcaacag tccatagttc aacacgctcc  29400
agccgaaact catcgcggga aggatgctac ccacgtggcc gtcgtaccag atcctcaggt  29460
aaatcaagtg gtgcccccctc cagaacacgc tgcccacgta catgatctcc ttgggcatgt  29520
ggcggttcac cacctcccgg taccacatca ccctctggtt gaacatgcag ccccggatga  29580
tcctgcggaa ccacagggcc agcaccgccc cgcccgccat gcagcgaaga gaccccgggt  29640
cccggcaatg gcaatggagg acccaccgct cgtacccgtg gatcatctgg gagctgaaca  29700
agtctatgtt ggcacagcac aggcatatgc tcatgcatct cttcagcact ctcaactcct  29760
cgggggtcaa aaccatatcc cagggcacgg ggaactcttg caggacagcg aaccccgcag  29820
aacagggcaa tcctcgcaca gaacttacat tgtgcatgga cagggtatcg caatcaggca  29880
gcaccgggtg atcctccacc agagaagcgc gggtctcggt ctcctcacag cgtggtaagg  29940
gggccggccg atacgggtga tggcgggacg cggctgatcg tgttcgcgac cgtgtcatga  30000
tgcagttgct ttcggacatt ttcgtacttg ctgtagcaga acctggtccg ggcgctgcac  30060
accgatcgcc ggcggcggtc tcggcgcttg gaacgctcgg tgttgaaatt gtaaaacagc  30120
cactctctca gaccgtgcag cagatctagg gcctcaggag tgatgaagat cccatcatgc  30180
ctgatggctc tgatcacatc gaccaccgtg gaatgggcca gacccagcca gatgatgcaa  30240
ttttgttggg tttcggtgac ggcgggggag ggaagaacag gaagaaccat gattaacttt  30300
taatccaaac ggtctcggag tacttcaaaa tgaagatcgc ggagatggca cctctcgccc  30360
ccgctgtgtt ggtggaaaat aacagccagg tcaaaggtga tacggttctc gagatgttcc  30420
acggtggctt ccagcaaagc ctccacgcgc acatccagaa acaagacaat agcgaaagcg  30480
ggagggttct ctaattcctc aatcatcatg ttacactcct gcaccatccc cagataattt  30540
tcatttttcc agccttgaat gattcgaact agttcgtgag gtaaatccaa gccagccatg  30600
ataaagagct cgcgcagagc gccctccacc ggcattctta agcacaccct cataattcca  30660
agatattctg ctcctggttc acctgcagca gattgacaag cggaatatca aaatctctgc  30720
cgcgatccct gagctcctcc ctcagcaata actgtaagta ctctttcata tcctctccga  30780
aatttttagc cataggacca ccaggaataa gattagggca agccacagta cagataaacc  30840
gaagtcctcc ccagtgagca ttgccaaatg caagactgct ataagcatgc tggctagacc  30900
cggtgatatc ttccagataa ctggacagaa aatcgcccag gcaattttta agaaaatcaa  30960
caaaagaaaa atcctccagg tggacgttta gagcctcggg aacaacgatg aagtaaatgc  31020
aagcggtgcg ttccagcatg gttagttagc tgatctgtag aaaaaacaaa aatgaacatt  31080
aaaccatgct agcctggcga acaggtgggt aaatcgttct ctccagcacc aggcaggcca  31140
cggggtctcc ggcgcgaccc tcgtaaaaat tgtcgctatg attgaaaacc atcacagaga  31200
gacgttcccg gtggccggcg tgaatgattc gacaagatga atacaccccc ggaacattgg  31260
cgtccgcgag tgaaaaaaag cgcccgagga agcaataagg cactacaatg ctcagtctca  31320
agtccagcaa agcgatgcca tgcggatgaa gcacaaaatt ctcaggtgcg tacaaaatgt  31380
aattactccc ctcctgcaca ggcagcaaag cccccgatcc ctccaggtac acatacaaag  31440
cctcagcgtc catagcttac cgagcagcag cacacaacag gcgcaagagt cagagaaagg  31500
ctgagctcta acctgtccac ccgctctctg ctcaatatat agcccagatc tacactgacg  31560
taaaggccaa agtctaaaaa tacccgccaa ataatcacac acgcccagca cacgcccaga  31620
aaccggtgac acactcaaaa aaatacgcgc acttcctcaa acgcccaaaa ctgccgtcat  31680
ttccgggttc ccacgctacg tcatcaaaac acgactttca aattccgtcg accgttaaaa  31740
acgtcacccg ccccgcccct aacggtcgcc cgtctctcag ccaatcagcg ccccgcatcc  31800
ccaaattcaa acacctcatt tgcatattaa cgcgcacaaa aagtttgagg tatattattg  31860
```

-continued

```
atgatgg                                                             31867

SEQ ID NO: 12           moltype = DNA  length = 32788
FEATURE                 Location/Qualifiers
misc_feature            1..32788
                        note = Description of Artificial Sequence: Synthetic
                         polynucleotide
source                  1..32788
                        mol_type = other DNA
                        organism = synthetic construct
SEQUENCE: 12
ccatcttcaa taatatacct caaacttttt gtgcgcgtta atatgcaaat gaggcgtttg  60
aatttgggga ggaagggcgg tgattggtcg agggatgagc gaccgttagg ggcggggcga  120
gtgacgtttt gatgacgtgg ttgcgaggag gagccagttt gcaagttctc gtgggaaaag  180
tgacgtcaaa cgaggtgtgg tttgaacacg gaaatactca attttcccgc gctctctgac  240
aggaaatgag gtgtttctgg gcggatgcaa gtgaaaacgg gccattttcg cgcgaaaact  300
gaatgaggaa gtgaaaatct gagtaatttc gcgtttatgg cagggaggag tatttgccga  360
gggccgagta gactttgacc gattacgtgg gggtttcgat taccgtgttt ttcacctaaa  420
tttccgcgta cggtgtcaaa gtccggtgtt tttacgtagg tgtcagctga tcgccagggt  480
atttaaacct gcgctctcca gtcaagaggc cactcttgag tgccagcgag aagagttttc  540
tcctccgcgc cgcgagtcag atctacactt tgaaagtagg gataacaggg taatgacatt  600
gattattgac tagttgttaa tagtaatcaa ttacggggtc attagttcat agcccatata  660
tggagttccg cgttacataa cttacggtaa atggcccgcc tggctgaccg cccaacgacc  720
cccgcccatt gacgtcaata atgacgtatg ttcccatagt aacgccaata gggactttcc  780
attgacgtca atgggtggag tatttacggt aaactgccca cttggcagta catcaagtgt  840
atcatatgcc aagtccgccc cctattgacg tcaatgacgg taaatggccc gcctggcatt  900
atgcccagta catgacctta cgggactttc ctacttggca gtacatctac gtattagtca  960
tcgctattac catggtgatg cggttttggc agtacaccaa tgggcgtgga tagcggtttg  1020
actcacgggg atttccaagt ctccacccca ttgacgtcaa tgggagtttg ttttggcacc  1080
aaaatcaacg ggactttcca aaatgtcgta ataaccccgc cccgttgacg caaatgggcg  1140
gtaggcgtgt acggtgggag gtctatataa gcagagctcg tttagtgaac cgtcagatcg  1200
cctggaacgc catccacgct gttttgacct ccatagaaga cagcgatcgc gccaccatgg  1260
ccgggatgtt ccaggcactg tccgaaggct gcacaccccta tgatattaac cagatgctga  1320
atgtcctggg agaccaccag gtctctggcc tggagcagct ggagagcatc atcaacttcg  1380
agaagctgac cgagtggaca agctccaatg tgatgcctat cctgtcccca ctgaccaagg  1440
gcatcctggg cttcgtgttt accctgacag tgccttctga gcggggcctg tcttgcatca  1500
gcgaggcaga cgcaaccaca ccagagtccg ccaatctggg cgaggagatc ctgtctcagc  1560
tgtacctgtg gccccgggtg acatatcact ccccttctta cgcctatcac cagttcgagc  1620
ggagagccaa gtacaagaga cacttcccag gctttggcca gtctctgctg ttcggctacc  1680
ccgtgtacgt gttcggcgat tgcgtgcagg gcgactggga tgccatccgg tttagatact  1740
gcgcaccacc tggatatgca ctgctgaggt gtaacgacac caattattcc gccctgctgg  1800
cagtgggcgc cctggagggc cctcgcaatc aggattggct gggcgtgcca aggcagctgg  1860
tgacacgcat gcaggccatc cagaacgcag gcctgtgcac cctggtggca atgctggagg  1920
agacaatctt ctggctgcag gcctttctga tggccctgac cgacagcggc cccaagacaa  1980
acatcatcgt ggattcccag tacgtgatgg gcatctccaa gccttctttc caggagtttg  2040
tggactggga gaacgtgagc ccagagctga attccaccga tcagccattc tggcaggcag  2100
gaatcctggc aaggaacctg gtgcctatgg tggccacagt gcagggccag aatctgaagt  2160
accagggcca gagcctggtc atcagcgcct ccatcatcgt gtttaacctg ctggagctgg  2220
agggcgacta tcgggacgat ggcaacgtgt gggtgcacac cccactgagc cccagaacac  2280
tgaacgcctg ggtgaaggcc gtggaggaga agaagggcat cccagtgcac ctggagctgg  2340
cctccatgac caatatggag ctgatgtcta gcatcgtgca ccagcaggtg aggacatacg  2400
gacccgtgtt catgtgcctg ggaggcctgc tgaccatggt ggcaggagcc gtgtggctga  2460
cagtgcgggt gctggagctg ttcagagccg cccagctggc caacgatgtg gtgctgcaga  2520
tcatggagct gtgcggagca gcctttcgcc aggtgtgcca caccacagtg ccatggccca  2580
atgcctccct gacccccaag tggaacaatg agacaacaca gcctcagatc gccaactgta  2640
gcgtgtacga cttcttcgtg tggctgcact actatagcgt gagggatacc ctgtggcccc  2700
gcgtgacata ccacatgaat aagtacgcct atcacatgct ggagaggcgc gccaagtata  2760
agagaggccc tggcccaggc gcaaagtttg tggcagcatg gaccctgaag gccgccgccg  2820
gccccggccc cggccagtat atcaaggcta acagtaagtt cattggaatc acagagctgg  2880
gacccggacc tggataatga gtttaaactc ccatttaaat gtgagggtta atgcttcgag  2940
cagacatgat aagatacatt gatgagtttg gacaaaccac aactagaatg cagtgaaaaa  3000
aatgctttat ttgtgaaatt tgtgatgcta ttgctttatt tgtaaccatt ataagctgca  3060
ataaacaagt taacaacaac aattgcattc attttatgtt tcaggttcag ggggagatgt  3120
gggaggtttt ttaaagcaag taaaacctct acaaatgtgg taaaataact ataacggtcc  3180
taaggtagcg agtgagtagt gttctggggc gggggaggac ctgcatgagg gccagaataa  3240
ctgaaatctg tgcttttctg tgtgttgcag cagcatgagc ggaagcggct cctttgaggg  3300
aggggtattc agcccttatc tgacggggcg tctcccctcc tgggcgggag tgcgtcagaa  3360
tgtgatggga tccacggtgg acggccggcc cgtgcagccc gcgaactctt caaccctgac  3420
ctatgcaacc ctgagctctt cgtcgttgga cgcagctgcc gccgcagctg ctgcatctgc  3480
cgccagcgcc gtgcgcggaa tggccatggg cgccggctac tacggcactc tggtggccaa  3540
ctcgagttcc accaataatc ccgccagcct gaacgaggag aagctgttgc tgctgatggc  3600
ccagctcgag gccttgaccc agcgcctggg cgagctgacc cagcaggtgg ctcagctgca  3660
ggagcagacg cgggccgcgg ttgccacggt gaaatccaaa taaaaaatga atcaataaat  3720
aaacggagac ggttgttgat tttaacacag agtctgaatc tttatttgat ttttcgcgcg  3780
cggtaggccc tggaccaccg gtctcgatca ttgagcaccc ggtggatctt ttccaggacc  3840
cggtagaggt gggcttggat gttgaggtac atgggcatga gcccgtcccg ggggtggagg  3900
tagctccatt gcagggcctc gtgctcgggg gtggtgttgt aaatcaccca gtcatagcag  3960
gggcgcaggg catggtgttg cacaatatct ttgaggagga gactgatggc cacgggcagc  4020
cctttggtgt aggtgtttac aaatctgttg agctgggagg gatgcatgcg gggggagatg  4080
```

-continued

```
aggtgcatct tggcctggat cttgagattg gcgatgttac cgcccagatc ccgcctgggg  4140
ttcatgttgt gcaggaccac cagcacggtg tatccggtgc acttggggaa tttatcatgc  4200
aacttggaag ggaaggcgtg aaagaatttg gcgacgcctt tgtgcccgcc caggttttcc  4260
atgcactcat ccatgatgat ggcgatgggc ccgtgggcgg cggcctgggc aaagacgttt  4320
cgggggtcgg acacatcata gttgtggtcc tgggtgaggt catcataggc cattttaatg  4380
aatttggggc ggagggtgcc ggactggggg acaaaggtac cctcgatccc gggggcgtag  4440
ttcccctcac agatctgcat ctcccaggct ttgagctcgg aggggggat catgtccacc  4500
tgcggggcga taaagaacac ggtttccggg gcgggggaga tgagctgggc cgaaagcaag  4560
ttccggagca gctgggactt gccgcagccg gtggggccgt agatgacccc gatgaccggc  4620
tgcaggtggt agttgaggga gagacagctg ccgtcctccc ggaggagggg ggccacctcg  4680
ttcatcatct cgcgcacgtg catgttctcg cgcaccagtt ccgccaggag gcgctctccc  4740
cccagggata ggagctcctg gagcgaggcg aagtttttca gcggcttgag tccgtcggcc  4800
atgggcattt tggagagggt ttgttgcaag agttccaggc ggtcccagag ctcggtgatg  4860
tgctctacgg catctcgatc cagcagacct cctcgtttcg cgggttggga cggctgcggg  4920
agtagggcac cagacgatgg gcgtccagcg cagccagggt ccggtccttc cagggtcgca  4980
gcgtccgcgt cagggtggtc tccgtcacgg tgaaggggtg cgcgccgggc tgggcgcttg  5040
cgagggtgcg cttcaggctc atccggctgg tcgaaaaccg ctcccgatcg gcgccctgcg  5100
cgtcggccag gtagcaattg accatgagtt cgtagttgag cgcctcggcc gcgtggcctt  5160
tggcgcggag cttacctttg gaagtctgcc cgcaggcggg acagaggagg gacttgaggg  5220
cgtagagctt gggggcgagg aagacggact cgggggcgta ggcgtccgcg ccgcagtggg  5280
cgcagacggt ctcgcactcc acgagccagg tgaggtcggg ctggtcgggg tcaaaaacca  5340
gtttcccgcc gttctttttg atgcgtttct tacctttggt ctccatgagc tcgtgtcccc  5400
gctgggtgac aaagaggctg tccgtgtccc cgtagaccga ctttatgggc cggtcctcga  5460
gcggtgtgcc gcggtcctcc tcgtagagga accccgccca ctccgagacg aaagcccggg  5520
tccaggccag cacgaaggag gccacgtggg acgggtagcg gtcgttgtcc accagcgggt  5580
ccaccttttc cagggtatgc aaacacatgt cccctcgtc cacatccagg aaggtgattg  5640
gcttgtaagt gtaggccacg tgaccggggg tcccggccgg gggggtataa aagggtgcgg  5700
gtccctgctc gtcctcactg tcttccggat cgctgtccag gagcgccagc tgttggggta  5760
ggtattccct ctcgaaggcg ggcatgacct cggcactcag gttgtcagtt tctagaaacg  5820
aggaggattt gatattgacg gtgccggcgg agatgccttt caagagcccc tcgtccatct  5880
ggtcagaaaa gacgatcttt ttgttgtcga gcttggtggc gaaggagccg tagagggcgt  5940
tggagaggag cttggcgatg gagcgcatgg tctggttttt ttccttgtcg gcgcgctcct  6000
tggcggcgat gttgagctgc acgtactcgc gcgccacgca cttccattcg gggaagacgg  6060
tggtcagctc gtcgggcacg attctgacct gccagccccg attatgcagg gtgatgaggt  6120
ccacactggt ggccacctcg ccgcgcaggg gctcattagt ccagcagagg cgtccgccct  6180
tgcgcgagca gaagggggc agggggtcca gcatgacctc gtcggggggg tcggcatcga  6240
tggtgaagat gccgggcagg aggtcggggt caaagtagct gatggaagtg gccagatcgt  6300
ccagggcagc ttgccattcg cgcacggcca gcgcgctctc gtagggactg aggggcgtgc  6360
cccagggcat gggatgggta agcgcggagg cgtacatgcc gcagatgtcg tagacgtaga  6420
ggggctcctc gaggatgccg atgtaggtgg ggtagcagcg cccccgcgg atgctggcgc  6480
gcacgtagtc atacagctcg tgcgaggggg cgaggagccc cgggcccagg ttggtgcgac  6540
tgggcttttc ggcgcggtag acgatctggc ggaaaatggc atgcgagttg gaggagatgg  6600
tgggcctttg gaagatgttg aagtgggcgt ggggcagtcc gaccgagtcg cggatgaagt  6660
gggcgtagga gtcttgcagc ttggcgacga gctcggcggt gactaggacg tccagagcgc  6720
agtagtcgag ggtctcctgg atgatgtcat acttgagctg tccctttgt ttccacagct  6780
cgcggttgag aaggaactct tcgcggtcct tccagtactc ttcgaggggg aacccgtcct  6840
gatctgcacg gtaagagcct agcatgtaga actggttgac ggccttgtag gcgcagcagc  6900
ccttctccac ggggagggcg taggcctggg cggccttgcg cagggaggtg tgcgtgaggg  6960
cgaaagtgtc cctgaccatg accttgagga actggtgctt gaagtcgata tcgtcgcagc  7020
cccctgctc ccagagctgg aagtccgtgc gcttcttgta ggcggggttg ggcaaagcga  7080
aagtaacatc gttgaagagg atcttgcccg cgcggggcat aaagttgcga gtgatgcgga  7140
aaggttgggg cacctcggcc cggttgttga tgacctgggc ggcgagcacg atctcgtcga  7200
agccgttgat gttgtggccc acgatgtaga gttccacgaa tcgcggacgg cccttgacgt  7260
ggggcagttt cttgagctcc tcgtaggtga gctcgtcggg gtcgctgagc ccgtgctgct  7320
cgagcgccca gtcggcgaga tgggggttgg cgcggaggaa ggaagtccag agatccacgg  7380
ccagggcggt ttgcagacgg tcccggtact gacggaactg ctgcccgacg gccatttttt  7440
cgggggtgac gcagtagaag gtgcggggt ccccgtgcca gcgatcccat ttgagctgga  7500
gggcgagatc gagggcgagc tcgacgagcc ggtcgtcccc ggagagtttc atgaccagca  7560
tgaaggggac gagctgcttg ccgaaggacc ccatccaggt gtaggtttcc acatcgtagg  7620
tgaggaagag cctttcggtg cgaggatgcg agccgatggg gaagaactgg atctcctgcc  7680
accaattgga ggaatggctg ttgatgtgat ggaagtagaa atgccgacgg cgcgccgaac  7740
actcgtgctt gtgtttatac aagcggccac agtgctcgca acgctgcacg ggatgcacgt  7800
gctgcacgag ctgtacctga gttcctttga cgaggaattt cagtgggaag tggagtcgtg  7860
gcgcctgcat ctcgtgctgt actacgtcgt ggtggtcggc ctggccctct tctgcctcga  7920
tggtggtcat gctgacgagc ccgcgcggga ggcaggtcca gacctcggcg cgagcgggtc  7980
ggagagcgag gacgagggcg cgcaggccgg agctgtccag ggtcctgaga cgctgcggag  8040
tcaggtcagt gggcagcggc ggcgcgcggt tgacttgcag gagtttttcc agggcgcgcg  8100
ggaggtccag atggtacttg atctccaccg cgccattggt ggcgacgtcg atggcttgca  8160
gggtcccgtg cccctggggt gtgaccaccg tcccccgttt cttcttgggc ggctggggcg  8220
acgggggcgg tgcctcttcc atggttagaa gcggcggcga ggacgcgcgc cgggcggcag  8280
gggcggctcg gggcccggag gcaggggcgg caggggcacg tcggcgccgc gcgcgggtag  8340
gttctggtac tgcgcccgga gaagactggc gtgagcgacg acgcgacggt tgacgtcctg  8400
gatctgacgc ctctgggtga aggccacggg acccgtgagt ttgaacctga aagagagttc  8460
gacagaatca atctcggtat cgttgacggc ggcctgccgc aggatctctt gcacgtcgcc  8520
cgagttgtcc tggtaggcga tctcggtcat gaactgctcg atctcctcct cttgaaggtc  8580
tccgcggccg gcgcgctcca cggtggccgc gaggtcgttg gagatgcggc ccatgagctg  8640
cgagaaggcg ttcatgcccg cctcgttcca gacgcggctg tagaccacga cgccctcggg  8700
atcgcgggcg cgcatgacca cctgggcgag gttgagctcc acgtggcgcg tgaagaccgc  8760
gtagttgcag aggcgctggt agaggtagtt gagcgtggtg gcgatgtgct cggtgacgaa  8820
```

-continued

```
gaaatacatg atccagcggc ggagcggcat ctcgctgacg tcgcccagcg cctccaaacg  8880
ttccatggcc tcgtaaaagt ccacggcgaa gttgaaaaac tgggagttgc gcgccgagac  8940
ggtcaactcc tcctccagaa gacggatgag ctcggcgatg gtggcgcgca cctcgcgctc  9000
gaaggccccc gggagttcct ccacttcctc ttcttcctcc tccactaaca tctcttctac  9060
ttcctcctca ggcggcagtg gtggcggggg agggggcctg cgtcgccggc ggcgcacggg  9120
cagacggtcg atgaagcgct cgatggtctc gccgcgccgg cgtcgcatgg tctcggtgac  9180
ggcgcgcccg tcctcgcggg gccgcagcgt gaagacgccg ccgcgcatct ccaggtggcc  9240
gggggggtcc ccgttgggca gggagagggc gctgacgatg catcttatca attgccccgt  9300
agggactccg cgcaaggacc tgagcgtctc gagatccacg ggatctgaaa accgctgaac  9360
gaaggcttcg agccagtcgc agtcgcaagg taggctgagc acggtttctt ctggcgggtc  9420
atgttggttg ggagcggggc gggcgatgct gctggtgatg aagttgaaat aggcggttct  9480
gagacggcgg atggtggcga ggagcaccag gtctttgggc ccggcttgct ggatgcgcag  9540
acggtcggcc atgccccagg cgtggtcctg acacctggcc aggtccttgt agtagtcctg  9600
catgagccgc tccacgggca cctcctcctc gcccgcgcgg ccgtgcatgc gcgtgagccc  9660
gaagccgcgc tggggctgga cgagcgccag gtcggcgacg acgcgctcgg cgaggatggc  9720
ttgctggatc tgggtgaggg tggtctggaa gtcatcaaag tcgacgaagc ggtggtaggc  9780
tccggtgttg atggtgtagg agcagttggc catgacggac cagttgacgg tctggtggcc  9840
cggacgcacg agctcgtggt acttgaggcg cgagtaggcg cgcgtgtcga agatgtagtc  9900
gttgcaggtg cgcaccaggt actggtagcc gatgaggaag tgcggcggcg gctggcggta  9960
gagcggccat cgctcggtgg cgggggcgcc gggcgcgagg tcctcgagca tggtgcggtg  10020
gtagccgtag atgtacctgg acatccaggt gatgccggcg gcggtggtgg aggcgcgcgg  10080
gaactcgcgg acgcggttcc agatgttgcg cagcggcagg aagtagttca tggtgggcac  10140
ggtctggccc gtgaggcgcg cgcagtcgtg gatgctctat acgggcaaaa acgaaagcgg  10200
tcagcggctc gactccgtgg cctggaggct aagcgaacgg gttgggctgc gcgtgtaccc  10260
cggttcgaat ctcgaatcag gctggagccg cagctaacgt ggtattggca ctcccgtctc  10320
gacccaagcc tgcaccaacc ctccaggata cggaggcggg tcgttttgca acttttttt  10380
ggaggccgga tgagactagt aagcgcggaa agcggccgac cgcgatggct cgctgccgta  10440
gtctggagaa gaatcgccag ggttgcgttg cggtgtgccc cggttcgagg ccggccggat  10500
tccgcggcta acgagggcgt ggctgccccg tcgtttccaa gaccccatag ccagccgact  10560
tctccagtta cggagcgagc ccctcttttg ttttgtttgt ttttgccaga tgcatcccgt  10620
actgcggcag atgcgccccc accaccctcc accgcaacaa cagccccctc cacagccggc  10680
gcttctgccc ccgccccagc agcaacttcc agccacgacc gccgcggccg ccgtgagcgg  10740
ggctggacag agttatgatc accagctggc cttggaagag ggcgaggggc tggcgcgcct  10800
gggggcgtcg tcgccggagc ggcacccgcg cgtgcagatg aaaagggacg ctcgcgaggc  10860
ctacgtgccc aagcagaacc tgttcagaga caggagcggc gaggagcccg aggagatgcg  10920
cgcggcccgg ttccacgcgg ggcgggagct gcggcgcggc ctggaccgaa agagggtgct  10980
gagggacgag gatttcgagg cggacgagct gacggggatc agccccgcgc gcgcgcacgt  11040
ggccgcggcc aacctggtca cggcgtacga gcagaccgtg aaggaggaga gcaacttcca  11100
aaaatccttc aacaaccacg tgcgcaccct gatcgcgcgc gaggaggtga ccctgggcct  11160
gatgcacctg tgggacctgc tggaggccat cgtgcagaac cccaccagca agccgctgac  11220
ggcgcagctg ttcctggtgg tgcagcatag tcgggacaac gaagcgttca gggaggcgct  11280
gctgaatatc accgagcccg agggccgctg gctcctggac ctggtgaaca ttctgcagag  11340
catcgtggtg caggagcgcg ggctgccgct gtccgagaag ctggcggcca tcaacttctc  11400
ggtgctgagt ttgggcaagt actacgctag gaagatctac aagaccccgt acgtgcccat  11460
agacaaggag gtgaagatcg acgggtttta catgcgcatg accctgaaag tgctgaccct  11520
gagcgacgat ctgggggtgt accgcaacga caggatgcac cgtgcggtga gcgccagcag  11580
gcggcgcgag ctgagcgacc aggagctgat gcatagtctg cagcgggccc tgaccggggc  11640
cgggaccgag ggggagagct actttgacat gggcgcggac ctgcactggc agcccagccg  11700
ccgggccttg gaggcggcgg caggacccta cgtagaagag gtggacgatg aggtggacga  11760
ggagggcgag tacctggaag actgatggcg cgaccgtatt tttgctagat gcaacaacaa  11820
cagccacctc ctgatcccgc gatgcgggcg gcgctgcaga gccagccgtc cggcattaac  11880
tcctcggacg attggaccca ggccatgcaa cgcatcatgg cgctgacgac ccgcaacccc  11940
gaagccttta gacagcagcc ccaggccaac cggctctcgg ccatcctgga ggccgtggtg  12000
ccctcgcgct ccaaccccac gcacgagaag gtcctggcca tcgtgaacgc gctggtggag  12060
aacaaggcca tccgcggcga cgaggccggc ctggtgtaca acgcgctgct ggagcgcgtg  12120
gcccgctaca acagcaccaa cgtgcagacc aacctggacc gcatggtgac cgacgtgcgc  12180
gaggccgtgg cccagcgcga gcggttccac cgcgagtcca acctgggatc catggtggcg  12240
ctgaacgcct tcctcagcac ccagcccgcc aacgtgcccc ggggccagga ggactacacc  12300
aacttcatca gcgccctgcg cctgatggtg accgaggtgc cccagagcga ggtgtaccag  12360
tccgggccgg actacttctt ccagaccagt cgccagggct tgcagaccgt gaacctgagc  12420
caggctttca agaacttgca gggcctgtgg ggcgtgcagg ccccggtcgg ggaccgcgcg  12480
acggtgtcga gcctgctgac gccgaactcg cgcctgctgc tgctgctggt ggccccccttc  12540
acggacagcg gcagcatcaa ccgcaactcg tacctgggct acctgattaa cctgtaccgc  12600
gaggccatcg gccaggcgca cgtggacgag cagacctacc aggagatcac ccacgtgagc  12660
cgcgccctgg gccaggacga cccgggcaac ctggaagcca ccctgaactt tttgctgacc  12720
aaccggtcgc agaagatccc gccccagtac gcgctcagca ccgaggagga gcgcatcctg  12780
cgttacgtgc agcagagcgt gggcctgttc ctgatgcagg agggggccac ccccagcgcc  12840
gcgctcgaca tgaccgcgcg caacatggag cccagcatgt acgccagcaa ccgcccgttc  12900
atcaataaac tgatggacta cttgcatcgg gcggccgcca tgaactctga ctatttcacc  12960
aacgccatcc tgaatcccca ctggctcccg ccgccggggt tctacacggg cgagtacgac  13020
atgcccgacc ccaatgacgg gttcctgtgg gacgatgtgg acagcagcgt gttctccccc  13080
cgaccgggtg ctaacgagcg ccccttgtgg aagaaggaag gcagcgaccg acgcccgtcc  13140
tcggcgctgt ccggccgcga gggtgctgcc gcggcggtgc ccgaggccgc cagtcctttc  13200
ccgagcttgc ccttctcgct gaacagtatc cgcagcagcg agctgggcag gatcacgcgc  13260
ccgcgcttgc tgggcgaaga ggagtacttg aatgactcgc tgttgagacc cgagcgggag  13320
aagaacttcc ccaataacgg gatagaaagc ctggtggaca agatgagccg ctggaagacg  13380
tatgcgcagg agcacaggga cgatccccgg gcgtcgcagg gggccacgag ccggggcagc  13440
gccgcccgta aacgccggtg gcacgacagg cagcggggac agatgtggga cgatgaggac  13500
tccgccgacg acagcagcgt gttggacttg ggtgggagtg gtaacccgtt cgctcacctg  13560
```

-continued

```
cgcccccgta tcgggcgcat gatgtaagag aaaccgaaaa taaatgatac tcaccaaggc  13620
catggcgacc agcgtgcgtt cgtttcttct ctgttgttgt tgtatctagt atgatgaggc  13680
gtgcgtaccc ggagggtcct cctccctcgt acgagagcgt gatgcagcag gcgatggcgg  13740
cggcggcgat gcagcccccg ctggaggctc cttacgtgcc cccgcggtac ctggcgccta  13800
cggaggggcg gaacagcatt cgttactcgg agctggcacc cttgtacgat accacccggt  13860
tgtacctggt ggacaacaag tcggcggaca tcgcctcgct gaactaccag aacgaccaca  13920
gcaacttcct gaccaccgtg gtgcagaaca atgacttcac ccccacggag gccagcaccc  13980
agaccatcaa ctttgacgag cgctcgcggt ggggcggcca gctgaaaacc atcatgcaca  14040
ccaacatgcc caacgtgaac gagttcatgt acagcaacaa gttcaaggcg cgggtgatgg  14100
tctcccgcaa gacccccaat ggggtgacag tgacagagga ttatgatggt agtcaggatg  14160
agctgaagta tgaatgggtg gaatttgagc tgcccgaagg caacttctcg gtgaccatga  14220
ccatcgacct gatgaacaac gccatcatcg acaattactt ggcggtgggg cggcagaacg  14280
gggtgctgga gagcgacatc ggcgtgaagt tcgacactag gaacttcagg ctgggctggg  14340
accccgtgac cgagctggtc atgcccgggg tgtacaccaa cgaggctttc catcccgata  14400
ttgtcttgct gcccggctgc ggggtggact tcaccgagag ccgcctcagc aacctgctgg  14460
gcattcgcaa gaggcagccc ttccaggaag gcttccagat catgtacgag gatctggagg  14520
ggggcaacat ccccgcgctc ctggatgtcg acgcctatga gaaaagcaag gaggatgcag  14580
cagctgaagc aactgcagcc gtagctaccg cctctaccga ggtcaggggc gataattttg  14640
caagcgccgc agcagtggca gcggccgagg cggctgaaac cgaaagtaag atagtcattc  14700
agccggtgga gaaggatagc aagaacagga gctacaacgt actaccggac aagataaaca  14760
ccgcctaccg cagctggtac ctagcctaca actatggcga ccccgagaag ggcgtgcgct  14820
cctggacgct gctcaccacc tcggacgtca cctgcggcgt ggagcaagtc tactggtcgc  14880
tgcccgacat gatgcaagac ccggtcacct tccgctccac gcgtcaagtt agcaactacc  14940
cggtggtggg cgccgagctc ctgcccgtct actccaagag cttcttcaac gagcaggccg  15000
tctactcgca gcagctgcgc gccttcacct cgcttacgca cgtcttcaac cgcttccccg  15060
agaaccagat cctcgtccgc ccgcccgcgc ccaccattac caccgtcagt gaaaacgttc  15120
ctgctctcac agatcacggg accctgccgc tgcgcagcag tatccgggga gtccagcgcg  15180
tgaccgttac tgacgccaga cgccgcacct gcccctacgt ctacaaggcc ctgggcatag  15240
tcgcgccgcg cgtcctctcg agccgcacct tctaaatgtc cattctcatc tcgcccagta  15300
ataacaccgg ttggggcctg cgcgcgccca gcaagatgta cggaggcgct cgccaacgct  15360
ccacgcaaca ccccgtgcgc gtgcgcgggc acttccgcgc tccctggggc gccctcaagg  15420
gccgcgtgcg gtcgcgcacc accgtcgacg acgtgatcga ccaggtggtg gccgacgcgc  15480
gcaactacac ccccgccgcc gcgcccgtct ccaccgtgga cgccgtcatc gacagcgtgg  15540
tggccgacgc gcgccggtac gcccgcgcca agagccggcg gcggcgcatc gcccggcggc  15600
accggagcac ccccgccatg cgcgcggcgc gagccttgct gcgcagggcc aggcgcacgg  15660
gacgcagggc catgctcagg gcggccagac gcgcggcttc aggcgccagc gccggcagga  15720
cccggagacg cgcggccacg gcggcggcag cggccatcgc cagcatgtcc cgcccgcggc  15780
gagggaacgt gtactgggtg cgcgacgccg ccaccggtgt gcgcgtgccc gtgcgcaccc  15840
gcccccctcg cacttgaaga tgttcacttc gcgatgttga tgtgtcccag cggcgaggag  15900
gatgtccaag cgcaaattca aggaagagat gctccaggtc atcgcgcctg agatctacgg  15960
ccctgcggtg gtgaaggagg aaagaaagcc ccgcaaaatc aagcgggtca aaaaggacaa  16020
aaaggaagaa gaaagtgatg tggacggatt ggtggagttt gtgcgcgagt tcgccccccg  16080
gcggcgcgtg cagtggcgcg ggcggaaggt gcaaccggtg ctgagacccg gcaccaccgt  16140
ggtcttcacg cccggcgagc gctccggcac cgcttccaag cgctcctacg acgaggtgta  16200
cggggatgat gatattctgg agcaggcggc cgagcgcctg ggcgagtttg cttacggcaa  16260
gcgcagccgt tccgcaccga aggaagaggc ggtgtccatc ccgctggacc acggcaaccc  16320
cacgccgagc ctcaagcccg tgaccttgca gcaggtgctg ccgaccgcgg cgccgcgccg  16380
ggggttcaag cgcgagggcg aggatctgta ccccaccatg cagctgatgg tgcccaagcg  16440
ccagaagctg gaagacgtgc tggagaccat gaaggtggac ccggacgtgc agcccgaggt  16500
caaggtgcgg cccatcaagc aggtggcccc gggcctgggc gtgcagaccg tggacatcaa  16560
gattcccacg gagcccatgg aaacgcagac cgagcccatg atcaagccca gcaccagcac  16620
catggaggtg cagacggatc cctggatgcc atcggctcct agtcgaagac cccggcgcaa  16680
gtacggcgcg gccagcctgc tgatgcccaa ctacgcgctg catccttcca tcatccccac  16740
gccgggctac cgcggcacgc gcttctaccg cggtcatacc agcagccgcc gccgcaagac  16800
caccactcgc cgccgccgtc gccgcaccgc cgctgcaacc accoctgccg ccctggtgcg  16860
gagagtgtac cgccgcggcc gcgcacctct gaccctgccg cgcgcgcgct accacccgag  16920
catcgccatt taaactttcg cctgctttgc agatcaatgg ccctcacatg ccgccttcgc  16980
gttcccatta cgggctaccg aggaagaaaa ccgcgccgta gaaggctggc ggggaacggg  17040
atgcgtcgcc accaccaccg gcggcggcgc gccatcagca agcggttggg gggaggcttc  17100
ctgcccgcgc tgatccccat catcgccgcg gcgatcgggg cgatccccgg cattgcttcc  17160
gtggcggtgc aggcctctca gcgccactga gacacacttg gaaacatctt gtaataaacc  17220
aatggactct gacgctcctg gtcctgtgat gtgttttcgt agacagatgg aagacatcaa  17280
tttttcgtcc ctggctccgc gacacggcac gcggccgttc atgggcacct ggagcgacat  17340
cggcaccagc caactgaacg gggcgccctt caattggagc agtctctgga gcgggcttaa  17400
gaatttcggg tccacgctta aacctatgg cagcaaggcg tggaacagca ccacagggca  17460
ggcgctgagg gataagctga aagagcagaa cttccagcag aaggtggtcg atgggctcgc  17520
ctcgggcatc aacggggtgg tggacctggc caaccaggcc gtgcagcggc agatcaacag  17580
ccgcctggac ccggtgccgc ccgccggctc cgtggagatg ccgcaggtgg aggaggagct  17640
gcctcccctg gacaagcggg gcgagaagcg accccgcccc gatgcggagg agacgctgct  17700
gacgcacacg gacgagccgc ccccgtacga ggaggcggtg aaactgggtc tgcccaccac  17760
gcggcccatc gcgcccctgg ccaccggggt gctgaaaccc gaaaagcccg cgaccctgga  17820
cttgcctcct ccccagcctt cccgcccctc tacagtggct aagcccctgc cgccggtggc  17880
cgtggcccgc gcgcgacccg gggcaccgc ccgccctcat gcgaactggc agagcactct  17940
gaacagcatc gtgggtctgg gagtgcagag tgtgaagcgc cgccgctgct attaaaccta  18000
ccgtagcgct taacttgctt gtctgtgtgt gtatgtatta tgtcgccgcc gccgctgtcc  18060
accagaagga ggagtgaaga ggcgcgtcgc cgagttgcaa gatggccacc ccatcgatgc  18120
tgccccagtg ggcgtacatg cacatcgccg gacaggacgc ttcggagtac ctgagtccgg  18180
gtctggtgca gtttgcccgc gccacagaca cctacttcag tctggggaac aagtttagga  18240
accccacggt ggcgcccacg cacgatgtga ccaccgaccg cagccagcgg ctgacgctgc  18300
```

-continued

```
gcttcgtgcc cgtggaccgc gaggacaaca cctactcgta caaagtgcgc tacacgctgg  18360
ccgtgggcga caaccgcgtg ctggacatgg ccagcaccta ctttgacatc cgcggcgtgc  18420
tggatcgggg ccctagcttc aaaccctact ccggcaccgc ctacaacagt ctggccccca  18480
agggagcacc caacacttgt cagtggacat ataaagccga tggtgaaact gccacagaaa  18540
aaacctatac atatggaaat gcacccgtgc agggcattaa catcacaaaa gatggtattc  18600
aacttggaac tgacaccgat gatcagccaa tctacgcaga taaaacctat cagcctgaac  18660
ctcaagtggg tgatgctgaa tggcatgaca tcactggtac tgatgaaaag tatggaggca  18720
gagctcttaa gcctgatacc aaaatgaagc cttgttatgg ttcttttgcc aagcctacta  18780
ataaagaagg aggtcaggca aatgtgaaaa caggaacagg cactactaaa gaatatgaca  18840
tagacatggc tttctttgac aacagaagtg cggctgctgc tggcctagct ccagaaattg  18900
ttttgtatac tgaaaatgtg gatttggaaa ctccagatac ccatattgta tacaaagcag  18960
gcacagatga cagcagctct tctattaatt tgggtcagca agccatgccc aacagaccta  19020
actacattgg tttcagagac aactttatcg ggctcatgta ctacaacagc actggcaata  19080
tgggggtgct ggccggtcag gcttctcagc tgaatgctgt ggttgacttg caagacagaa  19140
acaccgagct gtcctaccag ctcttgcttg actctctggg tgacagaacc cggtatttca  19200
gtatgtggaa tcaggcggtg gacagctatg atcctgatgt gcgcattatt gaaaatcatg  19260
gtgtggagga tgaacttccc aactattgtt tccctctgga tgctgttggc agaacagata  19320
cttatcaggg aattaaggct aatggaactg atcaaaccac atggaccaaa gatgacagtg  19380
tcaatgatgc taatgagata ggcaagggta atccattcgc catggaaatc aacatccaag  19440
ccaacctgtg gaggaacttc ctctacgcca acgtggccct gtacctgccc gactcttaca  19500
agtacacgcc ggccaatgtt accctgccca ccaacaccaa cacctacgat tacatgaacg  19560
gccgggtggt ggcgccctcg ctggtggact cctacatcaa catcggggcg cgctggtcgc  19620
tggatcccat ggacaacgtg aaccccttca accaccaccg caatgcgggg ctgcgctacc  19680
gctccatgct cctgggcaac gggcgctacg tgcccttcca catccaggtg ccccagaaat  19740
ttttcgccat caagagcctc ctgctcctgc ccgggtccta cacctacgag tggaacttcc  19800
gcaaggacgt caacatgatc ctgcagagct ccctcggcaa cgacctgcgc acggacgggg  19860
cctccatctc cttcaccagc atcaacctct acgccacctt cttccccatg gcgcacaaca  19920
cggcctccac gctcgaggcc atgctgcgca acgacaccaa cgaccagtcc ttcaacgact  19980
acctctcggc ggccaacatg ctctacccca tcccggccaa cgccaccaac gtgcccatct  20040
ccatcccctc gcgcaactgg gccgccttcc gcggctggtc cttcacgcgt ctcaagacca  20100
aggagacgcc ctcgctgggc tccgggttcg acccctactt cgtctactcg ggctccatcc  20160
cctacctcga cggcaccttc tacctcaacc acaccttcaa gaaggtctcc atcaccttcg  20220
actcctccgt cagctggccc ggcaacgacc ggctcctgac gcccaacgag ttcgaaatca  20280
agcgcaccgt cgacggcgag ggctacaacg tggcccagtg caacatgacc aaggactggt  20340
tcctggtcca gatgctggcc cactacaaca tcggctacca gggcttctac gtgcccgagg  20400
gctacaagga ccgcatgtac tccttcttcc gcaacttcca gcccatgagc cgccaggtgg  20460
tggacgaggt caactacaag gactaccagg ccgtcaccct ggcctaccag cacaacaact  20520
cgggcttcgt cggctacctc gcgcccacca tgcgccaggg ccagccctac cccgccaact  20580
acccctaccc gctcatcggc aagagcgccg tcaccagcgt cacccagaaa aagttcctct  20640
gcgacagggt catgtggcgc atccccttct ccagcaactt catgtccatg ggcgcgctca  20700
ccgacctcgg ccagaacatg ctctatgcca actccgccca cgcgctagac atgaatttcg  20760
aagtcgaccc catggatgag tccacccttc tctatgttgt cttcgaagtc ttcgacgtcg  20820
tccgagtgca ccagccccac cgcggcgtca tcgaggccgt ctacctgcgc acccccttct  20880
cggccggtaa cgccaccacc taagctcttg cttcttgcaa gccatggccg cgggctccgg  20940
cgagcaggag ctcagggcca tcatccgcga cctgggctgc gggccctact tcctgggcac  21000
cttcgataag cgcttcccgg gattcatggc cccgcacaag ctggcctgcg ccatcgtcaa  21060
cacggccggc cgcgagaccg ggggcgagca ctggctggcc ttcgcctgga acccgcgctc  21120
gaacacctgc tacctcttcg acccctccgg gttctcggac gagcgcctca agcagatcta  21180
ccagttcgag tacgagggcc tgctgcgccg cagcgccctg gccaccgagg accgctgcgt  21240
caccctggaa aagtccaccc agaccgtgca gggtccgcgc tcggccgcct gcgggctctt  21300
ctgctgcatg ttcctgcacg ccttcgtgca ctggcccgac cgccccatgg acaagaaccc  21360
caccatgaac ttgctgacgg gggtgcccaa cggcatgctc cagtcgcccc aggtggaacc  21420
caccctgcgc cgcaaccagg aggcgctcta ccgcttcctc aactcccact ccgcctactt  21480
tcgctcccac cgcgcgcgca tcgagaaggc caccgccttc gaccgcatga atcaagacat  21540
gtaaaccgtg tgtgtatgtt aaatgtcttt aataaacagc actttcatgt tacacatgca  21600
tctgagatga tttatttaga aatcgaaagg gttctgccgg gtctcggcat ggcccgcggg  21660
cagggacacg ttgcggaact ggtacttggc cagccacttg aactcgggga tcagcagttt  21720
gggcagcggg gtgtcgggga aggagtcggt ccacagcttc cgcgtcagtt gcagggcgcc  21780
cagcaggtcg ggcgcggaga tcttgaaatc gcagttggga cccgcgttct gcgcgcggga  21840
gttgcggtac acggggttgc agcactggaa caccatcagg gccgggtgct tcacgctcgc  21900
cagcaccgtc gcgtcggtga tgctctccac gtcgaggtcc tcggcgttgg ccatcccgaa  21960
gggggtcatc ttgcaggtct gccttcccat ggtgggcacg cacccgggct tgtggttgca  22020
atcgcagtgc agggggatca gcatcatctg ggcctggtcg gcgttcatcc ccgggtacat  22080
ggccttcatg aaagcctcca attgcctgaa cgcctgctgg gccttggctc cctcggtgaa  22140
gaagaccccg caggacttgc tagagaactg gttggtggcg cacccggcgt cgtgcacgca  22200
gcagcgcgcg tcgttgttgg ccagctgcac cacgctgcgc ccccagcggt tctgggtgat  22260
cttggcccgg tcggggttct ccttcagcgc gcgctgcccg ttctcgctcg ccacatccat  22320
ctcgatcatg tgctccttct ggatcatggt ggtcccgtgc aggcaccgca gcttgccctc  22380
ggcctcggtg cacccgtgca gccacagcgc gcacccggtg cactcccagt tcttgtgggc  22440
gatctgggaa tgcgcgtgca cgaagccctg caggaagcgg cccatcatgg tggtcagggt  22500
cttgttgcta gtgaaggtca gcggaatgcc gcggtgctcc tcgttgatgt acaggtggca  22560
gatgcggcgg tacacctcgc cctgctcggg catcagctgg aagttggctt tcaggtcggt  22620
ctccacgcgg tagcggtcca tcagcatagt catgatttcc ataccttct cccaggccga  22680
gacgatgggc aggctcatag ggttcttcac catcatctta gcgctagcag ccgcggccag  22740
ggggtcgctc tcgtccaggg tctcaaagct ccgcttgccg tccttctcgg tgatccgcac  22800
cggggggtag ctgaagccca cggccgccag ctcctcctcg gcctgtcttt cgtcctcgct  22860
gtcctggctg acgtcctgca ggaccacatg cttggtcttg cggggtttct tcttgggcgg  22920
cagcggcggc ggagatgttg gagatggcga gggggagcgc gagttctcgc tcaccactac  22980
tatctcttcc tcttcttggt ccgaggccac gcggcggtag gtatgtctct tcgggggcag  23040
```

```
aggcggaggc gacgggctct cgccgccgcg acttggcgga tggctggcag agccccttcc  23100
gcgttcgggg gtgcgctccc ggcggcgctc tgactgactt cctccgcggc cggccattgt  23160
gttctcctag ggaggaacaa caagcatgga gactcagcca tcgccaacct cgccatctgc  23220
ccccaccgcc gacgagaagc agcagcagca gaatgaaagc ttaaccgccc cgccgcccag  23280
ccccgccacc tccgacgcgg ccgtcccaga catgcaagag atggaggaat ccatcgagat  23340
tgacctgggc tatgtgacgc ccgcggagca cgaggaggag ctggcagtgc gcttttcaca  23400
agaagagata caccaagaac agccagagca ggaagcagag aatgagcaga gtcaggctgg  23460
gctcgagcat gacggcgact acctccacct gagcgggggg gaggacgcgc tcatcaagca  23520
tctggcccgg caggccacca tcgtcaagga tgcgctgctc gaccgcaccg aggtgcccct  23580
cagcgtggag gagctcagcc gcgcctacga gttgaacctc ttctcgccgc gcgtgccccc  23640
caagcgccag cccaatggca cctgcgagcc caacccgcgc ctcaacttct acccggtctt  23700
cgcggtgccc gaggccctgg ccacctacca catctttttc aagaaccaaa agatccccgt  23760
ctcctgccgc gccaaccgca cccgcgccga cgccctttc aacctgggtc ccggcgcccg  23820
cctacctgat atcgcctcct tggaagaggt tcccaagatc ttcgagggtc tgggcagcga  23880
cgagactcgg gccgcgaacg ctctgcaagg agaaggagga gagcatgagc accacagcgc  23940
cctggtcgag ttggaaggcg acaacgcgcg gctggcggtg ctcaaacgca cggtcgagct  24000
gacccatttc gcctacccgg ctctgaacct gccccccaaa gtcatgagcg cggtcatgga  24060
ccaggtgctc atcaagcgcg cgtcgcccat ctccgaggac gagggcatgc aagactccga  24120
ggagggcaag cccgtggtca gcgacgagca gctggcccgg tggctgggtc ctaatgctag  24180
tccccagagt ttggaagagc ggcgcaaact catgatggcc gtggtcctgg tgaccgtgga  24240
gctggagtgc ctgcgccgct tcttcgccga cgcggagacc ctgcgcaagg tcgaggagaa  24300
cctgcactac ctcttcaggc acgggttcgt gcgccaggcc tgcaagatct ccaacgtgga  24360
gctgaccaac ctggtctcct acatgggcat cttgcacgag aaccgcctgg ggcagaacgt  24420
gctgcacacc accctgcgcg gggaggcccg gcgcgactac atccgcgact gcgtctacct  24480
ctacctctgc cacacctggc agacgggcat gggcgtgtgg cagcagtgtc tggaggagca  24540
gaacctgaaa gagctctgca agctcctgca gaagaacctc aagggtctgt ggaccgggtt  24600
cgacgagcgc accaccgcct cggacctggc cgacctcatt ttccccgagc gcctcaggct  24660
gacgctgcgc aacggcctgc ccgactttat gagccaaagc atgttgcaaa actttcgctc  24720
tttcatcctc gaacgctccg gaatcctgcc cgccacctgc tccgcgctgc cctcggactt  24780
cgtgccgctg accttccgcg agtgcccccc gccgctgtgg agccactgct acctgctgcg  24840
cctggccaac tacctggcct accactcgga cgtgatcgag gacgtcagcg gcgagggcct  24900
gctcgagtgc cactgccgct gcaacctctg cacgccgcac cgctccctgg cctgcaaccc  24960
ccagctgctg agcgagaccc agatcatcgg caccttcgag ttgcaagggc ccagcgaagg  25020
cgagggttca gccgccaagg ggggtctgaa actcaccccg ggctgtgga cctcggccta  25080
cttgcgcaag ttcgtgcccg aggactacca tcccttcgag atcaggttct acgaggacca  25140
atcccatccg cccaaggccg agctgtcggc ctgcgtcatc acccaggggg cgatcctggc  25200
ccaattgcaa gccatccaga aatcccgcca agaattcttg ctgaaaaagg gccgcggggt  25260
ctacctcgac ccccagaccg gtgaggagct caaccccggc ttcccccagg atgccccgag  25320
gaaacaagaa gctgaaagtg gagctgccgc ccgtggagga tttggaggaa gactgggaga  25380
acagcagtca ggcagaggag gaggagatgg aggaagactg ggacagcact caggcagagg  25440
aggacagcct gcaagacagt ctggaggaag acgaggagga ggcagaggag gaggtggaag  25500
aagcagccgc cgccagaccg tcgtcctcgg cgggggagaa agcaagcagc acggatacca  25560
tctccgctcc gggtcggggt cccgctcgac cacacagtag atgggacgag accggacgat  25620
tcccgaaccc caccacccag accggtaaga aggagcggca gggatacaag tcctggcggg  25680
ggcacaaaaa cgccatcgtc tcctgcttgc aggcctgcgg gggcaacatc tccttcaccc  25740
ggcgctacct gctcttccac cgcggggtga actttccccg caacatcttg cattactacc  25800
gtcacctcca cagcccctac tacttccaag aagaggcagc agcagcagaa aaagaccagc  25860
agaaaaccag cagctagaaa atccacagcg gcggcagcag gtggactgag gatcgcggcg  25920
aacgagccgg cgcaaacccg ggagctgagg aaccggatct ttcccaccct ctatgccatc  25980
ttccagcaga gtcgggggca ggagcaggaa ctgaaagtca agaaccgttc tctgcgctcg  26040
ctcacccgca gttgtctgta tcacaagagc gaagaccaac ttcagcgcac tctcgaggac  26100
gccgaggctc tcttcaacaa gtactgcgcg ctcactctta aagagtagcc cgcgcccgcc  26160
cagtcgcaga aaaaggcggg aattacgtca cctgtgccct tcgccctagc cgcctccacc  26220
catcatcatg agcaaagaga ttcccacgcc ttacatgtgg agctaccagc cccagatggg  26280
cctggccgcc ggtgccgccc aggactactc cacccgcatg aattggctca gcgccgggcc  26340
cgcgatgatc tcacgggtga atgacatccg cgcccaccga aaccagatac tcctagaaca  26400
gtcagcgctc accgccacgc cccgcaatca cctcaatccg cgtaattggc ccgccgccct  26460
ggtgtaccag gaaattcccc agcccacgac cgtactactt ccgcgagacg cccaggccga  26520
agtccagctg actaactcag gtgtccagct ggcgggcggc gccaccctgt gtcgtcaccg  26580
ccccgctcag ggtataaagc ggctggtgat ccggggcaga ggcacacagc tcaacgacga  26640
ggtggtgagc tcttcgctgg gtctgcgacc tgacggagtc ttccaactcg ccggatcggg  26700
gagatcttcc ttcacgcctc gtcaggccgt cctgactttg gagagttcgt cctcgcagcc  26760
ccgctcgggt ggcatcggca ctctccagtt cgtggaggag ttcactccct cggtctactt  26820
caacccctc tccggctccc ccggccacta cccggacgag ttcatcccga acttcgacgc  26880
catcagcgag tcggtggacg gctacgattg aatgtcccat ggtggcgcag ctgacctagc  26940
tcggcttcga cacctggacc actgccgccg cttccgctgc ttcgctcggg atctcgccga  27000
gtttgcctac tttgagctgc ccgaggagca ccctcagggc ccggcccacg gagtgcggat  27060
cgtcgtcgaa gggggcctcg actcccacct gcttcggatc ttcagccagc gtccgatcct  27120
ggtcgagcgc gagcaaggac agacccttct gactctgtac tgcatctgca accaccccgg  27180
cctgcatgaa agtctttgtt gtctgctgtg tactgagtat aataaaagct gagatcagcg  27240
actactccgg acttccgtgt gttcctgaat ccatcaacca gtctttgttc ttcaccggga  27300
acgagaccga gctccagctc cagtgtaagc cccacaagaa gtacctcacc tggctgttcc  27360
agggctcccc gatcgccgtt gtcaaccact gcgacaacga cggagtcctg ctgagcggcc  27420
ctgccaacct tactttttcc acccgcagaa gcaagctcca gctcttccaa cccttcctcc  27480
ccgggaccta tcagtgcgtc tcgggaccct gccatcacac cttccacctg atcccgaata  27540
ccacagcgtc gctccccgct actaacaacc aaactaacct ccaccaacgc caccgtcgcg  27600
acggccacaa tacatgccca tattagacta tgaggccgag ccacagcgac ccatgctccc  27660
cgctattagt tacttcaatc taaccggcgg agatgactga cccactggcc aacaacaacg  27720
tcaacgacct tctcctggac atggacggcc gcgcctcgga gcagcgactc gcccaacttc  27780
```

-continued gcattcgcca gcagcaggag agagccgtca aggagctgca ggatgcggtg gccatccacc 27840
agtgcaagag aggcatcttc tgcctggtga aacaggccaa gatctcctac gaggtcactc 27900
caaacgacca tcgcctctcc tacgagctcc tgcagcagcg ccagaagttc acctgcctgg 27960
tcggagtcaa ccccatcgtc atcacccagc agtctggcga taccaagggg tgcatccact 28020
gctcctgcga ctcccccgac tgcgtccaca ctctgatcaa gaccctctgc ggcctccgcg 28080
acctcctccc catgaactaa tcacccccttt atccagtgaa ataaagatca tattgatgat 28140
gattttacag aaataaaaaa taatcatttg atttgaaata aagatacaat catattgatg 28200
atttgagttt aacaaaaaaa taaagaatca cttacttgaa atctgatacc aggtctctgt 28260
ccatgttttc tgccaacacc acttcactcc cctcttccca gctctggtac tgcaggcccc 28320
ggcgggctgc aaacttcctc cacacgctga aggggatgtc aaattcctcc tgtccctcaa 28380
tcttcatttt atcttctatc agatgtccaa aaagcgcgtc cgggtggatg atgacttcga 28440
ccccgtctac ccctacgatg cagacaacgc accgaccgtg cccttcatca acccccccctt 28500
cgtctcttca gatggattcc aagagaagcc cctgggggtg ttgtccctgc gactggccga 28560
ccccgtcacc accaagaacg gggaaatcac cctcaagctg ggagaggggg tggacctcga 28620
ttcctcggga aaactcatct ccaacacggc caccaaggcc gccgcccctc tcagtttttc 28680
caacaacacc atttccctta acatggatca ccccttttac actaaagatg gaaaattatc 28740
cttacaagtt tctccaccat taaatatact gagaacaagc attctaaaca cactagcttt 28800
aggttttgga tcaggtttag gactccgtgg ctctgccttg gcagtacagt tagtctctcc 28860
acttacattt gatactgatg gaaacataaa gcttacctta gacagaggtt tgcatgttac 28920
aacaggagat gcaattgaaa gcaacataag ctgggctaaa ggtttaaaat ttgaagatgg 28980
agccatagca accaacattg gaaatgggtt agagtttgga agcagtagta cagaaacagg 29040
tgttgatgat gcttacccaa tccaagttaa acttggatct ggccttagct ttgacagtac 29100
aggagccata atggctggta acaaagaaga cgataaactc actttgtgga caacacctga 29160
tccatcacca aactgtcaaa tactcgcaga aaatgatgca aaactaacac tttgcttgac 29220
taaatgtggt agtcaaatac tggccactgt gtcagtctta gttgtaggaa gtggaaacct 29280
aaaccccatt actggcaccg taagcagtgc tcaggtgttt ctacgttttg atgcaaacgg 29340
tgttctttta acagaacatt ctacactaaa aaaatactgg gggtataggc agggagatag 29400
catagatggc actccatata ccaatgctgt aggattcatg cccaatttaa aagcttatcc 29460
aaagtcacaa agttctacta ctaaaaataa tatagtaggg caagtataca tgaatggaga 29520
tgtttcaaaa cctatgcttc tcactataac cctcaatggt actgatgaca gcaacagtac 29580
atattcaatg tcattttcat acacctggac taatggaagc tatgttggag caacatttgg 29640
ggctaactct tataccttct catacatcgc ccaagaatga acactgtatc ccaccctgca 29700
tgccaaccct tcccacccca ctctgtggaa caaactctga aacacaaaat aaaataaagt 29760
tcaagtgttt tattgattca acagttttac aggattcgag cagttatttt tcctccaccc 29820
tcccaggaca tggaatacac caccctctcc ccccgcacag ccttgaacat ctgaatgcca 29880
ttggtgatgg acatgctttt ggtctccacg ttccacacag tttcagagcg agccagtctc 29940
gggtcggtca gggagatgaa accctccggg cactcccgca tctgcacctc acagctcaac 30000
agctgaggat tgtcctcggt ggtcgggatc acggttatct ggaagaagca gaagagcggc 30060
ggtgggaatc atagtccgcg aacgggatcg gccggtggtg tcgcatcagg ccccgcagca 30120
gtcgctgccg ccgccgctcc gtcaagctgc tgctcagggg gtccgggtcc agggactccc 30180
tcagcatgat gcccacggcc ctcagcatca gtcgtctggt gcggcgggcg cagcagcgca 30240
tgcggatctc gctcaggtcg ctgcagtacg tgcaacacag aaccaccagg ttgttcaaca 30300
gtccatagtt caacacgctc cagccgaaac tcatcgcggg aaggatgcta cccacgtggc 30360
cgtcgtacca gatcctcagg taaatcaagt ggtgcccccct ccagaacacg ctgcccacgt 30420
acatgatctc cttgggcatg tggcggttca ccacctcccg gtaccacatc accctctggt 30480
tgaacatgca gccccggatg atcctgcgga accacagggc cagcaccgcc ccgcccgcca 30540
tgcagcgaag agaccccggg tcccggcaat ggcaatggag gacccaccgc tcgtacccgt 30600
ggatcatctg ggagctgaac aagtctatgt tggcacagca caggcatatg ctcatgcatc 30660
tcttcagcac tctcaactcc tcgggggtca aaaccatatc ccagggcacg gggaactctt 30720
gcaggacagc gaaccccgca gaacagggca atcctcgcac agaacttaca ttgtgcatgg 30780
acagggtatc gcaatcaggc agcaccgggt gatcctccac cagagaagcg cgggtctcgg 30840
tctcctcaca gcgtggtaag ggggccggcc gatacgggtg atggcgggac gcggctgatc 30900
gtgttcgcga ccgtgtcatg atgcagttgc tttcggacat tttcgtactt gctgtagcag 30960
aacctggtcc gggcgctgca caccgatcgc cggcggcggt ctcggcgctt ggaacgctcg 31020
gtgttgaaat tgtaaaacag ccactctctc agaccgtgca gcagatctag ggcctcagga 31080
gtgatgaaga tcccatcatg cctgatggct ctgatcacat cgaccaccgt ggaatgggcc 31140
agacccagcc agatgatgca attttgttgg gtttcggtga cggcggggga gggaagaaca 31200
ggaagaacca tgattaactt ttaatccaaa cggtctcgga gtacttcaaa atgaagatcg 31260
cggagatggc acctctcgcc cccgctgtgt tggtggaaaa taacagccag gtcaaaggtg 31320
atacggttct cgagatgttc cacggtggct tccagcaaag cctccacgcg cacatccaga 31380
aacaagacaa tagcgaaagc gggagggttc tctaattcct caatcatcat gttacactcc 31440
tgcaccatcc ccagataatt ttcatttttc cagccttgaa tgattcgaac tagttcgtga 31500
ggtaaatcca agccagccat gataaagagc tcgcgcagag cgccctccac cggcattctt 31560
aagcacaccc tcataattcc aagatattct gctcctggtt cacctgcagc agattgacaa 31620
gcggaatatc aaaatctctg ccgcgatccc tgagctcctc cctcagcaat aactgtaagt 31680
actctttcat atcctctccg aaatttttag ccataggacc accaggaata agattagggc 31740
aagccacagt acagataaac cgaagtcctc cccagtgagc attgccaaat gcaagactgc 31800
tataagcatg ctggctagac ccggtgatat cttccagata actggacaga aaatcgccca 31860
ggcaattttt aagaaaatca acaaaagaaa aatcctccag gtggacgttt agagcctcgg 31920
gaacaacgat gaagtaaatg caagcggtgc gttccagcat ggttagttag ctgatctgta 31980
gaaaaaacaa aaatgaacat taaaccatgc tagcctggcg aacaggtggg taaatcgttc 32040
tctccagcac caggcaggcc acggggtctc cggcgcgacc ctcgtaaaaa ttgtcgctat 32100
gattgaaaac catcacagag agacgttccc ggtggccggc gtgaatgatt cgacaagatg 32160
aatacacccc cggaacattg gcgtccgcga gtgaaaaaaa gcgcccgagg aagcaataag 32220
gcactacaat gctcagtctc aagtccagca aagcgatgcc atgcggatga agcacaaaat 32280
tctcaggtgc gtacaaaatg taattactcc cctcctgcac aggcagcaaa gcccccgatc 32340
cctccaggta cacatacaaa gcctcagcgt ccatagctta ccgagcagca gcacacaaca 32400
ggcgcaagag tcagagaaag gctgagctct aacctgtcca cccgctctct gctcaatata 32460
tagcccagat ctacactgac gtaaaggcca aagtctaaaa atacccgcca aataatcaca 32520

```
cacgcccagc acacgcccag aaaccggtga cacactcaaa aaaatacgcg cacttcctca  32580
aacgcccaaa actgccgtca tttccgggtt cccacgctac gtcatcaaaa cacgactttc  32640
aaattccgtc gaccgttaaa aacgtcaccc gccccgcccc taacggtcgc ccgtctctca  32700
gccaatcagc gccccgcatc cccaaattca aacacctcat ttgcatatta acgcgcacaa  32760
aaagtttgag gtatattatt gatgatgg                                    32788

SEQ ID NO: 13          moltype = DNA  length = 30684
FEATURE                Location/Qualifiers
misc_feature           1..30684
                       note = Description of Artificial Sequence: Synthetic
                        polynucleotide
source                 1..30684
                       mol_type = other DNA
                       organism = synthetic construct
SEQUENCE: 13
ccatcttcaa taatatacct caaacttttt gtgcgcgtta atatgcaaat gaggcgtttg  60
aatttgggga ggaagggcgg tgattggtcg agggatgagc gaccgttagg ggcggggcga  120
gtgacgtttt gatgacgtgg ttgcgaggag gagccagttt gcaagttctc gtgggaaaag  180
tgacgtcaaa cgaggtgtgg tttgaacacg gaaatactca attttcccgc gctctctgac  240
aggaaatgag gtgtttctgg gcggatgcaa gtgaaaacgg gccattttcg cgcgaaaact  300
gaatgaggaa gtgaaaatct gagtaatttc gcgtttatgg cagggaggag tatttgccga  360
gggccgagta gactttgacc gattacgtgg gggtttcgat taccgtgttt ttcacctaaa  420
tttccgcgta cggtgtcaaa gtccggtgtt tttacgtagg tgtcagctga tcgccagggt  480
atttaaacct gcgctctcca gtcaagaggc cactcttgag tgccagcgag aagagttttc  540
tcctccgcgc cgcgagtcag atctacactt tgaaagtagg gataacaggg taatgacatt  600
gattattgac tagttgttaa tagtaatcaa ttacggggtc attagttcat agcccatata  660
tggagttccg cgttacataa cttacggtaa atggcccgcc tggctgaccg cccaacgacc  720
cccgcccatt gacgtcaata atgacgtatg ttcccatagt aacgccaata gggactttcc  780
attgacgtca atgggtggag tatttacggt aaactgccca cttggcagta catcaagtgt  840
atcatatgcc aagtccgccc cctattgacg tcaatgacgg taaatggccc gcctggcatt  900
atgcccagta catgacctta cgggactttc ctacttggca gtacatctac gtattagtca  960
tcgctattac catggtgatg cggttttggc agtacaccaa tgggcgtgga tagcggtttg  1020
actcacgggg atttccaagt ctccacccca ttgacgtcaa tgggagtttg ttttggcacc  1080
aaaatcaacg ggactttcca aaatgtcgta ataaccccgc cccgttgacg caaatgggcg  1140
gtaggcgtgt acggtgggag gtctatataa gcagagctcg tttagtgaac cgtcagatcg  1200
cctggaacgc catccacgct gttttgacct ccatagaaga cagcgatcgc gccaccatgg  1260
tgagcaaggg cgaggagctg ttcaccgggg tggtgcccat cctggtcgag ctggacggcg  1320
acgtaaacgg ccacaagttc agcgtgtccg gcgagggcga gggcgatgcc acctacggca  1380
agctgaccct gaagttcatc tgcaccaccg gcaagctgcc cgtgccctgg cccaccctcg  1440
tgaccaccct gacctacggc gtgcagtgct tcagccgcta ccccgaccac atgaagcagc  1500
acgacttctt caagtccgcc atgcccgaag gctacgtcca ggagcgcacc atcttcttca  1560
aggacgacgg caactacaag acccgcgccg aggtgaagtt cgagggcgac accctggtga  1620
accgcatcga gctgaagggc atcgacttca aggaggacgg caacatcctg gggcacaagc  1680
tggagtacaa ctacaacagc cacaacgtct atatcatggc cgacaagcag aagaacggca  1740
tcaaggtgaa cttcaagatc cgccacaaca tcgaggacgg cagcgtgcag ctcgccgacc  1800
actaccagca gaacaccccc atcggcgacg gccccgtgct gctgcccgac aaccactacc  1860
tgagcaccca gtccgccctg agcaaagacc ccaacgagaa gcgcgatcac atggtcctgc  1920
tggagttcgt gaccgccgcc gggatcactc tcggcatgga cgagctttac aagtagtgag  1980
tttaaactcc catttaaatg tgagggttaa tgcttcgagc agacatgata agatacattg  2040
atgagtttgg acaaaccaca actagaatgc agtgaaaaaa atgctttatt tgtgaaattt  2100
gtgatgctat tgctttattt gtaaccatta taagctgcaa taaacaagtt aacaacaaca  2160
attgcattca ttttatgttt caggttcagg gggagatgtg ggaggttttt taaagcaagt  2220
aaaacctcta caaatgtggt aaaataacta taacggtcct aaggtagcga gtgagtagtg  2280
ttctggggcg ggggaggacc tgcatgaggg ccagaataac tgaaatctgt gcttttctgt  2340
gtgttgcagc agcatgagcg gaagcggctc ctttgaggga ggggtattca gcccttatct  2400
gacggggcgt ctcccctcct gggcgggagt gcgtcagaat gtgatgggat ccacggtgga  2460
cggccggccc gtgcagcccg cgaactcttc aaccctgacc tatgcaaccc tgagctcttc  2520
gtcgttggac gcagctgccg ccgcagctgc tgcatctgcc gccagcgccg tgcgcggaat  2580
ggccatgggc gccggctact acggcactct ggtggccaac tcgagttcca ccaataatcc  2640
cgccagcctg aacgaggaga agctgttgct gctgatggcc cagctcgagg ccttgaccca  2700
gcgcctgggc gagctgaccc agcaggtggc tcagctgcag gagcagacgc gggccgcggt  2760
tgccacggtg aaatccaaat aaaaaatgaa tcaataaata aacggagacg gttgttgatt  2820
ttaacacaga gtctgaatct ttatttgatt tttcgcgcgc ggtaggccct ggaccaccgg  2880
tctcgatcat tgagcacccg gtggatcttt tccaggaccc ggtagaggtg ggcttggatg  2940
ttgaggtaca tgggcatgag cccgtcccgg gggtggaggt agctccattg cagggcctcg  3000
tgctcggggg tggtgttgta aatcacccag tcatagcagg ggcgcagggc atggtgttgc  3060
acaatatctt tgaggaggag actgatggcc acgggcagcc ctttggtgta ggtgtttaca  3120
aatctgttga gctgggaggg atgcatgcgg ggggagatga ggtgcatctt ggcctggatc  3180
ttgagattgg cgatgttacc gcccagatcc cgcctggggt tcatgttgtg caggaccacc  3240
agcacggtgt atccggtgca cttggggaat ttatcatgca acttggaagg gaaggcgtga  3300
aagaatttgg cgacgccttt gtgcccgccc aggttttcca tgcactcatc catgatgatg  3360
gcgatgggcc cgtgggcggc ggcctgggca aagacgtttc gggggtcgga cacatcatag  3420
ttgtggtcct gggtgaggtc atcataggcc attttaatga atttggggcg gagggtgccg  3480
gactggggga caaaggtacc ctcgatcccg ggggcgtagt tcccctcaca gatctgcatc  3540
tcccaggctt tgagctcgga ggggggggatc atgtccacct gcggggcgat aaagaacacg  3600
gtttccgggg cgggggagat gagctgggcc gaaagcaagt tccggagcag ctgggacttg  3660
ccgcagccgg tggggccgta gatgaccccg atgaccggct gcaggtggta gttgagggag  3720
agacagctgc cgtcctcccg gaggaggggg gccacctcgt tcatcatctc gcgcacgtgc  3780
atgttctcgc gcaccagttc cgccaggagg cgctctcccc ccagggatag gagctcctgg  3840
```

```
agcgaggcga agtttttcag cggcttgagt ccgtcggcca tgggcatttt ggagagggtt  3900
tgttgcaaga gttccaggcg gtcccagagc tcggtgatgt gctctacggc atctcgatcc  3960
agcagacctc ctcgtttcgc gggttgggac ggctgcggga gtagggcacc agacgatggg  4020
cgtccagcgc agccagggtc cggtccttcc agggtcgcag cgtccgcgtc agggtggtct  4080
ccgtcacggt gaaggggtgc gcgccgggct gggcgcttgc gagggtgcgc ttcaggctca  4140
tccggctggt cgaaaaccgc tcccgatcgg cgccctgcgc gtcggccagg tagcaattga  4200
ccatgagttc gtagttgagc gcctcggccg cgtggccttt ggcgcggagc ttacctttgg  4260
aagtctgccc gcaggcggga cagaggaggg acttgagggc gtagagcttg gggcgagga   4320
agacggactc gggggcgtag gcgtccgcgc cgcagtgggc gcagacggtc tcgcactcca  4380
cgagccaggt gaggtcgggc tggtcggggt caaaaaccag tttcccgccg ttctttttga  4440
tgcgtttctt acctttggtc tccatgagct cgtgtccccg ctgggtgaca aagaggctgt  4500
ccgtgtcccc gtagaccgac tttatgggcc ggtcctcgag cggtgtgccg cggtcctcct  4560
cgtagaggaa ccccgcccac tccgagacga aagcccgggt ccaggccagc acgaaggagg  4620
ccacgtggga cgggtagcgg tcgttgtcca ccagcgggtc caccttttcc agggtatgca  4680
aacacatgtc cccctcgtcc acatccagga aggtgattgg cttgtaagtg taggccacgt  4740
gaccgggggt cccggccggg ggggtataaa agggtgcggg tccctgctcg tcctcactgt  4800
cttccggatc gctgtccagg agcgccagct gttggggtag gtattccctc tcgaaggcgg  4860
gcatgacctc ggcactcagg ttgtcagttt ctagaaacga ggaggatttg atattgacgg  4920
tgccggcgga gatgcctttc aagagcccct cgtccatctg gtcagaaaag acgatctttt  4980
tgttgtcgag cttggtggcg aaggagccgt agagggcgtt ggagaggagc ttggcgatgg  5040
agcgcatggt ctggtttttt tccttgtcgg cgcgctcctt ggcggcgatg ttgagctgca  5100
cgtactcgcg cgccacgcac ttccattcgg ggaagacggt ggtcagctcg tcgggcacga  5160
ttctgacctg ccagccccga ttatgcaggg tgatgaggtc cacactggtg gccacctcgc  5220
cgcgcagggg ctcattagtc cagcagaggc gtccgccctt gcgcgagcag aaggggggca  5280
gggggtccag catgacctcg tcgggggggt cggcatcgat ggtgaagatg ccgggcagga  5340
ggtcggggtc aaagtagctg atggaagtgg ccagatcgtc cagggcagct tgccattcgc  5400
gcacggccag cgcgcgctcg tagggactga ggggcgtgcc ccagggcatg ggatgggtaa  5460
gcgcggaggc gtacatgccg cagatgtcgt agacgtagag gggctcctcg aggatgccga  5520
tgtaggtggg gtagcagcgc cccccgcgga tgctggcgcg cacgtagtca tacagctcgt  5580
gcgagggggc gaggagcccc gggcccaggt tggtgcgact gggcttttcg gcgcggtaga  5640
cgatctggcg gaaaatggca tgcgagttgg aggagatggt gggcctttgg aagatgttga  5700
agtgggcgtg gggcagtccg accgagtcgc ggatgaagtg ggcgtaggag tcttgcagct  5760
tggcgacgag ctcggcggtg actaggacgt ccagagcgca gtagtcgagg gtctcctgga  5820
tgatgtcata cttgagctgt ccctttttgtt tccacagctc gcggttgaga aggaactctt  5880
cgcggtcctt ccagtactct tcgaggggga acccgtcctg atctgcacgg taagagccta  5940
gcatgtagaa ctggttgacg gccttgtagg cgcagcagcc cttctccacg gggagggcgt  6000
aggcctgggc ggccttgcgc agggaggtgt gcgtgagggc gaaagtgtcc ctgaccatga  6060
ccttgaggaa ctggtgcttg aagtcgatat cgtcgcagcc cccctgctcc cagagctgga  6120
agtccgtgcg cttcttgtag gcggggttgg gcaaagcgaa agtaacatcg ttgaagagga  6180
tcttgcccgc gcggggcata aagttgcgag tgatgcggaa aggttggggc acctcggccc  6240
ggttgttgat gacctgggcg gcgagcacga tctcgtcgaa gccgttgatg ttgtggccca  6300
cgatgtagag ttccacgaat cgcggacggc ccttgacgtg gggcagtttc ttgagctcct  6360
cgtaggtgag ctcgtcgggg tcgctgagcc cgtgctgctc gagcgcccag tcggcgagat  6420
gggggttggc gcggaggaag gaagtccaga gatccacggc cagggcggtt tgcagacggt  6480
cccggtactg acggaactgc tgcccgacgg ccattttttc gggggtgacg cagtagaagg  6540
tgcgggggtc cccgtgccag cgatcccatt tgagctggag ggcgagatcg agggcgagct  6600
cgacgagccg gtcgtccccg gagagtttca tgaccagcat gaaggggacg agctgcttgc  6660
cgaaggaccc catccaggtg taggtttcca catcgtaggt gaggaagagc ctttcggtgc  6720
gaggatgcga gccgatgggg aagaactgga tctcctgcca ccaattggag gaatggctgt  6780
tgatgtgatg gaagtagaaa tgccgacggc gcgccgaaca ctcgtgcttg tgtttataca  6840
agcggccaca gtgctcgcaa cgctgcacgg gatgcacgtg ctgcacgagc tgtacctgag  6900
ttcctttgac gaggaatttc agtgggaagt ggagtcgtgg cgcctgcatc tcgtgctgta  6960
ctacgtcgtg gtggtcggcc tggccctctt ctgcctcgat ggtggtcatg ctgacgagcc  7020
cgcgcgggag gcaggtccag acctcggcgc gagcgggtcg gagagcgagg acgagggcgc  7080
gcaggccgga gctgtccagg gtcctgagac gctgcggagt caggtcagtg ggcagcggcg  7140
gcgcgcggtt gacttgcagg agtttttcca gggcgcgcgg gaggtccaga tggtacttga  7200
tctccaccgc gccattggtg gcgacgtcga tggcttgcag ggtcccgtgc cctggggtg   7260
tgaccaccgt cccccgtttc ttcttgggcg gctggggcga cgggggcggt gcctcttcca  7320
tggttagaag cggcggcgag gacgcgcgcc gggcggcagg ggcggctcgg ggcccggagg  7380
caggggcggc aggggcacgt cggcgccgcg cgcgggtagg ttctggtact gcgcccggag  7440
aagactggcg tgagcgacga cgcgacggtt gacgtcctgg atctgacgcc tctgggtgaa  7500
ggccacggga cccgtgagtt tgaacctgaa agagagttcg acagaatcaa tctcggtatc  7560
gttgacggcg gcctgccgca ggatctcttg cacgtcgccc gagttgtcct ggtaggcgat  7620
ctcggtcatg aactgctcga tctcctcctc ttgaaggtct ccgcggccgg cgcgctccac  7680
ggtggccgcg aggtcgttgg agatgcggcc catgagctgc gagaaggcgt tcatgcccgc  7740
ctcgttccag acgcggctgt agaccacgac gccctcggga tcgcgggcgc gcatgaccac  7800
ctgggcgagg ttgagctcca cgtggcgcgt gaagaccgcg tagttgcaga ggcgctggta  7860
gaggtagttg agcgtggtgg cgatgtgctc ggtgacgaag aaatacatga tccagcggcg  7920
gagcggcatc tcgctgacgt cgcccagcgc ctccaaacgt tccatggcct cgtaaaagtc  7980
cacggcgaag ttgaaaaact gggagttgcg cgccgagacg gtcaactcct cctccagaag  8040
acggatgagc tcggcgatgg tggcgcgcac ctcgcgctcg aaggcccccg ggagttcctc  8100
cacttcctct tcttcctcct ccactaacat ctcttctact tcctcctcag gcggcagtgg  8160
tggcgggggga gggggcctgc gtcgccggcg gcgcacgggc agacggtcga tgaagcgctc  8220
gatggtctcg ccgcgccggc gtcgcatggt ctcggtgacg gcgcgcccgt cctcgcgggg  8280
ccgcagcgtg aagacgccgc cgcgcatctc caggtggccg ggggggtccc cgttgggcag  8340
ggagagggcg ctgacgatgc atcttatcaa ttgccccgta gggactccgc gcaaggacct  8400
gagcgtctcg agatccacgg gatctgaaaa ccgctgaacg aaggcttcga gccagtcgca  8460
gtcgcaaggt aggctgagca cggtttcttc tggcgggtca tgttggttgg gagcggggcg  8520
ggcgatgctg ctggtgatga agttgaaata ggcggttctg agacggcgga tggtggcgag  8580
```

```
gagcaccagg tctttgggcc cggcttgctg gatgcgcaga cggtcggcca tgccccaggc  8640
gtggtcctga cacctggcca ggtccttgta gtagtcctgc atgagccgct ccacgggcac  8700
ctcctcctcg cccgcgcggc cgtgcatgcg cgtgagcccg aagccgcgct ggggctggac  8760
gagcgccagg tcggcgacga cgcgctcggc gaggatggct tgctggatct gggtgagggt  8820
ggtctggaag tcatcaaagt cgacgaagcg gtggtaggct ccggtgttga tggtgtagga  8880
gcagttggcc atgacggacc agttgacggt ctggtggccc ggacgcacga gctcgtggta  8940
cttgaggcgc gagtaggcgc gcgtgtcgaa gatgtagtcg ttgcaggtgc gcaccaggta  9000
ctggtagccg atgaggaagt gcggcggcgg ctggcggtag agcggccatc gctcggtggc  9060
gggggcgccg ggcgcgaggt cctcgagcat ggtgcggtgg tagccgtaga tgtacctgga  9120
catccaggtg atgccggcgg cggtggtgga ggcgcgcggg aactcgcgga cgcggttcca  9180
gatgttgcgc agcggcagga agtagttcat ggtgggcacg gtctggcccg tgaggcgcgc  9240
gcagtcgtgg atgctctata cgggcaaaaa cgaaagcggt cagcggctcg actccgtggc  9300
ctggaggcta agcgaacggg ttgggctgcg cgtgtacccc ggttcgaatc tcgaatcagg  9360
ctggagccgc agctaacgtg gtattggcac tcccgtctcg acccaagcct gcaccaaccc  9420
tccaggatac ggaggcgggt cgttttgcaa cttttttttg gaggccggat gagactagta  9480
agcgcggaaa gcggccgacc gcgatggctc gctgccgtag tctggagaag aatcgccagg  9540
gttgcgttgc ggtgtgcccc ggttcgaggc cggccggatt ccgcggctaa cgagggcgtg  9600
gctgccccgt cgtttccaag accccatagc cagccgactt ctccagttac ggagcgagcc  9660
cctcttttgt tttgtttgtt tttgccagat gcatcccgta ctgcggcaga tgcgccccca  9720
ccaccctcca ccgcaacaac agccccctcc acagccggcg cttctgcccc cgccccagca  9780
gcaacttcca gccacgaccg ccgcggccgc cgtgagcggg gctggacaga gttatgatca  9840
ccagctggcc ttggaagagg gcgaggggct ggcgcgcctg ggggcgtcgt cgccggagcg  9900
gcacccgcgc gtgcagatga aagggacgc tcgcgaggcc tacgtgccca agcagaacct  9960
gttcagagac aggagcggcg aggagcccga ggagatgcgc gcggcccggt tccacgcggg  10020
gcgggagctg cggcgcggcc tggaccgaaa gagggtgctg agggacgagg atttcgaggc  10080
ggacgagctg acggggatca gccccgcgcg cgcgcacgtg gccgcggcca acctggtcac  10140
ggcgtacgag cagaccgtga aggaggagag caacttccaa aaatccttca acaaccacgt  10200
gcgcaccctg atcgcgcgcg aggaggtgac cctgggcctg atgcacctgt gggacctgct  10260
ggaggccatc gtgcagaacc ccaccagcaa gccgctgacg gcgcagctgt tcctggtggt  10320
gcagcatagt cgggacaacg aagcgttcag ggaggcgctg ctgaatatca ccgagcccga  10380
gggccgctgg ctcctggacc tggtgaacat tctgcagagc atcgtggtgc aggagcgcgg  10440
gctgccgctg tccgagaagc tggcggccat caacttctcg gtgctgagtt tgggcaagta  10500
ctacgctagg aagatctaca agaccccgta cgtgcccata gacaaggagg tgaagatcga  10560
cgggttttac atgcgcatga ccctgaaagt gctgaccctg agcgacgatc tgggggtgta  10620
ccgcaacgac aggatgcacc gtgcggtgag cgccagcagg cggcgcgagc tgagcgacca  10680
ggagctgatg catagtctgc agcgggccct gaccggggcc gggaccgagg gggagagcta  10740
ctttgacatg ggcgcggacc tgcactggca gcccagccgc cgggccttgg aggcggcggc  10800
aggaccctac gtagaagagg tggacgatga ggtggacgag gagggcgagt acctggaaga  10860
ctgatggcgc gaccgtattt ttgctagatg caacaacaac agccacctcc tgatcccgcg  10920
atgcgggcgg cgctgcagag ccagccgtcc ggcattaact cctcggacga ttggacccag  10980
gccatgcaac gcatcatggc gctgacgacc cgcaaccccg aagcctttag acagcagccc  11040
caggccaacc ggctctcggc catcctggag gccgtggtgc cctcgcgctc caaccccacg  11100
cacgagaagg tcctggccat cgtgaacgcg ctggtggaga acaaggccat ccgcggcgac  11160
gaggccggcc tggtgtacaa cgcgctgctg gagcgcgtgg cccgctacaa cagcaccaac  11220
gtgcagacca acctggaccg catggtgacc gacgtgcgcg aggccgtggc ccagcgcgag  11280
cggttccacc gcgagtccaa cctgggatcc atggtggcgc tgaacgcctt cctcagcacc  11340
cagcccgcca acgtgccccg gggccaggag gactacacca acttcatcag cgccctgcgc  11400
ctgatggtga ccgaggtgcc ccagagcgag gtgtaccagt ccgggccgga ctacttcttc  11460
cagaccagtc gccagggctt gcagaccgtg aacctgagcc aggctttcaa gaacttgcag  11520
ggcctgtggg gcgtgcaggc cccggtcggg gaccgcgcga cggtgtcgag cctgctgacg  11580
ccgaactcgc gcctgctgct gctgctggtg gccccccttca cggacagcgg cagcatcaac  11640
cgcaactcgt acctgggcta cctgattaac ctgtaccgcg aggccatcgg ccaggcgcac  11700
gtggacgagc agacctacca ggagatcacc cacgtgagcc gcgccctggg ccaggacgac  11760
ccgggcaacc tggaagccac cctgaacttt ttgctgacca accggtcgca gaagatcccg  11820
ccccagtacg cgctcagcac cgaggaggag cgcatcctgc gttacgtgca gcagagcgtg  11880
ggcctgttcc tgatgcagga gggggccacc cccagcgccg cgctcgacat gaccgcgcgc  11940
aacatggagc ccagcatgta cgccagcaac cgcccgttca tcaataaact gatggactac  12000
ttgcatcggg cggccgccat gaactctgac tatttcacca acgccatcct gaatccccac  12060
tggctcccgc cgccggggtt ctacacgggc gagtacgaca tgcccgaccc caatgacggg  12120
ttcctgtggg acgatgtgga cagcagcgtg ttctcccccc gaccgggtgc taacgagcgc  12180
cccttgtgga agaaggaagg cagcgaccga cgcccgtcct cggcgctgtc cggccgcgag  12240
ggtgctgccg cggcggtgcc cgaggccgcc agtcctttcc cgagcttgcc cttctcgctg  12300
aacagtatcc gcagcagcga gctgggcagg atcacgcgcc cgcgcttgct gggcgaagag  12360
gagtacttga atgactcgct gttgagaccc gagcgggaga agaacttccc caataacggg  12420
atagaaagcc tggtggacaa gatgagccgc tggaagacgt atgcgcagga gcacagggac  12480
gatccccggg cgtcgcaggg ggccacgagc cggggcagcg ccgcccgtaa acgccggtgg  12540
cacgacaggc agcggggaca gatgtgggac gatgaggact ccgccgacga cagcagcgtg  12600
ttggacttgg gtgggagtgg taacccgttc gctcacctgc gcccccgtat cgggcgcatg  12660
atgtaagaga aaccgaaaat aaatgatact caccaaggcc atggcgacca gcgtgcgttc  12720
gtttcttctc tgttgttgtt gtatctagta tgatgaggcg tgcgtacccg gagggtcctc  12780
ctccctcgta cgagagcgtg atgcagcagg cgatggcggc ggcggcgatg cagcccccgc  12840
tggaggctcc ttacgtgccc ccgcggtacc tggcgcctac ggaggggcgg aacagcattc  12900
gttactcgga gctggcaccc ttgtacgata ccacccggtt gtacctggtg gacaacaagt  12960
cggcggacat cgcctcgctg aactaccaga acgaccacag caacttcctg accaccgtgg  13020
tgcagaacaa tgacttcacc cccacggagg ccagcaccca gaccatcaac tttgacgagc  13080
gctcgcggtg gggcggccag ctgaaaacca tcatgcacac caacatgccc aacgtgaacg  13140
agttcatgta cagcaacaag ttcaaggcgc gggtgatggt ctcccgcaag acccccaatg  13200
gggtgacagt gacagaggat tatgatggta gtcaggatga gctgaagtat gaatgggtgg  13260
aatttgagct gcccgaaggc aacttctcgg tgaccatgac catcgacctg atgaacaacg  13320
```

```
ccatcatcga caattacttg gcggtggggc ggcagaacgg ggtgctggag agcgacatcg  13380
gcgtgaagtt cgacactagg aacttcaggc tgggctggga ccccgtgacc gagctggtca  13440
tgcccggggt gtacaccaac gaggctttcc atcccgatat tgtcttgctg cccggctgcg  13500
gggtggactt caccgagagc cgcctcagca acctgctggg cattcgcaag aggcagccct  13560
tccaggaagg cttccagatc atgtacgagg atctggaggg gggcaacatc cccgcgctcc  13620
tggatgtcga cgcctatgag aaaagcaagg aggatgcagc agctgaagca actgcagccg  13680
tagctaccgc ctctaccgag gtcaggggcg ataattttgc aagcgccgca gcagtggcag  13740
cggccgaggc ggctgaaacc gaaagtaaga tagtcattca gccggtggag aaggatagca  13800
agaacaggag ctacaacgta ctaccggaca agataaacac cgcctaccgc agctggtacc  13860
tagcctacaa ctatggcgac cccgagaagg gcgtgcgctc ctggacgctg ctcaccacct  13920
cggacgtcac ctgcggcgtg gagcaagtct actggtcgct gcccgacatg atgcaagacc  13980
cggtcacctt ccgctccacg cgtcaagtta gcaactaccc ggtggtgggc gccgagctcc  14040
tgcccgtcta ctccaagagc ttcttcaacg agcaggccgt ctactcgcag cagctgcgcg  14100
ccttcacctc gcttacgcac gtcttcaacc gcttccccga gaaccagatc ctcgtccgcc  14160
cgcccgcgcc caccattacc accgtcagtg aaaacgttcc tgctctcaca gatcacggga  14220
ccctgccgct gcgcagcagt atccggggag tccagcgcgt gaccgttact gacgccagac  14280
gccgcacctg cccctacgtc tacaaggccc tgggcatagt cgcgccgcgc gtcctctcga  14340
gccgcacctt ctaaatgtcc attctcatct cgcccagtaa taacaccggt tggggcctgc  14400
gcgcgcccag caagatgtac ggaggcgctc gccaacgctc cacgcaacac cccgtgcgcg  14460
tgcgcgggca cttccgcgct ccctggggcg ccctcaaggg ccgcgtgcgg tcgcgcacca  14520
ccgtcgacga cgtgatcgac caggtggtgg ccgacgcgcg caactacacc cccgccgccg  14580
cgcccgtctc caccgtggac gccgtcatcg acagcgtggt ggccgacgcg cgccggtacg  14640
cccgcgccaa gagccggcgg cggcgcatcg cccggcggca ccggagcacc cccgccatgc  14700
gcgcggcgcg agccttgctg cgcagggcca ggcgcacggg acgcagggcc atgctcaggg  14760
cggccagacg cgcggcttca ggcgccagcg ccggcaggac ccggagacgc gcggccacgg  14820
cggcggcagc ggccatcgcc agcatgtccc gcccgcggcg agggaacgtg tactgggtgc  14880
gcgacgccgc caccggtgtg cgcgtgcccg tgcgcacccg ccccccctcgc acttgaagat  14940
gttcacttcg cgatgttgat gtgtcccagc ggcgaggagg atgtccaagc gcaaattcaa  15000
ggaagagatg ctccaggtca tcgcgcctga gatctacggc cctgcggtgg tgaaggagga  15060
aagaaagccc cgcaaaatca agcgggtcaa aaaggacaaa aaggaagaag aaagtgatgt  15120
ggacggattg gtggagtttg tgcgcgagtt cgccccccgg cggcgcgtgc agtggcgcgg  15180
gcggaaggtg caaccggtgc tgagacccgg caccaccgtg gtcttcacgc ccggcgagcg  15240
ctccggcacc gcttccaagc gctcctacga cgaggtgtac ggggatgatg atattctgga  15300
gcaggcggcc gagcgcctgg gcgagtttgc ttacggcaag cgcagccgtt ccgcaccgaa  15360
ggaagaggcg gtgtccatcc cgctggacca cggcaacccc acgccgagcc tcaagcccgt  15420
gaccttgcag caggtgctgc cgaccgcggc gccgcgccgg gggttcaagc gcgagggcga  15480
ggatctgtac cccaccatgc agctgatggt gcccaagcgc cagaagctgg aagacgtgct  15540
ggagaccatg aaggtggacc cggacgtgca gcccgaggtc aaggtgcggc ccatcaagca  15600
ggtggccccg ggcctgggcg tgcagaccgt ggacatcaag attcccacgg agcccatgga  15660
aacgcagacc gagcccatga tcaagcccag caccagcacc atggaggtgc agacggatcc  15720
ctggatgcca tcggctccta gtcgaagacc ccggcgcaag tacggcgcgg ccagcctgct  15780
gatgcccaac tacgcgctgc atccttccat catccccacg ccgggctacc gcggcacgcg  15840
cttctaccgc ggtcatacca gcagccgccg ccgcaagacc accactcgcc gccgccgtcg  15900
ccgcaccgcc gctgcaacca cccctgccgc cctggtgcgg agagtgtacc gccgcggccg  15960
cgcacctctg accctgccgc gcgcgcgcta ccacccgagc atcgccattt aaactttcgc  16020
ctgctttgca gatcaatggc cctcacatgc cgccttcgcg ttcccattac gggctaccga  16080
ggaagaaaac cgcgccgtag aaggctggcg gggaacggga tgcgtcgcca ccaccaccgg  16140
cggcggcgcg ccatcagcaa gcggttgggg ggaggcttcc tgcccgcgct gatccccatc  16200
atcgccgcgg cgatcggggc gatccccggc attgcttccg tggcggtgca ggcctctcag  16260
cgccactgag acacacttgg aaacatcttg taataaacca atggactctg acgctcctgg  16320
tcctgtgatg tgttttcgta gacagatgga agacatcaat ttttcgtccc tggctccgcg  16380
acacggcacg cggccgttca tgggcacctg gagcgacatc ggcaccagcc aactgaacgg  16440
gggcgccttc aattggagca gtctctggag cgggcttaag aatttcgggt ccacgcttaa  16500
aacctatggc agcaaggcgt ggaacagcac cacagggcag gcgctgaggg ataagctgaa  16560
agagcagaac ttccagcaga aggtggtcga tgggctcgcc tcgggcatca acggggtggt  16620
ggacctggcc aaccaggccg tgcagcggca gatcaacagc cgcctggacc cggtgccgcc  16680
cgccggctcc gtggagatgc cgcaggtgga ggaggagctg cctcccctgg acaagcgggg  16740
cgagaagcga ccccgccccg atgcggagga gacgctgctg acgcacacgg acgagccgcc  16800
cccgtacgag gaggcggtga aactgggtct gcccaccacg cggcccatcg cgcccctggc  16860
caccggggtg ctgaaacccg aaaagcccgc gaccctggac ttgcctcctc cccagccttc  16920
ccgcccctct acagtggcta agcccctgcc gccggtggcc gtggcccgcg cgcgacccgg  16980
gggcaccgcc cgccctcatg cgaactggca gagcactctg aacagcatcg tgggtctggg  17040
agtgcagagt gtgaagcgcc gccgctgcta ttaaacctac cgtagcgctt aacttgcttg  17100
tctgtgtgtg tatgtattat gtcgccgccg ccgctgtcca ccagaaggag gagtgaagag  17160
gcgcgtcgcc gagttgcaag atggccaccc catcgatgct gccccagtgg gcgtacatgc  17220
acatcgccgg acaggacgct tcggagtacc tgagtccggg tctggtgcag tttgcccgcg  17280
ccacagacac ctacttcagt ctggggaaca agtttaggaa ccccacggtg gcgcccacgc  17340
acgatgtgac caccgaccgc agccagcggc tgacgctgcg cttcgtgccc gtggaccgcg  17400
aggacaacac ctactcgtac aaagtgcgct acacgctggc cgtgggcgac aaccgcgtgc  17460
tggacatggc cagcacctac tttgacatcc gcggcgtgct ggatcggggc cctagcttca  17520
aaccctactc cggcaccgcc tacaacagtc tggcccccaa gggagcaccc aacacttgtc  17580
agtggacata taaagccgat ggtgaaactg ccacagaaaa aacctataca tatggaaatg  17640
cacccgtgca gggcattaac atcacaaaag atggtattca acttggaact gacaccgatg  17700
atcagccaat ctacgcagat aaaacctatc agcctgaacc tcaagtgggt gatgctgaat  17760
ggcatgacat cactggtact gatgaaaagt atggaggcag agctcttaag cctgatacca  17820
aaatgaagcc ttgttatggt tcttttgcca agcctactaa taaagaagga ggtcaggcaa  17880
atgtgaaaac aggaacaggc actactaaag aatatgacat agacatggct ttctttgaca  17940
acagaagtgc ggctgctgct ggcctagctc cagaaattgt tttgtatact gaaaatgtgg  18000
atttggaaac tccagatacc catattgtat acaaagcagg cacagatgac agcagctctt  18060
```

```
ctattaattt gggtcagcaa gccatgccca acagacctaa ctacattggt ttcagagaca  18120
actttatcgg gctcatgtac tacaacagca ctggcaatat gggggtgctg gccggtcagg  18180
cttctcagct gaatgctgtg gttgacttgc aagacagaaa caccgagctg tcctaccagc  18240
tcttgcttga ctctctgggt gacagaaccc ggtatttcag tatgtggaat caggcggtgg  18300
acagctatga tcctgatgtg cgcattattg aaaatcatgg tgtggaggat gaacttccca  18360
actattgttt ccctctggat gctgttggca gaacagatac ttatcaggga attaaggcta  18420
atggaactga tcaaaccaca tggaccaaag atgacagtgt caatgatgct aatgagatag  18480
gcaagggtaa tccattcgcc atggaaatca acatccaagc caacctgtgg aggaacttcc  18540
tctacgccaa cgtggccctg tacctgcccg actcttacaa gtacacgccg gccaatgtta  18600
ccctgcccac caacaccaac acctacgatt acatgaacgg ccgggtggtg gcgccctcgc  18660
tggtggactc ctacatcaac atcggggcgc gctggtcgct ggatcccatg gacaacgtga  18720
acccctcaa ccaccaccgc aatgcggggc tgcgctaccg ctccatgctc ctgggcaacg  18780
ggcgctacgt gcccttccac atccaggtgc cccagaaatt tttcgccatc aagagcctcc  18840
tgctcctgcc cgggtcctac acctacgagt ggaacttccg caaggacgtc aacatgatcc  18900
tgcagagctc cctcggcaac gacctgcgca cggacggggc ctccatctcc ttcaccagca  18960
tcaacctcta cgccaccttc ttccccatgg cgcacaacac ggcctccacg ctcgaggcca  19020
tgctgcgcaa cgacaccaac gaccagtcct tcaacgacta cctctcggcg gccaacatgc  19080
tctaccccat cccggccaac gccaccaacg tgcccatctc catcccctcg cgcaactggg  19140
ccgccttccg cggctggtcc ttcacgcgtc tcaagaccaa ggagacgccc tcgctgggct  19200
ccgggttcga cccctacttc gtctactcgg gctccatccc ctacctcgac ggcaccttct  19260
acctcaacca caccttcaag aaggtctcca tcaccttcga ctcctccgtc agctggcccg  19320
gcaacgaccg gctcctgacg cccaacgagt tcgaaatcaa gcgcaccgtc gacggcgagg  19380
gctacaacgt ggcccagtgc aacatgacca aggactggtt cctggtccag atgctggccc  19440
actacaacat cggctaccag ggcttctacg tgcccgaggg ctacaaggac cgcatgtact  19500
ccttcttccg caacttccag cccatgagcc gccaggtggt ggacgaggtc aactacaagg  19560
actaccaggc cgtcaccctg gcctaccagc acaacaactc gggcttcgtc ggctacctcg  19620
cgcccaccat gcgccagggc cagccctacc ccgccaacta cccctacccg ctcatcggca  19680
agagcgccgt caccagcgtc acccagaaaa agttcctctg cgacagggtc atgtggcgca  19740
tcccttctc cagcaacttc atgtccatgg gcgcgctcac cgacctcggc cagaacatgc  19800
tctatgccaa ctccgcccac gcgctagaca tgaatttcga agtcgacccc atggatgagt  19860
ccaccttct ctatgttgtc ttcgaagtct tcgacgtcgt ccgagtgcac cagccccacc  19920
gcggcgtcat cgaggccgtc tacctgcgca cccccttctc ggccggtaac gccaccacct  19980
aagctcttgc ttcttgcaag ccatggccgc gggctccggc gagcaggagc tcagggccat  20040
catccgcgac ctgggctgcg ggccctactt cctgggcacc ttcgataagc gcttcccggg  20100
attcatggcc ccgcacaagc tggcctgcgc catcgtcaac acggccggcc gcgagaccgg  20160
gggcgagcac tggctggcct tcgcctggaa cccgcgctcg aacacctgct acctcttcga  20220
cccttcggg ttctcggacg agcgcctcaa gcagatctac cagttcgagt acgagggcct  20280
gctgcgccgc agcgccctgg ccaccgagga ccgctgcgtc accctggaaa agtccaccca  20340
gaccgtgcag ggtccgcgct cggccgcctg cgggctcttc tgctgcatgt tcctgcacgc  20400
cttcgtgcac tggcccgacc gccccatgga caagaacccc accatgaact tgctgacggg  20460
ggtgcccaac ggcatgctcc agtcgcccca ggtggaaccc accctgcgcc gcaaccagga  20520
ggcgctctac cgcttcctca actcccactc cgcctacttt cgctcccacc gcgcgcgcat  20580
cgagaaggcc accgccttcg accgcatgaa tcaagacatg taaaccgtgt gtgtatgtta  20640
aatgtcttta ataaacagca ctttcatgtt acacatgcat ctgagatgat ttatttagaa  20700
atcgaaaggg ttctgccggg tctcggcatg gcccgcgggc agggacacgt tgcggaactg  20760
gtacttggcc agccacttga actcggggat cagcagtttg ggcagcgggg tgtcggggaa  20820
ggagtcggtc cacagcttcc gcgtcagttg cagggcgccc agcaggtcgg gcgcggagat  20880
cttgaaatcg cagttgggac ccgcgttctg cgcgcgggag ttgcggtaca cggggttgca  20940
gcactggaac accatcaggg ccgggtgctt cacgctcgcc agcaccgtcg cgtcggtgat  21000
gctctccacg tcgaggtcct cggcgttggc catcccgaag gggtcatct tgcaggtctg  21060
ccttcccatg gtgggcacgc acccgggctt gtggttgcaa tcgcagtgca gggggatcag  21120
catcatctgg gcctggtcgg cgttcatccc cgggtacatg gccttcatga aagcctccaa  21180
ttgcctgaac gcctgctggg ccttggctcc ctcggtgaag aagaccccgc aggacttgct  21240
agagaactgg ttggtggcgc acccggcgtc gtgcacgcag cagcgcgcgt cgttgttggc  21300
cagctgcacc acgctgcgcc cccagcggtt ctgggtgatc ttggcccggt cggggttctc  21360
cttcagcgcg cgctgcccgt tctcgctcgc cacatccatc tcgatcatgt gctccttctg  21420
gatcatggtg gtcccgtgca ggcaccgcag cttgccctcg gcctcggtgc acccgtgcag  21480
ccacagcgcg cacccggtgc actcccagtt cttgtgggcg atctgggaat gcgcgtgcac  21540
gaagccctgc aggaagcggc ccatcatggt ggtcagggtc ttgttgctag tgaaggtcag  21600
cggaatgccg cggtgctcct cgttgatgta caggtggcag atgcggcggt acacctcgcc  21660
ctgctcgggc atcagctgga agttggcttt caggtcggtc tccacgcggt agcggtccat  21720
cagcatagtc atgatttcca tacccttctc ccaggccgag acgatgggca ggctcatagg  21780
gttcttcacc atcatcttag cgctagcagc cgcggccagg gggtcgctct cgtccagggt  21840
ctcaaagctc cgcttgccgt ccttctcggt gatccgcacc ggggggtagc tgaagcccac  21900
ggccgccagc tcctcctcgg cctgtctttc gtcctcgctg tcctggctga cgtcctgcag  21960
gaccacatgc ttggtcttgc ggggtttctt cttgggcggc agcggcggcg gagatgttgg  22020
agatggcgag gggggagcgcg agttctcgct caccactact atctcttcct cttcttggtc  22080
cgaggccacg cggcggtagg tatgtctctt cgggggcaga ggcggaggcg acgggctctc  22140
gccgccgcga cttggcggat ggctggcaga gccccttccg cgttcggggg tgcgctcccg  22200
gcggcgctct gactgacttc ctccgcggcc ggccattgtg ttctcctagg gaggaacaac  22260
aagcatggag actcagccat cgccaacctc gccatctgcc cccaccgccg acgagaagca  22320
gcagcagcag aatgaaagct taaccgcccc gccgcccagc cccgccacct ccgacgcggc  22380
cgtcccagac atgcaagaga tggaggaatc catcgagatt gacctgggct atgtgacgcc  22440
cgcggagcac gaggaggagc tggcagtgcg cttttcacaa gaagagatac accaagaaca  22500
gccagagcag gaagcagaga atgagcagag tcaggctggg ctcgagcatg acggcgacta  22560
cctccacctg agcgggggggg aggacgcgct catcaagcat ctggcccggc aggccaccat  22620
cgtcaaggat gcgctgctcg accgcaccga ggtgcccctc agcgtggagg agctcagccg  22680
cgcctacgag ttgaacctct tctcgccgcg cgtgcccccc aagcgccagc ccaatggcac  22740
ctgcgagccc aacccgcgcc tcaacttcta cccggtcttc gcggtgcccg aggccctggc  22800
```

```
cacctaccac atctttttca agaaccaaaa gatccccgtc tcctgccgcg ccaaccgcac  22860
ccgcgccgac gcccttttca acctgggtcc cggcgcccgc ctacctgata tcgcctcctt  22920
ggaagaggtt cccaagatct tcgagggtct gggcagcgac gagactcggg ccgcgaacgc  22980
tctgcaagga gaaggaggag agcatgagca ccacagcgcc ctggtcgagt tggaaggcga  23040
caacgcgcgg ctggcggtgc tcaaacgcac ggtcgagctg acccatttcg cctacccggc  23100
tctgaacctg ccccccaaag tcatgagcgc ggtcatggac caggtgctca tcaagcgcgc  23160
gtcgcccatc tccgaggacg agggcatgca agactccgag gagggcaagc ccgtggtcag  23220
cgacgagcag ctggcccggt ggctgggtcc taatgctagt ccccagagtt tggaagagcg  23280
gcgcaaactc atgatggccg tggtcctggt gaccgtggag ctggagtgcc tgcgccgctt  23340
cttcgccgac gcggagaccc tgcgcaaggt cgaggagaac ctgcactacc tcttcaggca  23400
cgggttcgtg cgccaggcct gcaagatctc caacgtggag ctgaccaacc tggtctccta  23460
catgggcatc ttgcacgaga accgcctggg gcagaacgtg ctgcacacca ccctgcgcgg  23520
ggaggcccgg cgcgactaca tccgcgactg cgtctacctc tacctctgcc acacctggca  23580
gacgggcatg ggcgtgtggc agcagtgtct ggaggagcag aacctgaaag agctctgcaa  23640
gctcctgcag aagaacctca agggtctgtg gaccgggttc gacgagcgca ccaccgcctc  23700
ggacctggcc gacctcattt tccccgagcg cctcaggctg acgctgcgca acggcctgcc  23760
cgactttatg agccaaagca tgttgcaaaa ctttcgctct ttcatcctcg aacgctccgg  23820
aatcctgccc gccacctgct ccgcgctgcc ctcggacttc gtgccgctga ccttccgcga  23880
gtgccccccg ccgctgtgga gccactgcta cctgctgcgc ctggccaact acctggccta  23940
ccactcggac gtgatcgagg acgtcagcgg cgagggcctg ctcgagtgcc actgccgctg  24000
caacctctgc acgccgcacc gctccctggc ctgcaacccc cagctgctga gcgagaccca  24060
gatcatcggc accttcgagt tgcaagggcc cagcgaaggc gagggttcag ccgccaaggg  24120
gggtctgaaa ctcaccccgg ggctgtggac ctcggcctac ttgcgcaagt tcgtgcccga  24180
ggactaccat cccttcgaga tcaggttcta cgaggaccaa tcccatccgc ccaaggccga  24240
gctgtcggcc tgcgtcatca cccagggggc gatcctggcc caattgcaag ccatccagaa  24300
atcccgccaa gaattcttgc tgaaaaaggg ccgcggggtc tacctcgacc cccagaccgg  24360
tgaggagctc aaccccggct tcccccagga tgccccgagg aaacaagaag ctgaaagtgg  24420
agctgccgcc cgtggaggat ttggaggaag actgggagaa cagcagtcag gcagaggagg  24480
aggagatgga ggaagactgg gacagcactc aggcagagga ggacagcctg caagacagtc  24540
tggaggaaga cgaggaggag gcagaggagg aggtggaaga agcagccgcc gccagaccgt  24600
cgtcctcggc gggggagaaa gcaagcagca cggataccat ctccgctccg ggtcggggtc  24660
ccgctcgacc acacagtaga tgggacgaga ccggacgatt cccgaacccc accacccaga  24720
ccggtaagaa ggagcggcag ggatacaagt cctggcgggg gcacaaaaac gccatcgtct  24780
cctgcttgca ggcctgcggg ggcaacatct ccttcacccg gcgctacctg ctcttccacc  24840
gcggggtgaa ctttccccgc aacatcttgc attactaccg tcacctccac agcccctact  24900
acttccaaga agaggcagca gcagcagaaa aagaccagca gaaaaccagc agctagaaaa  24960
tccacagcgg cggcagcagg tggactgagg atcgcggcga acgagccggc gcaaacccgg  25020
gagctgagga accggatctt tcccaccctc tatgccatct tccagcagag tcgggggcag  25080
gagcaggaac tgaaagtcaa gaaccgttct ctgcgctcgc tcacccgcag ttgtctgtat  25140
cacaagagcg aagaccaact tcagcgcact ctcgaggacg ccgaggctct cttcaacaag  25200
tactgcgcgc tcactcttaa agagtagccc gcgcccgccc agtcgcagaa aaaggcggga  25260
attacgtcac ctgtgccctt cgccctagcc gcctccaccc atcatcatga gcaaagagat  25320
tcccacgcct tacatgtgga gctaccagcc ccagatgggc ctggccgccg gtgccgccca  25380
ggactactcc acccgcatga attggctcag cgccgggccc gcgatgatct cacgggtgaa  25440
tgacatccgc gcccaccgaa accagatact cctagaacag tcagcgctca ccgccacgcc  25500
ccgcaatcac ctcaatccgc gtaattggcc cgccgccctg gtgtaccagg aaattcccca  25560
gcccacgacc gtactacttc cgcgagacgc ccaggccgaa gtccagctga ctaactcagg  25620
tgtccagctg gcgggcggcg ccaccctgtg tcgtcaccgc cccgctcagg gtataaagcg  25680
gctggtgatc cggggcagag gcacacagct caacgacgag gtggtgagct cttcgctggg  25740
tctgcgacct gacggagtct tccaactcgc cggatcgggg agatcttcct tcacgcctcg  25800
tcaggccgtc ctgactttgg agagttcgtc ctcgcagccc cgctcgggtg gcatcggcac  25860
tctccagttc gtggaggagt tcactccctc ggtctacttc aacccctct ccggctcccc  25920
cggccactac ccggacgagt tcatcccgaa cttcgacgcc atcagcgagt cggtggacgg  25980
ctacgattga aactaatcac ccccttatcc agtgaaataa agatcatatt gatgatgatt  26040
ttacagaaat aaaaaataat catttgattt gaaataaaga tacaatcata ttgatgattt  26100
gagtttaaca aaaaaataaa gaatcactta cttgaaatct gataccaggt ctctgtccat  26160
gttttctgcc aacaccactt cactcccctc ttcccagctc tggtactgca ggccccggcg  26220
ggctgcaaac ttcctccaca cgctgaaggg gatgtcaaat tcctcctgtc cctcaatctt  26280
cattttatct tctatcagat gtccaaaaag cgcgtccggg tggatgatga cttcgacccc  26340
gtctacccct acgatgcaga caacgcaccg accgtgccct tcatcaaccc cccttcgtc  26400
tcttcagatg gattccaaga gaagcccctg gggtgttgt ccctgcgact ggccgacccc  26460
gtcaccacca agaacgggga aatcaccctc aagctgggag agggggtgga cctcgattcc  26520
tcgggaaaac tcatctccaa cacggccacc aaggccgccg cccctctcag tttttccaac  26580
aacaccattt cccttaacat ggatcacccc ttttacacta aagatggaaa attatcctta  26640
caagtttctc caccattaaa tatactgaga acaagcattc taaacacact agctttaggt  26700
tttggatcag gtttaggact ccgtggctct gccttggcag tacagttagt ctctccactt  26760
acatttgata ctgatggaaa cataaagctt accttagaca gaggtttgca tgttacaaca  26820
ggagatgcaa ttgaaagcaa cataagctgg gctaaaggtt taaaatttga agatggagcc  26880
atagcaacca acattggaaa tgggttagag tttggaagca gtagtacaga aacaggtgtt  26940
gatgatgctt acccaatcca agttaaactt ggatctggcc ttagctttga cagtacagga  27000
gccataatgg ctggtaacaa agaagacgat aaactcactt tgtggacaac acctgatcca  27060
tcaccaaact gtcaaatact cgcagaaaat gatgcaaaac taacactttg cttgactaaa  27120
tgtggtagtc aaatactggc cactgtgtca gtcttagttg taggaagtgg aaacctaaac  27180
cccattactg gcaccgtaag cagtgctcag gtgtttctac gttttgatgc aaacggtgtt  27240
cttttaacag aacattctac actaaaaaaa tactgggggt ataggcaggg agatagcata  27300
gatggcactc catataccaa tgctgtagga ttcatgccca atttaaaagc ttatccaaag  27360
tcacaaagtt ctactactaa aaataatata gtagggcaag tatacatgaa tggagatgtt  27420
tcaaaaccta tgcttctcac tataaccctc aatggtactg atgacagcaa cagtacatat  27480
tcaatgtcat tttcatacac ctggactaat ggaagctatg ttggagcaac atttggggct  27540
```

```
aactcttata ccttctcata catcgcccaa gaatgaacac tgtatcccac cctgcatgcc  27600
aacccttccc accccactct gtggaacaaa ctctgaaaca caaaataaaa taaagttcaa  27660
gtgttttatt gattcaacag ttttacagga ttcgagcagt tatttttcct ccaccctccc  27720
aggacatgga atacaccacc ctctccccc gcacagcctt gaacatctga atgccattgg  27780
tgatggacat gcttttggtc tccacgttcc acacagtttc agagcgagcc agtctcgggt  27840
cggtcaggga gatgaaaccc tccgggcact cccgcatctg cacctcacag ctcaacagct  27900
gaggattgtc ctcggtggtc gggatcacgg ttatctggaa gaagcagaag agcggcggtg  27960
ggaatcatag tccgcgaacg ggatcggccg gtggtgtcgc atcaggcccc gcagcagtcg  28020
ctgccgccgc cgctccgtca agctgctgct caggggggtcc gggtccaggg actccctcag  28080
catgatgccc acggccctca gcatcagtcg tctggtgcgg cgggcgcagc agcgcatgcg  28140
gatctcgctc aggtcgctgc agtacgtgca acacagaacc accaggttgt tcaacagtcc  28200
atagttcaac acgctccagc cgaaactcat cgcgggaagg atgctaccca cgtggccgtc  28260
gtaccagatc ctcaggtaaa tcaagtggtg ccccctccag aacacgctgc ccacgtacat  28320
gatctccttg ggcatgtggc ggttcaccac ctcccggtac cacatcaccc tctggttgaa  28380
catgcagccc cggatgatcc tgcggaacca cagggccagc accgccccgc ccgccatgca  28440
gcgaagagac cccgggtccc ggcaatggca atggaggacc caccgctcgt acccgtggat  28500
catctgggag ctgaacaagt ctatgttggc acagcacagg catatgctca tgcatctctt  28560
cagcactctc aactcctcgg gggtcaaaac catatcccag ggcacgggga actcttgcag  28620
gacagcgaac cccgcagaac agggcaatcc tcgcacagaa cttacattgt gcatggacag  28680
ggtatcgcaa tcaggcagca ccgggtgatc ctccaccaga gaagcgcggg tctcggtctc  28740
ctcacagcgt ggtaaggggg ccggccgata cgggtgatgg cgggacgcgg ctgatcgtgt  28800
tcgcgaccgt gtcatgatgc agttgctttc ggacattttc gtacttgctg tagcagaacc  28860
tggtccgggc gctgcacacc gatcgccggc ggcggtctcg gcgcttggaa cgctcggtgt  28920
tgaaattgta aaacagccac tctctcagac cgtgcagcag atctagggcc tcaggagtga  28980
tgaagatccc atcatgcctg atggctctga tcacatcgac caccgtggaa tgggccagac  29040
ccagccagat gatgcaattt tgttgggttt cggtgacggc gggggaggga agaacaggaa  29100
gaaccatgat taacttttaa tccaaacggt ctcggagtac ttcaaaatga agatcgcgga  29160
gatggcacct ctcgcccccg ctgtgttggt ggaaaaataac agccaggtca aaggtgatac  29220
ggttctcgag atgttccacg gtggcttcca gcaaagcctc cacgcgcaca tccagaaaca  29280
agacaatagc gaaagcggga gggttctcta attcctcaat catcatgtta cactcctgca  29340
ccatccccag ataattttca tttttccagc cttgaatgat tcgaactagt tcctgaggta  29400
aatccaagcc agccatgata aagagctcgc gcagagcgcc ctccaccggc attcttaagc  29460
acaccctcat aattccaaga tattctgctc ctggttcacc tgcagcagat tgacaagcgg  29520
aatatcaaaa tctctgccgc gatccctgag ctcctccctc agcaataact gtaagtactc  29580
tttcatatcc tctccgaaat ttttagccat aggaccacca ggaataagat tagggcaagc  29640
cacagtacag ataaaccgaa gtcctcccca gtgagcattg ccaaatgcaa gactgctata  29700
agcatgctgg ctagacccgg tgatatcttc cagataactg gacagaaaat cgcccaggca  29760
atttttaaga aaatcaacaa aagaaaaatc ctccaggtgg acgtttagag cctcgggaac  29820
aacgatgaag taaatgcaag cggtgcgttc cagcatggtt agttagctga tctgtagaaa  29880
aaacaaaaat gaacattaaa ccatgctagc ctggcgaaca ggtgggtaaa tcgttctctc  29940
cagcaccagg caggccacgg ggtctccggc gcgaccctcg taaaaattgt cgctatgatt  30000
gaaaaccatc acagagagac gttcccggtg gccggcgtga atgattcgac aagatgaata  30060
cacccccgga acattggcgt ccgcgagtga aaaaaagcgc ccgaggaagc aataaggcac  30120
tacaatgctc agtctcaagt ccagcaaagc gatgccatgc ggatgaagca caaaattctc  30180
aggtgcgtac aaaatgtaat tactcccctc ctgcacaggc agcaaagccc ccgatccctc  30240
caggtacaca tacaaagcct cagcgtccat agcttaccga gcagcagcac acaacaggcg  30300
caagagtcag agaaaggctg agctctaacc tgtccacccg ctctctgctc aatatatagc  30360
ccagatctac actgacgtaa aggccaaagt ctaaaaatac ccgccaaata atcacacacg  30420
cccagcacac gcccagaaac cggtgacaca ctcaaaaaaa tacgcgcact tcctcaaacg  30480
cccaaaactg ccgtcatttc cgggttccca cgctacgtca tcaaaacacg actttcaaat  30540
tccgtcgacc gttaaaaacg tcacccgccc cgcccctaac ggtcgcccgt ctctcagcca  30600
atcagcgccc cgcatcccca aattcaaaca cctcatttgc atattaacgc gcacaaaaag  30660
tttgaggtat attattgatg atgg                                        30684
```

```
SEQ ID NO: 14          moltype = DNA  length = 8602
FEATURE                Location/Qualifiers
misc_feature           1..8602
                       note = Description of Artificial Sequence: Synthetic
                        polynucleotide
source                 1..8602
                       mol_type = other DNA
                       organism = synthetic construct
SEQUENCE: 14
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct cgccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
```

-continued

```
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaagccgatg  1620
tcgacttgat gttacaagag gctggggccg gctcagtgga gacacctcgt ggcttgataa  1680
aggttaccag ctacgctggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg ttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg acttttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gcccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
```

-continued

```
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga cccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gactctagaa tagtctttaa  7560
ttaaagtccg ccatatgagg ccaccatgca gatcttcgtg aagaccctga ccggcaagac  7620
catcacccta gaggtggagc ccagtgacac catcgagaac gtgaaggcca agatccagga  7680
taaagagggc atcccccctg accagcagag gctgatcttt gccggcaagc agctggaaga  7740
tggccgcacc ctctctgatt acaacatcca gaaggagtca accctgcacc tggtccttcg  7800
cctgagaggt ggcgctgctt acagtataat caactttgaa aaactggctg cttacggcat  7860
cctgggcttt gtgtttacac tggctgccta cctgctgttt ggctatcctg tgtacgtggc  7920
cgcttatgga ctgtgtaccc tggtggccat gctggctgct tacaatctgg tgcctatggt  7980
ggccacagtg gccgcctatt gtcttggcgg actgctgaca atggtggcag cctacagccc  8040
gagctatgcg tatcatcagt ttgcagccta cggcccagga ccaggcgcta aatttgtggc  8100
tgcctggaca ctgaaagccg ccgctggacc aggtcctgga cagtacatca aggccaacag  8160
caagttcatc ggcatcaccg aactcggccc aggaccaggc tatccctacg atgtgcctga  8220
ttacgcctga tagtgatgat tcgaacggcc gtatcacgcc caaacattta cagccgcggt  8280
gtcaaaaacc gcgtggacgt ggttaacatc cctgctggga ggatcagccg taattattat  8340
aattggcttg gtgctggcta ctattgtggc catgtacgtg ctgaccaacc agaaacataa  8400
ttgaatacag cagcaattgg caagctgctt acatagaact cgcggcgatt ggcatgccgc  8460
cttaaaattt ttattttatt ttttcttttc ttttccgaat cggattttgt ttttaatatt  8520
tcaaaaaaaa aaaaaaaaaa aaaaaaaaaa aaaaaaaaaa aaaaaaaaaa aaaaaaaaaa  8580
aaaaaaaaaa aaaaaaaaaa aa                                            8602

SEQ ID NO: 15          moltype = DNA  length = 9595
FEATURE                Location/Qualifiers
misc_feature           1..9595
                       note = Description of Artificial Sequence: Synthetic
                        polynucleotide
source                 1..9595
                       mol_type = other DNA
                       organism = synthetic construct
SEQUENCE: 15
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct cgccgccgtc atgagcgacc  420
ctgacctgga aactgagact atgtgcctcc acgacgacga gtcgtgtcgc tacgaagggc  480
aagtcgctgt ttaccaggat gtatacgcgg ttgacggacc gacaagtctc tatcaccaag  540
ccaataaggg agttagagtc gcctactgga taggctttga caccacccct tttatgttta  600
agaacttggc tggagcatat ccatcatact ctaccaactg ggccgacgaa accgtgttaa  660
cggctcgtaa cataggccta tgcagctctg acgttatgga gcggtcacgt agagggatgt  720
ccattcttag aaagaagtat ttgaaaccat ccaacaatgt tctattctct gttggctcga  780
ccatctacca cgagaagagg gacttactga ggagctggca cctgccgtct gtatttcact  840
tacgtggcaa gcaaaattac acatgtcggt gtgagactat agttagttgc gacgggtacg  900
tcgttaaaag aatagctatc agtccaggcc tgtatgggaa gccttcaggc tatgctgcta  960
cgatgcaccg cgagggattc ttgtgctgca aagtgacaga cacattgaac ggggagaggg  1020
tctcttttcc cgtgtgcacg tatgtgccag ctacattgtg tgaccaaatg actggcatac  1080
tggcaacaga tgtcagtgcg gacgacgcgc aaaaactgct ggttgggctc aaccagcgta  1140
tagtcgtcaa cggtcgcacc cagagaaaca ccaataccat gaaaaattac cttttgcccg  1200
```

-continued

```
tagtggccca ggcatttgct aggtgggcaa aggaatataa ggaagatcaa gaagatgaaa  1260
ggccactagg actacgagat agacagttag tcatggggtg ttgttgggct tttagaaggc  1320
acaagataac atctatttat aagcgcccgg atacccaaac catcatcaaa gtgaacagcg  1380
atttccactc attcgtgctg cccaggatag gcagtaacac attggagatc gggctgagaa  1440
caagaatcag gaaaatgtta gaggagcaca aggagccgtc acctctcatt accgccgagg  1500
acgtacaaga agctaagtgc gcagccgatg aggctaagga ggtgcgtgaa gccgaggagt  1560
tgcgcgcagc tctaccacct ttggcagctg atgttgagga gcccactctg gaagccgatg  1620
tcgacttgat gttacaagag gctggggccg gctcagtgga gacacctcgt ggcttgataa  1680
aggttaccag ctacgctggc gaggacaaga tcggctctta cgctgtgctt tctccgcagg  1740
ctgtactcaa gagtgaaaaa ttatcttgca tccaccctct cgctgaacaa gtcatagtga  1800
taacacactc tggccgaaaa gggcgttatg ccgtggaacc ataccatggt aaagtagtgg  1860
tgccagaggg acatgcaata cccgtccagg actttcaagc tctgagtgaa agtgccacca  1920
ttgtgtacaa cgaacgtgag ttcgtaaaca ggtacctgca ccatattgcc acacatggag  1980
gagcgctgaa cactgatgaa gaatattaca aaactgtcaa gcccagcgag cacgacggcg  2040
aatacctgta cgacatcgac aggaaacagt gcgtcaagaa agaactagtc actgggctag  2100
ggctcacagg cgagctggtg gatcctccct tccatgaatt cgcctacgag agtctgagaa  2160
cacgaccagc cgctccttac caagtaccaa ccataggggt gtatggcgtg ccaggatcag  2220
gcaagtctgg catcattaaa agcgcagtca ccaaaaaaga tctagtggtg agcgccaaga  2280
aagaaaactg tgcagaaatt ataagggacg tcaagaaaat gaaagggctg gacgtcaatg  2340
ccagaactgt ggactcagtg ctcttgaatg gatgcaaaca ccccgtagag accctgtata  2400
ttgacgaagc ttttgcttgt catgcaggta ctctcagagc gctcatagcc attataagac  2460
ctaaaaaggc agtgctctgc ggggatccca aacagtgcgg tttttttaac atgatgtgcc  2520
tgaaagtgca ttttaaccac gagatttgca cacaagtctt ccacaaaagc atctctcgcc  2580
gttgcactaa atctgtgact tcggtcgtct caaccttgtt ttacgacaaa aaaatgagaa  2640
cgacgaatcc gaaagagact aagattgtga ttgacactac cggcagtacc aaacctaagc  2700
aggacgatct cattctcact tgtttcagag ggtgggtgaa gcagttgcaa atagattaca  2760
aaggcaacga aataatgacg gcagctgcct ctcaagggct gacccgtaaa ggtgtgtatg  2820
ccgttcggta caaggtgaat gaaaatcctc tgtacgcacc cacctcagaa catgtgaacg  2880
tcctactgac ccgcacggag gaccgcatcg tgtggaaaac actagccggc gacccatgga  2940
taaaaacact gactgccaag taccctggga atttcactgc cacgatagag gagtggcaag  3000
cagagcatga tgccatcatg aggcacatct tggagagacc ggaccctacc gacgtcttcc  3060
agaataaggc aaacgtgtgt tgggccaagg ctttagtgcc ggtgctgaag accgctggca  3120
tagacatgac cactgaacaa tggaacactg tggattattt tgaaacggac aaagctcact  3180
cagcagagat agtattgaac caactatgcg tgaggttctt tggactcgat ctggactccg  3240
gtctattttc tgcacccact gttccgttat ccattaggaa taatcactgg gataactccc  3300
cgtcgcctaa catgtacggg ctgaataaag aagtggtccg tcagctctct cgcaggtacc  3360
cacaactgcc tcgggcagtt gccactggaa gagtctatga catgaacact ggtacactgc  3420
gcaattatga tccgcgcata aacctagtac ctgtaaacag aagactgcct catgctttag  3480
tcctccacca taatgaacac ccacagagtg actttcttc attcgtcagc aaattgaagg  3540
gcagaactgt cctggtggtc ggggaaaagt tgtccgtccc aggcaaaatg gttgactggt  3600
tgtcagaccg gcctgaggct accttcagag ctcggctgga tttaggcatc ccaggtgatg  3660
tgcccaaata tgacataata tttgttaatg tgaggacccc atataaatac catcactatc  3720
agcagtgtga agaccatgcc attaagctta gcatgttgac caagaaagct tgtctgcatc  3780
tgaatcccgg cggaacctgt gtcagcatag gttatggtta cgctgacagg gccagcgaaa  3840
gcatcattgg tgctatagcg cggcagttca agttttcccg ggtatgcaaa ccgaaatcct  3900
cacttgaaga gacggaagtt ctgtttgtat tcattgggta cgatcgcaag gccccgtacgc  3960
acaatcctta caagctttca tcaaccttga ccaacattta tacaggttcc agactccacg  4020
aagccggatg tgcaccctca tatcatgtgg tgcgaggggga tattgccacg gccaccgaag  4080
gagtgattat aaatgctgct aacagcaaag gacaacctgg cggaggggtg tgcggagcgc  4140
tgtataagaa attcccggaa agcttcgatt tacagccgat cgaagtagga aaagcgcgac  4200
tggtcaaagg tgcagctaaa catatcattc atgccgtagg accaaacttc aacaaagttt  4260
cggaggttga aggtgacaaa cagttggcag aggcttatga gtccatcgct aagattgtca  4320
acgataacaa ttacaagtca gtagcgattc cactgttgtc caccggcatc ttttccggga  4380
acaaagatcg actaacccaa tcattgaacc atttgctgac agctttagac accactgatg  4440
cagatgtagc catatactgc agggacaaga aatgggaaat gactctcaag gaagcagtgg  4500
ctaggagaga agcagtggag gagatatgca tatccgacga ctcttcagtg acagaacctg  4560
atgcagagct ggtgagggtg catccgaaga gttctttggc tggaaggaag ggctacagca  4620
caagcgatgg caaaactttc tcatatttgg aagggaccaa gtttcaccag gcggccaagg  4680
atatagcaga aattaatgcc atgtggcccg ttgcaacgga ggccaatgag caggtatgca  4740
tgtatatcct cggagaaagc atgagcagta ttaggtcgaa atgccccgtc gaagagtcgg  4800
aagcctccac accacctagc acgctgcctt gcttgtgcat ccatgccatg actccagaaa  4860
gagtacagcg cctaaaagcc tcacgtccag aacaaattac tgtgtgctca tcctttccat  4920
tgccgaagta tagaatcact ggtgtgcaga agatccaatg ctcccagcct atattgttct  4980
caccgaaagt gcctgcgtat attcatccaa ggaagtatct cgtggaaaca ccaccggtag  5040
acgagactcc ggagccatcg gcagagaacc aatccacaga ggggacacct gaacaaccac  5100
cacttataac cgaggatgag accaggacta gaacgcctga gccgatcatc atcgaagagg  5160
aagaagagga tagcataagt ttgctgtcag atggcccgac ccaccaggtg ctgcaagtcg  5220
aggcagacat tcacgggccg ccctctgtat ctagctcatc ctggtccatt cctcatgcat  5280
ccgactttga tgtggacagt ttatccatac ttgacaccct ggagggagct agcgtgacca  5340
gcggggcaac gtcagccgag actaactctt acttcgcaaa gagtatggag tttctggcgc  5400
gaccggtgcc tgcgcctcga acagtattca ggaaccctcc acatcccgct ccgcgcacaa  5460
gaacaccgtc acttgcaccc agcagggcct gctcgagaac cagcctagtt tccaccccgc  5520
caggcgtgaa tagggtgatc actagagagg agctcgaggc gcttaccccg tcacgcactc  5580
ctagcaggtc ggtctcgaga accagcctgg tctccaaccc gccaggcgta aatagggtga  5640
ttacaagaga ggagtttgag gcgttcgtag cacaacaaca atgacggttt gatgcgggtg  5700
catacatctt ttcctccgac accggtcaag ggcatttaca acaaaaatca gtaaggcaaa  5760
cggtgctatc cgaagtggtg ttggagagga ccgaattgga gatttcgtat gccccgcgcc  5820
tcgaccaaga aaaagaagaa ttactacgca agaaattaca gttaaatccc acacctgcta  5880
acagaagcag ataccagtcc aggaaggtgg agaacatgaa agccataaca gctagacgta  5940
```

-continued

```
ttctgcaagg cctagggcat tatttgaagg cagaaggaaa agtggagtgc taccgaaccc  6000
tgcatcctgt tcctttgtat tcatctagtg tgaaccgtgc cttttcaagc cccaaggtcg  6060
cagtggaagc ctgtaacgcc atgttgaaag agaactttcc gactgtggct tcttactgta  6120
ttattccaga gtacgatgcc tatttggaca tggttgacgg agcttcatgc tgcttagaca  6180
ctgccagttt ttgccctgca aagctgcgca gctttccaaa gaaacactcc tatttggaac  6240
ccacaatacg atcggcagtg ccttcagcga tccagaacac gctccagaac gtcctggcag  6300
ctgccacaaa aagaaattgc aatgtcacgc aaatgagaga attgcccgta ttggattcgg  6360
cggcctttaa tgtggaatgc ttcaagaaat atgcgtgtaa taatgaatat tgggaaacgt  6420
ttaaagaaaa ccccatcagg cttactgaag aaaacgtggt aaattacatt accaaattaa  6480
aaggaccaaa agctgctgct ctttttgcga agacacataa tttgaatatg ttgcaggaca  6540
taccaatgga caggtttgta atggacttaa agagagacgt gaaagtgact ccaggaacaa  6600
aacatactga agaacggccc aaggtacagg tgatccaggc tgccgatccg ctagcaacag  6660
cgtatctgtg cggaatccac cgagagctgg ttaggagatt aaatgcggtc ctgcttccga  6720
acattcatac actgtttgat atgtcggctg aagactttga cgctattata gccgagcact  6780
tccagcctgg ggattgtgtt ctggaaactg acatcgcgtc gtttgataaa agtgaggacg  6840
acgccatggc tctgaccgcg ttaatgattc tggaagactt aggtgtggac gcagagctgt  6900
tgacgctgat tgaggcggct ttcggcgaaa tttcatcaat acatttgccc actaaaacta  6960
aatttaaatt cggagccatg atgaaatctg gaatgttcct cacactgttt gtgaacacag  7020
tcattaacat tgtaatcgca agcagagtgt tgagagaacg gctaaccgga tcaccatgtg  7080
cagcattcat tggagatgac aatatcgtga aaggagtcaa atcggacaaa ttaatggcag  7140
acaggtgcgc cacctggttg aatatggaag tcaagattat agatgctgtg gtgggcgaga  7200
aagcgcctta tttctgtgga gggtttattt tgtgtgactc cgtgaccggc acagcgtgcc  7260
gtgtggcaga ccccctaaaa aggctgttta agcttggcaa acctctggca gcagacgatg  7320
aacatgatga tgacaggaga agggcattgc atgaagagtc aacacgctgg aaccgagtgg  7380
gtattctttc agagctgtgc aaggcagtag aatcaaggta tgaaaccgta ggaacttcca  7440
tcatagttat ggccatgact actctagcta gcagtgttaa atcattcagc tacctgagag  7500
gggcccctat aactctctac ggctaacctg aatggactac gactctagaa tagtctttaa  7560
ttaaagtccg ccatatgaga tggaagatgc caaaaacatt aagaagggcc cagcgccatt  7620
ctacccactc gaagacggga ccgccggcga gcagctgcac aaagccatga agcgctacgc  7680
cctggtgccc ggcaccatcg cctttaccga cgcacatatc gaggtggaca ttacctacgc  7740
cgagtacttc gagatgagcg ttcggctggc agaagctatg aagcgctatg ggctgaatac  7800
aaaccatcgg atcgtggtgt gcagcgagaa tagcttgcag ttcttcatgc ccgtgttggg  7860
tgccctgttc atcggtgtgg ctgtggcccc agctaacgac atctacaacg agcgcgagct  7920
gctgaacagc atgggcatca gccagcccac cgtcgtattc gtgagcaaga aagggctgca  7980
aaagatcctc aacgtgcaaa agaagctacc gatcatacaa aagatcatca tcatggatag  8040
caagaccgac taccagggct tccaaagcat gtacaccttc gtgacttccc atttgccacc  8100
cggcttcaac gagtacgact tcgtgcccga gagcttcgac cgggacaaaa ccatcgccct  8160
gatcatgaac agtagtggca gtaccggatt gcccaagggc gtagccctac cgcaccgcac  8220
cgcttgtgtc cgattcagtc atgcccgcga ccccatcttc ggcaaccaga tcatccccga  8280
caccgctatc ctcagcgtgg tgccatttca ccacggcttc ggcatgttca ccacgctggg  8340
ctacttgatc tgcggctttc gggtcgtgct catgtaccgc ttcgaggagg agctattctt  8400
gcgcagcttg caagactata agattcaatc tgccctgctg gtgcccacac tatttagctt  8460
cttcgctaag agcactctca tcgacaagta cgacctaagc aacttgcacg agatcgccag  8520
cggcggggcg ccgctcagca aggaggtagg tgaggccgtg gccaaacgct tccacctacc  8580
aggcatccgc cagggctacg gcctgacaga aacaaccagc gccattctga tcacccccga  8640
aggggacgac aagcctggcg cagtaggcaa ggtggtgccc ttcttcgagg ctaaggtggt  8700
ggacttggac accggtaaga cactgggtgt gaaccagcgc ggcgagctgt gcgtccgtgg  8760
ccccatgatc atgagcggct acgttaacaa ccccgaggct acaaacgctc tcatcgacaa  8820
ggacggctgg ctgcacagcg gcgacatcgc ctactgggac gaggacgagc acttcttcat  8880
cgtggaccgg ctgaagagcc tgatcaaata caagggctac caggtagccc cagccgaact  8940
ggagagcatc ctgctgcaac accccaacat cttcgacgcc ggggtcgccg gcctgcccga  9000
cgacgatgcc ggcgagctgc ccgccgcagt cgtcgtgctg gaacacggta aaaccatgac  9060
cgagaaggag atcgtggact atgtggccag ccaggttaca accgccaaga agctgcgcgg  9120
tggtgttgtg ttcgtggacg aggtgcctaa aggactgacc ggcaagttgg acgcccgcaa  9180
gatccgcgag attctcatta aggccaagaa gggcggcaag atcgccgtgt aattcgaacg  9240
gccgtatcac gcccaaacat ttacagccgc ggtgtcaaaa accgcgtgga cgtggttaac  9300
atccctgctg ggaggatcag ccgtaattat tataattggc ttggtgctgg ctactattgt  9360
ggccatgtac gtgctgacca accagaaaca taattgaata cagcagcaat tggcaagctg  9420
cttacataga actcgcggcg attggcatgc cgccttaaaa ttttatttt attttttctt  9480
ttcttttccg aatcggattt tgtttttaat atttcaaaaa aaaaaaaaaa aaaaaaaaaa  9540
aaaaaaaaaa aaaaaaaaaa aaaaaaaaaa aaaaaaaaaa aaaaaaaaaa aaaaa       9595
```

```
SEQ ID NO: 16           moltype = AA  length = 139
FEATURE                 Location/Qualifiers
REGION                  1..139
                        note = Description of Artificial Sequence: Synthetic
                         polypeptide
source                  1..139
                        mol_type = protein
                        organism = synthetic construct
SEQUENCE: 16
PSSLSASVGD RVTITCRASQ SINSYLDWYQ QKPGKAPKLL IYAASSLQSG VPSRFSGSGS  60
GTDFTLTISS LQPEDFATYY CQQYYSTPFT FGPGTKVEIK RTVAAPSVFI FPPSDEQLKS  120
GTASVVCLLN NFYPREAKV                                               139

SEQ ID NO: 17           moltype = AA  length = 167
FEATURE                 Location/Qualifiers
REGION                  1..167
                        note = Description of Artificial Sequence: Synthetic
```

```
                       polypeptide
source                 1..167
                       mol_type = protein
                       organism = synthetic construct
SEQUENCE: 17
GVVQPGRSLR LSCAASGFTF SSYGMHWVRQ APGKGLEWVA VIWYDGSNKY YADSVKGRFT  60
ISRDNSKNTL YLQMNSLRAE DTAVYYCARD PRGATLYYYY YGMDVWGQGT TVTVSSASTK  120
GPSVFPLAPC SRSTSESTAA LGCLVKDYFP EPVTVSWNSG ALTSGVH                167

SEQ ID NO: 18          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 18
GFTFSSYGMH                                                         10

SEQ ID NO: 19          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 19
VIWYDGSNKY YADSV                                                   15

SEQ ID NO: 20          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 20
DPRGATLYYY YYGMDV                                                  16

SEQ ID NO: 21          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 21
RASQSINSYL D                                                       11

SEQ ID NO: 22          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 22
AASSLQS                                                            7

SEQ ID NO: 23          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 23
QQYYSTPFT                                                          9

SEQ ID NO: 24          moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 24
EIVLTQSPGT LSLSPGERAT LSCRASQRVS SSYLAWYQQK PGQAPRLLIY DASSRATGIP  60
```

-continued

```
DRFSGSGSGT DFTLTISRLE PEDFAVYYCQ QYGSLPWTFG QGTKVEIK              108

SEQ ID NO: 25           moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 25
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                 121

SEQ ID NO: 26           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 26
RYWMS                                                             5

SEQ ID NO: 27           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 27
NIKQDGSEKY YVDSVKG                                                17

SEQ ID NO: 28           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 28
EGGWFGELAF DY                                                     12

SEQ ID NO: 29           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 29
RASQRVSSSY LA                                                     12

SEQ ID NO: 30           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 30
DASSRAT                                                           7

SEQ ID NO: 31           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 31
QQYGSLPWT                                                         9

SEQ ID NO: 32           moltype = DNA  length = 2019
FEATURE                 Location/Qualifiers
misc_feature            1..2019
                        note = Description of Artificial Sequence: Synthetic
```

```
                         polynucleotide
source                  1..2019
                        mol_type = other DNA
                        organism = synthetic construct
SEQUENCE: 32
gcccgggcat ttaaatgcga tcgcatcgat tacgactcta gaatagtcta gtccgcaggc  60
caccatgcag atcttcgtga agaccctgac cggcaagacc atcaccctag aggtggagcc  120
cagtgacacc atcgagaacg tgaaggccaa gatccaggat aaagagggca tcccccctga  180
ccagcagagg ctgatctttg ccggcaagca gctggaagat ggccgcaccc tctctgatta  240
caacatccag aaggagtcaa ccctgcacct ggtccttcgc ctgagaggtg ccatgtttca  300
ggcgctgagc gaaggctgca ccccgtatga tattaaccag atgctgaacg tgctgggcga  360
tcatcaggtc tcaggccttg agcagcttga gagtataatc aactttgaaa aactgactga  420
atggaccagt tctaatgtta tgcctatcct gtctcctctg acaaagggca tcctgggctt  480
cgtgtttacc ctgaccgtgc cttctgagag aggacttagc tgcattagcg aagcggatgc  540
gaccacccccg gaaagcgcga acctgggcga agaaattctg agccagctgt atctttggcc  600
aagggtgacc taccattccc ctagttatgc ttaccaccaa tttgaaagac gagccaaata  660
taaaagacac ttccccggct ttggccagag cctgctgttt ggctaccctg tgtacgtgtt  720
cggcgattgc gtgcagggcg attgggatgc gattcgcttt cgctattgcg cgccgccggg  780
ctatgcgctg ctgcgctgca acgataccaa ctatagcgct ctgctggctg tgggggccct  840
agaaggaccc aggaatcagg actggcttgg tgtcccaaga caacttgtaa ctcggatgca  900
ggctattcag aatgccggcc tgtgtaccct ggtggccatg ctggaagaga caatcttctg  960
gctgcaagcg tttctgatgg cgctgaccga tagcggcccg aaaaccaaca ttattgtgga  1020
tagccagtat gtgatgggca ttagcaaacc gagctttcag gaatttgtgg attgggaaaa  1080
cgtgagcccg gaactgaaca gcaccgatca gccgttttgg caagccggaa tcctggccag  1140
aaatctggtg cctatggtgg ccacagtgca gggccagaac ctgaagtacc agggtcagtc  1200
actagtcatc tctgcttcta tcattgtctt caacctgctg gaactggaag gtgattatcg  1260
agatgatggc aacgtgtggg tgcatacccc gctgagcccg cgcaccctga acgcgtgggt  1320
gaaagcggtg gaagaaaaaa aaggtattcc agttcaccta gagctggcca gtatgaccaa  1380
catggagctc atgagcagta ttgtgcatca gcaggtcaga acatacggcc ccgtgttcat  1440
gtgtctcggc ggactgctta caatggtggc tggtgctgtg tggctgacag tgcgagtgct  1500
cgagctgttc cgggccgcgc agctggccaa cgacgtggtc ctccagatca tggagctttg  1560
tggtgcagcg tttcgccagg tgtgccatac caccgtgccg tggccgaacg cgagcctgac  1620
cccgaaatgg aacaacgaaa ccacccagcc ccagatcgcc aactgcagcg tgtatgactt  1680
ttttgtgtgg ctccattatt attctgttcg agacacactt tggccaaggg tgacctacca  1740
tatgaacaaa tatgcgtatc atatgctgga aagacgagcc aaatataaaa gaggaccagg  1800
acctggcgct aaatttgtgg ccgcctggac actgaaagcc gctgctggtc ctggacctgg  1860
ccagtacatc aaggccaaca gcaagttcat cggcatcacc gaactcggac ccggaccagg  1920
ctgatgattt cgaaatttaa ataagcttgc ggccgctagg gataacaggg taattatcac  1980
gcccaaacat ttacagccgc ggtgtcaaaa accgcgtgg                        2019

SEQ ID NO: 33           moltype = AA  length = 619
FEATURE                 Location/Qualifiers
REGION                  1..619
                        note = Description of Artificial Sequence: Synthetic
                         polypeptide
source                  1..619
                        mol_type = protein
                        organism = synthetic construct
SEQUENCE: 33
MQIFVKTLTG KTITLEVEPS DTIENVKAKI QDKEGIPPDQ QRLIFAGKQL EDGRTLSDYN  60
IQKESTLHLV LRLRGAMFQA LSEGCTPYDI NQMLNVLGDH QVSGLEQLES IINFEKLTEW  120
TSSNVMPILS PLTKGILGFV FTLTVPSERG LSCISEADAT TPESANLGEE ILSQLYLWPR  180
VTYHSPSYAY HQFERRAKYK RHFPGFGQSL LFGYPVYVFG DCVQGDWDAI RFRYCAPPGY  240
ALLRCNDTNY SALLAVGALE GPRNQDWLGV PRQLVTRMQA IQNAGLCTLV AMLEETIFWL  300
QAFLMALTDS GPKTNIIVDS QYVMGISKPS FQEFVDWENV SPELNSTDQP FWQAGILARN  360
LVPMVATVQG QNLKYQGQSL VISASIIVFN LLELEGDYRD DGNVWVHTPL SPRTLNAWVK  420
AVEEKKGIPV HLELASMTNM ELMSSIVHQQ VRTYGPVFMC LGGLLTMVAG AVWLTVRVLE  480
LFRAAQLAND VVLQIMELCG AAFRQVCHTT VPWPNASLTP KWNNETTQPQ IANCSVYDFF  540
VWLHYYSVRD TLWPRVTYHM NKYAYHMLER RAKYKRGPGP GAKFVAAWTL KAAAGPGPGQ  600
YIKANSKFIG ITELGPGPG                                              619

SEQ ID NO: 34           moltype = DNA  length = 1638
FEATURE                 Location/Qualifiers
misc_feature            1..1638
                        note = Description of Artificial Sequence: Synthetic
                         polynucleotide
source                  1..1638
                        mol_type = other DNA
                        organism = synthetic construct
SEQUENCE: 34
atggccggga tgttccaggc actgtccgaa ggctgcacac cctatgatat taaccagatg  60
ctgaatgtcc tgggagacca ccaggtctct ggcctggagc agctggagag catcatcaac  120
ttcgagaagc tgaccgagtg gacaagctcc aatgtgatgc ctatcctgtc cccactgacc  180
aagggcatcc tgggcttcgt gtttaccctg acagtgcctt ctgagcgggg cctgtcttgc  240
atcagcgagg cagacgcaac cacaccagag tccgccaatc tgggcgagga gatcctgtct  300
cagctgtacc tgtggccccg ggtgacatat cactcccctt cttacgccta tcaccagttc  360
gagcggagag ccaagtacaa gagacacttc ccaggctttg gccagtctct gctgttcggc  420
taccccgtgt acgtgttcgg cgattgcgtg cagggcgact gggatgccat ccggtttaga  480
tactgcgcac cacctggata tgcactgctg aggtgtaacg acaccaatta ttccgccctg  540
```

```
ctggcagtgg gcgccctgga gggccctcgc aatcaggatt ggctgggcgt gccaaggcag  600
ctggtgacac gcatgcaggc catccagaac gcaggcctgt gcaccctggt ggcaatgctg  660
gaggagacaa tcttctggct gcaggccttt ctgatggccc tgaccgacag cggccccaag  720
acaaacatca tcgtggattc ccagtacgtg atgggcatct ccaagccttc tttccaggag  780
tttgtggact gggagaacgt gagcccagag ctgaattcca ccgatcagcc attctggcag  840
gcaggaatcc tggcaaggaa cctggtgcct atggtggcca cagtgcaggg ccagaatctg  900
aagtaccagg gccagagcct ggtcatcagc gcctccatca tcgtgtttaa cctgctggag  960
ctggagggcg actatcggga cgatggcaac gtgtgggtgc acaccccact gagccccaga  1020
acactgaacg cctgggtgaa ggccgtggag gagaagaagg gcatcccagt gcacctggag  1080
ctggcctcca tgaccaatat ggagctgatg tctagcatcg tgcaccagca ggtgaggaca  1140
tacggacccg tgttcatgtg cctgggaggc ctgctgacca tggtggcagg agccgtgtgg  1200
ctgacagtgc gggtgctgga gctgttcaga gccgcccagc tggccaacga tgtggtgctg  1260
cagatcatgg agctgtgcgg agcagccttt cgccaggtgt gccacaccac agtgccatgg  1320
cccaatgcct ccctgacccc caagtggaac aatgagacaa cacagcctca gatcgccaac  1380
tgtagcgtgt acgacttctt cgtgtggctg cactactata gcgtgaggga taccctgtgg  1440
ccccgcgtga cataccacat gaataagtac gcctatcaca tgctggagag gcgcgccaag  1500
tataagagag gccctggccc aggcgcaaag tttgtggcag catggaccct gaaggccgcc  1560
gccggccccg gccccggcca gtatatcaag gctaacagta agttcattgg aatcacagag  1620
ctgggacccg gacctgga                                                1638
```

```
SEQ ID NO: 35          moltype = AA  length = 546
FEATURE                Location/Qualifiers
REGION                 1..546
                       note = Description of Artificial Sequence: Synthetic
                        polypeptide
source                 1..546
                       mol_type = protein
                       organism = synthetic construct
SEQUENCE: 35
MAGMFQALSE GCTPYDINQM LNVLGDHQVS GLEQLESIIN FEKLTEWTSS NVMPILSPLT  60
KGILGFVFTL TVPSERGLSC ISEADATTPE SANLGEEILS QLYLWPRVTY HSPSYAYHQF  120
ERRAKYKRHF PGFGQSLLFG YPVYVFGDCV QGDWDAIRFR YCAPPGYALL RCNDTNYSAL  180
LAVGALEGPR NQDWLGVPRQ LVTRMQAIQN AGLCTLVAML EETIFWLQAF LMALTDSGPK  240
TNIIVDSQYV MGISKPSFQE FVDWENVSPE LNSTDQPFWQ AGILARNLVP MVATVQGQNL  300
KYQGQSLVIS ASIIVFNLLE LEGDYRDDGN VWVHTPLSPR TLNAWVKAVE EKKGIPVHLE  360
LASMTNMELM SSIVHQQVRT YGPVFMCLGG LLTMVAGAVW LTVRVLELFR AAQLANDVVL  420
QIMELCGAAF RQVCHTTVPW PNASLTPKWN NETTQPQIAN CSVYDFFVWL HYYSVRDTLW  480
PRVTYHMNKY AYHMLERRAK YKRGPGPGAK FVAAWTLKAA AGPGPGQYIK ANSKFIGITE  540
LGPGPG                                                        546
```

```
SEQ ID NO: 36          moltype = DNA  length = 2019
FEATURE                Location/Qualifiers
misc_feature           1..2019
                       note = Description of Artificial Sequence: Synthetic
                        polynucleotide
source                 1..2019
                       mol_type = other DNA
                       organism = synthetic construct
SEQUENCE: 36
gcccgggcat ttaaatgcga tcgcatcgat tacgactcta gaatagtcta gtccgcaggc  60
caccatgcag atcttcgtga agaccctgac cggcaagacc atcaccctag aggtggagcc  120
cagtgacacc atcgagaacg tgaaggccaa gatccaggat aaagagggca tcccccctga  180
ccagcagagg ctgatctttg ccggcaagca gctggaagat ggccgcaccc tctctgatta  240
caacatccag aaggagtcaa ccctgcacct ggtccttcgc ctgagaggtg ccatgtttca  300
ggcgctgagc gaaggctgca ccccgtatga tattaaccag atgctgaacg tgctgggcga  360
tcatcagttt aagcacatca aagcctttga ccggacattt gctaacaacc caggtcccat  420
ggttgtgttt gccacacctg ggcctatcct gtctcctctg acaaagggca tcctgggctt  480
cgtgtttacc ctgaccgtgc cttctgagag aggacttagc tgcattagcg aagcggatgc  540
gaccaccccg gaaagcgcga acctgggcga agaaattctg agccagctgt atctttggcc  600
aagggtgacc taccattccc ctagttatgc ttaccaccaa tttgaaagac gagccaaata  660
taaaagacac ttccccggct ttggccagag cctgctgttt ggctaccctg tgtacgtgtt  720
cggcgattgc gtgcagggcg attgggatgc gattcgcttt cgctattgcg cgccgccggg  780
ctatgcgctg ctgcgctgca acgataccaa ctatagcgct ctgctggctg tgggggccct  840
agaaggaccc aggaatcagg actggcttgg tgtcccaaga caacttgtaa ctcggatgca  900
ggctattcag aatgccggcc tgtgtaccct ggtggccatg ctggaagaga caatcttctg  960
gctgcaagcg tttctgatgg cgctgaccga tagcggcccg aaaaccaaca ttattgtgga  1020
tagccagtat gtgatgggca ttagcaaacc gagctttcag gaatttgtgg attgggaaaa  1080
cgtgagcccg gaactgaaca gcaccgatca gccgttttgg caagccggaa tcctggccag  1140
aaatctggtg cctatggtgg ccacagtgca gggccagaac ctgaagtacc agggtcagtc  1200
actagtcatc tctgcttcta tcattgtctt caacctgctg gaactggaag gtgattatcg  1260
agatgatggc aacgtgtggg tgcatacccc gctgagcccg cgcaccctga acgcgtgggt  1320
gaaagcggtg gaagaaaaaa aaggtattcc agttcaccta gagctggcca gtatgaccaa  1380
catggagctc atgagcagta ttgtgcatca gcaggtcaga acatacggcc ccgtgttcat  1440
gtgtctcggc ggactgctta caatggtggc tggtgctgtg tggctgacag tgcgagtgct  1500
cgagctgttc cgggccgcgc agctggccaa cgacgtggtc ctccagatca tggagctttg  1560
tggtgcagcg tttcgccagg tgtgccatac caccgtgccg tggccgaacg cgagcctgac  1620
cccgaaatgg aacaacgaaa ccacccagcc ccagatcgcc aactgcagcg tgtatgactt  1680
ttttgtgtgg ctccattatt attctgttcg agacacactt tggccaaggg tgacctacca  1740
tatgaacaaa tatgcgtatc atatgctgga aagacgagcc aaatataaaa gaggaccagg  1800
```

```
acctggcgct aaatttgtgg ccgcctggac actgaaagcc gctgctggtc ctggacctgg  1860
ccagtacatc aaggccaaca gcaagttcat cggcatcacc gaactcggac ccggaccagg  1920
ctgatgattt cgaaatttaa ataagcttgc ggccgctagg gataacaggg taattatcac  1980
gcccaaacat ttacagccgc ggtgtcaaaa accgcgtgg                          2019

SEQ ID NO: 37          moltype = AA  length = 619
FEATURE                Location/Qualifiers
REGION                 1..619
                       note = Description of Artificial Sequence: Synthetic
                        polypeptide
source                 1..619
                       mol_type = protein
                       organism = synthetic construct
SEQUENCE: 37
MQIFVKTLTG KTITLEVEPS DTIENVKAKI QDKEGIPPDQ QRLIFAGKQL EDGRTLSDYN  60
IQKESTLHLV LRLRGAMFQA LSEGCTPYDI NQMLNVLGDH QFKHIKAFDR TFANNPGPMV  120
VFATPGPILS PLTKGILGFV FTLTVPSERG LSCISEADAT TPESANLGEE ILSQLYLWPR  180
VTYHSPSYAY HQFERRAKYK RHFPGFGQSL LFGYPVYVFG DCVQGDWDAI RFRYCAPPGY  240
ALLRCNDTNY SALLAVGALE GPRNQDWLGV PRQLVTRMQA IQNAGLCTLV AMLEETIFWL  300
QAFLMALTDS GPKTNIIVDS QYVMGISKPS FQEFVDWENV SPELNSTDQP FWQAGILARN  360
LVPMVATVQG QNLKYQGQSL VISASIIVFN LLELEGDYRD DGNVWVHTPL SPRTLNAWVK  420
AVEEKKGIPV HLELASMTNM ELMSSIVHQQ VRTYGPVFMC LGGLLTMVAG AVWLTVRVLE  480
LFRAAQLAND VVLQIMELCG AAFRQVCHTT VPWPNASLTP KWNNETTQPQ IANCSVYDFF  540
VWLHYYSVRD TLWPRVTYHM NKYAYHMLER RAKYKRGPGP GAKFVAAWTL KAAAGPGPGQ  600
YIKANSKFIG ITELGPGPG                                                619

SEQ ID NO: 38          moltype = DNA  length = 228
FEATURE                Location/Qualifiers
misc_feature           1..228
                       note = Description of Artificial Sequence: Synthetic
                        polynucleotide
source                 1..228
                       mol_type = other DNA
                       organism = synthetic construct
SEQUENCE: 38
atgcagatct tcgtgaagac cctgaccggc aagaccatca ccctagaggt ggagcccagt  60
gacaccatcg agaacgtgaa ggccaagatc caggataaag agggcatccc ccctgaccag  120
cagaggctga tctttgccgg caagcagctg gaagatggcc gcaccctctc tgattacaac  180
atccagaagg agtcaaccct gcacctggtc cttcgcctga gaggtggc                228

SEQ ID NO: 39          moltype = DNA  length = 228
FEATURE                Location/Qualifiers
misc_feature           1..228
                       note = Description of Artificial Sequence: Synthetic
                        polynucleotide
source                 1..228
                       mol_type = other DNA
                       organism = synthetic construct
SEQUENCE: 39
atgcagatct tcgtgaagac cctgaccggc aagaccatca ccctagaggt ggagcccagt  60
gacaccatcg agaacgtgaa ggccaagatc caggataaag agggcatccc ccctgaccag  120
cagaggctga tctttgccgg caagcagctg gaagatggcc gcaccctctc tgattacaac  180
atccagaagg agtcaaccct gcacctggtc cttcgcctga gaggtgcc                228

SEQ ID NO: 40          moltype = DNA  length = 78
FEATURE                Location/Qualifiers
source                 1..78
                       mol_type = other DNA
                       organism = Homo sapiens
SEQUENCE: 40
atggccgtca tggcgccccg aaccctcgtc ctgctactct cgggggctct ggccctgacc  60
cagacctggg cgggctct                                                 78

SEQ ID NO: 41          moltype = DNA  length = 201
FEATURE                Location/Qualifiers
source                 1..201
                       mol_type = other DNA
                       organism = Homo sapiens
SEQUENCE: 41
ccgtcttccc agcccaccat ccccatcgtg ggcatcattg ctggcctggt tctctttgga  60
gctgtgatca ctggagctgt ggtcgctgct gtgatgtgga ggaggaagag ctcagataga  120
aaaggaggga gctactctca ggctgcaagc agtgacagtg cccagggctc tgatgtgtct  180
ctcacagctt gtaaagtgtg a                                             201

SEQ ID NO: 42          moltype = DNA  length = 60
FEATURE                Location/Qualifiers
misc_feature           1..60
                       note = Description of Artificial Sequence: Synthetic
                        oligonucleotide
```

```
source                  1..60
                        mol_type = other DNA
                        organism = synthetic construct
SEQUENCE: 42
atggagaccg atacactgct gctgtgggtg ctgctcctgt gggtgccagg aagcacaggc  60

SEQ ID NO: 43           moltype = DNA  length = 3178
FEATURE                 Location/Qualifiers
source                  1..3178
                        mol_type = other DNA
                        organism = Homo sapiens
SEQUENCE: 43
ggcaccgatt cggggcctgc ccggacttcg ccgcacgctg cagaacctcg cccagcgccc  60
accatgcccc ggcagctcag cgcggcggcc gcgctcttcg cgtccctggc cgtaattttg  120
cacgatggca gtcaaatgag agcaaaagca tttccagaaa ccagagatta ttctcaacct  180
actgcagcag caacagtaca ggacataaaa aaacctgtcc agcaaccagc taagcaagca  240
cctcaccaaa ctttagcagc aagattcatg gatggtcata tcacctttca aacagcggcc  300
acagtaaaaa ttccaacaac taccccagca actacaaaaa acactgcaac caccagccca  360
attacctaca ccctggtcac aacccaggcc acacccaaca actcacacac agctcctcca  420
gttactgaag ttacagtcgg ccctagctta gccccttatt cactgccacc caccatcacc  480
ccaccagctc atacagctgg aaccagttca tcaaccgtca gccacacaac tgggaacacc  540
actcaaccca gtaaccagac caccettcca gcaactttat cgatagcact gcacaaaagc  600
acaaccggtc agaagcctga tcaacccacc catgccccag gaacaacggc agctgcccac  660
aataccaccc gcacagctgc acctgcctcc acggttcctg ggcccaccct tgcacctcag  720
ccatcgtcag tcaagactgg aatttatcag gttctaaacg gaagcagact ctgtataaaa  780
gcagagatgg ggatacagct gattgttcaa gacaaggagt cggtttttc acctcggaga  840
tacttcaaca tcgaccccaa cgcaacgcaa gcctctggga actgtggcac ccgaaaatcc  900
aaccttctgt tgaattttca gggcggattt gtgaatctca catttaccaa ggatgaagaa  960
tcatattata tcagtgaagt gggagcctat ttgaccgtct cagatccaga gacagtttac  1020
caaggaatca aacatgcggt ggtgatgttc cagacagcag tcgggcattc cttcaagtgc  1080
gtgagtgaac agagcctcca gttgtcagcc cacctgcagg tgaaaacaac cgatgtccaa  1140
cttcaagcct ttgattttga agatgaccac tttggaaatg tggatgagtg ctcgtctgac  1200
tacacaattg tgcttcctgt gattggggcc atcgtggttg gtctctgcct tatgggtatg  1260
ggtgtctata aaatccgcct aaggtgtcaa tcatctggat accagagaat ctaattgttg  1320
cccgggggga atgaaaataa tggaatttag agaactcttt catcccttcc aggatggatg  1380
ttgggaaatt ccctcagagt gtgggtcctt caaacaatgt aaaccaccat cttctattca  1440
aatgaagtga gtcatgtgtg atttaagttc aggcagcaca tcaatttcta aatacttttt  1500
gtttatttta tgaaagatat agtgagctgt ttattttcta gtttccttta gaatatttta  1560
gccactcaaa gtcaacattt gagatatgtt gaattaacat aatatatgta aagtagaata  1620
agccttcaaa ttataaacca agggtcaatt gtaactaata ctactgtgtg tgcattgaag  1680
attttatttt acccttgatc ttaacaaagc ctttgctttg ttatcaaatg gactttcagt  1740
gcttttacta tctgtgtttt atggtttcat gtaacataca tattcctggt gtagcactta  1800
actccttttc cactttaaat ttgtttttgt tttttgagac ggagtttcac tcttgtcacc  1860
caggctggag tacagtggca cgatctcggc ttatggcaac ctccgcctcc cgggttcaag  1920
tgattctcct gcttcagctt cccgagtagc tgggattaca ggcacacact accacgcctg  1980
gctaattttt gtatttttat tatagacggg tttcaccatg ttggccagac tggtcttgaa  2040
ctcttgacct caggtgatcc acccacctca gcctcccaaa gtgctgggat tacaggcatg  2100
agccattgcg cccggcctta aatgtttttt ttaatcatca aaaagaacaa catatctcag  2160
gttgtctaag tgtttttatg taaaaccaac aaaaagaaca aatcagctta tattttttat  2220
cttgatgact cctgctccag aattgctaga ctaagaatta ggtggctaca gatggtagaa  2280
ctaaacaata agcaagagac aataataatg gcccttaatt attaacaaag tgccagagtc  2340
taggctaagc actttatcta tatctcattt cattctcaca acttataagt gaatgagtaa  2400
actgagactt aagggaactg aatcacttaa atgtcacctg gctaactgat ggcagagcca  2460
gagcttgaat tcatgttggt ctgacatcaa ggtctttggt cttctcccta caccaagtta  2520
cctacaagaa caatgacacc acactctgcc tgaaggctca cacctcatac cagcatacgc  2580
tcaccttaca gggaaatggg tttatccagg atcatgagac attagggtag atgaaaggag  2640
agctttgcag ataacaaaat agcctatcct taataaatcc tccactctct ggaaggagac  2700
tgaggggctt tgtaaaacat tagtcagttg ctcattttta tgggattgct tagctgggct  2760
gtaaagatga aggcatcaaa taaactcaaa gtatttttaa attttttga taatagagaa  2820
acttcgctaa ccaactgttc tttcttgagt gtatagcccc atcttgtggt aacttgctgc  2880
ttctgcactt catatccata tttcctattg ttcactttat tctgtagagc agcctgccaa  2940
gaattttatt tctgctgttt tttttgctgc taaagaaagg aactaagtca ggatgttaac  3000
agaaaagtcc acataaccct agaattctta gtcaaggaat aattcaagtc agcctagaga  3060
ccatgttgac tttcctcatg tgtttcctta tgactcagta agttggcaag gtcctgactt  3120
tagtcttaat aaaacattga attgtagtaa aggtttttgc aataaaaact tactttgg    3178

SEQ ID NO: 44           moltype = DNA  length = 1858
FEATURE                 Location/Qualifiers
source                  1..1858
                        mol_type = other DNA
                        organism = Mus sp.
SEQUENCE: 44
attccggagg tgaaaaacaa tggcacaacg tgtataatgg ccagcttctc tgcctccttt  60
ctgaccacct acgagactgc gaatggttct cagatcgtga acatttccct gccagcctct  120
gcagaagtac tgaaaaatgg cagttcttgt ggtaaagaaa atgtttctga ccccagcctc  180
acaattactt ttggaagagg atatttactg acactcaact tcacaaaaaa tacaacacgt  240
tacagtgtcc agcatatgta ttttacatat aacttgtcag atacagaaca ttttcccaat  300
gccatcagca aagagatcta caccatggat tccacaactg acatcaaggc agacatcaac  360
aaagcatacc ggtgtgtcag tgatatccgg gtctacatga agaatgtgac cgttgtgctc  420
```

```
cgggatgcca ctatccaggc ctacctgtcg agtggcaact tcagcaagga agagacacac  480
tgcacacagg atggaccttc cccaaccact gggccaccca gcccctcacc accacttgtg  540
cccacaaacc ccactgtatc caagtacaat gttactggta acaacggaac ctgcctgctg  600
gcctctatgg cactgcaact gaatatcacc tacctgaaaa aggacaacaa gacggtgacc  660
agagcgttca acatcagccc aaatgacaca tctagtggga gttgcggtat caacttggtg  720
accctgaaag tggagaacaa gaacagagcc ctggaattgc agtttgggat gaatgccagc  780
tctagcctgt ttttcttgca aggagtgcgc ttgaatatga ctcttcctga tgccctagtg  840
cccacattca gcatctccaa ccattcactg aaagctcttc aggccactgt gggaaactca  900
tacaagtgca acactgagga acacatcttt gtcagcaaga tgctctccct caatgtcttc  960
agtgtgcagg tccaggcttt caaggtggac agtgacaggt ttgggtctgt ggaagagtgt  1020
gttcaggatg gtaacaacat gttgatcccc attgctgtgg gcggtgccct ggcagggctg  1080
atcctcatcg tcctcattgc ctacctcatt ggcaggaaga ggagtcacgc cggctatcag  1140
accatctagc ctggtgggca ggtgcaccag agatgcacag gggcctgttc tcacatcccc  1200
aagcttagat aggtgtggaa gggaggcaca ctttctggca aactgtttta aaatctgctt  1260
tatcaaatgt gaagttcatc ttgcaacatt tactatgcac aaaggaataa ctattgaaat  1320
gacggtgtta attttgctaa ctgggttaaa tattgatgag aaggctccac tgatttgact  1380
tttaagactt ggtgtttggt tcttcattct tttactcaga tttaagccta tcaaagggat  1440
actctggtcc agaccttggc ctggcaaggg tggctgatgg ttaggctgca cacacttaag  1500
aagcaacggg agcagggaag gcttgcacac aggcacgcac agggtcaacc tctggacact  1560
tggcttgggc tacctggcct tggggggggct gaactctggc atctggctgg gtacacaccc  1620
ccccaatttc tgtgctctgc caccccgtgag ctgccacttt cctaaataga aaatggcatt  1680
atttttattt actttttgt aaagtgattt ccagtcttgt gttggcgttc agggtggccc  1740
tgtctctgca ctgtgtacaa taatagattc acactgctga cgtgtcttgc agcgtaggtg  1800
ggttgtacac tgggcatcag ctcacgtaat gcattgcctg taacgatgct aataaaaa    1858

SEQ ID NO: 45           moltype = DNA  length = 2339
FEATURE                 Location/Qualifiers
source                  1..2339
                        mol_type = other DNA
                        organism = Homo sapiens
SEQUENCE: 45
ggcccaaccg ccgcccgcgc ccccgctctc cgcaccgtac ccggccgcct cgcgccatgg  60
cggcccccgg cagcgcccgg cgacccctgc tgctgctact gctgttgctg ctgctcggcc  120
tcatgcattg tgcgtcagca gcaatgttta tggtgaaaaa tggcaacggg accgcgtgca  180
taatggccaa cttctctgct gccttctcag tgaactacga caccaagagt ggccctaaga  240
acatgacctt tgacctgcca tcagatgcca cagtggtgct caaccgcagc tcctgtggaa  300
aagagaacac ttctgacccc agtctcgtga ttgcttttgg aagaggacat acactcactc  360
tcaatttcac gagaaatgca acacgttaca gcgtccagct catgagtttt gtttataact  420
tgtcagacac acaccttttc cccaatgcga gctccaaaga aatcaagact gtggaatcta  480
taactgacat cagggcagat atagataaaa aatacagatg tgttagtggc acccaggtcc  540
acatgaacaa cgtgaccgta acgctccatg atgccaccat ccaggcgtac ctttccaaca  600
gcagcttcag caggggagag acacgctgtg aacaagacag gccttcccca accacagcgc  660
cccctgcgcc acccagcccc tcgccctcac ccgtgcccaa gagcccctct gtggacaagt  720
acaacgtgag cggcaccaac gggacctgcc tgctggccag catggggctg cagctgaacc  780
tcacctatga gaggaaggac aacacgacgg tgacaaggct tctcaacatc aaccccaaca  840
agacctcggc cagcgggagc tgcggcgccc acctggtgac tctggagctg cacagcgagg  900
gcaccaccgt cctgctcttc cagttcggga tgaatgcaag ttctagccgg tttttcctac  960
aaggaatcca gttgaataca attcttcctg acgccagaga ccctgccttt aaagctgcca  1020
acggctccct gcgagcgctg caggccacag tcggcaattc ctacaagtgc aacgcggagg  1080
agcacgtccg tgtcacgaag gcgttttcag tcaatatatt caaagtgtgg gtccaggctt  1140
tcaaggtgga aggtggccag tttggctctg tggaggagtg tctgctggac gagaacagca  1200
tgctgatccc catcgctgtg ggtggtgccc tggcggggct ggtcctcatc gtcctcatcg  1260
cctacctcgt cggcaggaag aggagtcacg caggctacca gactatctag cctggtgcac  1320
gcaggcacag cagctgcagg ggcctctgtt cctttctctg ggcttagggt cctgtcgaag  1380
gggaggcaca ctttctggca aacgtttctc aaatctgctt catccaatgt gaagttcatc  1440
ttgcagcatt tactatgcac aacagagtaa ctatcgaaat gacggtgtta attttgctaa  1500
ctgggttaaa tattttgcta actggttaaa cattaatatt taccaaagta ggattttgag  1560
ggtgggggtg ctctctctga gggggtgggg gtgccgctgt ctctgagggg tgggggtgcc  1620
gctgtctctg aggggtgggg gtgccgctct ctctgagggg gtgggggtgc cgctttctct  1680
gagggggtgg gggtgccgct ctctctgagg gggtgggggt gctgctctct ccgaggggtg  1740
gaatgccgct gtctctgagg ggtgggggtg ccgctctaaa ttggctccat atcatttgag  1800
tttagggttc tggtgtttgg tttcttcatt ctttactgca ctcagattta agccttacaa  1860
agggaaagcc tctggccgtc acacgtagga cgcatgaagg tcactcgtgg tgaggctgac  1920
atgctcacac attacaacag tagagaggga aaatcctaag acagaggaac tccagagatg  1980
agtgtctgga gcgcttcagt tcagctttaa aggccaggac gggccacacg tggctggcgg  2040
cctcgttcca gtggcggcac gtccttgggc gtctctaatg tctgcagctc aagggctggc  2100
actttttaa atataaaaat gggtgttatt tttatttttt tttgtaaagt gatttttggt  2160
cttctgttga cattcggggt gatcctgttc tgcgctgtgt acaatgtgag atcggtgcgt  2220
tctcctgatg ttttgccgtg gcttggggat tgtacacggg accagctcac gtaatgcatt  2280
gcctgtaaca atgtaataaa aagcctcttt cttttaaaaa aaaaaaaaaa aaaaaaaaa   2339

SEQ ID NO: 46           moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
```

```
SEQUENCE: 46
cagtacatca aggccaacag caagttcatc ggcatcaccg aactc                 45

SEQ ID NO: 47          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 47
QYIKANSKFI GITEL                                                  15

SEQ ID NO: 48          moltype = DNA  length = 39
FEATURE                Location/Qualifiers
misc_feature           1..39
                       note = Description of Artificial Sequence: Synthetic
                        oligonucleotide
source                 1..39
                       mol_type = other DNA
                       organism = synthetic construct
SEQUENCE: 48
gctaaatttg tggctgcctg gacactgaaa gccgccgct                        39

SEQ ID NO: 49          moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 49
AKFVAAWTLK AAA                                                    13

SEQ ID NO: 50          moltype = DNA  length = 593
FEATURE                Location/Qualifiers
source                 1..593
                       mol_type = other DNA
                       organism = Woodchuck hepatitis virus
SEQUENCE: 50
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaagctga cgtcctttcc atggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc tgt         593

SEQ ID NO: 51          moltype = DNA  length = 589
FEATURE                Location/Qualifiers
misc_feature           1..589
                       note = Description of Artificial Sequence: Synthetic
                        polynucleotide
source                 1..589
                       mol_type = other DNA
                       organism = synthetic construct
SEQUENCE: 51
tctccccccc ccccctctcc ctcccccccc cctaacgtta ctggccgaag ccgcttggaa  60
taaggccggt gtgcgtttgt ctatatgtta ttttccacca tattgccgtc ttttggcaat  120
gtgagggccc ggaaacctgg ccctgtcttc ttgacgagca ttcctagggg tctttcccct  180
ctcgccaaag gaatgcaagg tctgttgaat gtcgtgaagg aagcagttcc tctggaagct  240
tcttgaagac aaacaacgtc tgtagcgacc ctttgcaggc agcggaaccc cccacctggc  300
gacaggtgcc tctgcggcca aaagccacgt gtataagata cacctgcaaa ggcggcacaa  360
ccccagtgcc acgttgtgag ttggatagtt gtggaaagag tcaaatggct ctcctcaagc  420
gtattcaaca aggggctgaa ggatgcccag aaggtacccc attgtatggg atctgatctg  480
gggcctcggt gcacatgctt tacatgtgtt tagtcgaggt taaaaaaacg tctaggcccc  540
ccgaaccacg gggacgtggt tttcctttga aaaacacgat gataatatg              589

SEQ ID NO: 52          moltype = DNA  length = 720
FEATURE                Location/Qualifiers
misc_feature           1..720
                       note = Description of Artificial Sequence: Synthetic
                        polynucleotide
source                 1..720
                       mol_type = other DNA
                       organism = synthetic construct
```

-continued

```
SEQUENCE: 52
atggtgagca agggcgagga gctgttcacc ggggtggtgc ccatcctggt cgagctggac  60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccctgaccta cggcgtgcag tgcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaagtag  720

SEQ ID NO: 53          moltype = DNA  length = 1563
FEATURE                Location/Qualifiers
misc_feature           1..1563
                       note = Description of Artificial Sequence: Synthetic
                        polynucleotide
source                 1..1563
                       mol_type = other DNA
                       organism = synthetic construct
SEQUENCE: 53
atgctgctgc tgctgctgct gctgggcctg aggctacagc tctccctggg catcatccca  60
gttgaggagg agaacccgga cttctggaac cgcgaggcag ccgaggccct gggtgccgcc  120
aagaagctgc agcctgcaca gacagccgcc aagaacctca tcatcttcct gggcgatggg  180
atgggggtgt ctacggtgac agctgccagg atcctaaaag ggcagaagaa ggacaaactg  240
gggcctgaga taccccctggc catggaccgc ttcccatatg tggctctgtc caagacatac  300
aatgtagaca aacatgtgcc agacagtgga gccacagcca cggcctacct gtgcggggtc  360
aagggcaact tccagaccat tggcttgagt gcagccgccc gctttaacca gtgcaacacg  420
acacgcggca acgaggtcat ctccgtgatg aatcgggcca agaaagcagg gaagtcagtg  480
ggagtggtaa ccaccacacg agtgcagcac gcctcgccag ccggcaccta cgcccacacg  540
gtgaaccgca actggtactc ggacgccgac gtgcctgcct cggcccgcca ggaggggtgc  600
caggacatcg ctacgcagct catctccaac atggacattg acgtgatcct aggtggaggc  660
cgaaagtaca tgtttcgcat gggaacccca gaccctgagt acccagatga ctacagccaa  720
ggtgggacca ggctggacgg gaagaatctg gtgcaggaat ggctggcgaa gcgccagggt  780
gcccggtatg tgtggaaccg cactgagctc atgcaggctt ccctggaccc gtctgtgacc  840
catctcatgg gtctctttga gcctggagac atgaaatacg agatccaccg agactccaca  900
ctggacccct ccctgatgga gatgacagag gctgccctgc gcctgctgag caggaacccc  960
cgcggcttct tcctcttcgt ggagggtggt cgcatcgacc atggtcatca tgaaagcagg  1020
gcttaccggg cactgactga gacgatcatg ttcgacgacg ccattgagag ggcgggccag  1080
ctcaccagcg aggaggacac gctgagcctc gtcactgccg accactccca cgtcttctcc  1140
ttcggaggct acccccctgcg agggagctcc atcttcgggc tggcccctgg caaggcccgg  1200
gacaggaagg cctacacggt cctcctatac ggaaacggtc caggctatgt gctcaaggac  1260
ggcgcccggc cggatgttac cgagagcgag agcgggagcc ccgagtatcg gcagcagtca  1320
gcagtgcccc tggacgaaga gacccacgca ggcgaggacg tggcggtgtt cgcgcgcggc  1380
ccgcaggcgc acctggttca cggcgtgcag gagcagacct tcatagcgca cgtcatggcc  1440
ttcgccgcct gcctggagcc ctacaccgcc tgcgacctgg cgccccccgc cggcaccacc  1500
gacgccgcgc acccgggtta ctctagagtc ggggcggccg gccgcttcga gcagacatga  1560
taa                                                               1563

SEQ ID NO: 54          moltype = DNA  length = 1653
FEATURE                Location/Qualifiers
misc_feature           1..1653
                       note = Description of Artificial Sequence: Synthetic
                        polynucleotide
source                 1..1653
                       mol_type = other DNA
                       organism = synthetic construct
SEQUENCE: 54
atggaagatg ccaaaaacat taagaagggc ccagcgccat tctacccact cgaagacggg  60
accgccggcg agcagctgca caaagccatg aagcgctacg ccctggtgcc cggcaccatc  120
gcctttaccg acgcacatat cgaggtggac attacctacg ccgagtactt cgagatgagc  180
gttcggctgg cagaagctat gaagcgctat gggctgaata caaaccatcg gatcgtggtg  240
tgcagcgaga atagcttgca gttcttcatg cccgtgttgg gtgccctgtt catcggtgtg  300
gctgtggccc cagctaacga catctacaac gagcgcgagc tgctgaacag catgggcatc  360
agccagccca ccgtcgtatt cgtgagcaag aaagggctgc aaaagatcct caacgtgcaa  420
aagaagctac cgatcataca aaagatcatc atcatggata gcaagaccga ctaccagggc  480
ttccaaagca tgtacacctt cgtgacttcc catttgccac ccggcttcaa cgagtacgac  540
ttcgtgcccg agagcttcga ccgggacaaa accatcgccc tgatcatgaa cagtagtggc  600
agtaccggat tgcccaaggg cgtagcccta ccgcaccgca ccgcttgtgt ccgattcagt  660
catgcccgcg accccatctt cggcaaccag atcatccccg acaccgctat cctcagcgtg  720
gtgccatttc accacggctt cggcatgttc accacgctgg gctacttgat ctgcggcttt  780
cgggtcgtgc tcatgtaccg cttcgaggag gagctattct tgcgcagctt gcaagactat  840
aagattcaat ctgccctgct ggtgcccaca ctatttagct tcttcgctaa gagcactctc  900
atcgacaagt acgacctaag caacttgcac gagatcgcca gcggcggggc gccgctcagc  960
aaggaggtag gtgaggccgt ggccaaacgc ttccacctac caggcatccg ccagggctac  1020
ggcctgacag aaacaaccag cgccattctg atcacccccg aaggggacga caagcctggc  1080
gcagtaggca aggtggtgcc cttcttcgag gctaaggtgg tggacttgga caccggtaag  1140
```

-continued

```
acactgggtg tgaaccagcg cggcgagctg tgcgtccgtg gccccatgat catgagcggc  1200
tacgttaaca accccgaggc tacaaacgct ctcatcgaca aggacggctg gctgcacagc  1260
ggcgacatcg cctactggga cgaggacgag cacttcttca tcgtggaccg gctgaagagc  1320
ctgatcaaat acaagggcta ccaggtagcc ccagccgaac tggagagcat cctgctgcaa  1380
caccccaaca tcttcgacgc cggggtcgcc ggcctgcccg acgacgatgc cggcgagctg  1440
cccgccgcag tcgtcgtgct ggaacacggt aaaaccatga ccgagaagga gatcgtggac  1500
tatgtggcca gccaggttac aaccgccaag aagctgcgcg gtggtgttgt gttcgtggac  1560
gaggtgccta aaggactgac cggcaagttg gacgcccgca agatccgcga gattctcatt  1620
aaggccaaga agggcggcaa gatcgccgtg taa                                1653

SEQ ID NO: 55          moltype = DNA  length = 66
FEATURE                Location/Qualifiers
source                 1..66
                       mol_type = other DNA
                       organism = Foot-and-mouth disease virus
SEQUENCE: 55
gtaaagcaaa cactgaactt tgaccttctc aagttggctg gagacgttga gtccaatcct  60
gggccc                                                            66

SEQ ID NO: 56          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 56
GPGPG                                                             5

SEQ ID NO: 57          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 57
SIINFEKL                                                          8

SEQ ID NO: 58          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 58
SPSYAYHQF                                                         9

SEQ ID NO: 59          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 59
YVYVADVAAK                                                        10

SEQ ID NO: 60          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 60
YEMFNDKS                                                          8

SEQ ID NO: 61          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 61
YEMFNDKSQR APDDKMF                                                17
```

-continued

```
SEQ ID NO: 62           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 62
YEMFNDKSF                                                                   9

SEQ ID NO: 63           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 63
HROEIFSHDF J                                                                11

SEQ ID NO: 64           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 64
FJIEJFOESS                                                                  10

SEQ ID NO: 65           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 65
NEIOREIREI                                                                  10

SEQ ID NO: 66           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 66
JFKSIFEMMS JDSSU                                                            15

SEQ ID NO: 67           moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 67
KNFLENFIES OFI                                                              13

SEQ ID NO: 68           moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 68
JFKSIFEMMS JDSSUIFLKS JFIEIFJ                                               27

SEQ ID NO: 69           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 69
FOEIFNDKSL DKFJI                                                            15
```

-continued

```
SEQ ID NO: 70           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 70
QCEIOWARE                                                         9

SEQ ID NO: 71           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 71
FIEUHFWI                                                          8

SEQ ID NO: 72           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 72
FEWRHRJTRU JR                                                     12

SEQ ID NO: 73           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 73
QIEJOEIJE                                                         9

SEQ ID NO: 74           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 74
FJELFISBOS JFIE                                                   14

SEQ ID NO: 75           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 75
QCEIOWAREF LKEIGJ                                                 16

SEQ ID NO: 76           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 76
IEFROEIFJE F                                                      11

SEQ ID NO: 77           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 77
```

```
IEFROEIFJ                                                   9

SEQ ID NO: 78          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 78
EFROEIFJE                                                   9

SEQ ID NO: 79          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 79
FROEIFJEF                                                   9

SEQ ID NO: 80          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 80
SINFEKL                                                     7

SEQ ID NO: 81          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 81
LLLLLVVVV                                                   9

SEQ ID NO: 82          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 82
EKLAAYLLL                                                   9

SEQ ID NO: 83          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 83
KLAAYLLLLL                                                  10

SEQ ID NO: 84          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 84
FEKLAAYL                                                    8

SEQ ID NO: 85          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
```

-continued

```
SEQUENCE: 85
AAYLLLLL                                                        8

SEQ ID NO: 86          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 86
YLLLLLVVV                                                       9

SEQ ID NO: 87          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 87
VVVVAAYSIN                                                      10

SEQ ID NO: 88          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 88
VVVVAAY                                                         7

SEQ ID NO: 89          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 89
AYSINFEK                                                        8

SEQ ID NO: 90          moltype = AA  length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 90
YNYSYWISIF AHTMWYNIWH VQWNK                                     25

SEQ ID NO: 91          moltype = AA  length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 91
IEALPYVFLQ DQFELRLLKG EQGNN                                     25

SEQ ID NO: 92          moltype = AA  length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 92
DSEETNTNYL HYCHFHWTWA QQTTV                                     25

SEQ ID NO: 93          moltype = AA  length = 25
FEATURE                Location/Qualifiers
REGION                 1..25
                       note = Description of Artificial Sequence: Synthetic peptide
source                 1..25
                       mol_type = protein
```

-continued

```
                         organism = synthetic construct
SEQUENCE: 93
GMLSQYELKD CSLGFSWNDP AKYLR                                             25

SEQ ID NO: 94            moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 94
VRIDKFLMYV WYSAPFSAYP LYQDA                                             25

SEQ ID NO: 95            moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 95
CVHIYNNYPR MLGIPFSVMV SGFAM                                             25

SEQ ID NO: 96            moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 96
FTFKGNIWIE MAGQFERTWN YPLSL                                             25

SEQ ID NO: 97            moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 97
ANDDTPDFRK CYIEDHSFRF SQTMN                                             25

SEQ ID NO: 98            moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 98
AAQYIACMVN RQMTIVYHLT RWGMK                                             25

SEQ ID NO: 99            moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 99
KYLKEFTQLL TFVDCYMWIT FCGPD                                             25

SEQ ID NO: 100           moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 100
AMHYRTDIHG YWIEYRQVDN QMWNT                                             25

SEQ ID NO: 101           moltype = AA  length = 25
FEATURE                  Location/Qualifiers
REGION                   1..25
                         note = Description of Artificial Sequence: Synthetic peptide
source                   1..25
```

```
                        mol_type = protein
                        organism = synthetic construct
SEQUENCE: 101
THVNEHQLEA VYRFHQVHCR FPYEN                                               25

SEQ ID NO: 102          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 102
QTFSECLFFH CLKVWNNVKY AKSLK                                               25

SEQ ID NO: 103          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 103
SFSSWHYKES HIALLMSPKK NHNNT                                               25

SEQ ID NO: 104          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 104
ILDGIMSRWE KVCTRQTRYS YCQCA                                               25

SEQ ID NO: 105          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 105
YRAAQMSKWP NKYFDFPEFM AYMPI                                               25

SEQ ID NO: 106          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 106
PRPGMPCQHH NTHGLNDRQA FDDFV                                               25

SEQ ID NO: 107          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 107
HNIISDETEV WEQAPHITWV YMWCR                                               25

SEQ ID NO: 108          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 108
AYSWPVVPMK WIPYRALCAN HPPGT                                               25

SEQ ID NO: 109          moltype = AA  length = 25
FEATURE                 Location/Qualifiers
REGION                  1..25
                        note = Description of Artificial Sequence: Synthetic peptide
```

-continued

```
source                 1..25
                       mol_type = protein
                       organism = synthetic construct
SEQUENCE: 109
HVMPHVAMNI CNWYEFLYRI SHIGR                                         25

SEQ ID NO: 110         moltype = AA  length = 484
FEATURE                Location/Qualifiers
REGION                 1..484
                       note = Description of Artificial Sequence: Synthetic
                        polypeptide
source                 1..484
                       mol_type = protein
                       organism = synthetic construct
SEQUENCE: 110
THVNEHQLEA VYRFHQVHCR FPYENAMHYQ MWNTYRAAQM SKWPNKYFDF PEFMAYMPIC  60
VHIYNNYPRM LGIPFSVMVS GFAMAYSWPV VPMKWIPYRA LCANHPPGTA NDDTPDFRKC  120
YIEDHSFRFS QTMNIEALPY VFLQDQFELR LLKGEQGNND SEETNTNYLH YCHFHWTWAQ  180
QTTVILDGIM SRWEKVCTRQ TRYSYCQCAF TFKGNIWIEM AGQFERTWNY PLSLSFSSWH  240
YKESHIALLM SPKKNHNNTQ TFSECLFFHC LKVWNNVKYA KSLKHVMPHV AMNICNWYEF  300
LYRISHIGRH NIISDETEVW EQAPHITWVY MWCRVRIDKF LMYVWYSAPF SAYPLYQDAK  360
YLKEFTQLLT FVDCYMWITF CGPDAAQYIA CMVNRQMTIV YHLTRWGMKY NYSYWISIFA  420
HTMWYNIWHV QWNKGMLSQY ELKDCSLGFS WNDPAKYLRP RPGMPCQHHN THGLNDRQAF  480
DDFV                                                                484

SEQ ID NO: 111         moltype = AA  length = 484
FEATURE                Location/Qualifiers
REGION                 1..484
                       note = Description of Artificial Sequence: Synthetic
                        polypeptide
source                 1..484
                       mol_type = protein
                       organism = synthetic construct
SEQUENCE: 111
IEALPYVFLQ DQFELRLLKG EQGNNILDGI MSRWEKVCTR QTRYSYCQCA HVMPHVAMNI  60
CNWYEFLYRI SHIGRTHVNE HQLEAVYRFH QVHCRFPYEN FTFKGNIWIE MAGQFERTWN  120
YPLSLAMHYQ MWNTSFSSWH YKESHIALLM SPKKNHNNTV RIDKFLMYVW YSAPFSAYPL  180
YQDAQTFSEC LFFHCLKVWN NVKYAKSLKY RAAQMSKWPN KYFDFPEFMA YMPIAYSWPV  240
VPMKWIPYRA LCANHPPGTC VHIYNNYPRM LGIPFSVMVS GFAMHNIISD ETEVWEQAPH  300
ITWVYMWCRA AQYIACMVNR QMTIVYHLTR WGMKYNYSYW ISIFAHTMWY NIWHVQWNKG  360
MLSQYELKDC SLGFSWNDPA KYLRKYLKEF TQLLTFVDCY MWITFCGPDA NDDTPDFRKC  420
YIEDHSFRFS QTMNDSEETN TNYLHYCHFH WTWAQQTTVP RPGMPCQHHN THGLNDRQAF  480
DDFV                                                                484

SEQ ID NO: 112         moltype = AA  length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 112
SSTPYLYYGT SSVSYQFPMV PGGDR                                         25

SEQ ID NO: 113         moltype = AA  length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 113
EMAGKIDLLR DSYIFQLFWR EAAEP                                         25

SEQ ID NO: 114         moltype = AA  length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 114
ALKQRTWQAL AHKYNSQPSV SLRDF                                         25

SEQ ID NO: 115         moltype = AA  length = 25
FEATURE                Location/Qualifiers
REGION                 1..25
                       note = Description of Artificial Sequence: Synthetic peptide
source                 1..25
```

```
                        mol_type = protein
                        organism = synthetic construct
SEQUENCE: 115
VSSHSSQATK DSAVGLKYSA STPVR                                    25

SEQ ID NO: 116          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 116
KEAIDAWAPY LPEYIDHVIS PGVTS                                    25

SEQ ID NO: 117          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 117
SPVITAPPSS PVFDTSDIRK EPMNI                                    25

SEQ ID NO: 118          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 118
PAEVAEQYSE KLVYMPHTFF IGDHA                                    25

SEQ ID NO: 119          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
SEQUENCE: 119
MADLDKLNIH SIIQRLLEVR GS                                       22

SEQ ID NO: 120          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 120
AAAYNEKSGR ITLLSLLFQK VFAQI                                    25

SEQ ID NO: 121          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 121
KIEEVRDAME NEIRTQLRRQ AAAHT                                    25

SEQ ID NO: 122          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 122
DRGHYVLCDF GSTTNKFQNP QTEGV                                    25

SEQ ID NO: 123          moltype = AA  length = 25
FEATURE                 Location/Qualifiers
REGION                  1..25
                        note = Description of Artificial Sequence: Synthetic peptide
```

```
source                  1..25
                        mol_type = protein
                        organism = synthetic construct
SEQUENCE: 123
QVDNRKAEAE EAIKRLSYIS QKVSD                                        25

SEQ ID NO: 124          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 124
CLSDAGVRKM TAAVRVMKRG LENLT                                        25

SEQ ID NO: 125          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 125
LPPRSLPSDP FSQVPASPQS QSSSQ                                        25

SEQ ID NO: 126          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 126
ELVLEDLQDG DVKMGGSFRG AFSNS                                        25

SEQ ID NO: 127          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 127
VTMDGVREED LASFSLRKRW ESEPH                                        25

SEQ ID NO: 128          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 128
IVGVMFFERA FDEGADAIYD HINEG                                        25

SEQ ID NO: 129          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 129
TVTPTPTPTG TQSPTPTPIT TTTTV                                        25

SEQ ID NO: 130          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 130
QEEMPPRPCG GHTSSSLPKS HLEPS                                        25

SEQ ID NO: 131          moltype = AA  length = 21
FEATURE                 Location/Qualifiers
REGION                  1..21
```

-continued

```
                        note = Description of Artificial Sequence: Synthetic peptide
source                  1..21
                        mol_type = protein
                        organism = synthetic construct
SEQUENCE: 131
PNIQAVLLPK KTDSHHKAKG K                                                 21

SEQ ID NO: 132          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 132
NLVPMVATV                                                               9

SEQ ID NO: 133          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 133
CLGGLLTMV                                                               9

SEQ ID NO: 134          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 134
GILGFVFTL                                                               9

SEQ ID NO: 135          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 135
LLFGYPVYV                                                               9

SEQ ID NO: 136          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 136
GLCTLVAML                                                               9

SEQ ID NO: 137          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 137
WLSLLVPFV                                                               9

SEQ ID NO: 138          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 138
FLLTRICT                                                                8

SEQ ID NO: 139          moltype = AA  length = 8
FEATURE                 Location/Qualifiers
```

```
REGION                  1..8
                        note = Description of Artificial Sequence: Synthetic peptide
source                  1..8
                        mol_type = protein
                        organism = synthetic construct
SEQUENCE: 139
WQAGILAR                                                                  8

SEQ ID NO: 140          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 140
QGQNLKYQ                                                                  8

SEQ ID NO: 141          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 141
WQAGILARNL VPMVATVQGQ NLKYQ                                               25

SEQ ID NO: 142          moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 142
gtggtgtgca gcgagaatag                                                     20

SEQ ID NO: 143          moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 143
cgctcgttgt agatgtcgtt ag                                                  22

SEQ ID NO: 144          moltype = DNA  length = 15
FEATURE                 Location/Qualifiers
misc_feature            1..15
                        note = Description of Artificial Sequence: Synthetic probe
source                  1..15
                        mol_type = other DNA
                        organism = synthetic construct
SEQUENCE: 144
ttcatgcccg tgttg                                                          15

SEQ ID NO: 145          moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 145
gtttttgatc cagacccaga tg                                                  22

SEQ ID NO: 146          moltype = DNA  length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 146
gcccattatt cagagcgagt a                                                   21

SEQ ID NO: 147          moltype = DNA  length = 14
```

```
FEATURE                Location/Qualifiers
misc_feature           1..14
                       note = Description of Artificial Sequence: Synthetic probe
source                 1..14
                       mol_type = other DNA
                       organism = synthetic construct
SEQUENCE: 147
tcaccaggat ccac                                                      14

SEQ ID NO: 148         moltype = DNA  length = 17
FEATURE                Location/Qualifiers
misc_feature           1..17
                       note = Description of Artificial Sequence: Synthetic primer
source                 1..17
                       mol_type = other DNA
                       organism = synthetic construct
SEQUENCE: 148
ccttgcacat gccggag                                                   17

SEQ ID NO: 149         moltype = DNA  length = 17
FEATURE                Location/Qualifiers
misc_feature           1..17
                       note = Description of Artificial Sequence: Synthetic primer
source                 1..17
                       mol_type = other DNA
                       organism = synthetic construct
SEQUENCE: 149
acagagcctc gcctttg                                                   17

SEQ ID NO: 150         moltype = DNA  length = 12
FEATURE                Location/Qualifiers
misc_feature           1..12
                       note = Description of Artificial Sequence: Synthetic probe
source                 1..12
                       mol_type = other DNA
                       organism = synthetic construct
SEQUENCE: 150
gtgagctggc gg                                                        12

SEQ ID NO: 151         moltype = DNA  length = 22
FEATURE                Location/Qualifiers
misc_feature           1..22
                       note = Description of Artificial Sequence: Synthetic primer
source                 1..22
                       mol_type = other DNA
                       organism = synthetic construct
SEQUENCE: 151
ctgaaagctc ggtttgctaa tg                                             22

SEQ ID NO: 152         moltype = DNA  length = 21
FEATURE                Location/Qualifiers
misc_feature           1..21
                       note = Description of Artificial Sequence: Synthetic primer
source                 1..21
                       mol_type = other DNA
                       organism = synthetic construct
SEQUENCE: 152
ccatgctgga agagacaatc t                                              21

SEQ ID NO: 153         moltype = DNA  length = 15
FEATURE                Location/Qualifiers
misc_feature           1..15
                       note = Description of Artificial Sequence: Synthetic probe
source                 1..15
                       mol_type = other DNA
                       organism = synthetic construct
SEQUENCE: 153
tggcgctgac cgata                                                     15

SEQ ID NO: 154         moltype = DNA  length = 22
FEATURE                Location/Qualifiers
misc_feature           1..22
                       note = Description of Artificial Sequence: Synthetic primer
source                 1..22
                       mol_type = other DNA
                       organism = synthetic construct
SEQUENCE: 154
tatgcctatc ctgtctcctc tg                                             22
```

-continued

```
SEQ ID NO: 155          moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 155
gctaatgcag ctaagtcctc tc                                           22

SEQ ID NO: 156          moltype = DNA  length = 15
FEATURE                 Location/Qualifiers
misc_feature            1..15
                        note = Description of Artificial Sequence: Synthetic probe
source                  1..15
                        mol_type = other DNA
                        organism = synthetic construct
SEQUENCE: 156
tgaccgtgcc ttctg                                                   15

SEQ ID NO: 157          moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 157
YEMFNDKSFQ RAPDDKMF                                                18

SEQ ID NO: 158          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 158
FEGRKUOOI                                                          9

SEQ ID NO: 159          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 159
PJFIOEJOIJ GEIO                                                    14

SEQ ID NO: 160          moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 160
AKFVAAWTLK AAA                                                     13

SEQ ID NO: 161          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 161
QYIKANSKFI GITE                                                    14

SEQ ID NO: 162          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 162
DLMGYIPAV                                                          9
```

```
SEQ ID NO: 163          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 163
FLPSDFFPSV                                                          10

SEQ ID NO: 164          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 164
FLLTRILTI                                                           9

SEQ ID NO: 165          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 165
FLLSLGIHL                                                           9

SEQ ID NO: 166          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 166
ILKEPVHGV                                                           9

SEQ ID NO: 167          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 167
YMLDLQPETT                                                          10

SEQ ID NO: 168          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 168
CINGVCWTV                                                           9

SEQ ID NO: 169          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 169
YLLPRRGPRL                                                          10

SEQ ID NO: 170          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 170
```

-continued

```
FLYALALLL                                                    9

SEQ ID NO: 171          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 171
AAGIGILTV                                                    9

SEQ ID NO: 172          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 172
SLLMWITQV                                                    9

SEQ ID NO: 173          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 173
KLGGALQAK                                                    9

SEQ ID NO: 174          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 174
RLRAEAQVK                                                    9

SEQ ID NO: 175          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 175
EENLLDFVRF                                                   10

SEQ ID NO: 176          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 176
EEYLQAFTY                                                    9

SEQ ID NO: 177          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 177
CTPYDINQM                                                    9

SEQ ID NO: 178          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
```

-continued

```
SEQUENCE: 178
TTPESANL                                                          8

SEQ ID NO: 179          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 179
CAPPGYALL                                                         9

SEQ ID NO: 180          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 180
SGPKTNIIV                                                         9

SEQ ID NO: 181          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 181
LSPRTLNAW                                                         9

SEQ ID NO: 182          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 182
TVPWPNASL                                                         9

SEQ ID NO: 183          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 183
EGPRNQDWL                                                         9

SEQ ID NO: 184          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 184
DWENVSPEL                                                         9

SEQ ID NO: 185          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 185
SIIVFNLL                                                          8

SEQ ID NO: 186          moltype = AA  length = 9
FEATURE                 Location/Qualifiers
REGION                  1..9
                        note = Description of Artificial Sequence: Synthetic peptide
source                  1..9
                        mol_type = protein
```

```
                        organism = synthetic construct
SEQUENCE: 186
ASMTNMELM                                                         9

SEQ ID NO: 187          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 187
AQLANDVVL                                                         9

SEQ ID NO: 188          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 188
SVYDFFVWL                                                         9

SEQ ID NO: 189          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 189
MNKYAYHML                                                         9

SEQ ID NO: 190          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 190
QYIKANSKFI GITEL                                                  15

SEQ ID NO: 191          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 191
SINFEKLAAY LLLLLVVVV                                              19

SEQ ID NO: 192          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 192
LLLLLVVVVA AYSINFEKL                                              19

SEQ ID NO: 193          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 193
SPSYVYHQF                                                         9
```

What is claimed is:

1. A method for inducing an immune response in a subject, comprising:

(A) administering a first vaccine composition, wherein the first vaccine composition comprises a chimpanzee adenovirus vector comprising a first neoantigen cassette; and (B) administering a second vaccine composition comprising an neoantigen expression system, wherein the neoantigen expression system comprises one or more vectors, wherein the one or more vectors each comprise:

(a) an RNA alphavirus backbone, wherein the RNA alphavirus backbone comprises:

(i) at least one promoter nucleotide sequence, and (ii) at least one polyadenylation (poly(A)) sequence; and (b) a second neoantigen cassette; and wherein the first neoantigen cassette and the second neoantigen cassette comprise at least one neoantigene-encoding nucleic acid sequence that is the same.

2. The method of claim 1, wherein the first neoantigen cassette and the second neoantigen cassette comprise the same neoantigene-encoding nucleic acid sequences.

3. The method of claim 1, wherein the second neoantigen cassette comprises at least one neoantigene-encoding nucleic acid sequence that is different with respect to any neoantigene-encoding nucleic acid sequences present in the first neoantigen cassette.

4. The method of claim 1, wherein the first vaccine composition is administered prior to the second vaccine composition.

5. The method of claim 1, wherein the first vaccine composition is administered is administered as a priming dose.

6. The method of claim 1, wherein the RNA alphavirus backbone comprises:

(a) the sequence of SEQ ID NO:3 further comprising a deletion between base pair 7544 and 11175, wherein the second neoantigen cassette is inserted to replace the deletion between base pair 7544 and 11175, and/or (b) the sequence set forth in SEQ ID NO:6, wherein the second neoantigen cassette is inserted at position 7544 of the sequence set forth in SEQ ID NO:6.

7. The method of claim 1, wherein one or both of the first neoantigen cassette and the second neoantigen cassette comprise junctional epitope sequences encoded by adjacent neoantigen-encoding nucleic acid sequences in the respective neoantigen cassettes, wherein at least one or each junctional epitope sequence has an affinity of greater than 500 nM for MHC, and optionally wherein at least one or each junctional epitope sequence is non-self.

8. The method of claim 1, wherein the chimpanzee adenovirus vector comprises a ChAdV68-based vector.

9. The method of claim 1, wherein one or both of the first neoantigen cassette and the second neoantigen cassette comprise at least two neoantigen-encoding nucleic acid sequences, wherein each neoantigen-encoding nucleic acid sequence comprises an epitope-encoding nucleic acid sequence, and wherein each of the at least two neoantigen-encoding nucleic acid sequences within the first neoantigen cassette and the second neoantigen cassette, respectively, is linked directly to one another.

10. The method of claim 9, wherein each neoantigen-encoding nucleic acid sequence comprises:

(A) the epitope-encoding nucleic acid sequence corresponding to the respective neoantigen-encoding nucleic acid sequence;

(B) a 5' linker sequence that encodes a N-terminal amino acid sequence, and wherein the 5' linker sequence encodes a peptide that is between 2-20 amino acids in length; and (C) a 3' linker sequence that encodes a C-terminal amino acid sequence, and wherein the 3' linker sequence encodes a peptide that is between 2-20 amino acids in length.

11. The method of claim 10, wherein:

(A) the 5' linker sequence comprises a native 5' linker sequence that encodes a native N-terminal amino acid sequence of the epitope encoded by the epitope-encoding nucleic acid sequence, and (B) the 3' linker sequence comprises a native 3' linker sequence that encodes a native C-terminal amino acid sequence of the epitope encoded by the epitope-encoding nucleic acid sequence.

12. The method of claim 1, wherein the at least one neoantigen-encoding nucleic acid sequence that is the same comprises an MHC class I epitope-encoding nucleic acid sequence.

13. The method of claim 1, wherein the at least one neoantigene-encoding nucleic acid sequence that is the same comprises an epitope-encoding nucleic acid sequence comprising an alteration that makes the encoded epitope sequence distinct from a corresponding peptide sequence encoded by a wild-type nucleic acid sequence, optionally wherein the alteration is selected from the group consisting of: a point mutation, a frameshift mutation, a non-frameshift mutation, a deletion mutation, an insertion mutation, a splice variant, a genomic rearrangement, a proteasome-generated spliced neoantigen, and combinations thereof.

14. The method of claim 13, wherein the encoded epitope comprising the alteration has (1) increased binding affinity to its corresponding MHC allele relative to the translated, corresponding wild-type nucleic acid sequence, (2) has increased binding stability to its corresponding MHC allele relative to the translated, corresponding wild-type nucleic acid sequence, and/or (3) has an increased likelihood of presentation on its corresponding MHC allele relative to the translated, corresponding wild-type nucleic acid sequence.

15. The method of claim 1, wherein an ordered sequence of each element of one or both of the first neoantigen cassette and the second neoantigen cassette is described in the formula, from 5' to 3', comprising:

$$P_a\text{-}(L5_b\text{-}N_c\text{-}L3_d)_X\text{-}(G5_e\text{-}U_f)_Y\text{-}G3_g$$

wherein P comprises a second promoter nucleotide sequence, where a=0 or 1,

N comprises an epitope-encoding nucleic acid sequences, where c=1,

L5 comprises a 5' linker sequence, where b=0 or 1,

L3 comprises a 3' linker sequence, where d=0 or 1,

G5 comprises at least one nucleic acid sequence encoding a GPGPG amino acid linker sequence (SEQ ID NO:56), where e=0 or 1, G3 comprises at least one second nucleic acid sequence encoding a GPGPG amino acid linker sequence (SEQ ID NO:56), where g=0 or 1, U comprises at least one MHC class II neoantigen-encoding nucleic acid sequence, where f=1, X=2 to 400, and Y=0, 1, or 2; optionally (i) wherein for each X the corresponding N is distinct; and/or (ii) wherein for each Y the corresponding U is distinct.

16. The method of claim 15, wherein:

a=0, b=1, d=1, e=1, g=1, X≥2, Y≥0, the at least one promoter nucleotide sequence is a single 26S promoter nucleotide sequence provided by the RNA alphavirus backbone, the at least one polyadenylation poly(A) sequence is a poly(A) sequence of at least 80 consecutive A nucleotides provided by the RNA alphavirus backbone, the epitope encoded by the epitope-encoding nucleic acid sequence comprises an MHC class I epitope, wherein the MHC class I epitope encoded by each N is 7-15 amino acids in length, U is each of a PADRE class II sequence and a Tetanus toxoid MHC class II sequence, the RNA alphavirus backbone is:

(a) the sequence of SEQ ID NO:3 further comprising a deletion between base pair 7544 and 11175, wherein the second neoantigen cassette is inserted to replace the deletion between base pair 7544 and 11175, and/or (b) the sequence set forth in SEQ ID NO:6, wherein the second neoantigen cassette is inserted at position 7544 of the sequence set forth in SEQ ID NO:6 the sequence set forth in SEQ ID NO:6, and each of the MHC class I neoantigen-encoding nucleic acid sequences encodes a polypeptide that is between 8 and 35 amino acids in length.

17. The method of claim 1, wherein the at least one neoantigen-encoding nucleic acid sequence that is the same comprises an epitope-encoding nucleic acid sequence that encodes an epitope that is capable of being presented by an MHC allele on the surface of a cell of the subject, optionally wherein the cell is a tumor cell optionally selected from the group consisting of: lung cancer, melanoma, breast cancer, ovarian cancer, prostate cancer, kidney cancer, gastric cancer, colon cancer, testicular cancer, head and neck cancer, pancreatic cancer, bladder cancer, brain cancer, B-cell lymphoma, acute myelogenous leukemia, adult acute lymphoblastic leukemia, chronic myelogenous leukemia, chronic lymphocytic leukemia, T cell lymphocytic leukemia, non-small cell lung cancer, and small cell lung cancer.

18. The method of claim 9, wherein the at least two neoantigen-encoding nucleic acid sequence comprises at least 2-10, 11-20, 15-20, 11-100, 11-200, 11-300, 11-400, 11, 12, 13, 14, 15, 16, 17, 18, 19, 20, 2, 3, 4, 5, 6, 7, 8, 9, 10 nucleic acid sequences, or up to 400 nucleic acid sequences, optionally wherein at least two of the neoantigen-encoding nucleic acid sequences comprise an epitope-encoding nucleic acid sequence that encodes epitopes that are capable of being presented by an MHC allele on the surface of a cell of the subject.

19. The method of claim 1, wherein the method further comprises administering (1) an adjuvant, and/or (2) an immune modulator, optionally wherein the immune modulator is an anti-CTLA4 antibody or an antigen-binding fragment thereof, an anti-PD-1 antibody or an antigen-binding fragment thereof, an anti-PD-L1 antibody or an antigen-binding fragment thereof, an anti-4-1BB antibody or an antigen-binding fragment thereof, or an anti-OX-40 antibody or an antigen-binding fragment thereof.

20. The method of claim 1, wherein the method comprises treating a subject known or suspected of having cancer, and wherein the method further comprises obtaining or having obtained at least one of exome, transcriptome, or whole genome nucleotide sequencing data from the subject, optionally exome, transcriptome, or whole genome tumor nucleotide sequencing data from a tumor of the subject.

* * * * *